(12) United States Patent
Thottathil

(10) Patent No.: US 10,226,456 B2
(45) Date of Patent: Mar. 12, 2019

(54) METHODS AND COMPOSITIONS FOR PREVENTING OPIOID ABUSE

(71) Applicant: Waterville Valley Technologies, Inc., Providence, RI (US)

(72) Inventor: John K. Thottathil, Mundelein, IL (US)

(73) Assignee: 3ST Research LLC, Westfield, NJ (US)

( * ) Notice: Subject to any disclaimer, the term of this patent is extended or adjusted under 35 U.S.C. 154(b) by 0 days.

(21) Appl. No.: 15/139,836

(22) Filed: Apr. 27, 2016

(65) Prior Publication Data

US 2016/0326182 A1 Nov. 10, 2016

Related U.S. Application Data

(60) Provisional application No. 62/153,157, filed on Apr. 27, 2015.

(51) Int. Cl.
   *A61K 31/485* (2006.01)
   *C07D 489/08* (2006.01)
   *A61K 47/54* (2017.01)

(52) U.S. Cl.
   CPC .......... *A61K 31/485* (2013.01); *A61K 47/542* (2017.08); *C07D 489/08* (2013.01)

(58) Field of Classification Search
   USPC ........................... 514/1.1, 1.3, 282, 289, 295
   See application file for complete search history.

(56) References Cited

U.S. PATENT DOCUMENTS

| | | |
|---|---|---|
| 4,673,679 A | 6/1987 | Aungst |
| 7,375,083 B2 | 5/2008 | Mickle |
| 8,816,083 B2 | 8/2014 | Mickle |
| 2004/0058946 A1 | 3/2004 | Buchwald et al. |
| 2005/0075361 A1 | 4/2005 | Wang |
| 2005/0080012 A1 | 4/2005 | Mickle |
| 2010/0286186 A1* | 11/2010 | Franklin ............... A61K 31/485 514/282 |
| 2011/0040072 A1* | 2/2011 | Mickle ................. A61K 9/0019 530/330 |
| 2011/0053971 A1 | 3/2011 | Guillaume et al. |
| 2014/0200235 A1 | 7/2014 | Riggs-Sauthier |
| 2016/0326182 A1 | 11/2016 | Peltier |
| 2017/0151228 A1 | 6/2017 | Thottathil |
| 2017/0152266 A1 | 6/2017 | Thottathil |
| 2017/0196851 A1 | 7/2017 | Thottathil |

FOREIGN PATENT DOCUMENTS

WO    WO 03/032990 A2 *    4/2003    ........... A61K 31/485

OTHER PUBLICATIONS

Non-Final Office Action in U.S. Appl. No. 14/953,392 dated Jan. 13, 2017, 15 pages.
Non-Final Office Action in U.S. Appl. No. 14/956,143 dated Dec. 28, 2016, 12 pages.
PCT International Search Report and Written Opinion in PCT/US16/63834 dated Jan. 31, 2017, 17 pages.
PCT International Search Report and Written Opinion in PCT/US16/63836 dated Jan. 24, 2017, 17 pages.
Aquina, et al., "OxyContin Abuse and Overdose", Postgrad Med. vol. 121, Issue 2, Mar. 2009, 163-67, Abstract.
Final Office Action in U.S. Appl. No. 14/953,392, dated Oct. 19, 2017, 14 pages.
Final Office Action in U.S. Appl. No. 14/956,143, dated Jul. 17, 2017, 18 pages.
PCT International Search Report and Written Opinion in PCT/US18/24476 dated May 17, 2018, 24 pages.

* cited by examiner

*Primary Examiner* — Pancham Bakshi
(74) *Attorney, Agent, or Firm* — Servilla Whitney LLC

(57) ABSTRACT

Abuse-resistant opioid compounds, drug delivery systems, pharmaceutical compositions comprising an opioid covalently bound to a chemical moiety are provided. Methods of delivering an active ingredient to a subject and methods of preventing opioid abuse are also provided.

5 Claims, 14 Drawing Sheets

METHODS AND COMPOSITIONS FOR PREVENTING OPIOID ABUSE

FIELD OF THE INVENTION

The following invention generally relates to the field of preventing the overuse and/or abuse of certain medicines, and in particular, opioid compounds.

BACKGROUND OF THE INVENTION

Opioids reduce pain by decreasing perception of pain, decreasing reaction to pain, and increasing pain tolerance. They have long been used in the treatment of acute and chronic pain. Opioid use may produce side effects such as feelings of euphoria, and, as such, opioids are among the most misused and abused medications. Attempts to create abuse-resistant opioids have been made (e.g., crush-resistant formulations), but skilled illicit chemists have thus far been able to extract the opioids from these formulations.

Therefore there at least remains a need in the art for the availability of new methods and compositions for preventing opioid abuse.

SUMMARY OF THE INVENTION

One or more embodiments of the invention may address one or more of the aforementioned problems. The present invention addresses some of the needs mentioned above by using abuse-resistant opioid compounds comprising an opioid covalently bound to a chemical moiety. For example, certain embodiments according to the present invention provide abuse-resistant opioid compounds. In some embodiments, the abuse-resistant opioid compound may comprise an opioid covalently bound to a chemical moiety.

In another aspect, the present invention provides a drug delivery system including abuse-resistant opioid compounds. In such embodiments, the abuse-resistant opioid compound comprises an opioid covalently bound to a chemical moiety.

In another aspect, the present invention provides a pharmaceutical composition including abuse-resistant opioid compounds wherein the abuse-resistant opioid compounds comprise an opioid covalently bound to a chemical moiety.

In another aspect, the present invention provides a method of delivering an active ingredient to a subject by administering a therapeutically effective amount of an opioid compound to a subject.

In another aspect, the present invention provides a method of preventing opioid abuse by administering a therapeutically effective amount of an opioid compound to a subject.

BRIEF DESCRIPTION OF THE DRAWINGS

The present invention now will be described more fully hereinafter with reference to the accompanying drawings, in which some, but not all embodiments of the invention are shown. The present invention may be embodied in many different forms and should not be construed as limited to the embodiments set forth herein; rather, these embodiments are provided so that this disclosure will satisfy applicable legal requirements and demonstrate exemplary embodiments of the invention. Repeat use of reference characters in the present specification and drawings is intended to represent same or analogous features or elements of the invention.

DETAILED DESCRIPTION OF PREFERRED EMBODIMENTS

Figure 1:
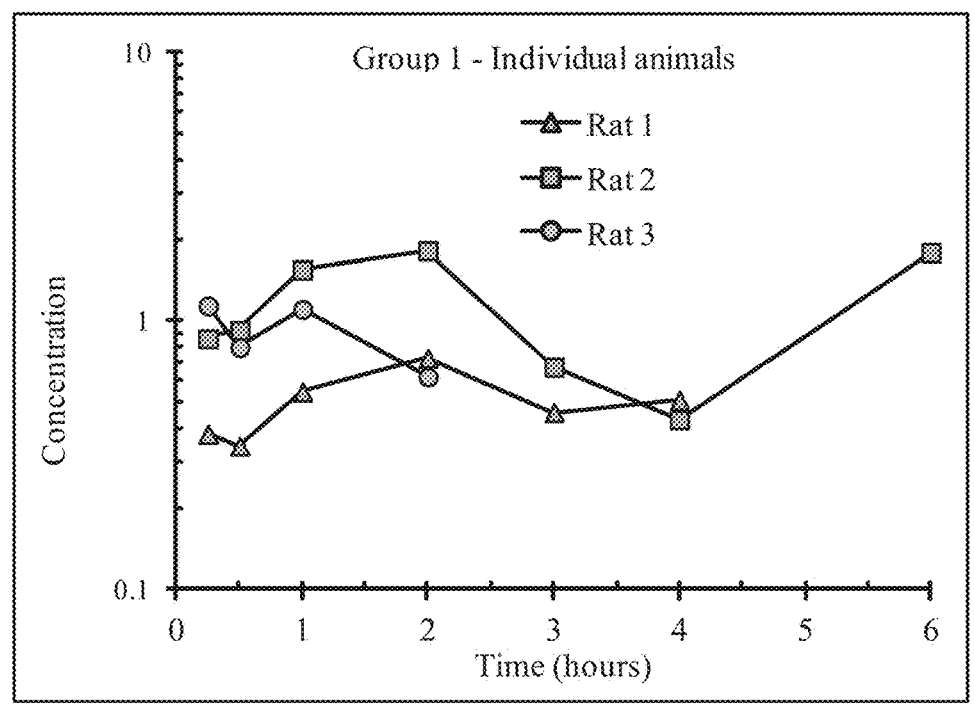
FIG. 1 illustrates plasma concentrations of oxymorphone at dose 1.77 mg/kg Oxymorphone HCl Oral for individual animals.
Figure 2:
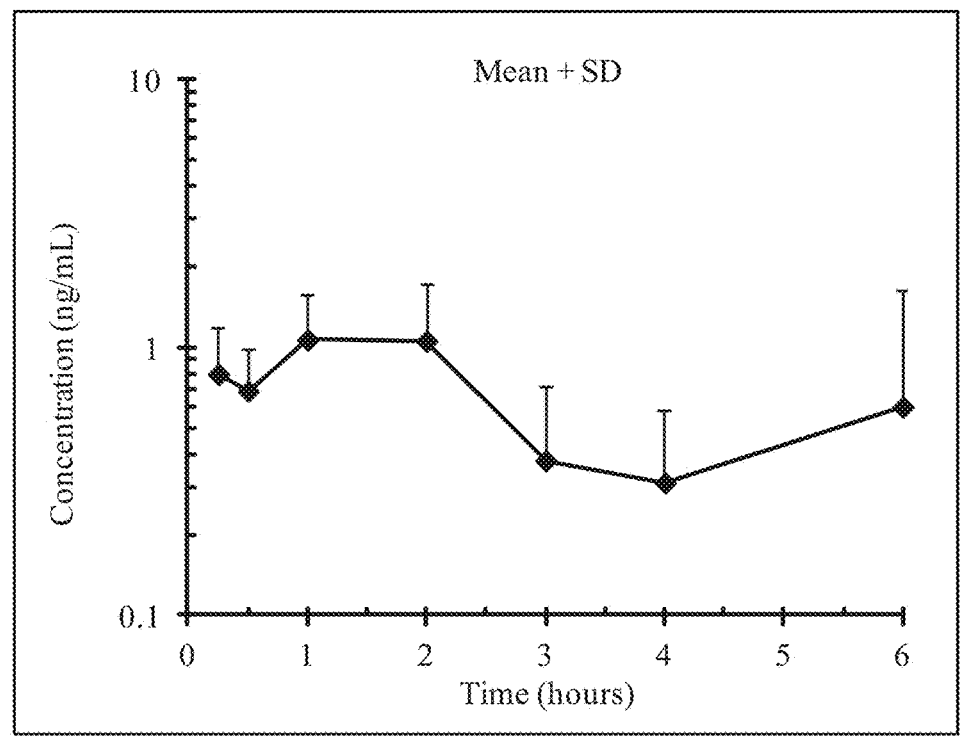
FIG. 2 illustrates mean and standard deviation plasma concentrations of oxymorphone at dose 1.77 mg/kg Oxymorphone HCl Oral.
Figure 3:
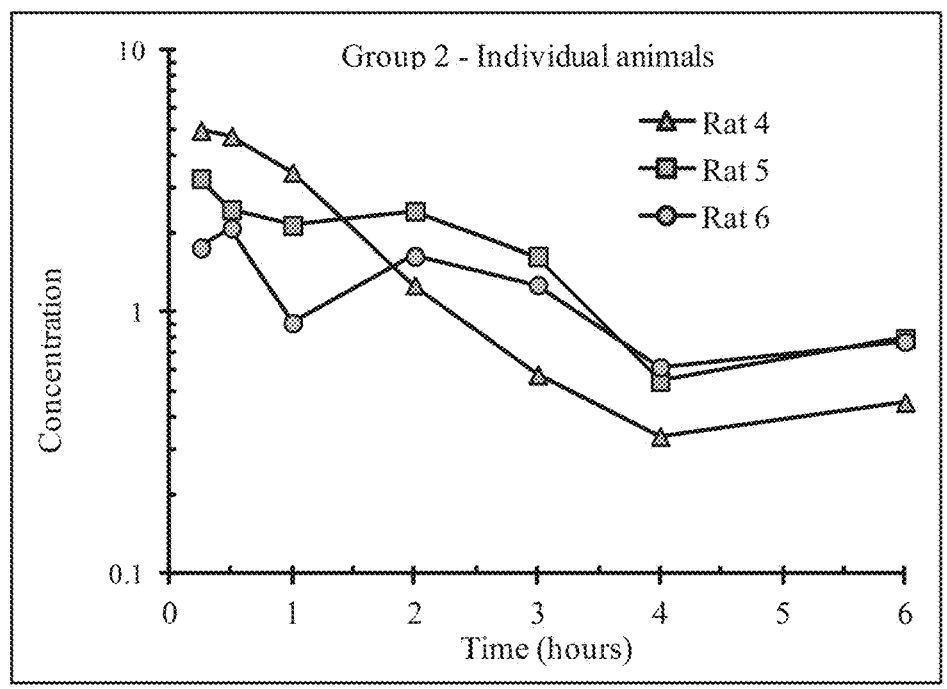
FIG. 3 illustrates plasma concentrations of oxymorphone at dose 3.54 mg/kg Oxymorphone HCl Oral for individual animals.
Figure 4:
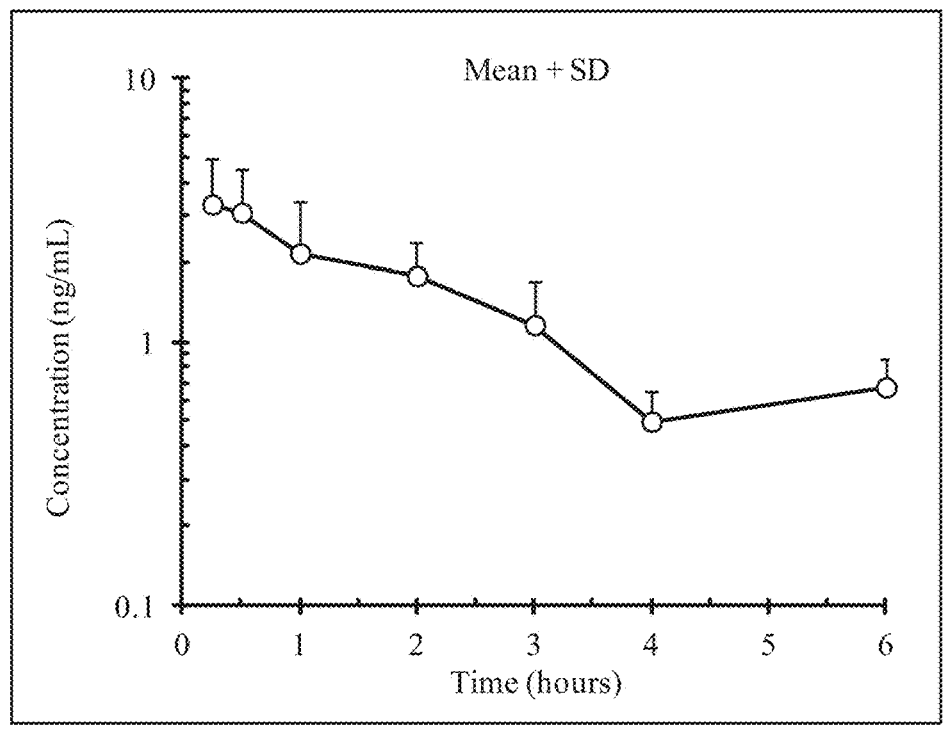
FIG. 4 illustrates mean and standard deviation plasma concentrations of oxymorphone at dose 3.54 mg/kg Oxymorphone HCl Oral.
Figure 5:
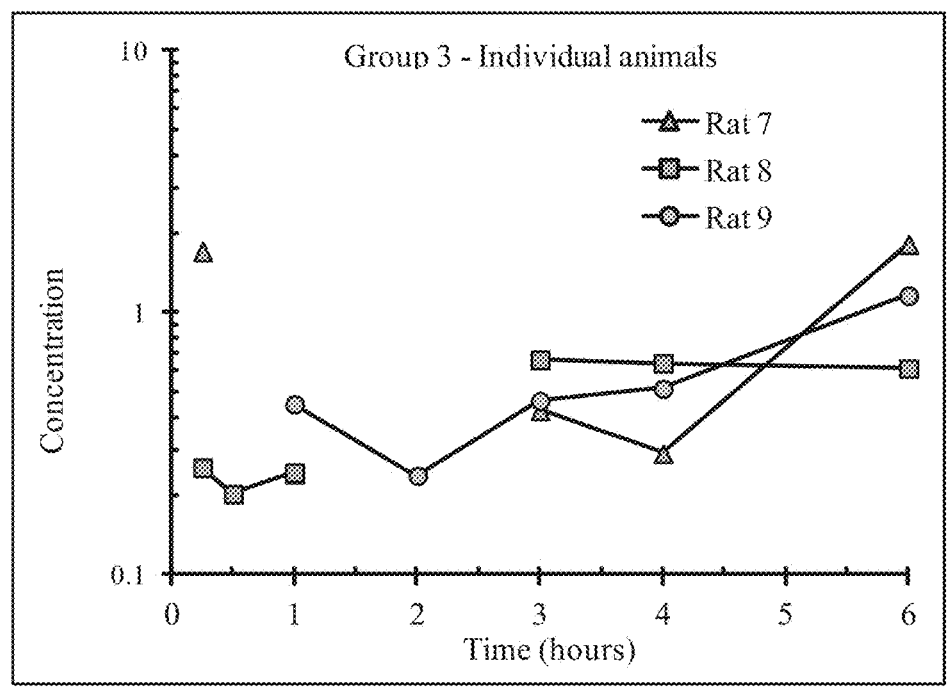
FIG. 5 illustrates plasma concentrations of oxymorphone at dose 7.12 mg/kg Oxymorphone Oleate (Ex No. B3) Oral for individual animals.
Figure 6:
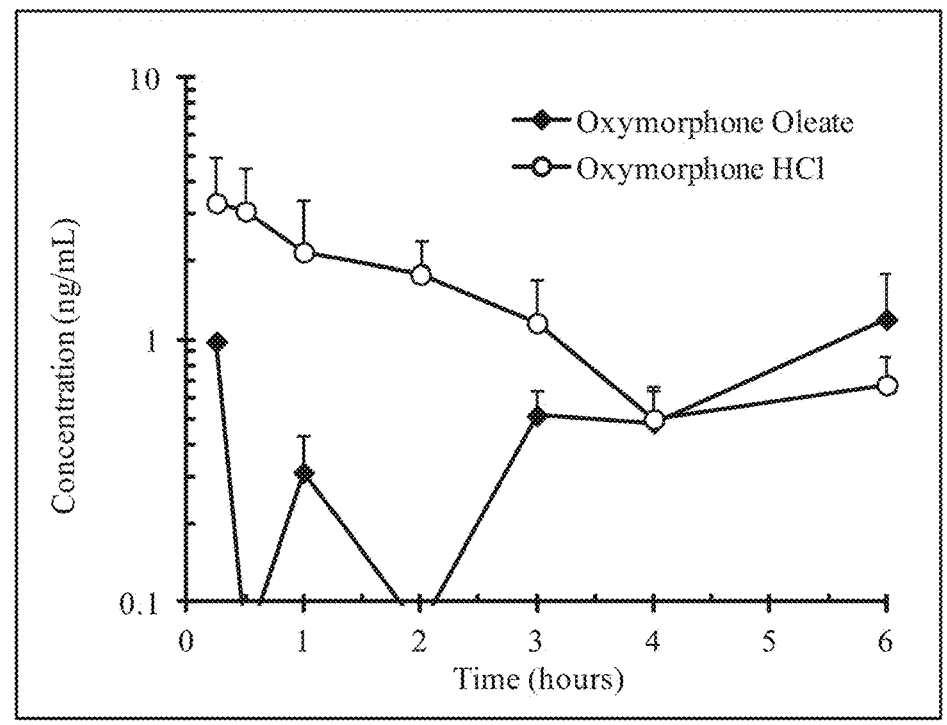
FIG. 6 illustrates mean and standard deviation plasma concentrations of oxymorphone at dose 7.12 mg/kg Oxymorphone Oleate (Ex No. B3) Oral.
Figure 7:
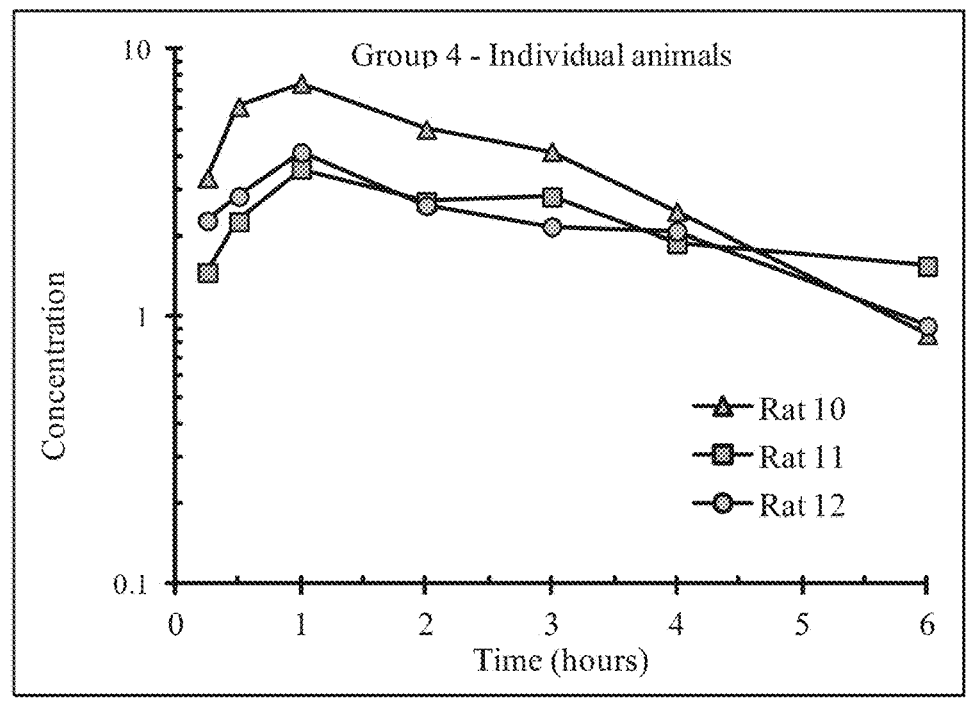
FIG. 7 illustrates plasma concentrations of oxymorphone at dose 5.56 mg/kg Oxymorphone Malate (Ex No. B5) Oral for individual animals.
Figure 8:
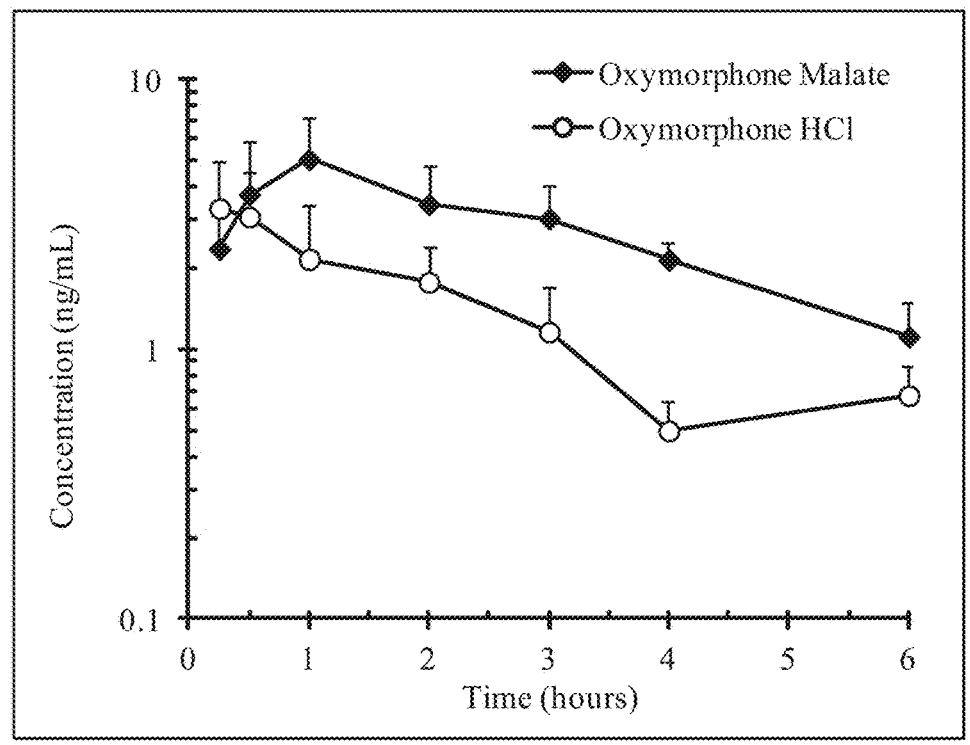
FIG. 8 illustrates mean and standard deviation plasma concentrations of oxymorphone at dose 5.56 mg/kg Oxymorphone Malate (Ex No. B5) Oral.
Figure 9:
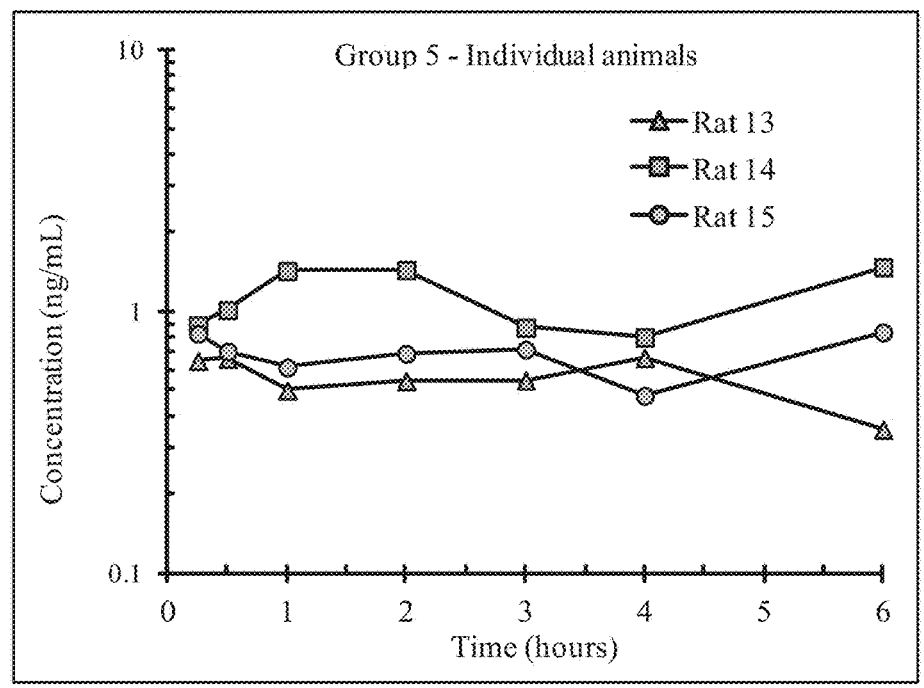
FIG. 9 illustrates plasma concentrations of oxymorphone at dose 6.72 mg/kg Oxymorphone Mandelate (Ex No. B1a) Oral for individual animals.
Figure 10:
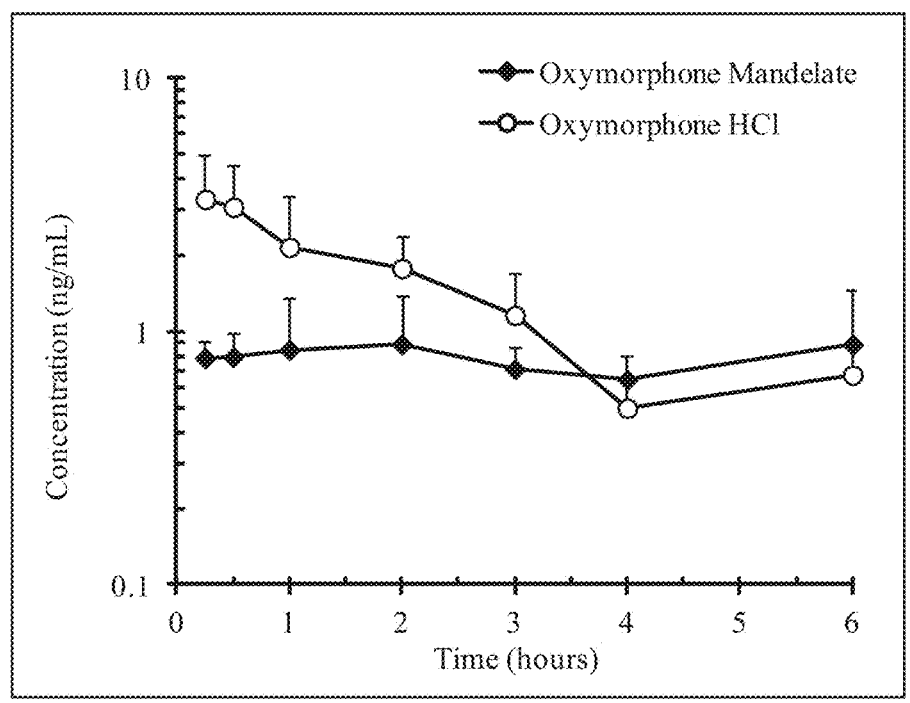
FIG. 10 illustrates mean and standard deviation plasma concentrations of oxymorphone at dose 6.72 mg/kg Oxymorphone Mandelate (Ex No. B1a) Oral.
Figure 11:
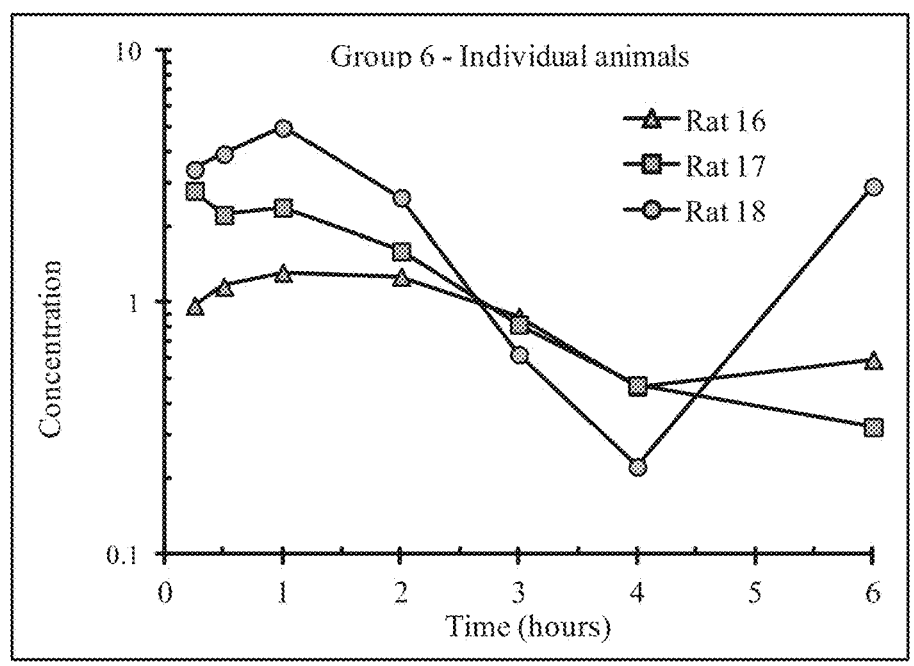
FIG. 11 illustrates plasma concentrations of oxymorphone at dose 5.48 mg/kg Oxymorphone Mandelate (Ex No. B1b) Oral for individual animals.
Figure 12:
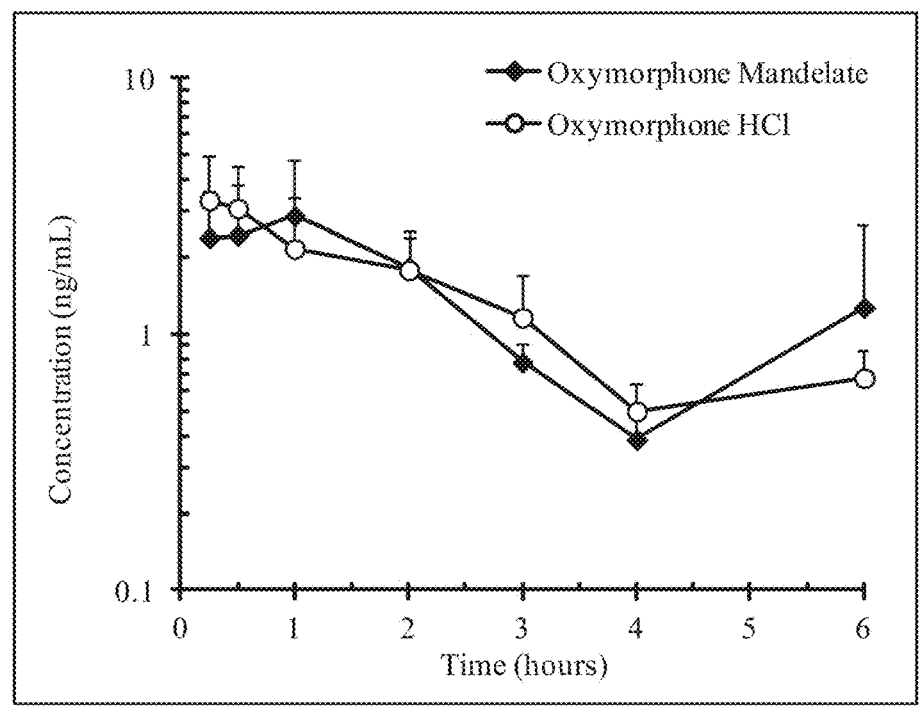
FIG. 12 illustrates mean and standard deviation plasma concentrations of oxymorphone at dose 5.48 mg/kg Oxymorphone Mandelate (Ex No. B1b) Oral.
Figure 13:
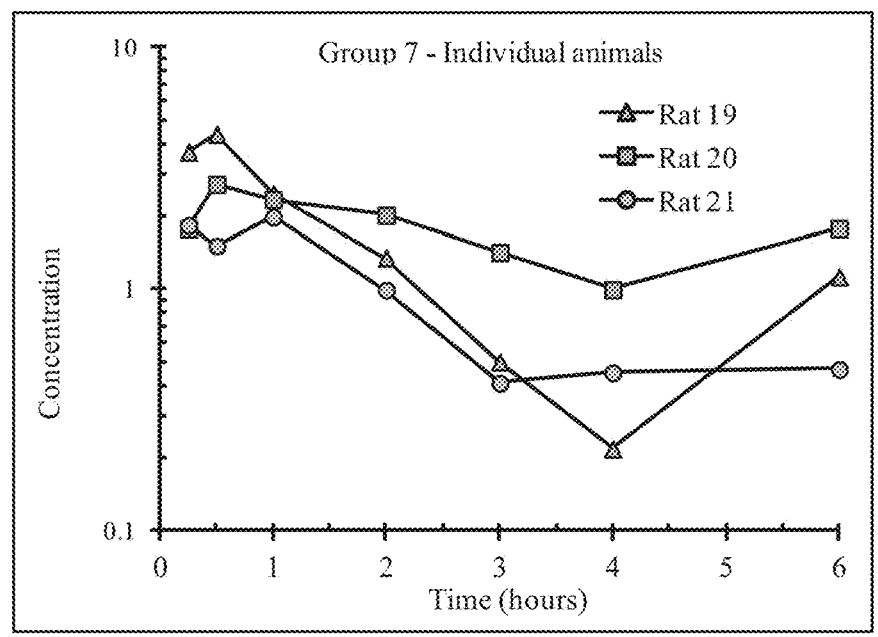
FIG. 13 illustrates plasma concentrations of oxymorphone at dose 6.01 mg/kg Oxymorphone Lactate (Ex No. B2a) Oral for individual animals.
Figure 14:
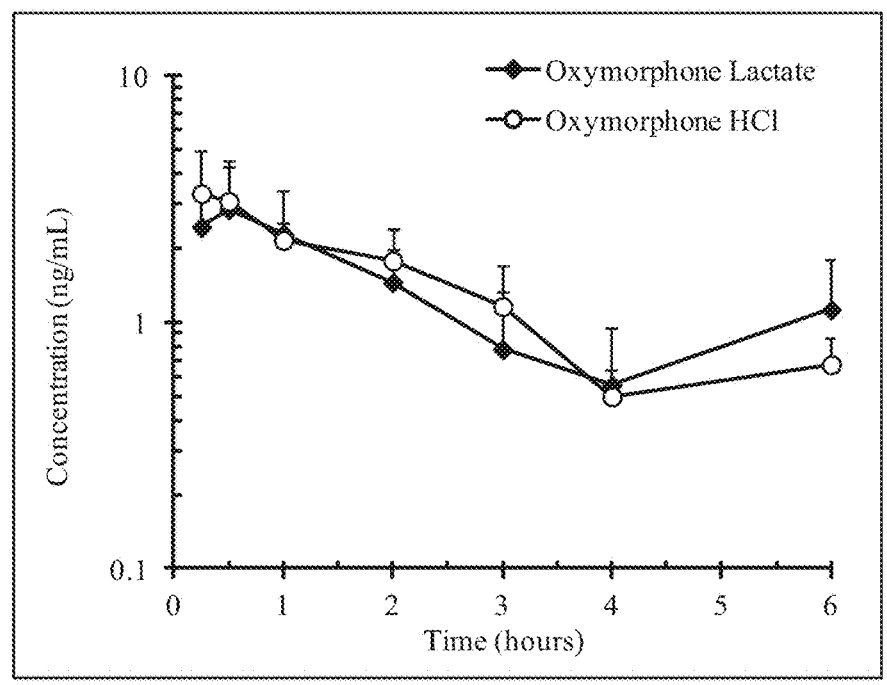
FIG. 14 illustrates mean and standard deviation plasma concentrations of oxymorphone at dose 6.01 mg/kg Oxymorphone Lactate (Ex No. B2a) Oral.
Figure 15:
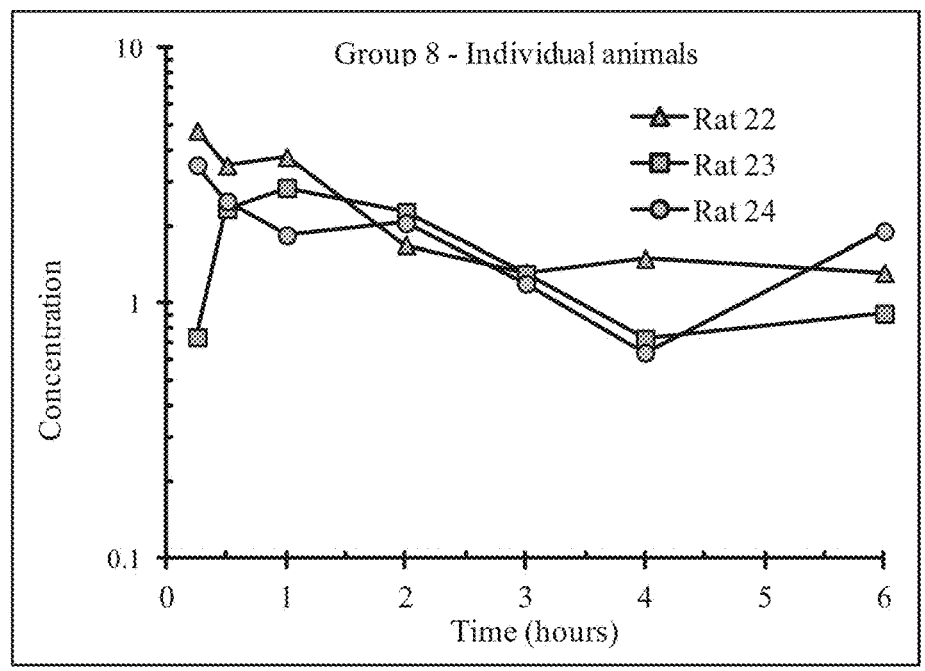
FIG. 15 illustrates plasma concentrations of oxymorphone at dose 4.93 mg/kg Oxymorphone Lactate (Ex No. B2b) Oral for individual animals.
Figure 16:
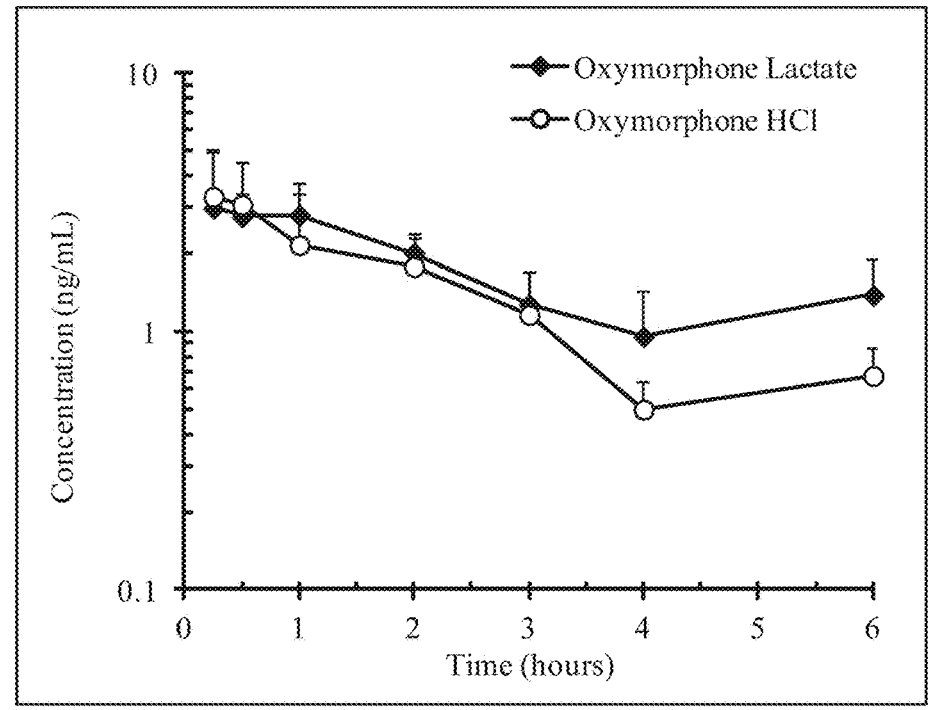
FIG. 16 illustrates mean and standard deviation plasma concentrations of oxymorphone at dose 4.93 mg/kg Oxymorphone Lactate (Ex No. B2b) Oral.
Figure 17:
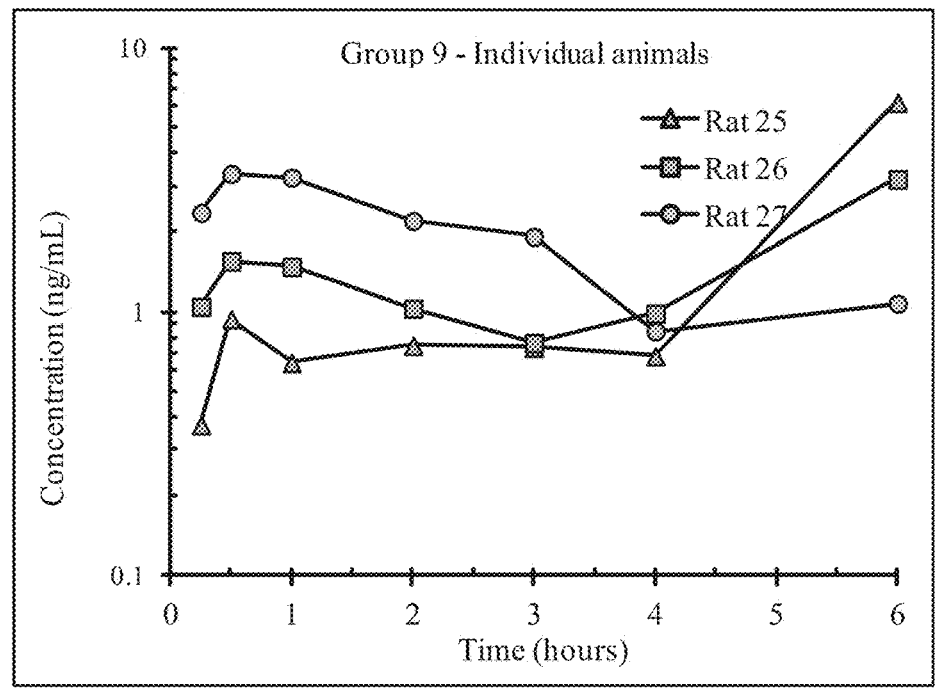
FIG. 17 illustrates plasma concentrations of oxymorphone at dose 7.4 mg/kg Oxymorphone Stearate (Ex No. B4) Oral for individual animals.
Figure 18:
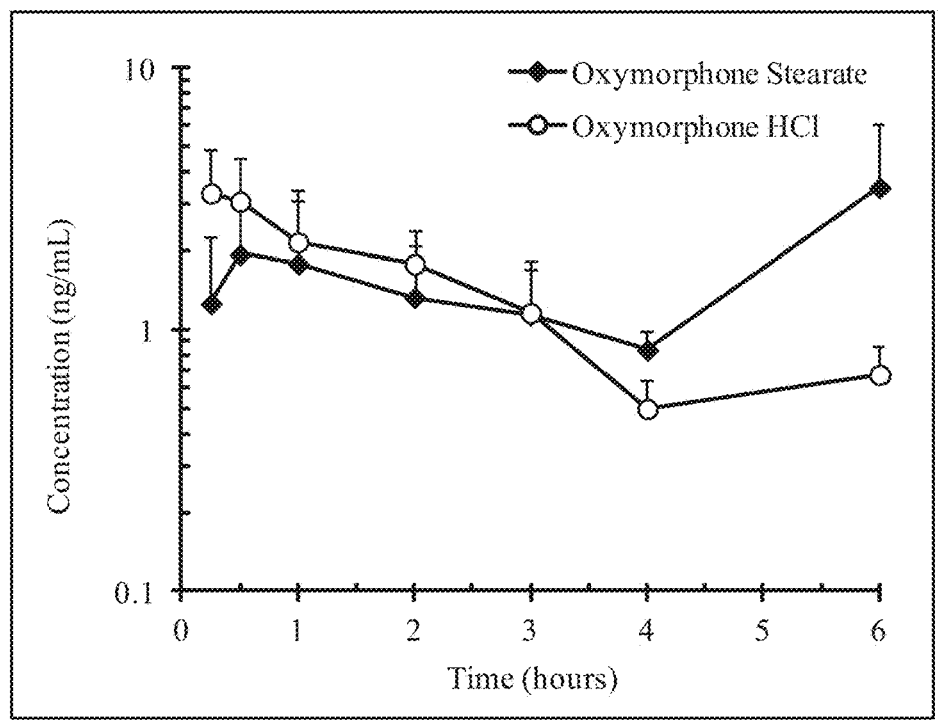
FIG. 18 illustrates mean and standard deviation plasma concentrations of oxymorphone at dose 7.4 mg/kg Oxymorphone Stearate (Ex No. B4) Oral.
Figure 19:
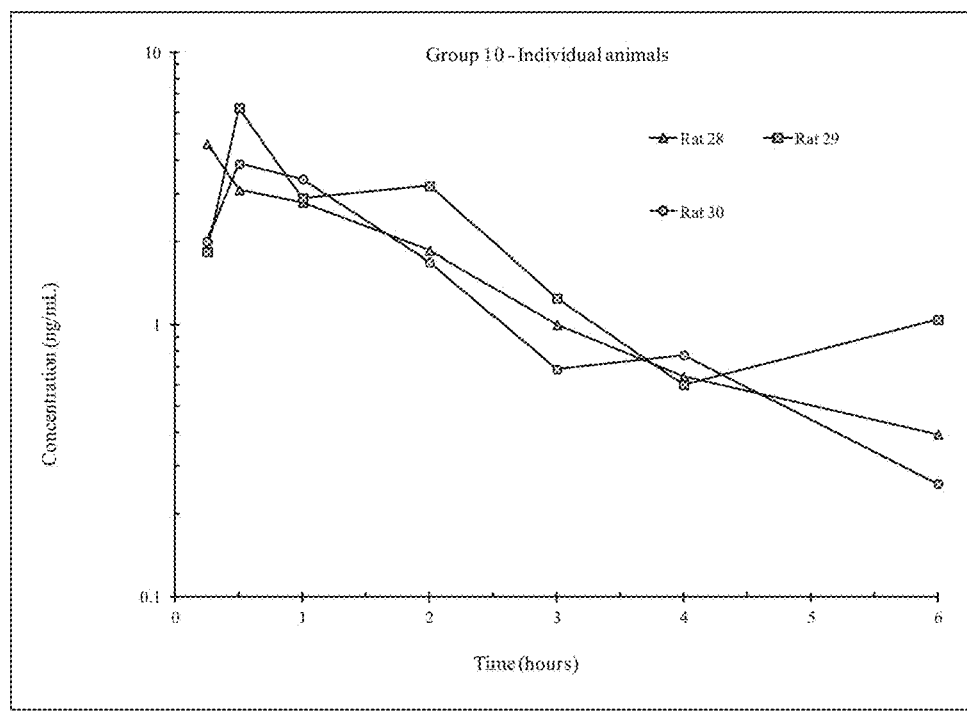
FIG. 19 illustrates plasma concentrations of oxymorphone at dose 6.16 mg/kg Oxymorphone Alanine (Ex No. B6) Oral.
Figure 20:
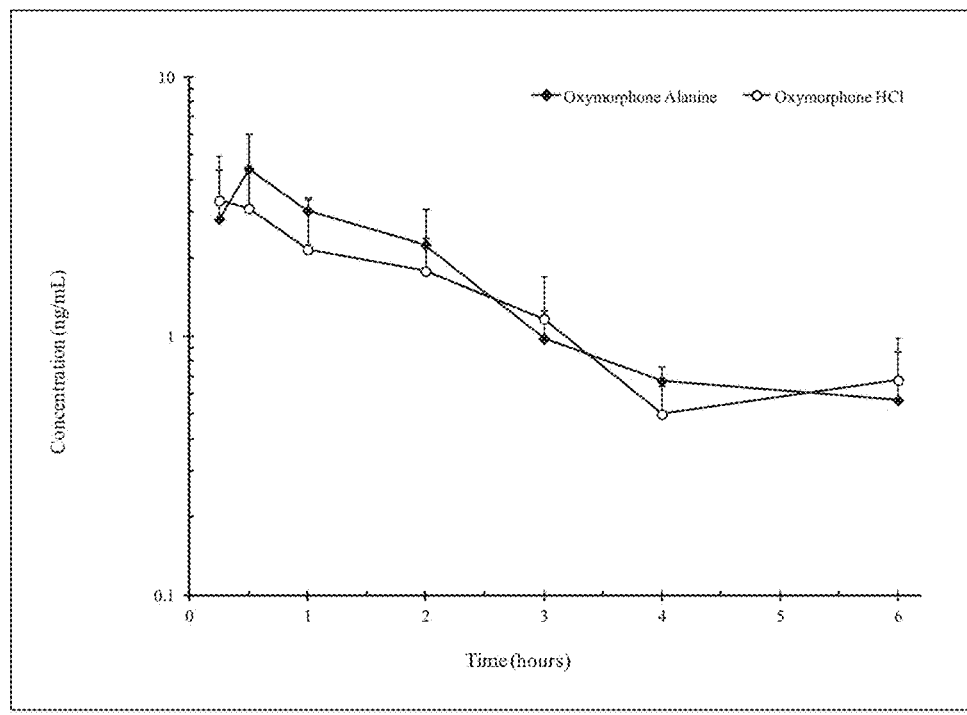
FIG. 20 illustrates mean and standard deviation plasma concentrations of oxymorphone at dose 6.16 mg/kg Oxymorphone Alanine (Ex No. B6) Oral.
Figure 21:
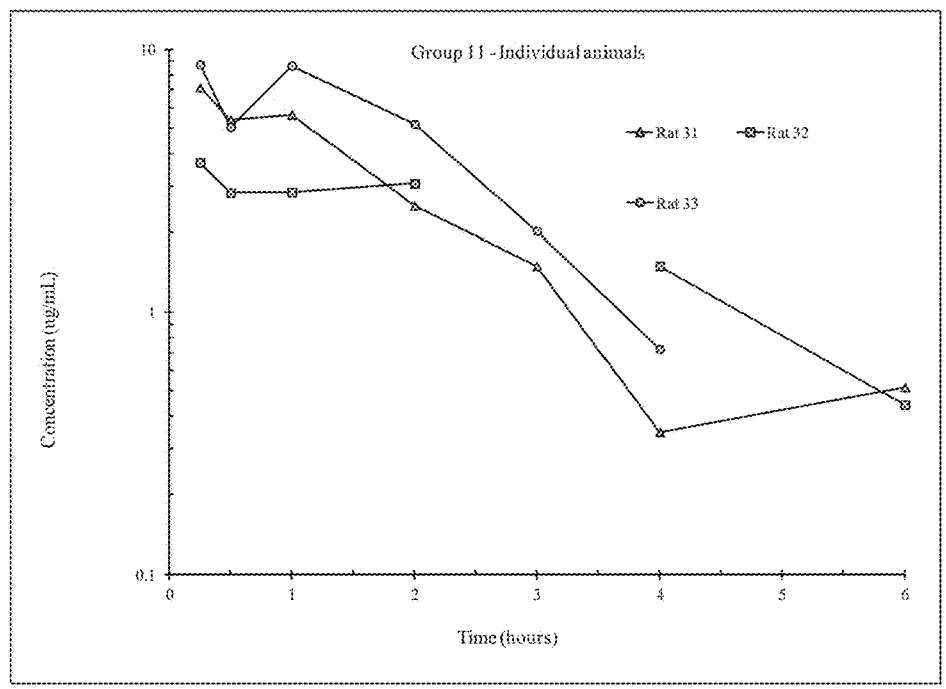
FIG. 21 illustrates plasma concentrations of oxymorphone at dose 5.41 mg/kg Oxymorphone Alanine (Ex No. B7) Oral.
Figure 22:
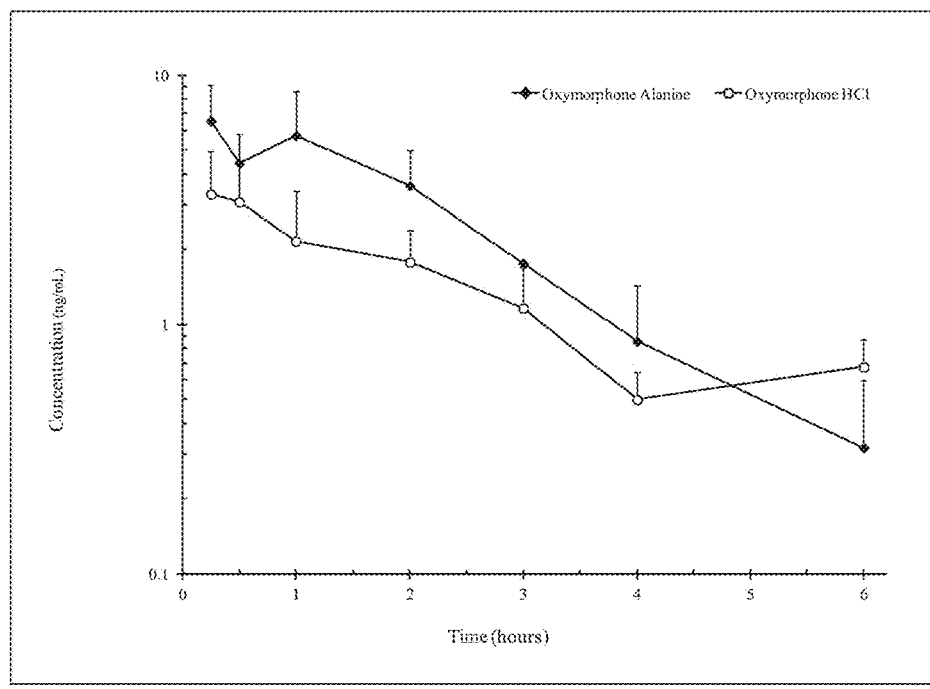
FIG. 22 illustrates mean and standard deviation plasma concentrations of oxymorphone at dose 5.41 mg/kg Oxymorphone Alanine (Ex No. B7) Oral.
Figure 23:
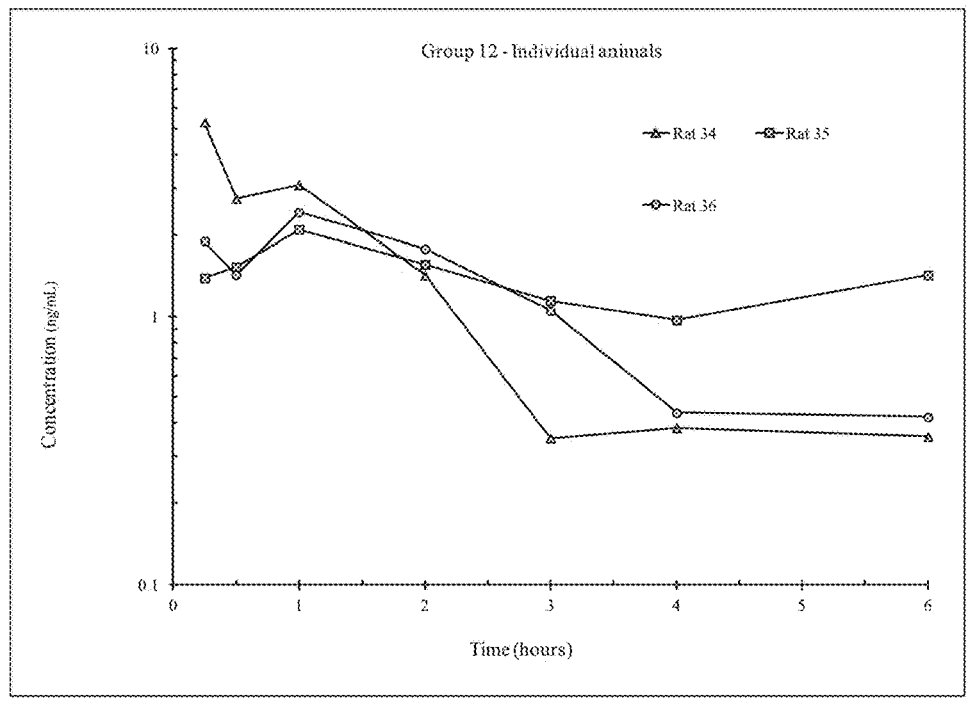
FIG. 23 illustrates plasma concentrations of oxymorphone at dose 6.01 mg/kg Oxymorphone Mandelate (Ex No. B8) Oral.
Figure 24:
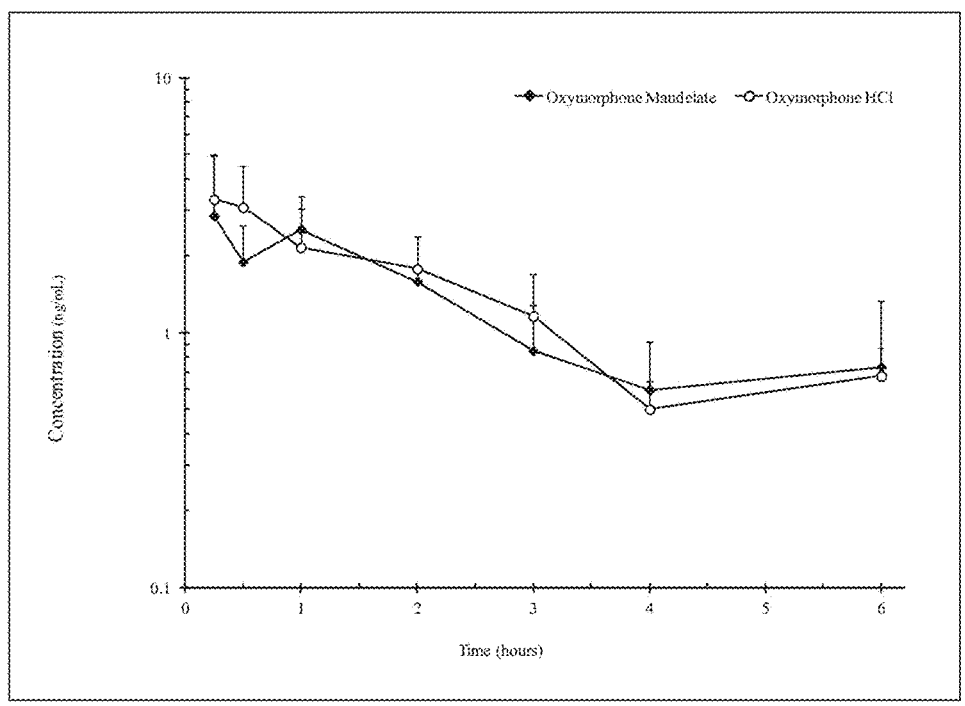
FIG. 24 illustrates mean and standard deviation plasma concentrations of oxymorphone at dose 6.01 mg/kg Oxymorphone Mandelate (Ex No. B8) Oral.
Figure 25:
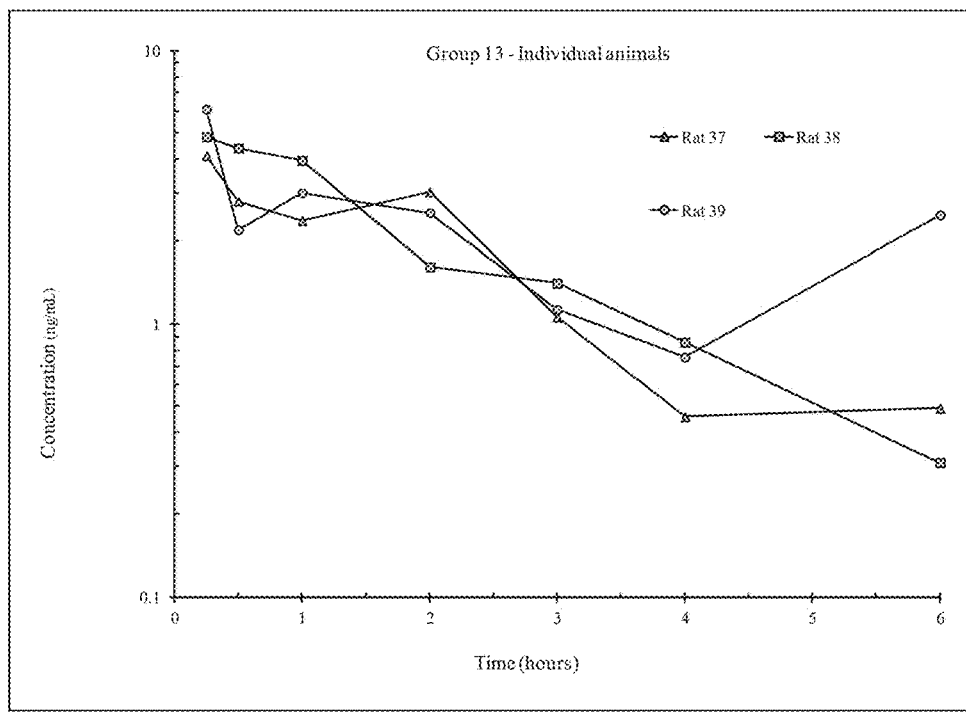
FIG. 25 illustrates plasma concentrations of oxymorphone at dose 6.02 mg/kg Oxymorphone Malate (Ex No. B9) Oral.
Figure 26:
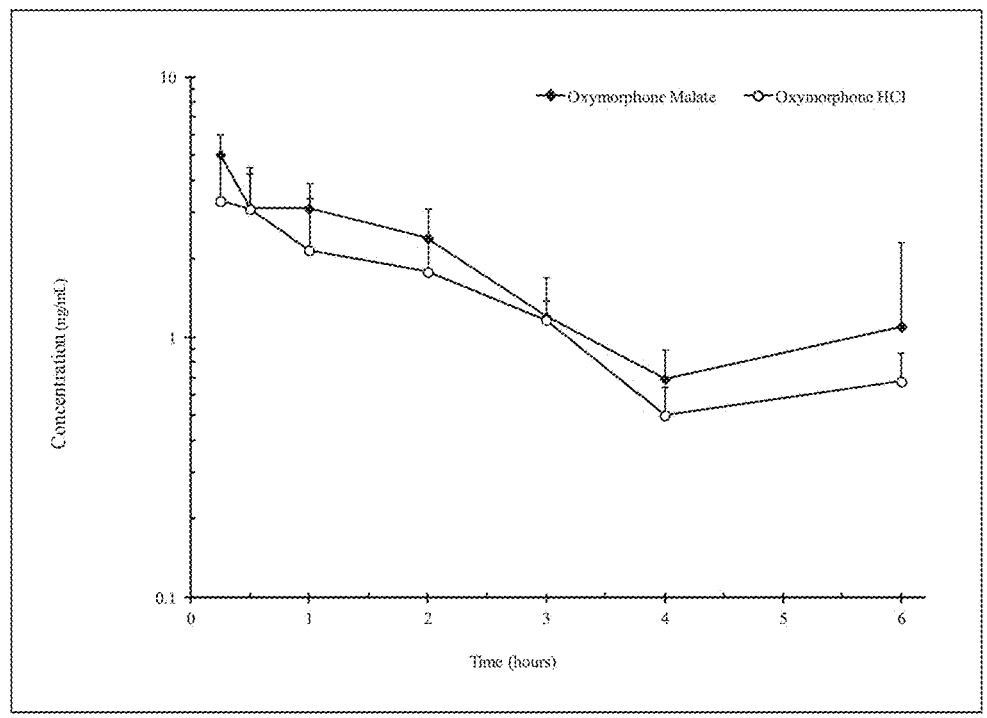
FIG. 26 illustrates mean and standard deviation plasma concentrations of oxymorphone at dose 6.02 mg/kg Oxymorphone Malate (Ex No. B9) Oral.
Figure 27:
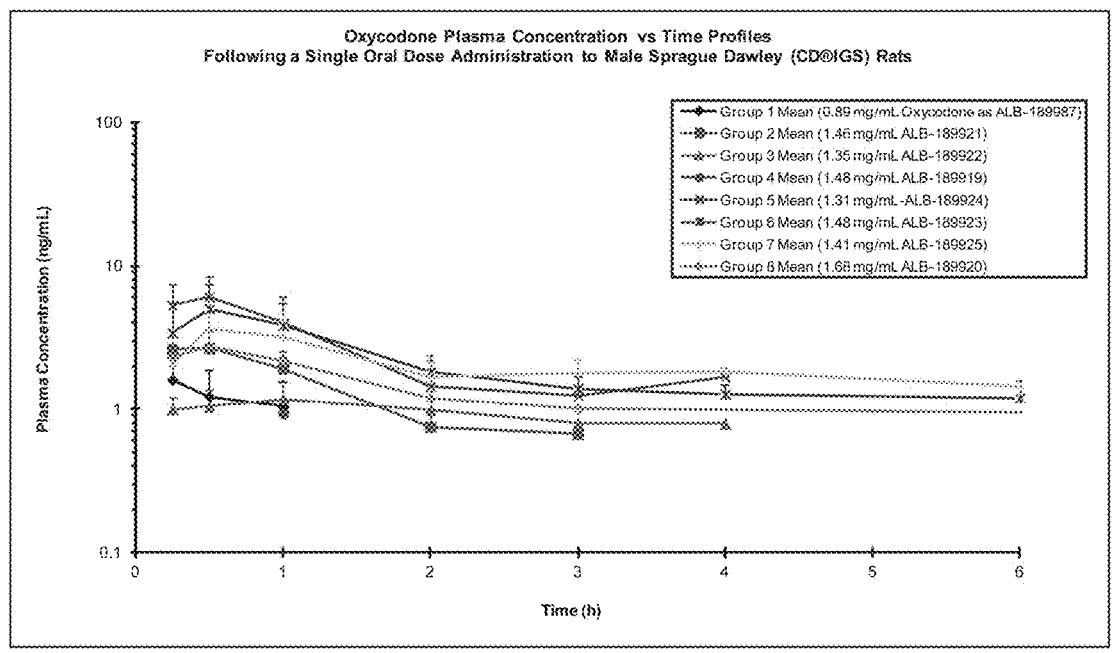
FIG. 27 illustrates average plasma concentrations of oxycodone in rats at various doses of opioid compounds according to certain embodiments of the present invention.

Reference will now be made in detail to exemplary embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

As used herein, the term "composition" may comprise any composition containing one or more opioid compounds. The composition may comprise a dry formulation, an aqueous solution, or a sterile composition. Compositions comprising the opioid compounds described herein may be stored in freeze-dried form and may be associated with a stabilizing agent such as a carbohydrate. In use, the composition may be deployed in an aqueous solution containing salts, e.g., NaCl, detergents such as sodium dodecyl sulfate (SDS), and other components.

The term "alkyl", as used herein, may refer to linear or branched alkyl groups. Exemplary alkyl groups include methyl, ethyl, n-propyl, iso-propyl, n-butyl, iso-butyl, t-butyl, n-pentyl, iso-pentyl, hexyl, heptyl, octyl and the like. Unless otherwise specified, an alkyl group typically has from about 1 to about 10 carbon atoms.

The term "alkoxy", as used herein, may refer to an —O (alkyl) group, where alkyl is as defined above. Exemplary alkyl groups include methoxy, ethoxy, prepay, butoxy, iso-propoxy, iso-butoxy, and the like. Unless otherwise specified, an alkoxy group typically has from 1 to about 10 carbon atoms.

The term "amine", as used herein, may refer to a primary, secondary, or tertiary amino group. The secondary and tertiary amine may contain alkyl, cycloalkyl or aryl substitutions. Some examples of amines include $NH_2$, NHMe, $NMe_2$, NH(cyclopropyl), and the like. Unless otherwise specified, the alkyl or cycloalkyl group on an amine typically has from 1 to about 8 carbon atoms.

The term "aryl", as used herein, may refer to an optionally substituted monocyclic or polycyclic aromatic ring system of about 6 to about 14 carbon atoms. Exemplary aryl groups include phenyl, naphthyl, and the like. Unless otherwise specified, an aryl group typically has from 6 to about 14 carbon atoms.

The term "salts", as used herein, may refer to any acid or base salt, pharmaceutically acceptable solvates, or any complex of the compound that, when administered to a recipient, is capable of providing (directly or indirectly) a compound as described herein. It should be appreciated, however, that salts that are not pharmaceutically acceptable also lie within the scope of the invention. The preparation of salts can be carried out using known methods.

For example, pharmaceutically acceptable salts of compounds contemplated herein as being useful may be synthesized by conventional chemical methods using a parent compound containing a base or an acid functionality. Generally, such salts may be prepared, for example, by making free acid or base forms of the compounds and reacting with a stoichiometric quantity of the appropriate base or acid in water or in an organic solvent, or in a mixture of the two. Generally, non-aqueous media such as one or more of solvents such as ether, ethyl acetate, ethanol, isopropanol or acetonitrile may be utilized. Examples of acid addition salts include one or more of mineral acid addition salts such as hydrochloride, hydrobromide, hydroiodide, sulphate, phosphate, and organic acid addition salts such as one or more of acetate, maleate, fumarate, citrate, oxalate, succinate, tartrate, malate, mandelate, methanesulphonate and p-toluenesulphonate. Examples of base addition salts include one or more of inorganic salts such as sodium, potassium, calcium, ammonium, magnesium, and lithium salts, and organic base salts such as one or more of ethylenediamine, ethanolamine, N,N-dialkyl-ethanolamine, triethanolamine, and basic amino acid salts.

As used herein, the term "peptide" may refer to a single amino acid, a dipeptide, a tripeptide, an oligopeptide, a polypeptide, or a carrier peptide. An oligopeptide includes from 2 to 70 amino acids.

The terms "decreased", "reduced", "diminished", or "lowered", as used herein, include at least a 10% change in pharmacological activity with greater percentage changes being preferred for reduction in abuse potential and overdose potential. For instance, the change may also be greater than 25%, 35%, 45%, 55%, 65%, 75%, 85%, 95%, 96%, 97%, 98%, 99%, or other increments greater than 10%.

The term "similar pharmacological activity", as used herein, may indicate that two compounds exhibit curves that have substantially the same AUC, $C_{max}$, $T_{max}$, $C_{min}$, and/or $t_{1/2}$ parameters, within, in certain exemplary embodiments, about 30% of each other, and in further exemplary embodiments within about 25%, 20%, 10%, 5%, 2%, 1%, or other increments less than 30%.

For ease of reference, the present invention will be described in terms of administration to human subjects. It will be understood, however, that such descriptions are not limited to administration to humans, but will also include administration to other animals unless explicitly stated otherwise.

In one aspect, the present invention provides abuse-resistant opioid compounds comprising an opioid covalently bound to at least one chemical moiety. The opioid compounds can also be characterized as conjugates in that they possess a covalent attachment. The opioid compounds may also be characterized as conditionally bioreversible derivatives ("CBDs") in that, according to certain embodiments, the opioid compound remains inactive until oral administration releases the opioid from the at least one chemical moiety.

In accordance with certain embodiments of the present invention, the opioid compound may be represented by Formula I:

$$O\text{-}X_n\text{—}Z_m \quad (I)$$

wherein O is an opioid; each X is an independent chemical moiety; each Z is an independent chemical moiety that acts as an adjuvant and is a different chemical moiety from at least one X; n is from 1 to 50; and m is from 0 to 50. In further embodiments, n may be from 1 to 10, and m may be from 0 to 10.

In some embodiments, m may be 0. In such embodiments, the opioid compound may be represented by Formula II:

$$O\text{-}X_n \quad (II)$$

wherein O is an opioid; each X is an independent chemical moiety; and n is from 1 to 50. Formula II can also be written to designate the chemical moiety that is physically attached to the opioid:

$$O\text{-}X_1\text{—}(X)_{n-1} \quad (III)$$

wherein O is an opioid; $X_1$ is a chemical moiety; each X is an independent chemical moiety that is the same or different from $X_1$; and n is from 1 to 50. In further embodiments, n may be from 1 to 10.

In accordance with certain embodiments of the present invention, the opioid O may be any of the natural or synthetic derivatives of *Papaver somniferum* such as oxymorphone or oxycodone, or any derivative, analog, or salt thereof. In some embodiments, the opioid O may be selected from the group consisting of a natural opioid, an ester of morphine opioid, an ether of morphine opioid, a semi-synthetic opioid, a synthetic opioid, and an endogenous opioid peptide. As such, exemplary opioids include, but are not limited to, morphine; codeine; thebaine; oripavine; diacetylmorphine; 2,4-dinitrophenylmorphine; methylenedioxydimethylamphetamine; chlomaltrexamine; dihydromorphine; hydromorphinol; nicomorphine; dipropanoylmorphine; desomorphine; acetylproprionylmorphine; methyldesorphine; N-phenethylnormorphine; 14-hydroxy-dihydrocodeine (RAM-318); 7,8-dihydro-14-hydroxy-N-phenethylnormorphine (RAM-378); dibenzoylmorphine; diacetyldihydromorphine; dibenzoylmorphine; 6-monoacetylcodeine (6-MAC); acetyldihydrocodeine; dihydrocodeine; nalbuphine; nicocodeine; nicodicodeine; oxymorphazone; 1-iodomorphine; morphine-6-glycuronide (M6G); 6-monoacetylmorphine (6-MAM); norcodeine; normorphine; genomorphine; dextrallorphan (DXA); cyclorphan; dihydroheterocodeine; pholcodine; myrophine; 14-cinnamoyloxycodeinone; 14-ethoxymetopon; 14-methoxymetopon; 14-phenylpropoxymetopon (PPOM); 7-spiroindanyloxymorphone; acetylmorphine; codeinone; conorphone; codoxime; thebacon; metopon; N-phenethyl-14-ethoxymetopon; morphinone; benzylmorphine; codeine methylbromide; ethylmorphine; heterocodeine; hydromorphone; hydrocodone; oxycodone; oxymorphone; pentamorphone; semorphone; chloromorphide; ethylmorphine; buprenorphine; fentanyl; alphamethylfentanyl; alfentanil; sufentanil; remifentanil; carfentanyl; ohmefentanyl; pethidine; ketobemidone; desmethylprodine (MPPP); allylprodine; prodine; 1-methyl-4-phenyl-4-propionoxypiperidine (PEPAP); propoxyphene; dextropropoxyphene; dextromoramide; bezitramide; piritramide; levorphanol; methadone; dipipanone; levomethadyl acetate (LAAM); difenoxin; diphenoxylate; loperamide; dezocine; pentazocine; phenazocine; dihydroetorphine; etorphine; butorphanol; nalbuphine; levomethorphan; levophenacylmorphan; norlevorphanol; oxilorphan; phenomorphan; furethylnorlevorphanol; xorphanol; butorphanol; cyprodime; drotebanol; 7-PET; acetorphine; BU-48; cyprenorphine; norbuprenorphine; lefetamine; meptazinol; mitragynine; tilidine; tramadol; tapentadol; dextropropoxyphene; endorphins; enkephalins; dynorphins; and endomorphins. In some embodiments, the opioid is oxymorphone. In further embodiments, the opioid is oxycodone.

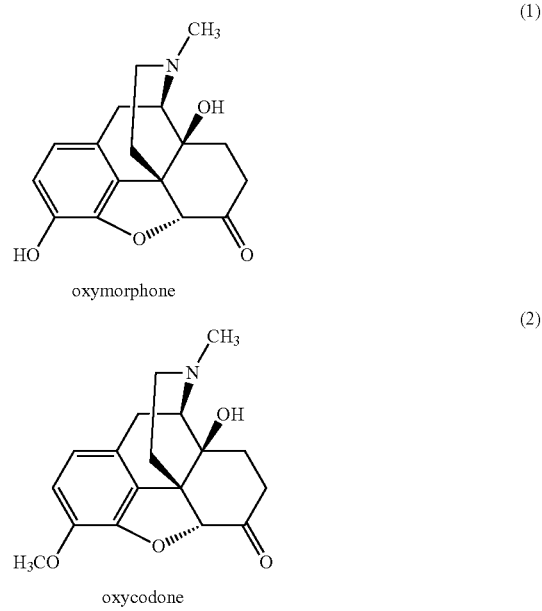

The opioid can have any stereogenic configuration, including both dextro- and levo-isomers.

According to certain embodiments of the present invention, the opioid may be an opioid salt. Pharmaceutically acceptable salts, e.g., non-toxic, inorganic and organic acid addition salts, are known in the art. Exemplary salts include, but are not limited to, 2-hydroxyethanesulfonate, 2-naphthalenesulfonate, 3-hydroxy-2-naphthoate, 3-phenylpropionate, acetate, adipate, alginate, amsonate, aspartate, benzenesulfonate, benzoate, besylate, bicarbonate, bisulfate, bitartrate, borate, butyrate, calcium edetate, camphorate, camphorsulfonate, camsylate, carbonate, citrate, clavulariate, cyclopentanepropionate, digluconate, dodecylsulfate, edetate, edisylate, estolate, esylate, ethanesulfonate, finnarate, gluceptate, glucoheptanoate, gluconate, glutamate, glycerophosphate, glycollylarsanilate, hemisulfate, heptanoate, hexafluorophosphate, hexanoate, hexylresorcinate, hydrabamine, hydrobromide, hydrochloride, hydroiodide, hydroxynaphthoate, iodide, isothionate, lactate, lactobionate, laurate, laurylsulphonate, malate, maleate, mandelate, mesylate, methanesulfonate, methylbromide, methylnitrate, methylsulfate, mucate, naphthylate, napsylate, nicotinate, nitrate, N-methylglucamine ammonium salt, oleate, oxalate, palmitate, pamoate, pantothenate, pectinate, persulfate, phosphate, phosphateldiphosphate, picrate, pivalate, polygalacturonate, propionate, p-toluenesulfonate, saccharate, salicylate, stearate, subacetate, succinate, sulfate, sulfosaliculate, suramate, tannate, tartrate, teoclate, thiocyanate, tosylate, triethiodide, undecanoate, and valerate salts, and the like.

According to certain embodiments of the present invention, the opioid is bound to one or more chemical moieties, denominated X. A chemical moiety can be any moiety that decreases the pharmacological activity of the opioid while bound to the chemical moiety as compared to unbound (free) opioid. The attached chemical moiety can be either naturally occurring or synthetic. The chemical moiety is safe for human consumption. Safe for human consumption, as used herein, may generally refer to the Food and Drug Administration (FDA) designation of a consumable as generally recognized as safe ("GRAS"). In this regard, the chemical moiety is regarded as safe under the conditions of its intended use by experts and, as such, is exempted from Federal Food, Drug, and Cosmetic Act (FFDCA) food additive tolerance requirements.

Exemplary chemical moieties may include, but are not limited to, peptides, including single amino acids, dipeptides, tripeptides, oligopeptides, and polypeptides; carboxylic acids, including α-hydroxy acids and dicarboxylic acids; and fatty acids. In some embodiments, X may be a carboxylic acid. In such embodiments, X may comprise lactic acid, mandelic acid, malic acid, tartaric acid, succinic acid, citric acid, or sorbic acid. In other embodiments, X may be a peptide. In such embodiments, X may comprise an amino acid including, but not limited to, alanine (Ala or A), arginine (Arg or R), asparagine (Asn or N), aspartic acid (Asp or D), cysteine (Cys or C), glycine (Gly or G), glutamic acid (Glu or E), glutamine (Gln or Q), histidine (His or H), isoleucine (Ile or I), leucine (Leu or L), lysine (Lys or K), methionine (Met or M), proline (Pro or P), phenylalanine (Phe or F), serine (Ser or S), tryptophan (Trp or W), threonine (Thr or T), tyrosine (Tyr or Y), and valine (Val or V), or a dipeptide including, but not limited to, carnosine. Each amino acid can be any one of the L- or D-enantiomers. In further embodiments, X may comprise at least one of alanine, proline, or carnosine. In other embodiments, X may be a fatty acid. In such embodiments, X may comprise oleic acid or stearic acid.

According to certain embodiments, the opioid may be bound to another chemical moiety Z. In such embodiments, Z may be an adjuvant analgesic. Exemplary embodiments of Z are listed below in Table 1.

In accordance with certain embodiments of the present invention, the abuse-resistant opioid compound may be represented by Formula IV:

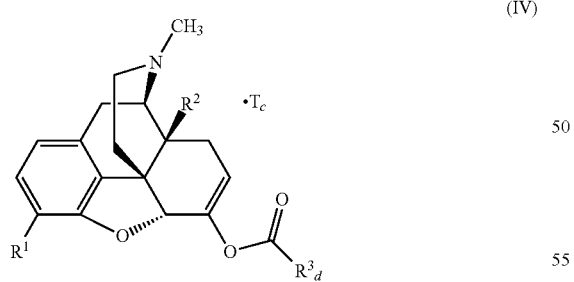

(IV)

wherein $R^1$ is selected from the group consisting of hydroxy, alkoxy, and —OC(O)-alkoxy; $R^2$ is selected from the group consisting of hydroxy and —OC(O)$R^4$; $R^3$ and $R^4$ are selected from the group consisting of —CHR$^5$R$^6$, —C$_a$H$_b$, —C$_2$H$_3$R$^7$R$^8$, —C$_2$H$_4$NHC(O)C$_2$H$_3$R$^9$R$^{10}$, —C$_2$H$_4$NC(O)C$_2$H$_3$R$^{11}$R$^{12}$, —C$_2$H$_4$NC(O)CHR$^{23}$R$^{24}$, —C$_2$H$_3$CHR$^{29}$R$^{30}$, —C$_2$H$_4$NHC(O)(CH)$_2$C(O)OH, —C$_2$H$_4$C(O)OCHR$^{31}$R$^{32}$, —C$_2$H$_4$NHC(O)CHR$^{33}$R$^{34}$, and —C$_3$H$_5$R$^{35}$R$^{36}$; $R^5$ is selected from the group consisting of hydroxy, —OC(O)-alkoxy, —NHC(O)CHR$^{17}$R$^{18}$, —NHC(O)C$_2$H$_3$R$^{19}$R$^{20}$, —OC(O)CHR$^{21}$R$^{22}$, 4-methylimidazole, —OC(O)C$_2$H$_4$NH$_2$, —OC(O)C$_2$H$_4$NHC(O)CHR$^{25}$R$^{26}$, —OC(O)C$_2$H$_3$R$^{27}$R$^{28}$, —OC(O)(CH$_2$)$_{16}$CH$_3$, —OC(O)C$_2$H$_4$C(O)OH, —OC(O)(CH$_2$)$_7$(CH$_2$)$_7$CH$_3$, —CH$_2$COOH, —OC(O)CH$_3$, —CHR$^{37}$R$^{38}$, —CH$_2$C(O)OCHR$^{39}$R$^{40}$, —OC(O)C$_3$H$_5$R$^{41}$R$^{42}$, —CH$_2$C(O)OC$_2$H$_5$, —OC(O)C$_2$H$_4$NHC(O)C$_4$H$_7$NH, —OC(O)C$_4$H$_7$NH, —OC(O)C$_2$H$_3$NHC(O)C$_2$H$_3$R$^{43}$R$^{44}$, —OC(O)C$_2$H$_4$CHR$^{45}$R$^{46}$, and —OC(O)C$_2$H$_4$NHC(O)C$_3$H$_5$R$^{47}$R$^{48}$; $R^6$ is selected from the group consisting of alkyl, hydroxy, aryl, —CH$_2$COOH, —NHC(O)C$_2$H$_4$NH$_2$, —C(O)(CH$_2$)$_7$(CH)$_2$(CH$_2$)$_7$CH$_3$, —C(O)CH$_2$)$_{16}$CH$_3$, —CH$_2$C(O)CHR$^{49}$R$^{50}$, —CH$_2$C(O)OC$_4$H$_9$, —OC(O)CH$_3$, —OC(O)C$_2$H$_4$C(O)OH, —NHC(O)C$_2$H$_4$NHC(O)CHR$^{51}$R$^{52}$, and —OC(O)(CH$_2$)$_{16}$CH$_3$; $R^7$ is selected from the group consisting of hydroxy, amino, —OC(O)CH$_3$, —NHC(O)CHR$^{53}$R$^{54}$, —OC(O)CHR$^{55}$R$^{56}$, and —OC(O)C$_2$H$_3$R$^{57}$R$^{58}$; $R^8$ is selected from the group consisting of carboxyl, hydroxy, —C(O)OC$_4$H$_9$, —OC(O)CH$_3$, and —C(O)OCHR$^{59}$R$^{60}$; $R^9$ is selected from the group consisting of hydroxy, carboxyl, —NHC(O)CHR$^{61}$R$^{62}$, and —C(O)OCH$^{63}$RR$^{64}$R$^{10}$, $R^{12}$, $R^{29}$, $R^{31}$, $R^{35}$, $R^{39}$, $R^{42}$, $R^{44}$, $R^{46}$, $R^4$, $R^{57}$, $R^{59}$, $R^{63}$, $R^{69}$, $R^{73}$, $R^{75}$ are each independently carboxyl; $R^{11}$, $R^{43}$, $R^{52}$, $R^{53}$, $R^{56}$, $R^{58}$, $R^{70}$, $R^{77}$, $R^{79}$, $R^{84}$ are each independently hydroxy; $R^{17}$, $R^{24}$, $R^{34}$ are each independently selected from the group consisting of hydroxy, aryl, and alkyl; $R^{18}$ is selected from the group consisting of —CH$_2$COOH and hydroxy; $R^{19}$ and $R^{20}$ are each independently selected from the group consisting of hydroxy and carboxyl; $R^{21}$ is selected from the group consisting of alkyl, aryl, substituted aryl, hydroxy, amino, —OC(O)CH$_3$, —NHC(O)CHR$^{67}$R$^{68}$, —NHC(O)C$_2$H$_3$CHR$^{69}$R$^{70}$, and —NHC(O)C$_4$H$_7$NH; $R^{22}$ is selected from the group consisting of alkyl, hydroxy, amino, —NHC(O)CHR$^{71}$R$^{72}$, —CH$_2$COOH, —OC(O)(CH$_2$)$_{16}$CH$_3$, —OC(O)CH$_3$, —CH$_2$COOH, —(CH$_2$)$_2$COOH, —CH$_2$C(O)OC$_4$H$_9$, —CHR$^{73}$R$^{74}$, —NHC(O)C$_4$H$_7$NH, —OC(O)(CH$_2$)$_7$(CH)$_2$(CH$_2$)$_7$CH$_3$, and —CHR$^{75}$R$^{76}$; $R^{23}$ is selected from the group consisting of hydroxy, aryl, —CH$_2$COOH, and —OC(O)(CH$_2$)$_7$(CH)$_2$(CH$_2$)$_7$CH$_3$; $R^{25}$ is selected from the group consisting of alkyl, —C$_2$H$_4$C(O)OH, substituted aryl, and amino; $R^{26}$ is selected from the group consisting of alkyl, hydroxy, amino, substituted aryl, —NHC(O)CH$_3$, and —(CH$_2$)$_2$COOH; $R^{27}$ is selected from the group consisting of carboxyl, —NHC(O)CHR$^{77}$R$^{78}$, and —C(O)OC$_4$H$_9$; $R^{28}$ is selected from the group consisting of amino, hydroxy, carboxyl, and —OC(O)CH$_3$; $R^{30}$ is —NHC(O)CHR$^{79}$R$^{80}$; $R^{32}$ is selected from the group consisting of aryl, —CH$_2$COOH, and alkyl; $R^{33}$ is selected from the group consisting of —CH$_2$COOH and hydroxy; $R^{36}$ is NHC(O)CHR$^{83}$R$^{84}$; $R^{37}$, $R^{61}$, $R^{74}$ are each independently selected from the group consisting of hydroxy and —OC(O)CH$_3$; $R^{38}$ is selected from the group consisting of carboxyl and —C(O)OCHR$^{81}$R$^{82}$; $R^{41}$, $R^{45}$, and $R^{47}$ are each independently amino; $R^{40}$, $R^{62}$, $R^{64}$ are each independently selected from the group consisting of alkyl and aryl; $R^{49}$ and $R^{76}$ are each independently —OC(O)CH$_3$; $R^{50}$, $R^{51}$, $R^{54}$, $R^{55}$, $R^{60}$, $R^{78}$, $R^{80}$, $R^{83}$ are each independently alkyl; $R^{67}$ is selected from the group consisting of alkyl and —NHC(O)CH$_3$; $R^{68}$ is selected from the group consisting of hydroxy and —(CH$_2$)$_4$NH$_2$; $R^{71}$ is selected from the group consisting of hydroxy, —NHC(O)CH₃, and amino; $R^{72}$ is selected from the group consisting of alkyl and —C₄HNH₂; $R^{81}$ is selected from the group consisting of carboxyl, aryl, and —CH₂COOH; $R^{82}$ is selected from the group consisting of alkyl, aryl, carboxyl, and —CH₂COOH; T is a pharmaceutically acceptable salt; a is from 1 to 30; b is from 1 to 50; c is from 0 to 5; and d is from 1 to 10.

According to certain embodiments, the abuse-resistant opioid compound may be selected from one or more of:

| Ex, No. | Structure | Mass Spec | ¹H NMR Data |
|---|---|---|---|
| A1 | 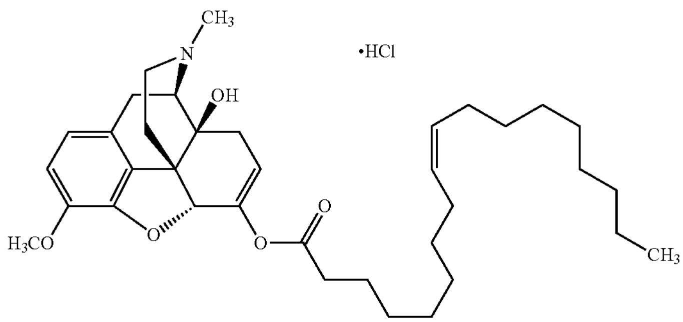 [SMILES: CCCCCCCC/C=C\CCCCCCCC(=O)OC1=CC[C@@]2(O)[C@H]3Cc4ccc(OC)c5c4[C@@]2(CCN3C)[C@H]1O5 ; Cl] | 580 | ¹H NMR (300 MHz, CDCl₃) δ 9.99 (s, 1H), 6.78 (d, J = 8.4 Hz, 1H), 6.70 (d, J = 8.1 Hz, 1H), 5.57 (apparent d, J = 4.5 Hz, 1H), 5.40-5.30 (m, 2H), 5.05 (s, 1H), 4.35 (br s, 1H), 3.86 (s, 3H), 3.48 (d, J = 10.2 Hz, 1H), 3.27-3.20 (m, 2H), 3.10-2.84 (m, 5H), 2.72-2.66 (m, 1H), 2.43 (t, J = 7.2 Hz, 2H), 2.12 (d, J = 17.7 Hz, 1H), 2.02-2.01 (m, 4H), 1.74-1.61 (m, 4H), 1.32-1.27 (m, 20H), 0.88 (t, J = 6.6 Hz, 3H) |
| A2 | 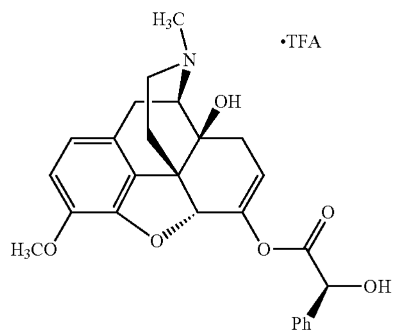 [SMILES: COc1ccc2c3c1O[C@H]1C(OC(=O)[C@@H](O)c4ccccc4)=CC[C@@]4(O)[C@@H](C2)N(C)CC[C@]314 ; "·TFA"] | 450 | ¹H NMR (300 MHz, DMSO-d₆) δ 9.14 (br s, 1H), 7.46-7.40 (m, 2H), 7.39-7.31 (m, 3H), 6.83 (d, J = 8.4 Hz, 2H), 6.73 (d, J = 8.1 Hz, 1H), 6.28-6.24 (m, 2H), 5.48-5.45 (m, 1H), 5.27 (d, J = 5.7 Hz, 1H), 4.92 (s, 1H), 3.68 (s, 3H), 3.64-3.62 (m, 1H), 3.44-3.38 (m, 1H), 3.13-3.05 (m, 2H), 2.82 (br s, 3H), 2.27-2.19 (m, 1H), 2.09-2.03 (m, 1H), 1.61 (d, J = 12.6 Hz, 1H) |
| A3 | 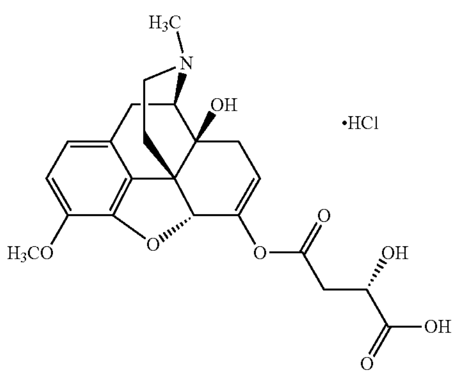 [SMILES: COc1ccc2c3c1O[C@H]1C(OC(=O)C[C@H](O)C(=O)O)=CC[C@@]4(O)[C@@H](C2)N(C)CC[C@]314 ; Cl] | 432 | ¹H NMR (300 MHz, DMSO-d₆) δ 12.7 (br s, 1H), 9.18 (br s, 1H), 6.82 (d, J = 8.1 Hz, 1H), 6.75 (d, J = 8.1 Hz, 1H), 6.29 (s, 1H), 5.62 (br s, 1H), 5.52 (d, J = 4.5 Hz, 1H), 4.98 (s, 1H), 4.33 (br s, 1H), 3.76 (s, 3H), 3.57 (s, 3H), 3.15-3.06 (m, 2H), 2.89-2.84 (m, 4H), 2.73-2.63 (m, 1H), 2.29 (dd, J = 6.3, 18.0 Hz, 1H), 2.33-2.25 (m, 1H), 1.63 (d, J = 11.4 Hz, 1H) |
| A4a | 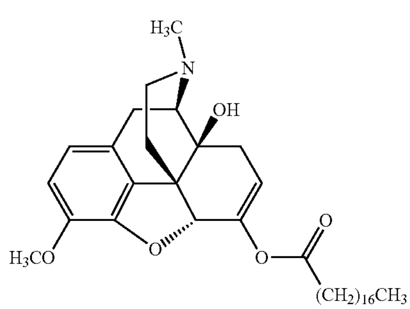 | 582 | ¹H NMR (300 MHz, CDCl₃) δ 6.71 (d, J = 8.1 Hz, 1H), 6.62 (d, J = 8.1 Hz, 1H), 5.57 (dd, J = 4.8, 3.9 Hz, 1H), 5.01 (s, 1H), 4.72 (br s, 1H), 3.84 (s, 3H), 3.17 (d, J = 18.6 Hz, 1H), 2.85 (d, J = 6.3 Hz, 1H), 2.62 (dd, J = 18.9, 6.6 Hz, 1H), 2.47-2.18 (m, 8H), 2.16-2.15 (m, 2H), 1.70-1.59 (m, 3H), 1.30-1.25 (m, 28H), 0.88 (t, J = 6.3 Hz, 3H) |

-continued

| Ex. No. | Structure | Mass Spec | ¹H NMR Data |
|---|---|---|---|
| A4b | (structure) | 554 | ¹H NMR (300 MHz, CDCl$_3$) δ 6.71 (d, J = 8.1 Hz, 1H), 6.62 (d, J = 8.4 Hz, 1H), 5.57 (dd, J = 4.5, 3.6 Hz, 1H), 5.01 (s, 1H), 3.84 (s, 3H), 3.17 (d, J = 18.6 Hz, 1H), 2.85 (d, J = 6.3 Hz, 1H), 2.62 (dd, J = 18.6, 6.3 Hz, 1H), 2.47-2.35 (m, 6H), 2.32-2.22 (m, 2H), 2.16-2.15 (m, 2H), 1.68-1.59 (m, 3H), 1.30-1.25 (m, 24H), 0.88 (t, J = 6.3 Hz, 3H) |
| A5 | (structure) ·TFA | 388 | ¹H NMR (300 MHz, DMSO-d$_6$) δ 9.18 (s, 1H), 6.86 (d, J = 8.1 Hz, 1H), 6.75 (d, J = 8.4 Hz, 1H), 6.30 (s, 1H), 5.60 (d, J = 6.0 Hz, 1H), 5.54 (dd, J = 6.0, 2.1 Hz, 1H), 5.00 (s, 1H), 4.33-4.24 (m, 1H), 3.75 (s, 3H), 3.64 (d, J = 6.6 Hz, 1H), 3.43 (d, J = 19.8 Hz, 1H), 3.11 (dd, J = 18.9, 6.6 Hz, 2H), 2.84 (d, J = 3.9 Hz, 3H), 2.69-2.57 (m, 1H), 2.49-2.41 (m, 1H), 2.32-2.24 (m, 1H), 2.07 (d, J = 17.7 Hz, 1H), 1.64 (d, J = 11.7 Hz, 1H), 1.35 (d, J = 6.9 Hz, 3H) |
| A6 | (structure) ·HCl | 459 | ¹H NMR (300 MHz, DMSO-d$_6$) δ 9.23 (br s, 1H), 8.48 (s, 3H), 6.87 (d, J = 8.4 Hz, 1H), 6.76 (d, J = 8.1 Hz, 1H), 6.36 (s, 1H), 5.61 (dd, J = 6.0, 1.8 Hz, 1H), 5.35 (q, J = 6.9 Hz, 1H), 5.01 (s, 1H), 4.24-4.22 (m, 1H), 3.76 (s, 3H), 3.69 (d, J = 6.0 Hz, 1H), 3.43 (d, J = 20.1 Hz, 1H), 3.12 (dd, J = 19.2, 6.9 Hz, 1H), 2.85 (s, 3H), 2.64-2.57 (m, 1H), 2.49-2.27 (m, 2H, partially obscured by solvent peak), 2.06 (apparent d, J = 18.0 Hz, 1H), 1.63 (d, J = 11.1 Hz, 1H), 1.56 (d, J = 6.9 Hz, 3H), 1.48 (d, J = 7.2 Hz, 3H) |
| A7 | (structure) ·TFA | 460 | ¹H NMR (300 MHz, DMSO-d$_6$) δ 9.18 (br s, 1H), 6.86 (d, J = 8.1 Hz, 1H), 6.75 (d, J = 8.4 Hz, 1H), 6.30 (s, 1H), 5.59 (dd, J = 5.7, 1.8 Hz, 1H), 5.50 (br s, 1H), 5.17 (q, J = 6.9 Hz, 1H), 5.00 (s, 1H), 4.25-4.22 (m, 1H), 3.75 (s, 3H), 3.65 (d, J = 6.0 Hz, 1H), 3.46-3.38 (m, 1H, partially obscured by water peak), 3.16-3.07 (m, 2H), 2.84 (apparent d, J = 5.1 Hz, 3H), 2.69-2.57 (m, 1H), 2.49-2.26 (m, 2H, partially obscured by solvent peak), 2.07 (apparent d, J = 18.0 Hz, 1H), 1.65 (d, J = 11.4 Hz, 1H), 1.51 (d, J = 11.4 Hz, 1H), 1.31 (d, J = 6.6 Hz, 3H) |

-continued

| Ex, No. | Structure | Mass Spec | ¹H NMR Data |
|---|---|---|---|
| A8 | 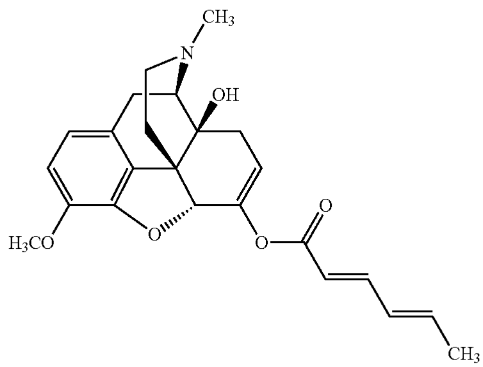 [SMILES: C/C=C/C=C/C(=O)OC1=CC[C@@]2(O)[C@H]3Cc4ccc(OC)c5c4[C@@]2(CCN3C)[C@H]1O5] | 410 | ¹H NMR (300 MHz, CDCl₃) δ 7.35-7.26 (m, 1H), 6.71 (d, J = 8.4 Hz, 1H), 6.62 (d, J = 8.1 Hz, 1H), 6.26-6.10 (m, 2H), 5.85 (d, J = 15.3 Hz, 1H), 5.64 (overlapping dd, J = 3.9 Hz, 1H), 5.06 (s, 1H), 4.72 (br s, 1H), 3.84 (s, 3H), 3.18 (d, J = 18.6 Hz, 1H), 2.86 (d, J = 6.3 Hz, 1H), 2.63 (dd, J = 18.6, 6.3 Hz, 1H), 2.47-2.42 (m, 1H), 2.38 (s, 3H), 2.33-2.19 (m, 2H), 2.18-2.16 (m, 2H), 1.87 (d, J = 5.4 Hz, 3H), 1.63 (dd, J = 13.5, 3.0 Hz, 1H) |
| A9 | 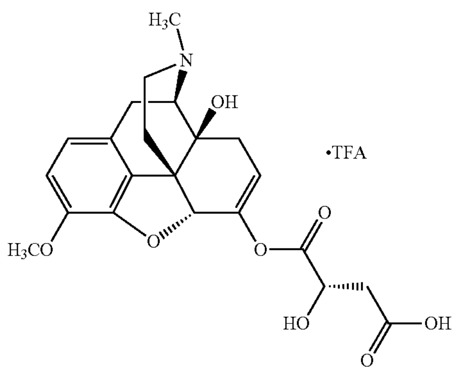 [SMILES: COc1ccc2c3c1O[C@H]1C(OC(=O)[C@@H](O)CC(=O)O)=CC[C@@]4(O)[C@@H](C2)N(C)CC[C@]314 ; "·TFA"] | 432 | ¹H NMR (300 MHz, DMSO-d₆) δ 12.43 (br s, 1H), 9.18 (br s, 1H), 6.86 (d, J = 8.4 Hz, 1H), 6.75 (d, J = 8.1 Hz, 1H), 6.29 (br s, 1H), 5.90 (br s, 1H), 5.55-5.54 (m, 1H), 4.97 (s, 1H), 4.47 (br s, 1H), 3.75 (s, 3H), 3.62 (s, 1H), 3.45-3.37 (m, 1H), 3.12-3.06 (m, 2H), 2.83 (s, 1H), 2.74-2.53 (m, 3H), 2.33-2.22 (m, 1H), 2.07 (d, J = 18.3 Hz, 1H), 1.63 (d, J = 12.3 Hz, 1H), one proton obscured by solvent peaks |
| A10 | 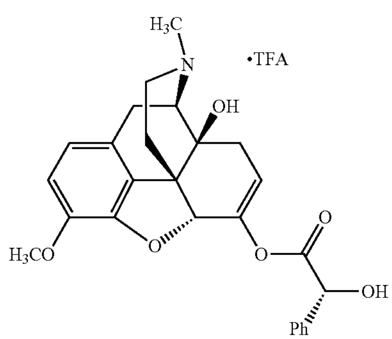 [SMILES: COc1ccc2c3c1O[C@H]1C(OC(=O)[C@H](O)c4ccccc4)=CC[C@@]4(O)[C@@H](C2)N(C)CC[C@]314 ; "·TFA"] | 450 | ¹H NMR (300 MHz, DMSO-d₆) δ 9.16 (br s, 1H), 7.49-7.33 (m, 5H), 6.84 (d, J = 8.1 Hz, 1H), 6.73 (d, J = 8.1 Hz, 1H), 6.28-6.24 (m, 2H), 5.44-5.41 (m, 1H), 5.28 (d, J = 5.1 Hz, 1H), 4.95 (s, 1H), 3.68 (s, 3H), 3.64-3.62 (m, 1H), 3.44-3.35 (m, 1H), 3.13-3.04 (m, 2H), 2.83 (s, 3H), 2.69-2.54 (m, 1H), 2.44-2.43 (m, 1H), 2.34 (dd, J = 18.0, 5.4 Hz, 1H), 2.04 (d, J = 18.0 Hz, 1H) |
| A11 | 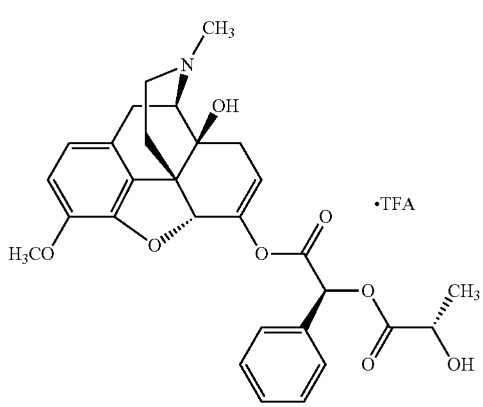 [SMILES: COc1ccc2c3c1O[C@H]1C(OC(=O)[C@@H](OC(=O)[C@H](C)O)c4ccccc4)=CC[C@@]4(O)[C@@H](C2)N(C)CC[C@]314 ; "·TFA"] | 522 | ¹H NMR (300 MHz, DMSO-d₆) δ 9.15 (br s, 1H), 7.57-7.55 (m, 2H), 7.48-7.45 (m, 3H), 6.81 (d, J = 8.1 Hz, 1H), 6.72 (d, J = 8.1 Hz, 1H), 6.31 (br s, 1H), 6.15 (s, 1H), 5.57-5.53 (m, 2H), 4.94 (s, 1H), 4.34-4.26 (m, 1H), 3.64 (br s, 4H), 3.44-3.37 (m, 1H, partially obscured by water peak), 3.13-3.05 (m, 2H), 2.82 (s, 3H), 2.62-2.57 (m, 1H), 2.49-2.39 (m, 1H, partially obscured by solvent peak), 2.30-2.22 (m, 1H), 2.08-2.02 (m, 1H), 1.62 (d, J = 12.0 Hz, 1H), 1.37 (d, J = 6.6 Hz, 3H) |

-continued

| Ex. No. | Structure | Mass Spec | ¹H NMR Data |
|---|---|---|---|
| A12 | (structure with •TFA) | 459 | ¹H NMR (300 MHz, DMSO-$d_6$) δ 9.22 (br s, 1H), 8.09 (d, J = 6.9 Hz, 1H), 6.86 (d, J = 8.4 Hz, 1H), 6.75 (d, J = 8.1 Hz, 1H), 6.28 (s, 1H), 5.53-5.50 (m, 1H), 5.00 (s, 1H), 4.39-4.34 (m, 1H), 4.03-3.99 (m, 1H), 3.75 (s, 3H), 3.64 (d, J = 5.7 Hz, 1H), 3.50-3.35 (m, 2H), 3.13-3.06 (m, 2H), 2.84 (d, J = 4.5 Hz, 3H), 2.75-2.55 (m, 1H), 2.32-2.24 (m, 1H), 2.06 (d, J = 18.0 Hz, 1H), 1.59 (d, J = 11.7 Hz, 1H), 1.40 (d, J = 7.2 Hz, 3H), 1.22 (d, J = 10.5 Hz, 3H) |
| A13 | (structure with •HCl) | 485 | ¹H NMR (300 MHz, DMSO-$d_6$) δ 9.93 (br s, 1H), 9.22 (br s, 1H), 9.02 (br s, 1H), 6.87 (d, J = 8.4 Hz, 1H), 6.76 (d, J = 8.1 Hz, 1H), 6.35 (s, 1H), 5.62 (dd, J = 5.7, 1.8 Hz, 1H), 5.35 (q, J = 7.2 Hz, 1H), 4.99 (s, 1H), 4.54 (br s, 1H), 3.75 (s, 3H), 3.69 (d, J = 5.7 Hz, 1H), 3.42-3.37 (m, 1H, partially obscured by water peak), 3.25 (br s, 2H), 3.16-3.07 (m, 2H), 2.85 (apparent d, J = 4.8 Hz, 3H), 2.65-2.57 (m, 1H), 2.49-2.27 (m, 3H, partially obscured by solvent peak), 2.18-1.88 (m, 4H), 1.63 (d, J = 12.0 Hz, 1H), 1.57 (d, J = 7.2 Hz, 3H) |
| A14 | (structure with •3TFA) | | ¹H NMR (300 MHz, DMSO-$d_6$) δ 9.22 (br s, 1H), 9.01 (s, 1H), 8.85 (d, J = 7.2 Hz, 1H), 7.77 (br s, 3H), 7.49 (s, 1H), 6.88 (d, J = 8.4 Hz, 1H), 6.77 (d, J = 8.4 Hz, 1H), 6.35 (br s, 1H), 5.53-5.51 (m, 1H), 4.94 (s, 1H), 4.69 (q, J = 8.1 Hz, 1H), 3.75 (s, 3H), 3.67 (d, J = 6.3 Hz, 1H), 3.44 (d, J = 20.1 Hz, 1H), 3.23-3.09 (m, 4H), 3.00-2.92 (m, 2H), 2.85 (s, 3H), 2.70-2.55 (m, 1H), 2.30 (dd, J = 18.6, 6.6 Hz, 1H), 2.04 (d, J = 17.7 Hz, 1H), 1.62 (, J = 11.4 Hz, 1H), two protons not observed |
| A15 | (structure with •HCl) | 459 | ¹H NMR (300 MHz, DMSO-$d_6$) δ 9.24 (br s, 1H), 8.02 (br s, 3H), 6.86 (d, J = 8.4 Hz, 1H), 6.76 (d, J = 8.4 Hz, 1H), 6.38 (s, 1H), 5.59 (dd, J = 6.0, 1.8 Hz, 1H), 5.17 (q, J = 7.2 Hz, 1H), 4.99 (s, 1H), 3.76 (s, 3H), 3.70 (d, J = 6.0 Hz, 1H), 3.43 (d, J = 20.1 Hz, 1H), 3.16-3.04 (m, 4H), 2.85-2.79 (m, 5H), 2.65-2.57 (m, 1H), 2.49-2.27 (m, 2H, partially obscured by solvent peak), 2.05 (apparent d, J = 18.0 Hz, 1H), 1.63 (d, J = 10.8 Hz, 1H), 1.52 (d, J = 7.2 Hz, 3H) |

| Ex. No. | Structure | Mass Spec | ¹H NMR Data |
|---|---|---|---|
| A16 | (structure with •2HCl) | 521 | ¹H NMR (300 MHz, DMSO-d$_6$, Mixture of diastereomers) δ 9.22 (br s, 1H), 8.03 (br s, 3H), 7.57-7.56 (m, 2H), 7.49-7.46 (m, 3H), 6.86-6.80 (m, 1H), 6.76-6.72 (m, 1H), 6.38 (s, 1H), 6.14 (s, 0.66H), 6.13 (s, 0.34H), 5.55 (dd, J = 6.3, 2.1 Hz, 0.66H), 5.47 (dd, J = 6.0, 1.8 Hz, 0.34H), 4.96 (s, 0.66H), 4.93 (s, 0.34H), 3.72 (s, 1.02H), 3.70-3.68 (m, 1H), 3.64 (s, 1.98H), 3.41 (d, J = 20.1 Hz, 1H), 3.14-3.07 (m, 4H), 2.89-2.83 (m, 5H), 2.63-2.59 (m, 1H), 2.49-2.27 (m, 2H, partially obscured by solvent peak), 2.04 (apparent d, J = 18.3 Hz, 1H), 1.61 (d, J = 11.7 Hz, 1H) |
| A17 | (structure with •TFA) | 521 | ¹H NMR (300 MHz, DMSO-d$_6$) δ 8.13 (t, J = 6.0 Hz, 1H), 7.42-7.24 (m, 7H), 6.83 (d, J = 8.1 Hz, 1H), 6.72 (d, J = 8.1 Hz, 1H), 6.20 (d, J = 4.8 Hz, 1H), 5.47-5.45 (m, 1H), 4.93 (s, 1H), 4.89 (d, J = 4.8 Hz, 1H), 3.74 (s, 3H), 3.41-3.28 (m, 2H), 3.10-2.80 (m, 2H), 2.78-2.60 (m, 5H), 2.46-2.33 (m, 2H), 2.30-2.12 (m, 1H), 2.02 (d, J = 18.0 Hz, 1H), 1.60-1.50 (m, 1H), one proton not observed |
| A18 | (structure with •TFA) | 459 | ¹H NMR (300 MHz, DMSO-d$_6$) δ 9.22 (br s, 1H), 8.09 (d, J = 6.9 Hz, 1H), 6.86 (d, J = 8.4 Hz, 1H), 6.75 (d, J = 8.1 Hz, 1H), 6.28 (s, 1H), 5.53-5.50 (m, 1H), 5.00 (s, 1H), 4.39-4.34 (m, 1H), 4.03-3.99 (m, 1H), 3.75 (s, 3H), 3.64 (d, J = 5.7 Hz, 1H), 3.50-3.35 (m, 2H), 3.13-3.06 (m, 2H), 2.84 (d, J = 4.5 Hz, 3H), 2.75-2.55 (m, 1H), 2.32-2.24 (m, 1H), 2.06 (d, J = 18.0 Hz, 1H), 1.59 (d, J = 11.7 Hz, 1H), 1.40 (d, J = 7.2 Hz, 3H), 1.22 (d, J = 10.5 Hz, 3H) |
| A19 | (structure with •HCl) | 566 | ¹H NMR (300 MHz, DMSO-d$_6$, Mixture of diastereomers) δ 7.56-7.54 (m, 2H), 7.46-7.44 (m, 3H), 6.75-6.62 (m, 1H), 6.09 (s, 0.68H), 6.05 (s, 0.32H), 5.54 (dd, J = 5.4, 2.4 Hz, 0.68H), 5.42 (dd, J = 5.4, 2.4 Hz, 0.32H), 4.81 (s, 1H), 4.29-4.25 (m, 1H), 3.70 (s, 0.96H), 3.61 (s, 2.04H), 3.13 (d, J = 18.9 Hz, 1H), 2.93-2.83 (m, 2H), 2.73-2.59 (m, 2H), 2.49-2.40 (m, 1H, partially obscured by solvent peak), 2.38 (s, 3H), 2.31-1.95 (m, 5H), 1.39 (d, J = 10.8 Hz, 1H), CO$_2$H, HCl, and two OH protons not observed |

-continued

| Ex. No. | Structure | Mass Spec | ¹H NMR Data |
|---|---|---|---|
| A20 | 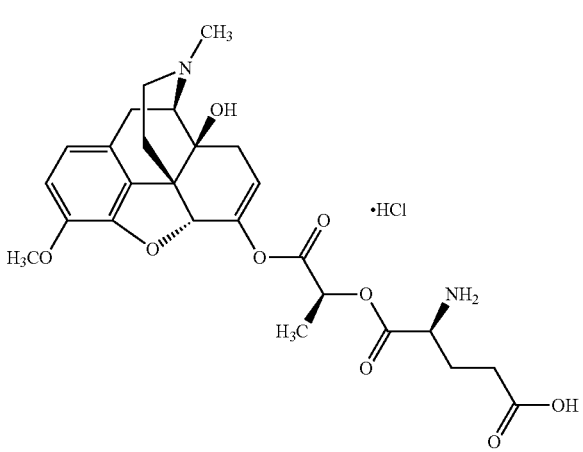 [SMILES: COc1ccc2c3c1O[C@H]1C(OC(=O)[C@H](C)OC(=O)[C@@H](N)CCC(=O)O)=CC[C@@]4(O)[C@@H](C2)N(C)CC[C@]314 ; Cl] | 517 | ¹H NMR (300 MHz, DMSO-d₆) δ 9.09 (br s, 1H), 8.52 (br s, 2H), 6.86 (d, J = 8.4 Hz, 1H), 6.76 (d, J = 8.1 Hz, 1H), 6.31 (br s, 1H), 5.63-5.60 (m, 1H), 5.35 (q, J = 6.9 Hz, 1H), 5.02 (s, 1H), 4.20 (apparent t, J = 6.6 Hz, 1H), 3.75 (s, 3H), 3.65 (br s, 1H), 3.43 (d, J = 19.8 Hz, 1H, partially obscured by water peak), 3.14-3.05 (m, 2H), 2.83 (s, 3H), 2.62-2.56 (m, 1H), 2.49-2.27 (m, 3H, partially obscured by solvent peak), 2.10-2.04 (m, 3H), 1.65-1.58 (m, 1H), 1.57 (d, J = 7.2 Hz, 3H), CO₂H proton not observed, one proton obscured by solvent peaks |
| A21 | 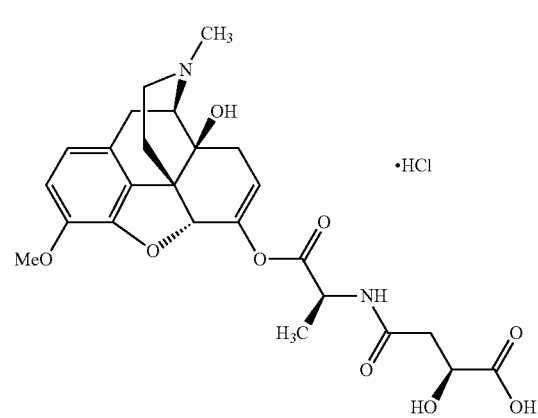 [SMILES: COc1ccc2c3c1O[C@H]1C(OC(=O)[C@H](C)NC(=O)C[C@H](O)C(=O)O)=CC[C@@]4(O)[C@@H](C2)N(C)CC[C@]314 ; Cl] | 503 | ¹H NMR (300 MHz, DMSO-d₆) δ 12.5 (br s, 1H), 9.21 (br s, 1H), 8.45 (d, J = 6.3 Hz, 1H), 6.85 (d, J = 8.4 Hz, 1H), 6.75 (d, J = 8.1 Hz, 1H), 6.34 (s, 1H), 5.54-5.52 (m, 1H), 4.99 (s, 1H), 4.37-4.31 (m, 2H), 3.75 (s, 3H), 3.69-3.65 (m, 2H), 3.39 (s, 3H), 3.13-3.07 (m, 2H), 2.84 (d, J = 4.5 Hz, 3H), 2.28 (d, J = 6.3 Hz, 1H), 2.05 (d, J = 17.7 Hz, 1H), 1.63 (d, J = 11.1 Hz, 1H), 1.36 (d, J = 7.5 Hz, 3H), 1.25 (d, J = 7.5 Hz, 1H) |
| A22 | 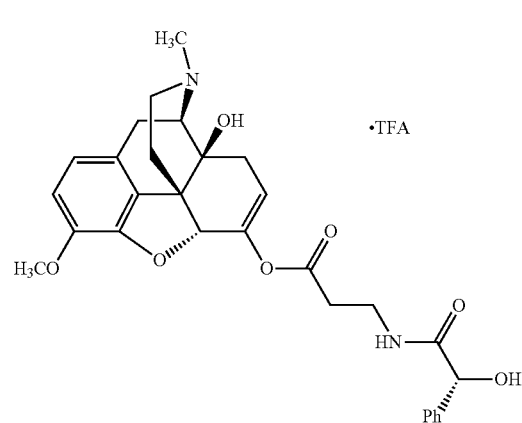 [SMILES: COc1ccc2c3c1O[C@H]1C(OC(=O)CCNC(=O)[C@H](O)c4ccccc4)=CC[C@@]4(O)[C@@H](C2)N(C)CC[C@]314 ; "·TFA"] | 521 | ¹H NMR (300 MHz, DMSO-d₆) δ 9.16 (br s, 1H), 8.13 (t, J = 6.3 Hz, 1H), 7.34-7.31 (m, 2H), 7.29-7.23 (m, 3H), 6.86 (d, J = 8.4 Hz, 1H), 6.75 (d, J = 8.1 Hz, 1H), 6.26 (s, 1H), 6.21 (d, J = 4.5 Hz, 1H), 5.50-5.48 (m, 1H), 4.97 (s, 1H), 4.89 (d, J = 4.2 Hz, 1H), 3.75 (m, 3H), 3.64-3.63 (m, 1H), 3.46-3.33 (m, 3H), 3.15-3.06 (m, 2H), 2.84 (d, J = 4.5 Hz, 3H), 2.63 (t, J = 6.9 Hz, 3H), 2.28-2.22 (m, 1H), 2.05 (d, J = 17.7 Hz, 1H), 1.63 (d, J = 12.9 Hz, 1H) |

-continued

| Ex, No. | Structure | Mass Spec | ¹H NMR Data |
|---|---|---|---|
| A23 | 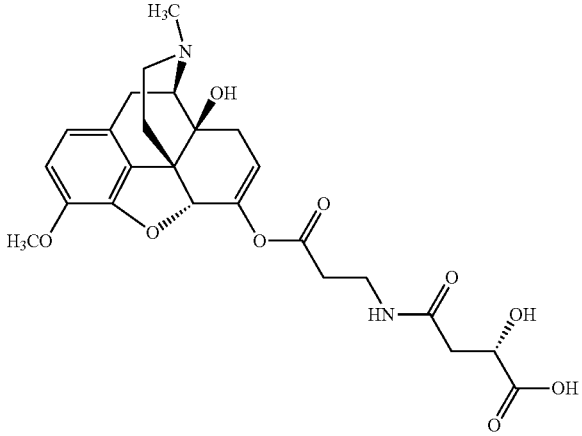 [SMILES: COc1ccc2c3c1O[C@H]1C(OC(=O)CCNC(=O)C[C@H](O)C(=O)O)=CC[C@@]4(O)[C@@H](C2)N(C)CC[C@]314] | 503 | $^1$H NMR (300 MHz, DMSO-$d_6$) δ 8.05 (t, J = 5.4H, 1H), 6.75 (d, J = 8.1 Hz, 1H), 6.66 (d, J = 8.1 Hz, 1H), 5.55-5.52 (m, 1H), 4.87 (s, 1H), 4.24-4.20 (m, 1H), 3.73 (s, 3H), 3.14 (d, J = 18.9 Hz, 2H), 2.91 (d, J = 6.0 Hz, 1H), 2.73-2.55 (m, 3H), 2.48-2.42 (m, 2H), 2.39-2.20 (m, 5H), 2.17-1.90 (m, 3H), 1.40 (d, J = 11.1 Hz, 1H), CO$_2$H and two OH protons not observed, one proton obscured by solvent peaks |
| A24 | 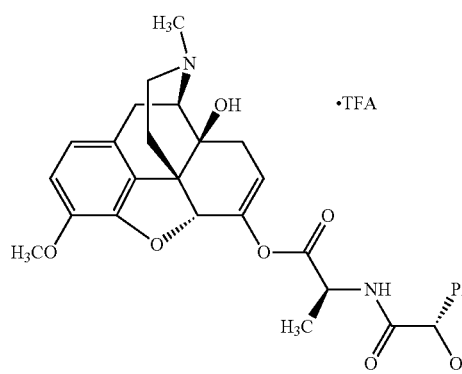 | 521 | $^1$H NMR (300 MHz, DMSO-$d_6$) δ 9.15 (br s, 1H), 8.43 (d, J = 6.9 Hz, 1H), 7.43-7.40 (m, 2H), 7.34-7.21 (m, 3H), 6.85 (d, J = 8.1 Hz, 1H), 6.75 (d, J = 8.4 Hz, 1H), 6.27-6.22 (m, 2H), 5.41-5.40 (m, 1H), 4.96 (d, J = 4.8 Hz, 2H), 4.40-4.35 (m, 1H), 3.75 (s, 3H), 3.70-3.55 (m, 1H), 3.50-3.35 (m, 1H), 3.20-3.00 (m, 2H), 2.83 (s, 3H), 2.27-2.22 (m, 1H), 2.05-1.99 (m, 1H), 1.65-1.61 (m, 1H), 1.40 (d, J = 7.2 Hz, 3H), one proton obscured by solvent peaks |
| A25 | 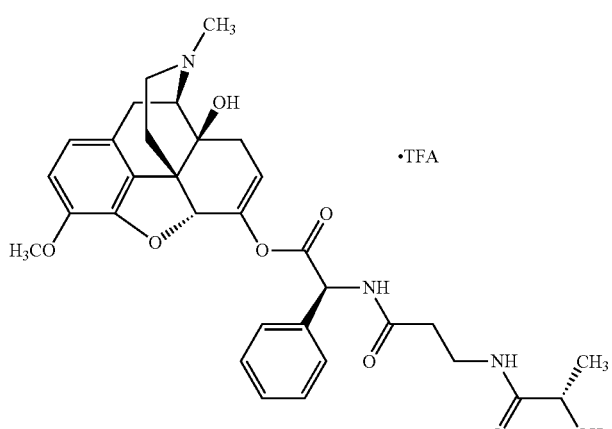 | 593 | $^1$H NMR (300 MHz, DMSO-$d_6$, Mixture of diastereomers) δ 9.17 (br s, 1H), 7.82-7.79 (m, 1H), 7.57-7.54 (m, 2H), 7.47-7.45 (m, 3H), 6.86-6.80 (m, 1H), 6.74-6.71 (m, 1H), 6.30 (s, 1H), 6.09 (s, 0.64H), 6.07 (s, 0.36H), 5.56-5.46 (m, 2H), 4.96 (s, 0.64H), 4.93 (s, 0.36H), 3.98-3.90 (m, 1H), 3.71 (s, 1.08H), 3.63 (s, 1.92H), 3.62 (br s, 1H), 3.46-3.32 (m, 3H, partially obscured by water peak), 3.14-3.05 (m, 2H), 2.83 (s, 3H), 2.65-2.61 (m, 2H), 2.49-2.39 (m, 2H, partially obscured by solvent peak), 2.30-2.24 (m, 1H), 2.09-2.03 (m, 1H), 1.65-1.61 (m, 1H), 1.19-1.16 (m, 3H) |

| Ex. No. | Structure | Mass Spec | ¹H NMR Data |
|---|---|---|---|
| A26 | 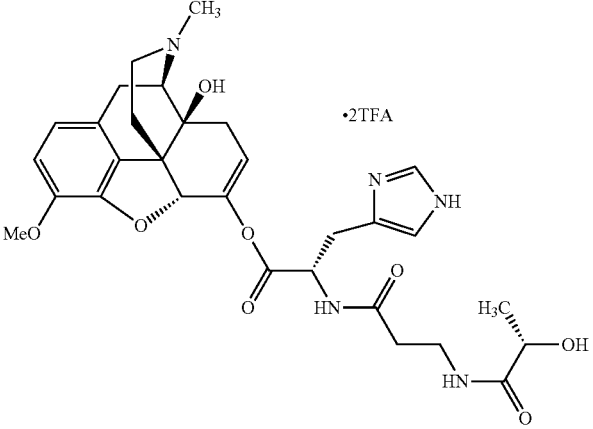 [SMILES: COc1ccc2c3c1O[C@H]1C(OC(=O)[C@H](Cc4c[nH]cn4)NC(=O)CCNC(=O)[C@H](C)O)=CC[C@@]4(O)[C@@H](C2)N(C)CC[C@]314 ; "·2TFA"] | 596 | ¹H NMR (300 MHz, DMSO-d₆) δ 9.19 (br s, 1H), 8.94 (s, 1H), 8.59 (d, J = 7.5 Hz, 1H), 7.72 (t, J = 7.2 Hz, 1H), 7.45 (s, 1H), 6.87 (d, J = 8.4 Hz, 1H), 6.76 (d, J = 8.1 Hz, 1H), 6.29 (s, 1H), 5.53-5.51 (m, 2H), 4.96 (s, 1H), 4.68-4.65 (m, 1H), 3.98-3.88 (m, 1H), 3.75 (s, 3H), 3.60-3.70 (m, 1H), 3.25-3.23 (m, 3H), 3.15-3.10 (m, 4H), 2.85 (s, 3H), 2.33-2.28 (m, 3H), 2.07-2.02 (m, 1H), 1.63 (d, J = 11.1 Hz, 1H), 1.228-1.24 (m, 2H), 1.17 (d, J = 6.9 Hz, 3H) |
| A27 | 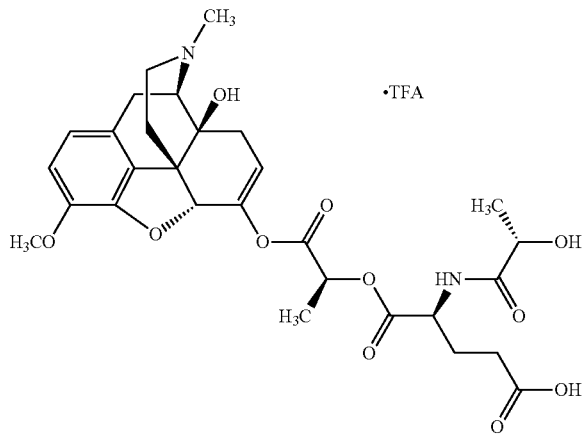 [SMILES: COc1ccc2c3c1O[C@H]1C(OC(=O)[C@H](C)OC(=O)[C@H](CCC(=O)O)NC(=O)[C@H](C)O)=CC[C@@]4(O)[C@@H](C2)N(C)CC[C@]314 ; "·TFA"] | 589 | ¹H NMR (300 MHz, DMSO-d₆) δ 12.19 (br s, 1H), 9.17 (br s, 1H), 7.99 (d, J = 7.8 Hz, 1H), 6.86 (d, J = 8.4 Hz, 1H), 6.75 (d, J = 8.4 Hz, 1H), 6.30 (s, 1H), 5.60 (dd, J = 6.0, 2.1 Hz, 1H), 5.54 (br s, 1H), 5.16 (q, J = 6.9 Hz, 1H), 5.01 (s, 1H), 4.42-4.34 (m, 1H), 4.01 (q, J = 6.9 Hz, 1H), 3.75 (s, 3H), 3.65 (d, J = 6.3 Hz, 1H), 3.43 (d, J = 20.1 Hz, 1H, partially obscured by water peak), 3.16-3.07 (m, 2H), 2.84 (apparent d, J = 4.8 Hz, 3H), 2.66-2.57 (m, 1H), 2.49-2.43 (m, 1H, partially obscured by solvent peak), 2.37-2.23 (m, 3H), 2.15-2.05 (m, 2H), 1.97-1.85 (m, 1H), 1.64 (d, J = 10.8 Hz, 1H), 1.52 (d, J = 6.9 Hz, 3H), 1.22 (d, J = 6.9 Hz, 3H) |
| A28 | 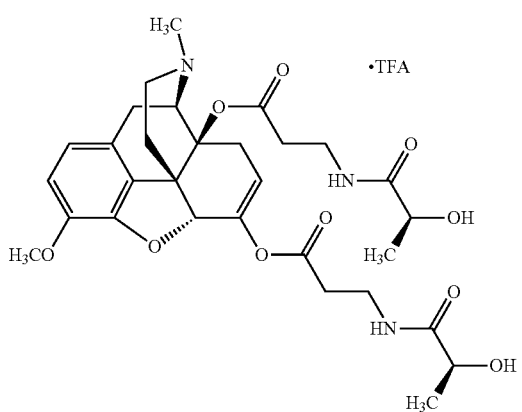 [SMILES: COc1ccc2c3c1O[C@H]1C(OC(=O)CCNC(=O)[C@H](C)O)=CC[C@@]4(OC(=O)CCNC(=O)[C@H](C)O)[C@@H](C2)N(C)CC[C@]314 ; "·TFA"] | 602 | ¹H NMR (300 MHz, DMSO-d₆) δ 9.44 (br s, 1H), 7.89 (dt, J = 12.9, 6.0 Hz, 2H) 6.92 (d, J = 8.4 Hz, 1H), 6.79 (d, J = 8.4 Hz, 1H), 5.51-5.49 (m, 2H), 5.10 (s, 1H), 4.76 (d, J = 5.4 Hz, 1H), 3.98-3.94 (m, 2H), 3.77 (s, 3H), 3.40-3.20 (m, 7H), 3.04-2.96 (m, 4H), 2.65-2.61 (m, 3H), 2.09 (d, J = 18.3 Hz, 1H), 1.81 (d, J = 12.0 Hz, 1H), 1.21 (d, J = 4.5 Hz, 3H), 1.19 (d, J = 4.2 Hz, 6H) |

-continued

| Ex. No. | Structure | Mass Spec | ¹H NMR Data |
|---|---|---|---|
| A29 | (structure) ·2HCl | 521 | ¹H NMR (300 MHz, DMSO-$d_6$, Mixture of diastereomers) δ 9.19 (br s, 1H), 7.91 (br s, 3H), 7.57-7.55 (m, 2H), 7.48-7.46 (m, 3H), 6.87-6.81 (m, 1H), 6.76-6.72 (m, 1H), 6.32 (s, 1H), 6.14 (s, 0.42H), 6.13 (s, 0.58H), 5.56-5.54 (m, 0.42H), 5.48-5.46 (m, 0.58H), 4.96 (s, 0.42H), 4.92 (s, 0.58H), 3.72 (s, 1.74H), 3.67 (br s, 1H), 3.75 (s, 1.26H), 3.42 (d, J = 20.4 Hz, 1H), 3.14-3.07 (m, 4H), 2.86-2.83 (m, 5H), 2.64-2.57 (m, 1H), 2.49-2.33 (m, 2H, partially obscured by solvent peak), 2.08-2.00 (m, 1H), 1.61 (d, J = 12.6 Hz, 1H) |
| A30 | (structure) ·TFA | 503 | ¹H NMR (300 MHz, DMSO-$d_6$) δ 12.96 (br s, 1H), 9.17 (br s, 1H), 8.01 (d, J = 8.4 Hz, 1H), 6.86 (d, J = 8.4 Hz, 1H), 6.75 (d, J = 8.4 Hz, 1H), 6.27 (s, 1H), 5.65 (br s, 1H), 5.51 (dd, J = 6.0, 2.1 Hz, 1H), 4.97 (s, 1H), 4.66 (q, J = 8.1 Hz, 1H), 4.01 (q, J = 6.6 Hz, 1H), 3.75 (s, 3H), 3.64 (d, J = 6.0 Hz, 1H), 3.15-3.01 (m, 3H), 2.96 (d, J = 6.3 Hz, 1H), 2.91 (d, J = 6.3 Hz, 1H), 2.84 (d, J = 4.5 Hz, 3H), 2.75-2.55 (m, 1H), 2.32-2.24 (m, 1H), 2.06 (d, J = 18.0 Hz, 1H), 1.64 (d, J = 10.2 Hz, 1H), 1.21 (d, J = 6.6 Hz, 3H) |
| A31 | (structure) ·HCl | 633 | ¹H NMR (300 MHz, DMSO-$d_6$) δ 8.41 (d, J = 7.2 Hz, 1H), 6.75 (d, J = 8.1 Hz, 1H), 6.67 (d, J = 8.1 Hz, 1H), 5.57 (dd, J = 5.7, 2.4 Hz, 1H), 5.14 (q, J = 7.2 Hz, 1H), 4.87 (s, 1H), 4.41-4.34 (m, 1H), 4.23 (dd, J = 8.1, 4.8 Hz, 1H), 3.73 (s, 3H), 3.15 (d, J = 18.9 Hz, 1H), 2.95 (d, J = 5.4 Hz, 1H), 2.73-2.63 (m, 1H), 2.49-2.24 (m, 9H, partially obscured by solvent peak), 2.16-1.96 (m, 4H), 1.88-1.76 (m, 1H), 1.52 (d, J = 7.2 Hz, 3H), two CO$_2$H, HCl, and two OH protons not observed, one proton obscured by solvent peaks |

-continued

| Ex, No. | Structure | Mass Spec | ¹H NMR Data |
|---|---|---|---|
| A32 | 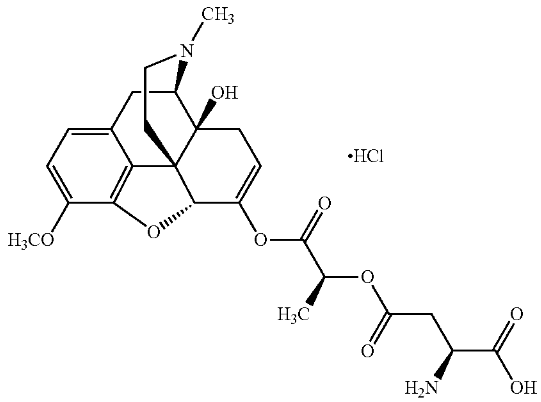 [SMILES: COc1ccc2c3c1O[C@H]1C(OC(=O)[C@H](C)OC(=O)C[C@H](N)C(=O)O)=CC[C@@]4(O)[C@@H](C2)N(C)CC[C@]314 ; Cl] | 503 | ¹H NMR (300 MHz, DMSO-d₆) δ 7.77 (br s, 1H), 6.84 (d, J = 8.1 Hz, 1H), 6.74 (d, J = 8.4 Hz, 1H), 5.60-5.58 (m, 1H), 5.13 (q, J = 6.9 Hz, 1H), 4.99 (s, 1H), 3.76 (s, 3H), 3.64-3.52 (m, 2H), 3.04-2.91 (m, 4H), 2.76-2.63 (m, 5H), 2.49-2.40 (m, 1H, partially obscured by solvent peak), 2.28-2.22 (m, 1H), 2.06 (apparent d, J = 17.4 Hz, 1H), 1.60 (d, J = 9.9 Hz, 1H), 1.51 (d, J = 6.9 Hz, 3H), CO₂H, NH₂, and OH protons not observed |
| A33 | 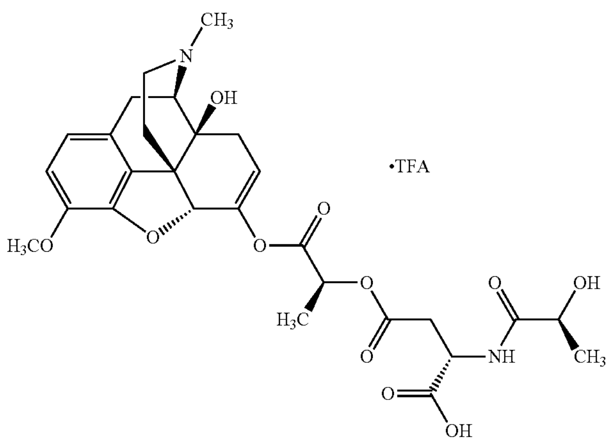 [SMILES: COc1ccc2c3c1O[C@H]1C(OC(=O)[C@H](C)OC(=O)C[C@H](NC(=O)[C@H](C)O)C(=O)O)=CC[C@@]4(O)[C@@H](C2)N(C)CC[C@]314 ; "·TFA"] | 575 | ¹H NMR (300 MHz, DMSO-d₆) δ 7.94 (d, J = 8.1 Hz, 1H), 6.77 (d, J = 8.1 Hz, 1H), 6.68 (d, J = 8.1 Hz, 1H), 5.64 (d, J = 5.1 Hz, 1H), 5.57 (dd, J = 5.7, 2.1 Hz, 1H), 5.11 (q, J = 6.9 Hz, 1H), 4.90 (s, 1H), 4.62-4.55 (m, 1H), 4.00-3.94 (m, 1H), 3.74 (s, 3H), 3.20 (d, J = 19.8 Hz, 1H, partially obscured by water peak), 3.08 (br s, 1H), 2.89-2.78 (m, 3H), 2.63-2.57 (m, 1H), 2.49-2.31 (m, 2H, partially obscured by solvent peak), 2.17-1.97 (m, 2H), 1.48 (d, J = 6.9 Hz, 3H), 1.47-1.45 (m, 1H), 1.19 (d, J = 6.6 Hz, 3H), CO₂H and CH₃CO₂H protons not observed, four protons obscured by solvent peaks |
| A34 | 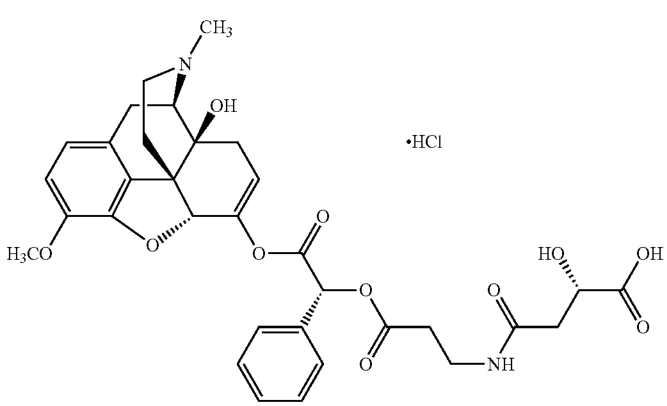 [SMILES: COc1ccc2c3c1O[C@H]1C(OC(=O)[C@H](OC(=O)CCNC(=O)C[C@H](O)C(=O)O)c4ccccc4)=CC[C@@]4(O)[C@@H](C2)N(C)CC[C@]314 ; Cl] | 637 | ¹H NMR (300 MHz, DMSO-d₆, Mixture of diastereomers) δ 8.04 (br s, 1H), 7.56-7.54 (m, 2H), 7.46-7.44 (m, 3H), 6.75-6.69 (m, 1H), 6.66-6.62 (m, 1H), 6.06 (s, 1H), 5.55-5.52 (m, 0.43H), 5.43-5.41 (m, 0.57H), 4.80 (s, 1H), 4.24-4.19 (m, 1H), 3.70 (s, 1.71H), 3.61 (s, 1.29H), 3.16-3.09 (m, 1H, partially obscured by water peak), 2.90 (br s, 1H), 2.67-2.58 (m, 2H), 2.49-2.22 (m, 8H, partially obscured by solvent peak), 2.12-1.93 (m, 3H), 1.39 (d, J = 11.4 Hz, 1H), CO₂H and HCl protons not observed, four protons obscured by solvent peaks |

-continued

| Ex, No. | Structure | Mass Spec | ¹H NMR Data |
|---|---|---|---|
| A35 | 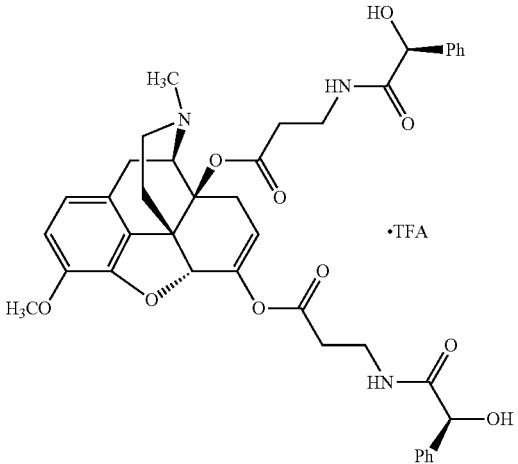 [SMILES: COc1ccc2c3c1O[C@H]1C(OC(=O)CCNC(=O)[C@@H](O)c4ccccc4)=CC[C@@]4(OC(=O)CCNC(=O)[C@@H](O)c5ccccc5)[C@@H](C2)N(C)CC[C@]314 ; "·TFA"] | 726 | ¹H NMR (300 MHz, DMSO-$d_6$) δ 9.41 (br s, 1H), 8.24 (t, J = 5.7 Hz, 1H), 8.16 (t, J = 5.7 Hz, 1H), 7.40-7.21 (m, 10H), 6.92 (d, J = 8.4 Hz, 1H), 6.79 (d, J = 8.4 Hz, 1H), 6.26 (br s, 2H), 5.37-5.35 (m, 1H), 5.07 (s, 1H), 4.91 (d, J = 6.0 Hz, 2H), 4.70 (d, J = 6.0 Hz, 1H), 3.77 (s, 3H), 3.52 (d, J = 20.1 Hz, 1H), 3.38-3.18 (m, 6H), 2.99-2.87 (m, 4H), 2.82-2.52 (m, 5H), 2.05 (d, J = 18.9 Hz, 1H), 1.78 (d, J = 13.5 Hz, 1H) |
| A36 | 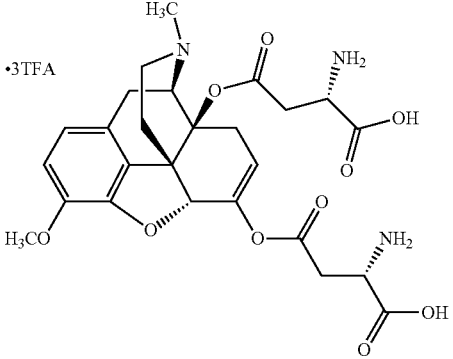 [SMILES: "·3TFA" ; COc1ccc2c3c1O[C@H]1C(OC(=O)C[C@H](N)C(=O)O)=CC[C@@]4(OC(=O)C[C@H](N)C(=O)O)[C@@H](C2)N(C)CC[C@]314] | 546 | ¹H NMR (300 MHz, DMSO-$d_6$) δ 8.85-7.92 (br s, 6H), 6.92 (d, J = 8.1 Hz, 1H), 6.80 (d, J = 8.4 Hz, 1H), 5.54-5.52 (m, 1H), 5.07 (s, 1H), 4.67 (d, J = 6.0 Hz, 1H), 4.27 (t, J = 5.7 Hz, 1H), 3.93 (t, J = 8.7 Hz, 1H), 3.77 (s, 3H), 3.50 (d, J = 20.1 Hz, 1H), 3.21-2.97 (m, 5H), 2.81 (s, 3H), 2.77-2.65 (m, 4H), 2.13 (d, J = 18.3 Hz, 1H), 1.77 (d, J = 11.4 Hz, 1H), two $CO_2H$ protons not observed |
| A37 | 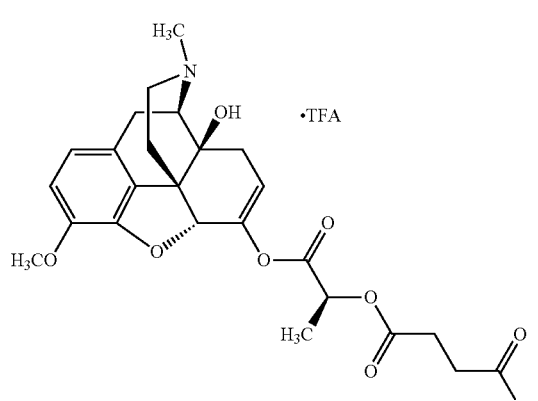 | 488 | ¹H NMR (300 MHz, DMSO-$d_6$) δ 12.25 (br s, 1H), 9.19 (s, 1H), 6.86 (d, J = 8.4 Hz, 1H), 6.75 (d, J = 8.4 Hz, 1H), 6.31 (br s, 1H), 5.59-5.57 (m, 1H), 5.11 (q, J = 6.9 Hz, 1H), 4.99 (s, 1H), 3.75 (s, 3H), 3.65 (d, J = 6.0 Hz, 2H), 3.43 (d, J = 19.8 Hz, 1H), 3.14-3.31 (m, 2H), 2.84 (d, J = 4.5 Hz, 3H), 2.62-2.60 (m, 3H), 2.48-2.40 (m, 2H), 2.29 (dd, J = 17.7, 11.7 Hz, 1H), 2.06 (d, J = 18.0 Hz, 1H), 1.65 (d, J = 11.1 Hz, 1H), 1.49 (d, J = 3.9 Hz, 3H) |

-continued

| Ex. No. | Structure | Mass Spec | ¹H NMR Data |
|---|---|---|---|
| A38 | 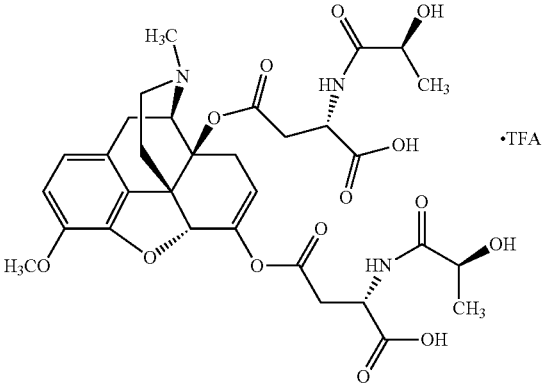 [SMILES: COc1ccc2c3c1O[C@H]1C(OC(=O)C[C@H](NC(=O)[C@H](C)O)C(=O)O)=CC[C@@]4(OC(=O)C[C@H](NC(=O)[C@H](C)O)C(=O)O)[C@@H](C2)N(C)CC[C@]314 ; "·TFA"] | 690 | ¹H NMR (300 MHz, DMSO-d$_6$) δ 12.96 (br s, 2H), 9.35 (br s, 1H), 8.03 (d, J = 8.4 Hz, 1H), 7.93 (d, J = 7.8 Hz, 1H), 6.89 (d, J = 8.1 Hz, 1H), 6.77 (d, J = 8.4 Hz, 1H), 5.68 (br s, 2H), 5.44-5.42 (m, 1H), 5.03 (s, 1H), 4.69-4.62 (m, 3H), 4.03-3.97 (m, 2H), 3.76 (s, 3H), 3.28-3.13 (m, 1H), 3.16-3.07 (m, 2H), 3.04-2.82 (m, 8H), 2.73-2.63 (m, 2H), 2.11 (d, J = 18.3 Hz, 1H), 1.76 (d, J = 12.9 Hz, 1H), 1.20 (d, J = 9.0 Hz, 6H) |
| A39 | 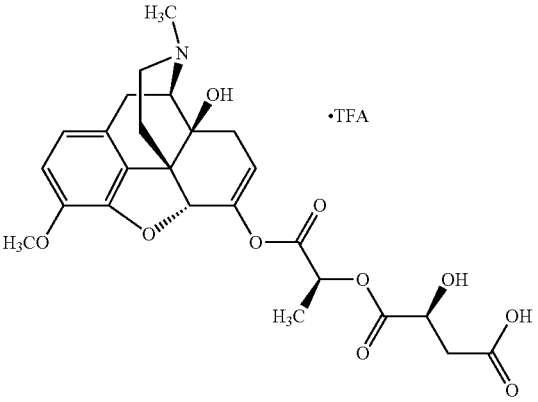 [SMILES: COc1ccc2c3c1O[C@H]1C(OC(=O)[C@H](C)OC(=O)[C@@H](O)CC(=O)O)=CC[C@@]4(O)[C@@H](C2)N(C)CC[C@]314 ; "·TFA"] | 504 | ¹H NMR (300 MHz, DMSO-d$_6$) δ 12.36 (br s, 1H), 9.19 (br s, 1H), 6.86 (d, J = 8.4 Hz, 1H), 6.75 (d, J = 8.4 Hz, 1H), 6.31 (s, 1H), 5.83 (br s, 1H), 5.60-5.58 (m, 1H), 5.18 (q, J = 16.2 Hz, 1H), 5.00 (s, 1H), 4.73 (dd, J = 8.7, 3.9 Hz, 1H), 3.75 (s, 3H), 3.65 (d, J = 6.3 Hz, 1H), 3.43 (d, J = 20.1 Hz, 1H), 3.14-3.07 (m, 2H), 2.84 (d, J = 4.8 Hz, 3H), 2.78-2.58 (m, 2H), 2.33-2.26 (m, 1H), 2.07 (d, J = 17.7 Hz, 1H), 1.65 (d, J = 11.4 Hz, 1H), 1.51 (d, J = 7.2 Hz, 3H), one proton obscured by solvent peaks |
| A40 | 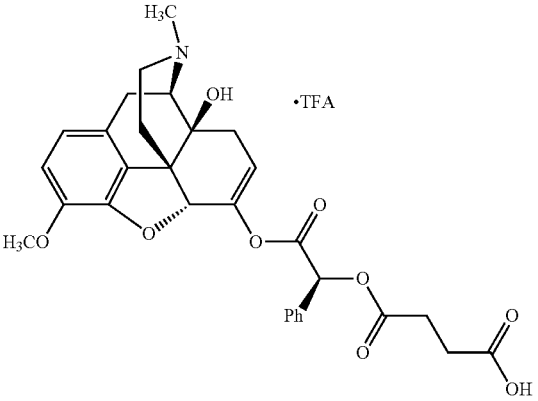 [SMILES: COc1ccc2c3c1O[C@H]1C(OC(=O)[C@@H](OC(=O)CCC(=O)O)c4ccccc4)=CC[C@@]4(O)[C@@H](C2)N(C)CC[C@]314 ; "·TFA"] | 550 | ¹H NMR (300 MHz, DMSO-d$_6$) δ 12.28 (br s, 1H), 9.16 (br s, 1H), 7.56-7.54 (m, 2H), 7.50-7.45 (m, 3H), 6.81 (d, J = 8.4 Hz, 1H), 6.72 (d, J = 8.4 Hz, 1H), 6.31 (s, 1H), 6.10 (s, 1H), 5.55-5.53 (m, 1H), 4.95 (s, 1H), 3.64 (s, 3H), 3.41 (d, J = 19.8 Hz, 1H), 3.14-3.05 (m, 2H), 2.83 (d, J = 4.5 Hz, 3H), 2.69-2.66 (m, 3H), 2.56-2.49 (m, 2H), 2.45-2.40 (m, 1H), 2.30-2.22 (m, 1H), 2.05 (d, J = 18.3 Hz, 1H), 1.62 (d, J = 11.4 Hz, 1H) |
| A41 | 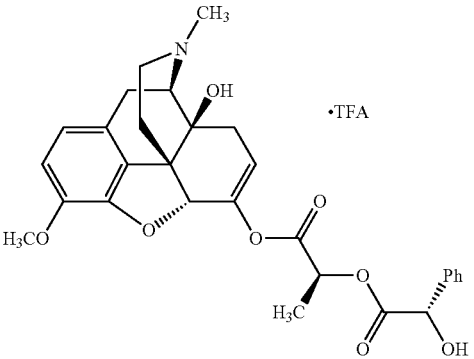 [SMILES: COc1ccc2c3c1O[C@H]1C(OC(=O)[C@H](C)OC(=O)[C@@H](O)c4ccccc4)=CC[C@@]4(O)[C@@H](C2)N(C)CC[C@]314 ; "·TFA"] | 522 | ¹H NMR (300 MHz, DMSO-d$_6$) δ 9.17 (br s, 1H), 7.46-7.42 (m, 2H), 7.37-7.27 (m, 3H), 6.85 (d, J = 8.4 Hz, 1H), 6.74 (d, J = 8.1 Hz, 1H), 6.26 (s, 1H), 6.15 (d, J = 5.4 Hz, 1H), 5.50-5.48 (m, 1H), 5.23-5.16 (m, 1H), 4.84 (s, 1H), 3.72 (s, 3H), 3.64 (br s, 1H), 3.42 (d, J = 20.1 Hz, 1H), 3.15-3.06 (m, 2H), 2.84 (s, 3H), 2.64-2.57 (m, 1H), 2.49-2.40 (m, 1H, partially obscured by solvent peak), 2.34-2.23 (m, 1H), 2.04 (apparent d, J = 18.3 Hz, 1H), 1.62 (d, J = 8.7 Hz, 1H), 1.48 (d, J = 6.9 Hz, 3H) |

-continued

| Ex, No. | Structure | Mass Spec | ¹H NMR Data |
|---|---|---|---|
| A42 | 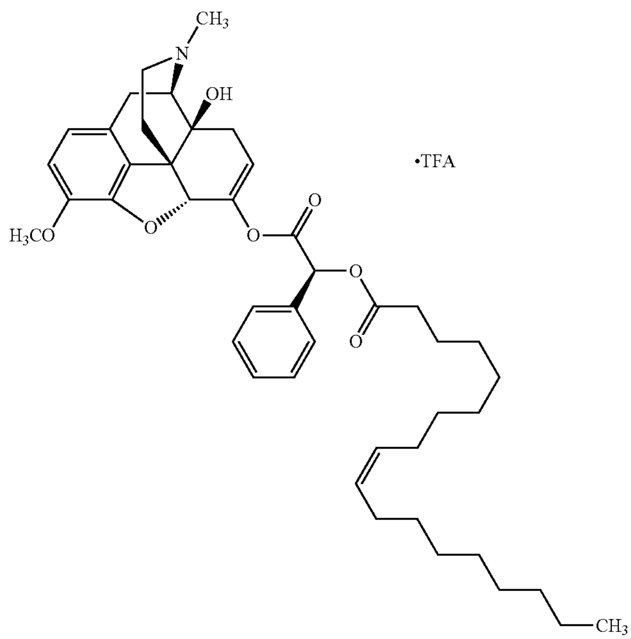 [SMILES: CCCCCCCC/C=C\CCCCCCCC(=O)O[C@H](C(=O)OC1=CC[C@@]2(O)[C@H]3Cc4ccc(OC)c5c4[C@@]2(CCN3C)[C@H]1O5)c1ccccc1 ; "·TFA"] | 714 | ¹H NMR (300 MHz, DMSO-d₆, Mixture of diastereomers) δ 9.17 (br s, 1H), 7.56-7.53 (m, 2H), 7.46-7.44 (m, 3H), 6.85-6.79 (m, 1H), 6.75-6.71 (m, 1H), 6.29 (s, 1H), 6.09 (s, 0.49H), 6.07 (s, 0.51H), 5.53 (dd, J = 6.0, 2.1 Hz, 0.49H), 5.45 (dd, J = 6.0, 2.1 Hz, 0.51H), 5.33-5.30 (m, 2H), 4.94 (s, 0.49H), 4.90 (s, 0.51H), 3.71 (s, 1.47H), 3.64 (br s, 2.53H), 3.45-3.38 (m, 1H), 3.13-3.05 (m, 2H), 2.82 (s, 3H), 2.64-2.55 (m, 1H), 2.49-2.40 (m, 3H, partially obscured by solvent peak), 2.28-2.22 (m, 1H), 2.07-1.96 (m, 5H), 1.64-1.54 (m, 3H), 1.32-1.24 (m, 20H), 0.84 (t, J = 6.6 Hz, 3H) |
| A43 | 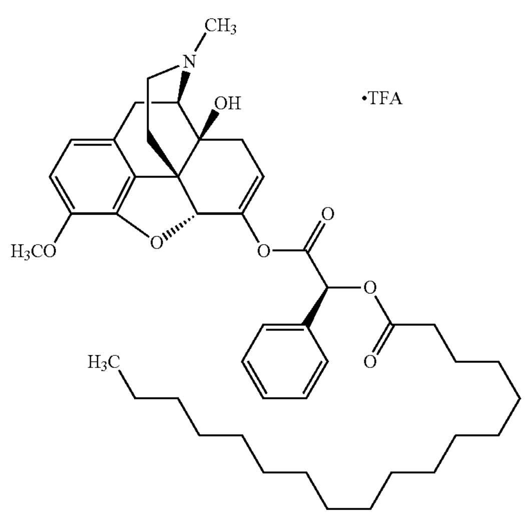 [SMILES: CCCCCCCCCCCCCCCCCC(=O)O[C@H](C(=O)OC1=CC[C@@]2(O)[C@H]3Cc4ccc(OC)c5c4[C@@]2(CCN3C)[C@H]1O5)c1ccccc1 ; "·TFA"] | 716 | ¹H NMR (300 MHz, DMSO-d₆, Mixture of diastereomers) δ 9.17 (br s, 1H), 7.56-7.53 (m, 2H), 7.46-7.44 (m, 3H), 6.86-6.80 (m, 1H), 6.75-6.71 (m, 1H), 6.30 (hr s, 1H), 6.09 (s, 0.51H), 6.07 (s, 0.49H), 5.53 (dd, J = 6.0, 2.1 Hz, 0.51H), 5.45 (dd, J = 6.0, 2.1 Hz, 0.49H), 4.94 (s, 0.51H), 4.90 (s, 0.49H), 3.71 (s, 1.53H), 3.64 (br s, 2.47H), 3.45-3.35 (m, 1H), 3.13-3.05 (m, 2H), 2.83 (apparent d, J = 4.5 Hz, 3H), 2.67-2.55 (m, 1H), 2.49-2.40 (m, 3H, partially obscured by solvent peak), 2.30-2.22 (m, 1H), 2.08-2.01 (m, 1H), 1.64-1.51 (m, 3H), 1.32-1.23 (m, 28H), 0.85 (t, J = 6.6 Hz, 3H) |

-continued

| Ex, No. | Structure | Mass Spec | ¹H NMR Data |
|---|---|---|---|
| A44 | 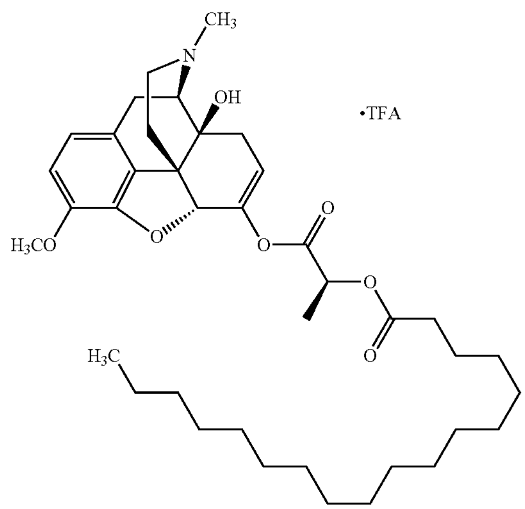 [SMILES: CCCCCCCCCCCCCCCCCC(=O)O[C@@H](C)C(=O)OC1=CC[C@@]2(O)[C@H]3Cc4ccc(OC)c5c4[C@@]2(CCN3C)[C@H]1O5 ; "·TFA"] | 654 | ¹H NMR (300 MHz, DMSO-d$_6$) δ 9.17 (br s, 1H), 6.85 (d, J = 8.4 Hz, 1H), 6.75 (d, J = 8.4 Hz, 1H), 6.29 (br s, 1H), 5.58 (dd, J = 5.7, 1.8 Hz, 1H), 5.10 (q, J = 6.9 Hz, 1H), 4.99 (s, 1H), 3.75 (s, 3H), 3.64 (br s, 1H), 3.43 (d, J = 19.5 Hz, 1H), 3.16-3.07 (m, 2H), 2.84 (s, 3H), 2.64-2.57 (m, 1H), 2.49-2.42 (m, 1H, partially obscured by solvent peak), 2.06 (d, J = 18.0 Hz, 1H), 1.66-1.51 (m, 3H), 1.49 (d, J = 6.9 Hz, 3H), 1.32-1.23 (m, 28H), 0.85 (t, J = 6.6 Hz, 3H) |
| A45 | 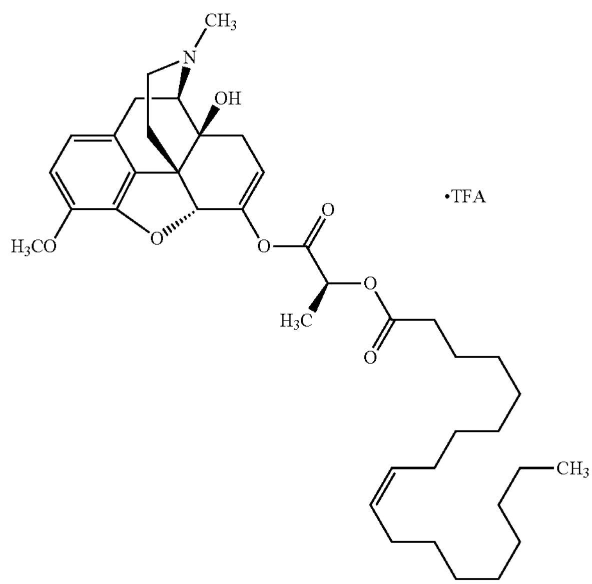 [SMILES: CCCCCCCC/C=C\CCCCCCCC(=O)O[C@@H](C)C(=O)OC1=CC[C@@]2(O)[C@H]3Cc4ccc(OC)c5c4[C@@]2(CCN3C)[C@H]1O5 ; "·TFA"] | 652 | ¹H NMR (300 MHz, DMSO-d$_6$) δ 9.23 (br s, 1H), 6.85 (d, J = 8.4 Hz, 1H), 6.75 (d, J = 8.4 Hz, 1H), 6.39 (br s, 1H), 5.58-5.56 (m, 1H), 5.37-5.27 (m, 2H), 5.10 (q, J = 6.9 Hz, 1H), 4.99 (s, 1H), 3.75 (s, 3H), 3.68 (d, J = 6.0 Hz, 1H), 3.43 (d, J = 19.8 Hz, 1H), 3.16-3.07 (m, 2H), 2.85 (s, 3H), 2.64-2.58 (m, 1H), 2.49-2.42 (m, 1H, partially obscured by solvent peak), 2.39-2.27 (m, 3H), 2.09-1.97 (m, 5H), 1.63 (d, J = 11.7 Hz, 1H), 1.54-1.48 (m, 5H), 1.26-1.24 (m, 20H), 0.85 (t, J = 6.3 Hz, 3H) |
| A46 | 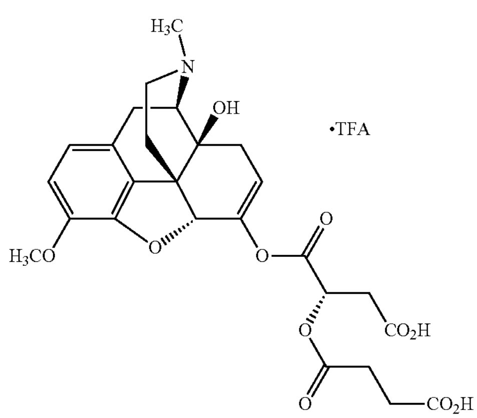 [SMILES: COc1ccc2c3c1O[C@H]1C(OC(=O)[C@H](CC(=O)O)OC(=O)CCC(=O)O)=CC[C@@]4(O)[C@@H](C2)N(C)CC[C@]314 ; "·TFA"] | 532 | ¹H NMR (300 MHz, DMSO-d$_6$) δ 12.71 (br s, 1H), 12.32 (br s, 1H), 9.17 (br s, 1H), 6.85 (d, J = 8.4 Hz, 1H), 6.75 (d, J = 8.4 Hz, 1H), 6.30 (s, 1H), 5.59 (dd, J = 5.7, 1.8 Hz, 1H), 5.42 (t, J = 5.4 Hz, 1H), 4.96 (s, 1H), 3.75 (s, 3H), 3.65 (d, J = 6.0 Hz, 1H), 3.16-3.07 (m, 3H), 2.90-2.84 (m, 5H), 2.73-2.59 (m, 3H), 2.33-2.25 (m, 1H), 2.07 (d, J = 18.0 Hz, 1H), 1.64 (d, J = 11.4 Hz, 1H), three protons obscured by solvent peaks |

| Ex. No. | Structure | Mass Spec | $^1$H NMR Data |
|---|---|---|---|
| A47 | (structure) ·TFA | 517 | $^1$H NMR (300 MHz, DMSO-d$_6$) δ 12.81 (br s, 1H), 9.17 (br s, 1H), 7.85 (d, J = 8.1 Hz, 1H), 6.86 (d, J = 8.4 Hz, 1H), 6.75 (d, J = 8.1 Hz, 1H), 6.27 (s, 1H), 5.55-5.53 (m, 2H), 5.00 (s, 1H), 4.35-4.27 (m, 1H), 4.00 (q, J = 6.9 Hz, 1H), 3.75 (s, 3H), 3.64 (d, J = 6.0 Hz, 1H), 3.15-3.06 (m, 2H), 2.84 (d, J = 4.2 Hz, 3H), 2.73-2.55 (m, 1H), 2.32-2.24 (m, 1H), 2.14-1.89 (m, 3H), 1.63 (d, J = 11.4 Hz, 1H), 1.22 (d, J = 6.9 Hz, 3H), four protons obscured by solvent peaks |
| A48 | (structure) ·TFA | 564 | $^1$H NMR (300 MHz, CDCl$_3$) δ 9.15 (br s, 1H), 7.59-7.54 (m, 2H), 7.49-7.76 (m, 3H), 6.82 (d, J = 8.4 Hz, 1H), 6.73 (d, J = 8.4 Hz, 1H), 6.30 (br s, 1H), 6.22 (s, 1H), 5.53 (dd, J = 6.0, 1.8 Hz, 1H), 5.15 (q, J = 6.9 Hz, 1H), 4.95 (s, 1H), 3.64 (s, 3H), 3.41 (d, J = 19.8 Hz, 1H), 3.14-3.05 (m, 2H), 2.83 (d, J = 4.8 Hz, 3H), 2.70-2.53 (m, 1H), 2.46-2.38 (m, 1H), 2.30-2.22 (m, 1H), 2.08 (s, 3H), 2.06-2.00 (m, 1H), 1.62 (d, J = 11.1 Hz, 1H), 1.53 (d, J = 6.9 Hz, 3H) |
| A49 | (structure) ·TFA | 698 | $^1$H NMR (300 MHz, DMSO-d$_6$) δ 12.76 (br s, 1H), 9.17 (br s, 1H), 6.84 (d, J = 8.1 Hz, 1H), 6.74 (d, J = 8.1 Hz, 1H), 6.31 (s, 1H), 5.59 (dd, J = 6.0, 3.9 Hz, 1H), 5.41 (t, J = 6.3 Hz, 1H), 4.96 (s, 1H), 3.75 (s, 3H), 3.65 (d, J = 6.3 Hz, 1H), 3.13-3.06 (m, 2H), 2.90-2.84 (m, 5H), 2.70-2.52 (m, 2H), 2.33 (t, J = 7.2 Hz, 2H), 2.27-2.25 (m, 1H), 1.64 (d, J = 11.7 Hz, 1H), 1.56-1.51 (m, 2H), 1.23 (br s, 30H), 0.88 (t, J = 6.3 Hz, 3H) |
| A50 | (structure) ·TFA | 430 | $^1$H NMR (300 MHz, CDCl$_3$) δ 9.18 (br s, 1H), 6.86 (d, J = 8.4 Hz, 1H), 6.75 (d, J = 8.1 Hz, 1H), 6.31 (s, 1H), 5.58 (dd, J = 5.7, 1.8 Hz, 1H), 5.09 (q, J = 6.9 Hz, 1H), 4.99 (s, 1H), 3.76 (s, 3H), 3.65 (d, J = 6.0 Hz, 1H), 3.43 (d, J = 20.1 Hz, 1H), 3.16-3.07 (m, 2H), 2.84 (d, J = 4.8 Hz, 3H), 2.72-2.52 (m, 1H), 2.49-2.43 (m, 1H, partially obscured by solvent peak), 2.29 (dd, J = 18.0, 6.6 Hz, 1H), 2.10 (s, 3H), 2.30-2.22 (m, 1H), 1.65 (d, J = 11.4 Hz, 1H), 1.49 (d, J = 6.9 Hz, 3H) |

| Ex, No. | Structure | Mass Spec | $^1$H NMR Data |
|---|---|---|---|
| A51 | 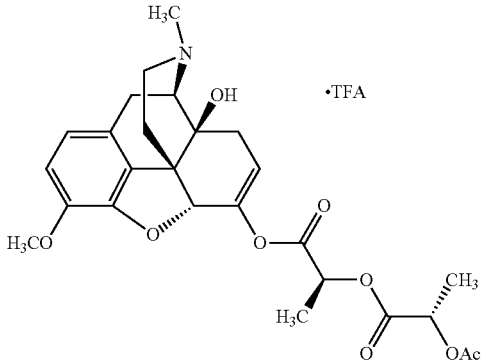 [SMILES: COc1ccc2c3c1O[C@H]1C(OC(=O)[C@H](C)OC(=O)[C@H](C)OC(C)=O)=CC[C@@]4(O)[C@@H](C2)N(C)CC[C@]314 ; "·TFA"] | 502 | $^1$H NMR (300 MHz, CDCl$_3$) δ 9.17 (br s, 1H), 6.86 (d, J = 8.1 Hz, 1H), 6.75 (d, J = 8.4 Hz, 1H), 6.30 (s, 1H), 5.59 (dd, J = 5.7, 1.8 Hz, 1H), 5.24 (q, J = 6.9 Hz, 1H), 5.07 (q, J = 7.2 Hz, 1H), 4.99 (s, 1H), 3.75 (s, 3H), 3.65 (d, 6.0 Hz, 1H), 3.16-3.07 (m, 2H), 2.84 (d, J = 4.8 Hz, 3H), 2.72-2.58 (m, 1H), 2.44-2.40 (m, 1H), 2.30 (dd, J = 18.3, 6.0 Hz, 1H), 2.08 (s, 3H), 2.12-2.02 (m, 1H), 1.65 (d, J = 13.2 Hz, 1H), 1.53 (d, J = 6.9 Hz, 3H), 1.47 (d, J = 6.9 Hz, 3H), one proton obscured by the solvent peaks |
| A52 | 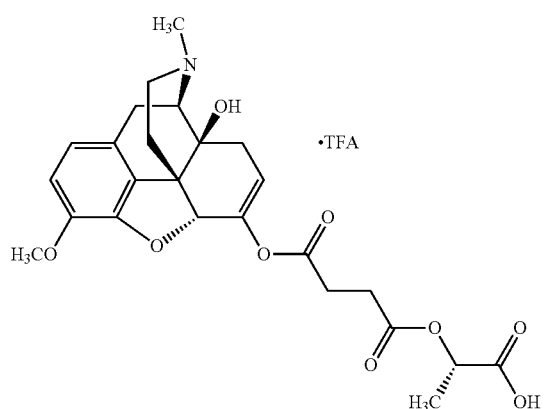 | 488 | $^1$H NMR (300 MHz, DMSO-d$_6$) δ 13.02 (br s, 1H), 9.18 (br s, 1H), 6.86 (d, J = 8.4 Hz, 1H), 6.75 (d, J = 8.4 Hz, 1H), 6.28 (br s, 1H), 5.53 (dd, J = 6.0, 1.8 Hz, 1H), 4.98 (s, 1H), 4.92 (q, J = 6.9 Hz, 1H), 3.75 (s, 3H), 3.64 (d, J = 6.3 Hz, 1H), 3.43 (d, J = 19.8 Hz, 1H), 3.15-3.06 (m, 2H), 2.84 (d, J = 3.9 Hz, 3H), 2.73-2.58 (m, 5H), 2.46-2.40 (m, 1H), 2.32-2.20 (m, 1H), 2.05 (d, J = 18.3 Hz, 1H), 1.64 (d, J = 11.1 Hz, 1H), 1.40 (d, J = 6.9 Hz, 3H) |
| A53 | 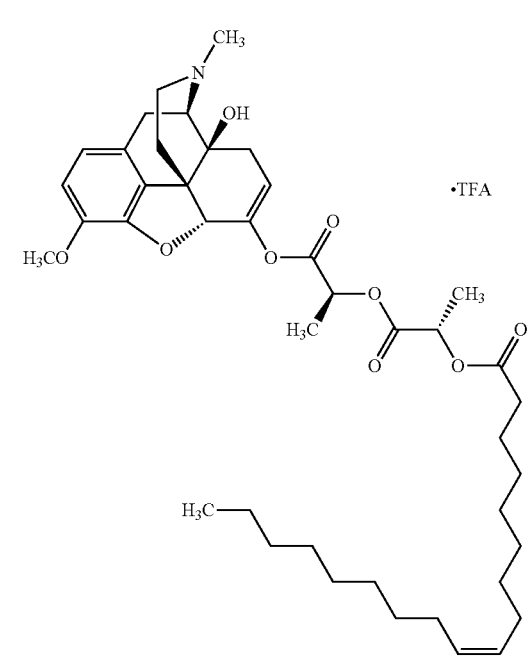 [SMILES: CCCCCCCC/C=C\CCCCCCCC(=O)O[C@@H](C)C(=O)O[C@@H](C)C(=O)OC1=CC[C@@]2(O)[C@H]3Cc4ccc(OC)c5c4[C@@]2(CCN3C)[C@H]1O5 ; "·TFA"] | 724 | $^1$H NMR (300 MHz, DMSO-d$_6$) δ 9.22 (br s, 1H), 6.85 (d, J = 8.4 Hz, 1H), 6.75 (d, J = 8.4 Hz, 1H), 6.34 (br s, 1H), 5.59-5.58 (m, 1H), 5.37-5.30 (m, 2H), 5.24 (q, J = 6.9 Hz, 1H), 5.08 (q, J = 6.9 Hz, 1H), 4.99 (s, 1H), 3.75 (s, 3H), 3.65 (br s, 1H), 3.42 (d, J = 20.1 Hz, 1H), 3.15-3.06 (m, 2H), 2.84 (s, 3H), 2.64-2.58 (m, 1H), 2.49-2.43 (m, 1H, partially obscured by solvent peak), 2.37-2.26 (m, 3H), 2.09-1.95 (m, 5H), 1.63 (d, J = 11.7 Hz, 1H), 1.54-1.45 (m, 8H), 1.26-1.24 (m, 20H), 0.85 (t, J = 6.3 Hz, 3H) |

-continued

| Ex. No. | Structure | Mass Spec | ¹H NMR Data |
|---|---|---|---|
| A54 | 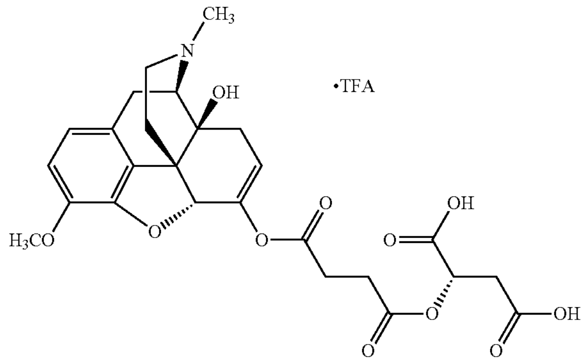 [SMILES: COc1ccc2c3c1O[C@H]1C(OC(=O)CCC(=O)O[C@@H](CC(=O)O)C(=O)O)=CC[C@@]4(O)[C@@H](C2)N(C)CC[C@]314 ; "·TFA"] | 532 | ¹H NMR (300 MHz, DMSO-$d_6$) δ 13.23 (br s, 1H), 12.59 (br s, 1H), 9.17 (br s, 1H), 6.86 (d, J = 8.4 Hz, 1H), 6.75 (d, J = 8.4 Hz, 1H), 6.27 (s, 1H), 5.53 (dd, J = 6.3, 2.1 Hz, 1H), 5.22 (dd, J = 7.8, 4.5 Hz, 1H), 4.99 (s, 1H), 3.75 (s, 3H), 3.64 (d, J = 6.3 Hz, 1H), 3.46-3.39 (m, 1H, partially obscured by water peak), 3.15-3.06 (m, 2H), 2.84 (s, 3H), 2.80-2.66 (m, 7H), 2.49-2.43 (m, 1H, partially obscured by solvent peak), 2.27 (dd, J = 17.7, 6.3 Hz, 1H), 2.06 (apparent d, J = 18.0 Hz, 1H), 1.64 (d, J = 11.7 Hz, 1H) |
| A55 | 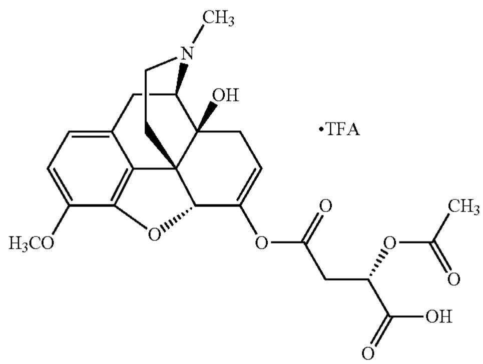 [SMILES: COc1ccc2c3c1O[C@H]1C(OC(=O)C[C@H](OC(C)=O)C(=O)O)=CC[C@@]4(O)[C@@H](C2)N(C)CC[C@]314 ; "·TFA"] | 474 | ¹H NMR (300 MHz, DMSO-$d_6$) δ 13.38 (br s, 1H), 9.17 (br s, 1H), 6.86 (d, J = 8.4 Hz, 1H), 6.75 (d, J = 8.4 Hz, 1H), 6.29 (s, 1H), 5.56 (dd, J = 5.7, 1.8 Hz, 1H), 5.26 (dd, J = 8.4, 4.2 Hz, 1H), 4.99 (s, 1H), 3.74 (s, 3H), 3.65 (d, J = 6.3 Hz, 1H), 3.43 (d, J = 20.1 Hz, 1H, partially obscured by water peak), 3.16-3.06 (m, 3H), 2.98 (dd, J = 16.8, 8.4 Hz, 1H), 2.84 (apparent d, J = 3.9 Hz, 3H), 2.65-2.57 (m, 1H), 2.49-2.42 (m, 1H, partially obscured by solvent peak), 2.28 (dd, J = 17.7, 6.3 Hz, 1H), 2.09 (s, 3H), 2.09-2.04 (m, 1H), 1.65 (d, J = 11.1 Hz, 1H) |
| A56 | 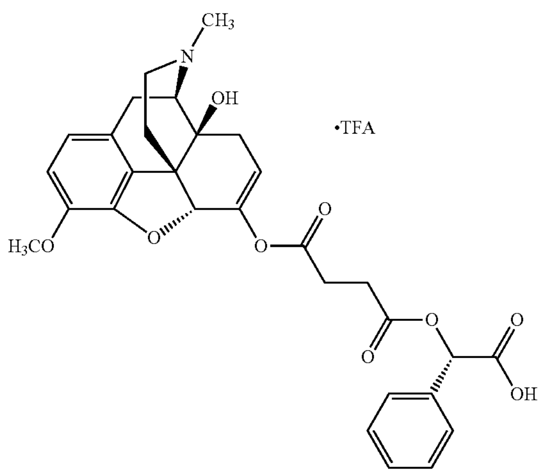 [SMILES: COc1ccc2c3c1O[C@H]1C(OC(=O)CCC(=O)O[C@H](C(=O)O)c4ccccc4)=CC[C@@]4(O)[C@@H](C2)N(C)CC[C@]314 ; "·TFA"] | 550 | ¹H NMR (300 MHz, DMSO-$d_6$) δ 13.29 (br s, 1H), 9.18 (br s, 1H), 7.46-7.40 (m, 5H), 6.86 (d, J = 8.4 Hz, 1H), 6.75 (d, J = 8.4 Hz, 1H), 6.29 (br s, 1H), 5.84 (s, 1H), 5.50-5.46 (m, 1H), 4.96 (s, 1H), 3.74 (s, 3H), 3.64 (d, J = 6.0 Hz, 1H), 3.43 (d, J = 19.8 Hz, 1H), 3.15-3.06 (m, 2H), 2.84 (apparent d, J = 3.3 Hz, 3H), 2.76 (s, 4H), 2.65-2.58 (m, 1H), 2.43 (dd, J = 12.9, 4.2 Hz, 1H), 2.26 (dd, J = 17.7, 6.0 Hz, 1H), 2.04 (apparent d, J = 17.7 Hz, 1H), 1.63 (d, J = 12.0 Hz, 1H) |
| A57 | 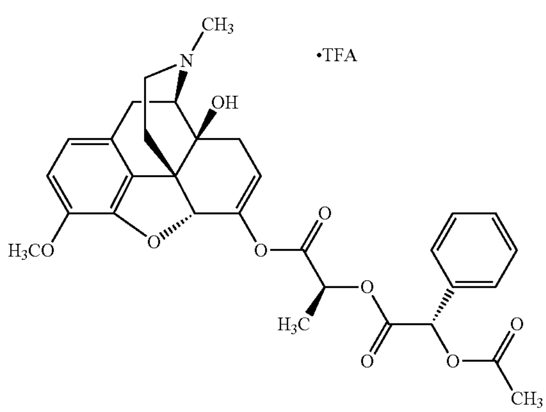 [SMILES: COc1ccc2c3c1O[C@H]1C(OC(=O)[C@H](C)OC(=O)[C@@H](OC(C)=O)c4ccccc4)=CC[C@@]4(O)[C@@H](C2)N(C)CC[C@]314 ; "·TFA"] | 564 | ¹H NMR (300 MHz, DMSO-$d_6$) δ 9.19 (br s, 1H), 7.52-7.48 (m, 2H), 7.42-7.37 (m, 3H), 6.86 (d, J = 8.4 Hz, 1H), 6.75 (d, J = 8.1 Hz, 1H), 6.28 (s, 1H), 6.06 (s, 1H), 5.47 (dd, J = 5.7, 1.8 Hz, 1H), 5.28 (q, J = 6.9 Hz, 1H), 4.82 (s, 1H), 3.73 (s, 3H), 3.64 (d, J = 6.0 Hz, 1H), 3.42 (d, J = 20.1 Hz, 1H), 3.15-3.06 (m, 2H), 2.84 (apparent d, J = 4.8 Hz, 3H), 2.68-2.57 (m, 1H), 2.49-2.35 (m, 1H, partially obscured by solvent peak), 2.27 (dd, J = 18.0, 6.0 Hz, 1H), 2.14 (s, 3H), 2.04 (apparent d, J = 17.7 Hz, 1H), 1.62 (d, J = 12.0 Hz, 1H), 1.48 (d, J = 6.9 Hz, 3H) |

| Ex. No. | Structure | Mass Spec | $^1$H NMR Data |
|---|---|---|---|
| A58 | 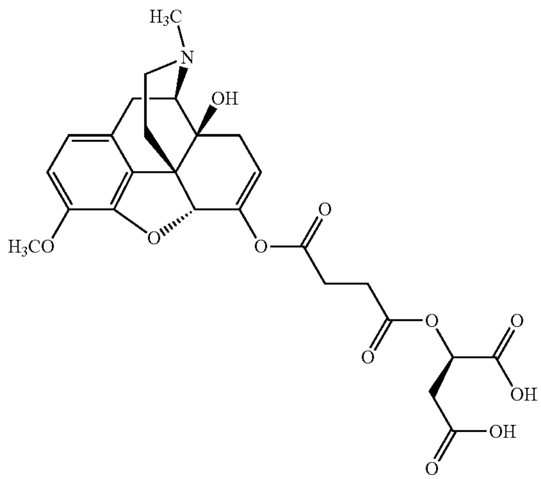 [SMILES: COc1ccc2c3c1O[C@H]1C(OC(=O)CCC(=O)O[C@H](CC(=O)O)C(=O)O)=CC[C@@]4(O)[C@@H](C2)N(C)CC[C@]314] | 530 | $^1$H NMR (300 MHz, DMSO-$d_6$) δ 6.81 (d, J = 8.1 Hz, 1H), 6.70 (d, J = 8.1 Hz, 1H), 5.53 (dd, J = 5.7, 2.1 Hz, 1H), 5.09-5.06 (m, 1H), 4.93 (s, 1H), 3.74 (s, 3H), 3.28 (d, J = 18.9 Hz, 1H), 2.83-2.61 (m, 9H), 2.37-2.13 (m, 6H), 2.02 (d, J = 18 Hz, 1H), 1.52 (d, J = 9.9 Hz, 1H), two CO$_2$H and OH protons not observed |
| A59 | 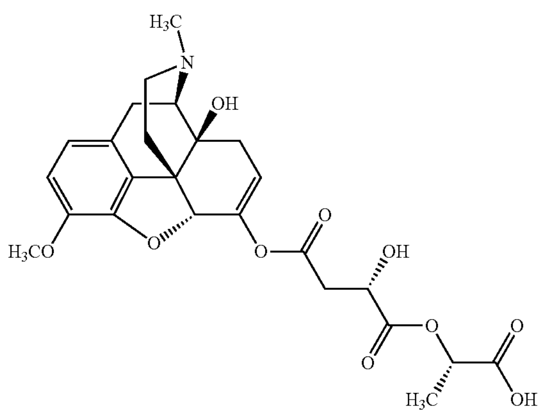 [SMILES: COc1ccc2c3c1O[C@H]1C(OC(=O)C[C@H](O)C(=O)O[C@@H](C)C(=O)O)=CC[C@@]4(O)[C@@H](C2)N(C)CC[C@]314] | 504 | $^1$H NMR (300 MHz, DMSO-$d_6$) δ 6.75 (d, J = 8.4 Hz, 1H), 6.66 (d, J = 8.4 Hz, 1H), 5.91 (s, 1H), 5.52 (dd, J = 5.7, 2.4 Hz, 1H), 4.95 (dd, J = 13.8, 6.9 Hz, 1H), 4.86 (s, 1H), 4.49-4.47 (m, 1H), 3.74 (s, 3H), 3.13 (d, J = 18.9 Hz, 1H), 2.97-2.89 (m, 2H), 2.69-2.61 (m, 2H), 2.46-2.42 (m, 1H), 2.28-2.22 (m, 2H), 2.12-2.00 (m, 4H), 1.42-1.38 (m, 4H), CO$_2$H and OH protons not observed |
| A60a | 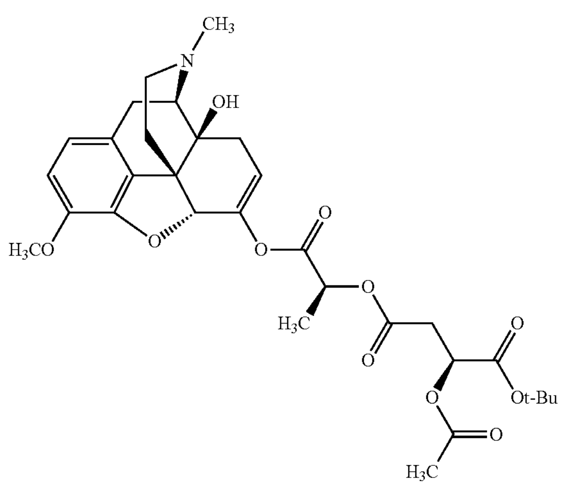 [SMILES: COc1ccc2c3c1O[C@H]1C(OC(=O)[C@H](C)OC(=O)C[C@H](OC(C)=O)C(=O)OC(C)(C)C)=CC[C@@]4(O)[C@@H](C2)N(C)CC[C@]314] | 602 | $^1$H NMR (300 MHz, DMSO-$d_6$) δ 6.73 (d, J = 8.4 Hz, 1H), 6.65 (d, J = 8.1 Hz, 1H), 5.55 (dd, J = 5.4, 2.4 Hz, 1H), 5.21-5.13 (m, 2H), 4.83 (s, 1H), 4.72 (s, 1H), 3.73 (s, 3H), 3.10 (d, J = 18.6 Hz, 1H), 2.97-2.94 (m, 2H), 2.83 (d, J = 6.0 Hz, 1H), 2.60 (dd, J = 18.9, 6.0 Hz, 1H), 2.41 (dd, J = 11.4, 3.9 Hz, 1H), 2.31 (s, 3H), 2.22 (dd, J = 12.6, 4.8 Hz, 1H), 2.10-1.94 (m, 3H), 2.04 (s, 3H), 1.49 (d, J = 6.9 Hz, 3H) 1.41 (s, 9H), 1.39 (d, J = 12.3 Hz, 1H) |

| Ex. No. | Structure | Mass Spec | ¹H NMR Data |
|---|---|---|---|
| A60b | (morphinan structure with methoxy, OH, N-CH₃, and ester side chain bearing lactate-malate-acetate) ·TFA | 546 | ¹H NMR (300 MHz, DMSO-d₆) δ 13.37 (br s, 1H), 9.18 (br s, 1H), 6.85 (d, J = 8.4 Hz, 1H), 6.75 (d, J = 8.4 Hz, 1H), 6.30 (s, 1H), 5.59 (dd, J = 5.7, 1.8 Hz, 1H), 5.27 (dd, J = 7.8, 4.5 Hz, 1H), 5.18 (q, J = 7.2 Hz, 1H), 5.00 (s, 1H), 3.75 (s, 3H), 3.65 (d, J = 6.3 Hz, 1H), 3.43 (d, J = 19.8 Hz, 1H, partially obscured by water peak), 3.16-3.07 (m, 2H), 3.05-2.90 (m, 2H), 2.84 (apparent d, J = 3.0 Hz, 3H), 2.66-2.55 (m, 1H), 2.49-2.43 (m, 1H, partially obscured by solvent peak), 2.34-2.26 (m, 1H), 2.10-2.04 (m, 1H), 2.04 (s, 3H), 1.65 (d, J = 11.1 Hz, 1H), 1.50 (d, J = 7.2 Hz, 3H) |
| A61 | (morphinan structure with methoxy, OH, N-CH₃, and ester side chain bearing di-acetoxy succinate) ·TFA | 532 | ¹H NMR (300 MHz, DMSO-d₆) δ 13.87 (br s, 1H), 9.17 (br s, 1H), 6.88 (d, J = 8.4 Hz, 1H), 6.76 (d, J = 8.4 Hz, 1H), 6.34 (s, 1H), 5.77 (d, J = 3.0 Hz, 1H), 5.68 (d, J = 3.0 Hz, 1H), 5.56 (dd, J = 6.3, 2.1 Hz, 1H), 4.88 (s, 1H), 3.76 (s, 3H), 3.65 (d, J = 6.3 Hz, 1H), 3.43 (d, J = 20.1 Hz, 1H), 3.16-3.07 (m, 2H), 2.84 (apparent d, J = 3.3 Hz, 3H), 2.64-2.57 (m, 1H), 2.49-2.43 (m, 1H, partially obscured by solvent peak), 2.33-2.25 (m, 1H), 2.18 (s, 3H), 2.14 (s, 3H), 2.11-2.05 (m, 1H), 1.65 (d, J = 11.4 Hz, 1H) |
| A62 | (morphinan structure with methoxy, OH, N-CH₃, and ester side chain bearing phenyl-OAc-malate) ·TFA | 608 | ¹H NMR (300 MHz, DMSO-d₆; Mixture of diastereomers) δ 7.58-7.53 (m, 2H), 7.48-7.44 (m, 3H), 6.75-6.71 (m, 0.8H), 6.69-6.64 (m, 1.2H), 6.21 (s, 0.4H), 6.12 (s, 0.6H), 5.53-5.47 (m, 0.8H), 5.45-5.43 (m, 1.2H), 4.81 (s, 0.6H), 4.78 (s, 0.4H), 3.70 (s, 1.8H), 3.60 (s, 1.2H), 3.12 (d, J = 18.3 Hz, 1H), 3.00-3.72 (m, 5H), 2.46-2.42 (m, 1H), 2.35 (s, 3H), 2.28-1.99 (m, 6H), 1.38 (d, J = 12.6 Hz, 1H), CO₂H, CF₃CO₂H, and OH protons not observed |

| Ex, No. | Structure | Mass Spec | $^1$H NMR Data |
|---|---|---|---|
| A63 | 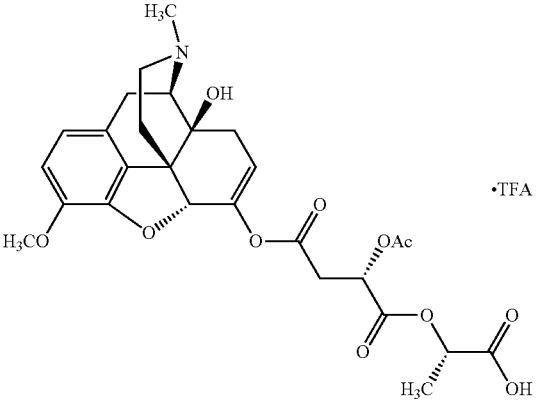 [SMILES: COc1ccc2c3c1O[C@H]1C(OC(=O)C[C@H](OC(C)=O)C(=O)O[C@@H](C)C(=O)O)=CC[C@@]4(O)[C@@H](C2)N(C)CC[C@]314 ; "·TFA"] | 546 | $^1$H NMR (300 MHz, DMSO-$d_6$) δ 6.81 (d, J = 8.4 Hz, 1H), 6.71 (d, J = 8.4 Hz, 1H), 5.57 (dd, J = 5.7, 2.1 Hz, 1H), 5.39 (dd, J = 9.6, 3.2 Hz, 1H), 5.04 (dd, J = 14.1, 6.9 Hz, 1H), 4.95 (s, 1H), 3.73 (s, 3H), 3.29-3.26 (m, 1H), 3.17 (d, J = 17.1 Hz, 1H), 3.00-2.72 (m, 3H), 2.64-2.62 (m, 3H), 2.39-2.37 (m, 3H), 2.22-2.00 (m, 2H), 2.11 (s, 3H), 1.53 (d, J = 9.9 Hz, 1H), 1.43 (d, J = 6.9 Hz, 3H), CO$_2$H, CF$_3$CO$_2$H, and OH protons not observed |
| A64 | 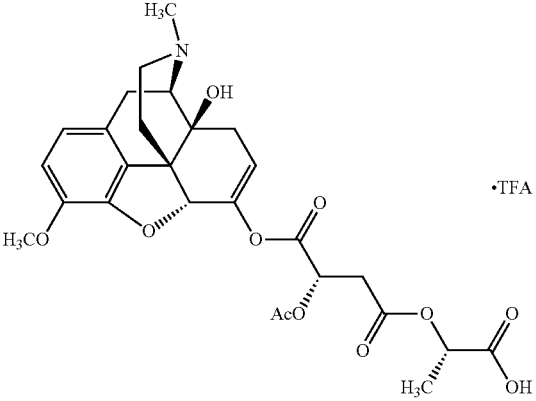 [SMILES: COc1ccc2c3c1O[C@H]1C(OC(=O)[C@H](CC(=O)O[C@@H](C)C(=O)O)OC(C)=O)=CC[C@@]4(O)[C@@H](C2)N(C)CC[C@]314 ; "·TFA"] | 546 | $^1$H NMR (300 MHz, DMSO-$d_6$) δ 6.77 (d, J = 8.4 Hz, 1H), 6.68 (d, J = 8.4 Hz, 1H), 5.61 (dd, J = 5.7, 2.4 Hz, 1H), 5.45 (dd, J = 6.9, 2.1 Hz, 1H), 4.99 (dd, J = 14.1, 6.9 Hz, 1H), 4.87 (s, 1H), 3.74 (s, 3H), 3.19 (d, J = 19.2 Hz, 1H), 3.12-2.99 (m, 5H), 2.79-2.59 (m, 2H), 2.47-2.46 (m, 1H), 2.37-1.97 (m, 7H), 1.45 (d, J = 12.6 Hz, 1H), 1.40 (d, J = 7.2 Hz, 3H), CO$_2$H, CF$_3$CO$_2$H, and OH protons not observed |
| A65 | 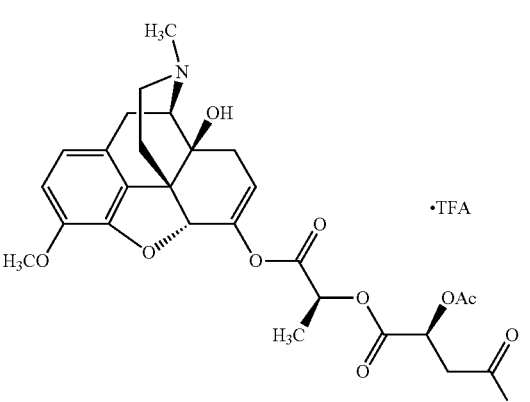 | 546 | $^1$H NMR (300 MHz, DMSO-$d_6$) δ 12.8 (s, 1H), 9.19 (s, 1H), 6.86 (d, J = 8.4 Hz, 1H), 6.76 (d, J = 8.1 Hz, 1H), 6.31 (s, 1H), 5.59 (dd, J = 6.0, 1.8 Hz, 1H), 5.36 (dd, J = 9.0, 3.6 Hz, 1H), 5.26 (dd, J = 14.1, 6.9 Hz, 1H), 5.00 (s, 1H), 3.75 (s, 3H), 3.65 (d, J = 6.3 Hz, 1H), 3.43 (d, J = 20.1 Hz, 1H), 3.16-3.07 (m, 2H), 2.96-2.72 (m, 5H), 2.62-2.52 (m, 1H), 2.46-2.42 (m, 1H), 2.34-2.26 (m, 1H), 2.09 (s, 3H), 2.06 (d, J = 16.0 Hz, 1H), 1.64 (d, J = 11.1 Hz, 1H), 1.52 (d, J = 6.9 Hz, 3H) |

-continued

| Ex. No. | Structure | Mass Spec | ¹H NMR Data |
|---|---|---|---|
| A66 | 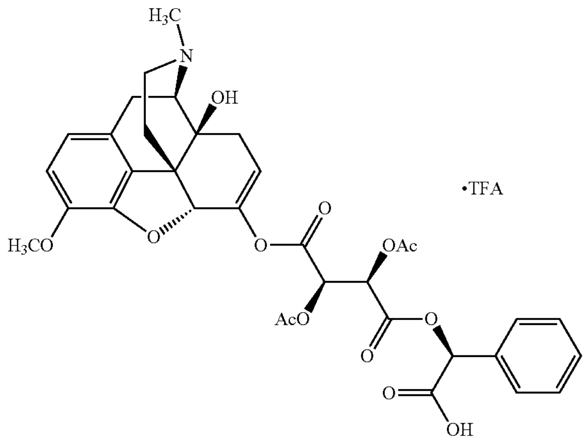 [SMILES: COc1ccc2c3c1O[C@H]1C(OC(=O)[C@H](OC(C)=O)[C@@H](OC(C)=O)C(=O)O[C@H](C(=O)O)c4ccccc4)=CC[C@@]4(O)[C@@H](C2)N(C)CC[C@]314 ; "·TFA"] | 666 | ¹H NMR (300 MHz, DMSO-$d_6$) δ 13.5 (s, 1H), 9.18 (s, 1H), 7.46-7.41 (m, 5H), 6.88 (d, J = 8.4 Hz, 1H), 6.76 (d, J = 8.4 Hz, 1H), 6.35 (s, 1H), 6.01 (s, 1H), 5.92 (dd, J = 24.6, 2.7 Hz, 1H), 5.55 (dd, J = 6.0, 2.1 Hz, 1H), 4.87 (s, 1H), 3.75 (s, 3H), 3.65 (d, J = 6.0 Hz, 1H), 3.43 (d, J = 20.1 Hz, 1H), 3.16-3.07 (m, 2H), 2.84 (d, J = 3.6 Hz, 3H), 2.64-2.61 (m, 1H), 2.41-2.32 (m, 2H), 2.32-2.27 (m, 1H), 2.20 (s, 3H), 2.08 (d, J = 18.3 Hz, 1H), 2.00 (s, 3H), 1.64 (d, J = 11.7 Hz, 1H) |
| A67 | 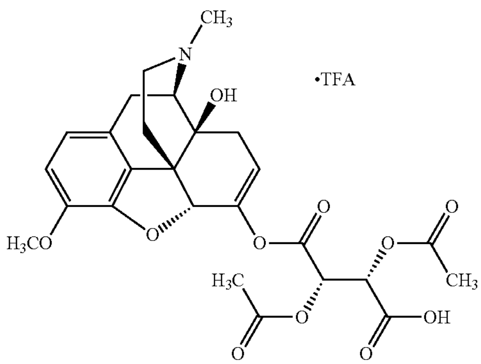 [SMILES: COc1ccc2c3c1O[C@H]1C(OC(=O)[C@@H](OC(C)=O)[C@H](OC(C)=O)C(=O)O)=CC[C@@]4(O)[C@@H](C2)N(C)CC[C@]314 ; "·TFA"] | 532 | ¹H NMR (300 MHz, DMSO-$d_6$) δ 13.87 (br s, 1H), 9.18 (br s, 1H), 6.84 (d, J = 8.4 Hz, 1H), 6.75 (d, J = 8.1 Hz, 1H), 6.33 (s, 1H), 5.80 (d, J = 3.0 Hz, 1H), 5.59 (dd, J = 5.7, 1.8 Hz, 1H), 5.56 (d, J = 3.0 Hz, 1H), 5.00 (s, 1H), 3.72 (s, 3H), 3.65 (d, J = 6.3 Hz, 1H), 3.43 (d, J = 19.8 Hz, 1H), 3.16-3.07 (m, 2H), 2.84 (apparent d, J = 2.7 Hz, 3H), 2.65-2.58 (m, 1H), 2.49-2.43 (m, 1H, partially obscured by solvent peak), 2.34-2.25 (m, 1H), 2.17 (s, 3H), 2.15 (s, 3H), 2.11-2.05 (m, 1H), 1.66 (d, J = 10.8 Hz, 1H) |
| A68a | 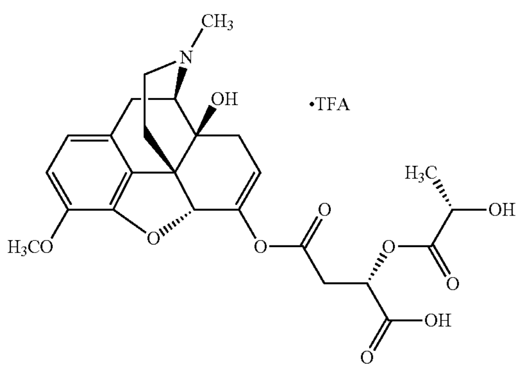 [SMILES: COc1ccc2c3c1O[C@H]1C(OC(=O)C[C@H](OC(=O)[C@H](C)O)C(=O)O)=CC[C@@]4(O)[C@@H](C2)N(C)CC[C@]314 ; "·TFA"] | 504 | ¹H NMR (300 MHz, DMSO-$d_6$) δ 13.42 (br s, 1H), 9.18 (br s, 1H), 6.86 (d, J = 8.4 Hz, 1H), 6.75 (d, J = 8.4 Hz, 1H), 6.29 (s, 1H), 5.56-5.55 (m, 1H), 5.46 (br s, 1H), 5.31 (dd, J = 8.1, 4.2 Hz, 1H), 4.99 (s, 1H), 4.21 (q, J = 6.9 Hz, 1H), 3.75 (s, 3H), 3.64 (d, J = 6.3 Hz, 1H), 3.48-3.40 (m, 1H, partially obscured by water peak), 3.15-2.96 (m, 4H), 2.84 (apparent d, J = 4.2 Hz, 3H), 2.66-2.58 (m, 1H), 2.49-2.42 (m, 1H, partially obscured by solvent peak), 2.32-2.24 (m, 1H), 2.07 (apparent d, J = 18.0 Hz, 1H), 1.64 (d, J = 11.7 Hz, 1H), 1.31 (d, J = 6.9 Hz, 3H) |
| A68b | 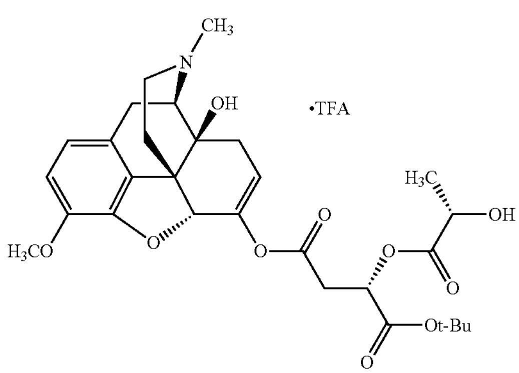 [SMILES: COc1ccc2c3c1O[C@H]1C(OC(=O)C[C@H](OC(=O)[C@H](C)O)C(=O)OC(C)(C)C)=CC[C@@]4(O)[C@@H](C2)N(C)CC[C@]314 ; "·TFA"] | 560 | ¹H NMR (300 MHz, CDCl$_3$) δ 9.18 (br s, 1H), 6.86 (d, J = 8.4 Hz, 1H), 6.75 (d, J = 8.4 Hz, 1H), 6.27 (s, 1H), 5.56-5.54 (m, 1H), 5.48 (br s, 1H), 5.24 (dd, J = 7.5, 4.8 Hz, 1H), 4.99 (s, 1H), 4.21 (q, J = 6.6 Hz, 1H), 3.74 (s, 3H), 3.64 (d, J = 6.0 Hz, 1H), 3.46-3.40 (m, 1H, partially obscured by water peak), 3.15-2.97 (m, 4H), 2.85 (apparent d, J = 4.8 Hz, 3H), 2.66-2.57 (m, 1H), 2.49-2.42 (m, 1H, partially obscured by solvent peak), 2.33-2.24 (m, 1H), 2.07 (apparent d, J = 18.3 Hz, 1H), 1.64 (d, J = 12.0 Hz, 1H), 1.41 (s, 9H), 1.32 (d, J = 6.9 Hz, 3H) |

| Ex. No. | Structure | Mass Spec | $^1$H NMR Data |
|---|---|---|---|
| A69 | 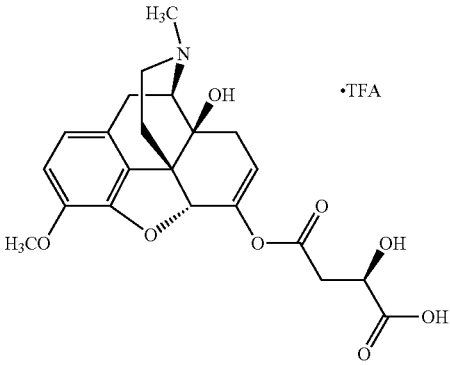 [SMILES: COc1ccc2c3c1O[C@H]1C(OC(=O)C[C@@H](O)C(=O)O)=CC[C@@]4(O)[C@@H](C2)N(C)CC[C@]314 ; "·TFA"] | 432 | $^1$H NMR (300 MHz, DMSO-$d_6$) δ 12.7 (s, 1H), 9.19 (s, 1H), 6.86 (d, J = 8.4 Hz, 1H), 6.75 (d, J = 8.4 Hz, 1H), 6.28 (s, 1H), 5.63 (s, 1H), 5.53-5.51 (m, 1H), 4.98 (s, 1H), 4.34 (dd, J = 7.8, 2.1 Hz, 1H), 3.76 (s, 3H), 3.64 (d, J = 6.3 Hz, 1H), 3.43 (d, J = 20.1 Hz, 1H), 3.15-3.07 (m, 2H), 2.89-2.82 (m, 2.72-2.61 (m, 2H), 2.46-2.42 (m, 1H), 2.33-2.26 (m, 1H), 2.05 (d, J = 18.0 Hz, 1H), 1.64 (d, J = 11.5 Hz, 1H) |
| A70 | 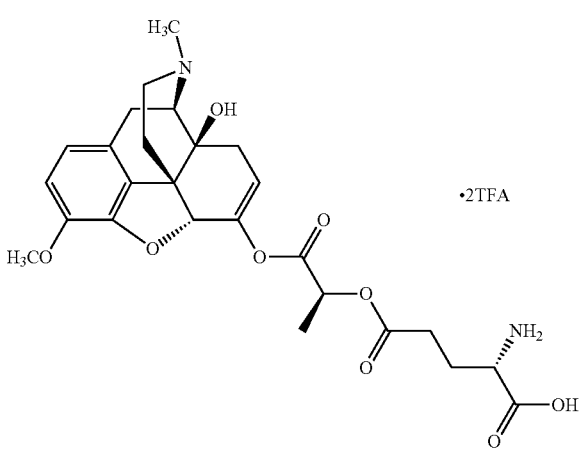 [SMILES: COc1ccc2c3c1O[C@H]1C(OC(=O)[C@H](C)OC(=O)CC[C@H](N)C(=O)O)=CC[C@@]4(O)[C@@H](C2)N(C)CC[C@]314 ; "·2TFA"] | 517 | $^1$H NMR (300 MHz, DMSO-$d_6$) δ 9.20 (s, 1H), 8.29 (s, 3H), 6.86 (d, J = 8.4 Hz, 1H), 6.76 (d, J = 8.1 Hz, 1H), 6.34 (s, 1H), 5.60-5.58 (m, 1H), 5.14 (dd, J = 13.8, 7.2 Hz, 1H), 5.00 (s, 1H), 3.76 (s, 3H), 3.66 (d, J = 6.3 Hz, 1H), 3.43 (d, J = 20.1 Hz, 1H), 3.16-3.07 (m, 2H), 2.85 (s, 3H), 2.72-2.61 (m, 3H), 2.46-2.42 (m, 1H), 2.33-2.26 (m, 1H), 2.15-1.99 (m, 3H), 2.07 (d, J = 18.0 Hz, 1H), 1.64 (d, J = 11.5 Hz, 1H), 1.51 (d, J = 7.2 Hz, 3H), CO$_2$H proton not observed |
| A71 | 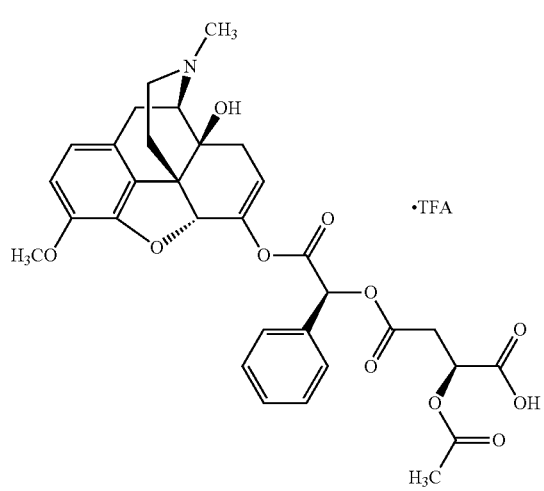 [SMILES: COc1ccc2c3c1O[C@H]1C(OC(=O)[C@@H](OC(=O)C[C@H](OC(C)=O)C(=O)O)c4ccccc4)=CC[C@@]4(O)[C@@H](C2)N(C)CC[C@]314 ; "·TFA"] | 608 | $^1$H NMR (300 MHz, DMSO-$d_6$) δ 13.40 (br s, 1H), 9.16 (br s, 1H), 7.57-7.54 (m, 2H), 7.48-7.46 (m, 3H), 6.81 (d, J = 8.4 Hz, 1H), 6.73 (d, J = 8.4 Hz, 1H), 6.29 (s, 1H), 6.17 (s, 1H), 5.55 (dd, J = 6.0, 2.1 Hz, 1H), 5.33 (dd, J = 8.7, 3.9 Hz, 1H), 4.95 (s, 1H), 3.75 (br s, 4H), 3.44-3.38 (m, 1H, partially obscured by water peak), 3.14-2.97 (m, 4H), 2.83 (apparent d, J = 4.2 Hz, 3H), 2.68-2.57 (m, 1H), 2.49-2.40 (m, 1H, partially obscured by solvent peak), 2.31-2.22 (m, 1H), 2.09-2.04 (m, 1H), 2.04 (s, 3H), 1.63 (d, J = 12.0 Hz, 3H) |

-continued

| Ex, No. | Structure | Mass Spec | ¹H NMR Data |
|---|---|---|---|
| A72 | (structure) | 648 | ¹H NMR (300 MHz, DMSO-d₆) δ 13.5 (s, 1H), 12.6 (s, 1H), 9.18 (s, 1H), 6.88 (d, J = 8.1 Hz, 1H), 6.77 (d, J = 8.1 Hz, 1H), 6.34 (s, 1H), 5.85 (d, J = 2.7 Hz, 1H), 5.78 (d, J = 2.7 Hz, 1H), 5.55 (dd, J = 6.0, 2.1 Hz, 1H), 5.30 (dd, J = 8.4, 3.6 Hz, 1H), 4.88 (s, 1H), 3.75 (s, 3H), 3.65 (d, J = 6.0 Hz, 1H), 3.43 (d, J = 20.1 Hz, 1H), 3.16-3.07 (m, 2H), 2.90-2.80 (m, 5H), 2.64-2.61 (m, 1H), 2.41-2.32 (m, 1H), 2.32-2.27 (m, 1H), 2.20 (s, 3H), 2.12 (s, 3H), 2.08 (d, J = 18.3 Hz, 1H), 1.64 (d, J = 11.7 Hz, 1H) |
| A73 | (structure) | 548 | ¹H NMR (300 MHz, DMSO-d₆) δ 13.41 (br s, 1H), 12.69 (br s, 1H), 9.19 (br s, 1H), 6.86 (d, J = 8.4 Hz, 1H), 6.75 (d, J = 8.1 Hz, 1H), 6.31 (br s, 1H), 5.57 (dd, J = 5.7, 1.5 Hz, 1H), 5.55 (br s, 1H), 5.30 (dd, J = 7.8, 4.5 Hz, 1H), 4..99 (s, 1H), 4.32 (dd, J = 7.8, 4.2 Hz, 1H), 3.75 (s, 3H), 3.65 (d, J = 6.3 Hz, 1H), 3.43 (d, J = 20.1 Hz, 1H), 3.16-2.95 (m, 4H), 2.84 (s, 3H), 2.81-2.58 (m, 3H), 2.49-2.43 (m, 1H, partially obscured by solvent peak), 2.32-2.24 (m, 1H), 2.07 (apparent d, J = 18.0 Hz, 1H), 1.64 (d, J = 11.1 Hz, 1H) |
| A74 | (structure) | 556 | ¹H NMR (300 MHz, DMSO-d₆) δ 9.20 (br s, 2H), 8.61 (t, J = 5.7 Hz, 1H), 8.54 (br s, 1H), 6.86 (d, J = 8.4 Hz, 1H), 6.76 (d, J = 8.1 Hz, 1H), 6.31 (br s, 1H), 5.59 (dd, J = 6.0, 2.1 Hz, 1H), 5.12 (q, J = 7.2 Hz, 1H), 5.00 (s, 1H), 4.13-4.09 (m, 1H), 3.76 (s, 3H), 3.66 (d, J = 6.0 Hz, 1H), 3.51-3.29 (m, 4H), 3.22-3.07 (m, 4H), 2.85 (apparent d, J = 4.5 Hz, 3H), 2.70-2.58 (m, 2H), 2.49-2.41 (m, 1H, partially obscured by solvent peak), 2.34-2.19 (m, 2H), 2.06 (apparent d, J = 18.0 Hz, 1H), 1.92-1.77 (m, 3H), 1.64 (d, J = 11.1 Hz, 1H), 1.51 (d, J = 6.9 Hz, 3H) |

-continued

| Ex. No. | Structure | Mass Spec | ¹H NMR Data |
|---|---|---|---|
| A75 | 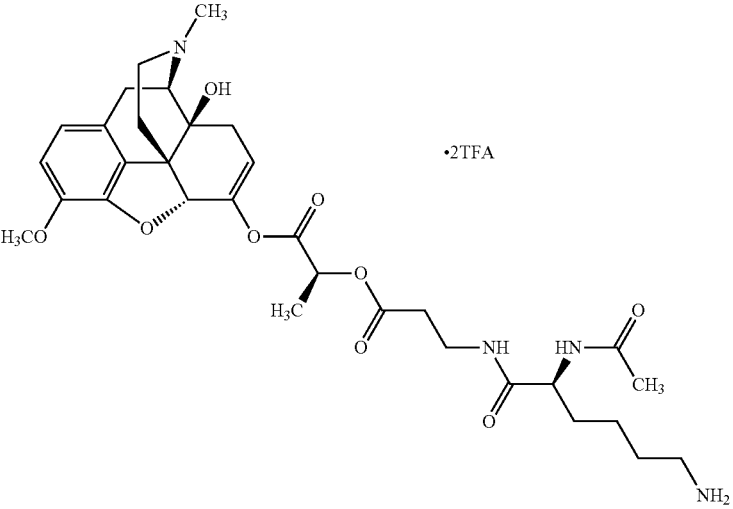 [SMILES: COc1ccc2c3c1O[C@H]1C(OC(=O)[C@H](C)OC(=O)CCNC(=O)[C@H](CCCCN)NC(C)=O)=CC[C@@]4(O)[C@@H](C2)N(C)CC[C@]314 ; "·2TFA"] | 629 | ¹H NMR (300 MHz, DMSO-d$_6$) δ 9.19 (br s, 1H), 8.05-7.98 (m, 2H), 7.65 (br s, 3H), 6.86 (d, J = 8.4 Hz, 1H), 6.76 (d, J = 8.4 Hz, 1H), 6.32 (s, 1H), 5.59 (dd, J = 5.7, 1.8 Hz, 1H), 5.10 (q, J = 6.9 Hz, 1H), 5.00 (s, 1H), 4.19-4.12 (m, 1H), 3.75 (s, 3H), 3.66 (d, J = 6.0 Hz, 1H), 3.43 (d, J = 19.8 Hz, 1H), 3.35-3.25 (m, 2H), 3.16-3.07 (m, 2H), 2.85 (apparent d, J = 4.5 Hz, 3H), 2.79-2.70 (m, 2H), 2.65-2.53 (m, 3H, partially obscured by solvent peak), 2.49-2.43 (m, 1H, partially obscured by solvent peak), 2.34-2.26 (m, 1H), 2.06 (apparent d, J = 18.3 Hz, 1H), 1.84 (s, 3H), 1.67-1.40 (m, 8H), .33-1.20 (m, 2H) |
| A76 | 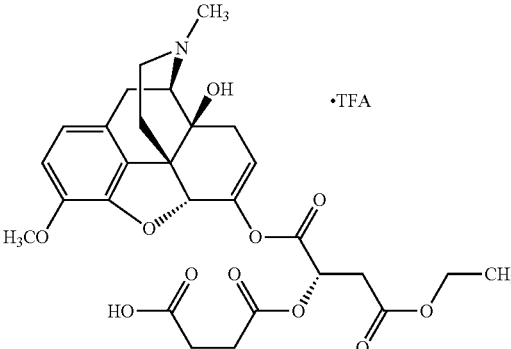 | 560 | ¹H NMR (300 MHz, DMSO-d$_6$) δ 12.28 (br s, 1H), 9.19 (br s, 1H), 6.85 (d, J = 8.4 Hz, 1H), 6.75 (d, J = 8.4 Hz, 1H), 6.31 (s, 1H), 5.61 (dd, J = 5.7, 1.8 Hz, 1H), 5.47 (t, J = 5.4 Hz, 1H), 4.96 (s, 1H), 4.13 (q, J = 6.9 Hz, 2H), 3.74 (s, 3H), 3.65 (d, J = 6.0 Hz, 1H), 3.43 (d, J = 19.8 Hz, 1H), 3.16-3.07 (m, 2H), 2.98 (d, J = 6.6 Hz, 2H), 2.84 (apparent d, J = 4.8 Hz, 3H), 2.69-2.58 (m, 3H), 2.49-2.43 (m, 1H, partially obscured by solvent peak), 2.34-2.26 (m, 1H), 2.07 (apparent d, J = 18.3 Hz, 1H), 1.65 (d, J = 10.8 Hz, 1H), 1.21 (t, J = 6.9 Hz, 3H), two protons obscured by the solvent peaks |
| A77 | 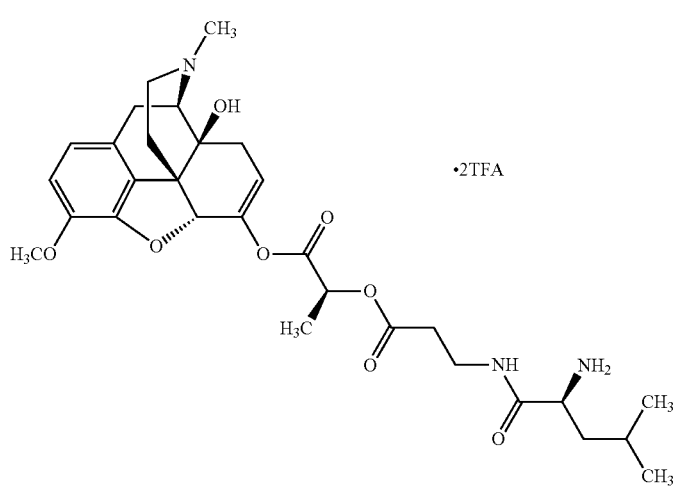 [SMILES: COc1ccc2c3c1O[C@H]1C(OC(=O)[C@H](C)OC(=O)CCNC(=O)[C@@H](N)CC(C)C)=CC[C@@]4(O)[C@@H](C2)N(C)CC[C@]314 ; "·2TFA"] | 572 | ¹H NMR (300 MHz, DMSO-d$_6$) δ 9.19 (br s, 1H), 8.63 (t, J = 5.4 Hz, 1H), 8.11 (br s, 3H), 6.86 (d, J = 8.4 Hz, 1H), 6.76 (d, J = 8.4 Hz, 1H), 6.32 (br s, 1H), 5.59 (dd, J = 5.7, 1.8 Hz, 1H), 5.13 (q, J = 6.9 Hz, 1H), 5.00 (s, 1H), 3.76 (s, 3H), 3.67-3.65 (m, 2H), 3.53-3.40 (m, 2H), 3.35-3.24 (m, 1H), 3.16-3.07 (m, 2H), 2.85 (apparent d, J = 4.5 Hz, 3H), 2.73-2.59 (m, 3H), 2.49-2.43 (m, 1H, partially obscured by solvent peak), 2.34-2.26 (m, 1H), 2.06 (apparent d, J = 18.3 Hz, 4H), 1.66-1.50 (m, 7H), 0.90-0.87 (m, 6H) |

-continued

| Ex. No. | Structure | Mass Spec | $^1$H NMR Data |
|---|---|---|---|
| A78 | 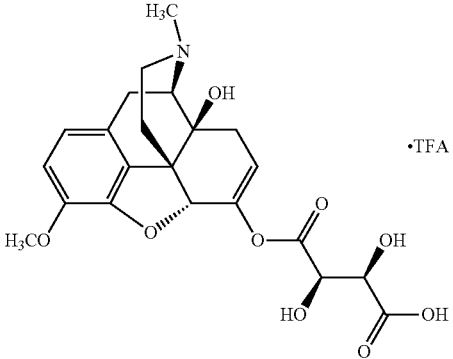 [SMILES: COc1ccc2c3c1O[C@H]1C(OC(=O)[C@H](O)[C@@H](O)C(=O)O)=CC[C@@]4(O)[C@@H](C2)N(C)CC[C@]314 ; "·TFA"] | 448 | $^1$H NMR (300 MHz, DMSO-d$_6$) δ 12.8 (s, 1H), 9.20 (s, 1H), 6.86 (d, J = 8.4 Hz, 1H), 6.75 (d, J = 8.4 Hz, 1H), 6.30 (s, 1H), 5.71 (s, 1H), 5.54 (dd, J = 6.0, 2.1 Hz, 1H), 5.31 (s, 1H), 5.04 (s, 1H), 4.55 (s, 1H), 4.41 (s, 1H), 3.75 (s, 3H), 3.64 (d, J = 6.3 Hz, 1H), 3.43 (d, J = 19.8 Hz, 1H), 3.15-3.07 (m, 2H), 2.85 (d, J = 3.3 Hz, 3H), 2.69-2.62 (m, 1H), 2.49-2.43 (m, 1H), 2.32-2.26 (m, 1H), 2.07 (d, J = 18.3 Hz, 1H), 1.65 (d, J = 11.1 Hz, 1H) |
| A79 | 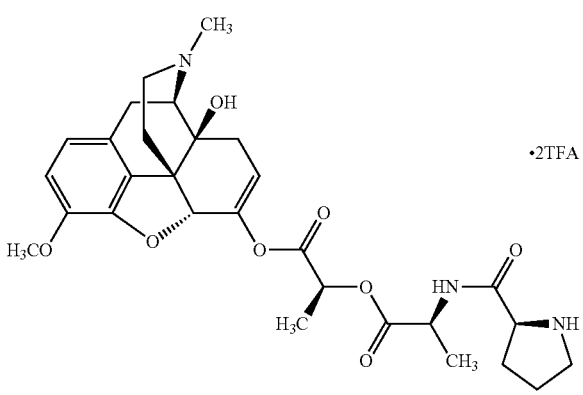 [SMILES: COc1ccc2c3c1O[C@H]1C(OC(=O)[C@H](C)OC(=O)[C@H](C)NC(=O)[C@@H]4CCCN4)=CC[C@@]4(O)[C@@H](C2)N(C)CC[C@]314 ; "·2TFA"] | 556 | $^1$H NMR (300 MHz, DMSO-d$_6$) δ 9.21 (s, 2H), 8.96 (d, J = 6.6 Hz, 1H), 8.55 (s, 1H), 6.86 (d, J = 8.1 Hz, 1H), 6.75 (d, J = 8.1 Hz, 1H), 6.30 (s, 1H), 5.59 (dd, J = 6.0, 2.1 Hz, 1H), 5.19 (dd, J = 14, 7.2 Hz, 1H), 4.99 (s, 1H), 4.48-4.39 (m, 1H), 4.25-4.18 (m, 1H), 3.76 (s, 3H), 3.66 (d, J = 6.0 Hz, 1H), 3.43 (d, J = 19.8 Hz, 1H), 3.23-3.07 (m, 4H), 2.85 (d, J = 4.5 Hz, 3H), 2.69-2.57 (m, 1H), 2.49-2.41 (m, 1H), 2.33-2.26 (m, 2H), 2.06 (d, J = 18 Hz, 1H), 1.93-1.84 (m, 3H), 1.64 (d, J = 11.1 Hz, 1H), 1.52 (d, J = 6.9 Hz, 3H), 1.41 (d, J = 7.2 Hz, 3H) |
| A80 | 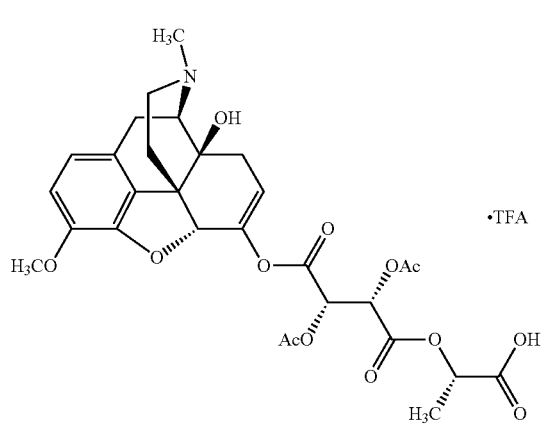 [SMILES: COc1ccc2c3c1O[C@H]1C(OC(=O)[C@@H](OC(C)=O)[C@H](OC(C)=O)C(=O)O[C@@H](C)C(=O)O)=CC[C@@]4(O)[C@@H](C2)N(C)CC[C@]314 ; "·TFA"] | 604 | $^1$H NMR (300 MHz, DMSO-d$_6$) δ 13.2 (s, 1H), 9.17 (s, 1H), 6.88 (d, J = 8.4 Hz, 1H), 6.77 (d, J = 8.4 Hz, 1H), 6.35 (s, 1H), 5.87 (dd, J = 13.5, 2.7 Hz, 2H), 5.57 (dd, J = 6.3, 2.1 Hz, 1H), 5.04 (dd, J = 13.8, 1.2 Hz, 1H), 4.88 (s, 1H), 3.76 (s, 3H), 3.65 (d, J = 6.3 Hz, 1H), 3.41 (d, J = 20.1 Hz, 1H), 3.16-3.07 (m, 2H), 2.84 (d, J = 3.6 Hz, 3H), 2.64-2.61 (m, 1H), 2.46-2.42 (m, 1H), 2.33-2.26 (m, 1H), 2.21 (s, 3H), 2.15 (s, 3H), 2.08 (d, J = 18.0 Hz, 1H), 1.64 (d, J = 11.1 Hz, 1H), 1.38 (d, J = 7.2 Hz, 3H) |

-continued

| Ex, No. | Structure | Mass Spec | ¹H NMR Data |
|---|---|---|---|
| A81 | 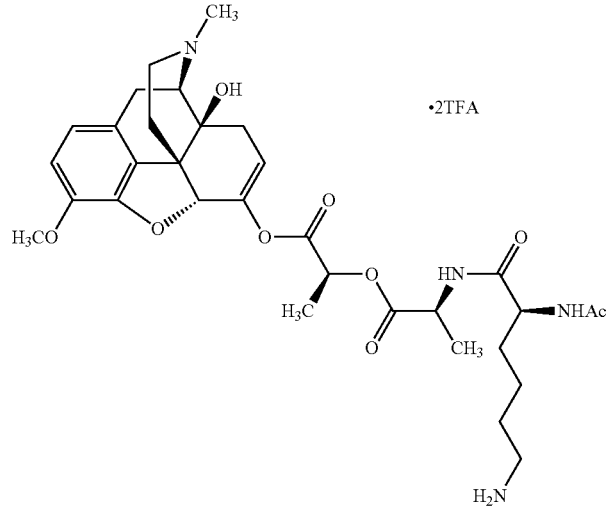 [SMILES: COc1ccc2c3c1O[C@H]1C(OC(=O)[C@H](C)OC(=O)[C@H](C)NC(=O)[C@H](CCCCN)NC(C)=O)=CC[C@@]4(O)[C@@H](C2)N(C)CC[C@]314 ; "·2TFA"] | 629 | ¹H NMR (300 MHz, DMSO-$d_6$) δ 9.19 (s, 1H), 8.42 (d, J = 6.6 Hz, 1H), 8.00 (d, J = 8.4 Hz, 1H), 7.64 (s, 3H), 6.86 (d, J = 8.4 Hz, 1H), 6.76 (d, J = 8.4 Hz, 1H), 6.30 (s, 1H), 5.57 (dd, J = 6.0, 2.1 Hz, 1H), 5.15 (dd, J = 14, 6.9 Hz, 1H), 4.99 (s, 1H), 4.34-4.25 (m, 2H), 3.75 (s, 3H), 3.66 (d, J = 6.0 Hz, 1H), 3.43 (d, J = 19.8 Hz, 1H), 3.16-3.07 (m, 2H), 2.85 (d, J = 4.5 Hz, 3H), 2.76-2.62 (m, 2H), 2.33-2.26 (m, 2H), 2.06 (d, J = 18 Hz, 1H), 1.84 (s, 3H), 1.66-1.34 (m, 14H) |
| A82 | 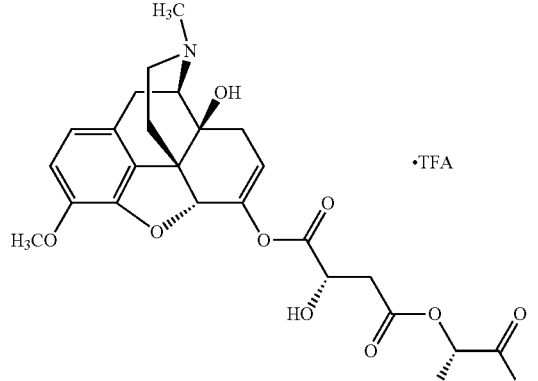 | 504 | ¹H NMR (300 MHz, DMSO-$d_6$) δ 13.1 (s, 1H), 9.17 (s, 1H), 6.87 (d, J = 8.4 Hz, 1H), 6.76 (d, J = 8.4 Hz, 1H), 6.29 (s, 1H), 6.00 (s, 1H), 5.57 (dd, J = 6.0, 1.8 Hz, 1H), 4.98 (d, J = 4.5 Hz, 1H), 4.96 (dd, J = 14.1, 6.9 Hz, 1H), 4.54-4.50 (m, 1H), 3.76 (s, 3H), 3.64 (d, J = 5.7 Hz, 1H), 3.43 (d, J = 20.1 Hz, 1H), 3.16-3.07 (m, 2H), 2.85-2.78 (m, 5H), 2.65-2.61 (m, 1H), 2.46-2.42 (m, 1H), 2.33-2.25 (m, 1H), 2.07 (d, J = 18.0 Hz, 1H), 1.64 (d, J = 11.1 Hz, 1H), 1.40 (d, J = 6.9 Hz, 3H) |
| A83 | 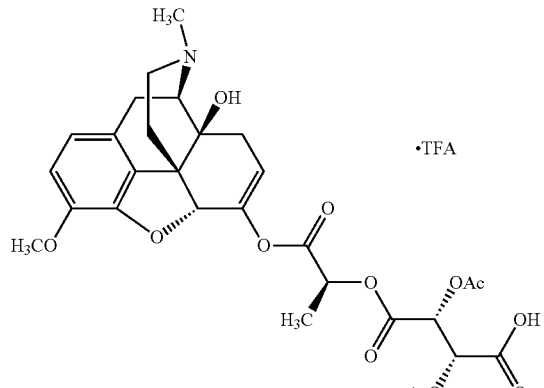 | 604 | ¹H NMR (300 MHz, DMSO-$d_6$) δ 13.9 (s, 1H), 9.19 (s, 1H), 6.85 (d, J = 8.1 Hz, 1H), 6.75 (d, J = 8.1 Hz, 1H), 6.32 (s, 1H), 5.72 (d, J = 3.0 Hz, 1H), 5.66-5.60 (m, 2H), 5.29 (dd, J = 13.8, 6.9 Hz, 1H), 5.03 (s, 1H), 3.74 (s, 3H), 3.65 (d, J = 6.3 Hz, 1H), 3.41 (d, J = 20.1 Hz, 1H), 3.16-3.07 (m, 2H), 2.84 (d, J = 3.6 Hz, 3H), 2.64-2.61 (m, 1H), 2.46-2.42 (m, 1H), 2.33-2.26 (m, 1H), 2.13 (s, 3H), 2.11 (s, 3H), 2.06 (d, J = 18.0 Hz, 1H), 1.65 (d, J = 11.1 Hz, 1H), 1.46 (d, J = 6.9 Hz, 3H) |

| Ex, No. | Structure | Mass Spec | ¹H NMR Data |
|---|---|---|---|
| A84 | 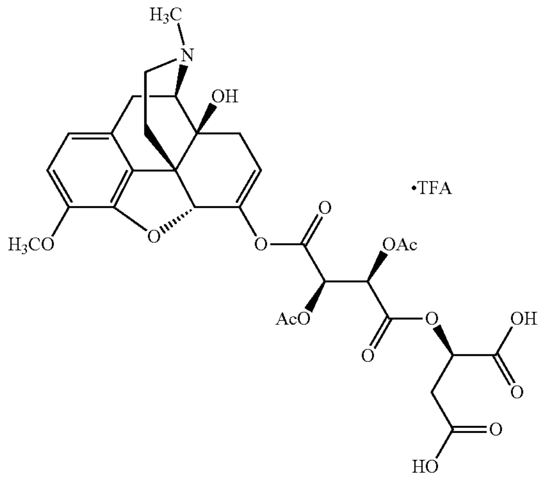 [SMILES: COc1ccc2c3c1O[C@H]1C(OC(=O)[C@H](OC(C)=O)[C@@H](OC(C)=O)C(=O)O[C@H](CC(=O)O)C(=O)O)=CC[C@@]4(O)[C@@H](C2)N(C)CC[C@]314 ; "·TFA"] | 648 | ¹H NMR (300 MHz, DMSO-d$_6$) δ 13.5 (s, 1H), 12.7 (s, 1H), 9.17 (s, 1H), 6.88 (d, J = 8.4 Hz, 1H), 6.77 (d, J = 8.4 Hz, 1H), 6.33 (s, 1H), 5.80 (dd, J = 9.6, 2.7 Hz, 2H), 5.57 (dd, J = 6.0, 2.1 Hz, 1H), 5.35 (dd, J = 7.8, 1.2 Hz, 1H), 4.89 (s, 1H), 3.75 (s, 3H), 3.65 (d, J = 6.3 Hz, 1H), 3.41 (d, J = 20.1 Hz, 1H), 3.15-3.07 (m, 2H), 2.93-2.80 (m, 5H), 2.64-2.61 (m, 1H), 2.41-2.32 (m, 1H), 2.32-2.26 (m, 1H), 2.27 (s, 3H), 2.07 (s, 3H), 2.06 (d, J = 18.3 Hz, 1H), 1.64 (d, J = 11.4 Hz, 1H) |
| A85 | 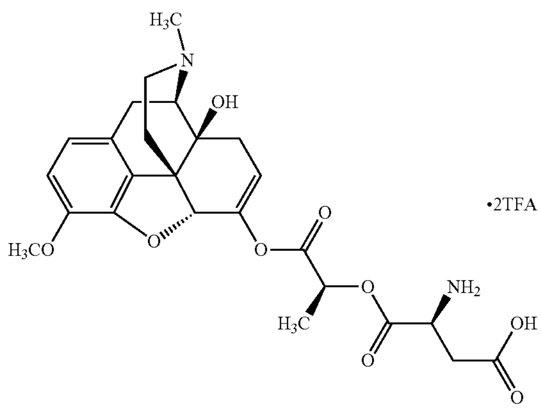 [SMILES: COc1ccc2c3c1O[C@H]1C(OC(=O)[C@H](C)OC(=O)[C@@H](N)CC(=O)O)=CC[C@@]4(O)[C@@H](C2)N(C)CC[C@]314 ; "·2TFA"] | 503 | ¹H NMR (300 MHz, DMSO-d$_6$) δ 13.2 (s, 1H), 9.20 (s, 1H), 8.48 (s, 3H), 6.87 (d, J = 8.4 Hz, 1H), 6.76 (d, J = 8.4 Hz, 1H), 6.32 (s, 1H), 5.62-5.59 (m, 1H), 5.39-5.30 (m, 1H), 5.00 (d, J = 7.5 Hz, 1H), 4.48-4.45 (m, 1H), 3.76 (s, 3H), 3.66 (d, J = 6.3 Hz, 1H), 3.44 (d, J = 20.1 Hz, 1H), 3.16-3.07 (m, 2H), 2.96-2.85 (m, 5H), 2.64-2.61 (m, 1H), 2.46-2.42 (m, 1H), 2.33-2.26 (m, 1H), 2.07 (d, J = 18.0 Hz, 1H), 1.64 (d, J = 12.6 Hz, 1H), 1.55 (d, J = 7.2 Hz, 3H) |
| A86 | 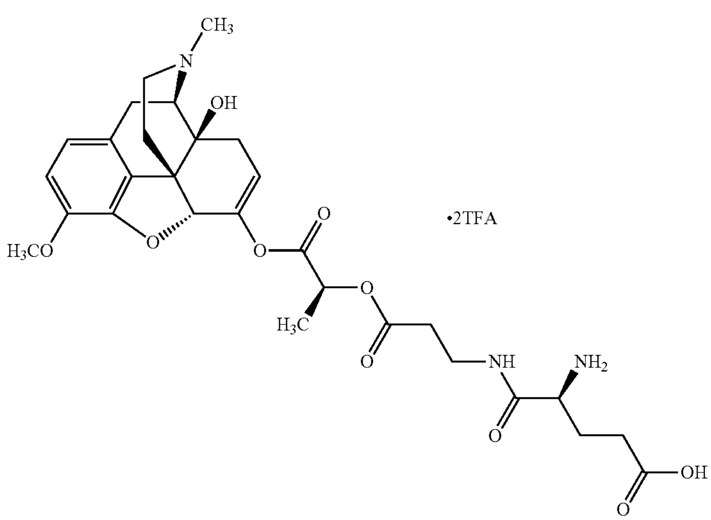 [SMILES: COc1ccc2c3c1O[C@H]1C(OC(=O)[C@H](C)OC(=O)CCNC(=O)[C@@H](N)CCC(=O)O)=CC[C@@]4(O)[C@@H](C2)N(C)CC[C@]314 ; "·2TFA"] | 588 | ¹H NMR (300 MHz, DMSO-d$_6$) δ 12.35 (br s, 1H), 9.19 (br s, 1H), 8.61 (t, J = 5.4 Hz, 1H), 8.13 (br s, 3H), 6.86 (d, J = 8.4 Hz, 1H), 6.76 (d, J = 8.4 Hz, 1H), 6.31 (br s, 1H), 5.59 (dd, J = 5.7, 1.8 Hz, 1H), 5.12 (q, J = 7.2 Hz, 1H), 5.00 (s, 1H), 3.76 (s, 3H), 3.75-3.71 (m, 1H), 3.66 (d, J = 6.3 Hz, 1H), 3.53-3.40 (m, 3H), 3.35-3.25 (m, 1H), 3.16-3.07 (m, 2H), 2.85 (apparent d, J = 3.6 Hz, 3H), 2.67-2.55 (m, 2H), 2.49-2.42 (m, 1H, partially obscured by solvent peak), 2.35-2.26 (m, 3H), 2.09-2.03 (m, 1H), 1.95-1.89 (m, 2H), 1.64 (d, J = 11.1 Hz, 1H), 1.51 (d, J = 7.2 Hz, 3H) |

| Ex, No. | Structure | Mass Spec | ¹H NMR Data |
|---|---|---|---|
| A87 | 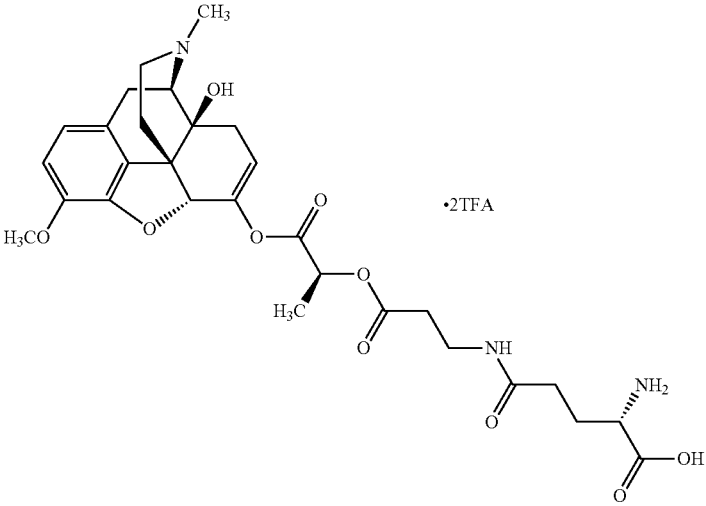 [SMILES: COc1ccc2c3c1O[C@H]1C(OC(=O)[C@H](C)OC(=O)CCNC(=O)CC[C@H](N)C(=O)O)=CC[C@@]4(O)[C@@H](C2)N(C)CC[C@]314 ; "·2TFA"] | 588 | ¹H NMR (300 MHz, DMSO-$d_6$) δ 9.19 (br s, 1H), 8.26 (br s, 3H), 8.10 (t, J = 5.7 Hz, 1H), 6.86 (d, J = 8.4 Hz, 1H), 6.76 (d, J = 8.4 Hz, 1H), 6.32 (br s, 1H), 5.58 (dd, J = 5.7, 1.8 Hz, 1H), 5.11 (q, J = 7.2 Hz, 1H), 5.00 (s, 1H), 3.93 (br s, 1H), 3.75 (s, 3H), 3.66 (d, J = 6.3 Hz, 1H), 3.47-3.40 (m, 2H, partially obscured by water peak), 3.36-3.27 (m, 2H), 3.16-3.07 (m, 2H), 2.85 (s, 3H), 2.63-2.55 (m, 2H), 2.49-2.43 (m, 1H, partially obscured by solvent peak), 2.34-2.17 (m, 3H), 2.09-1.93 (m, 3H), 1.64 (d, J = 11.1 Hz, 1H), 1.50 (d, J = 7.2 Hz, 3H), $CO_2H$ proton not observed |
| A88 | 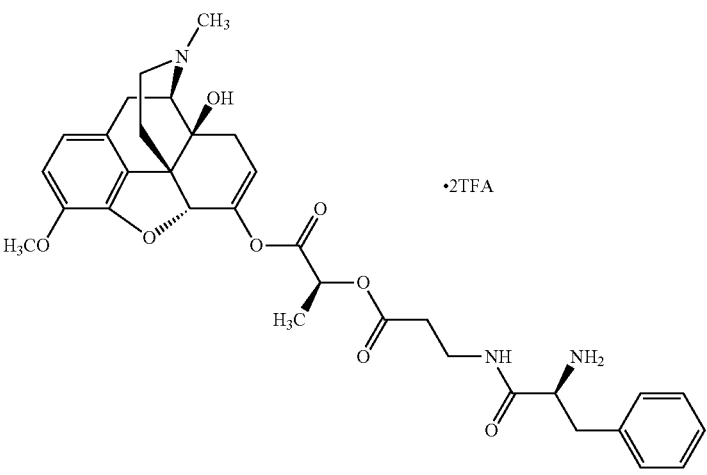 [SMILES: COc1ccc2c3c1O[C@H]1C(OC(=O)[C@H](C)OC(=O)CCNC(=O)[C@@H](N)Cc4ccccc4)=CC[C@@]4(O)[C@@H](C2)N(C)CC[C@]314 ; "·2TFA"] | 606 | ¹H NMR (300 MHz, DMSO-$d_6$) δ 9.18 (br s, 1H), 8.48 (t, J = 5.7 Hz, 1H), 8.17 (br s, 3H), 7.37-7.26 (m, 3H), 7.23-7.20 (m, 2H), 6.86 (d, J = 8.4 Hz, 1H), 6.76 (d, J = 8.4 Hz, 1H), 6.29 (br s, 1H), 5.58 (dd, J = 6.0, 2.1 Hz, 1H), 5.09 (q, J = 7.2 Hz, 1H), 4.99 (s, 1H), 3.94 (br s, 1H), 3.75 (s, 3H), 3.65 (d, J = 6.3 Hz, 1H), 3.45-3.40 (m, 3H, partially obscured by water peak), 3.24-3.07 (m, 4H), 2.99-2.96 (m, 2H), 2.85 (apparent d, J = 4.2 Hz, 3H), 2.68-2.55 (m, 1H), 2.49-2.41 (m, 1H, partially obscured by solvent peak), 2.37-2.25 (m, 1H), 2.05 (apparent d, J = 17.7 Hz, 1H), 1.64 (d, J = 13.2 Hz, 1H), 1.52 (d, J = 6.9 Hz, 3H) |

In further embodiments, the abuse-resistant opioid compound may be selected from one or more of:

| Ex, No. | Structure | Mass Spec | ¹H NMR Data |
|---|---|---|---|
| B1a | 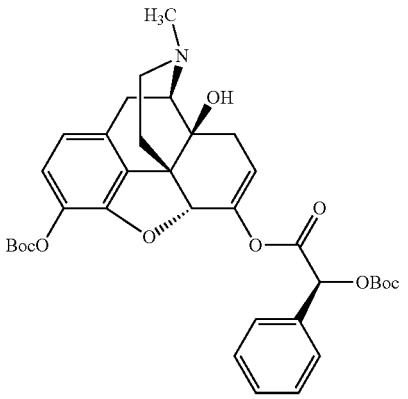 | 636 | ¹H NMR (300 MHz, DMSO-$d_6$) δ 7.54-7.51 (m, 2H), 7.46-7.44 (m, 3H), 6.90 (d, J = 8.1 Hz, 0.14H), 6.87 (d, J = 8.1 Hz, 0.86H), 6.72 (d, J = 8.4 Hz, 0.14H), 6.71 (d, J = 8.1 Hz, 0.86H), 5.98 (s, 0.14H), 5.97 (s, 0.86H), 5.57 (dd, J = 5.4, 2.1 Hz, 0.86H), 5.42-5.41 (m, 0.14H), 4.86 (s, 0.86H), 4.83 (s, 0.14H), 4.76 (br s, 1H), 3.14 (d, J = 19.2 Hz, 1H), 2.86-2.84 (m, 1H), 2.69-2.61 (m, 1H), 2.43-2.41 (m, 1H), 2.31 (s, 3H), 2.27-2.23 (m, 1H), 2.11-1.94 (m, 3H), 1.47 (s, 1.26H), 1.46 (s, 7.74H), 1.43 (s, 9H), 1.39-1.33 (m, 1H) |

-continued

| Ex, No. | Structure | Mass Spec | $^1$H NMR Data |
|---|---|---|---|
| B1b | 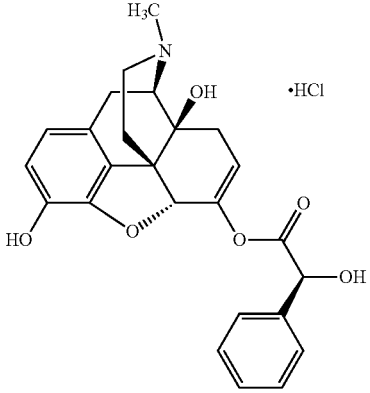 [SMILES: CN1CCC[C@]23c4c5ccc(O)c4O[C@H]2C(OC(=O)[C@@H](O)c2ccccc2)=CC[C@@]3(O)[C@H]1C5 ; Cl] ·HCl | 436 | $^1$H NMR (300 MHz, DMSO-$d_6$) δ 9.30 (s, 1H), 9.12 (br s, 1H), 7.50-7.47 (m, 2H), 7.42-7.31 (m, 3H), 6.68 (d, J = 8.1 Hz, 1H), 6.62 (d, J = 8.1 Hz, 1H), 6.26 (d, J = 5.7 Hz, 1H), 6.24 (s, 1H), 5.48-5.45 (m, 1H), 5.27 (d, J = 5.4 Hz, 1H), 4.87 (s, 1H), 3.61-3.60 (m, 1H), 3.40-3.34 (m, 1H), 3.07-3.01 (m, 2H), 2.82 (d, J = 4.5 Hz, 3H), 2.64-2.57 (m, 1H), 2.43-2.38 (m, 1H), 2.28-2.18 (m, 1H), 2.09-2.03 (m, 1H), 1.62-1.58 (m, 1H) |
| B2a | 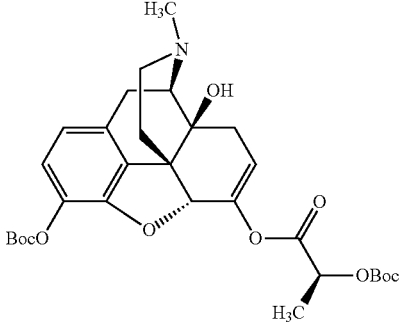 | 574 | $^1$H NMR (300 MHz, DMSO-$d_6$) δ 6.88 (d, J = 8.4 Hz, 1H), 6.72 (d, J = 8.4 Hz, 1H), 5.58 (dd, J = 5.7, 2.4 Hz, 1H), 4.99-4.92 (m, 2H), 4.78 (s, 1H), 3.15 (d, J = 18.9 Hz, 1H), 2.87-2.86 (m, 1H), 2.73-2.62 (m, 1H), 2.49-2.41 (m, 1H), 2.32 (s, 3H), 2.29-2.23 (m, 1H), 2.12-1.95 (m, 2H), 1.47-1.22 (m, 23H) |
| B2b | 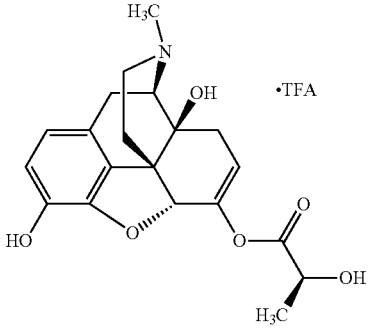 [SMILES: C[C@H](O)C(=O)OC1=CC[C@@]2(O)[C@H]3Cc4ccc(O)c5c4[C@@]2(CCCN3C)[C@H]1O5] ·TFA | 374 | $^1$H NMR (300 MHz, DMSO-$d_6$) δ 9.29 (s, 1H), 9.19 (br s, 1H), 6.67 (d, J = 8.1 Hz, 1H), 6.61 (d, J = 8.1 Hz, 1H), 6.21 (br s, 1H), 5.60-5.53 (m, 2H), 4.94 (s, 1H), 4.30-4.25 (m, 1H), 3.57 (br s, 1H), 3.04-2.99 (m, 2H), 2.79 (s, 3H), 2.65-2.35 (m, 2H), 2.29-2.22 (m, 1H), 2.09-2.02 (m, 1H), 1.62-1.57 (m, 1H), 1.36 (d, J = 6.9 Hz, 3H), one proton obscured by solvent peaks |
| B3 | 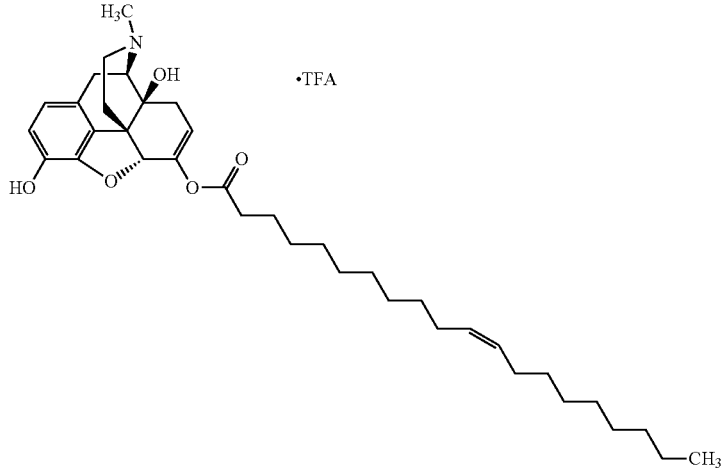 ·TFA | 566 | $^1$H NMR (300 MHz, DMSO-$d_6$) δ 9.29 (s, 1H), 9.15 (br s, 1H), 6.67 (d, J = 8.1 Hz, 1H), 6.62 (d, J = 8.1 Hz, 1H), 6 22 (s, 1H), 5.51-5.49 (m, 1H), 5.34-5.31 (m, 2H), 4.95 (s, 1H), 3.62- 3.60 (m, 1H), 3.37 (d, J = 19.8 Hz, 1H), 3.11-3.02 (m, 2H), 2.84 (d, J = 4.8 Hz, 3H), 2.78-2.56 (m, 1H), 2.45-2.40 (m, 3H), 3.37 (dd, J = 18.0, 6.0 Hz, 1H), 2.08-1.98 (m, 5H), 1.63- 1.52 (m, 3H), 1.28-1.24 (br m, 20H), 0.85 (t, J = 6.3 Hz, 3H) |

| Ex, No. | Structure | Mass Spec | ¹H NMR Data |
|---|---|---|---|
| B4 | ·TFA, (CH₂)₁₆CH₃ | 568 | ¹H NMR (300 MHz, DMSO-d₆) δ 9.28 (s, 1H), 9.14 (br s, 1H), 6.67 (d, J = 8.1 Hz, 1H), 6.61 (d, J = 8.1 Hz, 1H), 6.21 (s, 1H), 5.52-5.49 (m, 1H), 4.95 (s, 1H), 3.62-3.60 (m, 1H), 3.41-3.33 (m, 1H), 3.11-3.02 (m, 2H), 2.84 (d, J = 4.8 Hz, 3H), 2.73-2.63 (m, 1H), 2.45-2.40 (m, 3H), 2.30-2.22 (m, 1H), 2.08-2.03 (m, 1H), 1.63-1.54 (m, 3H), 1.33-1.24 (br m, 28H), 0.85 (t, J = 6.3 Hz, 3H) |
| B5 | ·1.6TFA | 418 | ¹H NMR (300 MHz, DMSO-d₆) δ 12.7 (br s, 1H), 9.32 (s, 1H), 9.16 (s, 1H), 6.67 (d, J = 8.1 Hz, 1H), 6.62 (d, J = 8.1 Hz, 1H), 6.24 (s, 1H), 5.52 (dd, J = 5.9, 1.9 Hz, 1H), 4.95 (s, 1H), 4.35 (dd, J = 7.4, 5.0 Hz, 1H), 3.61 (d, J = 8.4 Hz, 1H), 3.13-3.00 (m, 2H), 2.90-2.80 (m, 4H), 2.74-2.59 (m, 2H), 2.50-2.40 (m, 1H), 2.27 (dd, J = 17.9, 6.1 Hz, 1H), 2.05 (d, J = 17.9 Hz, 1H), 1.62 (d, J = 10.9 Hz, 1H), one proton obscured by solvent peaks |
| B6 | ·TFA | 445 | ¹H NMR (300 MHz, DMSO-d₆) δ 9.28 (s, 1H), 9.16 (br s, 1H), 8.10 (d, J = 7.1 Hz, 1H), 6.68 (d, J = 8.1 Hz, 1H), 6.62 (d, J = 8.1 Hz, 1H), 6.24 (s, 1H), 5.57-5.49 (m, 2H), 4.96 (s, 1H), 4.41-4.31 (m, 1H), 4.06-4.97 (m, 1H), 3.61 (d, J = 6.1 Hz, 1H), 3.36 (d, partially obscured by solvent peak, 1H), 3.11-3.01 (m, 2H), 2.84 (apparent d, J = 3.9 Hz, 3H), 2.69-2.60 (m, 1H), 2.43 (dd, J = 13.1, 5.0 Hz, 1H), 2.27 (dd, J = 18.0, 6.0 Hz, 1H), 2.05 (d, J = 18.0 Hz, 1H), 1.62 (d, J = 10.7 Hz, 1H), 1.41 (d, J = 7.2 Hz, 3H), 1.22 (d, J = 6.8 Hz, 3H) |
| B7 | 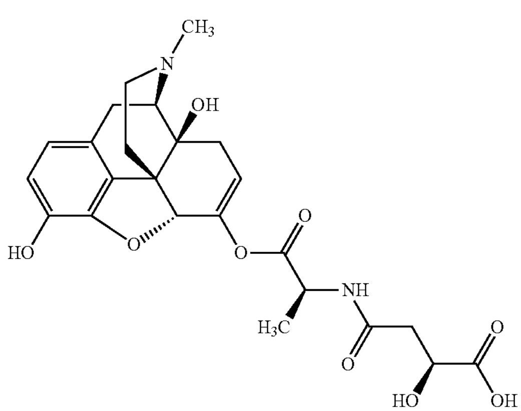 [SMILES: C[C@H](NC(=O)C[C@H](O)C(=O)O)C(=O)OC1=CC[C@@]2(O)[C@H]3Cc4ccc(O)c5c4[C@@]2(CCCN3C)[C@H]1O5] | 489 | ¹H NMR (300 MHz, DMSO-d₆) δ 8.54 (d, J = 6.8 Hz, 1H), 6.58 (d, J = 8.1 Hz, 1H), 6.53 (d, J = 8.1 Hz, 1H), 5.51 (dd, J = 5.6, 2.5 Hz, 1H), 4.83 (s, 1H), 4.37-4.27 (m, 1H), 4.22 (dd, J = 8.4, 4.3 Hz, 1H), 3.10 (d, J = 18.9 Hz, 1H), 2.93 (d, J = 5.6 Hz, 1H), 2.64 (dd, J = 18.9, 5.9 Hz, 1H), 2.48-2.40 (m, 2H), 2.39 (s, 3H), 2.34-1.93 (m, 5H), 1.45-1.33 (m, 4H), CO₂H and three OH protons not observed |

| Ex, No. | Structure | Mass Spec | 1H NMR Data |
|---|---|---|---|
| B8 | 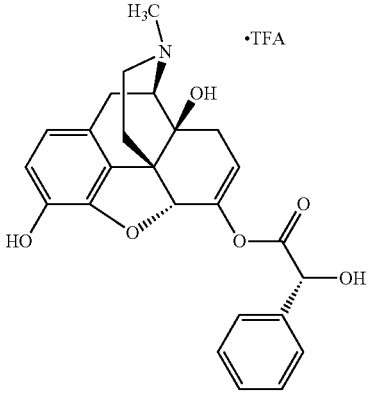 [SMILES: CN1CCC[C@]23c4c5ccc(O)c4O[C@H]2C(OC(=O)[C@H](O)c2ccccc2)=CC[C@@]3(O)[C@H]1C5] | 436 | $^1$H NMR (300 MHz, DMSO-d$_6$) δ 9.34 (s, 1H), 9.14 (br s, 1H), 7.50-7.41 9 m, 2H), 7.40-7.30 9 m, 3H), 6.68 (d, J = 8.1 Hz, 1H), 6.61 (d, J = 8.1 Hz, 1H), 6.25 (d, J = 5.4 Hz 1H), 6.21 (s, 1H), 5.32 (dd, J = 23.7, 3.9 Hz, 1H), 4.97 (s, 1H), 3.60 (d, J = 6.0 Hz, 1H), 3.09-3.00 (m, 2H), 2.83 (d, J = 4.2 Hz, 3H), 2.72-2.52 (m, 1H), 2.22 (dd, J = 18.3, 6.3 Hz, 1H), 2.01 (d, J = 17.7 Hz, 1H), 1.62 (d, J = 11.1 Hz, 1H) |
| B9 | 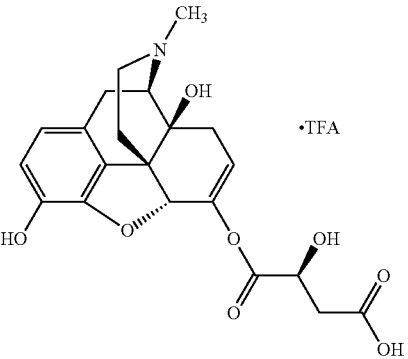 [SMILES: CN1CCC[C@]23c4c5ccc(O)c4O[C@H]2C(OC(=O)[C@@H](O)CC(=O)O)=CC[C@@]3(O)[C@H]1C5] | 418 | $^1$H NMR (300 MHz, DMSO-d$_6$) δ 12.43 (br s, 1H), 9.30 (s, 1H), 9.16 (br s, 1H), 6.69-6.64 (m, 2H), 6.25 (s, 1H), 5.90 (s, 1H), 5.55 (s, 1H), 4.93 (s, 1H), 4.49 (s, 1H), 3.62 (s, 1H), 3.18-3.00 (m, 2H), 2.83 (s, 3H), 2.80-2.58 (m, 3H), 2.29-2.26 (m, 1H), 2.07 (d, J = 18.0 Hz, 1H), 1.62 (d, J = 13.2 Hz, 1H), two protons obscured by solvent peaks |
| B10 | 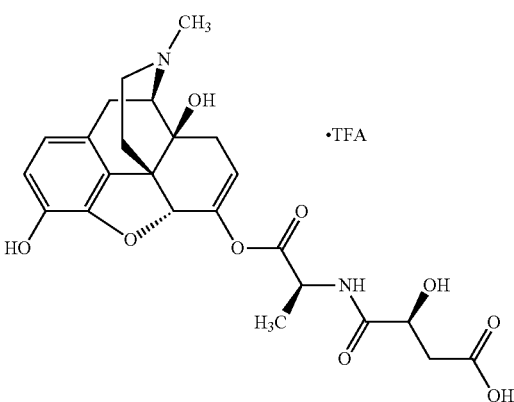 [SMILES: C[C@H](NC(=O)[C@@H](O)CC(=O)O)C(=O)OC1=CC[C@@]2(O)[C@H]3Cc4ccc(O)c5c4[C@@]2(CCCN3C)[C@H]1O5] | 489 | 1H NMR (300 MHz, DMSO-d$_6$) δ 8.21 (d, J = 7.3 Hz, 1H), 6.57 (d, J = 8.1 Hz, 1H), 6.52 (d, J = 8.1 Hz, 1H), 5.51 (dd, J = 4.4, 2.8 Hz, 1H), 4.83 (s, 1H), 4.43-4.32 (m, 1H), 4.27 (dd, J = 8.8, 3.7 Hz, 1H), 3.08 (d, J = 18.6 Hz, 1H), 2.85 (d, J = 5.8 Hz, 1H), 2.65-2.54 (m, 2H), 2.48-2.38 (m, 1H), 2.34 (s, 3H), 2.30-2.17 (m, 2H), 2.10 (d, J = 8.7 Hz, 1H), 2.07-1.98 (m, 2H), 1.43-1.34 (m, 4H), CO$_2$H, CF$_3$CO$_2$H, and three OH protons not observed |

| Ex. No. | Structure | Mass Spec | ¹H NMR Data |
|---|---|---|---|
| B11 | 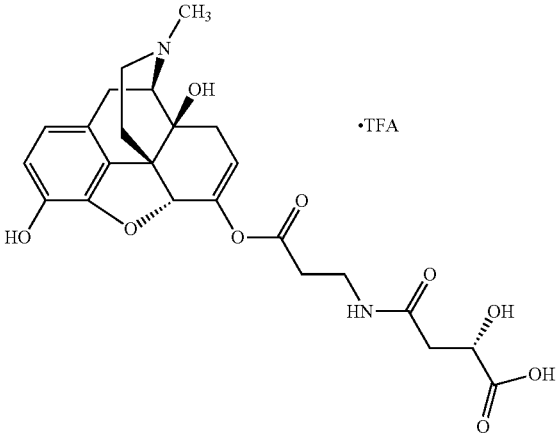 [SMILES: CN1CCC[C@]23c4c5ccc(O)c4O[C@H]2C(OC(=O)CCNC(=O)C[C@H](O)C(=O)O)=CC[C@@]3(O)[C@H]1C5] •TFA | 489 | ¹H NMR (300 MHz, DMSO-d$_6$) δ 8.08 (t, J = 5.6 Hz, 1H), 6.58 (d, J = 8.1 Hz, 1H), 6.53 (d, J = 8.1 Hz, 1H), 5.53 (dd, J = 5.5, 2.6 Hz, 1H), 4.85 (s, 1H), 4.22 (dd, J = 8.1, 4.5 Hz, 1H), 3.41-3.24 (m, 2H), 3.12 (d, J = 18.8 Hz, 1H), 2.95 (d, J = 6.0 Hz, 1H), 2.70-2.51 (m, 4H), 2.49-4.22 (m, 1H), 2.40 (s, 3H), 2.35-1.95 (m, 5H), 1.41 (d, J = 12.2 Hz, 1H), CO$_2$H and three OH protons not observed |
| B12 | 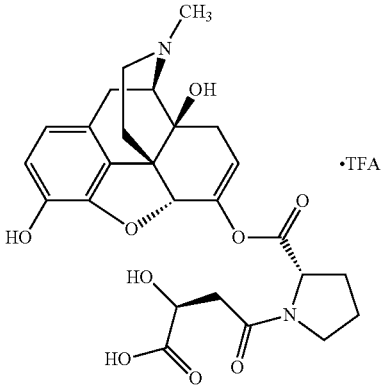 [SMILES: CN1CCC[C@]23c4c5ccc(O)c4O[C@H]2C(OC(=O)[C@@H]2CCCN2C(=O)C[C@H](O)C(=O)O)=CC[C@@]3(O)[C@H]1C5] •TFA | 515 | ¹H NMR (300 MHz, DMSO-d$_6$) δ 6.58 (d, J = 8.1 Hz, 1H), 6.53 (d, J = 8.1 Hz, 1H), 5.51 (dd, J = 5.5, 2.5 Hz, 1H), 4.86-4.83 (m, 1H), 4.39 (dd, J = 8.7, 3.5 Hz, 1H), 4.29-4.24 (m, 1H), 3.65-3.54 (m, 2H), 3.10 (d, J = 18.8 Hz, 1H), 2.93 (d, J = 5.9 Hz, 1H), 2.69-2.60 (m, 3H), 2.39 (s, 3H), 2.30-2.20 (m, 2H), 2.15 (d, J = 13.4 Hz, 1H), 2.10-1.92 (m, 5H), 1.40 (d, J = 11.1 Hz, 1H), five protons not observed |
| B13 | 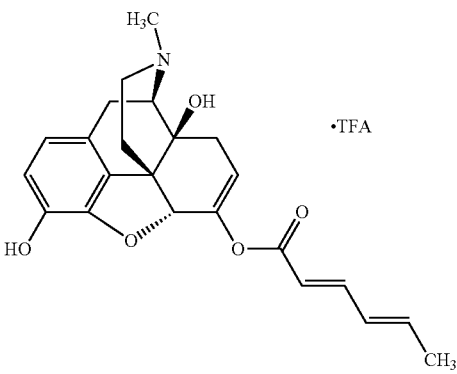 [SMILES: C/C=C/C=C/C(=O)OC1=CC[C@@]2(O)[C@H]3Cc4ccc(O)c5c4[C@@]2(CCCN3C)[C@H]1O5] •TFA | 396 | ¹H NMR (300 MHz, DMSO-d$_6$) δ 9.32 (s, 1H), 9.15 (br s, 1H), 7.37-7.28 (m, 1H), 6.67 (d, J = 8.1 Hz, 1H), 6.62 (d, J = 8.1 Hz, 1H), 6.38-6.35 (m, 2H), 6.24 (s, 1H), 5.98 (d, J = 15.0 Hz, 1H), 5.59-5.57 (m, 1H), 5.03 (s, 1H), 3.63-3.61 (m, 1H), 3.41-3.33 (m, 1H), 3.09-3.05 (m, 2H), 2.84 (d, J = 4.5 Hz, 3H), 2.67-2.60 (m, 1H), 2.49-2.41 (m, 1H), 2.31-2.23 (m, 1H), 2.11-2.05 (m, 1H), 1.85 (d, J = 4.5 Hz, 3H), 1.65-1.60 (m, 1H) |
| B14 | 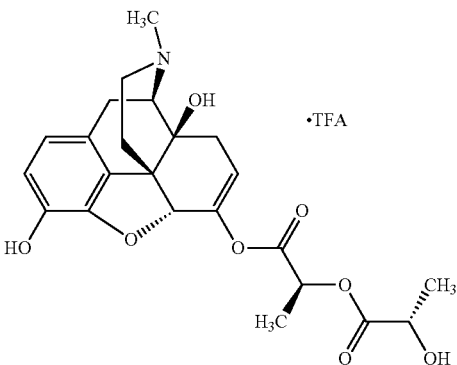 [SMILES: C[C@H](O)C(=O)O[C@@H](C)C(=O)OC1=CC[C@@]2(O)[C@H]3Cc4ccc(O)c5c4[C@@]2(CCCN3C)[C@H]1O5] •TFA | 446 | ¹H NMR (300 MHz, DMSO-d$_6$) 9.29 (s, 1H), 9.15 (br s, 1H), 6.68 (d, J = 8.4 Hz, 1H), 6.62 (d, J = 8.1 Hz, 1H), 6.25 (br s, 1H), 5.59-5.55 (m, 1H), 5.50 (d, J = 5.7 Hz, 1H), 5.15 (q, J = 6.9 Hz, 1H), 4.96 (s, 1H), 4.29-4.20 (m, 1H), 3.62 (br s, 1H), 3.41-3.33 (m, 1H), 3.10-3.03 (m, 2H), 2.83 (s, 3H), 2.68-2.56 (m, 1H), 2.46-2.41 (m, 1H), 2.33-2.25 (m, 1H), 2.09-2.03 (m, 1H), 1.64-1.60 (m, 1H), 1.53 (d, J = 6.9 Hz, 3H), 1.32 (d, J = 6.6 Hz, 3H) |

-continued

| Ex, No. | Structure | Mass Spec | $^1$H NMR Data |
|---|---|---|---|
| B15 | 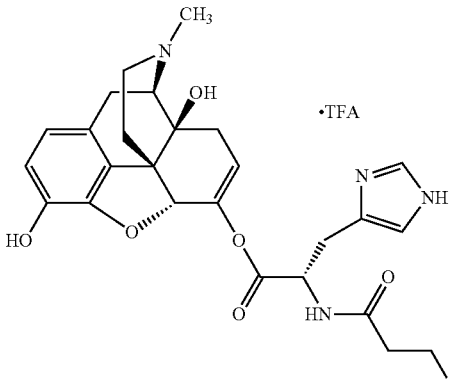 | 510 | $^1$H NMR (300 MHz, DMSO-d$_6$) δ 9.40 (br s, 1H), 9.18 (br s, 1H), 8.94 (br s, 1H), 8.82 (d, J = 7.2 Hz, 1H), 7.73 (br s, 3H), 7.47 (s, 1H), 6.70 (d, J = 8.1 Hz, 1H), 6.63 (d, J = 8.1 Hz, 1H), 6.27 (s, 1H), 5.53-5.51 (m, 1H), 4.91 (s, 1H), 4.69 (q, J = 7.2 Hz, 1H), 3.63 (d, J = 4.8 Hz, 1H), 3.39 (d, J = 19.8 Hz, 1H), 3.28-2.93 (m, 7H), 2.85 (s, 3H), 2.74-2.55 (m, 1H), 2.29 (dd, J = 17.7, 6.0 Hz, 1H), 2.04 (d, J = 18.0 Hz, 1H), three protons not observed |
| B16 | 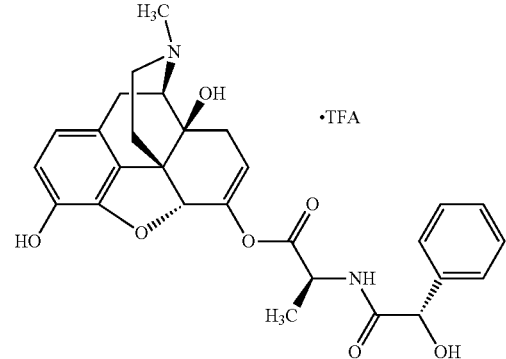 [SMILES: C[C@H](NC(=O)[C@@H](O)c1ccccc1)C(=O)OC1=CC[C@@]2(O)[C@H]3Cc4ccc(O)c5c4[C@@]2(CCCN3C)[C@H]1O5] | 507 | $^1$H NMR (300 MHz, DMSO-d$_6$) δ 9.29 (s, 1H), 9.17 (br s, 1H), 8.43 (d, J = 7.2 Hz, 1H), 7.47-7.10 (m, 5H), 6.65 (q, J = 8.1 Hz, 2H), 6.27-6.23 (m, 2H), 5.48 (dd, J = 6.0, 2.1 Hz, 1H), 4.95 (d, J = 4.5 Hz, 1H), 4.91 (s, 1H), 4.36 (m, 1H), 3.59 (m, 1H), 3.09-3.00 (m, 2H), 2.82 (s, 3H), 2.72-2.38 (m, 3H), 2.28-2.20 (m, 1H), 2.06-2.00 (m, 1H), 1.63-1.60 (m, 1H), 1.41 (d, J = 7.2 Hz, 3H) |
| B17 | 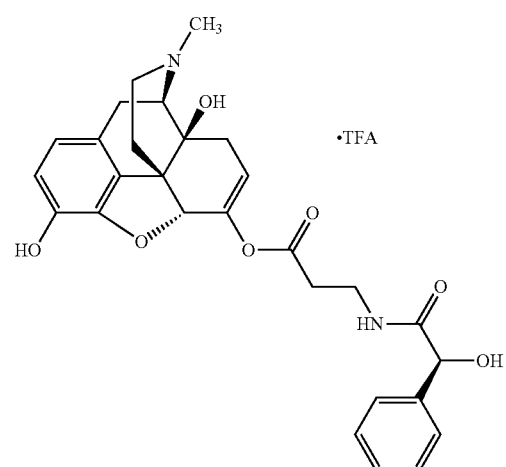 | 507 | $^1$H NMR (300 MHz, DMSO-d$_6$) δ 9.31 (s, 1H), 9.15 (s, 1H), 8.15 (t, J = 5.8 Hz, 1H), 7.41-7.37 (m, 2H), 7.33-7.23 (m, 3H), 6.65 (q, J = 7.9 Hz, 2H), 6.22-6.20 (m, 2H), 5.46 (dd, J = 5.8, 1.9 Hz, 1H), 4.94 (s, 1H), 4.90 (d, J = 4.5 Hz, 1H), 3.60 (s, 1H), 3.40-3.32 (m, 2H), 3.13-3.00 (m, 2H), 2.83 (s, 3H), 2.62 (t, J = 7.0 Hz, 3H), 2.50-2.38 (m, 1H), 2.28-2.19 (m, 1H), 2.03 (d, J = 18.0 Hz, 1H), 1.61 (d, J = 12.3 Hz, 1H) |

-continued

| Ex. No. | Structure | Mass Spec | ¹H NMR Data |
|---|---|---|---|
| B18 | (structure) ·2TFA | 459 | ¹H NMR (300 MHz, DMSO-d₆) δ 9.32 (s, 1H), 9.16 (s, 1H), 7.78 (s, 3H), 6.66 (q, J = 10.5 Hz, 2H), 6.23 (s, 1H), 5.59 (dd, J = 6.0, 4.2 Hz, 1H), 5.17 (q, J = 6.9 Hz, 1H), 3.62 (m, 1H), 3.08 (m, 4H), 2.63-2.84 (m, 6H), 2.45-2.49 (m, 4H), 2.05 (d, J = 18.3 Hz, 1H), 1.61 (d, J = 12.3 Hz, 1H), 1.54 (d, J = 6.9 Hz, 3H) |
| B19 | (structure) ·2TFA | 487 | ¹H NMR (300 MHz, DMSO-d₆) δ 9.31 (s, 1H), 9.13 (br s, 1H), 8.32 (br s, 3H), 6.06 (apparent q, J = 9.6 Hz, 2H), 6.21 (s, 1H), 5.60 (dd, J = 6.0, 2.1 Hz, 1H), 5.34 (q, J = 7.2 Hz, 1H), 4.96 (s, 1H), 4.11 (t, J = 6.6 Hz, 1H), 3.71-3.53 (m, 1H, partially obscured by water peak), 3.07-3.04 (m, 2H), 2.83 (s, 3H), 2.63-2.41 (m, 3H), 2.33-2.25 (m, 1H), 2.06 (d, J = 18.0 Hz, 1H), 1.91-1.57 (m, 4H), 1.58 (d, J = 7.2 Hz, 3H), 0.93 (t, J = 6.3 Hz, 6H) |
| B20 | (structure) ·TFA | 445 | ¹H NMR (300 MHz, DMSO-d₆) δ 9.30 (s, 1H), 9.15 (s, 1H), 7.84 (t, J = 5.9 Hz, 1H), 6.67 (d, J = 8.1 Hz, 1H), 6.62 (d, J = 8.1 Hz, 1H), 6.23 (s, 1H), 5.56-5.51 (m, 2H), 4.96 (s, 1H), 4.00-3.91 (m, 1H), 3.61 (d, J = 5.4 Hz, 1H), 3.42-3.31 (m, 3H), 3.12-3.00 (m, 2H), 2.83 (s, 3H), 2.62 (t, J = 6.9 Hz, 3H), 2.50-2.39 (m, 1H), 2.26 (dd, J = 17.7, 6.0 Hz, 1H), 2.06 (d, J = 17.7 Hz, 1H), 1.62 (d, J = 11.6 Hz, 1H), 1.20 (d, J 6.8 Hz, 3H) |
| B21 | (structure) ·2TFA | 507 | ¹H NMR (300 MHz, DMSO-d₆) δ 9.31 (s, 1H), 9.13 (s, 1H), 7.79 (s, 3H), 7.59-7.56 (m, 2H), 7.49-7.47 (m, 3H), 6.64 (q, J = 11.4 Hz, 2H), 6.23 (s, 1H), 6.15 (s, 1H), 5.59 (dd, J = 6.0, 2.1 Hz, 1H), 4.87 (s, 1H), 3.61 (m, 1H), 3.10 (m, 4H), 2.85-2.83 (m, 5H), 2.65-2.43 (m, 3H), 2.29-2.21 (m, 1H), 2.06 (d, J = 18.3 Hz, 1H), 1.62-1.58 (m, 1H) |

| Ex, No. | Structure | Mass Spec | ¹H NMR Data |
|---|---|---|---|
| B22 | 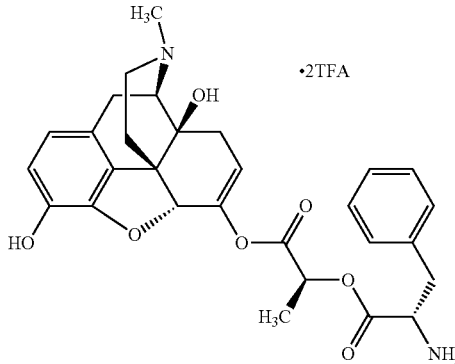 •2TFA | 521 | ¹H NMR (300 MHz, DMSO-d6) δ 9.31 (s, 1H), 9.15 (s, 1H), 8.35 (s, 3H), 7.35-7.27 (m, 5H), 6.66 (apparent q, J = 9.6 Hz, 2H), 6.24 (s, 1H), 5.59 (dd, J = 6.0, 2.1 Hz, 1H), 5.30 (q, J = 7.2 Hz, 1H), 4.97 (s, 1H), 4.44 (t, J = 6.6 Hz, 1H), 3.62 (m, 1H), 3.25-3.05 (m, 5H), 2.84 (s, 3H), 2.64 (m, 1H), 2.29-2.26 (m, 1H), 2.07 (d, J = 18.3 Hz, 1H), 1.64-1.61 (m, 1H), 1.51 (d, J = 6.9 Hz, 3H), one proton obscured by solvent peaks |
| B23 | 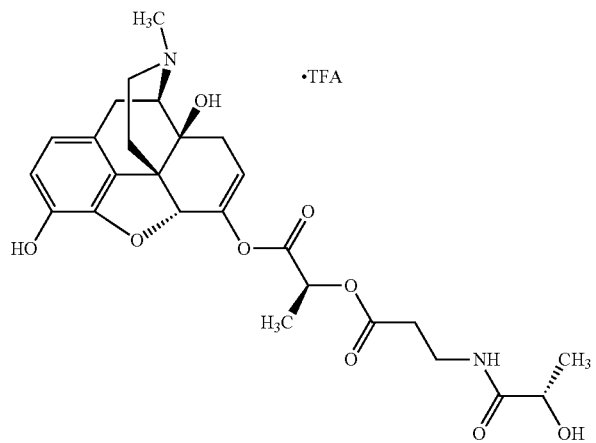 [SMILES: C[C@H](O)C(=O)NCCC(=O)O[C@@H](C)C(=O)OC1=CC[C@@]2(O)[C@H]3Cc4ccc(O)c5c4[C@@]2(CCCN3C)[C@H]1O5] •TFA | 517 | ¹H NMR (300 MHz, DMSO-d₆) δ 9.28 (s, 1H), 9.15 (s, 1H), 7.79 (t, J = 6.0 Hz, 1H), 6.65 (apparent q, J = 8.4 Hz, 1H), 6.25 (s, 1H), 5.58 (dd, J = 6.0, 2.1 Hz, 1H), 5.11 (q, J = 7.2 Hz, 1H), 4.96 (s, 1H), 3.94 (m, 1H), 3.62 (m, 1H), 3.38 (m, 4H), 3.05 (m, 2H), 2.83 (s, 3H), 2.64 (m, 1H), 2.57 (t, J = 6.9 Hz, 2H), 2.42 (m, 2H), 2.29 (m, 1H), 2.06 (d, J = 18.0 Hz, 1H), 1.63 (d, J = 11.4 Hz, 1H), 1.52 (d, J = 9.6 Hz, 3H), 1.19 (d, J = 9.6 Hz, 3H) |
| B24 | 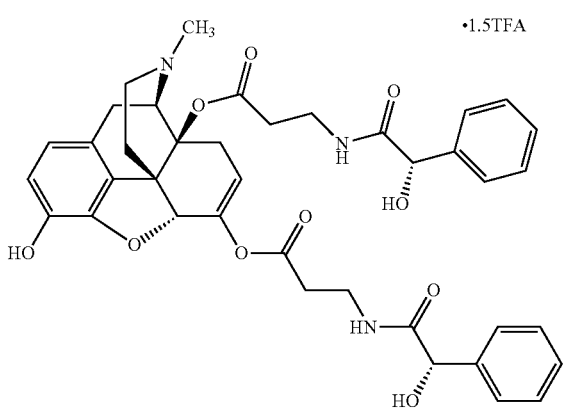 [SMILES: CN1CCC[C@]23c4c5ccc(O)c4O[C@H]2C(OC(=O)CCNC(=O)[C@@H](O)c2ccccc2)=CC[C@@]3(OC(=O)CCNC(=O)[C@@H](O)c2ccccc2)[C@H]1C5] •1.5TFA | 712 | ¹H NMR (300 MHz, DMSO-d₆) δ 9.46 (broad s, 1.5H), 8.24-8.15 (m, 2H), 7.41-7.20 (m, 10H), 6.72 (d, J = 8.2 Hz, 1H), 6.66 (d, J = 8.2 Hz, 1H), 5.36 (dd, J = 6.3, 1.8 Hz, 1H), 5.03 (s, 1H), 4.92-4.90 (m, 2H), 4.68 (d, J = 6.3 Hz, 1H), 3.46-3.10 (m, 8H), 3 00-2.71 (m, 5H), 2.69-2.51 (m, 4H), 2.43-2.35 (m, 1H), 2.05 (d, J = 18.6 Hz, 1H), 1.76 (d, J = 12.6 Hz, 1H |

| Ex, No. | Structure | Mass Spec | ¹H NMR Data |
|---|---|---|---|
| B25 | (structure shown) ·2TFA | 489 | ¹H NMR (300 MHz, DMSO-$d_6$) δ 8.33 (br s, 3H), 6.63 (apparent q, J = 8.1 Hz, 2H), 5.58 (dd, J = 6.0, 2.1 Hz, 1H), 5.01 (q, J = 6.9 Hz, 1H), 4.88 (s, 1H), 3.71 (m, 1H), 3.55 (m, 1H), 3.04-2.97 (m, 4H), 2.79-2.72 (m, 4H), 2.63-2.40 (m, 2H), 2.28-2.22 (m, 1H), 2.04 (d, J = 18.3 Hz, 1H), 1.60 (d, J = 12.6 Hz, 1H), 1.52 (d, J = 6.9 Hz, 3H), $CO_2H$ and two OH protons not observed |
| B26 | (structure shown) ·1.6TFA | 588 | ¹H NMR (300 MHz, DMSO-$d_6$) δ 9.70-9.40 (m, 1.6H), 7.92-7.84 (m, 2H), 6.73 (d, J = 8.2 Hz, 1H), 6.67 (d, J = 8.2 Hz, 1H), 5.50 (dd, J = 6.3, 1.6 Hz, 1H), 5.06 (s, 1H), 4.73 (d, J = 5.7 Hz, 1H), 4.01-3.91 (m, 2H), 3.45-3.13 (m, 10H), 3.17-2.89 (m, 4H), 2.87-2.70 (m, 1H), 2.69-2.52 (m, 4H), 2.47-2.36 (m, 1H), 2.09 (d, J = 18.6 Hz, 1H), 1.78 (d, J = 12.7 Hz, 1H), 1.21 (d, J = 2.7 Hz, 3H), 1.19 (d, J = 2.7 Hz, 3H) |
| B27 | (structure shown) ·TFA | 559 | ¹H NMR (300 MHz, DMSO-$d_6$) δ 9.30 (s, 1H), 9.14 (br s,1H), 7.89 (d, J = 8.1 Hz, 1H), 6.66 (apparent q, J = 8.1 Hz, 1H), 6.23 (s, 1H), 5.58 (dd, J = 6.0, 2.1 Hz, 1H), 5.53 (br s, 1H), 5.15 (q, J = 6.9 Hz, 1H), 4.96 (s, 1H), 4.40 (m, 1H), 4.01 (m, 1H), 3.62 (m, 1H), 3.11-3.03 (m, 2H), 2.84 (d, J = 4.5 Hz, 3H), 2.65 (m, 1H), 2.43 (m, 2H), 2.27 (m, 1H), 2.06 (d, J = 17.7 Hz, 1H), 1.75-1.61 (m, 4H), 1.53 (d, J = 6.9 Hz, 3H), 1.21 (d, J = 6.9 Hz, 3H), 0.91 (d, J = 6.0 Hz, 3H), 0.86 (d, J = 5.7 Hz, 3H), one proton obscured by solvent peaks |

| Ex, No. | Structure | Mass Spec | $^1$H NMR Data |
|---|---|---|---|
| B28 | 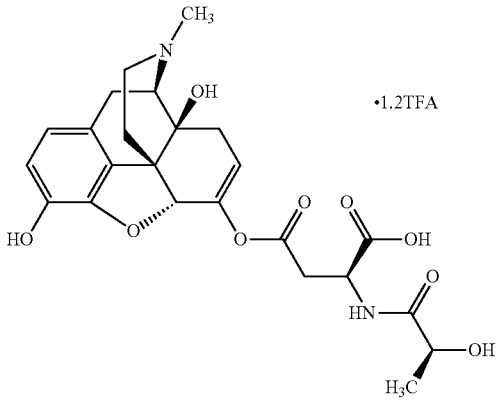 [SMILES: C[C@H](O)C(=O)N[C@@H](CC(=O)OC1=CC[C@@]2(O)[C@H]3Cc4ccc(O)c5c4[C@@]2(CCCN3C)[C@H]1O5)C(=O)O] | 489 | $^1$H NMR (300 MHz, DMSO-d$_6$) δ 12.99 (br s, 1H), 9.29 (s, 1H), 9.16 (s, 1H), 8.05 (d, J = 8.4 Hz, 1H), 6.67 (d, J = 8.2 Hz, 1H), 6.63 (d, J = 8.2 Hz, 1H), 6 23 (s, 1H), 5.69 (br s, 1H), 5.52-5.49 (m, 1H), 4.94 (s, 1H), 4.72-4.64 (m, 1H), 4.02 (q, J = 6.8 Hz, 1H), 3.61 (d, J = 6.1 Hz, 1H), 3.13-3.00 (m, 3H), 3.00-2.87 (m, 2H), 2.87-2.78 (m, 3H), 2.78-2.55 (m, 1H), 2.48-2.38 (m, 1H), 2.27 (dd, J = 17.8, 6.1 Hz, 1H), 2.05 (d, J = 17.8 Hz, 1H), 1.62 (d, J = 12.0 Hz, 1H), 1.22 (d, J = 6.8 Hz, 1H), two protons obscured by solvent peaks |
| B29 | 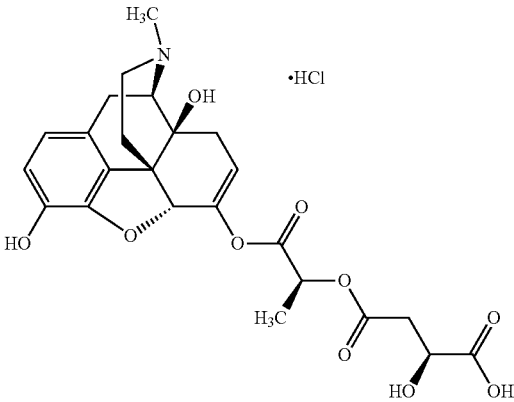 [SMILES: C[C@H](OC(=O)C[C@H](O)C(=O)O)C(=O)OC1=CC[C@@]2(O)[C@H]3Cc4ccc(O)c5c4[C@@]2(CCCN3C)[C@H]1O5 ; Cl] | 490 | $^1$H NMR (300 MHz, DMSO-d$_6$) δ 6.57 (apparent q, J = 7.8 Hz, 2H), 5.56 (dd, J = 5.7, 2.4 Hz, 1H), 5.10 (q, J = 6.9 Hz, 1H), 4.84 (s, 1H), 4.24 (dd, J = 8.1, 4.2 Hz, 1H), 3.14 (d, J = 18.9 Hz, 1H), 3.01 (m, 1H), 2.79 (dd, J = 15.6, 4.2 Hz, 1H), 2.75-2.54 (m, 3H), 2.44 (s, 3H), 2.33-2.13 (m, 2H), 2.09-1.96 (m, 2H), 1.50 (d, J = 6.9 Hz, 3H), 1.42 (m, 1H), CO$_2$H, HCl, and OH protons not observed |
| B30 | 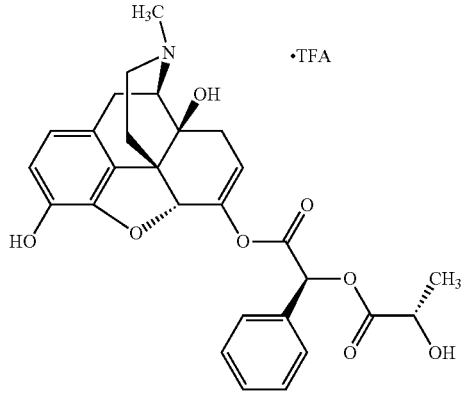 [SMILES: C[C@H](O)C(=O)O[C@H](C(=O)OC1=CC[C@@]2(O)[C@H]3Cc4ccc(O)c5c4[C@@]2(CCCN3C)[C@H]1O5)c1ccccc1 ; "·TFA"] | 508 | $^1$H NMR (300 MHz, DMSO-d$_6$) δ 9.26 (s, 1H), 9.13 (s, 1H), 7.60-7.56 (m, 2H), 7.49-7.46 (m, 3H), 6.64 (apparent q, J = 8.1 Hz, 2H), 6.24 (s, 1H), 6.14 (s, 1H), 5.60-5.54 (m, 2H), 4.87 (s, 1H), 4.31 (m, 1H), 3.03 (m, 1H), 2.82 (m, 3H), 2.64-2.39 (m, 3H), 2.30-2.22 (m, 1H), 2.05 (d, J = 18.0 Hz, 1H), 1.59 (d, J = 11.4 Hz, 3H), 1.38 (d, J = 6.9 Hz, 3H) |

| Ex. No. | Structure | Mass Spec | ¹H NMR Data |
|---|---|---|---|
| B31 | 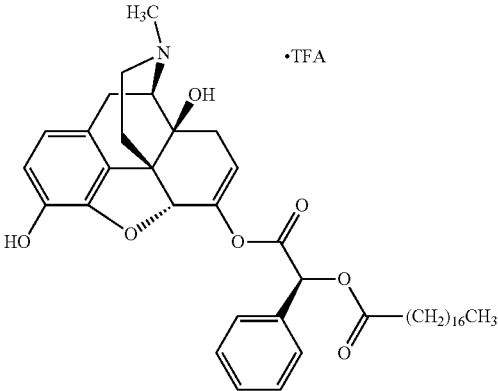 | 702 | ¹H NMR (300 MHz, DMSO-$d_6$) δ 9.25 (s, 1H), 9.13 (s, 1H), 7.58-7.55 (m, 2H), 7.47-7.44 (m, 3H), 6.63 (q, J = 8.1 Hz, 2H), 6.23 (s, 1H), 6.09 (s, 1H), 5.58 (dd, J = 8.3, 2.1 Hz, 1H), 4.86 (s, 1H), 3.06 (m, 1H), 2.82 (d, J = 4.8 Hz, 3H), 2.64-2.22 (m, 6H), 2.05 (m, 1H), 2.58 (m, 3H), 1.23 (m, 30H 0.85 (t, J = 6.9 Hz, 3H) |
| B32 | 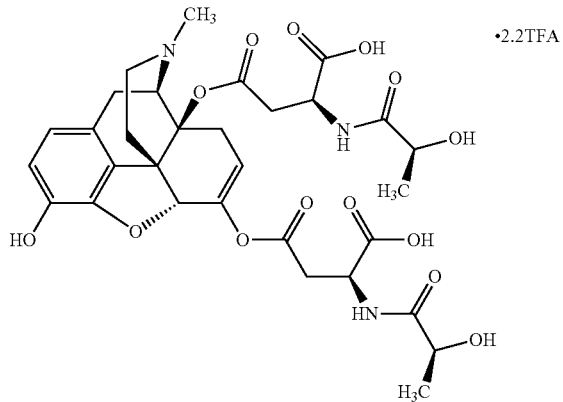 [SMILES: C[C@H](O)C(=O)N[C@@H](CC(=O)OC1=CC[C@@]2(OC(=O)C[C@H](NC(=O)[C@H](C)O)C(=O)O)[C@H]3Cc4ccc(O)c5c4[C@@]2(CCCN3C)[C@H]1O5)C(=O)O ; "·2.2TFA"] | 676 | ¹H NMR (300 MHz, DMSO-$d_6$) δ 12.97 (br s, 1H), 9.40 (br s, 2H), 8.10 (d, J = 8.4 Hz, 1H), 7.95 (d, J = 8.0 Hz, 1H), 6.72 (d, J = 8.2 Hz, 1H), 6.66 (d, J = 8.2 Hz, 1H), 5.42 (dd, J = 6.1, 1.7 Hz, 1H), 5.01 (s, 1H), 4.76-4.60 (m, 3H), 4.06-3.98 (m, 2H), 2.30-3.10 (m, 4H), 3.09-2.56 (m, 10H), 2.48-2.33 (m, 2H), 2.11 (d, J = 19.0 Hz, 1H), 1.78 (d, J = 12.8 Hz, 1H), 1.21 (d, J = 6.8 Hz, 6H) |
| B33 | 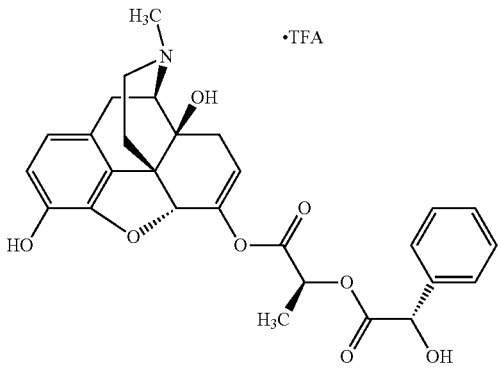 [SMILES: C[C@H](OC(=O)[C@@H](O)c1ccccc1)C(=O)OC1=CC[C@@]2(O)[C@H]3Cc4ccc(O)c5c4[C@@]2(CCCN3C)[C@H]1O5 ; "·TFA"] | 508 | ¹H NMR (300 MHz, DMSO-$d_6$) δ 9.29 (s, 1H), 9.14 (s, 1H), 7.46-7.43 (m, 2H), 7.38-7.27 (m, 3H), 6.64 (apparent q, J = 8.1 Hz, 2H), 6.21 (s, 1H), 6.16 (d, J = 5.7 Hz, 1H), 5.49 (dd, J = 5.7, 2.1 Hz, 1H), 5.24-5.15 (m, 2H), 4.82 (s, 1H), 3.06 (m, 1H), 2.83 (d, J = 4.2 Hz, 3H), 2.63-2.22 (m, 6H), 2.03 (d, J = 18.0 Hz, 1H), 1.60 (d, J = 10.2 Hz, 1H), 1.50 (d, J = 6.9 Hz, 3H) |
| B34 | 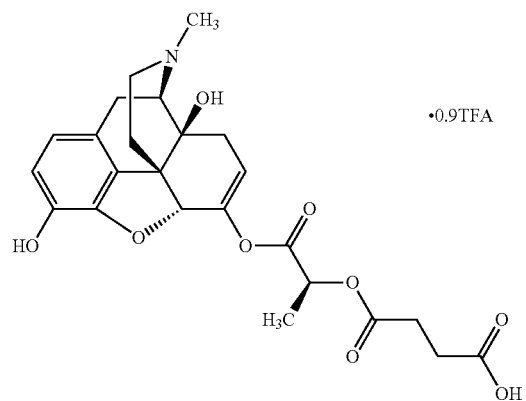 [SMILES: C[C@H](OC(=O)CCC(=O)O)C(=O)OC1=CC[C@@]2(O)[C@H]3Cc4ccc(O)c5c4[C@@]2(CCCN3C)[C@H]1O5 ; "·0.9TFA"] | 474 | ¹H NMR (300 MHz, DMSO-$d_6$) δ 9.26 (br s, 1H), 6.66 (d, J = 8.2 Hz, 1H), 6.60 (d, J = 8.2 Hz, 1H), 5.57 (dd, J = 5.8, 2.0 Hz, 1H), 5.11 (q, J = 7.0 Hz, 1H), 4.92 (s, 1H), 3.02-2.78 (m, 2H), 2.8-2.58 (m, 5H), 2.50-2.31 (m, 1H), 2.24 (dd, J = 17.8, 5.4 Hz, 1H), 2.04 (d, J = 19.9 Hz, 1H), 1.57 (d, J = 11.3 Hz, 1H), 1.51 (d, J = 7.0 Hz, 3H), CO$_2$H and OH protons not observed, five protons obscured by solvent peaks |

-continued

| Ex. No. | Structure | Mass Spec | ¹H NMR Data |
|---|---|---|---|
| B35 | 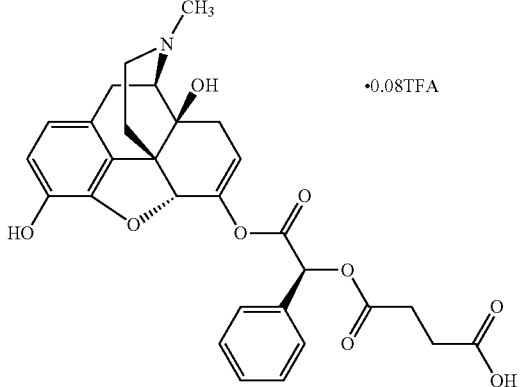 [SMILES: CN1CCC[C@]23c4c5ccc(O)c4O[C@H]2C(OC(=O)[C@@H](OC(=O)CCC(=O)O)c2ccccc2)=CC[C@@]3(O)[C@H]1C5 ; "·0.08TFA"] •0.08TFA | 536 | ¹H NMR (300 MHz, DMSO-d₆) δ 7.59-7.51 (m, 2H), 7.50-7.40 (m, 3H), 6.57 (d, J = 8.1 Hz, 1H), 6.51 (d, J = 8.1 Hz, 1H), 6.07 (s, 1H), 5.55 (dd, J = 5.5, 2.6 Hz, 1H), 4.70 (s, 1H), 3.20-3.03 (m, 2H), 3.84 (d, J = 6.0 Hz, 1H), 2.74-2.63 (m, 2H), 2.62-2.54 (m, 3H), 2.43 (dd, J = 10.9, 3.6 Hz, 1H), 2.32 (s, 3H), 2.19 (dd, J = 12.3, 4.5 Hz, 1H), 2.13-1.93 (m, 3H), 1.36 (d, J = 10.8 Hz, 1H), CO₂H and OH protons not observed |
| B36 | 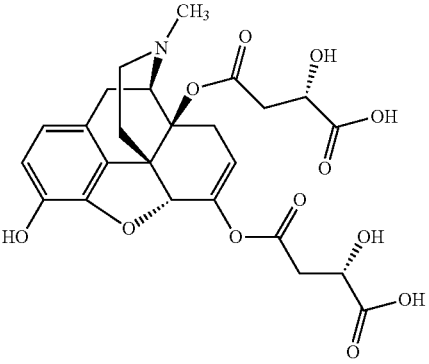 [SMILES: CN1CCC[C@]23c4c5ccc(O)c4O[C@H]2C(OC(=O)C[C@H](O)C(=O)O)=CC[C@@]3(OC(=O)C[C@H](O)C(=O)O)[C@H]1C5] | 534 | ¹H NMR (300 MHz, DMSO-d₆) δ 9.44 (br s, 1H), 9.31 (br s, 1H), 9.15 (br s, 1H), 6.75-6.58 (m, 3H), 5.46-5.41 (m, 2H), 5.02 (s, 1H), 4.69 (d, J = 5.9 Hz, 1H), 4.25-4.33 (m, 3H), 3.60-2.60 (m, 11H), 2.47-2.37 (m, 1H), 2.10 (d, J = 19.3 Hz, 1H), 1.77 (d, J = 11.4 Hz, 1H) |
| B37 | 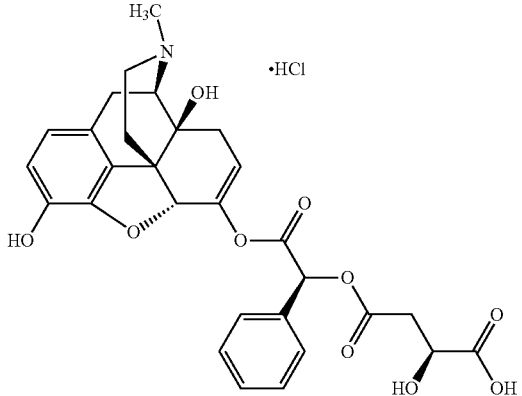 [SMILES: CN1CCC[C@]23c4c5ccc(O)c4O[C@H]2C(OC(=O)[C@@H](OC(=O)C[C@H](O)C(=O)O)c2ccccc2)=CC[C@@]3(O)[C@H]1C5 ; Cl] •HCl | 552 | ¹H NMR (300 MHz, DMSO-d₆) δ 7.59-7.54 (m, 2H), 7.48-7.44 (m, 3H), 6.55 (apparent q, J = 7.8 Hz, 2H), 6.08 (s, 1H), 5.56 (dd, J = 5.7, 2.4 Hz, 1H), 4.74 (s, 1H), 4.26 (dd, J = 8.4, 4.2 Hz, 1H), 3.15 (s, 1H), 3.09 (s, 1H), 2.97 (d, J = 5.7 Hz, 1H), 2.88 (dd, J = 15.9, 4.2 Hz, 1H), 2.73-1.95 (m, 6H), 2.41 (s, 3H), 1.40 (d, J = 11.1 Hz, 1H), CO₂H, HCl, and three OH protons not observed |
| B38 | 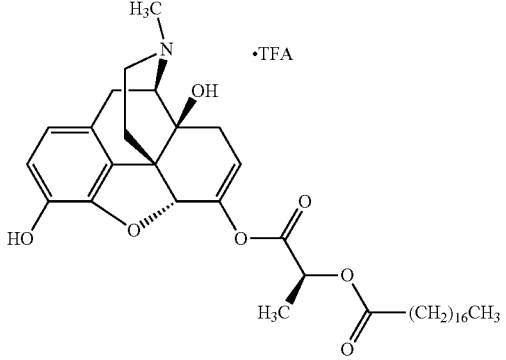 •TFA | 640 | ¹H NMR (300 MHz, DMSO-d₆) δ 9.27 (s, 1H), 9.13 (s, 1H), 6.65 (apparent q, J = 8.1 Hz, 2H), 6.23 (s, 1H), 5.57 (dd, J = 6.3, 2.1 Hz, 1H), 5.09 (q, J = 6.9 Hz, 1H), 4.95 (s, 1H), 3.09 (m, 1H), 2.84 (d, J = 3.9 Hz, 3H), 2.63-2.26 (m, 5H), 2.05 (d, J = 18.0 Hz, 1H), 1.64-1.49 (m, 7H), 1.23 (m, 30H), 0.85 (t, J = 6.6 Hz, 3H) |

| Ex, No. | Structure | Mass Spec | $^1$H NMR Data |
|---|---|---|---|
| B39 | 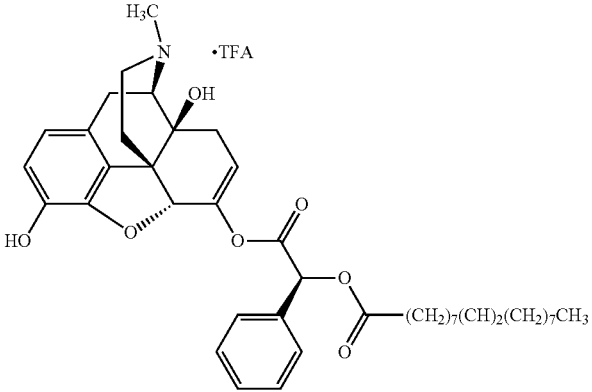 | 700 | $^1$H NMR (300 MHz, DMSO-d$_6$) δ 9.25 (s, 1H), 9.12 (s, 1H), 7.58-7.54 (m, 2H), 7.48-7.45 (m, 3H), 6.64 (q, J = 8.1 Hz, 2H), 6.23 (s, 1H), 6.09 (s, 1H), 5.58 (dd, J = 8.3, 2.1 Hz, 1H), 5.32 (t, J = 4.8 Hz, 2H), 4.86 (s, 1H), 3.04 (m, 1H), 2.82 (d, J = 4.8 Hz, 3H), 2.64-2.22 (m, 3H), 2.08-1.96 (m, 5H), 1.60-1.40 (m, 4H), 1.23 (m, 24H), 0.85 (t, J = 6.9 Hz, 3H) |
| B40 | 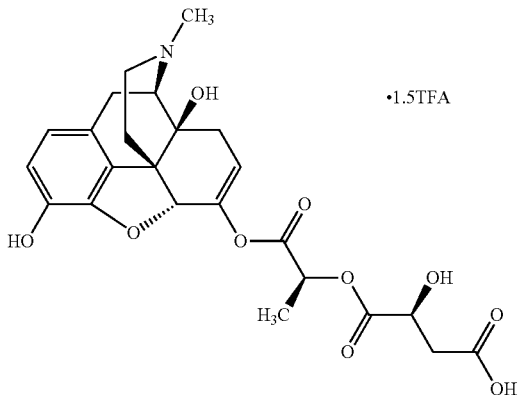 [SMILES: C[C@H](OC(=O)[C@@H](O)CC(=O)O)C(=O)OC1=CC[C@@]2(O)[C@H]3Cc4ccc(O)c5c4[C@@]2(CCCN3C)[C@H]1O5 ; "·1.5TFA"] | 490 | $^1$H NMR (300 MHz, DMSO-d$_6$) δ 12.39 (br s, 1H), 9.30 (s, 1H), 9.17 (s, 1H), 6.69 (d, J = 8.1 Hz, 1H), 6.62 (d, J = 8.1 Hz, 1H), 6.28 (s, 1H), 5.84 (br s, 1H), 5.59 (dd, J = 5.9, 2.0 Hz, 1H), 5.17 (q, J = 7.0 Hz, 1H), 4.97 (s, 1H), 4.47 (dd, J = 8.6, 4.0 Hz, 1H), 3.63 (d, J = 6.2 Hz, 1H), 3.13-3.00 (m, 2H), 2.84 (d, J = 3.3 Hz, 3H), 2.72 (dd, J = 16.0, 4.2 Hz, 1H), 2.69-2.57 (m, 1H), 2.50-2.40 (m, 1H), 2.29 (dd, J = 18.0, 6.0 Hz, 1H), 2.06 (d, J = 18.0 Hz, 1H), 1.62 (d, J = 11.2 Hz, 1H), 1.53 (d, J = 7.0 Hz, 3H), two protons obscured by solvent peaks |
| B41 | 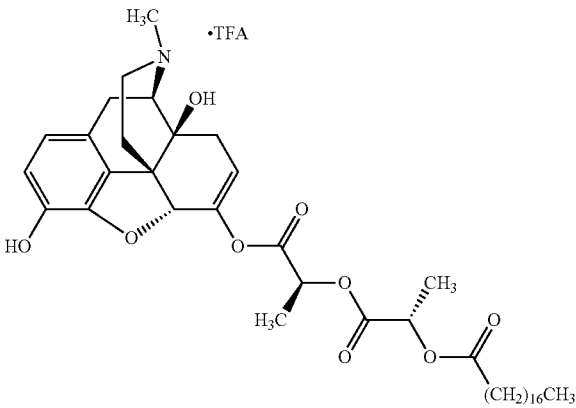 | 712 | $^1$H NMR (300 MHz, DMSO-d$_6$) δ 9.27 (s, 1H), 9.13 (s, 1H), 6.65 (apparent q, J = 8.1 Hz, 2H), 6.23 (s, 1H), 5.58 (dd, J = 6.3, 2.1 Hz, 1H), 5.23 (q, J = 6.9 Hz, 1H), 5.08 (q, J = 7.2 Hz, 1H), 4.95 (s, 1H), 3.06 (m, 1H), 2.83 (d, J = 4.8 Hz, 3H), 2.63-2.25 (m, 5H), 2.06 (d, J = 17.4 Hz, 1H), 1.64-1.46 (m, 10H), 1.23 (m, 30H), 0.85 (t, J = 6.9 Hz, 3H) |

-continued

| Ex. No. | Structure | Mass Spec | ¹H NMR Data |
|---|---|---|---|
| B42 | 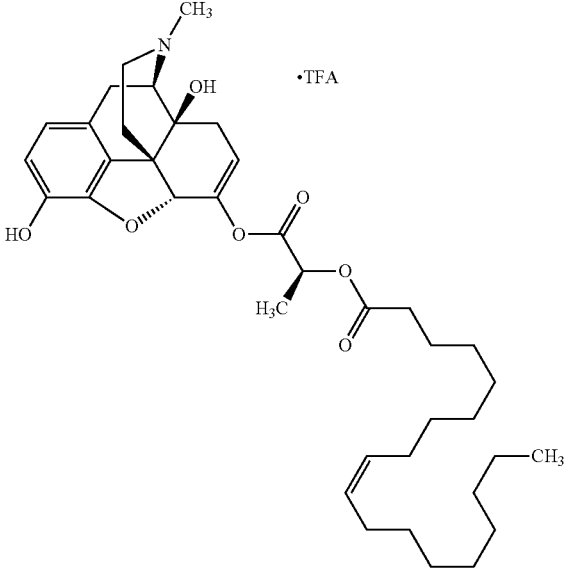 [SMILES: CCCCCCCC/C=C\CCCCCCCC(=O)O[C@@H](C)C(=O)OC1=CC[C@@]2(O)[C@H]3Cc4ccc(O)c5c4[C@@]2(CCCN3C)[C@H]1O5 ; "·TFA"] ·TFA | 638 | ¹H NMR (300 MHz, DMSO-d₆) δ 9.27 (s, 1H), 9.14 (s, 1H), 6.65 (apparent q, J = 8.1 Hz, 2H), 6.23 (s, 1H), 5.57 (dd, J = 5.7, 2.1 Hz, 1H), 5.32 (t, J = 4.5 Hz, 2H), 5.09 (q, J = 7.2 Hz, 1H), 4.95 (s, 1H), 3.09 (m, 1H), 2.83 (d, J = 4.5 Hz, 3H), 2.67-2.24 (m, 7H), 2.09-1.95 (m, 5H), 1.64-1.49 (m, 6H), 1.25 (m, 21H), 0.85 (t, J = 6.3 Hz, 3H) |
| B43a | 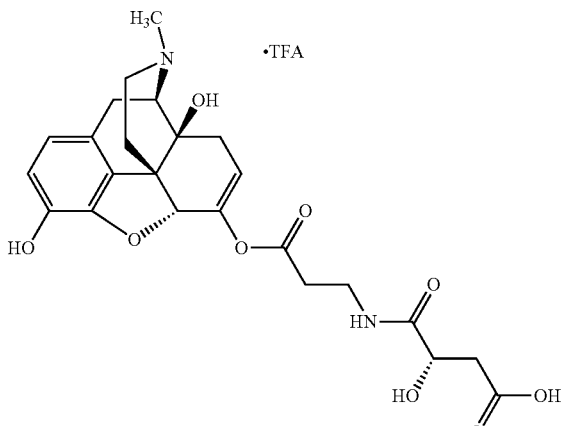 ·TFA | 508 | ¹H NMR (300 MHz, DMSO-d₆) δ 12.23 (br s, 1H), 9.30 (s, 1H), 9.15 (s, 1H), 7.97 (t, J = 6.0 Hz, 1H), 6.64 (apparent q, J = 8.1 Hz, 2H), 6.22 (s, 1H), 5.85 (s, 1H), 5.55 (dd, J = 6.0, 2.1 Hz, 1H), 4.96 (s, 1H), 4.22 (dd, J = 8.7, 3.6 Hz, 1H), 3.62-3.43 (m, 5H), 3.11-3.02 (m, 1H), 2.84 (d, J = 4.8 Hz, 3H), 2.66-2.60 (m, 4H), 2.49- 2.23 (m, 3H), 2.05 (d, J = 17.7 Hz, 1H), 1.62 (d, J = 10.5 Hz, 1H) |
| B43b | 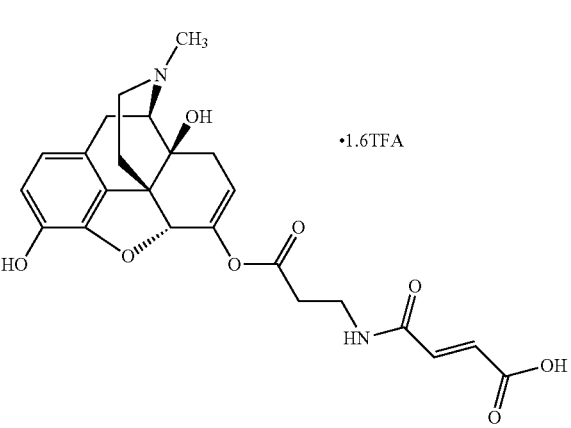 [SMILES: CN1CCC[C@]23c4c5ccc(O)c4O[C@H]2C(OC(=O)CCNC(=O)/C=C/C(=O)O)=CC[C@@]3(O)[C@H]1C5 ; "·1.6TFA"] ·1.6TFA | 471 | ¹H NMR (300 MHz, DMSO-d₆) 12.86 (br s, 1H), 9.30 (s, 1H), 9.15 (s, 1H), 8.65 (t, J = 5.5 Hz, 1H), 6.92 (d, J = 15.5 Hz, 1H), 6.68 (d, J = 8.1 Hz, 1H), 6.62 (d, J = 8.1 Hz, 1H), 6.53 (d, J = 15.5 Hz, 1H), 6.21 (s, 1H), 5.55 (dd, J = 6.0, 2.0 Hz, 1H), 4.96 (s, 1H), 3.61 (d, J = 6.3 Hz, 1H), 3.50-3.42 (m, 2H), 3.13-3.01 (m, 3H), 2.84 (d, J = 4.7 Hz, 3H), 2.70-2.62 (m, 3H), 2.50- 2.40 (m, 1H), 2.32-2.22 (m, 1H), 2.06 (d, J = 17.5 Hz, 1H), 1.62 (d, J = 11.3 Hz, 1H) |

-continued

| Ex, No. | Structure | Mass Spec | ¹H NMR Data |
|---|---|---|---|
| B44 | 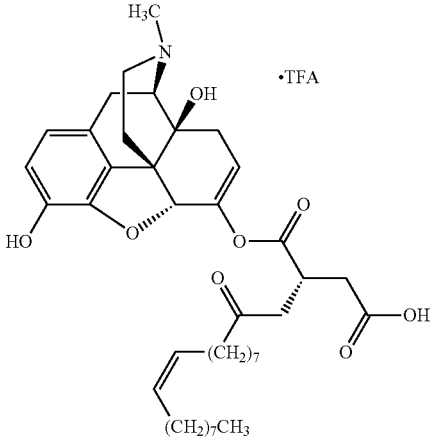 | 680 | ¹H NMR (300 MHz, DMSO-d$_6$) δ 12.75 (br s, 1H), 9.26 (s, 1H), 9.13 (s, 1H), 6.64 (apparent q, J = 8.1 Hz, 2H), 6.23 (s, 1H), 5.59 (dd, J = 6.0, 2.1 Hz, 1H), 5.40 (dd, J = 7.8, 4.2 Hz, 1H), 5.32 (t, J = 4.5 Hz, 2H), 4.93 (s, 1H), 3.62-3.41 (m, 1H), 3.04-2.88 (m, 4H), 2.84 (d, J = 4.5 Hz, 3H), 2.66-2.24 (m, 6H), 2.09-1.97 (m, 4H), 1.64-1.52 (m, 3H), 1.25 (m, 23H), 0.85 (t, J = 6.9 Hz, 3H) |
| B45 | 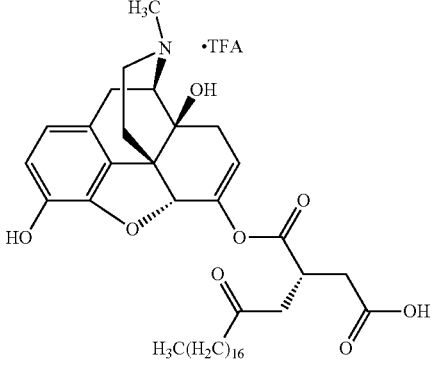 | 682 | ¹H NMR (300 MHz, DMSO-d$_6$) δ 12.77 (s, 1H), 9.26 (s, 1H), 9.14 (s, 1H), 6.65 (q, J = 8.1 Hz, 2H), 6.24 (s, 1H), 5.59 (dd, J = 6.0, 2.1 Hz, 1H), 5.40 (dd, J = 7.8, 4.2 Hz, 1H), 4.92 (s, 1H), 3.04-2.83 (m, 6H), 2.63-2.24 (m, 6H), 2.06 (d, J = 18.0 Hz, 1H), 1.64-1.52 (m, 3H), 1.25 (m, 31H), 0.85 (t, J = 6.9 Hz, 3H) |
| B46 | 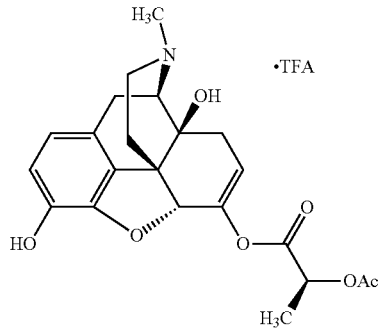 [SMILES: CC(=O)O[C@@H](C)C(=O)OC1=CC[C@@]2(O)[C@H]3Cc4ccc(O)c5c4[C@@]2(CCCN3C)[C@H]1O5 ; "·TFA"] | 416 | ¹H NMR (300 MHz, DMSO-d$_6$) δ 9.28 (s, 1H), 9.14 (s, 1H), 6.65 (q, J = 8.1 Hz, 2H), 6.25 (s, 1H), 5.58 (dd, J = 6.0, 2.1 Hz, 1H), 5.08 (q, J = 6.9 Hz, 1H), 4.95 (s, 1H), 3.05 (m, 1H), 2.83 (d, J = 4.2 Hz, 3H), 2.67-2.24 (m, 6H), 2.11-2.03 (m, 4H), 1.62 (d, J = 12.6 Hz, 1H), 1.51 (d, J = 7.2 Hz, 3H) |
| B47 | 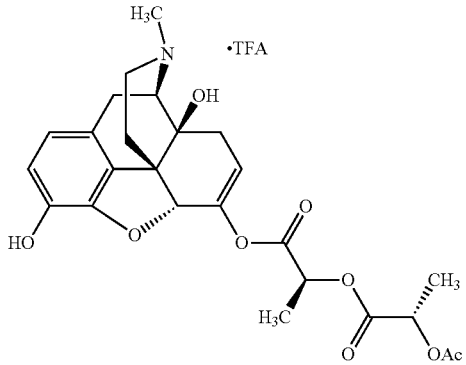 [SMILES: CC(=O)O[C@@H](C)C(=O)O[C@@H](C)C(=O)OC1=CC[C@@]2(O)[C@H]3Cc4ccc(O)c5c4[C@@]2(CCCN3C)[C@H]1O5 ; "·TFA"] | 488 | ¹H NMR (300 MHz, DMSO-d$_6$) δ 9.27 (s, 1H), 9.14 (s, 1H), 6.65 (q, J = 8.1 Hz, 2H), 6.24 (s, 1H), 5.58 (dd, J = 5.7, 1.8 Hz, 1H), 5.23 (q, J = 6.9 Hz, 1H), 5.07 (q, J = 7.2 Hz, 1H), 4.95 (s, 1H), 3.05 (m, 1H), 2.82 (s, 3H), 2.63-2.24 (m, 6H), 2.08-2.03 (m, 4H), 1.62 (d, J = 12.3 Hz, 1H), 1.54 (d, J = 7.2 Hz, 3H), 1.47 (d, J = 7.2 Hz, 3H) |

| Ex, No. | Structure | Mass Spec | $^1$H NMR Data |
|---|---|---|---|
| B48 | 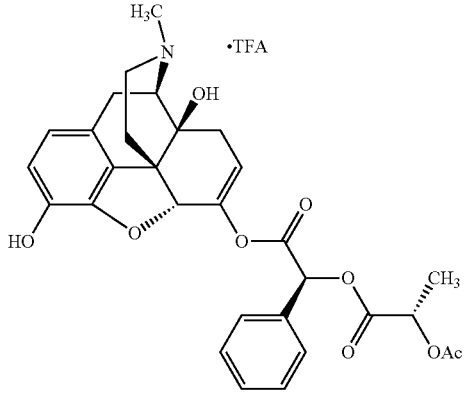 [SMILES: CC(=O)O[C@@H](C)C(=O)O[C@H](C(=O)OC1=CC[C@@]2(O)[C@H]3Cc4ccc(O)c5c4[C@@]2(CCCN3C)[C@H]1O5)c1ccccc1 ; "·TFA"] | 550 | $^1$H NMR (300 MHz, DMSO-$d_6$) δ 9.25 (s, 1H), 9.12 (s, 1H), 7.60-7.55 (m, 2H), 7.52-7.46 (m, 3H), 6.65 (q, J = 8.1 Hz, 2H), 6.24 (s, 1H), 6.21 (s, 1H), 5.58 (dd, J = 6.0, 2.1 Hz, 1H), 5.15 (q, J = 6.9 Hz, 1H), 4.86 (s, 1H), 3.03 (m, 1H), 2.82 (s, 3H), 2.63-2.22 (m, 6H), 2.08-2.02 (m, 4H), 1.62 (d, J = 13.5 Hz, 1H), 1.54 (d, J = 7.2 Hz, 3H) |
| B49 | 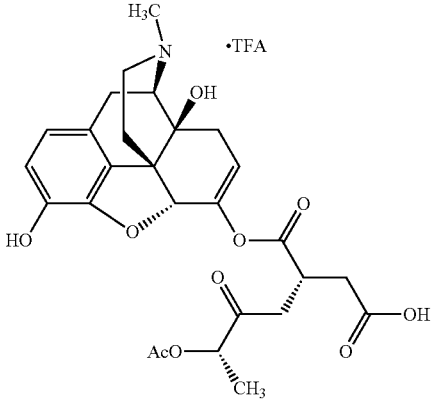 [SMILES: CC(=O)O[C@@H](C)C(=O)C[C@@H](CC(=O)O)C(=O)OC1=CC[C@@]2(O)[C@H]3Cc4ccc(O)c5c4[C@@]2(CCCN3C)[C@H]1O5 ; "·TFA"] | 530 | $^1$H NMR (300 MHz, DMSO-$d_6$) δ 12.82 (s, 1H), 9.27 (s, 1H), 9.15 (s, 1H), 6.65 (apparent q, J = 8.1 Hz, 2H), 6.25 (s, 1H), 5.59 (dd, J = 6.0, 2.1 Hz, 1H), 5.50 (t, J = 5.4 Hz, 1H), 5.08 (q, J = 7.2 Hz, 1H), 4.91 (s, 1H), 3.04 (m, 1H), 2.95 (d, J = 6.0 Hz, 2H), 2.84 (d, J = 4.5 Hz, 3H), 2.67-2.25 (m, 8H), 2.08-2.03 (m, 4H), 1.62 (d, J = 11.7 Hz, 1H), 1.46 (d, J = 6.9 Hz, 3 H) |
| B50 | 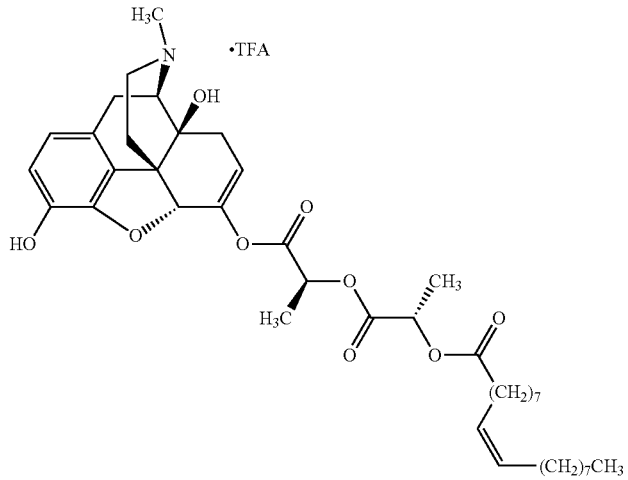 | 710 | $^1$H NMR (300 MHz, DMSO-$d_6$) δ 9.27 (s, 1H), 9.14 (s, 1H), 6.65 (apparent q, J = 8.1 Hz, 2H), 6.23 (s, 1H), 5.57 (dd, J = 6.3, 2.1 Hz, 1H), 5.32 (t, J = 4.5 Hz, 1H), 5.22 (q, J = 6.9 Hz, 1H), 5.08 (q, J = 7.2 Hz, 1H), 4.95 (s, 1H), 3.06 (m, 1H), 2.84 (d, J = 4.5Hz, 3H), 2.63-2.25 (m, 8H), 2.09-1.95 (m, 4H), 1.64-1.46 (m, 10H), 1.23 m, 21H), 0.85 (t, J = 6.6 Hz, 3H) |

| Ex. No. | Structure | Mass Spec | ¹H NMR Data |
|---|---|---|---|
| B51 | 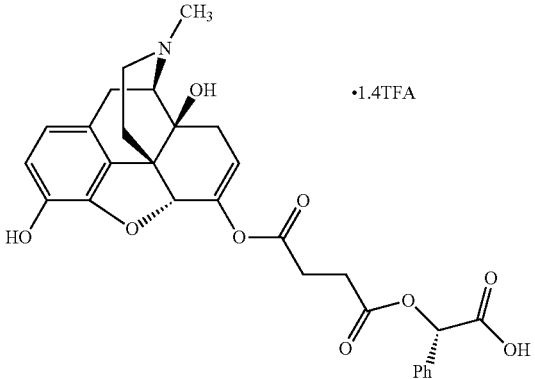 [SMILES: CN1CCC[C@]23c4c5ccc(O)c4O[C@H]2C(OC(=O)CCC(=O)O[C@H](C(=O)O)c2ccccc2)=CC[C@@]3(O)[C@H]1C5 ; "·1.4TFA"] •1.4TFA | 536 | ¹H NMR (300 MHz, DMSO-$d_6$) δ 9.30 (s, 1H), 9.15 (br s, 1H), 7.50-7.44 (m, 2H), 7.44-7.40 (m, 3H), 6.68 (d, J = 8.2 Hz, 1H), 6.62 (d, J = 8.2 Hz, 1H), 6.22 (s, 1H), 5.85 (s, 1H), 5.49 (dd, J = 6.0, 1.9 Hz, 1H), 4.93 (s, 1H), 3.61 (d, J = 6.3 Hz, 1H), 3.12-3.01 (m, 2H), 2.84 (s, 3H), 2.79-2.70 (m, 4H), 2.70-2.58 (m, 1H), 2.42 (dd, J = 13.3, 4.7 Hz, 1H), 2.25 (dd, J = 17.1, 7.1 Hz, 1H), 2.04 (d, J = 17.1 Hz, 1H), 1.61 (d, J = 11.2 Hz, 1H), $CO_2H$ proton not observed, one proton obscured by solvent peaks |
| B52 | 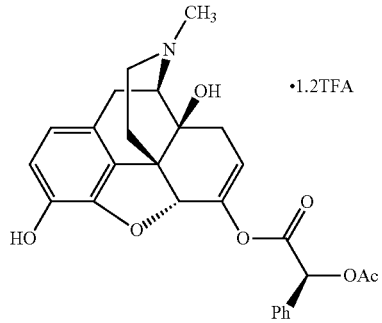 [SMILES: CC(=O)O[C@H](C(=O)OC1=CC[C@@]2(O)[C@H]3Cc4ccc(O)c5c4[C@@]2(CCCN3C)[C@H]1O5)c1ccccc1 ; "·1.2TFA"] •1.2TFA | 478 | ¹H NMR (300 MHz, DMSO-$d_6$) δ 9.29 (s, 1H), 9.15 (br s, 1H), 7.60-7.51 (m, 2H), 7.51-7.43 (m, 3H), 6.68 (d, J = 8.1 Hz, 1H), 6.61 (d, J = 8.1 Hz, 1H), 6.27 (s, 1H), 6.08 (s, 1H), 5.58 (dd, J = 6.0, 1.9 Hz, 1H), 4.87 (s, 1H), 3.61 (d, J = 6.1 Hz, 1H), 3.11-3.00 (m, 2H), 2.83 (d, J = 4.6 Hz, 3H), 2.70-2.55 (m, 1H), 2.42 (dd, J = 12.8, 4.2 Hz, 1H), 2.26 (dd, J = 18.0, 6.1 Hz, 1H), 2.17 (s, 3H), 2.05 (d, J = 18.0 Hz, 1H), 1.60 (d, J = 11.1 Hz, 1H), one proton obscured by solvent peaks |
| B53 | 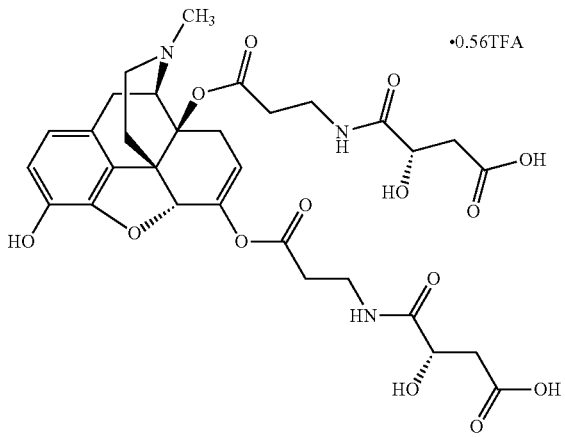 [SMILES: CN1CCC[C@]23c4c5ccc(O)c4O[C@H]2C(OC(=O)CCNC(=O)[C@@H](O)CC(=O)O)=CC[C@@]3(OC(=O)CCNC(=O)[C@@H](O)CC(=O)O)[C@H]1C5 ; "·0.56TFA"] •0.56TFA | 676 | ¹H NMR (300 MHz, DMSO-$d_6$) δ 9.55 (br s, 2H), 8.03-7.97 (m, 2H), 6.73 (d, J = 8.2 Hz, 1H), 6.66 (d, J = 8.2 Hz, 1H), 5.50 (dd, J = 6.7, 1.8 Hz, 1H), 5.06 (s, 1H), 4.73 (d, J = 6.0 Hz, 1H), 4.26-4.21 (m, 2H), 3.45-3.13 (m, 10H), 3.08-2.90 (m, 4H), 2.86-2.70 (m, 1H), 2.70-2.53 (m, 5H), 2.45-2.25 (m, 3H), 2.09 (d, J = 18.6 Hz, 1H), 1.78 (d, J = 13.5 Hz, 1H), $CO_2H$ protons not observed |

-continued

| Ex, No. | Structure | Mass Spec | ¹H NMR Data |
|---|---|---|---|
| B54 | 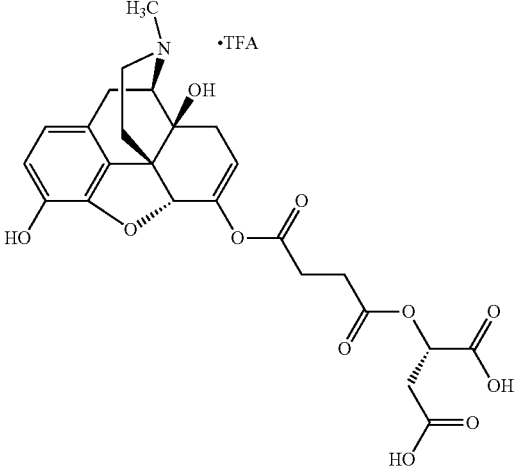 [SMILES: CN1CCC[C@]23c4c5ccc(O)c4O[C@H]2C(OC(=O)CCC(=O)O[C@@H](CC(=O)O)C(=O)O)=CC[C@@]3(O)[C@H]1C5 ; "·TFA"] | 518 | ¹H NMR (300 MHz, DMSO-d$_6$) δ 12.3 (s, 1H), 12.6 (s, 1H), 9.30 (s, 1H), 9.14 (s, 1H), 6.65 (apparent q, J = 8.1 Hz, 2H), 6.22 (s, 1H), 5.53 (dd, J = 6.3, 2.1 Hz, 1H), 5.23 (dd, J = 7.8, 4.5 Hz, 1H), 4.95 (s, 1H), 3.06 (m, 1H), 2.91-2.66 (m, 11H), 2.47 (m, 3H), 2.27 (m, 1H), 2.06 (d, J = 18.0 Hz, 1H), 1.63 (d, J = 11.7 Hz, 1H) |
| B55 | 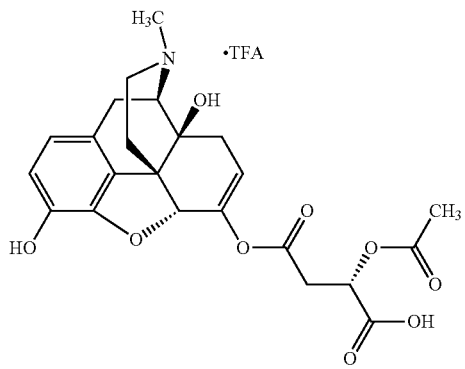 [SMILES: CC(=O)O[C@@H](CC(=O)OC1=CC[C@@]2(O)[C@H]3Cc4ccc(O)c5c4[C@@]2(CCCN3C)[C@H]1O5)C(=O)O ; "·TFA"] | 460 | ¹H NMR (300 MHz, DMSO-d$_6$) δ 13.4 (br s, 1H), 9.29 (s, 1H), 9.14 (br s, 1H), 6.65 (apparent q, J = 8.1 Hz, 2H), 6.24 (s, 1H), 5.55 (dd, J = 5.7, 2.1 Hz, 1H), 5.28 (dd, J = 8.4, 4.5 Hz, 1H), 4.96 (s, 1H), 3.12-2.94 (m, 4H), 2.84 (d, J = 3.6 Hz, 3H), 2.67-2.42 (m, 4H), 2.27 (dd, J = 17.7, 6.0 Hz, 1H), 2.09-2.03 (m, 4H), 1.63 (d, J = 11.7 Hz, 1H) |
| B56 | 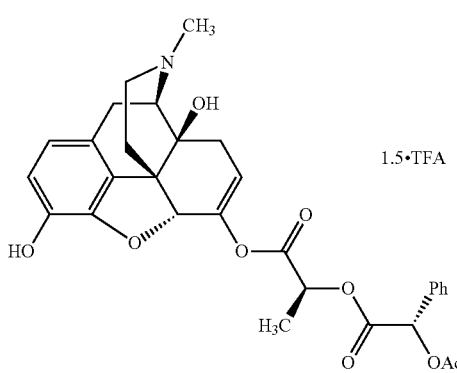 [SMILES: CC(=O)O[C@H](C(=O)O[C@@H](C)C(=O)OC1=CC[C@@]2(O)[C@H]3Cc4ccc(O)c5c4[C@@]2(CCCN3C)[C@H]1O5)c1ccccc1 ; "1.5·TFA"] | 550 | ¹H NMR (300 MHz, DMSO-d$_6$) δ 9.30 (br s, 1H), 9.16 (br s, 1H), 7.53-7.49 (m, 2H), 7.42-7.39 (m, 3H), 6.68 (d, J = 8.2 Hz, 1H), 6.63 (d, J = 8.2 Hz, 1H), 6.25 (s, 1H), 6.06 (s, 1H), 5.46 (dd, J = 5.9, 2.0 Hz, 1H), 5.26 (q, J = 7.1 Hz, 1H), 4.79 (s, 1H), 6.61 (d, J = 6.1 Hz, 1H), 3.36 (d, J = 20.0 Hz, 1H), 3.12-3.01 (m, 2H), 2.87-2.82 (m, 3H), 2.69-2.57 (m, 1H), 2.41 (dd, J = 13.2, 4.7 Hz, 1H), 2.26 (dd, J = 18.0, 6.2 Hz, 1H), 2.13 (s, 3H), 2.03 (d, J = 18.0 Hz, 1H), 1.59 (d, J = 10.9 Hz, 1H), 1.50 (d, J = 7.1 Hz, 3H) |

| Ex, No. | Structure | Mass Spec | ¹H NMR Data |
|---|---|---|---|
| B57 | ·1.4TFA | 474 | ¹H NMR (300 MHz, DMSO-d₆) δ 13.05 (br s, 1H), 9.33 (br s, 1H), 9.18 (br s, 1H), 6.68 (d, J = 8.2 Hz, 1H), 6.62 (d, J = 8.2 Hz, 1H), 6.28 (s, 1H), 5.52 (dd, J = 5.7, 1.8 Hz, 1H), 4.98-4.89 (m, 2H), 3.63 (d, J = 6.2 Hz, 1H), 3.37 (d, J = 19.9 Hz, 1H), 3.13-3.00 (m, 2H), 3.84 (s, 3H), 2.76-2.55 (m, 5H), 2.43 (dd, J = 13.2, 4.6 Hz, 1H), 2.27 (dd, J = 17.9, 6.1 Hz, 1H), 2.05 (d, J = 16.2 Hz, 1H), 1.62 (d, J = 11.0 Hz, 1H), 1.40 (d, J = 7.1 Hz, 3H) |
| B58 | ·1.2TFA | 531 | ¹H NMR (300 MHz, DMSO-d₆) δ 9.28 (br s, 1H), 9.16 (br s, 1H), 8.45 (d, J = 8.3 Hz, 1H), 6.68 (d, J = 8.2 Hz, 1H), 6.63 (d, J = 8.2 Hz, 1H), 6.24 (s, 1H), 5.52 (dd, J = 5.9, 1.9 Hz, 1H), 4.98 (q, J = 6.8 Hz, 1H), 4.93 (s, 1H), 4.65 (q, J = 6.9 Hz, 1H), 3.61 (d, J = 6.3 Hz, 1H), 3.11-2.93 (m, 3H), 2.91-2.74 (m, 4H), 2.70-2.58 (m, 1H), 2.48-2.39 (m, 1H), 2.28 (dd, J = 17.7, 6.2 Hz, 1H), 2.06 (d, J = 14.0 Hz, 1H), 1.62 (d, J = 11.0 Hz, 1H), 1.33 (d, J = 6.9 Hz, 3H), CO₂H proton not observed, four protons obscured by solvent peaks |
| B59 | ·TFA | 800 | ¹H NMR (300 MHz, DMSO-d₆, Mixture of diastereomers) δ 9.35 (s, 1H), 8.48 (d, J = 8.4 Hz, 0.18H), 8.43 (d, J = 8.3 Hz, 0.82H), 8.25 (d, J = 7.2 Hz, 1H), 7.44-7.17 (m, 10H), 6.69 (d, J = 8.2 Hz, 1H), 6.63 (d, J = 8.2 Hz, 1H), 6.41-6.30 (m, 2H), 5.34 (d, J = 5.9 Hz, 0.18H), 5.25 (d, J = 4.5 Hz, 0.82H), 5.00-4.89 (m, 3H), 4.74-4.47 (m, 3H), 3.18-2.94 (m, 4H), 2.93-2.67 (m, 8H), 2.45-2.43 (m, 2H), 2.09-1.98 (m, 1H), 1.73-1.61 (m, 1H), CO₂H protons not observed |

| Ex, No. | Structure | Mass Spec | ¹H NMR Data |
|---|---|---|---|
| B60 | 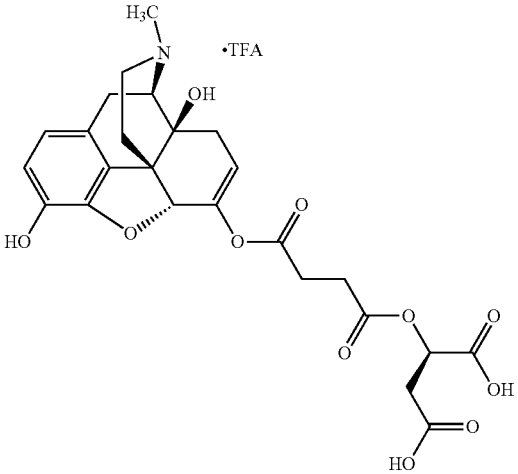 [SMILES: CN1CCC[C@]23c4c5ccc(O)c4O[C@H]2C(OC(=O)CCC(=O)O[C@H](CC(=O)O)C(=O)O)=CC[C@@]3(O)[C@H]1C5 ; "·TFA"] | 518 | ¹H NMR (300 MHz, DMSO-d$_6$) δ 13.2 (br s, 1H), 12.6 (br s, 1H), 9.30 (s, 1H), 9.17 (br s, 1H), 6.64 (q, J = 8.1 Hz, 2H), 6.24 (br s, 1H), 5.53 (dd, J = 6.3, 2.1 Hz, 1H), 5.22 (dd, J = 7.8, 4.5 Hz, 1H), 4.95 (s, 1H), 3.41-3.32 (m, 1H), 3.04 (m, 1H), 2.86-2.61 (m, 10H), 2.51-2.42 (m, 3H), 2.26 (m, 1H), 2.06 (d, J = 18.0 Hz, 1H), 1.62 (d, J = 10.8 Hz, 1H) |
| B61a | 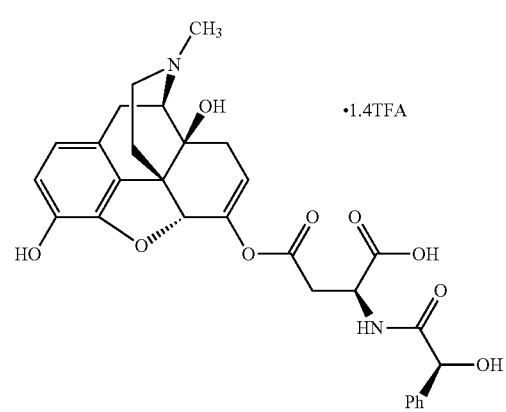 [SMILES: CN1CCC[C@]23c4c5ccc(O)c4O[C@H]2C(OC(=O)C[C@H](NC(=O)[C@@H](O)c2ccccc2)C(=O)O)=CC[C@@]3(O)[C@H]1C5 ; "·1.4TFA"] | 551 | ¹H NMR (300 MHz, DMSO-d$_6$) δ 13.01 (br s,1H), 9.30 (br s, 1H), 9.15 (br s, 1H), 8.37 (d, J = 8.3 Hz, 1H), 7.46-7.18 (m, 5H), 6.68 (d, J = 8.1 Hz, 1H), 6.62 (d, J = 8.1 Hz, 1H), 6.38 (br s, 1H), 6.21 (s, 1H), 5.35 (d, J = 4.2 Hz, 1H), 4,96 (s, 1H), 4.89 (s, 1H), 4.67 (q, J = 6.3 Hz, 1H), 3.64-3.58 (m, 1H), 3.18-2.79 (m, 8H), 2.77-2.60 (m, 2H), 2.30-2.18 (dd, J = 17.6, 6.1 Hz, 1H), 2.03 (d, J = 18.32 Hz, 1H), 1.62 (d, J = 12.2 Hz, 1H) |
| B61b | 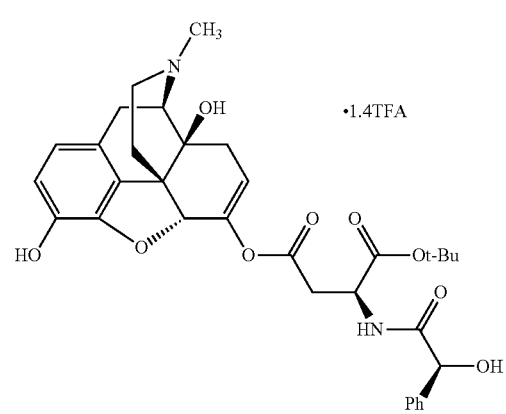 [SMILES: CN1CCC[C@]23c4c5ccc(O)c4O[C@H]2C(OC(=O)C[C@H](NC(=O)[C@@H](O)c2ccccc2)C(=O)OC(C)(C)C)=CC[C@@]3(O)[C@H]1C5 ; "·1.4TFA"] | 607 | ¹H NMR (300 MHz, DMSO-d$_6$) δ 9.29 (br s, 1H), 9.14 (br s, 1H), 8.41 (d, J = 8.1 Hz, 1H), 7.43-7.38 (m, 2H), 7.34-7.24 (m, 3H), 6.68 (d, J = 8.1 Hz, 1H), 6.63 (d, J = 8.1 Hz, 1H), 6.32 (br s, 1H), 6.22 (s, 1H), 5.41-5.39 (m, 1H), 4.96 (s, 1H), 4.90 (s, 1H), 4.61-4.52 (m, 1H), 3.63-3.59 (m, 1H), 3.12-2.95 (m, 3H), 2.88-2.78 (m, 4H), 2.70-2.59 (m, 1H), 2.45-2.40 (m, 1H), 2.25 (dd, J = 17.5, 6.3 Hz, 1H), 2.04 (d, J = 18.6 Hz, 1H), 1.62 (d, J = 11.6 Hz, 1H), 1.33 (s, 9H), one proton obscured by solvent peaks |

| Ex. No. | Structure | Mass Spec | ¹H NMR Data |
|---|---|---|---|
| B62 | 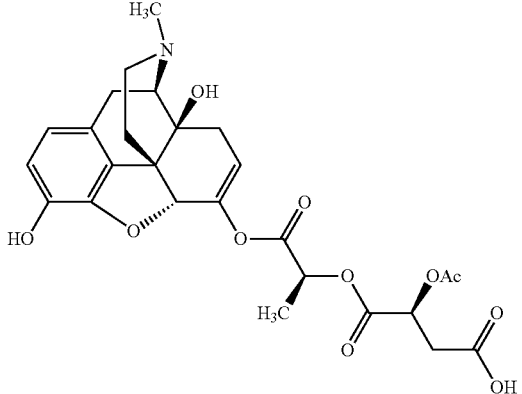 [SMILES: CC(=O)O[C@@H](CC(=O)O)C(=O)O[C@@H](C)C(=O)OC1=CC[C@@]2(O)[C@H]3Cc4ccc(O)c5c4[C@@]2(CCCN3C)[C@H]1O5] | 532 | ¹H NMR (300 MHz, DMSO-$d_6$) δ 6.55 (apparent q, J = 8.1 Hz, 2H), 5.56 (dd, J = 5.7, 2.4 Hz, 1H), 5.35 (dd, J = 9.0, 3.6 Hz, 1H), 5.23 (q, J = 8.1 Hz, 1H), 3.09 (d, J = 18.6 Hz, 1H), 2.94-2.72 (m, 3H), 2.60 (dd, J = 18.6, 6.3 Hz, 1H), 2.51-2.44 (m, 4H), 2.35 (s, 3H), 2.27 (m, 1H), 2.13-2.00 (m, 6H), 1.53 (d, J = 6.9 Hz, 3H), 1.39 (d, J = 10.8 Hz, 1H), CO$_2$H proton not observed |
| B63 | 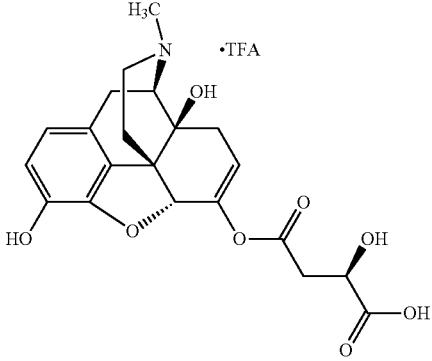 [SMILES: CN1CCC[C@]23c4c5ccc(O)c4O[C@H]2C(OC(=O)C[C@@H](O)C(=O)O)=CC[C@@]3(O)[C@H]1C5] | 418 | ¹H NMR (300 MHz, DMSO-$d_6$) δ 12.7 (s, 1H), 9.31 (s, 1H), 9.15 (br s, 1H), 6.65 (apparent q, J = 7.8 Hz, 2H), 6.22 (s, 1H), 5.64 (s, 1H), 5.52 (dd, J = 6.0, 2.1 Hz, 1H), 4.95 (s, 1H), 4.35 (m, 1H), 3.41-3.33 (m, 2H), 3.03 (m, 1H), 2.89 (d, J = 4.5 Hz, 1H), 2.83 (s, 3H), 2.72-2.61 (m, 1H), 2.44-2.42 (m, 1H), 2.27 (m, 1H), 2.06 (d, J = 17.7 Hz, 3H), 1.63 (d, J = 10.8 Hz, 1H) |
| B64 | 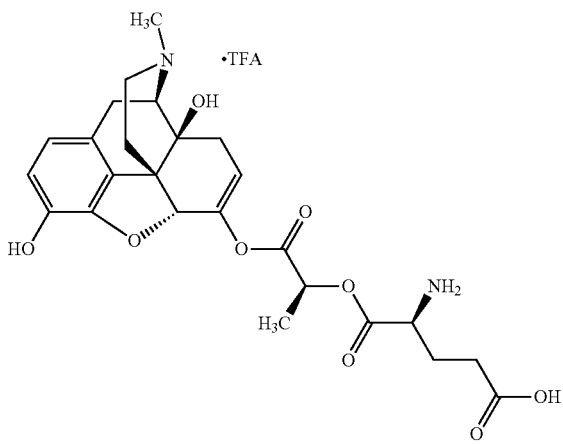 [SMILES: C[C@H](OC(=O)[C@@H](N)CCC(=O)O)C(=O)OC1=CC[C@@]2(O)[C@H]3Cc4ccc(O)c5c4[C@@]2(CCCN3C)[C@H]1O5] | 503 | ¹H NMR (300 MHz, DMSO-$d_6$) δ 12.3 (br s, 1H), 9.32 (br s, 1H), 9.16 (br s, 1H), 8.44 (br s, 3H), 6.66 (apparent q, J = 8.1 Hz, 2H), 6.25 (s, 1H), 5.61 (dd, J = 6.0, 2.1 Hz, 1H), 5.34 (q, J = 7.2 Hz, 1H), 4.99 (s, 1H), 4.23 (m, 1H), 3.62 (m, 3H), 3.08 (m, 1H), 2.84 (s, 3H), 2.63-2.26 (m, 4H), 2.11-2.05 (m, 3H), 1.76 (m, 1H), 1.63-1.58 (m, 4H) |

-continued

| Ex, No. | Structure | Mass Spec | ¹H NMR Data |
|---|---|---|---|
| B65 | 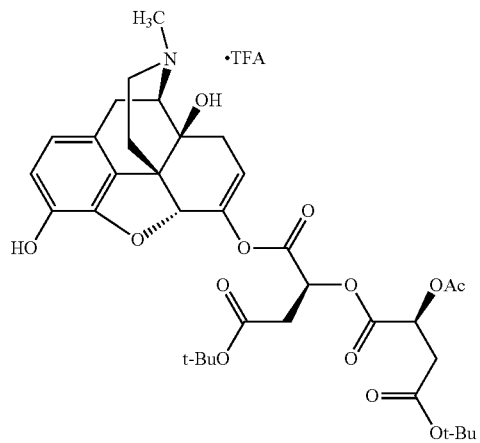 [SMILES: CC(=O)O[C@@H](CC(=O)OC(C)(C)C)C(=O)O[C@@H](CC(=O)OC(C)(C)C)C(=O)OC1=CC[C@@]2(O)[C@H]3Cc4ccc(O)c5c4[C@@]2(CCCN3C)[C@H]1O5] ·TFA | 688 | ¹H NMR (300 MHz, DMSO-d₆) δ 9.26 (s, 1H), 9.14 (br s, 1H), 6.65 (apparent q, J = 8.1 Hz, 2H), 6.23 (s, 1H), 5.62 (dd, J = 6.0, 2.4 Hz, 1H), 5.52 (dd, J = 7.2, 4.5 Hz, 1H), 5.36 (dd, J = 8.7, 3.9 Hz, 1H), 4.92 (s, 1H), 3.62-3.31 (m, 1H), 3.11-3.01 (m, 2H), 2.97-2.63 (m, 8H), 2.47-2.27 (m, 2H), 2.08-2.03 (m, 4H), 1.63 (m, 1H), 1.44 (s, 9H), 1.39 (s, 9H), one proton obscured by solvent peaks |
| B66 | 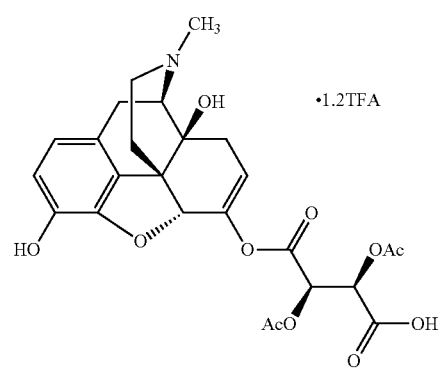 [SMILES: CC(=O)O[C@@H](C(=O)O)[C@@H](OC(C)=O)C(=O)OC1=CC[C@@]2(O)[C@H]3Cc4ccc(O)c5c4[C@@]2(CCCN3C)[C@H]1O5] ·1.2TFA | 518 | ¹H NMR (300 MHz, DMSO-d₆) δ 9.34 (s, 1H), 9.15 (br s, 1H), 6.68 (d, J = 8.1 Hz, 1H), 6.63 (d, J = 8.1 Hz, 1H), 6.29 (br s, 1H), 5.77 (d, J = 2.8 Hz, 1H), 5.68 (d, J = 2.8 Hz, 1H), 5.52 (d, J = 4.1 Hz, 1H), 4.83 (s, 1H), 3.62 (d, J = 6.0 Hz, 1H), 3.12-3.01 (m, 3H), 2.83 (s, 3H), 2.70-2.56 (m, 1H), 2.46-2.39 (m, 1H), 2.28 (dd, J = 17.7, 6.0 Hz, 1H), 2.19 (s, 3H), 2.15 (s, 3H), 2.07 (d, J = 16.4 Hz, 1H), 1.62 (d, J = 11.2 Hz, 1H), CO₂H proton not observed |
| B67 | 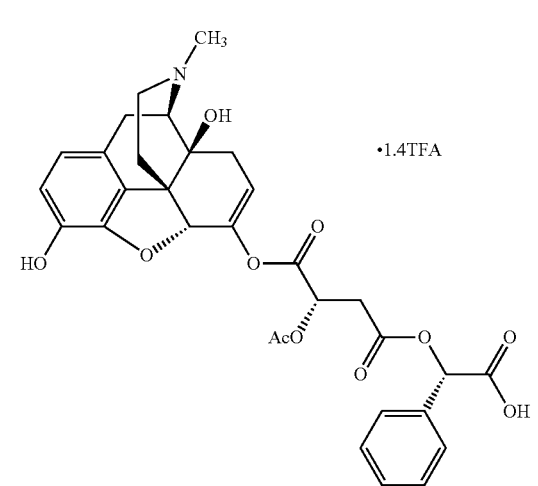 [SMILES: CC(=O)O[C@@H](CC(=O)O[C@H](C(=O)O)c1ccccc1)C(=O)OC1=CC[C@@]2(O)[C@H]3Cc4ccc(O)c5c4[C@@]2(CCCN3C)[C@H]1O5] ·1.4TFA | 594 | ¹H NMR (300 MHz, DMSO-d₆) δ 9.30 (s, 1H), 9.15 (s, 1H), 7.51-7.39 (m, 5H), 6.68 (d, J = 8.1 Hz, 1H), 6.63 (d, J = 8.1 Hz, 1H), 6.27 (s, 1H), 5.92-5.87 (m, 1H), 5.61-5.47 (m, 2H), 4.94 (m, 0.7H), 4.90 (s, 0.3H), 3.62 (d, J = 6.4 Hz, 1H), 3.24-3.01 (m, 5H), 2.83 (s, 3H), 2.71-2.56 (m, 1H), 2.48-2.36 (m, 1H), 2.33-2.21 (m, 1H), 2.12-2.02 (m, 4H), 1.66-1.57 (m, 1H), CO₂H proton not observed |

| Ex. No. | Structure | Mass Spec | $^1$H NMR Data |
|---|---|---|---|
| B68 | 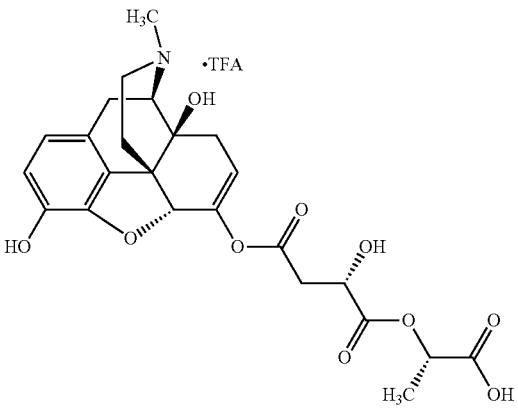 [SMILES: C[C@H](OC(=O)[C@@H](O)CC(=O)OC1=CC[C@@]2(O)[C@H]3Cc4ccc(O)c5c4[C@@]2(CCCN3C)[C@H]1O5)C(=O)O] | 490 | $^1$H NMR (300 MHz, DMSO-d) δ 13.1 (br s, 1H), 9.30 (s, 1H), 9.14 (br s, 1H), 6.64 (apparent q, J = 8.1 Hz, 2H), 6.22 (s, 1H), 5.96 (d, J = 6.3 Hz, 1H), 5.55 (dd, J = 6.0, 1.8 Hz, 1H), 5.03-4.97 (m, 2H), 4.52 (m, 1H), 3.41-3.33 (m, 1H), 3.04 (m, 1H), 2.95 (dd, J = 15.9, 4.2 Hz, 1H), 2.84 (s, 3H), 2.73-2.64 (m, 2H), 2.51-2.42 (m, 3H), 2.27 (m, 1H), 2.05 (d, J = 17.7 Hz, 1H), 1.63 (m, 1H), 1.42 (d, J = 6.9 Hz, 3H) |
| B69 | 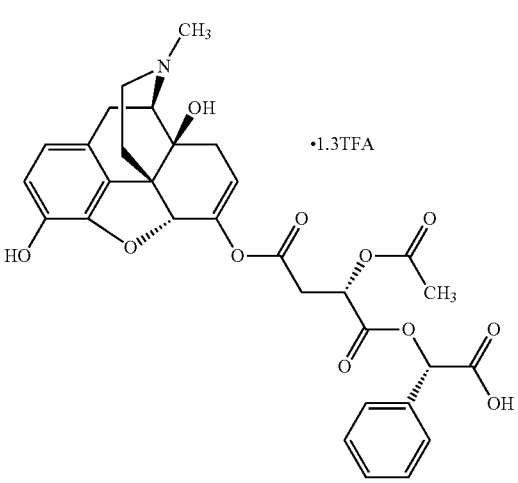 [SMILES: CC(=O)O[C@@H](CC(=O)OC1=CC[C@@]2(O)[C@H]3Cc4ccc(O)c5c4[C@@]2(CCCN3C)[C@H]1O5)C(=O)O[C@H](C(=O)O)c1ccccc1] | 594 | $^1$H NMR (300 MHz, DMSO-d$_6$) δ 9.30 (br s, 1H), 9.15 (br s, 1H), 7.52-7.39 (m, 5H), 6.68 (d, J = 8.2 Hz, 1H), 6.63 (d, J = 8.2 Hz, 1H), 6.23 (s, 1H), 5.97 (s, 1H), 5.57-5.47 (m, 2H), 4.96 (s, 1H), 6.31 (d, J = 6.0 Hz, 1H), 3.12-3.00 (m, 4H), 2.84 (s, 3H), 2.71-2.49 (m, 1H), 2.50-2.40 (m, 1H), 2.34-2.21 (m, 1H), 2.15-2.00 (m, 4H), 1.63 (d, J = 11.8 Hz, 1H), CO$_2$H proton not observed |
| B70 | 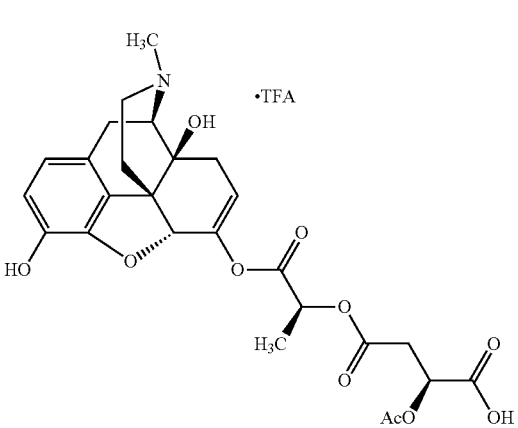 [SMILES: CC(=O)O[C@@H](CC(=O)O[C@@H](C)C(=O)OC1=CC[C@@]2(O)[C@H]3Cc4ccc(O)c5c4[C@@]2(CCCN3C)[C@H]1O5)C(=O)O] | 532 | $^1$H NMR (300 MHz, DMSO-d$_6$) δ 13.3 (br s, 1H), 9.29 (s, 1H), 9.15 (br s, 1H), 6.65 (apparent q, J = 8.1 Hz, 2H), 6.24 (s, 1H), 5.58 (dd, J = 5.7, 2.1 Hz, 1H), 5.27 (dd, J = 8.4, 4.5 Hz, 1H), 5.18 (q, J = 6.9 Hz, 1H), 4.97 (s, 1H), 3.11-2.96 (m, 4H), 2.83 (d, J = 3.9 Hz, 3H), 2.73-2.41 (m, 4H), 2.29 (m, 1H), 2.09-2.04 (m, 4H), 1.63 (m, 1H), 1.52 (d, J = 7.2 Hz, 3H) |

| Ex, No. | Structure | Mass Spec | ¹H NMR Data |
|---|---|---|---|
| B71 | 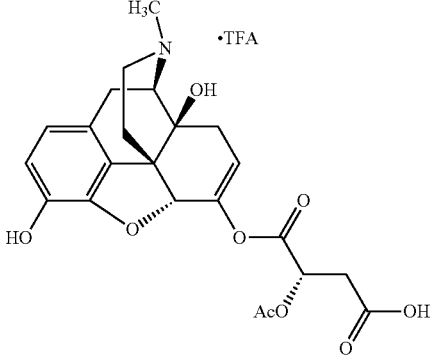 [SMILES: CC(=O)O[C@@H](CC(=O)O)C(=O)OC1=CC[C@@]2(O)[C@H]3Cc4ccc(O)c5c4[C@@]2(CCCN3C)[C@H]1O5] | 460 | ¹H NMR (300 MHz, DMSO-$d_6$) δ 12.8 (br s, 1H), 9.29 (s, 1H), 9.16 (br s, 1H), 6.65 (apparent q, J = 8.1 Hz, 2H), 6.26 (s, 1H), 5.60 (dd, J = 5.7, 2.1 Hz, 1H), 5.39 (dd, J = 7.2, 4.2 Hz, 1H), 4.92 (s, 1H), 3.62-3.34 (m, 1H), 3.11-2.83 (m, 7H), 2.73-2.39 (m, 3H), 2.29 (m, 1H), 2.11 (s, 3H), 2.06 (m, 1H), 1.62 (m, 1H) |
| B72 | 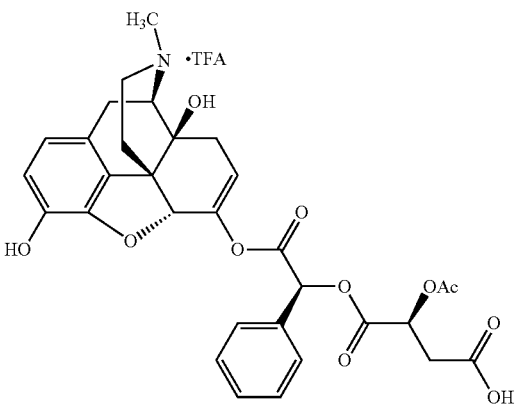 [SMILES: CC(=O)O[C@@H](CC(=O)O)C(=O)O[C@H](C(=O)OC1=CC[C@@]2(O)[C@H]3Cc4ccc(O)c5c4[C@@]2(CCCN3C)[C@H]1O5)c1ccccc1] | 594 | ¹H NMR (300 MHz, DMSO-$d_6$) δ 12.8 (br s, 1H), 9.34 (s, 1H), 9.27 (br s, 1H), 7.60-7.54 (m, 2H), 7.49-7.45 (m, 3H), 6.68 (d, J = 8.1 Hz, 1H), 6.66 (d, J = 8.1 Hz, 1H), 6.24 (s, 2H), 5.58 (dd, J = 5.7, 2.1 Hz, 1H), 5.44 (dd, J = 9.0, 3.6 Hz, 1H), 4.86 (s, 1H), 3.40-3.33 (m, 2H), 3.07-2.99 (m, 2H), 2.89-2.82 (m, 4H), 2.63-2.39 (m, 4H), 2.25 (m, 1H), 2.09-2.02 (m, 3H), 1.59 (m, 1H) |
| B73 | 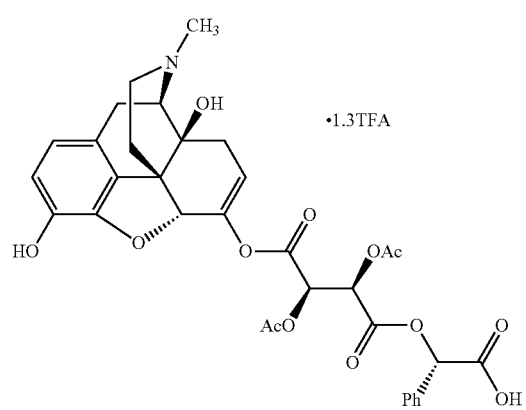 [SMILES: CC(=O)O[C@@H](C(=O)OC1=CC[C@@]2(O)[C@H]3Cc4ccc(O)c5c4[C@@]2(CCCN3C)[C@H]1O5)[C@@H](OC(C)=O)C(=O)O[C@H](C(=O)O)c1ccccc1] | 652 | ¹H NMR (300 MHz, DMSO-$d_6$) δ 9.35 (s, 1H), 9.15 (br s, 1H), 7.46-7.40 (m, 5H), 6.68 (d, J = 8.2 Hz, 1H), 6.63 (d, J = 8.2 Hz, 1H), 6.30 (s, 1H), 6.01 (s, 1H), 5.96 (d, J = 2.7 Hz, 1H), 5.86 (d, J = 2.7 Hz, 1H), 5.56-5.51 (m, 1H), 4.83 (s, 1H), 3.62 (d, J = 6.2 Hz, 1H), 3.11-3.01 (m, 1H), 3.83 (s, 3H), 2.70-2.54 (m, 1H), 2.49-2.39 (m, 1H), 2.32-2.16 (m, 5H), 2.07 (d, J = 18.0 Hz, 1H), 2.01 (s, 3H), 1.62 (d, J = 12.0 Hz, 1H), $CO_2H$ proton not observed |

| Ex. No. | Structure | Mass Spec | ¹H NMR Data |
|---|---|---|---|
| B74 | 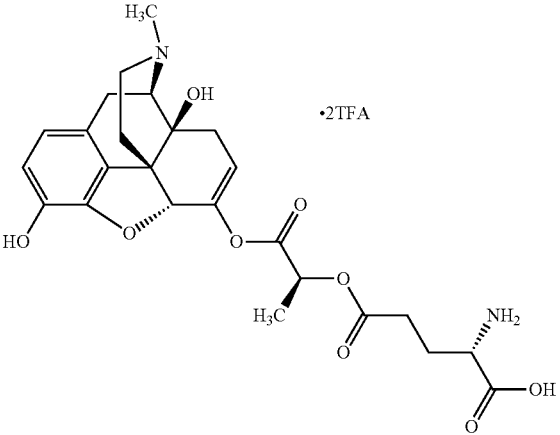 [SMILES: C[C@H](OC(=O)CC[C@H](N)C(=O)O)C(=O)OC1=CC[C@@]2(O)[C@H]3Cc4ccc(O)c5c4[C@@]2(CCCN3C)[C@H]1O5] •2TFA | 503 | ¹H NMR (300 MHz, DMSO-$d_6$) δ 9.30 (br s, 1H), 9.16 (br s, 1H), 8.27 (br s, 3H), 6.66 (apparent q, J = 8.1 Hz, 2H), 6.26 (s, 1H), 5.58 (dd, J = 6.0, 2.1 Hz, 1H), 5.13 (q, J = 4.2 Hz, 1H), 4.96 (s, 1H), 3.96 (m, 1H), 3.44 (m, 2H), 3.05 (m, 1H), 2.84 (s, 3H), 2.73-2.41 (m, 5H), 2.28 (m, 1H), 2.18-2.00 (m, 3H), 1.62 (m, 1H), 1.53 (d, J = 7.2 Hz, 3H), CO$_2$H proton not observed |
| B75 | 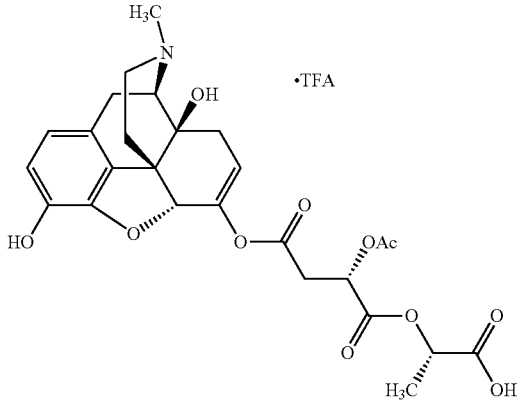 [SMILES: CC(=O)O[C@@H](CC(=O)OC1=CC[C@@]2(O)[C@H]3Cc4ccc(O)c5c4[C@@]2(CCCN3C)[C@H]1O5)C(=O)O[C@@H](C)C(=O)O] •TFA | 532 | ¹H NMR (300 MHz, DMSO-$d_6$) δ 13.2 (br s, 1H), 9.29 (s, 1H), 9.15 (br s, 1H), 6.65 (apparent q, J = 8.1 Hz, 2H), 6.23 (s, 1H), 5.58 (dd, J = 6.3, 2.1 Hz, 1H), 5.42 (dd, J = 9.3, 3.6 Hz, 1H), 5.09-4.97 (m, 2H), 3.43-3.33 (m, 1H), 3.18 (dd, J = 17.1, 3.6 Hz, 1H), 3.11-2.93 (m, 3H), 2.84 (s, 3H), 2.73-2.42 (m, 3H), 2.28 (m, 1H), 2.13-2.04 (m, 4H), 1.63 (m, 1H), 1.43 (d, J = 7.2 Hz, 3H) |
| B76 | 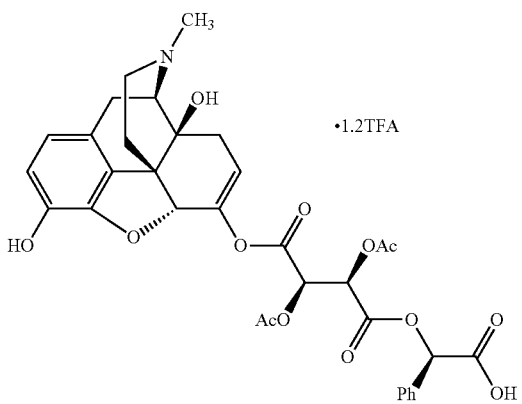 [SMILES: CC(=O)O[C@@H](C(=O)OC1=CC[C@@]2(O)[C@H]3Cc4ccc(O)c5c4[C@@]2(CCCN3C)[C@H]1O5)[C@@H](OC(C)=O)C(=O)O[C@@H](C(=O)O)c1ccccc1] •1.2TFA | 652 | ¹H NMR (300 MHz, DMSO-$d_6$) δ 13.51 (br s, 1H), 9.33 (s, 1H), 9.15 (br s, 1H), 7.51-7.40 (m, 5H), 6.67 (d, J = 8.2 Hz, 1H), 6.62 (d, J = 8.2 Hz, 1H), 6.30 (s, 1H), 6.03 (d, J = 2.7 Hz, 1H), 5.98-5.94 (m, 2H), 5.56-5.53 (m, 1H), 4.83 (s, 1H), 3.62 (d, J = 6.0 Hz, 1H), 3.40-3.33 (m, 1H), 3.12-3.02 (m, 2H), 3.83 (apparent d, J = 3.5 Hz, 3H), 2.67-2.56 (m, 1H), 2.47-2.38 (m, 1H), 2.31-2.21 (m, 4H), 2.11 (s, 3H), 2.08 (d, J = 17.7 Hz, 1H), 1.63 (d, J = 11.1 Hz, 1H) |

-continued

| Ex, No. | Structure | Mass Spec | ¹H NMR Data |
|---|---|---|---|
| B77 | 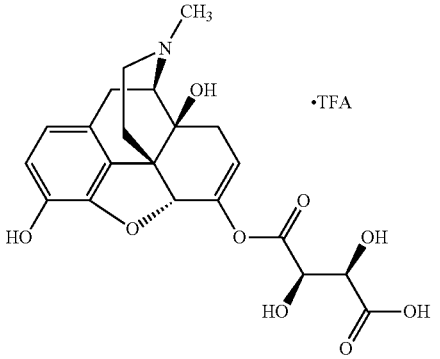 [SMILES: CN1CCC[C@]23c4c5ccc(O)c4O[C@H]2C(OC(=O)[C@H](O)[C@@H](O)C(=O)O)=CC[C@@]3(O)[C@H]1C5] | 434 | ¹H NMR (300 MHz, CD$_3$OD) δ 6.65-6.57 (m, 2H), 5.55 (dd, J = 5.4, 2.8 Hz, 1H), 4.99 (s, 1H), 4.65 (d, J = 2.2 Hz, 1H), 4.53 (d, J = 2.2 Hz, 1H), 3.56 (d, J = 6.5 Hz, 1H), 3.35 (d, J = 20.0 Hz, 1H), 3.13-3.03 (m, 2H), 2.83 (s, 3H), 2.82-2.74 (m, 1H), 2.57 (dt, J = 13.4, 4.9 Hz, 1H), 2.25-2.17 (m, 2H), 1.71 (dd, J = 13.5, 3.0 Hz, 1H), CO$_2$H, CF$_3$CO$_2$H, and four OH protons not observed |
| B78 | 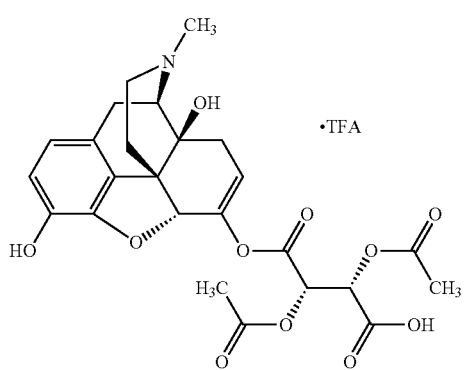 [SMILES: CC(=O)O[C@H](C(=O)O)[C@H](OC(C)=O)C(=O)OC1=CC[C@@]2(O)[C@H]3Cc4ccc(O)c5c4[C@@]2(CCCN3C)[C@H]1O5] | 518 | ¹H NMR (300 MHz, DMSO-d$_6$) δ 9.24 (br s, 1H), 9.16 (br s, 1H), 6.87 (d, J = 8.2 Hz, 1H), 6.62 (d, J = 8.2 Hz, 1H), 6.30 (s, 1H), 5.82 (d, J = 2.9 Hz, 1H), 5.60 (dd, J = 6.0, 1.9 Hz, 1H), 5.56 (d, J = 2.9 Hz, 1H), 4.94 (s, 1H), 3.63 (d, J = 6.0 Hz, 1H), 3.42-3.30 (m, 1H), 3.11-3.02 (m, 2H), 2.84 (apparent d, J = 3.8 Hz, 3H), 2.70-2.56 (m, 1H), 2.48-2.39 (m, 1H), 2.28 (d, J = 18.0, 6.1 Hz, 1H), 2.18 (s, 3H), 2.15 (s, 3H), 2.11-2.02 (m, 1H), 1.63 (d, J = 11.3 Hz, 1H), CO$_2$H proton not observed |
| B79 | 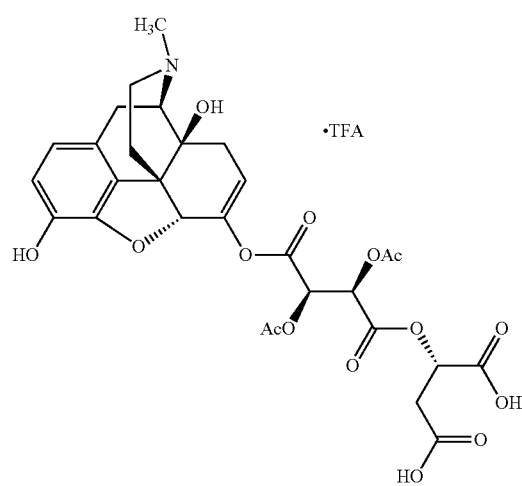 [SMILES: CC(=O)O[C@@H](C(=O)OC1=CC[C@@]2(O)[C@H]3Cc4ccc(O)c5c4[C@@]2(CCCN3C)[C@H]1O5)[C@@H](OC(C)=O)C(=O)O[C@@H](CC(=O)O)C(=O)O] | 634 | ¹H NMR (300 MHz, DMSO-d$_6$) δ 9.35 (s, 1H), 9.15 (br s, 1H), 6.64 (apparent q, J = 8.1 Hz, 2H), 6.27 (br s, 1H), 5.85 (d, J = 2.7 Hz, 1H), 5.77 (d, J = 2.7 Hz, 1H), 5.53 (dd, J = 5.7, 1.8 Hz, 1H), 5.29 (dd, J = 8.4, 3.9 Hz, 1H), 4.83 (s, 1H), 3.32 (m, 1H), 3.03 (m, 1H), 2.90-2.63 (m, 6H), 2.51-2.41 (m, 3H), 2.27 (m, 1H), 2.21 (s, 3H), 2.13 (s, 3H), 2.04 (m, 1H), 1.62 (m, 1H), CO$_2$H protons not observed |

| Ex, No. | Structure | Mass Spec | ¹H NMR Data |
|---|---|---|---|
| B80 | 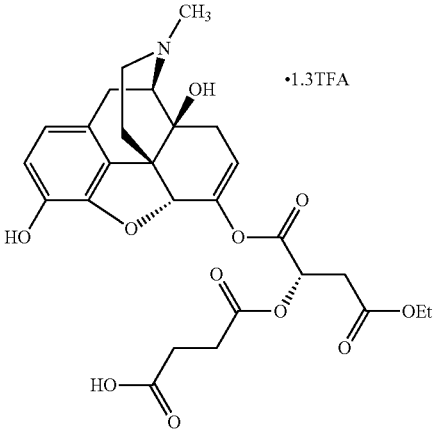 [SMILES: CCOC(=O)C[C@H](OC(=O)CCC(=O)O)C(=O)OC1=CC[C@@]2(O)[C@H]3Cc4ccc(O)c5c4[C@@]2(CCCN3C)[C@H]1O5] •1.3TFA | 546 | ¹H NMR (300 MHz, DMSO-d$_6$) δ 12.30 (br s, 1H), 9.30 (br s, 1H), 9.17 (br s, 1H), 6.68 (d, J = 8.2 Hz, 1H), 6.63 (d, J = 8.2 Hz, 1H), 6.27 (s, 1H), 5.60 (dd, J = 6.0, 1.9 Hz, 1H), 5.45 (t, J = 5.9 Hz, 1H), 4.93 (s, 1H), 4.14 (q, J = 7.1 Hz, 2H), 3.62 (d, J = 6.0 Hz, 1H), 3.14-2.98 (m, 4H), 2.84 (apparent d, J = 4.7 Hz, 3H), 2.70-2.57 (m, 3H), 2.43 (dd, J = 13.3, 4.5 Hz, 1H), 2.28 (dd, J = 17.9, 6.0 Hz, 1H), 2.05 (d, J = 17.9 Hz, 1H), 1.63 (d, J = 11.1 Hz, 1H), 1.21 (t, J = 7.1 Hz, 3H), three protons obscured by solvent peaks |
| B81 | 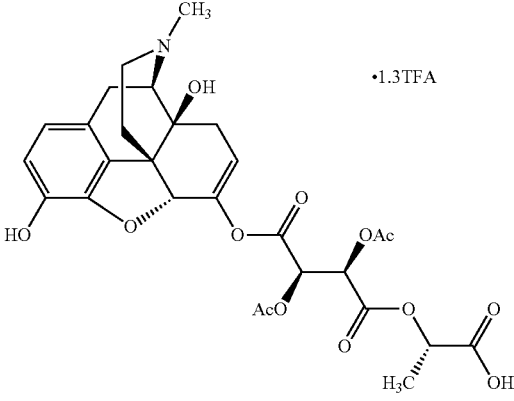 [SMILES: CC(=O)O[C@@H](C(=O)OC1=CC[C@@]2(O)[C@H]3Cc4ccc(O)c5c4[C@@]2(CCCN3C)[C@H]1O5)[C@@H](OC(C)=O)C(=O)O[C@@H](C)C(=O)O] •1.3TFA | 590 | ¹H NMR (300 MHz, DMSO-d$_6$) δ 9.37 (br s, 1H), 9.17 (br s, 1H), 6.68 (d, J = 8.2 Hz, 1H), 6.63 (d, J = 8.2Hz, 1H), 6.33 (br s, 1H), 5.89 (d, J = 2.7 Hz, 1H), 5.85 (d, J = 2.7 Hz, 1H), 5.55-5.53 (m, 1H), 5.05 (q, J = 7.0 Hz, 1H), 4.84 (s, 1H), 3.63 (d, J = 6.2 Hz, 1H), 3.11-3.03 (m, 2H), 3.83 (apparent d, J = 1.8 Hz, 3H), 2.71-2.57 (m, 1H), 2.47-2.39 (m, 1H), 2.43 (dd, J = 18.0, 6.3 Hz, 1H), 2.22 (s, 3H), 2.15 (s, 3H), 2.07 (d, J = 18.0 Hz, 1H), 1.62 (d, J = 11.2 Hz, 1H), 1.39 (d, J = 7.0 Hz, 3H), CO$_2$H proton not observed |
| B82 | 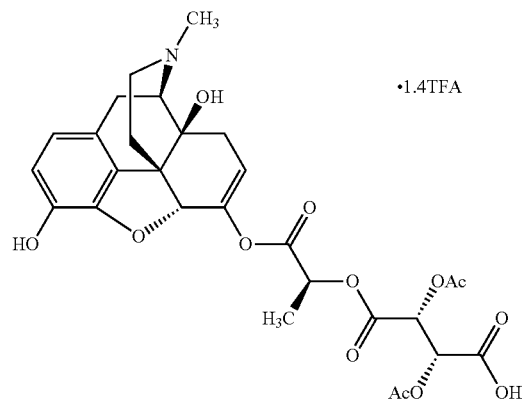 [SMILES: CC(=O)O[C@@H](C(=O)O)[C@@H](OC(C)=O)C(=O)O[C@@H](C)C(=O)OC1=CC[C@@]2(O)[C@H]3Cc4ccc(O)c5c4[C@@]2(CCCN3C)[C@H]1O5] •1.4TFA | 590 | ¹H NMR (300 MHz, DMSO-d$_6$) δ 13.9 (br s, 1H), 9.29 (br s, 1H), 9.17 (br s 1H), 6.68 (d, J = 8.2 Hz, 1H), 6.63 (d, J = 8.2 Hz, 1H), 6.26 (s, 1H), 5.72 (d, J = 2.8 Hz, 1H), 5.62 (d, J = 2 8 Hz, 1H), 5.59 (dd, J = 6.0, 2.2 Hz, 1H), 5.28 (q, J = 7.0 Hz, 1H), 5.00 (s, 1H), 3.62 (d, J = 6.3 Hz, 1H), 3.37 (d, J = 20.0 Hz, 1H), 3.13-3.01 (m, 2H), 2.83 (apparent d, J = 4.6 Hz, 3H), 2.70-2.57 (m, 1H), 2.43 (dd, J = 14.5, 4.7 Hz, 1H), 2.29 (dd, J = 17.9, 6.4 Hz, 1H), 2.14 (s, 3H), 2.11-2.02 (m, 4H), 1.63 (d, J = 10.8 Hz, 1H), 1.50 (d, J = 7.0 Hz, 3H) |

| Ex, No. | Structure | Mass Spec | ¹H NMR Data |
|---|---|---|---|
| B83 | 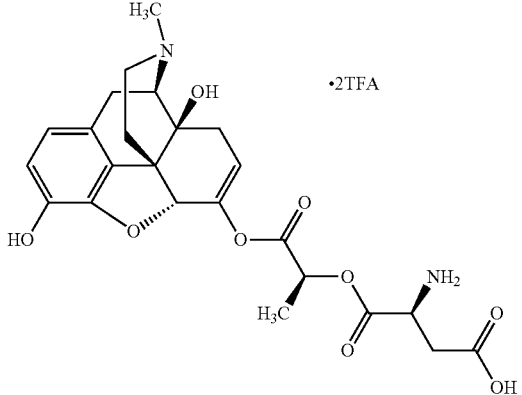 [SMILES: C[C@H](OC(=O)[C@@H](N)CC(=O)O)C(=O)OC1=CC[C@@]2(O)[C@H]3Cc4ccc(O)c5c4[C@@]2(CCCN3C)[C@H]1O5] •2TFA | 489 | ¹H NMR (300 MHz, DMSO-$d_6$) δ 9.15 (br s, 2H), 8.44 (br s, 2H), 6.66 (apparent q, J = 8.1 Hz, 2H), 6.26 (s, 2H), 5.59 (m, 1H), 5.33 (q, J = 7.2 Hz, 1H), 4.98 (s, 1H), 4.45 (m, 1H), 3.35 (m, 2H), 3.11-2.88 (m, 4H), 2.84 (s, 3H), 2.73-2.42 (m, 3H), 2.29 (m, 1H), 2.06 (m, 1H), 1.64-1.53 (m, 4H) |
| B84 | 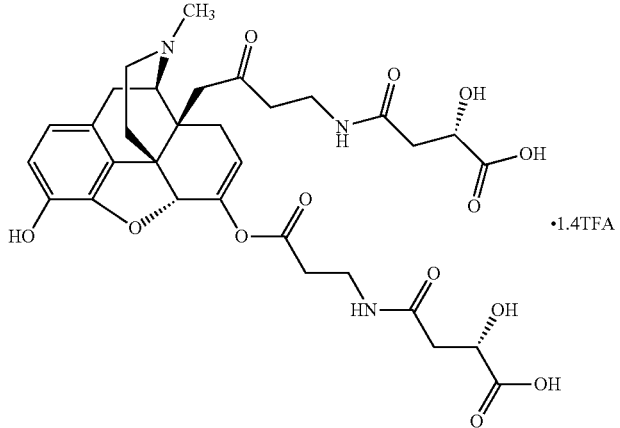 [SMILES: CN1CCC[C@]23c4c5ccc(O)c4O[C@H]2C(OC(=O)CCNC(=O)C[C@H](O)C(=O)O)=CC[C@@]3(CC(=O)CCNC(=O)C[C@H](O)C(=O)O)[C@H]1C5] •1.4TFA | 676 | ¹H NMR (300 MHz, DMSO-$d_6$) δ 12.5 (br s, 2H), 9.51-9.28 (m, 2H), 8.13 (t, J = 5.7 Hz, 1H), 8.02 (t, J = 5.5 Hz, 1H), 6.72 (d, J = 8.2 Hz, 1H), 6.66 (d, J = 8.2 Hz, 1H), 5.50 (dd, J = 6.6, 1.7 Hz, 1H), 5.06 (s, 1H), 4.78-4.65 (m, 1H), 4.32-4.27 (m, 2H), 3.56-3.43 (m, 2H), 3.40-3.15 (m, 6H), 3.08-2.88 (m, 4H), 2.87-2.69 (m, 2H), 2.67-2.57 (m, 3H), 2.48-2.30 (m, 4H), 2.08 (d, J = 18.8 Hz, 1H), 1.78 (d, J = 12.9 Hz, 1H), two protons obscured by solvent peaks |
| B85 | 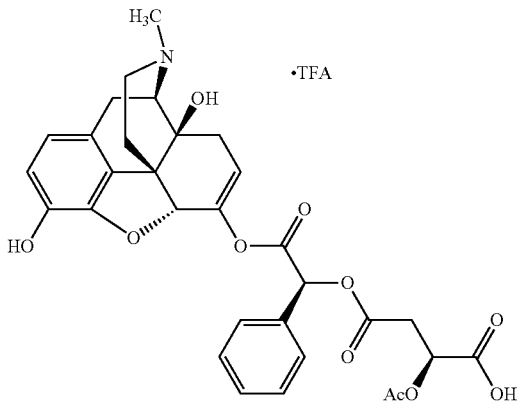 [SMILES: CC(=O)O[C@@H](CC(=O)O[C@H](C(=O)OC1=CC[C@@]2(O)[C@H]3Cc4ccc(O)c5c4[C@@]2(CCCN3C)[C@H]1O5)c1ccccc1)C(=O)O] •TFA | 594 | ¹H NMR (300 MHz, DMSO-$d_6$) δ 13.4 (br s, 1H), 9.28 (s, 1H), 9.14 (br s, 1H), 7.59-7.54 (m, 2H), 7.52-7.45 (m, 3H), 6.64 (apparent q, J = 8.1 Hz, 2H), 6.25 (s, 1H), 6.17 (s, 1H), 5.60 (dd, J = 5.7, 2.1 Hz, 1H), 5.31 (dd, J = 8.7, 3.9 Hz, 1H), 4.87 (s, 1H), 3.62-3.33 (m, 2H), 3.14-2.96 (m, 4H), 2.82 (d, J = 4.2 Hz, 3H), 2.64-2.38 (m, 2H), 2.25 (m, 1H), 2.09-2.02 (m, 4H), 1.60 (m, 1H) |

| Ex, No. | Structure | Mass Spec | ¹H NMR Data |
|---|---|---|---|
| B86 | ·TFA | 634 | ¹H NMR (300 MHz, DMSO-d$_6$) δ 13.5 (br s, 1H), 12.8 (br s, 1H), 9.36 (s, 1H), 9.16 (br s, 1H), 6.65 (apparent q, J = 8.1 Hz, 2H), 6.28 (br s, 1H), 5.82 (d, J = 2.4 Hz, 1H), 5.78 (d, J = 2.4 Hz, 1H), 5.54 (dd, J = 6.0, 1.8 Hz, 1H), 5.35 (dd, J = 7.5, 3.9 Hz, 1H), 4.84 (s, 1H), 3.62-3.34 (m, 2H), 3.02 (m, 1H), 2.93-2.72 (m, 5H), 2.63-2.40 (m, 3H), 2.27 (m, 1H), 2.22 (s, 3H), 2.11 (s, 3H), 2.07 (m, 1H), 1.62 (m, 1H) |
| B87 | ·2TFA | 615 | ¹H NMR (300 MHz, DMSO-d$_6$) δ 9.30 (s, 1H), 9.16 (br s, 1H), 8.05-7.98 (m, 2H), 7.64 (br s, 3H), 6.65 (apparent q, J = 8.1 Hz, 2H), 6.25 (s, 2H), 5.58 (dd, J = 5.7, 1.8 Hz, 1H), 5.10 (q, J = 7.2 Hz, 1H), 4.96 (s, 1H), 4.15 (m, 1H), 3.67-3.27 (m, 4H), 3.11-3.03 (m, 2H), 2.84 (d, J = 4.8 Hz, 3H), 2.78-2.72 (m, 2H), 2.67-2.46 (m, 2H), 2.29 (m, 1H), 2.06 (m, 1H), 1.84 (s, 3H), 1.65-1.25 (m, 11H) |
| B88 | ·1.3TFA | 506 | ¹H NMR (300 MHz, DMSO-d$_6$) δ 12.83 (br s, 1H), 9.30 (br s, 1H), 9.17 (br s, 1H), 6.69 (d, J = 8.1 Hz, 1H), 6.63 (d, J = 8.1 Hz, 1H), 6.27 (s, 1H), 5.60 (dd, J = 6.0, 2.0 Hz, 1H), 5.18 (q, J = 7.0 Hz, 1H), 4.99 (s, 1H), 4.48 (d, J = 2.2 Hz, 1H), 4.39 (d, J = 2.1 Hz, 1H), 3.63 (d, J = 6.3 Hz, 1H), 3.38 (d, J = 20.0 Hz, 1H), 3.14-3.00 (m, 2H), 2.84 (apparent d, J = 4.2 Hz, 3H), 2.70-2.57 (m, 1H), 2.44 (dd, J = 13.6, 4.9 Hz, 1H), 2.29 (dd, J = 17.9, 6.1 Hz, 1H), 2.07 (d, J = 17.9 Hz, 1H), 1.63 (d, J = 11.3 Hz, 1H), 1.53 (d, J = 7.0 Hz, 3H), two protons obscured by solvent peaks |

-continued

| Ex. No. | Structure | Mass Spec | $^1$H NMR Data |
|---|---|---|---|
| B89 | 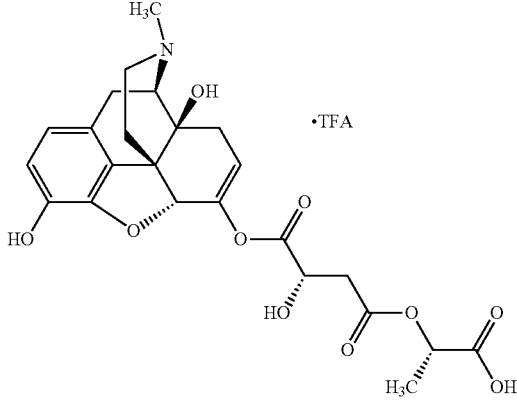 [SMILES: C[C@H](OC(=O)C[C@H](O)C(=O)OC1=CC[C@@]2(O)[C@H]3Cc4ccc(O)c5c4[C@@]2(CCCN3C)[C@H]1O5)C(=O)O] ·TFA | 490 | $^1$H NMR (300 MHz, DMSO-$d_6$) δ 9.30 (s, 1H), 9.14 (br s, 1H), 6.64 (apparent q, J = 8.4 Hz, 2H), 6.24 (br s, 1H), 5.97 (d, J = 6.0 Hz, 1H), 5.57 (d, J = 3.9 Hz, 1H), 5.00-4.93 (m, 2H), 4.53 (m, 1H), 3.41-3.33 (m, 2H), 3.05 (m, 1H), 2.89-2.72 (m, 6H), 2.63- 2.41 (m, 3H), 2.27 (m, 1H), 2.07 (m, 1H), 1.62 (m, 1H), 1.40 (d, J = 7.2 Hz, 3H) |
| B90 | 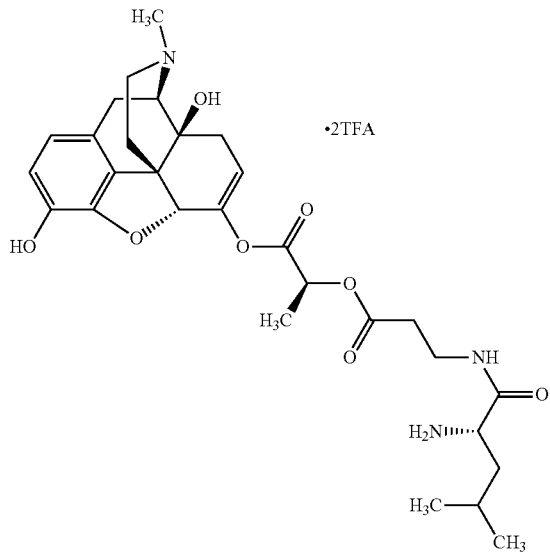 [SMILES: CC(C)C[C@H](N)C(=O)NCCC(=O)O[C@@H](C)C(=O)OC1=CC[C@@]2(O)[C@H]3Cc4ccc(O)c5c4[C@@]2(CCCN3C)[C@H]1O5] ·2TFA | 558 | $^1$H NMR (300 MHz, DMSO-$d_6$) δ 9.31 (s, 1H), 9.16 (br s, 1H), 8.62 (t, J = 5.4 Hz, 1H), 8.09 (br s, 3H), 6.65 (apparent q, J = 8.1 Hz, 2H), 6.24 (s, 1H), 5.58 (dd, J = 6.0, 2.1 Hz, 1H), 5.12 (q, J = 6.9 Hz, 1H), 4.96 (s, 1H), 3.67-3.27 (m, 4H), 3.05 (m, 1H), 2.84 (d, J = 4.8 Hz, 3H), 2.63-2.41 (m, 6H), 2.28 (m, 1H), 2.05 (m, 1H), 1.64- 1.52 (m, 7H), 0.89 (dd, J = 6.0, 2.1 Hz, 6H) |
| B91 | 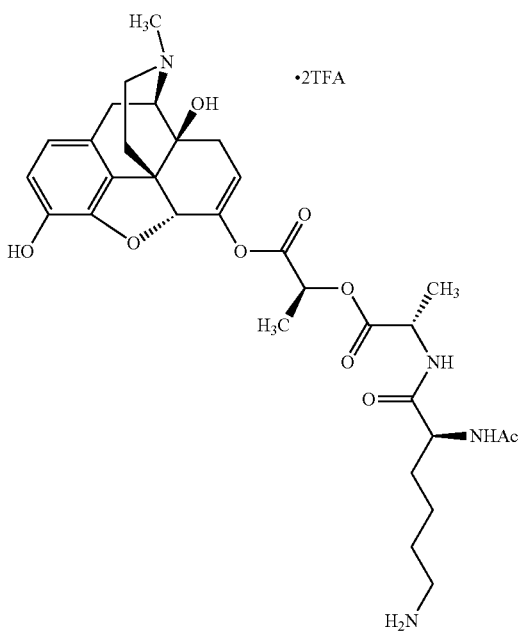 [SMILES: CC(=O)N[C@@H](CCCCN)C(=O)N[C@@H](C)C(=O)O[C@@H](C)C(=O)OC1=CC[C@@]2(O)[C@H]3Cc4ccc(O)c5c4[C@@]2(CCCN3C)[C@H]1O5] ·2TFA | 615 | $^1$H NMR (300 MHz, DMSO-$d_6$) δ 9.30 (s, 1H), 9.16 (br s, 1H), 8.43 (d, J = 6.3 Hz, 1H), 7.99 (d, J = 7.8 Hz, 1H), 7.61 (br s, 3H), 6.65 (apparent q, J = 8.1 Hz, 2H), 6.22 (s, 1H), 5.57 (dd, J = 6.0, 2.1 Hz, 1H), 5.14 (q, J = 6.9 Hz, 1H), 4.35-4.30 (m, 3H), 3.46- 3.33 (m, 2H), 3.11 (m, 1H), 2.84 (d, J = 5.1 Hz, 3H), 2.74-2.41 (m, 3H), 2.27 (m, 1H), 2.07 (m, 1H), 1.84 (s, 3H), 1.64-1.32 (m, 14H) |

-continued

| Ex, No. | Structure | Mass Spec | ¹H NMR Data |
|---|---|---|---|
| B92 | 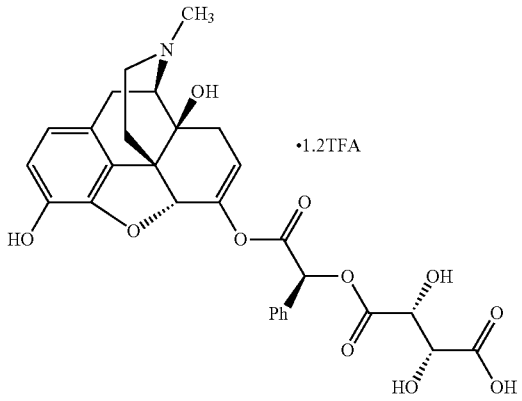 [SMILES: CN1CCC[C@]23c4c5ccc(O)c4O[C@H]2C(OC(=O)[C@@H](OC(=O)[C@H](O)[C@@H](O)C(=O)O)c2ccccc2)=CC[C@@]3(O)[C@H]1C5] ·1.2TFA | 568 | ¹H NMR (300 MHz, DMSO-$d_6$) δ 12.86 (br s, 1H), 9.30 (br s, 1H), 9.14 (br s, 1H), 7.62-7.56 (m, 2H), 7.50-7.43 (d, 3H), 6.68 (d, J = 8.1 Hz, 1H), 6.62 (d, J = 8.1 Hz, 1H), 6.27 (s, 1H), 6.16 (s, 1H), 5.61 (dd, J = 6.0, 2.0 Hz, 1H), 4.90 (s, 1H), 4.58 (d, J = 2.0 Hz, 1H), 4.38 (d, J = 2.3 Hz, 1H), 3.61 (d, J = 6.2 Hz, 1H), 3.37 (d, J = 19.8 Hz, 1H), 3.13-3.00 (m, 2H), 2.83 (d, J = 4.3 Hz, 3H), 2.68-2.56 (m, 1H), 2.41 (dd, J = 13.0, 4.7 Hz, 1H), 2.26 (dd, J = 18.0, 6.2 Hz, 1H), 2.07 (d, J = 18.0 Hz, 1H), 1.60 (d, J = 10.8 Hz, 1H), two protons obscured by solvent peaks |
| B93 | 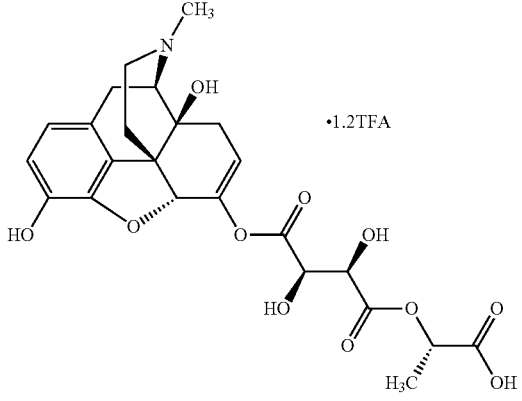 [SMILES: C[C@H](OC(=O)[C@H](O)[C@@H](O)C(=O)OC1=CC[C@@]2(O)[C@H]3Cc4ccc(O)c5c4[C@@]2(CCCN3C)[C@H]1O5)C(=O)O] ·1.2TFA | 506 | ¹H NMR (300 MHz, DMSO-$d_6$) δ 13.4 (br s, 1H), 9.32 (s, 1H), 9.17 (br s, 1H), 6.69 (d, J = 8.2 Hz, 1H), 6.63 (d, J = 8.2 Hz, 1H), 6.26 (s, 1H), 5.83 (br s, 2H), 5.56 (dd, J = 5.9, 1.9 Hz, 1H), 5.03 (s, 1H), 4.99 (q, J = 7.1 Hz, 1H), 4.62 (s, 1H), 4.56 (s, 1H), 3.62 (d, J = 6.1 Hz, 1H), 3.38 (d, J = 20.0 Hz, 1H), 3.13-3.01 (m, 2H), 2.84 (apparent d, J = 4.1 Hz, 3H), 2.71-2.58 (m, 1H), 2.45 (dd, J = 14.1, 5.6 Hz, 1H), 2.30 (dd, J = 18.0, 6.1 Hz, 1H), 2.06 (d, J = 18.0 Hz, 1H), 1.64 (d, J = 10.7 Hz, 1H), 1.43 (d, J = 7.1 Hz, 3H) |
| B94 | 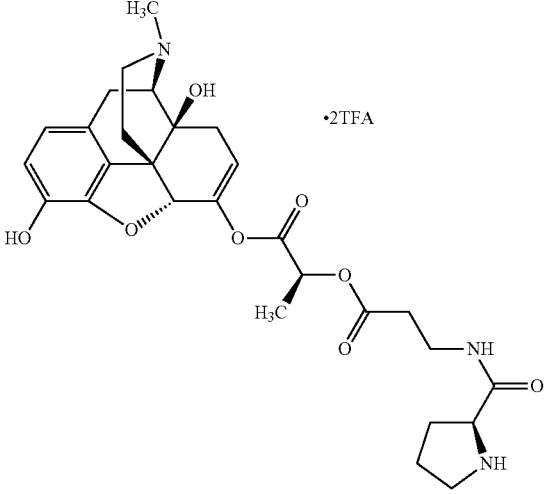 [SMILES: C[C@H](OC(=O)CCNC(=O)[C@@H]1CCCN1)C(=O)OC1=CC[C@@]2(O)[C@H]3Cc4ccc(O)c5c4[C@@]2(CCCN3C)[C@H]1O5] ·2TFA | 542 | ¹H NMR (300 MHz, DMSO-$d_6$) δ 9.31 (s, 1H), 9.19 (br s, 2H), 8.61 (t, J = 5.7 Hz, 1H), 8.54 (br s, 1H), 6.66 (apparent q, J = 8.1 Hz, 2H), 6.25 (s, 1H), 5.58 (dd, J = 6.0, 2.1 Hz, 1H), 5.12 (q, J = 6.9 Hz, 1H), 4.96 (s, 1H), 4.13-3.03 (m, 10H), 2.84 (d, J = 4.5 Hz, 3H), 2.64-2.19 (m, 5H), 2.05 (m, 1H), 1.92-1.77 (m, 3H), 1.62 (m, 1H), 1.53 (d, J = 7.2 Hz, 3H) |

| Ex, No. | Structure | Mass Spec | ¹H NMR Data |
|---|---|---|---|
| B95a | 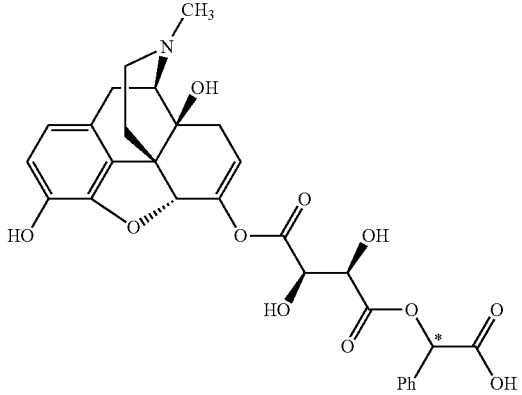<br>Isomer A: •1.5TFA | 568 | ¹H NMR (300 MHz, DMSO-$d_6$) δ 13.38 (br s,1H), 9.32 (s, 1H), 9.17 (br s, 1H), 7.54-7.47 (m, 2H), 7.47-7.39 (m, 3H), 6.69 (d, J = 8.2 Hz, 1H), 6.63 (d, J = 8.2 Hz, 1H), 6.26 (s, 1H), 5.99-5.80 (m, 3H), 5.54 (dd, J = 6.1, 2.0 Hz, 1H), 5.02 (s, 1H), 4.67 (d, J = 1.6 Hz, 1H), 4.59 (d, J = 1.5 Hz, 1H), 3.62 (d, J = 7.1 Hz, 1H), 3.38 (d, J = 18.7 Hz, 1H), 3.13-3.00 (m, 2H), 2.84 (s, 3H), 2.70-2.57 (m, 1H), 2.43 (dd, J = 14.2, 5.5 Hz, 1H), 2.28 (dd, J = 17.5, 6.2 Hz, 1H), 2.05 (d, J = 17.7 Hz, 1H), 1.63 (d, J = 10.5 Hz, 1H) |
| B95b | 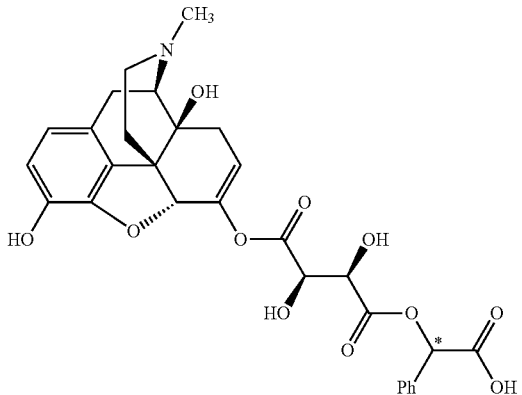<br>Isomer B: •2.0TFA | 568 | ¹H NMR (300 MHz, DMSO-$d_6$) δ 13.28 (br s, 1H), 9.32 (s, 1H), 9.15 (br s, 1H), 7.56-7.47 (m, 2H), 7.47-7.37 (m, 3H), 6.68 (d, J = 8.2 Hz, 1H), 6.63 (d, J = 8.2 Hz, 1H), 6.29 (br s, 1H), 5.94-5.89 (m, 3H), 5.56-5.35 (m, 1H), 5.03 (s, 1H), 4.70 (s, 1H), 4.64 (dd, J = 8.0, 2.4 Hz, 1H), 3.61 (d, J = 5.6 Hz, 1H), 3.41-3.38 (m, 1H), 3.14-2.99 (m, 2H), 2.83 (s, 3H), 2.71-2.58 (m, 1H), 2.47-2.38 (m, 1H), 2.27 (dd, J = 17.4, 6.5 Hz, 1H), 2.05 (d, J = 18.0 Hz, 1H), 1.63 (d, J = 12.8 Hz, 1H) |
| B96 | 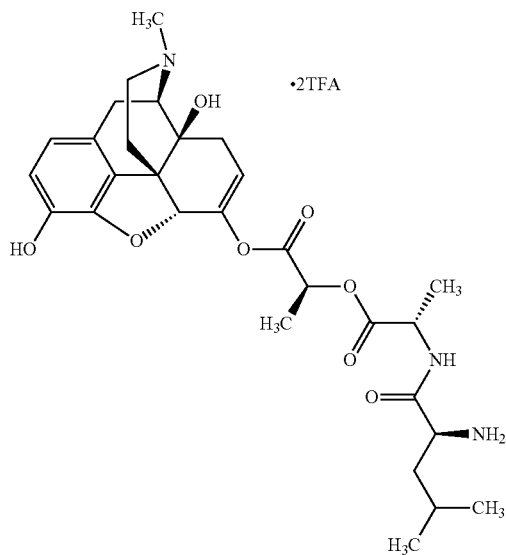 [SMILES: CC(C)C[C@H](N)C(=O)N[C@@H](C)C(=O)O[C@@H](C)C(=O)OC1=CC[C@@]2(O)[C@H]3Cc4ccc(O)c5c4[C@@]2(CCCN3C)[C@H]1O5] | 558 | ¹H NMR (300 MHz, DMSO-$d_6$) δ 9.32 (s, 1H), 9.15 (br s, 1H), 8.93 (d, J = 6.9 Hz, 1H), 8.13 (br s, 3H), 6.65 (apparent q, J = 8.1 Hz, 2H), 6.24 (s, 1H), 5.58 (dd, J = 6.0, 2.1 Hz, 1H), 5.19 (q, J = 6.9 Hz, 1H), 4.95 (s, 1H), 4.47 (m, 1H), 3.75 (m, 1H), 3.64-3.52 (m, 2H), 3.05 (m, 1H), 2.84 (d, J = 4.5 Hz, 3H), 2.73-2.41 (m, 3H), 2.27 (m, 1H), 2.07 (m, 1H), 1.73-1.51 (m, 7H), 1.41 (d, J = 7.5 Hz, 3H), 0.91 (t, J = 6.6 Hz, 6H) |

| Ex, No. | Structure | Mass Spec | ¹H NMR Data |
|---|---|---|---|
| B97 | 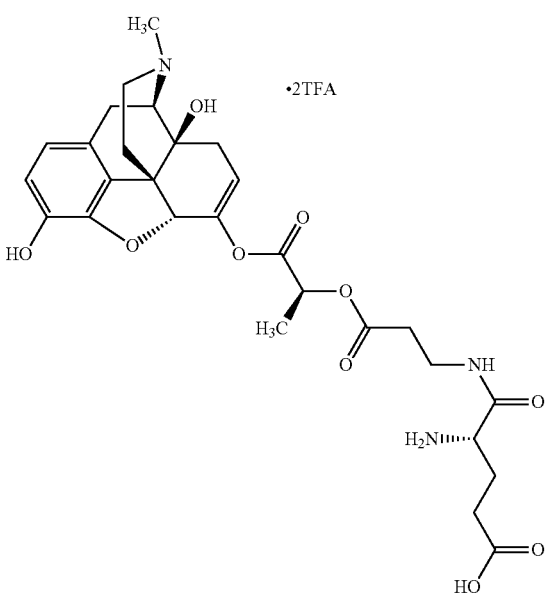 [SMILES: C[C@H](OC(=O)CCNC(=O)[C@@H](N)CCC(=O)O)C(=O)OC1=CC[C@@]2(O)[C@H]3Cc4ccc(O)c5c4[C@@]2(CCCN3C)[C@H]1O5] •2TFA | 574 | ¹H NMR (300 MHz, DMSO-d$_6$) δ 12.35 (br s, 1H), 9.32 (s, 1H), 9.17 (br s, 1H), 8.61 (t, J = 5.4 Hz, 1H), 8.14 (br s, 3H), 6.66 (apparent q, J = 8.1 Hz, 2H), 6.26 (s, 1H), 5.58 (dd, J = 6.0, 2.1 Hz, 1H), 5.11 (q, J = 7.2 Hz, 1H), 4.96 (s, 1H), 3.74 (m, 1H), 3.67-3.27 (m, 4H), 3.06 (m, 1H), 2.84 (s, 3H), 2.63-2.41 (m, 5H), 2.32-2.26 (m, 3H), 2.05 (m, 1H), 1.96-1.88 (m, 2H), 1.62 (m, 1H), 1.53 (d, J = 7.2 Hz, 3H) |
| B98 | 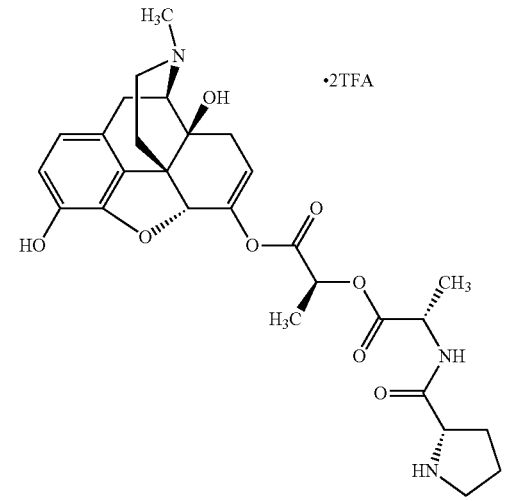 [SMILES: C[C@H](NC(=O)[C@@H]1CCCN1)C(=O)O[C@@H](C)C(=O)OC1=CC[C@@]2(O)[C@H]3Cc4ccc(O)c5c4[C@@]2(CCCN3C)[C@H]1O5] •2TFA | 542 | ¹H NMR (300 MHz, DMSO-d$_6$) δ 9.32 (s, 1H), 9.25 (br s, 1H), 9.17 (br s, 1H), 8.97 (d, J = 6.6 Hz, 1H), 8.56 (br s, 1H), 6.66 (apparent q, J = 8.1 Hz, 2H), 6.25 (s, 1H), 5.58 (dd, J = 6.0, 2.4 Hz, 1H), 5.18 (q, J = 6.9 Hz, 1H), 4.95 (s, 1H), 4.44 (m, 1H), 4.21 (m, 1H), 3.67-3.03 (m, 4H), 2.84 (d, J = 4.5 Hz, 3H), 2.72-2.41 (m, 3H), 2.31-2.27 (m, 2H), 2.07 (m, 1H), 1.91-1.84 (m, 3H), 1.62 (m, 1H), 1.54 (d, J = 7.2 Hz, 3H), 1.41 (d, J = 7.2 Hz, 3H) |

| Ex, No. | Structure | Mass Spec | ¹H NMR Data |
|---|---|---|---|
| B99 | 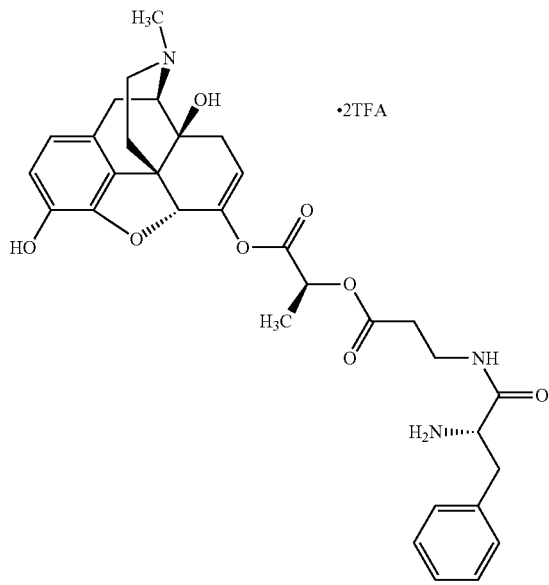 [SMILES: C[C@H](OC(=O)CCNC(=O)[C@@H](N)Cc1ccccc1)C(=O)OC1=CC[C@@]2(O)[C@H]3Cc4ccc(O)c5c4[C@@]2(CCCN3C)[C@H]1O5] | 592 | ¹H NMR (300 MHz, DMSO-$d_6$) δ 9.32 (s, 1H), 9.16 (br s, 1H), 8.49 (t, J = 5.4 Hz, 1H), 8.19 (br s, 3H), 7.37-7.24 (m, 5H), 6.65 (apparent q, J = 8.1 Hz, 2H), 6.25 (s, 1H), 5.57 (dd, J = 5.7, 1.8 Hz, 1H), 5.08 (q, J = 6.9 Hz, 1H), 3.94 (m, 1H), 3.64-3.16 (m, 6H), 3.11-2.92 (m, 4H), 2.84 (d, J = 3.3 Hz, 3H), 2.73-2.24 (m, 3H), 2.28 (m, 1H), 2.05 (m, 1H), 1.61 (m, 1H), 1.53 (d, J = 7.2 Hz, 3H) |

In further embodiments, the abuse-resistant opioid compound may be selected from one or more of:

| Ex, No. | Structure | Name |
|---|---|---|
| C1 | 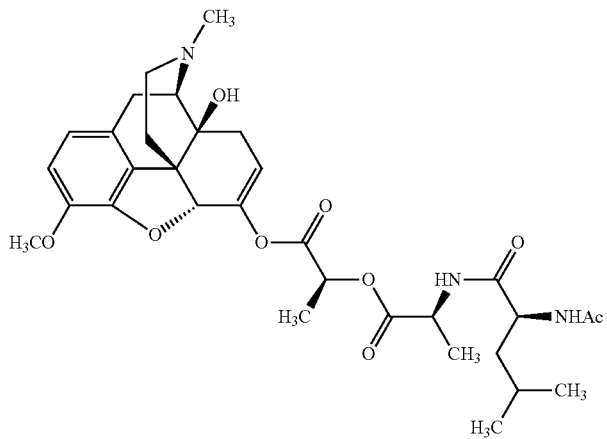 [SMILES: COc1ccc2c3c1O[C@H]1C(OC(=O)[C@H](C)OC(=O)[C@H](C)NC(=O)[C@H](CC(C)C)NC(C)=O)=CC[C@@]4(O)[C@@H](C2)N(C)CCC[C@]314] | (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(((S)-2-((S)-2-acetamido-4-methylpentanamido)propanoyl)oxy)propanoate |

| Ex, No. | Structure | Name |
|---|---|---|
| C2 | 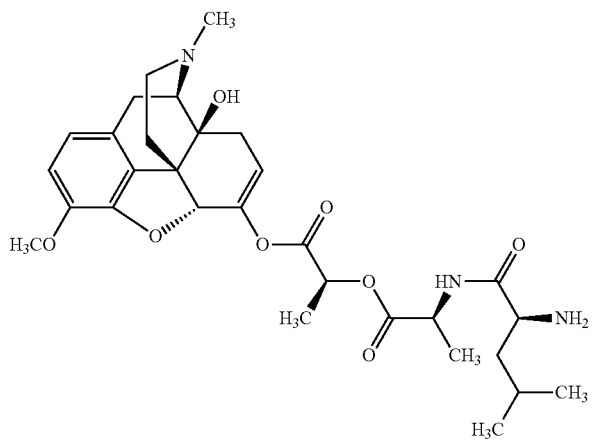 [SMILES: COc1ccc2c3c1O[C@H]1C(OC(=O)[C@H](C)OC(=O)[C@H](C)NC(=O)[C@@H](N)CC(C)C)=CC[C@@]4(O)[C@@H](C2)N(C)CCC[C@]314] | (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(((S)-2-((S)-2-amino-4-methylpentanamido)propanoyl)oxy)propanoate |
| C3 | 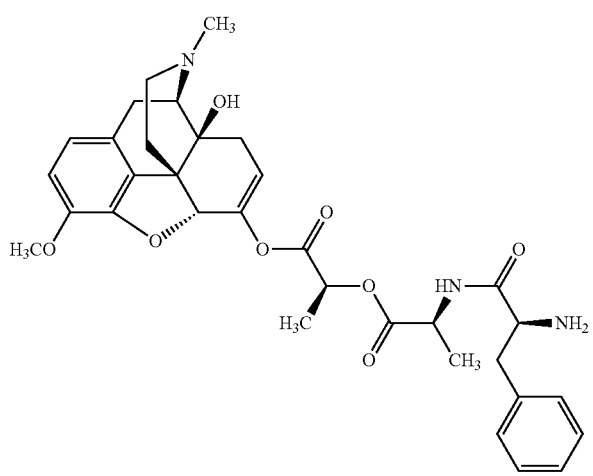 [SMILES: COc1ccc2c3c1O[C@H]1C(OC(=O)[C@H](C)OC(=O)[C@H](C)NC(=O)[C@@H](N)Cc4ccccc4)=CC[C@@]4(O)[C@@H](C2)N(C)CCC[C@]314] | (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(((S)-2-((S)-2-amino-3-phenylpropanamido)propanoyl)oxy)propanoate |
| C4 | 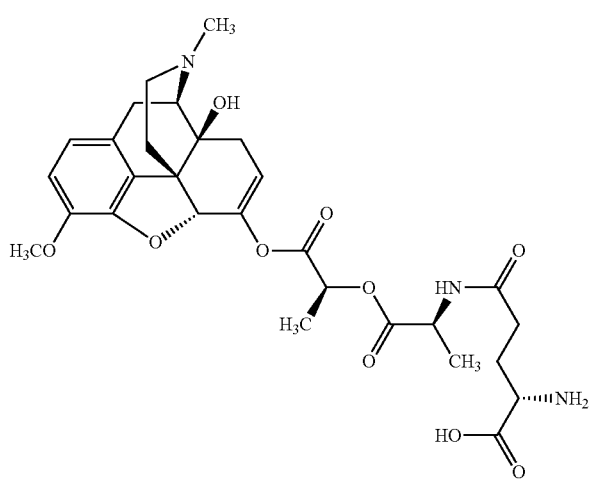 [SMILES: COc1ccc2c3c1O[C@H]1C(OC(=O)[C@H](C)OC(=O)[C@H](C)NC(=O)CC[C@H](N)C(=O)O)=CC[C@@]4(O)[C@@H](C2)N(C)CCC[C@]314] | (S)-2-amino-5-(((S)-1-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl)amino)-5-oxopentanoic acid |

| Ex, No. | Structure | Name |
|---|---|---|
| C5 | 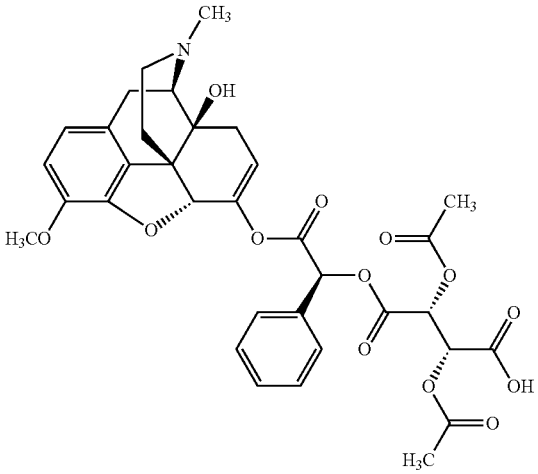 [SMILES: COc1ccc2c3c1O[C@H]1C(OC(=O)[C@@H](OC(=O)[C@H](OC(C)=O)[C@@H](OC(C)=O)C(=O)O)c4ccccc4)=CC[C@@]4(O)[C@@H](C2)N(C)CCC[C@]314] | (2R,3R)-2,3-diacetoxy-4-(((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid |
| C6 | 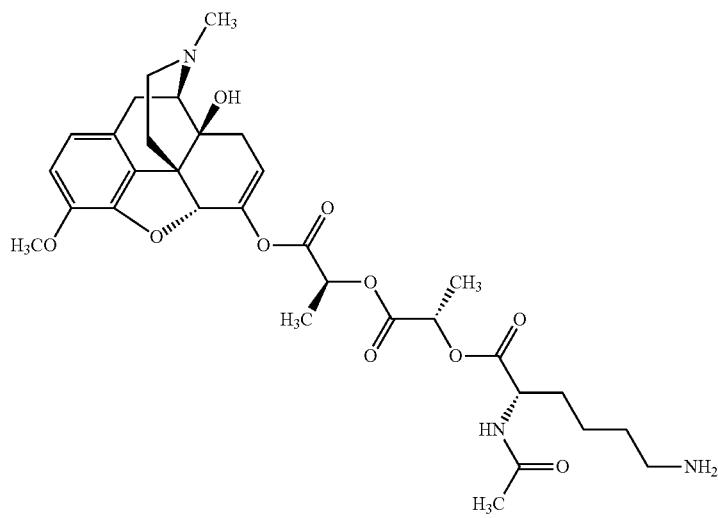 [SMILES: COc1ccc2c3c1O[C@H]1C(OC(=O)[C@H](C)OC(=O)[C@H](C)OC(=O)[C@H](CCCCN)NC(C)=O)=CC[C@@]4(O)[C@@H](C2)N(C)CCC[C@]314] | (S)-(S)-1-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl 2-acetamido-6-aminohexanoate |
| C7 | 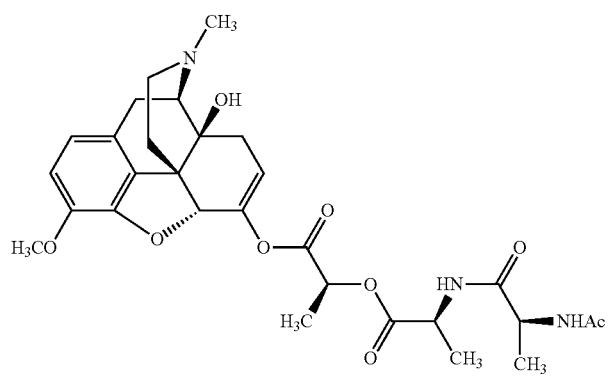 [SMILES: COc1ccc2c3c1O[C@H]1C(OC(=O)[C@H](C)OC(=O)[C@H](C)NC(=O)[C@H](C)NC(C)=O)=CC[C@@]4(O)[C@@H](C2)N(C)CCC[C@]314] | (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(((S)-2-((S)-2-acetamidopropanamido)propanoyl)oxy)propanoate |

| Ex, No. | Structure | Name |
|---|---|---|
| C8 | 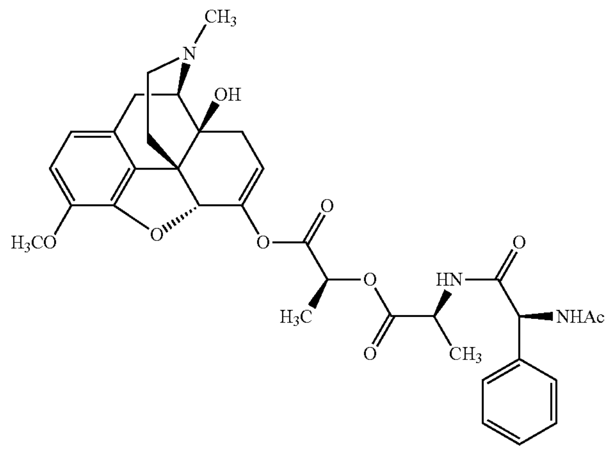 [SMILES: COc1ccc2c3c1O[C@H]1C(OC(=O)[C@H](C)OC(=O)[C@H](C)NC(=O)[C@@H](NC(C)=O)c4ccccc4)=CC[C@@]4(O)[C@@H](C2)N(C)CCC[C@]314] | (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(((S)-2-((S)-2-acetamido-2-phenylacetamido)propanoyl)oxy)propanoate |
| C9 | 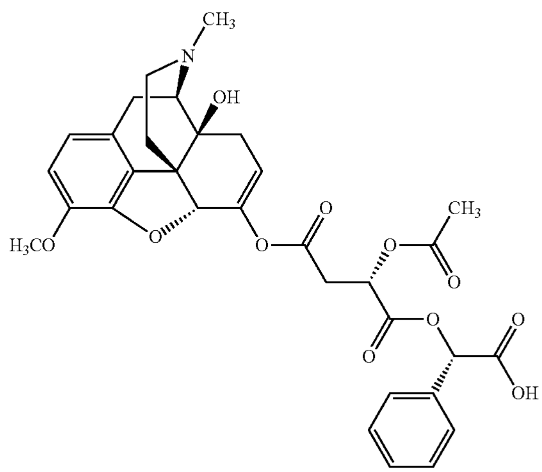 [SMILES: COc1ccc2c3c1O[C@H]1C(OC(=O)C[C@H](OC(C)=O)C(=O)O[C@H](C(=O)O)c4ccccc4)=CC[C@@]4(O)[C@@H](C2)N(C)CCC[C@]314] | (S)-2-(((S)-2-acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]-isoquinolin-7-yl)oxy)-4-oxobutanoyl)oxy)-2-phenylacetic acid |
| C10 | 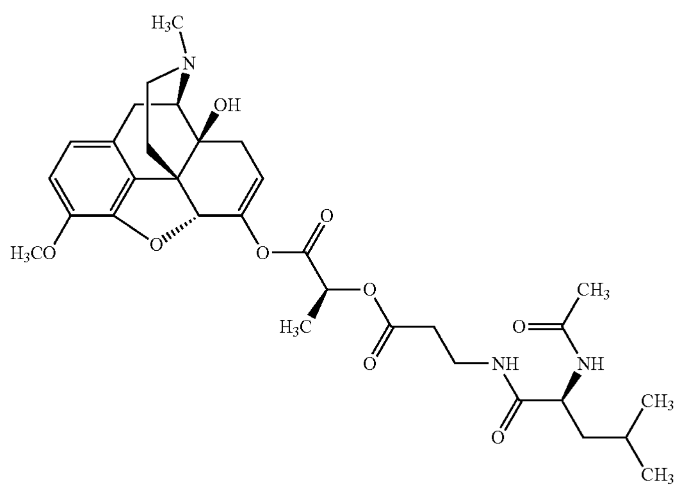 [SMILES: COc1ccc2c3c1O[C@H]1C(OC(=O)[C@H](C)OC(=O)CCNC(=O)[C@H](CC(C)C)NC(C)=O)=CC[C@@]4(O)[C@@H](C2)N(C)CCC[C@]314] | (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-((S)-2-acetamido-4-methylpentanamido)propanoyl)oxy)propanoate |

-continued

| Ex. No. | Structure | Name |
|---|---|---|
| C11 | 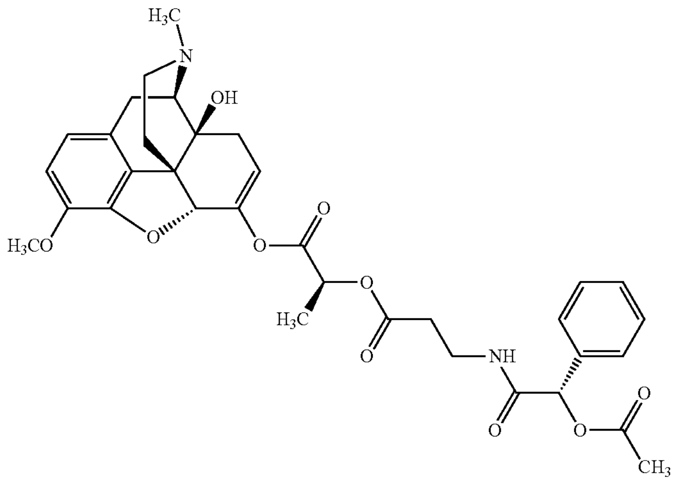 [SMILES: COc1ccc2c3c1O[C@H]1C(OC(=O)[C@H](C)OC(=O)CCNC(=O)[C@@H](OC(C)=O)c4ccccc4)=CC[C@@]4(O)[C@@H](C2)N(C)CCC[C@]314] | (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-((S)-2-acetoxy-2-phenylacetamido)propanoyl)oxy)propanoate |
| C12 | 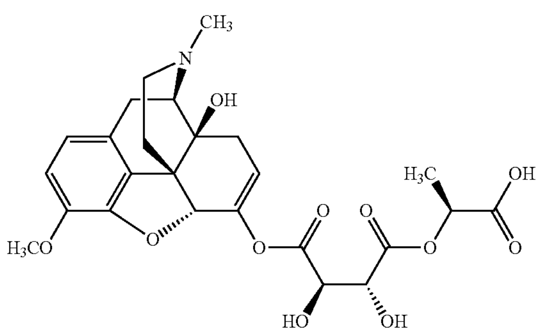 [SMILES: COc1ccc2c3c1O[C@H]1C(OC(=O)[C@H](O)[C@@H](O)C(=O)O[C@@H](C)C(=O)O)=CC[C@@]4(O)[C@@H](C2)N(C)CCC[C@]314] | (S)-2-(((2R,3R)-2(3-dihydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoic acid |
| C13 | 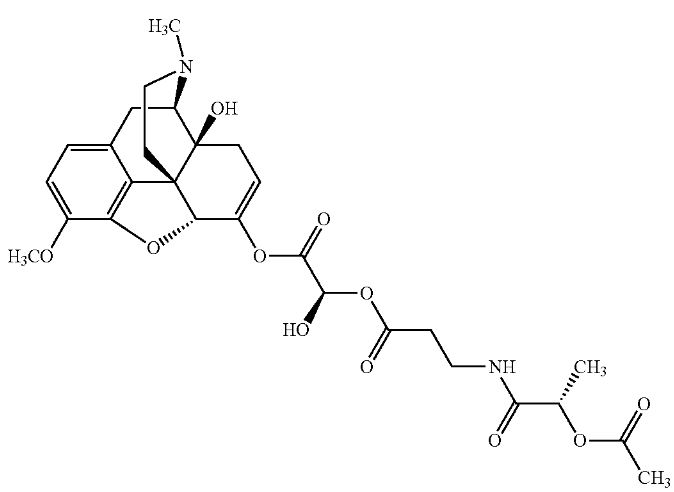 [SMILES: COc1ccc2c3c1O[C@H]1C(OC(=O)[C@H](O)OC(=O)CCNC(=O)[C@H](C)OC(C)=O)=CC[C@@]4(O)[C@@H](C2)N(C)CCC[C@]314] | (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-((S)-2-acetoxypropanamido)propanoyl)oxy)propanoate |

-continued

| Ex, No. | Structure | Name |
|---|---|---|
| C14 | 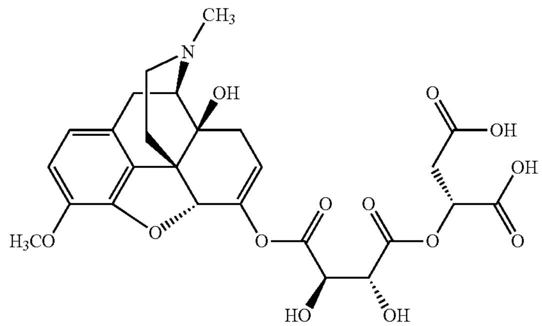 [SMILES: COc1ccc2c3c1O[C@H]1C(OC(=O)[C@H](O)[C@@H](O)C(=O)O[C@H](CC(=O)O)C(=O)O)=CC[C@@]4(O)[C@@H](C2)N(C)CCC[C@]314] | (R)-2-(((2R)3R)-2,3-dihydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid |
| C15 | 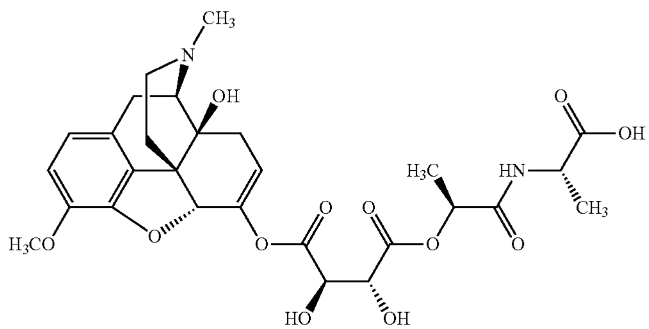 [SMILES: COc1ccc2c3c1O[C@H]1C(OC(=O)[C@H](O)[C@@H](O)C(=O)O[C@@H](C)C(=O)N[C@@H](C)C(=O)O)=CC[C@@]4(O)[C@@H](C2)N(C)CCC[C@]314] | (S)-2-((S)-2-(((2R,3R)-2,3-dihydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanamido)propanoic acid |
| C16 | 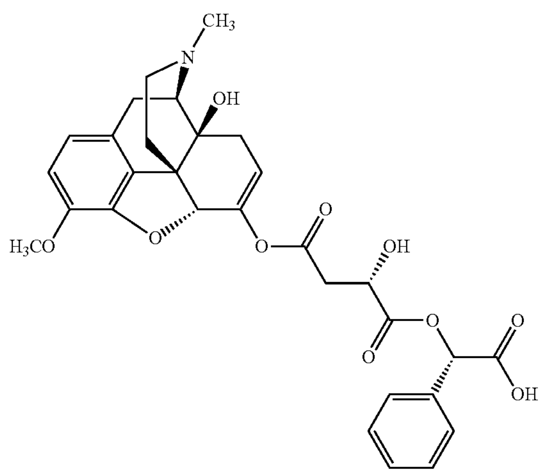 [SMILES: COc1ccc2c3c1O[C@H]1C(OC(=O)C[C@H](O)C(=O)O[C@H](C(=O)O)c4ccccc4)=CC[C@@]4(O)[C@@H](C2)N(C)CCC[C@]314] | (S)-2-(((S)-2-hydroxy-4-((((4R,4aS,7aR,12bS-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid |
| C17 | 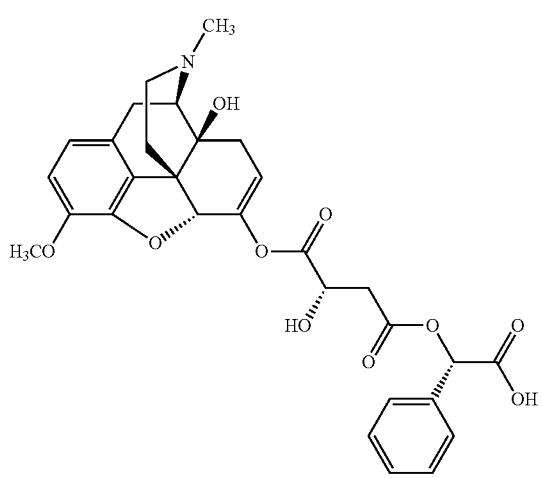 [SMILES: COc1ccc2c3c1O[C@H]1C(OC(=O)[C@@H](O)CC(=O)O[C@H](C(=O)O)c4ccccc4)=CC[C@@]4(O)[C@@H](C2)N(C)CCC[C@]314] | (S)-2-(((S)-3-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)4-oxobutanoyl)oxy)-2-phenylacetic acid |

| Ex, No. | Structure | Name |
|---|---|---|
| C18 | 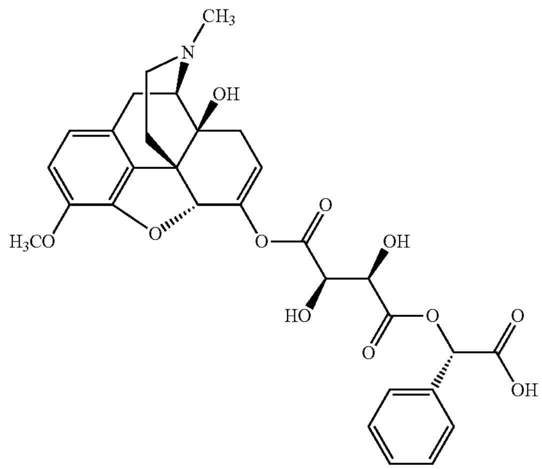 [SMILES: COc1ccc2c3c1O[C@H]1C(OC(=O)[C@H](O)[C@@H](O)C(=O)O[C@H](C(=O)O)c4ccccc4)=CC[C@@]4(O)[C@@H](C2)N(C)CCC[C@]314] | (S)-2-(((2R,3R)-2,3-dihydroxy-4-(((4R(4aS,7aR,12bS)-4a-hydroxy-9-methoxy-3-methyl-2,3,4,4a,5,7a-hexahydro-1H-4,12-ethanobenzofuro[3,2-e]isoquinolin-7-yl)oxy)-4-oxobutanoyl)oxy)-2-phenylacetic acid |
| C19 | 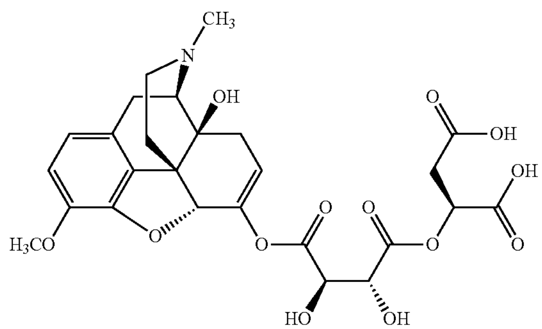 [SMILES: COc1ccc2c3c1O[C@H]1C(OC(=O)[C@H](O)[C@@H](O)C(=O)O[C@@H](CC(=O)O)C(=O)O)=CC[C@@]4(O)[C@@H](C2)N(C)CCC[C@]314] | (S)-2-(((2R,3R)-2,3-dihydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy) succinic acid |
| C20 | 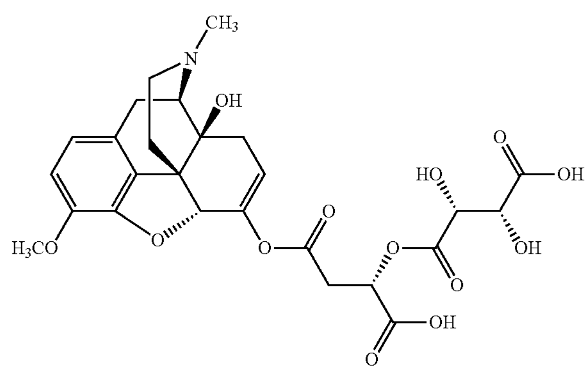 [SMILES: COc1ccc2c3c1O[C@H]1C(OC(=O)C[C@H](OC(=O)[C@H](O)[C@@H](O)C(=O)O)C(=O)O)=CC[C@@]4(O)[C@@H](C2)N(C)CCC[C@]314] | (2R,3R)-4-((S)-1-carboxy-3-(((4R,4a,5,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-3-oxopropoxy)-2,3-dihydroxy-4-oxobutanoic acid |
| C21 | 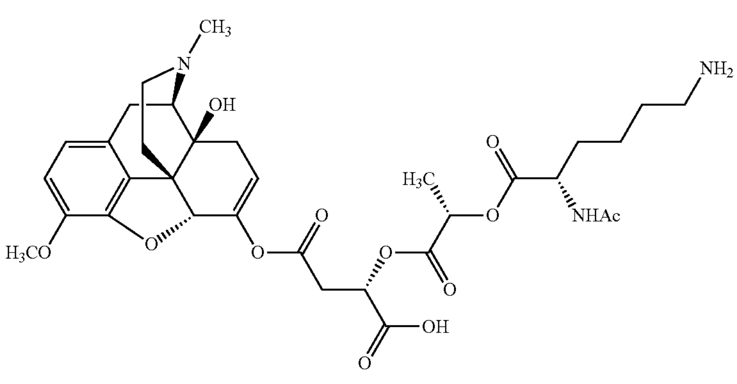 [SMILES: COc1ccc2c3c1O[C@H]1C(OC(=O)C[C@H](OC(=O)[C@H](C)OC(=O)[C@H](CCCCN)NC(C)=O)C(=O)O)=CC[C@@]4(O)[C@@H](C2)N(C)CCC[C@]314] | (S)-2-(((S)-2-(((S)-2-acetamido-6-aminohexanoyl)oxy)propanoyl)oxy)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid |

-continued

| Ex, No. | Structure | Name |
|---|---|---|
| C22 | 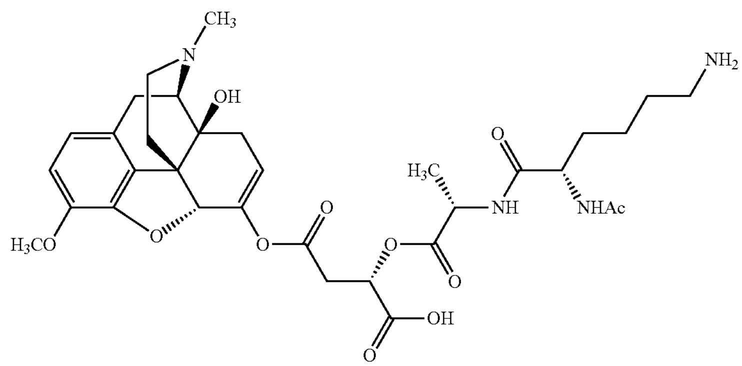 [SMILES: COc1ccc2c3c1O[C@H]1C(OC(=O)C[C@H](OC(=O)[C@H](C)NC(=O)[C@H](CCCCN)NC(C)=O)C(=O)O)=CC[C@@]4(O)[C@@H](C2)N(C)CCC[C@]314] | (S)-2-(((S)-2-((S)-2-acetamido-6-aminohexanamido)propanoyl)oxy)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid |
| C23 | 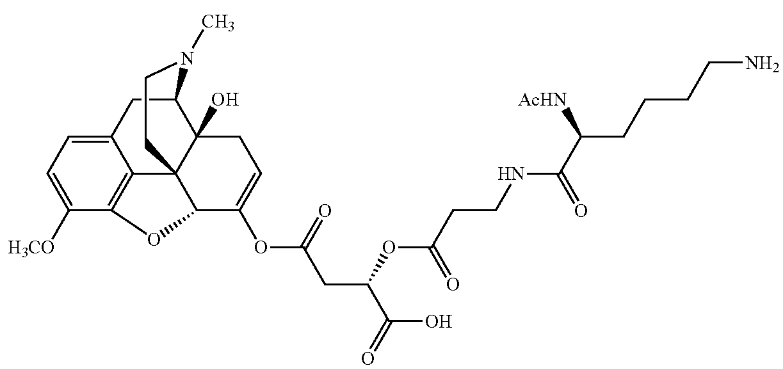 [SMILES: COc1ccc2c3c1O[C@H]1C(OC(=O)C[C@H](OC(=O)CCNC(=O)[C@H](CCCCN)NC(C)=O)C(=O)O)=CC[C@@]4(O)[C@@H](C2)N(C)CCC[C@]314] | (S)-2-((3-((S)-2-acetamido-6-aminohexanamido)propanoyl)oxy)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid |
| C24 | 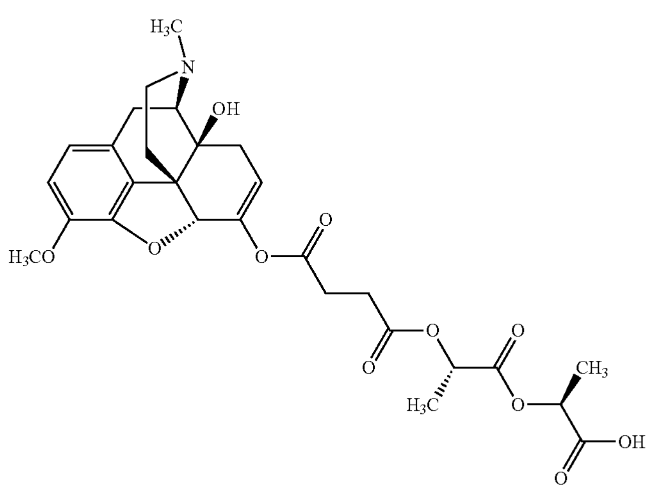 [SMILES: COc1ccc2c3c1O[C@H]1C(OC(=O)CCC(=O)O[C@@H](C)C(=O)O[C@@H](C)C(=O)O)=CC[C@@]4(O)[C@@H](C2)N(C)CCC[C@]314] | (S)-2-(((S)-2-((4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)propanoic acid |

-continued

| Ex, No. | Structure | Name |
|---|---|---|
| C25 | 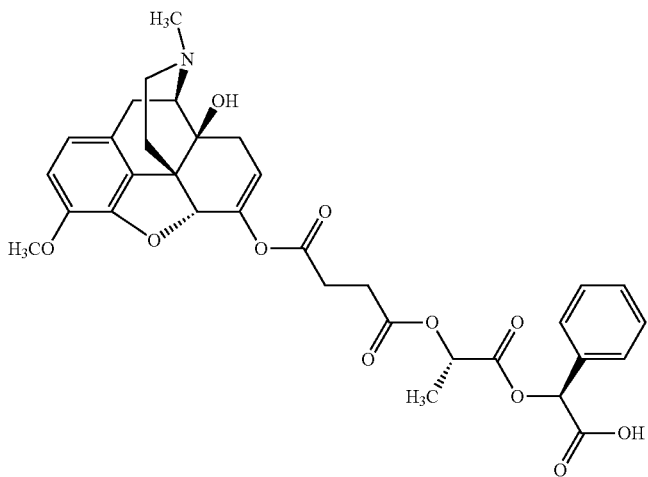 [SMILES: COc1ccc2c3c1O[C@H]1C(OC(=O)CCC(=O)O[C@@H](C)C(=O)O[C@H](C(=O)O)c4ccccc4)=CC[C@@]4(O)[C@@H](C2)N(C)CCC[C@]314] | (S)-2-(((S)-2-((4-(((4R, 4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)-2-phenylacetic acid |
| C26 | 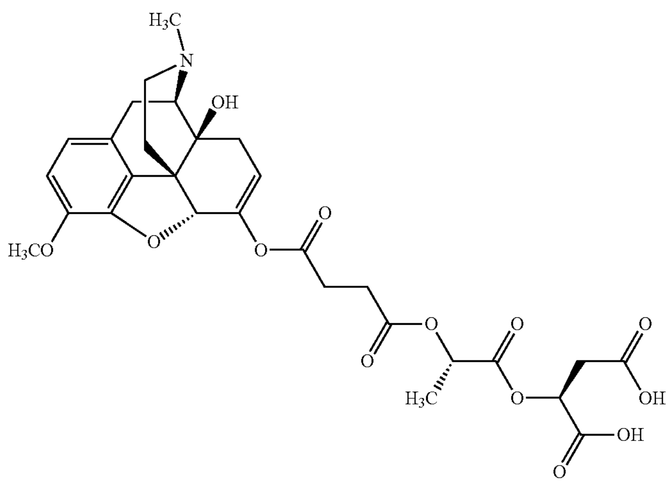 [SMILES: COc1ccc2c3c1O[C@H]1C(OC(=O)CCC(=O)O[C@@H](C)C(=O)O[C@@H](CC(=O)O)C(=O)O)=CC[C@@]4(O)[C@@H](C2)N(C)CCC[C@]314] | (S)-2-(((S)-2-((4-(((4R, 4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |
| C27 | 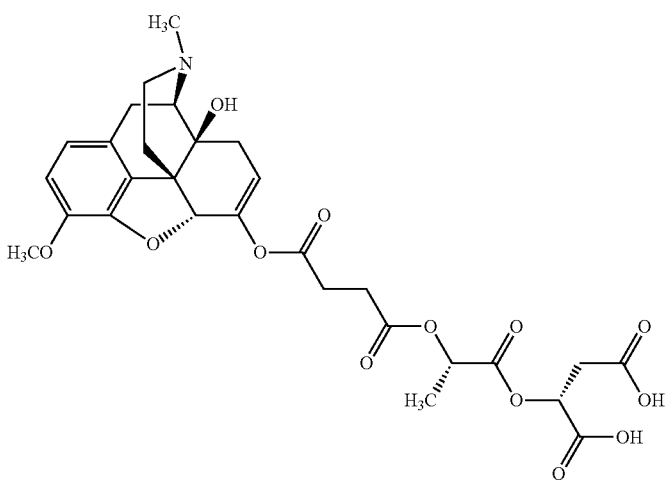 [SMILES: COc1ccc2c3c1O[C@H]1C(OC(=O)CCC(=O)O[C@@H](C)C(=O)O[C@H](CC(=O)O)C(=O)O)=CC[C@@]4(O)[C@@H](C2)N(C)CCC[C@]314] | (R)-2-(((S)-2-((4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |

-continued

| Ex, No. | Structure | Name |
|---|---|---|
| C28 | 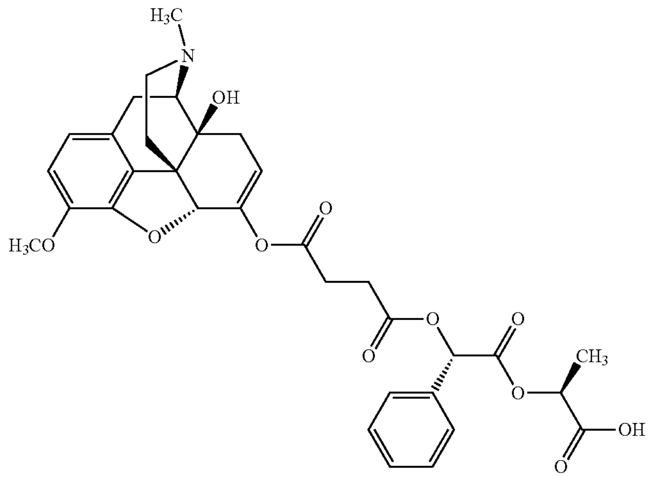 [SMILES: COc1ccc2c3c1O[C@H]1C(OC(=O)CCC(=O)O[C@H](C(=O)O[C@@H](C)C(=O)O)c4ccccc4)=CC[C@@]4(O)[C@@H](C2)N(C)CCC[C@]314] | (S)-2-((S)-2-((4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)propanoic acid |
| C29 | 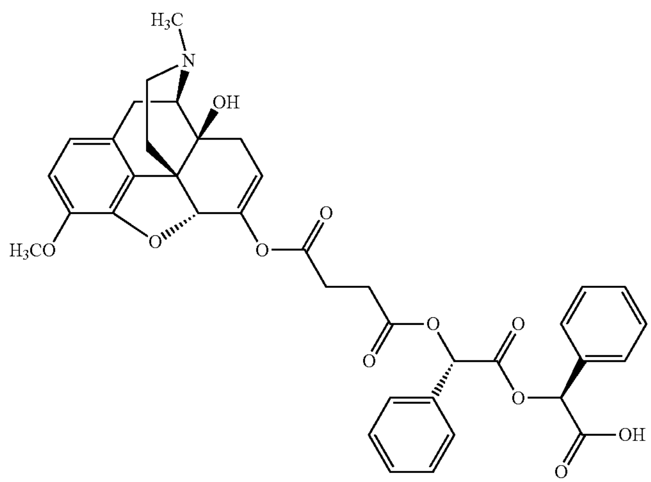 [SMILES: COc1ccc2c3c1O[C@H]1C(OC(=O)CCC(=O)O[C@H](C(=O)O[C@H](C(=O)O)c4ccccc4)c4ccccc4)=CC[C@@]4(O)[C@@H](C2)N(C)CCC[C@]314] | (S)-2-((S)-2-((4-(((4R,4aS,7aR,12bS)-4a-hydroxy-9-methoxy-3-methyl-2,3,4,4a,5,7a-hexahydro-1H-4,12-methanobenzofuro[3,2-e]isoqulnolin-7-yl)oxy)-4-oxobutanoyl)oxy)-2-phenylacetoxy)-2-phenylacetic acid |
| C30 | 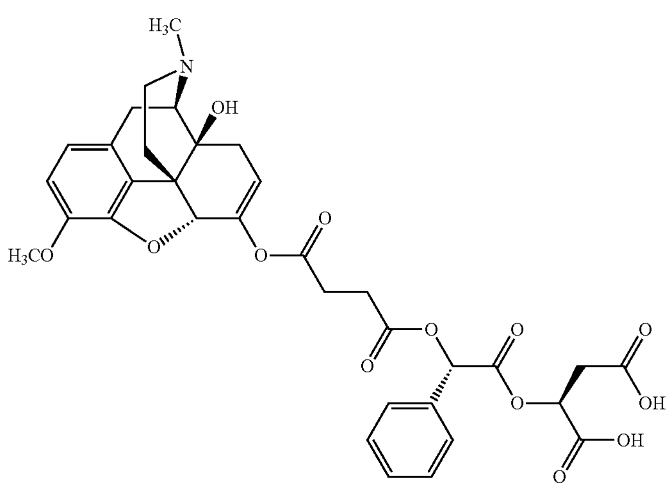 [SMILES: COc1ccc2c3c1O[C@H]1C(OC(=O)CCC(=O)O[C@H](C(=O)O[C@@H](CC(=O)O)C(=O)O)c4ccccc4)=CC[C@@]4(O)[C@@H](C2)N(C)CCC[C@]314] | (S)-2-((S)-2-((4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)succinic acid |

-continued

| Ex, No. | Structure | Name |
|---|---|---|
| C31 | 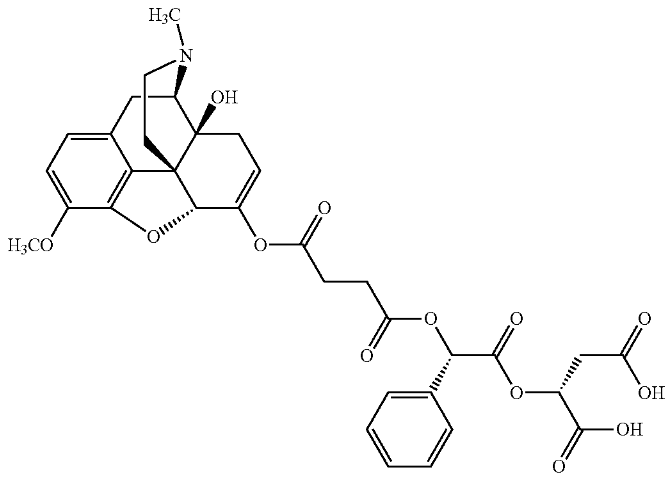 [SMILES: COc1ccc2c3c1O[C@H]1C(OC(=O)CCC(=O)O[C@H](C(=O)O[C@H](CC(=O)O)C(=O)O)c4ccccc4)=CC[C@@]4(O)[C@@H](C2)N(C)CCC[C@]314] | (R)-2-((S)-2-((4-(((4R,4aS, 7aR,12bS)-4a-hydroxy-9-methoxy-3-methyl-2,3,4,4a, 5,7a-hexahydro-1H-4,12-methanobenzofuro[3,2-e] isoquinolin-7-yl)oxy)-4-oxobutanoyl)oxy)-2-phenylacetoxy)succinic acid |
| C32 | 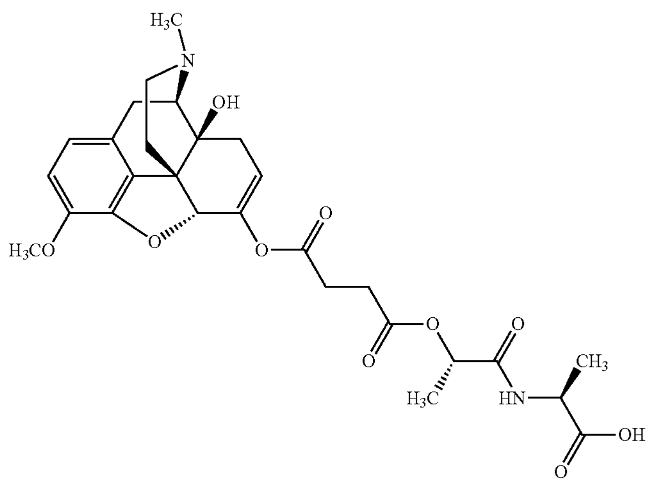 [SMILES: COc1ccc2c3c1O[C@H]1C(OC(=O)CCC(=O)O[C@@H](C)C(=O)N[C@@H](C)C(=O)O)=CC[C@@]4(O)[C@@H](C2)N(C)CCC[C@]314] | (S)-2-((S)-2-((4-(((4R,4aS, 7aR,12bS)-4a-hydroxy-9-methoxy-3-methyl-2,3,4,4a, 5,7a-hexahydro-1H-4,12-methanobenzofuro[3,2-e] isoquinolin-7-yl)oxy)-4-oxobutanoyl)oxy) propanamido)propanoic acid |
| C33 | 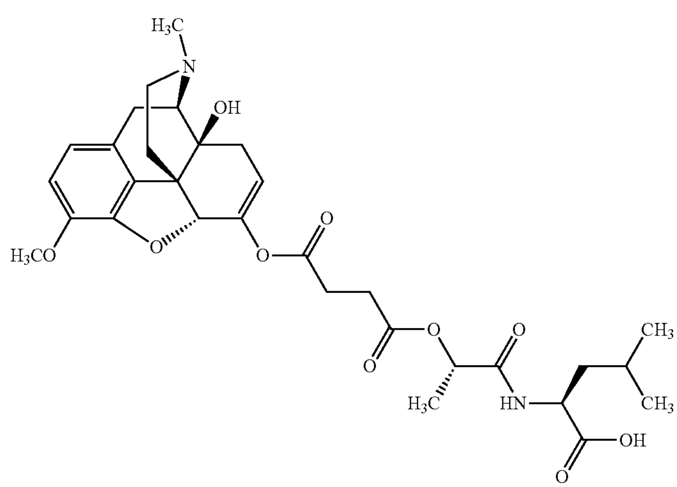 [SMILES: COc1ccc2c3c1O[C@H]1C(OC(=O)CCC(=O)O[C@@H](C)C(=O)N[C@@H](CC(C)C)C(=O)O)=CC[C@@]4(O)[C@@H](C2)N(C)CCC[C@]314] | (S)-2-((S)-2-((4-(((4R,4aS, 7aR,12bS)-4a-hydroxy-9-methoxy-3-methyl-2,3,4,4a, 5,7a-hexahydro-1H-4,12-methanobenzofuro[3,2-e] isoquinolin-7-yl)oxy)-4-oxobutanoyl)oxy) propanamido)-4-methylpentanoic acid |

-continued

| Ex. No. | Structure | Name |
|---|---|---|
| C34 | 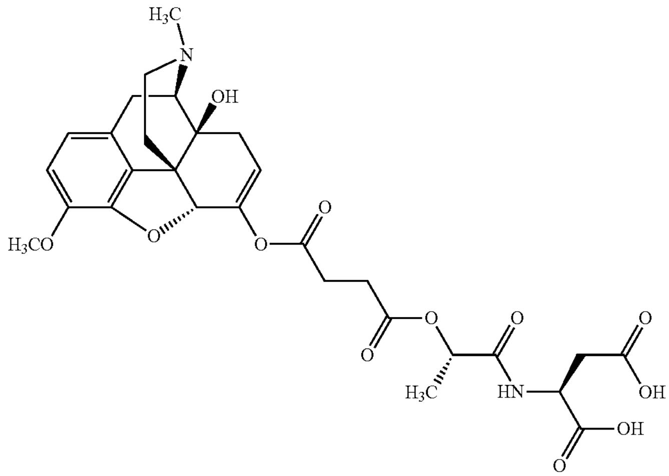 [SMILES: COc1ccc2c3c1O[C@H]1C(OC(=O)CCC(=O)O[C@@H](C)C(=O)N[C@@H](CC(=O)O)C(=O)O)=CC[C@@]4(O)[C@@H](C2)N(C)CCC[C@]314] | (S)-2-((S)-2-((4-(((4R,4aS, 7aR,12bS)-4a-hydroxy-9-methoxy-3-methyl-2,3,4,4a, 5,7a-hexahydro-1H-4,12-methanobenzofuro[3,2-e] isoquinolin-7-yl)oxy)-4-oxobutanoyl)oxy) propanamido)succinic acid |
| C35 | 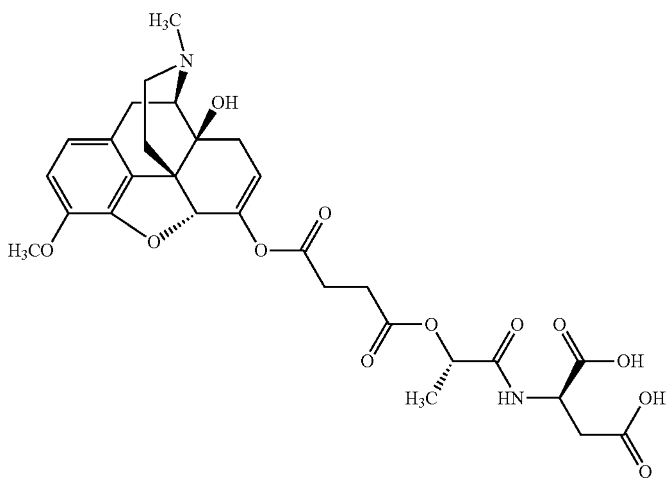 [SMILES: COc1ccc2c3c1O[C@H]1C(OC(=O)CCC(=O)O[C@@H](C)C(=O)N[C@H](CC(=O)O)C(=O)O)=CC[C@@]4(O)[C@@H](C2)N(C)CCC[C@]314] | (R)-2-((S)-2-((4-(((4R,4aS, 7aR,12bS)-4a-hydroxy-9-methoxy-3-methyl-2,3,4,4a, 5,7a-hexahydro-1H-4,12-methanobenzofuro[3,2-e] isoquinolin-7-yl)oxy)-4-oxobutanoyl)oxy) propanamido)succinic acid |
| C36 | 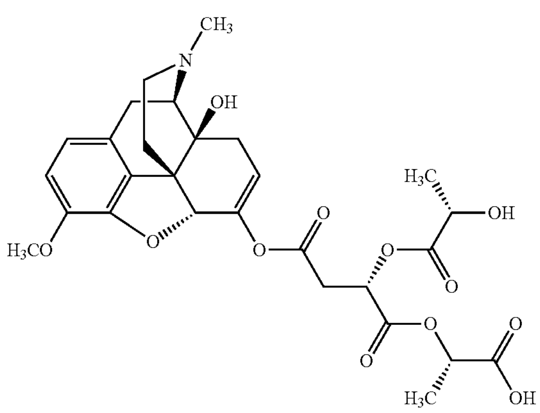 [SMILES: COc1ccc2c3c1O[C@H]1C(OC(=O)C[C@H](OC(=O)[C@H](C)O)C(=O)O[C@@H](C)C(=O)O)=CC[C@@]4(O)[C@@H](C2)N(C)CCC[C@]314] | (S)-2-(((S)-4-(((4R,4aS, 7aR,12bS)-4a-hydroxy-9-methoxy-3-methyl-2,3,4,4a, 5,7a-hexahydro-1H-4,12-methanobenzofuro[3,2-e] isoquinolin-7-yl)oxy)-2-(((S)-2-hydroxypropanoyl) oxy)-4-oxobutanoyl)oxy) propanoic acid |

-continued

| Ex, No. | Structure | Name |
|---|---|---|
| C37 | 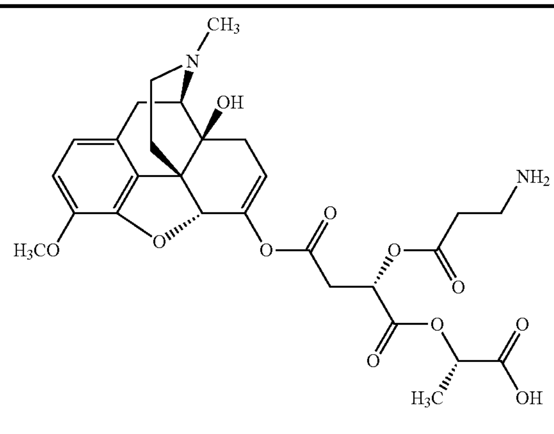 | (S)-2-(((S)-2-((3-amino-propanoyl)oxy)-4-(((4R,4aS,7aR,12bS)-4a-hydroxy-9-methoxy-3-methyl-2,3,4,4a,5,7a-hexahydro-1H-4,12-methanobenzofuro(3,2-e]isoquinolin-7-yl)oxy)-4-oxobutanoyl)oxy)propanoic acid |
| C38 | 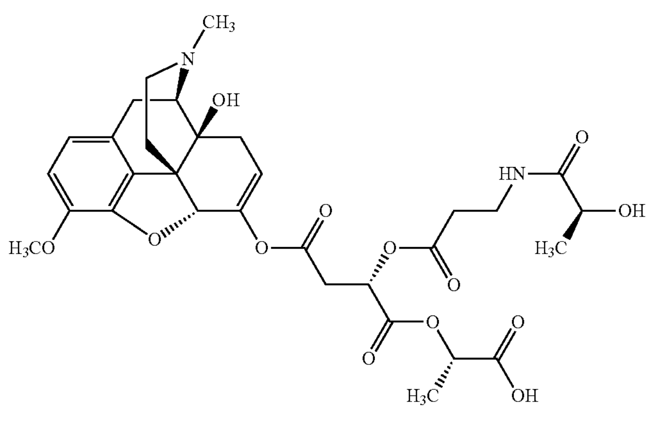 [SMILES: COc1ccc2c3c1O[C@H]1C(OC(=O)C[C@H](OC(=O)CCNC(=O)[C@H](C)O)C(=O)O[C@@H](C)C(=O)O)=CC[C@@]4(O)[C@@H](C2)N(C)CCC[C@]314] | (S)-2-(((S)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-((3-((S)-2-hydroxy-propanamido)propanoyl)oxy)-4-oxobutanoyl)oxy)propanoic acid |
| C39 | 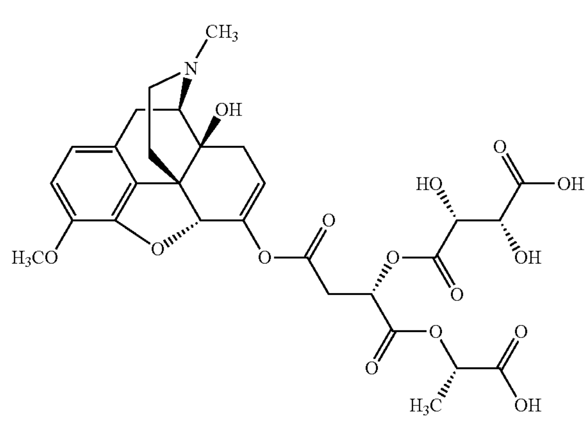 [SMILES: COc1ccc2c3c1O[C@H]1C(OC(=O)C[C@H](OC(=O)[C@H](O)[C@@H](O)C(=O)O)C(=O)O[C@@H](C)C(=O)O)=CC[C@@]4(O)[C@@H](C2)N(C)CCC[C@]314] | (2R,3R)-4-(((S)-1-((S)-1-carboxyethoxy)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1,4-dioxobutan-2-yl)oxy)-2,3-dihydroxy-4-oxobutanoic acid |

-continued

| Ex. No. | Structure | Name |
|---|---|---|
| C40 | 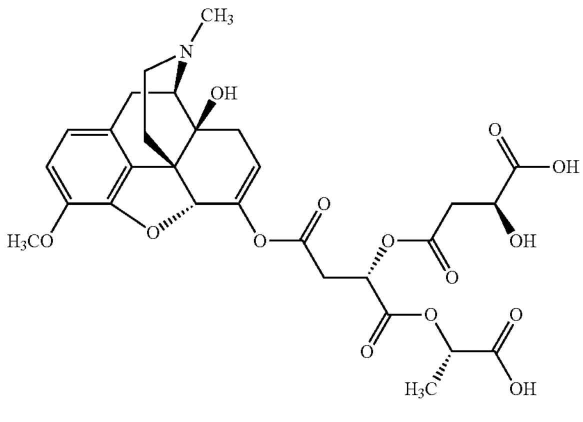 [SMILES: COc1ccc2c3c1O[C@H]1C(OC(=O)C[C@H](OC(=O)C[C@H](O)C(=O)O)C(=O)O[C@@H](C)C(=O)O)=CC[C@@]4(O)[C@@H](C2)N(C)CCC[C@]314] | (S)-4-(((S)-1-((S)-1-carboxyethoxy)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1,4-dioxobutan-2-yl)oxy)-2-hydroxy-4-oxobutanoic acid |
| C41 | 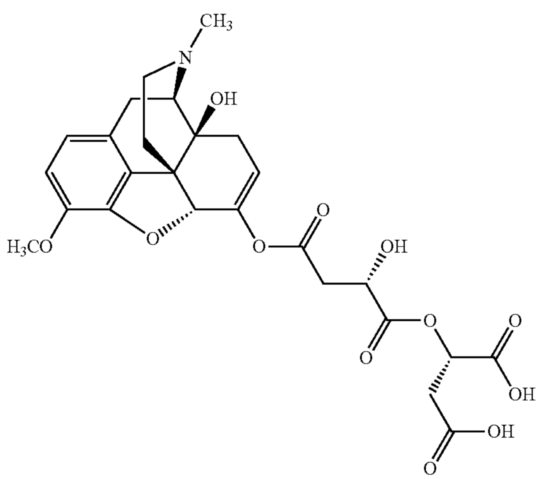 [SMILES: COc1ccc2c3c1O[C@H]1C(OC(=O)C[C@H](O)C(=O)O[C@@H](CC(=O)O)C(=O)O)=CC[C@@]4(O)[C@@H](C2)N(C)CCC[C@]314] | (S)-2-(((S)-2-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid |
| C42 | 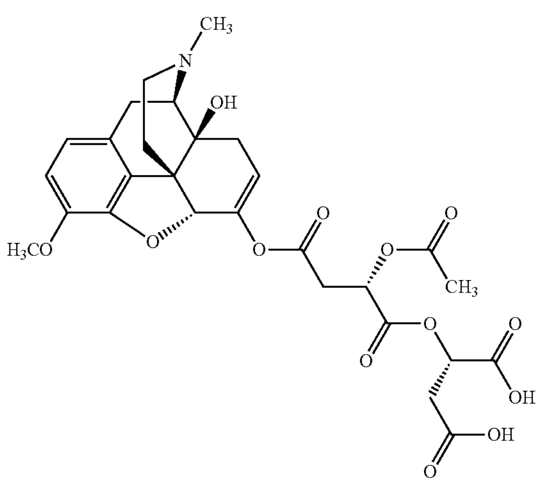 [SMILES: COc1ccc2c3c1O[C@H]1C(OC(=O)C[C@H](OC(C)=O)C(=O)O[C@@H](CC(=O)O)C(=O)O)=CC[C@@]4(O)[C@@H](C2)N(C)CCC[C@]314] | (S)-2-(((S)-2-acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid |

| Ex. No. | Structure | Name |
|---|---|---|
| C43 | 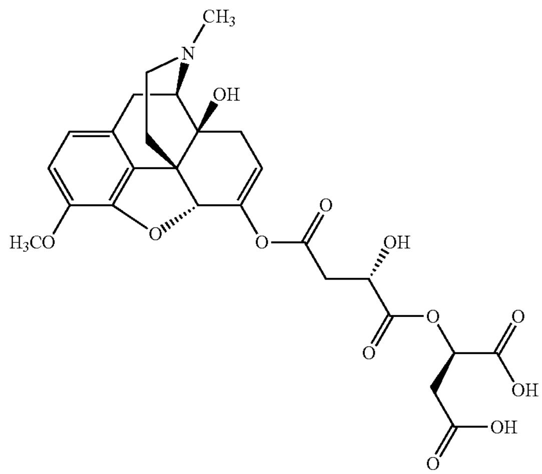 [SMILES: COc1ccc2c3c1O[C@H]1C(OC(=O)C[C@H](O)C(=O)O[C@H](CC(=O)O)C(=O)O)=CC[C@@]4(O)[C@@H](C2)N(C)CCC[C@]314] | (R)-2-(((S)-2-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy) succinic acid |
| C44 | 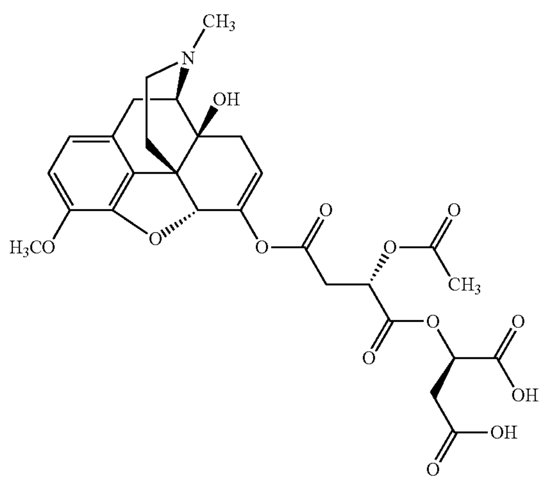 [SMILES: COc1ccc2c3c1O[C@H]1C(OC(=O)C[C@H](OC(C)=O)C(=O)O[C@H](CC(=O)O)C(=O)O)=CC[C@@]4(O)[C@@H](C2)N(C)CCC[C@]314] | (R)-2-(((S)-2-acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy) succinic acid |
| C45 | 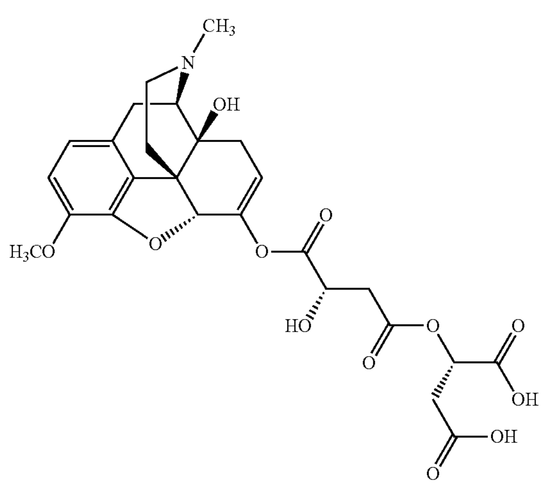 [SMILES: COc1ccc2c3c1O[C@H]1C(OC(=O)[C@@H](O)CC(=O)O[C@@H](CC(=O)O)C(=O)O)=CC[C@@]4(O)[C@@H](C2)N(C)CCC[C@]314] | (S)-2-(((S)-3-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy) succinic acid |

-continued

| Ex. No. | Structure | Name |
|---|---|---|
| C46 | 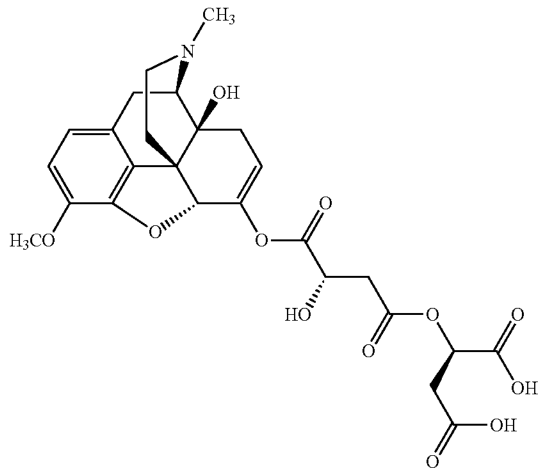 [SMILES: COc1ccc2c3c1O[C@H]1C(OC(=O)[C@@H](O)CC(=O)O[C@H](CC(=O)O)C(=O)O)=CC[C@@]4(O)[C@@H](C2)N(C)CCC[C@]314] | (R)-2-(((S)-3-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid |
| C47 | 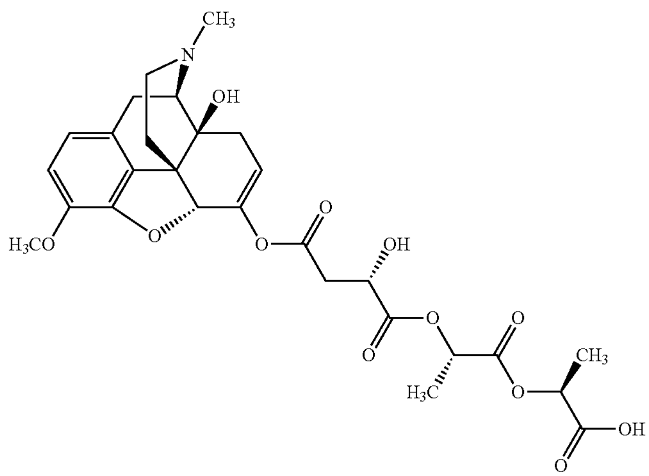 [SMILES: COc1ccc2c3c1O[C@H]1C(OC(=O)C[C@H](O)C(=O)O[C@@H](C)C(=O)O[C@@H](C)C(=O)O)=CC[C@@]4(O)[C@@H](C2)N(C)CCC[C@]314] | (S)-2-(((S)-2-(((S)-2-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)propanoic acid |
| C48 | 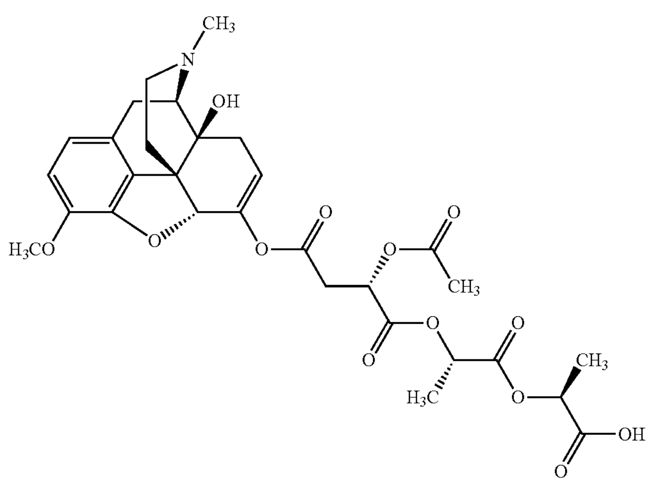 [SMILES: COc1ccc2c3c1O[C@H]1C(OC(=O)C[C@H](OC(C)=O)C(=O)O[C@@H](C)C(=O)O[C@@H](C)C(=O)O)=CC[C@@]4(O)[C@@H](C2)N(C)CCC[C@]314] | (S)-2-(((S)-2-(((S)-2-acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)propanoic acid |

| Ex, No. | Structure | Name |
|---|---|---|
| C49 | 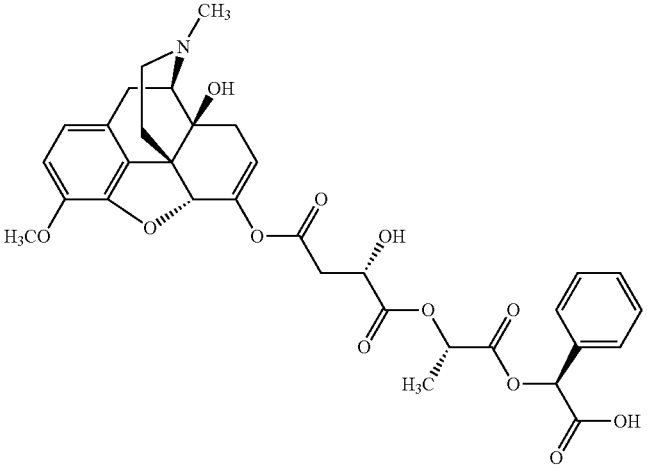 [SMILES: COc1ccc2c3c1O[C@H]1C(OC(=O)C[C@H](O)C(=O)O[C@@H](C)C(=O)O[C@H](C(=O)O)c4ccccc4)=CC[C@@]4(O)[C@@H](C2)N(C)CCC[C@]314] | (S)-2-(((S)-2-(((S)-2-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)-2-phenylacetic acid |
| C50 | 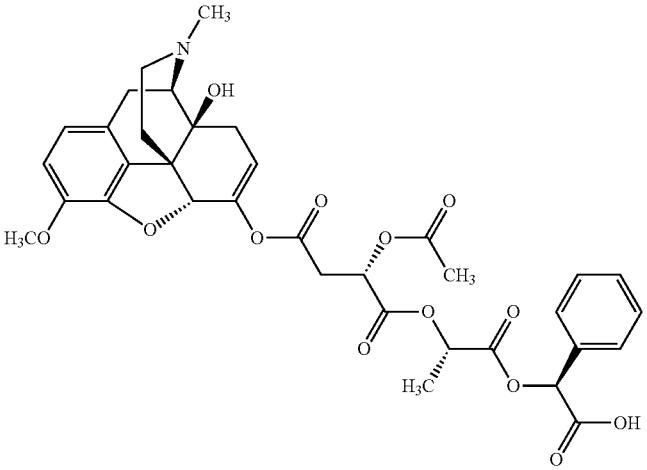 [SMILES: COc1ccc2c3c1O[C@H]1C(OC(=O)C[C@H](OC(C)=O)C(=O)O[C@@H](C)C(=O)O[C@H](C(=O)O)c4ccccc4)=CC[C@@]4(O)[C@@H](C2)N(C)CCC[C@]314] | (S)-2-(((S)-2-(((S)-2-acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)-2-phenylacetic acid |
| C51 | 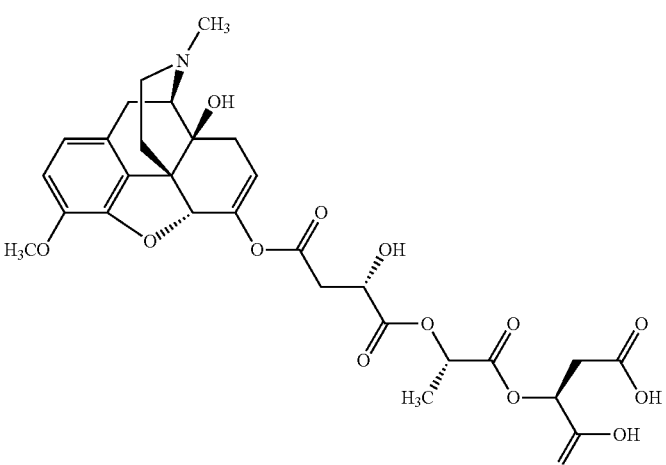 | (S)-2-(((S)-2-(((S)-2-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |

| Ex, No. | Structure | Name |
|---|---|---|
| C52 | 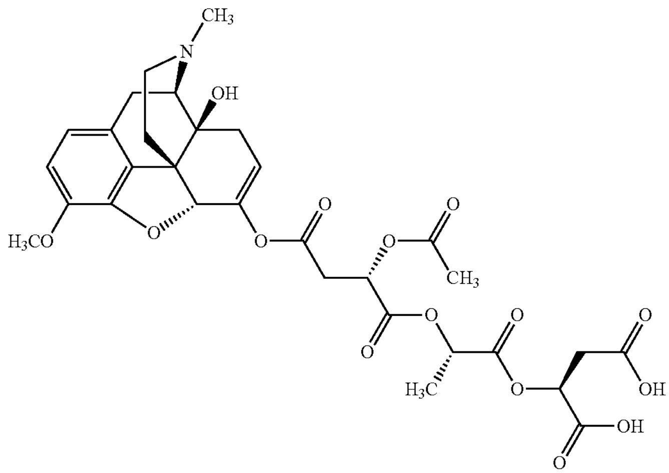 [SMILES: COc1ccc2c3c1O[C@H]1C(OC(=O)C[C@H](OC(C)=O)C(=O)O[C@@H](C)C(=O)O[C@@H](CC(=O)O)C(=O)O)=CC[C@@]4(O)[C@@H](C2)N(C)CCC[C@]314] | (S)-2-(((S)-2-(((S)-2-acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |
| C53 | 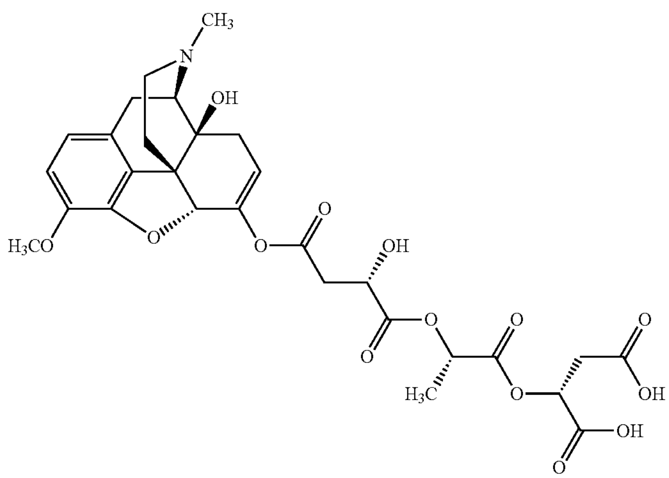 [SMILES: COc1ccc2c3c1O[C@H]1C(OC(=O)C[C@H](O)C(=O)O[C@@H](C)C(=O)O[C@H](CC(=O)O)C(=O)O)=CC[C@@]4(O)[C@@H](C2)N(C)CCC[C@]314] | (R)-2-(((S)-2-(((S)-2-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |
| C54 | 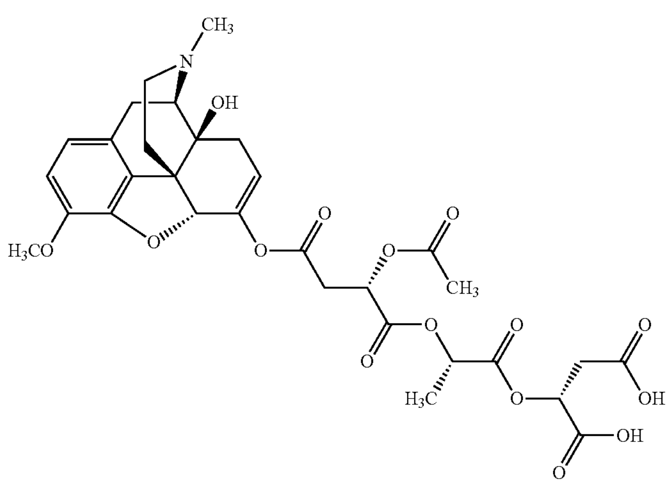 [SMILES: COc1ccc2c3c1O[C@H]1C(OC(=O)C[C@H](OC(C)=O)C(=O)O[C@@H](C)C(=O)O[C@H](CC(=O)O)C(=O)O)=CC[C@@]4(O)[C@@H](C2)N(C)CCC[C@]314] | (R)-2-(((S)-2-(((S)-2-acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |

| Ex, No. | Structure | Name |
|---|---|---|
| C55 | 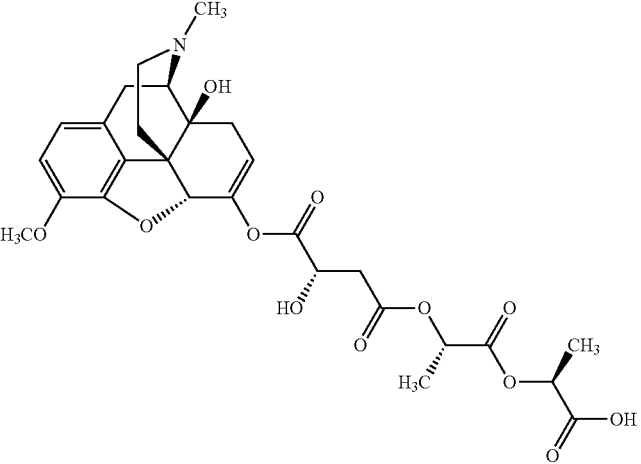 [SMILES: COc1ccc2c3c1O[C@H]1C(OC(=O)[C@@H](O)CC(=O)O[C@@H](C)C(=O)O[C@@H](C)C(=O)O)=CC[C@@]4(O)[C@@H](C2)N(C)CCC[C@]314] | (S)-2-((((S)-2-(((S)-3-hydroxy-4-((((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy) propanoyl)oxy) propanoic acid |
| C56 | 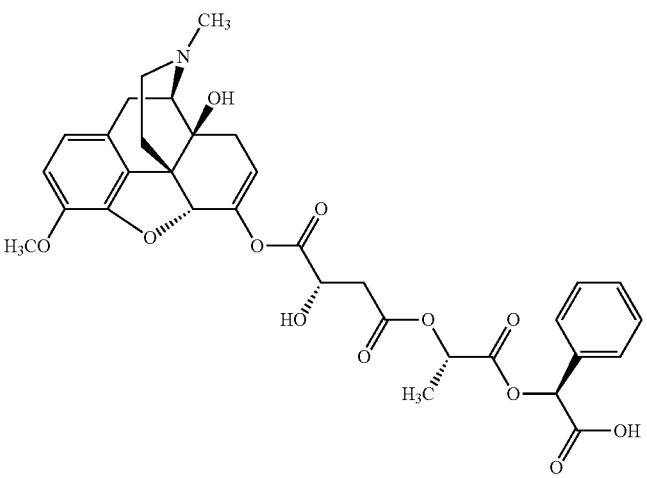 [SMILES: COc1ccc2c3c1O[C@H]1C(OC(=O)[C@@H](O)CC(=O)O[C@@H](C)C(=O)O[C@H](C(=O)O)c4ccccc4)=CC[C@@]4(O)[C@@H](C2)N(C)CCC[C@]314] | (S)-2-(((S)-2-(((S)-3-hydroxy-4-((((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy) propanoyl)oxy)-2-phenylacetic acid |
| C57 | 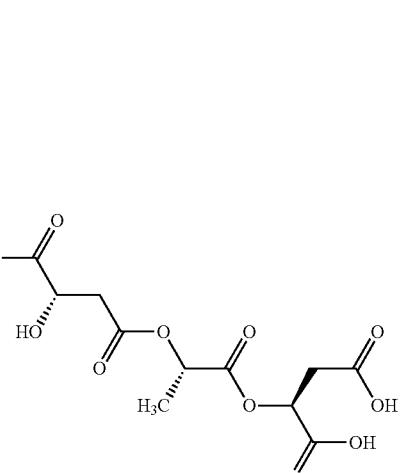 | (S)-2-(((S)-2-(((S)-3-hydroxy-4-((((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy) propanoyl)oxy) succinic acid |

| Ex, No. | Structure | Name |
|---|---|---|
| C58 | 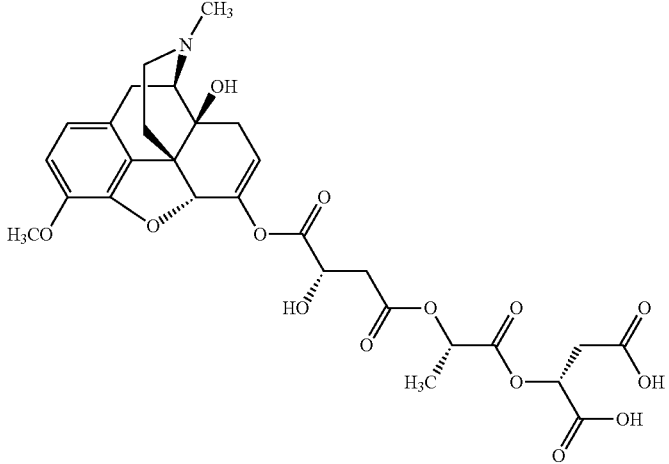 [SMILES: COc1ccc2c3c1O[C@H]1C(OC(=O)[C@@H](O)CC(=O)O[C@@H](C)C(=O)O[C@H](CC(=O)O)C(=O)O)=CC[C@@]4(O)[C@@H](C2)N(C)CCC[C@]314] | (R)-2-(((S)-2-(((S)-3-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy) succinic acid |
| C59 | 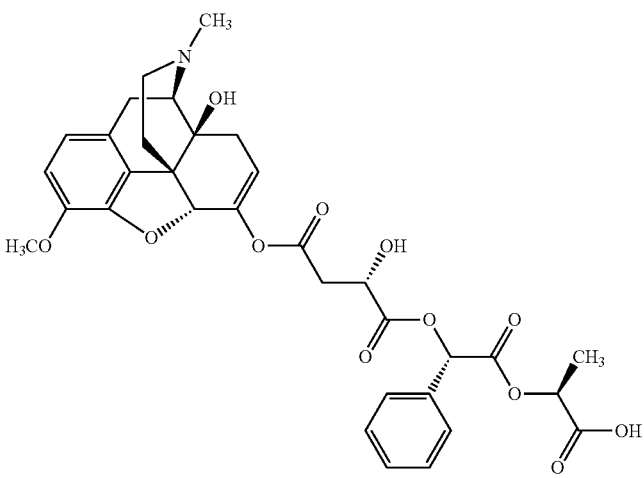 [SMILES: COc1ccc2c3c1O[C@H]1C(OC(=O)C[C@H](O)C(=O)O[C@H](C(=O)O[C@@H](C)C(=O)O)c4ccccc4)=CC[C@@]4(O)[C@@H](C2)N(C)CCC[C@]314] | (S)-2-((S)-2-(((S)-2-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyt)oxy)-2-phenylacetoxy) propanoic acid |
| C60 | 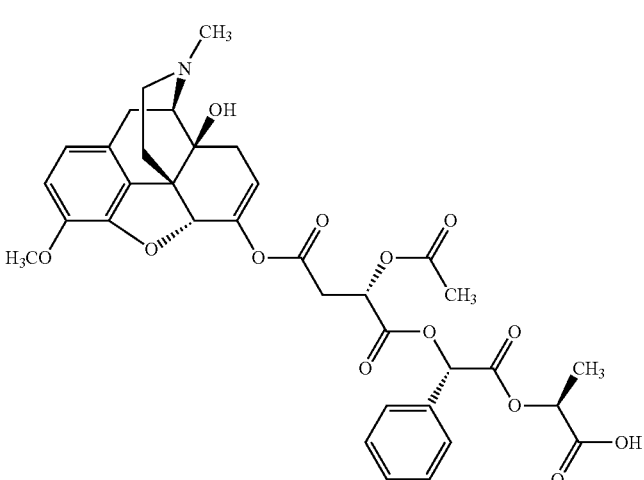 | (S)-2-((S)-2-(((S)-2-acetoxy-4-(((4R,4aS,7aR,12bS)-4a-hydroxy-9-methoxy-3-methyl-2,3,4,4a,5,7a-hexahydro-1H-4,12-methano-benzofuro[3,2-e]isoquinolin-7-yl)oxy)-4-oxobutanoyt)oxy)-2-phenylacetoxy) propanoic acid |

-continued

| Ex, No. | Structure | Name |
|---|---|---|
| C61 | 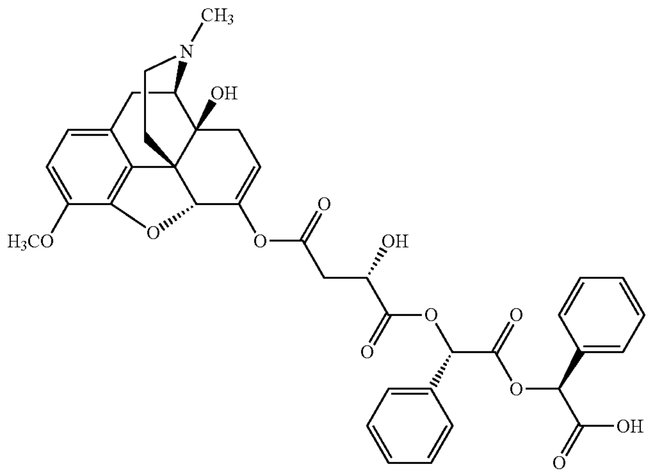 [SMILES: COc1ccc2c3c1O[C@H]1C(OC(=O)C[C@H](O)C(=O)O[C@H](C(=O)O[C@H](C(=O)O)c4ccccc4)c4ccccc4)=CC[C@@]4(O)[C@@H](C2)N(C)CCC[C@]314] | (S)-2-((S)-2-(((S)-2-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyt)oxy)-2-phenylacetoxy)-2-phenylacetic acid |
| C62 | 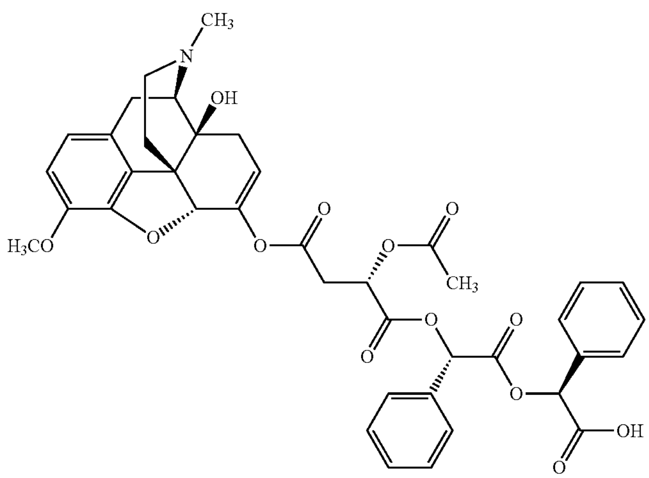 [SMILES: COc1ccc2c3c1O[C@H]1C(OC(=O)C[C@H](OC(C)=O)C(=O)O[C@H](C(=O)O[C@H](C(=O)O)c4ccccc4)c4ccccc4)=CC[C@@]4(O)[C@@H](C2)N(C)CCC[C@]314] | (S)-2-((S)-2-(((S)-2-acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)-2-phenylacetic acid |
| C63 | 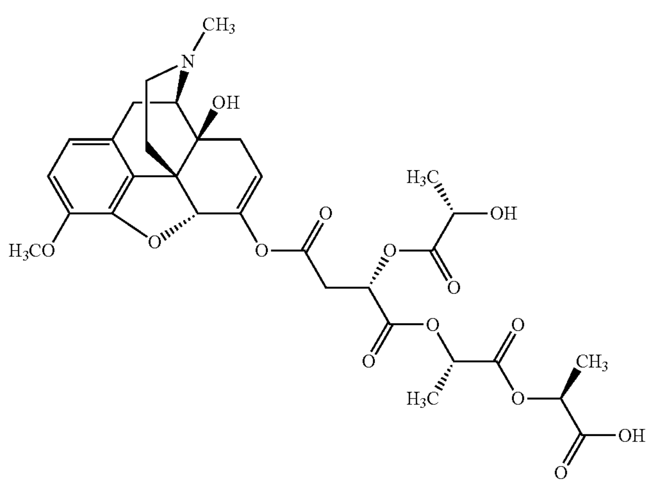 [SMILES: COc1ccc2c3c1O[C@H]1C(OC(=O)C[C@H](OC(=O)[C@H](C)O)C(=O)O[C@@H](C)C(=O)O[C@@H](C)C(=O)O)=CC[C@@]4(O)[C@@H](C2)N(C)CCC[C@]314] | (S)-2-(((S)-2-(((S)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-(((S)-2-hydroxypropanoyl)oxy)-4-oxobutanoyl)oxy)propanoyl)oxy)propanoic acid |

-continued

| Ex, No. | Structure | Name |
|---|---|---|
| C64 | 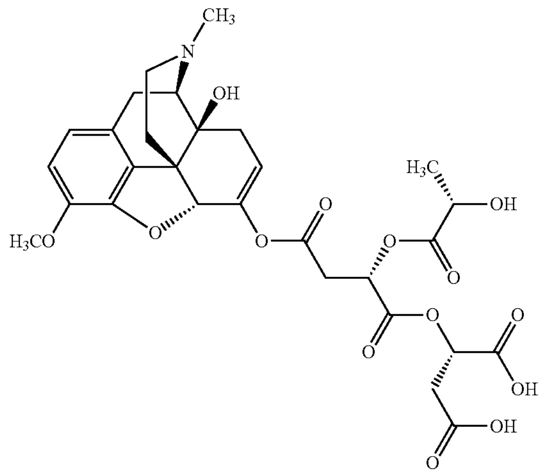 [SMILES: COc1ccc2c3c1O[C@H]1C(OC(=O)C[C@H](OC(=O)[C@H](C)O)C(=O)O[C@@H](CC(=O)O)C(=O)O)=CC[C@@]4(O)[C@@H](C2)N(C)CCC[C@]314] | (S)-2-(((S)-4-(((4R,4aS, 7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-(((S)-2-hydroxy-propanoyt)oxy)-4-oxobutanoyl)oxy) succinic acid |
| C65 | 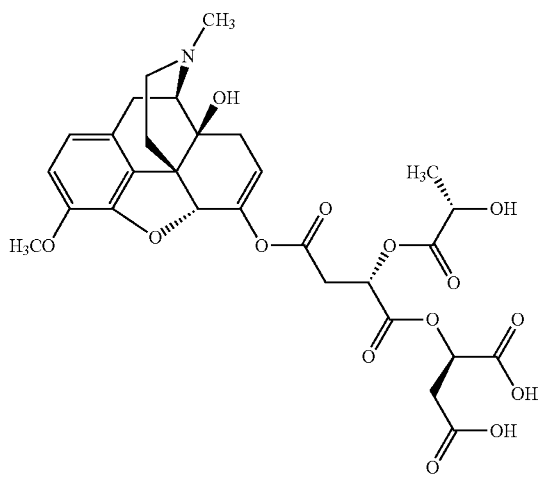 [SMILES: COc1ccc2c3c1O[C@H]1C(OC(=O)C[C@H](OC(=O)[C@H](C)O)C(=O)O[C@H](CC(=O)O)C(=O)O)=CC[C@@]4(O)[C@@H](C2)N(C)CCC[C@]314] | (R)-2-(((S)-4-(((4R,4aS, 7aR,12bS)-4a-hydroxy-9-methoxy-3-methyl-2,3,4,4a, 5,7a-hexahydro-1H-4,12-methanobenzofuro (3,2-e]isoquinolin-7-yl) oxy)-2-(((S)-2-hydroxypropanoyl)oxy)-4-oxobutanoyl)oxy) succinic acid |
| C66 | 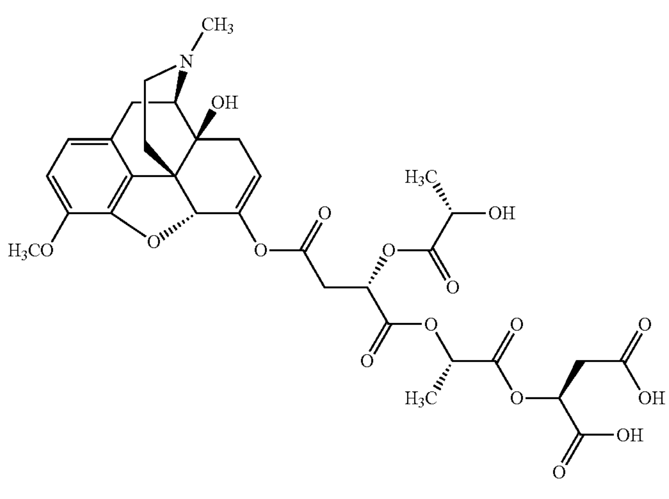 [SMILES: COc1ccc2c3c1O[C@H]1C(OC(=O)C[C@H](OC(=O)[C@H](C)O)C(=O)O[C@@H](C)C(=O)O[C@@H](CC(=O)O)C(=O)O)=CC[C@@]4(O)[C@@H](C2)N(C)CCC[C@]314] | (S)-2-(((S)-2-(((S)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-(((S)-2-hydroxypropanoyl)oxy)-4-oxobutanoyl)oxy)propanoyl)oxy)succinic acid |

| Ex, No. | Structure | Name |
|---|---|---|
| C67 | 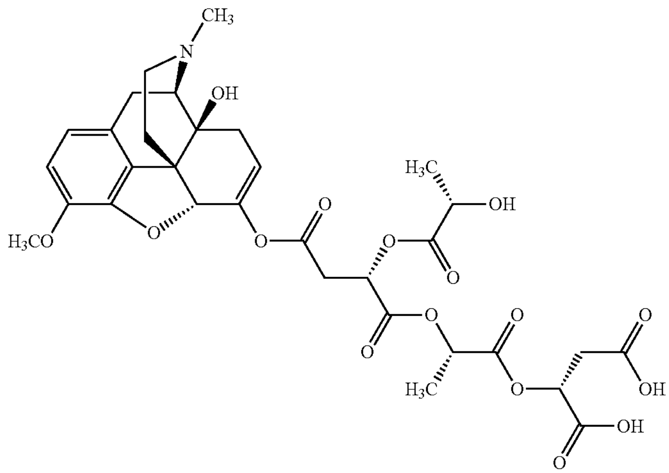 [SMILES: COc1ccc2c3c1O[C@H]1C(OC(=O)C[C@H](OC(=O)[C@H](C)O)C(=O)O[C@@H](C)C(=O)O[C@H](CC(=O)O)C(=O)O)=CC[C@@]4(O)[C@@H](C2)N(C)CCC[C@]314] | (R)-2-(((S)-2-(((S)-4-(((4R,4aS,7aR,12bS)-4a-hydroxy-9-methoxy-3-methoxy-3-methyl-2,3,4,4a,5,7a-hexahydro-1H-4,12-methanobenzofuro[3,2-e]isoquinolin-7-yl)oxy)-2-(((S)-2-hydroxypropanoyl)oxy)-4-oxobutanoyl)oxy)propanoyl)oxy)succinic acid |
| C68 | 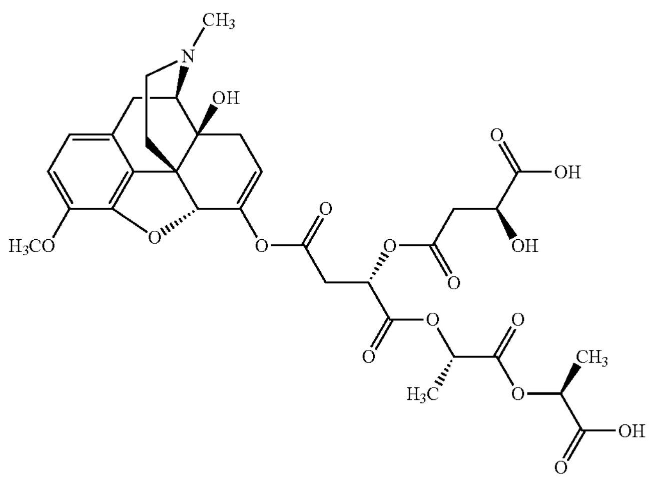 [SMILES: COc1ccc2c3c1O[C@H]1C(OC(=O)C[C@H](OC(=O)C[C@H](O)C(=O)O)C(=O)O[C@@H](C)C(=O)O[C@@H](C)C(=O)O)=CC[C@@]4(O)[C@@H](C2)N(C)CCC[C@]314] | (S)-4-(((S)-1-(((S)-1-((S)-1-carboxyethoxy)-1-oxopropan-2-yl)oxy)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1,4-dioxobutan-2-yl)oxy)-2-hydroxy-4-oxobutanoic acid |
| C69 | 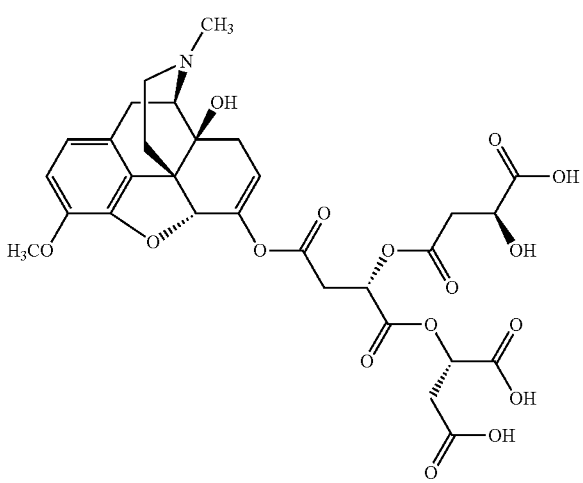 [SMILES: COc1ccc2c3c1O[C@H]1C(OC(=O)C[C@H](OC(=O)C[C@H](O)C(=O)O)C(=O)O[C@@H](CC(=O)O)C(=O)O)=CC[C@@]4(O)[C@@H](C2)N(C)CCC[C@]314] | (S)-2-(((S)-2-(((S)-3-carboxy-3-hydroxy-propanoyl)oxy)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid |

-continued

| Ex, No. | Structure | Name |
|---|---|---|
| C70 | 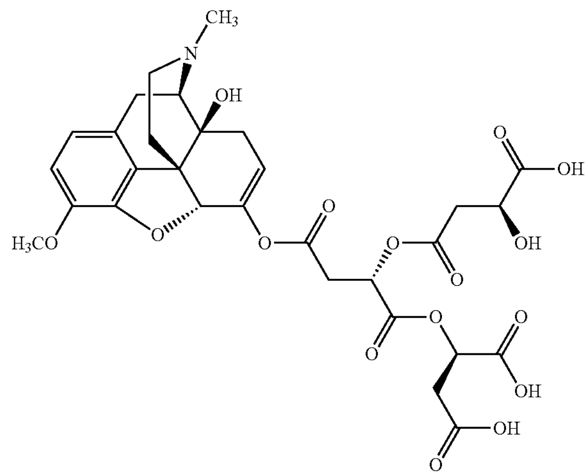 [SMILES: COc1ccc2c3c1O[C@H]1C(OC(=O)C[C@H](OC(=O)C[C@H](O)C(=O)O)C(=O)O[C@H](CC(=O)O)C(=O)O)=CC[C@@]4(O)[C@@H](C2)N(C)CCC[C@]314] | (R)-2-(((S)-2-(((S)-3-carboxy-3-hydroxy-propanoyl)oxy)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid |
| C71 | 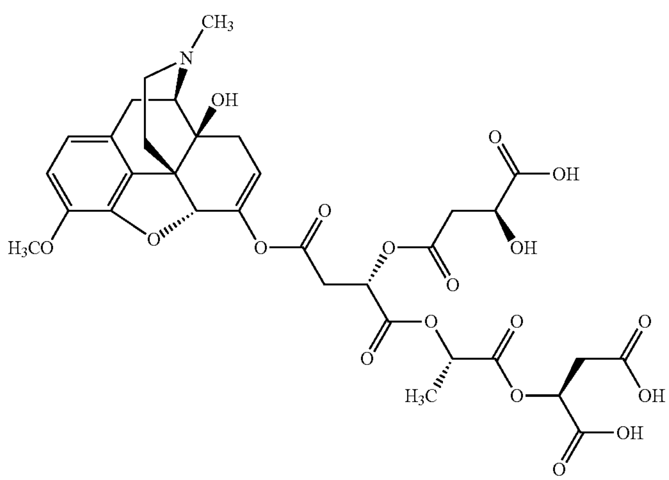 [SMILES: COc1ccc2c3c1O[C@H]1C(OC(=O)C[C@H](OC(=O)C[C@H](O)C(=O)O)C(=O)O[C@@H](C)C(=O)O[C@@H](CC(=O)O)C(=O)O)=CC[C@@]4(O)[C@@H](C2)N(C)CCC[C@]314] | (S)-2-(((S)-2-(((S)-2-(((S)-3-carboxy-3-hydroxypropanoyl)oxy)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |
| C72 | 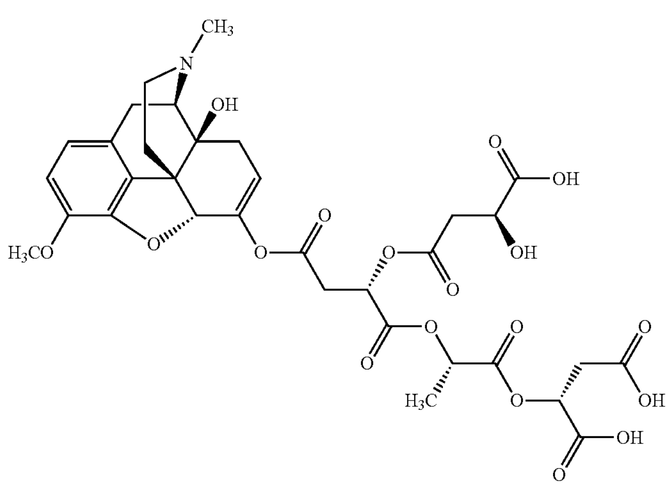 [SMILES: COc1ccc2c3c1O[C@H]1C(OC(=O)C[C@H](OC(=O)C[C@H](O)C(=O)O)C(=O)O[C@@H](C)C(=O)O[C@H](CC(=O)O)C(=O)O)=CC[C@@]4(O)[C@@H](C2)N(C)CCC[C@]314] | (R)-2-(((S)-2-(((S)-2-(((S)-3-carboxy-3-hydroxypropanoyl)oxy)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |

-continued

| Ex, No. | Structure | Name |
|---|---|---|
| C73 | 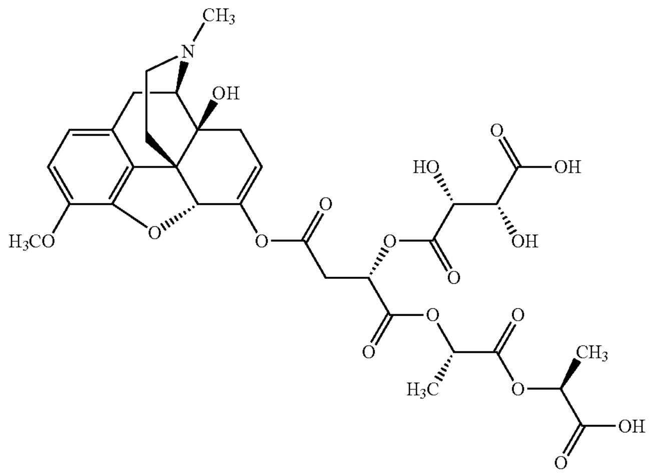 [SMILES: COc1ccc2c3c1O[C@H]1C(OC(=O)C[C@H](OC(=O)[C@H](O)[C@@H](O)C(=O)O)C(=O)O[C@@H](C)C(=O)O[C@@H](C)C(=O)O)=CC[C@@]4(O)[C@@H](C2)N(C)CCC[C@]314] | (2R,3R)-4-(((S)-1-(((S)-1-((S)-1-carboxyethoxy)-1-oxopropan-2-yl)oxy)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1,4-dioxobutan-2-yl)oxy)-2,3-dihydroxy-4-oxobutanoic acid |
| C74 | 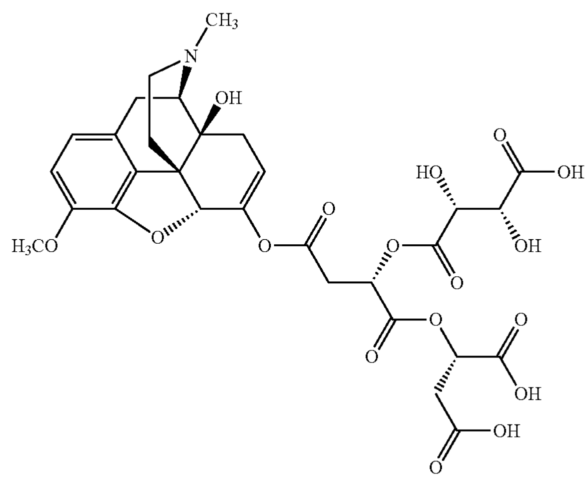 [SMILES: COc1ccc2c3c1O[C@H]1C(OC(=O)C[C@H](OC(=O)[C@H](O)[C@@H](O)C(=O)O)C(=O)O[C@@H](CC(=O)O)C(=O)O)=CC[C@@]4(O)[C@@H](C2)N(C)CCC[C@]314] | (S)-2-(((S)-2-(((2R,3R)-3-carboxy-2,3-dihydroxypropanoyl)oxy)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid |
| C75 | 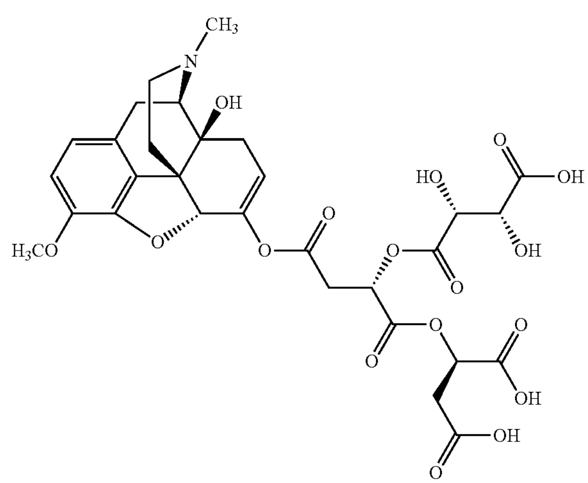 [SMILES: COc1ccc2c3c1O[C@H]1C(OC(=O)C[C@H](OC(=O)[C@H](O)[C@@H](O)C(=O)O)C(=O)O[C@H](CC(=O)O)C(=O)O)=CC[C@@]4(O)[C@@H](C2)N(C)CCC[C@]314] | (R)-2-(((S)-2-(((2R,3R)-3-carboxy-2,3-dihydroxypropanoyl)oxy)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid |

| Ex, No. | Structure | Name |
|---|---|---|
| C76 | 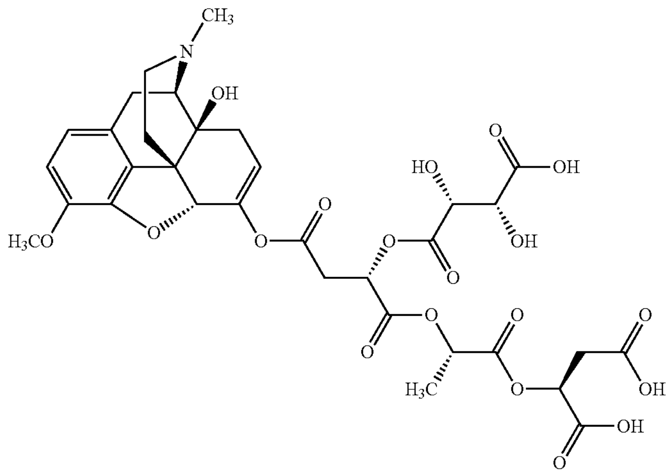 [SMILES: COc1ccc2c3c1O[C@H]1C(OC(=O)C[C@H](OC(=O)[C@H](O)[C@@H](O)C(=O)O)C(=O)O[C@@H](C)C(=O)O[C@@H](CC(=O)O)C(=O)O)=CC[C@@]4(O)[C@@H](C2)N(C)CCC[C@]314] | (S)-2-(((S)-2-(((S)-2-(((2R,3R)-3-carboxy-2,3-dihydroxy-propanoyl)oxy)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |
| C77 | 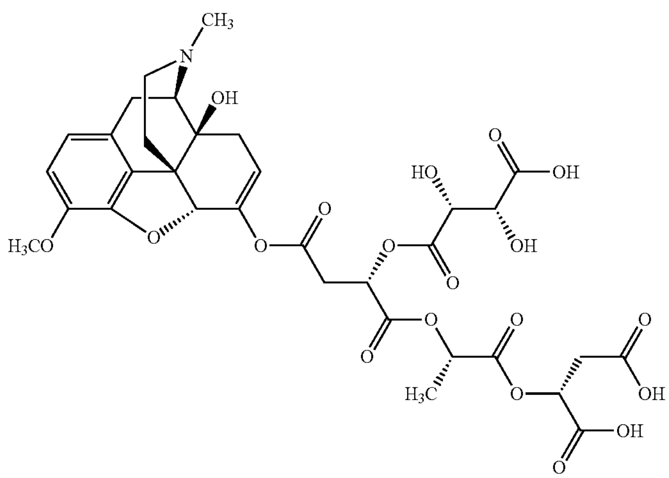 [SMILES: COc1ccc2c3c1O[C@H]1C(OC(=O)C[C@H](OC(=O)[C@H](O)[C@@H](O)C(=O)O)C(=O)O[C@@H](C)C(=O)O[C@H](CC(=O)O)C(=O)O)=CC[C@@]4(O)[C@@H](C2)N(C)CCC[C@]314] | (R)-2-(((S)-2-(((S)-2-(((2R,3R)-3-carboxy-2,3-dihydroxy-propanoyl)oxy)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |
| C78 | 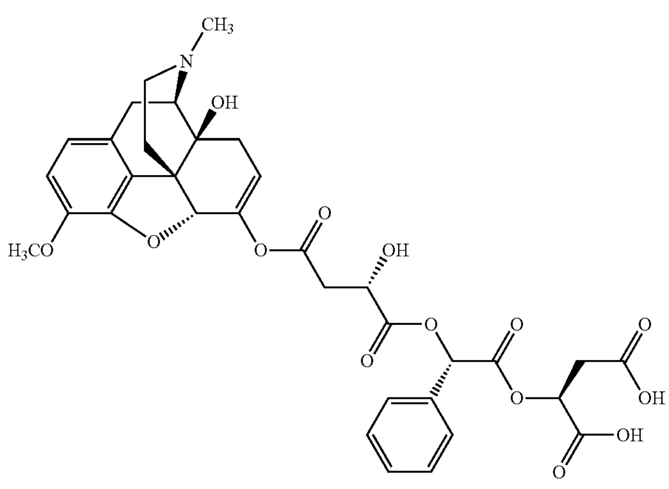 [SMILES: COc1ccc2c3c1O[C@H]1C(OC(=O)C[C@H](O)C(=O)O[C@H](C(=O)O[C@@H](CC(=O)O)C(=O)O)c4ccccc4)=CC[C@@]4(O)[C@@H](C2)N(C)CCC[C@]314] | (S)-2-((S)-2-(((S)-2-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)succinic acid |

-continued

| Ex, No. | Structure | Name |
|---|---|---|
| C79 | 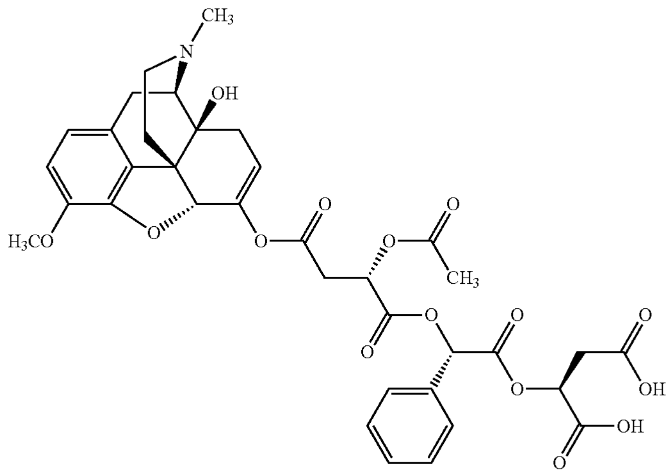 [SMILES: COc1ccc2c3c1O[C@H]1C(OC(=O)C[C@H](OC(C)=O)C(=O)O[C@H](C(=O)O[C@@H](CC(=O)O)C(=O)O)c4ccccc4)=CC[C@@]4(O)[C@@H](C2)N(C)CCC[C@]314] | (S)-2-((S)-2-(((S)-2-acetoxy-4-(((4R,4aS,7aR,12bS)-4a-hydroxy-9-methoxy-3-methyl-2,3,4,4a,5,7a-hexahydro-1H-4,12-methanoben2ofuro[3,2-e]isoquinolin-7-yl)oxy)-4-oxobutanoyl)oxy)-2-phenylacetoxy) succinic acid |
| C80 | 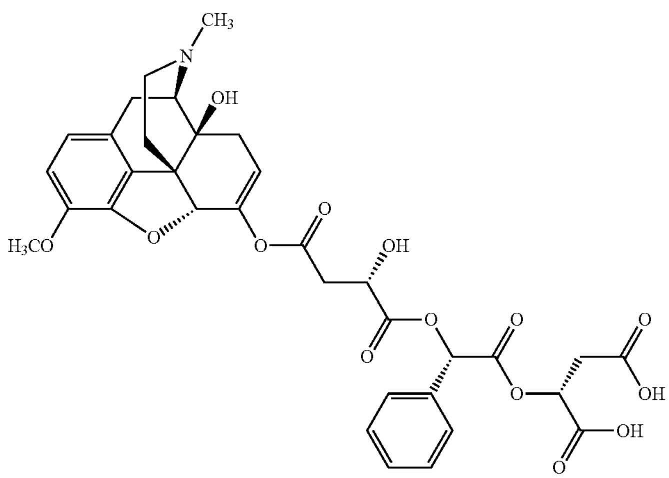 [SMILES: COc1ccc2c3c1O[C@H]1C(OC(=O)C[C@H](O)C(=O)O[C@H](C(=O)O[C@H](CC(=O)O)C(=O)O)c4ccccc4)=CC[C@@]4(O)[C@@H](C2)N(C)CCC[C@]314] | (R)-2-((S)-2-(((S)-2-hydroxy-4-(((4R,4aS,7aR,12bS)-4a-hydroxy-9-methoxy-3-methyl-2,3,4,4a,5,7a-hexahydro-1H-4,2-methanobenzofuro[3,2-e]isoquinolin-7-yl)oxy)-4-oxobutanoyl)oxy)-2-phenylacetoxy) succinic acid |
| C81 | 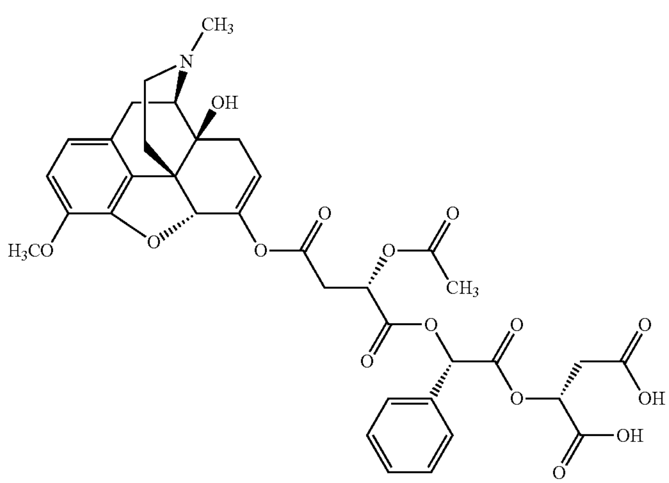 [SMILES: COc1ccc2c3c1O[C@H]1C(OC(=O)C[C@H](OC(C)=O)C(=O)O[C@H](C(=O)O[C@H](CC(=O)O)C(=O)O)c4ccccc4)=CC[C@@]4(O)[C@@H](C2)N(C)CCC[C@]314] | (R)-2-((S)-2-(((S)-2-acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy) succinic acid |

| Ex, No. | Structure | Name |
|---|---|---|
| C82 | 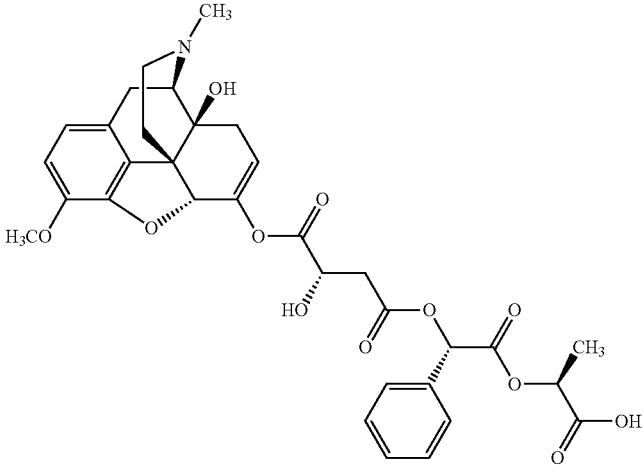 [SMILES: COc1ccc2c3c1O[C@H]1C(OC(=O)[C@@H](O)CC(=O)O[C@H](C(=O)O[C@@H](C)C(=O)O)c4ccccc4)=CC[C@@]4(O)[C@@H](C2)N(C)CCC[C@]314] | (S)-2-((S)-2-(((S)-3-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)propanoic acid |
| C83 | 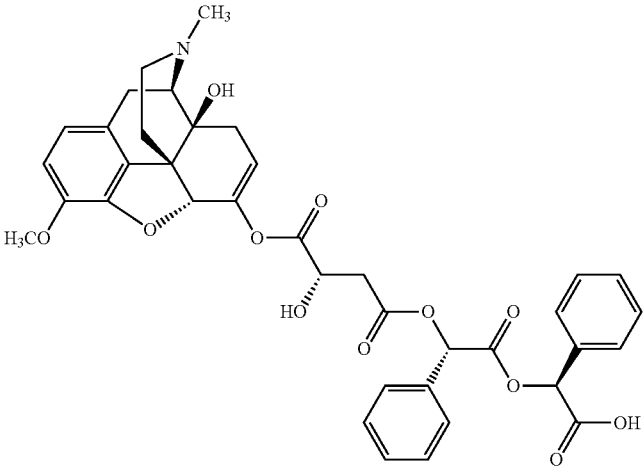 [SMILES: COc1ccc2c3c1O[C@H]1C(OC(=O)[C@@H](O)CC(=O)O[C@H](C(=O)O[C@H](C(=O)O)c4ccccc4)c4ccccc4)=CC[C@@]4(O)[C@@H](C2)N(C)CCC[C@]314] | (S)-2-((S)-2-(((S)-3-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)-2-phenylacetic acid |
| C84 | 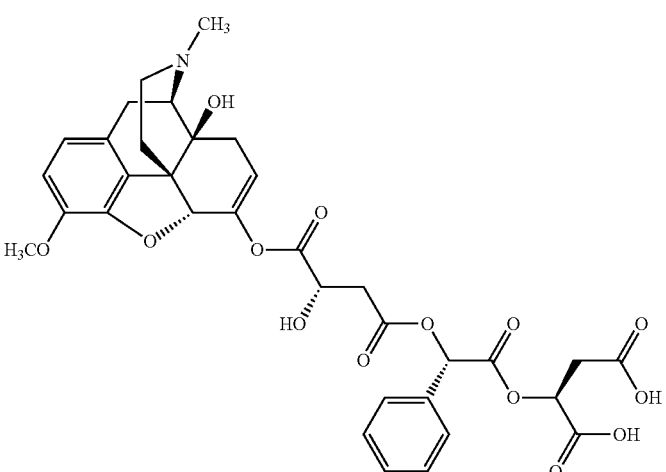 | (S)-2-((S)-2-(((S)-3-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)succinic acid |

| Ex, No. | Structure | Name |
|---|---|---|
| C85 | 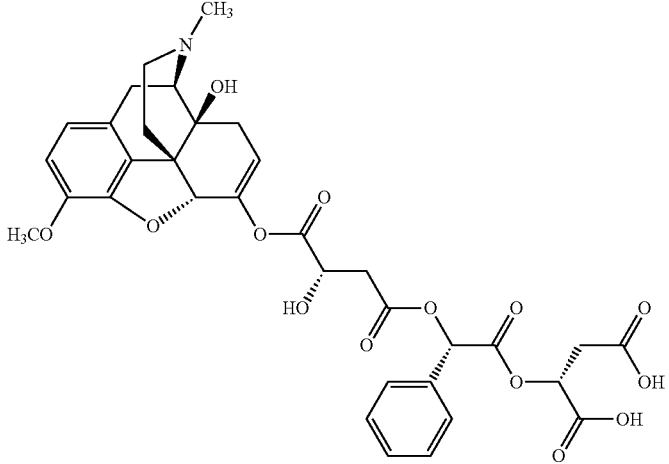 [SMILES: COc1ccc2c3c1O[C@H]1C(OC(=O)[C@@H](O)CC(=O)O[C@H](C(=O)O[C@H](CC(=O)O)C(=O)O)c4ccccc4)=CC[C@@]4(O)[C@@H](C2)N(C)CCC[C@]314] | (R)-2-((S)-2-(((S)-3-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)succinic acid |
| C86 | 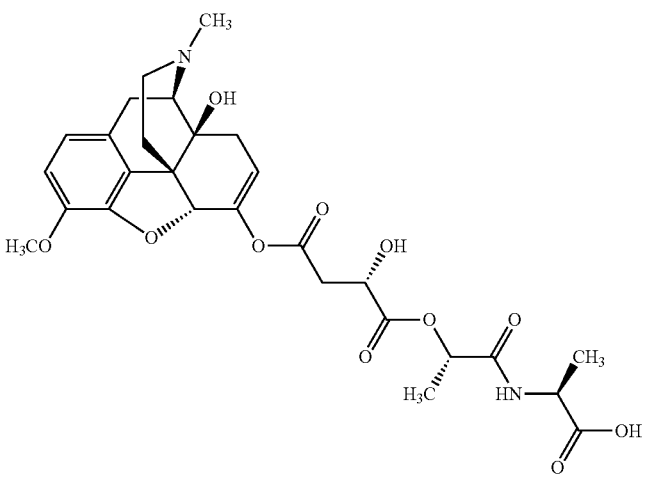 [SMILES: COc1ccc2c3c1O[C@H]1C(OC(=O)C[C@H](O)C(=O)O[C@@H](C)C(=O)N[C@@H](C)C(=O)O)=CC[C@@]4(O)[C@@H](C2)N(C)CCC[C@]314] | (S)-2-((S)-2-(((S)-2-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanamido)propanoic acid |
| C87 | 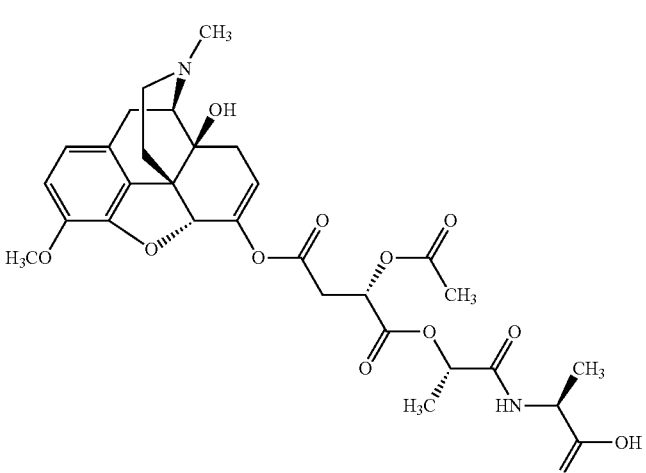 | (S)-2-((S)-2-(((S)-2-acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanamido)propanoic acid |

| Ex, No. | Structure | Name |
|---|---|---|
| C88 | 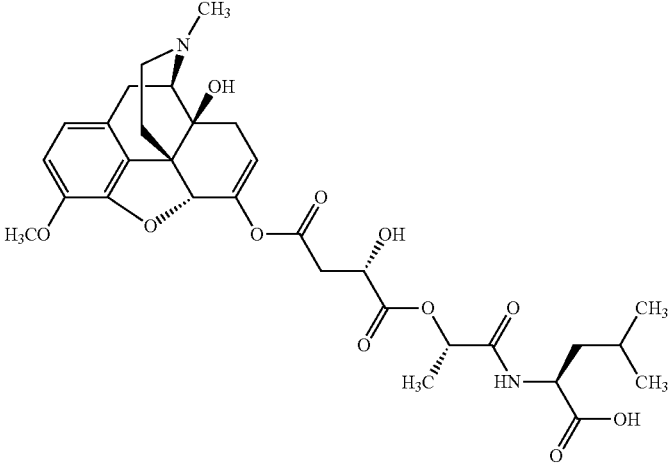 [SMILES: COc1ccc2c3c1O[C@H]1C(OC(=O)C[C@H](O)C(=O)O[C@@H](C)C(=O)N[C@@H](CC(C)C)C(=O)O)=CC[C@@]4(O)[C@@H](C2)N(C)CCC[C@]314] | (S)-2-((S)-2-(((S)-2-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanamido)-4-methylpentanoic acid |
| C89 | 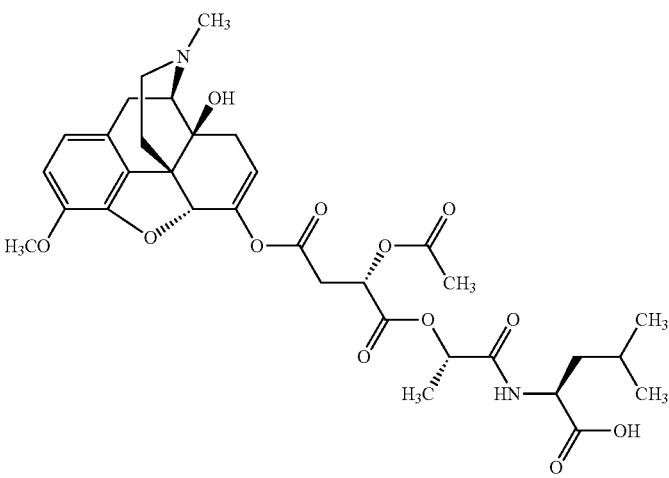 [SMILES: COc1ccc2c3c1O[C@H]1C(OC(=O)C[C@H](OC(C)=O)C(=O)O[C@@H](C)C(=O)N[C@@H](CC(C)C)C(=O)O)=CC[C@@]4(O)[C@@H](C2)N(C)CCC[C@]314] | (S)-2-((S)-2-(((S)-2-acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanamido)-4-methylpentanoic acid |
| C90 | 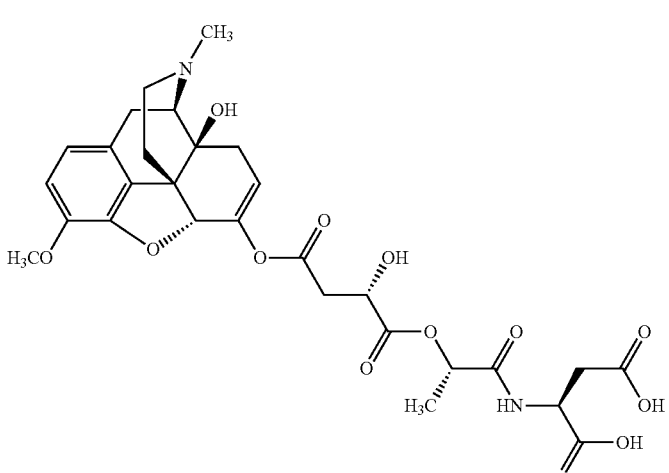 | (S)-2-((S)-2-(((S)-2-hydroxy-4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanamido)succinic acid |

| Ex, No. | Structure | Name |
|---|---|---|
| C91 | 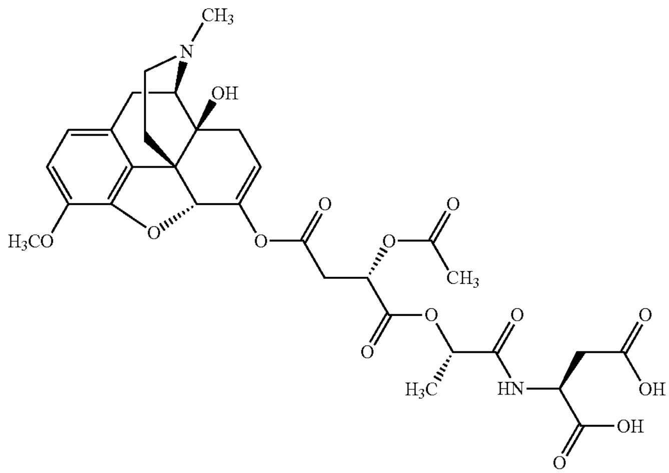 [SMILES: COc1ccc2c3c1O[C@H]1C(OC(=O)C[C@H](OC(C)=O)C(=O)O[C@@H](C)C(=O)N[C@@H](CC(=O)O)C(=O)O)=CC[C@@]4(O)[C@@H](C2)N(C)CCC[C@]314] | (S)-2-((S)-2-(((S)-2-acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanamido)succinic acid |
| C92 | 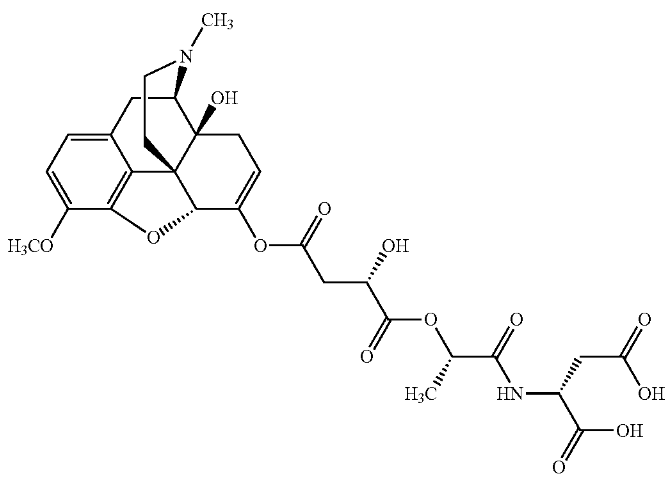 [SMILES: COc1ccc2c3c1O[C@H]1C(OC(=O)C[C@H](O)C(=O)O[C@@H](C)C(=O)N[C@H](CC(=O)O)C(=O)O)=CC[C@@]4(O)[C@@H](C2)N(C)CCC[C@]314] | (R)-2-((S)-2-(((S)-2-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanamido)succinic acid |
| C93 | 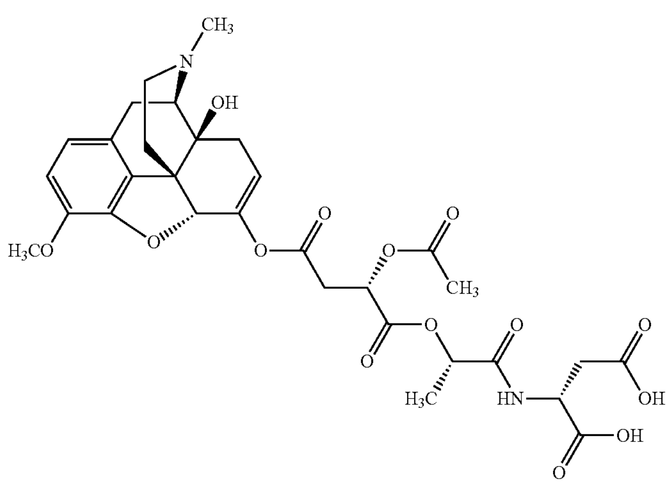 [SMILES: COc1ccc2c3c1O[C@H]1C(OC(=O)C[C@H](OC(C)=O)C(=O)O[C@@H](C)C(=O)N[C@H](CC(=O)O)C(=O)O)=CC[C@@]4(O)[C@@H](C2)N(C)CCC[C@]314] | (R)-2-((S)-2-(((S)-2-acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanamido)succinic acid |

| Ex. No. | Structure | Name |
|---|---|---|
| C94 | 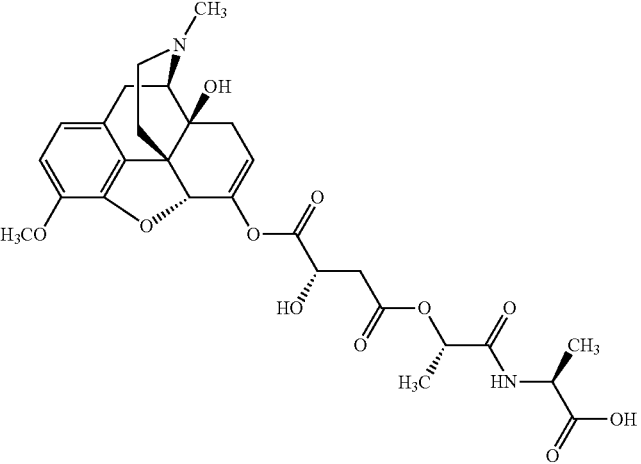 [SMILES: COc1ccc2c3c1O[C@H]1C(OC(=O)[C@@H](O)CC(=O)O[C@@H](C)C(=O)N[C@@H](C)C(=O)O)=CC[C@@]4(O)[C@@H](C2)N(C)CCC[C@]314] | (S)-2-((S)-2-(((S)-3-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanamido)propanoic acid |
| C95 | 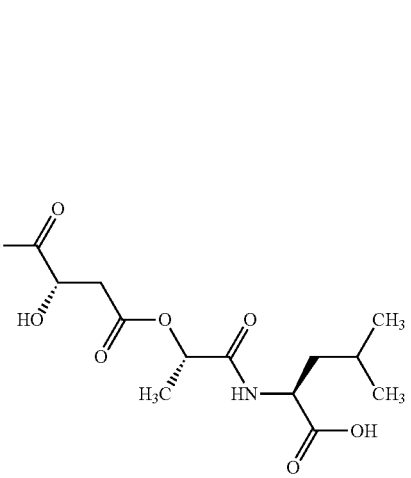 | (S)-2-((S)-2-(((S)-3-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanamido)-4-methylpentanoic acid |
| C96 | 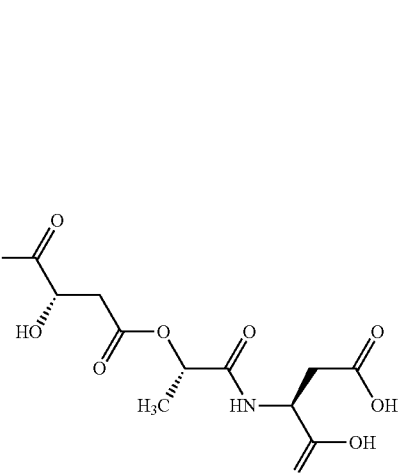 | (S)-2-((S)-2-(((S)-3-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanamido)succinic acid |

-continued

| Ex, No. | Structure | Name |
|---|---|---|
| C97 | 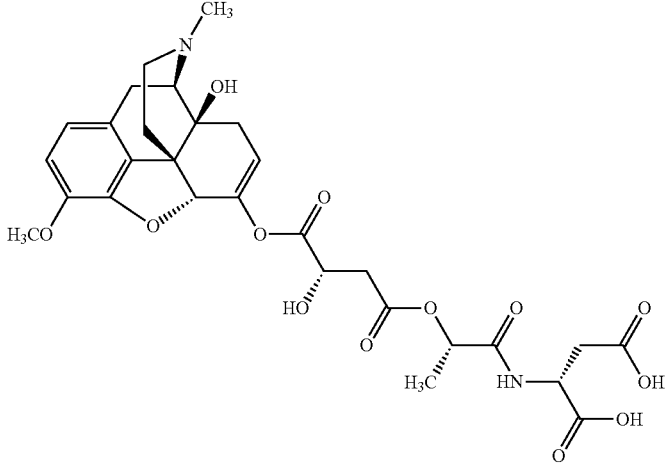 [SMILES: COc1ccc2c3c1O[C@H]1C(OC(=O)[C@@H](O)CC(=O)O[C@@H](C)C(=O)N[C@H](CC(=O)O)C(=O)O)=CC[C@@]4(O)[C@@H](C2)N(C)CCC[C@]314] | (R)-2-((S)-2-(((S)-3-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanamido)succinic acid |
| C98 | 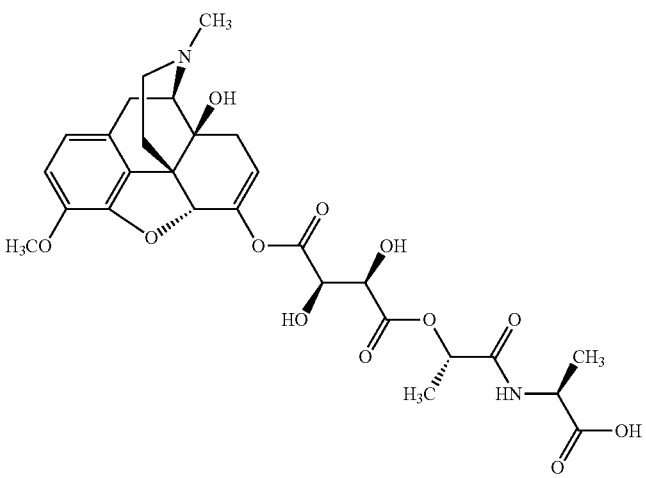 [SMILES: COc1ccc2c3c1O[C@H]1C(OC(=O)[C@H](O)[C@@H](O)C(=O)O[C@@H](C)C(=O)N[C@@H](C)C(=O)O)=CC[C@@]4(O)[C@@H](C2)N(C)CCC[C@]314] | (S)-2-(((S)-2-(((2R,3R)-2,3-dihydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)propanoic acid |
| C99 | 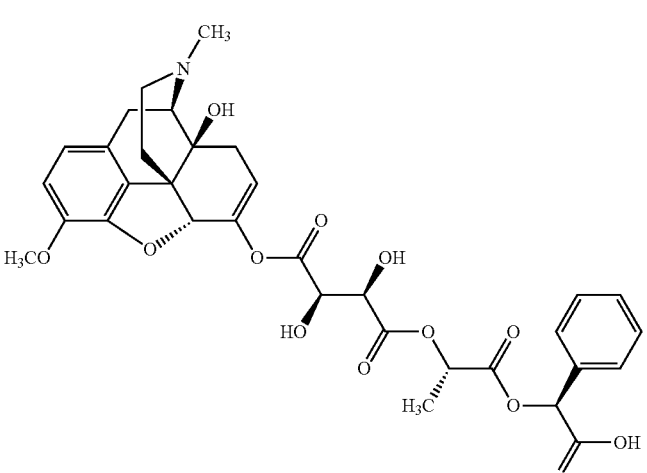 | (S)-2-(((S)-2-(((2R,3R)-2,3-dihydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)-2-phenylacetic acid |

| Ex. No. | Structure | Name |
|---|---|---|
| C100 | 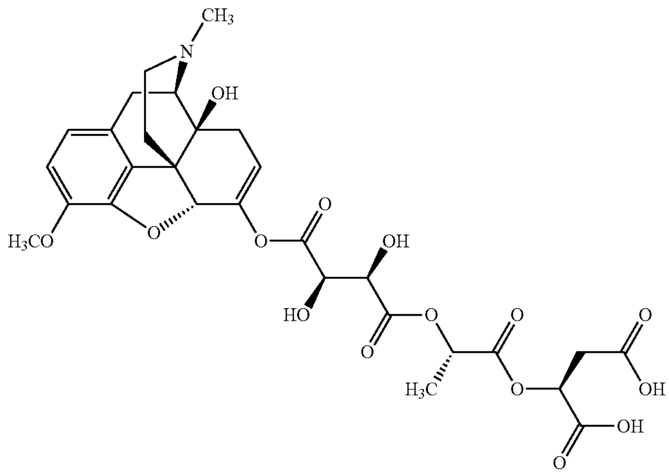 [SMILES: COc1ccc2c3c1O[C@H]1C(OC(=O)[C@H](O)[C@@H](O)C(=O)O[C@@H](C)C(=O)O[C@@H](CC(=O)O)C(=O)O)=CC[C@@]4(O)[C@@H](C2)N(C)CCC[C@]314] | (S)-2-(((S)-2-(((2R,3R)-2,3-dihydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |
| C101 | 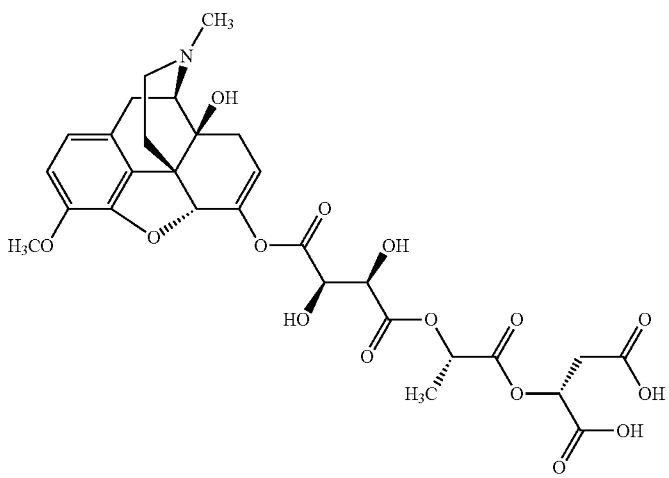 [SMILES: COc1ccc2c3c1O[C@H]1C(OC(=O)[C@H](O)[C@@H](O)C(=O)O[C@@H](C)C(=O)O[C@H](CC(=O)O)C(=O)O)=CC[C@@]4(O)[C@@H](C2)N(C)CCC[C@]314] | (R)-2-(((S)-2-(((2R,3R)-2,3-dihydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |
| C102 | 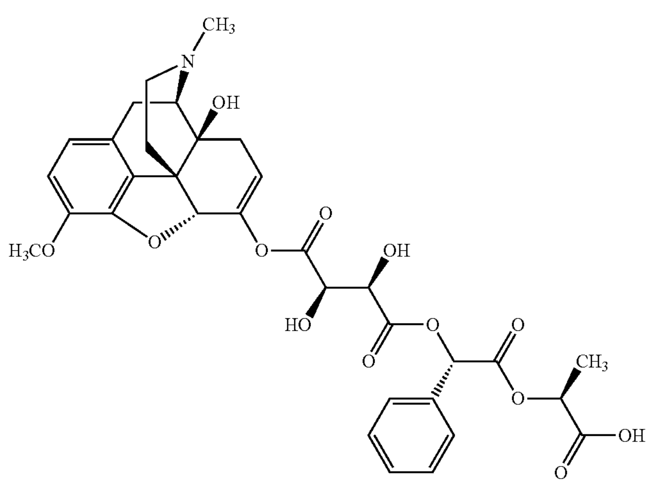 [SMILES: COc1ccc2c3c1O[C@H]1C(OC(=O)[C@H](O)[C@@H](O)C(=O)O[C@H](C(=O)O[C@@H](C)C(=O)O)c4ccccc4)=CC[C@@]4(O)[C@@H](C2)N(C)CCC[C@]314] | (S)-2-(((S)-2-(((2R,3R)-2,3-dihydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)propanoic acid |

| Ex, No. | Structure | Name |
|---|---|---|
| C103 | 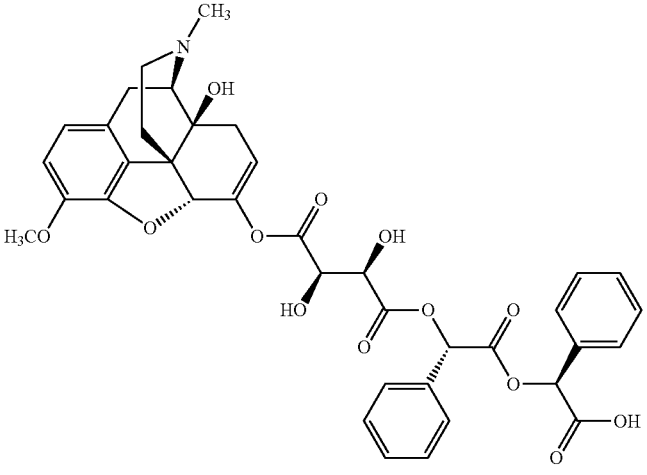 [SMILES: COc1ccc2c3c1O[C@H]1C(OC(=O)[C@H](O)[C@@H](O)C(=O)O[C@H](C(=O)O[C@H](C(=O)O)c4ccccc4)c4ccccc4)=CC[C@@]4(O)[C@@H](C2)N(C)CCC[C@]314] | (S)-2-((S)-2-(((2R,3R)-2,3-dihydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)-2-phenylacetic acid |
| C104 | 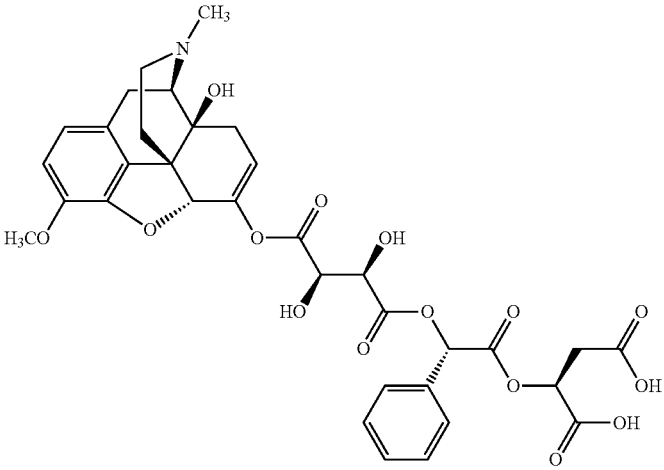 [SMILES: COc1ccc2c3c1O[C@H]1C(OC(=O)[C@H](O)[C@@H](O)C(=O)O[C@H](C(=O)O[C@@H](CC(=O)O)C(=O)O)c4ccccc4)=CC[C@@]4(O)[C@@H](C2)N(C)CCC[C@]314] | (S)-2-((S)-2-(((2R,3R)-2,3-dihydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)succinic acid |
| C105 | 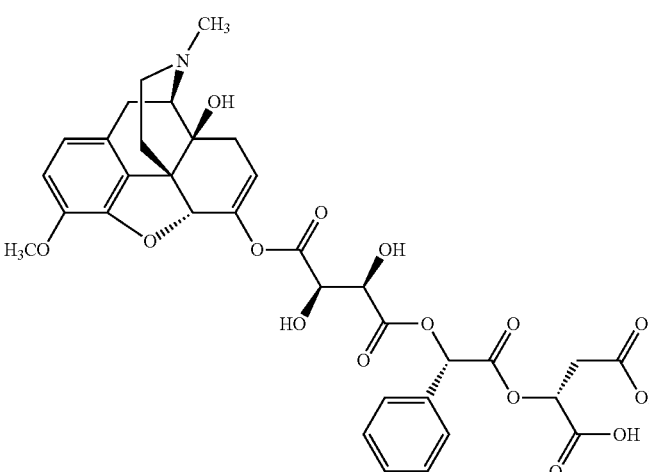 | (R)-2-((S)-2-(((2R,3R)-2,3-dihydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)succinic acid |

| Ex, No. | Structure | Name |
|---|---|---|
| C106 | 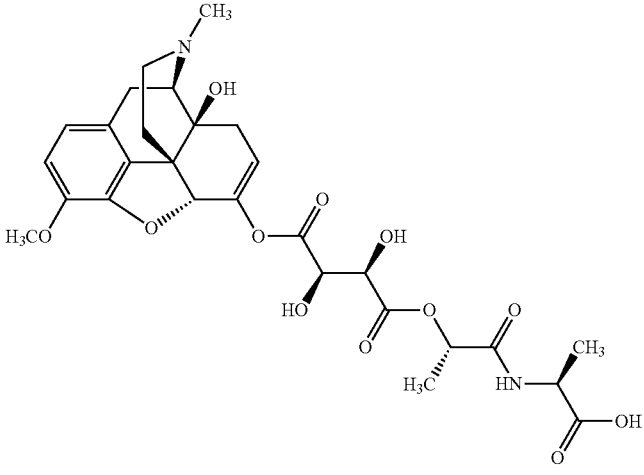 [SMILES: COc1ccc2c3c1O[C@H]1C(OC(=O)[C@H](O)[C@@H](O)C(=O)O[C@@H](C)C(=O)N[C@@H](C)C(=O)O)=CC[C@@]4(O)[C@@H](C2)N(C)CCC[C@]314] | (S)-2-((S)-2-(((2R,3R)-2,3-dihydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanamido)propanoic acid |
| C107 | 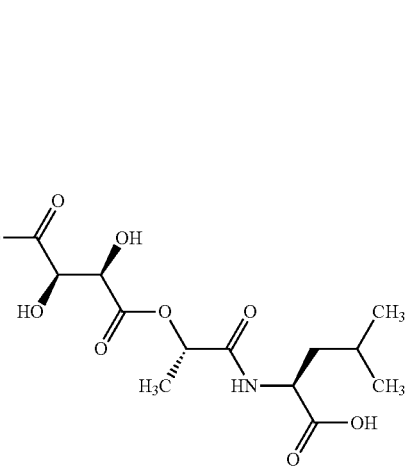 | (S)-2-((S)-2-(((2R,3R)-2,3-dihydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanamido)-4-methylpentanoic acid |
| C108 | 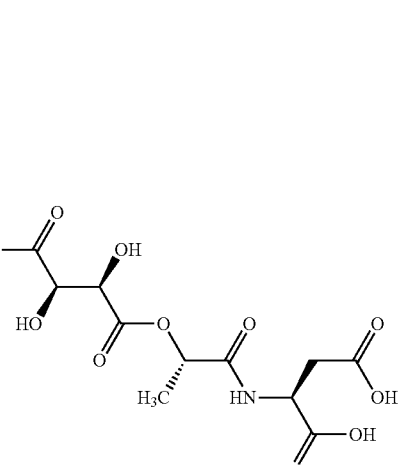 | (S)-2-((S)-2-(((2R,3R)-2,3-dihydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanamido)succinic acid |

| Ex. No. | Structure | Name |
|---|---|---|
| C109 | 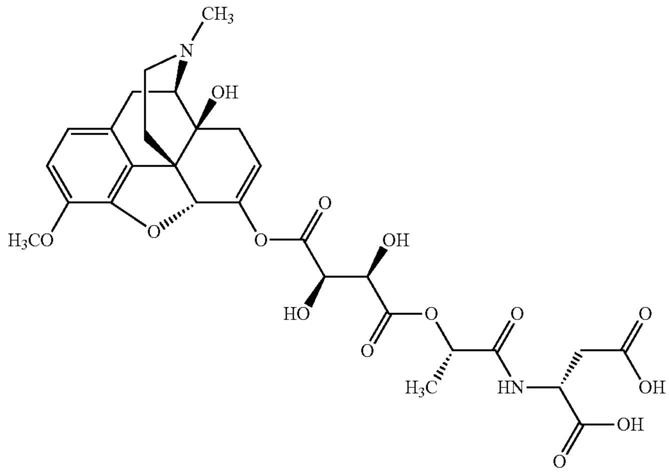 [SMILES: COc1ccc2c3c1O[C@H]1C(OC(=O)[C@H](O)[C@@H](O)C(=O)O[C@@H](C)C(=O)N[C@H](CC(=O)O)C(=O)O)=CC[C@@]4(O)[C@@H](C2)N(C)CCC[C@]314] | (R)-2-((S)-2-(((2R,3R)-2,3-dihydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanamido)succinic acid |

In further embodiments, the abuse-resistant opioid compound may be selected from one or more of:

| Ex. No. | Structure | Name |
|---|---|---|
| D1 | 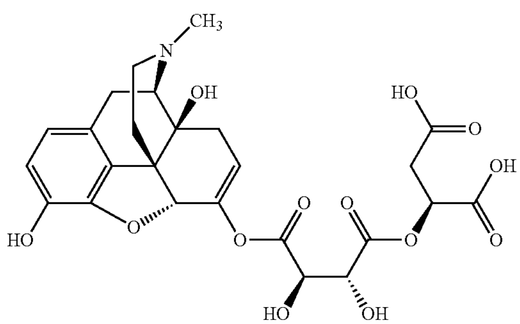 [SMILES: CN1CC[C@]23c4c5ccc(O)c4O[C@H]2C(OC(=O)[C@H](O)[C@@H](O)C(=O)O[C@@H](CC(=O)O)C(=O)O)=CC[C@@]3(O)[C@H]1C5] | (S)-2-(((2R,3R)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy)succinic acid |
| D2 | 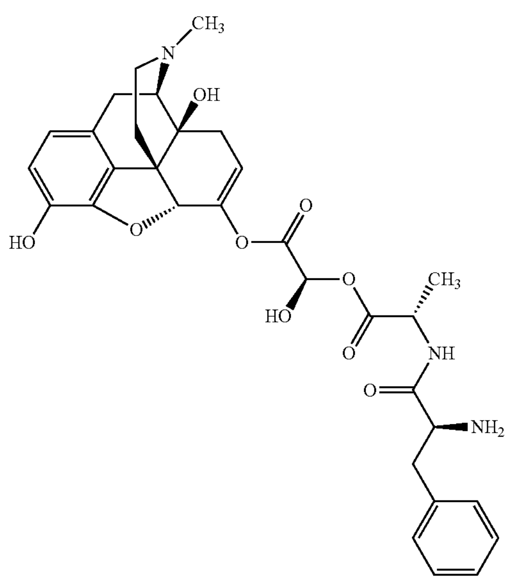 [SMILES: C[C@H](NC(=O)[C@@H](N)Cc1ccccc1)C(=O)O[C@@H](O)C(=O)OC1=CC[C@@]2(O)[C@H]3Cc4ccc(O)c5c4[C@@]2(CCN3C)[C@H]1O5] | (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-(((S)-2-((S)-2-amino-3-phenylpropanamido)propanoyl)oxy)propanoate |

| Ex. No. | Structure | Name |
|---|---|---|
| D3 | 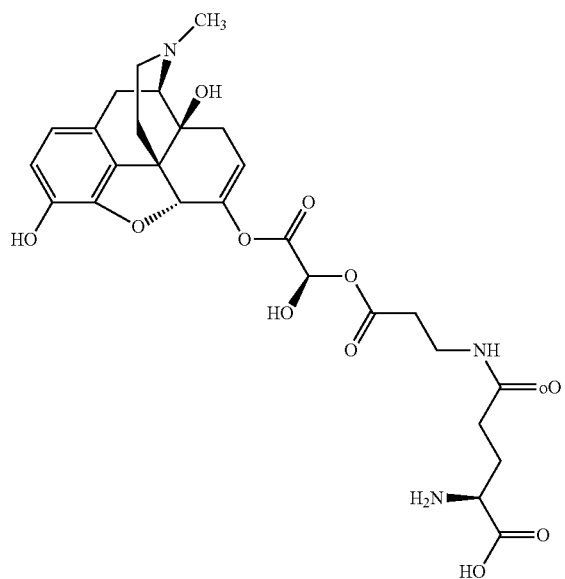 | (S)-2-amino-5-((3-(((S)-1-(((4R,4aS,7aR,12bS)-4a,9-dihydroxy-3-methyl-2,3,4,4a,5,7-hexahydro-1H-4,12-methanobenzofuro[3,2-e]isoquinolin-7-yl)oxy)-1-oxopropan-2-yl)oxy)-3-oxopropyl)amino)-5-oxopentanoic acid |
| D4 | 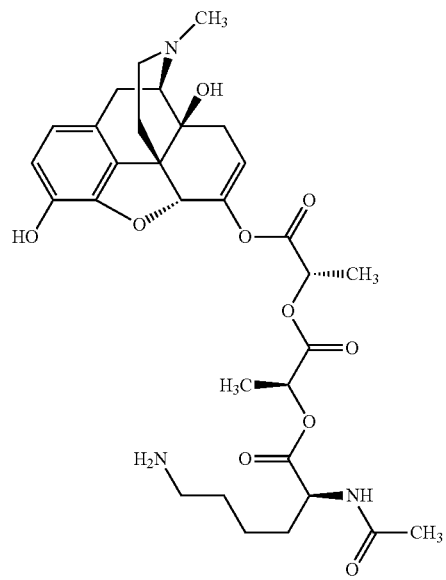 [SMILES: CC(=O)N[C@@H](CCCCN)C(=O)O[C@@H](C)C(=O)O[C@@H](C)C(=O)OC1=CC[C@@]2(O)[C@H]3Cc4ccc(O)c5c4[C@@]2(CCN3C)[C@H]1O5] | (S)-(S)-1-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl 2-actamido-6-aminohexanoate |

-continued
| Ex. No. | Structure | Name |
|---|---|---|
| D5 | 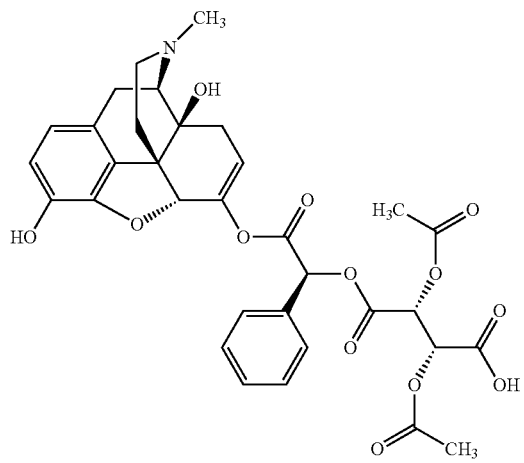 [SMILES: CC(=O)O[C@@H](C(=O)O)[C@@H](OC(C)=O)C(=O)O[C@H](C(=O)OC1=CC[C@@]2(O)[C@H]3Cc4ccc(O)c5c4[C@@]2(CCN3C)[C@H]1O5)c1ccccc1] | (2R,3R)-2,3-diacetoxy-4-((S)-2-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid |
| D6 | 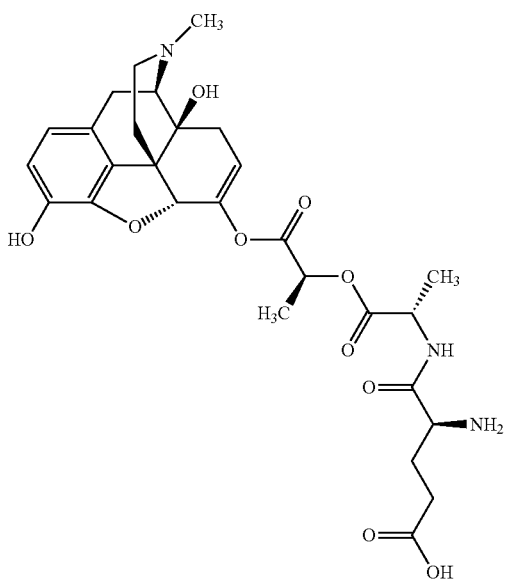 [SMILES: C[C@H](NC(=O)[C@@H](N)CCC(=O)O)C(=O)O[C@@H](C)C(=O)OC1=CC[C@@]2(O)[C@H]3Cc4ccc(O)c5c4[C@@]2(CCN3C)[C@H]1O5] | (S)-4-amino-5-(((S)-1-(((S)-1-(((4R,4aS,7aR,12bS)-4a,9-dihydroxy-3-methyl-2,3,4,4a,5,7a-hexahydro-1H-4,12-methano-benzofuro[3,2-e]isoquinolin-7-yl)oxy)-1-oxopropan-2-yl)oxy)-1-oxopropan-2-yl)amino)-5-oxopentanoic acid |

| Ex. No. | Structure | Name |
|---|---|---|
| D7 | 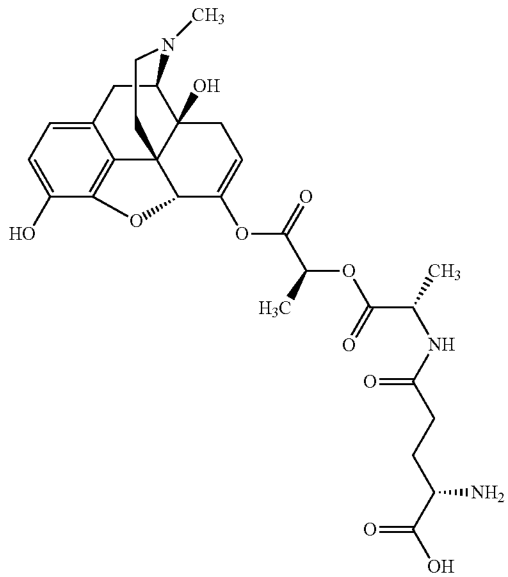 [SMILES: C[C@H](NC(=O)CC[C@H](N)C(=O)O)C(=O)O[C@@H](C)C(=O)OC1=CC[C@@]2(O)[C@H]3Cc4ccc(O)c5c4[C@@]2(CCN3C)[C@H]1O5] | (S)-2-amino-5-(((S)-1-(((S)-1-(((4R,4aS,7aR,12bS)-4a,9-dihydroxy-3-methyl-2,3,4,4a,5,7a-hexahydro-1H-4,12-methano-benzofuro[3,2-e]isoquinolin-7-yl)oxy)-1-oxopropan-2-yl)oxy)-1-oxopropan-2-yl)amino)-5-oxopentanoic acid |
| D8 | 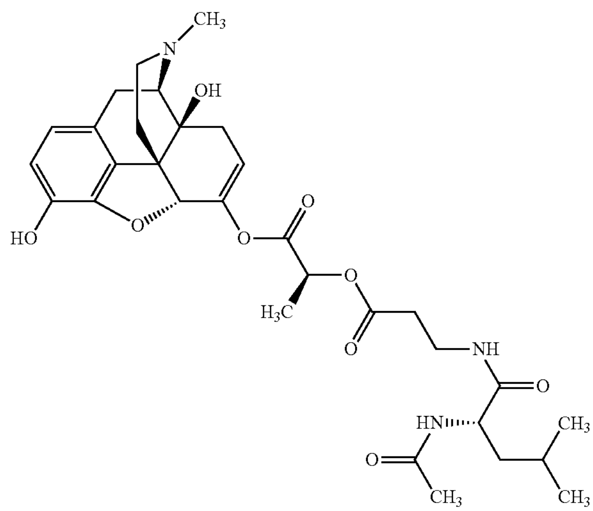 [SMILES: CC(=O)N[C@@H](CC(C)C)C(=O)NCCC(=O)O[C@@H](C)C(=O)OC1=CC[C@@]2(O)[C@H]3Cc4ccc(O)c5c4[C@@]2(CCN3C)[C@H]1O5] | (S)-(4R,4aS,7aR,12bs)-4a,9-dihydroxy-3-methyl-2,3,4,4a,5,7a-hexahydro-1H-4,12-methanobenzofuro[3,2-e]isoquinolin-7-yl 2-((3-((S)-2-acetamido-4-methylpentanamido)propanoyl)oxy)propanoate |
| D9 | 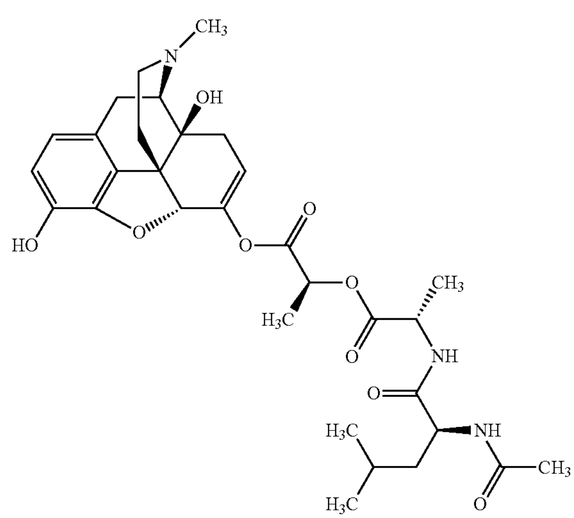 [SMILES: CC(=O)N[C@@H](CC(C)C)C(=O)N[C@@H](C)C(=O)O[C@@H](C)C(=O)OC1=CC[C@@]2(O)[C@H]3Cc4ccc(O)c5c4[C@@]2(CCN3C)[C@H]1O5] | (S)-(4R,4aS,7aR,12bS)-4a,9-dihydro-3-methyl-2,3,4,4a,5,7a-hexahydro-1H-4,12-methanobenzofuro[3,2-e]isoquinolin-7-yl 2-(((S)-2-((S)-2-acetamido-4-methyl-pentanamido)propanoyl)oxy)propanoate |

| Ex. No. | Structure | Name |
|---|---|---|
| D10 | 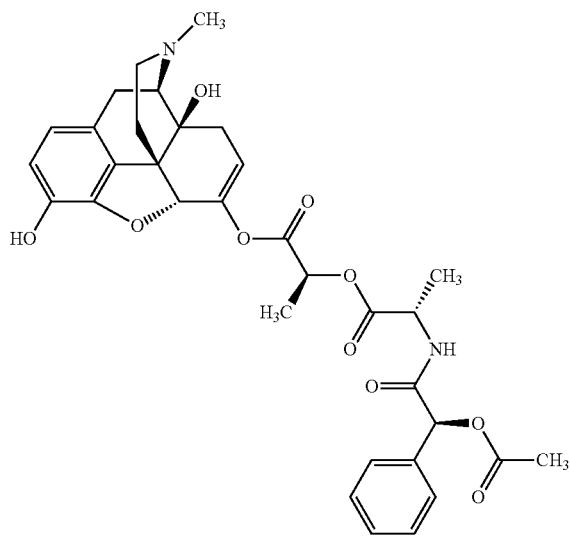 [SMILES: CC(=O)O[C@H](C(=O)N[C@@H](C)C(=O)O[C@@H](C)C(=O)OC1=CC[C@@]2(O)[C@H]3Cc4ccc(O)c5c4[C@@]2(CCN3C)[C@H]1O5)c1ccccc1] | (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-(((S)-2-((S)-2-acetoxy-2-phenylacetamido)propanoyl)oxy)propanoate |
| D11 | 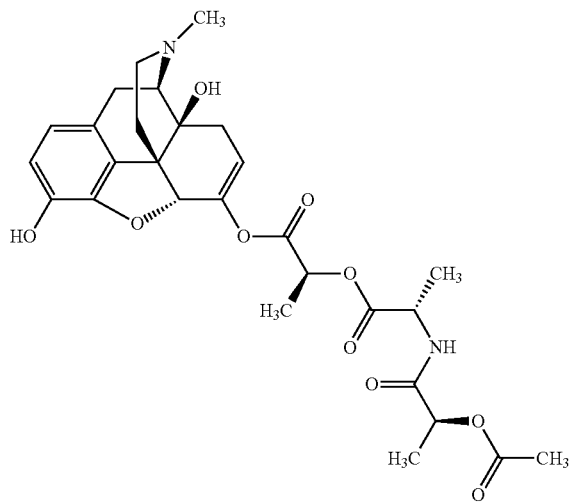 [SMILES: CC(=O)O[C@@H](C)C(=O)N[C@@H](C)C(=O)O[C@@H](C)C(=O)OC1=CC[C@@]2(O)[C@H]3Cc4ccc(O)c5c4[C@@]2(CCN3C)[C@H]1O5] | (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-(((S)-2-((S)-2-acetoxypropanamido)propanoyl)oxy)propanoate |
| D12 | 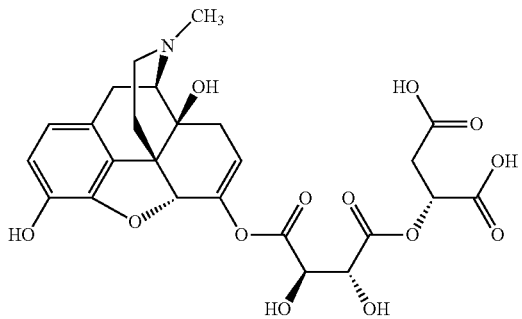 [SMILES: CN1CC[C@]23c4c5ccc(O)c4O[C@H]2C(OC(=O)[C@H](O)[C@@H](O)C(=O)O[C@H](CC(=O)O)C(=O)O)=CC[C@@]3(O)[C@H]1C5] | (R)-2-(((2R,3R)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy)succinic acid |

| Ex. No. | Structure | Name |
|---|---|---|
| D13 | 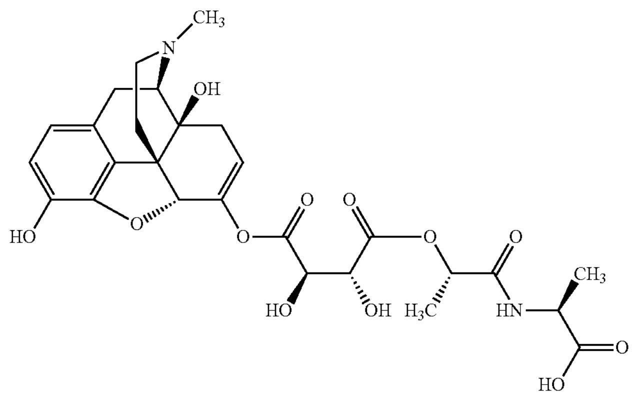 [SMILES: C[C@H](NC(=O)[C@H](C)OC(=O)[C@H](O)[C@@H](O)C(=O)OC1=CC[C@@]2(O)[C@H]3Cc4ccc(O)c5c4[C@@]2(CCN3C)[C@H]1O5)C(=O)O] | (S)-2-((S)-2-(((2R,3R)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy)propanamido)propanoic acid |
| D14 | 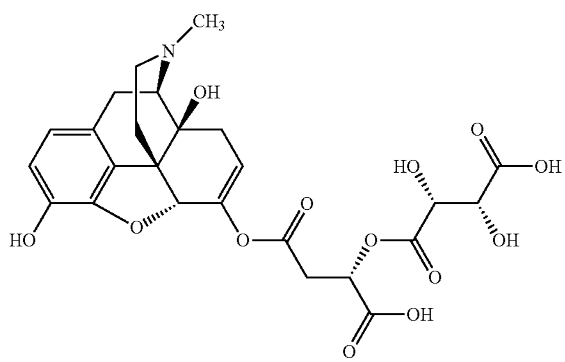 [SMILES: CN1CC[C@]23c4c5ccc(O)c4O[C@H]2C(OC(=O)C[C@H](OC(=O)[C@H](O)[C@@H](O)C(=O)O)C(=O)O)=CC[C@@]3(O)[C@H]1C5] | (2R,3R)-4-((S)-1-carboxy-3-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-oxopropoxy)-2,3-dihydroxy-4-oxobutanoic acid |
| D15 | 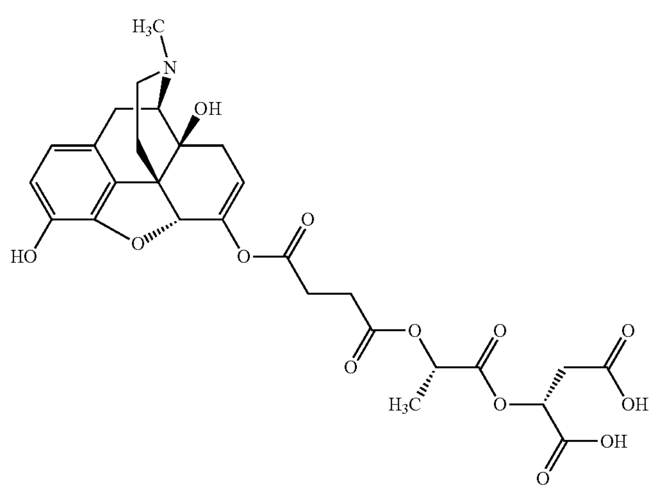 [SMILES: C[C@H](OC(=O)CCC(=O)OC1=CC[C@@]2(O)[C@H]3Cc4ccc(O)c5c4[C@@]2(CCN3C)[C@H]1O5)C(=O)O[C@H](CC(=O)O)C(=O)O] | (R)-2-(((S)-2-((4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |

| Ex. No. | Structure | Name |
|---|---|---|
| D16 | 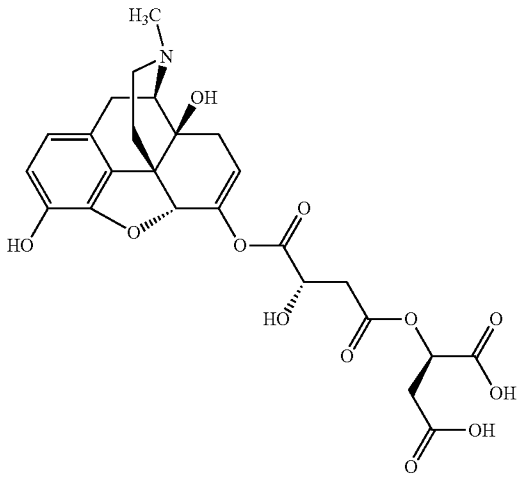 [SMILES: CN1CC[C@]23c4c5ccc(O)c4O[C@H]2C(OC(=O)[C@@H](O)CC(=O)O[C@H](CC(=O)O)C(=O)O)=CC[C@@]3(O)[C@H]1C5] | (R)-2-(((S)-4-(((4R,4aS, 7aR,12bS)-4a,9-dihydroxy-3-methyl-2,3,4,4a,5,7a-hexahydro-1H-4,12-methanobenzofuro [3,2-e]isoquinolin-7-yl)oxy)-3-hydroxy-4-oxobutanoyl) oxy)succinic acid |
| D17 | 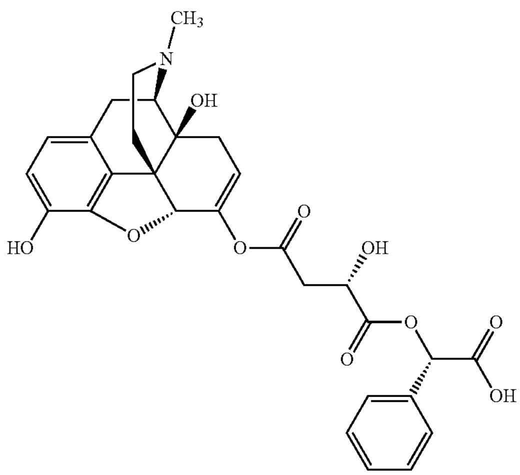 [SMILES: CN1CC[C@]23c4c5ccc(O)c4O[C@H]2C(OC(=O)C[C@H](O)C(=O)O[C@H](C(=O)O)c2ccccc2)=CC[C@@]3(O)[C@H]1C5] | (S)-2-(((S)-4-(((4R,4aS,7aR,12bS)-4a,9-dihydroxy-3-methyl-2,3,4,4a,5,7a-hexahydro-1H-4,12-methanobenzofuro[3,2-e] isoquinolin-7-yl)oxy)-2-hydroxy-4-oxobutanoyl)oxy)-2-phenylacetic acid |
| D18 | 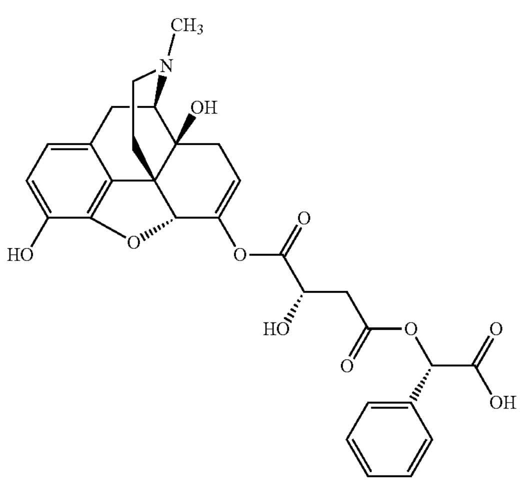 [SMILES: CN1CC[C@]23c4c5ccc(O)c4O[C@H]2C(OC(=O)[C@@H](O)CC(=O)O[C@H](C(=O)O)c2ccccc2)=CC[C@@]3(O)[C@H]1C5] | (S)-2-(((S)-4-(((4R,4aS,7aR, 12bS)-4a,9-dihydroxy-3-methyl-2,3,4,4a,5,7a-hexahydro-1H-4,12-methanobenzofuro [3,2-e]isoquinolin-7-yl)oxy)-3-hydroxy-4-oxobutanoyl)oxy)-2-phenylacetic acid |

-continued

| Ex. No. | Structure | Name |
|---|---|---|
| D19 | 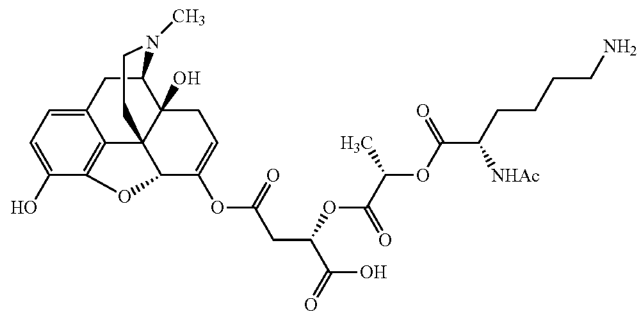 [SMILES: CC(=O)N[C@@H](CCCCN)C(=O)O[C@@H](C)C(=O)O[C@@H](CC(=O)OC1=CC[C@@]2(O)[C@H]3Cc4ccc(O)c5c4[C@@]2(CCN3C)[C@H]1O5)C(=O)O] | (S)-2-(((S)-2-(((S)-2-acetamido-6-aminohexanoyl)oxy)propanoyl)oxy)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoic acid |
| D20 | 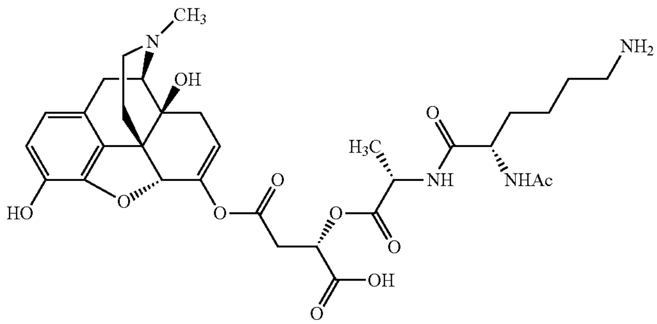 [SMILES: CC(=O)N[C@@H](CCCCN)C(=O)N[C@@H](C)C(=O)O[C@@H](CC(=O)OC1=CC[C@@]2(O)[C@H]3Cc4ccc(O)c5c4[C@@]2(CCN3C)[C@H]1O5)C(=O)O] | (S)-2-(((S)-2-((S)-2-acetamido-6-amino-hexanamido)propanoyl)oxy)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoic acid |
| D21 | 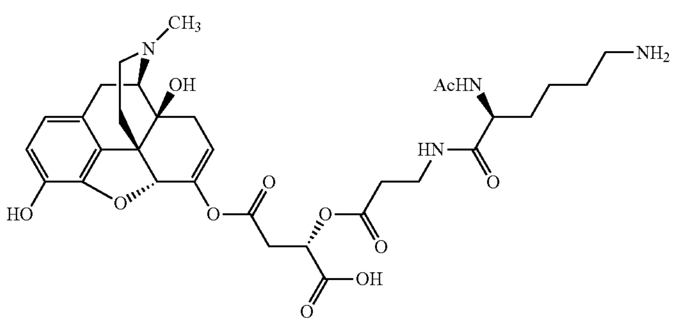 [SMILES: CC(=O)N[C@@H](CCCCN)C(=O)NCCC(=O)O[C@@H](CC(=O)OC1=CC[C@@]2(O)[C@H]3Cc4ccc(O)c5c4[C@@]2(CCN3C)[C@H]1O5)C(=O)O] | (S)-2-((3-((S)-2-acetamido-6-amino-hexanamido)propanoyl)oxy)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoic acid |
| D22 | 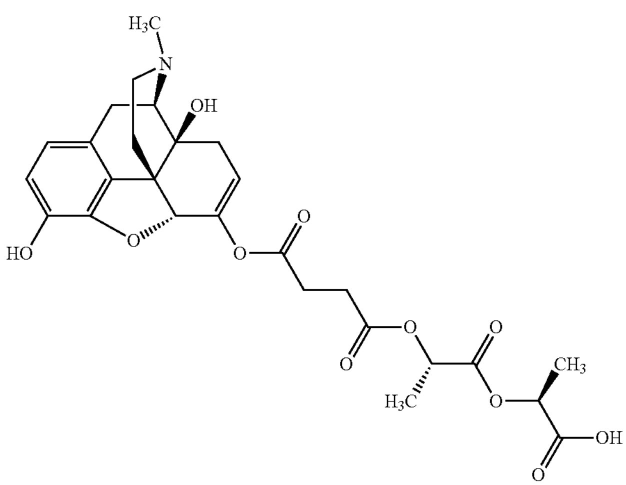 [SMILES: C[C@H](OC(=O)[C@H](C)OC(=O)CCC(=O)OC1=CC[C@@]2(O)[C@H]3Cc4ccc(O)c5c4[C@@]2(CCN3C)[C@H]1O5)C(=O)O] | (S)-2-(((S)-2-((4-(((4R,4aS,7aR,12bS)-4a,9-dihydroxy-3-methyl-2,3,4,4a,5,7a-hexahydro-1H-4,12-methano-benzofuro[3,2-e]isoquinolin-7-yl)oxy)-4-oxobutanoyl)oxy)propanoyl)oxy)propanoic acid |

-continued

| Ex. No. | Structure | Name |
|---|---|---|
| D23 | 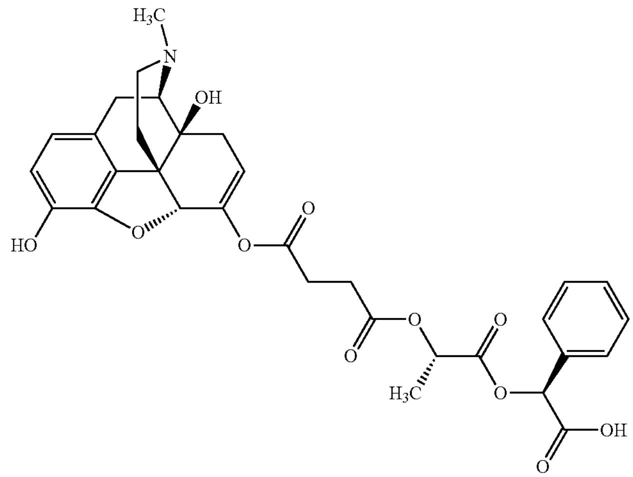 [SMILES: C[C@H](OC(=O)CCC(=O)OC1=CC[C@@]2(O)[C@H]3Cc4ccc(O)c5c4[C@@]2(CCN3C)[C@H]1O5)C(=O)O[C@H](C(=O)O)c1ccccc1] | (S)-2-(((S)-2-((4-(((4R,4aS, 7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)-2-phenylacetic acid |
| D24 | 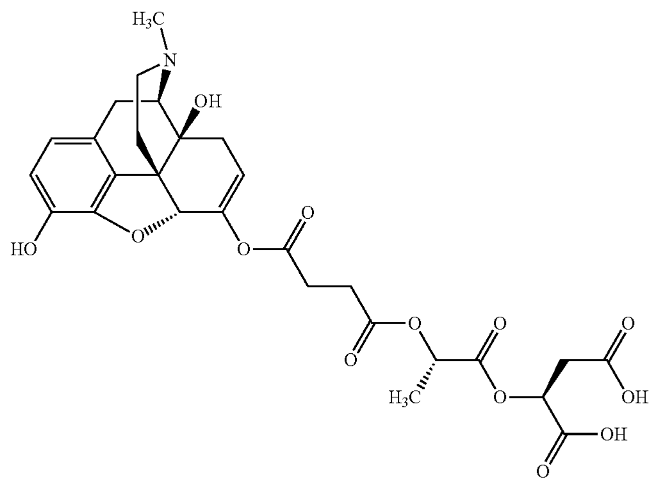 [SMILES: C[C@H](OC(=O)CCC(=O)OC1=CC[C@@]2(O)[C@H]3Cc4ccc(O)c5c4[C@@]2(CCN3C)[C@H]1O5)C(=O)O[C@@H](CC(=O)O)C(=O)O] | (S)-2-(((S)-2-((4-(((4R,4aS, 7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |
| D25 | 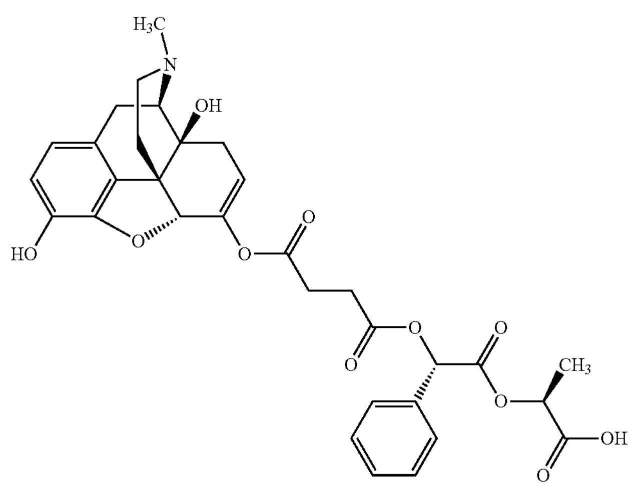 [SMILES: C[C@H](OC(=O)[C@@H](OC(=O)CCC(=O)OC1=CC[C@@]2(O)[C@H]3Cc4ccc(O)c5c4[C@@]2(CCN3C)[C@H]1O5)c1ccccc1)C(=O)O] | (S)-2-((S)-2-((4-(((4R,4aS, 7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)propanoic acid |

-continued

| Ex. No. | Structure | Name |
|---|---|---|
| D26 | 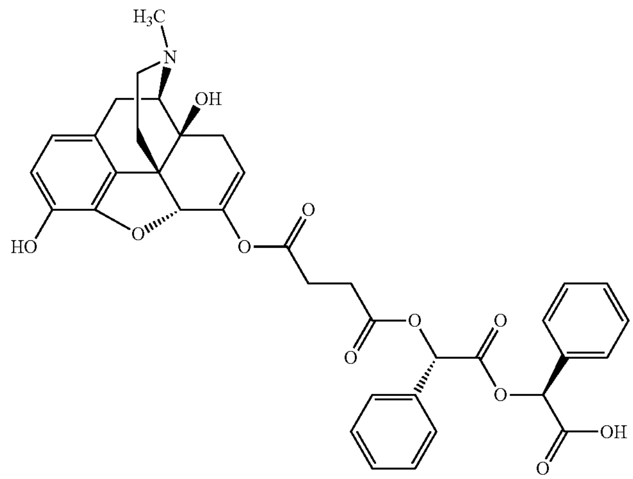 [SMILES: CN1CC[C@]23c4c5ccc(O)c4O[C@H]2C(OC(=O)CCC(=O)O[C@H](C(=O)O[C@H](C(=O)O)c2ccccc2)c2ccccc2)=CC[C@@]3(O)[C@H]1C5] | (S)-2-((S)-2-((4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)-2-phenylacetic acid |
| D27 | 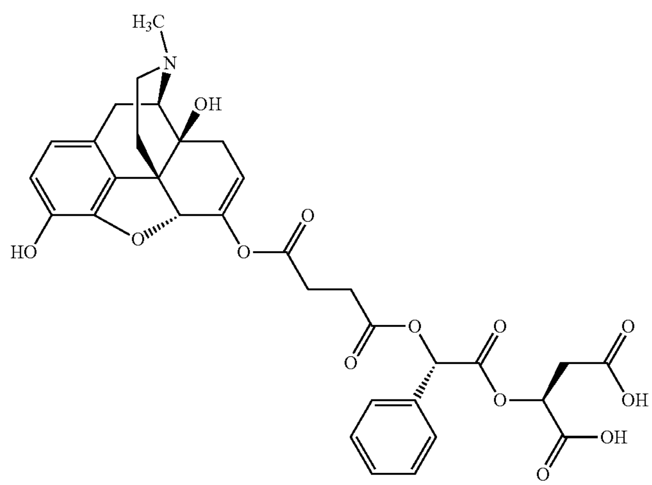 [SMILES: CN1CC[C@]23c4c5ccc(O)c4O[C@H]2C(OC(=O)CCC(=O)O[C@H](C(=O)O[C@@H](CC(=O)O)C(=O)O)c2ccccc2)=CC[C@@]3(O)[C@H]1C5] | (S)-2-((S)-2-((4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)succinic acid |
| D28 | 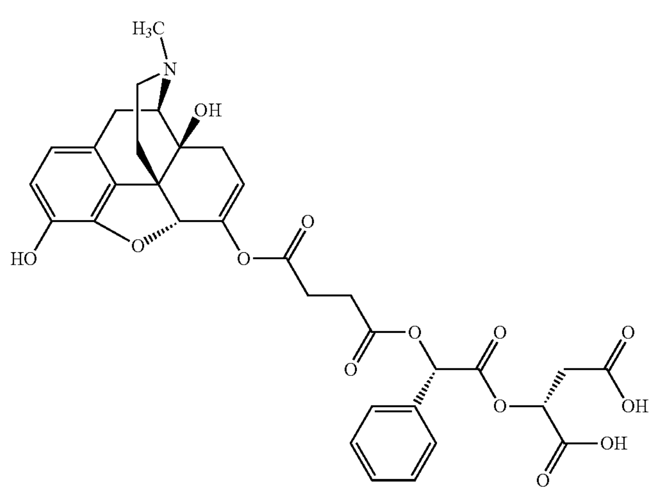 [SMILES: CN1CC[C@]23c4c5ccc(O)c4O[C@H]2C(OC(=O)CCC(=O)O[C@H](C(=O)O[C@H](CC(=O)O)C(=O)O)c2ccccc2)=CC[C@@]3(O)[C@H]1C5] | (R)-2-((S)-2-((4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)succinic acid |

| Ex. No. | Structure | Name |
|---|---|---|
| D29 | 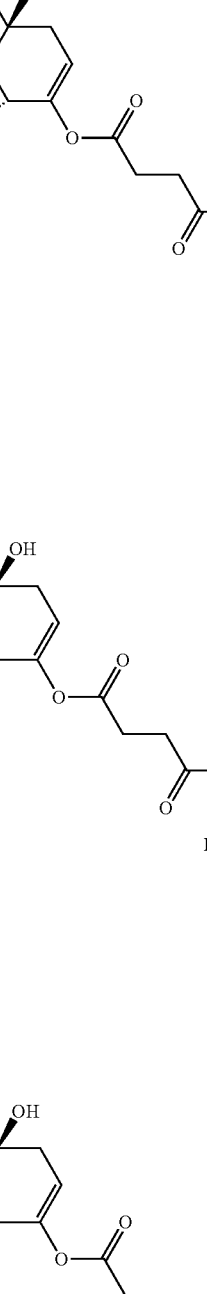 | (S)-2-((S)-2-((4-((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanamido)propanoic acid |
| D30 | 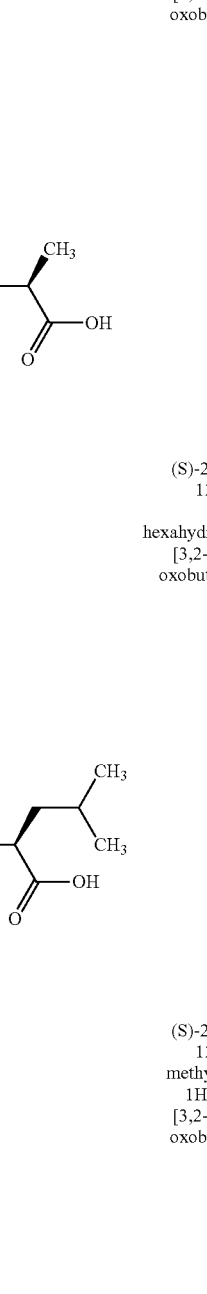 | (S)-2-((S)-2-((4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanamido)-4-methylpentanoic acid |
| D31 | 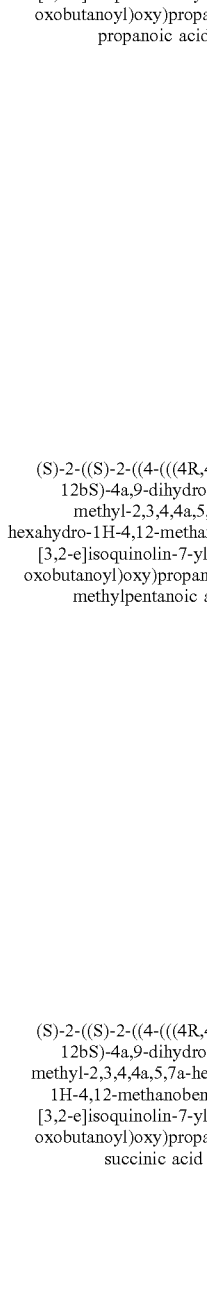 | (S)-2-((S)-2-((4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanamido)succinic acid |

-continued

| Ex. No. | Structure | Name |
|---|---|---|
| D32 | 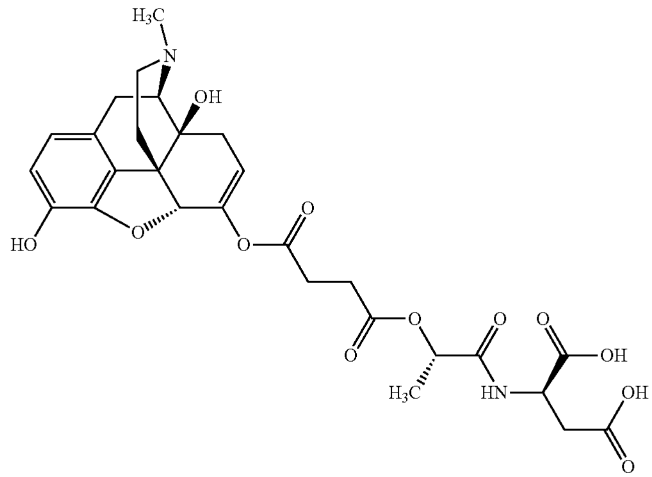 [SMILES: C[C@H](OC(=O)CCC(=O)OC1=CC[C@@]2(O)[C@H]3Cc4ccc(O)c5c4[C@@]2(CCN3C)[C@H]1O5)C(=O)N[C@H](CC(=O)O)C(=O)O] | (R)-2-((S)-2-((4-(((4R,4aS,7aR, 12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy) propanamido)succinic acid |
| D33 | 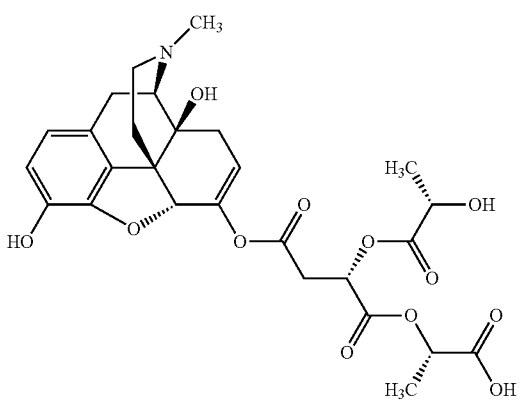 [SMILES: C[C@H](O)C(=O)O[C@@H](CC(=O)OC1=CC[C@@]2(O)[C@H]3Cc4ccc(O)c5c4[C@@]2(CCN3C)[C@H]1O5)C(=O)O[C@@H](C)C(=O)O] | (S)-2-(((S)-4-(((4R,4aS,7aR, 12bS)-4a,9-dihydroxy-3-methyl-2,3,4,4a,5,7a-hexahydro-1H-4,12-methanobenzofuro [3,2-e]isoquinolin-7-yl)oxy)-2-(((S)-2-hydroxypropanoyl)oxy)-4-oxobutanoyl)oxy)propanoic acid |
| D34 | 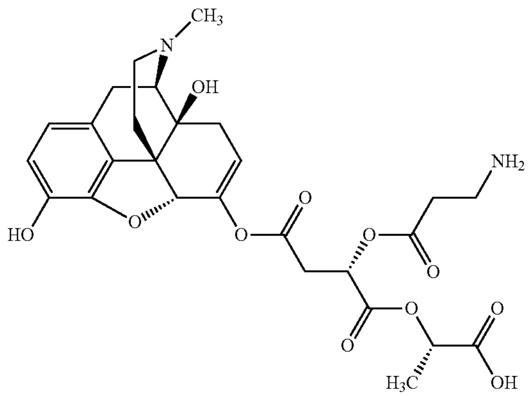 [SMILES: C[C@H](OC(=O)[C@H](CC(=O)OC1=CC[C@@]2(O)[C@H]3Cc4ccc(O)c5c4[C@@]2(CCN3C)[C@H]1O5)OC(=O)CCN)C(=O)O] | (S)-2-(((S)-2-((3-aminopropanoyl) oxy)-4-(((4R,4aS,7aR,12bS)-4a,9-dihydroxy-3-methyl-2,3,4,4a,5,7a-hexahydro-1H-4,12-methanobenzofuro [3,2-e]isoquinolin-7-yl)oxy)-4-oxobutanoyl)oxy)propanoic acid |

| Ex. No. | Structure | Name |
|---|---|---|
| D35 | 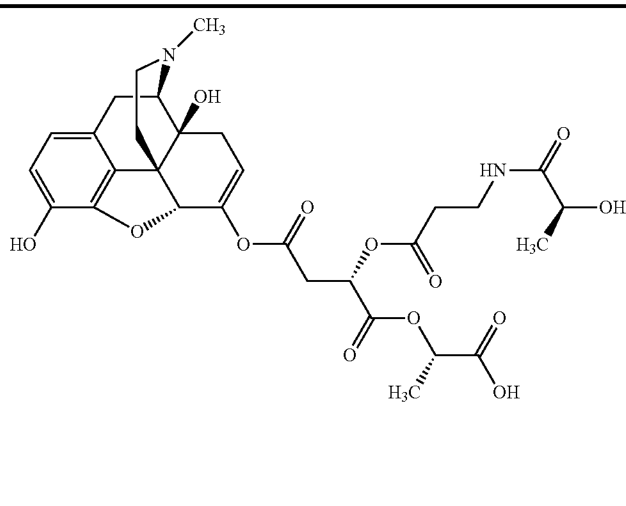 | (S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-((3-((S)-2-hydroxypropanamido)propanoyl)oxy)-4-oxobutanoyl)oxy)propanoic acid |
| D36 | 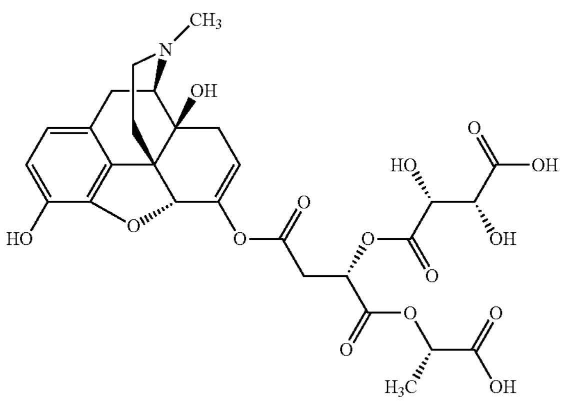 [SMILES: C[C@H](OC(=O)[C@H](CC(=O)OC1=CC[C@@]2(O)[C@H]3Cc4ccc(O)c5c4[C@@]2(CCN3C)[C@H]1O5)OC(=O)[C@H](O)[C@@H](O)C(=O)O)C(=O)O] | (2R,3R)-4-(((S)-1-((S)-1-carboxyethoxy)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1,4-dioxobutan-2-yl)oxy)-2,3-dihydroxy-4-oxobutanoic acid |
| D37 | 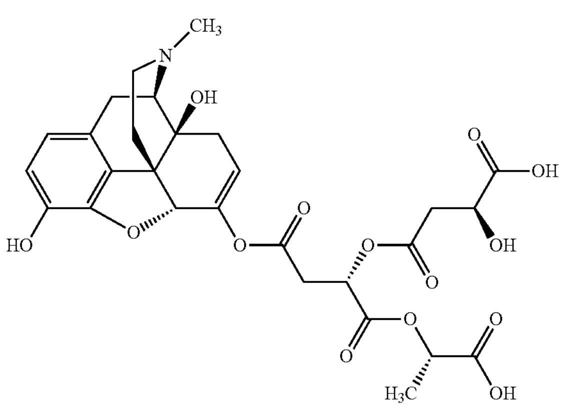 [SMILES: C[C@H](OC(=O)[C@H](CC(=O)OC1=CC[C@@]2(O)[C@H]3Cc4ccc(O)c5c4[C@@]2(CCN3C)[C@H]1O5)OC(=O)C[C@H](O)C(=O)O)C(=O)O] | (S)-4-(((S)-1-((S)-1-carboxyethoxy)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1,4-dioxobutan-2-yl)oxy)-2-hydroxy-4-oxobutanoic acid |

| Ex. No. | Structure | Name |
|---|---|---|
| D38 | 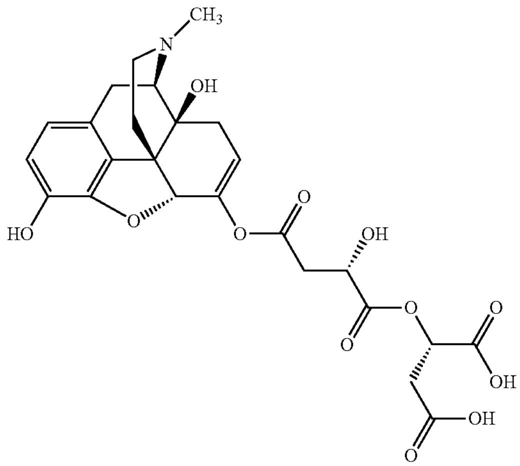 [SMILES: CN1CC[C@]23c4c5ccc(O)c4O[C@H]2C(OC(=O)C[C@H](O)C(=O)O[C@@H](CC(=O)O)C(=O)O)=CC[C@@]3(O)[C@H]1C5] | (S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-hydroxy-4-oxobutanoyl)oxy)succinic acid |
| D39 | 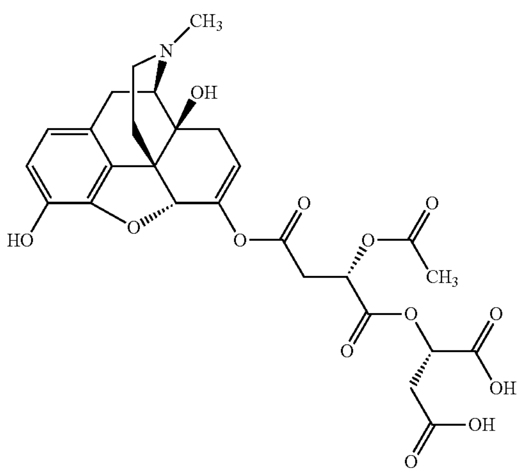 [SMILES: CC(=O)O[C@@H](CC(=O)OC1=CC[C@@]2(O)[C@H]3Cc4ccc(O)c5c4[C@@]2(CCN3C)[C@H]1O5)C(=O)O[C@@H](CC(=O)O)C(=O)O] | (S)-2-(((S)-2-acetoxy-4-(((4R,4aS,7aR,12bS)-4a,9-dihydroxy-3-methyl-2,3,4,4a,5,7a-hexahydro-1H-4,12-methano-benzofuro[3,2-e]isoquinolin-7-yl)oxy)-4-oxobutanoyl)oxy)succinic acid |
| D40 | 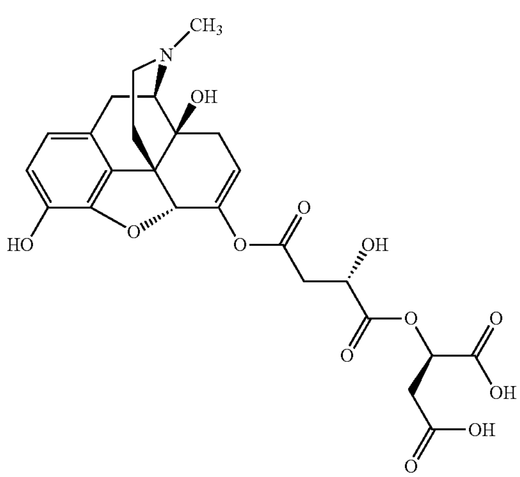 [SMILES: CN1CC[C@]23c4c5ccc(O)c4O[C@H]2C(OC(=O)C[C@H](O)C(=O)O[C@H](CC(=O)O)C(=O)O)=CC[C@@]3(O)[C@H]1C5] | (R)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-hydroxy-4-oxobutanoyl)oxy) succinic acid |

-continued

| Ex. No. | Structure | Name |
|---|---|---|
| D41 | 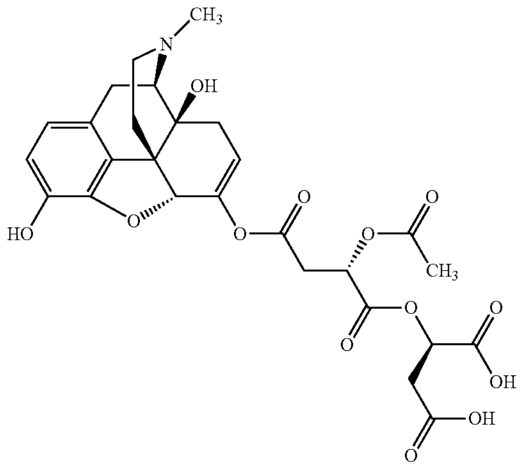 [SMILES: CC(=O)O[C@@H](CC(=O)OC1=CC[C@@]2(O)[C@H]3Cc4ccc(O)c5c4[C@@]2(CCN3C)[C@H]1O5)C(=O)O[C@H](CC(=O)O)C(=O)O] | (R)-2-(((S)-2-acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)succinic acid |
| D42 | 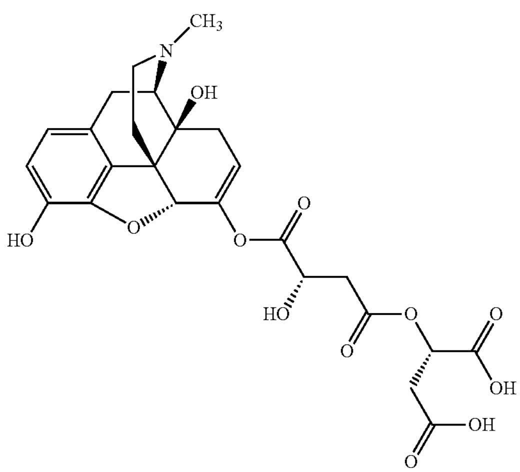 [SMILES: CN1CC[C@]23c4c5ccc(O)c4O[C@H]2C(OC(=O)[C@@H](O)CC(=O)O[C@@H](CC(=O)O)C(=O)O)=CC[C@@]3(O)[C@H]1C5] | (S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-hydroxy-4-oxobutanoyl)oxy)succinic acid |
| D43 | 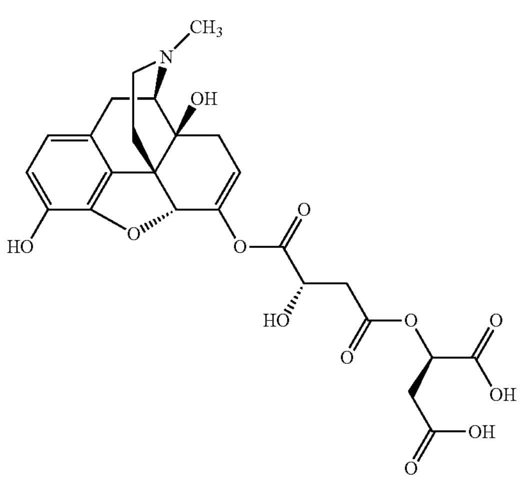 [SMILES: CN1CC[C@]23c4c5ccc(O)c4O[C@H]2C(OC(=O)[C@@H](O)CC(=O)O[C@H](CC(=O)O)C(=O)O)=CC[C@@]3(O)[C@H]1C5] | (R)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-hydroxy-4-oxobutanoyl)oxy)succinic acid |

| Ex. No. | Structure | Name |
|---|---|---|
| D44 | 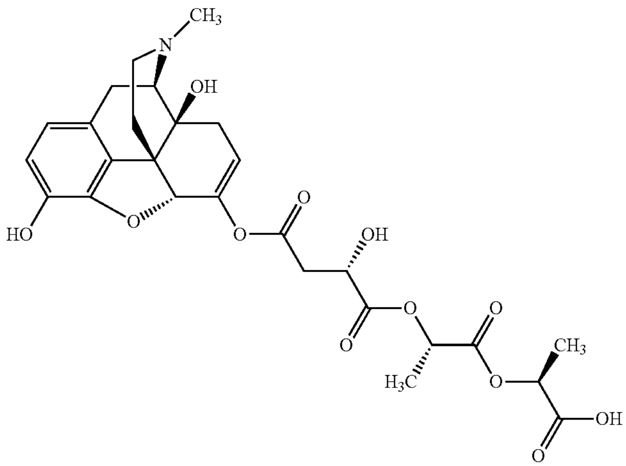 [SMILES: C[C@H](OC(=O)[C@H](C)OC(=O)[C@@H](O)CC(=O)OC1=CC[C@@]2(O)[C@H]3Cc4ccc(O)c5c4[C@@]2(CCN3C)[C@H]1O5)C(=O)O] | (S)-2-(((S)-2-(((S)-4-(((4R,4aS,7aR,12bS)-4a,9-dihydroxy-3-methyl-2,3,4,4a,5,7a-hexahydro-1H-4,12-methanobenzo-furo[3,2-e]isoquinolin-7-yl)oxy)-2-hydroxy-4-oxobutanoyl)oxy)propanoyl)oxy)propanoic acid |
| D45 | 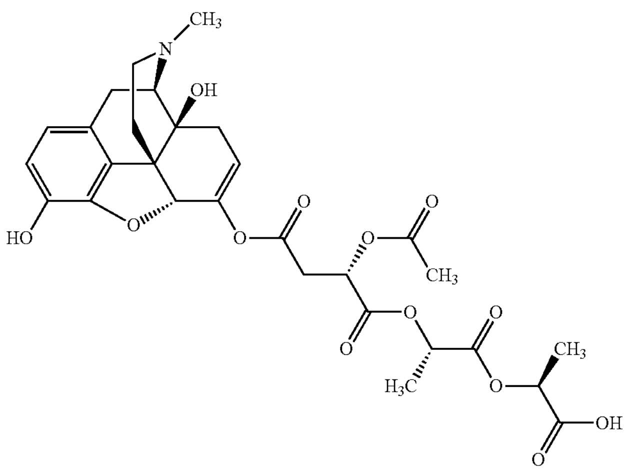 [SMILES: CC(=O)O[C@@H](CC(=O)OC1=CC[C@@]2(O)[C@H]3Cc4ccc(O)c5c4[C@@]2(CCN3C)[C@H]1O5)C(=O)O[C@@H](C)C(=O)O[C@@H](C)C(=O)O] | (S)-2-(((S)-2-(((S)-2-acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)propanoic acid |
| D46 | 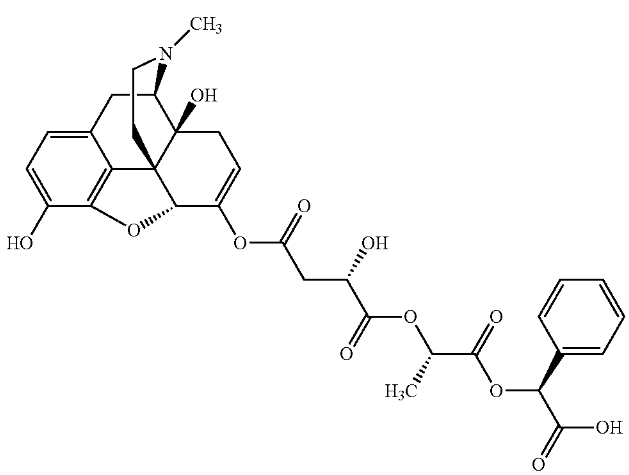 [SMILES: C[C@H](OC(=O)[C@@H](O)CC(=O)OC1=CC[C@@]2(O)[C@H]3Cc4ccc(O)c5c4[C@@]2(CCN3C)[C@H]1O5)C(=O)O[C@H](C(=O)O)c1ccccc1] | (S)-2-(((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-hydroxy-4-oxobutanoyl)oxy)propanoyl)oxy)-2-phenylacetic acid |

-continued

| Ex. No. | Structure | Name |
|---|---|---|
| D47 | 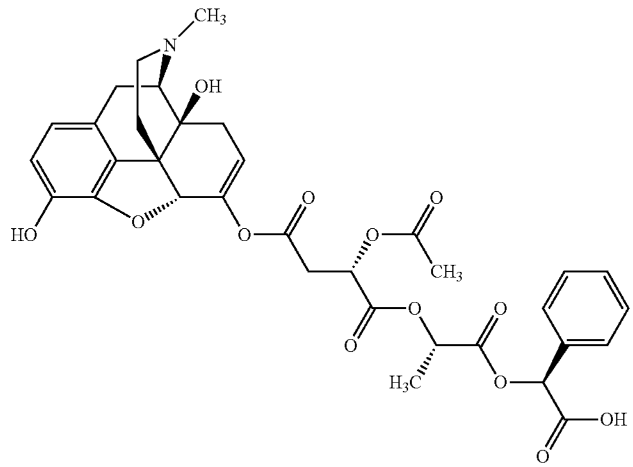 [SMILES: CC(=O)O[C@@H](CC(=O)OC1=CC[C@@]2(O)[C@H]3Cc4ccc(O)c5c4[C@@]2(CCN3C)[C@H]1O5)C(=O)O[C@@H](C)C(=O)O[C@H](C(=O)O)c1ccccc1] | (S)-2-(((S)-2-(((S)-2-acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)-2-phenylacetic acid |
| D48 | 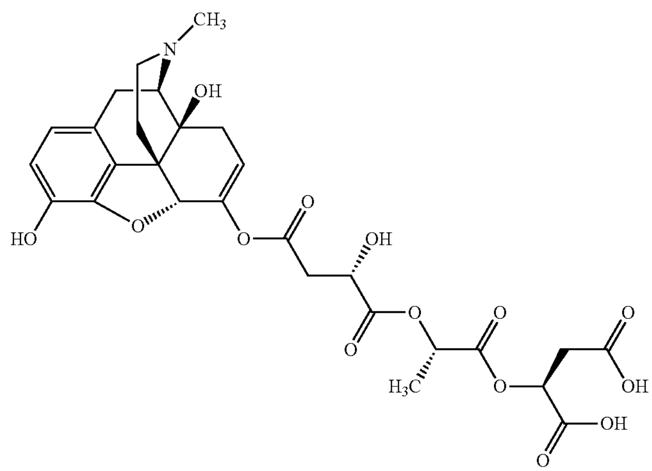 [SMILES: C[C@H](OC(=O)[C@@H](O)CC(=O)OC1=CC[C@@]2(O)[C@H]3Cc4ccc(O)c5c4[C@@]2(CCN3C)[C@H]1O5)C(=O)O[C@@H](CC(=O)O)C(=O)O] | (S)-2-(((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-hydroxy-4-oxobutanoyl)oxy)propanoyl)oxy)succinic acid |
| D49 | 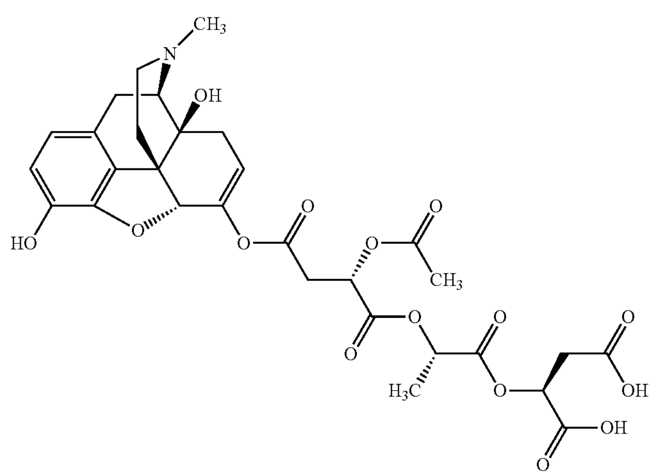 [SMILES: CC(=O)O[C@@H](CC(=O)OC1=CC[C@@]2(O)[C@H]3Cc4ccc(O)c5c4[C@@]2(CCN3C)[C@H]1O5)C(=O)O[C@@H](C)C(=O)O[C@@H](CC(=O)O)C(=O)O] | (S)-2-(((S)-2-(((S)-2-acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |

| Ex. No. | Structure | Name |
|---|---|---|
| D50 | 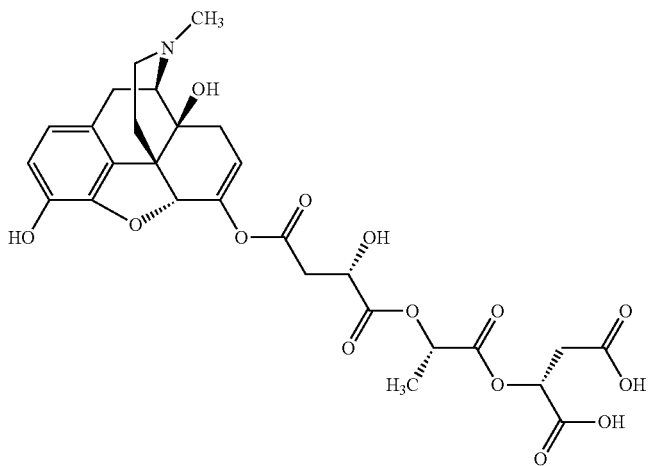 [SMILES: C[C@H](OC(=O)[C@@H](O)CC(=O)OC1=CC[C@@]2(O)[C@H]3Cc4ccc(O)c5c4[C@@]2(CCN3C)[C@H]1O5)C(=O)O[C@H](CC(=O)O)C(=O)O] | (R)-2-(((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-hydroxy-4-oxobutanoyl)oxy)propanoyl)oxy)succinic acid |
| D51 | 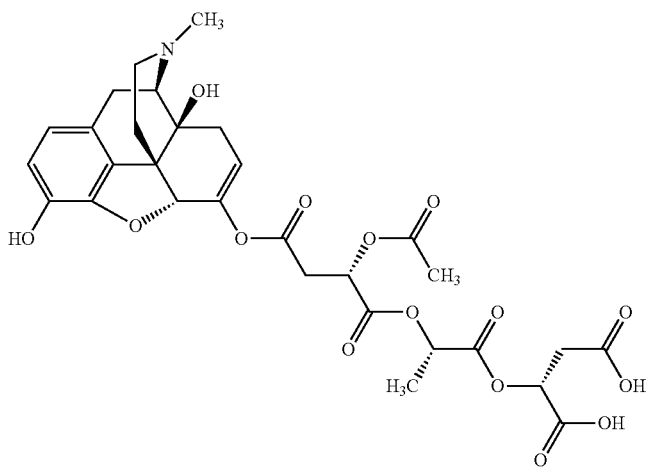 [SMILES: CC(=O)O[C@@H](CC(=O)OC1=CC[C@@]2(O)[C@H]3Cc4ccc(O)c5c4[C@@]2(CCN3C)[C@H]1O5)C(=O)O[C@@H](C)C(=O)O[C@H](CC(=O)O)C(=O)O] | (R)-2-(((S)-2-(((S)-2-acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |
| D52 | 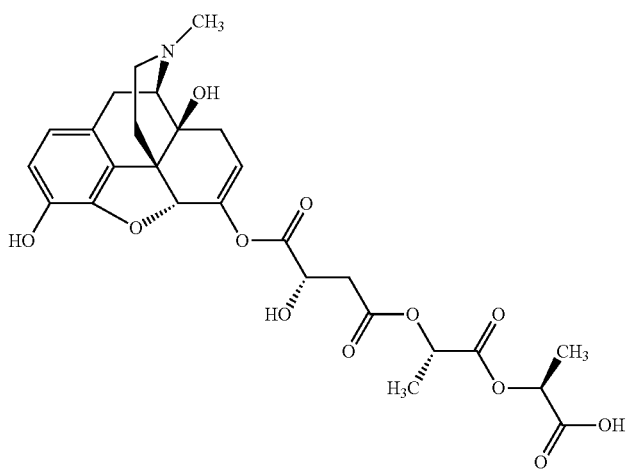 [SMILES: C[C@H](OC(=O)[C@H](C)OC(=O)C[C@H](O)C(=O)OC1=CC[C@@]2(O)[C@H]3Cc4ccc(O)c5c4[C@@]2(CCN3C)[C@H]1O5)C(=O)O] | (S)-2-(((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-hydroxy-4-oxobutanoyl)oxy)propanoyl)oxy)propanoic acid |

| Ex. No. | Structure | Name |
|---|---|---|
| D53 | 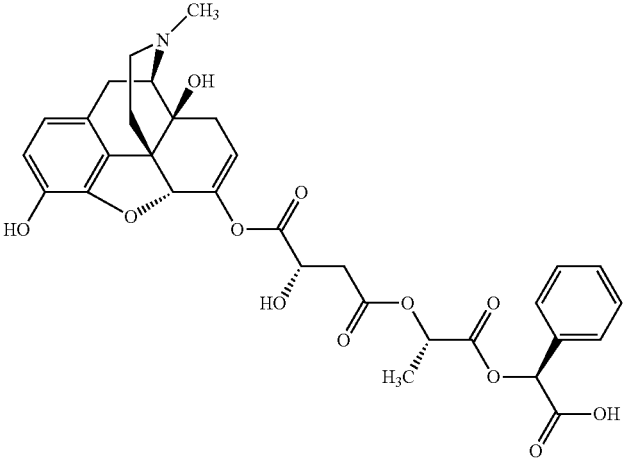 [SMILES: C[C@H](OC(=O)C[C@H](O)C(=O)OC1=CC[C@@]2(O)[C@H]3Cc4ccc(O)c5c4[C@@]2(CCN3C)[C@H]1O5)C(=O)O[C@H](C(=O)O)c1ccccc1] | (S)-2-(((S)-2-(((S)-4-(((4R, 4aS,7aR,12bS)-4a,9-dihydroxy-3-methyl-2,3,4,4a, 5,7a-hexahydro-1H-4,12-methanobenzofuro[3,2-e] isoquinolin-7-yl)oxy)-3-hydroxy-4-oxobutanoyl) oxy)propanoyl)oxy)-2-phenylacetic acid |
| D54 | 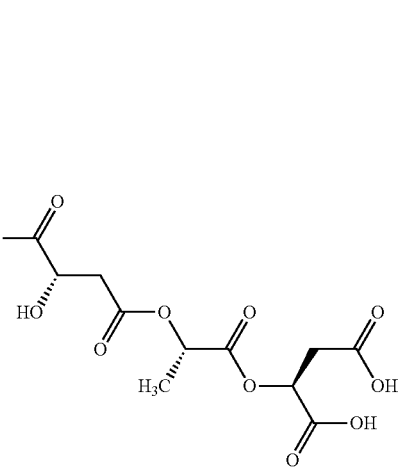 | (S)-2-(((S)-2-(((S)-4-(((4R,4aS,7aR,12bS)-4a,9-dihydroxy-3-methyl-2,3,4, 4a,5,7a-hexahydro-1H-4,12-methanobenzofuro[3,2-e] isoquinolin-7-yl)oxy)-3-hydroxy-4-oxobutanoyl)oxy) propanoyl)oxy)succinic acid |
| D55 | 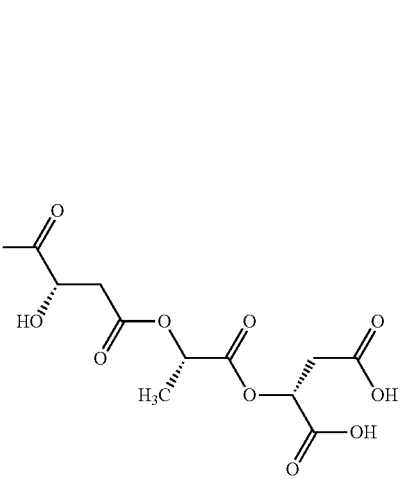 | (R)-2-(((S)-2-(((S)-4-(((4R,4aS,7aR,12bS)-4a,9-dihydroxy-3-methyl-2,3,4,4a, 5,7a-hexahydro-1H-4,12-methanobenzofuro[3,2-e] isoquinolin-7-yl)oxy)-3-hydroxy-4-oxobutanoyl)oxy) propanoyl)oxy)succinic acid |

-continued

| Ex. No. | Structure | Name |
|---|---|---|
| D56 | 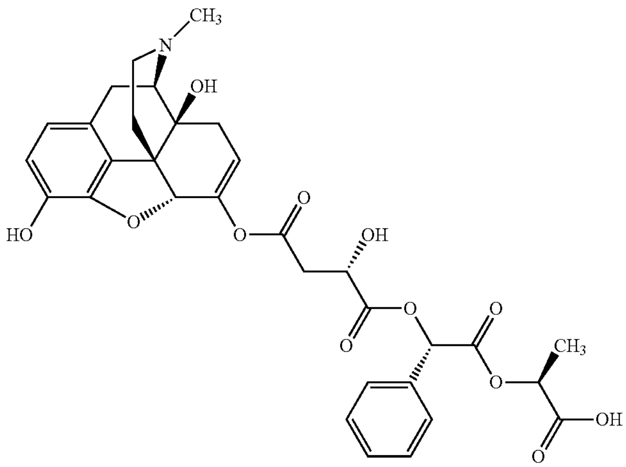 [SMILES: C[C@H](OC(=O)[C@@H](OC(=O)[C@@H](O)CC(=O)OC1=CC[C@@]2(O)[C@H]3Cc4ccc(O)c5c4[C@@]2(CCN3C)[C@H]1O5)c1ccccc1)C(=O)O] | (S)-2-((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-hydroxy-4-oxobutanoyl)oxy)-2-phenylacetoxy)propanoic acid |
| D57 | 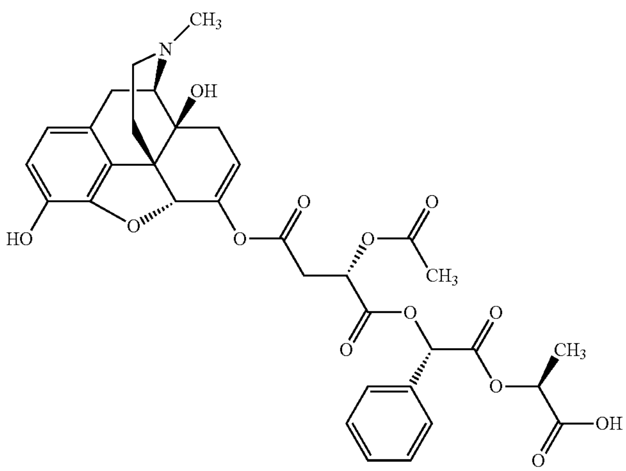 [SMILES: CC(=O)O[C@@H](CC(=O)OC1=CC[C@@]2(O)[C@H]3Cc4ccc(O)c5c4[C@@]2(CCN3C)[C@H]1O5)C(=O)O[C@H](C(=O)O[C@@H](C)C(=O)O)c1ccccc1] | (S)-2-((S)-2-(((S)-2-acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)propanoic acid |
| D58 | 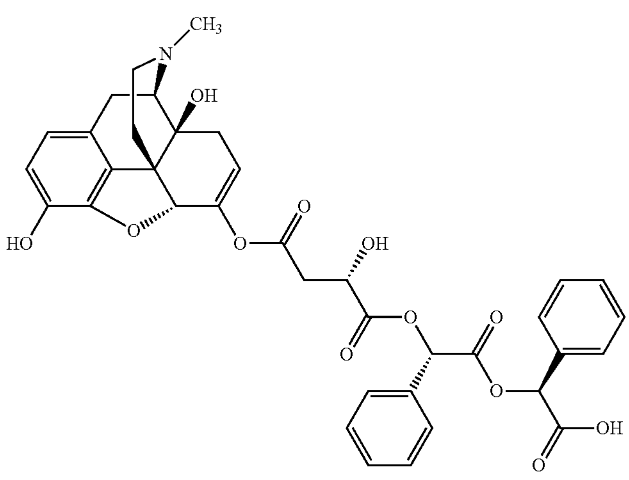 [SMILES: CN1CC[C@]23c4c5ccc(O)c4O[C@H]2C(OC(=O)C[C@H](O)C(=O)O[C@H](C(=O)O[C@H](C(=O)O)c2ccccc2)c2ccccc2)=CC[C@@]3(O)[C@H]1C5] | (S)-2-((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-hydroxy-4-oxobutanoyl)oxy)-2-phenylacetoxy)-2-phenylacetic acid |

-continued

| Ex. No. | Structure | Name |
|---|---|---|
| D59 | 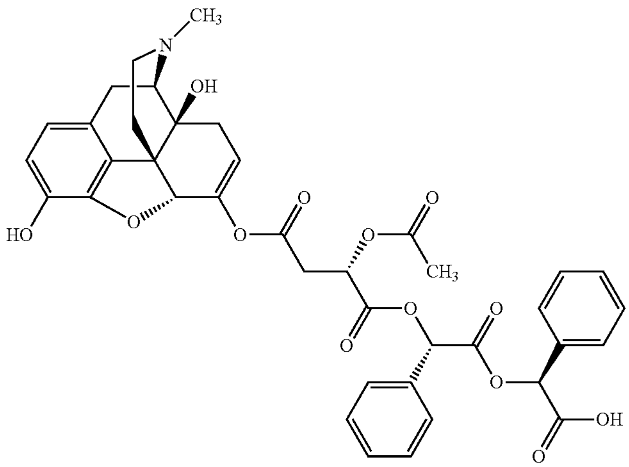 [SMILES: CC(=O)O[C@@H](CC(=O)OC1=CC[C@@]2(O)[C@H]3Cc4ccc(O)c5c4[C@@]2(CCN3C)[C@H]1O5)C(=O)O[C@H](C(=O)O[C@H](C(=O)O)c1ccccc1)c1ccccc1] | (S)-2-((S)-2-(((S)-2-acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)-2-phenylacetic acid |
| D60 | 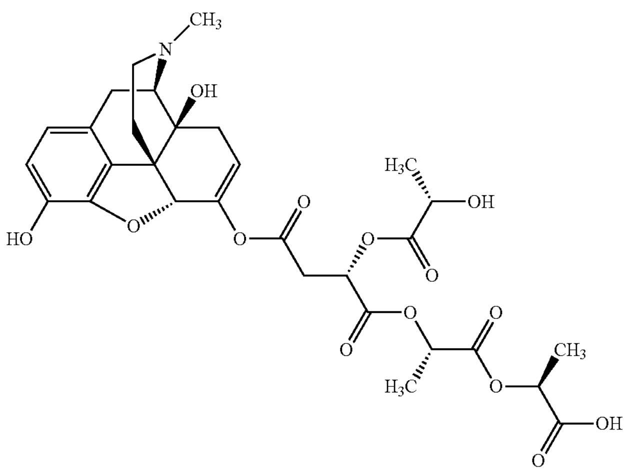 [SMILES: C[C@H](O)C(=O)O[C@@H](CC(=O)OC1=CC[C@@]2(O)[C@H]3Cc4ccc(O)c5c4[C@@]2(CCN3C)[C@H]1O5)C(=O)O[C@@H](C)C(=O)O[C@@H](C)C(=O)O] | (S)-2-(((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-(((S)-2-hydroxypropanoyl)oxy)-4-oxobutanoyl)oxy)propanoyl)oxy)propanoic acid |
| D61 | 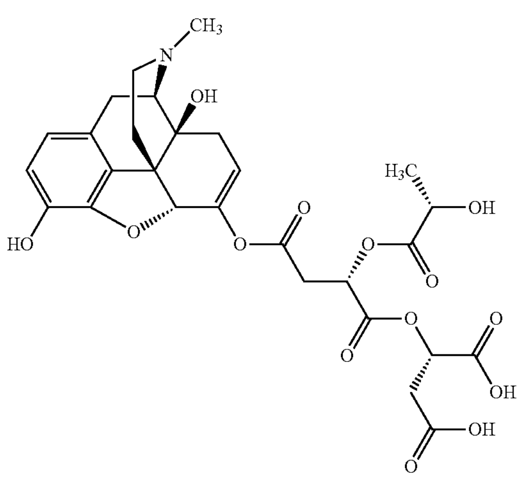 [SMILES: C[C@H](O)C(=O)O[C@@H](CC(=O)OC1=CC[C@@]2(O)[C@H]3Cc4ccc(O)c5c4[C@@]2(CCN3C)[C@H]1O5)C(=O)O[C@@H](CC(=O)O)C(=O)O] | (S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-(((S)-2-hydroxypropanoyl)oxy)-4-oxobutanoyl)oxy)succinic acid |

-continued

| Ex. No. | Structure | Name |
| --- | --- | --- |
| D62 | 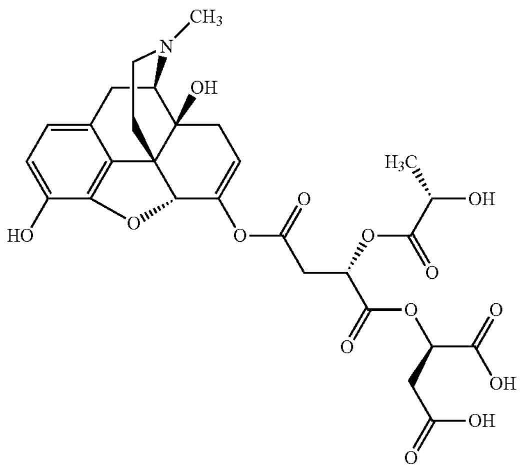 [SMILES: C[C@H](O)C(=O)O[C@@H](CC(=O)OC1=CC[C@@]2(O)[C@H]3Cc4ccc(O)c5c4[C@@]2(CCN3C)[C@H]1O5)C(=O)O[C@H](CC(=O)O)C(=O)O] | (R)-2-(((S)-4-(((4R,4aS,7aR, 12bS)-4a,9-dihydroxy-3-methyl-2,3,4,4a,5,7a-hexahydro-1H-4,12-methanobenzofuro [3,2-e]isoquinolin-7-yl)oxy)-2-(((S)-2-hydroxypropanoyl)oxy)-4-oxobutanoyl)oxy)succinic acid |
| D63 | 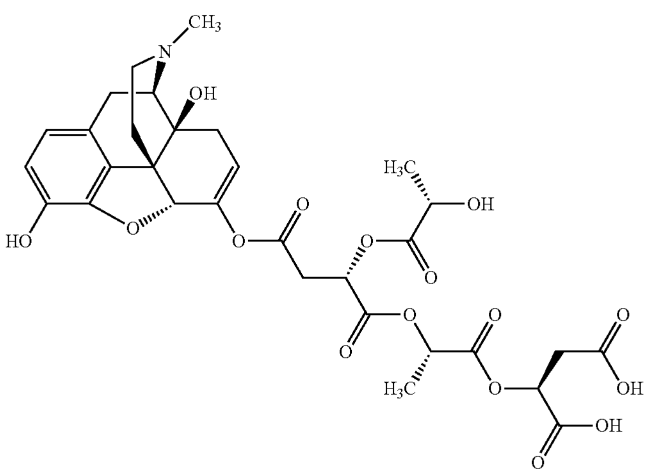 [SMILES: C[C@H](O)C(=O)O[C@@H](CC(=O)OC1=CC[C@@]2(O)[C@H]3Cc4ccc(O)c5c4[C@@]2(CCN3C)[C@H]1O5)C(=O)O[C@@H](C)C(=O)O[C@@H](CC(=O)O)C(=O)O] | (S)-2-(((S)-2-(((S)-4-(((4R, 4aS,7aR,12bS)-4a,9-dihydroxy-3-methyl-2,3,4,4a,5,7a-hexahydro-1H-4,12-methanobenzofuro[3,2-e] isoquinolin-7-yl)oxy)-2-(((S)-2-hydroxypropanoyl)oxy)-4-oxobutanoyl)oxy)propanoyl) oxy)succinic acid |
| D64 | 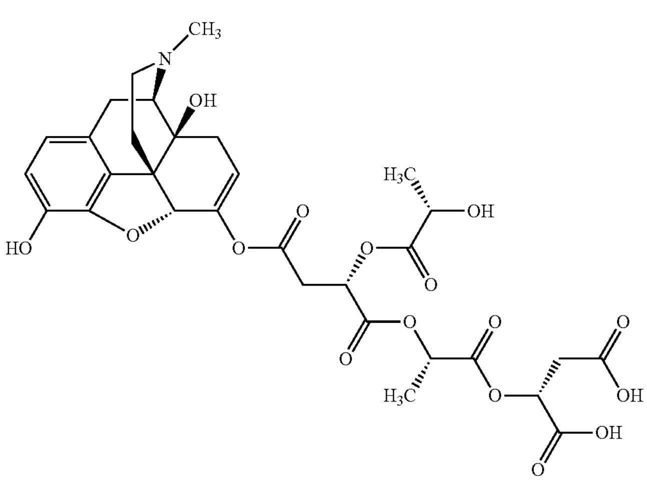 [SMILES: C[C@H](O)C(=O)O[C@@H](CC(=O)OC1=CC[C@@]2(O)[C@H]3Cc4ccc(O)c5c4[C@@]2(CCN3C)[C@H]1O5)C(=O)O[C@@H](C)C(=O)O[C@H](CC(=O)O)C(=O)O] | (R)-2-(((S)-2-(((S)-4-(((4R, 4aS,7aR,12bS)-4a,9-dihydroxy-3-methyl-2,3,4,4a,5,7a-hexa-hydro-1H-4,12-methanobenzofuro [3,2-e]isoquinolin-7-yl)oxy)-2-(((S)-2-hydroxypropanoyl)oxy)-4-oxobutanoyl)oxy)propanoyl) oxy)succinic acid |

| Ex. No. | Structure | Name |
|---|---|---|
| D65 | 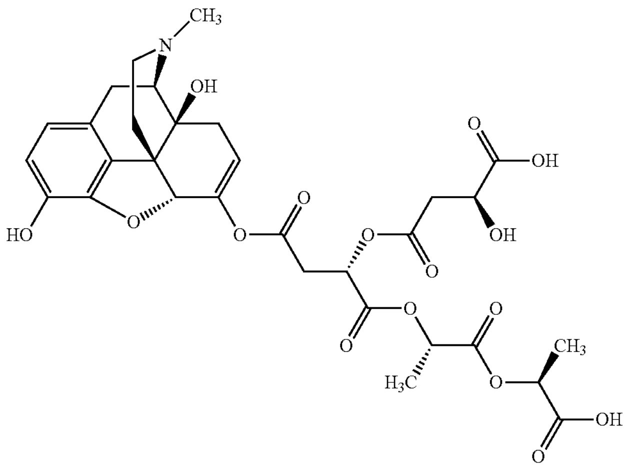 [SMILES: C[C@H](OC(=O)[C@H](C)OC(=O)[C@H](CC(=O)OC1=CC[C@@]2(O)[C@H]3Cc4ccc(O)c5c4[C@@]2(CCN3C)[C@H]1O5)OC(=O)C[C@H](O)C(=O)O)C(=O)O] | (S)-4-(((S)-1-(((S)-1-((S)-1-carboxyethoxy)-1-oxopropan-2-yl)oxy)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1,4-dioxobutan-2-yl)oxy)-2-hydroxy-4-oxobutanoic acid |
| D66 | 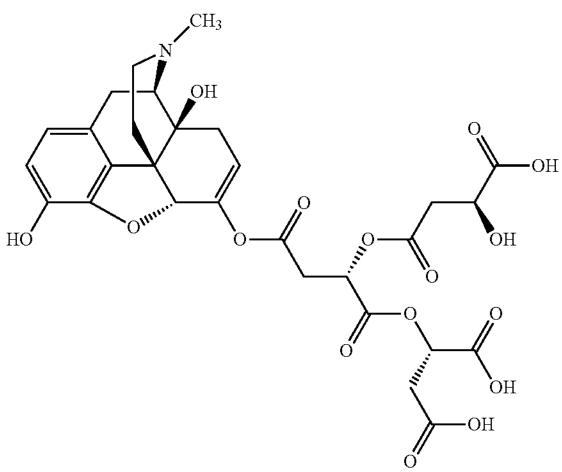 [SMILES: CN1CC[C@]23c4c5ccc(O)c4O[C@H]2C(OC(=O)C[C@H](OC(=O)C[C@H](O)C(=O)O)C(=O)O[C@@H](CC(=O)O)C(=O)O)=CC[C@@]3(O)[C@H]1C5] | (S)-2-(((S)-2-(((S)-3-carboxy-3-hydroxypropanoyl)oxy)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)succinic acid |
| D67 | 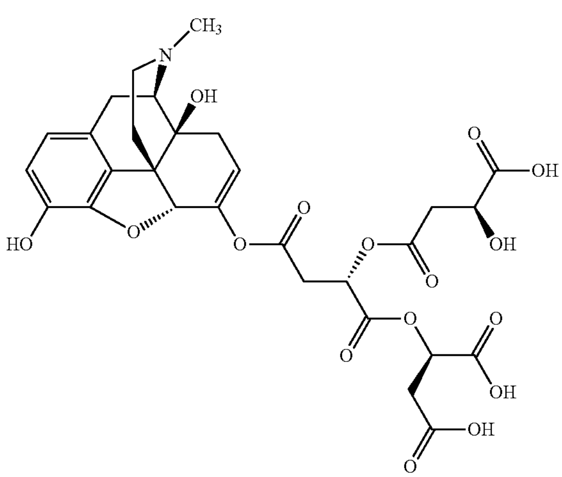 [SMILES: CN1CC[C@]23c4c5ccc(O)c4O[C@H]2C(OC(=O)C[C@H](OC(=O)C[C@H](O)C(=O)O)C(=O)O[C@H](CC(=O)O)C(=O)O)=CC[C@@]3(O)[C@H]1C5] | (R)-2-(((S)-2-(((S)-3-carboxy-3-hydroxypropanoyl)oxy)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)succinic acid |

| Ex. No. | Structure | Name |
|---|---|---|
| D68 | 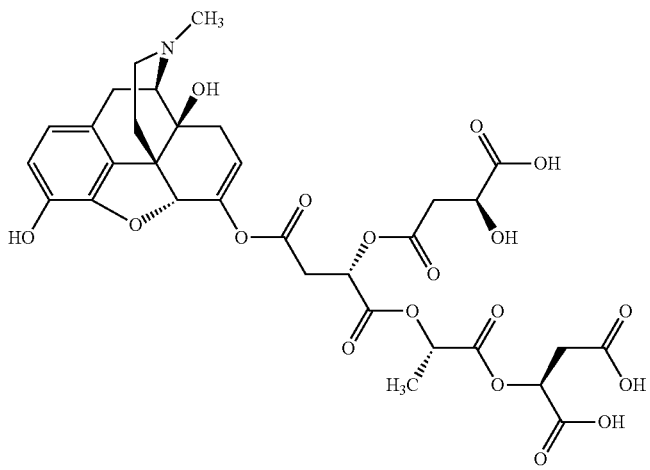 [SMILES: C[C@H](OC(=O)[C@H](CC(=O)OC1=CC[C@@]2(O)[C@H]3Cc4ccc(O)c5c4[C@@]2(CCN3C)[C@H]1O5)OC(=O)C[C@H](O)C(=O)O)C(=O)O[C@@H](CC(=O)O)C(=O)O] | (S)-2-(((S)-2-(((S)-2-(((S)-3-carboxy-3-hydroxypropanoyl)oxy)-4-(((4R,4aS,7aR,12bS)-4a,9-dihydroxy-3-methyl-2,3,4,4a,5,7a-hexahydro-1H-4,12-methano-benzofuro[3,2-e]isoquinolin-7-yl)oxy)-4-oxobutanoyl)oxy)propanoyl)oxy)succinic acid |
| D69 | 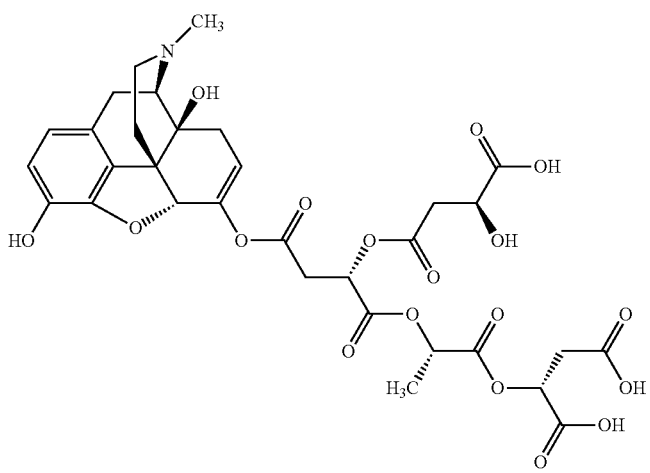 [SMILES: C[C@H](OC(=O)[C@H](CC(=O)OC1=CC[C@@]2(O)[C@H]3Cc4ccc(O)c5c4[C@@]2(CCN3C)[C@H]1O5)OC(=O)C[C@H](O)C(=O)O)C(=O)O[C@H](CC(=O)O)C(=O)O] | (R)-2-(((S)-2-(((S)-2-(((S)-3-carboxy-3-hydroxypropanoyl)oxy)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |
| D70 | 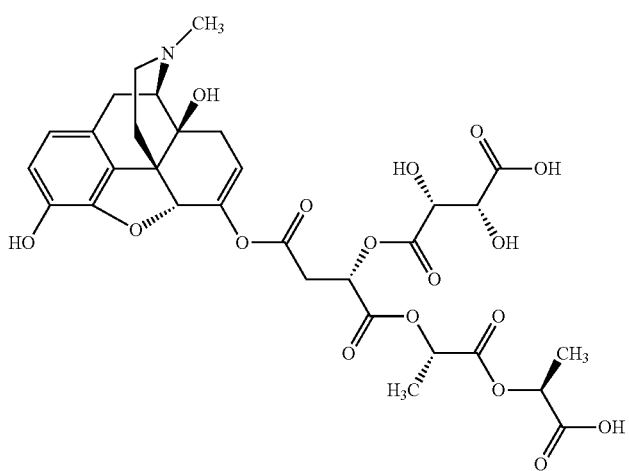 [SMILES: C[C@H](OC(=O)[C@H](C)OC(=O)[C@H](CC(=O)OC1=CC[C@@]2(O)[C@H]3Cc4ccc(O)c5c4[C@@]2(CCN3C)[C@H]1O5)OC(=O)[C@H](O)[C@@H](O)C(=O)O)C(=O)O] | (2R,3R)-4-(((S)-1-((S)-1-carboxyethoxy)-1-oxopropan-2-yl)oxy)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1,4-dioxobutan-2-yl)oxy)-2,3-dihydroxy-4-oxobutanoic acid |

-continued

| Ex. No. | Structure | Name |
|---|---|---|
| D71 | 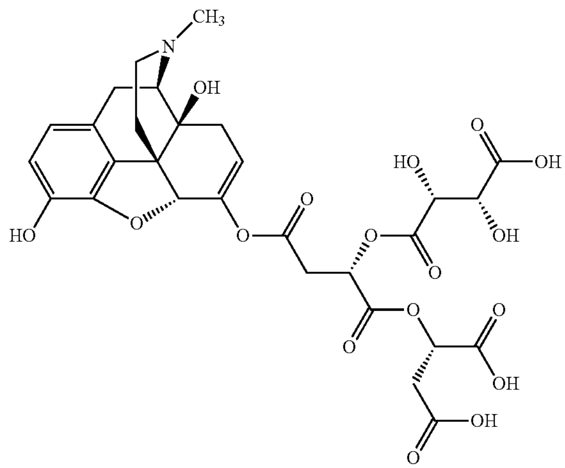 [SMILES: CN1CC[C@]23c4c5ccc(O)c4O[C@H]2C(OC(=O)C[C@H](OC(=O)[C@H](O)[C@@H](O)C(=O)O)C(=O)O[C@@H](CC(=O)O)C(=O)O)=CC[C@@]3(O)[C@H]1C5] | (S)-2-(((S)-2-(((2R,3R)-3-carboxy-2,3-dihydroxypropanoyl)oxy)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)succinic acid |
| D72 | 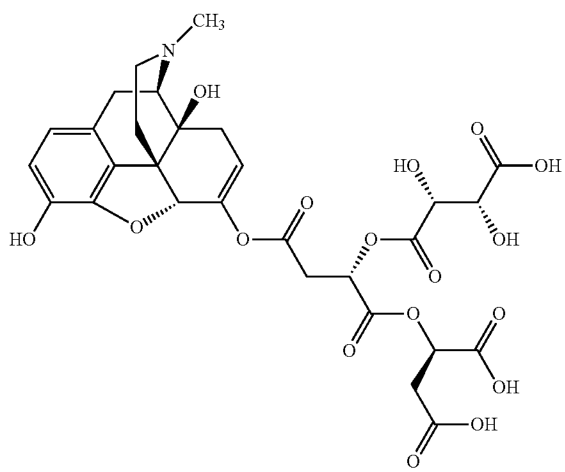 [SMILES: CN1CC[C@]23c4c5ccc(O)c4O[C@H]2C(OC(=O)C[C@H](OC(=O)[C@H](O)[C@@H](O)C(=O)O)C(=O)O[C@H](CC(=O)O)C(=O)O)=CC[C@@]3(O)[C@H]1C5] | (R)-2-(((S)-2-(((2R,3R)-3-carboxy-2,3-dihydroxypropanoyl)oxy)-4-(((4R,4aS,7aR,12bS)-4a,9-dihydroxy-3-methyl-2,3,4,4a,5,7a-hexahydro-1H-4,12-methano-benzofuro[3,2-e]isoquinolin-7-yl)oxy)-4-oxobutanoyl)oxy)succinic acid |
| D73 | 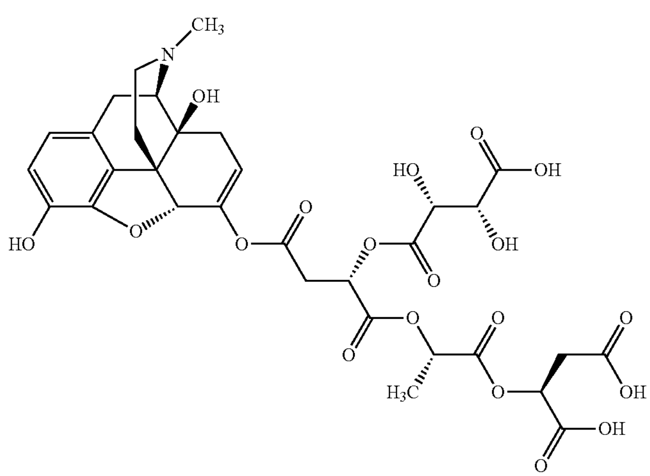 [SMILES: C[C@H](OC(=O)[C@H](CC(=O)OC1=CC[C@@]2(O)[C@H]3Cc4ccc(O)c5c4[C@@]2(CCN3C)[C@H]1O5)OC(=O)[C@H](O)[C@@H](O)C(=O)O)C(=O)O[C@@H](CC(=O)O)C(=O)O] | (S)-2-(((S)-2-(((S)-2-(((2R,3R)-3-carboxy-2,3-dihydroxypropanoyl)oxy)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanoyl)oxy)succinic acid |

| Ex. No. | Structure | Name |
|---|---|---|
| D74 | 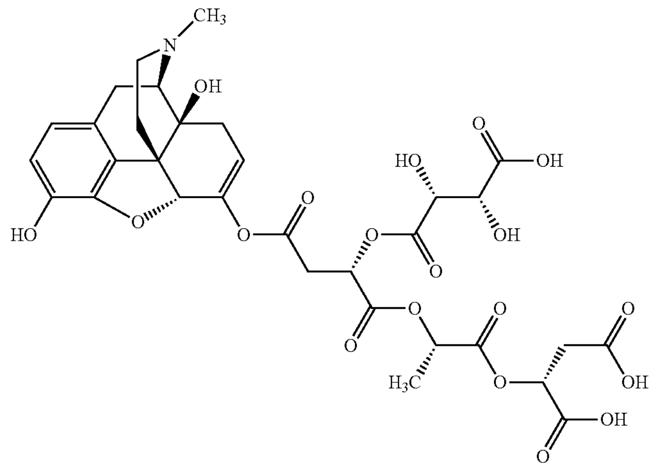 [SMILES: C[C@H](OC(=O)[C@H](CC(=O)OC1=CC[C@@]2(O)[C@H]3Cc4ccc(O)c5c4[C@@]2(CCN3C)[C@H]1O5)OC(=O)[C@H](O)[C@@H](O)C(=O)O)C(=O)O[C@H](CC(=O)O)C(=O)O] | (R)-2-(((S)-2-(((S)-2-(((2R, 3R)-3-carboxy-2,3-dihydroxy-propanoyl)oxy)-4-(((4R,4aS,7aR, 12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy) propanoyl)oxy)succinic acid |
| D75 | 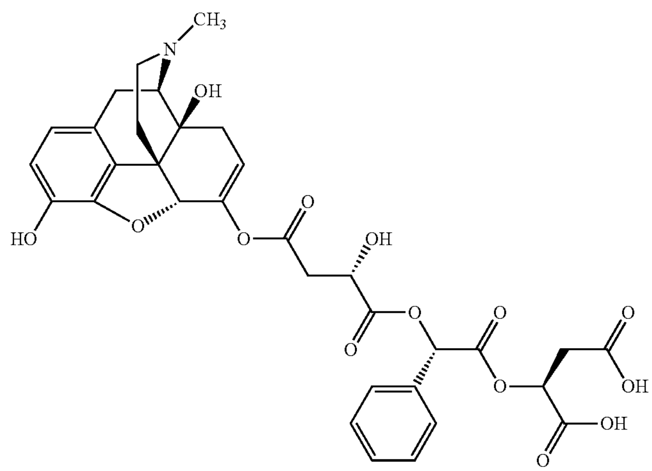 [SMILES: CN1CC[C@]23c4c5ccc(O)c4O[C@H]2C(OC(=O)C[C@H](O)C(=O)O[C@H](C(=O)O[C@@H](CC(=O)O)C(=O)O)c2ccccc2)=CC[C@@]3(O)[C@H]1C5] | (S)-2-((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-hydroxy-4-oxobutanoyl)oxy)-2-phenylacetoxy)succinc acid |
| D76 | 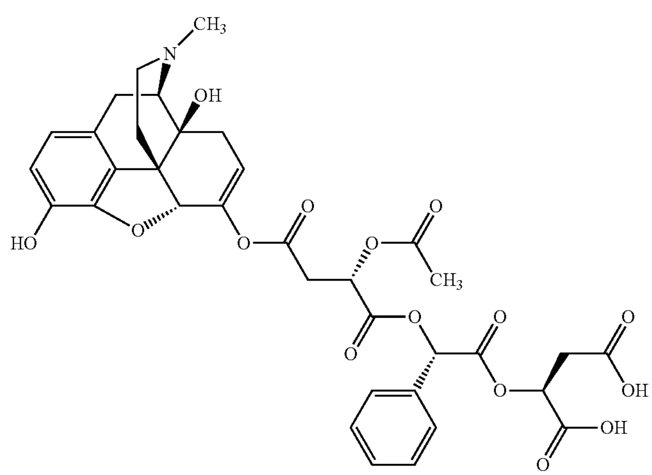 [SMILES: CC(=O)O[C@@H](CC(=O)OC1=CC[C@@]2(O)[C@H]3Cc4ccc(O)c5c4[C@@]2(CCN3C)[C@H]1O5)C(=O)O[C@H](C(=O)O[C@@H](CC(=O)O)C(=O)O)c1ccccc1] | (S)-2-((S)-2-(((S)-2-acetoxy-4-(((4R,4aS,7aR,12bS)-4a,9-dihydroxy-3-methyl-2,3,4,4a,5,7a-hexahydro-1H-4,12-methano-benzofuro[3,2-e]isoquinolin-7-yl)oxy)-4-oxobutanoyl)oxy)-2-phenylacetoxy)succinic acid |

-continued

| Ex. No. | Structure | Name |
|---|---|---|
| D77 | 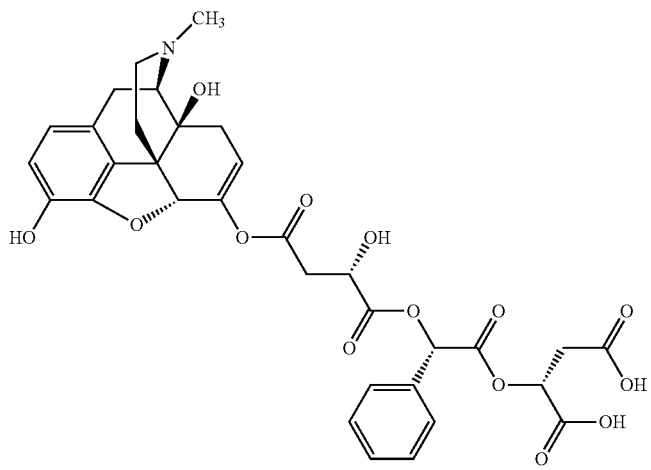 [SMILES: CN1CC[C@]23c4c5ccc(O)c4O[C@H]2C(OC(=O)C[C@H](O)C(=O)O[C@H](C(=O)O[C@H](CC(=O)O)C(=O)O)c2ccccc2)=CC[C@@]3(O)[C@H]1C5] | (R)-2-((S)-2-(((S)-4-(((4R, 4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-hydroxy-4-oxobutanoyl)oxy)-2-phenylacetoxy)succinic acid |
| D78 | 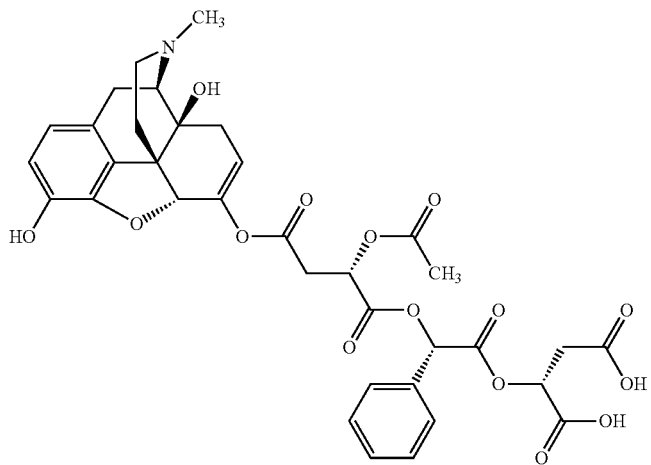 [SMILES: CC(=O)O[C@@H](CC(=O)OC1=CC[C@@]2(O)[C@H]3Cc4ccc(O)c5c4[C@@]2(CCN3C)[C@H]1O5)C(=O)O[C@H](C(=O)O[C@H](CC(=O)O)C(=O)O)c1ccccc1] | (R)-2-((S)-2-(((S)-2-acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetoxy)succinic acid |
| D79 | 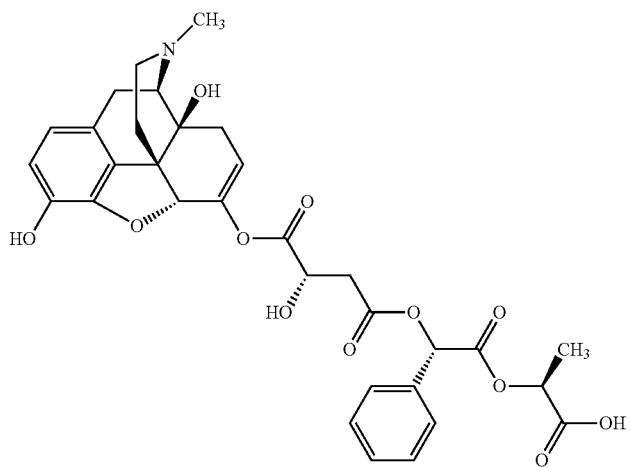 [SMILES: C[C@H](OC(=O)[C@@H](OC(=O)C[C@H](O)C(=O)OC1=CC[C@@]2(O)[C@H]3Cc4ccc(O)c5c4[C@@]2(CCN3C)[C@H]1O5)c1ccccc1)C(=O)O] | (S)-2-((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-hydroxy-4-oxobutanoyl)oxy)-2-phenylacetoxy)propanoic acid |

-continued

| Ex. No. | Structure | Name |
|---|---|---|
| D80 | 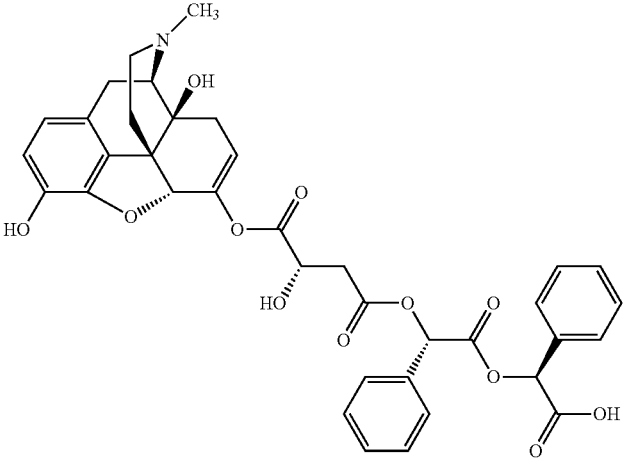 [SMILES: CN1CC[C@]23c4c5ccc(O)c4O[C@H]2C(OC(=O)[C@@H](O)CC(=O)O[C@H](C(=O)O[C@H](C(=O)O)c2ccccc2)c2ccccc2)=CC[C@@]3(O)[C@H]1C5] | (S)-2-((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-hydroxy-4-oxobutanoyl)oxy)-2-phenylacetoxy)-2-phenylacetic acid |
| D81 | 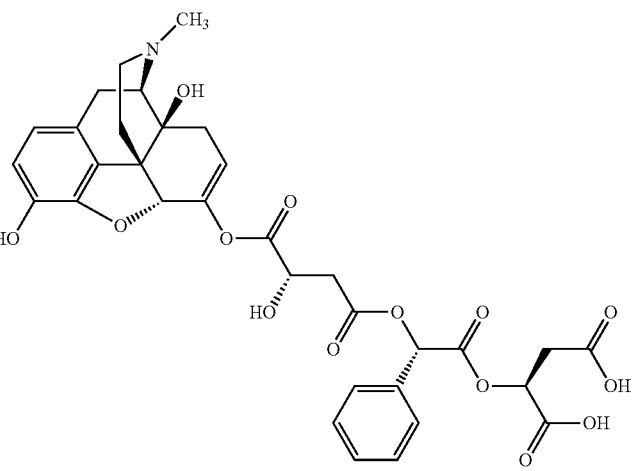 | (S)-2-((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-hydroxy-4-oxobutanoyl)oxy)-2-phenylacetoxy)succinic acid |
| D82 | 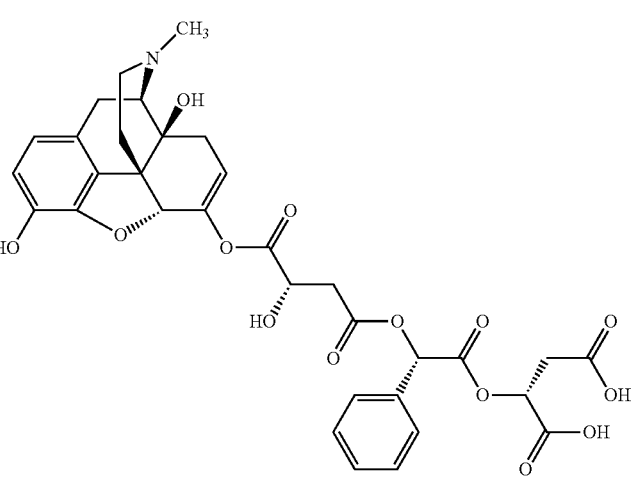 | (R)-2-((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-hydroxy-4-oxobutanoyl)oxy)-2-phenylacetoxy)succinic acid |

| Ex. No. | Structure | Name |
|---|---|---|
| D83 | 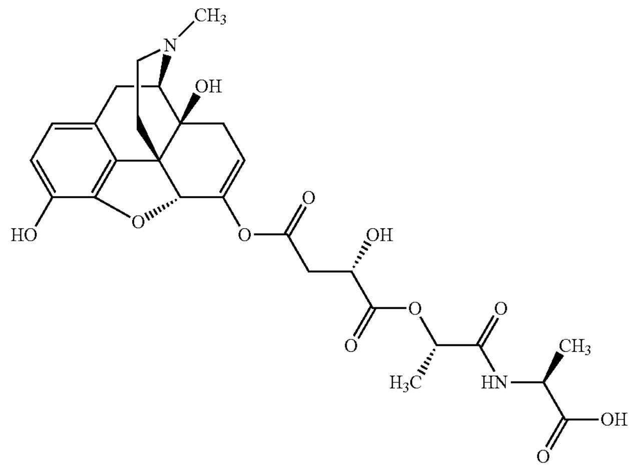 [SMILES: C[C@H](NC(=O)[C@H](C)OC(=O)[C@@H](O)CC(=O)OC1=CC[C@@]2(O)[C@H]3Cc4ccc(O)c5c4[C@@]2(CCN3C)[C@H]1O5)C(=O)O] | (S)-2-((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-hydroxy-4-oxobutanoyl)oxy)propanamido)propanoic acid |
| D84 | 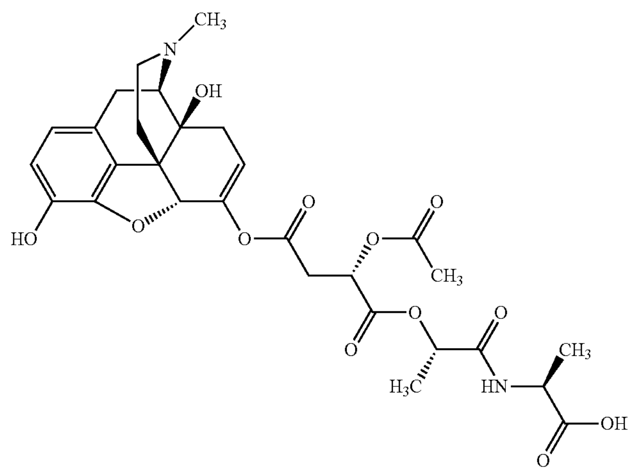 [SMILES: CC(=O)O[C@@H](CC(=O)OC1=CC[C@@]2(O)[C@H]3Cc4ccc(O)c5c4[C@@]2(CCN3C)[C@H]1O5)C(=O)O[C@@H](C)C(=O)N[C@@H](C)C(=O)O] | (S)-2-((S)-2-(((S)-2-acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanamido)propanoic acid |
| D85 | 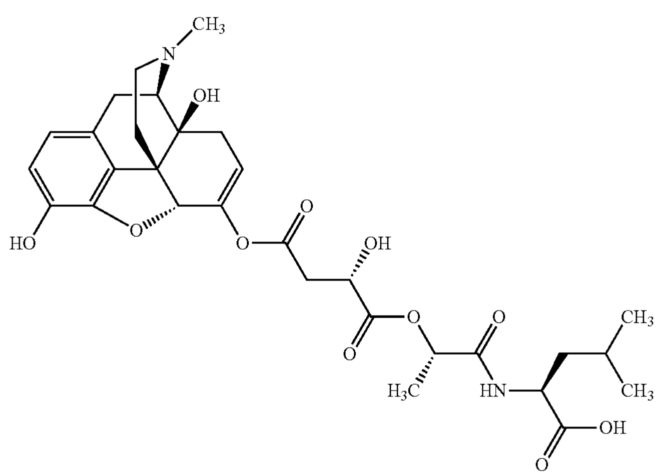 [SMILES: CC(C)C[C@H](NC(=O)[C@H](C)OC(=O)[C@@H](O)CC(=O)OC1=CC[C@@]2(O)[C@H]3Cc4ccc(O)c5c4[C@@]2(CCN3C)[C@H]1O5)C(=O)O] | (S)-2-((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-hydroxy-4-oxobutanoyl)oxy)propanamido)-4-methylpentanoic acid |

| Ex. No. | Structure | Name |
|---|---|---|
| D86 | 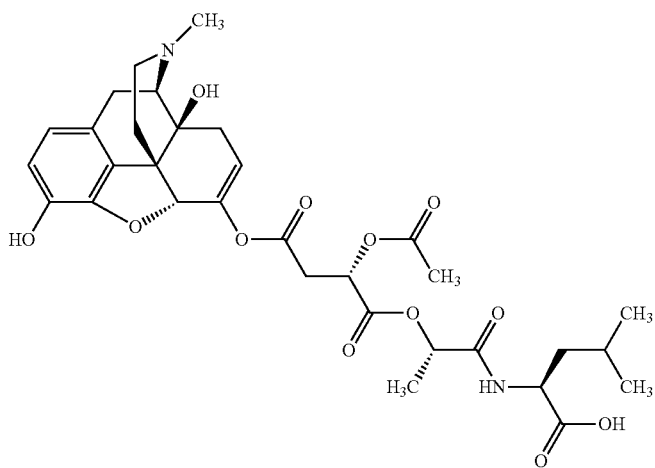 [SMILES: CC(=O)O[C@@H](CC(=O)OC1=CC[C@@]2(O)[C@H]3Cc4ccc(O)c5c4[C@@]2(CCN3C)[C@H]1O5)C(=O)O[C@@H](C)C(=O)N[C@@H](CC(C)C)C(=O)O] | (S)-2-((S)-2-(((S)-2-acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanamido)-4-methylpentanoic acid |
| D87 | 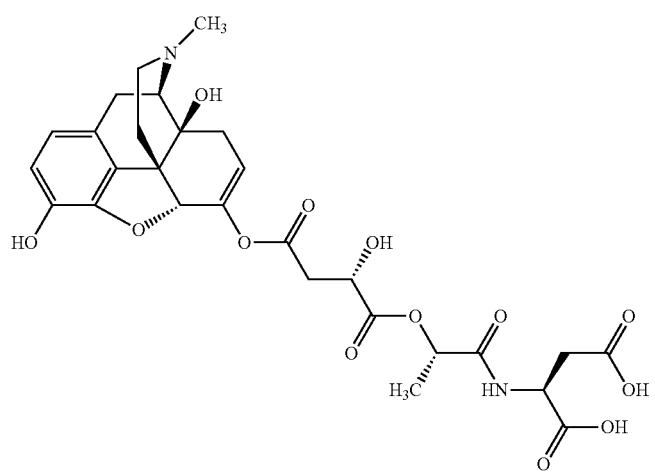 [SMILES: C[C@H](OC(=O)[C@@H](O)CC(=O)OC1=CC[C@@]2(O)[C@H]3Cc4ccc(O)c5c4[C@@]2(CCN3C)[C@H]1O5)C(=O)N[C@@H](CC(=O)O)C(=O)O] | (S)-2-((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-hydroxy-4-oxobutanoyl)oxy)propanamido)succinic acid |
| D88 | 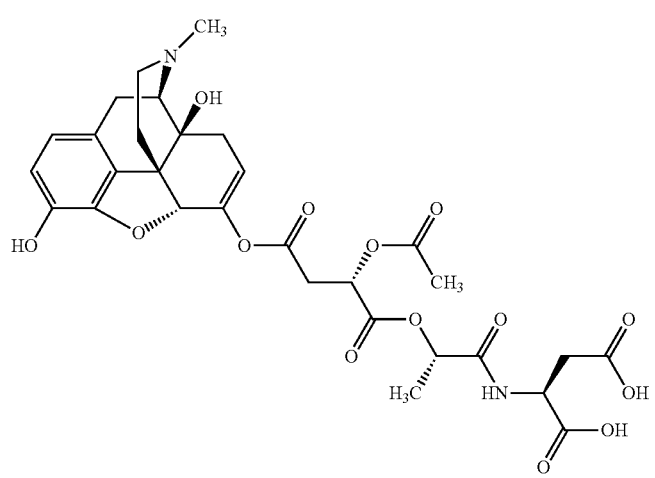 [SMILES: CC(=O)O[C@@H](CC(=O)OC1=CC[C@@]2(O)[C@H]3Cc4ccc(O)c5c4[C@@]2(CCN3C)[C@H]1O5)C(=O)O[C@@H](C)C(=O)N[C@@H](CC(=O)O)C(=O)O] | (S)-2-((S)-2-(((S)-2-acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanamido)succinic acid |

-continued

| Ex. No. | Structure | Name |
|---|---|---|
| D89 | 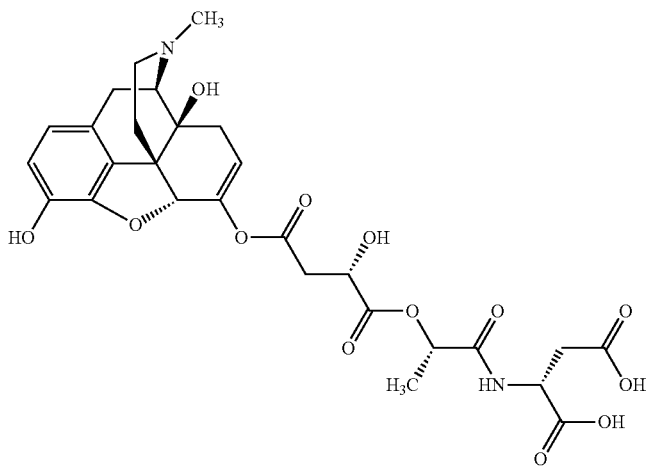 [SMILES: C[C@H](OC(=O)[C@@H](O)CC(=O)OC1=CC[C@@]2(O)[C@H]3Cc4ccc(O)c5c4[C@@]2(CCN3C)[C@H]1O5)C(=O)N[C@H](CC(=O)O)C(=O)O] | (R)-2-((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-hydroxy-4-oxobutanoyl)oxy)propanamido)succinic acid |
| D90 | 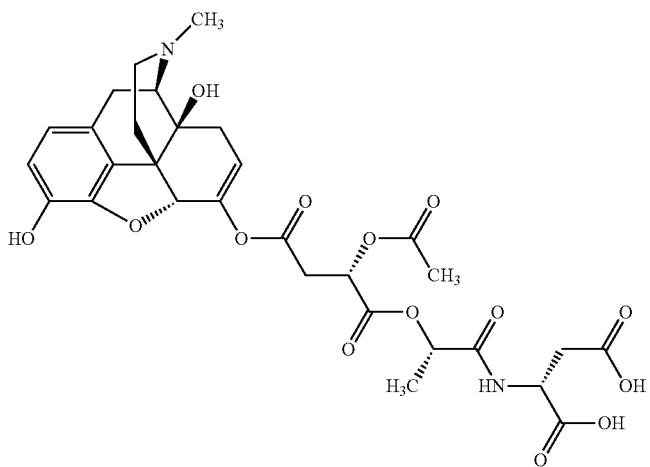 [SMILES: CC(=O)O[C@@H](CC(=O)OC1=CC[C@@]2(O)[C@H]3Cc4ccc(O)c5c4[C@@]2(CCN3C)[C@H]1O5)C(=O)O[C@@H](C)C(=O)N[C@H](CC(=O)O)C(=O)O] | (R)-2-((S)-2-(((S)-2-acetoxy-4-(((4R,4aS,7aR,12bS)-4a,9-dihydroxy-3-methyl-2,3,4,4a,5,7a-hexahydro-1H-4,12-methano-benzofuro[3,2-e]isoquinolin-7-yl)oxy)-4-oxobutanoyl)oxy)propanamido)succinic acid |
| D91 | 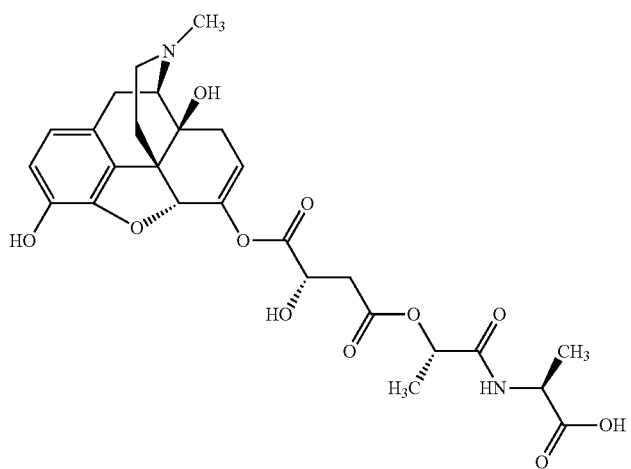 [SMILES: C[C@H](NC(=O)[C@H](C)OC(=O)C[C@H](O)C(=O)OC1=CC[C@@]2(O)[C@H]3Cc4ccc(O)c5c4[C@@]2(CCN3C)[C@H]1O5)C(=O)O] | (S)-2-((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-hydroxy-3-oxobutanoyl)oxy)propanamido)propanoic acid |

-continued

| Ex. No. | Structure | Name |
|---|---|---|
| D92 | 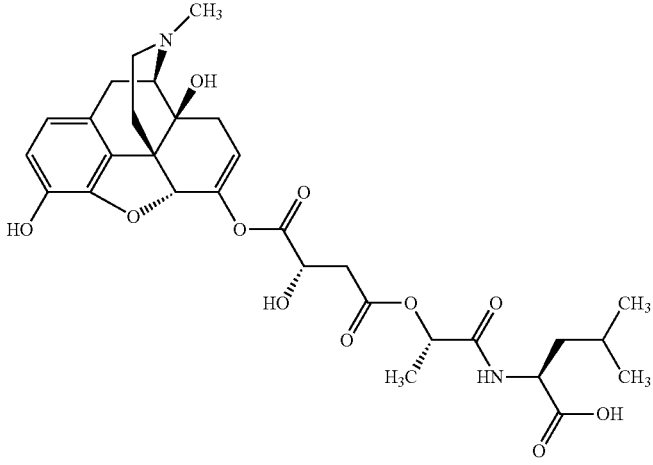 [SMILES: CC(C)C[C@H](NC(=O)[C@H](C)OC(=O)C[C@H](O)C(=O)OC1=CC[C@@]2(O)[C@H]3Cc4ccc(O)c5c4[C@@]2(CCN3C)[C@H]1O5)C(=O)O] | (S)-2-((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-hydroxy-4-oxobutanoyl)oxy)propanamido)-4-methylpentanoic acid |
| D93 | 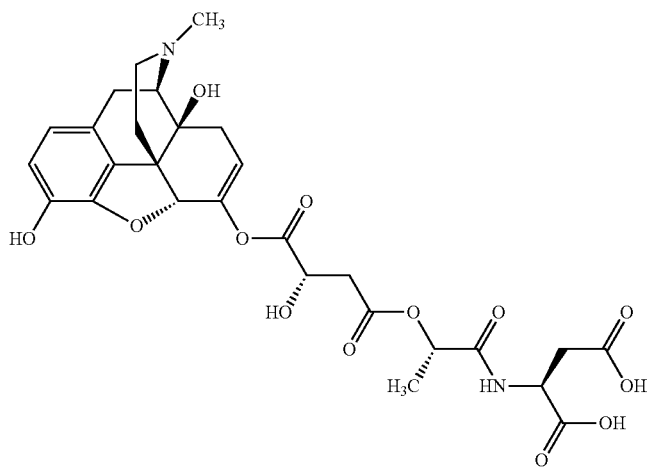 [SMILES: C[C@H](OC(=O)C[C@H](O)C(=O)OC1=CC[C@@]2(O)[C@H]3Cc4ccc(O)c5c4[C@@]2(CCN3C)[C@H]1O5)C(=O)N[C@@H](CC(=O)O)C(=O)O] | (S)-2-((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-hydroxy-4-oxobutanoyl)oxy)propanamido)succinic acid |
| D94 | 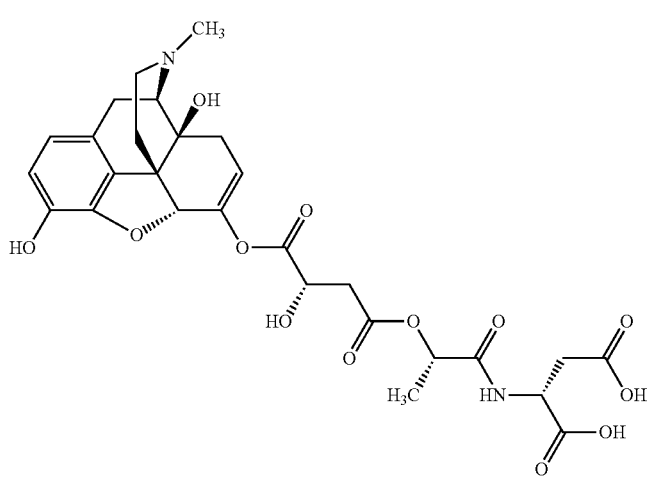 [SMILES: C[C@H](OC(=O)C[C@H](O)C(=O)OC1=CC[C@@]2(O)[C@H]3Cc4ccc(O)c5c4[C@@]2(CCN3C)[C@H]1O5)C(=O)N[C@H](CC(=O)O)C(=O)O] | (R)-2-((S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-hydroxy-4-oxobutanoyl)oxy)propanamido)succinic acid |

| Ex. No. | Structure | Name |
|---|---|---|
| D95 | 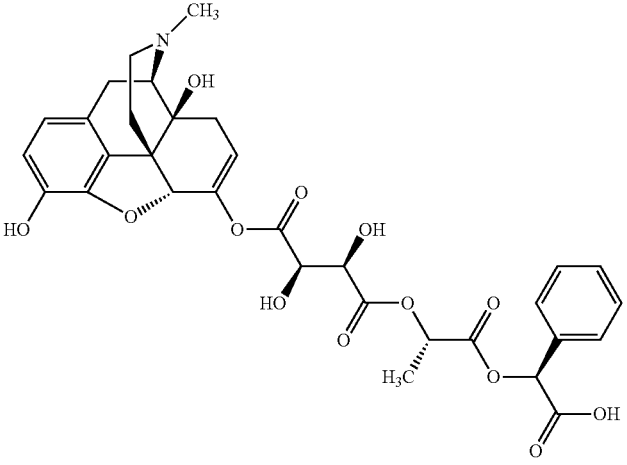 [SMILES: C[C@H](OC(=O)[C@H](O)[C@@H](O)C(=O)OC1=CC[C@@]2(O)[C@H]3Cc4ccc(O)c5c4[C@@]2(CCN3C)[C@H]1O5)C(=O)O[C@H](C(=O)O)c1ccccc1] | (S)-2-(((S)-2-(((2R,3R)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy)propanoyl)oxy)-2-phenylacetic acid |
| D96 | 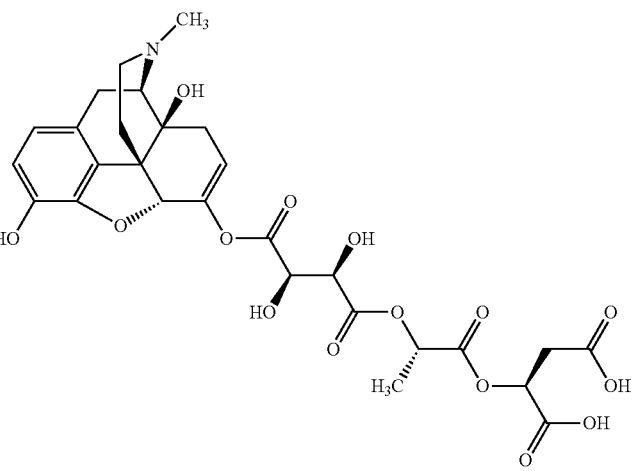 | (S)-2-(((S)-2-(((2R,3R)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy)propanoyl)oxy)succinic acid |
| D97 | 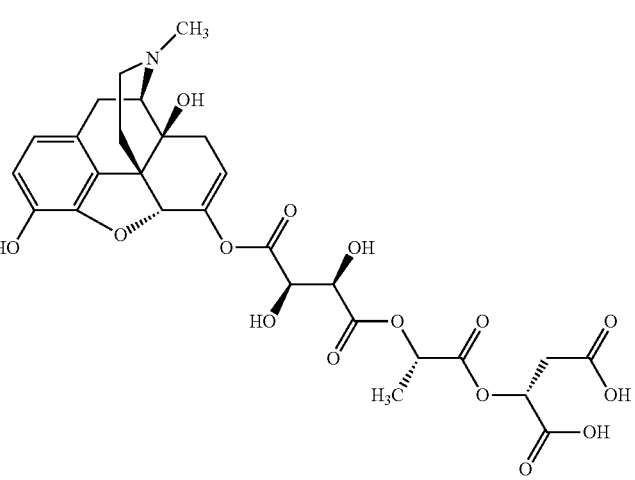 | (R)-2-(((S)-2-(((2R,3R)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy)propanoyl)oxy)succinic acid |

-continued

| Ex. No. | Structure | Name |
|---|---|---|
| D98 | 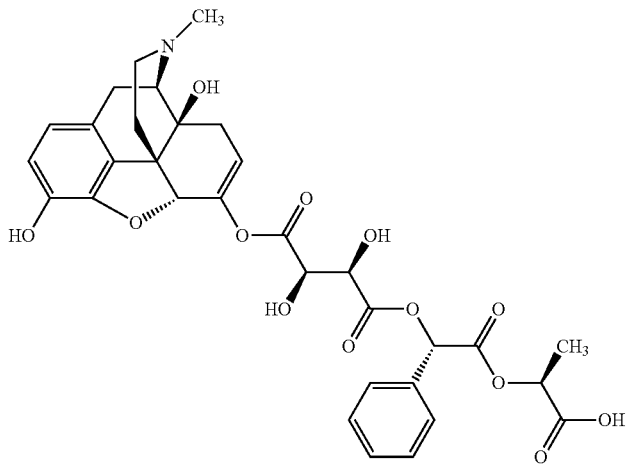 [SMILES: C[C@H](OC(=O)[C@@H](OC(=O)[C@H](O)[C@@H](O)C(=O)OC1=CC[C@@]2(O)[C@H]3Cc4ccc(O)c5c4[C@@]2(CCN3C)[C@H]1O5)c1ccccc1)C(=O)O] | (S)-2-((S)-2-(((2R,3R)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy)-2-phenylacetoxy)propanoic acid |
| D99 | 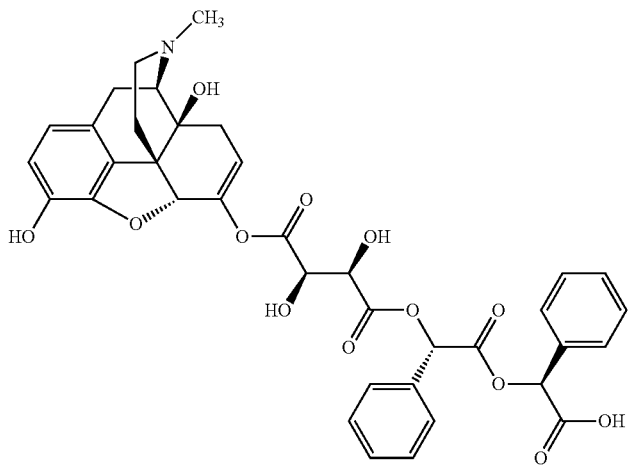 [SMILES: CN1CC[C@]23c4c5ccc(O)c4O[C@H]2C(OC(=O)[C@H](O)[C@@H](O)C(=O)O[C@H](C(=O)O[C@H](C(=O)O)c2ccccc2)c2ccccc2)=CC[C@@]3(O)[C@H]1C5] | (S)-2-((S)-2-(((2R,3R)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy)-2-phenylacetoxy)-2-phenylacetic acid |
| D100 | 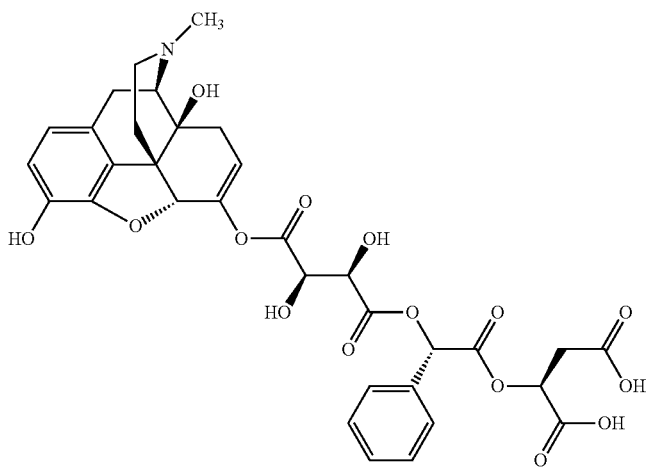 [SMILES: CN1CC[C@]23c4c5ccc(O)c4O[C@H]2C(OC(=O)[C@H](O)[C@@H](O)C(=O)O[C@H](C(=O)O[C@@H](CC(=O)O)C(=O)O)c2ccccc2)=CC[C@@]3(O)[C@H]1C5] | (S)-2-((S)-2-(((2R,3R)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy)-2-phenylacetoxy)succinic acid |

-continued

| Ex. No. | Structure | Name |
|---|---|---|
| D101 | 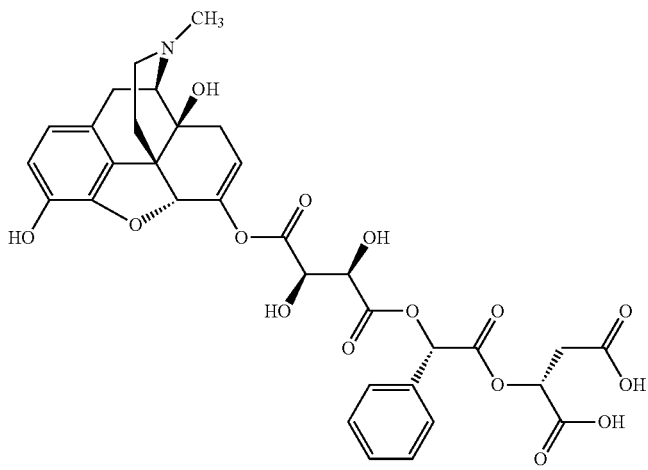 [SMILES: CN1CC[C@]23c4c5ccc(O)c4O[C@H]2C(OC(=O)[C@H](O)[C@@H](O)C(=O)O[C@H](C(=O)O[C@H](CC(=O)O)C(=O)O)c2ccccc2)=CC[C@@]3(O)[C@H]1C5] | (R)-2-((S)-2-(((2R,3R)-4-(((4R, 4aS,7aR,12bS)-4a,9-dihydroxy-3-methyl-2,3,4,4a,5,7a-hexahydro-1H-4,12-methanobenzofuro [3,2-e]isoquinolin-7-yl)oxy)-2,3-dihydroxy-4-oxobutanoyl)oxy)-2-phenylacetoxy)succinic acid |
| D102 | 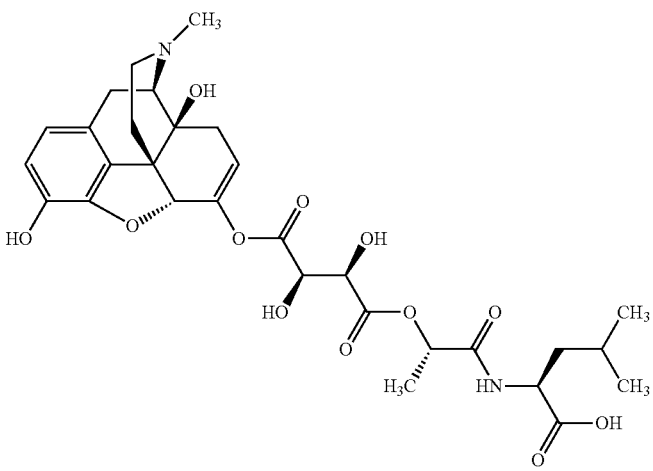 [SMILES: CC(C)C[C@H](NC(=O)[C@H](C)OC(=O)[C@H](O)[C@@H](O)C(=O)OC1=CC[C@@]2(O)[C@H]3Cc4ccc(O)c5c4[C@@]2(CCN3C)[C@H]1O5)C(=O)O] | (S)-2-((S)-2-(((2R,3R)-4-(((4R, 4aS,7aR,12bS)-4a,9-dihydroxy-3-methyl-2,3,4,4a,5,7a-hexahydro-1H-4,12-methanobenzofuro [3,2-e]isoquinolin-7-yl)oxy)-2,3-dihydroxy-4-oxobutanoyl)oxy) propanamido)-4-methylpentanoic acid |
| D103 | 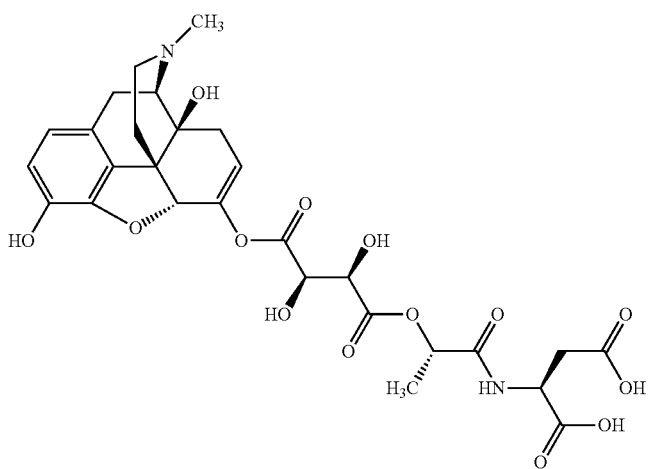 [SMILES: C[C@H](OC(=O)[C@H](O)[C@@H](O)C(=O)OC1=CC[C@@]2(O)[C@H]3Cc4ccc(O)c5c4[C@@]2(CCN3C)[C@H]1O5)C(=O)N[C@@H](CC(=O)O)C(=O)O] | (S)-2-((S)-2-(((2R,3R)-4-(((4R, 4aS,7aR,12bS)-4a,9-dihydroxy-3-methyl-2,3,4,4a,5,7a-hexahydro-1H-4,12-methanobenzofuro [3,2-e]isoquinolin-7-yl)oxy)-2,3-dihydroxy-4-oxobutanoyl)oxy) propanamido)succinic acid |

| Ex. No. | Structure | Name |
|---|---|---|
| D104 | 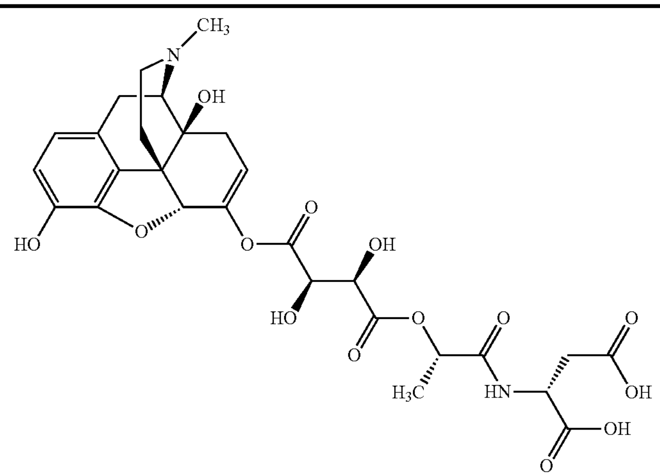 | (R)-2-((S)-2-(((2R,3R)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy)propanamido)succinic acid |

As such, in another aspect, certain embodiments of the present invention provide a drug delivery system comprising an abuse-resistant opioid compound. In such embodiments, as described above, the abuse-resistant opioid compound comprises an opioid covalently bound to a chemical moiety.

In another aspect, certain embodiments of the present invention provide a method of preventing opioid abuse. In such embodiments, the method comprises administering a therapeutically effective amount of an opioid compound (a compound of one of the formulas described above) to a subject. In some embodiments, the opioid compound may exhibit one or more of the following advantages over free opioids. The opioid compound may prevent overdose by exhibiting a reduced pharmacological activity when administered at higher than therapeutic doses, e.g., higher than the prescribed dose. Yet when the opioid compound is administered at therapeutic doses, the opioid compound may retain similar pharmacological activity to that achieved by administering unbound opioids, e.g., Opana® ER. Also, the opioid compound may prevent abuse by exhibiting stability under conditions likely to be employed by illicit chemists attempting to release the amphetamine. The opioid compound may prevent abuse by exhibiting reduced bioavailability when it is administered via parenteral routes, particularly the intravenous ("shooting"), intranasal ("snorting"), and/or inhalation ("smoking") routes that are often employed in illicit use. In particular, the chemical moiety X may not release the opioid until the opioid compound reaches the intestinal tract. Thus, the opioid compound may not be administered via routes typically associated with opioid abuse. As such, the opioid compound may reduce the euphoric effect associated with opioid abuse. Additionally, the opioid compound may prevent and/or reduce the potential of abuse and/or overdose when the opioid compound is used in a manner inconsistent with the manufacturer's instructions, e.g., consuming the opioid compound at a higher than therapeutic dose or via a non-oral route of administration.

According to certain embodiments of the present invention, the opioid compound remains inactive until oral administration releases the opioid. Without being bound by theory, it is believed that the opioid compound is inactive because the attachment of the chemical moiety reduces binding between the opioid and its biological target sites (e.g., opioid receptors located in the intestinal tract, brain, spinal cord, and peripheral sensory neurons). The opioid compound is activated by oral administration, that is, the opioid is released from the chemical moiety by hydrolysis, e.g., by enzymes in the intestinal tract. Because oral administration facilitates activation, activation is reduced or does not occur when the opioid compound is administered via parenteral routes often employed by illegal users. Further, it is believed that the opioid compound is resistant to abuse and/or overdose due to a natural gating mechanism at the site of hydrolysis, namely the intestinal tract. This gating mechanism is thought to allow the release of therapeutic amounts of opioid from the opioid compound but limit the release of higher amounts of opioid.

In another aspect, certain embodiments of the present invention provide a method of delivering an active ingredient to a subject. In such embodiments, the method comprises administering a therapeutically effective amount of an opioid compound to a subject (i.e. an amount sufficient to prevent, ameliorate, and/or eliminate the symptoms of a disease. In some embodiments, this method can be used to treat any disease that may benefit from opioid-type drugs including, but not limited to: acute and/or chronic back pain, chronic cancer pain, fibromyalgia, headaches, migraines, acute and/or chronic nerve pain, rheumatoid arthritis, and shortness of breath from cancer or cardiopulmonary syndromes (e.g., COPD).

In accordance with certain embodiments of the present invention, the method of delivering an active ingredient to a subject may further comprise administering at least one adjuvant analgesic in addition to administering an opioid compound. In such embodiments, the at least one adjuvant analgesic and the opioid compound can be formulated into a single dosage form, or they may be formulated together or separately among multiple dosage forms. The at least one adjuvant analgesic and the opioid compound can be administered simultaneously or sequentially in any order. Exemplary combination therapies include the administration of the drugs listed in Table 1:

TABLE 1

Exemplary drug therapies contemplated for use in combination with an opioid compound

| Condition | Exemplary Drug Class | Specific exemplary drugs |
|---|---|---|
| Back Pain | Antidepressant (TCA, SSRI) | Elavil ®, Prozac ®, Paxil ®, Zoloft ®, Effexor ®, Serzone ®. |
|  | Muscle Relaxants | Soma ®, Flexeril ®, Skelaxin ®. |
|  | α-2-Adrenergic Agonist | Zanaflex ® |
| Cancer Pain | Steroid | Corticosteroids |
| Fibromyalgia | Anticonvulsant | Neurontin ®, Lyrica ®. |
| Headache | Antidepressant (TCA, SSRI) | Elavil ®, Prozac ®, Paxil ®, Zoloft ®, Effexor ®, Serzone ®. |
|  | Anticonvulsant | Depakote ®, Topamax ®. |
|  | α-2-Adrenergic Agonist | Zanaflex ® |
| Migraine | Antidepressant (TCA, SSRI) | Elavil ®, Prozac ®, Paxil ®, Zoloft ®, Effexor ®, Serzone ®. |
|  | Anticonvulsant | Neurontin ®, Lyrica ®. |
|  | Steroid | Corticosteroids |
| Nerve Pain | Antidepressant (TCA, SSRI) | Elavil ®, Prozac ®, Paxil ®, Zoloft ®, Effexor ®, Serzone ®. |
|  | Anticonvulsant | Neurontin ®, Lyrica ®, Tegretol ®, Dilantin ®, Depakote ®, Klonopin ®, Topamax ®, Lamictal ®. |
|  | α-2-Adrenergic Agonist | Zanaflex ®, Catapres ®. |
|  | Local Anesthetic | Mexiletine |
|  | Muscle Relaxant | Baclofen |
|  | NDMA Receptor Agonist | Dextromethorphan, Ketamine, Amantadine |
|  | Topical Pain Reliever | Lidoderm ®, Capsaicin |
| Rheumatoid Arthritis | Antidepressant (TCA, SSRI) | Elavil ®, Prozac ®, Paxil ®, Zoloft ®, Effexor ®, Serzone ®. |
|  | Topical Pain Reliever | Capsaicin |
| Shortness of Breath | Steroid | Corticosteroids |

In another aspect, certain embodiments of the present invention provide a pharmaceutical composition comprising an abuse-resistant opioid compound and at least one pharmaceutical additive. In such embodiments, the abuse-resistant opioid compound may comprise an opioid covalently bound to a chemical moiety. Additionally, in such embodiments, the at least one pharmaceutical additive may include a wide range of materials including, but not limited to, diluents and bulking substances, binders and adhesives, lubricants, glidants, plasticizers, disintegrants, carrier solvents, buffers, colorants, flavorings, sweeteners, preservatives and stabilizers, and other pharmaceutical additives known in the art.

Diluents increase the bulk of a dosage form and may make the dosage form easier to handle. Exemplary diluents include, but are not limited to, lactose, dextrose, saccharose, cellulose, starch, and calcium phosphate for solid dosage forms, e.g., tablets and capsules; olive oil and ethyl oleate for soft capsules; water and vegetable oil for liquid dosage forms, e.g., suspensions and emulsions. Additional suitable diluents include, but are not limited to, sucrose, dextrates, dextrin, maltodextrin, microcrystalline cellulose (e.g., Avicel®), microfine cellulose, powdered cellulose, pregelatinized starch (e.g., Starch 1500®), calcium phosphate dihydrate, soy polysaccharide (e.g., Emcosoy®), gelatin, silicon dioxide, calcium sulfate, calcium carbonate, magnesium carbonate, magnesium oxide, sorbitol, mannitol, kaolin, polymethacrylates (e.g., Eudragit®), potassium chloride, sodium chloride, and talc. In some embodiments, r the ranges for the amount of diluent by weight percent may include about 40% to about 90%, about 50% to about 85%, about 55% to about 80%, about 50% to about 60%, and increments therein.

In embodiments where the pharmaceutical composition is compacted into a solid dosage form, e.g., a tablet, a binder can help the ingredients hold together. Binders include, but are not limited to, sugars such as sucrose, lactose, and glucose; corn syrup; soy polysaccharide, gelatin; povidone (e.g., Kollidon®, Plasdone®); Pullulan; cellulose derivatives such as microcrystalline cellulose, hydroxypropylmethyl cellulose (e.g., Methocel®), hydroxypropyl cellulose (e.g., Klucel®), ethylcellulose, hydroxyethyl cellulose, carboxymethylcellulose sodium, and methylcellulose; acrylic and methacrylic acid co-polymers; carbomer (e.g., Carbopol®); polyvinylpolypyrrolidine, polyethylene glycol (Carbowax®); pharmaceutical glaze; alginates such as alginic acid and sodium alginate; gums such as acacia, guar gum, and arabic gums; tragacanth; dextrin and maltodextrin; milk derivatives such as whey; starches such as pregelatinized starch and starch paste; hydrogenated vegetable oil; and magnesium aluminum silicate.

For tablet dosage forms, the pharmaceutical composition is subjected to pressure from a punch and dye. Among other purposes, a lubricant can help prevent the composition from sticking to the punch and dye surfaces. A lubricant can also be used in the coating of a coated dosage form. Lubricants include, but are not limited to, magnesium stearate, calcium stearate, zinc stearate, powdered stearic acid, glyceryl monostearate, glyceryl palmitostearate, glyceryl behenate, silica, magnesium silicate, colloidal silicon dioxide, titanium dioxide, sodium benzoate, sodium lauryl sulfate, sodium stearyl fumarate, hydrogenated vegetable oil, talc, polyethylene glycol, and mineral oil. In certain embodiments, the amount of lubricant by weight percent may be less than about 5%, 4%, 3%, 2%, 1.5%, 1%, or 0.5%, or increments therein.

Glidants may improve the flowability of non-compacted solid dosage forms and may improve the accuracy of dosing. Glidants include, but are not limited to, colloidal silicon dioxide, fumed silicon dioxide, silica gel, talc, magnesium trisilicate, magnesium or calcium stearate, powdered cellulose, starch, and tribasic calcium phosphate.

Plasticizers may include both hydrophobic and hydrophilic plasticizers such as, but not limited to, diethyl phthalate, butyl phthalate, diethyl sebacate, dibutyl sebacate, triethyl citrate, acetyltriethyl citrate, acetyltributyl citrate, cronotic acid, propylene glycol, castor oil, triacetin, polyethylene glycol, propylene glycol, glycerin, and sorbitol. Plasticizers are particularly useful for pharmaceutical compositions containing a polymer and in soft capsules and film-coated tablets.

Disintegrants can increase the dissolution rate of a pharmaceutical composition. Disintegrants include, but are not limited to, alginates such as alginic acid and sodium alginate, carboxymethylcellulose calcium, carboxymethylcellulose sodium (e.g., Ac-Di-Sol®, Primellose®), colloidal silicon dioxide, croscarmellose sodium, crospovidone (e.g., Kollidon®, Polyplasdone®), polyvinylpolypyrrolidine (Plasone-XL®), guar gum, magnesium aluminum silicate, methyl cellulose, microcrystalline cellulose, polacrilin potassium, powdered cellulose, starch, pregelatinized starch, sodium starch glycolate (e.g., Explotab®, Primogel®). In some embodiments, the ranges for the amount of disintegrant by weight percent may include about 1% to about 10%, about 1% to about 5%, about 2% to about 3%, and increments therein.

In embodiments where the pharmaceutical composition is formulated for a liquid dosage form, the pharmaceutical composition may include one or more solvents. Suitable solvents include, but are not limited to, water; alcohols such as ethanol and isopropyl alcohol; methylene chloride; vegetable oil; polyethylene glycol; propylene glycol; and glycerin.

The pharmaceutical composition may comprise a buffer. Buffers include, but are not limited to, lactic acid, citric acid, acetic acid, sodium lactate, sodium citrate, and sodium acetate.

Any pharmaceutically acceptable colorant can be used to improve appearance or to help identify the pharmaceutical composition. Exemplary colorants include D&C Red No. 28, D&C Yellow No. 10, FD&C Blue No. 1, FD&C Red No. 40, FD&C Green #3, FD&C Yellow No. 6, and edible inks. Preferred colors for gelatin capsules include white, medium orange, and light blue.

Flavorings improve palatability and may be particularly useful for chewable tablet or liquid dosage forms. Flavorings include, but are not limited to maltol, vanillin, ethyl vanillin, menthol, citric acid, fumaric acid, ethyl maltol, and tartaric acid. Sweeteners include, but are not limited to, sorbitol, saccharin, sodium saccharin, sucrose, aspartame, fructose, mannitol, and invert sugar.

The pharmaceutical compositions of the invention may also include one or more preservatives and/or stabilizers to improve storagability. These include, but are not limited to, alcohol, sodium benzoate, butylated hydroxy toluene, butylated hydroxyanisole, and ethylenediamine tetraacetic acid.

Other pharmaceutical additives may include gelling agents such as colloidal clays; thickening agents such as gum tragacanth and sodium alginate; wetting agents such as lecithin, polysorbates, and laurylsulphates; humectants; antioxidants such as vitamin E, caronene, and BHT; adsorbents; effervescing agents; emulsifying agents, viscosity enhancing agents; surface active agents such as sodium lauryl sulfate, dioctyl sodium sulfosuccinate, triethanolamine, polyoxyethylene sorbitan, poloxalkol, and quaternary ammonium salts; and other miscellaneous excipients such as lactose, mannitol, glucose, fructose, xylose, galactose, sucrose, maltose, xylitol, sorbitol, chloride, sulfate and phosphate salts of potassium, sodium, and magnesium.

The pharmaceutical compositions may be manufactured according to any method known to those of skill in the art of pharmaceutical manufacture such as, for example, wet granulation, dry granulation, encapsulation, direct compression, slugging, etc. For instance, a pharmaceutical composition may be prepared by mixing the opioid compound with one or more pharmaceutical additives with an aliquot of liquid, preferably water, to form a wet granulation. The wet granulation can be dried to obtain granules. The resulting granulation can be milled, screened, and blended with various pharmaceutical additives such as water-insoluble polymers and additional hydrophilic polymers. In some embodiments, an opioid compound may be mixed with a hydrophilic polymer and an aliquot of water, then dried to obtain granules of opioid compound encapsulated by hydrophilic polymer.

After granulation, the pharmaceutical composition may be encapsulated, e.g., in a gelatin capsule. The gelatin capsule can contain, for example, kosher gelatin, titanium dioxide, and optional colorants. Alternatively, the pharmaceutical composition may be tableted, e.g., compressed and optionally coated with a protective coating that dissolves or disperses in gastric juices.

The pharmaceutical compositions of the invention may be administered by a variety of dosage forms. Any biologically-acceptable dosage form known in the art, and combinations thereof, are contemplated. Examples of preferred dosage forms include, without limitation, tablets including chewable tablets, film-coated tablets, quick dissolve tablets, effervescent tablets, multi-layer tablets, and bi-layer tablets; caplets; powders including reconstitutable powders; granules; dispersible granules; particles; microparticles; capsules including soft and hard gelatin capsules; lozenges; chewable lozenges; cachets; beads; liquids; solutions; suspensions; emulsions; elixirs; and syrups.

The pharmaceutical composition is administered orally. Oral administration permits the maximum release of opioid, provides sustained release of opioid, and maintains abuse resistance by only releasing the opioid from the chemical moiety upon reaching the intestinal tract.

Oral dosage forms may be presented as discrete units, such as capsules, caplets, or tablets. In certain embodiments, a solid oral dosage form comprising an opioid compound that is smaller in size compared to a solid oral dosage form containing a therapeutically equivalent amount of unbound opioid may be used. In some embodiment, the oral dosage form may comprise a gelatin capsule of size 2, size 3, or smaller (e.g., size 4). The smaller size of the opioid compound dosage forms promotes ease of swallowing.

Soft gel or soft gelatin capsules may be prepared, for example, by dispersing the formulation in an appropriate vehicle (e.g., vegetable oil) to form a high viscosity mixture. This mixture then is encapsulated with a gelatin based film. The industrial units so formed are then dried to a constant weight.

Chewable tablets can be prepared by mixing the opioid compound with excipients designed to form a relatively soft, flavored tablet dosage form that is intended to be chewed. Conventional tablet machinery and procedures (e.g., direct compression, granulation, and slugging) can be utilized.

Film-coated tablets can be prepared by coating tablets using techniques such as rotating pan coating methods and air suspension methods to deposit a contiguous film layer on a tablet.

Compressed tablets can be prepared by mixing the opioid compound with excipients that add binding qualities. The mixture can be directly compressed, or it can be granulated and then compressed.

In other embodiments, the pharmaceutical composition may alternatively be formulated into a liquid dosage form, such as a solution or suspension in an aqueous or non-aqueous liquid. The liquid dosage form can be an emulsion, such as an oil-in-water liquid emulsion or a water-in-oil liquid emulsion. The oils can be administered by adding the purified and sterilized liquids to a prepared enteral formula, which then is placed in the feeding tube of a patient who is unable to swallow.

For oral administration, fine powders or granules containing diluting, dispersing, and/or surface-active agents can be presented in a draught, in water or a syrup, in capsules or sachets in the dry state, in a non-aqueous suspension wherein suspending agents may be included, or in a suspension in water or a syrup. Liquid dispersions for oral administration can be syrups, emulsions, or suspensions. The syrups, emulsions, or suspensions can contain a carrier, for example, a natural gum, agar, sodium alginate, pectin, methylcellulose, carboxymethylcellulose, saccharose, saccharose with glycerol, mannitol, sorbitol, and polyvinyl alcohol.

The dose range of the opioid compound for humans will depend on a number of factors including the age, weight, and condition of the patient. Tablets and other dosage forms provided in discrete units can contain a daily dose, or an appropriate fraction thereof, of one or more opioid compounds. The dosage form can contain a dose of about 2.5 mg to about 500 mg, about 10 mg to about 250 mg, about 10 mg to about 100 mg, about 10 mg to about 75 mg, or increments therein of one or more of the opioid compounds.

In certain embodiments, the pharmaceutical compositions of the invention may be administered in a partial, i.e., fractional dose, one or more times during a 24 hour period. Fractional, single, double, or other multiple doses can be taken simultaneously or at different times during a 24 hour period. The doses can be uneven doses with regard to one another or with regard to the individual components at different administration times. Preferably, a single dose is administered once daily. The dose can be administered in a fed or fasted state.

The dosage units of the pharmaceutical composition can be packaged according to market need, for example, as unit doses, rolls, bulk bottles, blister packs, and so forth. The pharmaceutical package, e.g., blister pack, can further include or be accompanied by indicia allowing individuals to identify the identity of the pharmaceutical composition, the prescribed indication (e.g., pain), and/or the time periods (e.g., time of day, day of the week, etc.) for administration. The blister pack or other pharmaceutical package can also include a second pharmaceutical product for combination therapy.

EXAMPLES

The present disclosure is further illustrated by the following examples, which in no way should be construed as being limiting. That is, the specific features described in the following examples are merely illustrative and not limiting.

Compound Synthesis

The following outlines synthesis of exemplary compounds of the invention. The suggested methodologies are not intended to be limiting. The variations of these synthetic methodologies or methodologies reported in literature can be adopted to synthesize molecules within the scope of invention.

HPLC Conditions:

| | Method A |
|---|---|
| Column: | Phenomenex Luna C8(2) column (150 × 4.6 mm, 5 micron) |
| Mobile Phase A: | Water containing 0.1% v/v Trifluoroacetic Acid |
| Mobile Phase B: | Acetonitrile containing 0.1% v/v Trifluoroacetic Acid |
| Detection: | 254 nm |

Method A Gradient

| Time (min) | Flow (mL/min) | % A | % B |
|---|---|---|---|
| 0.0 | 1.0 | 100.0 | 0.0 |
| 15.0 | 1.0 | 0.0 | 100.0 |
| 22.0 | 1.0 | 0.0 | 100.0 |

Method B Gradient

| Time (min) | Flow (mL/min) | % A | % B |
|---|---|---|---|
| 0.0 | 1.0 | 100.0 | 0.0 |
| 12.0 | 1.0 | 0.0 | 30.0 |
| 20.0 | 1.0 | 0.0 | 30.0 |

Scheme 1: (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl oleate hydrochloride

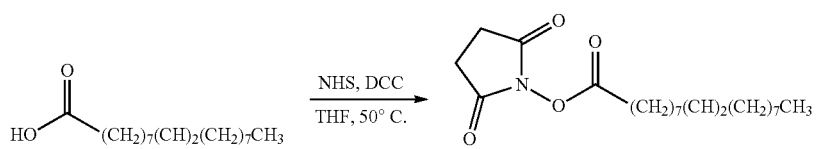

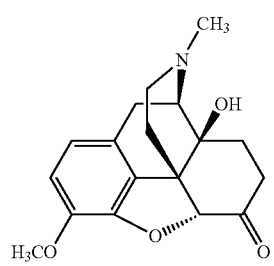

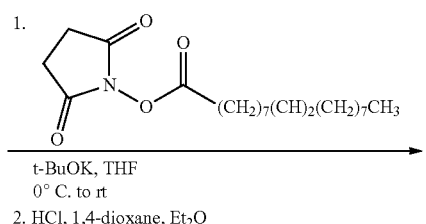

t-BuOK, THF
0° C. to rt
2. HCl, 1,4-dioxane, Et$_2$O

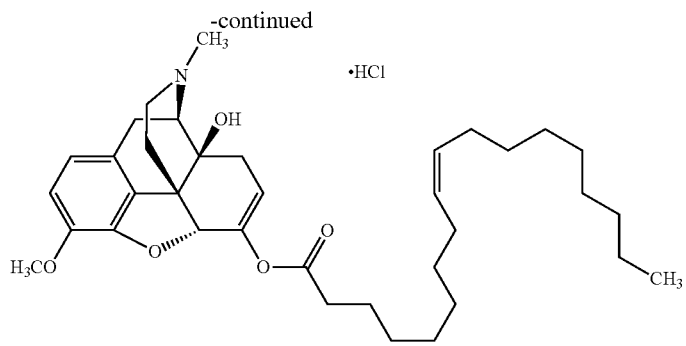

Preparation 2,5-Dioxopyrrolidin-1-yl oleate

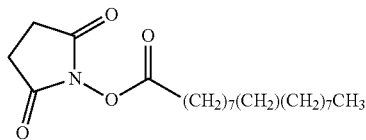

A solution of oleic acid (1.00 g, 3.54 mmol) and N-hydroxysuccinimide (407 mg, 3.54 mmol) in tetrahydrofuran (10 mL) was treated dropwise with a solution of N,N'-dicyclohexylcarbodiimide (730 mg, 3.54 mmol) in tetrahydrofuran (10 mL). The mixture was heated at 50° C. under a nitrogen atmosphere for 2 h. After this time, the reaction mixture was cooled to room temperature and filtered to remove the solid dicyclohexylurea byproduct. The filtrate was concentrated under reduced pressure and dried under vacuum overnight to provide 2,5-dioxopyrrolidin-1-yl oleate (3.54 g, 83%) as a white semi-solid: $^1$H NMR (300 MHz, DMSO-$d_6$) δ 5.32 (m, 2H), 2.81 (s, 4H), 2.65 (t, J=7.2 Hz, 2H), 1.99-1.95 (m, 4H), 1.63-1.95 (m, 3H), 1.24-1.18 (m, 19H), 0.85 (t, J=6.3 Hz, 3H).

Preparation of (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl oleate hydrochloride

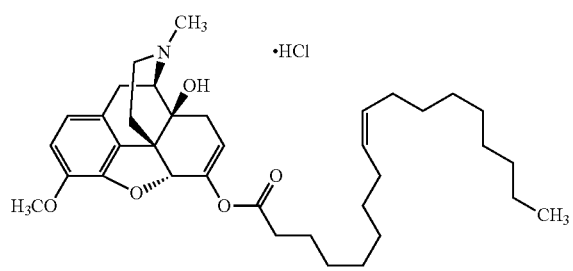 [SMILES: CCCCCCCC/C=C\CCCCCCCC(=O)OC1=CC[C@@]2(O)[C@H]3Cc4ccc(OC)c5c4[C@@]2(CCN3C)[C@H]1O5 ; Cl]

A suspension of oxycodone (380 mg, 1.20 mmol) in tetrahydrofuran (5 mL) was cooled in an ice bath and treated dropwise with a 1.0 M solution of potassium tert-butoxide in tetrahydrofuran (1.5 mL, 1.5 mmol). After addition was complete, the mixture was stirred at ambient temperature for 15 min. The mixture was re-cooled in the ice bath and treated dropwise with a solution of 2,5-dioxopyrrolidin-1-yl octadec-9-enoate (502 mg, 1.32 mmol) in tetrahydrofuran (5 mL) over 15 min. After addition was complete, the mixture was stirred at ambient temperature for 15 min. After this time, the reaction mixture was re-cooled in the ice bath, treated with saturated aqueous ammonium chloride (50 mL), and extracted with ethyl acetate (2×50 mL). The combined organics were washed with saturated sodium bicarbonate (2×25 mL) and brine (25 mL), dried over sodium sulfate, filtered, and concentrated under reduced pressure. The crude residue was purified by column chromatography (silica gel, 0-10% methanol/methylene chloride) followed by reversed phase column chromatography (15 g C18 column, 10-100% acetonitrile/water) to provide (4R,4aS,7aR,12bS)-4α-hydroxy-9-methoxy-3-methyl-2,3,4,4a,5,7a-hexahydro-1H-4,12-methanobenzofuro[3,2-e]isoquinolin-7-yl oleate (169 mg, 24%) as a colorless oil. Approximately half of this material was dissolved in diethyl ether (1 mL) and treated with a 4.0 M solution of hydrogen chloride in 1,4-dioxane (0.3 mL). The solution was diluted with hexanes (5 mL) and concentrated under reduced pressure until a white precipitate formed. The solids were isolated by filtration, washed with diethyl ether, and dried under vacuum to provide (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl oleate hydrochloride (59 mg, 8%) as a white solid: $^1$H NMR (300 MHz, CDCl$_3$) δ 9.99 (s, 1H), 6.78 (d, J=8.4 Hz, 1H), 6.70 (d, J=8.1 Hz, 1H), 5.57 (apparent d, J=4.5 Hz, 1H), 5.40-5.30 (m, 2H), 5.05 (s, 1H), 4.35 (br s, 1H), 3.86 (s, 3H), 3.48 (d, J=10.2 Hz, 1H), 3.27-3.20 (m, 2H), 3.10-2.84 (m, 5H), 2.72-2.66 (m, 1H), 2.43 (t, J=7.2 Hz, 2H), 2.12 (d, J=17.7 Hz, 1H), 2.02-2.01 (m, 4H), 1.74-1.61 (m, 4H), 1.32-1.27 (m, 20H), 0.88 (t, J=6.6 Hz, 3H); ESI MS m/z 580 [C$_{36}$H$_{53}$NO$_5$+H]$^+$; HPLC (Method A) 98.9% (AUC), $t_R$=15.36 min.

Scheme 2: (S)-(4R, 4aS, 7aR, 12bS)-4a-Hydroxy-9-methoxy-3-methyl-2, 3, 4, 4a, 5, 7a-hexahydro-1H-4, 12-methanobenzofuro[3,2-e]isoquinolin-7-yl 2-hydroxy-2-phenylacetate

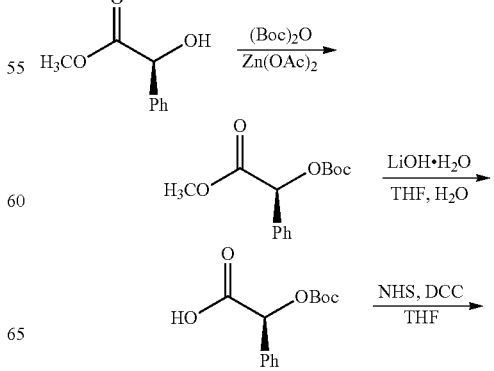

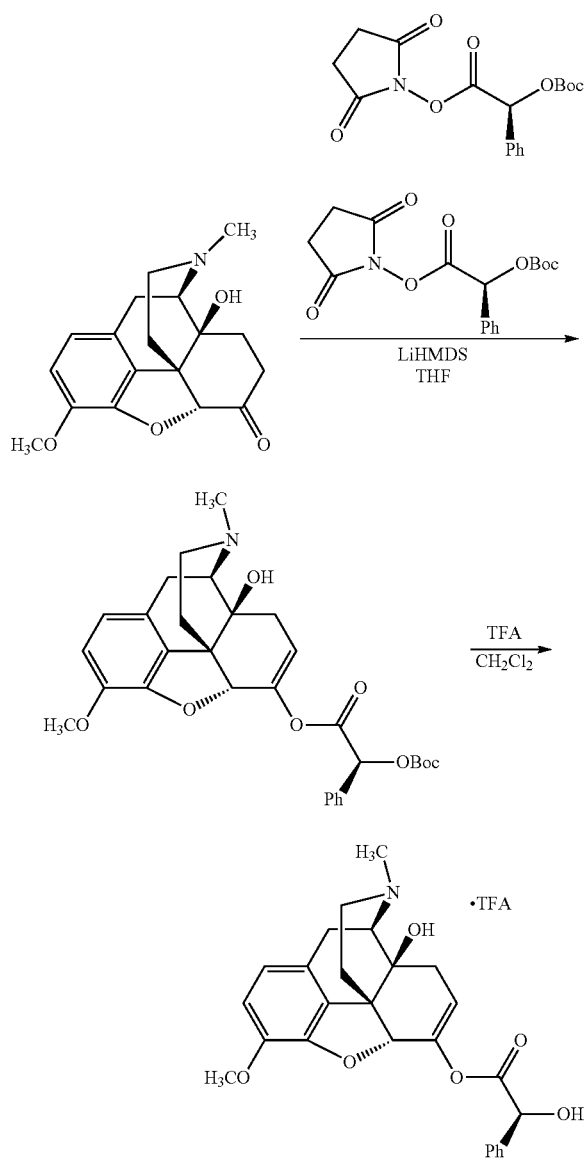

Preparation of (S)-Methyl 2-((tert-butoxycarbonyl)oxy)-2-phenylacetate

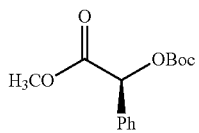

(S)-Methyl 2-hydroxy-2-phenylacetate (30.0 g, 180 mmol), di-tert-butyl dicarbonate (43.3 g, 198 mmol), and zinc acetate (3.96 g, 18.0 mmol) were combined and heated at 55° C. under a nitrogen atmosphere for 48 h. After this time, the reaction mixture was cooled to ambient temperature. The mixture was diluted with water (400 mL) and extracted with methylene chloride (3×200 mL). The combined organics were washed with brine (200 mL), dried over sodium sulfate, filtered, and concentrated under reduced pressure to provide (S)-methyl 2-((tert-butoxycarbonyl)oxy)-2-phenylacetate (39.2 g, 82%) as a colorless oil: $^1$H NMR (500 MHz, CDCl$_3$) δ 7.37-7.32 (m, 5H), 5.80 (s, 1H), 3.74 (s, 3H), 1.51 (s, 9H).

Preparation of (S)-2-((tert-Butoxycarbonyl)oxy)-2-phenylacetic acid

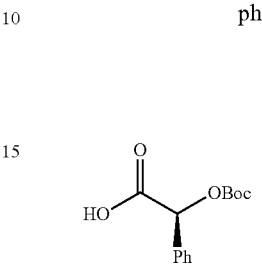

A solution of (S)-methyl 2-((tert-butoxycarbonyl)oxy)-2-phenylacetate (9.06 g, 34.0 mmol) in a mixture of tetrahydrofuran (106 mL) and water (53 mL) was treated with lithium hydroxide hydrate (4.30 g, 102 mmol) and stirred at ambient temperature for 3 h. After this time, the volatiles were removed under reduced pressure. The aqueous mixture was diluted with water (50 mL) and extracted with diethyl ether (100 mL). The aqueous layer was cooled in an ice bath, acidified to pH ~3 with 1 M hydrochloric acid, and extracted with ethyl acetate (3×100 mL). The combined organics were dried over sodium sulfate, filtered, and concentrated under reduced pressure to provide (S)-2-((tert-butoxycarbonyl)oxy)-2-phenylacetic acid (8.40 g, 98%) as a white solid: $^1$H NMR (500 MHz, CDCl$_3$) δ 7.50 (7.47 (m, 2H), 7.48-7.37 (m, 3H), 5.82 (s, 1H), 1.50 (s, 9H), CO$_2$H proton not observed.

Preparation of (S)-2,5-Dioxopyrrolidin-1-yl 2-((tert-butoxycarbonyl)oxy)-2-phenylacetate

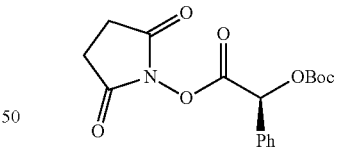

A solution of (S)-2-((tert-butoxycarbonyl)oxy)-2-phenylacetic acid (8.02 g, 31.8 mmol) in tetrahydrofuran (107 mL) was treated with N-hydroxysuccinimide (4.03 g, 35.0 mmol) and N,N'-dicyclohexylcarbodiimide (7.22 g, 16.4 mmol) and stirred under a nitrogen atmosphere for 3 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-2,5-dioxopyrrolidin-1-yl 2-((tert-butoxycarbonyl)oxy)-2-phenylacetate (8.20 g, 74%) as a white powder: $^1$H NMR (500 MHz, DMSO) δ 7.58-7.56 (m, 2H), 7.49-7.45 (m, 3H), 6.39 (s, 1H), 2.93-2.76 (m, 4H), 1.45 (s, 9H).

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((tert-butoxycabonyl)oxy)-2-phenylacetate

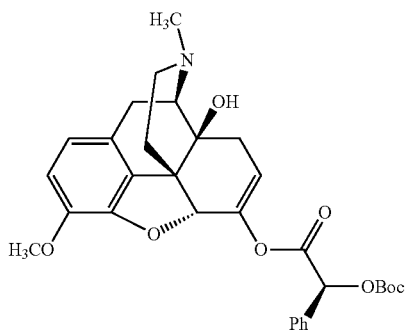

A suspension of oxycodone (0.200 g, 0.634 mmol) in tetrahydrofuran (6.5 mL) was cooled in an ice bath and treated dropwise with a 1.0 M solution of lithium bis(trimethylsilyl)amide in tetrahydrofuran (0.7 mL, 0.7 mmol). The mixture was stirred at 0° C. for 15 min and then treated dropwise with a solution of (S)-2,5-dioxopyrrolidin-1-yl 2-((tert-butoxycarbonyl)oxy)-2-phenylacetate (0.190 g, 0.661 mmol) in tetrahydrofuran (2 mL). The mixture was stirred at 0° C. for 1 h. After this time, the reaction mixture was treated with saturated aqueous ammonium chloride (50 mL) and extracted with ethyl acetate (3×75 mL). The combined organics were dried over sodium sulfate, filtered, and concentrated under reduced pressure. The crude residue was purified by column chromatography (silica gel, 0-5% methanol/methylene chloride) to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((tert-butoxycabonyl)oxy)-2-phenylacetate (0.100 g, 29%) as a colorless oil: ESI MS m/z 550 $[C_{31}H_{35}NO_8+H]^+$.

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-hydroxy-2-phenylacetate

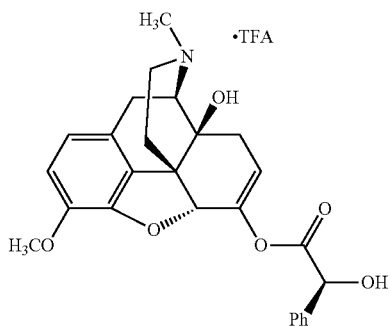 [SMILES: COc1ccc2c3c1O[C@H]1C(OC(=O)[C@@H](O)c4ccccc4)=CC[C@@]4(O)[C@@H](C2)N(C)CC[C@]314]

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((tert-butoxycabonyl)oxy)-2-phenylacetate (0.100 g, 0.182 mmol) in methylene chloride (2 mL) was treated with trifluoroacetic acid (2 mL) and stirred under a nitrogen atmosphere at ambient temperature for 1 h. After this time, the reaction mixture was concentrated under reduced pressure. The residue was triturated with diethyl ether to give a white powder. This material was purified by reversed phase column chromatography (50 g C18 column, 5-50% acetonitrile/water) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-hydroxy-2-phenylacetate 2,2,2-trifluoroacetate (41 mg, 50%) as a fluffy white solid: $^1$H NMR (300 MHz, DMSO-$d_6$) δ 9.14 (br s, 1H), 7.46-7.40 (m, 2H), 7.39-7.31 (m, 3H), 6.83 (d, J=8.4 Hz, 2H), 6.73 (d, J=8.1 Hz, 1H), 6.28-6.24 (m, 2H), 5.48-5.45 (m, 1H), 5.27 (d, J=5.7 Hz, 1H), 4.92 (s, 1H), 3.68 (s, 3H), 3.64-3.62 (m, 1H), 3.44-3.38 (m, 1H), 3.13-3.05 (m, 2H), 2.82 (br s, 3H), 2.27-2.19 (m, 1H), 2.09-2.03 (m, 1H), 1.61 (d, J=12.6 Hz, 1H); ESI MS m/z 450 $[C_{26}H_{27}NO_6+H]^+$; HPLC (Method A) 98.4% (AUC), $t_R$=8.62 min.

Scheme 3: (S)-2-Hydroxy-4-(((4R, 4aS, 7aR, 12bS)-4a-hydroxy-9-methoxy-3-methyl-2, 3, 4, 4a, 5, 7a-hexahydro-1H-4, 12-methanobenzofuro[3,2-e]isoquinolin-7-yl)oxy)-4-oxobutanoic acid hydrochloride

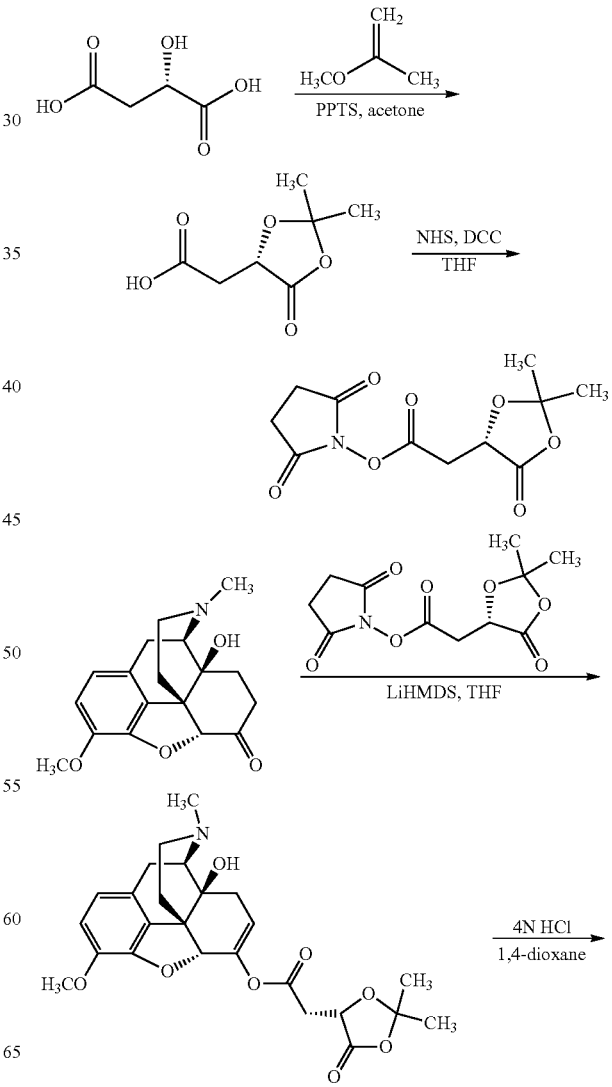

-continued

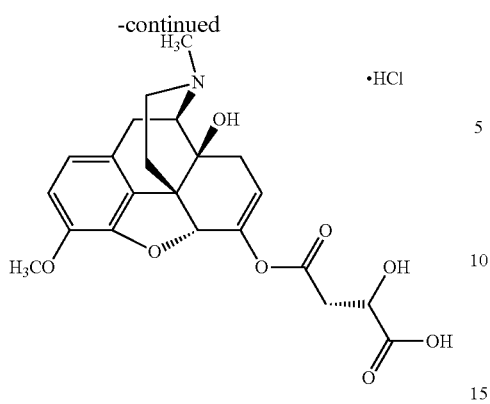

Preparation of (S)-2-(2,2-Dimethyl-5-oxo-1,3-dioxolan-4-yl)acetic acid

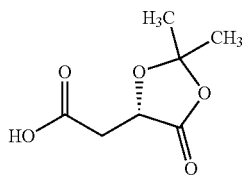

A solution of (S)-2-hydroxysuccinic acid (25.0 g, 186 mmol) and 2-methoxypropene (71.4 mL, 746 mmol) in acetone (400 mL) at 0° C. was slowly treated with pyridinium p-toluenesulfonate (4.68 g, 18.6 mmol). The reaction mixture was warmed to ambient temperature then heated at 35° C. for overnight. After this time, the volatiles were removed under reduced pressure. The residue was triturated in heptane/ethyl acetate (150 mL, 1:1) and filtered. The filtrate was diluted with ethyl acetate (300 mL) and washed with water (150 mL). The organic layer was dried over sodium sulfate, filtered and concentrated at reduced pressure to give (S)-2-(2,2-dimethyl-5-oxo-1,3-dioxolan-4-yl)acetic acid (27.9 g, 86%) as a light brown solid: $^1$H NMR (500 MHz, CDCl$_3$) δ 4.72 (apparent t, J=3.5 Hz, 1H), 3.00 (dd, J=17.0, 3.5 Hz, 1H), 2.56 (dd, J=17.0, 6.5 Hz, 1H), 1.57 (s, 3H), 1.50 (s, 3H).

Preparation of (S)-2,5-Dioxopyrrolidin-1-yl 2-(2,2-dimethyl-5-oxo-1,3-dioxolan-4-yl)aceate

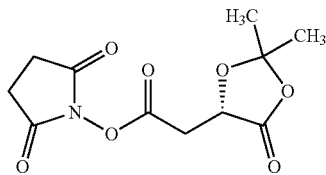 [SMILES: CC1(C)OC(=O)[C@H](CC(=O)ON2C(=O)CCC2=O)O1]

The combined organics were washed with brine (50 mL), dried over sodium sulfate, filtered, and concentrated under reduced pressure to provide (S)-methyl 2-((tert-butoxycarbonyl)oxy)propanoate (18.5 g, quantitative) as a colorless oil: $^1$H NMR (300 MHz, DMSO-d$_6$) δ 4.98 (apparent t, J=4.5 Hz, 1H), 3.34-3.32 (m, 2H), 2.81 (s, 4H), 1.55 (s, 3H), 1.53 (s, 3H).

Preparation of (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((S)-2,2-dimethyl-5-oxo-1,3-dioxolan-4-yl)acetate

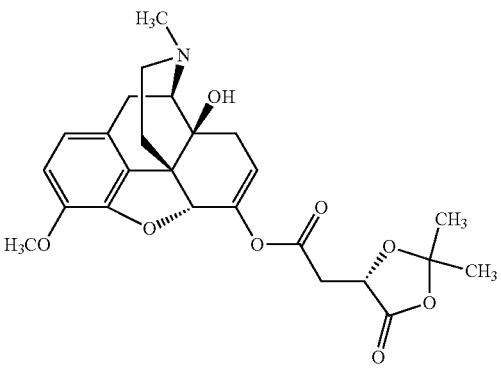 [SMILES: COc1ccc2c3c1O[C@H]1C(OC(=O)C[C@@H]4OC(C)(C)OC4=O)=CC[C@@]4(O)[C@@H](C2)N(C)CC[C@]314]

A suspension of oxycodone (0.500 g, 1.58 mmol) in tetrahydrofuran (10 mL) was cooled in an ice bath and treated dropwise with a 1.0 M solution of lithium bis(trimethylsilyl)amide in tetrahydrofuran (1.74 mL, 1.74 mmol). The reaction mixture was stirred at 0° C. for 15 min then was treated dropwise with a solution of (S)-2,5-dioxopyrrolidin-1-yl 2-(2,2-dimethyl-5-oxo-1,3-dioxolan-4-yl)acetate (0.473 g, 1.74 mmol) in tetrahydrofuran (5 mL). The reaction was stirred at 0° C. for 3 h. After this time, the reaction mixture was poured into saturated aqueous ammonium chloride (50 mL) and extracted with ethyl acetate (3×100 mL). The combined organics were dried over sodium sulfate, filtered, and concentrated under reduced pressure. The crude residue was purified by column chromatography (silica gel, 0-5% methanol/methylene chloride) to provide (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((S)-2,2-dimethyl-5-oxo-1,3-dioxolan-4-yl)acetate (0.390 g, 52%) as a light yellow oil: $^1$H NMR (300 MHz, CDCl$_3$) δ 6.72 (d, J=8.4 Hz, 1H), 6.62 (d, J=8.1 Hz, 1H), 5.69-5.66 (m, 1H), 4.99 (s, 1H), 4.74 (dd, J=6.9, 3.6 H, 1H), 3.85 (s, 3H), 3.17 (d, J=18.6 Hz, 1H), 3.08 (dd, J=17.1, 3.6 Hz, 1H), 2.94-2.86 (m, 2H), 2.68-2.60 (m, 2H), 2.50-2.43 (m, 1H), 2.39 (s, 3H), 2.34-2.24 (m, 2H), 2.18-2.14 (m, 2H), 1.62 (s, 3H), 1.56 (s, 3H), OH proton not observed; ESI MS m/z 472 [C$_{25}$H$_{29}$NO$_5$+H]$^+$.

Preparation (S)-2-Hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid hydrochloride

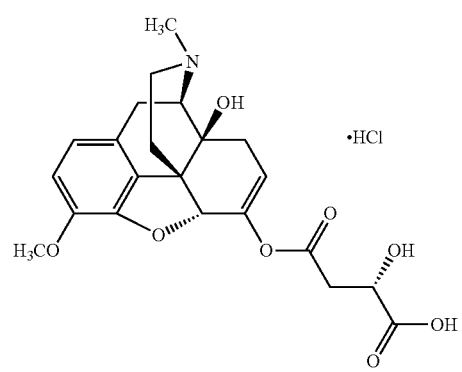 [SMILES: COc1ccc2c3c1O[C@H]1C(OC(=O)C[C@H](O)C(=O)O)=CC[C@@]4(O)[C@@H](C2)N(C)CC[C@]314 ; Cl]

A solution of (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((S)-2,2-dimethyl-5-oxo-1,3-dioxolan-4-yl)acetate (0.050 g, 0.11 mmol) in 1,4-dioxane (5 mL) was treated with 4 N hydrogen chloride in 1,4-dioxane (0.8 mL) and 4 drops of water. The reaction mixture was stirred at ambient temperature for 1 h. Additional 4 N hydrogen chloride in 1,4-dioxane (0.25 mL) and water (2 drops) were added and stirring continued for another 1 h. After this time, the reaction mixture was concentrated under reduced pressure. The residue was triturated with diethyl ether, filtered and dried under vacuum at ambient temperature for six days to provide (S)-2-hydroxy-4-(((4R,4aS,7aR, 12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid hydrochloride (41 mg, 89%) as an off-white solid: $^1$H NMR (300 MHz, DMSO-$d_6$) δ 12.7 (br s, 1H), 9.18 (br s, 1H), 6.82 (d, J=8.1 Hz, 1H), 6.75 (d, J=8.1 Hz, 1H), 6.29 (s, 1H), 5.62 (br s, 1H), 5.52 (d, J=4.5 Hz, 1H), 4.98 (s, 1H), 4.33 (br s, 1H), 3.76 (s, 3H), 3.57 (s, 3H), 3.15-3.06 (m, 2H), 2.89-2.84 (m, 4H), 2.73-2.63 (m, 1H), 2.29 (dd, J=6.3, 18.0 Hz, 1H), 2.33-2.25 (m, 1H), 1.63 (d, J=11.4 Hz, 1H); ESI MS m/z 432 $[C_{22}H_{25}NO_8+H]^+$.

Scheme 4: (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl stearate and (4R,4aS,7aR,12bS)-4a-Hydroxy-9-methoxy-3-methyl-2,3,4,4a,5,7a-hexahydro-1H-4, 12-methanobenzofuro[3,2-e]isoquinolin-7yl palmitate

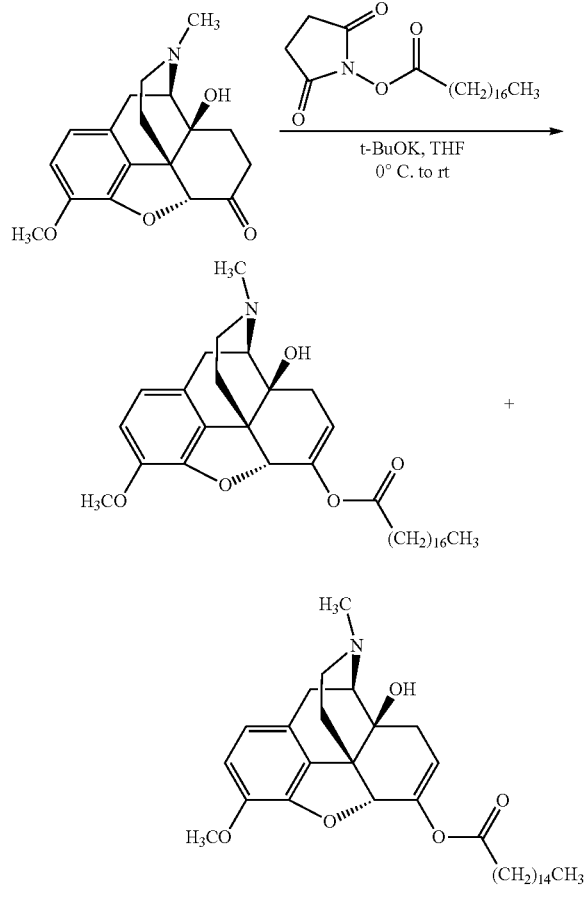

Preparation of (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl stearate and (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl palmitate

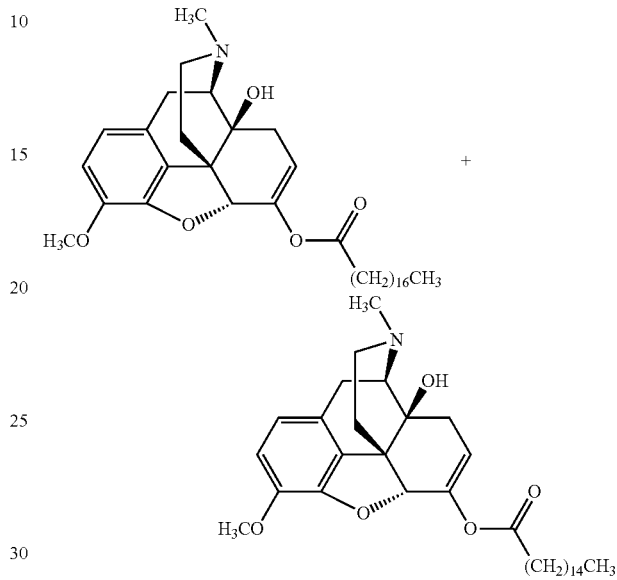

A suspension of oxycodone (478 mg, 1.52 mmol) in tetrahydrofuran (5 mL) was cooled in an ice bath and treated dropwise with a 1.0 M solution of potassium tert-butoxide in tetrahydrofuran (2.0 mL, 2.0 mmol). After addition was complete, the mixture was stirred at ambient temperature for 15 min. The mixture was re-cooled in the ice bath and treated dropwise with a solution of 2,5-dioxopyrrolidin-1-yl stearate (644 mg, 1.69 mmol) in tetrahydrofuran (5 mL) over 10 min. After addition was complete, the mixture was stirred at ambient temperature for 30 min. After this time, the reaction mixture was re-cooled in the ice bath, treated with saturated aqueous ammonium chloride (50 mL), and extracted with ethyl acetate (2×50 mL). The combined organics were dried over sodium sulfate, filtered, and concentrated under reduced pressure. The crude residue was purified by column chromatography (silica gel, 0-10% methanol/methyl tert-butyl ether) to provide material contaminated with stearic acid. This material was dissolved in methylene chloride (50 ml), washed with saturated sodium bicarbonate (2×25 mL) and brine (25 mL), dried over sodium sulfate, filtered, and concentrated under reduced pressure. This residue was purified by reversed phase column chromatography (50 g C18 column, 30-100% acetonitrile/water) to provide two compounds. Each compound was freeze dried to afford (4R,4aS,7aR,12bS)-4a-hydroxy-9-methoxy-3-methyl-2,3,4,4a,5, 7a-hexahydro-1H-4,12-methanobenzofuro[3,2-e]isoquinolin-7-yl stearate (92 mg, 10%) as a fluffy white solid: $^1$H NMR (300 MHz, CDCl$_3$) δ 6.71 (d, J=8.1 Hz, 1H), 6.62 (d, J=8.1 Hz, 1H), 5.57 (dd, J=4.8, 3.9 Hz, 1H), 5.01 (s, 1H), 4.72 (br s, 1H), 3.84 (s, 3H), 3.17 (d, J=18.6 Hz, 1H), 2.85 (d, J=6.3 Hz, 1H), 2.62 (dd, J=18.9, 6.6 Hz, 1H), 2.47-2.18 (m, 8H), 2.16-2.15 (m, 2H), 1.70-1.59 (m, 3H), 1.30-1.25 (m, 28H), 0.88 (t, J=6.3 Hz, 3H); ESI MS m/z 582 $[C_3H_{55}NO_5+H]^+$; HPLC (Method A) 97.9% (AUC), $t_R$=16.03 min; and (4R, 4aS, 7aR, 12bS)-4a- hydroxy-9-methoxy-3-methyl-2,3,4,4a,5,7a-hexahydro-1H-4,12-methanobenzofuro[3,2-e]isoquinolin-7-yl palmitate (105 mg, 12%) as a fluffy white solid: $^1$H NMR (300 MHz, CDCl$_3$) δ 6.71 (d, J=8.1 Hz, 1H), 6.62 (d, J=8.4 Hz, 1H), 5.57 (dd, J=4.5, 3.6 Hz, 1H), 5.01 (s, 1H), 3.84 (s, 3H), 3.17 (d, J=18.6 Hz, 1H), 2.85 (d, J=6.3 Hz, 1H), 2.62 (dd, J=18.6, 6.3 Hz, 1H), 2.47-2.35 (m, 6H), 2.322.22 (m, 2H), 2.16-2.15 (m, 2H), 1.68-1.59 (m, 3H), 1.30-1.25 (m, 24H), 0.88 (t, J=6.3 Hz, 3H), OH proton not observed; ESI MS m/z 554 [C$_{34}$H$_{51}$NO$_5$=H]$^+$; HPLC (Method A) 96.9% (AUC), t$_R$=15.20 min.

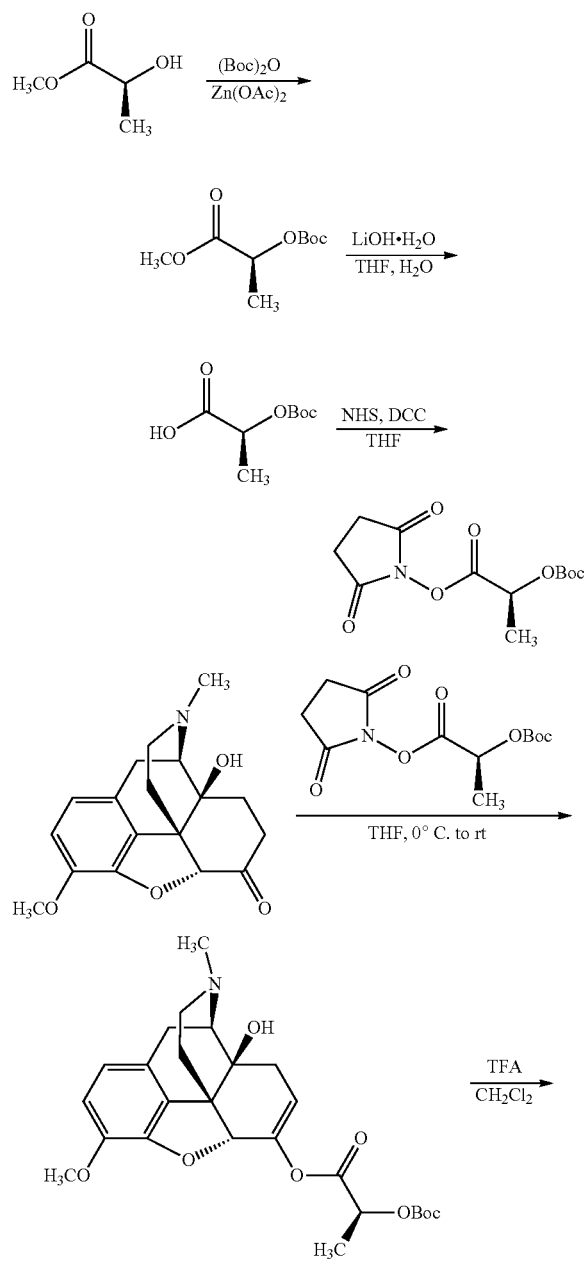

Scheme 5: (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-hydroxypropanoate trifluoroacetic acid salt

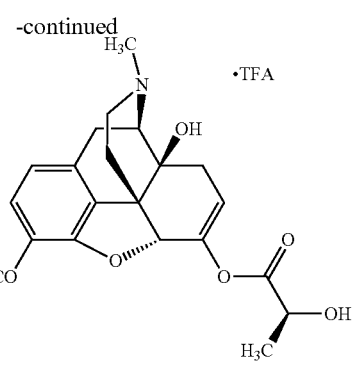

Preparation of (S)-Methyl 2-((tert-butoxycarbonyl)oxy)propanoate (S)-Methyl 2-hydroxypropanoate (5.01 g, 48.2 mmol), di-tert-butyl dicarbonate (11.63 g, 53.29 mmol), and zinc acetate (1.05 g, 4.78 mmol) were combined and heated at 55° C. under a nitrogen atmosphere for 48 h. After this time, the reaction mixture was cooled to room temperature. The mixture was diluted with water (50 mL) and extracted with methylene chloride (2×50 mL). The combined organics were washed with brine (50 mL), dried over sodium sulfate, filtered, and concentrated under reduced pressure to provide (S)-methyl 2-((tert-butoxycarbonyl)oxy)propanoate (8.03 g, 82%) as a colorless oil: $^1$H NMR (500 MHz, CDCl$_3$) δ 4.96 (q, J=7.0 Hz, 1H), 3.77 (s, 3H), 1.52 (d, J=6.5 Hz, 3H), 1.50 (s, 9H).

Preparation of (S)-2-((tert-Butoxycarbonyl)oxy)propanoic acid

A solution of (S)-methyl 2-((tert-butoxycarbonyl)oxy)propanoate (7.00 g, 34.3 mmol) in tetrahydrofuran (100 mL) and water (50 mL) was treated with lithium hydroxide hydrate (1.45 g, 34.5 mmol) and stirred at ambient temperature for 16 h. After this time, the volatiles were removed under reduced pressure. The aqueous mixture was diluted with water (50 mL) and extracted with diethyl ether (100 mL). The aqueous layer was cooled in an ice bath, acidified to pH ~3 with 0.5 M hydrochloric acid, and extracted with diethyl ether (3×100 mL). The combined organics were dried over sodium sulfate, filtered, and concentrated under reduced pressure to provide of (S)-2-((tert-butoxycarbonyl)oxy)propanoic acid (2.83 g, 43%) as a white solid: $^1$H NMR (500 MHz, CDCl$_3$) δ 4.99 (q, J=7.0 Hz, 1H), 1.56 (d, J=7.5 Hz, 3H), 1.50 (s, 9H).

Preparation of (S)-2,5-Dioxopyrrolidin-1-yl 2-((tert-butoxycarbonyl)oxy)propanoate

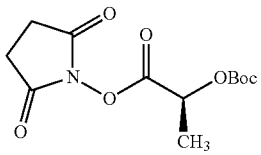

A solution of (S)-2-((tert-butoxycarbonyl)oxy)propanoic acid (2.83 g, 14.9 mmol) in tetrahydrofuran (50 mL) was treated with N-hydroxysuccinimide (1.88 g, 16.3 mmol) and N,N'-dicyclohexylcarbodiimide (3.38 g, 16.4 mmol) and stirred under a nitrogen atmosphere for 3 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-2,5-dioxopyrrolidin-1-yl 2-((tert-butoxycarbonyl)oxy)propanoate (3.54 g, 83%) as a white powder: $^1$H NMR (500 MHz, CDCl$_3$) δ 5.24 (q, J=7.0 Hz, 1H), 2.84 (s, 4H), 1.69 (d, J=7.0 Hz, 3H), 1.51 (s, 9H).

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((tert-butoxycarbonyl)oxy)propanoate

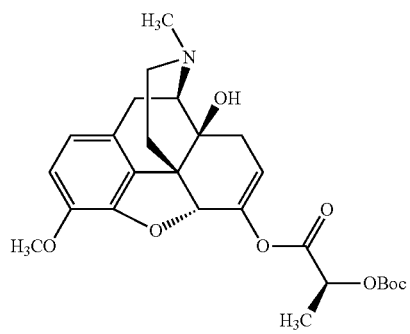

A suspension of oxycodone (201 mg, 0.637 mmol) in tetrahydrofuran (3 mL) was cooled in an ice bath and treated dropwise with a 1.0 M solution of potassium tert-butoxide in tetrahydrofuran (0.7 mL, 0.7 mmol). After addition was complete, the mixture was stirred at ambient temperature for 15 min. The mixture was re-cooled in the ice bath and treated dropwise with a solution of (S)-2,5-dioxopyrrolidin-1-yl 2-((tert-butoxycarbonyl)oxy)propanoate (190 mg, 0.661 mmol) in tetrahydrofuran (2 mL). After addition was complete, the mixture was stirred at ambient temperature for 15 min. After this time, the reaction mixture was treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (silica gel, 0-5% methanol/methylene chloride) to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((tert-butoxycarbonyl)oxy)propanoate (156 mg, 50%) as a colorless residue: $^1$H NMR (300 MHz, CDCl$_3$) δ 6.71 (d, J=8.1 Hz, 1H), 6.61 (d, J=8.4 Hz, 1H), 5.66 (dd, J=5.1, 3.3 Hz, 1H), 5.07-4.99 (m, 2H), 3.84 (s, 3H), 3.17 (d, J=18.6 Hz, 1H), 2.85 (d, J=6.3 Hz, 1H), 2.63 (dd, J=18.6, 6.6 Hz, 1H), 2.47-2.35 (m, 1H), 2.38 (s, 3H), 2.31-2.22 (m, 2H), 2.18-2.16 (2H), 1.63-1.69 (m, 1H), 1.60 (d, J=7.2 Hz, 3H), 1.50 (s, 9H); ESI MS m/z 488 [C$_{26}$H$_{33}$NO$_8$+H]$^+$.

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-hydroxypropanoate trifluoroacetic acid salt

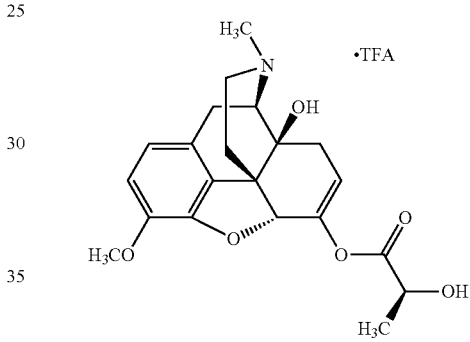

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((tert-butoxycarbonyl)oxy)propanoate (71 mg, 0.15 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. The residue was triturated with diethyl ether to give a white powder. This material was purified by reversed phase column chromatography (15 g C18 column, 10-100% acetonitrile/water) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-hydroxypropanoate trifluoroacetic acid salt (36 mg, 51%) as a fluffy white solid: $^1$H NMR (300 MHz, DMSO-d$_6$) δ 9.18 (s, 1H), 6.86 (d, J=8.1 Hz, 1H), 6.75 (d, J=8.4 Hz, 1H), 6.30 (s, 1H), 5.60 (d, J=6.0 Hz, 1H), 5.54 (dd, J=6.0, 2.1 Hz, 1H), 5.00 (s, 1H), 4.33-4.24 (m, 1H), 3.75 (s, 3H), 3.64 (d, J=6.6 Hz, 1H), 3.43 (d, J=19.8 Hz, 1H), 3.11 (dd, J=18.9, 6.6 Hz, 2H), 2.84 (d, J=3.9 Hz, 3H), 2.69-2.57 (m, 1H), 2.49-2.41 (m, 1H), 2.32-2.24 (m, 1H), 2.07 (d, J=17.7 Hz, 1H), 1.64 (d, J=11.7 Hz, 1H), 1.35 (d, J=6.9 Hz, 3H); ESI MS m/z 388 [C$_{21}$H$_{25}$NO$_6$+H]$^+$; HPLC (Method A) 98.3% (AUC), t$_R$=7.32 min.

Scheme 6: (S)-(4R,4aS,7aR,12bS)-4a-Hydroxy-9-methoxy-3-methyl-2,3,4,4a,5,7a-hexahydro-1H-4, 12-methanobenzofuro[3,2-e]isoquinolin-7-yl 2-(((S)-2-aminopropanoyl)oxy)propanoate hydrochloride

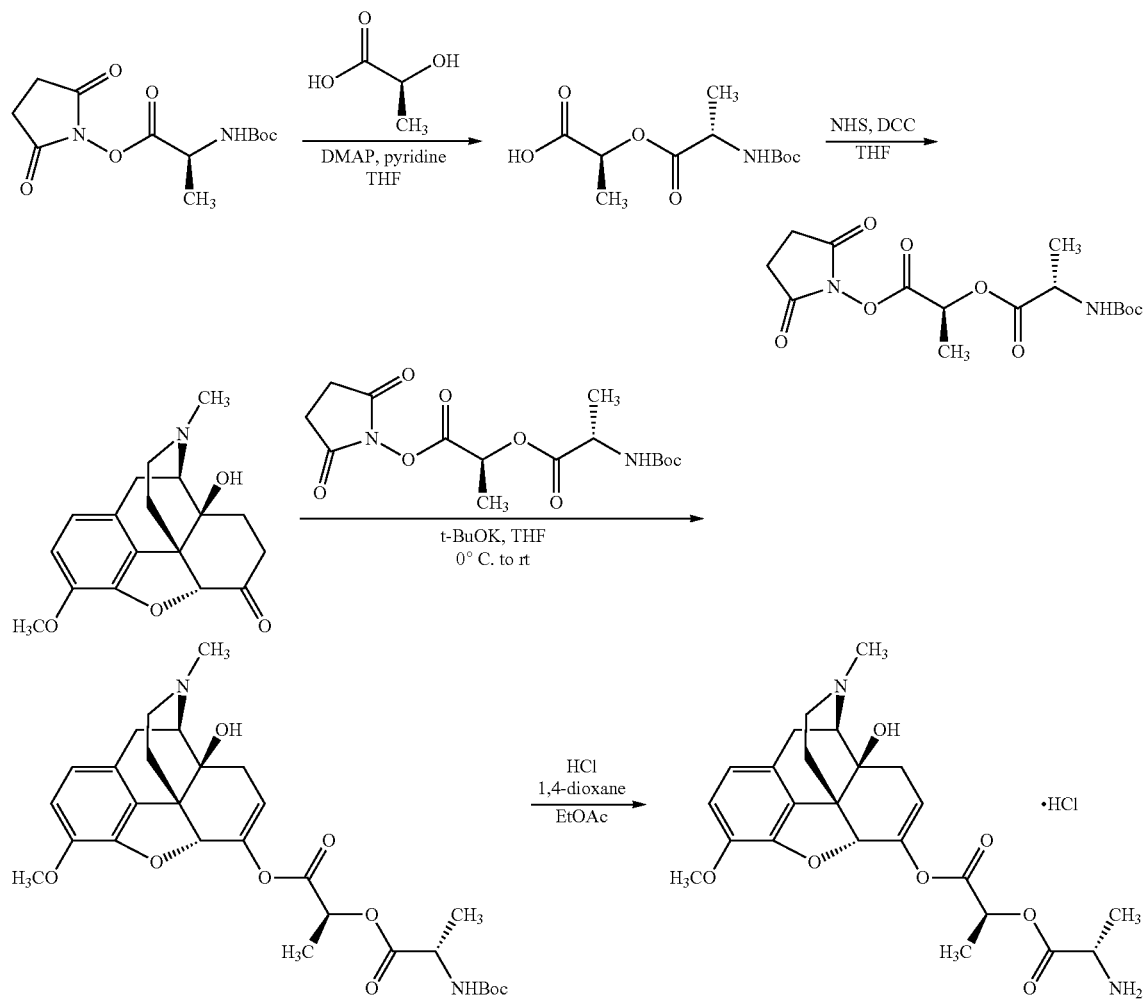

Preparation of (S)-2-(((S)-2-((tert-Butoxycarbonyl)amino)propanoyl)oxy)propanoic acid

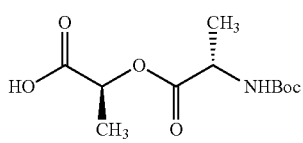

A solution of (S)-2,5-dioxopyrrolidin-1-yl 2-((tert-butoxycarbonyl)amino)propanoate (1.00 g, 3.49 mmol), lactic acid (391 mg, 4.34 mmol), and 4-dimethylaminopyridine (51 mg, 0.42 mmol) in tetrahydrofuran (17 mL) was treated with pyridine (0.33 g, 4.2 mmol) and heated at 50° C. under a nitrogen atmosphere for 17 h. After this time, the reaction mixture was cooled to room temperature and concentrated under reduced pressure. The residue was dissolved in ethyl acetate (50 mL) and washed with aqueous 10% citric acid (2×25 mL) and water (25 mL). The organic layer was extracted with saturated aqueous sodium bicarbonate (2×25 mL). The combined aqueous bicarbonate layers were acidified to pH ~2 with 6 N hydrochloric acid and extracted with ethyl acetate (4×25 mL). The combined organics were dried over sodium sulfate, filtered, and concentrated under reduced pressure to provide (S)-2-(((S)-2-((tert-butoxycarbonyl)amino)propanoyl)oxy)propanoic acid (862 mg, 95%) as a colorless oil: $^1$H NMR (300 MHz, CDCl$_3$) δ 5.23-5.17 (m, 1H), 5.03-5.01 (m, 1H), 4.38-4.33 (m, 1H), 1.56 (d, J=7.2 Hz, 3H), 1.45-1.44 (m, 12H), CO$_2$H proton not observed; ESIMS m/z 260 [C$_{11}$H$_{19}$NO$_6$–H]$^-$.

Preparation of (S)-2,5-Dioxopyrrolidin-1-yl 2-(((S)-2-((tert-butoxycarbonyl)amino)propanoyl)oxy)propanoate

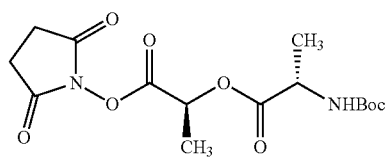 [SMILES: C[C@H](NC(=O)OC(C)(C)C)C(=O)O[C@@H](C)C(=O)ON1C(=O)CCC1=O]

A solution of (S)-2-(((S)-2-((tert-butoxycarbonyl)amino)propanoyl)oxy)propanoic acid (820 mg, 3.14 mmol) in tetrahydrofuran (10 mL) was treated with N-hydroxysuccinimide (401 mg, 3.48 mmol) and N,N'-dicyclohexylcarbodiimide (717 mg, 3.48 mmol) and stirred under a nitrogen atmosphere for 2 h. After this time, the reaction mixture was filtered to remove the solid dicyclohexylurea byproduct. The solid was washed with diethyl ether, and the combined filtrate and washings were concentrated under reduced pressure to provide (S)-2,5-dioxopyrrolidin-1-yl 2-(((S)-2-((tert-butoxycarbonyl)amino)propanoyl)oxy)propanoate (1.15 g, quantitative) as a colorless crushable foam: $^1$H NMR (300 MHz, CDCl$_3$) δ 5.52-5.43 (m, 1H), 5.02-5.00 (m, 1H), 4.42-4.33 (m, 1H), 2.84 (br s, 4H), 1.71 (d, J=7.2 Hz, 3H), 1.46-1.44 (m, 12H).

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(((S)-2-((tert-butoxycarbonyl)amino)propanoyl)oxy)propanoate

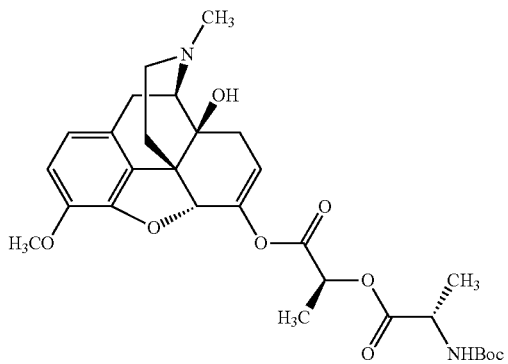 [SMILES: COc1ccc2c3c1O[C@H]1C(OC(=O)[C@H](C)OC(=O)[C@H](C)NC(=O)OC(C)(C)C)=CC[C@@]4(O)[C@@H](C2)N(C)CC[C@]314]

A suspension of oxycodone (480 mg, 1.52 mmol) in tetrahydrofuran (5 mL) was cooled in an ice bath and treated dropwise with a 1.0 M solution of potassium tert-butoxide in tetrahydrofuran (1.8 mL, 1.8 mmol). After addition was complete, the mixture was stirred at ambient temperature for 30 min. The mixture was re-cooled in the ice bath and treated dropwise with a solution of (S)-2,5-dioxopyrrolidin-1-yl 2-(((S)-2-((tert-butoxycarbonyl)amino)propanoyl)oxy)propanoate (601 mg, 1.68 mmol) in tetrahydrofuran (5 mL). After addition was complete, the mixture was stirred at ambient temperature for 15 min. After this time, the reaction mixture was re-cooled in the ice bath and treated with saturated aqueous ammonium chloride (25 mL) and extracted with ethyl acetate (2×50 mL). The combined organics were washed with saturated sodium bicarbonate (25 mL), dried over sodium sulfate, filtered, and concentrated under reduced pressure. The crude residue was purified by column chromatography (silica gel, 0-10% methanol/methylene chloride) followed by reversed phase column chromatography (50 g C18 column, 10-100% acetonitrile/water) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(((S)-2-((tert-butoxycarbonyl)amino)propanoyl)oxy)propanoate (68 mg, 8%) as a fluffy white solid: ESI MS m/z 559 [C$_{29}$H$_{38}$N$_2$O$_9$+H]$^+$.

Preparation of (S)-(4R,4aS,7aR,12bS)-4a-Hydroxy-9-methoxy-3-methyl-2,3,4,4a,5,7a-hexahydro-H-4,12-methanobenzofuro[3,2-e]isoquinolin-7-yl 2-(((S)-2-aminopropanoyl)oxy)propanoate hydrochloride

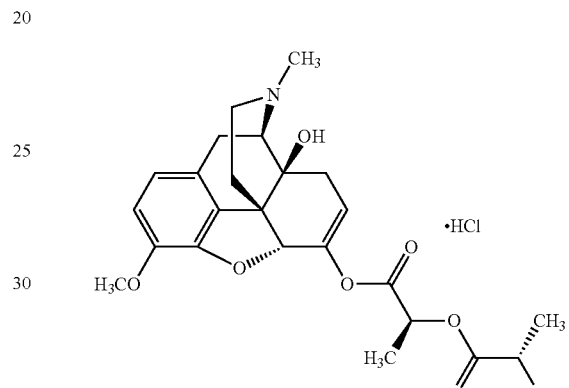

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(((S)-2-((tert-butoxycarbonyl)amino)propanoyl)oxy)propanoate (67 mg, 0.12 mmol) in ethyl acetate (1 mL) was treated with a 4.0 M solution of hydrogen chloride in 1,4-dioxane (1 mL) and stirred under a nitrogen atmosphere at ambient temperature for 3.5 h. After this time, the reaction mixture was diluted with diethyl ether (5 mL). The resulting precipitate was isolated by filtration, washed with diethyl ether (5 mL), and freeze-dried from acetonitrile/water to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(((S)-2-aminopropanoyl)oxy)propanoate hydrochloride (47 mg, 74%) as a fluffy white solid: $^1$H NMR (300 MHz, DMSO-d$_6$) δ 9.23 (br s, 1H), 8.48 (s, 3H), 6.87 (d, J=8.4 Hz, 1H), 6.76 (d, J=8.1 Hz, 1H), 6.36 (s, 1H), 5.61 (dd, J=6.0, 1.8 Hz, 1H), 5.35 (q, J=6.9 Hz, 1H), 5.01 (s, 1H), 4.24-4.22 (m, 1H), 3.76 (s, 3H), 3.69 (d, J=6.0 Hz, 1H), 3.43 (d, J=20.1 Hz, 1H), 3.12 (dd, J=19.2, 6.9 Hz, 1H), 2.85 (s, 3H), 2.64-2.57 (m, 1H), 2.49-2.27 (m, 2H, partially obscured by solvent peak), 2.06 (apparent d, J=18.0 Hz, 1H), 1.63 (d, J=11.1 Hz, 1H), 1.56 (d, J=6.9 Hz, 3H), 1.48 (d, J=7.2 Hz, 3H); ESI MS m/z 459 [C$_{24}$H$_{30}$N$_2$O$_7$+H]$^+$; HPLC (Method A) 95.1% (AUC), t$_R$=6.98 min.

Scheme 7: (S)-(4R,4aS,7aR,12bS)-4a-Hydroxy-9-methoxy-3-methyl-2,3,4,4a,5,7a-hexahydro-1H-4, 12-methanobenzofuro[3,2-e]isoquinolin-7-yl 2-(((S)-2-hydroxypropanoyl)oxy)propanoate trifluoroacetic acid salt

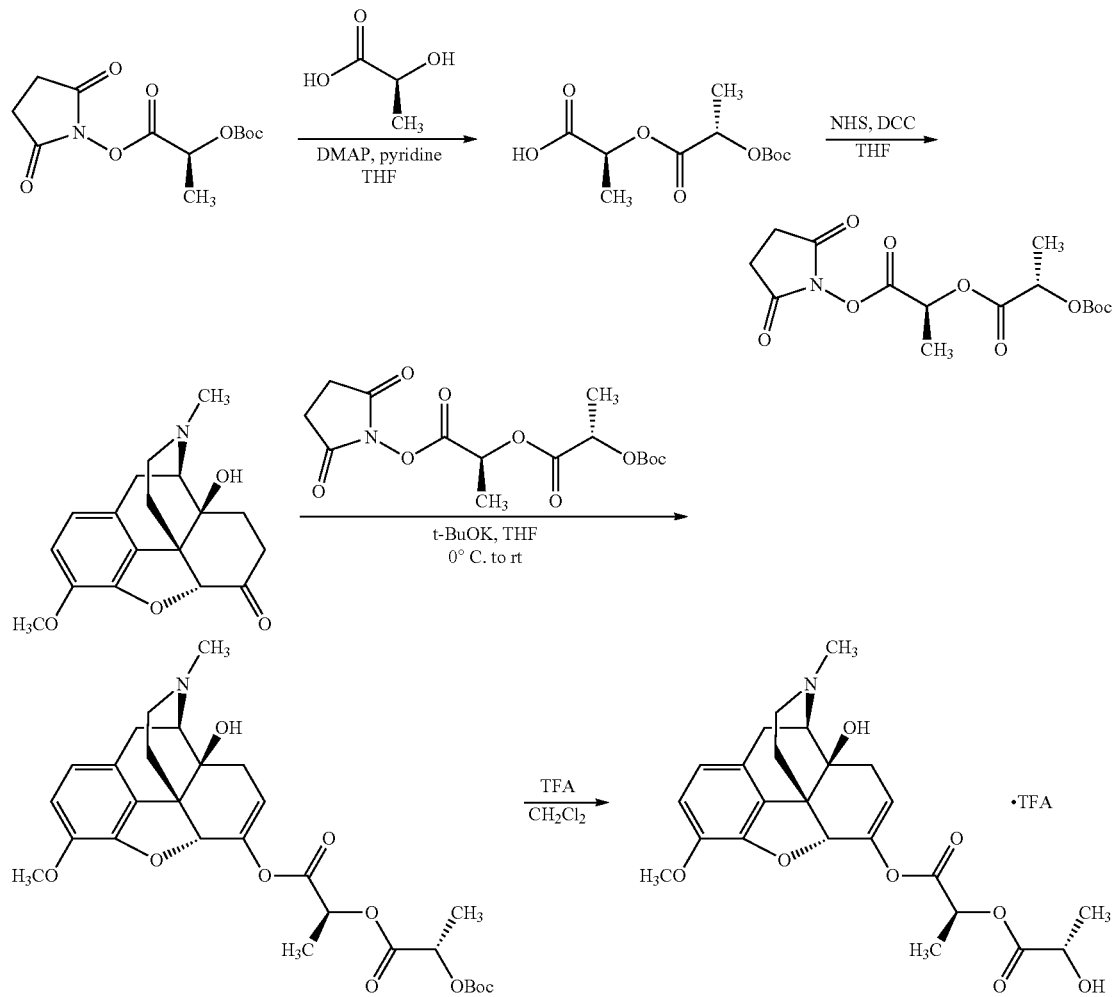

Preparation of (S)-2-(((S)-2-((tert-Butoxycarbonyl)oxy)propanoyl)oxy)propanoic acid

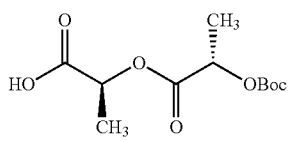

A solution of (S)-2,5-dioxopyrrolidin-1-yl 2-((tert-butoxycarbonyl)oxy)propanoate (1.00 g, 3.48 mmol), lactic acid (376 mg, 4.17 mmol), and 4-dimethylaminopyridine (53 mg, 0.43 mmol) in tetrahydrofuran (17 mL) was treated with pyridine (0.33 g, 4.2 mmol) and heated at 50° C. under a nitrogen atmosphere for 48 h. After this time, the reaction mixture was cooled to room temperature and concentrated under reduced pressure. The residue was dissolved in ethyl acetate (50 mL) and washed with aqueous 10% citric acid (2×25 mL) and water (25 mL). The organic layer was extracted with saturated aqueous sodium bicarbonate (2×25 mL). The combined aqueous bicarbonate layers were acidified to pH ~2 with 6 N hydrochloric acid and extracted with ethyl acetate (4×25 mL). The combined organics were dried over sodium sulfate, filtered, and concentrated under reduced pressure to provide (S)-2-(((S)-2-((tert-butoxycarbonyl)oxy)propanoyl)oxy)propanoic acid (659 mg, 72%) as a colorless oil: $^1$H NMR (300 MHz, CDCl$_3$) δ 5.27-5.17 (m, 1H), 4.98 (q, J=7.2 Hz, 1H), 1.60-1.55 (m, 6H), 1.50 (s, 9H), CO$_2$H proton not observed; ESI MS m/z 261 [C$_{11}$H$_{18}$O$_7$–H]$^-$.

Preparation of (S)-2,5-Dioxopyrrolidin-1-yl 2-(((S)-2-((tert-butoxycarbonyl)oxy)propanoyl)oxy)propanoate

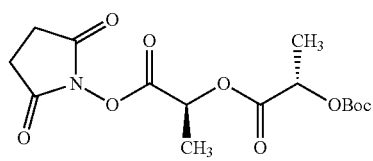

A solution of (S)-2-(((S)-2-((tert-butoxycarbonnyl)oxy)propanoic acid (659 mg, 2.51 mmol) in tetrahydrofuran (10 mL) was treated with N-hydroxysuccinimide (323 mg, 2.81 mmol) and N,N'-dicydohexylcarbodiimide (573 mg, 2.78 mmol) and stirred under a nitrogen atmosphere for 3 h. After this time, the reaction mixture was filtered to remove the solid dicyclohexylurea byproduct. The solid was washed with diethyl ether, and the combined filtrate and washings were concentrated under reduced pressure to provide (S)-2,5-dioxopyrrolidin-1-yl 2-(((S)-2-((tert-butoxycarbonyl)oxy)propanoyl)oxy)propanoate (813 g, 90%) as an off-white solid: $^1$H NMR (300 MHz, CDCl$_3$) δ 5.57-5.47 (m, 1H), 5.02-4.94 (m, 1H), 2.84 (br s, 4H), 1.73-1.69 (m, 3H), 1.60-1.55 (m, 3H), 1.49 (s, 9H).

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(((S)-2-((tert-butoxycarbonyl)oxy)propanoyl)oxy)propanoate

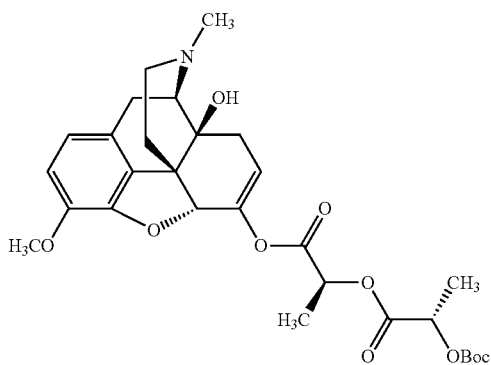

A suspension of oxycodone (602 mg, 1.91 mmol) in tetrahydrofuran (6 mL) was cooled in an ice bath and treated dropwise with a 1.0 M solution of potassium tert-butoxide in tetrahydrofuran (2.3 mL, 2.3 mmol). After addition was complete, the mixture was stirred at ambient temperature for 15 min. The mixture was re-cooled in the ice bath and treated dropwise with a solution of (S)-2,5-dioxopyrrolidin-1-yl 2-(((S)-2-((tert-butoxycarbonyl)oxy)propanoyl)oxy)propanoate (813 mg, 2.26 mmol) in tetrahydrofuran (6 mL). After addition was complete, the mixture was stirred at ambient temperature for 15 min. After this time, the reaction mixture was re-cooled in the ice bath and treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (silica gel, 0-10% methanol/methylene chloride) followed by reversed phase column chromatography (50 g C18 column, 10-100% acetonitrile/water) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(((S)-2-((tert-butoxycarbonyl)oxy)propanoyl)oxy)propanoate (98 mg, 9%) as a fluffy white solid: ESI MS m/z 560 [C$_{29}$H$_{37}$NO$_{10}$+H]$^+$.

Preparation of (S)-(4R,4aS,7aR,12bS)-4a-Hydroxy-9-methoxy-3-methyl-2,3,4,4a,5,7a-hexahydro-H-4,12-methanobenzofuro[3,2-e]isoquinolin-7-yl 2-(((S)-2-hydroxypropanoyl)oxy)propanoate trifluoroacetic acid salt

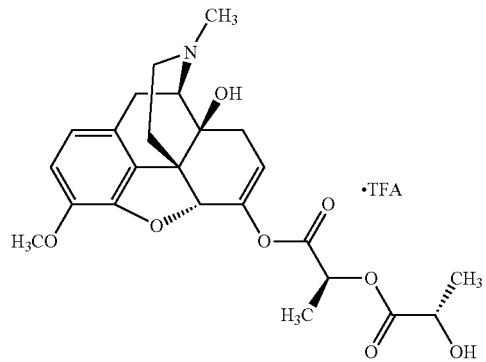 [SMILES: COc1ccc2c3c1O[C@H]1C(OC(=O)[C@H](C)OC(=O)[C@H](C)O)=CC[C@@]4(O)[C@@H](C2)N(C)CC[C@]314]

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(((S)-2-((tert-butoxycarbonyl)oxy)propanoyl)oxy)propanoate (94 mg, 0.17 mmol) in methylene chloride (2 mL) was treated with trifluoroacetic acid (1 mL) and stirred under a nitrogen atmosphere at ambient temperature for 1 h. After this time, the reaction mixture was concentrated under reduced pressure. The residue was purified by reversed phase column chromatography (C18 column, 10-100% acetonitrile/water) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(((S)-2-hydroxypropanoyl)oxy)propanoate trifluoroacetic acid salt (51 mg, 54%) as a fluffy white solid: $^1$H NMR (300 MHz, DMSO-d$_6$) δ 9.18 (br s, 1H), 6.86 (d, J=8.1 Hz, 1H), 6.75 (d, J=8.4 Hz, 1H), 6.30 (s, 1H), 5.59 (dd, J=5.7, 1.8 Hz, 1H), 5.50 (br s, 1H), 5.17 (q, J=6.9 Hz, 1H), 5.00 (s, 1H), 4.25-4.22 (m, 1H), 3.75 (s, 3H), 3.65 (d, J=6.0 Hz, 1H), 3.46-3.38 (m, 1H, partially obscured by water peak), 3.16-3.07 (m, 2H), 2.84 (apparent d, J=5.1 Hz, 3H), 2.69-2.57 (m, 1H), 2.49-2.26 (m, 2H, partially obscured by solvent peak), 2.07 (apparent d, J=18.0 Hz, 1H), 1.65 (d, J=11.4 Hz, 1H), 1.51 (d, J=11.4 Hz, 3H), 1.31 (d, J=6.6 Hz, 3H); ESI MS m/z 460 [C$_{24}$H$_{29}$NO$_8$+H]$^+$.

Scheme 8: (2E,4E)-(4R,4aS,7aR,12bS)-4a-Hydroxy-9-methoxy-3-methyl-2,3,4,4a,5,7a-hexahydro-1H-4, 12-methanobenzofuro[3,2-e]isoquinolin-7-yl hexa-2,4-dienoate

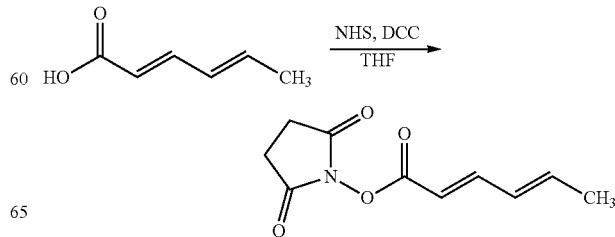

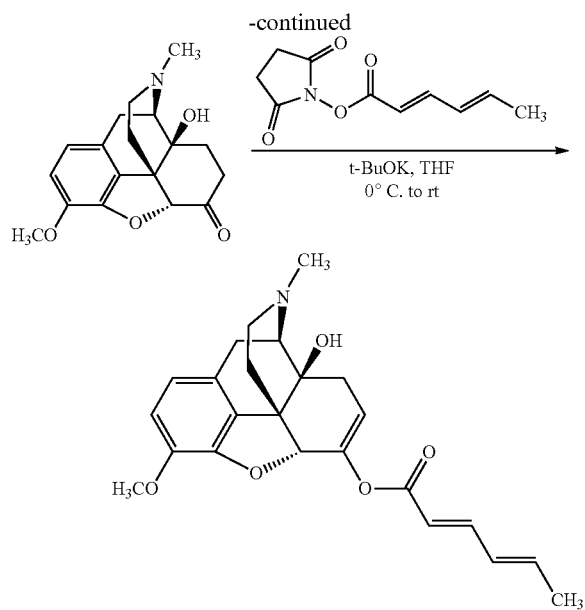

Preparation of (2E,4E)-2,5-Dioxopyrrolidin-1-yl hexa-2,4-dienoate

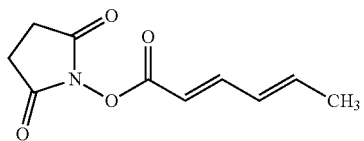

A solution of (2E,4E)-hexa-2,4-dienoic acid (2.00 g, 17.8 mmol) in tetrahydrofuran (50 mL) was treated with N-hydroxysuccinimide (2.26 g, 19.6 mmol) and N,N'-dicyclohexylcarbodiimide (4.04 g, 19.6 mmol) and stirred under a nitrogen atmosphere for 2.5 h. After this time, the reaction mixture was filtered to remove the solid dicyclohexylurea byproduct. The solid was washed with diethyl ether, and the combined filtrate and washings were concentrated under reduced pressure to provide (2E,4E)-2,5-dioxopyrrolidin-1-yl hexa-2,4-dienoate (5.14 g, quantitative) as a white solid: $^1$H NMR (300 MHz, CDCl$_3$) δ 7.53-5.44 (m, 1H), 6.31-6.27 (m, 2H), 5.93 (d, J=15.3 Hz, 1H), 2.85 (s, 4H), 1.91 (d, J=5.4 Hz, 3H).

Preparation of (2E,4E)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl hexa-2,4-dienoate

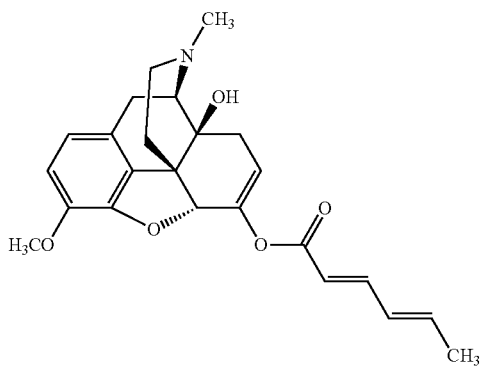 [SMILES: C/C=C/C=C/C(=O)OC1=CC[C@@]2(O)[C@H]3Cc4ccc(OC)c5c4[C@@]2(CCN3C)[C@H]1O5]

A suspension of oxycodone (487 mg, 1.54 mmol) in tetrahydrofuran (5 mL) was cooled in an ice bath and treated dropwise with a 1.0 M solution of potassium tert-butoxide in tetrahydrofuran (1.9 mL, 1.9 mmol). After addition was complete, the mixture was stirred at ambient temperature for 10 min. The mixture was re-cooled in the ice bath and treated dropwise with a solution of (2E,4E)-2,5-dioxopyrrolidin-1-yl hexa-2,4-dienoate (391 mg, 1.87 mmol) in tetrahydrofuran (5 mL). After addition was complete, the mixture was stirred at ambient temperature for 15 min. After this time, the reaction mixture was re-cooled in the ice bath and treated with saturated aqueous ammonium chloride (50 mL) and extracted with ethyl acetate (2×50 mL). The combined organics were washed with saturated sodium bicarbonate (25 mL) and brine (25 mL), dried over sodium sulfate, filtered, and concentrated under reduced pressure. The crude residue was purified by column chromatography (silica gel, 0-10% methanol/methylene chloride) followed by reversed phase column chromatography (50 g C18 column, 10-100% acetonitrile/water) and freeze dried to provide (2E,4E)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl hexa-2,4-dienoate (69 mg, 11%) as a fluffy white solid: $^1$H NMR (300 MHz, CDCl$_3$) δ 7.35-7.26 (m, 1H), 6.71 (d, J=8.4 Hz, 1H), 6.62 (d, J=8.1 Hz, 1H), 6.26-6.10 (m, 2H), 5.85 (d, J=15.3 Hz, 1H), 5.64 (overlapping dd, J=3.9 Hz, 1H), 5.06 (s, 1H), 4.72 (br s, 1H), 3.84 (s, 3H), 3.18 (d, J=18.6 Hz, 1H), 2.86 (d, J=6.3 Hz, 1H), 2.63 (dd, J=18.6, 6.3 Hz, 1H), 2.47-2.42 (m, 1H), 2.38 (s, 3H), 2.33-2.19 (m, 2H), 2.18-2.16 (m, 2H), 1.87 (d, J=5.4 Hz, 3H), 1.63 (dd, J=13.5, 3.0 Hz, 1H);ESI MS m/z 410 [C$_{24}$H$_{27}$NO$_5$+H]$^+$; HPLC (Method A)>99% (AUC), t$_R$=9.74 min.

Scheme 9: (S)-3-Hydroxy-4-(((4R, 4aS, 7aR, 12bS)-4a-hydroxy-9-methoxy-3-methyl-2, 3, 4, 4a, 5, 7a-hexahydro-1H-4,12-methanobenzofuro[3,2-e]isoquinolin-7-yl)oxy)-4-oxobutanoic acid trifluoroacetic acid salt

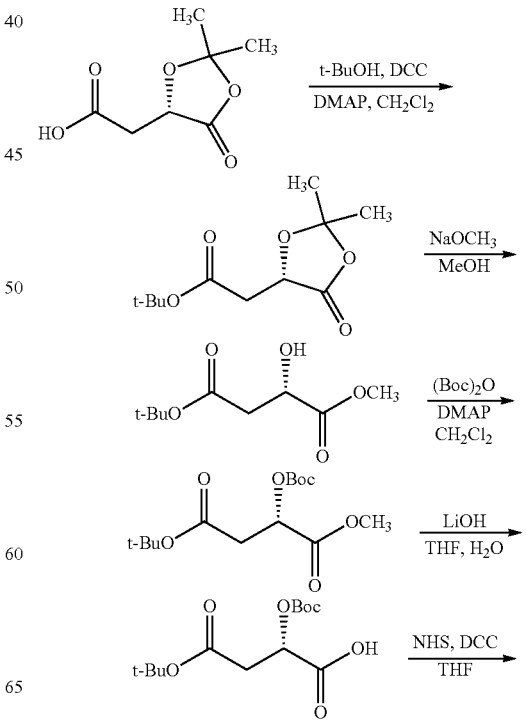

-continued

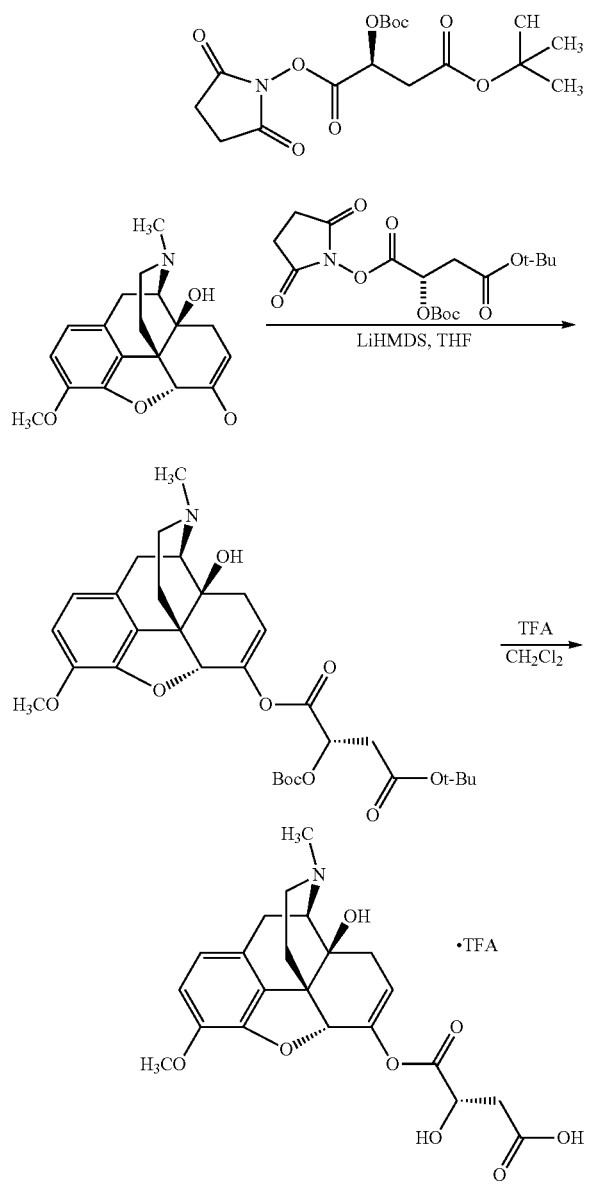

Preparation of (S)-tert-Butyl 2-(2,2-dimethyl-5-oxo-1,3-dioxolan-4-yl)acetate

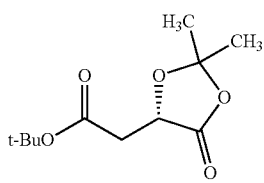 [SMILES: CC(C)(C)OC(=O)C[C@@H]1OC(C)(C)OC1=O]

A solution of (S)-2-(2,2-dimethyl-5-oxo-1,3-dioxolan-4-yl)acetic acid (7.50 g, 43.1 mmol) in methylene chloride (150 mL) was treated with N,N'-dicyclohexylcarbodiimide (10.7 g, 51.7 mmol), 4-dimethylaminopyridine (1.60 g, 12.9 mmol), and tert-butyl alcohol (6.2 mL, 64.7 mmol) and stirred under a nitrogen atmosphere for 2 h. After this time, the reaction mixture was filtered to remove the solid dicyclohexylurea byproduct. The filtrate was concentrated under reduced pressure. The crude residue was purified by column chromatography (silica gel, 0-10% ethyl acetate/heptanes) to provide (S)-tert-butyl 2-(2,2-dimethyl-5-oxo-1,3-dioxolan-4-yl)acetate (7.2 g, 73%) as an off-white solid: $^1$H NMR (300 MHz, CDCl$_3$) δ 4.66 (dd, J=6.3, 3.9 Hz, 1H), 2.84 (dd, J=16.8, 3.9 Hz, 1H), 2.72 (dd, J=16.8, 6.3 Hz, 1H), 1.63 (s, 3H), 1.56 (s, 3H), 1.47 (s, 9H).

Preparation of (S)-4-tert-Butyl 1-methyl 2-hydroxysuccinate

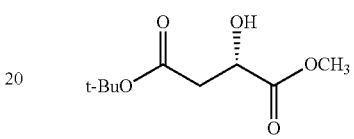

A solution of (S)-tert-butyl 2-(2,2-dimethyl-5-oxo-1,3-dioxolan-4-yl)acetate (6.80 g, 29.6 mmol) in methanol (100 mL) was cooled in an ice bath and treated portion-wise over 10 min with anhydrous sodium methoxide (1.76 g, 32.5 mmol). After addition was complete, the mixture was stirred at 0° C. for 1.5 h. After this time, the reaction mixture was treated with saturated aqueous ammonium chloride (100 mL) and extracted with ethyl acetate (3×100 mL). The combined organics were dried over sodium sulfate, filtered, concentrated under reduced pressure, and dried under vacuum to provide (S)-4-tert-butyl 1-methyl 2-hydroxysuccinate (5.2 g, 86%) as a yellow oil: $^1$H NMR (300 MHz, CDCl$_3$) δ 4.44 (dd, J=10.5, 5.4 Hz, 1H), 3.81 (s, 3H), 3.22 (d, J=5.4 Hz, 1H), 2.87-2.64 (m, 2H), 1.45 (s, 9H).

Preparation of (S)-4-tert-Butyl 1-methyl 2-((tert-butoxycarbonyl)oxy)succinate

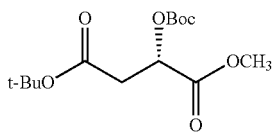

A solution of (S)-4-tert-butyl 1-methyl 2-hydroxysuccinate (5.30 g, 26.0 mmol) in methylene chloride (150 mL) was cooled in an ice bath under a nitrogen atmosphere and treated with 4-dimethylaminopyridine (0.317 g, 2.60 mmol) followed by di-tert-butyl dicarbonate (8.50 g, 40.0 mmol). After 2-3 min, the ice bath was removed, and the mixture was stirred at ambient temperature for 2 h. After this time, the reaction mixture was concentrated under reduced pressure and purified by column chromatography (silica gel, 0-5% ethyl acetate/heptanes) to provide (S)-4-tert-butyl 1-methyl 2-((tert-butoxycarbonyl)oxy)succinate (6.6 g, 83%) as a light yellow oil: $^1$H NMR (300 MHz, CDCl$_3$) δ 5.32 (dd, J=6.9, 6.0 Hz, 1H), 3.78 (s, 3H), 2.81-2.79 (m, 2H), 1.50 (s, 9H), 1.45 (s, 9H).

Preparation of (S)-4-(tert-Butoxy)-2-((tert-butoxycarbonyl)oxy)-4-oxobutanoic acid

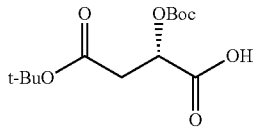

A solution of (S)-4-tert-butyl 1-methyl 2-((tert-butoxycarbonyl)oxy)succinate (6.60 g, 21.7 mmol) in tetrahydrofuran (74 mL) and water (37 mL) was cooled in an ice bath, treated with lithium hydroxide hydrate (1.09 g, 26.1 mmol), and stirred at 0° C. for 3 h. After this time, the reaction mixture was concentrated to remove the volatiles, acidified at 0° C. to pH ~3, and extracted with ethyl acetate (3×100 mL). The combined organics were dried over sodium sulfate, filtered, concentrated under reduced pressure, and dried under vacuum to provide (S)-4-(tert-butoxy)-2-((tert-butoxycarbonyl)oxy)-4-oxobutanoic acid (5.7 g, 90%): $^1$H NMR (300 MHz, CDCl$_3$) δ 5.32 (apparent t, J=6.0 Hz, 1H), 2.85 (apparent d, J=6.0 Hz, 2H), 1.50 (s, 9H), 1.46 (s, 9H), CO$_2$H proton not observed.

Preparation of (S)-4-tert-Butyl 1-(2,5-dioxopyrrolidin-1-yl) 2-((tert-butoxycarbonyl)oxy)succinate

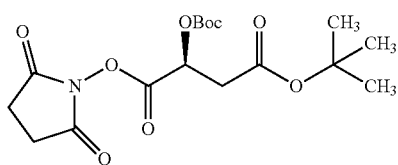

A solution of (S)-4-(tert-butoxy)-2-((tert-butoxycarbonyl)oxy)-4-oxobutanoic acid (525 mg, 1.81 mmol) in tetrahydrofuran (10 mL) was treated with N-hydroxysuccinimide (292 mg, 2.53 mmol) and N,N'-dicydohexylcarbodiimide (523 mg, 2.53 mmol) and stirred under a nitrogen atmosphere for 1 h. After this time, the reaction mixture was filtered to remove the solid dicyclohexylurea byproduct. The solid was washed with tetrahydrofuran (25 mL), and the combined filtrate and washings were concentrated under reduced pressure. The residue was triturated with tetrahydrofuran (25 mL) and filtered to remove the solids. The filtrate was concentrated under reduced pressure. The residue was triturated with diethyl ether and filtered to remove the solids. The filtrate was concentrated under reduced pressure and dried under vacuum to provide (S)-4-tert-butyl 1-(2,5-dioxopyrrolidin-1-yl) 2-((tert-butoxycarbonyl)oxy)succinate (702 mg, quantitative) as a light yellow oil: $^1$H NMR (300 MHz, CDCl$_3$) δ 5.61 (dd, J=8.1, 4.8 Hz, 1H), 2.98-2.94 (m, 2H), 2.84 (s, 4H), 1.51 (s, 9H), 1.47 (s, 9H).

Preparation of (S)-4-tert-Butyl 1-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-((tert-butoxycarbonyl)oxy)succinate

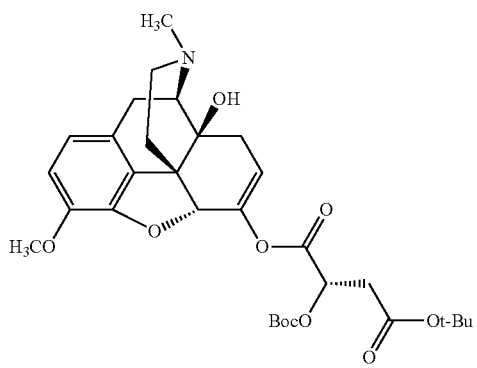

A suspension of oxycodone (0.438 g, 1.39 mmol) in tetrahydrofuran (10 mL) was cooled in an ice bath and treated dropwise with a 1.0 M solution of lithium bis(trimethylsilyl)amide in tetrahydrofuran (1.80 mL, 1.80 mmol). The reaction mixture was stirred at 0° C. for 15 min then was treated dropwise with a solution of (S)-4-tert-butyl 1-(2,5-dioxopyrrolidin-1-yl) 2-((tert-butoxycarbonyl)oxy)succinate (0.700 g, 1.81 mmol) in tetrahydrofuran (6 mL). The reaction mixture was stirred at 0° C. for 1 h. After this time, the reaction mixture was poured into saturated aqueous ammonium chloride (100 mL) and extracted with ethyl acetate (3×100 mL). The combined organics were dried over sodium sulfate, filtered, and concentrated under reduced pressure. The crude residue was purified by reversed phase column chromatography (50 g C18 column, 5-80% acetonitrile/water) and freeze dried to provide (S)-4-tert-butyl 1-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-((tert-butoxycarbonyl)oxy)succinate (0.133 g, 16%) as a white solid: ESI MS m/z 588 [C$_{31}$H$_{41}$NO$_{10}$+H]$^+$.

Preparation of (S)-3-Hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

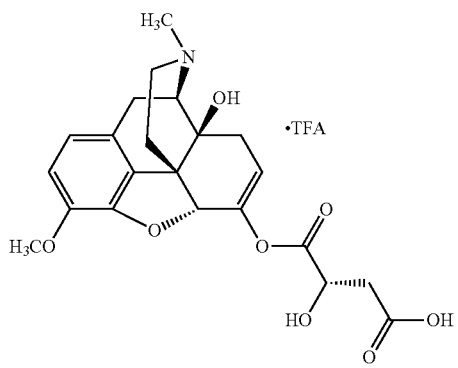 [SMILES: COc1ccc2c3c1O[C@H]1C(OC(=O)[C@@H](O)CC(=O)O)=CC[C@@]4(O)[C@@H](C2)N(C)CC[C@]314]

A solution of (S)-4-tert-butyl 1-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-((tert-butoxycarbonyl)oxy)succinate (0.070 g, 0.12 mmol) in dichloromethane (8 mL) was treated with trifluoroacetic acid (2.5 mL). The reaction mixture was stirred at ambient temperature for 1 h. After this time, the reaction mixture was concentrated under reduced pressure. The residue was triturated with diethyl ether, filtered and lyophilized to provide (S)-3-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt (0.044 g, 86%) as an off-white solid: $^1$H NMR (300 MHz, DMSO-$d_6$) δ 12.43 (br s, 1H), 9.18 (br s, 1H), 6.86 (d, J=8.4 Hz, 1H), 6.75 (d, J=8.1 Hz, 1H), 6.29 (br s, 1H), 5.90 (br s, 1H), 5.55-5.54 (m, 1H), 4.97 (s, 1H), 4.47 (br s, 1H), 3.75 (s, 3H), 3.62 (s, 1H), 3.45-3.37 (m, 1H), 3.12-3.06 (m, 2H), 2.83 (s, 3H), 2.74-2.53 (m, 3H), 2.33-2.22 (m, 1H), 2.07 (d, J=18.3 Hz, 1H), 1.63 (d, J=12.3 Hz, 1H), one proton obscured by solvent peaks; ESI MS m/z 432 $[C_{22}H_{25}NO_8+H]^+$.

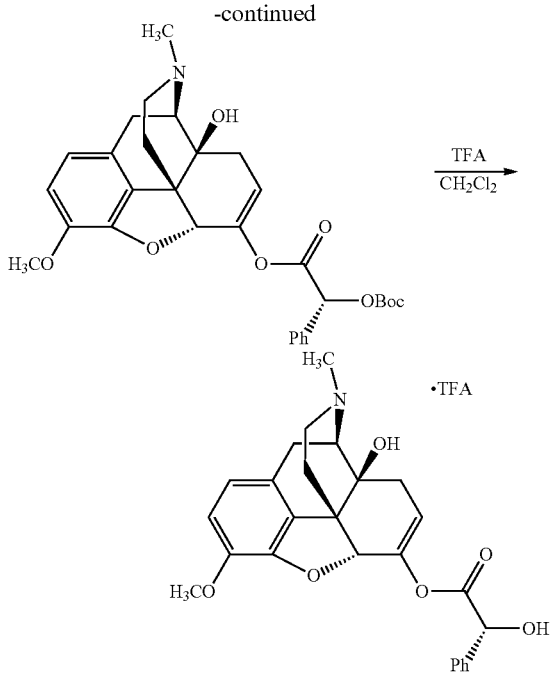

Scheme 10: (R)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-hydroxy-2-phenylacetate trifluoroacetic acid salt

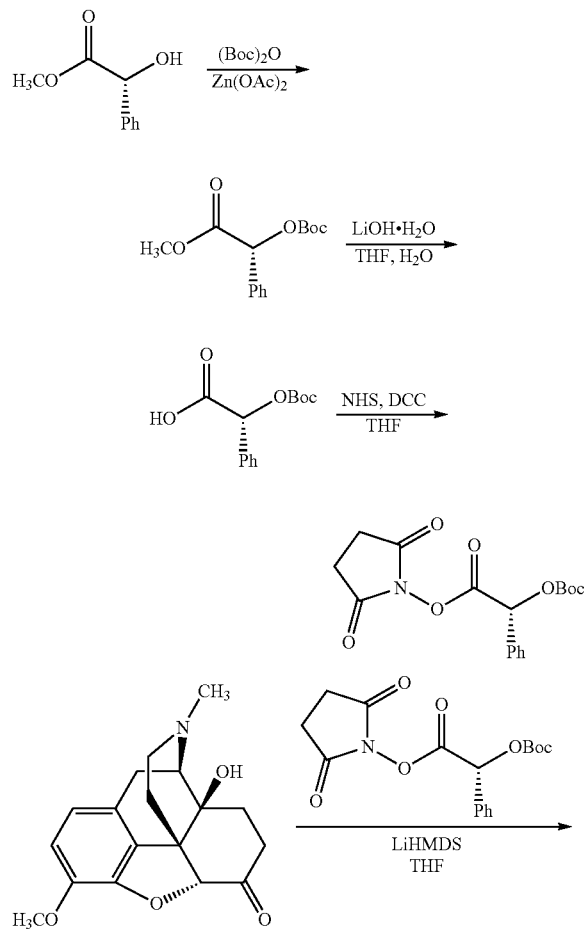

Preparation of (R)-Methyl 2-((tert-butoxycarbonyl)oxy)-2-phenylacetate

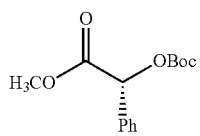

(R)-Methyl 2-hydroxy-2-phenylacetate (20.0 g, 120 mmol), di-tert-butyl dicarbonate (34.1 g, 156 mmol), and zinc acetate (3.96 g, 18.0 mmol) were combined and heated at 55° C. overnight under a nitrogen atmosphere. After this time, the reaction mixture was cooled to room temperature. The mixture was diluted with water (300 mL) and extracted with methylene chloride (3×150 mL). The combined organics were washed with brine (150 mL), dried over sodium sulfate, filtered, and concentrated under reduced pressure to provide (R)-methyl 2-((tert-butoxycarbonyl)oxy)-2-phenylacetate (31.4 g, 98%) as a colorless oil: $^1$H NMR (500 MHz, CDCl$_3$) δ 7.49-7.46 (m, 2H), 7.40-7.36 (m, 3H), 5.80 (s, 1H), 3.74 (s, 3H), 1.51 (s, 9H).

Preparation of (R)-2-((tert-Butoxycarbonyl)oxy)-2-phenylacetic acid

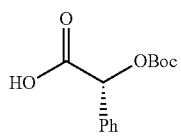

A solution of (R)-methyl 2-((tert-butoxycarbonyl)oxy)-2-phenylacetate (30.0 g, 110 mmol) in a mixture of tetrahydrofuran (300 mL) and water (150 mL) was treated with lithium hydroxide hydrate (9.45 g, 220 mmol) and stirred at ambient temperature for 3 h. After this time, the volatiles were removed under reduced pressure. The aqueous mixture was diluted with water (50 mL) and extracted with diethyl ether (150 mL). The aqueous layer was cooled in an ice bath, acidified to pH ~3 with 1.0 M hydrochloric acid, and extracted with ethyl acetate (3×150 mL). The combined organics were dried over sodium sulfate, filtered, and concentrated under reduced pressure to provide (R)-2-((tert-butoxycarbonyl)oxy)-2-phenylacetic acid (16.8 g, 61%) as a white solid: $^1$H NMR (300 MHz, CDCl$_3$) δ 7.51-7.44 (m, 2H), 7.41-7.36 (m, 3H), 5.25 (s, 1H), 1.51 (s, 9H), CO$_2$H proton not observed.

Preparation of (R)-2,5-Dioxopyrrolidin-1-yl 2-((tert-butoxycarbonyl)oxy)-2-phenylacetate

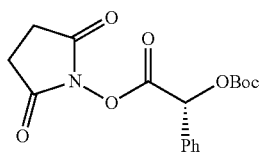

A solution of (R)-2-((tert-butoxycarbonyl)oxy)-2-phenylacetic acid (7.78 g, 30.8 mmol) in tetrahydrofuran (110 mL) was treated with N-hydroxysuccinimide (3.90 g, 34.0 mmol) and N,N'-dicyclohexylcarbodiimide (7.00 g, 34.0 mmol) and stirred under a nitrogen atmosphere for 3 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (R)-2,5-dioxopyrrolidin-1-yl 2-((tert-butoxycarbonyl)oxy)-2-phenylacetate (8.50 g, 79%) as a white solid: $^1$H NMR (300 MHz, CDCl$_3$) δ 7.57-7.55 (m, 2H), 7.44-7.42 (m, 3H), 6.15 (s, 1H), 2.80 (m, 4H), 1.52 (s, 9H).

Preparation of (R)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((tert-butoxycabonyl)oxy)-2-phenylacetate

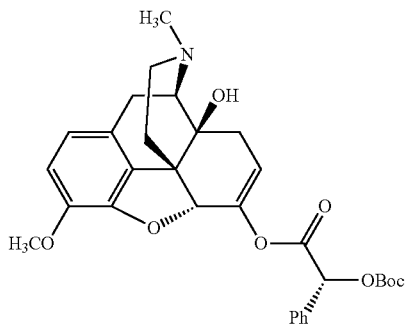

A suspension of oxycodone (0.350 g, 1.11 mmol) in tetrahydrofuran (8 mL) was cooled in an ice bath and treated dropwise with a 1.0 M solution of lithium bis(trimethylsilyl) amide in tetrahydrofuran (1.3 mL, 1.3 mmol). The mixture was stirred at 0° C. for 15 min and then treated dropwise with a solution of (R)-2,5-dioxopyrrolidin-1-yl 2-((tert-butoxycarbonyl)oxy)-2-phenylacetate (0.465 g, 1.33 mmol) in tetrahydrofuran (4 mL). The reaction mixture was stirred at 0° C. for 1 h. After this time, the mixture was poured into saturated aqueous ammonium chloride (75 mL) and extracted with ethyl acetate (2×100 mL). The combined organics were dried over sodium sulfate, filtered, and concentrated under reduced pressure. The crude residue was purified by column chromatography (silica gel, 0-5% methanol/methylene chloride) to provide (R)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((tert-butoxycabonyl)oxy)-2-phenylacetate (0.130 g, 21%) as a light yellow oil: $^1$H NMR (300 MHz, CDCl$_3$) δ 7.56-7.53 (m, 2H), 7.40-7.37 (m, 3H), 6.68 (d, J=8.1 Hz, 1H), 6.63 (d, J=8.4 Hz, 1H), 5.90 (s, 1H), 5.56 (apparent t, J=3.6 Hz, 1H), 4.89 (s, 1H), 3.77 (s, 3H), 3.14 (d, J=18.6 Hz, 1H), 2.83 (d, J=6.3 Hz, 1H), 2.60 (dd, J=18.6, 6.3 Hz, 1H), 2.44-2.40 (m, 1H), 2.36 (s, 3H), 2.27-2.12 (m, 4H), 1.35-1.55 (m, 2H), 1.50 (s, 9H).

Preparation of (R)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-hydroxy-2-phenylacetate trifluoroacetic acid salt

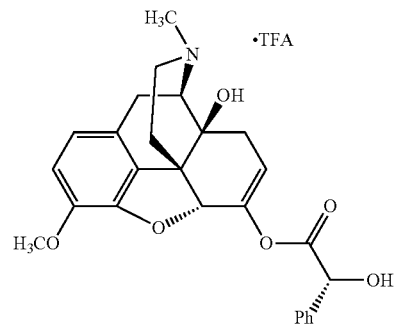 [SMILES: COc1ccc2c3c1O[C@H]1C(OC(=O)[C@H](O)c4ccccc4)=CC[C@@]4(O)[C@@H](C2)N(C)CC[C@]314]

A solution of (R)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((tert-butoxycabonyl)oxy)-2-phenylacetate (0.120 g, 0.218 mmol) in methylene chloride (3 mL) was treated with trifluoroacetic acid (2 mL) and stirred at ambient temperature for 1 h. After this time, the reaction mixture was concentrated under reduced pressure. The residue was triturated with diethyl ether to give a white powder. The powder was dissolved in water and freeze dried to provide (R)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-hydroxy-2-phenylacetate trifluoroacetic acid salt (83 mg, 50%) as a fluffy white solid: $^1$H NMR (300 MHz, DMSO-d$_6$) δ 9.16 (br s, 1H), 7.49-7.33 (m, 5H), 6.84 (d, J=8.1 Hz, 1H), 6.73 (d, J=8.1 Hz, 1H), 6.28-6.24 (m, 2H), 5.44-5.41 (m, 1H), 5.28 (d, J=5.1 Hz, 1H), 4.95 (s, 1H), 3.68 (s, 3H), 3.64-3.62 (m, 1H), 3.44-3.35 (m, 1H), 3.13-3.04 (m, 2H), 2.83 (s, 3H), 2.69-2.54 (m, 1H), 2.44-2.43 (m, 1H), 2.34 (dd, J=18.0, 5.4 Hz, 1H), 2.04 (d, J=18.0 Hz, 1H); ESI MS m/z 450 [C$_{26}$H$_{27}$NO$_6$+H]$^+$; HPLC (Method A) 95.2% (AUC), t$_R$=8.62 min.

Scheme 11: (S)-(S)-2-(((4R, 4aS, 7aR, 12bS)-4a-Hydroxy-9-methoxy-3-methyl-2, 3, 4, 4a, 5, 7a-hexahydro-1H-4, 12-methanobenzofuro[3,2-e]isoquinolin-7-yl)oxy)-2-oxo-1-phenylethyl 2-hydroxypropanoate trifluoroacetic acid salt

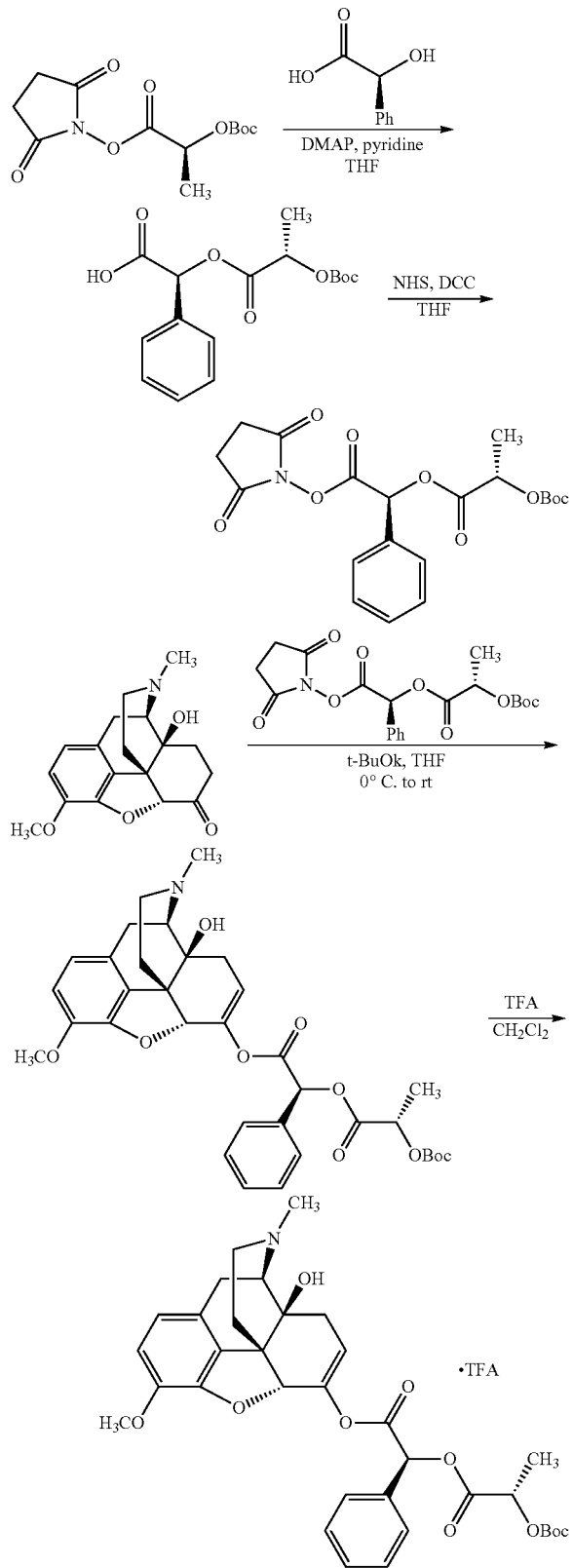

Preparation of (S)-2-(((S)-2-((tert-Butoxycarbonyl)oxy)propanoyl)oxy)-2-phenylacetic acid

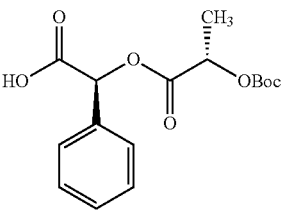

A solution of (S)-2,5-dioxopyrrolidin-1-yl 2-((tert-butoxycarbonyl)oxy)propanoate (2.00 g, 6.96 mmol), mandelic acid (1.28 g, 8.41 mmol), and 4-dimethylaminopyridine (87 mg, 0.71 mmol) in tetrahydrofuran (30 mL) was treated with pyridine (0.67 mL, 8.3 mmol) and heated at 50° C. under a nitrogen atmosphere for 20 h. After this time, the reaction mixture was cooled to room temperature and concentrated under reduced pressure. The residue was dissolved in ethyl acetate (50 mL) and washed with aqueous 10% citric acid (2×25 mL) and water (25 mL). The organic layer was extracted with saturated aqueous sodium bicarbonate (2×25 mL). The combined aqueous bicarbonate layers were acidified to pH ~2 with 6 N hydrochloric acid and extracted with ethyl acetate (4×25 mL). The combined organics were dried over sodium sulfate, filtered, and concentrated under reduced pressure to provide (S)-2-(((S)-2-((tert-butoxycarbonyl)oxy)propanoyl)oxy)-2-phenylacetic acid (1.71 g, 76%) as a colorless oil: $^1$H NMR (300 MHz, CDCl$_3$) δ 7.48-7.36 (m, 5H), 6.00 (s, 1H), 5.06 (q, J=6.9 Hz, 1H), 1.62 (d, J=6.9 Hz, 3H), 1.48 (s, 9H), CO$_2$H proton not observed; ESI MS m/z 647 [(2×C$_{16}$H$_{20}$O$_7$)–H]$^-$.

Preparation of (S)-(S)-2-((2,5-Dioxopyrrolidin-1-yl)oxy)-2-oxo-1-phenylethyl 2-((tert-butoxycarbonyl)oxy)propanoate

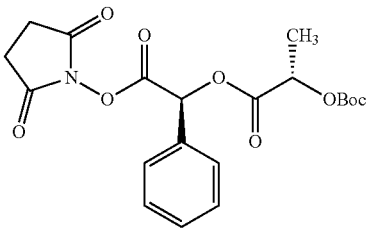

A solution of (S)-2-(((S)-2-((tert-butoxycarbonyl)oxy)propanoyl)oxy)-2-phenylacetic acid (1.71 g, 5.27 mmol) in tetrahydrofuran (20 mL) was treated with N-hydroxysuccinimide (667 mg, 5.80 mmol) and N,N'-dicyclohexylcarbodiimide (1.21 g, 5.86 mmol) and stirred under a nitrogen atmosphere for 2.5 h. After this time, the reaction mixture was filtered to remove the solid dicyclohexylurea byproduct.

The solid was washed with diethyl ether, and the combined filtrate and washings were concentrated under reduced pressure to provide (S)-(S)-2-((2,5-dioxopyrrolidin-1-yl)oxy)-2-oxo-1-phenylethyl 2-((tert-butoxycarbonyl)oxy)propanoate (2.21 g, 99%) as an white crushable foam: $^1$H NMR (300 MHz, CDCl$_3$) δ 7.55-7.51 (m, 2H), 7.47-7.42 (m, 3H), 6.39 (s, 1H), 5.05 (q, J=7.2 Hz, 1H), 2.80 (s, 4H), 1.61 (d, J=7.2 Hz, 3H), 1.48 (s, 9H).

Preparation of (S)-(S)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 2-((tert-butoxycarbonyl)oxy)propanoate

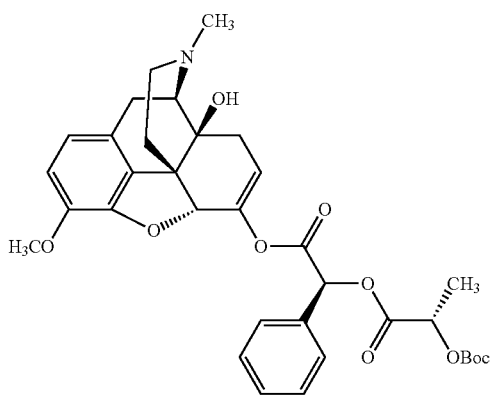

A suspension of oxycodone (503 mg, 1.60 mmol) in tetrahydrofuran (6 mL) was cooled in an ice bath and treated dropwise with a 1.0 M solution of potassium tert-butoxide in tetrahydrofuran (1.9 mL, 1.9 mmol). After addition was complete, the mixture was stirred at ambient temperature for 15 min. The mixture was re-cooled in the ice bath and treated dropwise with a solution of (S)-(S)-2-((2,5-dioxopyrrolidin-1-yl)oxy)-2-oxo-1-phenylethyl 2-((tert-butoxycarbonyl)oxy)propanoate (806 mg, 1.91 mmol) in tetrahydrofuran (6 mL). After addition was complete, the mixture was stirred at ambient temperature for 10 min. After this time, the reaction mixture was re-cooled in the ice bath and treated with saturated aqueous ammonium chloride (50 mL) and extracted with ethyl acetate (2×50 mL). The combined organics were washed with saturated sodium bicarbonate (25 mL) and brine (25 mL), dried over sodium sulfate, filtered, and concentrated under reduced pressure. The crude residue was purified by column chromatography (silica gel, 0-10% methanol/methylene chloride) followed by reversed phase column chromatography (50 g C18 column, 10-100% acetonitrile/water) and freeze dried to provide (S)-(S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 2-((tert-butoxycarbonyl)oxy)propanoate (51 mg, 5%) as a fluffy white solid: ESI MS m/z 622 [C$_{34}$H$_{39}$NO$_{10}$+H]$^+$.

Preparation of (S)-(S)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 2-hydroxypropanoate trifluoroacetic acid salt

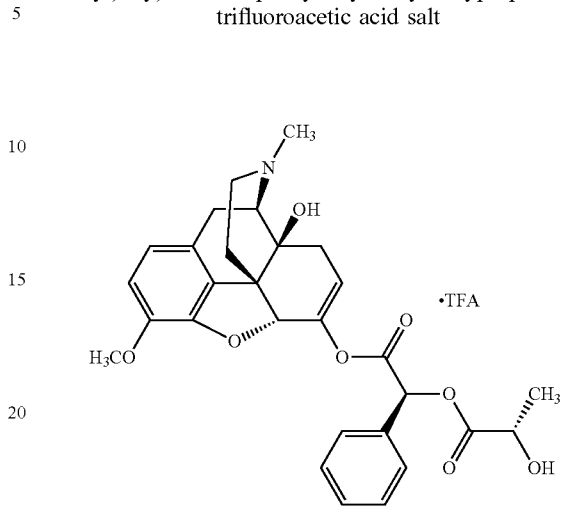

A solution of (S)-(S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 2-((tert-butoxycarbonyl)oxy)propanoate (50 mg, 0.080 mmol) in methylene chloride (2 mL) was treated with trifluoroacetic acid (1 mL) and stirred under a nitrogen atmosphere at ambient temperature for 30 min. After this time, the reaction mixture was concentrated under reduced pressure. The residue was purified by reversed phase column chromatography (C18 column, 10-100% acetonitrile/water) and freeze dried to provide (S)-(S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 2-hydroxypropanoate trifluoroacetic acid salt (23 mg, 46%) as a fluffy white solid: $^1$H NMR (300 MHz, DMSO-d$_6$) δ 9.15 (br s, 1H), 7.57-7.55 (m, 2H), 7.48-7.45 (m, 3H), 6.81 (d, J=8.1 Hz, 1H), 6.72 (d, J=8.1 Hz, 1H), 6.31 (br s, 1H), 6.15 (s, 1H), 5.57-5.53 (m, 2H), 4.94 (s, 1H), 4.34-4.26 (m, 1H), 3.64 (br s, 4H), 3.44-3.37 (m, 1H, partially obscured by water peak), 3.13-3.05 (m, 2H), 2.82 (s, 3H), 2.62-2.57 (m, 1H), 2.49-2.39 (m, 1H, partially obscured by solvent peak), 2.30-2.22 (m, 1H), 2.08-2.02 (m, 1H), 1.62 (d, J=12.0 Hz, 1H), 1.37 (d, J=6.6 Hz, 3H);ESI MS m/z 522 [C$_{29}$H$_{31}$ NO$_8$+H]$^+$.

Scheme 12: (S)-(4R,4aS,7aR,12bS)-4a-Hydroxy-9-methoxy-3-methyl-2,3,4,4a,5,7a-hexahydro-1H-4, 12-methanobenzofuro [3,2-e]isoquinolin-7-yl 2-((S)-2-hydroxypropanamido) propanoatetrifluoroacetic acid salt

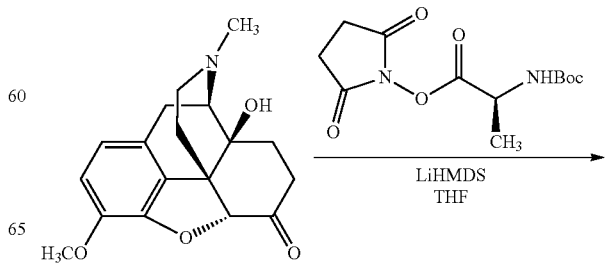

315
-continued

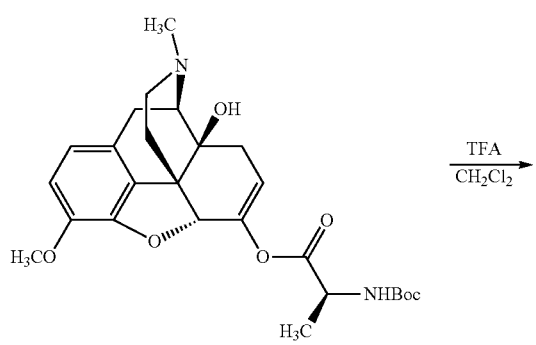

316

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((tert-butoxycarbonyl)amino)propanoate

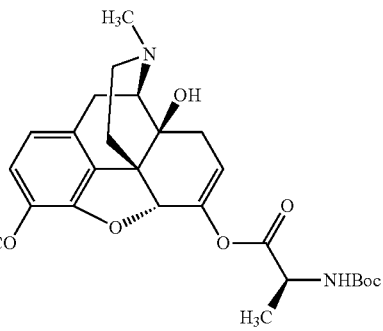

A suspension of oxycodone (0.500 g, 1.58 mmol) in tetrahydrofuran (10 mL) was cooled in an ice bath and treated dropwise with a 1.0 M solution of lithium bis(trimethylsilyl)amide in tetrahydrofuran (0.7 mL, 0.7 mmol). The mixture was stirred at 0° C. for 15 min and then treated dropwise with a solution of (S)-2,5-dioxopyrrolidin-1-yl 2-((tert-butoxycarbonyl)amino)propanoate (0.904 g, 3.16 mmol) in tetrahydrofuran (10 mL). The mixture was stirred 0° C. for 1 h. After this time, the reaction mixture was treated with saturated aqueous ammonium chloride (75 mL) and extracted with ethyl acetate (2×100 mL). The combined organics were dried over sodium sulfate, filtered, and concentrated under reduced pressure. The crude residue was purified by reversed phase chromatography (C18, 10-80% acetonitrile/water) to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((tert-butoxycarbonyl)amino)propanoate (0.225 g, 29%) as a white solid: $^1$H NMR (300 MHz, CDCl$_3$) δ 6.71 (d, J=8.1 Hz, 1H), 6.62 (d, J=8.4 Hz, 1H), 5.65-5.62 (m, 1H), 5.05 (br s, 1H), 4.99 (s, 1H), 4.45-4.35 (m, 1H), 3.84 (s, 3H), 3.17 (d, J=18.6 Hz, 1H), 2.86 (d, J=6.3 Hz, 1H), 2.63 (dd, J=18.9, 6.3 Hz, 1H), 2.47-2.42 (m, 1H), 2.38 (s, 3H), 2.35-2.22 (m, 2H), 2.18-2.16 (m, 2H), 1.64-1.59 (m, 1H), 1.48 (d, J=7.5 Hz, 3H), 1.45 (s, 9H), OH proton not observed.

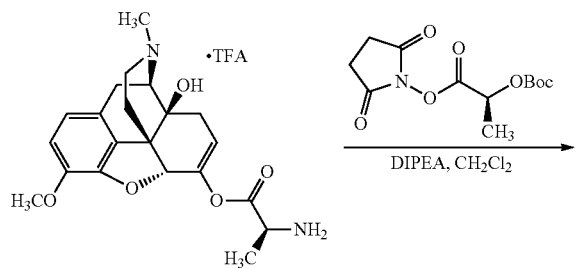

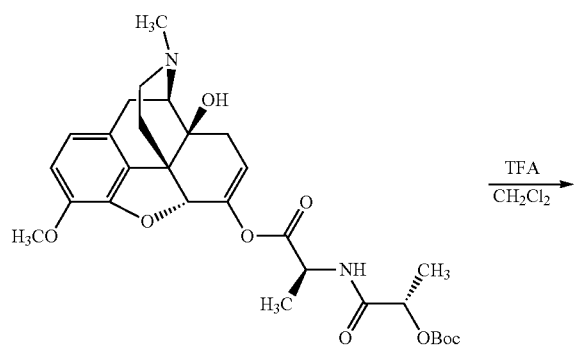

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-aminopropanoate bis(trifluoroacetic acid salt)

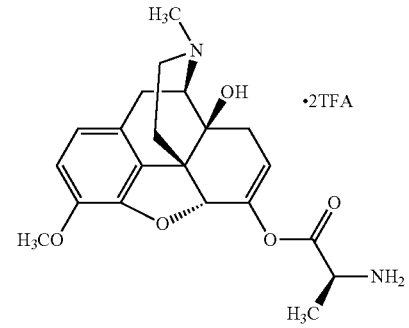 [SMILES: COc1ccc2c3c1O[C@H]1C(OC(=O)[C@H](C)N)=CC[C@@]4(O)[C@@H](C2)N(C)CC[C@]314]

317

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((tert-butoxycarbonyl)amino)propanoate (0.200 g, 0.410 mmol) in methylene chloride (6 mL) was treated with trifluoroacetic acid (3 mL) and stirred under a nitrogen atmosphere at ambient temperature for 0.5 h. After this time, the reaction mixture was concentrated under reduced pressure to give (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-aminopropanoate bis(trifluoroacetic acid salt) (0.343 g, quantitative) as a light yellow oil: ESI MS m/z 387 $[C_{21}H_{26}N_2O_5+H]^+$.

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((S)-2-((tert-butoxycarbonyl)oxy)propanamido)propanoate

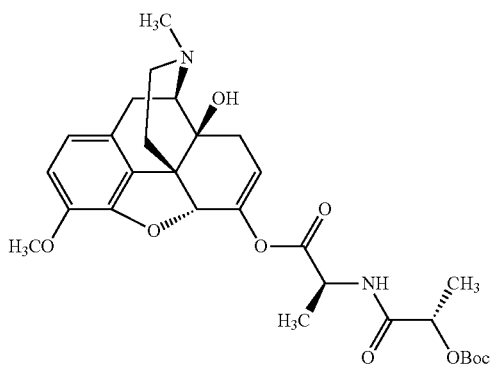

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-aminopropanoate bis(trifluoroacetic acid salt) (0.252 g, 0.411 mmol) in methylene chloride (8 mL) was cooled in an ice bath and treated with N,N-diisopropylethylamine (0.77 mL, 4.44 mmol) and (S)-2,5-dioxopyrrolidin-1-yl 2-((tert-butoxycarbonyl)oxy)propanoate (0.382 g, 1.33 mmol). The ice bath was removed, and the mixture was stirred at ambient temperature for 2 h. After this time, the reaction mixture was concentrated under reduced pressure. The residue was diluted in ethyl acetate (100 mL) and successively washed with 10% citric acid (75 mL), saturated sodium bicarbonate (75 mL) and brine (75 mL). The organic layer was dried over sodium sulfate, filtered and concentrated under reduced pressure. The crude residue was purified by column chromatography (silica gel, 0-4% methylene chloride/methanol) to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((S)-2-((tert-butoxycarbonyl)oxy)propanamido)propanoate (0.138 g, 60%) as a white foam: ESI MS m/z 559 $[C_{29}H_{38}N_2O_9+H]^+$.

318

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((S)-2-hydroxypropanamido)propanoate trifluoroacetic acid salt

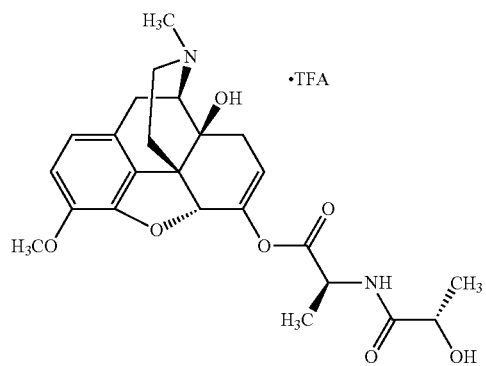 [SMILES: COc1ccc2c3c1O[C@H]1C(OC(=O)[C@H](C)NC(=O)[C@H](C)O)=CC[C@@]4(O)[C@@H](C2)N(C)CC[C@]314]

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((S)-2-((tert-butoxycarbonyl)oxy)propanamido)propanoate (0.080 g, 0.14 mmol) in methylene chloride (3 mL) was treated with trifluoroacetic acid (1.5 mL) and stirred at ambient temperature for 1 h. After this time, the reaction mixture was concentrated under reduced pressure. The residue was triturated with a mixture of methylene chloride/diethyl ether (1:1) and filtered to give (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((S)-2-hydroxypropanamido)propanoate trifluoroacetic acid salt (0.044 mg, 67%) as a white solid: $^1$H NMR (300 MHz, DMSO-$d_6$) δ 9.22 (br s, 1H), 8.09 (d, J=6.9 Hz, 1H), 6.86 (d, J=8.4 Hz, 1H), 6.75 (d, J=8.1 Hz, 1H), 6.28 (s, 1H), 5.53-5.50 (m, 1H), 5.00 (s, 1H), 4.39-4.34 (m, 1H), 4.03-3.99 (m, 1H), 3.75 (s, 3H), 3.64 (d, J=5.7 Hz, 1H), 3.50-3.35 (m, 2H), 3.13-3.06 (m, 2H), 2.84 (d, J=4.5 Hz, 3H), 2.75-2.55 (m, 1H), 2.32-2.24 (m, 1H), 2.06 (d, J=18.0 Hz, 1H), 1.59 (d, J=11.7 Hz, 1H), 1.40 (d, J=7.2 Hz, 3H), 1.22 (d, J=10.5 Hz, 3H); ESI MS m/z 459 $[C_{24}H_{30}N_2O_7+H]^+$.

Scheme 13: (S)-(S)-1-(((4R,4aS,7aR,12bS)-4a-Hydroxy-9-methoxy-3-methyl-2,3,4,4a,5,7a-hexahydro-1H-4, 12-methanobenzofuro[3,2-e]isoquinolin-7-yl)oxy)-1-oxopropan-2-yl pyrrolidine-2-carboxylate dihydrochloride

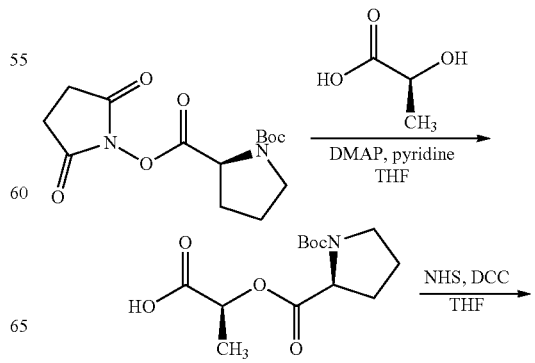

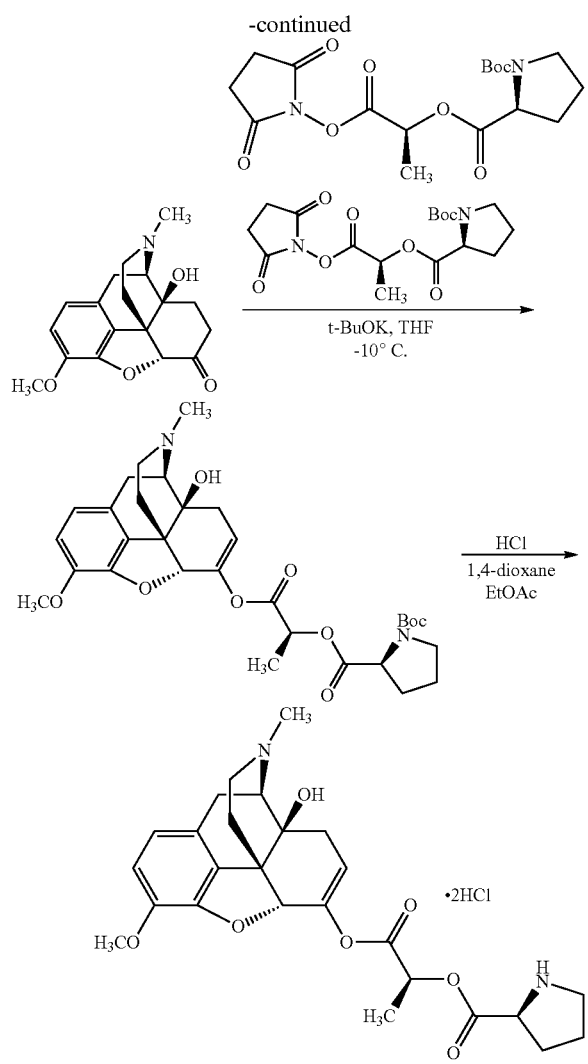

Preparation of (S)-2-(((S)-1-(tert-Butoxycarbonyl) pyrrolidine-2-carbonyl)oxy)propanoic acid

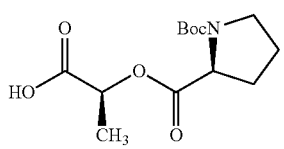

A solution of (S)-1-tert-butyl 2-(2,5-dioxopyrrolidin-1-yl) pyrrolidine-1,2-dicarboxylate (2.01 g, 6.44 mmol), lactic acid (699 mg, 7.76 mmol), and 4-dimethylaminopyridine (82 mg, 0.67 mmol) in tetrahydrofuran (30 mL) was treated with pyridine (0.62 mL, 7.7 mmol) and heated at 50° C. under a nitrogen atmosphere for 20 h. After this time, the reaction mixture was cooled to room temperature and concentrated under reduced pressure. The residue was dissolved in ethyl acetate (50 mL) and washed with aqueous 10% citric acid (2×25 mL) and water (25 mL). The organic layer was extracted with saturated aqueous sodium bicarbonate (2×25 mL). The combined aqueous bicarbonate layers were acidified to pH ~2 with 6 N hydrochloric acid and extracted with ethyl acetate (4×25 mL). The combined organics were dried over sodium sulfate, filtered, and concentrated under reduced pressure to provide (S)-2-(((S)-1-(tert-Butoxycarbonyl)pyrrolidine-2-carbonyl)oxy)propanoic acid (646 mg, 35%) as a colorless oil: $^1$H NMR (300 MHz, CDCl$_3$, Mixture of isomers) δ 5.29 (q, J=7.2 Hz, 0.51H), 5.21-5.14 (m, 0.49H), 4.38 (dd, J=8.4, 4.8 Hz, 0.51H), 4.38 (dd, J=8.4, 3.9 Hz, 0.49H), 3.62-3.36 (m, 2H), 2.34-2.22 (m, 1H), 2.19-2.06 (m, 1H), 1.98-1.87 (m, 2H), 1.57-1.41 (m, 12H), CO$_2$H proton not observed; ESI MS m/z 573 [(2× C$_{13}$H$_{21}$NO$_6$)−H]$^-$.

Preparation of (S)-1-tert-Butyl 2-((S)-1-((2,5-dioxopyrrolidin-1-yl)oxy)-1-oxopropan-2-yl) pyrrolidine-1,2-dicarboxylate

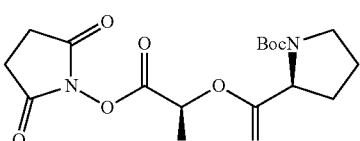

A solution of (S)-2-(((S)-1-(tert-butoxycarbonyl)pyrrolidine-2-carbonyl)oxy)propanoic acid (640 mg, 2.23 mmol) in tetrahydrofuran (10 mL) was treated with N-hydroxysuccinimide (283 mg, 2.46 mmol) and N,N'-dicyclohexylcarbodiimide (511 mg, 2.48 mmol) and stirred under a nitrogen atmosphere for 3 h. After this time, the reaction mixture was filtered to remove the solid dicyclohexylurea byproduct. The solid was washed with diethyl ether, and the combined filtrate and washings were concentrated under reduced pressure to provide (S)-1-tert-butyl 2-((S)-1-((2,5-dioxopyrrolidin-1-yl)oxy)-1-oxopropan-2-yl) pyrrolidine-1,2-dicarboxylate (957 mg, quantitative) as a tan foam: $^1$H NMR (300 MHz, CDCl$_3$, Mixture of isomers) δ 5.48 (q, J=6.9 Hz, 1H), 4.41 (dd, J=8.4, 3.9 Hz, 0.50H), 4.31 (dd, J=8.4, 3.9 Hz, 0.50H), 3.60-3.37 (m, 2H), 2.85-2.84 (m, 4H), 2.27-2.11 (m, 2H), 1.98-1.89 (m, 2H), 1.70 (d, J=6.9 Hz, 3H), 1.45 (s, 4.5H), 1.43 (s, 4.5H).

Preparation of (S)-1-tert-Butyl 2-((S)-1-(((4R,4aS, 7aR,12bS)-4a-hydroxy-9-methoxy-3-methyl-2,3,4, 4a,5,7a-hexahydro-1H-4,12-methanobenzofuro[3,2-e]isoquinolin-7-yl)oxy)-1-oxopropan-2-yl) pyrrolidine-1,2-dicarboxylate

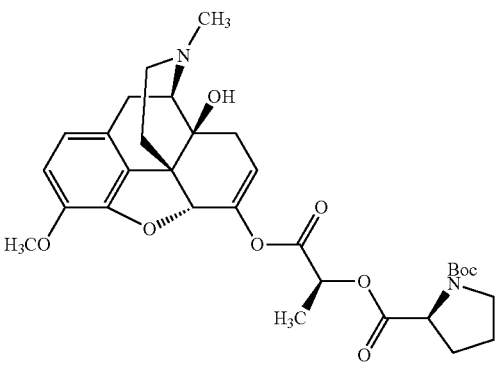 [SMILES: COc1ccc2c3c1O[C@H]1C(OC(=O)[C@H](C)OC(=O)[C@@H]4CCCN4C(=O)OC(C)(C)C)=CC[C@@]4(O)[C@@H](C2)N(C)CC[C@]314]

A suspension of oxycodone (634 mg, 2.01 mmol) in tetrahydrofuran (7 mL) was cooled in an ice bath and treated dropwise with a 1.0 M solution of potassium tert-butoxide in tetrahydrofuran (2.4 mL, 2.4 mmol). After addition was complete, the mixture was stirred in the ice bath for 5 min and at ambient temperature for 5 min. The mixture was re-cooled in an ice/brine bath and treated dropwise with a solution of (S)-1-tert-butyl 2-((S)-1-((2,5-dioxopyrrolidin-1-yl)oxy)-1-oxopropan-2-yl) pyrrolidine-1,2-dicarboxylate (932 mg, 2.43 mmol) in tetrahydrofuran (7 mL). After addition was complete, the mixture was stirred in the ice/brine bath for 20 min. After this time, the reaction mixture was treated with saturated aqueous ammonium chloride (50 mL) and extracted with ethyl acetate (2×50 mL). The combined organics were washed with saturated sodium bicarbonate (50 mL) and brine (50 mL), dried over sodium sulfate, filtered, and concentrated under reduced pressure. The crude residue was purified by column chromatography (silica gel, 0-10% methanol/methylene chloride) followed by reversed phase column chromatography (150 g C18 column, 20-100% acetonitrile/water) and freeze dried to provide (S)-1-tert-butyl 2-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) pyrrolidine-1,2-dicarboxylate (185 mg, 16%) as a fluffy white solid: ESI MS m/z 585 [$C_{31}H_{40}N_2O_9$+H]$^+$.

Preparation of (S)-(S)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl pyrrolidine-2-carboxylate dihydrochloride

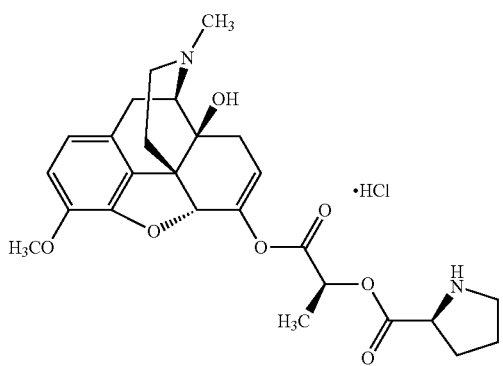 [SMILES: COc1ccc2c3c1O[C@H]1C(OC(=O)[C@H](C)OC(=O)[C@@H]4CCCN4)=CC[C@@]4(O)[C@@H](C2)N(C)CC[C@]314 ; Cl]

A solution of (S)-1-tert-butyl 2-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) pyrrolidine-1,2-dicarboxylate (88 mg, 0.15 mmol) in ethyl acetate (1 mL) was treated with a 4.0 M solution of hydrogen chloride in 1,4-dioxane (1 mL) and stirred under a nitrogen atmosphere at ambient temperature for 1 h. After this time, the reaction mixture was diluted with diethyl ether and sonicated to produce a solid precipitate. The solid was isolated by filtration, washed with diethyl ether, and dried under vacuum to provide (S)-(S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl pyrrolidine-2-carboxylate dihydrochloride (90 mg, quantitative) as a white solid: $^1$H NMR (300 MHz, DMSO-d$_6$) δ 9.93 (br s, 1H), 9.22 (br s, 1H), 9.02 (br s, 1H), 6.87 (d, J=8.4 Hz, 1H), 6.76 (d, J=8.1 Hz, 1H), 6.35 (s, 1H), 5.62 (dd, J=5.7, 1.8 Hz, 1H), 5.35 (q, J=7.2 Hz, 1H), 4.99 (s, 1H), 4.54 (br s, 1H), 3.75 (s, 3H), 3.69 (d, J=5.7 Hz, 1H), 3.42-3.37 (m, 1H, partially obscured by water peak), 3.25 (br s, 2H), 3.16-3.07 (m, 2H), 2.85 (apparent d, J=4.8 Hz, 3H), 2.65-2.57 (m, 1H), 2.49-2.27 (m, 3H, partially obscured by solvent peak), 2.18-1.88 (m, 4H), 1.63 (d, J=12.0 Hz, 1H), 1.57 (d, J=7.2 Hz, 3H);ESI MS m/z 485 [$C_{26}H_{32}N_2O_7$+H]$^+$; HPLC (Method A) 98.0% (AUC), $t_R$=7.07 min.

Scheme 14: (S)-(4R, 4aS, 7aR, 12bS)-4a-Hydroxy-9-methoxy-3-methyl-2, 3, 4, 4a, 5, 7a-hexahydro-1H-4, 12-methanobenzofuro[3,2-e]isoquinolin-7-yl 2-(3-aminopropanamido)-3-(1H-imidazo-4-yl)propanoate tris(trifluoroacetic acid salt)

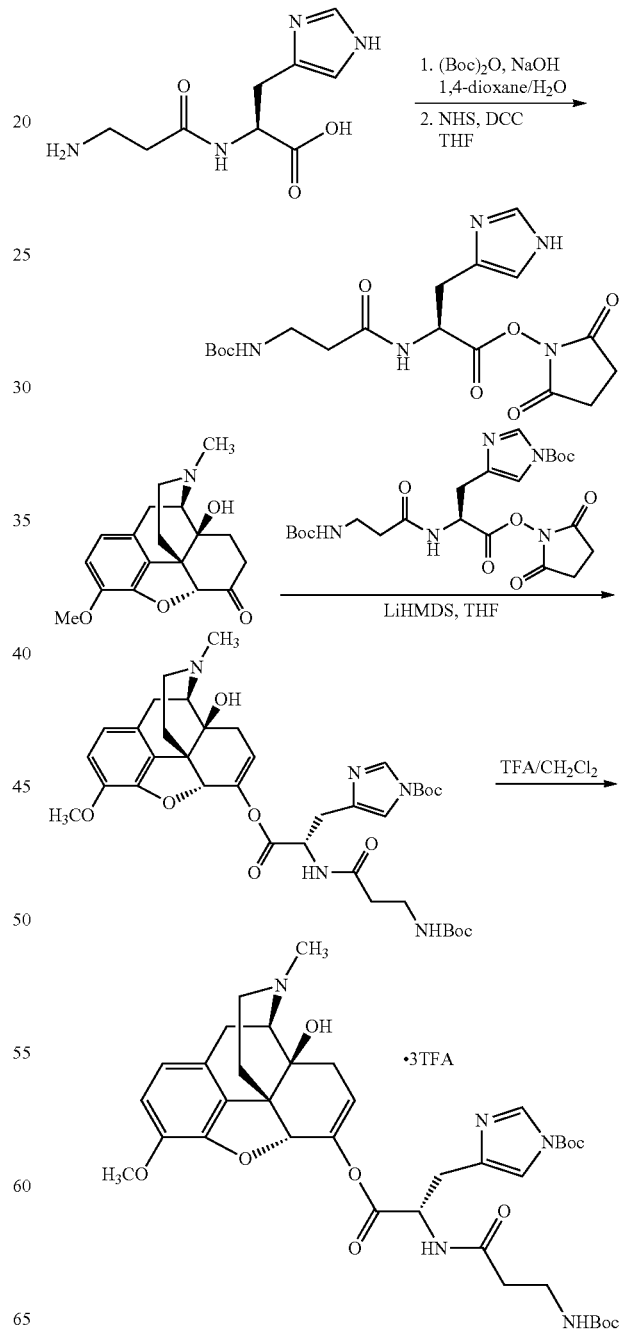

Preparation of (S)-3-(1-(tert-Butoxycarboyl)-1H-imidazol-4-yl)-2-(3-((tert-butoxycarbonyl)amino)propanamido)propanoic acid

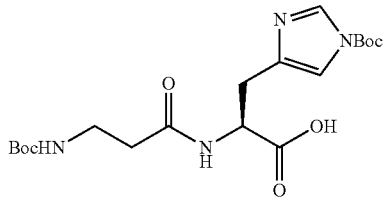 [SMILES: CC(C)(C)OC(=O)NCCC(=O)N[C@@H](Cc1cn(C(=O)OC(C)(C)C)cn1)C(=O)O]

A suspension of (S)-2-(3-aminopropanamido)-3-(1H-imidazol-4-yl)propanoic acid (3.00 g, 13.3 mmol) in a mixture of 1,4-dioxane/water (13.5 mL, 2:1) was stirred at ambient temperature until a clear solution was obtained (~10 minutes). The mixture was treated dropwise with a solution of 1 M aqueous NaOH (4.40 mL, 4.42 mmol). The reaction mixture was cooled to 0° C. and treated with di-tert-butyl dicarbonate (2.12 g, 9.72 mmol). The ice bath was removed and stirring continued at ambient temperature for 2 h. After this time, the volatiles were removed under reduced pressure. The residue was diluted with water (40 mL) and ethyl acetate (60 mL), acidified to pH ~3 with 1.0 M potassium bisulfate and extracted with ethyl acetate (3×100 mL). The combined organics were dried over sodium sulfate, filtered, and concentrated under reduced pressure to provide (S)-3-(1-(tert-butoxycarboyl)-1H-imidazol-4-yl)-2-(3-((tert-butoxycarbonyl)amino)propanamido)propanoic acid (1.70 g, 90%) as a white solid: $^1$H NMR (300 MHz, CDCl$_3$) δ 8.15 (s, 1H), 7.21 (s, 1H), 6.69-6.67 (br s, 1H), 5.28 (s, 1H), 4.72-4.66 (m, 1H), 3.46-3.40 (m, 2H), 3.26 (dd, J=11.7, 5.7 Hz, 1H), 3.13 (dd, J=15.0, 6.3 Hz, 1H), 2.46 (t, J=26.3 Hz, 2H), 1.61 (s, 9H), 1.44 (s, 9H), CO$_2$H proton not observed.

Preparation of (S)-tert-Butyl 4-(2-(3-((tert-butoxycarbonyl)amino)propanamido)-3-((2,5-dioxopyrrolidin-1-yl)oxy)-3-oxopropyl)-1H-Imidazole-1-carboxylate

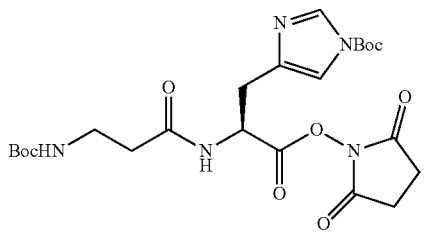 [SMILES: CC(C)(C)OC(=O)NCCC(=O)N[C@@H](Cc1cn(C(=O)OC(C)(C)C)cn1)C(=O)ON1C(=O)CCC1=O]

A solution of (S)-3-(1-(tert-butoxycarboyl)-1H-imidazol-4-yl)-2-(3-((tert-butoxycarbonyl)amino)propanamido)propanoic acid (4.90 g, 11.5 mmol) in tetrahydrofuran (60 mL) was treated with N-hydroxysuccinimide (1.70 g, 14.9 mmol) and N,N'-dicyclohexylcarbodiimide (3.08 g, 14.9 mmol) and stirred under a nitrogen atmosphere for 3 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-tert-butyl 4-(2-(3-((tert-butoxycarbonyl)amino)propanamido)-3-((2,5-dioxopyrrolidin-1-yl)oxy)-3-oxopropyl)-1H-imidazole-1-carboxylate (7.20 g, quantitative) as a white foam: $^1$H NMR (300 MHz, CDCl$_3$) δ 8.02 (s, 1H), 7.41 (s, 1H), 5.72 (br s, 1H), 5.17-5.11 (m, 1H), 3.51-3.3.41 (m, 2H), 3.21 (d, J=4.8 Hz, 2H), 2.82 (m, 5H), 2.49-2.44 (m, 2H), 1.61 (s, 9H), 1.42 (s, 9H).

Preparation of tert-Butyl 4-((S)-2-(3-((tert-butoxycarbonyl)amino)propanamido)-3-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-3-oxopropyl)-1H-imidazole-1-carboxylate

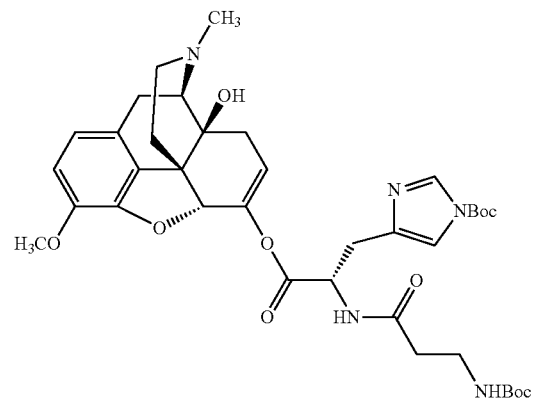 [SMILES: COc1ccc2c3c1O[C@H]1C(OC(=O)[C@H](Cc4cn(C(=O)OC(C)(C)C)cn4)NC(=O)CCNC(=O)OC(C)(C)C)=CC[C@@]4(O)[C@@H](C2)N(C)CC[C@]314]

A suspension of oxycodone (0.500 g, 1.58 mmol) in tetrahydrofuran (8 mL) was cooled in an ice bath and treated dropwise with a 1.0 M solution of lithium bis(trimethylsilyl)amide in tetrahydrofuran (3.20 mL, 3.20 mmol). The mixture was stirred at 0° C. for 15 min and then treated dropwise with a solution of(S)-tert-butyl 4-(2-(3-((tert-butoxycarbonyl)amino)propanamido)-3-((2,5-dioxopyrrolidin-1-yl)oxy)-3-oxopropyl)-1H-imidazole-1-carboxylate (1.66 g, 3.17 mmol) in tetrahydrofuran (8 mL). The reaction mixture was stirred at 0° C. for 1 h. After this time, the mixture was poured into saturated aqueous ammonium chloride (75 mL) and extracted with ethyl acetate (2×100 mL). The combined organics were dried over sodium sulfate, filtered, and concentrated under reduced pressure. The crude residue was purified by reversed phase chromatography (C18, 10-75% acetonitrile/water) and lyophilized to provide tert-butyl 4-((S)-2-(3-((tert-butoxycarbonyl)amino)propanamido)-3-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-3-oxopropyl)-1H-imidazole-1-carboxylate (0.331 g, 29%) as a white solid: $^1$H NMR (300 MHz, CDCl$_3$) δ 8.02 (s, 1H), 7.38 (s, 1H), 6.70 (d, J=6.6 Hz, 1H), 6.71 (d, J=6.6 Hz, 1H), 6.71 6.62 (d, J=8.4 Hz, 1H), 6.02 (br s, 1H), 5.58-5.55 (m, 1H), 4.97-4.90 (m, 2H), 3.85 (s, 3H), 3.58-3.38 (m, 2H), 3.20-3.13 (m, 3H), 2.85 (d, J=6.3 Hz, 1H), 2.62 (dd, J=18.6, 6.3 Hz, 1H), 2.46-2.40 (m, 3H), 2.38 (s, 3H), 2.33-2.21 (m, 2H), 2.16-2.14 (m, 2H), 1.58 (s, 9H), 1.43 (s, 9H).

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(3-aminopropanamido)-3-(1H-Imidazo-4-yl)propanoate tris(trifluoroacetic acid salt)

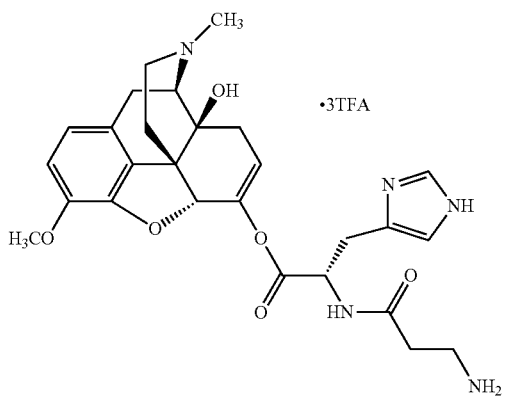 [SMILES: COc1ccc2c3c1O[C@H]1C(OC(=O)[C@H](Cc4c[nH]cn4)NC(=O)CCN)=CC[C@@]4(O)[C@@H](C2)N(C)CC[C@]314]

A solution of tert-butyl 4-((S)-2-(3-((tert-butoxycarbonyl)amino)propanamido)-3-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-3-oxopropyl)-1H-imidazole-1-carboxylate (100 mg, 0.138 mmol) in methylene chloride (4 mL) was treated with trifluoroacetic acid (1.5 mL) and stirred under a nitrogen atmosphere at ambient temperature for 1 h. After this time, the reaction mixture was concentrated under reduced pressure. The residue was triturated with diethyl ether then freeze dried from water to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(3-aminopropanamido)-3-(1H-imidazo-4-yl)propanoate tris(trifluoroacetic acid salt) (98.6 mg, quantitative) as an off-white solid: $^1$H NMR (300 MHz, DMSO-$d_6$) δ 9.22 (br s, 1H), 9.01 (s, 1H), 8.85 (d, J=7.2 Hz, 1H), 7.77 (br s, 3H), 7.49 (s, 1H), 6.88 (d, J=8.4 Hz, 1H), 6.77 (d, J=8.4 Hz, 1H), 6.35 (br s, 1H), 5.53-5.51 (m, 1H), 4.94 (s, 1H), 4.69 (q, J=8.1 Hz, 1H), 3.75 (s, 3H), 3.67 (d, J=6.3 Hz, 1H), 3.44 (d, J=20.1 Hz, 1H), 3.23-3.09 (m, 4H), 3.00-2.92 (m, 2H), 2.85 (s, 3H), 2.70-2.55 (m, 1H), 2.30 (dd, J=18.6, 6.6 Hz, 1H), 2.04 (d, J=17.7 Hz, 1H), 1.62 (d, J=11.4 Hz, 1H), two protons not observed; ESI MS m/z 524 $[C_{27}H_{33}N_5O_6+H]^+$.

Scheme 15: (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((3-aminopropanoyl)oxy)propanoate hydrochloride

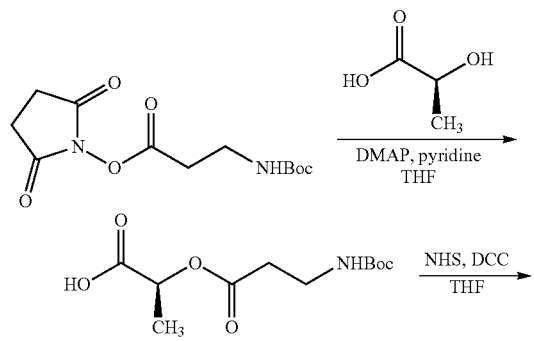

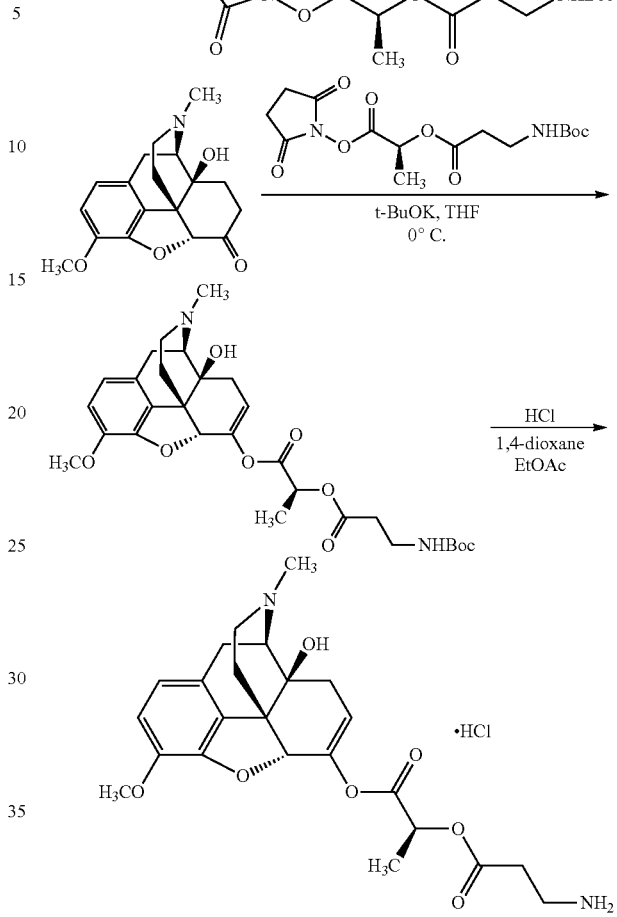

Preparation of (S)-2-((3-((tert-Butoxycarbonyl)amino)propanoyl)oxy)propanoic acid

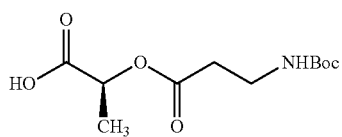

A solution of 2,5-dioxopyrrolidin-1-yl 3-((tert-butoxycarbonyl)amino)propanoate (1.00 g, 3.49 mmol), lactic acid (389 mg, 4.32 mmol), and 4-dimethylaminopyridine (45 mg, 0.37 mmol) in tetrahydrofuran (17 mL) was treated with pyridine (0.34 mL, 4.2 mmol) and heated at 50° C. under a nitrogen atmosphere for 17 h. After this time, the reaction mixture was cooled to room temperature and concentrated under reduced pressure. The residue was dissolved in ethyl acetate (50 mL) and washed with aqueous 10% citric acid (2×25 mL) and water (25 mL). The organic layer was extracted with saturated aqueous sodium bicarbonate (2×25 mL). The combined aqueous bicarbonate layers were acidified to pH ~2 with 6 N hydrochloric acid and extracted with ethyl acetate (4×25 mL). The combined organics were dried over sodium sulfate, filtered, and concentrated under reduced pressure to provide (S)-2-((3-((tert-butoxycarbonyl)amino)propanoyl)oxy)propanoic acid (489 mg, 54%) as a colorless oil: $^1$H NMR (300 MHz, CDCl$_3$) δ 5.18 (q, J=7.2 Hz, 1H), 5.11 (br s, 1H), 3.49-3.39 (m, 2H), 2.61-2.59 (m, 2H), 1.55 (d, J=7.2 Hz, 3H), 1.44 (s, 9H), CO$_2$H proton not observed; ESI MS m/z 260 [C$_{11}$H$_{19}$NO$_6$–H]$^-$.

Preparation of (S)-2,5-Dioxopyrrolidin-1-yl 2-((3-((tert-butoxycarbonyl)amino)propanoyl)oxy)propanoate

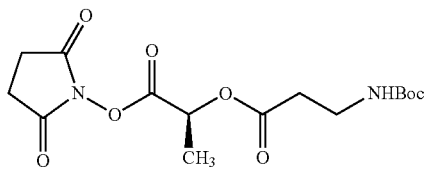

A solution of (S)-2-((3-((tert-butoxycarbonyl)amino)propanoyl)oxy)propanoic acid (489 mg, 1.87 mmol) in tetrahydrofuran (9 mL) was treated with N-hydroxysuccinimide (240 mg, 2.09 mmol) and N,N'-dicyclohexylcarbodiimide (426 mg, 2.06 mmol) and stirred under a nitrogen atmosphere for 3 h. After this time, the reaction mixture was filtered to remove the solid dicyclohexylurea byproduct. The solid was washed with diethyl ether, and the combined filtrate and washings were concentrated under reduced pressure to provide (S)-2,5-dioxopyrrolidin-1-yl 2-((3-((tert-butoxycarbonyl)amino)propanoyl)oxy)propanoate (773 mg, quantitative) as an off-white foam: $^1$H NMR (300 MHz, CDCl$_3$) δ 5.40 (q, J=6.9 Hz, 1H), 5.16-5.11 (m, 1H), 3.46-3.42 (m, 2H), 2.85 (s, 4H), 2.65-2.62 (m, 2H), 1.69 (d, J=6.9 Hz, 3H), 1.43 (s, 9H).

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((3-((tert-butoxycarbonyl)amino)propanoyl)oxy)propanoate

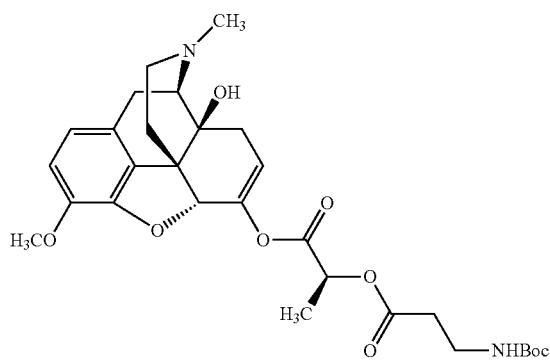 [SMILES: COc1ccc2c3c1O[C@H]1C(OC(=O)[C@H](C)OC(=O)CCNC(=O)OC(C)(C)C)=CC[C@@]4(O)[C@@H](C2)N(C)CC[C@]314]

A suspension of oxycodone (560 mg, 1.78 mmol) in tetrahydrofuran (6 mL) was cooled in an ice bath and treated dropwise with a 1.0 M solution of potassium tert-butoxide in tetrahydrofuran (2.1 mL, 2.1 mmol). After addition was complete, the mixture was stirred in the ice bath for 1 h. The mixture was treated dropwise with a solution of (S)-2,5-dioxopyrrolidin-1-yl 2-((3-((tert-butoxycarbonyl)amino) propanoyl)oxy)propanoate (761 mg, 2.12 mmol) in tetrahydrofuran (6 mL). After addition was complete, the mixture was stirred in the ice bath for 15 min. After this time, the reaction mixture was treated with saturated aqueous ammonium chloride (50 mL) and extracted with ethyl acetate (2×50 mL). The combined organics were washed with saturated sodium bicarbonate (2×25 mL) and brine (2×25 mL), dried over sodium sulfate, filtered, and concentrated under reduced pressure. The crude residue was purified by column chromatography (silica gel, 0-10% methanol/methylene chloride) followed by reversed phase column chromatography (50 g C18 column, 10-100% acetonitrile/water) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-((tert-butoxycarbonyl)amino)propanoyl)oxy)propanoate (132 mg, 13%) as a fluffy white solid: ESI MS m/z 559 [C$_{29}$H$_{38}$N$_2$O$_9$+H]$^+$.

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((3-aminopropanoyl)oxy)propanoate hydrochloride

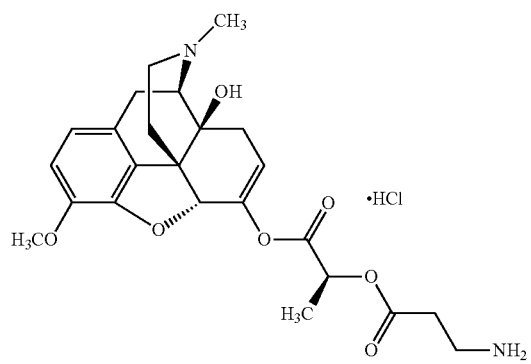 [SMILES: COc1ccc2c3c1O[C@H]1C(OC(=O)[C@H](C)OC(=O)CCN)=CC[C@@]4(O)[C@@H](C2)N(C)CC[C@]314 ; Cl]

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-((tert-butoxycarbonyl)amino)propanoyl)oxy)propanoate (35 mg, 0.063 mmol) in ethyl acetate (1 mL) was treated with a 4.0 M solution of hydrogen chloride in 1,4-dioxane (1 mL) and stirred under a nitrogen atmosphere at ambient temperature for 1 h. After this time, the reaction mixture was diluted with diethyl ether and sonicated to produce a solid precipitate. The solid was isolated by filtration, washed with diethyl ether, dried under vacuum, and freeze-dried from water to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-aminopropanoyl)oxy)propanoate hydrochloride (27 mg, 81%) as a white solid: $^1$H NMR (300 MHz, DMSO-d$_6$) δ 9.24 (br s, 1H), 8.02 (br s, 3H), 6.86 (d, J=8.4 Hz, 1H), 6.76 (d, J=8.4 Hz, 1H), 6.38 (s, 1H), 5.59 (dd, J=6.0, 1.8 Hz, 1H), 5.17 (q, J=7.2 Hz, 1H), 4.99 (s, 1H), 3.76 (s, 3H), 3.70 (d, J=6.0 Hz, 1H), 3.43 (d, J=20.1 Hz, 1H), 3.16-3.04 (m, 4H), 2.85-2.79 (m, 5H), 2.65-2.57 (m, 1H), 2.49-2.27 (m, 2H, partially obscured by solvent peak), 2.05 (apparent d, J=18.0 Hz, 1H), 1.63 (d, J=10.8 Hz, 1H), 1.52 (d, J=7.2 Hz, 3H); ESI MS m/z 459 [C$_{24}$H$_{30}$N$_2$O$_7$+H]$^+$.

Scheme 16: (S)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-aminopropanoate dihydrochloride

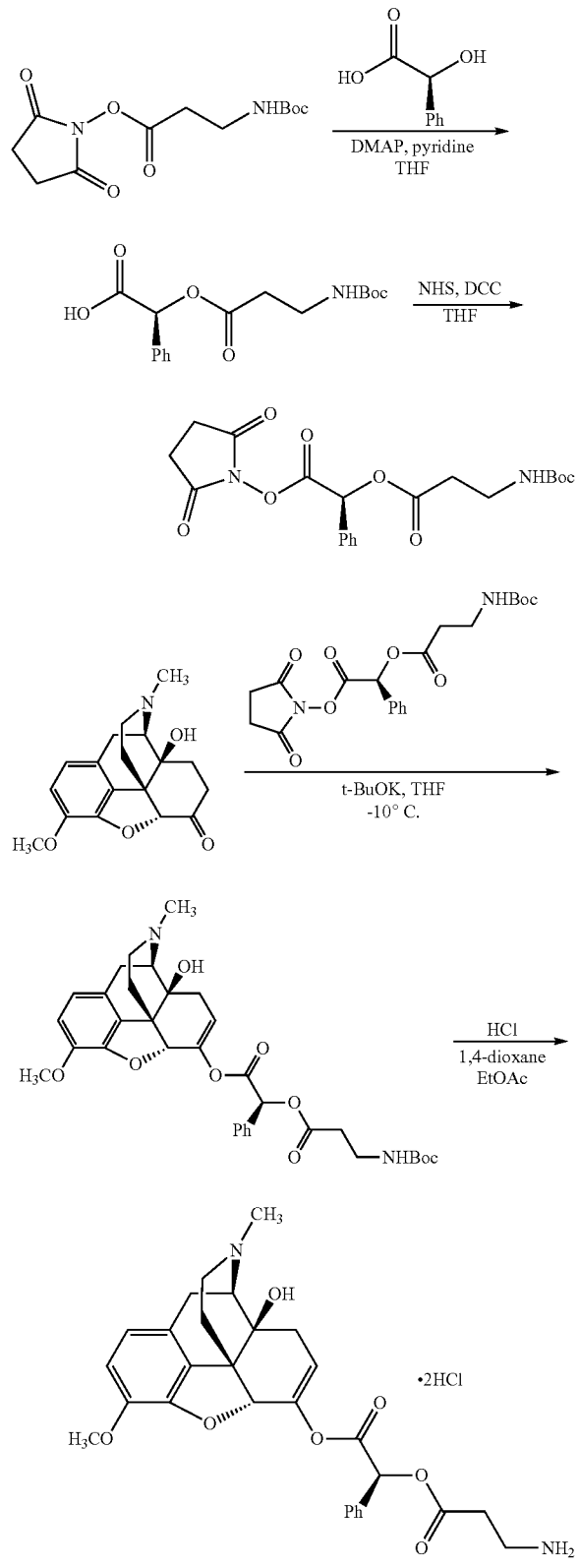

Preparation of (S)-2-((3-((tert-Butoxycarbonyl)amino)propanoyl)oxy)-2-phenylacetic acid

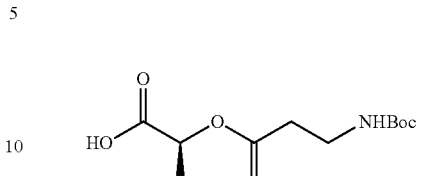

A solution of 2,5-dioxopyrrolidin-1-yl 3-((tert-butoxycarbonyl)amino)propanoate (1.04 g, 3.62 mmol), mandelic acid (457 mg, 3.00 mmol), and 4-dimethylaminopyridine (29 mg, 0.24 mmol) in tetrahydrofuran (18 mL) was treated with pyridine (0.40 mL, 5.0 mmol) and heated at 50° C. under a nitrogen atmosphere for 48 h. After this time, the reaction mixture was cooled to room temperature and concentrated under reduced pressure. The residue was dissolved in ethyl acetate (50 mL) and washed with aqueous 10% citric acid (2×25 mL) and water (25 mL). The organic layer was extracted with saturated aqueous sodium bicarbonate (2×25 mL). The combined aqueous bicarbonate layers were acidified to pH ~2 with 6 N hydrochloric acid and extracted with ethyl acetate (4×25 mL). The combined organics were dried over sodium sulfate, filtered, and concentrated under reduced pressure to provide (S)-2-((3-((tert-butoxycarbonyl)amino)propanoyl)oxy)-2-phenylacetic acid (791 mg, 81%) as a colorless oil: $^1$H NMR (300 MHz, CDCl$_3$) δ 7.50-7.36 (m, 5H), 5.99 (s, 1H), 5.18 (br s, 1H), 3.48-3.45 (m, 2H), 2.69-2.62 (m, 2H), 1.43 (s, 9H), CO$_2$H proton not observed.

Preparation of (S)-2-((2,5-Dioxopyrrolidin-1-yl)oxy)-2-oxo-1-phenylethyl 3-((tert-butoxycarbonyl)amino)propanoate

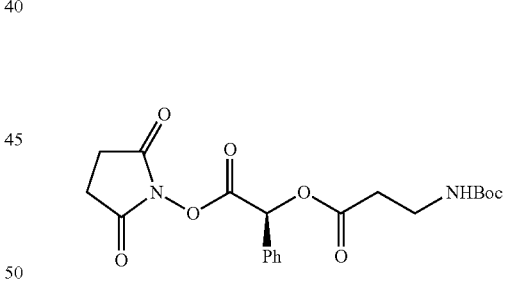

A solution of (S)-2-((3-((tert-butoxycarbonyl)amino)propanoyl)oxy)-2-phenylacetic acid (724 mg, 2.24 mmol) in tetrahydrofuran (12 mL) was treated with N-hydroxysuccinimide (298 mg, 2.59 mmol) and N,N'-dicyclohexylcarbodiimide (506 mg, 2.45 mmol) and stirred under a nitrogen atmosphere for 3 h. After this time, the reaction mixture was filtered to remove the solid dicyclohexylurea byproduct. The solid was washed with diethyl ether, and the combined filtrate and washings were concentrated under reduced pressure to provide (S)-2-((2,5-dioxopyrrolidin-1-yl)oxy)-2-oxo-1-phenylethyl 3-((tert-butoxycarbonyl)amino)propanoate (1.07 g, quantitative) as an off-white foam: $^1$H NMR (300 MHz, CDCl$_3$) δ 7.56-7.52 (m, 2H), 7.47-7.40 (m, 3H), 6.32 (s, 1H), 5.15 (t, J=5.7 Hz, 1H), 3.48-3.42 (m, 2H), 2.81 (s, 4H), 2.72-2.67 (m, 2H), 1.42 (s, 9H).

Preparation of (S)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-((tert-butoxycarbonyl)amino)propanoate

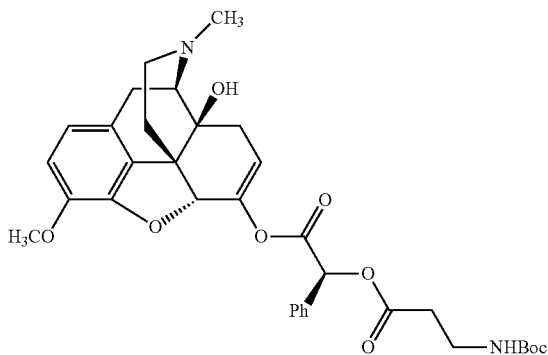 [SMILES: COc1ccc2c3c1O[C@H]1C(OC(=O)[C@@H](OC(=O)CCNC(=O)OC(C)(C)C)c4ccccc4)=CC[C@@]4(O)[C@@H](C2)N(C)CC[C@]314]

A suspension of oxycodone (645 mg, 2.05 mmol) in tetrahydrofuran (8 mL) was cooled in an ice bath and treated dropwise with a 1.0 M solution of potassium tert-butoxide in tetrahydrofuran (2.5 mL, 2.5 mmol). After addition was complete, the mixture was stirred in the ice bath for 5 min and at ambient temperature for 5 min. The mixture was re-cooled in an ice/brine bath and treated dropwise with a solution of (S)-2-((2,5-dioxopyrrolidin-1-yl)oxy)-2-oxo-1-phenylethyl 3-((tert-butoxycarbonyl)amino)propanoate (1.04 g, 2.47 mmol) in tetrahydrofuran (8 mL). After addition was complete, the mixture was stirred in the ice/brine bath for 45 min. After this time, the reaction mixture was treated with saturated aqueous ammonium chloride (50 mL) and extracted with ethyl acetate (2×50 mL). The combined organics were washed with saturated sodium bicarbonate (50 mL) and brine (50 mL), dried over sodium sulfate, filtered, and concentrated under reduced pressure. The crude residue was purified by column chromatography (silica gel, 0-10% methanol/methylene chloride) followed by reversed phase column chromatography (50 g C18 column, 30-100% acetonitrile/water) and freeze dried to provide (S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-((tert-butoxycarbonyl)amino)propanoate (128 mg, 10%) as a fluffy white solid: ESI MS m/z 621 $[C_{34}H_{40}N_2O_9+H]^+$.

Preparation of (S)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-aminopropanoate dihydrochloride

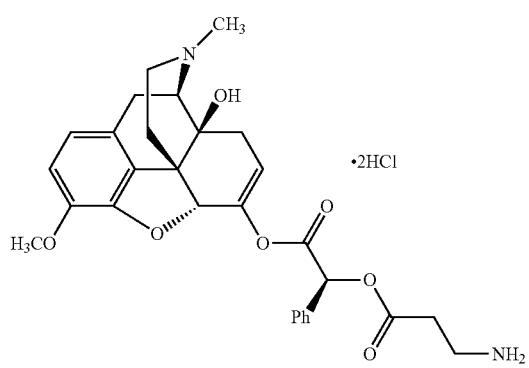 [SMILES: COc1ccc2c3c1O[C@H]1C(OC(=O)[C@@H](OC(=O)CCN)c4ccccc4)=CC[C@@]4(O)[C@@H](C2)N(C)CC[C@]314]

A solution of (S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-((tert-butoxycarbonyl)amino)propanoate (87 mg, 0.14 mmol) in ethyl acetate (1 mL) was treated with a 4.0 M solution of hydrogen chloride in 1,4-dioxane (1 mL) and stirred under a nitrogen atmosphere at ambient temperature for 1.5 h. After this time, the reaction mixture was diluted with diethyl ether and sonicated to produce a solid precipitate. The solid was isolated by filtration, washed with diethyl ether, dried under vacuum, and freeze-dried from acetonitrile/water to provide (S)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-aminopropanoate dihydrochloride (51 mg, 61%) as a white solid: $^1$H NMR (300 MHz, DMSO-$d_6$, Mixture of diastereomers) δ 9.22 (br s, 1H), 8.03 (br s, 3H), 7.57-7.56 (m, 2H), 7.49-7.46 (m, 3H), 6.86-6.80 (m, 1H), 6.76-6.72 (m, 1H), 6.38 (s, 1H), 6.14 (s, 0.66H), 6.13 (s, 0.34H), 5.55 (dd, J=6.3, 2.1 Hz, 0.66H), 5.47 (dd, J=6.0, 1.8 Hz, 0.34H), 4.96 (s, 0.66H), 4.93 (s, 0.34H), 3.72 (s, 1.02H), 3.70-3.68 (m, 1H), 3.64 (s, 1.98H), 3.41 (d, J=20.1 Hz, 1H), 3.14-3.07 (m, 4H), 2.89-2.83 (m, 5H), 2.63-2.59 (m, 1H), 2.49-2.27 (m, 2H, partially obscured by solvent peak), 2.04 (apparent d, J=18.3 Hz, 1H), 1.61 (d, J=11.7 Hz, 1H);ESI MS m/z 521 $[C_{29}H_{32}N_2O_7+H]^+$; HPLC (Method A) 95.0% (AUC), $t_R$=7.95 min.

Scheme 17: (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 3-((S)-2-hydroxy-2-phenylacetamido)propanoate trifluoroacetic acid salt

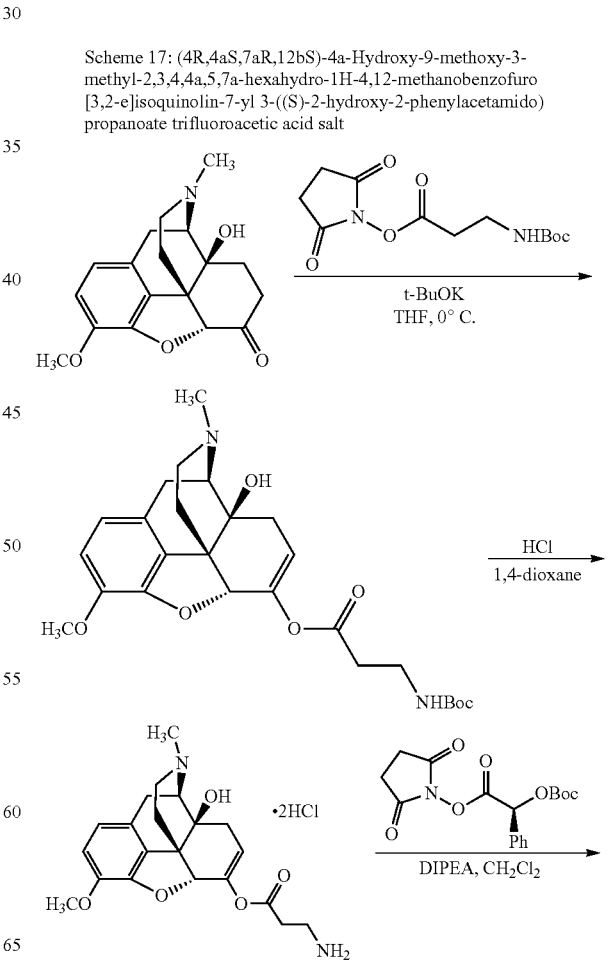

-continued

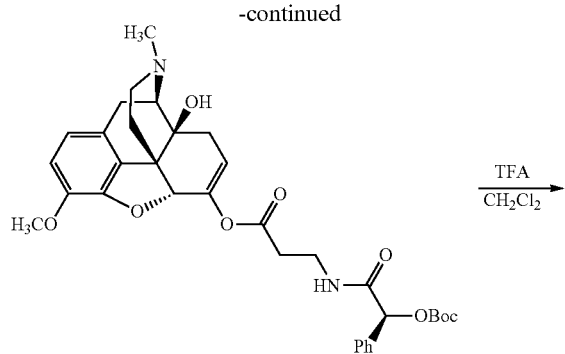

Preparation of (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 3-((tert-butoxycarbonyl)amino)propanoate

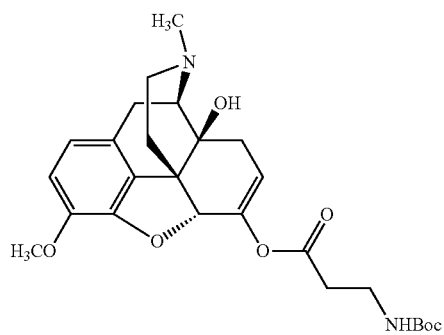 [SMILES: COc1ccc2c3c1O[C@H]1C(OC(=O)CCNC(=O)OC(C)(C)C)=CC[C@@]4(O)[C@@H](C2)N(C)CC[C@]314]

A suspension of oxycodone (1.02 g, 3.23 mmol) in tetrahydrofuran (10 mL) was cooled in an ice bath and treated with a 1.0 M solution of potassium tert-butoxide in tetrahydrofuran (3.55 mL, 3.55 mmol). After addition was complete, the mixture was stirred under nitrogen atmosphere in the ice bath for 45 min and at ambient temperature for 20 min. The solution was re-cooled in an ice/brine bath, treated dropwise with a solution of 2,5-dioxopyrrolidin-1-yl 3-((tert-butoxycarbonyl)amino)propanoate (0.972 g, 3.39 mmol) in tetrahydrofuran (10 mL), and stirred for 2 h. After this time, the reaction mixture was treated with saturated aqueous ammonium chloride (75 mL) and extracted with ethyl acetate (3×100 mL). The combined organics were washed with saturated aqueous ammonium chloride (100 mL), saturated sodium bicarbonate (2×100 mL), and brine (2×100 mL); dried over sodium sulfate; filtered; and concentrated under reduced pressure to provide (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-((tert-butoxycarbonyl)amino)propanoate (1.20 g, 76%) as a yellow oil: ESI MS m/z 487 $[C_{26}H_{34}N_2O_7+H]^+$.

Preparation of (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 3-aminopropanoate dihydrochloride

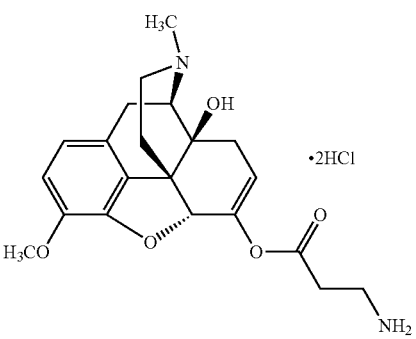 [SMILES: COc1ccc2c3c1O[C@H]1C(OC(=O)CCN)=CC[C@@]4(O)[C@@H](C2)N(C)CC[C@]314]

A solution of (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-((tert-butoxycarbonyl)amino)propanoate (0.500 g, 1.06 mmol) in 1,4-dioxane (1 mL) was treated with 4 N hydrogen chloride in 1,4-dioxane (5 mL) at ambient temperature and stirred for 2 h. After this time, the resulting precipitate was isolated by filtration, washed with 1,4-dioxane (15 mL), and dried under vacuum to provide (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-aminopropanoate dihydrochloride (0.560 g, quantitative) as an off-white solid: ESI MS m/z 387 $[C_{21}H_{26}N_2O_5+H]^+$.

Preparation of (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 3-((S)-2-((tert-butoxycarbonyl)oxy)-2-phenylacetamido)propanoate

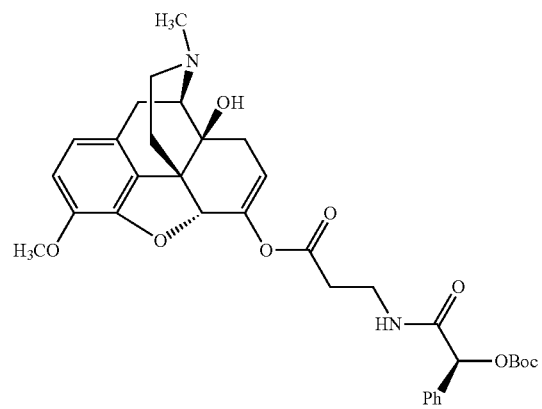

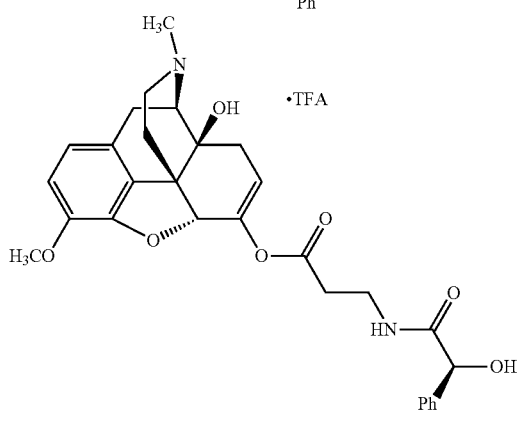

A mixture of (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-aminopropanoate dihydrochloride (0.500 g, 1.09 mmol), (S)-2,5-dioxopyrrolidin-1-yl 2-((tert-butoxycarbonyl)oxy)-2-phenylacetate (0.570 g, 1.63 mmol), and N,N-diisopropylethylamine (0.95 mL, 5.4 mmol) in methylene chloride (10 mL) was stirred at ambient temperature for 1 h. After this time, the reaction mixture was concentrated under reduced pressure. The crude residue was purified by column chromatography (silica gel, 0-4% methanol/methylene chloride) to provide (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-((S)-2-((tert-butoxycarbonyl)oxy)-2-phenylacetamido)propanoate (0.360 g, 53%) as a light yellow oil: ESI MS m/z 621 $[C_{34}H_{40}N_2O_9+H]^+$.

Preparation of (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 3-((S)-2-hydroxy-2-phenylacetamido)propanoate trifluoroacetic acid salt

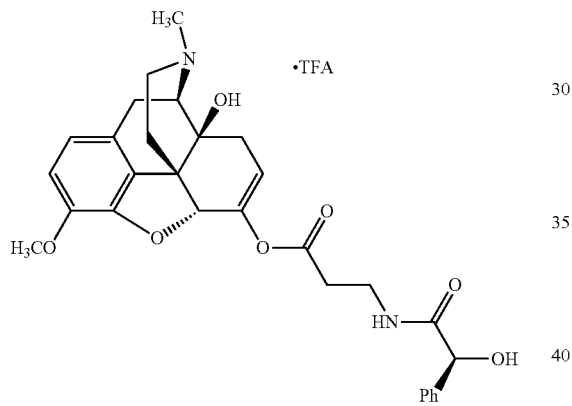

A solution of (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-((S)-2-((tert-butoxycarbonyl)oxy)-2-phenylacetamido)propanoate (0.100 g, 0.161 mmol) in methylene chloride (3 mL) was treated with trifluoroacetic acid (1 mL) and stirred under a nitrogen atmosphere at ambient temperature for 1 h. After this time, the reaction mixture was concentrated under reduced pressure. The crude residue was purified by reversed phase column chromatography (50 g C18 column, 5-50% acetonitrile/water) and freeze dried to provide (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-((S)-2-hydroxy-2-phenylacetamido)propanoate trifluoroacetic acid salt (0.026 g, 32%) as a white solid: $^1$H NMR (300 MHz, DMSO-$d_6$) δ 8.13 (t, J=6.0 Hz, 1H), 7.42-7.24 (m, 7H), 6.83 (d, J=8.1 Hz, 1H), 6.72 (d, J=8.1 Hz, 1H), 6.20 (d, J=4.8 Hz, 1H), 5.47-5.45 (m, 1H), 4.93 (s, 1H), 4.89 (d, J=4.8 Hz, 1H), 3.74 (s, 3H), 3.41-3.28 (m, 2H), 3.10-2.80 (m, 2H), 2.78-2.60 (m, 5H), 2.46-2.33 (m, 2H), 2.30-2.12 (m, 1H), 2.02 (d, J=18.0 Hz, 1H), 1.60-1.50 (m, 1H), one proton not observed; ESI MS m/z 521 $[C_{29}H_{32}N_2O_7+H]^+$; HPLC (Method A) 91.8% (AUC), $t_R$=8.15 min.

Scheme 18: (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 3-((S)-2-hydroxypropanamido)propanoate trifluoroacetic acid salt

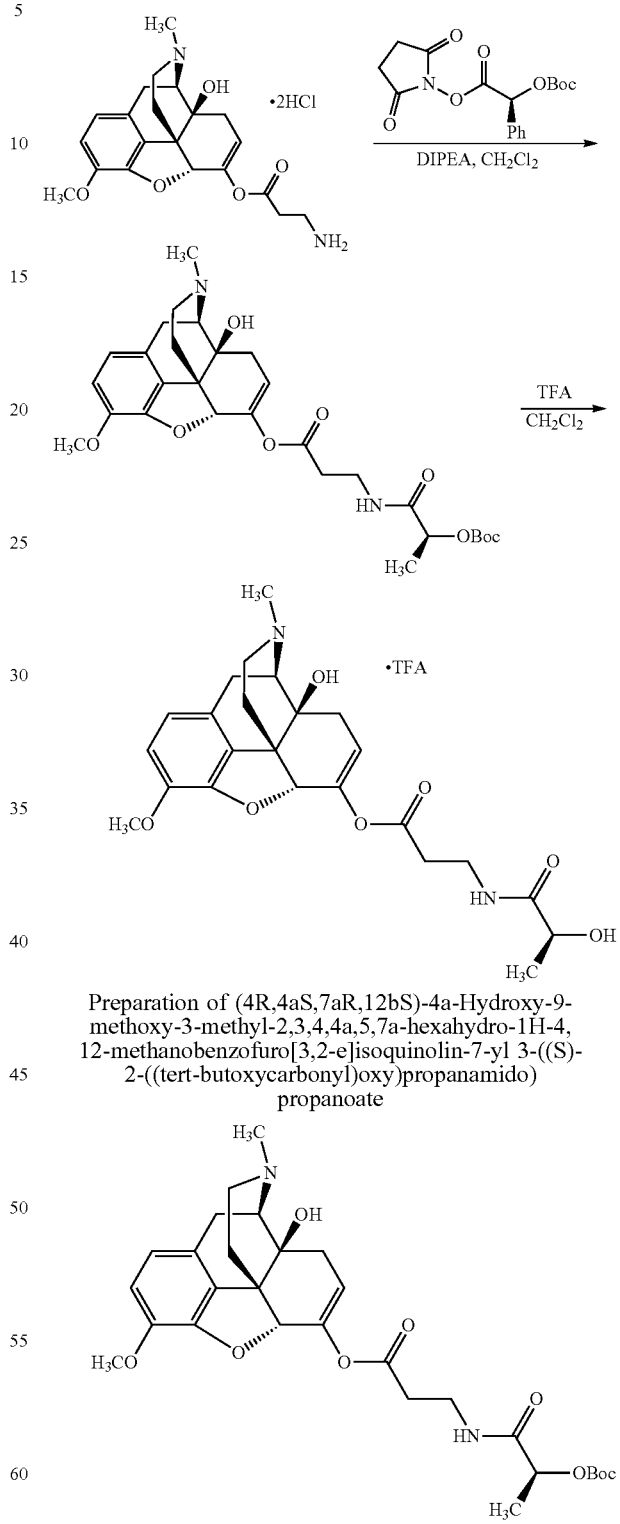

Preparation of (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 3-((S)-2-((tert-butoxycarbonyl)oxy)propanamido)propanoate

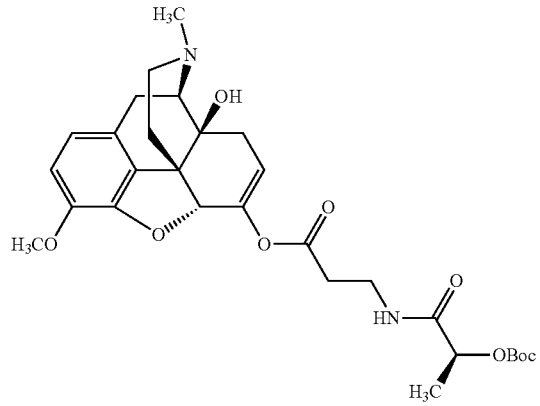

A mixture of (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-aminopropanoate dihydrochloride (0.500 g, 1.09 mmol), (S)-2,5-dioxopyrrolidin-1-yl 2-((tert-butoxycarbonyl)oxy)propanoate (0.469 g, 1.63 mmol) and N,N-diisopropylethylamine (0.95 mL, 5.44 mmol) in methylene chloride (10 mL) was stirred at ambient temperature for 2 h. After this time, the reaction mixture was concentrated under reduced pressure. The crude residue was purified by column chromatography (silica gel, 0-4% methanol/methylene chloride) to provide (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-((S)-2-((tert-butoxycarbonyl)oxy)propanamido)propanoate (0.260 g, 43%) as a white foam: ESI MS m/z 559 $[C_{29}H_{38}N_2O_9+H]^+$;

Preparation of (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 3-((S)-2-hydroxypropanamido)propanoate trifluoroacetic acid salt

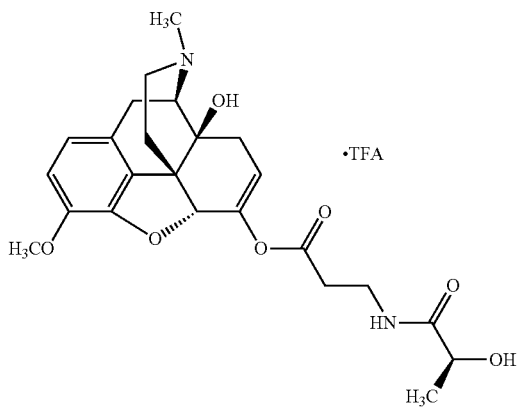 [SMILES: COc1ccc2c3c1O[C@H]1C(OC(=O)CCNC(=O)[C@H](C)O)=CC[C@@]4(O)[C@@H](C2)N(C)CC[C@]314]

A solution of (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-((S)-2-((tert-butoxycarbonyl)oxy)propanamido)propanoate (0.080 g, 0.143 mmol) in methylene chloride (3 mL) was treated with trifluoroacetic acid (1.5 mL) and stirred under a nitrogen atmosphere at ambient temperature for 1 h. After this time, the reaction mixture was concentrated under reduced pressure. The residue was triturated with a mixture of methylene chloride/diethyl ether (1:1) and filtered to give (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-((S)-2-hydroxypropanamido)propanoatetrifluoroacetic acid salt (0.044 mg, 67%) as a white solid: $^1$H NMR (300 MHz, DMSO-$d_6$) δ 9.22 (br s, 1H), 8.09 (d, J=6.9 Hz, 1H), 6.86 (d, J=8.4 Hz, 1H), 6.75 (d, J=8.1 Hz, 1H), 6.28 (s, 1H), 5.53-5.50 (m, 1H), 5.00 (s, 1H), 4.39-4.34 (m, 1H), 4.03-3.99 (m, 1H), 3.75 (s, 3H), 3.64 (d, J=5.7 Hz, 1H), 3.50-3.35 (m, 2H), 3.13-3.06 (m, 2H), 2.84 (d, J=4.5 Hz, 3H), 2.75-2.55 (m, 1H), 2.32-2.24 (m, 1H), 2.06 (d, J=18.0 Hz, 1H), 1.59 (d, J=11.7 Hz, 1H), 1.40 (d, J=7.2 Hz, 3H), 1.22 (d, J=10.5 Hz, 3H); ESI MS m/z 459 $[C_{24}H_{30}N_2O_7+H]^+$; HPLC (Method A) 93.9% (AUC), $t_R$=7.41 min.

Scheme 19: (S)-2-Hydroxy-4-((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid hydrochloride

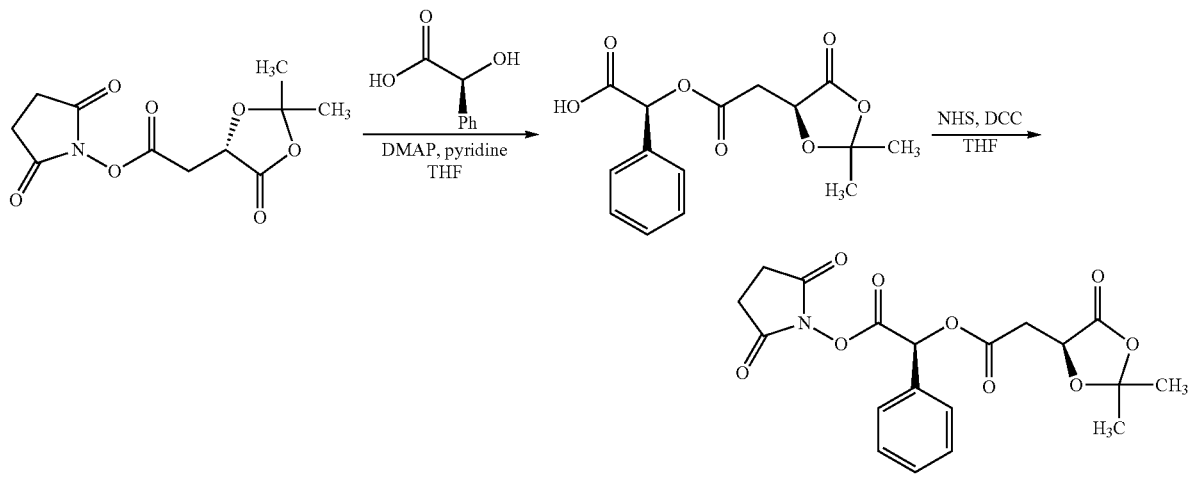

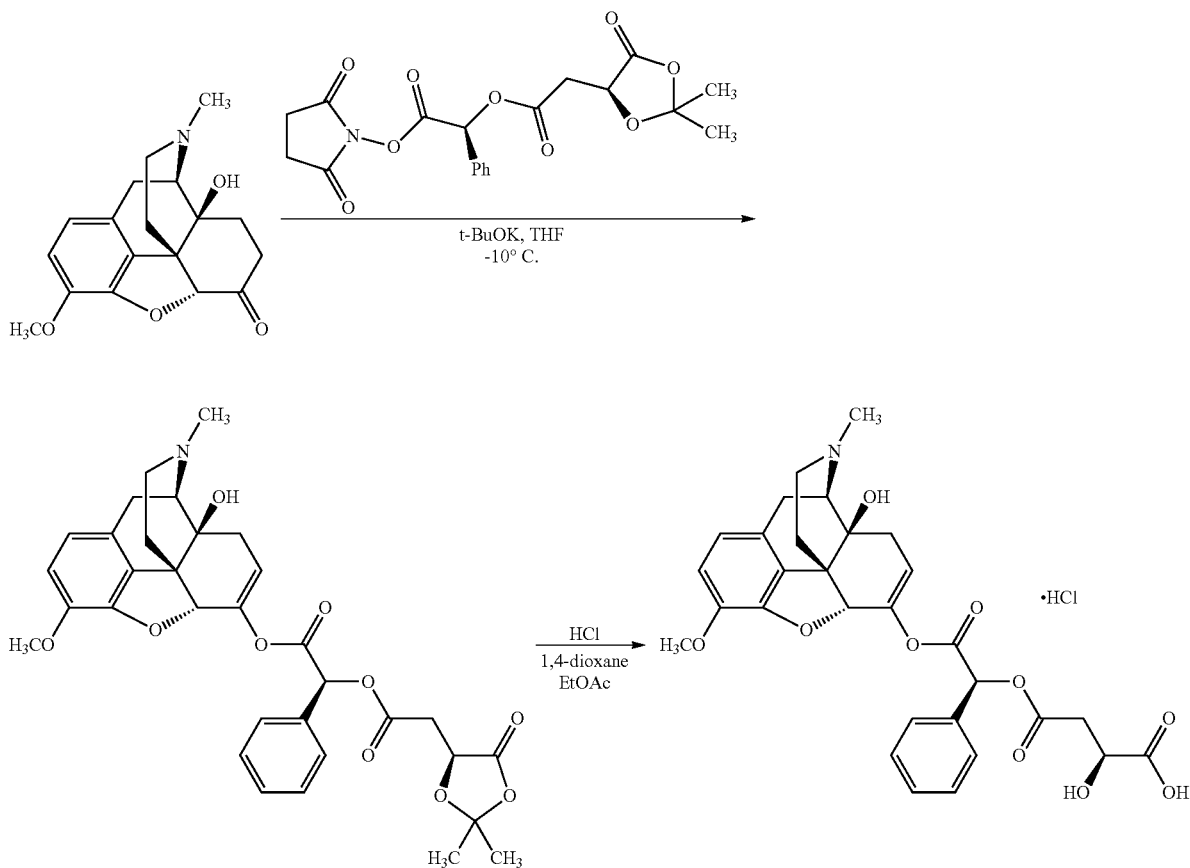

Preparation of (S)-2-(2-((S)-2,2-Dimethyl-5-oxo-1,3-dioxolan-4-yl)acetoxy)-2-phenylacetic acid

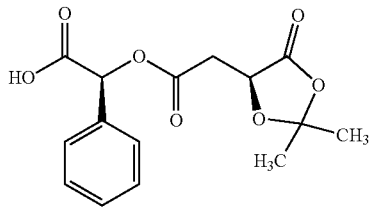 [SMILES: CC1(C)OC(=O)[C@H](CC(=O)O[C@H](C(=O)O)c2ccccc2)O1]

A solution of (S)-2,5-dioxopyrrolidin-1-yl 2-(2,2-dimethyl-5-oxo-1,3-dioxolan-4-yl)acetate (2.01 g, 7.41 mmol), mandelic acid (1.35 g, 8.87 mmol), and 4-dimethylaminopyridine (100 mg, 0.819 mmol) in tetrahydrofuran (30 mL) was treated with pyridine (0.70 mL, 8.7 mmol) and heated at 50° C. under a nitrogen atmosphere for 16 h. After this time, the reaction mixture was cooled to room temperature and concentrated under reduced pressure. The residue was dissolved in ethyl acetate (50 mL) and washed with aqueous 10% citric acid (2×25 mL) and water (25 mL). The organic layer was extracted with saturated aqueous sodium bicarbonate (2×25 mL). The combined aqueous bicarbonate layers were acidified to pH ~2 with 6 N hydrochloric acid and extracted with ethyl acetate (4×25 mL). The combined organics were dried over sodium sulfate, filtered, and concentrated under reduced pressure to provide crude (S)-2-(2-((S)-2,2-dimethyl-5-oxo-1,3-dioxolan-4-yl)acetoxy)-2-phenylacetic acid (1.55 g, 68%) as a white semisolid. The material was recrystallized from diethyl ether/ethyl acetate/heptanes to give the product (258 mg) as a white crystalline solid: $^1$H NMR (300 MHz, CDCl$_3$) δ 7.49-7.45 (m, 2H), 7.42-7.40 (m, 3H), 6.00 (s, 1H), 4.76 (dd, J=6.3, 3.6 Hz, 1H), 3.14 (dd, J=17.1, 3.6 Hz, 1H), 2.93 (dd, J=17.1, 6.3 Hz, 1H), 1.55 (s, 6H), CO$_2$H proton not observed; ESI MS m/z 615 [(2×C$_{15}$H$_{16}$O$_7$)−H]$^-$.

Preparation of (S)-2,5-Dioxopyrrolidin-1-yl 2-(2-((S)-2,2-dimethyl-5-oxo-1,3-dioxolan-4-yl)acetoxy)-2-phenylacetate

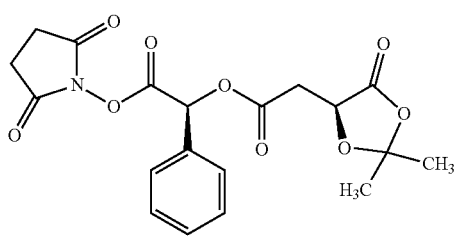 [SMILES: CC1(C)OC(=O)[C@H](CC(=O)O[C@H](C(=O)ON2C(=O)CCC2=O)c2ccccc2)O1]

A solution of (S)-2-(2-((S)-2,2-dimethyl-5-oxo-1,3-dioxolan-4-yl)acetoxy)-2-phenylacetic acid (258 mg, 0.836 mmol) in tetrahydrofuran (4 mL) was treated with N-hydroxysuccinimide (107 mg, 0.930 mmol) and N,N'-dicyclohexylcarbodiimide (191 mg, 0.926 mmol) and stirred under a nitrogen atmosphere for 3 h. After this time, the reaction mixture was filtered to remove the solid dicyclohexylurea byproduct. The solid was washed with diethyl ether, and the combined filtrate and washings were concentrated under reduced pressure to provide (S)-2,5-dioxopyrrolidin-1-yl 2-(2-((S)-2,2-dimethyl-5-oxo-1,3-dioxolan-4-yl)acetoxy)-2-phenylacetate (372 mg, quantitative) as an off-white foam: $^1$H NMR (300 MHz, CDCl$_3$) δ 7.55-7.52 (m, 2H), 7.46-7.44 (m, 3H), 6.38 (s, 1H), 4.77 (dd, J=6.6, 3.6 Hz, 1H), 3.14 (dd, J=17.4, 3.6 Hz, 1H), 2.92 (dd, J=17.4, 6.6 Hz, 1H), 2.81 (s, 4H), 1.57 (s, 3H), 1.56 (s, 3H).

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(2-((S)-2,2-d methyl-5-oxo-1,3-dioxolan-4-yl)acetoxy)-2-phenylacetate

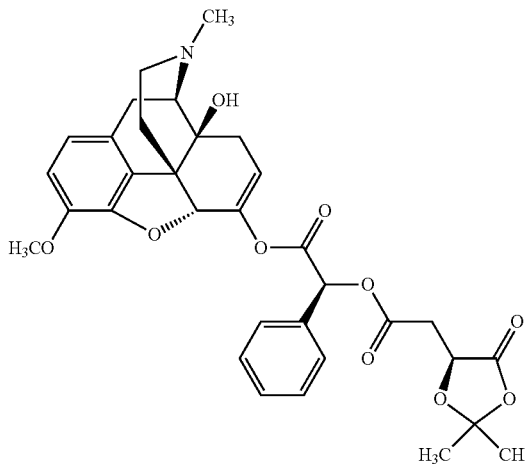

A suspension of oxycodone (241 mg, 0.764 mmol) in tetrahydrofuran (4 mL) was cooled in an ice bath and treated dropwise with a 1.0 M solution of potassium tert-butoxide in tetrahydrofuran (0.92 mL, 0.92 mmol). After addition was complete, the mixture was stirred in the ice bath for 10 min and at ambient temperature for 5 min. The mixture was re-cooled in an ice/brine bath and treated dropwise with a solution of (S)-2,5-dioxopyrrolidin-1-yl 2-(2-((S)-2,2-dimethyl-5-oxo-1,3-dioxolan-4-yl)acetoxy)-2-phenylacetate (370 mg, 0.913 mmol) in tetrahydrofuran (4 mL). After addition was complete, the mixture was stirred in the ice bath for 40 min. After this time, the reaction mixture was treated with saturated aqueous ammonium chloride (25 mL) and extracted with ethyl acetate (2×25 mL). The combined organics were washed with saturated sodium bicarbonate (25 mL) and brine (25 mL), dried over sodium sulfate, filtered, and concentrated under reduced pressure. The crude residue was purified by column chromatography (silica gel, 0-10% methanol/methylene chloride) followed by reversed phase column chromatography (15.5 g C18 column, 30-100% acetonitrile/water) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(2-((S)-2,2-dimethyl-5-oxo-1,3-dioxolan-4-yl)acetoxy)-2-phenylacetate (49 mg, 11%) as a fluffy white solid: ESI MS m/z 606 [C$_{33}$H$_{35}$NO$_{10}$+H]$^+$.

Preparation of (S)-2-Hydroxy-4-((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid hydrochloride

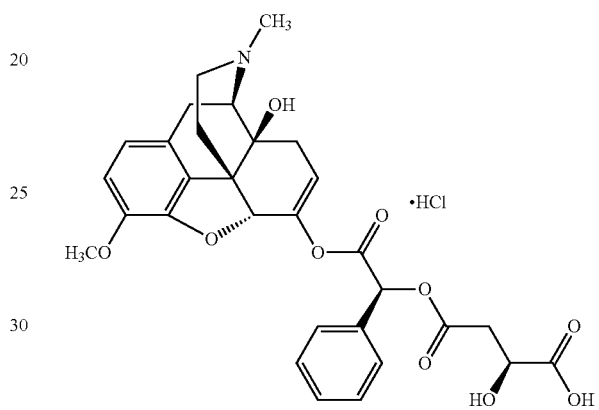

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(2-((S)-2,2-dimethyl-5-oxo-1,3-dioxolan-4-yl)acetoxy)-2-phenylacetate (47 mg, 0.078 mmol) in 1,4-dioxane (4 mL) was treated with a 4.0 M solution of hydrogen chloride in 1,4-dioxane (0.5 mL) followed by water (4 drops) and stirred under a nitrogen atmosphere at ambient temperature for 15 min. After this time, the reaction mixture was partially concentrated under reduced pressure, diluted with acetonitrile and water, and freeze dried. The crude product was purified by reversed phase column chromatography (15.5 g C18 column, 5-80% acetonitrile/water) and freeze dried to provide (S)-2-hydroxy-4-((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid hydrochloride (28 mg, 60%) as a white solid: $^1$H NMR (300 MHz, DMSO-d$_6$, Mixture of diastereomers) δ 7.56-7.54 (m, 2H), 7.46-7.44 (m, 3H), 6.75-6.62 (m, 1H), 6.09 (s, 0.68H), 6.05 (s, 0.32H), 5.54 (dd, J=5.4, 2.4 Hz, 0.68H), 5.42 (dd, J=5.4, 2.4 Hz, 0.32H), 4.81 (s, 1H), 4.29-4.25 (m, 1H), 3.70 (s, 0.96H), 3.61 (s, 2.04H), 3.13 (d, J=18.9 Hz, 1H), 2.93-2.83 (m, 2H), 2.73-2.59 (m, 2H), 2.49-2.40 (m, 1H, partially obscured by solvent peak), 2.38 (s, 3H), 2.31-1.95 (m, 5H), 1.39 (d, J=10.8 Hz, 1H), CO$_2$H, HCl, and two OH protons not observed; ESI MS m/z 566 [C$_{30}$H$_{31}$NO$_{10}$+H]$^+$; HPLC (Method A) 95.5% (AUC), t$_R$=8.86 min.

Scheme 20: (S)-4-Amino-5-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopenatnoic acid hydrochloride
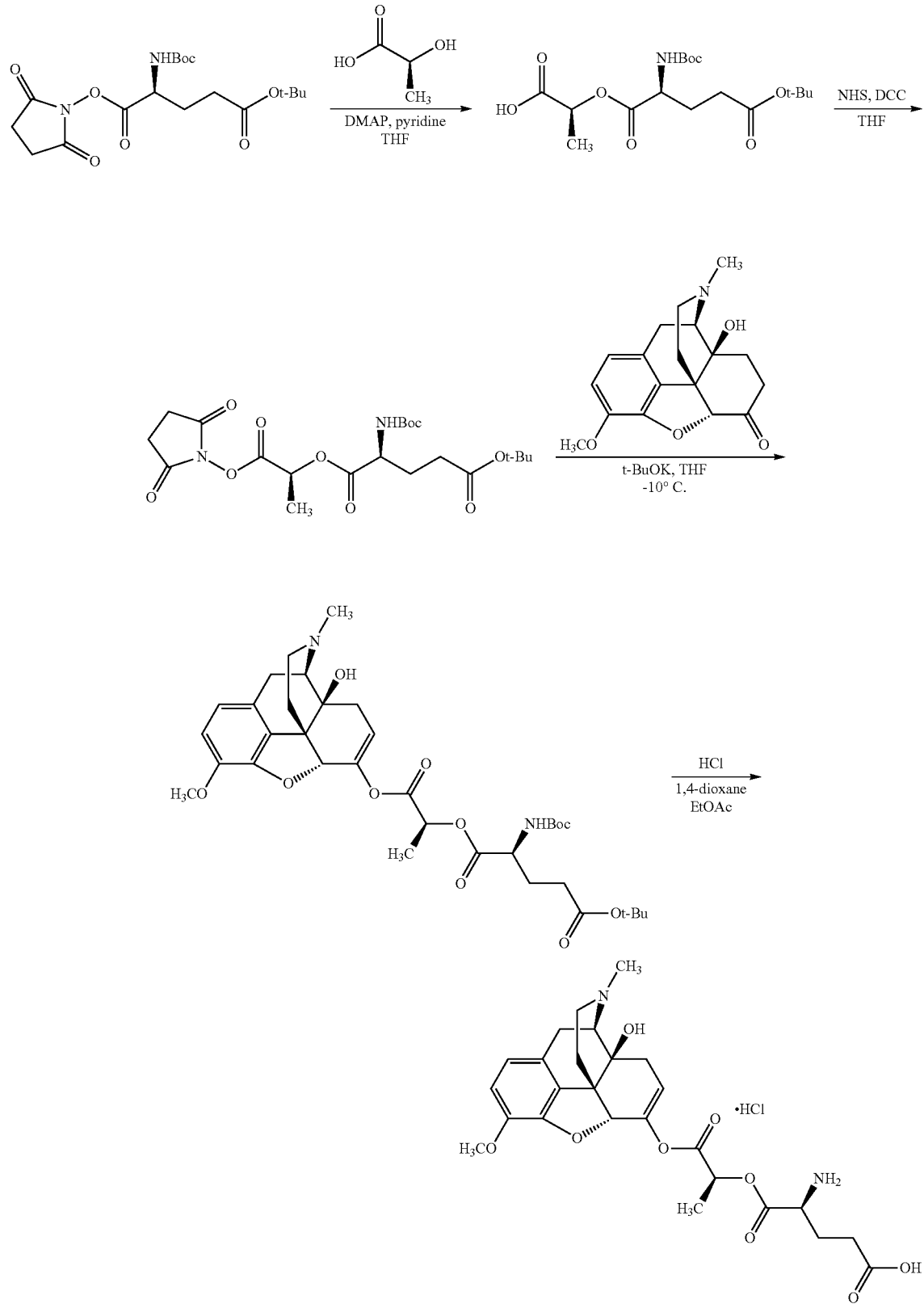

Preparation of (S)-2-(((S)-5-(tert-Butoxy)-2-((tert-butoxycarbonyl)amino)-5-oxopentanoyl)oxy)propanoic acid

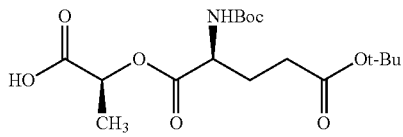 [SMILES: C[C@H](OC(=O)[C@H](CCC(=O)OC(C)(C)C)NC(=O)OC(C)(C)C)C(=O)O]

A solution of (S)-5-tert-butyl 1-(2,5-dioxopyrrolidin-1-yl) 2-((tert-butoxycarbonyl)amino)pentanedioate (3.01 g, 7.52 mmol), lactic acid (678 mg, 7.53 mmol), and 4-dimethylaminopyridine (93 mg, 0.76 mmol) in tetrahydrofuran (40 mL) was treated with pyridine (0.61 mL, 7.6 mmol) and heated at 50° C. under a nitrogen atmosphere for 48 h. After this time, the reaction mixture was cooled to room temperature and concentrated under reduced pressure. The residue was dissolved in ethyl acetate (100 mL) and washed with aqueous 10% citric acid (2×50 mL) and water (50 mL). The organic layer was extracted with saturated aqueous sodium bicarbonate (2×50 mL). The combined aqueous bicarbonate layers were acidified to pH ~1 with 6 N hydrochloric acid and extracted with ethyl acetate (4×50 mL). The combined organics were dried over sodium sulfate, filtered, and concentrated under reduced pressure to provide (S)-2-(((S)-5-(tert-butoxy)-2-((tert-butoxycarbonyl)amino)-5-oxopentanoyl)oxy)propanoic acid (2.49 g, 88%) as a colorless oil: $^1$H NMR (300 MHz, CDCl$_3$) δ 5.24-5.14 (m, 2H), 4.35-4.32 (m, 1H), 2.43-2.37 (m, 2H), 2.26-2.15 (m, 1H), 2.03-1.93 (m, 1H), 1.56 (d, J=7.2 Hz, 3H), 1.45 (s, 9H), 1.44 (s, 9H), CO$_2$H proton not observed.

Preparation of (S)-5-tert-Butyl 1-((S)-1-((2,5-dioxopyrrolidin-1-yl)oxy)-1-oxopropan-2-yl) 2-((tert-butoxycarbonyl)amino)pentanedioate

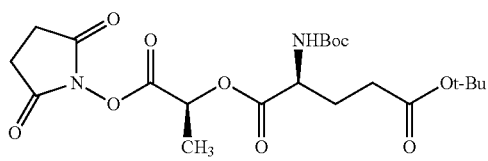 [SMILES: C[C@H](OC(=O)[C@H](CCC(=O)OC(C)(C)C)NC(=O)OC(C)(C)C)C(=O)ON1C(=O)CCC1=O]

A solution of (S)-2-(((S)-5-(tert-butoxy)-2-((tert-butoxycarbonyl)amino)-5-oxopentanoyl)oxy)propanoic acid (2.47 mg, 6.59 mmol) in tetrahydrofuran (33 mL) was treated with N-hydroxysuccinimide (836 mg, 7.26 mmol) and N,N'-dicyclohexylcarbodiimide (1.51 mg, 7.32 mmol) and stirred under a nitrogen atmosphere for 3 h. After this time, the reaction mixture was filtered to remove the solid dicyclohexylurea byproduct. The solid was washed with diethyl ether, and the combined filtrate and washings were concentrated under reduced pressure to provide (S)-5-tert-butyl 1-((S)-1-((2,5-dioxopyrrolidin-1-yl)oxy)-1-oxopropan-2-yl) 2-((tert-butoxycarbonyl)amino)pentanedioate 3.36 g, quantitative) as a tan foam: $^1$H NMR (300 MHz, CDCl$_3$) δ 5.45 (q, J=6.9 Hz, 1H), 5.20-5.12 (m, 1H), 4.43-4.33 (m, 1H), 2.84 (s, 4H), 2.39-2.34 (m, 2H), 2.0-2.15 (m, 1H), 2.02-1.90 (m, 1H), 1.71 (d, J=6.9 Hz, 3H), 1.44 (s, 9H), 1.43 (s, 9H).

Preparation of (S)-5-tert-Butyl 1-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-((tert-butoxycarbonyl)amino)pentanedioate

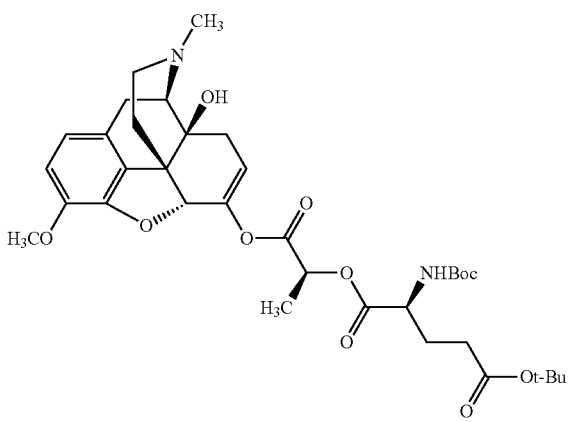 [SMILES: COc1ccc2c3c1O[C@H]1C(OC(=O)[C@H](C)OC(=O)[C@H](CCC(=O)OC(C)(C)C)NC(=O)OC(C)(C)C)=CC[C@@]4(O)[C@@H](C2)N(C)CC[C@]314]

A suspension of oxycodone (705 mg, 2.24 mmol) in tetrahydrofuran (9 mL) was cooled in an ice bath and treated dropwise with a 1.0 M solution of potassium tert-butoxide in tetrahydrofuran (2.7 mL, 2.7 mmol). After addition was complete, the mixture was stirred in the ice bath for 5 min and at ambient temperature for 5 min. The mixture was re-cooled in an ice/brine bath and treated dropwise with a solution of (S)-5-tert-butyl 1-((S)-1-((2,5-dioxopyrrolidin-1-yl)oxy)-1-oxopropan-2-yl) 2-((tert-butoxycarbonyl)amino)pentanedioate (1.28 g, 2.71 mmol) in tetrahydrofuran (9 mL). After addition was complete, the mixture was stirred in the ice/brine bath for 45 min. After this time, the reaction mixture was treated with saturated aqueous ammonium chloride (50 mL) and extracted with ethyl acetate (2×50 mL). The combined organics were washed with saturated sodium bicarbonate (2×25 mL) and brine (25 mL), dried over sodium sulfate, filtered, and concentrated under reduced pressure. The crude residue was purified by column chromatography (silica gel, 0-10% methanol/methylene chloride) followed by reversed phase column chromatography (150 g C18 column, 20-100% acetonitrile/water) and freeze dried to provide (S)-5-tert-butyl 1-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-((tert-butoxycarbonyl)amino)pentanedioate (219 mg, 15%) as a fluffy white solid: ESI MS m/z 673 [C$_{35}$H$_{48}$N$_2$O$_{11}$+H]$^+$.

Preparation of (S)-4-Amino-5-(((S)-1-(((4R,4aS, 7aR,12bS)-4a-hydroxy-9-methoxy-3-methyl-2,3,4, 4a,5,7a-hexahydro-1H-4,12-methanobenzofuro[3,2-e]isoquinolin-7-yl)oxy)-1-oxopropan-2-yl)oxy)-5-oxopentanoic acid hydrochloride

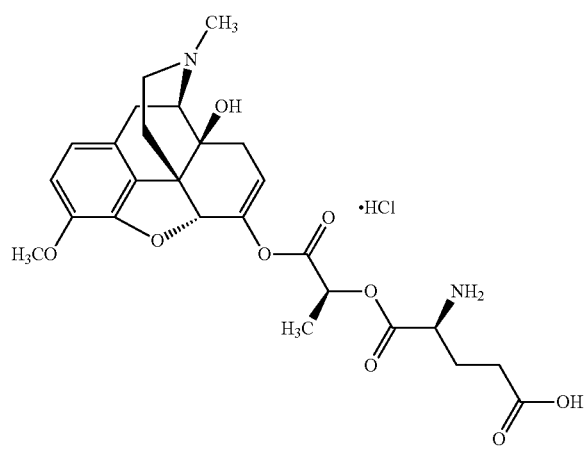 [SMILES: COc1ccc2c3c1O[C@H]1C(OC(=O)[C@H](C)OC(=O)[C@@H](N)CCC(=O)O)=CC[C@@]4(O)[C@@H](C2)N(C)CC[C@]314 ; Cl]

A solution of (S)-5-tert-butyl 1-((S)-1-(((4R,4aS,7aR, 12bS)-4a-hydroxy-9-methoxy-3-methyl-2,3,4,4a,5,7a-hexahydro-1H-4,12-methanobenzofuro[3,2-e]isoquinolin-7-yl) oxy)-1-oxopropan-2-yl) 2-((tert-butoxycarbonyl)amino) pentanedioate (145 mg, 0.216 mmol) in ethyl acetate (2 mL) was treated with a 4.0 M solution of hydrogen chloride in 1,4-dioxane (2 mL) and stirred under a nitrogen atmosphere at ambient temperature for 2 h. After this time, the reaction mixture was diluted with diethyl ether and sonicated to produce a solid precipitate. The solid was isolated by filtration, washed with diethyl ether, dried under vacuum, and freeze-dried from acetonitrile/water to provide (S)-4-amino-5-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid hydrochloride (48 mg, 38%) as a white solid: $^1$H NMR (300 MHz, DMSO-$d_6$) δ 9.09 (br s, 1H), 8.52 (br s, 2H), 6.86 (d, J=8.4 Hz, 1H), 6.76 (d, J=8.1 Hz, 1H), 6.31 (br s, 1H), 5.63-5.60 (m, 1H), 5.35 (q, J=6.9 Hz, 1H), 5.02 (s, 1H), 4.20 (apparent t, J=6.6 Hz, 1H), 3.75 (s, 3H), 3.65 (br s, 1H), 3.43 (d, J=19.8 Hz, 1H, partially obscured by water peak), 3.14-3.05 (m, 2H), 2.83 (s, 3H), 2.62-2.56 (m, 1H), 2.49-2.27 (m, 3H, partially obscured by solvent peak), 2.10-2.04 (m, 3H), 1.65-1.58 (m, 1H), 1.57 (d, J=7.2 Hz, 3H), CO$_2$H proton not observed, one proton obscured by solvent peaks; ESI MS m/z 517 [C$_{26}$H$_{32}$N$_2$O$_9$+H]$^+$; HPLC (Method A) 97.0% (AUC), $t_R$=6.88 min.

Scheme 21: (S)-2-hydroxy-4-(((S)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)amino)-4-oxobutanoic acid hydrochloride

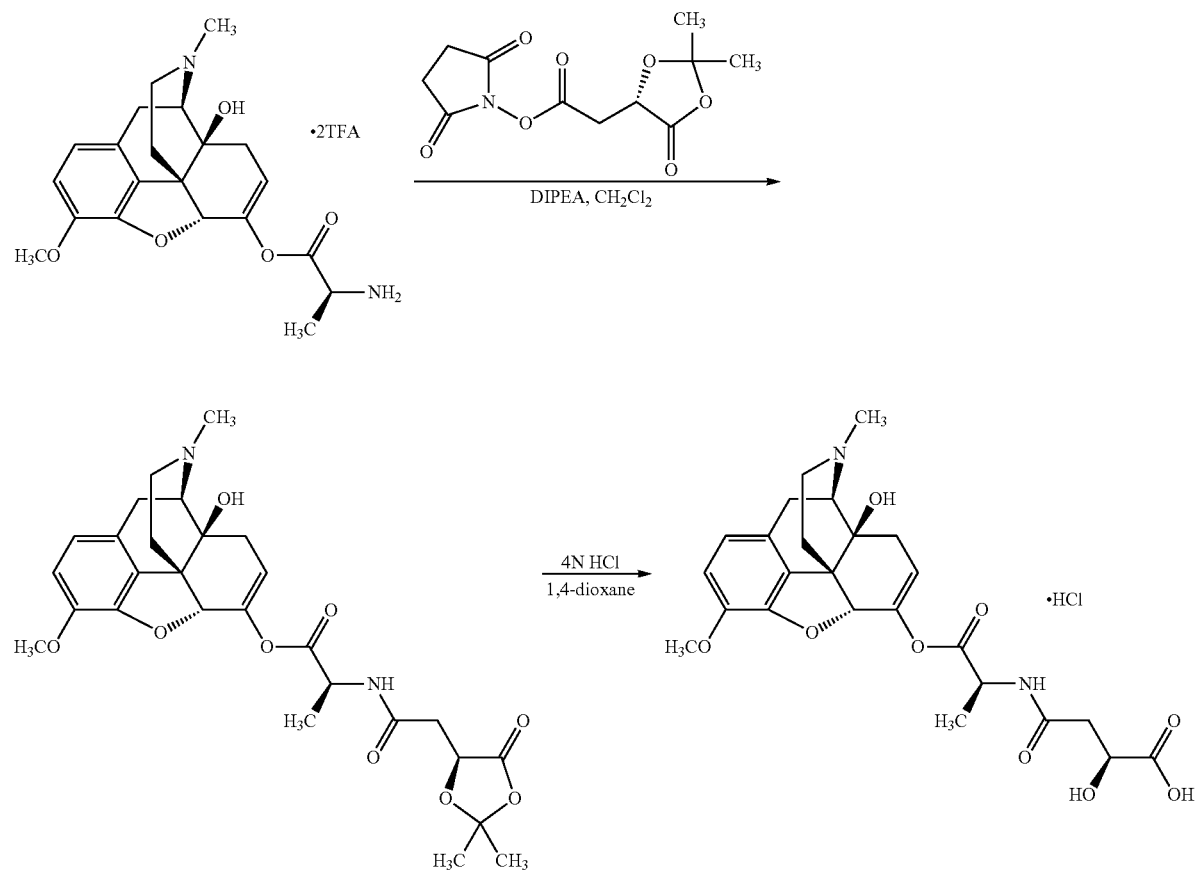

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(2-((S)-2,2-dimethyl-5-oxo-1,3-dioxolan-4-yl)acetamido)propanoate

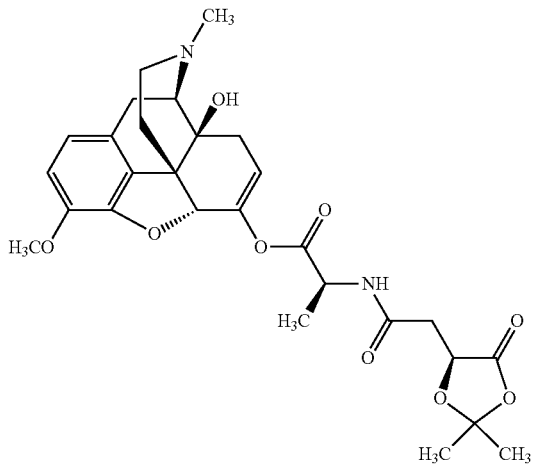 [SMILES: COc1ccc2c3c1O[C@H]1C(OC(=O)[C@H](C)NC(=O)C[C@@H]4OC(C)(C)OC4=O)=CC[C@@]4(O)[C@@H](C2)N(C)CC[C@]314]

A mixture of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-aminopropanoate (190 g, 0.309 mmol), (S)-2,5-dioxopyrrolidin-1-yl 2-(2,2-dimethyl-5-oxo-1,3-dioxolan-4-yl)acetate (0.106 g, 0.392 mmol) and pyridine (0.08 mL, 1 mmol) in methylene chloride (4 mL) was stirred at ambient temperature for 3 h. After this time, the reaction was concentrated under reduced pressure and purified by column chromatography (silica gel, 0-20% methanol/methylene chloride) to provide (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(2-((S)-2,2-dimethyl-5-oxo-1,3-dioxolan-4-yl)acetamido)propanoate (0.050 g, 30%) as a yellow solid: $^1$H NMR (300 MHz, CDCl$_3$) δ 9.17 (br s, 1H), 8.60 (d, J=6.6 Hz, 1H), 6.86 (d, J=8.4 Hz, 1H), 6.75 (d, J=8.4 Hz, 1H), 6.28 (s, 1H), 5.52 (m, 1H), 4.98 (s, 1H), 4.83-4.80 (m, 1H), 4.35-4.31 (m, 1H), 3.76 (s, 3H), 3.65-3.63 (m, 1H), 3.42 (d, J=19.5 Hz, 1H), 3.16-3.07 (m, 2H), 2.85-2.84 (m, 3H), 2.75-2.55 (m, 3H), 2.30-2.24 (m, 1H), 2.06 (d, J=17.4 Hz, 1H), 1.64 (d, J=12.3 Hz, 1H), 1.50 (s, 6H), 1.37 (d, J=7.2 Hz, 3H).

Preparation of (S)-2-hydroxy-4-(((S)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)amino)-4-oxobutanoic acid hydrochloride

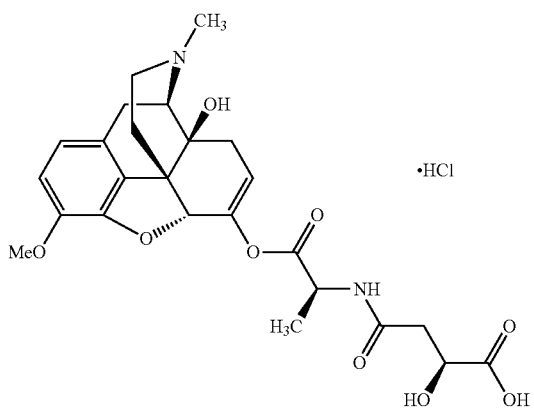 [SMILES: COc1ccc2c3c1O[C@H]1C(OC(=O)[C@H](C)NC(=O)C[C@H](O)C(=O)O)=CC[C@@]4(O)[C@@H](C2)N(C)CC[C@]314 ; Cl]

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(2-((S)-2,2-dimethyl-5-oxo-1,3-dioxolan-4-yl)acetamido)propanoate (0.040 g, 0.074 mmol) in 1,4-dioxane (4 mL) was treated with 4 N hydrogen chloride in 1,4-dioxane (0.5 mL) and 4 drops of water. The reaction mixture was stirred at ambient temperature for 0.5 h. After this time, the reaction mixture was concentrated under reduced pressure. The residue was triturated with diethyl ether and freeze dried from water to provide (S)-2-hydroxy-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)amino)-4-oxobutanoic acid hydrochloride (40 mg, quantitative) as an off-white solid: $^1$H NMR (300 MHz, DMSO-d$_6$) δ 12.5 (br s, 1H), 9.21 (br s, 1H), 8.45 (d, J=6.3 Hz, 1H), 6.85 (d, J=8.4 Hz, 1H), 6.75 (d, J=8.1 Hz, 1H), 6.34 (s, 1H), 5.54-5.52 (m, 1H), 4.99 (s, 1H), 4.37-4.31 (m, 2H), 3.75 (s, 3H), 3.69-3.65 (m, 2H), 3.39 (s, 3H), 3.13-3.07 (m, 2H), 2.84 (d, J=4.5 Hz, 3H), 2.28 (d, J=6.3 Hz, 1H), 2.05 (d, J=17.7 Hz, 1H), 1.63 (d, J=11.1 Hz, 1H), 1.36 (d, J=7.5 Hz, 3H), 1.25 (d, J=7.5 Hz, 1H); ESI MS m/z 503 [C$_{25}$H$_{30}$N$_2$O$_9$+H]$^+$; HPLC (Method A) 92.3% (AUC), t$_R$=7.03 min.

Scheme 22: (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 3-((R)-2-hydroxy-2-phenylacetamido)propanoate trifluoroacetic acid salt

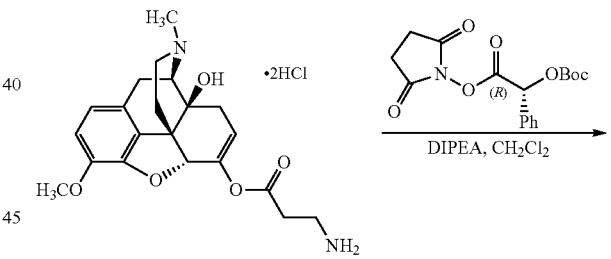

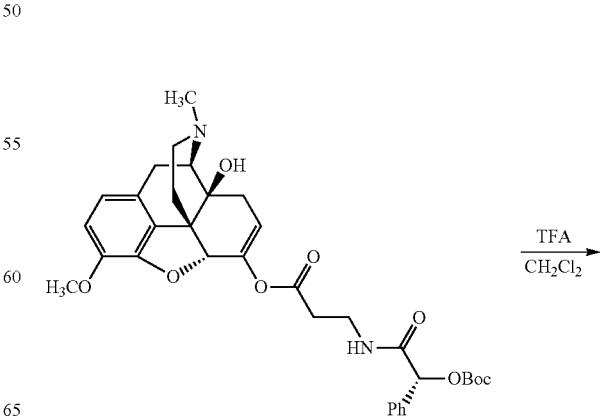

-continued

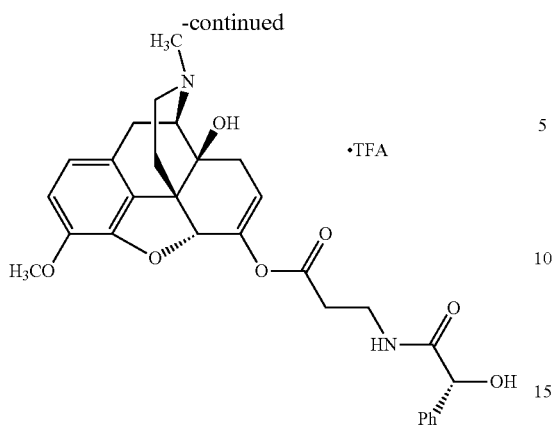

Preparation of (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 3-((R)-2-((tert-butoxycarbonyl)oxy)-2-phenylacetamido)propanoate

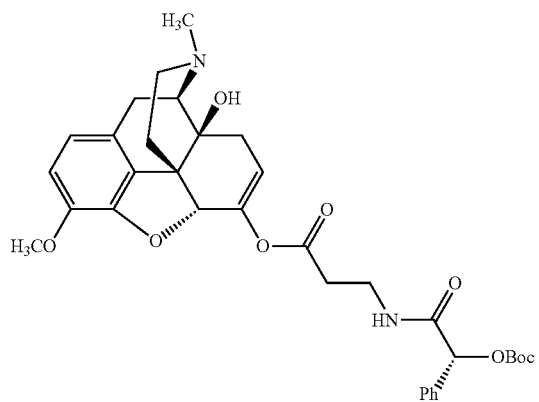

A solution of (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-aminopropanoate dihydrochloride (0.245 g, 0.533 mmol), (R)-2,5-dioxopyrrolidin-1-yl 2-((tert-butoxycarbonyl)oxy)-2-phenylacetate (0.279, 0.800 mmol), and N,N-diisopropylethylamine (0.46 mL, 2.7 mmol) in methylene chloride (5 mL) was stirred at ambient temperature for 2 h. After this time, the reaction was concentrated under reduced pressure. The crude residue was diluted with ethyl acetate (3×75 mL) and washed with water. The combined organics were dried over sodium sulfate, filtered, and concentrated under reduced pressure to give (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-((R)-2-((tert-butoxycarbonyl)oxy)-2-phenylacetamido)propanoate (0.095 g, 29%) as a colorless oil: ESI MS m/z 621 $[C_{34}H_{40}N_2O_9+H]^+$.

Preparation of (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 3-((R)-2-hydroxy-2-phenylacetamido)propanoatetrifluoroacetic acid salt

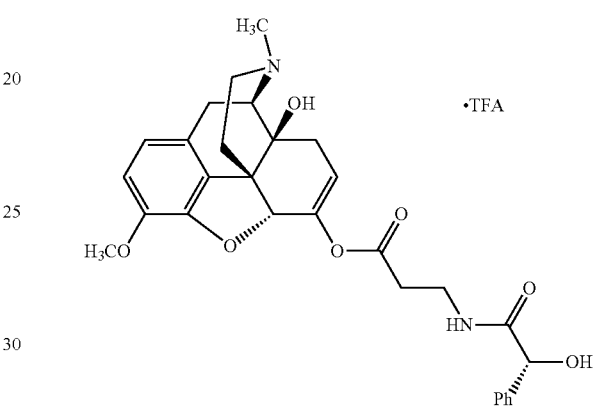

A solution of (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-((R)-2-((tert-butoxycarbonyl)oxy)-2-phenylacetamido)propanoate (0.065 g, 0.105 mmol) in dichloromethane (2 mL) was treated with trifluoroacetic acid (0.6 mL) and stirred at ambient temperature for 1 h. After this time, the reaction mixture was concentrated under reduced pressure. The crude residue was purified by reversed phase column chromatography (50 g C18 column, 5-25% acetonitrile/water) and freeze dried to provide (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-((R)-2-hydroxy-2-phenylacetamido)propanoatetrifluoroacetic acid salt (0.015 mg, 27%) as an off-white solid: $^1$H NMR (300 MHz, DMSO-$d_6$) δ 9.16 (br s, 1H), 8.13 (t, J=6.3 Hz, 1H), 7.34-7.31 (m, 2H), 7.29-7.23 (m, 3H), 6.86 (d, J=8.4 Hz, 1H), 6.75 (d, J=8.1 Hz, 1H), 6.26 (s, 1H), 6.21 (d, J=4.5 Hz, 1H), 5.50-5.48 (m, 1H), 4.97 (s, 1H), 4.89 (d, J=4.2 Hz, 1H), 3.75 (m, 3H), 3.64-3.63 (m, 1H), 3.46-3.33 (m, 3H), 3.15-3.06 (m, 2H), 2.84 (d, J=4.5 Hz, 3H), 2.63 (t, J=6.9 Hz, 3H), 2.28-2.22 (m, 1H), 2.05 (d, J=17.7 H, 1H), 1.63 (d, J=12.9 Hz, 1H); ESI MS m/z 521 $[C_{29}H_{32}N_2O_7+H]^+$; HPLC (Method A) >99% (AUC), $t_R$=8.16 min.

Scheme 23: (S)-2-Hydroxy-4-((3-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-3-oxopropyl)amino)-4-oxobutanoic acid
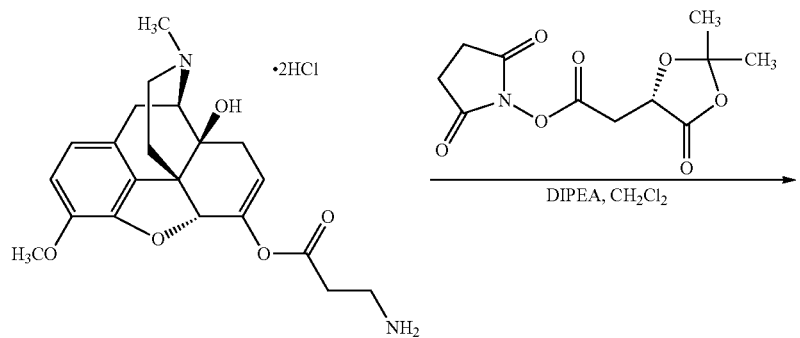
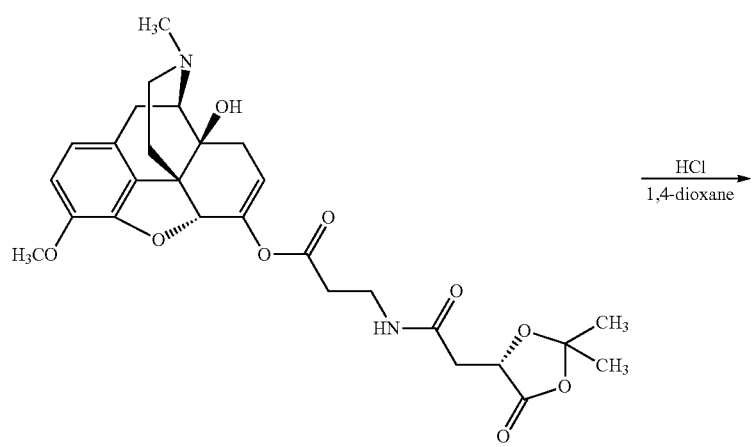
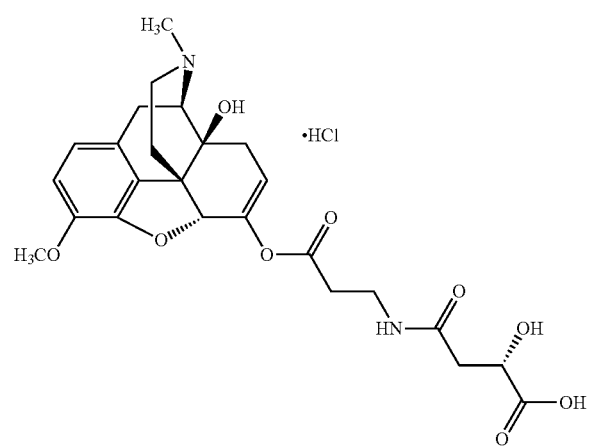

Preparation of (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 3-(2-((S)-2,2-dimethyl-5-oxo-1,3-dioxolan-4-yl)acetamido)propanoate

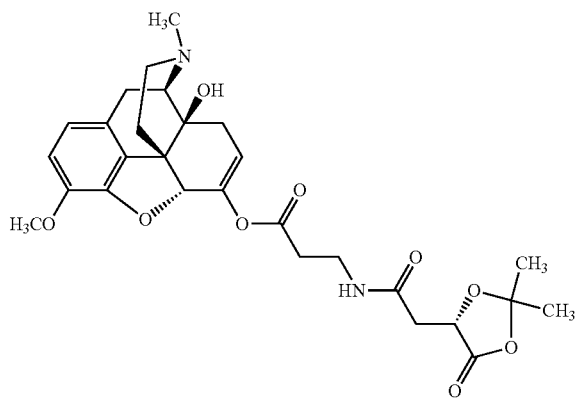 [SMILES: COc1ccc2c3c1O[C@H]1C(OC(=O)CCNC(=O)C[C@@H]4OC(C)(C)OC4=O)=CC[C@@]4(O)[C@@H](C2)N(C)CC[C@]314]

A solution of (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-aminopropanoate dihydrochloride (0.550 g, 1.19 mmol), (S)-2,5-dioxopyrrolidin-1-yl 2-(2,2-dimethyl-5-oxo-1,3-dioxolan-4-yl)acetate (0.487 g, 1.79 mmol), and N,N-diisopropylethylamine (1.0 mL, 6.0 mmol) in methylene chloride (10 mL) was stirred at ambient temperature for 2 h. After this time, the reaction was concentrated under reduced pressure. The crude residue was purified by column chromatography (silica gel, 0-4% methanol/methylene chloride) to provide (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-(2-((S)-2,2-dimethyl-5-oxo-1,3-dioxolan-4-yl)acetamido)propanoate (0.240 g, 37%) as a colorless oil: ESI MS m/z 543 $[C_{28}H_{34}N_2O_9+H]^+$.

Preparation of (S)-2-Hydroxy-4-((3-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-3-oxopropyl)amino)-4-oxobutanoic acid

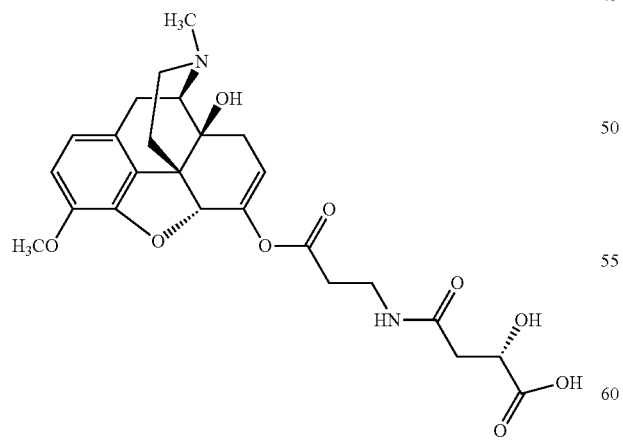

A solution of (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 3-(2-((S)-2,2-dimethyl-5-oxo-1,3-dioxolan-4-yl)acetamido)propanoate (0.115 g, 0.212 mmol) in 1,4-dioxane (4 mL) was treated with 4 N hydrogen chloride in 1,4-dioxane (0.4 mL) and 4 drops of water. The reaction mixture was stirred at ambient temperature for 1 h. Additional 4 N hydrogen chloride in 1,4-dioxane (0.25 mL) and water (2 drops) were added and stirring was continued for another 1 h. After this time, the reaction mixture was concentrated under reduced pressure. The crude residue was triturated with diethyl ether, filtered, and purified by reversed phase column chromatography (50 g C18 column, 5-15% acetonitrile/water) and freeze dried to provide (S)-2-hydroxy-4-((3-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-3-oxopropyl)amino)-4-oxobutanoic acid (0.038 mg, 36%) as an off-white solid: $^1$H NMR (300 MHz, DMSO-$d_6$) δ 8.05 (t, J=5.4 H, 1H), 6.75 (d, J=8.1 Hz, 1H), 6.66 (d, J=8.1 Hz, 1H), 5.55-5.52 (m, 1H), 4.87 (s, 1H), 4.24-4.20 (m, 1H), 3.73 (s, 3H), 3.14 (d, J=18.9 Hz, 2H), 2.91 (d, J=6.0 Hz, 1H), 2.73-2.55 (m, 3H), 2.48-2.42 (m, 2H), 2.39-2.20 (m, 5H), 2.17-1.90 (m, 3H), 1.40 (d, J=11.1 Hz, 1H), $CO_2H$ and two OH protons not observed, one proton obscured by solvent peaks; ESI MS m/z 503 $[C_{25}H_{30}N_2O_9+H]^+$; HPLC (Method A) 98.9% (AUC), $t_R$=7.06 min.

Scheme 24: (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((S)-2-hydroxy-2-phenylacetamido)propanoate trifluoroacetic acid salt

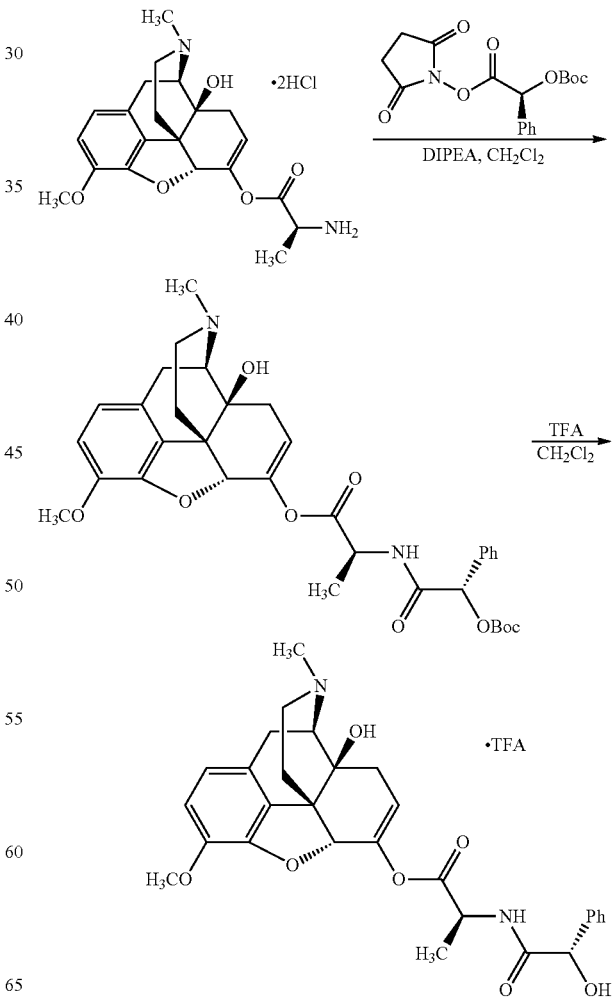

357

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((S)-2-((tert-butoxycarbonyl)oxy)-2-phenylacetamido)propanoate

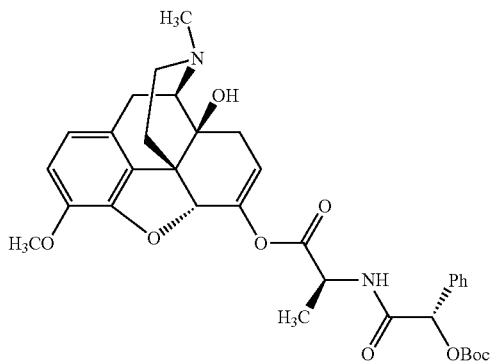

A mixture of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-aminopropanoate dihydrochloride (0.500 g, 1.09 mmol), (S)-2,5-dioxopyrrolidin-1-yl 2-((tert-butoxycarbonyl)oxy)-2-phenylacetate (0.571 g, 1.63 mmol), and N,N-diisopropylethylamine (0.95 mL, 5.4 mmol) in methylene chloride (10 mL) was stirred at ambient temperature for 1 h. After this time, the reaction mixture was concentrated under reduced pressure. The crude residue was purified by column chromatography (silica gel, 0-4% methanol/methylene chloride) to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((S)-2-((tert-butoxycarbonyl)oxy)-2-phenylacetamido)propanoate, (0.567 g, 84%) as a light yellow oil: ESI MS m/z 621 $[C_{34}H_{40}N_2O_9+H]^+$.

358

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((S)-2-hydroxy-2-phenylacetamido)propanoatetrifluoroacetic acid salt

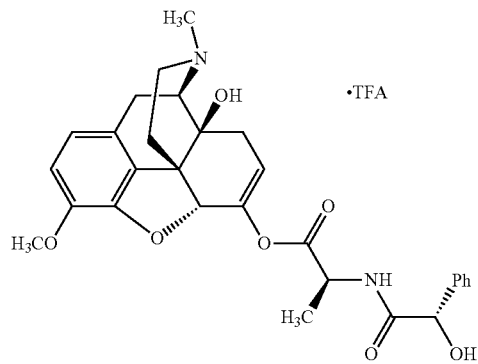 [SMILES: COc1ccc2c3c1O[C@H]1C(OC(=O)[C@H](C)NC(=O)[C@@H](O)c4ccccc4)=CC[C@@]4(O)[C@@H](C2)N(C)CC[C@]314]

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((S)-2-((tert-butoxycarbonyl)oxy)-2-phenylacetamido)propanoate (0.110 g, 0.177 mmol) in methylene chloride (3 mL) was treated with trifluoroacetic acid (1 mL) and stirred at ambient temperature for 1 h. After this time, the reaction mixture was concentrated under reduced pressure. The crude residue was purified by reversed phase column chromatography (50 g C18 column, 5-25% acetonitrile/water) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((S)-2-hydroxy-2-phenylacetamido)propanoatetrifluoroacetic acid salt (0.020 mg, 22%) as a white solid: $^1$H NMR (300 MHz, DMSO-$d_6$) δ 9.15 (br s, 1H), 8.43 (d, J=6.9 Hz, 1H), 7.43-7.40 (m, 2H), 7.34-7.21 (m, 3H), 6.85 (d, J=8.1 Hz, 1H), 6.75 (d, J=8.4 Hz, 1H), 6.27-6.22 (m, 2H), 5.41-5.40 (m, 1H), 4.96 (d, J=4.8 Hz, 2H), 4.40-4.35 (m, 1H), 3.75 (s, 3H), 3.70-3.55 (m, 1H), 3.50-3.35 (m, 1H), 3.20-3.00 (m, 2H), 2.83 (s, 3H), 2.27-2.22 (m, 1H), 2.05-1.99 (m, 1H), 1.65-1.61 (m, 1H), 1.40 (d, J=7.2 Hz, 3H), one proton obscured by solvent peaks; ESI MS m/z 521 $[C_{29}H_{32}N_2O_7+H]^+$; HPLC (Method A) 94.2% (AUC), $t_R$=8.58 min.

Scheme 25: (S)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-((S)-2-hydroxypropanamido)propanoate trifluoroacetic acid salt

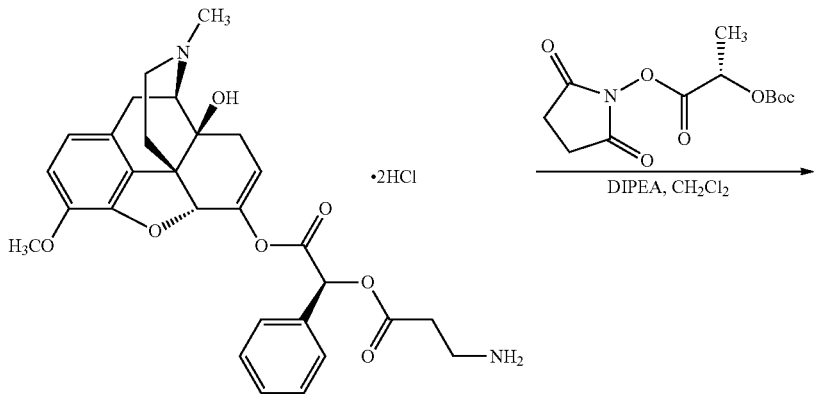

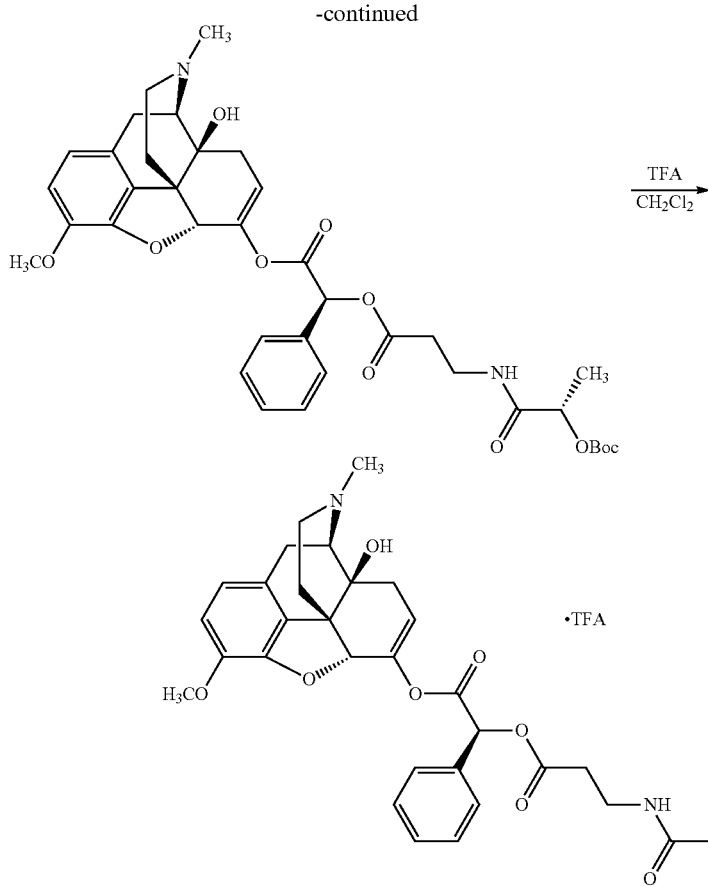

Preparation of (S)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-((S)-2-((tert-butoxycarbonyl)oxy)propanamido)propanoate

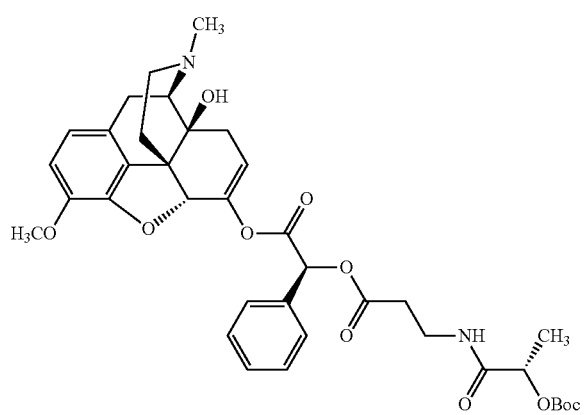

A suspension (S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-aminopropanoate dihydrochloride (50 mg, 0.084 mmol) and (S)-2,5-dioxopyrrolidin-1-yl 2-((tert-butoxycarbonyl)oxy)propanoate (36 mg, 0.13 mmol) in methylene chloride (2 mL) was treated with N,N-diisopropylethylamine (0.06 mL, 0.3 mmol) and stirred under a nitrogen atmosphere for 30 min. After this time, the reaction mixture was diluted with methylene chloride (10 mL) and washed with saturated aqueous ammonium chloride (10 mL). The organic layer was dried over sodium sulfate, filtered, and concentrated under reduced pressure. The crude residue was purified by reversed phase column chromatography (15.5 g C18 column, 20-100% acetonitrile/water) and freeze dried to provide (S)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-((S)-2-((tert-butoxycarbonyl)oxy)propanamido)propanoate (30 mg, 51%) as a fluffy white solid: ESI MS m/z 693 $[C_{37}H_{44}N_2O_{11}+H]^+$.

Preparation of (S)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-((S)-2-hydroxypropanamido)propanoate trifluoroacetic acid salt

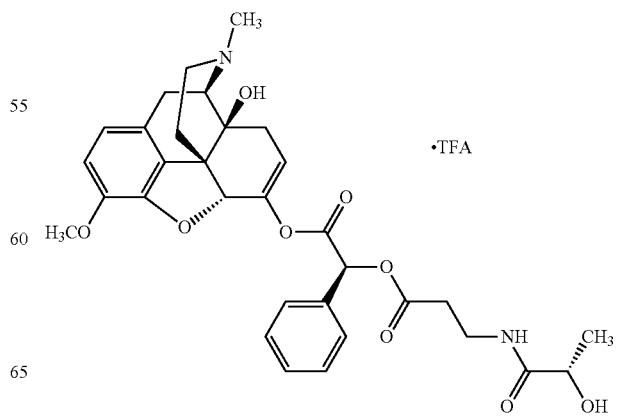

A solution of (S)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-((S)-2-((tert-butoxycarbonyl)oxy)propanamido)propanoate (30 mg, 0.043 mmol) in methylene chloride (1 mL) was treated with trifluoroacetic acid (0.5 mL) and stirred under a nitrogen atmosphere at ambient temperature for 30 min. After this time, the reaction mixture concentrated under reduced pressure. The residue was treated with diethyl ether (5 mL) and sonicated to produce a solid precipitate. The solid was isolated by filtration, washed with diethyl ether, dried under vacuum, and freeze-dried from acetonitrile/water. The crude product was purified by reversed phase column chromatography (15.5 g C18 column, 10-80% acetonitrile/water) and freeze dried to provide (S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-((S)-2-hydroxypropanamido)propanoate trifluoroacetic acid salt (23 mg, 77%) as a white solid: $^1$H NMR (300 MHz, DMSO-$d_6$, Mixture of diastereomers) δ 9.17 (br s, 1H), 7.82-7.79 (m, 1H), 7.57-7.54 (m, 2H), 7.47-7.45 (m, 3H), 6.86-6.80 (m, 1H), 6.74-6.71 (m, 1H), 6.30 (s, 1H), 6.09 (s, 0.64H), 6.07 (s, 0.36H), 5.56-5.46 (m, 2H), 4.96 (s, 0.64H), 4.93 (s, 0.36H), 3.98-3.90 (m, 1H), 3.71 (s, 1.08H), 3.63 (s, 1.92H), 3.62 (br s, 1H), 3.46-3.32 (m, 3H, partially obscured by water peak), 3.14-3.05 (m, 2H), 2.83 (s, 3H), 2.65-2.61 (m, 2H), 2.49-2.39 (m, 2H, partially obscured by solvent peak), 2.30-2.24 (m, 1H), 2.09-2.03 (m, 1H), 1.65-1.61 (m, 1H), 1.19-1.16 (m, 3H); ESI MS m/z 593 [$C_{32}H_{36}N_2O_9$+H]$^+$; HPLC (Method A) 98.2% (AUC), $t_R$=8.89 min.

Scheme 26: (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(3-((S)-2-hydroxypropanamido)propanamido)-3-(1H-imidazol-4-yl)propanoate bis(trifluoroacetic acid salt)

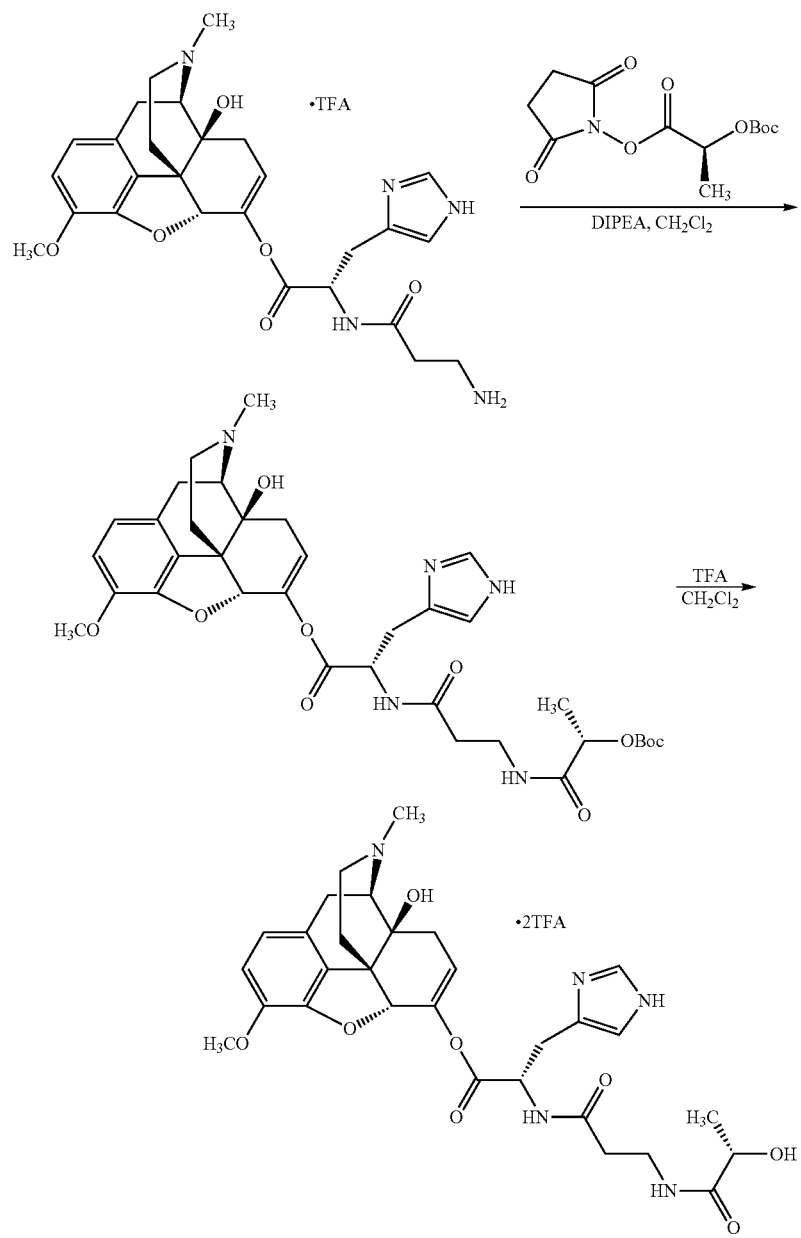

363

Preparation of (6S,13S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 13-((1H-imidazol-4-yl)methyl)-2,2,6-trimethyl-4,7,11-trioxo-3,5-dioxa-8,12-diazatetradecan-14-oate

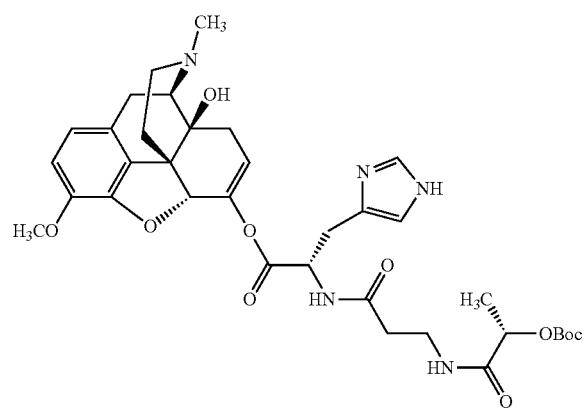

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(3-aminopropanamido)-3-(1H-imidazol-4-yl)propanoate trifluoroacetic acid salt (0.220 g, 0.250 mmol), (S)-2,5-dioxopyrrolidin-1-yl 2-((tert-butoxycarbonyl)oxy)propanoate (0.088 g, 0.31 mmol) and N,N-diisopropylethylamine (0.22 mL, 1.3 mmol) in methylene chloride (5 mL) was stirred at ambient temperature for 2 h. After this time, the reaction mixture was concentrated under reduced pressure. The residue was diluted in ethyl acetate (100 mL) and successively washed with water (75 mL) and brine (75 mL). The organic layer was dried over sodium sulfate, filtered, and concentrated under reduced pressure. The crude residue was purified by column chromatography (silica gel, 0-20% methanol/methylene chloride) to provide (6S,13S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 13-((1H-imidazol-4-yl)methyl)-2,2,6-trimethyl-4,7,11-trioxo-3,5-dioxa-8,12-diazatetradecan-14-oate (0.045 g, 26%) as a light yellow foam: ESI MS m/z 696 $[C_{35}H_{45}N_5O_{10}+H]^+$.

364

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(3-((S)-2-hydroxypropanamido)propanamido)-3-(1H-imidazol-4-yl)propanoate bis(trifluoroacetic acid salt)

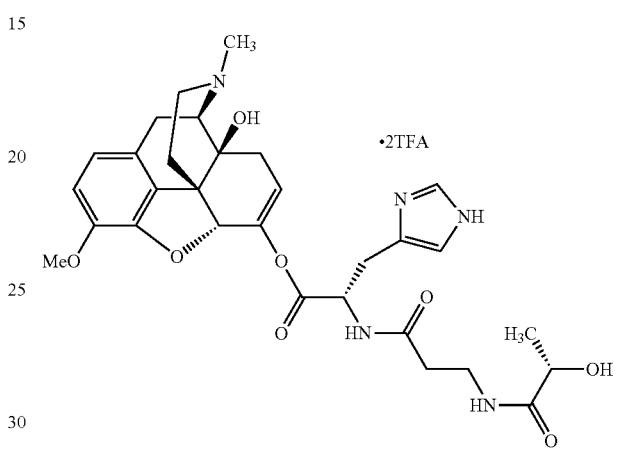

A solution of (6S,13S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 13-((1H-imidazol-4-yl)methyl)-2,2,6-trimethyl-4,7,11-trioxo-3,5-dioxa-8,12-diazatetradecan-14-oate (0.045 mg, 0.065 mmol) in methylene chloride (4 mL) was treated with trifluoroacetic acid (1 mL) and stirred under a nitrogen atmosphere at ambient temperature for 1 h. After this time, the reaction mixture was concentrated under reduced pressure. The crude residue was purified by reversed phase column chromatography (50 g C18 column, 5-60% acetonitrile/water) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(3-((S)-2-hydroxypropanamido)propanamido)-3-(1H-imidazol-4-yl)propanoate bis(trifluoroacetic acid salt) (99 mg, quantitative) as a white solid: $^1$H NMR (300 MHz, DMSO-$d_6$) δ 9.19 (br s, 1H), 8.94 (s, 1H), 8.59 (d, J=7.5 Hz, 1H), 7.72 (t, J=7.2 Hz, 1H), 7.45 (s, 1H), 6.87 (d, J=8.4 Hz, 1H), 6.76 (d, J=8.1 Hz, 1H), 6.29 (s, 1H), 5.53-5.51 (m, 2H), 4.96 (s, 1H), 4.68-4.65 (m, 1H), 3.98-3.88 (m, 1H), 3.75 (s, 3H), 3.60-3.70 (m, 1H), 3.25-3.23 (m, 3H), 3.15-3.10 (m, 4H), 2.85 (s, 3H), 2.33-2.28 (m, 3H), 2.07-2.02 (m, 1H), 1.63 (d, J=11.1 Hz, 1H), 1.228-1.24 (m, 2H), 1.17 (d, J=6.9 Hz, 3H); ESI MS m/z 596 $[C_{30}H_{37}N_5O_8+H]^+$.

Scheme 27: (S)-5-(((S)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-((S)-2-hydroxypropanamido)-5-oxopentanoic acid trifluoroacetic acid salt
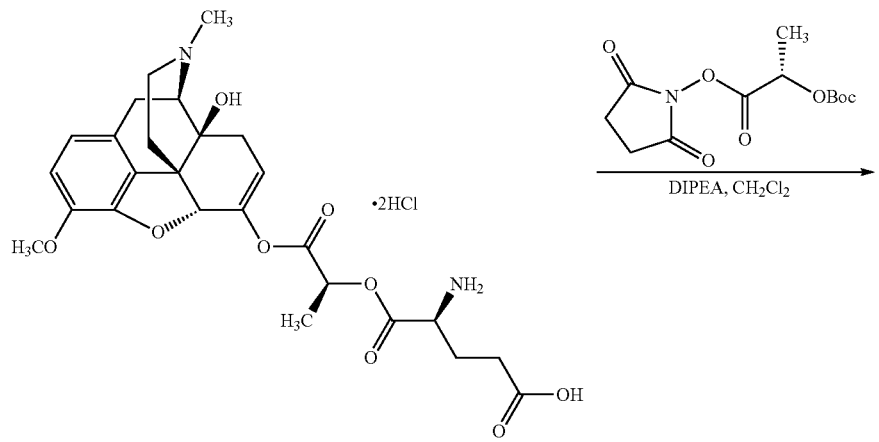
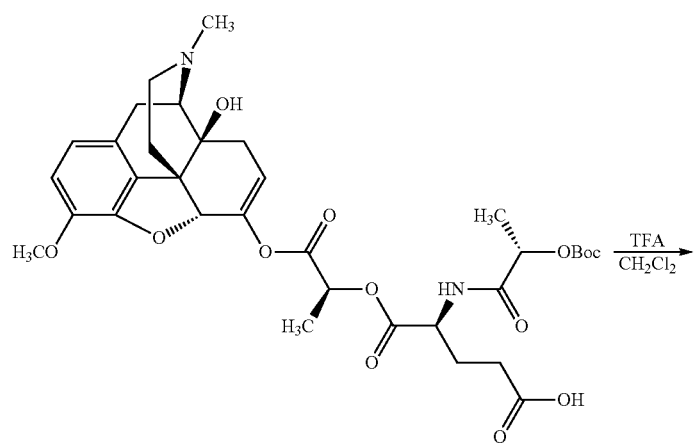
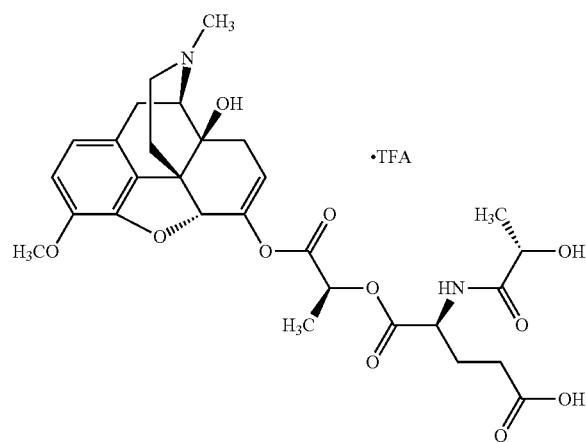

Preparation of (S)-4-((S)-2-((tert-Butoxycarbonyl)oxy)propanamido)-5-(((S)-1-(((4R,4aS,7aR,12bS)-4a-hexahydro-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid

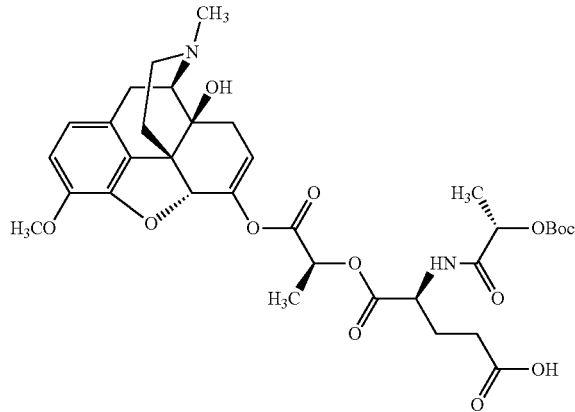

A suspension of (S)-4-amino-5-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid dihydrochloride (85 mg, 0.14 mmol) and (S)-2,5-dioxopyrrolidin-1-yl 2-((tert-butoxycarbonyl)oxy)propanoate (67 mg, 0.23 mmol) in methylene chloride (3 mL) was treated with N,N-diisopropylethylamine (0.10 mL, 0.57 mmol) and stirred under a nitrogen atmosphere for 30 min. After this time, the reaction mixture was diluted with methylene chloride (10 mL) and washed with saturated aqueous ammonium chloride (10 mL). The organic layer was dried over sodium sulfate, filtered, and concentrated under reduced pressure. The crude residue was purified by reversed phase column chromatography (15.5 g C18 column, 20-100% acetonitrile/water) and freeze dried to provide to provide (S)-4-((S)-2-((tert-butoxycarbonyl)oxy)propanamido)-5-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid (58 mg, 58%) as a fluffy white solid: ESI MS m/z 689 $[C_{34}H_{44}N_2O_{13}+H]^+$.

Preparation of (S)-5-(((S)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-((S)-2-hydroxypropanamido)-5-oxopentanoic acid trifluoroacetic acid salt

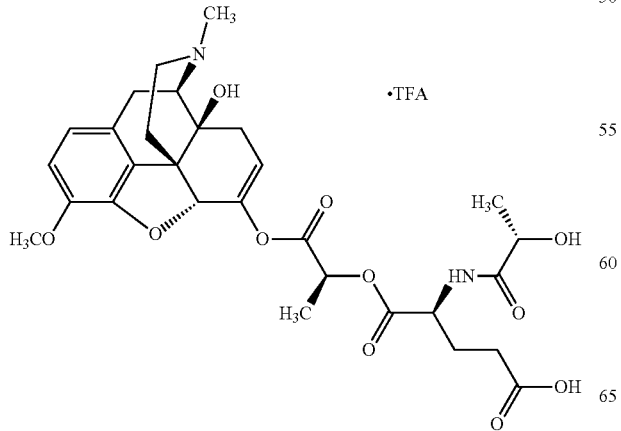

A solution of (S)-4-((S)-2-((tert-butoxycarbonyl)oxy)propanamido)-5-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid (54 mg, 0.078 mmol) in methylene chloride (1 mL) was treated with trifluoroacetic acid (0.5 mL) and stirred under a nitrogen atmosphere at ambient temperature for 45 min. After this time, the reaction mixture concentrated under reduced pressure. The residue was treated with diethyl ether (5 mL) and sonicated to produce a solid precipitate. The solid was isolated by filtration, washed with diethyl ether, dried under vacuum, and freeze-dried from acetonitrile/water to provide (S)-5-(((S)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-((S)-2-hydroxypropanamido)-5-oxopentanoic acid trifluoroacetic acid salt (44 mg, 81%) as a white solid: $^1$H NMR (300 MHz, DMSO-$d_6$) δ 12.19 (br s, 1H), 9.17 (br s, 1H), 7.99 (d, J=7.8 Hz, 1H), 6.86 (d, J=8.4 Hz, 1H), 6.75 (d, J=8.4 Hz, 1H), 6.30 (s, 1H), 5.60 (dd, J=6.0, 2.1 Hz, 1H), 5.54 (br s, 1H), 5.16 (q, J=6.9 Hz, 1H), 5.01 (s, 1H), 4.42-4.34 (m, 1H), 4.01 (q, J=6.9 Hz, 1H), 3.75 (s, 3H), 3.65 (d, J=6.3 Hz, 1H), 3.43 (d, J=20.1 Hz, 1H, partially obscured by water peak), 3.16-3.07 (m, 2H), 2.84 (apparent d, J=4.8 Hz, 3H), 2.66-2.57 (m, 1H), 2.49-2.43 (m, 1H, partially obscured by solvent peak), 2.37-2.23 (m, 3H), 2.15-2.05 (m, 2H), 1.97-1.85 (m, 1H), 1.64 (d, J=10.8 Hz, 1H), 1.52 (d, J=6.9 Hz, 3H), 1.22 (d, J=6.9 Hz, 3H); ESI MS m/z 589 $[C_{29}H_{36}N_2O_{11}+H]^+$; HPLC (Method A) 95.0% (AUC), $t_R$=7.63 min.

Scheme 28: (S)-(4R,4aS,7aR,12bS)-9-Methoxy-3-methyl-2,3,4,4a,5,7a-hexahydro-1H-4,12-methanobenzofuro[3,2-e]isoquinoline-4a,7-diyl bis(3-((S)-2-hydroxypropanamido)propanoate) trifluoroacetic acid salt

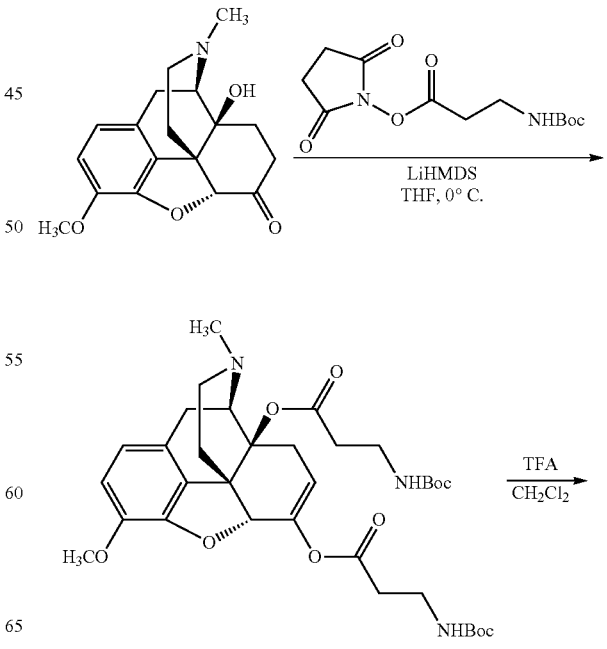

-continued

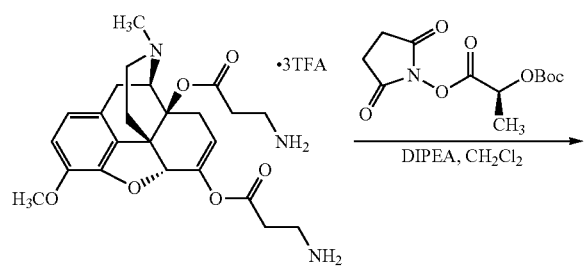

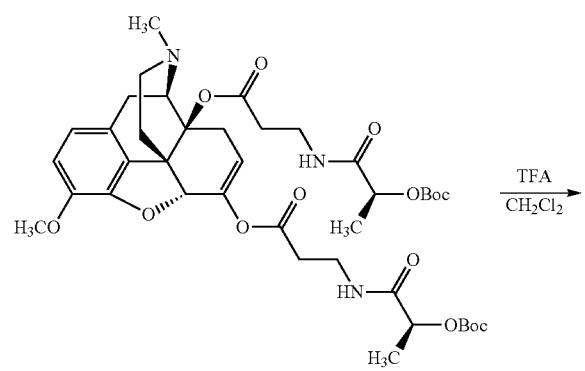

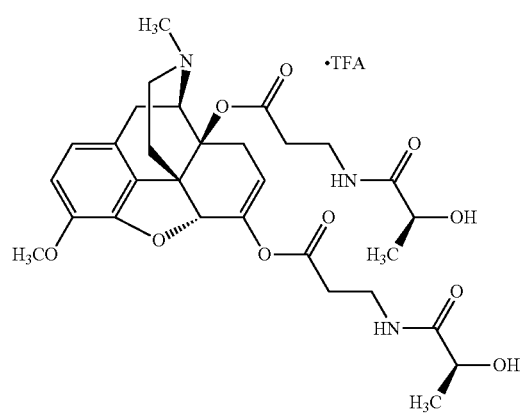

Preparation of (4R,4aS,7aR,12bS)-9-Methoxy-3-methyl-2,3,4,4a,5,7a-hexahydro-1H-4,12-methanobenzofuro[3,2-e]isoquinoline-4a,7-diyl bis(3-((tert-butoxycarbonyl)amino)propanoate)

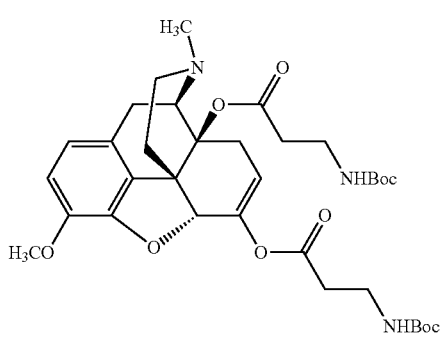 [SMILES: COc1ccc2c3c1O[C@H]1C(OC(=O)CCNC(=O)OC(C)(C)C)=CC[C@@]4(OC(=O)CCNC(=O)OC(C)(C)C)[C@@H](C2)N(C)CC[C@]314]

A suspension of oxycodone (0.490 g, 1.55 mmol) in tetrahydrofuran (10 mL) was cooled in an ice bath and treated with a 1.0 M solution of lithium bis(trimethylsilyl)amide in tetrahydrofuran (3.1 mL, 3.1 mmol). After addition was complete, the mixture was stirred under nitrogen atmosphere in the ice bath for 45 min and at ambient temperature for 20 min. The solution was re-cooled in an ice/brine bath, treated dropwise with a solution of 2,5-dioxopyrrolidin-1-yl 3-((tert-butoxycarbonyl)amino)propanoate (0.890 g, 3.11 mmol) in tetrahydrofuran (5 mL), and stirred for 2 h. After this time, the reaction mixture was treated with saturated aqueous ammonium chloride (75 mL) and extracted with ethyl acetate (3×100 mL). The combined organics were washed with saturated aqueous ammonium chloride (100 mL), saturated sodium bicarbonate (2×100 mL), and brine (2×100 mL); dried over sodium sulfate; filtered; and concentrated under reduced pressure to provide (4R,4aS,7aR,12bS)-9-methoxy-3-methyl-2,3,4,4a,5,7a-hexahydro-1H-4,12-methanobenzofuro[3,2-e]isoquinoline-4a,7-diyl bis(3-((tert-butoxycarbonyl)amino)propanoate) (0.990 g, 97%) as a yellow oil: ESI MS m/z 658 $[C_{34}H_{47}N_3O_{10}+H]^+$.

Preparation of (4R,4aS,7aR,12bS)-9-Methoxy-3-methyl-2,3,4,4a,5,7a-hexahydro-1H-4,12-methanobenzofuro[3,2-e]isoquinoline-4a,7-diyl bis(3-aminopropanoate) tris(trifluoroacetic acid salt)

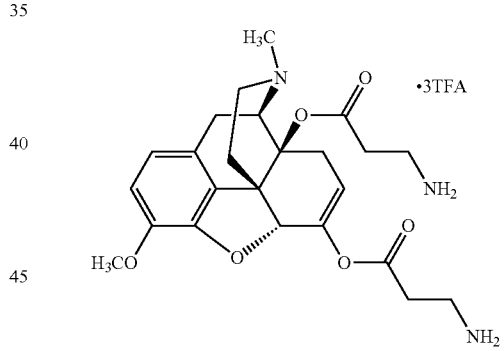

A solution of (4R,4aS,7aR,12bS)-9-methoxy-3-methyl-2,3,4,4a,5,7a-hexahydro-1H-4,12-methanobenzofuro[3,2-e]isoquinoline-4a,7-diyl bis(3-((tert-butoxycarbonyl)amino)propanoate) (0.990 g, 1.51 mmol) in methylene chloride (20 mL) was treated with trifluoroacetic acid (10 mL) and stirred under a nitrogen atmosphere at ambient temperature for 1 h. After this time, the reaction mixture was concentrated under reduced pressure and dried under vacuum to provide (4R,4aS,7aR,12bS)-9-methoxy-3-methyl-2,3,4,4a,5,7a-hexahydro-1H-4,12-methanobenzofuro[3,2-e]isoquinoline-4a,7-diyl bis(3-aminopropanoate) tris(trifluoroacetic acid salt) (1.50 g, quantitative) as a yellow oil: ESI MS m/z 458 $[C_{24}H_{31}N_3O_6+H]^+$.

Preparation of (S)-(4R,4aS,7aR,12bS)-9-Methoxy-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)propanamido)propanoate)

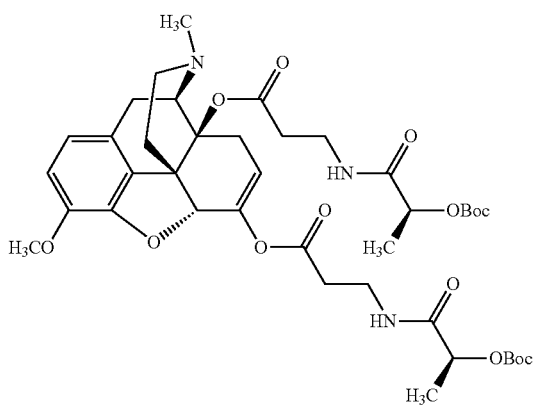

A mixture of (4R,4aS,7aR,12bS)-9-methoxy-3-methyl-2,3,4,4a,5,7a-hexahydro-1H-4,12-methanobenzofuro[3,2-e]isoquinoline-4a,7-diyl bis(3-aminopropanoate) tris(trifluoroacetic acid salt)(0.580 g, 0.725 mmol), (S)-2,5-dioxopyrrolidin-1-yl 2-((tert-butoxycarbonyl)oxy)propanoate (0.521 g, 1.81 mmol) and N,N-diisopropylethylamine (0.63 mL, 3.6 mmol) in methylene chloride (10 mL) was stirred at ambient temperature for 2 h. After this time, the reaction was concentrated under reduced pressure. The crude residue was purified by column chromatography (silica gel, 0-6% methanol/methylene chloride) to provide (S)-(4R,4aS,7aR,12bS)-9-methoxy-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)propanamido)propanoate) (0.300 g, 52%) as a colorless oil: ESI MS m/z 802 $[C_{40}H_{55}N_3O_{14}+H]^+$.

Preparation of (S)-(4R,4aS,7aR,12bS)-9-Methoxy-3-methyl-2,3,4,4a,5,7a-hexahydro-1H-4,12-methanobenzofuro[3,2-e]isoquinoline-4a,7-diyl bis(3-((S)-2-hydroxypropanamido)propanoate) trifluoroacetic acid salt

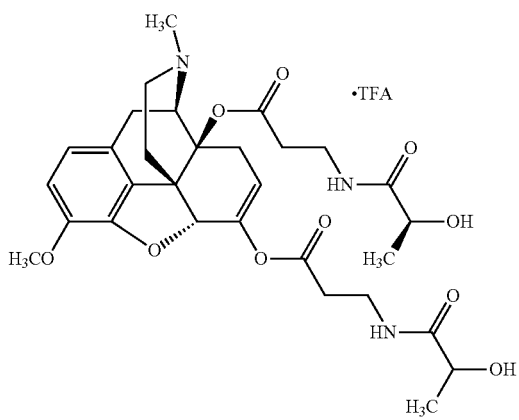 [SMILES: COc1ccc2c3c1O[C@H]1C(OC(=O)CCNC(=O)C(C)O)=CC[C@@]4(OC(=O)CCNC(=O)[C@H](C)O)[C@@H](C2)N(C)CC[C@]314]

A solution of (S)-(4R,4aS,7aR,12bS)-9-methoxy-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)propanamido)propanoate) (0.300 g, 0.374 mmol) in methylene chloride (5 mL) was treated with trifluoroacetic acid (2 mL) and stirred under a nitrogen atmosphere at ambient temperature for 1 h. After this time, the reaction mixture was concentrated under reduced pressure. The crude residue was purified by reverse phase chromatography (50 g C18 column, 5-25% acetonitrile/water with 0.1% trifluoroacetic acid) and freeze dried to provide (S)-(4R,4aS,7aR,12bS)-9-methoxy-3-methyl-2,3,4,4a,5,7a-hexahydro-1H-4,12-methanobenzofuro[3,2-e]isoquinoline-4a,7-diyl bis(3-((S)-2-hydroxypropanamido)propanoate) trifluoroacetic acid salt (0.070 mg, 31%) as a white solid: $^1$H NMR (300 MHz, DMSO-$d_6$) δ 9.44 (br s, 1H), 7.89 (dt, J=12.9, 6.0 Hz, 2H) 6.92 (d, J=8.4 Hz, 1H), 6.79 (d, J=8.4 Hz, 1H), 5.51-5.49 (m, 2H), 5.10 (s, 1H), 4.76 (d, J=5.4 Hz, 1H), 3.98-3.94 (m, 2H), 3.77 (s, 3H), 3.40-3.20 (m, 7H), 3.04-2.96 (m, 4H), 2.65-2.61 (m, 3H), 2.09 (d, J=18.3 Hz, 1H), 1.81 (d, J=12.0 Hz, 1H), 1.21 (d, J=4.5 Hz, 3H), 1.19 (d, J=4.2 Hz, 6H); ESI MS m/z 602 $[C_{30}H_{39}N_3O_{10}+H]^+$; HPLC (Method A)>99% (AUC), $t_R$=7.25 min.

Scheme 29: (R)-2-(((4R,4aS,7aR,12bS)-4a-Hydroxy-9-methoxy-3-methyl-2,3,4,4a,5,7a-hexahydro-1H-4, 12-methanobenzofuro[3,2-e]isoquinolin-7-yl)oxy)-2-oxo-1-phenylethyl 3-aminopropanoate dihydrochloride

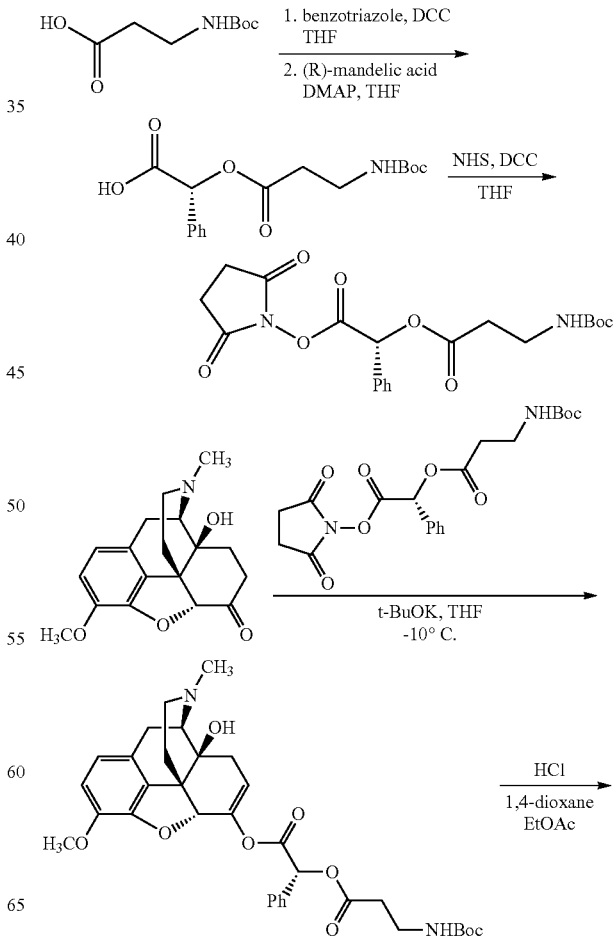

-continued

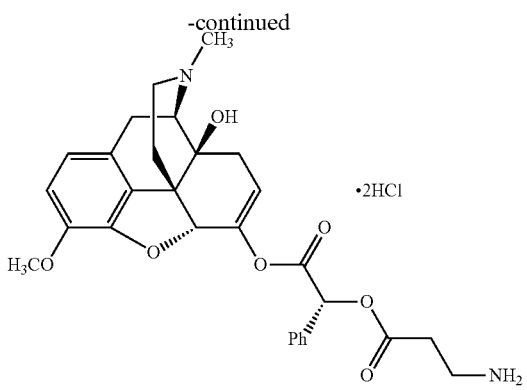

Preparation of (R)-2-((3-((tert-Butoxycarbonyl)amino)propanoyl)oxy)-2-phenylacetic acid

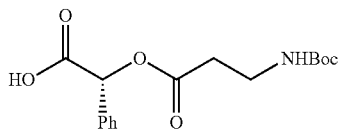 [SMILES: CC(C)(C)OC(=O)NCCC(=O)O[C@@H](C(=O)O)c1ccccc1]

A solution of 3-((tert-butoxycarbonyl)amino)propanoic acid (1.01 g, 5.31 mmol) and benzotriazole (703 mg, 5.90 mmol) in tetrahydrofuran (25 mL) was treated with N,N'-dicyclohexylcarbodiimide (1.20 g, 5.82 mmol) and stirred under a nitrogen atmosphere for 4 h. After this time, the reaction mixture was filtered to remove the solid dicyclohexylurea byproduct. The filtrate was cooled in an ice bath and treated with (R)-mandelic acid (511 mg, 3.36 mmol), and 4-dimethylaminopyridine (502 mg, 4.11 mmol) and stirred under a nitrogen atmosphere for 65 h. After this time, the reaction mixture was diluted with ethyl acetate (50 mL) and washed with aqueous 10% citric acid (2×25 mL) and water (25 mL). The organic layer was extracted with saturated aqueous sodium bicarbonate (3×25 mL). The combined aqueousbicarbonate layers were acidified to pH ~2 with 6 N hydrochloric acid and extracted with ethyl acetate (4×25 mL). The combined organics were dried over sodium sulfate, filtered, and concentrated under reduced pressure to provide (R)-2-((3-((tert-butoxycarbonyl)amino)propanoyl)oxy)-2-phenylacetic acid (1.23 g, quantitative) as a white semi-solid: $^1$H NMR (300 MHz, CDCl$_3$) δ 7.50-7.44 (m, 2H), 7.40-7.36 (m, 3H), 6.00 (s, 1H), 3.48-3.38 (m, 2H), 2.73-2.59 (m, 2H), 1.43 (s, 9H), CO$_2$H and NH protons not observed.

Preparation of (R)-2-((2,5-Dioxopyrrolidin-1-yl)oxy)-2-oxo-1-phenylethyl 3-((tert-butoxycarbonyl)amino)propanoate

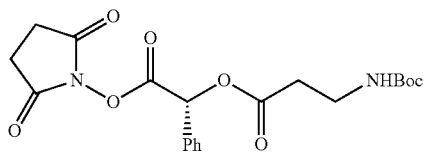 [SMILES: CC(C)(C)OC(=O)NCCC(=O)O[C@@H](C(=O)ON1C(=O)CCC1=O)c1ccccc1]

A solution of (R)-2-((3-((tert-butoxycarbonyl)amino)propanoyl)oxy)-2-phenylacetic acid (1.20 g, 3.36 mmol) in tetrahydrofuran (15 mL) was treated with N-hydroxysuccinimide (434 mg, 3.77 mmol) and N,N'-dicydohexylcarbodiimide (770 mg, 3.73 mmol) and stirred under a nitrogen atmosphere for 2 h. After this time, the reaction mixture was filtered to remove the solid dicyclohexylurea byproduct. The solid was washed with diethyl ether, and the combined filtrate and washings were concentrated under reduced pressure to provide (R)-2-((2,5-dioxopyrrolidin-1-yl)oxy)-2-oxo-1-phenylethyl 3-((tert-butoxycarbonyl)amino)propanoate (1.54 g, quantitative) as an amber foam: $^1$H NMR (300 MHz, CDCl$_3$) δ 7.56-7.53 (m, 2H), 7.46-7.44 (m, 3H), 6.32 (s, 1H), 5.14 (br s, 1H), 3.53-3.43 (m, 2H), 2.82 (br s, 4H), 2.72-2.62 (m, 2H), 1.43 (s, 9H).

Preparation of (R)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-((tert-butoxycarbonyl)amino)propanoate

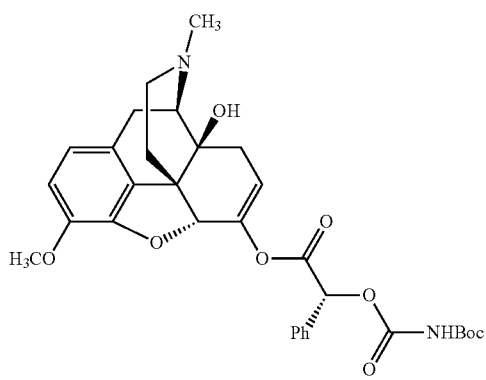 [SMILES: COc1ccc2c3c1O[C@H]1C(OC(=O)[C@H](OC(=O)NC(=O)OC(C)(C)C)c4ccccc4)=CC[C@@]4(O)[C@@H](C2)N(C)CC[C@]314]

A suspension of oxycodone (804 mg, 2.55 mmol) in tetrahydrofuran (10 mL) was cooled in an ice bath and treated dropwise with a 1.0 M solution of potassium tert-butoxide in tetrahydrofuran (3.0 mL, 3.0 mmol). After addition was complete, the mixture was stirred in the ice bath for 30 min and at ambient temperature for 5 min. The mixture was re-cooled in an ice/brine bath and treated dropwise with a solution of (R)-2-((2,5-dioxopyrrolidin-1-yl)oxy)-2-oxo-1-phenylethyl 3-((tert-butoxycarbonyl)amino)propanoate (1.54 g, 3.35 mmol) in tetrahydrofuran (8 mL). After addition was complete, the mixture was stirred in the ice/brine bath for 1 h. After this time, the reaction mixture was treated with saturated aqueous ammonium chloride (50 mL) and extracted with ethyl acetate (2×50 mL). The combined organics were washed with saturated sodium bicarbonate (25 mL) and brine (25 mL), dried over sodium sulfate, filtered, and concentrated under reduced pressure. The crude residue was purified by column chromatography (silica gel, 0-10% methanol/methylene chloride) followed by reversed phase column chromatography (150 g C18 column, 20-100% acetonitrile/water) and freeze dried to provide (R)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-((tert-butoxycarbonyl)amino)propanoate (111 mg, 7%) as a fluffy white solid: ESI MS m/z 621 [C$_{34}$H$_{40}$N$_2$O$_9$+H]$^+$.

Preparation of (R)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-aminopropanoate dihydrochloride

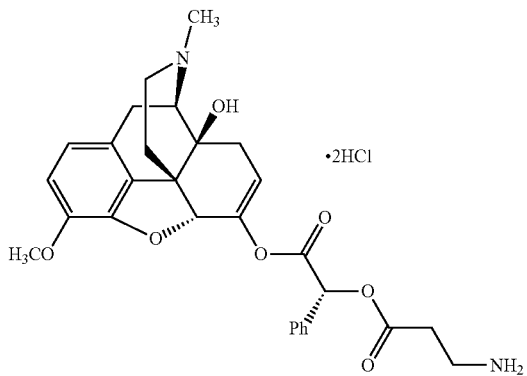 [SMILES: COc1ccc2c3c1O[C@H]1C(OC(=O)[C@H](OC(=O)CCN)c4ccccc4)=CC[C@@]4(O)[C@@H](C2)N(C)CC[C@]314]

A solution of (R)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-((tert-butoxycarbonyl)amino)propanoate (110 mg, 0.177 mmol) in ethyl acetate (3 mL) was treated with a 4.0 M solution of hydrogen chloride in 1,4-dioxane (3 mL) and stirred under a nitrogen atmosphere at ambient temperature for 2 h. After this time, the reaction mixture was diluted with diethyl ether and sonicated to produce a solid precipitate. The solid was isolated by filtration, washed with diethyl ether, dried under vacuum, and freeze-dried from water to provide (R)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-aminopropanoate dihydrochloride (91 mg, 87%) as a white solid: $^1$H NMR (300 MHz, DMSO-$d_6$, Mixture of diastereomers) δ 9.19 (br s, 1H), 7.91 (br s, 3H), 7.57-7.55 (m, 2H), 7.48-7.46 (m, 3H), 6.87-6.81 (m, 1H), 6.76-6.72 (m, 1H), 6.32 (s, 1H), 6.14 (s, 0.42H), 6.13 (s, 0.58H), 5.56-5.54 (m, 0.42H), 5.48-5.46 (m, 0.58H), 4.96 (s, 0.42H), 4.92 (s, 0.58H), 3.72 (s, 1.74H), 3.67 (br s, 1H), 3.75 (s, 1.26H), 3.42 (d, J=20.4 Hz, 1H), 3.14-3.07 (m, 4H), 2.86-2.83 (m, 5H), 2.64-2.57 (m, 1H), 2.49-2.33 (m, 2H, partially obscured by solvent peak), 2.08-2.00 (m, 1H), 1.61 (d, J=12.6 Hz, 1H); ESI MS m/z 521 $[C_{29}H_{32}N_2O_7+H]^+$; HPLC (Method A) 94.3% (AUC), $t_R$=7.92 min.

Scheme 30: (S)-4-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-((S)-2-hydroxypropanamido)-4-oxobutanoic acid trifluoroacetic acid salt

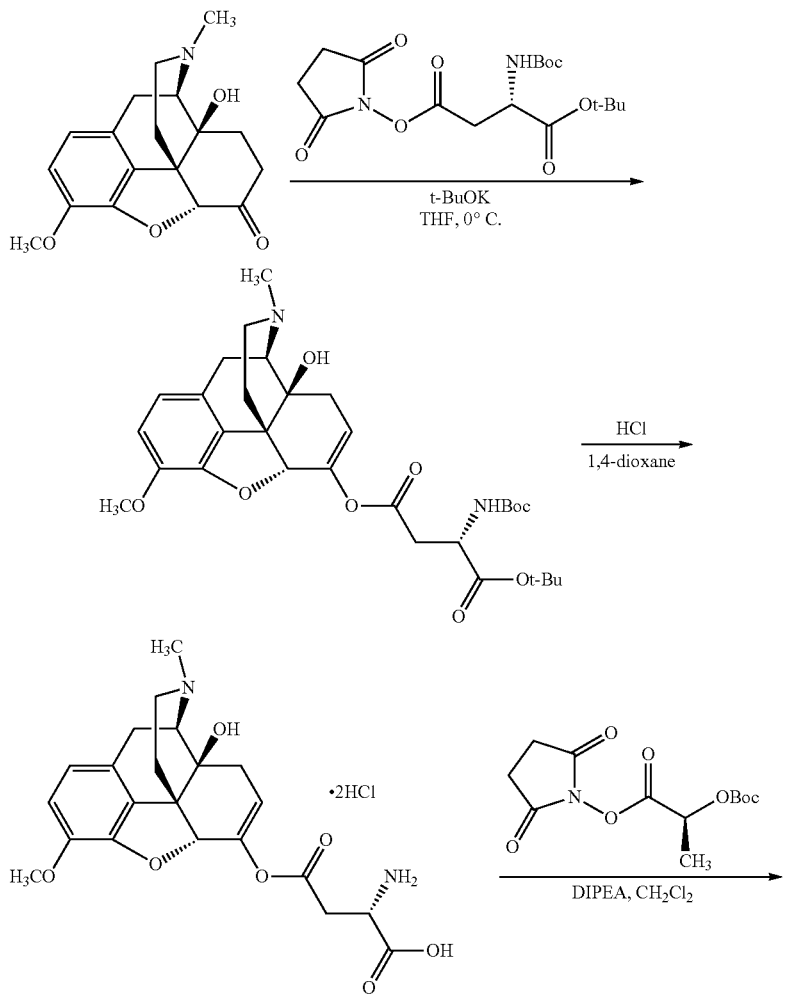

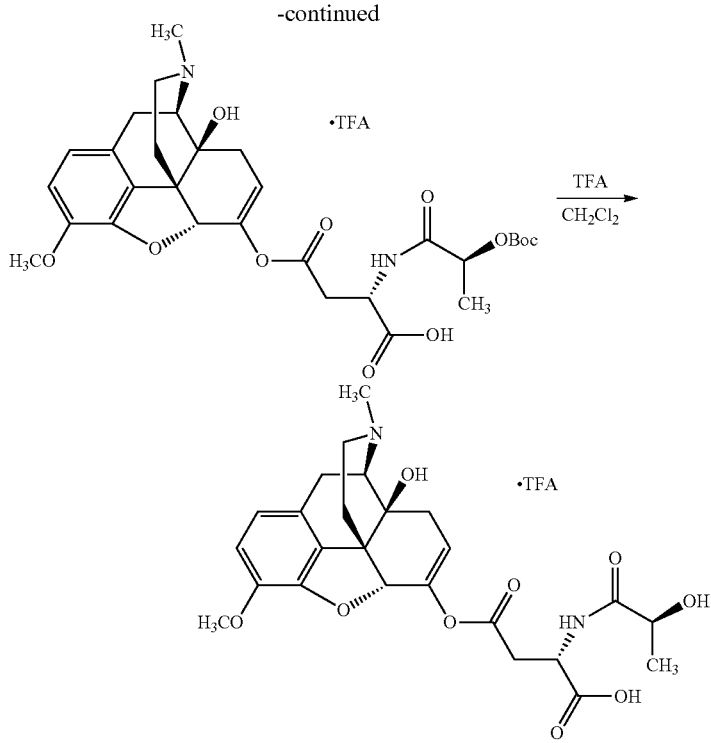

Preparation of (S)-1-tert-Butyl 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-((tert-butoxycarbonyl)amino)succinate A suspension of oxycodone (0.474 g, 1.50 mmol) in tetrahydrofuran (5 mL) was cooled in an ice bath and treated with a 1.0 M solution of potassium tert-butoxide in tetrahydrofuran (1.65 mL, 1.65 mmol). After addition was complete, the mixture was stirred under a nitrogen atmosphere in the ice bath for 25 min and at ambient temperature for 25 min. The solution was re-cooled in an ice/brine bath, and the mixture was treated with a solution of (S)-1-tert-butyl 4-(2,5-dioxopyrrolidin-1-yl) 2-((tert-butoxycarbonyl)amino)succinate (0.637 g, 1.64 mmol) in tetrahydrofuran (4 mL) and stirred for 2 h. After this time, the reaction mixture was treated with saturated aqueous ammonium chloride (50 mL) and extracted with ethyl acetate (2×50 mL). The combined organics were washed with saturated sodium bicarbonate (50 mL) and brine (50 mL), dried over sodium sulfate, filtered, and concentrated under reduced pressure. The crude residue was purified by column chromatography (silica gel, 0-4% methanol/methylene chloride) to provide (S)-1-tert-butyl 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-((tert-butoxycarbonyl)amino)succinate (0.485 g, 55%) as an off-white solid: ESI MS m/z 587 $[C_{31}H_{42}N_2O_9+H]^+$.

Preparation of (S)-2-Amino-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid dihydrochloride

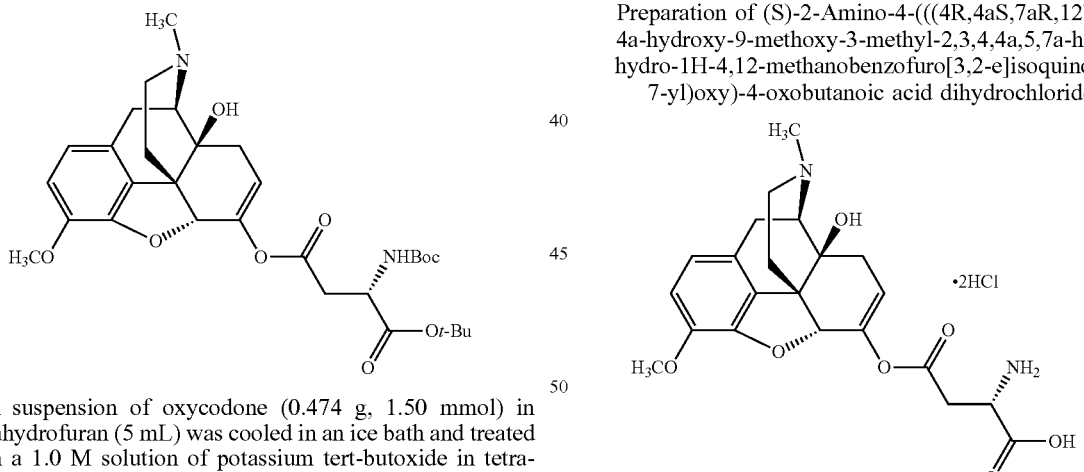

A solution of (S)-1-tert-butyl 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-((tert-butoxycarbonyl)amino)succinate (0.480 g, 0.818 mmol) in 1,4-dioxane (15 mL) was treated with 4 N hydrogen chloride in 1,4-dioxane (12 mL) at ambient temperature and stirred for 3 h. After this time, the reaction mixture was concentrated under reduced pressure and dried under vacuum to provide (S)-2-amino-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid dihydrochloride (0.460 g, quantitative) as a white solid: ESI MS m/z 387 $[C_{22}H_{26}N_2O_7+H]^+$.

Preparation of (S)-2-((S)-2-((tert-Butoxycarbonyl)oxy)propanamido)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid

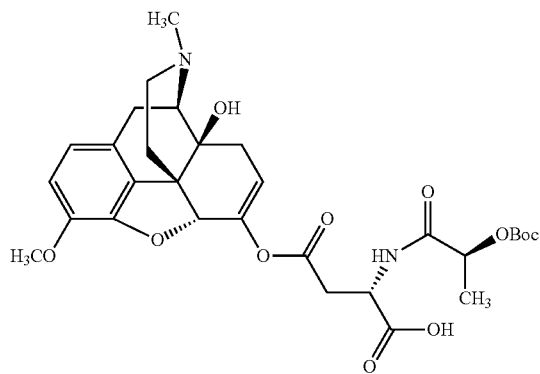

A mixture of (S)-2-amino-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid dihydrochloride (0.250 g, 0.496 mmol), (S)-2,5-dioxopyrrolidin-1-yl 2-((tert-butoxycarbonyl)oxy)propanoate (0.214 g, 0.745 mmol), and N,N-diisopropylethylamine (0.43 mL, 2.5 mmol) in methylene chloride (8 mL) was stirred at ambient temperature for 2 h. After this time, the reaction mixture was concentrated under reduced pressure. The crude residue was purified by reversed phase column chromatography (50 g C18 column, 5-100% acetonitrile/water) and freeze dried to provide (S)-2-((S)-2-((tert-butoxycarbonyl)oxy)propanamido)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid (0.050 g, 17%) as a white solid: ESI MS m/z 603 $[C_{30}H_{38}N_2O_{11}+H]^+$.

Preparation of (S)-4-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-((S)-2-hydroxypropanamido)-4-oxobutanoic acid trifluoroacetic acid salt

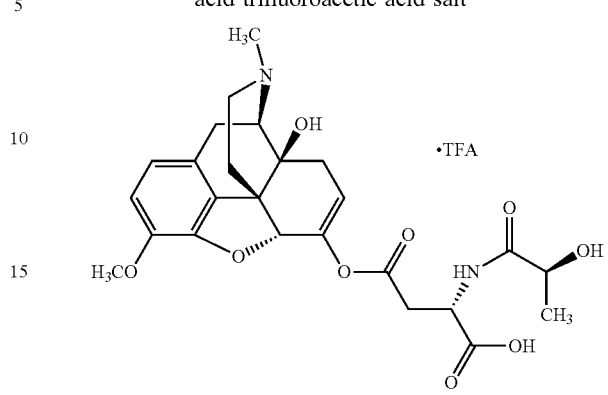

A solution of (S)-2-((S)-2-((tert-butoxycarbonyl)oxy)propanamido)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid (0.049 g, 0.074 mmol) in methylene chloride (3 mL) was treated with trifluoroacetic acid (1 mL) and stirred at ambient temperature for 1 h. After this time, the reaction mixture was concentrated under reduced pressure. The residue was purified by reverse chromatography (50 g C18 column, 5-25% acetonitrile/water, with 0.1% TFA) and freeze dried to provide (S)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-((S)-2-hydroxypropanamido)-4-oxobutanoic acid trifluoroacetic acid salt (0.032 g, 86%) as a white solid: $^1$H NMR (300 MHz, DMSO-$d_6$) δ 12.96 (br s, 1H), 9.17 (br s, 1H), 8.01 (d, J=8.4 Hz, 1H), 6.86 (d, J=8.4 Hz, 1H), 6.75 (d, J=8.4 Hz, 1H), 6.27 (s, 1H), 5.65 (br s, 1H), 5.51 (dd, J=6.0, 2.1 Hz, 1H), 4.97 (s, 1H), 4.66 (q, J=8.1 Hz, 1H), 4.01 (q, J=6.6 Hz, 1H), 3.75 (s, 3H), 3.64 (d, J=6.0 Hz, 1H), 3.15-3.01 (m, 3H), 2.96 (d, J=6.3 Hz, 1H), 2.91 (d, J=6.3 Hz, 1H), 2.84 (d, J=4.5 Hz, 3H), 2.75-2.55 (m, 1H), 2.32-2.24 (m, 1H), 2.06 (d, J=18.0 Hz, 1H), 1.64 (d, J=10.2 Hz, 1H), 1.21 (d, J=6.6 Hz, 3H); ESI MS m/z 503 $[C_{25}H_{30}N_2O_9+H]^+$; HPLC (Method A) 95.0% (AUC), $t_R$=7.03 min.

Scheme 31: (S)-4-((S)-3-Carboxy-3-hydroxypropanamido)-5-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid hydrochloride

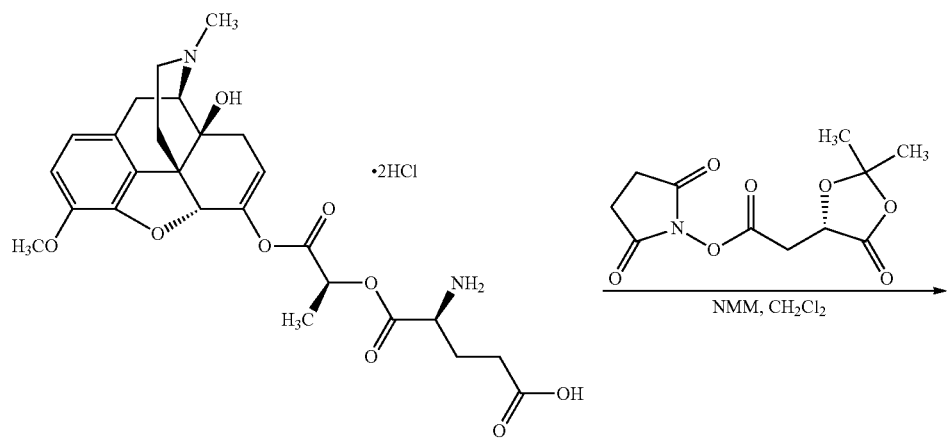

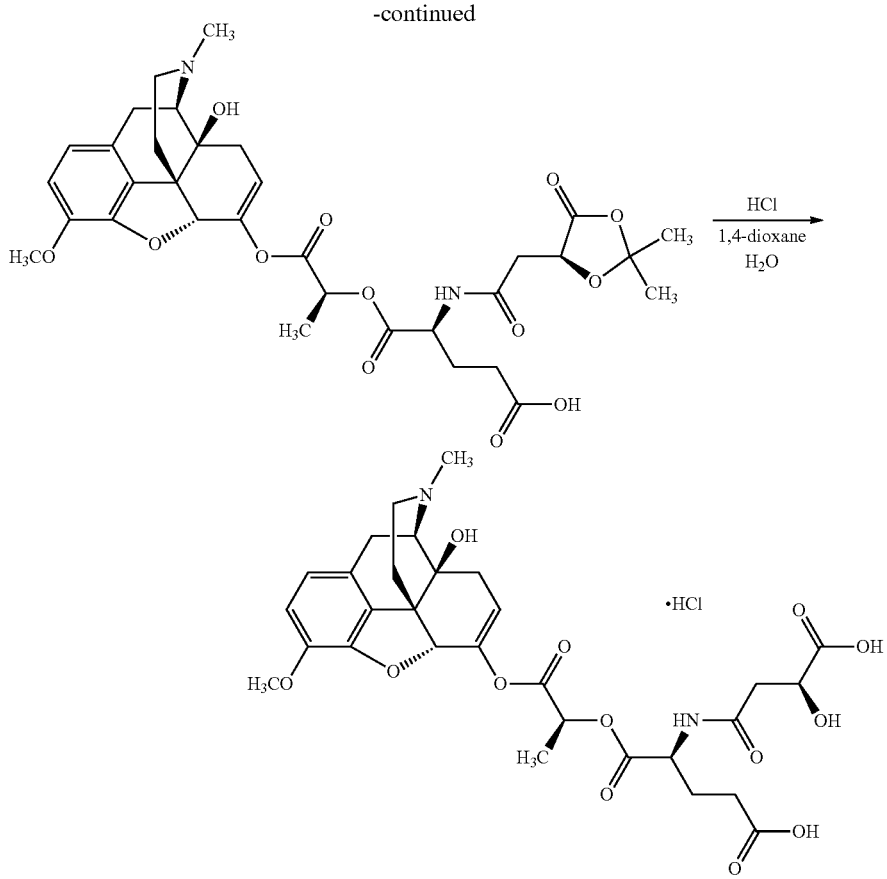

Preparation of (S)-4-(2-((S)-2,2-Dimethyl-5-oxo-1,3-dioxolan-4-yl)acetamido)-5-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid

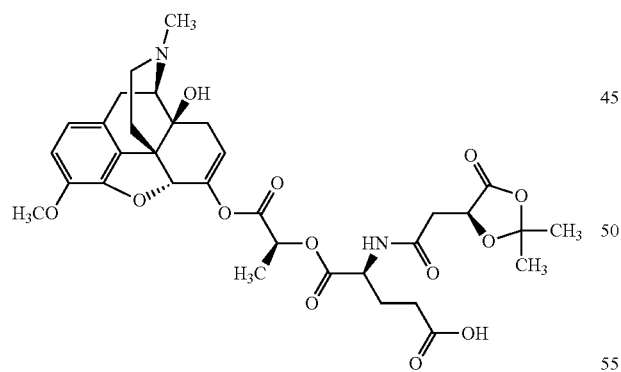

A suspension (S)-4-amino-5-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid dihydrochloride (207 mg, 0.351 mmol) and (S)-2,5-dioxopyrrolidin-1-yl 2-(2,2-dimethyl-5-oxo-1,3-dioxolan-4-yl)acetate (150 mg, 0.553 mmol) in methylene chloride (3 mL) was treated with N,N-diisopropylethylamine (0.24 mL, 1.4 mmol) and stirred under a nitrogen atmosphere for 15 min. After this time, the reaction mixture was diluted with methylene chloride (15 mL) and washed with saturated aqueous ammonium chloride (15 mL). The organic layer was dried over sodium sulfate, filtered, and concentrated under reduced pressure to provide (S)-4-(2-((S)-2,2-dimethyl-5-oxo-1,3-dioxolan-4-yl)acetamido)-5-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid (234 mg, 99%) as an off-white semi-solid: ESI MS m/z 673 $[C_{33}H_{40}N_2O_{13}+H]^+$.

Preparation of (S)-4-((S)-3-Carboxy-3-hydroxypropanamido)-5-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid hydrochloride

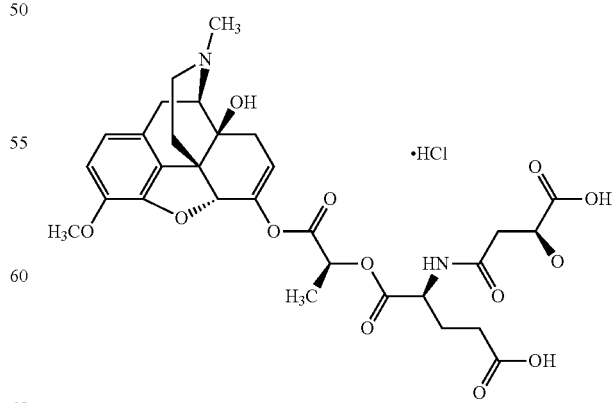

A solution of (S)-4-(2-((S)-2,2-dimethyl-5-oxo-1,3-dioxolan-4-yl)acetamido)-5-(((S)-1-(((4R,4aS,7aR,12bS)-4a- hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid (232 mg, 0.345 mmol) in 1,4-dioxane (5 mL) was treated with a 4.0 M solution of hydrogen chloride in 1,4-dioxane (0.5 mL) followed by water (5 drops) and stirred under a nitrogen atmosphere at ambient temperature for 10 min. After this time, the reaction mixture was partially concentrated under reduced pressure, diluted with acetonitrile, and freeze-dried. The crude product was purified by reversed phase column chromatography (50 g C18 column, 10-70% acetonitrile/water) and freeze dried to provide (S)-4-((S)-3-carboxy-3-hydroxypropanamido)-5-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid hydrochloride (59 mg, 26%) as a fluffy white solid: $^1$H NMR (300 MHz, DMSO-$d_6$) δ 8.41 (d, J=7.2 Hz, 1H), 6.75 (d, J=8.1 Hz, 1H), 6.67 (d, J=8.1 Hz, 1H), 5.57 (dd, J=5.7, 2.4 Hz, 1H), 5.14 (q, J=7.2 Hz, 1H), 4.87 (s, 1H), 4.41-4.34 (m, 1H), 4.23 (dd, J=8.1, 4.8 Hz, 1H), 3.73 (s, 3H), 3.15 (d, J=18.9 Hz, 1H), 2.95 (d, J=5.4 Hz, 1H), 2.73-2.63 (m, 1H), 2.49-2.24 (m, 9H, partially obscured by solvent peak), 2.16-1.96 (m, 4H), 1.88-1.76 (m, 1H), 1.52 (d, J=7.2 Hz, 3H), two CO$_2$H, HCl, and two OH protons not observed, one proton obscured by solvent peaks; ESI MS m/z 633 [C$_{30}$H$_{36}$N$_2$O$_{13}$+H]$^+$; HPLC (Method A) 96.9% (AUC), $t_R$=7.41 min.

Scheme 32: (S)-2-Amino-4-(((S)-1-(((4R,4aS,7aR,12bS)-4a-hydroxy-9-methoxy-3-methyl-2,3,4,4a,5,7a-hexahydro-1H-4, 12-methanobenzofuro[3,2-e]isoquinolin-7-yl)oxy)-1-oxopropan-2-yl)oxy)-4-oxobutanoic acid hydrochloride

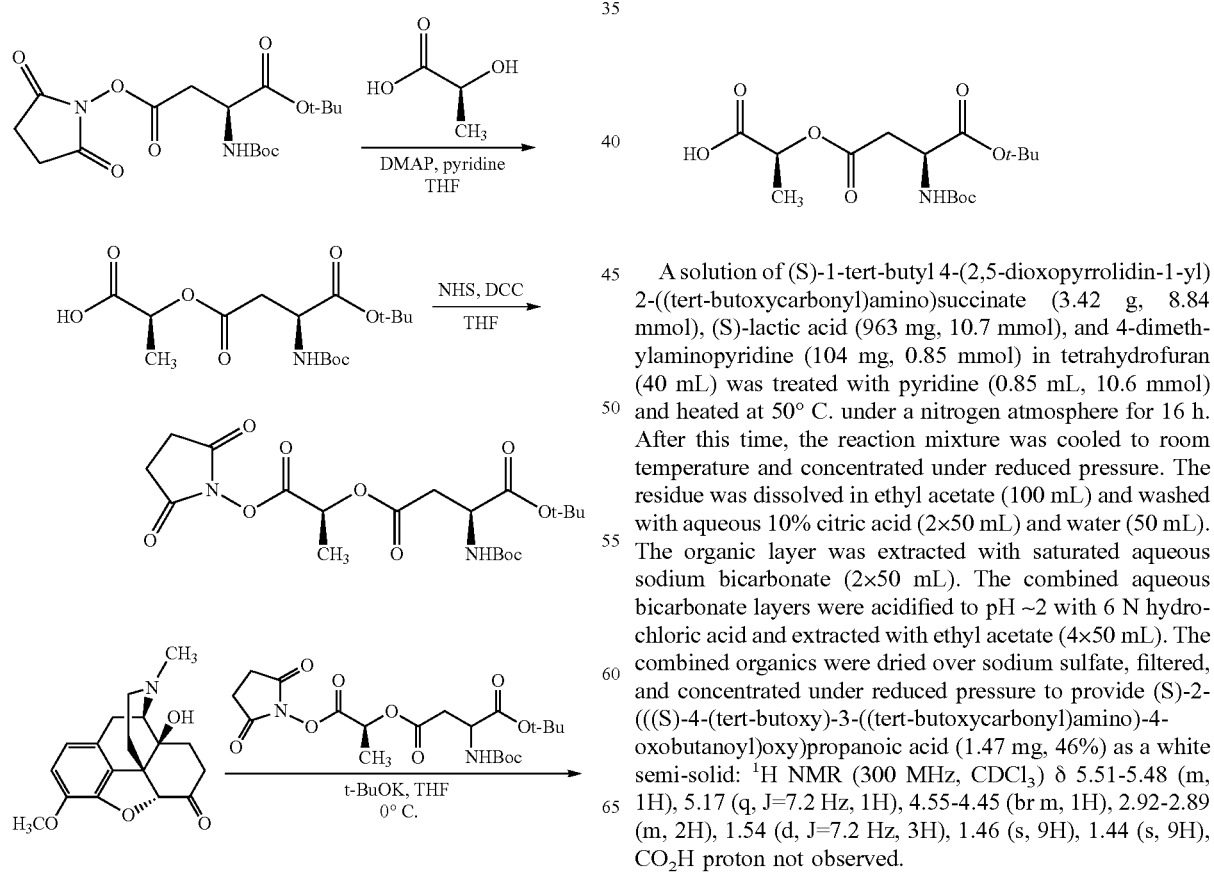

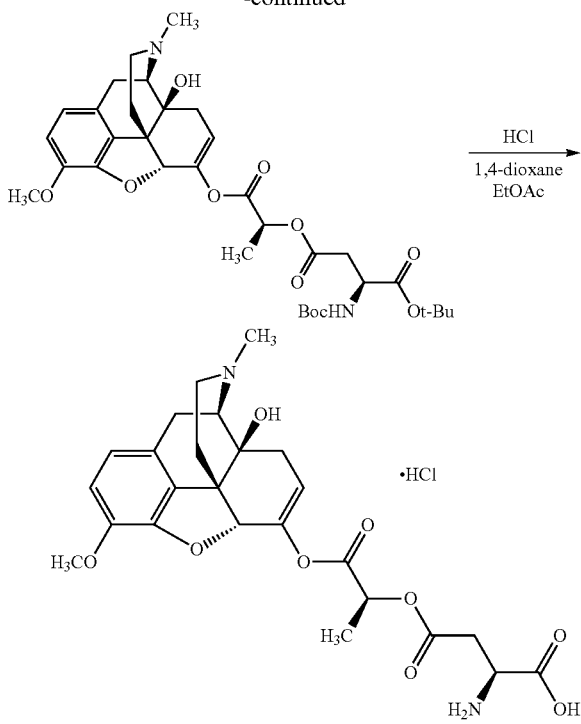

Preparation of (S)-2-(((S)-4-(tert-Butoxy)-3-((tert-butoxycarbonyl)amino)-4-oxobutanoyl)oxy)propanoic acid A solution of (S)-1-tert-butyl 4-(2,5-dioxopyrrolidin-1-yl) 2-((tert-butoxycarbonyl)amino)succinate (3.42 g, 8.84 mmol), (S)-lactic acid (963 mg, 10.7 mmol), and 4-dimethylaminopyridine (104 mg, 0.85 mmol) in tetrahydrofuran (40 mL) was treated with pyridine (0.85 mL, 10.6 mmol) and heated at 50° C. under a nitrogen atmosphere for 16 h. After this time, the reaction mixture was cooled to room temperature and concentrated under reduced pressure. The residue was dissolved in ethyl acetate (100 mL) and washed with aqueous 10% citric acid (2×50 mL) and water (50 mL). The organic layer was extracted with saturated aqueous sodium bicarbonate (2×50 mL). The combined aqueous bicarbonate layers were acidified to pH ~2 with 6 N hydrochloric acid and extracted with ethyl acetate (4×50 mL). The combined organics were dried over sodium sulfate, filtered, and concentrated under reduced pressure to provide (S)-2-(((S)-4-(tert-butoxy)-3-((tert-butoxycarbonyl)amino)-4-oxobutanoyl)oxy)propanoic acid (1.47 mg, 46%) as a white semi-solid: $^1$H NMR (300 MHz, CDCl$_3$) δ 5.51-5.48 (m, 1H), 5.17 (q, J=7.2 Hz, 1H), 4.55-4.45 (br m, 1H), 2.92-2.89 (m, 2H), 1.54 (d, J=7.2 Hz, 3H), 1.46 (s, 9H), 1.44 (s, 9H), CO$_2$H proton not observed.

Preparation of (S)-1-tert-Butyl 4-((S)-1-((2,5-dioxopyrrolidin-1-yl)oxy)-1-oxopropan-2-yl) 2-((tert-butoxycarbonyl)amino)succinate

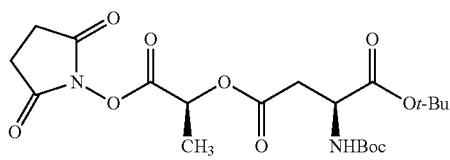 [SMILES: C[C@H](OC(=O)C[C@H](NC(=O)OC(C)(C)C)C(=O)OC(C)(C)C)C(=O)ON1C(=O)CCC1=O]

A solution of (S)-2-(((S)-4-(tert-butoxy)-3-((tert-butoxycarbonyl)amino)-4-oxobutanoyl)oxy)propanoic acid (1.47 g, 4.05 mmol) in tetrahydrofuran (20 mL) was treated with N-hydroxysuccinimide (513 mg, 4.46 mmol) and N,N'-dicyclohexylcarbodiimide (921 mg, 4.46 mmol) and stirred under a nitrogen atmosphere for 4 h. After this time, the reaction mixture was filtered to remove the solid dicyclohexylurea byproduct. The solid was washed with diethyl ether, and the combined filtrate and washings were concentrated under reduced pressure to provide (S)-1-tert-butyl 4-((S)-1-((2,5-dioxopyrrolidin-1-yl)oxy)-1-oxopropan-2-yl) 2-((tert-butoxycarbonyl)amino)succinate (2.04 g, quantitative) as a white foam: $^1$H NMR (300 MHz, CDCl$_3$) δ 5.54-5.48 (m, 1H), 5.42 (q, J=7.2 Hz, 1H), 4.51-4.45 (m, 1H), 3.08-2.82 (m, 6H), 1.68 (d, J=7.2 Hz, 3H), 1.46 (s, 9H), 1.44 (s, 9H).

Preparation of (S)-1-tert-Butyl 4-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-((tert-butoxycarbonyl)amino)succinate

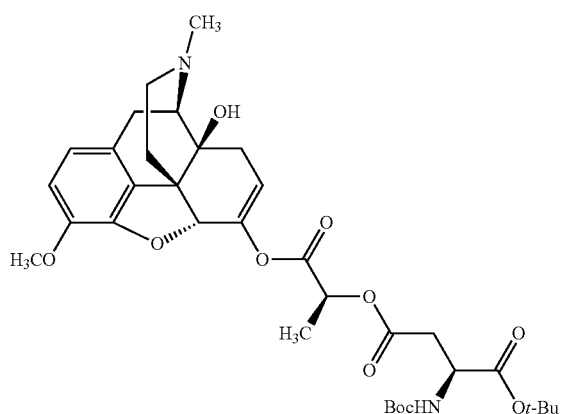 [SMILES: COc1ccc2c3c1O[C@H]1C(OC(=O)[C@H](C)OC(=O)C[C@H](NC(=O)OC(C)(C)C)C(=O)OC(C)(C)C)=CC[C@@]4(O)[C@@H](C2)N(C)CC[C@]314]

A suspension of oxycodone (574 mg, 1.82 mmol) in tetrahydrofuran (8 mL) was cooled in an ice bath and treated dropwise with a 1.0 M solution of potassium tert-butoxide in tetrahydrofuran (2.2 mL, 2.2 mmol). After addition was complete, the mixture was stirred in the ice bath for 1.5 h. The ice bath was replaced with an ice/brine bath, and the mixture was treated dropwise with a solution of (S)-1-tert-butyl 4-((S)-1-((2,5-dioxopyrrolidin-1-yl)oxy)-1-oxopropan-2-yl) 2-((tert-butoxycarbonyl)amino)succinate (992 mg, 2.16 mmol) in tetrahydrofuran (8 mL). After addition was complete, the mixture was stirred in the ice bath for 30 min. After this time, the reaction mixture was treated with saturated aqueous ammonium chloride (50 mL) and extracted with ethyl acetate (2×50 mL). The combined organics were washed with saturated sodium bicarbonate (50 mL) and brine (50 mL), dried over sodium sulfate, filtered, and concentrated under reduced pressure. The crude residue was purified by column chromatography (silica gel, 0-10% methanol/methylene chloride) followed by reversed phase column chromatography (150 g C18 column, 20-100% acetonitrile/water) and freeze dried to provide (S)-1-tert-butyl 4-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-((tert-butoxycarbonyl)amino)succinate (244 mg, 20%) as a fluffy white solid: ESI MS m/z 659 $[C_{34}H_{46}N_2O_{11}+H]^+$.

Preparation of (S)-2-Amino-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid hydrochloride

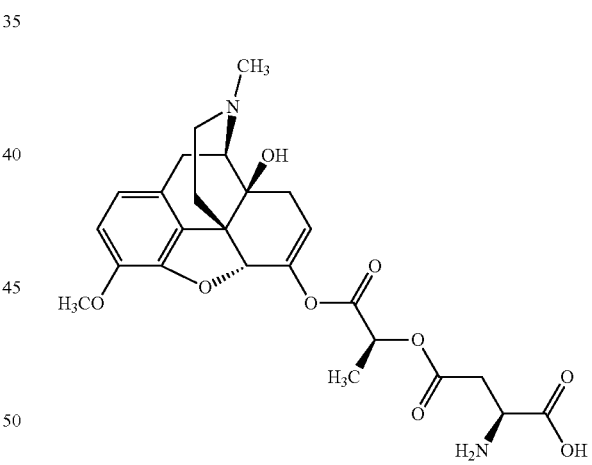

A solution of (S)-1-tert-butyl 4-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-((tert-butoxycarbonyl)amino)succinate (242 mg, 0.367 mmol) in ethyl acetate (3 mL) was treated with a 4.0 M solution of hydrogen chloride in 1,4-dioxane (3 mL) and stirred under a nitrogen atmosphere at ambient temperature for 16 h. After this time, the reaction mixture was diluted with diethyl ether and sonicated to produce a solid precipitate. The solid was isolated by filtration, washed with diethyl ether, and dried under vacuum. Half of the material was purified by reversed phase column chromatography (50 g C18 column, 10-50% acetonitrile/water) and freeze dried to provide (S)-2-amino-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid hydrochloride (30 mg, 30%) as a white solid: $^1$H NMR (300 MHz, DMSO-$d_6$) δ 7.77 (br s, 1H), 6.84 (d, J=8.1 Hz, 1H), 6.74 (d, J=8.4 Hz, 1H), 5.60-5.58 (m, 1H), 5.13 (q, J=6.9 Hz, 1H), 4.99 (s, 1H), 3.76 (s, 3H), 3.64-3.52 (m, 2H), 3.04-2.91 (m, 4H), 2.76-2.63 (m, 5H), 2.49-2.40 (m, 1H, partially obscured by solvent peak), 2.28-2.22 (m, 1H), 2.06 (apparent d, J=17.4 Hz, 1H), 1.60 (d, J=9.9 Hz, 1H), 1.51 (d, J=6.9 Hz, 3H),CO$_2$H, NH$_2$, and OH protons not observed;ESI MS m/z 503 [C$_{25}$H$_{30}$N$_2$O$_9$+H]$^+$; HPLC (Method A) 96.6% (AUC), $t_R$=6.89 min.

Scheme 33: (S)-4-(((S)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-2-((S)-2-hydroxypropanamido)-4-oxobutanoic acid trifluoroacetic acid salt

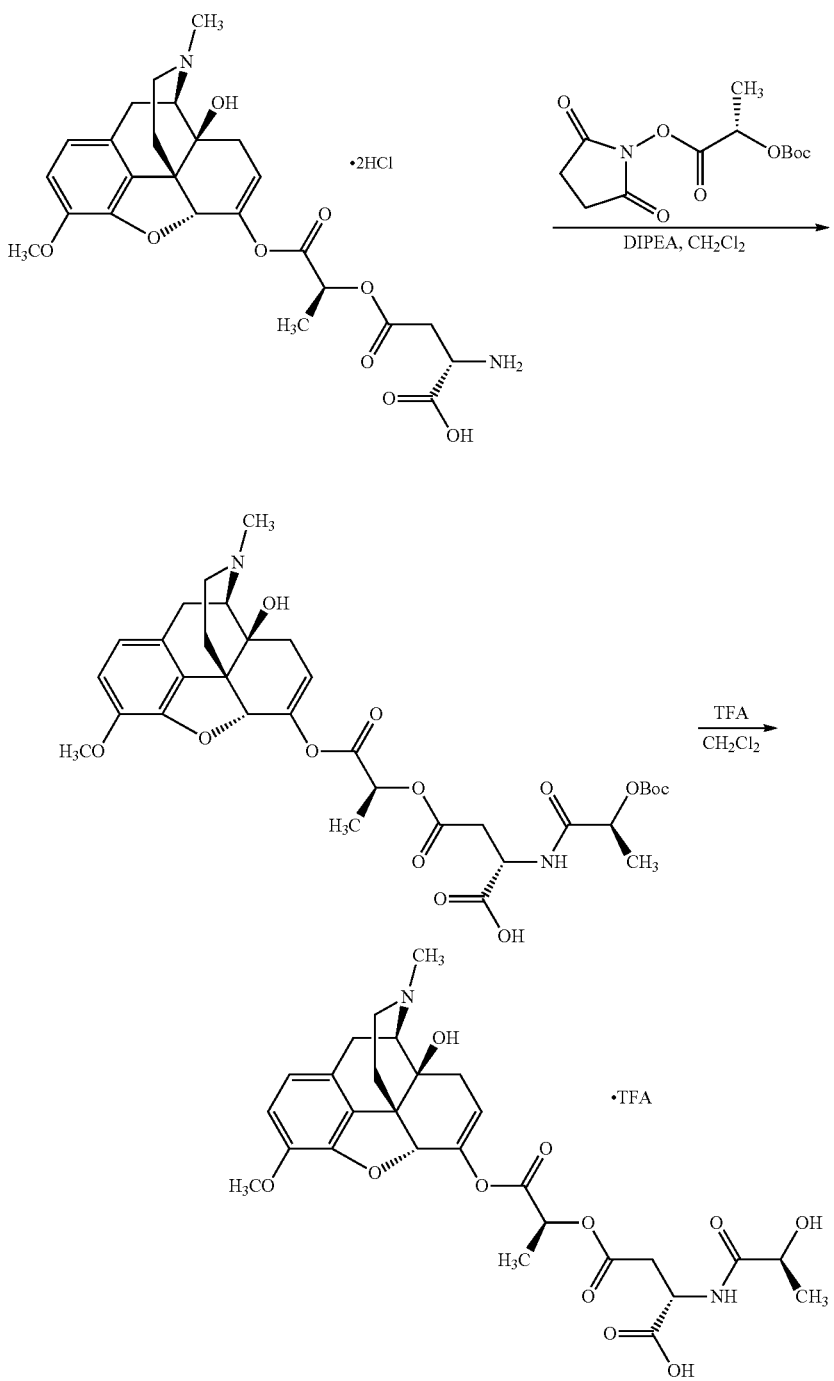

Preparation of (S)-2-((S)-2-((tert-Butoxycarbonyl)oxy)propanamido)-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid

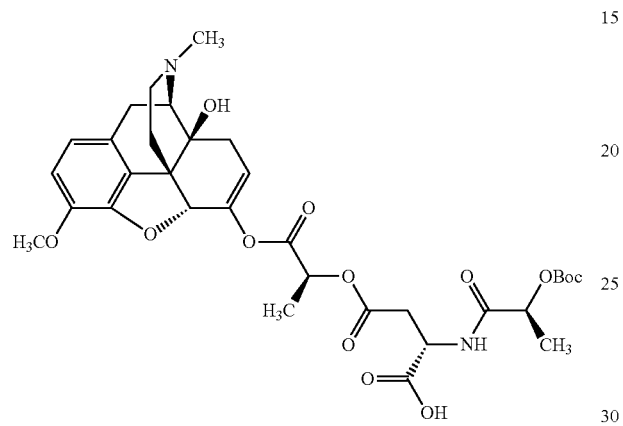

A suspension of (S)-2-amino-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-y)oxy)-1-oxopropan-2-yl)oxy)-4-oxobutanoic acid dihydrochloride (105 mg, 0.195 mmol) and (S)-2,5-dioxopyrrolidin-1-yl 2-((tert-butoxycarbonyl)oxy)propanoate (88 mg, 0.31 mmol) in methylene chloride (4 mL) was treated with N,N-diisopropylethylamine (0.08 mL, 0.5 mmol) and stirred under a nitrogen atmosphere for 15 min. After this time, the reaction mixture was diluted with methylene chloride (10 mL) and washed with saturated aqueous ammonium chloride (10 mL). The organic layer was dried over sodium sulfate, filtered, and concentrated under reduced pressure. The crude residue was purified by reversed phase column chromatography (50 g C18 column, 10-100% acetonitrile/water) and freeze dried to provide to provide (S)-2-((S)-2-((tert-butoxycarbonyl)oxy)propanamido)-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid (74 mg, 56%) as a fluffy white solid: ESI MS m/z 675 [$C_{33}H_{42}N_2O_{13}$+H]$^+$.

Preparation of (S)-4-(((S)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-2-((S)-2-hydroxypropanamido)-4-oxobutanoic acid trifluoroacetic acid salt

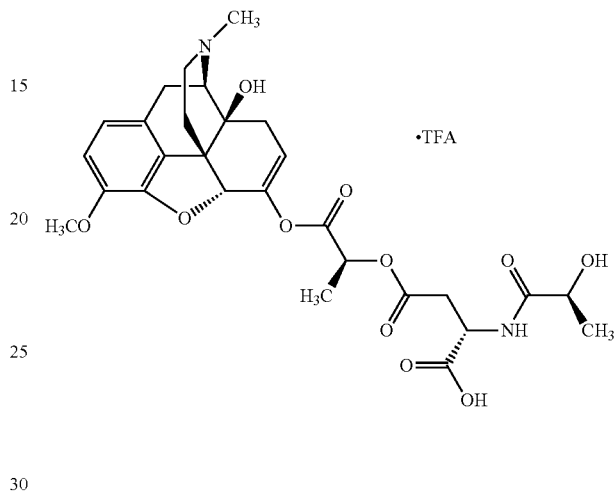

A solution of (S)-2-((S)-2-((tert-butoxycarbonyl)oxy)propanamido)-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid (73 mg, 0.11 mmol) in methylene chloride (2 mL) was treated with trifluoroacetic acid (0.5 mL) and stirred under a nitrogen atmosphere at ambient temperature for 30 min. After this time, the reaction mixture concentrated under reduced pressure. The residue was purified by reversed phase column chromatography (15.5 g C18 column, 10-70% acetonitrile/water) and freeze dried to provide to provide (S)-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-2-((S)-2-hydroxypropanamido)-4-oxobutanoic acid trifluoroacetic acid salt (42 mg, 58%) as a white solid: $^1$H NMR (300 MHz, DMSO-$d_6$) δ 7.94 (d, J=8.1 Hz, 1H), 6.77 (d, J=8.1 Hz, 1H), 6.68 (d, J=8.1 Hz, 1H), 5.64 (d, J=5.1 Hz, 1H), 5.57 (dd, J=5.7, 2.1 Hz, 1H), 5.11 (q, J=6.9 Hz, 1H), 4.90 (s, 1H), 4.62-4.55 (m, 1H), 4.00-3.94 (m, 1H), 3.74 (s, 3H), 3.20 (d, J=19.8 Hz, 1H, partially obscured by water peak), 3.08 (br s, 1H), 2.89-2.78 (m, 3H), 2.63-2.57 (m, 1H), 2.49-2.31 (m, 2H, partially obscured by solvent peak), 2.17-1.97 (m, 2H), 1.48 (d, J=6.9 Hz, 3H), 1.47-1.45 (m, 1H), 1.19 (d, J=6.6 Hz, 3H), $CO_2H$ and $CH_3CO_2H$ protons not observed, four protons obscured by solvent peaks; ESI MS m/z 575 [$C_{28}H_{34}N_2O_{11}$+H]$^+$; HPLC (Method A) 97.1% (AUC), $t_R$=7.78 min.

Scheme 34: (S)-2-Hydroxy-4-((3-((R)-2-(((4R,4aS,7aR,12bS)-4a-hydoxy-9-methoxy-3-methyl-2,3,4,4a,5,7a-hexahydro-1H-4,12-methanobenzofuro[3,2-e]isoquinolin-7-yl)oxy)-2-oxo-1-phenylethoxy)-3-oxopropyl)amino)-4-oxobutanoic acid hydrochloride
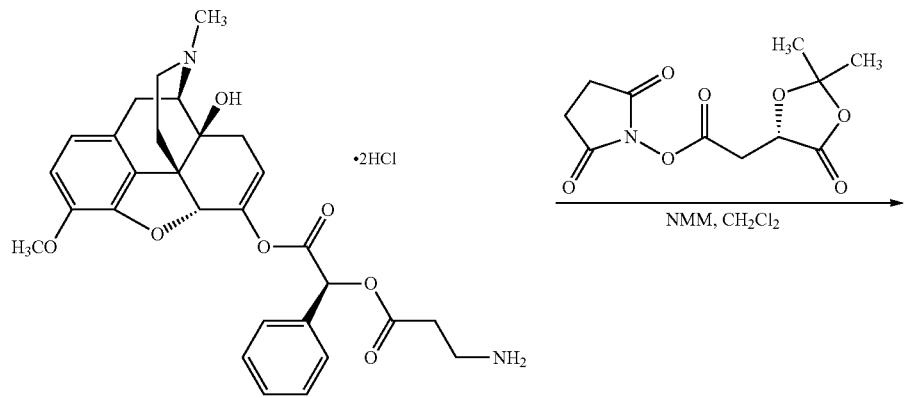
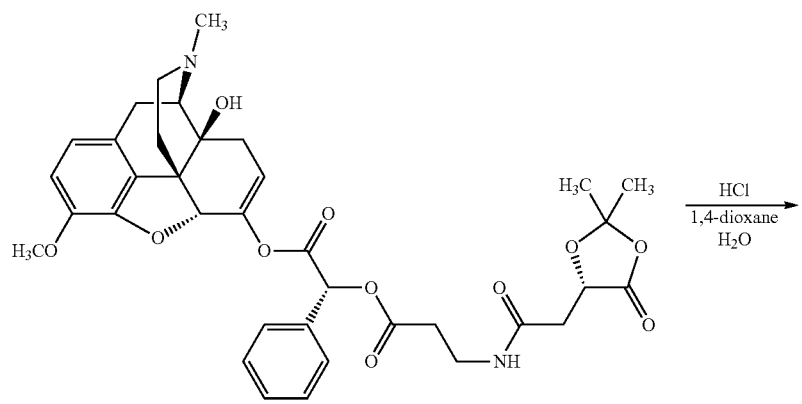
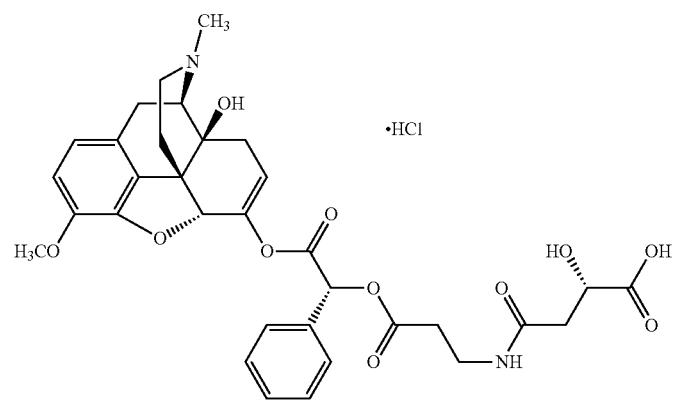

Preparation of (R)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-(2-((S)-2,2-dimethyl-5-oxo-1,3-dioxolan-4-yl)acetamido)propanoate

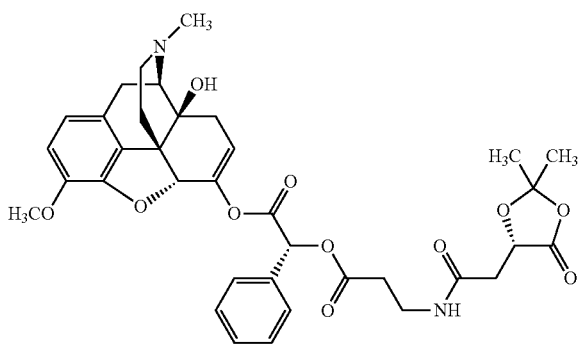 [SMILES: COc1ccc2c3c1O[C@H]1C(OC(=O)[C@H](OC(=O)CCNC(=O)C[C@@H]4OC(C)(C)OC4=O)c4ccccc4)=CC[C@@]4(O)[C@@H](C2)N(C)CC[C@]314]

A suspension (S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-aminopropanoate dihydrochloride (47 mg, 0.079 mmol) and (S)-2,5-dioxopyrrolidin-1-yl 2-(2,2-dimethyl-5-oxo-1,3-dioxolan-4-yl)acetate (32 mg, 0.12 mmol) in methylene chloride (2 mL) was treated with N-methylmorpholine (0.04 mL, 0.4 mmol) and stirred under a nitrogen atmosphere for 30 min. After this time, the reaction mixture was diluted with methylene chloride (10 mL) and washed with saturated aqueous ammonium chloride (10 mL). The organic layer was dried over sodium sulfate, filtered, and concentrated under reduced pressure to provide (R)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-(2-((S)-2,2-dimethyl-5-oxo-1,3-dioxolan-4-yl)acetamido)propanoate (65 mg, quantitative) as an off-white semi-solid: ESI MS m/z 677 $[C_{36}H_{40}N_2O_{11}+H]^+$.

Preparation of (S)-2-Hydroxy-4-((3-((R)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethoxy)-3-oxopropyl)amino)-4-oxobutanoic acid hydrochloride

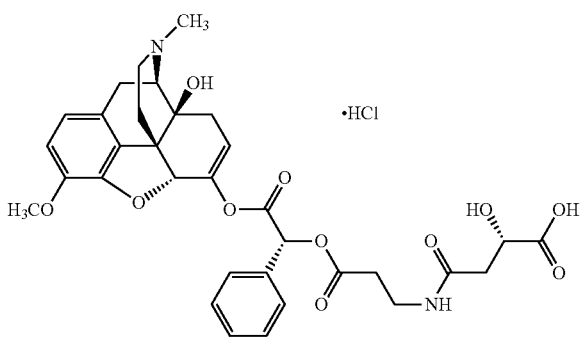 [SMILES: COc1ccc2c3c1O[C@H]1C(OC(=O)[C@H](OC(=O)CCNC(=O)C[C@H](O)C(=O)O)c4ccccc4)=CC[C@@]4(O)[C@@H](C2)N(C)CC[C@]314 ; Cl]

A solution of (R)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 3-(2-((S)-2,2-dimethyl-5-oxo-1,3-dioxolan-4-yl)acetamido)propanoate (54 mg, 0.079 mmol) in 1,4-dioxane (4 mL) was treated with a 4.0 M solution of hydrogen chloride in 1,4-dioxane (0.5 mL) followed by water (4 drops) and stirred under a nitrogen atmosphere at ambient temperature for 10 min. After this time, the reaction mixture was partially concentrated under reduced pressure, diluted with acetonitrile, and freeze dried. The crude product was purified by reversed phase column chromatography (15.5 g C18 column, 10-80% acetonitrile/water) and freeze dried to provide (S)-2-hydroxy-4-((3-((R)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethoxy)-3-oxopropyl)amino)-4-oxobutanoic acid hydrochloride (26 mg, 49%) as a fluffy white solid: $^1$H NMR (300 MHz, DMSO-$d_6$, Mixture of diastereomers) δ 8.04 (br s, 1H), 7.56-7.54 (m, 2H), 7.46-7.44 (m, 3H), 6.75-6.69 (m, 1H), 6.66-6.62 (m, 1H), 6.06 (s, 1H), 5.55-5.52 (m, 0.43H), 5.43-5.41 (m, 0.57H), 4.80 (s, 1H), 4.24-4.19 (m, 1H), 3.70 (s, 1.71H), 3.61 (s, 1.29H), 3.16-3.09 (m, 1H, partially obscured by water peak), 2.90 (br s, 1H), 2.67-2.58 (m, 2H), 2.49-2.22 (m, 8H, partially obscured by solvent peak), 2.12-1.93 (m, 3H), 1.39 (d, J=11.4 Hz, 1H),$CO_2H$ and HCl protons not observed, four protons obscured by solvent peaks; ESI MS m/z 637 $[C_{33}H_{36}N_2O_{11}+H]^+$;HPLC (Method A) 98.2% (AUC), $t_R$=8.52 min.

Scheme 35: (S)-(4R,4aS,7aR,12bS)-9-Methoxy-3-methyl-2,3,4,4a,5,7a-hexahydro-1H-4,12-methanobenzofuro[3,2-e]isoquinoline-4a,7-diyl bis(3-((S)-2-hydroxy-2-phenylacetamido)propanoate) trifluoroacetic acid salt

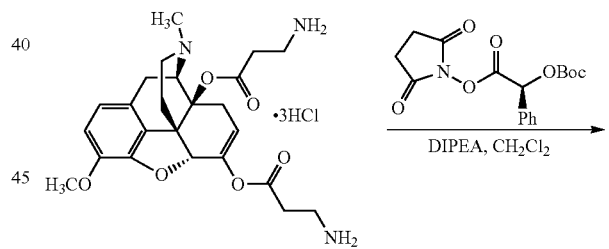

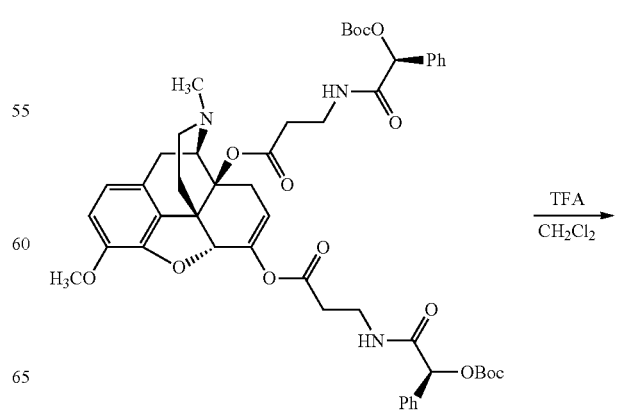

Preparation of (S)-(4R,4aS,7aR,12bS)-9-Methoxy-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)-2-phenylacetamido)propanoate)

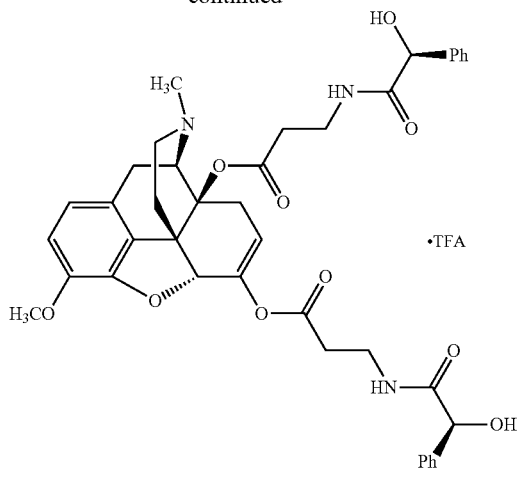

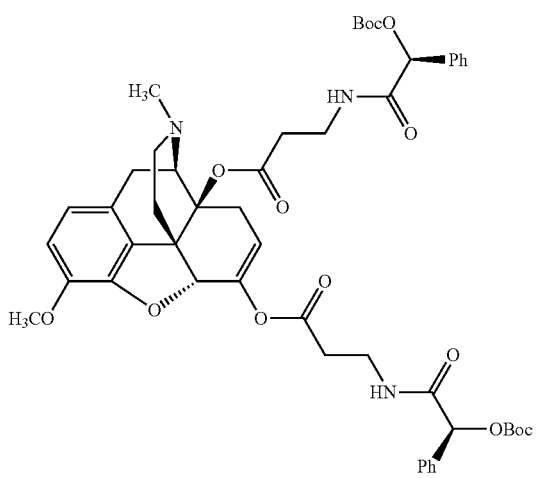

A mixture of (4R,4aS,7aR,12bS)-9-methoxy-3-methyl-2,3,4,4a,5,7a-hexahydro-1H-4,12-methanobenzofuro[3,2-e]isoquinoline-4a,7-diyl bis(3-aminopropanoate) tris(hydrochloride) (0.520 g, 1.14 mmol), (S)-2,5-dioxopyrrolidin-1-yl 2-((tert-butoxycarbonyl)oxy)-2-phenylacetate (0.595 g, 1.70 mmol) and N,N-diisopropylethylamine (0.98 mL, 5.7 mmol) in methylene chloride (15 mL) was stirred at ambient temperature for 2 h. After this time, the reaction mixture was concentrated under reduced pressure. The crude residue was purified by column chromatography (silica gel, 0-10% methanol/methylene chloride) to provide (S)-(4R,4aS,7aR,12bS)-9-methoxy-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)-2-phenylacetamido)propanoate) (0.400 g, 38%) as a yellow foam: ESI MS m/z 926 $[C_{50}H_{59}N_3O_{14}+H]^+$.

Preparation of (S)-(4R,4aS,7aR,12bS)-9-Methoxy-3-methyl-2,3,4,4a,5,7a-hexahydro-1H-4,12-methanobenzofuro[3,2-e]isoquinoline-4a,7-diyl bis(3-((S)-2-hydroxy-2-phenylacetamido)propanoate) trifluoroacetic acid salt

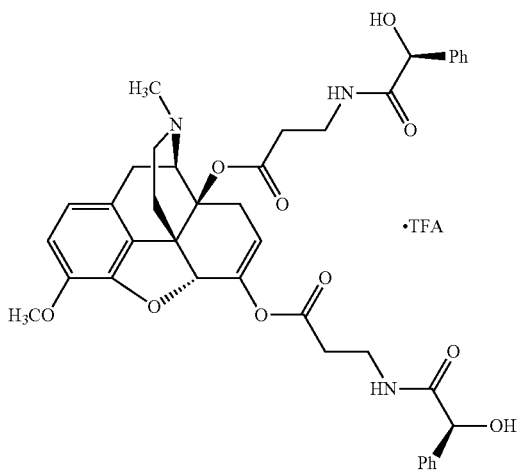 [SMILES: COc1ccc2c3c1O[C@H]1C(OC(=O)CCNC(=O)[C@@H](O)c4ccccc4)=CC[C@@]4(OC(=O)CCNC(=O)[C@@H](O)c5ccccc5)[C@@H](C2)N(C)CC[C@]314]

A solution of (S)-(4R,4aS,7aR,12bS)-9-methoxy-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)-2-phenylacetamido)propanoate) (0.400 g, 0.430 mmol) in methylene chloride (6 mL) was treated with trifluoroacetic acid (3 mL) and stirred under a nitrogen atmosphere at ambient temperature for 1 h. After this time, the reaction mixture was concentrated under reduced pressure. The crude residue was purified was purified by reversed phase column chromatography (50 g C18 column, 5-35% acetonitrile/water, with 0.1% trifluoroacetic acid) and freeze dried to provide (S)-(4R,4aS,7aR,12bS)-9-methoxy-3-methyl-2,3,4,4a,5,7a-hexahydro-1H-4,12-methanobenzofuro[3,2-e]isoquinoline-4a,7-diyl bis(3-((S)-2-hydroxy-2-phenylacetamido)propanoate) trifluoroacetic acid salt (0.0656 g, 21%) as a white solid: $^1$H NMR (300 MHz, DMSO-$d_6$) δ 9.41 (br s, 1H), 8.24 (t, J=5.7 Hz, 1H), 8.16 (t, J=5.7 Hz, 1H), 7.40-7.21 (m, 10H), 6.92 (d, J=8.4 Hz, 1H), 6.79 (d, J=8.4 Hz, 1H), 6.26 (br s, 2H), 5.37-5.35 (m, 1H), 5.07 (s, 1H), 4.91 (d, J=6.0 Hz, 2H), 4.70 (d, J=6.0 Hz, 1H), 3.77 (s, 3H), 3.52 (d, J=20.1 Hz, 1H), 3.38-3.18 (m, 6H), 2.99-2.87 (m, 4H), 2.82-2.52 (m, 5H), 2.05 (d, J=18.9 Hz, 1H), 1.78 (d, J=13.5 Hz, 1H); ESI MS m/z 726 $[C_{40}H_{43}N_3O_{10}+H]^+$; HPLC (Method A)>99% (AUC), $t_R$=9.14 min.

Scheme 36: (2S,2'S)-4,4'-(((4R,4aS,7aR,12bS)-9-Methoxy-3-methyl-2,3,4,4a,5,7a-hexahydro-1H-4, 12-methanobenzofuro[3,2-e]isoquinoline-4a,7-diyl)bis(oxy))bis(2-amino-4-oxobutanoic acid) tris(trifluoroacetic acid salt)

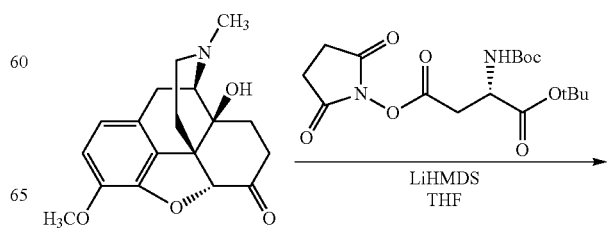

-continued

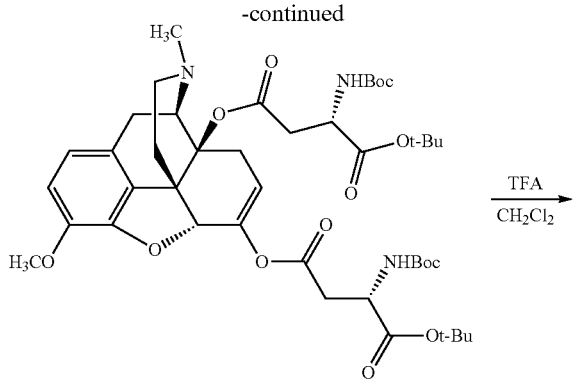

TFA
CH₂Cl₂

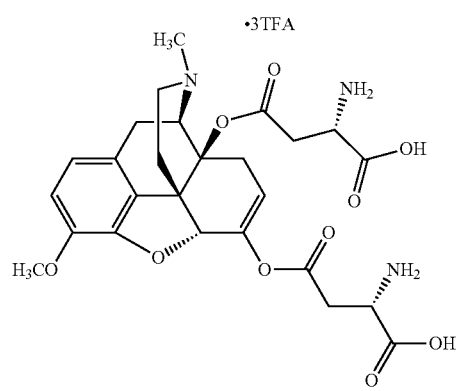

Preparation of (2S,2'S)-1-di-tert-Butyl O'4,O4-((4R, 4aS,7aR,12bS)-9-methoxy-3-methyl-2,3,4,4a,5,7a-hexahydro-1H-4,12-methanobenzofuro[3,2-e]isoquinoline-4a,7-diyl) bis(2-((tert-butoxycarbonyl)amino)succinate)

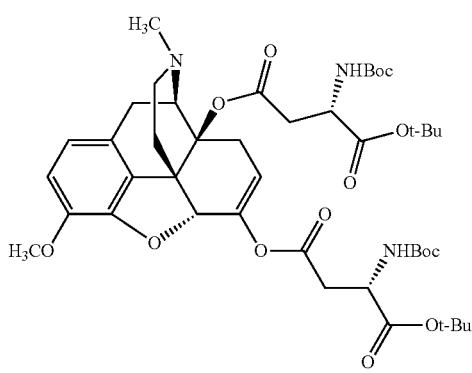 [SMILES: COc1ccc2c3c1O[C@H]1C(OC(=O)C[C@H](NC(=O)OC(C)(C)C)C(=O)OC(C)(C)C)=CC[C@@]4(OC(=O)C[C@H](NC(=O)OC(C)(C)C)C(=O)OC(C)(C)C)[C@@H](C2)N(C)CC[C@]314]

A suspension of oxycodone (0.600 g, 1.90 mmol) in tetrahydrofuran (8 mL) was cooled in an ice bath and treated dropwise with a 1.0 M solution of lithium bis(trimethylsilyl) amide in tetrahydrofuran (2.28 mL, 2.28 mmol). The mixture was stirred at 0° C. for 15 min and then treated dropwise with a solution of (S)-1-tert-butyl 4-(2,5-dioxopyrrolidin-1-yl) 2-((tert-butoxycarbonyl)amino)succinate (0.882 g, 2.28 mmol) in tetrahydrofuran (8 mL). The mixture was stirred at 0° C. for 1 h. After this time, the reaction mixture was treated with saturated aqueous ammonium chloride (100 mL) and extracted with ethyl acetate (3×100 mL). The combined organics were dried over sodium sulfate, filtered, and concentrated under reduced pressure. The crude residue was purified by column chromatography (silica gel, 0-3% methanol/methylene chloride) to provide (2S,2'S)-1-di-tert-butyl O'4,O4-((4R,4aS,7aR,12bS)-9-methoxy-3-methyl-2,3,4,4a, 5,7a-hexahydro-1H-4,12-methanobenzofuro[3,2-e]isoquinoline-4a,7-diyl) bis(2-((tert-butoxycarbonyl)amino)succinate)(0.490 g, 44%) as a white foam: ESI MS m/z 858 $[C_{44}H_{63}N_3O_{14}+H]^+$.

Preparation of (2S,2'S)-4,4'-(((4R,4aS,7aR,12bS)-9-Methoxy-3-methyl-2,3,4,4a,5,7a-hexahydro-1H-4,12-methanobenzofuro[3,2-e]isoquinoline-4a,7-diyl) bis(oxy))bis(2-amino-4-oxobutanoic acid) tris (trifluoroacetic acid salt)

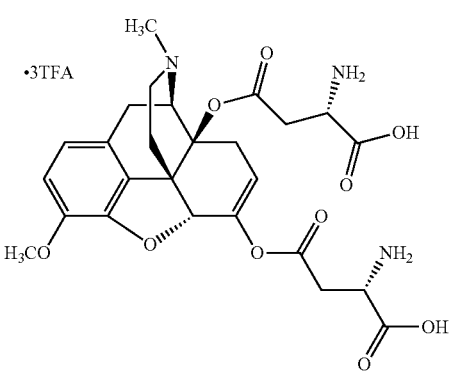 [SMILES: COc1ccc2c3c1O[C@H]1C(OC(=O)C[C@H](N)C(=O)O)=CC[C@@]4(OC(=O)C[C@H](N)C(=O)O)[C@@H](C2)N(C)CC[C@]314]

A solution of (2S,2'S)-1-di-tert-butyl O'4,O4-((4R,4aS, 7aR,12bS)-9-methoxy-3-methyl-2,3,4,4a,5,7a-hexahydro-1H-4,12-methanobenzofuro[3,2-e]isoquinoline-4a,7-diyl) bis(2-((tert-butoxycarbonyl)amino)succinate) (0.100 g, 0.116 mmol) in methylene chloride (8 mL) was treated with trifluoroacetic acid (2.5 mL) and stirred at ambient temperature for 1 h. After this time, the reaction mixture was concentrated under reduced pressure. The residue was purified by reversed phase column chromatography (50 g C18 column, 5-30% acetonitrile/water) and freeze dried to provide (2S,2'S)-4,4'-(((4R,4aS,7aR,12bS)-9-methoxy-3-methyl-2,3,4,4a,5,7a-hexahydro-1H-4,12-methanobenzofuro[3,2-e]isoquinoline-4a,7-diyl)bis(oxy))bis(2-amino-4-oxobutanoic acid)tris(trifluoroacetic acid salt)(0.0515 g, 81%) as a fluffy white solid: $^1$H NMR (300 MHz, DMSO-d$_6$) δ 8.85-7.92 (br s, 6H), 6.92 (d, J=8.1 Hz, 1H), 6.80 (d, J=8.4 Hz, 1H), 5.54-5.52 (m, 1H), 5.07 (s, 1H), 4.67 (d, J=6.0 Hz, 1H), 4.27 (t, J=5.7 Hz, 1H), 3.93 (t, J=8.7 Hz, 1H), 3.77 (s, 3H), 3.50 (d, J=20.1 Hz, 1H), 3.21-2.97 (m, 5H), 2.81 (s, 3H), 2.77-2.65 (m, 4H), 2.13 (d, J=18.3 Hz, 1H), 1.77 (d, J=11.4 Hz, 1H), two CO$_2$H protons not observed; ESI MS m/z 546 $[C_{26}H_{31}N_3O_{10}+H]$;HPLC (Method A) 95.6% (AUC), $t_R$=6.11 min.

Scheme 37: 4-(((R)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt
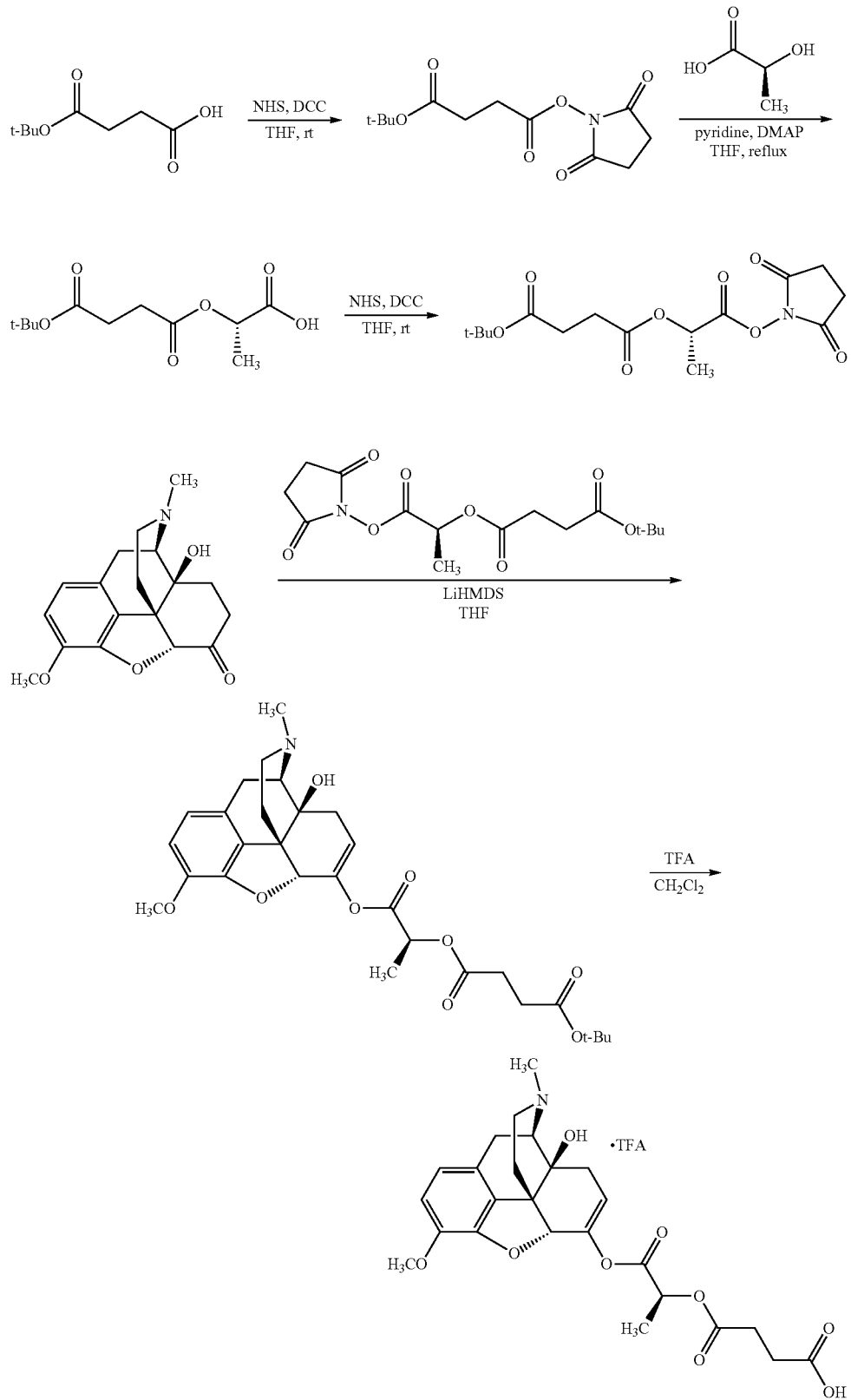

Preparation of tert-Butyl (2,5-dioxopyrrolidin-1-yl) succinate

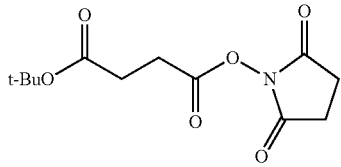 [SMILES: CC(C)(C)OC(=O)CCC(=O)ON1C(=O)CCC1=O]

A mixture of 4-(tert-butoxy)-4-oxobutanoic acid (9.75 g, 56.0 mmol) and N-hydroxysuccinimide (7.00 g, 60.8 mmol) in tetrahydrofuran (280 mL) at 0° C. was treated with N,N'-dicyclohexylcarbodiimide (12.5 g, 60.8 mmol). The ice bath was removed, and the reaction mixture was stirred at ambient temperature for 4 h. After this time, diethyl ether (100 mL) was added, and the mixture was filtered. The filtrate was concentrated under reduced pressure to provide tert-butyl (2,5-dioxopyrrolidin-1-yl) succinate (15.0 g) that was used without purification: $^1$H NMR (300 MHz, CDCl$_3$) δ 2.91 (t, J=7.2 Hz, 2H), 2.83 (s, 4H), 2.66 (t, J=7.2 Hz, 2H), 1.46 (s, 9H).

Preparation of (S)-2-((4-(tert-Butoxy)-4-oxobutanoyl)oxy)propanoic acid

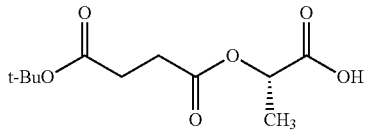

A mixture of tert-butyl (2,5-dioxopyrrolidin-1-yl) succinate (7.60 g, 28.0 mmol), (S)-2-hydroxypropanoic acid (3.00 g, 33.3 mmol), pyridine (2.7 mL, 33.5 mmol), and 4-dimethylaminopyridine (200 mg, 1.6 mmol) in tetrahydrofuran (120 mL) was stirred at reflux for 24 h. After this time, the mixture was cooled to room temperature, partially concentrated under reduced pressure, diluted with ethyl acetate, and washed with 10% citric acid. The organic layer was extracted with saturated sodium bicarbonate. The aqueous extract was carefully treated with 2N hydrochloric acid until acidic by pH paper analysis, and then extracted with ethyl acetate. The organic extracts were dried over sodium sulfate, filtered, and concentrated to give (S)-2-((4-(tert-butoxy)-4-oxobutanoyl)oxy)propanoic acid (4.84 g, 70%): ESI MS m/z 245 [C$_{11}$H$_{18}$O$_6$−H]$^-$

Preparation of (S)-tert-Butyl (1-((2,5-dioxopyrrolidin-1-yl)oxy)-1-oxopropan-2-yl) succinate

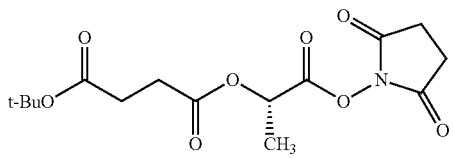 [SMILES: C[C@H](OC(=O)CCC(=O)OC(C)(C)C)C(=O)ON1C(=O)CCC1=O]

A mixture of (S)-2-((4-(tert-butoxy)-4-oxobutanoyl)oxy) propanoic acid (4.80 g, 19.5 mmol) and N-hydroxysuccinimide (2.50 g, 21.7 mmol) in tetrahydrofuran (100 mL) at 0° C. was treated with N,N'-dicyclohexylcarbodiimide (4.45 g, 21.6 mmol). The ice bath was removed, and the reaction mixture was stirred at ambient temperature for 4 h. After this time, diethyl ether (100 mL) was added, and the mixture was filtered. The filtrate was concentrated under reduced pressure to provide (S)-tert-butyl (1-((2,5-dioxopyrrolidin-1-yl) oxy)-1-oxopropan-2-yl) succinate (6.85 g) that was used without purification: $^1$H NMR (300 MHz, CDCl$_3$) δ 5.44 (q, J=7.1 Hz, 1H), 2.84 (s, 4H), 2.72-2.52 (m, 4H), 1.68 (d, J=7.1 Hz, 3H), 1.44 (s, 9H).

Preparation of tert-Butyl ((S)-1-(((4R,4aS,7aR,12bS)-4a-Hydroxy-9-methoxy-3-methyl-2,3,4,4a,5,7a-hexahydro-1H-4,12-methanobenzofuro[3,2-e] isoquinolin-7-yl)oxy)-1-oxopropan-2-yl) succinate

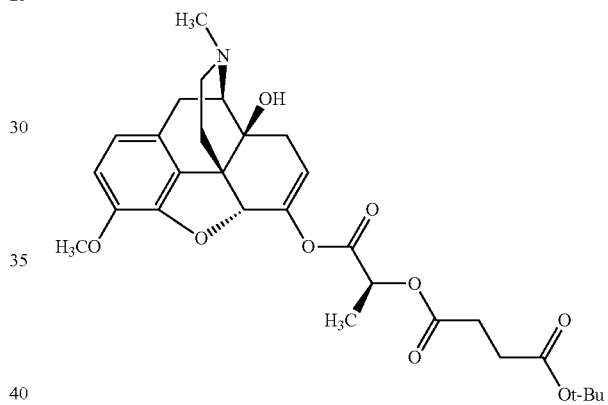

A suspension of oxycodone (0.600 g, 1.90 mmol) in tetrahydrofuran (6 mL) was cooled in an ice bath and treated dropwise with a 1.0 M solution of lithium bis(trimethylsilyl) amide in tetrahydrofuran (2.47 mL, 2.47 mmol). The mixture was stirred at 0° C. for 15 min and then treated dropwise with a solution of (S)-tert-butyl (1-((2,5-dioxopyrrolidin-1-yl)oxy)-1-oxopropan-2-yl) succinate (0.849 g, 2.47 mmol) in tetrahydrofuran (6 mL). The mixture was stirred at 0° C. for 1 h. After this time, the reaction mixture was treated with saturated aqueous ammonium chloride (100 mL) and extracted with ethyl acetate (3×100 mL). The combined organics were dried over sodium sulfate, filtered, and concentrated under reduced pressure. The crude residue was purified by reversed phase column chromatography (50 g C18 column, 5-100% acetonitrile/water) and freeze dried to provide tert-butyl ((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) succinate (0.460 g, 44%) as a colorless oil: ESI MS m/z 544 [C$_{29}$H$_{37}$NO$_9$+H]$^+$.

403

Preparation of 4-(((R)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt

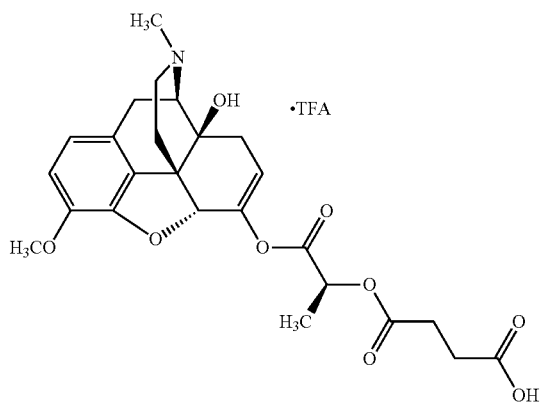 [SMILES: COc1ccc2c3c1O[C@H]1C(OC(=O)[C@H](C)OC(=O)CCC(=O)O)=CC[C@@]4(O)[C@@H](C2)N(C)CC[C@]314]

A solution of tert-butyl ((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) succinate (0.210 g, 0.386 mmol) in methylene chloride (6 mL) was treated with trifluoroacetic acid (3 mL) and stirred under a nitrogen atmosphere at ambient temperature for 1 h. After this time, the reaction mixture was concentrated under reduced pressure. The crude residue was purified by reversed phase column chromatography (50 g C18 column, 5-50% acetonitrile/water) and freeze dried to provide 4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt (0.098 g, 52%) as a fluffy white solid: $^1$H NMR (300 MHz, DMSO-$d_6$) δ 12.25 (br s, 1H), 9.19 (s, 1H), 6.86 (d, J=8.4 Hz, 1H), 6.75 (d, J=8.4 Hz, 1H), 6.31 (br s, 1H), 5.59-5.57 (m, 1H), 5.11 (q, J=6.9 Hz, 1H), 4.99 (s, 1H), 3.75 (s, 3H), 3.65 (d, J=6.0 Hz, 2H), 3.43 (d, J=19.8 Hz, 1H), 3.14-3.31 (m, 2H), 2.84 (d, J=4.5 Hz, 3H), 2.62-2.60 (m, 3H), 2.48-2.40 (m, 2H), 2.29 (dd, J=17.7, 11.7 Hz, 1H), 2.06 (d, J=18.0 Hz, 1H), 1.65 (d, J=11.1 Hz, 1H), 1.49 (d, J=3.9 Hz, 3H); ESI MS m/z 488 $[C_{25}H_{29}NO_9+H]^+$; HPLC (Method A) 97.3% (AUC), $t_R$=8.19 min.

Scheme 38: (S,2S,2'S)-4,4'-(((4R,4aS,7aR,12bS)-9-Methoxy-3-methyl-2,3,4,4a,5,7a-hexahydro-1H-4,12-methanobenzofuro[3,2-e]isoquinoline-4a,7-diyl)bis(oxy))bis(2-((S)-2-hydroxypropanamido)-4-oxobutanoic acid) trifluoroacetic acid salt

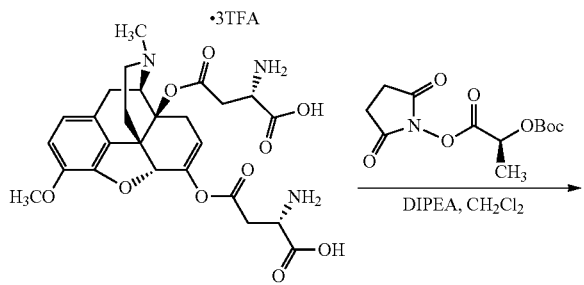

404

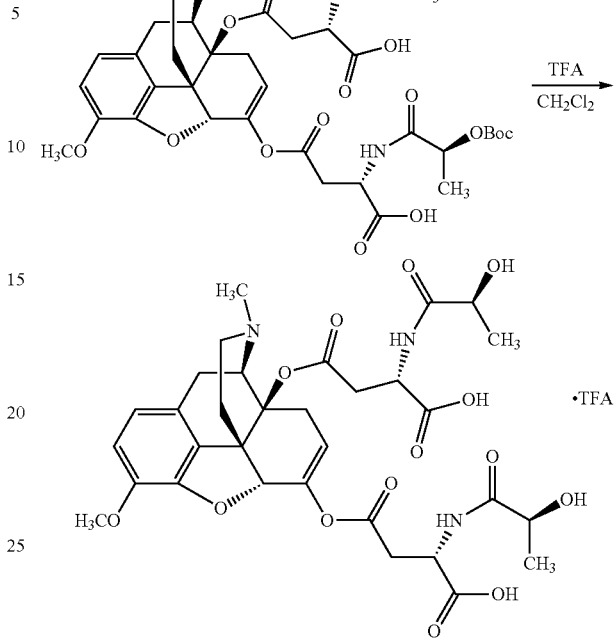

Preparation of (S,2S,2'S)-4,4'-(((4R,4aS,7aR,12bS)-9-Methoxy-3-methyl-2,3,4,4a,5,7a-hexahydro-1H-4,12-methanobonzofuro[3,2-e]isoquinolino-4a,7-diyl)bis(oxy))bis(2-((S)-2-((tert-butoxycarbonyl)oxy)propanamido)-4-oxobutanoic acid)

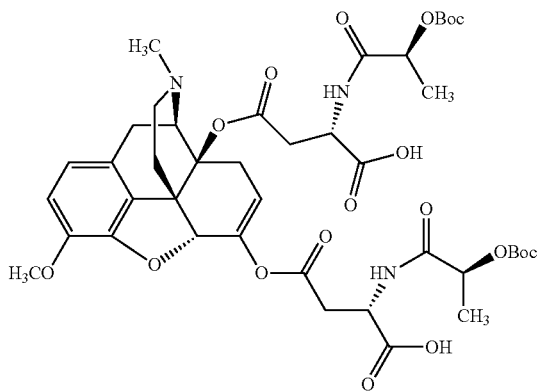

A mixture of (2S,2'S)-4,4'-(((4R,4aS,7aR,12bS)-9-Methoxy-3-methyl-2,3,4,4a,5,7a-hexahydro-1H-4,12-methanobenzofuro[3,2-e]isoquinoline-4a,7-diyl)bis(oxy))bis(2-amino-4-oxobutanoic acid) tris(trifluoroacetic acid salt)(0.200 g, 0.225 mmol), (S)-2,5-dioxopyrrolidin-1-yl 2-((tert-butoxycarbonyl)oxy)propanoate (0.194 g, 0.676 mmol), and N,N-diisopropylethylamine (0.23 mL, 1.4 mmol) in methylene chloride (5 mL) was stirred at ambient temperature for 2 h. After this time, the reaction was concentrated under reduced pressure to give (S,2S,2'S)-4,4'-(((4R,4aS,7aR,12bS)-9-methoxy-3-methyl-2,3,4,4a,5,7a-hexahydro-1H-4,12-methanobenzofuro[3,2-e]isoquinoline- 4a,7-diyl)bis(oxy))bis(2-((S)-2-((tert-butoxycarbonyl)oxy) propanamido)-4-oxobutanoic acid) (0.600 g, crude) as a white foam: ESI MS m/z 890 $[C_{42}H_5N_3O18+H]^+$.

Preparation of (S,2S,2'S)-4,4'-(((4R,4aS,7aR,12bS)-9-Methoxy-3-methyl-2,3,4,4a,5,7a-hexahydro-1H-4,12-methanobenzofuro[3,2-e]isoquinoline-4a,7-diyl) bis(oxy))bis(2-((S)-2-hydroxypropanamido)-4-oxobutanoic acid) trifluoroacetic acid salt

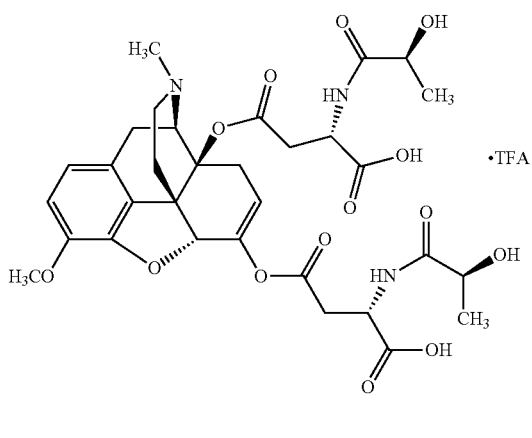 [SMILES: COc1ccc2c3c1O[C@H]1C(OC(=O)C[C@H](NC(=O)[C@H](C)O)C(=O)O)=CC[C@@]4(OC(=O)C[C@H](NC(=O)[C@H](C)O)C(=O)O)[C@@H](C2)N(C)CC[C@]314]

A solution of (S,2S,2'S)-4,4'-(((4R,4aS,7aR,12bS)-9-methoxy-3-methyl-2,3,4,4a,5,7a-hexahydro-1H-4,12-methanobenzofuro[3,2-e]isoquinoline-4a,7-diyl)bis(oxy)) bis(2-((S)-2-((tert-butoxycarbonyl)oxy)propanamido)-4-oxobutanoic acid)(0.600 g, crude) in methylene chloride (6 mL) was treated with trifluoroacetic acid (3 mL) and stirred at ambient temperature for 1 h. After this time, the reaction mixture was concentrated under reduced pressure. The residue was purified by reversed phase chromatography (50 g C18 column, 5-20% acetonitrile/water, with 0.1% trifluoroacetic acid) and freeze dried to provide (S,2S,2'S)-4,4'-(((4R,4aS,7aR,12bS)-9-methoxy-3-methyl-2,3,4,4a,5,7a-hexahydro-1H-4,12-methanobenzofuro[3,2-e]isoquinoline-4a,7-diyl)bis(oxy))bis(2-((S)-2-hydroxypropanamido)-4-oxobutanoic acid)trifluoroacetic acid salt (0.0135 g, 7% over two steps) as a white solid: $^1$H NMR (300 MHz, DMSO-$d_6$) δ 12.96 (br s, 2H), 9.35 (br s, 1H), 8.03 (d, J=8.4 Hz, 1H), 7.93 (d, J=7.8 Hz, 1H), 6.89 (d, J=8.1 Hz, 1H), 6.77 (d, J=8.4 Hz, 1H), 5.68 (br s, 2H), 5.44-5.42 (m, 1H), 5.03 (s, 1H), 4.69-4.62 (m, 3H), 4.03-3.97 (m, 2H), 3.76 (s, 3H), 3.28-3.13 (m, 1H), 3.16-3.07 (m, 2H), 3.04-2.82 (m, 8H), 2.73-2.63 (m, 2H), 2.11 (d, J=18.3 Hz, 1H), 1.76 (d, J=12.9 Hz, 1H), 1.20 (d, J=9.0 Hz, 6H); ESI MS m/z 690 $[C_{32}H_{39}N_3O_{14}+H]^+$; HPLC (Method A) 83.1% (AUC), $t_R$=7.13 min.

Scheme 39: (S)-3-Hydroxy-4-(((S)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt

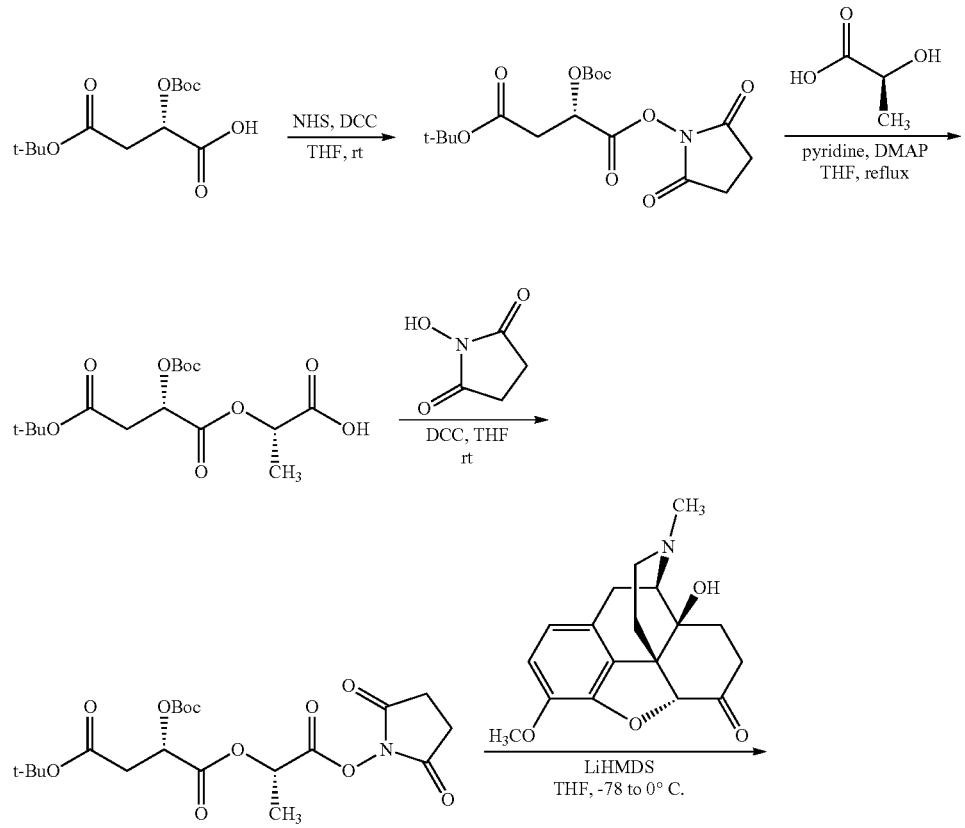

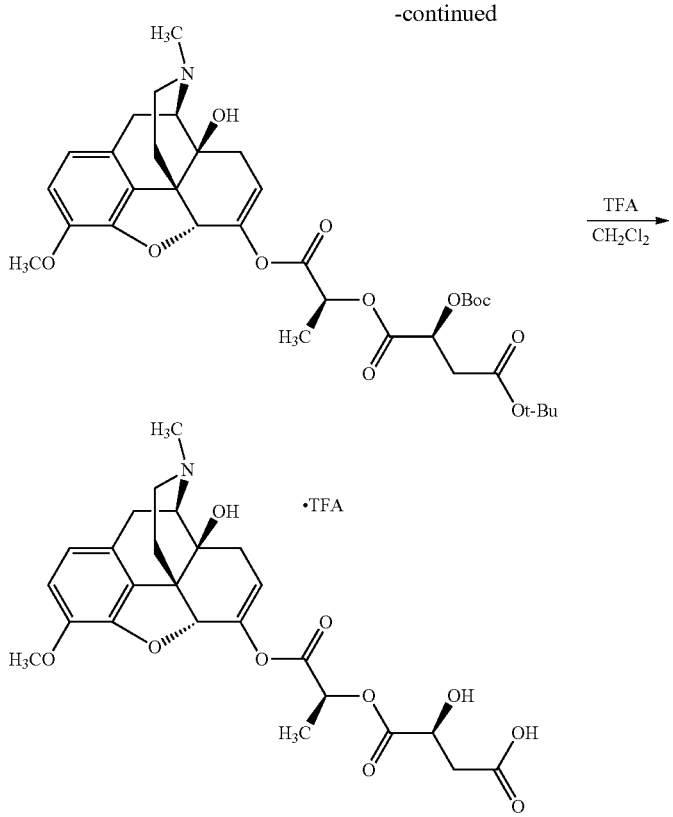

Preparation of (S)-4-tert-Butyl 1-(2,5-dioxopyrrolidin-1-yl) 2-((tert-butoxycarbonyl)oxy)succinate

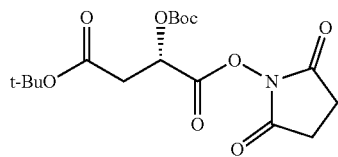

A mixture of (S)-4-(tert-butoxy)-2-((tert-butoxycarbonyl)oxy)-4-oxobutanoic acid (2.70 g, 9.31 mmol) and N-hydroxysuccinimide (1.25 g, 10.9 mmol) in tetrahydrofuran (50 mL) at 0° C. was treated with N,N'-dicyclohexylcarbodiimide (2.20 g, 10.7 mmol). The ice bath was removed, and the reaction mixture was stirred at ambient temperature for 4 h. After this time, diethyl ether (100 mL) was added, and the mixture was filtered. The filtrate was concentrated under reduced pressure to provide (S)-4-tert-butyl 1-(2,5-dioxopyrrolidin-1-yl) 2-((tert-butoxycarbonyl)oxy)succinate (3.78 g) that was used without purification: $^1$H NMR (300 MHz, CDCl$_3$) δ 5.61 (dd, J=8.0, 4.8 Hz, 1H), 2.98-2.93 (m, 2H), 2.84 (s, 4H), 1.51 (s, 9H), 1.47 (s, 9H).

Preparation of (S)-2-(((S)-4-(tert-Butoxy)-2-((tert-butoxycarbonyl)oxy)-4-oxobutanoyl)oxy)propanoic acid

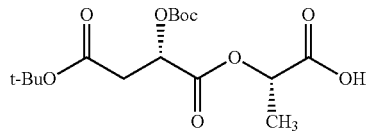

A mixture of (S)-4-tert-butyl 1-(2,5-dioxopyrrolidin-1-yl) 2-((tert-butoxycarbonyl)oxy)succinate (3.38 g, 8.73 mmol), (S)-2-hydroxypropanoic acid (1.20 g, 13.3 mmol), pyridine (1.1 mL, 14 mmol), and 4-dimethylaminopyridine (100 mg, 0.8 mmol) in tetrahydrofuran (40 mL) was stirred at reflux for 18 h. After this time, the mixture was cooled to room temperature, partially concentrated under reduced pressure, diluted with ethyl acetate, and washed with 10% citric acid. The organic layer was extracted with saturated sodium bicarbonate. The aqueous extract was carefully treated with 2N hydrochloric acid until acidic by pH paper analysis, and then extracted with ethyl acetate. The organic extracts were dried over sodium sulfate, filtered, and concentrated under reduced pressure to give (S)-2-(((S)-4-(tert-butoxy)-2-((tert-butoxycarbonyl)oxy)-4-oxobutanoyl)oxy)propanoic acid (1.58 g, 50%): $^1$H NMR (300 MHz, CDCl$_3$) δ 5.37-5.22 (m, 2H), 2.96-2.82 (m, 2H), 1.57 (d, J=7.1 Hz, 3H), 1.49 (s, 9H), 1.46 (s, 9H), CO$_2$H proton not observed.

Preparation of (S)-4-tert-Butyl 1-((S)-1-((2,5-dioxopyrrolidin-1-yl)oxy)-1-oxopropan-2-yl) 2-((tert-butoxycarbonyl)oxy)succinate A mixture of (S)-2-(((S)-4-(tert-butoxy)-2-((tert-butoxycarbonyl)oxy)-4-oxobutanoyl)oxy)propanoic acid (1.58 g, 4.36 mmol) and N-hydroxysuccinimide (550 mg, 4.78 mmol) in tetrahydrofuran (30 mL) at 0° C. was treated with N,N'-dicyclohexylcarbodiimide (990 mg, 4.80 mmol). The ice bath was removed, and the reaction mixture was stirred at ambient temperature for 4 h. After this time, diethyl ether (30 mL) was added, and the mixture was filtered. The filtrate was concentrated under reduced pressure to provide (S)-4-tert-butyl 1-((S)-1-((2,5-dioxopyrrolidin-1-yl)oxy)-1-oxopropan-2-yl) 2-((tert-butoxycarbonyl)oxy)succinate (2.2 g) that was used without purification: $^1$H NMR (300 MHz, CDCl$_3$) δ 5.56 (q, J=7.1 Hz, 1H), 3.37 (dd, J=8.8, 3.9 Hz, 1H), 2.98-2.93 (m, 2H), 2.84 (s, 4H), 1.72 (d, J=7.1 Hz, 3H), 1.50 (s, 9H), 1.46 (s, 9H).

Preparation of (S)-4-tert-Butyl 1-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-((tert-butoxycarbonyl)oxy)succinate

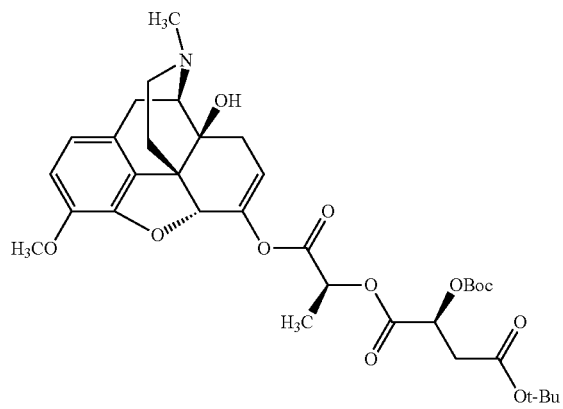

A suspension of oxycodone (0.550 g, 1.75 mmol) in tetrahydrofuran (5 mL) was cooled in an ice bath and treated with a 1.0 M solution of potassium tert-butoxide in tetrahydrofuran (1.95 mL, 1.95 mmol). After addition was complete, the mixture was stirred under a nitrogen atmosphere in the ice bath for 25 min and at ambient temperature for 25 min. The solution was re-cooled in a dry ice/acetone bath, and the mixture was treated with a solution of (S)-4-tert-butyl 1-((S)-1-((2,5-dioxopyrrolidin-1-yl)oxy)-1-oxopropan-2-yl) 2-((tert-butoxycarbonyl)oxy)succinate (0.900 g, 1.96 mmol) in tetrahydrofuran (5 mL). The temperature was allowed to slowly increase to 0° C. over 2 h. After this time, the reaction mixture was treated with saturated aqueous ammonium chloride (50 mL) and extracted with ethyl acetate (2×50 mL). The combined organics were washed with saturated sodium bicarbonate (50 mL) and brine (50 mL), dried over sodium sulfate, filtered, and concentrated under reduced pressure. The crude residue was purified by reversed phase column chromatography (150 g C18 column, 5-100% acetonitrile/water) and freeze dried to provide (S)-4-tert-butyl 1-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-((tert-butoxycarbonyl)oxy)succinate (273 mg, 24%) as a white solid: ESI MS m/z 660 [C$_{34}$H$_{45}$NO$_{12}$+H]$^+$.

Preparation of (S)-3-Hydroxy-4-(((S)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt

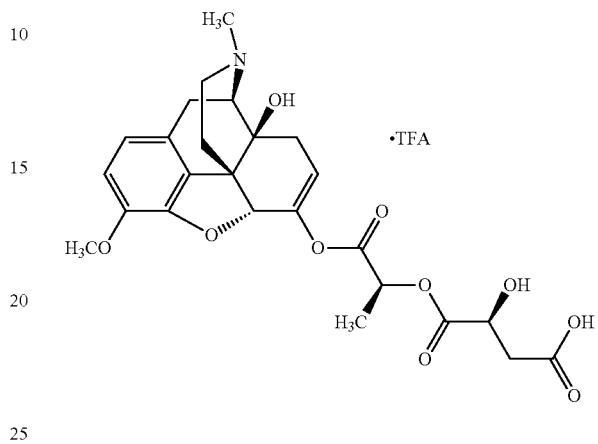

A solution of (S)-4-tert-butyl 1-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) oxy)-1-oxopropan-2-yl) 2-((tert-butoxycarbonyl)oxy) succinate (0.260 g, 0.390 mmol) in methylene chloride (6 mL) was treated with trifluoroacetic acid (3 mL) and stirred at ambient temperature for 1 h. After this time, the reaction mixture was concentrated under reduced pressure. The crude residue was purified by reversed phase column chromatography (50 g C18 column, 5-50% acetonitrile/water) and freeze dried to provide (S)-3-hydroxy-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt (0.122 g, 62%) as a white solid: $^1$H NMR (300 MHz, DMSO-d$_6$) δ 12.36 (br s, 1H), 9.19 (br s, 1H), 6.86 (d, J=8.4 Hz, 1H), 6.75 (d, J=8.4 Hz, 1H), 6.31 (s, 1H), 5.83 (br s, 1H), 5.60-5.58 (m, 1H), 5.18 (q, J=16.2 Hz, 1H), 5.00 (s, 1H), 4.73 (dd, J=8.7, 3.9 Hz, 1H), 3.75 (s, 3H), 3.65 (d, J=6.3 Hz, 1H), 3.43 (d, J=20.1 Hz, 1H), 3.14-3.07 (m, 2H), 2.84 (d, J=4.8 Hz, 3H), 2.78-2.58 (m, 2H), 2.33-2.26 (m, 1H), 2.07 (d, J=17.7 Hz, 1H), 1.65 (d, J=11.4 Hz, 1H), 1.51 (d, J=7.2 Hz, 3H), one proton obscured by solvent peaks; ESI MS m/z 504 [C$_{25}$H$_{29}$NO$_{10}$+H]$^+$;HPLC (Method A) 98.6% (AUC), t$_R$=7.62 min.

Scheme 40: 4-((R)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoroacetic acid salt

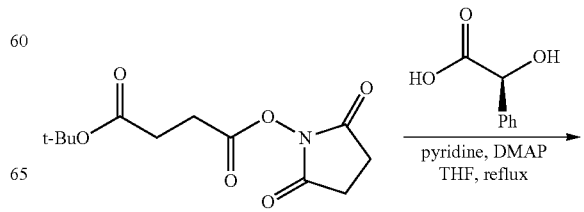

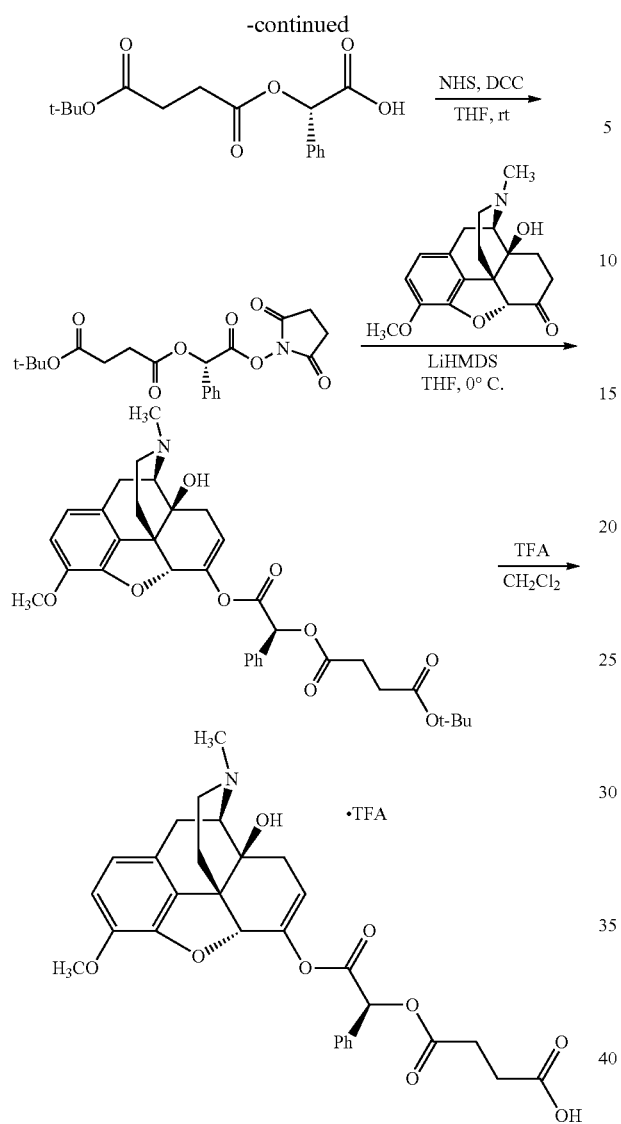

Preparation of (S)-2-((4-(tert-Butoxy)-4-oxobutanoyl)oxy)-2-phenylacetic acid

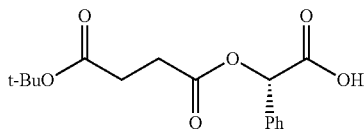

A mixture of tert-butyl (2,5-dioxopyrrolidin-1-yl) succinate (7.60 g, 28.0 mmol), (S)-2-hydroxy-2-phenylacetic acid (4.26 g, 28.0 mmol), pyridine (2.7 mL, 33.5 mmol), and 4-dimethylaminopyridine (200 mg, 1.6 mmol) in tetrahydrofuran (120 mL) was stirred at reflux for 48 h. After this time, the mixture was cooled to room temperature, partially concentrated under reduced pressure, diluted with ethyl acetate, and washed with 10% citric acid. The organic layer was extracted with saturated sodium bicarbonate. The aqueous extract was carefully treated with 2N hydrochloric acid until acidic by pH paper analysis, and then extracted with ethyl acetate. The organic extracts were dried over sodium sulfate, filtered, and concentrated to give (S)-2-((4-(tert-butoxy)-4-oxobutanoyl)oxy)-2-phenylacetic acid (6.00 g, 70%): $^1$H NMR (300 MHz, CDCl$_3$) δ 7.51-7.45 (m, 2H), 7.42-7.35 (m, 3H), 5.97 (s, 1H), 2.76-2.69 (m, 2H), 2.63-2.55 (m, 2H), 1.41 (s, 9H), CO$_2$H proton not observed.

Preparation of (S)-tert-Butyl (2-((2,5-dioxopyrrolidin-1-yl)oxy)-2-oxo-1-phenylethyl) succinate

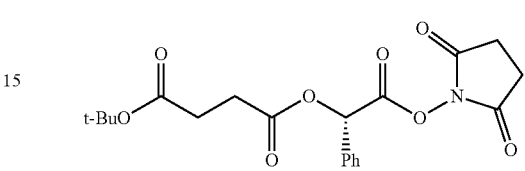

A mixture of (S)-2-((4-(tert-butoxy)-4-oxobutanoyl)oxy)-2-phenylacetic acid (6.00 g, 19.5 mmol) and N-hydroxysuccinimide (2.50 g, 21.7 mmol) in tetrahydrofuran (100 mL) at 0° C. was treated with N,N'-dicyclohexylcarbodiimide (4.45 g, 21.6 mmol). The ice bath was removed, and the reaction mixture was stirred at ambient temperature for 4 h. After this time, diethyl ether (100 mL) was added, and the mixture was filtered. The filtrate was concentrated under reduced pressure to provide (S)-tert-butyl (2-((2,5-dioxopyrrolidin-1-yl)oxy)-2-oxo-1-phenylethyl) succinate (8.33 g) that was used without purification: $^1$H NMR (300 MHz, CDCl$_3$) δ 7.57-7.51 (m, 2H), 7.46-7.40 (m, 3H), 6.35 (s, 1H), 2.80 (s, 4H), 2.77-2.71 (m, 2H), 2.63-2.56 (m, 2H), 1.41 (s, 9H).

Preparation of tert-butyl ((S)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl) succinate

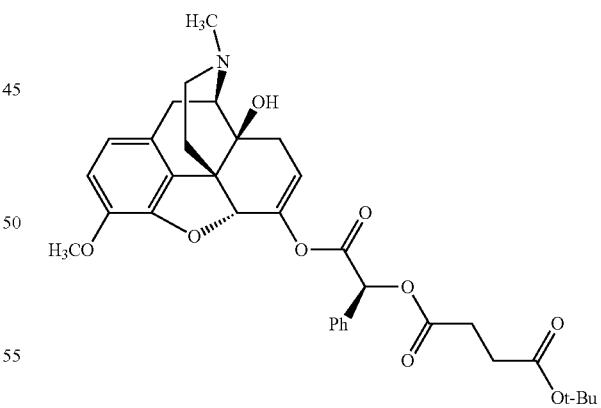

A suspension of oxycodone (0.600 g, 1.90 mmol) in tetrahydrofuran (6.0 mL) was cooled in an ice bath and treated dropwise with a 1.0 M solution of lithium bis(trimethylsilyl)amide in tetrahydrofuran (3.0 mL, 3.0 mmol). The mixture was stirred at 0° C. for 15 min and then treated dropwise with a solution of (S)-tert-butyl (2-((2,5-dioxopyrrolidin-1-yl)oxy)-2-oxo-1-phenylethyl) succinate (1.20 g, 3.04 mmol) in tetrahydrofuran (6 mL). The mixture was stirred at 0° C. for 1 h. After this time, the reaction mixture was treated with saturated aqueous ammonium chloride (100 mL) and extracted with ethyl acetate (3×100 mL). The combined organics were dried over sodium sulfate, filtered, and concentrated under reduced pressure. The crude residue was purified by reversed phase chromatography (150 g C18 column, 5-100% acetonitrile/water) and freeze dried to provide tert-butyl ((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl) succinate (0.540 g, 47%) as a colorless oil: ESI MS m/z 606 $[C_{34}H_{39}NO_9+H]^+$.

Preparation of 4-((R)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoroacetic acid salt

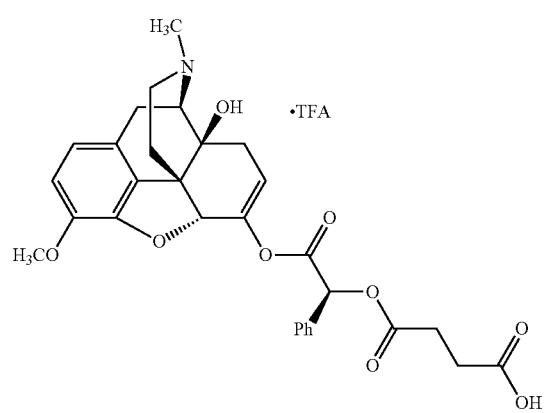 [SMILES: COc1ccc2c3c1O[C@H]1C(OC(=O)[C@@H](OC(=O)CCC(=O)O)c4ccccc4)=CC[C@@]4(O)[C@@H](C2)N(C)CC[C@]314]

A solution of tert-butyl ((R)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl) succinate (0.250 g, 0.413 mmol) in methylene chloride (6 mL) was treated with trifluoroacetic acid (3 mL) and stirred under a nitrogen atmosphere at ambient temperature for 1 h. After this time, the reaction mixture was concentrated under reduced pressure. The residue was purified by reversed phase column chromatography (50 g C18 column, 5-50% acetonitrile/water) and freeze dried to provide 4-((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoroacetic acid salt (0.100 mg, 44%) as a fluffy white solid: $^1$H NMR (300 MHz, DMSO-$d_6$) δ 12.28 (br s, 1H), 9.16 (br s, 1H), 7.56-7.54 (m, 2H), 7.50-7.45 (m, 3H), 6.81 (d, J=8.4 Hz, 1H), 6.72 (d, J=8.4 Hz, 1H), 6.31 (s, 1H), 6.10 (s, 1H), 5.55-5.53 (m, 1H), 4.95 (s, 1H), 3.64 (s, 3H), 3.41 (d, J=19.8 Hz, 1H), 3.14-3.05 (m, 2H), 2.83 (d, J=4.5 Hz, 3H), 2.69-2.66 (m, 3H), 2.56-2.49 (m, 2H), 2.45-2.40 (m, 1H), 2.30-2.22 (m, 1H), 2.05 (d, J=18.3 Hz, 1H), 1.62 (d, J=11.4 Hz, 1H); ESI MS m/z 550 $[C_{30}H_{31}NO_9+H]^+$; HPLC (Method A) 99.0% (AUC), $t_R$=9.30 min.

Scheme 41: (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((S)-2-hydroxy-2-phenylacetoxy)propanoate trifluoroacetic acid salt

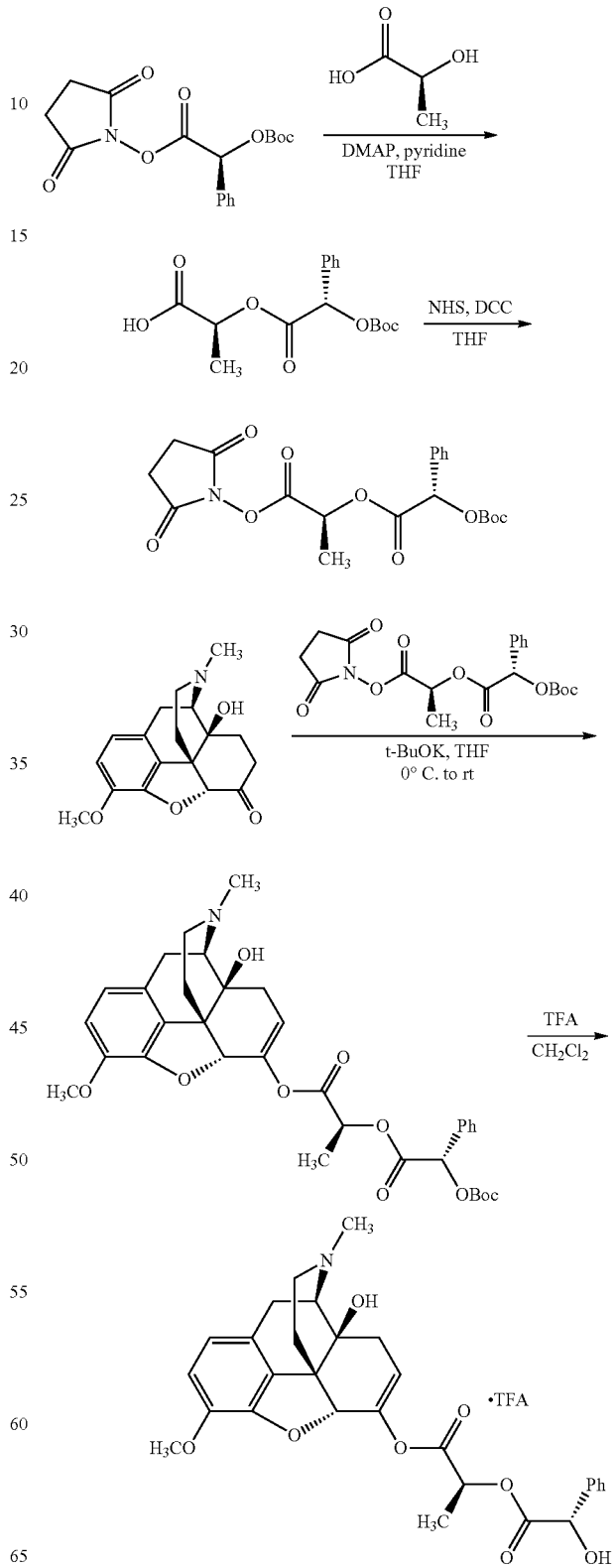

Preparation of (S)-2-((S)-2-((tert-Butoxycarbonyl)oxy)-2-phenylacetoxy)propanoic acid

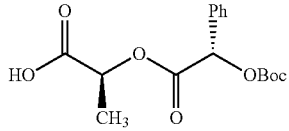

A solution of (S)-2,5-dioxopyrrolidin-1-yl 2-((tert-butoxycarbonyl)oxy)-2-phenylacetate (2.00 g, 5.73 mmol), lactic acid (627 mg, 6.96 mmol), and 4-dimethylaminopyridine (68 mg, 0.56 mmol) in tetrahydrofuran (25 mL) was treated with pyridine (0.56 g, 7.0 mmol) and heated at 50° C. under a nitrogen atmosphere for 16 h. After this time, the reaction mixture was cooled to room temperature and concentrated under reduced pressure. The residue was dissolved in ethyl acetate (50 mL) and washed with aqueous 10% citric acid (2×25 mL) and water (25 mL). The organic layer was extracted with saturated aqueous sodium bicarbonate (2×25 mL). The combined aqueous bicarbonate layers were acidified to pH ~2 with 6 N hydrochloric acid and extracted with ethyl acetate (4×25 mL). The combined organics were dried over sodium sulfate, filtered, and concentrated under reduced pressure to provide (S)-2-((S)-2-((tert-butoxycarbonyl)oxy)-2-phenylacetoxy)propanoic acid (1.42 g, 76%) as a colorless oil: $^1$H NMR (300 MHz, CDCl$_3$) δ 7.52-7.48 (m, 2H), 7.40-7.37 (m, 3H), 5.85 (s, 1H), 5.23 (q, J=6.9 Hz, 1H), 1.56-1.44 (m, 12H), CO$_2$H proton not observed; ESI MS m/z 647 [(2×C$_{16}$H$_{20}$O$_7$)–H]$^-$.

Preparation of (S)-2,5-Dioxopyrrolidin-1-yl 2-((S)-2-((tert-butoxycarbonyl)oxy)-2-phenylacetoxy)propanoate

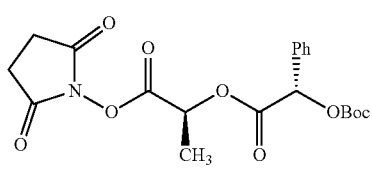

A solution of (S)-2-((S)-2-((tert-butoxycarbonyl)oxy)-2-phenylacetoxy)propanoic acid (1.42 g, 4.36 mmol) in tetrahydrofuran (20 mL) was treated with N-hydroxysuccinimide (558 mg, 4.85 mmol) and N,N'-dicyclohexylcarbodiimide (997 mg, 4.83 mmol) and stirred under a nitrogen atmosphere for 2.5 h. After this time, the reaction mixture was filtered to remove the solid dicyclohexylurea byproduct. The solid was washed with diethyl ether, and the combined filtrate and washings were concentrated under reduced pressure to provide (S)-2,5-dioxopyrrolidin-1-yl 2-((S)-2-((tert-butoxycarbonyl)oxy)-2-phenylacetoxy)propanoate (2.02 g, quantitative) as a white crushable foam: $^1$H NMR (300 MHz, CDCl$_3$) δ 7.51-7.45 (m, 2H), 7.40-7.34 (m, 3H), 5.85 (s, 1H), 5.53 (q, J=6.9 Hz, 1H), 2.82 (br s, 4H), 1.69 (d, J=6.9 Hz, 3H), 1.51 (s, 9H).

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((S)-2-((tert-butoxycarbonyl)oxy)-2-phenylacetoxy)propanoate

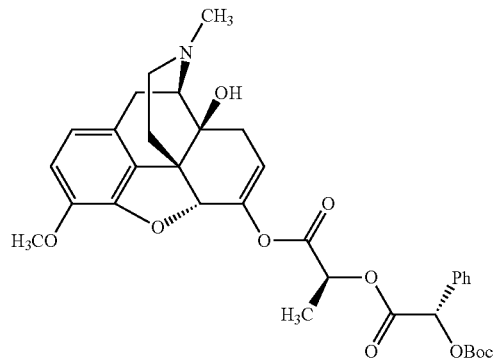

A suspension of oxycodone (502 mg, 1.59 mmol) in tetrahydrofuran (6 mL) was cooled in an ice bath and treated dropwise with a 1.0 M solution of potassium tert-butoxide in tetrahydrofuran (1.9 mL, 1.9 mmol). After addition was complete, the mixture was stirred in the ice bath for 10 min and at ambient temperature for 5 min. The mixture was re-cooled in the ice bath and treated dropwise with a solution of (S)-2,5-dioxopyrrolidin-1-yl 2-((S)-2-((tert-butoxycarbonyl)oxy)-2-phenylacetoxy)propanoate (806 mg, 1.91 mmol) in tetrahydrofuran (6 mL). After addition was complete, the mixture was stirred at ambient temperature for 10 min. After this time, the reaction mixture was re-cooled in the ice bath and treated with saturated aqueous ammonium chloride (50 mL) and extracted with ethyl acetate (2×50 mL). The combined organics were washed with saturated sodium bicarbonate (25 mL) and brine (25 mL), dried over sodium sulfate, filtered, and concentrated under reduced pressure. The crude residue was purified by column chromatography (silica gel, 0-10% methanol/methylene chloride) followed by reversed phase column chromatography (50 g C18 column, 20-100% acetonitrile/water) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((S)-2-((tert-butoxycarbonyl)oxy)-2-phenylacetoxy)propanoate (53 mg, 5%) as a fluffy white solid: ESI MS m/z 622 [C$_{34}$H$_{39}$NO$_{10}$+H]$^+$.

417

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((S)-2-hydroxy-2-phenylacetoxy)propanoate trifluoroacetic acid salt

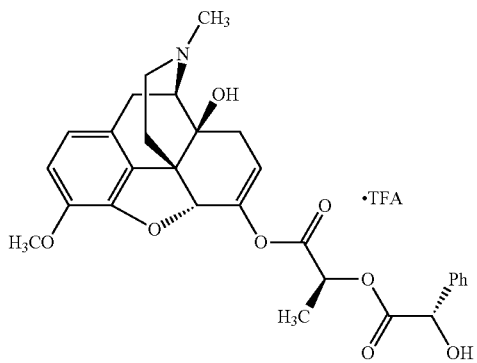 [SMILES: COc1ccc2c3c1O[C@H]1C(OC(=O)[C@H](C)OC(=O)[C@@H](O)c4ccccc4)=CC[C@@]4(O)[C@@H](C2)N(C)CC[C@]314]

418

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((S)-2-((tert-butoxycarbonyl)oxy)-2-phenylacetoxy)propanoate (53 mg, 0.085 mmol) in methylene chloride (2 mL) was treated with trifluoroacetic acid (0.5 mL) and stirred under a nitrogen atmosphere at ambient temperature for 20 min. After this time, the reaction mixture concentrated under reduced pressure. The residue was purified by reversed phase column chromatography (50 g C18 column, 10-70% acetonitrile/water) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((S)-2-hydroxy-2-phenylacetoxy)propanoate trifluoroacetic acid salt (24 mg, 45%) as a fluffy white solid: $^1$H NMR (300 MHz, DMSO-$d_6$) δ 9.17 (br s, 1H), 7.46-7.42 (m, 2H), 7.37-7.27 (m, 3H), 6.85 (d, J=8.4 Hz, 1H), 6.74 (d, J=8.1 Hz, 1H), 6.26 (s, 1H), 6.15 (d, J=5.4 Hz, 1H), 5.50-5.48 (m, 1H), 5.23-5.16 (m, 1H), 4.84 (s, 1H), 3.72 (s, 3H), 3.64 (br s, 1H), 3.42 (d, J=20.1 Hz, 1H), 3.15-3.06 (m, 2H), 2.84 (s, 3H), 2.64-2.57 (m, 1H), 2.49-2.40 (m, 1H, partially obscured by solvent peak), 2.34-2.23 (m, 1H), 2.04 (apparent d, J=18.3 Hz, 1H), 1.62 (d, J=8.7 Hz, 1H), 1.48 (d, J=6.9 Hz, 3H); ESI MS m/z 522 [C2H$_{31}$ NO$_8$+H]$^+$.

Scheme 42: (S)-2-(((4R,4aS,7aR,12bS)-4a-Hydroxy-9-methoxy-3-methyl-2,3,4,4a,5,7a-hexahydro-1H-4, 12-methanobenzofuro[3,2-e]isoquinolin-7-yl)oxy)-2-oxo-1-phenylethyl oleate trifluoroacetic acid salt

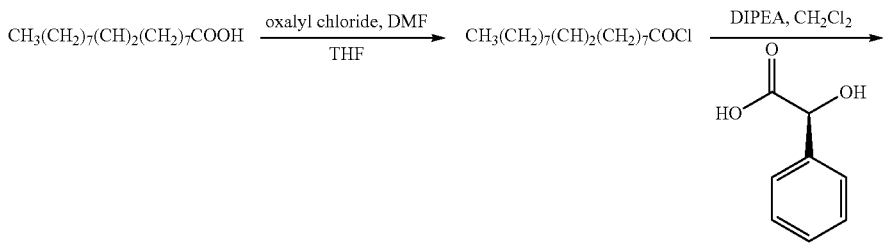

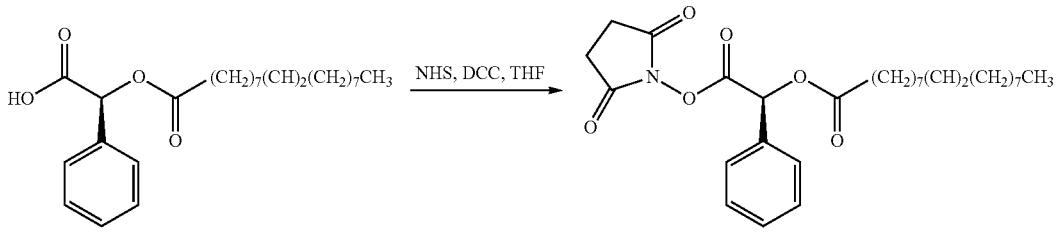

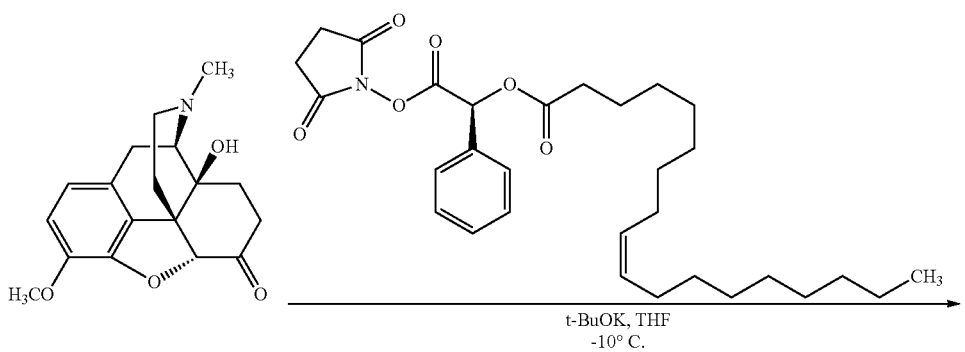

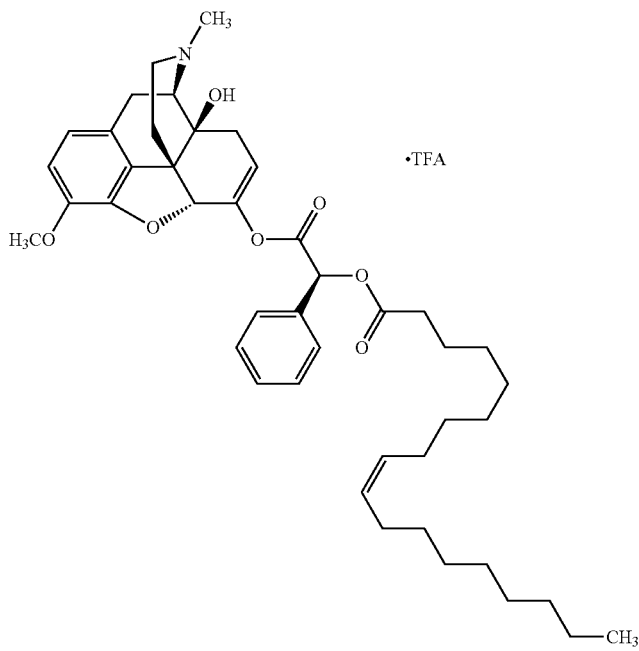

Preparation of (S,Z)-2-(Oleoyloxy)-2-phenylacetic acid

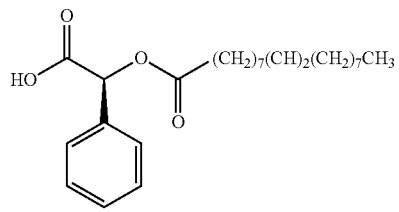

A solution of oleoyl chloride (2.13 g, 7.08 mmol) in methylene chloride (35 mL) was cooled in an ice bath and treated with (S)-mandelic acid (1.08 g, 7.08 mmol) and N,N-diisopropylethylamine (2.75 g, 21.2 mmol) and stirred under a nitrogen for 5 h. After this time, 10% aqueous citric acid (100 mL) was added, and the resulting mixture was extracted with ethyl acetate (2×100 mL). The combined organics were washed with brine (100 mL), dried over sodium sulfate, filtered, and concentrated under reduced pressure. The residue was purified by column chromatography (80 g silica gel column, 0-50% ethyl acetate/heptane) to provide of (S,Z)-2-(oleoyloxy)-2-phenylacetic acid (1.26 g, 42%) as a white solid: $^1$H NMR (300 MHz, DMSO-d$_6$) δ 7.50-7.46 (m, 2H), 7.41-7.37 (m, 3H), 5.95 (s, 1H), 5.36-5.32 (m, 2H), 2.47 (m, 2H), 1.99 (m, 4H), 1.66 (m, 2H), 1.27 (m, 20H), 0.87 (t, J=6.6 Hz, 3H),CO$_2$H proton not observed.

Preparation of (S)-2-((2,5-Dioxopyrrolidin-1-yl)oxy)-2-oxo-1-phenylethyl oleate

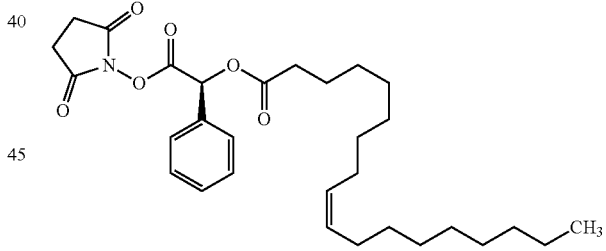

A solution of (S,Z)-2-(oleoyloxy)-2-phenylacetic acid (1.26 g, 3.02 mmol) in tetrahydrofuran (30 mL) was treated with N-hydroxysuccinimide (383 mg, 3.33 mmol) and N,N'-dicyclohexylcarbodiimide (686 mg, 3.33 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-2-((2,5-dioxopyrrolidin-1-yl)oxy)-2-oxo-1-phenylethyl oleate (1.68 g) as a white solid: $^1$H NMR (300 MHz, CDCl$_3$) δ 7.61-7.53 (m, 2H), 7.46-7.42 (m, 3H), 6.34 (s, 1H), 5.36-5.32 (m, 2H), 2.87 (s, 4H), 2.45 (m, 2H), 1.99 (m, 4H), 1.66 (m, 2H), 1.27 (m, 20H), 0.88 (t, J=6.6 Hz, 3H).

Preparation of (S)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl oleate trifluoroacetic acid salt Scheme 43: (S)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl stearate trifluoroacetic acid salt

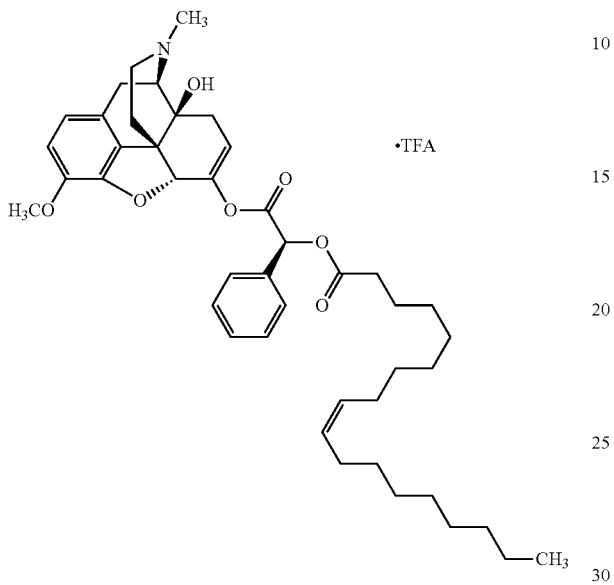

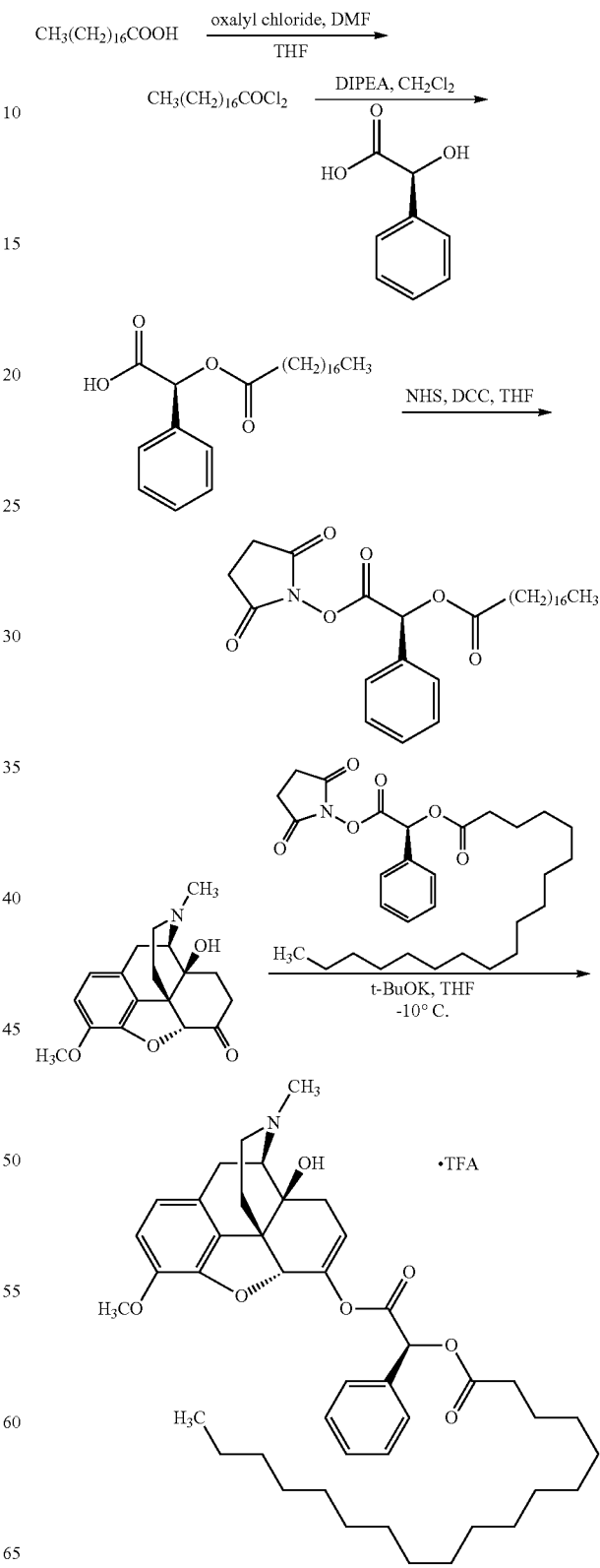

A suspension of oxycodone (461 mg, 1.46 mmol) in tetrahydrofuran (7 mL) was cooled in an ice bath and treated dropwise with a 1.0 M solution of potassium tert-butoxide in tetrahydrofuran (1.8 mL, 1.8 mmol). After addition was complete, the mixture was stirred in the ice bath for 45 min. The ice bath was replaced with an ice/brine bath, and the mixture was treated dropwise with a suspension of (S)-2-((2,5-dioxopyrrolidin-1-yl)oxy)-2-oxo-1-phenylethyl oleate (900 mg, 1.75 mmol) in tetrahydrofuran (7 mL). The mixture was stirred in the ice/brine bath under a nitrogen atmosphere for 45 min. After this time, the reaction mixture was treated with saturated aqueous ammonium chloride (50 mL) and extracted with ethyl acetate (2×50 mL). The combined organics were washed with saturated sodium bicarbonate (50 mL), water (50 mL), and brine (50 mL); dried over sodium sulfate; filtered; and concentrated under reduced pressure. The crude residue was purified by column chromatography (silica gel, 0-10% methanol/methylene chloride) followed by reversed phase column chromatography (150 g C18 column, 50-100% acetonitrile/water with 0.1% trifluoroacetic acid) and freeze dried to provide (S)-2-(((4R,4aS,7aR,12bS)-4α-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl oleate trifluoroacetic acid salt (265 mg, 22%) as a white solid: $^1$H NMR (300 MHz, DMSO-$d_6$, Mixture of diastereomers) δ 9.17 (br s, 1H), 7.56-7.53 (m, 2H), 7.46-7.44 (m, 3H), 6.85-6.79 (m, 1H), 6.75-6.71 (m, 1H), 6.29 (s, 1H), 6.09 (s, 0.49H), 6.07 (s, 0.51H), 5.53 (dd, J=6.0, 2.1 Hz, 0.49H), 5.45 (dd, J=6.0, 2.1 Hz, 0.51H), 5.33-5.30 (m, 2H), 4.94 (s, 0.49H), 4.90 (s, 0.51H), 3.71 (s, 1.47H), 3.64 (br s, 2.53H), 3.45-3.38 (m, 1H), 3.13-3.05 (m, 2H), 2.82 (s, 3H), 2.64-2.55 (m, 1H), 2.49-2.40 (m, 3H, partially obscured by solvent peak), 2.28-2.22 (m, 1H), 2.07-1.96 (m, 5H), 1.64-1.54 (m, 3H), 1.32-1.24 (m, 20H), 0.84 (t, J=6.6 Hz, 3H); ESI MS m/z 714 [$C_{44}H_{59}NO_7$+H]$^+$; HPLC (Method A)>99% (AUC), $t_R$=16.02 min.

Preparation of (S)-2-Phenyl-2-(stearoyloxy)acetic acid

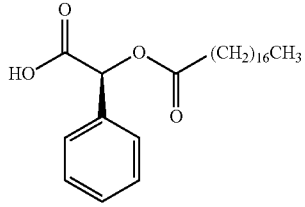

A solution of stearoyl chloride (364 mg, 1.20 mmol) in methylene chloride (5 mL) was cooled in an ice bath and treated with (S)-mandelic acid (182 mg, 1.20 mmol) and N,N-diisopropylethylamine (465 mg, 3.60 mmol) and stirred under a nitrogen atmosphere for 16 h. After this time, 10% aqueous citric acid (10 mL) was added, and the resulting mixture was extracted with ethyl acetate (2×20 mL). The combined organics were washed with brine (50 mL), dried over sodium sulfate, filtered, and concentrated under reduced pressure. The residue was purified by column chromatography (40 g silica gel column, 0-100% ethyl acetate/heptane) to provide of (S)-2-phenyl-2-(stearoyloxy)acetic acid (140 mg, 28%) as a white solid: $^1$H NMR (300 MHz, DMSO-d$_6$) δ 7.51-7.47 (m, 2H), 7.42-7.39 (m, 3H), 5.97 (s, 1H), 2.45 (m, 2H), 1.68 (m, 3H), 1.27 (m, 28H), 0.88 (t, J=6.6 Hz, 3H).

Preparation of (S)-2-((2,5-Dioxopyrrolidin-1-yl)oxy)-2-oxo-1-phenylethyl stearate

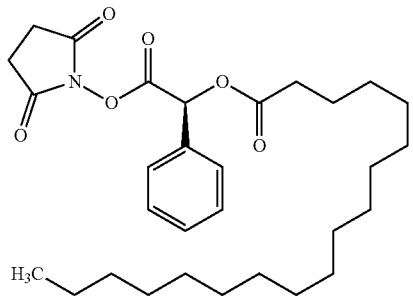 [SMILES: CCCCCCCCCCCCCCCCCC(=O)O[C@H](C(=O)ON1C(=O)CCC1=O)c1ccccc1]

A solution of (S)-2-phenyl-2-(stearoyloxy)acetic acid (140 mg, 0.334 mmol) in tetrahydrofuran (3 mL) was treated with N-hydroxysuccinimide (42 mg, 0.368 mmol) and N,N'-dicyclohexylcarbodiimide (76 mg, 0.368 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-2-((2,5-dioxopyrrolidin-1-yl)oxy)-2-oxo-1-phenylethyl stearate (191 mg) as a white powder: $^1$H NMR (300 MHz, CDCl$_3$) δ 7.56-7.53 (m, 2H), 7.46-7.43 (m, 3H), 6.34 (s, 1H), 2.81 (s, 4H), 2.46 (m, 2H), 1.68 (m, 2H), 1.24 (m, 28H), 0.88 (t, J=6.6 Hz, 3H).

Preparation of (S)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl stearate trifluoroacetic acid salt

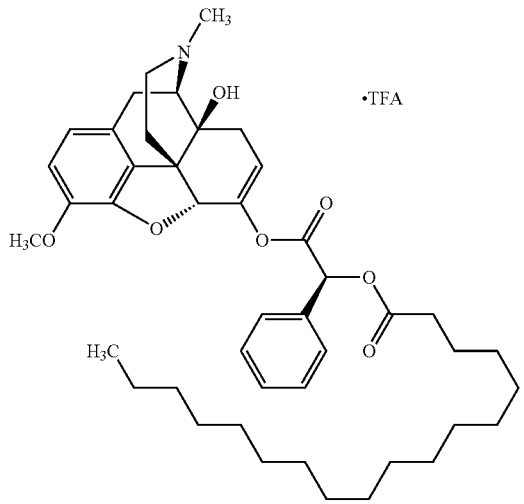 [SMILES: CCCCCCCCCCCCCCCCCC(=O)O[C@H](C(=O)OC1=CC[C@@]2(O)[C@H]3Cc4ccc(OC)c5c4[C@@]2(CCN3C)[C@H]1O5)c1ccccc1]

A suspension of oxycodone (515 mg, 1.63 mmol) in tetrahydrofuran (9 mL) was cooled in an ice bath and treated dropwise with a 1.0 M solution of potassium tert-butoxide in tetrahydrofuran (2.0 mL, 2.0 mmol). After addition was complete, the mixture was stirred in the ice bath for 45 min. The ice bath was replaced with an ice/brine bath, and the mixture was treated dropwise with a suspension of (S)-2-((2,5-dioxopyrrolidin-1-yl)oxy)-2-oxo-1-phenylethyl stearate (1.01 g, 1.96 mmol) in tetrahydrofuran (7 mL). The mixture was stirred in the ice/brine bath under a nitrogen atmosphere for 45 min. After this time, the reaction mixture was treated with saturated aqueous ammonium chloride (50 mL) and extracted with ethyl acetate (2×50 mL). The combined organics were washed with saturated sodium bicarbonate (50 mL), water (50 mL), and brine (50 mL); dried over sodium sulfate; filtered; and concentrated under reduced pressure. The crude residue was purified by column chromatography (silica gel, 0-10% methanol/methylene chloride) followed by reversed phase column chromatography (150 g C18 column, 50-100% acetonitrile/water with 0.1% trifluoroacetic acid) and freeze dried to (S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl stearate trifluoroacetic acid salt (430 mg, 32%) as a white solid: $^1$H NMR (300 MHz, DMSO-d$_6$, Mixture of diastereomers) δ 9.17 (br s, 1H), 7.56-7.53 (m, 2H), 7.46-7.44 (m, 3H), 6.86-6.80 (m, 1H), 6.75-6.71 (m, 1H), 6.30 (br s, 1H), 6.09 (s, 0.51H), 6.07 (s, 0.49H), 5.53 (dd, J=6.0, 2.1 Hz, 0.51H), 5.45 (dd, J=6.0, 2.1 Hz, 0.49H), 4.94 (s, 0.51H), 4.90 (s, 0.49H), 3.71 (s, 1.53H), 3.64 (br s, 2.47H), 3.45-3.35 (m, 1H), 3.13-3.05 (m, 2H), 2.83 (apparent d, J=4.5 Hz, 3H), 2.67-2.55 (m, 1H), 2.49-2.40 (m, 3H, partially obscured by solvent peak), 2.30-2.22 (m, 1H), 2.08-2.01 (m, 1H), 1.64-1.51 (m, 3H), 1.32-1.23 (m, 28H), 0.85 (t, J=6.6 Hz, 3H);ESI MS m/z 716 [C44H$_{61}$NO$_7$+H]$^+$; HPLC (Method A) 99.0% (AUC), t$_R$=16.53 min.

Scheme 44: (S)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl stearate trifluoroacetic acid salt

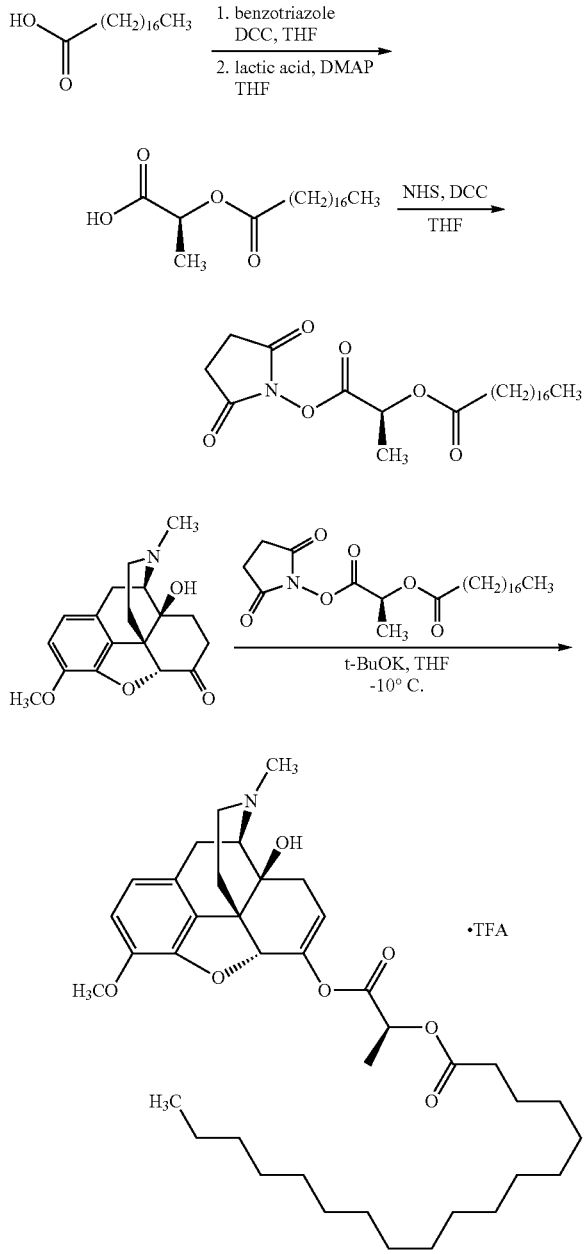

Preparation of (S)-2-(Stearoyloxy)propanoic acid

A solution of stearic acid (5.02 g, 17.6 mmol) and benzotriazole (2.31 g, 19.4 mmol) in tetrahydrofuran (80 mL) was treated with N,N'-dicyclohexylcarbodiimide (4.00 g, 19.4 mmol) and stirred under a nitrogen atmosphere for 5.5 h. After this time, the reaction mixture was filtered to remove the solid dicyclohexylurea byproduct, and the solids were washed with diethyl ether. The combined filtrate and washings were concentrated. The residue was dissolved in tetrahydrofuran (90 mL) and cooled in an ice bath. The mixture was treated with lactic acid (1.61 g, 17.9 mmol) and 4-dimethylaminopyridine (2.18 g, 17.8 mmol), and the ice bath was removed. The mixture was stirred at ambient temperature under a nitrogen atmosphere for 40 h. After this time, the reaction mixture was concentrated under reduced pressure. The residue was dissolved in ethyl acetate (250 mL) and washed with aqueous 10% citric acid (2×100 mL) and water (100 mL). The organic layer was extracted with saturated aqueous sodium bicarbonate (2×100 mL). The combined aqueous bicarbonate layers were acidified to pH ~1 with 6 N hydrochloric acid and extracted with ethyl acetate (2×100 mL). The combined organics were dried over sodium sulfate, filtered, and concentrated under reduced pressure. The residue was dissolved/suspended in heptanes (100 mL), filtered to remove undissolved solids, washed with aqueous 10% citric acid (50 mL), dried over sodium sulfate, filtered, and concentrated under reduced pressure to provide (S)-2-(stearoyloxy)propanoic acid (4.86 g, 77%) as a colorless oil: $^1$H NMR (300 MHz, CDCl$_3$) δ 5.12 (q, J=7.2 Hz, 1H), 2.41-2.32 (m, 2H), 1.67-1.52 (m, 5H), 1.31-1.27 (m, 28H), 0.88 (t, J=6.3 Hz, 3H), CO$_2$H proton not observed.

Preparation of (S)-1-((2,5-Dioxopyrrolidin-1-yl)oxy)-1-oxopropan-2-yl stearate

A solution of (S)-2-(stearoyloxy)propanoic acid (4.85 g, 13.6 mmol) in tetrahydrofuran (80 mL) was treated with N-hydroxysuccinimide (1.57 mg, 13.6 mmol) and N,N'-dicyclohexylcarbodiimide (2.80 g, 13.6 mmol) and stirred under a nitrogen atmosphere for 1.5 h. After this time, the reaction mixture was filtered to remove the solid dicyclohexylurea byproduct. The solid was washed with diethyl ether, and the combined filtrate and washings were concentrated under reduced pressure to provide (S)-1-((2,5-dioxopyrrolidin-1-yl)oxy)-1-oxopropan-2-yl stearate (6.69 g, quantitative) as a white crushable foam: $^1$H NMR (300 MHz, CDCl$_3$) δ 5.42 (q, J=7.2 Hz, 1H), 2.84 (br s, 4H), 2.42-2.37 (m, 2H), 1.73-1.53 (m, 5H), 1.31-1.27 (m, 28H), 0.88 (t, J=6.3 Hz, 3H).

Preparation of (S)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl stearate trifluoroacetic acid salt

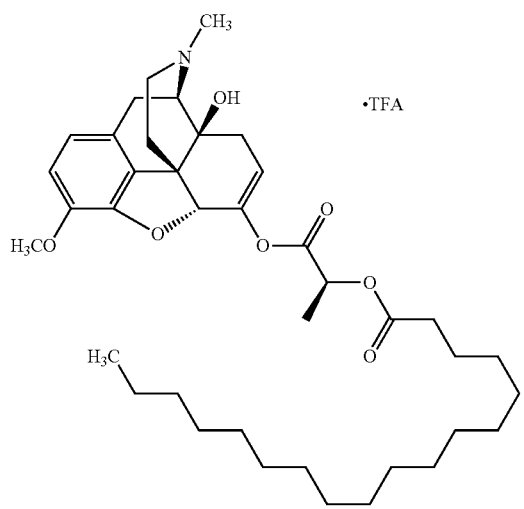 [SMILES: CCCCCCCCCCCCCCCCCC(=O)O[C@@H](C)C(=O)OC1=CC[C@@]2(O)[C@H]3Cc4ccc(OC)c5c4[C@@]2(CCN3C)[C@H]1O5]

A suspension of oxycodone (582 mg, 1.85 mmol) in tetrahydrofuran (9 mL) was cooled in an ice bath and treated dropwise with a 1.0 M solution of potassium tert-butoxide in tetrahydrofuran (2.3 mL, 2.3 mmol). After addition was complete, the mixture was stirred in the ice bath for 45 min. The ice bath was replaced with an ice/brine bath, and the mixture was treated dropwise with a solution of (S)-1-((2,5-dioxopyrrolidin-1-yl)oxy)-1-oxopropan-2-yl stearate (1.01 g, 2.23 mmol) in tetrahydrofuran (9 mL). The mixture was stirred in the ice/brine bath under a nitrogen atmosphere for 20 min. After this time, the reaction mixture was treated with saturated aqueous ammonium chloride (50 mL) and extracted with ethyl acetate (2×50 mL). The combined organics were washed with saturated sodium bicarbonate (50 mL) and brine (50 mL), dried over sodium sulfate, filtered, and concentrated under reduced pressure. The crude residue was purified by column chromatography (silica gel, 0-10% methanol/methylene chloride) followed by reversed phase column chromatography (150 g C18 column, 50-100% acetonitrile/water with 0.1% trifluoroacetic acid) and freeze dried to provide (S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl stearate trifluoroacetic acid salt (94 mg, 8%) as a white solid: $^1$H NMR (300 MHz, DMSO-$d_6$) δ 9.17 (br s, 1H), 6.85 (d, J=8.4 Hz, 1H), 6.75 (d, J=8.4 Hz, 1H), 6.29 (br s, 1H), 5.58 (dd, J=5.7, 1.8 Hz, 1H), 5.10 (q, J=6.9 Hz, 1H), 4.99 (s, 1H), 3.75 (s, 3H), 3.64 (br s, 1H), 3.43 (d, J=19.5 Hz, 1H), 3.16-3.07 (m, 2H), 2.84 (s, 3H), 2.64-2.57 (m, 1H), 2.49-2.42 (m, 1H, partially obscured by solvent peak), 2.06 (d, J=18.0 Hz, 1H), 1.66-1.51 (m, 3H), 1.49 (d, J=6.9 Hz, 3H), 1.32-1.23 (m, 28H), 0.85 (t, J=6.6 Hz, 3H); ESI MS m/z 654 $[C_{39}H_{59}NO_7+H]^+$; HPLC (Method A) 97.4% (AUC), $t_R$=16.31 min.

Scheme 45: (S)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl oleate trifluoroacetic acid salt

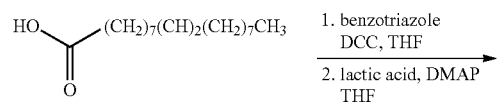

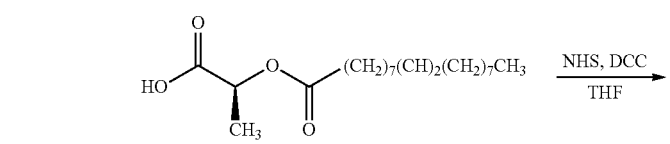

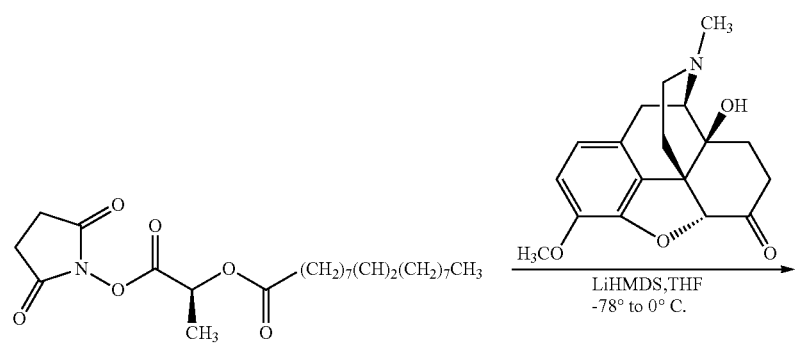

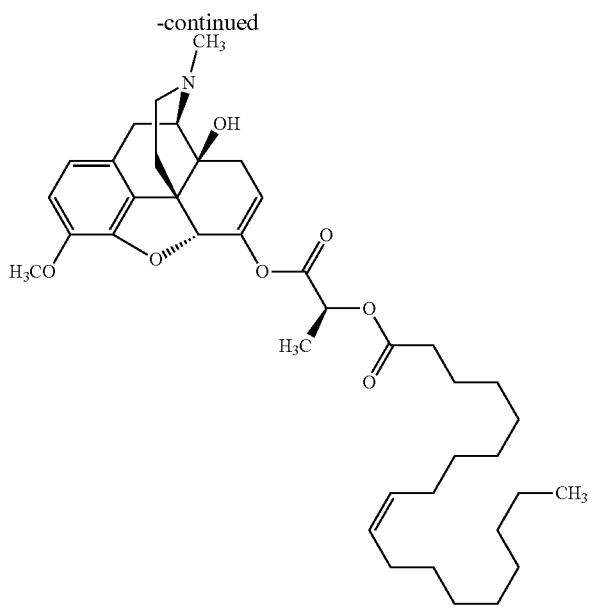

Preparation of (S,Z)-2-(Oleoyloxy)propanoic acid

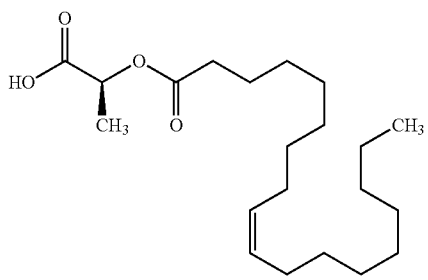 [SMILES: CCCCCCCC/C=C\CCCCCCCC(=O)O[C@@H](C)C(=O)O]

A solution of oleic acid (5.04 g, 17.9 mmol) and benzotriazole (2.35 g, 19.8 mmol) in tetrahydrofuran (80 mL) was treated with N,N'-dicyclohexylcarbodiimide (4.13 g, 20.0 mmol) and stirred under a nitrogen atmosphere for 16 h. After this time, the reaction mixture was filtered to remove the solid dicyclohexylurea byproduct, and the solids were washed with diethyl ether. The combined filtrate and washings were concentrated. The residue was dissolved in tetrahydrofuran (75 mL) and cooled in an ice bath. The mixture was treated with (S)-lactic acid (1.62 g, 18.0 mmol) and 4-dimethylaminopyridine (2.20 g, 18.0 mmol), and the ice bath was removed. The mixture was stirred at ambient temperature under a nitrogen atmosphere for 40 h. After this time, the reaction mixture was concentrated under reduced pressure. The residue was dissolved in ethyl acetate (250 mL) and washed with aqueous 10% citric acid (2×100 mL), water (100 mL), and brine (100 mL). The organic layer was extracted with saturated aqueous sodium bicarbonate (2×100 mL). The combined aqueous bicarbonate layers were acidified to pH ~1 with 6 N hydrochloric acid and extracted with ethyl acetate (2×100 mL). The combined organics were dried over sodium sulfate, filtered, and concentrated under reduced pressure. The residue was dissolved/suspended in heptanes (100 mL), washed with aqueous 10% citric acid (50 mL) and brine (50 mL), dried over sodium sulfate, filtered, and concentrated under reduced pressure to provide (S,Z)-2-(oleoyloxy)propanoic acid (4.50 g, 71%) as a colorless oil: $^1$H NMR (300 MHz, CDCl$_3$) δ 5.36-5.30 (m, 2H), 5.10 (q, J=5.4 Hz, 1H), 2.41-2.32 (m, 2H), 2.02-1.98 (m, 4H), 1.67-1.52 (m, 5H), 1.31-1.27 (m, 20H), 0.88 (t, J=6.3 Hz, 3H), CO$_2$H proton not observed.

Preparation of (S)-1-((2,5-Dioxopyrrolidin-1-yl)oxy)-1-oxopropan-2-yl oleate

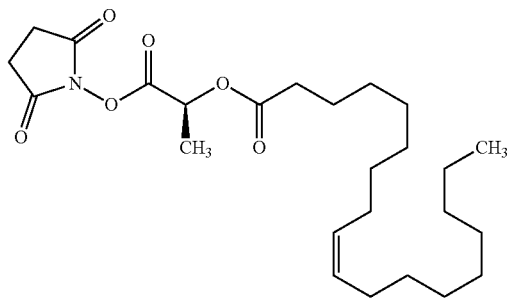 [SMILES: CCCCCCCC/C=C\CCCCCCCC(=O)O[C@@H](C)C(=O)ON1C(=O)CCC1=O]

A solution of (S,Z)-2-(oleoyloxy)propanoic acid (4.50 g, 12.7 mmol) in tetrahydrofuran (60 mL) was treated with N-hydroxysuccinimide (1.58 mg, 13.8 mmol) and N,N'-dicyclohexylcarbodiimide (2.91 g, 14.1 mmol) and stirred under a nitrogen atmosphere for 1.5 h. After this time, the reaction mixture was filtered to remove the solid dicyclohexylurea byproduct. The solid was washed with diethyl ether, and the combined filtrate and washings were concentrated under reduced pressure to provide (S)-1-((2,5-dioxopyrrolidin-1-yl)oxy)-1-oxopropan-2-yl oleate (6.20 g, quantitative) as an amber semi-solid: $^1$H NMR (300 MHz, CDCl$_3$) δ 5.42 (q, J=7.2 Hz, 1H), 5.36-5.32 (m, 2H), 2.84 (br s, 4H), 2.42-2.37 (m, 2H), 2.02-1.98 (m, 4H), 1.72-1.53 (m, 5H), 1.30-1.27 (m, 20H), 0.88 (t, J=6.3 Hz, 3H).

Preparation of (S)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl oleate trifluoroacetic acid salt

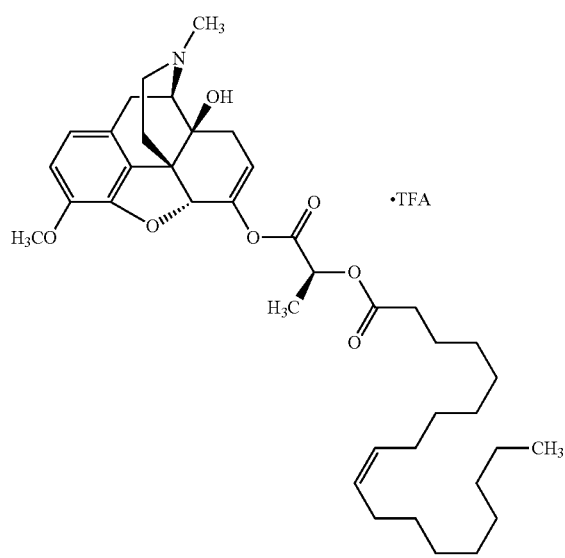 [SMILES: CCCCCCCC/C=C\CCCCCCCC(=O)O[C@@H](C)C(=O)OC1=CC[C@@]2(O)[C@H]3Cc4ccc(OC)c5c4[C@@]2(CCN3C)[C@H]1O5]

A suspension of oxycodone (0.50 g, 1.6 mmol) in tetrahydrofuran (5 mL) was cooled in an ice bath and treated with a 1.0 M solution of lithium bis(trimethylsilyl)amide in tetrahydrofuran (1.8 mL, 1.8 mmol). After addition was complete, the mixture was stirred under nitrogen atmosphere in the ice bath for 25 min and at ambient temperature for 25 min. The solution was re-cooled in a dry ice/acetone bath, and the mixture was treated with a solution of (S)-1-((2,5-dioxopyrrolidin-1-yl)oxy)-1-oxopropan-2-yl oleate (0.83 g, 1.8 mmol) in tetrahydrofuran (5 mL). The temperature was allowed to slowly increase to 0° C. over 2 h. After this time, the reaction mixture was treated with saturated aqueous ammonium chloride (50 mL) and extracted with ethyl acetate (2×50 mL). The combined organics were washed with saturated sodium bicarbonate (50 mL) and brine (50 mL), dried over sodium sulfate, filtered, and concentrated under reduced pressure. The crude residue was purified by column chromatography (silica gel, 0-10% methanol/methylene chloride) followed by reversed phase column chromatography (150 g C18 column, 50-100% acetonitrile/water with 0.1% trifluoroacetic acid) and freeze dried to provide (S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl oleate trifluoroacetic acid salt (343 mg, 28%) as a white solid: $^1$H NMR (300 MHz, DMSO-$d_6$) δ 9.23 (br s, 1H), 6.85 (d, J=8.4 Hz, 1H), 6.75 (d, J=8.4 Hz, 1H), 6.39 (br s, 1H), 5.58-5.56 (m, 1H), 5.37-5.27 (m, 2H), 5.10 (q, J=6.9 Hz, 1H), 4.99 (s, 1H), 3.75 (s, 3H), 3.68 (d, J=6.0 Hz, 1H), 3.43 (d, J=19.8 Hz, 1H), 3.16-3.07 (m, 2H), 2.85 (s, 3H), 2.64-2.58 (m, 1H), 2.49-2.42 (m, 1H, partially obscured by solvent peak), 2.39-2.27 (m, 3H), 2.09-1.97 (m, 5H), 1.63 (d, J=11.7 Hz, 1H), 1.54-1.48 (m, 5H), 1.26-1.24 (m, 20H), 0.85 (t, J=6.3 Hz, 3H); ESI MS m/z 652 $[C_{39}H_{57}NO_7+H]^+$; HPLC (Method A) 95.8% (AUC), $t_R$=15.64 min.

Scheme 46: (S)-3-((3-Carboxypropanoyl)oxy)-4-(((4R-4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

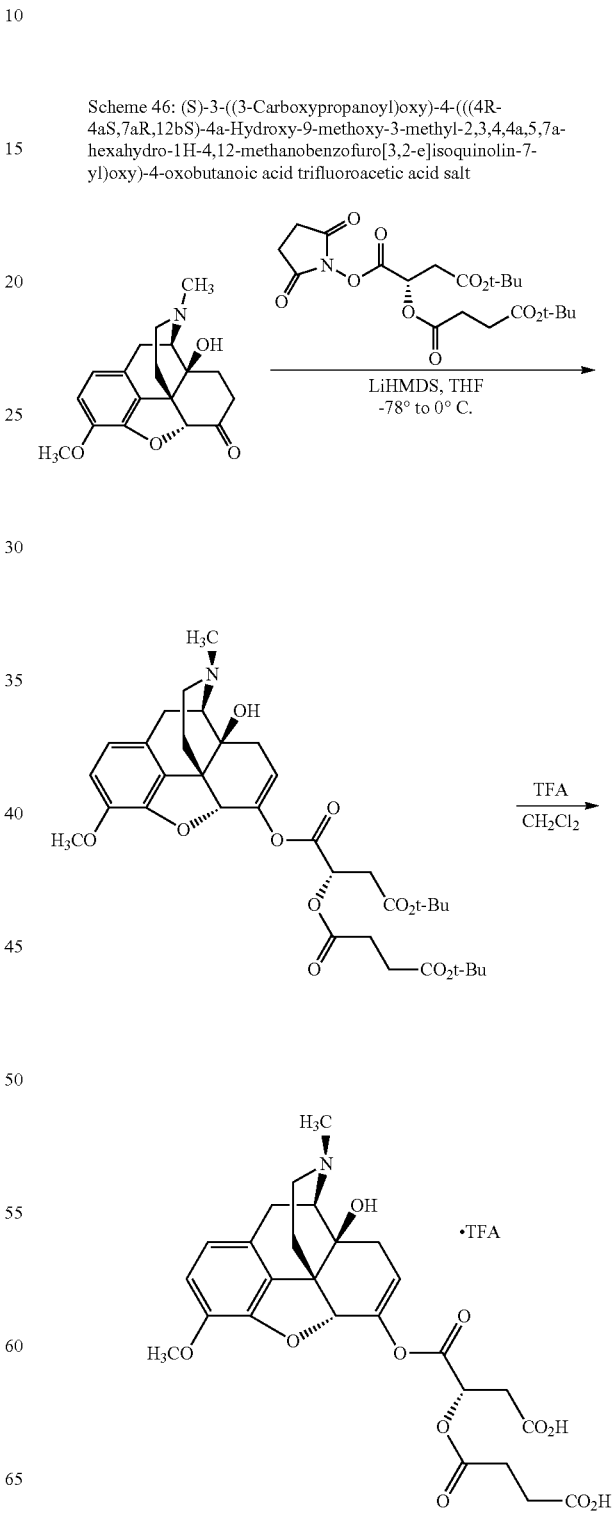

433

Preparation of (S)-4-tert-Butyl 1-((4R,4aS,7aR, 12bS)-4a-hydroxy-9-methoxy-3-methyl-2,3,4,4a,5, 7a-hexahydro-1H-4,12-methanobenzofuro[3,2-e] isoquinolin-7-yl) 2-((4-(tert-butoxy)-4-oxobutanoyl) oxy)succinate

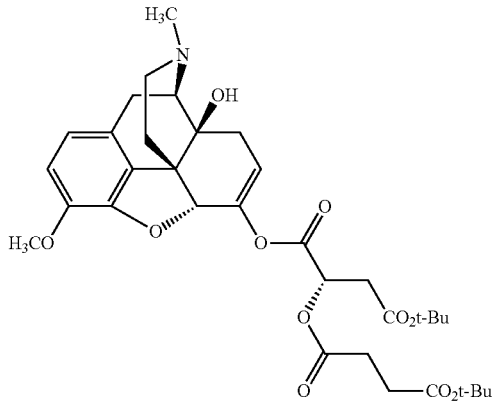 [SMILES: COc1ccc2c3c1O[C@H]1C(OC(=O)[C@H](CC(=O)OC(C)(C)C)OC(=O)CCC(=O)OC(C)(C)C)=CC[C@@]4(O)[C@@H](C2)N(C)CC[C@]314]

A suspension of oxycodone (0.500 g, 1.59 mmol) in tetrahydrofuran (5 mL) was cooled in an ice bath and treated with a 1.0 M solution of lithium bis(trimethylsilyl)amide in tetrahydrofuran (1.9 mL, 1.9 mmol). After addition was complete, the mixture was stirred under a nitrogen atmosphere in the ice bath for 25 min and at ambient temperature for 25 min. The solution was re-cooled in a dry ice/acetone bath, and the mixture was treated with a solution of (S)-4-tert-butyl 1-(2,5-dioxopyrrolidin-1-yl) 2-((4-(tert-butoxy)-4-oxobutanoyl)oxy)succinate (0.89 g, 2.0 mmol) in tetrahydrofuran (5 mL). The temperature was allowed to slowly increase to 0° C. over 2 h. After this time, the reaction mixture was treated with saturated aqueous ammonium chloride (50 mL) and extracted with ethyl acetate (2×50 mL). The combined organics were washed with saturated sodium bicarbonate (50 mL) and brine (50 mL), dried over sodium sulfate, filtered, and concentrated under reduced pressure. The crude residue was purified by reversed phase column chromatography (150 g C18 column, 5-100% acetonitrile/water) and freeze dried to provide (S)-4-tert-butyl 1-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-((4-(tert-butoxy)-4-oxobutanoyl)oxy)succinate (195 mg, 19%) as a white solid: ESI MS m/z 644 $[C_{34}H_{45}NO_{11}+H]^+$.

434

Preparation of (S)-3-((3-Carboxypropanoyl)oxy)-4-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-4-oxobutanoic acidtrifluoroacetic acid salt

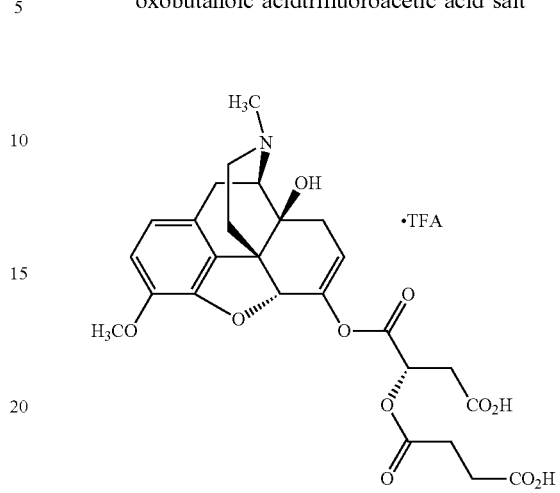

A solution of (S)-4-tert-butyl 1-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-((4-(tert-butoxy)-4-oxobutanoyl)oxy)succinate (0.195 g, 0.300 mmol) in methylene chloride (3 mL) was treated with trifluoroacetic acid (3 mL) and stirred under at ambient temperature for 1 h. After this time, the reaction mixture was concentrated under reduced pressure. The residue was purified twice by reversed phase column chromatography (50 g C18 column, 5-25% acetonitrile/water with 0.1% trifluoroacetic acid) and freeze dried to provide (S)-3-((3-carboxypropanoyl)oxy)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt (0.056 g, 35%) as a white solid: $^1$H NMR (300 MHz, DMSO-$d_6$) δ 12.71 (br s, 1H), 12.32 (br s, 1H), 9.17 (br s, 1H), 6.85 (d, J=8.4 Hz, 1H), 6.75 (d, J=8.4 Hz, 1H), 6.30 (s, 1H), 5.59 (dd, J=5.7, 1.8 Hz, 1H), 5.42 (t, J=5.4 Hz, 1H), 4.96 (s, 1H), 3.75 (s, 3H), 3.65 (d, J=6.0 Hz, 1H), 3.16-3.07 (m, 3H), 2.90-2.84 (m, 5H), 2.73-2.59 (m, 3H), 2.33-2.25 (m, 1H), 2.07 (d, J=18.0 Hz, 1H), 1.64 (d, J=11.4 Hz, 1H), three protons obscured by solvent peaks; ESI MS m/z 532 $[C_{26}H_{29}NO_{11}+H]^+$.

Scheme 47: (S)-5-(((4R,4aS,7aR,12bS)-4a-Hydroxy-9-methoxy-3-methyl-2,3,4,4a,5,7a-hexahydro-1H-4, 12-methanobenzofuro[3,2-e]isoquinolin-7-yl)oxy)-2-((S)-2-hydroxypropanamido)-5-oxopentanoic acid trifluoroacetic acid salt

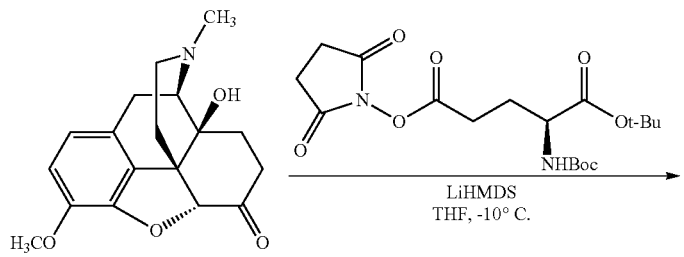

-continued
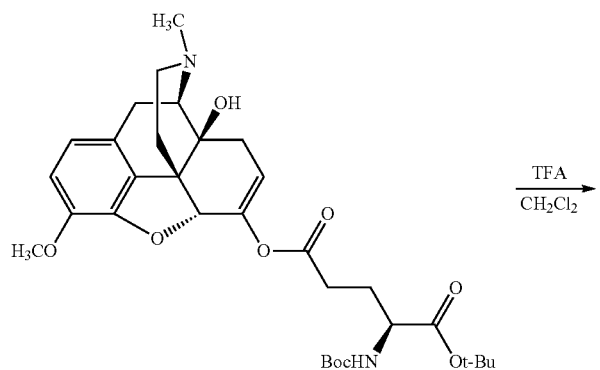
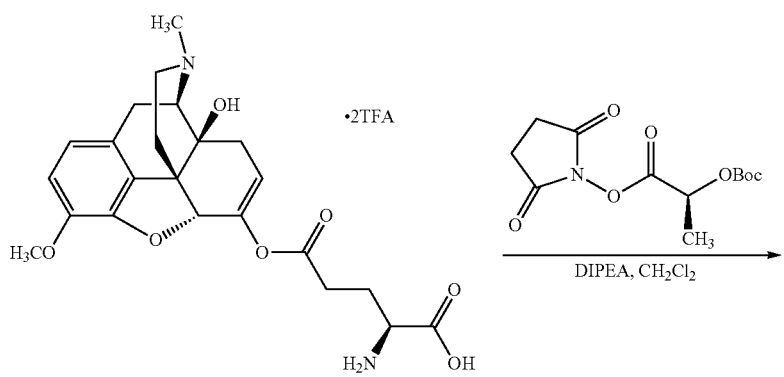
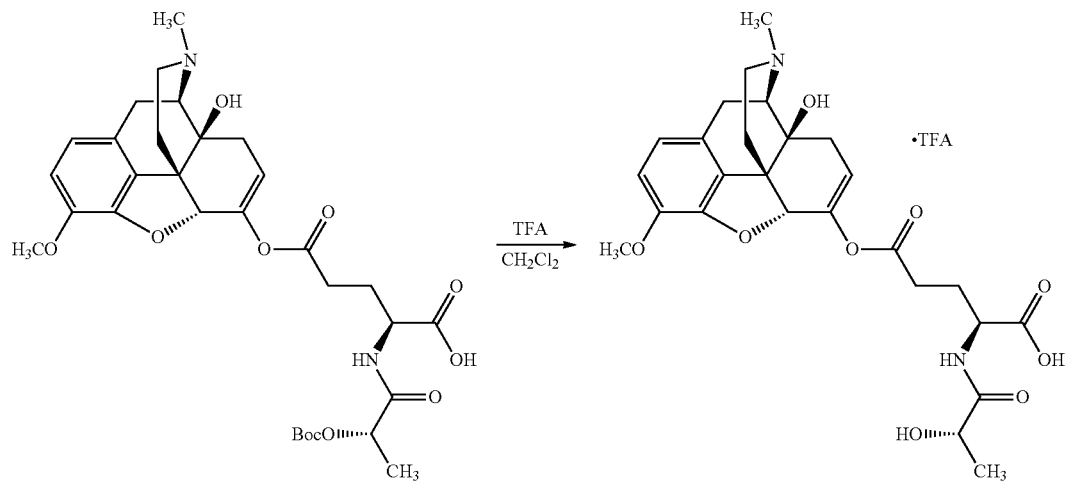

Preparation of (S)-1-tert-Butyl 5-((4R,4aS,7aR, 12bS)-4a-hydroxy-9-methoxy-3-methyl-2,3,4,4a,5, 7a-hexahydro-1H-4,12-methanobenzofuro[3,2-e] isoquinolin-7-yl) 2-((tert-butoxycarbonyl)amino) pentanedioate

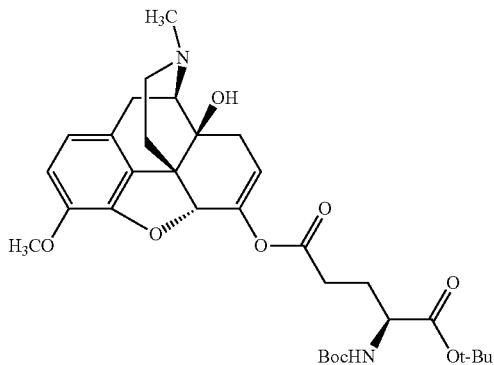 [SMILES: COc1ccc2c3c1O[C@H]1C(OC(=O)CC[C@H](NC(=O)OC(C)(C)C)C(=O)OC(C)(C)C)=CC[C@@]4(O)[C@@H](C2)N(C)CC[C@]314]

A suspension of oxycodone (0.450 g, 1.43 mmol) in tetrahydrofuran (6 mL) was cooled in an ice bath and treated with a 1.0 M solution of lithium bis(trimethylsilyl)amide in tetrahydrofuran (3.55 mL, 3.55 mmol). After addition was complete, the mixture was stirred under nitrogen atmosphere in the ice bath for 45 min and at ambient temperature for 20 min. The solution was re-cooled in an ice/brine bath, treated dropwise with a solution of (S)-1-tert-butyl 5-(2,5-dioxopyrrolidin-1-yl) 2-((tert-butoxycarbonyl)amino)pentanedioate (0.914 g, 2.28 mmol) in tetrahydrofuran (6 mL), and stirred for 2 h. After this time, the reaction mixture was treated with saturated aqueous ammonium chloride (75 mL) and extracted with ethyl acetate (3×100 mL). The combined organics were washed with saturated aqueous ammonium chloride (100 mL), saturated sodium bicarbonate (2×100 mL), and brine (2×100 mL); dried over sodium sulfate; filtered; and concentrated under reduced pressure. The crude residue was purified by reversed phase column chromatography (50 g C18 column, 5-100% acetonitrile/water) and freeze dried to provide (S)-1-tert-butyl 5-((4R,4aS,7aR, 12bS)-4a-hydroxy-9-methoxy-3-methyl-2,3,4,4a,5,7a-hexahydro-1H-4,12-methanobenzofuro[3,2-e]isoquinolin-7-yl) 2-((tert-butoxycarbonyl)amino)pentanedioate (0.371 g, 43%) as a colorless oil: ESI MS m/z 601 $[C_{32}H_{44}N_2O_9+H]^+$.

Preparation of (S)-2-Amino-5-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-5-oxopentanoic acid bis(trifluoroacetic acid salt)

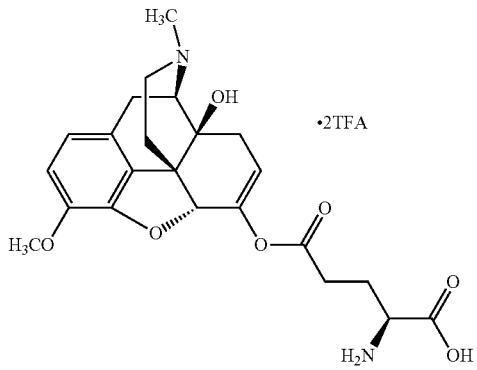 [SMILES: COc1ccc2c3c1O[C@H]1C(OC(=O)CC[C@H](N)C(=O)O)=CC[C@@]4(O)[C@@H](C2)N(C)CC[C@]314]

A solution of (S)-1-tert-butyl 5-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-((tert-butoxycarbonyl)amino)pentanedioate (0.371 g, 0.618 mmol) in methylene chloride (6 mL) was treated with trifluoroacetic acid (3 mL) and stirred under a nitrogen atmosphere at ambient temperature for 5 h. After this time, the reaction mixture was concentrated under reduced pressure and dried under vacuum to provide (S)-2-amino-5-(((4R,4aS,7aR, 12bS)-4a-hydroxy-9-methoxy-3-methyl-2,3,4,4a,5,7a-hexahydro-1H-4,12-methanobenzofuro[3,2-e]isoquinolin-7-yl) oxy)-5-oxopentanoic acid bis(trifluoroacetic acid salt)(0.500 g, quantitative) as a colorless oil: ESI MS m/z 445 $[C_{23}H_{28}N_2O_7+H]^+$.

Preparation of (S)-2-((S)-2-((tert-Butoxycarbonyl) oxy)propanamido)-5-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) oxy)-5-oxopentanoic acid

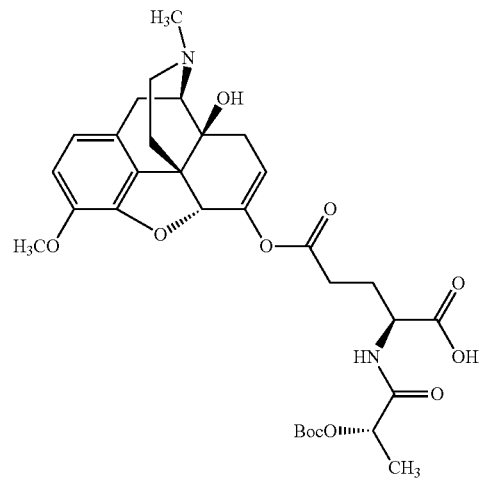

A mixture(S)-2-amino-5-(((4R,4aS,7aR,12bS)-4a-hydroxy-9-methoxy-3-methyl-2,3,4,4a,5,7a-hexahydro-1H-4, 12-methanobenzofuro[3,2-e]isoquinolin-7-yl)oxy)-5-oxopentanoic acid bis(trifluoroacetic acid salt)(0.220 g, 0.406 mmol), (S)-2,5-dioxopyrrolidin-1-yl 2-((tert-butoxycarbonyl)oxy)propanoate (0.175 g, 0.609 mmol) and N,N-diisopropylethylamine (0.35 mL, 2.0 mmol) in methylene chloride (5 mL) was stirred at ambient temperature for 2 h. After this time, the reaction mixture was concentrated under reduced pressure to give(S)-2-((S)-2-((tert-butoxycarbonyl) oxy)propanamido)-5-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-5-oxopentanoic acid (0.250 g, quantitative) as a colorless oil: ESI MS m/z 617 $[C_{31}H_{40}N_2O_{11}+H]^+$.

Preparation of (S)-5-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-((S)-2-hydroxypropanamido)-5-oxopentanoic acid trifluoroacetic acid salt

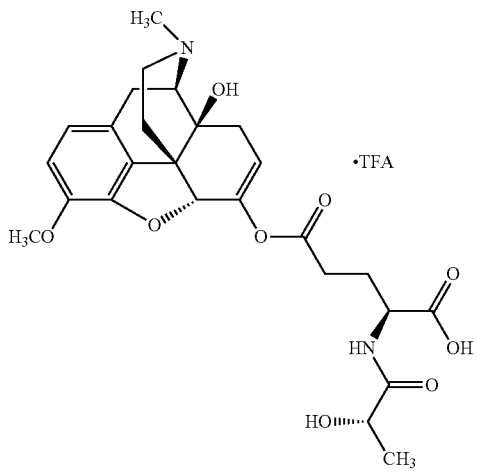 [SMILES: COc1ccc2c3c1O[C@H]1C(OC(=O)CC[C@H](NC(=O)[C@H](C)O)C(=O)O)=CC[C@@]4(O)[C@@H](C2)N(C)CC[C@]314]

A solution of (S)-2-((S)-2-((tert-butoxycarbonyl)oxy)propanamido)-5-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-5-oxopentanoic acid (0.250 g, 0.406) in methylene chloride (4 mL) was treated with trifluoroacetic acid (2 mL) and stirred under a nitrogen atmosphere at ambient temperature for 1 h. After this time, the reaction mixture was concentrated under reduced pressure. The residue was purified by reversed phase column chromatography (50 g C18 column, 5-25% acetonitrile/water, with 0.1% trifluoroacetic acid) and freeze dried to provide (S)-5-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-((S)-2-hydroxypropanamido)-5-oxopentanoic acid trifluoroacetic acid salt (0.067 g, 32%) as a white solid: $^1$H NMR (300 MHz, DMSO-$d_6$) δ 12.81 (br s, 1H), 9.17 (br s, 1H), 7.85 (d, J=8.1 Hz, 1H), 6.86 (d, J=8.4 Hz, 1H), 6.75 (d, J=8.1 Hz, 1H), 6.27 (s, 1H), 5.55-5.53 (m, 2H), 5.00 (s, 1H), 4.35-4.27 (m, 1H), 4.00 (q, J=6.9 Hz, 1H), 3.75 (s, 3H), 3.64 (d, J=6.0 Hz, 1H), 3.15-3.06 (m, 2H), 2.84 (d, J=4.2 Hz, 3H), 2.73-2.55 (m, 1H), 2.32-2.24 (m, 1H), 2.14-1.89 (m, 3H), 1.63 (d, J=11.4 Hz, 1H), 1.22 (d, J=6.9 Hz, 3H), four protons obscured by solvent peaks; ESI MS m/z 517 $[C_{26}H_{32}N_2O_9+H]^+$; HPLC (Method A) 96.5% (AUC), $t_R$=7.29 min.

Scheme 48: (S)-(S)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 2-acetoxypropanoate trifluoroacetic acid salt

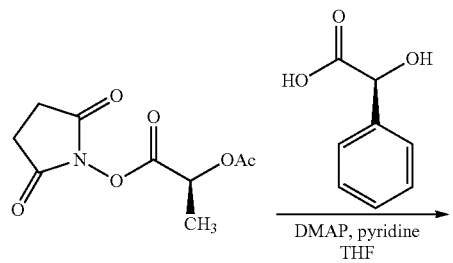

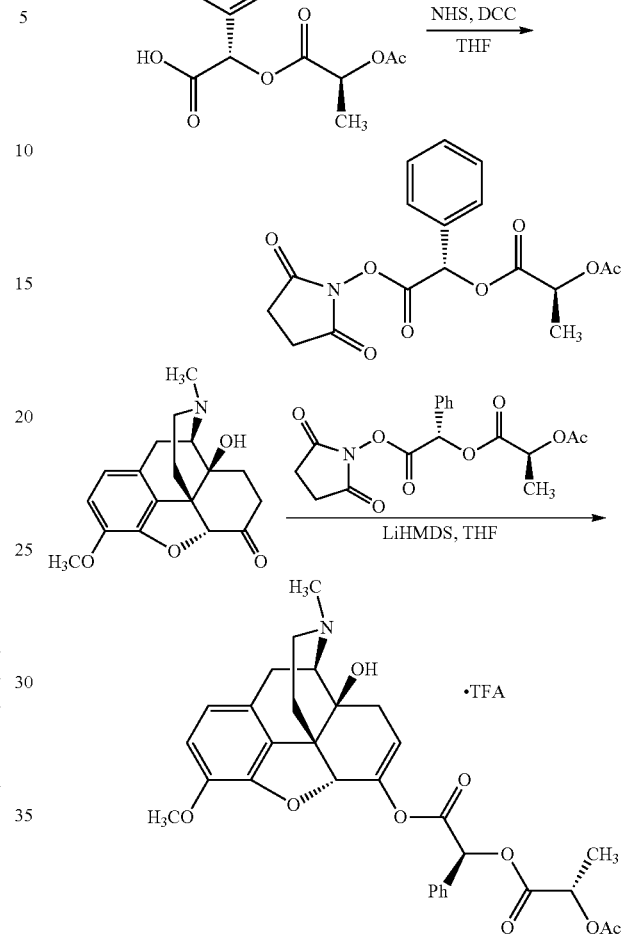

Preparation of (S)-2-(((S)-2-Acetoxypropanoyl)oxy)-2-phenylacetic acid

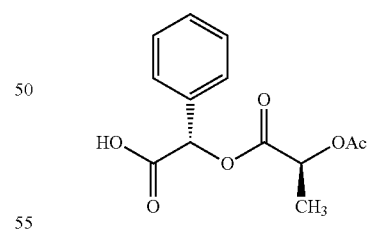

(S)-Mandelic acid (553 mg, 3.63 mmol), (S)-2,5-dioxopyrrolidin-1-yl 2-acetoxypropanoate (1.00 g, 4.36 mmol), 4-(dimethylamino)pyridine (44 mg, 0.363 mmol), pyridine (345 mg, 4.36 mmol) and tetrahydrofuran (15 mL) were combined and heated at 60° C. under a nitrogen atmosphere for 48 h. After this time, the solvent was removed under reduced pressure, and the residue was partitioned between ethyl acetate (20 mL) and 10% aqueous citric acid. The organic layer was separated and extracted with saturated aqueous sodium bicarbonate (20 ml). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (S)-2-(((S)-2-acetoxypropanoyl)oxy)-2-phenylacetic acid (1.02 g, 87%) as a colorless oil: $^1$H NMR (300 MHz, CDCl$_3$) δ 7.46-7.37 (m, 5H), 5.99 (s, 1H), 5.19 (q, J=7.2 Hz, 1H), 2.12 (s, 3H), 1.61 (d, J=6.9 Hz, 3H), CO$_2$H proton not observed.

Preparation of (S)-(S)-2-((2,5-Dioxopyrrolidin-1-yl)oxy)-2-oxo-1-phenylethyl 2-acetoxypropanoate

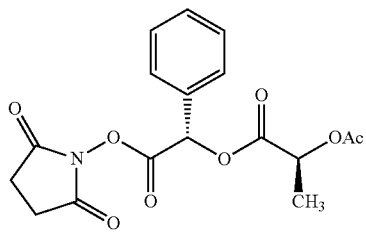 [SMILES: CC(=O)O[C@@H](C)C(=O)O[C@H](C(=O)ON1C(=O)CCC1=O)c1ccccc1]

A solution of (S)-2-(((S)-2-acetoxypropanoyl)oxy)-2-phenylacetic acid (1.02 g, 3.83 mmol) in tetrahydrofuran (40 mL) was treated with N-hydroxysuccinimide (485 mg, 4.21 mmol) and N,N'-dicyclohexylcarbodiimide (867 mg, 4.21 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-(S)-2-((2,5-dioxopyrrolidin-1-yl)oxy)-2-oxo-1-phenylethyl 2-acetoxypropanoate (1.65 g) as a white solid: $^1$H NMR (300 MHz, CDCl$_3$) δ 7.56-7.51 (m, 5H), 6.38 (s, 1H), 5.17 (q, J=7.2 Hz, 1H), 2.82 (s, 4H), 2.12 (s, 3H), 1.59 (d, J=6.9 Hz, 3H).

Preparation of (S)-(S)-2-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 2-acetoxypropanoatetrifluoroacetic acid salt

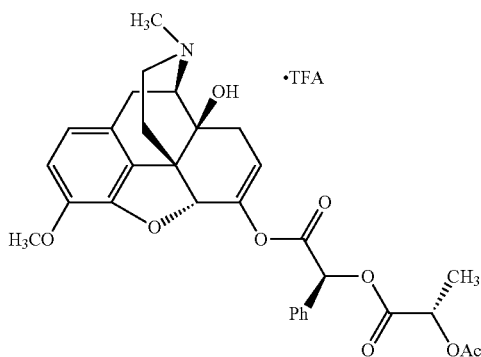 [SMILES: COc1ccc2c3c1O[C@H]1C(OC(=O)[C@@H](OC(=O)[C@H](C)OC(C)=O)c4ccccc4)=CC[C@@]4(O)[C@@H](C2)N(C)CC[C@]314]

A suspension of oxycodone (0.250 g, 0.793 mmol) in tetrahydrofuran (4 mL) was cooled in an ice bath and treated dropwise with a 1.0 M solution of lithium bis(trimethylsilyl)amide in tetrahydrofuran (1.03 mL, 1.03 mmol). The mixture was stirred at 0° C. for 15 min and then treated dropwise with a solution of (S)-(S)-2-((2,5-dioxopyrrolidin-1-yl)oxy)-2-oxo-1-phenylethyl 2-acetoxypropanoate (0.374 g, 1.03 mmol) in tetrahydrofuran (4 mL). The reaction mixture was stirred at 0° C. for 1 h. After this time, the mixture was poured into saturated aqueous ammonium chloride (75 mL) and extracted with ethyl acetate (2×100 mL). The combined organics were dried over sodium sulfate, filtered, and concentrated under reduced pressure. The crude residue was purified by reversed phase chromatography (C18, 10-100% acetonitrile/water with 0.1% trifluoroacetic acid) and lyophilized to provide (S)-(S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl 2-acetoxypropanoatetrifluoroacetic acid salt (0.120 g, 27%) as a white solid: $^1$H NMR (300 MHz, CDCl$_3$) δ 9.15 (br s, 1H), 7.59-7.54 (m, 2H), 7.49-7.76 (m, 3H), 6.82 (d, J=8.4 Hz, 1H), 6.73 (d, J=8.4 Hz, 1H), 6.30 (br s, 1H), 6.22 (s, 1H), 5.53 (dd, J=6.0, 1.8 Hz, 1H), 5.15 (q, J=6.9 Hz, 1H), 4.95 (s, 1H), 3.64 (s, 3H), 3.41 (d, J=19.8 Hz, 1H), 3.14-3.05 (m, 2H), 2.83 (d, J=4.8 Hz, 3H), 2.70-2.53 (m, 1H), 2.46-2.38 (m, 1H), 2.30-2.22 (m, 1H), 2.08 (s, 3H), 2.06-2.00 (m, 1H), 1.62 (d, J=11.1 Hz, 1H), 1.53 (d, J=6.9 Hz, 3H); ESI MS m/z 564 [C$_{31}$H$_{33}$NO$_9$+H]$^+$; HPLC (Method A) 97.4% (AUC), $t_R$=10.24 min.

Scheme 49: (S)-4-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-4-oxo-3-(stearoyloxy)butanoic acid trifluoroacetic acid salt

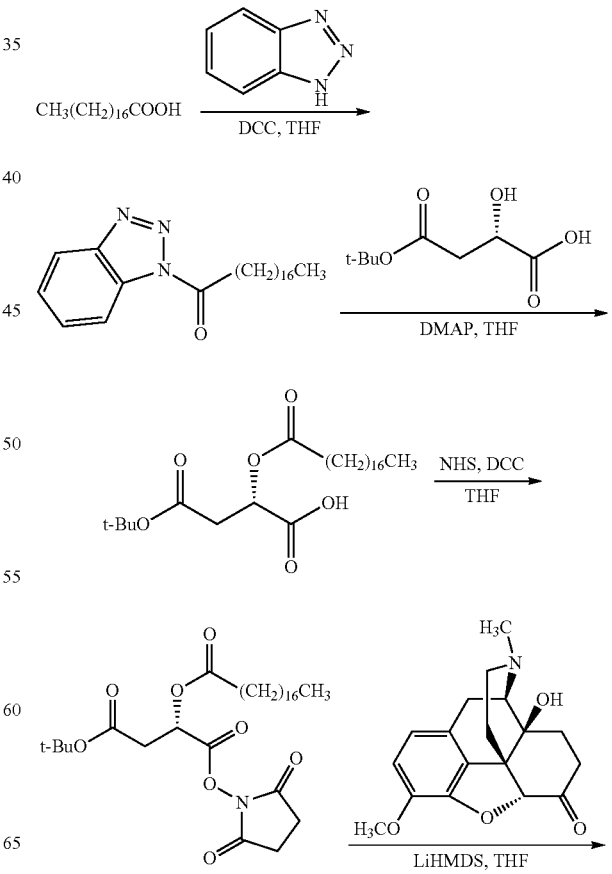

-continued

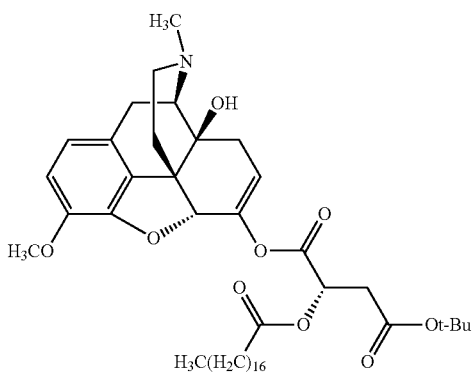

Preparation of 1-(1H-Benzo[d][1,2,3]triazol-1-yl)octadecan-1-one

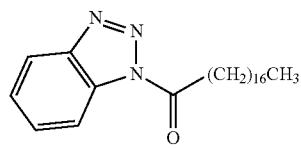

A solution of stearic acid (2.00 g, 7.03 mmol) in tetrahydrofuran (30 mL) was treated with 1H-benzo[d][1,2,3]triazole (921 mg, 7.73 mmol) and N,N'-dicyclohexylcarbodiimide (1.59 g, 7.73 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide 1-(1H-benzo[d][1,2,3]triazol-1-yl)octadecan-1-one (3.02 g) as a white solid, which was used without purification.

Preparation of (S)-4-(tert-Butoxy)-4-oxo-2-(stearoyloxy)butanoic acid

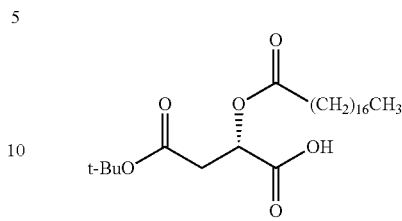

(S)-4-(tert-Butoxy)-2-hydroxy-4-oxobutanoic acid (247 mg, 1.30 mmol), 1-(1H-benzo[d][1,2,3]triazol-1-yl)octadecan-1-one (500 mg, 1.30 mmol), 4-(dimethylamino)pyridine (159 mg, 1.30 mmol), and tetrahydrofuran (10 mL) were combined and stirred at room temperature under a nitrogen atmosphere for 48 h. After this time, the solvent was removed under reduced pressure, and the residue was partitioned between ethyl acetate (30 mL) and 10% aqueous citric acid. The organic layer was separated and washed with water (50 mL), dried over sodium sulfate, filtered, and concentrated under reduced pressure. The crude residue was purified by column chromatography (40 g silica gel column, 0-50% ethyl acetate/heptane) to provide of (S)-4-(tert-butoxy)-4-oxo-2-(stearoyloxy)butanoic acid (430 mg, 72%) as a white solid: $^1$H NMR (300 MHz, CDCl$_3$) δ 5.47 (t, J=5.7 Hz, 1H), 2.84 (d, J=0.9 Hz, 2H), 2.38 (m, 2H), 1.62 (m, 2H), 1.45 (s, 9H), 1.25 (m, 28H), 0.88 (t, J=6.6 Hz, 3H), CO$_2$H proton not observed.

Preparation of (S)-4-tert-Butyl 1-(2,5-dioxopyrrolidin-1-yl) 2-(stearoyloxy)succinate

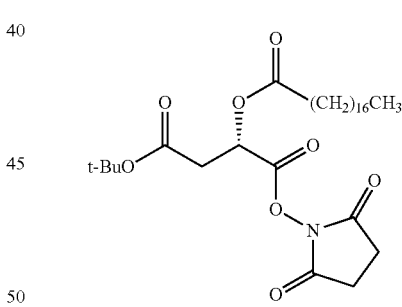

A solution of (S)-4-(tert-butoxy)-4-oxo-2-(stearoyloxy)butanoic acid (430 mg, 0.942 mmol) in tetrahydrofuran (10 mL) was treated with N-hydroxysuccinimide (119 mg, 1.04 mmol) and N,N'-dicyclohexylcarbodiimide (214 mg, 1.04 mmol) and stirred under a nitrogen atmosphere for 4 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-4-tert-butyl 1-(2,5-dioxopyrrolidin-1-yl) 2-(stearoyloxy)succinate (610 mg) as a white solid: $^1$H NMR (300 MHz, CDCl$_3$) δ 5.76 (dd, J=8.1, 1.8 Hz, 1H), 2.96 (m, 2H), 2.84 (s, 4H), 2.38 (m, 2H), 1.67 (m, 2H), 1.46 (s, 9H), 1.25 (m, 28H), 0.88 (t, J=6.3 Hz, 3H).

Preparation of (S)-4-tert-Butyl 1-((4R,4aS,7aR, 12bS)-4a-hydroxy-9-methoxy-3-methyl-2,3,4,4a,5, 7a-hexahydro-1H-4,12-methanobenzofuro[3,2-e] isoquinolin-7-yl) 2-(stearoyloxy)succinate

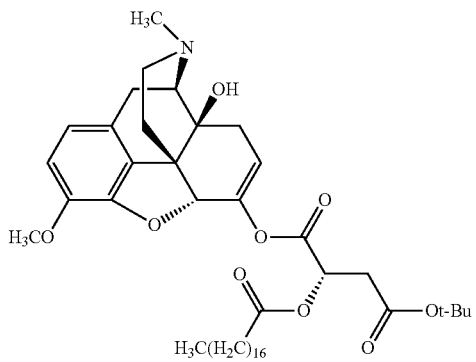

A suspension of oxycodone (0.300 g, 0.95 mmol) in tetrahydrofuran (5 mL) was cooled in an ice bath and treated dropwise with a 1.0 M solution of lithium bis(trimethylsilyl) amide in tetrahydrofuran (1.24 mL, 1.24 mmol). The mixture was stirred at 0° C. for 15 min and then treated dropwise with a solution of(S)-4-tert-butyl 1-(2,5-dioxopyrrolidin-1-yl) 2-(stearoyloxy)succinate (0.685 g, 1.23 mmol) in tetrahydrofuran (5 mL). The reaction mixture was stirred at 0° C. for 1 h. After this time, the mixture was poured into saturated aqueous ammonium chloride (100 mL) and extracted with ethyl acetate (2×100 mL). The combined organics were dried over sodium sulfate, filtered, and concentrated under reduced pressure. The crude residue was purified by reverse phase chromatography (C18, 10-100% acetonitrile/water) and lyophilized to provide (S)-4-tert-butyl 1-((4R,4aS,7aR, 12bS)-4a-hydroxy-9-methoxy-3-methyl-2,3,4,4a,5,7a-hexahydro-1H-4,12-methanobenzofuro[3,2-e]isoquinolin-7-yl) 2-(stearoyloxy)succinate (0.390 g, 54%) as a colorless oil: $^1$H NMR (300 MHz, CDCl$_3$) δ 6.81 (d, J=8.1 Hz, 1H), 6.72 (d, J=8.4 Hz, 1H), 5.65-5.62 (m, 1H), 5.51 (t, J=6.0 Hz, 1H), 3.80-3.60 (m, 1H), 3.86 (s, 3H), 3.41 (d, J=7.5 Hz, 1H), 3.24 (s, 1H), 3.21 (d, J=6.0 Hz, 1H), 2.93 (s, 3H), 2.89-2.79 (m, 4H), 2.41-2.35 (m, 3H), 2.21 (d, J=17.7 Hz, 1H), 1.78 (d, J=10.5 Hz, 1H), 1.66-1.61 (m, 2H), 1.46 (s, 9H), 1.25 (br s, 30H), 0.88 (t, J=6.3 Hz, 3H).

Preparation of (S)-4-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl) oxy)-4-oxo-3-(stearoyloxy)butanoic acid trifluoroacetic acid salt

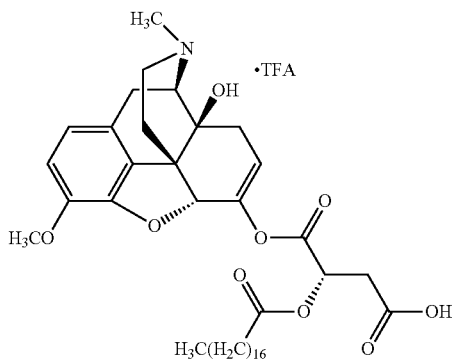

A solution of(S)-4-tert-butyl 1-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-(stearoyloxy)succinate (0.380 g, 0.504 mmol) in methylene chloride (6 mL) was treated with trifluoroacetic acid (3 mL) and stirred at ambient temperature for 1 h. After this time, the reaction mixture was concentrated under reduced pressure. The crude residue was purified by reversed phase chromatography (C18, 10-100% acetonitrile/water with 0.1% TFA) and freeze dried to provide (S)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxo-3-(stearoyloxy)butanoic acid trifluoroacetic acid salt (0.135 g, 38%) as an off-white solid: $^1$H NMR (300 MHz, DMSO-d$_6$) δ 12.76 (br s, 1H), 9.17 (br s, 1H), 6.84 (d, J=8.1 Hz, 1H), 6.74 (d, J=8.1 Hz, 1H), 6.31 (s, 1H), 5.59 (dd, J=6.0, 3.9 Hz, 1H), 5.41 (t, J=6.3 Hz, 1H), 4.96 (s, 1H), 3.75 (s, 3H), 3.65 (d, J=6.3 Hz, 1H), 3.13-3.06 (m, 2H), 2.90-2.84 (m, 5H), 2.70-2.52 (m, 2H), 2.33 (t, J=7.2 Hz, 2H), 2.27-2.25 (m, 1H), 1.64 (d, J=11.7 Hz, 1H), 1.56-1.51 (m, 2H), 1.23 (br s, 30H), 0.88 (t, J=6.3 Hz, 3H); ESI MS m/z 698 [C$_{40}$H$_{59}$NO$_9$+H]$^+$.

Scheme 50: (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-acetoxypropanoate trifluoroacetic acid salt

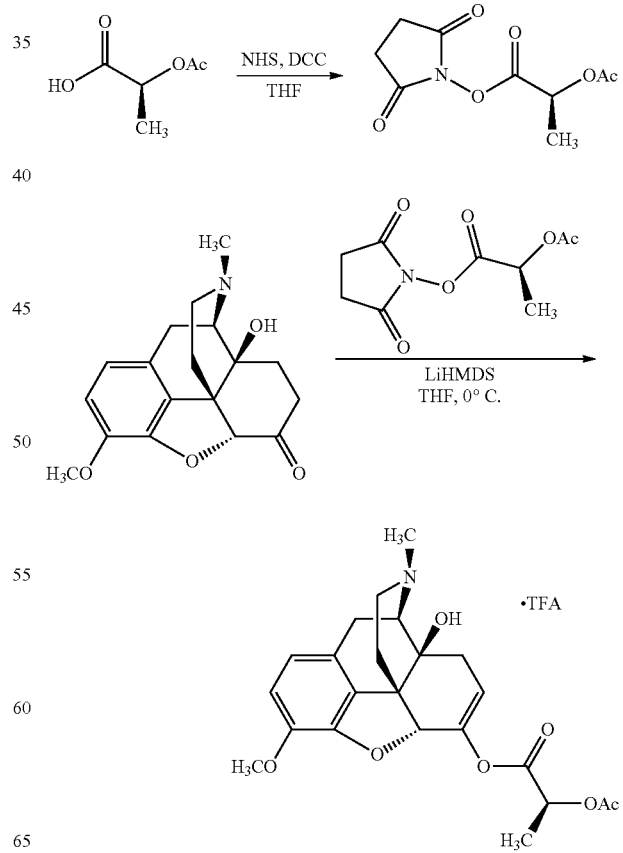

Preparation of (S)-2,5-Dioxopyrrolidin-1-yl 2-acetoxypropanoate

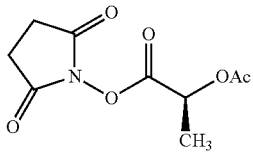 [SMILES: CC(=O)O[C@@H](C)C(=O)ON1C(=O)CCC1=O]

A solution of (S)-2-acetoxypropanoic acid (10.06 g, 76.15 mmol) in tetrahydrofuran (300 mL) was treated with N-hydroxysuccinimide (9.71 g, 84.4 mmol) and N,N'-dicyclohexylcarbodiimide (17.36 g, 84.14 mmol) and stirred under a nitrogen atmosphere for 4.5 h. After this time, the reaction mixture was filtered to remove the solid dicyclohexylurea byproduct. The solid was washed with diethyl ether, and the combined filtrate and washings were concentrated under reduced pressure. The crude residue was triturated with 5:1 diethyl ether/methylene chloride (120 mL). The resulting solid was isolated by filtration and washed with diethyl ether. The combined filtrate and washings were concentrated under reduced pressure to provide (S)-2,5-dioxopyrrolidin-1-yl 2-acetoxypropanoate (18.24 g, quantitative) as an off-white foam: $^1$H NMR (300 MHz, CDCl$_3$) δ 5.41 (t, J=7.2 Hz, 1H), 2.81 (s, 4H), 2.16 (s, 3H), 1.67 (d, J=7.2 Hz, 3H).

Preparation of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-acetoxypropanoate trifluoroacetic acid salt

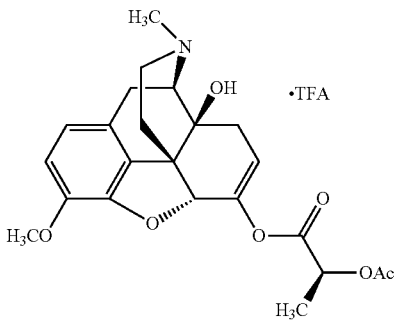 [SMILES: COc1ccc2c3c1O[C@H]1C(OC(=O)[C@H](C)OC(C)=O)=CC[C@@]4(O)[C@@H](C2)N(C)CC[C@]314]

A suspension of oxycodone (0.250 g, 0.793 mmol) in tetrahydrofuran (4 mL) was cooled in an ice bath and treated dropwise with a 1.0 M solution of lithium bis(trimethylsilyl) amide in tetrahydrofuran (1.03 mL, 1.03 mmol). The mixture was stirred at 0° C. for 15 min and then treated dropwise with a solution of (S)-2,5-dioxopyrrolidin-1-yl 2-acetoxypropanoate (0.236 g, 1.03 mmol) in tetrahydrofuran (4 mL). The reaction mixture was stirred at 0° C. for 1 h. After this time, the mixture was poured into saturated aqueous ammonium chloride (100 mL) and extracted with ethyl acetate (2×100 mL). The combined organics were dried over sodium sulfate, filtered, and concentrated under reduced pressure. The crude residue was purified by reverse phase chromatography (C18, 10-25% acetonitrile/water with 0.1% trifluoroacetic acid) and lyophilized to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-acetoxypropanoate trifluoroacetic acid salt (0.095 g, 28%) as a white solid: $^1$H NMR (300 MHz, CDCl$_3$) δ 9.18 (br s, 1H), 6.86 (d, J=8.4 Hz, 1H), 6.75 (d, J=8.1 Hz, 1H), 6.31 (s, 1H), 5.58 (dd, J=5.7, 1.8 Hz, 1H), 5.09 (q, J=6.9 Hz, 1H), 4.99 (s, 1H), 3.76 (s, 3H), 3.65 (d, J=6.0 Hz, 1H), 3.43 (d, J=20.1 Hz, 1H), 3.16-3.07 (m, 2H), 2.84 (d, J=4.8 Hz, 3H), 2.72-2.52 (m, 1H), 2.49-2.43 (m, 1H, partially obscured by solvent peak), 2.29 (dd, J=18.0, 6.6 Hz, 1H), 2.10 (s, 3H), 2.30-2.22 (m, 1H), 1.65 (d, J=11.4 Hz, 1H), 1.49 (d, J=6.9 Hz, 3H); ESI MS m/z 430 [C$_{23}$H$_{27}$NO$_7$+H]$^+$; HPLC (Method A) 97.8% (AUC), t$_R$=8.64 min.

Scheme 51: (S)-(4R,4aS,7aR,12bS)-4a-Hydroxy-9-methoxy-3-methyl-2,3,4,4a,5,7a-hexahydro-1H-4, 12-methanobenzofuro[3,2-e]isoquinolin-7-yl 2-(((S)-2-acetoxypropanoyl)oxy)propanoate

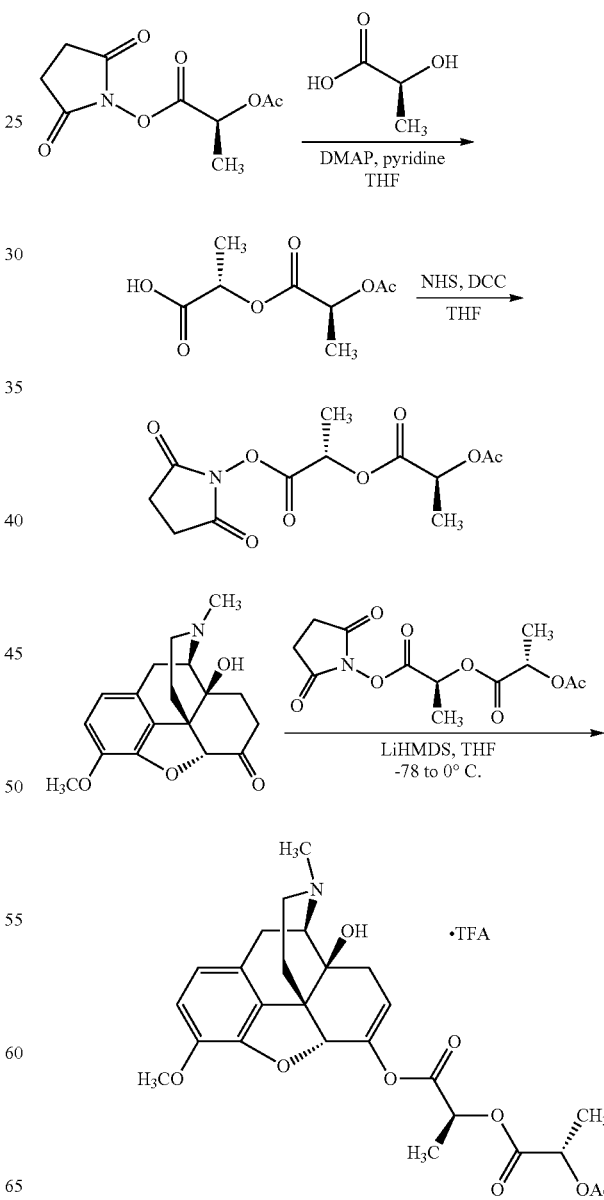

Preparation of (S)-2-(((S)-2-Acetoxypropanoyl)oxy) propanoic acid

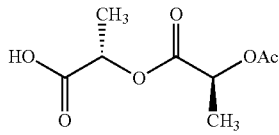

(S)-Lactic acid (472 mg, 5.24 mmol), (S)-2,5-dioxopyrrolidin-1-yl 2-acetoxypropanoate (1.00 g, 4.36 mmol), 4-(dimethylamino)pyridine (53 mg, 0.44 mmol), pyridine (414 mg, 5.24 mmol) and tetrahydrofuran (17 mL) were combined and heated at 80° C. under a nitrogen atmosphere for 24 h. After this time, the solvent was removed under reduced pressure, and the residue was partitioned between ethyl acetate (20 mL) and 10% aqueous citric acid. The organic layer was separated and extracted with saturated aqueous sodium bicarbonate (20 ml). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (S)-2-(((S)-2-acetoxypropanoyl)oxy)propanoic acid (323 mg, 36%) as a colorless oil: $^1$H NMR (300 MHz, CDCl$_3$) δ 5.23-5.08 (m, 2H), 2.14 (s, 3H), 1.60-1.48 (m, 6H), CO$_2$H proton not observed.

Preparation of (S)-2,5-Dioxopyrrolidin-1-yl 2-(((S)-2-acetoxypropanoyl)oxy)propanoate

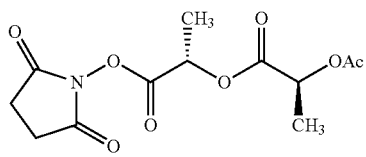 [SMILES: CC(=O)O[C@@H](C)C(=O)O[C@@H](C)C(=O)ON1C(=O)CCC1=O]

A solution of (S)-2-(((S)-2-acetoxypropanoyl)oxy)propanoic acid (323 mg, 1.58 mmol) in tetrahydrofuran (15 mL) was treated with N-hydroxysuccinimide (200 mg, 1.74 mmol) and N,N'-dicyclohexylcarbodiimide (358 mg, 1.74 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-2,5-dioxopyrrolidin-1-yl 2-(((S)-2-acetoxypropanoyl)oxy)propanoate (543 mg) as a colorless oil: $^1$H NMR (300 MHz, CDCl$_3$) δ 5.53 (q, J=5.4 Hz, 1H), 5.13 (q, J=5.4 Hz, 1H), 2.85 (s, 4H), 2.13 (s, 3H), 1.72 (m, 3H), 1.57 (m, 3H).

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(((S)-2-acetoxypropanoyl)oxy)propanoate

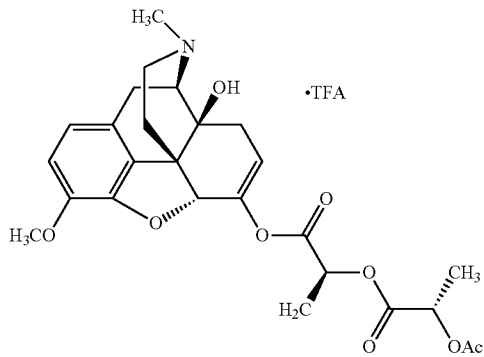 [SMILES: COc1ccc2c3c1O[C@H]1C(OC(=O)[C@H](C)OC(=O)[C@H](C)OC(C)=O)=CC[C@@]4(O)[C@@H](C2)N(C)CC[C@]314]

A suspension of oxycodone (0.600 g, 1.90 mmol) in tetrahydrofuran (5 mL) was cooled in an ice bath and treated with a 1.0 M solution of lithium bis(trimethylsilyl)amide in tetrahydrofuran (2.1 mL, 2.1 mmol). After addition was complete, the mixture was stirred under a nitrogen atmosphere in the ice bath for 25 min and at ambient temperature for 25 min. The solution was re-cooled in a dry ice/acetone bath, and the mixture was treated with a solution of (S)-2,5-dioxopyrrolidin-1-yl 2-(((S)-2-acetoxypropanoyl)oxy)propanoate (0.640 g, 2.12 mmol) in tetrahydrofuran (5 mL). The temperature was allowed to slowly increase to 0° C. over 2 h. After this time, the reaction mixture was treated with saturated aqueous ammonium chloride (75 mL) and extracted with ethyl acetate (2×100 mL). The combined organics were washed with saturated sodium bicarbonate (75 mL) and brine (75 mL), dried over sodium sulfate, filtered, and concentrated under reduced pressure. The crude residue was purified by reversed phase column chromatography (50 g C18 column, 10-100% acetonitrile/water with 0.1% trifluoroacetic acid) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(((S)-2-acetoxypropanoyl)oxy)propanoate (66 mg, 5%) as a white solid: $^1$H NMR (300 MHz, CDCl$_3$) δ 9.17 (br s, 1H), 6.86 (d, J=8.1 Hz, 1H), 6.75 (d, J=8.4 Hz, 1H), 6.30 (s, 1H), 5.59 (dd, J=5.7, 1.8 Hz, 1H), 5.24 (q, J=6.9 Hz, 1H), 5.07 (q, J=7.2 Hz, 1H), 4.99 (s, 1H), 3.75 (s, 3H), 3.65 (d, 6.0 Hz, 1H), 3.16-3.07 (m, 2H), 2.84 (d, J=4.8 Hz, 3H), 2.72-2.58 (m, 1H), 2.44-2.40 (m, 1H), 2.30 (dd, J=18.3, 6.0 Hz, 1H), 2.08 (s, 3H), 2.12-2.02 (m, 1H), 1.65 (d, J=13.2 Hz, 1H), 1.53 (d, J=6.9 Hz, 3H), 1.47 (d, J=6.9 Hz, 3H), one proton obscured by the solvent peaks; ESI MS m/z 502 [C$_{26}$H$_{31}$NO$_9$+H]$^+$; HPLC (Method A) 97.8% (AUC), t$_R$=8.64 min.

Scheme 52: (S)-2-((4-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt

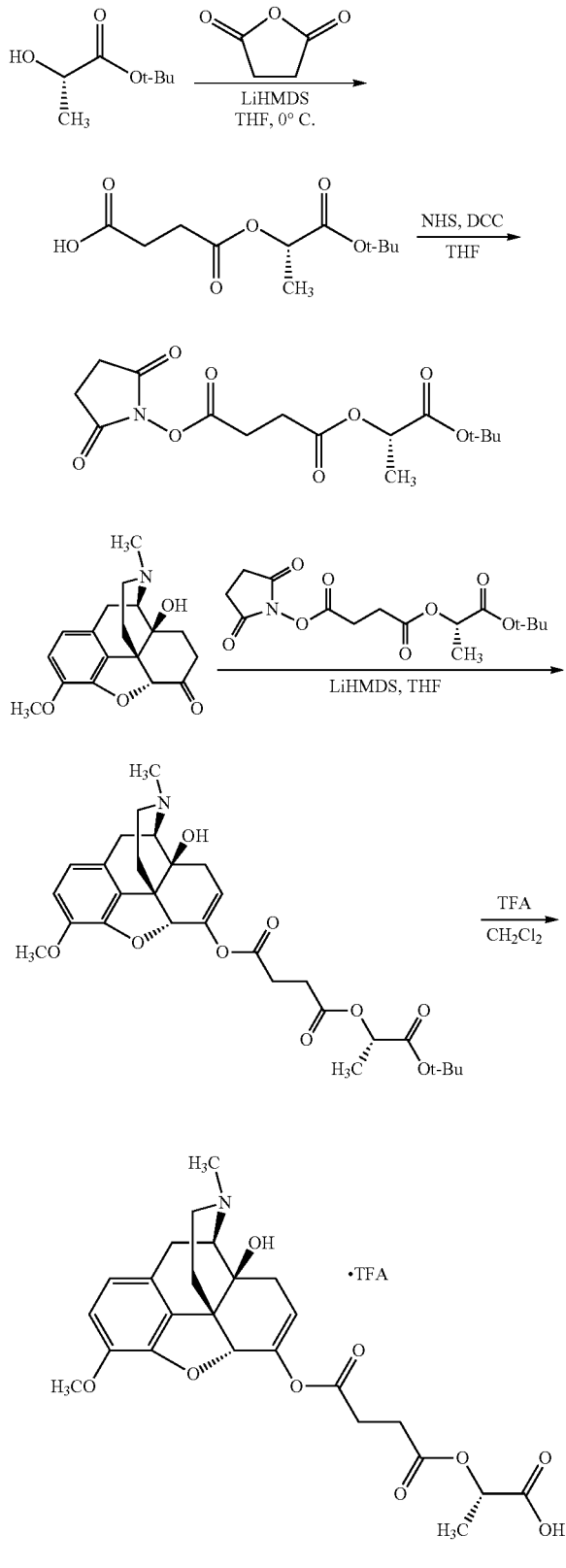

Preparation of (S)-4-((1-(tert-Butoxy)-1-oxopropan-2-yl)oxy)-4-oxobutanoic acid

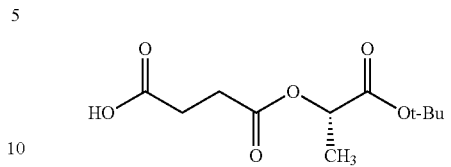

A solution of (S)-tert-butyl 2-hydroxypropanoate (3.40 g, 23.3 mmol) in tetrahydrofuran (50 mL) was cooled in an ice bath and treated with a 1.0 M solution of lithium bis(trimethylsilyl)amide in tetrahydrofuran (30.3 mL, 30.3 mmol) under a nitrogen atmosphere. After 10 min, the mixture was treated dropwise with a solution of succinic anhydride (2.80 g, 27.9 mmol) in tetrahydrofuran (25 mL) and stirred at 0° C. for 45 min. After this time, the reaction mixture was poured into saturated aqueous ammonium chloride and extracted with ethyl acetate. The combined organics were dried over sodium sulfate, filtered, and concentrated under reduced pressure. The crude residue was purified by column chromatography (silica gel, 0-20% methanol/methylene chloride) and triturated with ether, filtered, and concentrated under reduced pressure to provide (S)-4-((1-(tert-butoxy)-1-oxopropan-2-yl)oxy)-4-oxobutanoic acid (0.600 g, 10%) as a colorless oil: $^1$H NMR (300 MHz, DMSO-$d_6$) δ 12.18 (br s, 1H), 4.81 (q, J=7.2 Hz, 1H), 2.51-2.49 (m, 4H, partially obscured by solvent peak), 1.40 (s, 9H), 1.36 (d, J=7.2 Hz, 3H).

Preparation of (S)-1-(tert-Butoxy)-1-oxopropan-2-yl (2,5-dioxopyrrolidin-1-yl) succinate

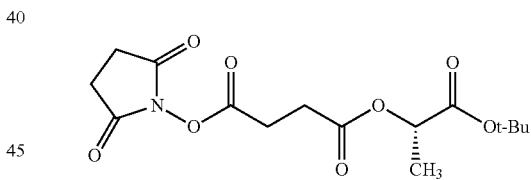

A solution of (S)-4-((1-(tert-butoxy)-1-oxopropan-2-yl)oxy)-4-oxobutanoic acid (0.700 mg, 2.84 mmol) in tetrahydrofuran (12 mL) was treated with N-hydroxysuccinimide (0.459 mg, 3.98 mmol) and N,N'-dicyclohexylcarbodiimide (0.822 mg, 3.98 mmol) and stirred under a nitrogen atmosphere for 5 h. After this time, the reaction mixture was filtered to remove the solid dicyclohexylurea byproduct. The solid was washed with diethyl ether, and the combined filtrate and washings were concentrated under reduced pressure. The crude residue was triturated with diethyl ether. The resulting solid was isolated by filtration and washed with diethyl ether. The combined filtrate and washings were concentrated under reduced pressure to provide (S)-1-(tert-butoxy)-1-oxopropan-2-yl (2,5-dioxopyrrolidin-1-yl) succinate (0.900 g, 92%) as a yellow oil: $^1$H NMR (300 MHz, CDCl$_3$) δ 5.00 (q, J=7.2 Hz, 1H), 2.99-2.96 (m, 2H), 2.85-2.80 (m, 6H), 1.48-1.45 (m, 12H).

453

Preparation of (S)-1-(tert-Butoxy)-1-oxopropan-2-yl ((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) succinate

454

Preparation of (S)-2-((4-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt

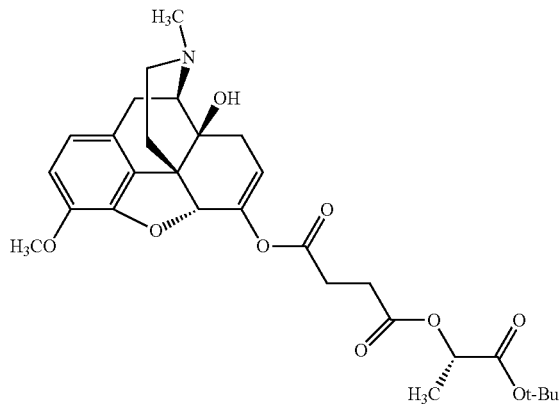 [SMILES: COc1ccc2c3c1O[C@H]1C(OC(=O)CCC(=O)O[C@@H](C)C(=O)OC(C)(C)C)=CC[C@@]4(O)[C@@H](C2)N(C)CC[C@]314]

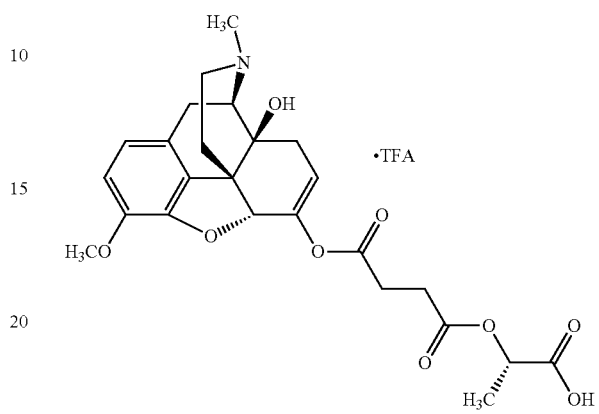

A suspension of oxycodone (0.350 g, 1.11 mmol) in tetrahydrofuran (5 mL) was cooled in an ice bath and treated dropwise with a 1.0 M solution of lithium bis(trimethylsilyl) amide in tetrahydrofuran (1.44 mL, 1.44 mmol). The mixture was stirred at 0° C. for 15 min and then treated dropwise with a solution of (S)-1-(tert-butoxy)-1-oxopropan-2-yl (2,5-dioxopyrrolidin-1-yl) succinate (0.496 g, 1.44 mmol) in tetrahydrofuran (5 mL). The reaction mixture was stirred at 0° C. for 1 h. After this time, the mixture was poured into saturated aqueous ammonium chloride (100 mL) and extracted with ethyl acetate (2×100 mL). The combined organics were dried over sodium sulfate, filtered, and concentrated under reduced pressure. The crude residue was purified by reverse phase chromatography (C18, 10-70% acetonitrile/water) and freeze dried to provide (S)-1-(tert-butoxy)-1-oxopropan-2-yl ((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) succinate (0.290 g, 48%) as a white solid: ESI MS m/z 544 $[C_{29}H_{37}NO_9+H]^+$.

A solution of (S)-1-(tert-butoxy)-1-oxopropan-2-yl ((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) succinate (0.280 g, 0.515 mmol) in methylene chloride (6 mL) was treated with trifluoroacetic acid (3 mL) and stirred under a nitrogen atmosphere at ambient temperature for 1 h. After this time, the reaction mixture was concentrated under reduced pressure. The residue was purified by reversed phase column chromatography (50 g C18 column, 5-30% acetonitrile/water, with 0.1% TFA) and freeze dried to provide (S)-2-((4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt (0.0200 g, 80%) as a white solid: $^1$H NMR (300 MHz, DMSO-$d_6$) δ 13.02 (br s, 1H), 9.18 (br s, 1H), 6.86 (d, J=8.4 Hz, 1H), 6.75 (d, J=8.4 Hz, 1H), 6.28 (br s, 1H), 5.53 (dd, J=6.0, 1.8 Hz, 1H), 4.98 (s, 1H), 4.92 (q, J=6.9 Hz, 1H), 3.75 (s, 3H), 3.64 (d, J=6.3 Hz, 1H), 3.43 (d, J=19.8 Hz, 1H), 3.15-3.06 (m, 2H), 2.84 (d, J=3.9 Hz, 3H), 2.73-2.58 (m, 5H), 2.46-2.40 (m, 1H), 2.32-2.20 (m, 1H), 2.05 (d, J=18.3 Hz, 1H), 1.64 (d, J=11.1 Hz, 1H), 1.40 (d, J=6.9 Hz, 3H); ESI MS m/z 488 $[C_{25}H_{29}NO_9+H]^+$; HPLC (Method A) 98.9% (AUC), $t_R$=8.17 min.

Scheme 53: (S)-1-(((S)-1-(((4R,4aS,7aR,12bS)-4a-Hydroxy-9-methoxy-3-methyl-2,3,4,4a,5,7a-hexahydro-1H-4, 12-methanobenzofuro[3,2-e]isoquinolin-7-yl)oxy)-1-oxopropan-2-yl)oxy)-1-oxopropan-2-yl oleate trifluoroacetic acid salt

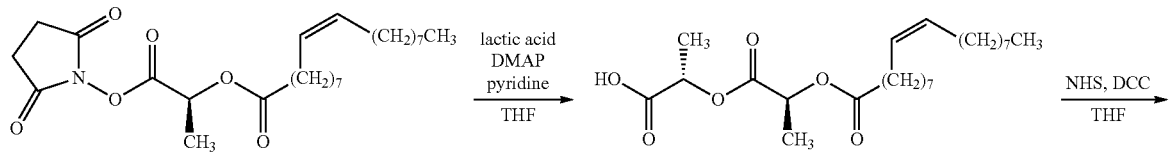

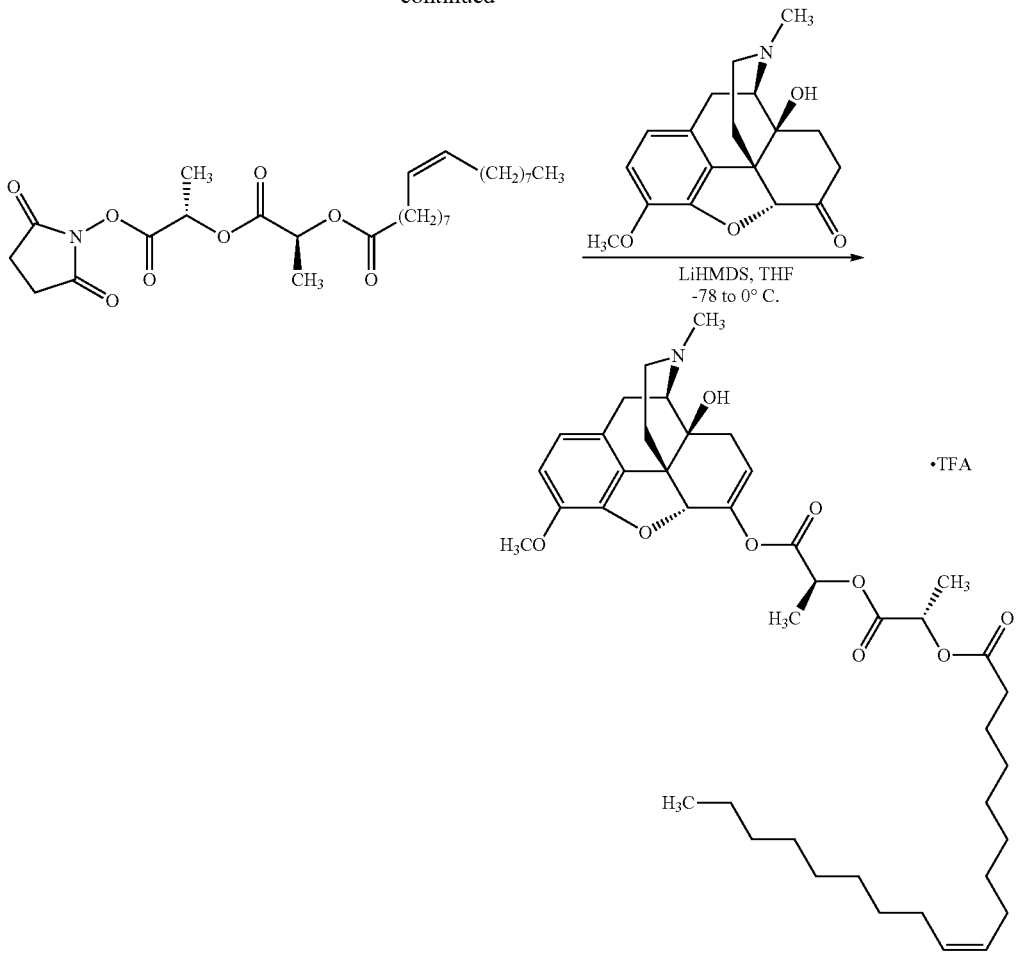

Preparation of (S)-2-(((S)-2-(Oleoyloxy)propanoyl)oxy)propanoic acid

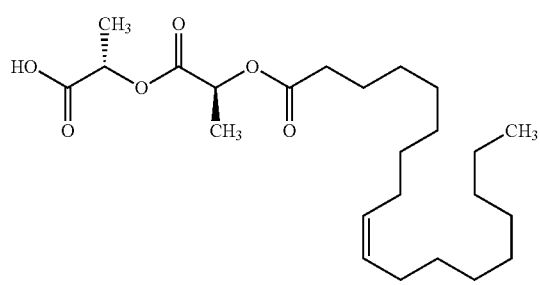 [SMILES: CCCCCCCC/C=C\CCCCCCCC(=O)O[C@@H](C)C(=O)O[C@@H](C)C(=O)O]

A solution of (S)-1-((2,5-dioxopyrrolidin-1-yl)oxy)-1-oxopropan-2-yl oleate (3.49 g, 7.73 mmol), (S)-lactic acid (764 mg, 8.48 mmol), and 4-dimethylaminopyridine (100 mg, 0.819 mmol) in tetrahydrofuran (35 mL) was treated with pyridine (0.69 g, 8.6 mmol) and heated at 50° C. under a nitrogen atmosphere for 64 h. After this time, the reaction mixture was cooled to room temperature and concentrated under reduced pressure. The residue was dissolved in methylene chloride (100 mL) and washed with aqueous 10% citric acid (2×50 mL). The organic layer was dried over sodium sulfate, filtered, and concentrated. The crude residue was purified by column chromatography (silica gel, 0-10% methanol/methylene chloride) to provide (S)-2-(((S)-2-(oleoyloxy)propanoyl)oxy)propanoic acid (835 mg, 25%) as a colorless oil: $^1$H NMR (300 MHz, CDCl$_3$) δ 5.36-5.29 (m, 2H), 5.24-5.08 (m, 2H), 2.41-2.35 (m, 2H), 2.02-1.98 (m, 4H), 1.67-1.60 (m, 2H), 1.58-1.52 (m, 6H), 1.30-1.27 (m, 20H), 0.88 (t, J=6.6 Hz, 3H), CO$_2$H proton not observed.

Preparation of (S)-1-(((S)-1-((2,5-Dioxopyrrolidin-1-yl)oxy)-1-oxopropan-2-yl)oxy)-1-oxopropan-2-yl oleate

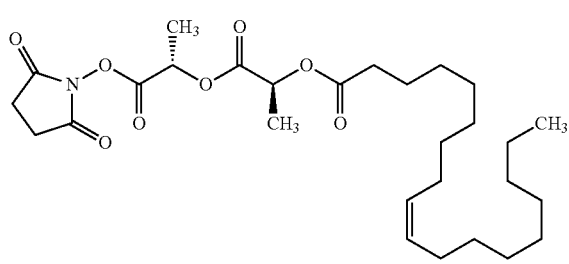 [SMILES: CCCCCCCC/C=C\CCCCCCCC(=O)O[C@@H](C)C(=O)O[C@@H](C)C(=O)ON1C(=O)CCC1=O]

A solution of (S)-2-(((S)-2-(oleoyloxy)propanoyl)oxy) propanoic acid (0.83 g, 2.0 mmol) in tetrahydrofuran (10 mL) was treated with N-hydroxysuccinimide (262 mg, 2.28 mmol) and N,N'-dicyclohexylcarbodiimide (446 mg, 2.16 mmol) and stirred under a nitrogen atmosphere for 3 h. After this time, the reaction mixture was filtered to remove the solid dicyclohexylurea byproduct. The solid was washed with diethyl ether, and the combined filtrate and washings were concentrated under reduced pressure to provide (S)-1-(((S)-1-((2,5-dioxopyrrolidin-1-yl)oxy)-1-oxopropan-2-yl)oxy)-1-oxopropan-2-yl oleate (1.07 g, quantitative) as a white semi-solid: $^1$H NMR (300 MHz, CDCl$_3$) δ 5.52 (q, J=7.2 Hz, 1H), 5.38-5.33 (m, 2H), 5.11 (q, J=7.2 Hz, 1H), 2.84 (br s, 4H), 2.42-2.35 (m, 2H), 2.02-1.98 (m, 4H), 1.72-1.53 (m, 8H), 1.30-1.27 (m, 20H), 0.88 (t, J=6.6 Hz, 3H).

Preparation of (S)-1-(((S)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl oleate trifluoroacetic acid salt

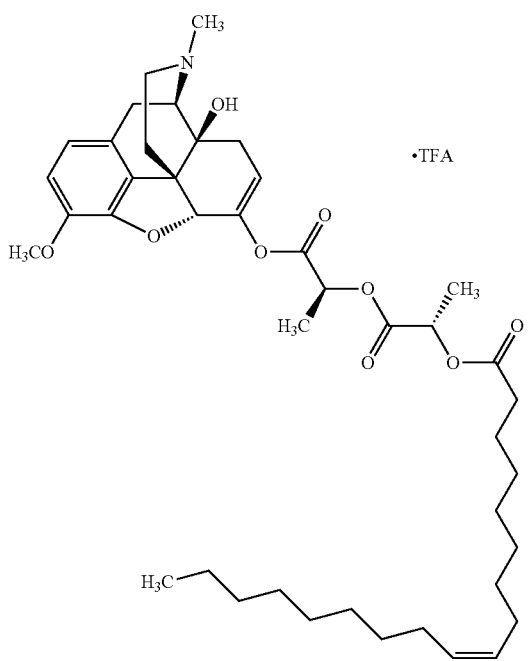 [SMILES: CCCCCCCC/C=C\CCCCCCCC(=O)O[C@@H](C)C(=O)O[C@@H](C)C(=O)OC1=CC[C@@]2(O)[C@H]3Cc4ccc(OC)c5c4[C@@]2(CCN3C)[C@H]1O5]

A suspension of oxycodone (0.27 g, 0.86 mmol) in tetrahydrofuran (5 mL) was cooled in an ice bath and treated with a 1.0 M solution of lithium bis(trimethylsilyl)amide in tetrahydrofuran (0.9 mL, 0.9 mmol). After addition was complete, the mixture was stirred under nitrogen atmosphere in the ice bath for 25 min and at ambient temperature for 25 min. The solution was re-cooled in a dry ice/acetone bath, and the mixture was treated with a solution of (S)-1-(((S)-1-((2,5-dioxopyrrolidin-1-yl)oxy)-1-oxopropan-2-yl)oxy)-1-oxopropan-2-yl oleate (0.50 g, 0.95 mmol) in tetrahydrofuran (5 mL). The temperature was allowed to slowly increase to 0° C. over 2 h. After this time, the reaction mixture was treated with saturated aqueous ammonium chloride (50 mL) and extracted with ethyl acetate (2×50 mL). The combined organics were washed with saturated sodium bicarbonate (50 mL) and brine (50 mL), dried over sodium sulfate, filtered, and concentrated under reduced pressure. The crude residue was purified by reversed phase column chromatography (150 g C18 column, 50-100% acetonitrile/water with 0.1% trifluoroacetic acid) and freeze dried to provide (S)-1-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl oleate trifluoroacetic acid salt (176 mg, 24%) as a white solid: $^1$H NMR (300 MHz, DMSO-d$_6$) δ 9.22 (br s, 1H), 6.85 (d, J=8.4 Hz, 1H), 6.75 (d, J=8.4 Hz, 1H), 6.34 (br s, 1H), 5.59-5.58 (m, 1H), 5.37-5.30 (m, 2H), 5.24 (q, J=6.9 Hz, 1H), 5.08 (q, J=6.9 Hz, 1H), 4.99 (s, 1H), 3.75 (s, 3H), 3.65 (br s, 1H), 3.42 (d, J=20.1 Hz, 1H), 3.15-3.06 (m, 2H), 2.84 (s, 3H), 2.64-2.58 (m, 1H), 2.49-2.43 (m, 1H, partially obscured by solvent peak), 2.37-2.26 (m, 3H), 2.09-1.95 (m, 5H), 1.63 (d, J=11.7 Hz, 1H), 1.54-1.45 (m, 8H), 1.26-1.24 (m, 20H), 0.85 (t, J=6.3 Hz, 3H); ESI MS m/z 724 [C$_{42}$H$_{61}$NO$_9$+H]$^+$; HPLC (Method A)>99% (AUC), t$_R$=15.93 min.

Scheme 54: (S)-2-((4-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid trifluoroacetic acid salt

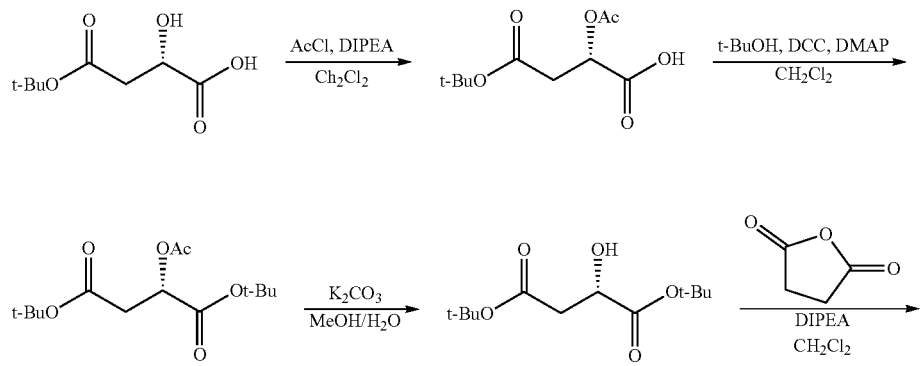

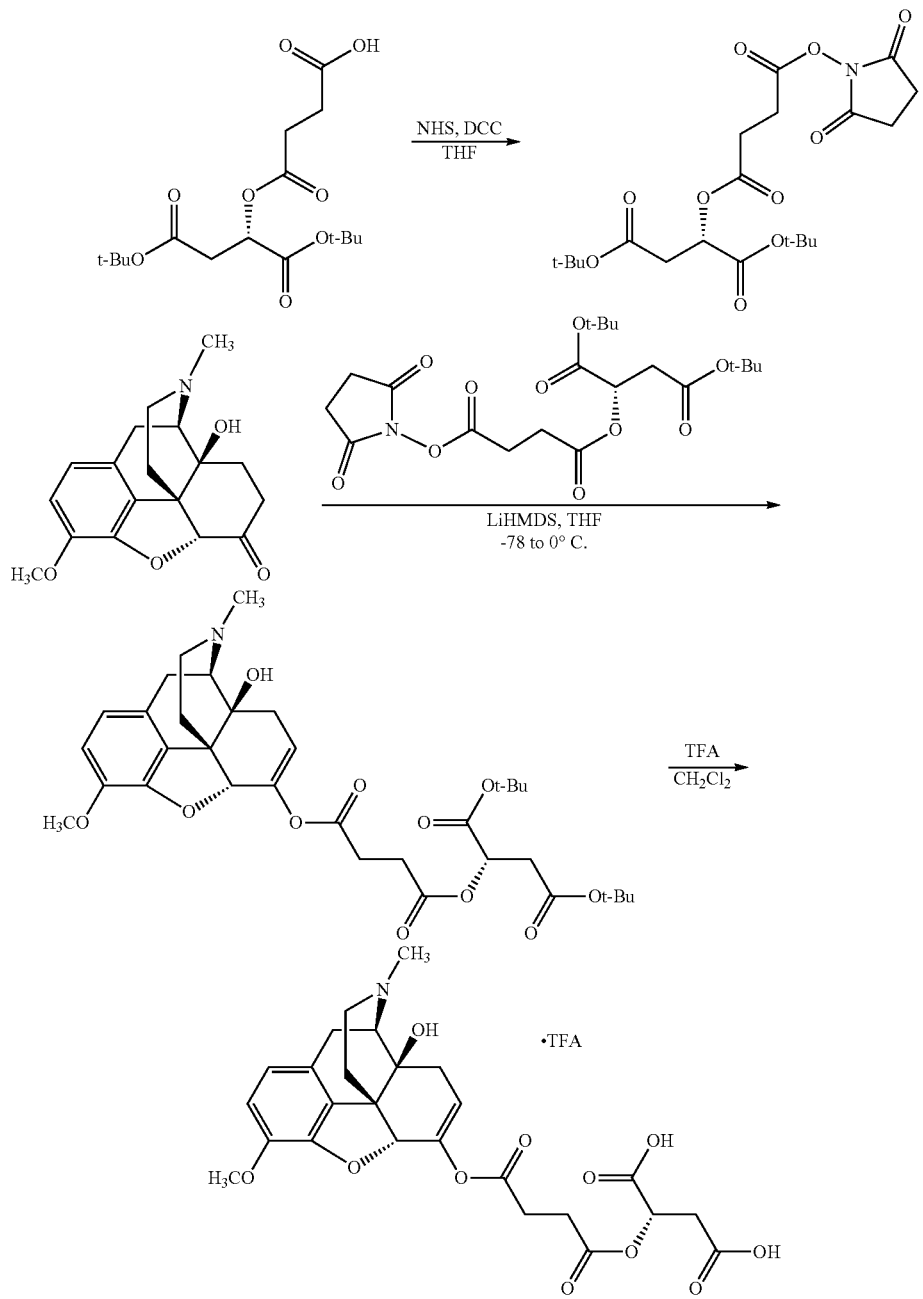

Preparation of (S)-2-Acetoxy-4-(tert-butoxy)-4-oxobutanoic acid

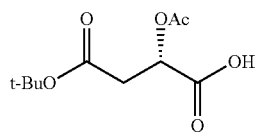

(S)-4-(tert-Butoxy)-2-hydroxy-4-oxobutanoic acid (4.88 g, 25.7 mmol), acetyl chloride (2.22 g, 28.2 mmol), N,N-diisopropylethylamine (3.99 g, 30.8 mmol), and methylene chloride (200 mL) were combined at 0° C. and stirred at room temperature under a nitrogen atmosphere for 16 h. After this time, 10% aqueous citric acid (100 mL) was added. The organic layer was separated and extracted with methylene chloride (2×100 mL). The combined organics were washed with brine (50 mL), dried over sodium sulfate, filtered, and concentrated under reduced pressure to provide (S)-2-acetoxy-4-(tert-butoxy)-4-oxobutanoic acid (4.59 g, 76%) as a light yellow oil: $^1$H NMR (300 MHz, CDCl$_3$) δ 5.46 (m, 1H), 2.83 (m, 2H), 2.14 (s, 3H), 1.46 (s, 9H), CO$_2$H proton not observed.

Preparation of (S)-Di-tert-butyl 2-acetoxysuccinate

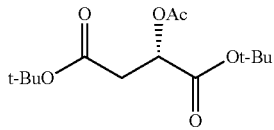

A solution of (S)-2-acetoxy-4-(tert-butoxy)-4-oxobutanoic acid (4.59 g, 19.8 mmol) and tert-butanol (3.22 g, 43.5 mmol) in methylene chloride (70 mL) was treated with N,N'-dicyclohexylcarbodiimide (5.31 g, 25.7 mmol) and 4-(dimethylamino)pyridine (798 mg, 6.53 mmol) at 0° C. and stirred at room temperature under a nitrogen atmosphere for 16 h. After this time, the reaction mixture was filtered to remove the solid dicyclohexylurea byproduct. The solid was washed with diethyl ether (100 mL), and the combined filtrate and washings were concentrated under reduced pressure. The crude residue was purified by column chromatography (80 g silica gel column, 0-30% ethyl acetate/heptane) to provide (S)-di-tert-butyl 2-acetoxysuccinate (3.44 g, 60%) as a colorless oil: $^1$H NMR (300 MHz, CDCl$_3$) δ 5.30 (dd, J=7.5, 5.4 Hz, 1H), 2.75 (m, 2H), 2.13 (s, 3H), 1.46 (s, 18H).

Preparation of (S)-Di-tert-butyl 2-hydroxysuccinate

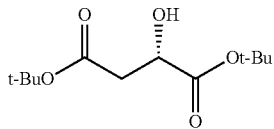

(S)-Di-tert-butyl 2-acetoxysuccinate (3.44 g, 11.9 mmol), potassium carbonate (4.94 g, 35.8 mmol), methanol (240 mL) and water (40 mL) were combined and stirred at 0° C. for 4 h. After this time, water (200 mL) was added, and the aqueous solution was extracted with methylene chloride (2×200 mL). The combined organics were washed with brine (50 mL), dried over sodium sulfate, filtered, and concentrated under reduced pressure to provide (S)-di-tert-butyl 2-hydroxysuccinate (2.71 g, 92%) as a colorless oil: $^1$H NMR (300 MHz, CDCl$_3$) δ 4.30 (dd, J=10.2, 5.7 Hz, 1H), 3.21 (d, J=5.4 Hz, 1H), 2.77-2.60 (m, 2H), 1.45 (s, 9H), 1.42 (s, 9H).

Preparation of (S)-4-((1,4-Di-tert-butoxy-1,4-dioxobutan-2-yl)oxy)-4-oxobutanoic acid

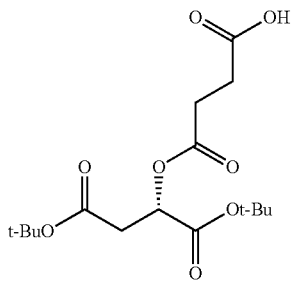 [SMILES: CC(C)(C)OC(=O)C[C@H](OC(=O)CCC(=O)O)C(=O)OC(C)(C)C]

(S)-Di-tert-butyl 2-hydroxysuccinate (428 mg, 1.74 mmol), dihydrofuran-2,5-dione (414 mg, 4.14 mmol), N,N-diisopropylethylamine (535 mg, 4.14 mmol), and methylene chloride (10 mL) were combined and stirred at room temperature under a nitrogen atmosphere for 16 h. After this time, 10% aqueous citric acid (100 mL) was added. The organic layer was separated and extracted with methylene chloride (2×50 mL). The combined organics were washed with brine (50 mL), dried over sodium sulfate, filtered, and concentrated under reduced pressure to provide (S)-4-((1,4-di-tert-butoxy-1,4-dioxobutan-2-yl)oxy)-4-oxobutanoic acid (534 mg, 95%) as a brown oil: $^1$H NMR (300 MHz, CDCl$_3$) δ 5.32 (dd, J=7.5, 5.1 Hz, 1H), 2.77-2.66 (m, 6H), 1.46 (s, 18H), CO$_2$H proton not observed.

Preparation of (S)-Di-tert-butyl 2-((4-((2,5-dioxopyrrolidin-1-yl)oxy)-4-oxobutanoyl)oxy)succinate

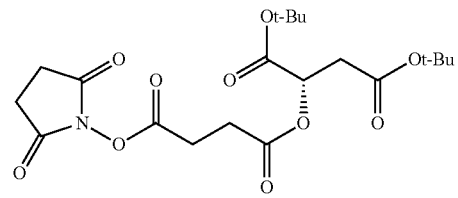 [SMILES: CC(C)(C)OC(=O)C[C@H](OC(=O)CCC(=O)ON1C(=O)CCC1=O)C(=O)OC(C)(C)C]

A solution of (S)-4-((1,4-di-tert-butoxy-1,4-dioxobutan-2-yl)oxy)-4-oxobutanoic acid (534 mg, 1.38 mmol) in tetrahydrofuran (15 mL) was treated with N-hydroxysuccinimide (159 mg, 1.38 mmol) and N,N'-dicyclohexylcarbodiimide (284 mg, 1.38 mmol) and stirred under a nitrogen atmosphere for 3 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-di-tert-butyl 2-((4-((2,5-dioxopyrrolidin-1-yl)oxy)-4-oxobutanoyl)oxy)succinate (684 mg) as a brown oil: $^1$H NMR (300 MHz, CDCl$_3$) δ 5.34 (dd, J=6.9, 5.7 Hz, 1H), 3.01-2.96 (m, 2H), 2.87-2.70 (m, 8H), 1.44 (s, 18H).

Preparation of (S)-Di-tert-butyl 2-((4-(((4R,4aS, 7aR,12bS)-4a-hydroxy-9-methoxy-3-methyl-2,3,4, 4a,5,7a-hexahydro-1H-4,12-methanobenzofuro[3,2-e]isoquinolin-7-yl)oxy)-4-oxobutanoyl)oxy) succinate

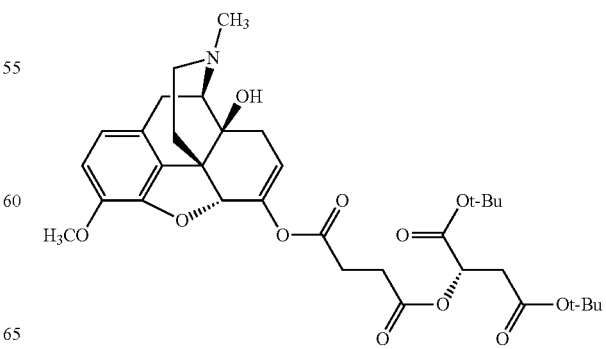

A suspension of oxycodone (0.22 g, 0.69 mmol) in tetrahydrofuran (5 mL) was cooled in an ice bath and treated with a 1.0 M solution of lithium bis(trimethylsilyl)amide in tetrahydrofuran (0.8 mL, 0.8 mmol). After addition was complete, the mixture was stirred under a nitrogen atmosphere in the ice bath for 25 min and at ambient temperature for 25 min. The solution was re-cooled in a dry ice/acetone bath, and the mixture was treated with a solution of (S)-di-tert-butyl 2-((4-((2,5-dioxopyrrolidin-1-yl)oxy)-4-oxobutanoyl)oxy)succinate (0.34 g, 0.77 mmol) in tetrahydrofuran (5 mL). The temperature was allowed to slowly increase to 0° C. over 2 h. After this time, the reaction mixture was treated with saturated aqueous ammonium chloride (50 mL) and extracted with ethyl acetate (2×50 mL). The combined organics were washed with saturated sodium bicarbonate (50 mL) and brine (50 mL), dried over sodium sulfate, filtered, and concentrated under reduced pressure. The crude residue was purified by reversed phase column chromatography (50 g C18 column, 10-100% acetonitrile/water) and freeze dried to provide (S)-di-tert-butyl 2-((4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinate (147 mg, 33%) as a white solid: ESI MS m/z 644 $[C_{34}H_{45}NO_{11}+H]^+$.

Preparation of (S)-2-((4-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid trifluoroacetic acid salt

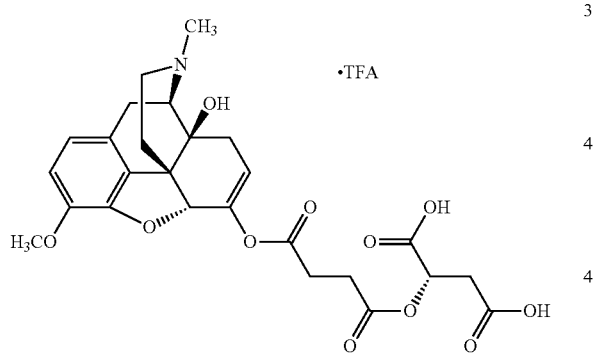

A solution of (S)-di-tert-butyl 2-((4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinate (136 mg, 0.211 mmol) in methylene chloride (4 mL) was treated with trifluoroacetic acid (1 mL) and stirred under a nitrogen atmosphere at ambient temperature for 7 h. After this time, the reaction mixture was concentrated under reduced pressure. The residue was purified by reversed phase column chromatography (C18 column, 10-70% acetonitrile/water with 0.1% trifluoroacetic acid) and freeze dried to provide (S)-2-((4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid trifluoroacetic acid salt (122 mg, 90%) as a white solid: $^1$H NMR (300 MHz, DMSO-$d_6$) δ 13.23 (br s, 1H), 12.59 (br s, 1H), 9.17 (br s, 1H), 6.86 (d, J=8.4 Hz, 1H), 6.75 (d, J=8.4 Hz, 1H), 6.27 (s, 1H), 5.53 (dd, J=6.3, 2.1 Hz, 1H), 5.22 (dd, J=7.8, 4.5 Hz, 1H), 4.99 (s, 1H), 3.75 (s, 3H), 3.64 (d, J=6.3 Hz, 1H), 3.46-3.39 (m, 1H, partially obscured by water peak), 3.15-3.06 (m, 2H), 2.84 (s, 3H), 2.80-2.66 (m, 7H), 2.49-2.43 (m, 1H, partially obscured by solvent peak), 2.27 (dd, J=17.7, 6.3 Hz, 1H), 2.06 (apparent d, J=18.0 Hz, 1H), 1.64 (d, J=11.7 Hz, 1H); ESI MS m/z 532 $[C_{26}H_{29}NO_{11}+H]^+$; HPLC (Method A)>99% (AUC), $t_R$=7.62 min.

Scheme 55: (S)-2-Acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

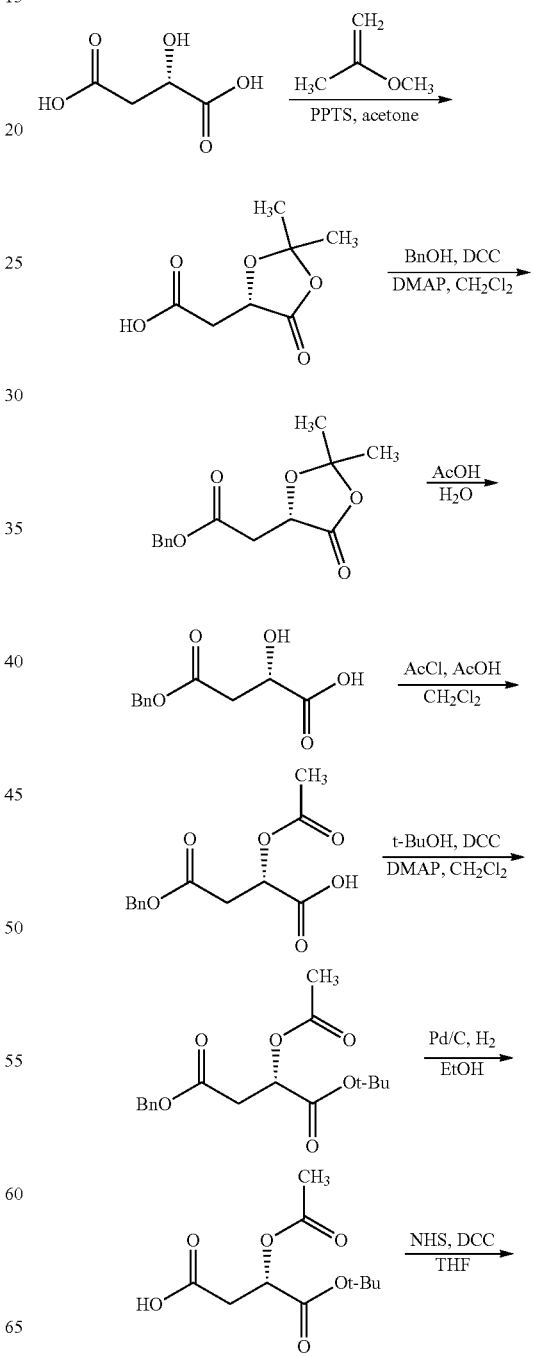

-continued

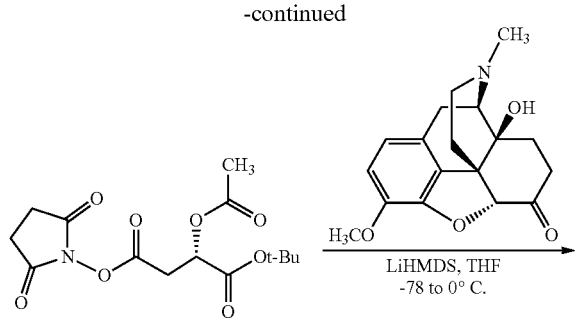

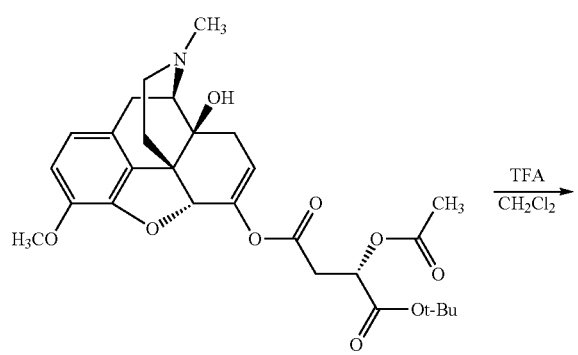

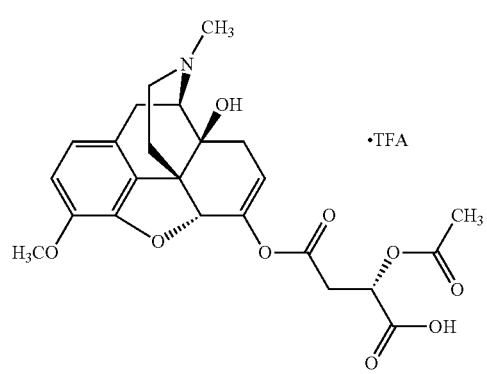

Preparation of (S)-2-(2,2-Dimethyl-5-oxo-1,3-dioxolan-4-yl)acetic acid

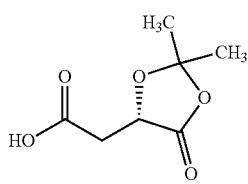

A solution of (S)-malic acid (30.28 g, 225.8 mmol) and pyridinium p-toluenesulfonate (5.16 g, 20.5 mmol) in acetone (17 mL) was cooled in an ice bath and treated with 2-methoxyprop-1-ene (85.0 mL, 888 mmol) under a nitrogen atmosphere. After 30 min, the ice bath was removed, and the mixture was heated at 35° C. for 16 h. After this time, the reaction mixture was cooled to room temperature and concentrated under reduced pressure. The residue was dissolved in ethyl acetate (500 mL), washed with 1:1 brine/water (4×200 mL), dried over sodium sulfate, filtered, and partially concentrated under reduced pressure to a volume of approximately 200 mL. The solution was treated with heptanes (200 mL) and cooled in an ice bath for 1 h. The resulting solids were isolated by filtration and washed with heptanes to provide (S)-2-(2,2-dimethyl-5-oxo-1,3-dioxolan-4-yl)acetic acid (23.14 g, 59%) as a white solid: $^1$H NMR (300 MHz, DMSO-$d_6$) δ 12.61 (s, 1H), 4.79 (dd, J=5.1, 4.8 Hz, 1H), 2.83-2.68 (m, 2H), 1.53 (s, 3H), 1.52 (s, 3H).

Preparation of (S)-Benzyl 2-(2,2-dimethyl-5-oxo-1,3-dioxolan-4-yl)acetate

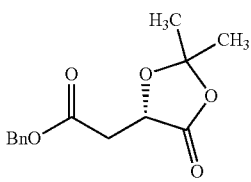 [SMILES: CC1(C)OC(=O)[C@H](CC(=O)OCc2ccccc2)O1]

A solution of (S)-2-(2,2-dimethyl-5-oxo-1,3-dioxolan-4-yl)acetic acid (10.08 g, 57.88 mmol) in methylene chloride (290 mL) was treated with benzyl alcohol (9.0 mL, 87 mmol), N,N'-dicyclohexylcarbodiimide (14.3 g, 69.2 mmol), and 4-dimethylaminopyridine (2.12 g, 17.4 mmol) and stirred under a nitrogen atmosphere for 1.5 h. After this time, the reaction mixture was filtered to remove the solid dicyclohexylurea byproduct. The solid was washed with methylene chloride, and the combined filtrate and washings were concentrated under reduced pressure. The crude residue was purified by column chromatography (silica gel, 0-20% ethyl acetate/heptanes) to provide (S)-benzyl 2-(2,2-dimethyl-5-oxo-1,3-dioxolan-4-yl)acetate (8.63 g, 56%) as a white solid: $^1$H NMR (300 MHz, DMSO-$d_6$) δ 7.41-7.30 (m, 5H), 5.13 (dd, J=14.4, 12.3 Hz, 2H), 4.87 (t, J=4.8 Hz, 1H), 3.02-2.89 (m, 2H), 1.52 (s, 3H), 1.49 (s, 3H).

Preparation of (S)-4-(Benzyloxy)-2-hydroxy-4-oxobutanoic acid

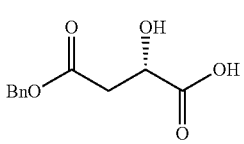

A solution of (S)-benzyl 2-(2,2-dimethyl-5-oxo-1,3-dioxolan-4-yl)acetate (8.63 g, 32.7 mmol) in acetic acid (50 mL) and water (25 mL) was heated at 60° C. for 1.5 h. After this time, the reaction mixture was concentrated under reduced pressure. The residue was dissolved in water and freeze dried to provide (S)-4-(benzyloxy)-2-hydroxy-4-oxobutanoic acid (7.32 g, quantitative) as a white solid: $^1$H NMR (300 MHz, DMSO-$d_6$) δ 12.57 (br s, 1H), 7.40-7.29 (m, 5H), 5.57 (br s, 1H), 5.11 (s, 2H), 4.33 (dd, J=7.8, 4.8 Hz, 1H), 2.77 (dd, J=15.6, 4.8 Hz, 1H), 2.61 (dd, J=15.6, 7.8 Hz, 1H); ESI MS m/z 223 $[C_{11}H_{12}O_5-H]^-$.

Preparation of (S)-2-Acetoxy-4-(benzyloxy)-4-oxobutanoic acid

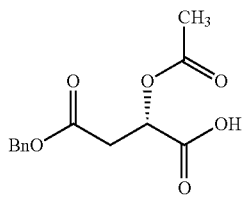 [SMILES: CC(=O)O[C@@H](CC(=O)OCc1ccccc1)C(=O)O]

A solution of (S)-4-(benzyloxy)-2-hydroxy-4-oxobutanoic acid (3.00 g, 13.4 mmol) in methylene chloride (15 mL) was treated with acetic acid (3 mL) and cooled in an ice bath under a nitrogen atmosphere. The solution was treated dropwise with acetyl chloride (1.05 mL, 14.8 mmol). After 15 min, the ice bath was removed, and the mixture was stirred at ambient temperature for 16 h. After this time, the reaction mixture was concentrated under reduced pressure and dried under vacuum to provide (S)-2-acetoxy-4-(benzyloxy)-4-oxobutanoic acid (4.12 g, quantitative) as a colorless oil: $^1$H NMR (300 MHz, DMSO-$d_6$) δ 7.39-7.33 (m, 5H), 5.25 (dd, J=8.1, 4.5 Hz, 1H), 5.14 (dd, J=14.4, 12.6 Hz, 2H), 3.00 (dd, J=16.5, 4.5 Hz, 1H), 2.89 (dd, J=16.5, 8.1 Hz, 1H), 2.02 (s, 3H), CO$_2$H proton not observed.

Preparation of (S)-4-Benzyl 1-tert-butyl 2-acetoxysuccinate

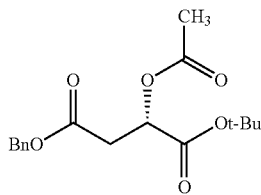 [SMILES: CC(=O)O[C@@H](CC(=O)OCc1ccccc1)C(=O)OC(C)(C)C]

A solution of (S)-2-acetoxy-4-(benzyloxy)-4-oxobutanoic acid (3.57 g, 13.4 mmol) in methylene chloride (60 mL) was treated with tert-butanol (4.5 mL, 47 mmol), N,N'-dicyclohexylcarbodiimide (4.30 g, 20.8 mmol), and 4-dimethylaminopyridine (462 mg, 3.78 mmol) and stirred under a nitrogen atmosphere for 5 h. After this time, the reaction mixture was filtered to remove the solid dicyclohexylurea byproduct. The solid was washed with diethyl ether, and the combined filtrate and washings were concentrated under reduced pressure. The crude residue was purified by column chromatography (silica gel, 0-20% ethyl acetate/heptanes) to provide (S)-4-benzyl 1-tert-butyl 2-acetoxysuccinate (2.78 g, 64%) as a colorless oil: $^1$H NMR (300 MHz, DMSO-$d_6$) δ 7.42-7.30 (m, 5H), 5.19-5.14 (m, 3H), 3.00-2.85 (m, 2H), 2.03 (s, 3H), 1.37 (s, 9H).

Preparation of (S)-3-Acetoxy-4-(tert-butoxy)-4-oxobutanoic acid

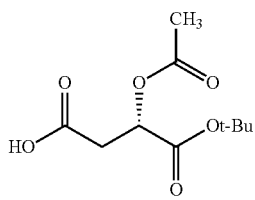 [SMILES: CC(=O)O[C@@H](CC(=O)O)C(=O)OC(C)(C)C]

A solution of (S)-4-benzyl 1-tert-butyl 2-acetoxysuccinate (1.02 g, 3.16 mmol) in ethanol (30 mL) was sparged with nitrogen gas for 30 min. The solution was treated with 5% palladium on carbon (214 mg) and sparged with hydrogen gas for 5 min. The mixture was stirred under a hydrogen atmosphere for 2 h. After this time, the reaction mixture was sparged with nitrogen gas for 5 min and filtered through diatomaceous earth. The filtrate was concentrated under reduced pressure to provide (S)-3-acetoxy-4-(tert-butoxy)-4-oxobutanoic acid (731 mg, 99%) as a colorless oil: $^1$H NMR (300 MHz, DMSO-$d_6$) δ 12.74 (br s, 1H), 5.10 (dd, J=8.1, 4.8 Hz, 1H), 2.81-2.64 (m, 2H), 2.06 (s, 3H), 1.40 (s, 9H).

Preparation of (S)-1-tert-Butyl 4-(2,5-dioxopyrrolidin-1-yl) 2-acetoxysuccinate

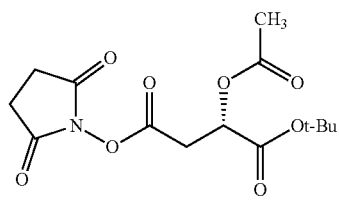 [SMILES: CC(=O)O[C@@H](CC(=O)ON1C(=O)CCC1=O)C(=O)OC(C)(C)C]

A solution of (S)-3-acetoxy-4-(tert-butoxy)-4-oxobutanoic acid (725 mg, 3.12 mmol) in tetrahydrofuran (15 mL) was treated with N-hydroxysuccinimide (396 mg, 3.44 mmol) and N,N'-dicyclohexylcarbodiimide (709 mg, 3.44 mmol) and stirred under a nitrogen atmosphere for 6 h. After this time, the reaction mixture was filtered to remove the solid dicyclohexylurea byproduct. The solid was washed with diethyl ether, and the combined filtrate and washings were concentrated under reduced pressure to provide (S)-1-tert-butyl 4-(2,5-dioxopyrrolidin-1-yl) 2-acetoxysuccinate (1.25 g, quantitative) as an off-white solid: $^1$H NMR (300 MHz, DMSO-$d_6$) δ 5.28 (dd, J=7.5, 4.8 Hz, 1H), 3.39-3.22 (m, 2H), 2.82 (s, 4H), 2.08 (s, 3H), 1.41 (s, 9H).

Preparation of (S)-1-tert-Butyl 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-acetoxysuccinate

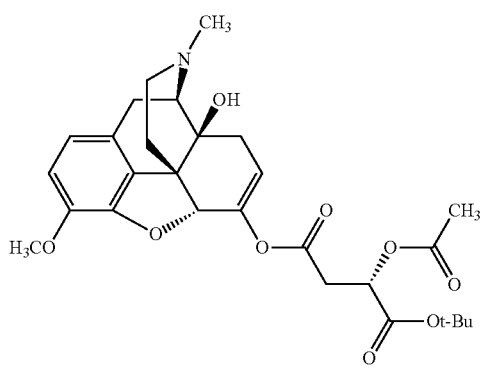 [SMILES: COc1ccc2c3c1O[C@H]1C(OC(=O)C[C@H](OC(C)=O)C(=O)OC(C)(C)C)=CC[C@@]4(O)[C@@H](C2)N(C)CC[C@]314]

A suspension of oxycodone (0.52 g, 1.7 mmol) in tetrahydrofuran (5 mL) was cooled in an ice bath and treated with a 1.0 M solution of lithium bis(trimethylsilyl)amide in tetrahydrofuran (1.8 mL, 1.8 mmol). After addition was complete, the mixture was stirred under nitrogen atmosphere in the ice bath for 25 min and at ambient temperature for 25 min. The solution was re-cooled in a dry ice/acetone bath, and the mixture was treated with a solution of (S)-1-tert-butyl 4-(2,5-dioxopyrrolidin-1-yl) 2-acetoxysuccinate (0.60 g, 1.8 mmol) in tetrahydrofuran (5 mL). The temperature was allowed to slowly increase to 0° C. over 2 h. After this time, the reaction mixture was treated with saturated aqueous ammonium chloride (50 mL) and extracted with ethyl acetate (2×50 mL). The combined organics were washed with saturated sodium bicarbonate (50 mL) and brine (50 mL), dried over sodium sulfate, filtered, and concentrated under reduced pressure. The crude residue was purified by reversed phase column chromatography (150 g C18 column, 10-100% acetonitrile/water) and freeze dried to provide (S)-1-tert-butyl 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-acetoxysuccinate (232 mg, 27%) as a white solid: ESI MS m/z 530 $[C_{28}H_{35}NO_9+H]^+$.

Preparation of (S)-2-Acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

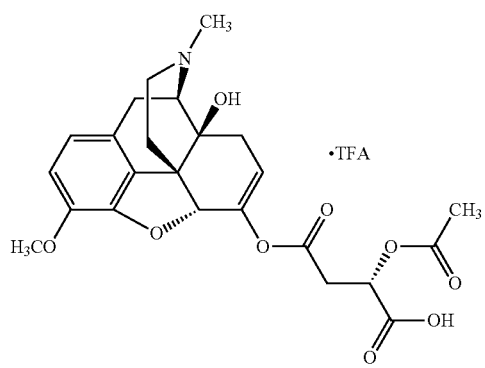 [SMILES: COc1ccc2c3c1O[C@H]1C(OC(=O)C[C@H](OC(C)=O)C(=O)O)=CC[C@@]4(O)[C@@H](C2)N(C)CC[C@]314]

A solution of (S)-1-tert-butyl 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-acetoxysuccinate (230 mg, 0.434 mmol) in methylene chloride (4 mL) was treated with trifluoroacetic acid (1 mL) and stirred under a nitrogen atmosphere at ambient temperature for 3 h. After this time, the reaction mixture was concentrated under reduced pressure. The residue was purified by reversed phase column chromatography (50 g C18 column, 10-70% acetonitrile/water with 0.1% trifluoroacetic acid) and freeze dried to provide (S)-2-acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid 2,2,2-trifluoroacetatetrifluoroacetic acid salt(225 mg, 88%) as a fluffy white solid: $^1$H NMR (300 MHz, DMSO-$d_6$) δ 13.38 (br s, 1H), 9.17 (br s, 1H), 6.86 (d, J=8.4 Hz, 1H), 6.75 (d, J=8.4 Hz, 1H), 6.29 (s, 1H), 5.56 (dd, J=5.7, 1.8 Hz, 1H), 5.26 (dd, J=8.4, 4.2 Hz, 1H), 4.99 (s, 1H), 3.74 (s, 3H), 3.65 (d, J=6.3 Hz, 1H), 3.43 (d, J=20.1 Hz, 1H, partially obscured by water peak), 3.16-3.06 (m, 3H), 2.98 (dd, J=16.8, 8.4 Hz, 1H), 2.84 (apparent d, J=3.9 Hz, 3H), 2.65-2.57 (m, 1H), 2.49-2.42 (m, 1H, partially obscured by solvent peak), 2.28 (dd, J=17.7, 6.3 Hz, 1H), 2.09 (s, 3H), 2.09-2.04 (m, 1H), 1.65 (d, J=11.1 Hz, 1H);ESI MS m/z 474 $[C_{24}H_{27}NO_9+H]^+$; HPLC (Method A) 96.7% (AUC), $t_R$=7.78 min.

Scheme 56: (S)-2-((4-(((4R,4aS,7aR,12bS)-4a-Hydroxy-9-methoxy-3-methyl-2,3,4,4a,5,7a-hexahydro-1H-4, 12-methanobenzofuro[3,2-e]isoquinolin-7-yl)oxy)-4-oxobutanoyl)oxy)-2-phenylacetic acid trifluoroacetic acid salt

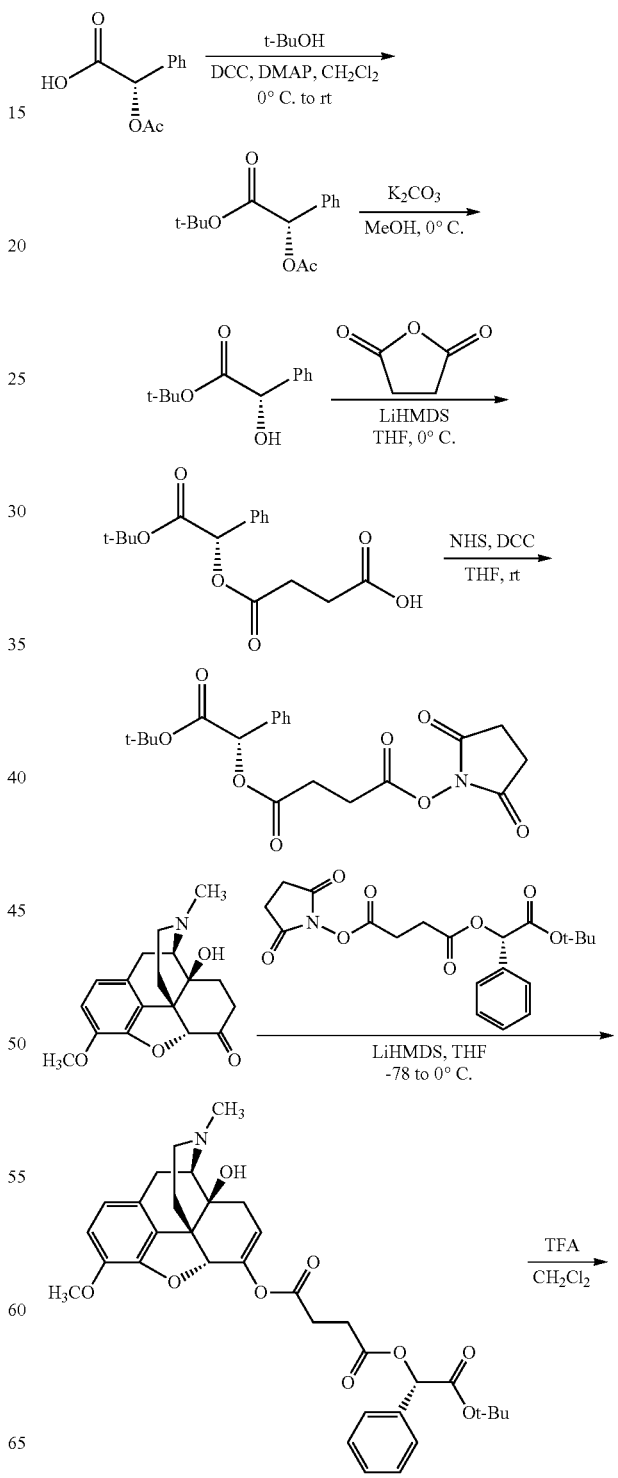

-continued

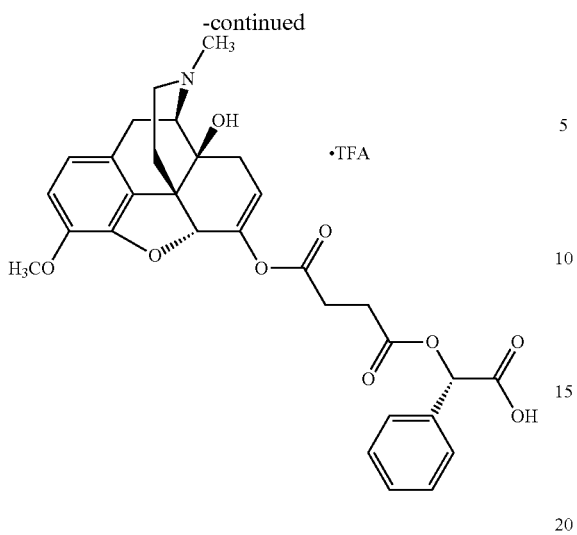

Preparation of (S)-tert-Butyl 2-acetoxy-2-phenylacetate

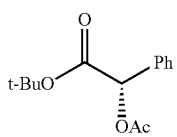

A mixture of (S)-2-acetoxy-2-phenylacetic acid (22.0 g, 104 mmol) and tert-butanol (19.0 g, 257 mmol) in methylene chloride (150 mL) at 0° C. was treated with N,N'-dicyclohexylcarbodiimide (28.0 g, 136 mmol). After stirring for 1 h, the ice bath was removed and the reaction mixture was stirred at ambient temperature for 18 h. After this time, the mixture was filtered and the filtrate was concentrated under reduced pressure. The residue was purified by column chromatography (330 g silica gel column, 5-20% ethyl acetate/heptane) to provide (S)-tert-butyl 2-acetoxy-2-phenylacetate (14.4 g, 52%): $^1$H NMR (300 MHz, CDCl$_3$) δ 7.48-7.43 (m, 2H), 7.40-7.35 (m, 3H), 5.80 (s, 1H), 2.18 (s, 3H), 1.40 (s, 9H).

Preparation of (S)-tert-Butyl 2-hydroxy-2-phenylacetate

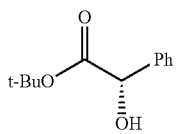

A solution of (S)-tert-butyl 2-acetoxy-2-phenylacetate (14.4 g, 54.1 mmol) in methanol (15 mL) was cooled to 0° C. and treated with a solution of sodium bicarbonate (22.5 g, 163 mmol) in water/methanol (3:2, 145 mL). The reaction mixture was stirred at 0° C. for 2 h, and then neutralized by addition of citric acid (10 g, 52 mmol). The mixture was partially concentrated under reduced pressure and then extracted with methylene chloride. The organic layer was washed with water and brine, dried over sodium sulfate, filtered, and concentrated under reduced pressure to provide (S)-tert-butyl 2-hydroxy-2-phenylacetate (11.2 g), which was used without purification: $^1$H NMR (300 MHz, CDCl$_3$) δ 7.43-7.29 (m, 5H), 5.03 (d, J=6.0 Hz, 1H), 3.50 (d, J=6.0 Hz, 1H), 1.41 (s, 9H).

Preparation of (S)-4-(2-(tert-Butoxy)-2-oxo-1-phenylethoxy)-4-oxobutanoic acid

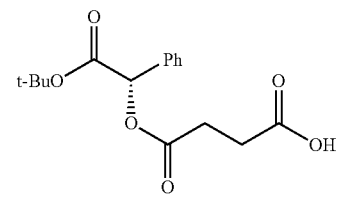 [SMILES: CC(C)(C)OC(=O)[C@@H](OC(=O)CCC(=O)O)c1ccccc1]

A solution of (S)-tert-butyl 2-hydroxy-2-phenylacetate (3.15 g, 15.1 mmol) in tetrahydrofuran (35 mL) at 0° C. was treated with a 1.0 M solution of lithium bis(trimethylsilyl)amide in tetrahydrofuran (16 mL, 16 mmol), and the mixture was stirred for 10 min. After this time, a solution of succinic anhydride (1.33 g, 16.6 mmol) in tetrahydrofuran (25 mL) was added, and the mixture was stirred at 0° C. for 1.5 h. After this time, the mixture was poured into a saturated solution of ammonium chloride and extracted with ethyl acetate. The organic extract was dried over sodium sulfate, filtered, and concentrated under reduced pressure to provide (S)-4-(2-(tert-butoxy)-2-oxo-1-phenylethoxy)-4-oxobutanoic acid (4.60 g): ESI MS m/z 634 [C$_{16}$H$_{20}$O$_6$+NH$_4$]$^+$.

Preparation of (S)-2-(tert-Butoxy)-2-oxo-1-phenylethyl (2,5-dioxopyrrolidin-1-yl) succinate

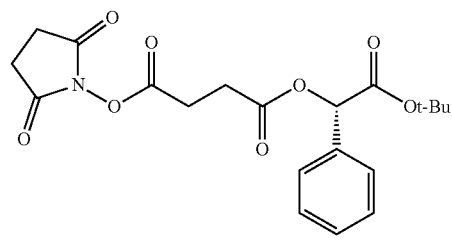 [SMILES: CC(C)(C)OC(=O)[C@@H](OC(=O)CCC(=O)ON1C(=O)CCC1=O)c1ccccc1]

A mixture of (S)-4-(2-(tert-butoxy)-2-oxo-1-phenylethoxy)-4-oxobutanoic acid (4.60 g, 15.0 mmol) and N-hydroxysuccinimide (1.90 g, 16.5 mmol) in tetrahydrofuran (75 mL) at 0° C. was treated with N,N'-dicyclohexylcarbodiimide (3.40 g, 16.5 mmol). The ice bath was removed, and the reaction mixture was stirred at ambient temperature for 4 h. After this time, diethyl ether (75 mL) was added, and the mixture was filtered. The filtrate was concentrated under reduced pressure to provide (S)-2-(tert-butoxy)-2-oxo-1-phenylethyl (2,5-dioxopyrrolidin-1-yl) succinate (10.0 g) that was used without purification: $^1$H NMR (300 MHz, CDCl$_3$) δ 7.47-7.42 (m, 2H), 7.42-7.35 (m, 3H), 5.84 (s, 1H), 3.06-2.98 (m, 2H), 2.93-2.88 (m, 2H), 2.83 (s, 4H), 1.39 (s, 9H).

Preparation of (S)-2-(tert-Butoxy)-2-oxo-1-phenylethyl ((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) succinate

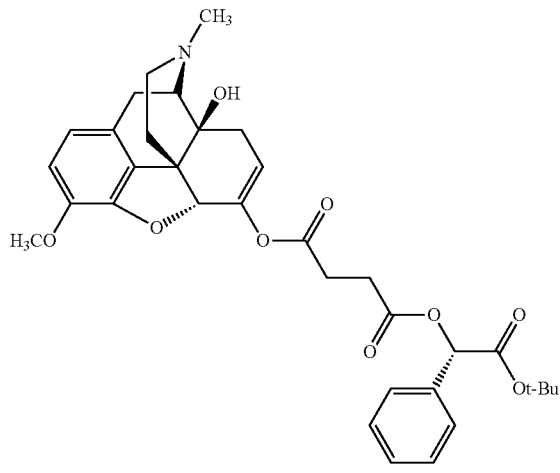

A suspension of oxycodone (530 mg, 1.68 mmol) in tetrahydrofuran (9 mL) was cooled in an ice bath and treated dropwise with a 1.0 M solution of lithium bis(trimethylsilyl)amide in tetrahydrofuran (2.0 mL, 2.0 mmol). After addition was complete, the mixture was stirred under nitrogen atmosphere in the ice bath for 10 min and at ambient temperature for 5 min. The solution was re-cooled in a dry ice/acetone bath, and the mixture was treated dropwise with a solution of (S)-2-(tert-butoxy)-2-oxo-1-phenylethyl (2,5-dioxopyrrolidin-1-yl) succinate (810 mg, 2.00 mmol) in tetrahydrofuran (7 mL). After addition was complete, the dry ice/acetone bath was replaced with a wet ice/brine bath, and the mixture was stirred for 20 min. After this time, the reaction mixture was treated with saturated aqueous ammonium chloride (50 mL) and extracted with ethyl acetate (2×50 mL). The combined organics were washed with saturated sodium bicarbonate (50 mL), water (50 mL), and brine (50 mL); dried over sodium sulfate; filtered; and concentrated under reduced pressure. The crude residue was purified by reversed phase column chromatography (150 g C18 column, 20-100% acetonitrile/water) and freeze dried to provide (S)-2-(tert-butoxy)-2-oxo-1-phenylethyl ((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) succinate (344 mg, 34%) as a white solid: ESI MS m/z 606 $[C_{34}H_{39}NO_9+H]^+$.

Preparation of (S)-2-((4-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt

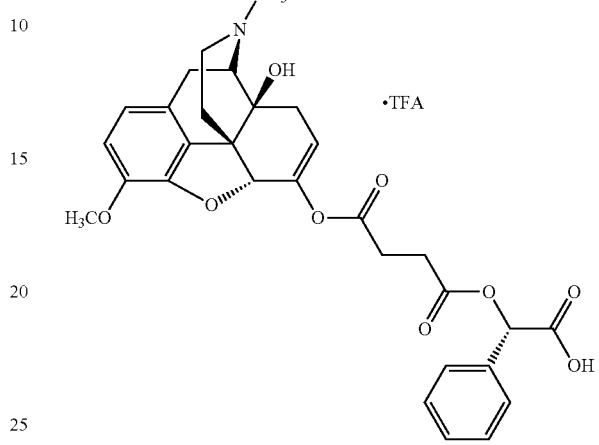

A solution of (S)-2-(tert-butoxy)-2-oxo-1-phenylethyl ((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) succinate (340 mg, 0.561 mmol) in methylene chloride (8 mL) was treated with trifluoroacetic acid (2 mL) and stirred under a nitrogen atmosphere at ambient temperature for 5 h. After this time, the reaction mixture was concentrated under reduced pressure. The residue was purified by reversed phase column chromatography (150 g C18 column, 10-100% acetonitrile/water with 0.1% trifluoroacetic acid) and freeze dried to provide (S)-2-((4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt (338 mg, 91%) as a white solid: $^1$H NMR (300 MHz, DMSO-$d_6$) δ 13.29 (br s, 1H), 9.18 (br s, 1H), 7.46-7.40 (m, 5H), 6.86 (d, J=8.4 Hz, 1H), 6.75 (d, J=8.4 Hz, 1H), 6.29 (br s, 1H), 5.84 (s, 1H), 5.50-5.46 (m, 1H), 4.96 (s, 1H), 3.74 (s, 3H), 3.64 (d, J=6.0 Hz, 1H), 3.43 (d, J=19.8 Hz, 1H), 3.15-3.06 (m, 2H), 2.84 (apparent d, J=3.3 Hz, 3H), 2.76 (s, 4H), 2.65-2.58 (m, 1H), 2.43 (dd, J=12.9, 4.2 Hz, 1H), 2.26 (dd, J=17.7, 6.0 Hz, 1H), 2.04 (apparent d, J=17.7 Hz, 1H), 1.63 (d, J=12.0 Hz, 1H); ESI MS m/z 550 $[C_{30}H_{31}NO_9+H]^+$; HPLC (Method A)>99% (AUC), $t_R$=9.29 min.

Scheme 57: (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((S)-2-acetoxy-2-phenylacetoxy)propanoate trifluoroacetic acid salt

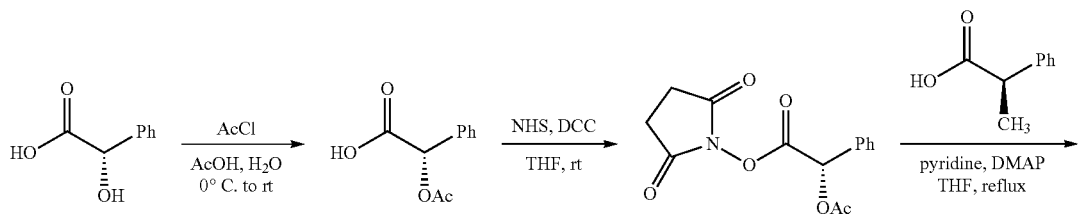

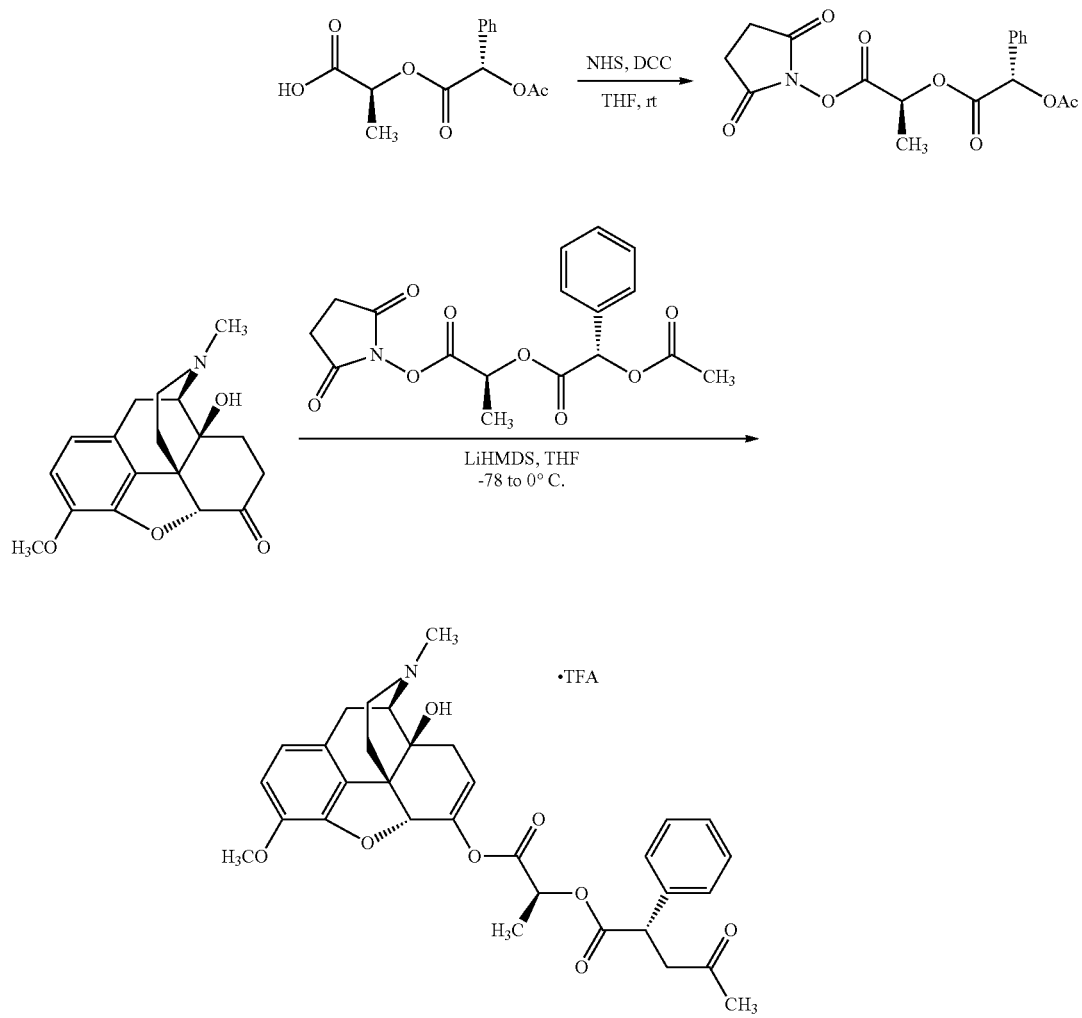

Preparation of (S)-2-Acetoxy-2-phenylacetic acid

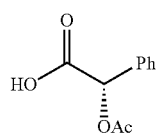

A solution of (S)-2-hydroxy-2-phenylacetic acid (16.4 g, 108 mmol) in acetic acid (30 mL) and water (1.3 mL) at 0° C. was treated dropwise with acetyl chloride (23.0 mL, 32.4 mmol). The reaction mixture was stirred at 0° C. for 1 h and then at room temperature for 18 h. After this time, the mixture was concentrated under reduced pressure, and the residue was dissolved in ethyl acetate, washed with water and brine, dried over sodium sulfate, filtered, and concentrated under reduced pressure to provide (S)-2-acetoxy-2-phenylacetic acid (22.0 g, 97%): $^1$H NMR (300 MHz, CDCl$_3$) δ 7.50-7.45 (m, 2H), 7.42-7.37 (m, 3H), 5.94 (s, 1H), 2.20 (s, 3H), CO$_2$H proton not observed.

Preparation of (S)-2,5-Dioxopyrrolidin-1-yl 2-acetoxy-2-phenylacetate

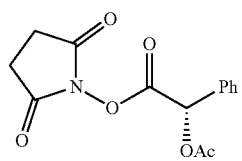 [SMILES: CC(=O)O[C@H](C(=O)ON1C(=O)CCC1=O)c1ccccc1]

A mixture of (S)-2-acetoxy-2-phenylacetic acid (6.50 g, 31.0 mmol) and N-hydroxysuccinimide (4.00 g, 34.8 mmol) in tetrahydrofuran (150 mL) at 0° C. was added N,N'-dicyclohexylcarbodiimide (7.00 g, 33.9 mmol). The ice bath was removed, and the reaction mixture was stirred at ambient temperature for 4 h. After this time, diethyl ether (100 mL) was added, and the mixture was filtered. The filtrate was concentrated under reduced pressure to provide (S)-2,5-dioxopyrrolidin-1-yl 2-acetoxy-2-phenylacetate (10.0 g) that was used without purification: $^1$H NMR (300 MHz, CDCl$_3$) δ 7.57-7.52 (m, 2H), 7.46-7.43 (m, 3H), 6.33 (s, 1H), 2.80 (s, 4H), 2.20 (s, 3H).

Preparation of (S)-2-((S)-2-Acetoxy-2-phenylacetoxy)propanoic acid

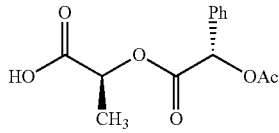

A mixture of (S)-2,5-dioxopyrrolidin-1-yl 2-acetoxy-2-phenylacetate (3.40 g, 11.6 mmol), (S)-2-hydroxypropanoic acid (1.30 g, 14.4 mmol), pyridine (1.1 mL, 13.6 mmol), and 4-dimethylaminopyridine (100 mg, 0.8 mmol) in tetrahydrofuran (50 mL) was stirred at reflux for 18 h. After this time, the mixture was cooled to room temperature, partially concentrated under reduced pressure, diluted with ethyl acetate, and washed with 10% citric acid. The organic layer was extracted with saturated sodium bicarbonate. The aqueous extract was carefully treated with 2N hydrochloric acid until acidic by pH paper analysis, and then extracted with ethyl acetate. The organic extracts were dried over sodium carbonate, filtered and concentrated. The residue was purified by reversed phase column chromatography (150 g C18 column, 5-100% acetonitrile/water) to provide (S)-2-((S)-2-acetoxy-2-phenylacetoxy)propanoic acid (1.15 g, 37%): ESI MS m/z 531 [2×($C_{13}H_{14}O_6$)−H]−.

Preparation of (S)-2,5-Dioxopyrrolidin-1-yl 2-((S)-2-acetoxy-2-phenylacetoxy)propanoate

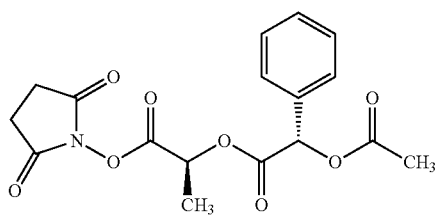

A mixture of (S)-2-((S)-2-acetoxy-2-phenylacetoxy)propanoic acid (1.15 g, 4.32 mmol) and N-hydroxysuccinimide (545 mg, 4.74 mmol) in tetrahydrofuran (20 mL) was treated with N,N'-dicyclohexylcarbodiimide (975 mg, 4.74 mmol), and the reaction mixture was stirred at ambient temperature for 4 h. After this time, diethyl ether (20 mL) was added, and the mixture was filtered. The filtrate was concentrated under reduced pressure to provide (S)-2,5-dioxopyrrolidin-1-yl 2-((S)-2-acetoxy-2-phenylacetoxy)propanoate (1.64 g) that was used without purification: $^1$H NMR (300 MHz, CDCl$_3$) δ 7.50-7.46 (m, 2H), 7.42-7.35 (m, 3H), 5.99 (s, 1H), 5.49 (q, J=7.1 Hz, 1H), 2.79 (s, 4H), 2.19 (s, 3H), 1.68 (d, J=7.1 Hz, 3H).

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((S)-2-acetoxy-2-phenylacetoxy)propanoate trifluoroacetic acid salt

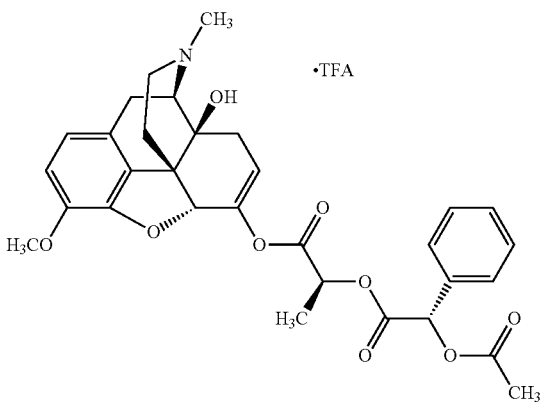 [SMILES: COc1ccc2c3c1O[C@H]1C(OC(=O)[C@H](C)OC(=O)[C@@H](OC(C)=O)c4ccccc4)=CC[C@@]4(O)[C@@H](C2)N(C)CC[C@]314]

A suspension of oxycodone (0.50 g, 1.6 mmol) in tetrahydrofuran (5 mL) was cooled in an ice bath and treated with a 1.0 M solution of lithium bis(trimethylsilyl)amide in tetrahydrofuran (1.8 mL, 1.8 mmol). After addition was complete, the mixture was stirred under nitrogen atmosphere in the ice bath for 25 min and at ambient temperature for 25 min. The solution was re-cooled in a dry ice/acetone bath, and the mixture was treated with a solution of (S)-2,5-dioxopyrrolidin-1-yl 2-((S)-2-acetoxy-2-phenylacetoxy)propanoate (0.67 g, 1.8 mmol) in tetrahydrofuran (5 mL). The temperature was allowed to slowly increase to 0° C. over 2 h. After this time, the reaction mixture was treated with saturated aqueous ammonium chloride (50 mL) and extracted with ethyl acetate (2×50 mL). The combined organics were washed with saturated sodium bicarbonate (50 mL) and brine (50 mL), dried over sodium sulfate, filtered, and concentrated under reduced pressure. The crude residue was purified by reversed phase column chromatography (150 g C18 column, 30-100% acetonitrile/water with 0.1% trifluoroacetic acid) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((S)-2-acetoxy-2-phenylacetoxy)propanoate trifluoroacetic acid salt (190 mg, 18%) as a white solid: $^1$H NMR (300 MHz, DMSO-d$_6$) δ 9.19 (br s, 1H), 7.52-7.48 (m, 2H), 7.42-7.37 (m, 3H), 6.86 (d, J=8.4 Hz, 1H), 6.75 (d, J=8.1 Hz, 1H), 6.28 (s, 1H), 6.06 (s, 1H), 5.47 (dd, J=5.7, 1.8 Hz, 1H), 5.28 (q, J=6.9 Hz, 1H), 4.82 (s, 1H), 3.73 (s, 3H), 3.64 (d, J=6.0 Hz, 1H), 3.42 (d, J=20.1 Hz, 1H), 3.15-3.06 (m, 2H), 2.84 (apparent d, J=4.8 Hz, 3H), 2.68-2.57 (m, 1H), 2.49-2.35 (m, 1H, partially obscured by solvent peak), 2.27 (dd, J=18.0, 6.0 Hz, 1H), 2.14 (s, 3H), 2.04 (apparent d, J=17.7 Hz, 1H), 1.62 (d, J=12.0 Hz, 1H), 1.48 (d, J=6.9 Hz, 3H); ESI MS m/z 564 [$C_{31}H_{33}NO_9$+H]+; HPLC (Method A) 98.2% (AUC), $t_R$=10.19 min.

Scheme 58: (R)-2-((4-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid
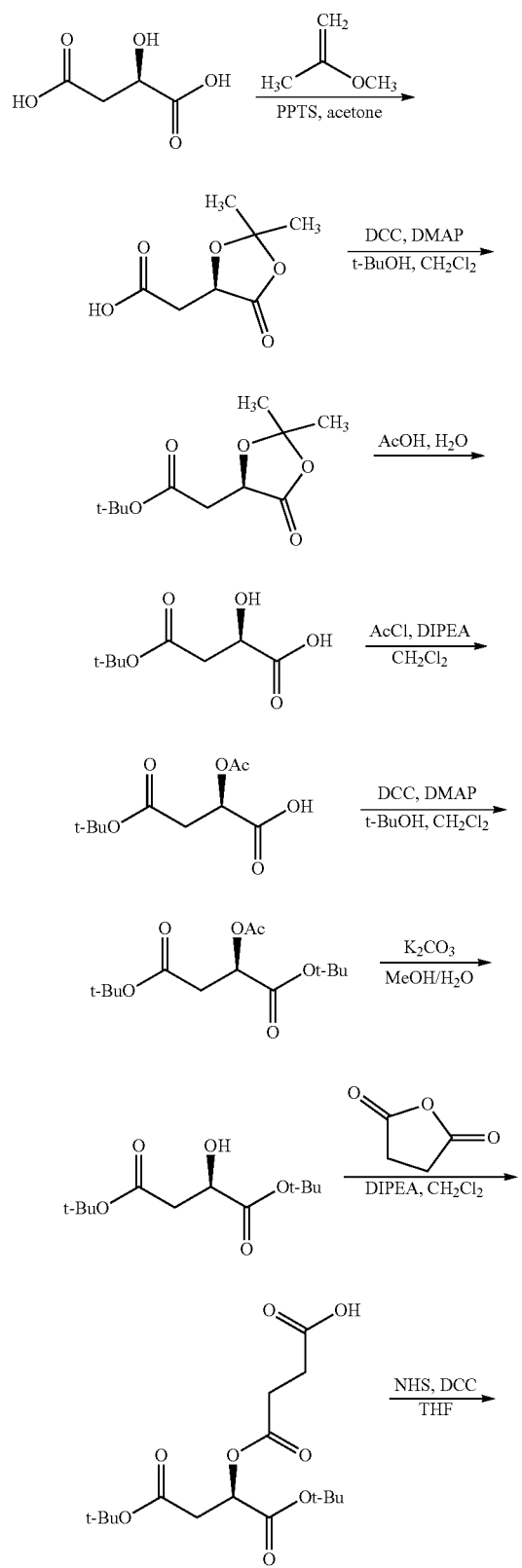
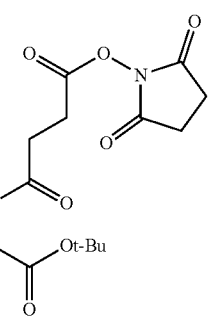
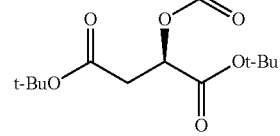
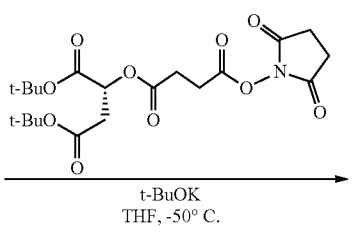
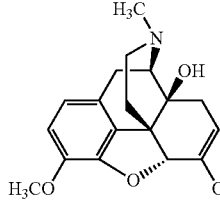
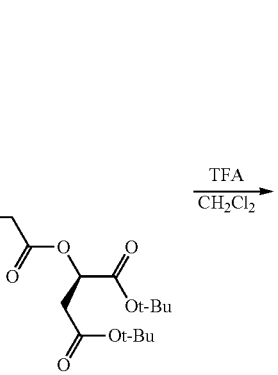
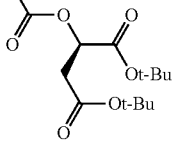
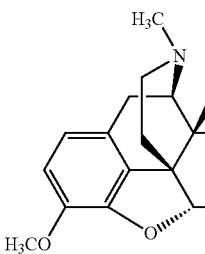
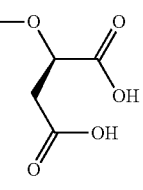

Preparation of (R)-2-(2,2-Dimethyl-5-oxo-1,3-di-oxolan-4-yl)acetic acid

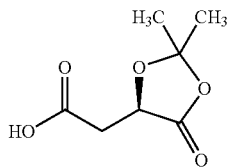

A solution of (R)-malic acid (4.50 g, 33.6 mmol), 2-methoxyprop-1-ene (9.68 g, 134 mmol) and pyridinium p-toluenesulfonate (844 mg, 3.36 mmol) in acetone (50 mL) was stirred at 35° C. for 16 h. After this time, water (200 mL) was added, and the aqueous solution was extracted with ethyl acetate (2×200 mL). The combined organics were dried over sodium sulfate, filtered, and concentrated under reduced pressure. The residue was recrystallized from ethyl acetate/heptane to provide (R)-2-(2,2-dimethyl-5-oxo-1,3-dioxolan-4-yl)acetic acid (2.92 g, 50%) as an off-white solid: $^1$H NMR (300 MHz, DMSO-$d_6$) δ 4.72 (dd, J=6.6, 3.9 Hz, 1H), 3.01 (dd, J=17.4, 3.9 Hz, 1H), 2.86 (dd, J=17.4, 6.6 Hz, 1H), 1.63 (s, 3H), 1.58 (s, 3H), CO$_2$H proton not observed.

Preparation of (R)-tert-Butyl 2-(2,2-dimethyl-5-oxo-1,3-dioxolan-4-yl)acetate

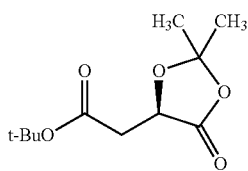 [SMILES: CC(C)(C)OC(=O)C[C@H]1OC(C)(C)OC1=O]

A solution of (R)-2-(2,2-dimethyl-5-oxo-1,3-dioxolan-4-yl)acetic acid (2.92 g, 16.8 mmol) and tert-butanol (1.86 g, 25.2 mmol) in methylene chloride (40 mL) was treated with N,N'-dicyclohexylcarbodiimide (4.16 g, 20.2 mmol) and 4-(dimethylamino)pyridine (616 mg, 5.04 mmol) and stirred at room temperature under a nitrogen atmosphere for 4 h. After this time, the reaction mixture was filtered to remove the solid dicyclohexylurea byproduct. The solid was washed with diethyl ether (100 mL), and the combined filtrate and washings were concentrated under reduced pressure. The crude residue was purified by column chromatography (80 g silica gel column, 0-30% ethyl acetate/heptane) to provide (R)-tert-butyl 2-(2,2-dimethyl-5-oxo-1,3-dioxolan-4-yl)acetate (3.19 g, 82%) as a white solid: $^1$H NMR (300 MHz, CDCl$_3$) δ 4.66 (dd, J=6.0, 3.9 Hz, 1H), 2.84 (dd, J=17.1, 4.2 Hz, 1H), 2.72 (dd, J=16.8, 6.3 Hz, 1H), 1.63 (s, 3H), 1.56 (s, 3H), 1.47 (s, 9H).

Preparation of (R)-4-(tert-Butoxy)-2-hydroxy-4-oxobutanoic acid

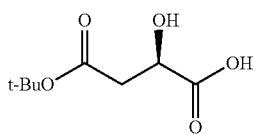 [SMILES: CC(C)(C)OC(=O)C[C@@H](O)C(=O)O]

A solution of (R)-tert-butyl 2-(2,2-dimethyl-5-oxo-1,3-dioxolan-4-yl)acetate (3.19 g, 13.9 mmol) in acetic acid (21 mL) and water (9 mL) was stirred at 60° C. for 4 h. After this time, the solvent was removed under reduced pressure. The residue was dried under vacuum to provide (R)-4-(tert-butoxy)-2-hydroxy-4-oxobutanoic acid (2.81 g) as a colorless oil: $^1$H NMR (300 MHz, DMSO-$d_6$) δ 4.48 (dd, J=5.7, 5.4 Hz, 1H), 2.83 (m, 2H), 1.48 (m, 9H), CO$_2$H and OH protons not observed.

Preparation of (R)-2-Acetoxy-4-(tert-butoxy)-4-oxobutanoic acid

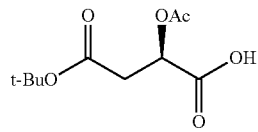 [SMILES: CC(=O)O[C@H](CC(=O)OC(C)(C)C)C(=O)O]

(R)-4-(tert-Butoxy)-2-hydroxy-4-oxobutanoic acid (2.81 g, 14.8 mmol), acetyl chloride (1.28 g, 16.3 mmol), N,N-diisopropylethylamine (5.74 g, 44.4 mmol), and methylene chloride (150 mL) were combined at 0° C. and then stirred at room temperature under a nitrogen atmosphere for 4 h. After this time, 10% aqueous citric acid (100 mL) was added. The organic layer was separated and extracted with methylene chloride (2×100 mL). The combined organics were washed with brine (50 mL), dried over sodium sulfate, filtered, and concentrated under reduced pressure to provide (R)-2-acetoxy-4-(tert-butoxy)-4-oxobutanoic acid (3.44 g) as a black oil, which was used without purification.

Preparation of (R)-Di-tert-butyl 2-acetoxysuccinate

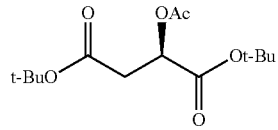 [SMILES: CC(=O)O[C@H](CC(=O)OC(C)(C)C)C(=O)OC(C)(C)C]

A solution of (R)-2-acetoxy-4-(tert-butoxy)-4-oxobutanoic acid (3.44 g, 14.8 mmol) and tert-butanol (2.41 g, 32.6 mmol) in methylene chloride (70 mL) was treated with N,N'-dicyclohexylcarbodiimide (3.69 g, 19.2 mmol) and 4-(dimethylamino)pyridine (597 mg, 4.88 mmol) and stirred at room temperature under a nitrogen atmosphere for 16 h. After this time, the reaction mixture was filtered to remove the solid dicyclohexylurea byproduct. The solid was washed with diethyl ether (100 mL), and the combined filtrate and washings were concentrated under reduced pressure. The crude residue was purified by column chromatography (80 g silica gel column, 0-30% ethyl acetate/heptane) to provide (R)-di-tert-butyl 2-acetoxysuccinate (1.70 g, 40%) as a colorless oil: $^1$H NMR (300 MHz, CDCl$_3$) δ 5.30 (dd, J=7.5, 5.4 Hz, 1H), 2.75 (m, 2H), 2.12 (s, 3H), 1.46 (s, 18H).

Preparation of (R)-Di-tert-butyl 2-hydroxysuccinate

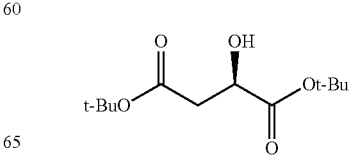

(R)-Di-tert-butyl 2-acetoxysuccinate (1.70 g, 5.90 mmol), potassium carbonate (2.44 g, 17.7 mmol), methanol (90 mL) and water (15 mL) were combined and stirred at 0° C. for 3 h. After this time, water (200 mL) was added, and the aqueous solution was extracted with methylene chloride (2×200 mL). The combined organics were washed with brine (50 mL), dried over sodium sulfate, filtered, and concentrated under reduced pressure to provide (R)-di-tert-butyl 2-hydroxysuccinate (1.16 g, 80%) as a white solid: $^1$H NMR (300 MHz, CDCl$_3$) δ 4.30 (dd, J=10.2, 5.7 Hz, 1H), 3.19 (d, J=5.4 Hz, 1H), 2.75-2.66 (m, 2H), 1.47 (s, 9H), 1.45 (s, 9H).

Preparation of (R)-4-((1,4-Di-tert-butoxy-1,4-dioxobutan-2-yl)oxy)-4-oxobutanoic acid

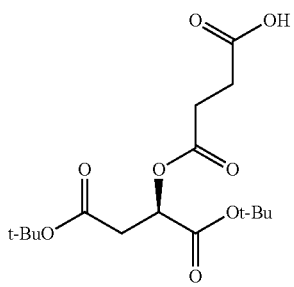 [SMILES: CC(C)(C)OC(=O)C[C@@H](OC(=O)CCC(=O)O)C(=O)OC(C)(C)C]

(R)-Di-tert-butyl 2-hydroxysuccinate (1.16 g, 4.71 mmol), dihydrofuran-2,5-dione (1.41 g, 14.1 mmol), N,N-diisopropylethylamine (1.82 g, 14.1 mmol), and methylene chloride (30 mL) were combined and stirred at room temperature under a nitrogen atmosphere for 16 h. After this time, 10% aqueous citric acid (100 mL) was added. The organic layer was separated and extracted with methylene chloride (2×50 mL). The combined organics were washed with brine (50 mL), dried over sodium sulfate, filtered, and concentrated under reduced pressure to provide (R)-4-((1,4-di-tert-butoxy-1,4-dioxobutan-2-yl)oxy)-4-oxobutanoic acid (2.05 g) as a brown oil: $^1$H NMR (300 MHz, CDCl$_3$) δ 5.32 (dd, J=7.5, 5.1 Hz, 1H), 2.77-2.66 (m, 6H), 1.45 (s, 18H), CO$_2$H proton not observed.

Preparation of (R)-Di-tert-butyl 2-((4-((2,5-dioxopyrrolidin-1-yl)oxy)-4-oxobutanoyl)oxy)succinate

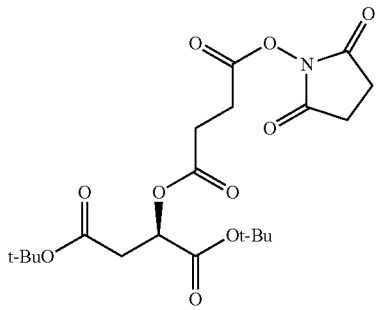 [SMILES: CC(C)(C)OC(=O)C[C@@H](OC(=O)CCC(=O)ON1C(=O)CCC1=O)C(=O)OC(C)(C)C]

A solution of (R)-4-((1,4-di-tert-butoxy-1,4-dioxobutan-2-yl)oxy)-4-oxobutanoic acid (2.05 g, 5.92 mmol) in tetrahydrofuran (60 mL) was treated with N-hydroxysuccinimide (681 mg, 5.92 mmol) and N,N'-dicyclohexylcarbodiimide (1.22 g, 5.92 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (R)-di-tert-butyl 2-((4-((2,5-dioxopyrrolidin-1-yl)oxy)-4-oxobutanoyl)oxy)succinate (2.75 g) as a brown oil: $^1$H NMR (300 MHz, CDCl$_3$) δ 5.34 (dd, J=6.9, 5.7 Hz, 1H), 3.01-2.96 (m, 2H), 2.87-2.70 (m, 8H), 1.45 (s, 18H).

Preparation of (R)-Di-tert-butyl 2-((4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinate

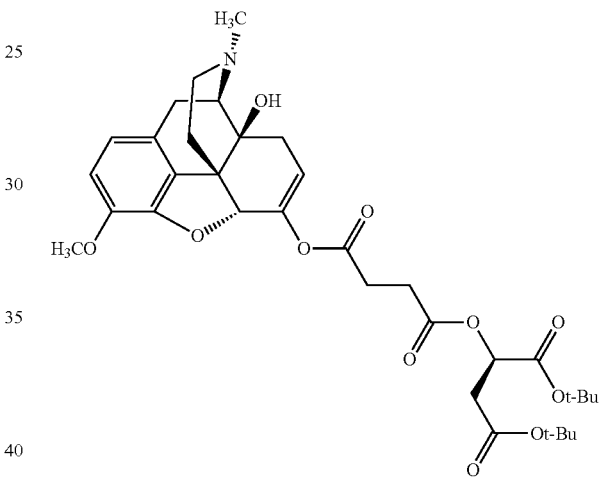

A suspension of oxycodone (500 mg, 1.59 mmol) in tetrahydrofuran (10 mL) was cooled to −50° C. and treated dropwise with a 1.0 M solution of potassium tert-butoxide in tetrahydrofuran (1.8 mL, 1.8 mmol). After addition was complete, the mixture was stirred at −50° C. for 45 min. The mixture was treated dropwise with a solution of (R)-di-tert-butyl 2-((4-((2,5-dioxopyrrolidin-1-yl)oxy)-4-oxobutanoyl)oxy)succinate (775 mg, 1.80 mmol) in tetrahydrofuran (8 mL). After addition was complete, the mixture was stirred at −50° C. for 30 min. After this time, the reaction mixture was treated with saturated aqueous ammonium chloride (20 mL) and extracted with ethyl acetate (3×20 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (R)-di-tert-butyl 2-((4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinate (144 mg, 15%) as a white solid: ESI MS m/z 644 [C$_{34}$H$_{45}$NO$_{11}$+H]$^+$.

485

Preparation of (R)-2-((4-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid

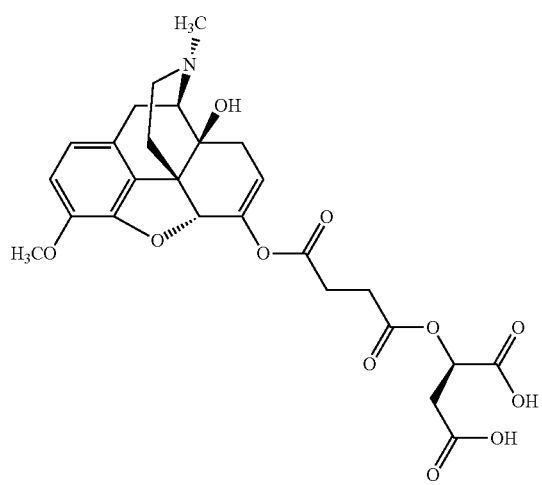

A solution of (R)-di-tert-butyl 2-((4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinate (144 mg, 0.220 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (R)-2-((4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid (102 mg, 86%) as a white solid: $^1$H NMR (300 MHz, DMSO-$d_6$) δ 6.81 (d, J=8.1 Hz, 1H), 6.70 (d, J=8.1 Hz, 1H), 5.53 (dd, J=5.7, 2.1 Hz, 1H), 5.09-5.06 (m, 1H), 4.93 (s, 1H), 3.74 (s, 3H), 3.28 (d, J=18.9 Hz, 1H), 2.83-2.61 (m, 9H), 2.37-2.13 (m, 6H), 2.02 (d, J=18 Hz, 1H), 1.52 (d, J=9.9 Hz, 1H), two $CO_2H$ and OH protons not observed; ESI MS m/z 530 $[C_{26}H_{29}NO_{11}+H]^+$; HPLC (Method A)>99% (AUC), $t_R$=7.64 min.

Scheme 59: (S)-2-(((S)-2-Hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoic acid

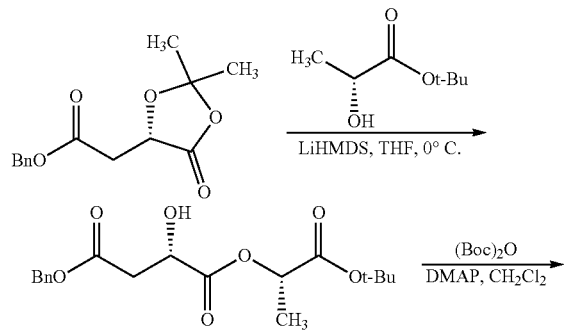

-continued

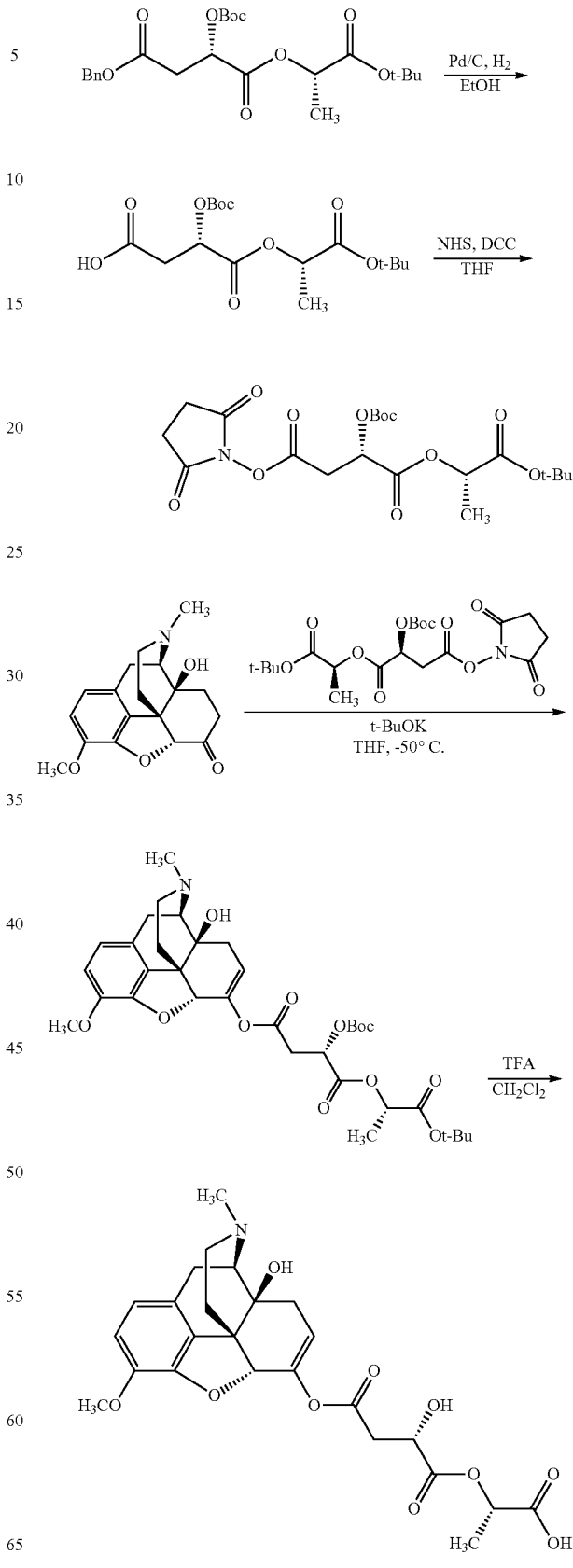

Preparation of (S)-4-Benzyl 1-((S)-1-(tert-butoxy)-1-oxopropan-2-yl) 2-hydroxysuccinate

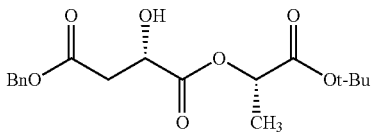

A solution of (S)-tert-butyl 2-hydroxypropanoate (1.11 g, 7.61 mmol) in tetrahydrofuran (15 mL) was cooled in an ice bath and treated dropwise with a 1.0 M solution of lithium bis(trimethylsilyl)amide in tetrahydrofuran (7.6 mL, 7.6 mmol). After addition was complete, the mixture was stirred at ambient temperature for 15 min. The mixture was re-cooled in the ice bath and treated dropwise with a solution of (S)-benzyl 2-(2,2-dimethyl-5-oxo-1,3-dioxolan-4-yl)acetate (2.01 g, 7.61 mmol) in tetrahydrofuran (10 mL). After addition was complete, the mixture was stirred at 0° C. for 4 h. After this time, the reaction mixture was treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (silica gel, 0-30% ethyl acetate/heptanes) to provide (S)-4-benzyl 1-((S)-1-(tert-butoxy)-1-oxopropan-2-yl) 2-hydroxysuccinate (0.89, 33%) as a colorless oil: $^1$H NMR (300 MHz, CDCl$_3$) δ 7.38-7.35 (m, 5H), 5.17 (d, J=1.0 Hz, 1H), 5.05 (dd, J=14.1, 8.4 Hz, 1H), 4.69-4.53 (m, 1H), 3.15 (dd, J=18.0, 6.0 Hz, 1H), 3.02 (dd, J=15.9, 3.9 Hz, 1H), 2.90-2.80 (m, 1H), 1.46 (d, J=8.1 Hz, 3H), 1.45 (s, 9H), OH proton not observed.

Preparation of (S)-4-Benzyl 1-((S)-1-(tert-butoxy)-1-oxopropan-2-yl) 2-((tert-butoxycarbonyl)oxy)succinate

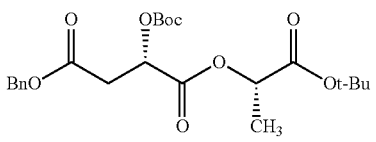

(S)-4-Benzyl 1-((S)-1-(tert-butoxy)-1-oxopropan-2-yl) 2-hydroxysuccinate (1.86 g, 5.28 mmol), di-tert-butyl dicarbonate (1.38 g, 6.34 mmol), and N,N-dimethylpyridin-4-amine (64 mg, 0.53 mmol) were combined and stirred in methylene chloride (60 mL) at ambient temperature for 3 h. After this time, the mixture was concentrated under reduced pressure. The crude residue was purified by column chromatography (silica gel, 0-30% ethyl acetate/heptanes) to provide (S)-4-benzyl 1-((S)-1-(tert-butoxy)-1-oxopropan-2-yl) 2-((tert-butoxycarbonyl)oxy)succinate (1.91 g, 80%) as a colorless oil: $^1$H NMR (300 MHz, CDCl$_3$) δ 7.38-7.33 (m, 5H), 5.41 (dd, J=9.6, 3.3 Hz, 1H), 5.21 (d, J=12.3 Hz, 1H), 5.13 (d, J=12.3 Hz, 1H), 5.02 (dd, J=14.1, 3.6 Hz, 1H), 3.12 (dd, J=17.8, 3.6 Hz, 1H), 2.95 (dd, J=18.1, 8.1 Hz, 1H), 1.49 (s, 9H), 1.45 (d, J=6.2 Hz, 3H), 1.44 (s, 9H).

Preparation of (S)-4-(((S)-1-(tert-Butoxy)-1-oxopropan-2-yl)oxy)-3-((tert-butoxycarbonyl)oxy)-4-oxobutanoic acid

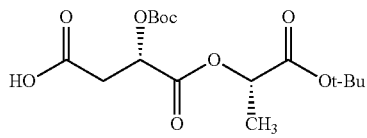

A solution of (S)-4-benzyl 1-((S)-1-(tert-butoxy)-1-oxopropan-2-yl) 2-((tert-butoxycarbonyl)oxy)succinate (0.27 g, 0.60 mmol) in ethyl alcohol (5 mL) was treated with palladium on carbon (10%, 30 mg). The mixture was stirred with under a hydrogen atmosphere at ambient temperature for 2 h. After this time, the reaction mixture was filtered and concentrated under reduced pressure to provide (S)-4-(((S)-1-(tert-butoxy)-1-oxopropan-2-yl)oxy)-3-((tert-butoxycarbonyl)oxy)-4-oxobutanoic acid (0.22 g, 99%) as a colorless oil: $^1$H NMR (300 MHz, CDCl$_3$) δ 5.38 (dd, J=9.3, 3.6 Hz, 1H), 5.05 (dd, J=14.1, 6.9 Hz, 1H), 3.13 (dd, J=17.1, 3.3 Hz, 1H), 2.95 (dd, J=17.1, 9.3 Hz, 1H), 1.50 (s, 9H), 1.47 (d, J=6.2 Hz, 3H), 1.46 (s, 9H), CO$_2$H proton not observed.

Preparation of (S)-1-((S)-1-(tert-Butoxy)-1-oxopropan-2-yl) 4-(2,5-dioxopyrrolidin-1-yl) 2-((tert-butoxycarbonyl)oxy)succinate

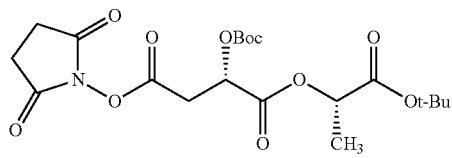

(S)-4-(((S)-1-(tert-Butoxy)-1-oxopropan-2-yl)oxy)-3-((tert-butoxycarbonyl)oxy)-4-oxobutanoic acid (0.21 g, 0.58 mmol), 1-hydroxypyrrolidine-2,5-dione (77 mg, 0.67 mmol) and dicyclohexylcarbodiimide (0.13 g, 0.64 mmol) were combined and stirred in tetrahydrofuran (4 mL) at ambient temperature for 4 h. After this time, the mixture was filtered and concentrated under reduced pressure to provide (S)-1-((S)-1-(tert-butoxy)-1-oxopropan-2-yl) 4-(2,5-dioxopyrrolidin-1-yl) 2-((tert-butoxycarbonyl)oxy)succinate (0.3 g, 99%) as a sticky solid: $^1$H NMR (300 MHz, CDCl$_3$) δ 5.45 (dd, J=9.6, 3.3 Hz, 1H), 5.05 (dd, J=14.1, 6.9 Hz, 1H), 3.46 (dd, J=17.1, 3.3 Hz, 1H), 3.18 (dd, J=17.1, 9.3 Hz, 1H), 2.87-2.82 (m, 4H), 1.50 (s, 9H), 1.47 (d, J=6.2 Hz, 3H), 1.46 (s, 9H).

489

Preparation of (S)-1-((S)-1-(tert-Butoxy)-1-oxopropan-2-yl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-((tert-butoxycarbonyl)oxy)succinate

490

Preparation of (S)-2-(((S)-2-Hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy) propanoic acid

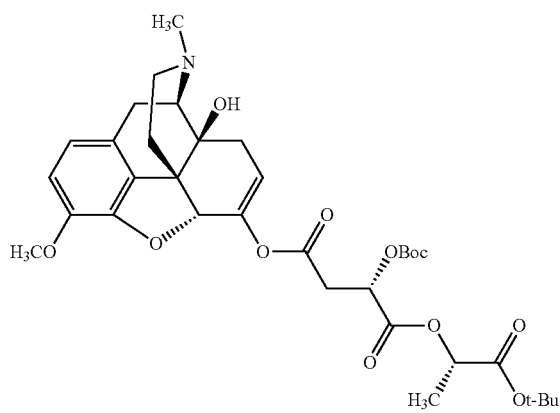

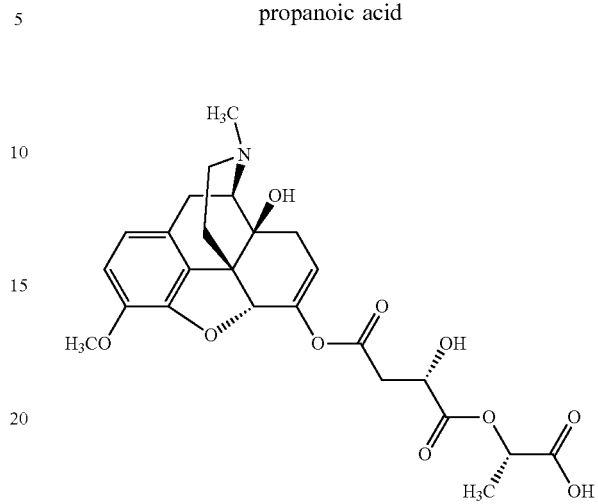

A suspension of oxycodone (500 mg, 1.59 mmol) in tetrahydrofuran (10 mL) was cooled to −50° C. and treated dropwise with a 1.0 M solution of potassium tert-butoxide in tetrahydrofuran (1.8 mL, 1.8 mmol). After addition was complete, the mixture was stirred at −50° C. for 45 min. The mixture was treated dropwise with a solution of (S)-1-((S)-1-(tert-butoxy)-1-oxopropan-2-yl) 4-(2,5-dioxopyrrolidin-1-yl) 2-((tert-butoxycarbonyl)oxy)succinate (800 mg, 1.8 mmol) in tetrahydrofuran (8 mL). After addition was complete, the mixture was stirred at −50° C. for 30 min. After this time, the reaction mixture was treated with saturated aqueous ammonium chloride (20 mL) and extracted with ethyl acetate (3×20 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (S)-1-((S)-1-(tert-butoxy)-1-oxopropan-2-yl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-((tert-butoxycarbonyl)oxy)succinate (77 mg, 7%) as a white solid: ESI MS m/z 660 $[C_{34}H_{45}NO_{12}+H]^+$.

A solution of (S)-1-((S)-1-(tert-butoxy)-1-oxopropan-2-yl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-((tert-butoxycarbonyl)oxy)succinate (77 mg, 0.12 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (S)-2-(((S)-2-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy) propanoic acid (34 mg, 58%) as a white solid: $^1$H NMR (300 MHz, DMSO-$d_6$) δ 6.75 (d, J=8.4 Hz, 1H), 6.66 (d, J=8.4 Hz, 1H), 5.91 (s, 1H), 5.52 (dd, J=5.7, 2.4 Hz, 1H), 4.95 (dd, J=13.8, 6.9 Hz, 1H), 4.86 (s, 1H), 4.49-4.47 (m, 1H), 3.74 (s, 3H), 3.13 (d, J=18.9 Hz, 1H), 2.97-2.89 (m, 2H), 2.69-2.61 (m, 2H), 2.46-2.42 (m, 1H), 2.28-2.22 (m, 2H), 2.12-2.00 (m, 4H), 1.42-1.38 (m, 4H), CO$_2$H and OH protons not observed; ESI MS m/z 504 $[C_{25}H_{29}NO_{10}+H]^+$; HPLC (Method A)>99% (AUC), $t_R$=7.58 min.

Scheme 60: (S)-1-tert-Butyl 4-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-acetoxysuccinate and (S)-2-Acetoxy-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxybutanic acid trifluoroacetic acid salt

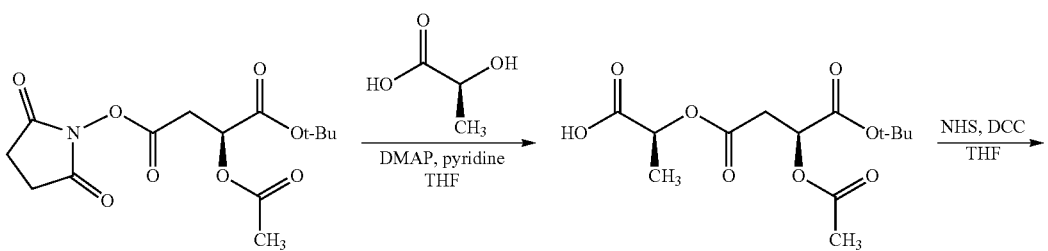

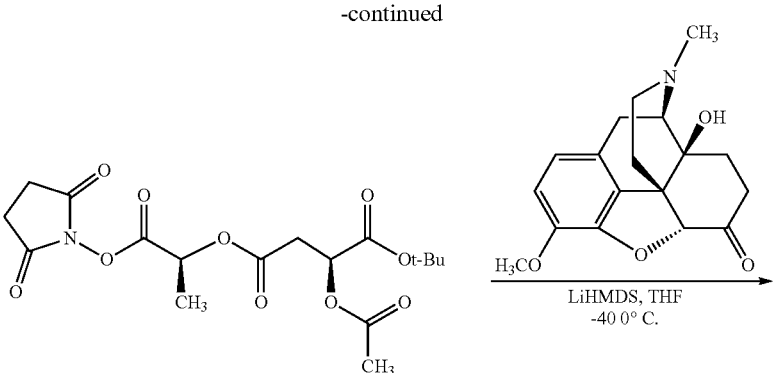

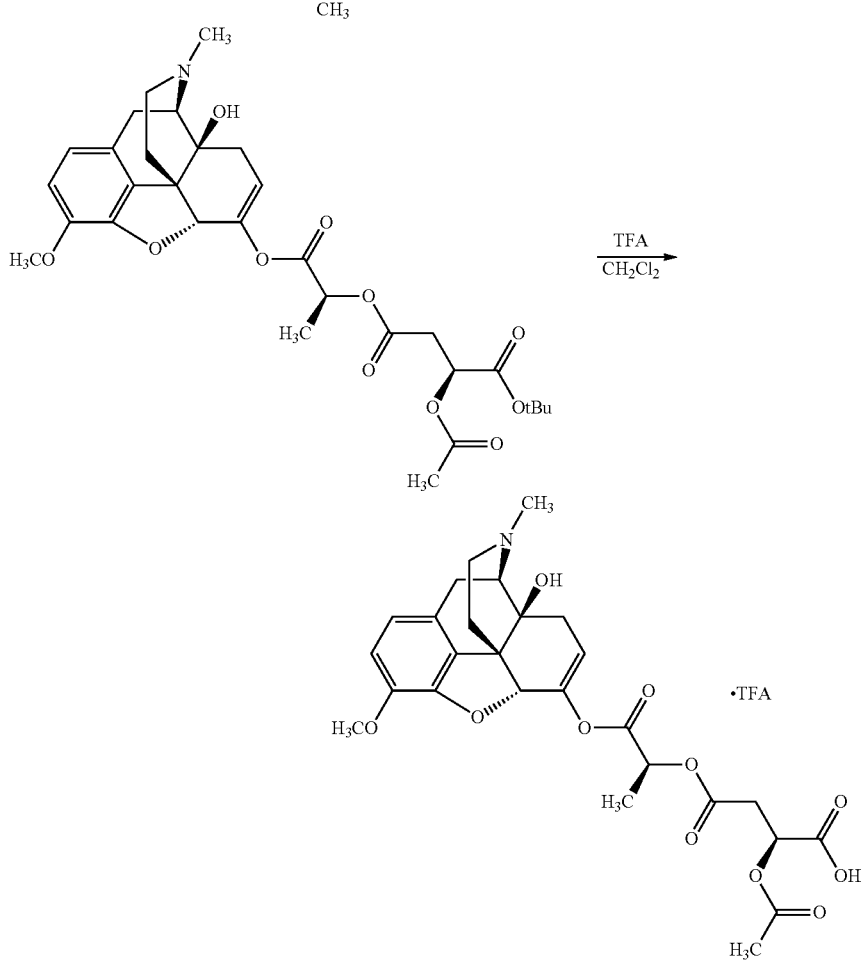

Preparation of (S)-2-(((S)-3-Acetoxy-4-(tert-butoxy)-4-oxobutanoyl)oxy)propanoic acid

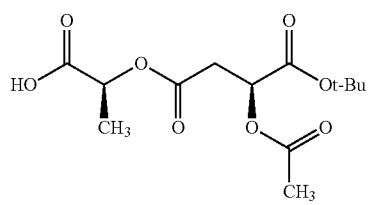 [SMILES: CC(=O)O[C@@H](CC(=O)O[C@@H](C)C(=O)O)C(=O)OC(C)(C)C]

A solution of (S)-1-tert-butyl 4-(2,5-dioxopyrrolidin-1-yl) 2-acetoxysuccinate (1.46 g, 4.44 mmol), lactic acid (447 mg, 4.96 mmol), and 4-dimethylaminopyridine (57 mg, 0.47 mmol) in tetrahydrofuran (30 mL) was treated with pyridine (0.72 g, 8.9 mmol) and heated at 50° C. under a nitrogen atmosphere for 48 h. After this time, the reaction mixture was cooled to room temperature and concentrated under reduced pressure. The residue was dissolved in ethyl acetate (50 mL) and washed with aqueous 10% citric acid (2×25 mL) and water (25 mL), dried over sodium sulfate, filtered, and concentrated under reduced pressure. The crude residue was purified by column chromatography (silica gel, 0-10% methanol/methylene chloride) to (S)-2-(((S)-3-acetoxy-4-(tert-butoxy)-4-oxobutanoyl)oxy)propanoic (455 mg, 34%) as a colorless oil: $^1$H NMR (300 MHz, DMSO-$d_6$) δ 13.07

(br s, 1H), 5.17 (dd, J=7.8, 4.8 Hz, 1H), 4.96 (q, J=6.9 Hz, 1H), 2.98-2.83 (m, 2H), 2.05 (s, 3H), 1.41 (s, 9H), 1.39 (d, J=6.9 Hz, 3H).

Preparation of (S)-1-tert-Butyl 4-((S)-1-((2,5-dioxopyrrolidin-1-yl)oxy)-1-oxopropan-2-yl) 2-acetoxysuccinate

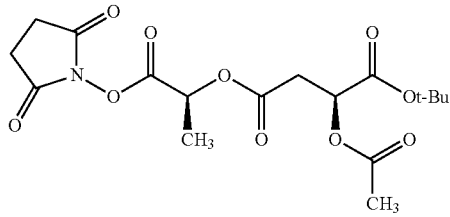 [SMILES: CC(=O)O[C@@H](CC(=O)O[C@@H](C)C(=O)ON1C(=O)CCC1=O)C(=O)OC(C)(C)C]

A solution of (S)-2-(((S)-3-acetoxy-4-(tert-butoxy)-4-oxobutanoyl)oxy)propanoic (450 mg, 1.48 mmol) in tetrahydrofuran (15 mL) was treated with N-hydroxysuccinimide (185 mg, 1.61 mmol) and N,N'-dicyclohexylcarbodiimide (338 mg, 1.64 mmol) and stirred under a nitrogen atmosphere for 7 h. After this time, the reaction mixture was filtered to remove the solid dicyclohexylurea byproduct. The solid was washed with diethyl ether, and the combined filtrate and washings were concentrated under reduced pressure to provide (S)-1-tert-butyl 4-((S)-1-((2,5-dioxopyrrolidin-1-yl)oxy)-1-oxopropan-2-yl) 2-acetoxysuccinate (703 mg, quantitative) as an off-white solid: $^1$H NMR (300 MHz, DMSO-$d_6$) δ 5.52 (q, J=6.9 Hz, 1H), 5.18 (dd, J=7.5, 5.1 Hz, 1H), 3.05-2.91 (m, 2H), 2.82 (br s, 4H), 2.05 (s, 3H), 1.56 (d, J=6.9 Hz, 3H), 1.41 (s, 9H).

Preparation of (S)-1-tert-Butyl 4-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-acetoxysuccinate A suspension of oxycodone (415 mg, 1.32 mmol) in tetrahydrofuran (6 mL) was cooled in an ice bath and treated dropwise with a 1.0 M solution of lithium bis(trimethylsilyl)amide in tetrahydrofuran (1.4 mL, 1.4 mmol). After stirring at 0° C. for 45 min, the ice bath was replaced with a dry ice/acetonitrile bath (−45° C.). The mixture was treated dropwise with a solution of (S)-1-tert-butyl 4-((S)-1-((2,5-dioxopyrrolidin-1-yl)oxy)-1-oxopropan-2-yl) 2-acetoxysuccinate (590 mg, 1.47 mmol) in tetrahydrofuran (7 mL) and stirred for 1 h. After this time, the dry ice/acetonitrile bath was replaced with a wet ice/brine bath, and the reaction mixture was treated with saturated aqueous ammonium chloride (50 mL) and extracted with ethyl acetate (2×50 mL). The combined organics were washed with saturated sodium bicarbonate (50 mL) and brine (50 mL), dried over sodium sulfate, filtered, and concentrated under reduced pressure. The crude residue was purified by reversed phase column chromatography (50 g C18 column, 10-100% acetonitrile/water) and freeze dried to provide (S)-1-tert-butyl 4-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-acetoxysuccinate (241 mg, 30%) as a fluffy white solid: $^1$H NMR (300 MHz, DMSO-$d_6$) δ 6.73 (d, J=8.4 Hz, 1H), 6.65 (d, J=8.1 Hz, 1H), 5.55 (dd, J=5.4, 2.4 Hz, 1H), 5.21-5.13 (m, 2H), 4.83 (s, 1H), 4.72 (s, 1H), 3.73 (s, 3H), 3.10 (d, J=18.6 Hz, 1H), 2.97-2.94 (m, 2H), 2.83 (d, J=6.0 Hz, 1H), 2.60 (dd, J=18.9, 6.0 Hz, 1H), 2.41 (dd, J=11.4, 3.9 Hz, 1H), 2.31 (s, 3H), 2.22 (dd, J=12.6, 4.8 Hz, 1H), 2.10-1.94 (m, 3H), 2.04 (s, 3H), 1.49 (d, J=6.9 Hz, 3H) 1.41 (s, 9H), 1.39 (d, J=12.3 Hz, 1H);ESI MS m/z 602 $[C_{31}H_{39}NO_{11}+H]^+$; HPLC (Method A) 96.6% (AUC), $t_R$=10.46 min.

Preparation of (S)-2-Acetoxy-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt

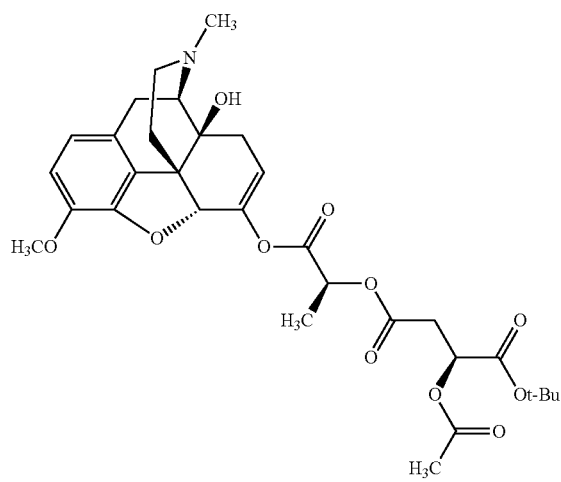 [SMILES: COc1ccc2c3c1O[C@H]1C(OC(=O)[C@H](C)OC(=O)C[C@H](OC(C)=O)C(=O)OC(C)(C)C)=CC[C@@]4(O)[C@@H](C2)N(C)CC[C@]314]

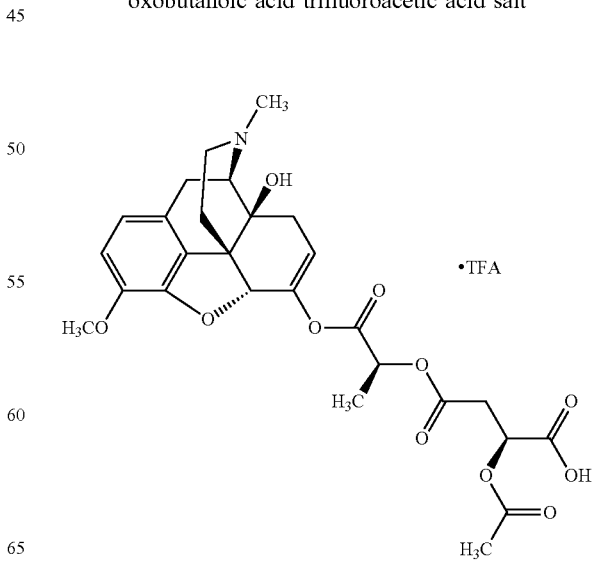

A solution of (S)-1-tert-butyl 4-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-acetoxysuccinate (196 mg, 0.326 mmol) in methylene chloride (4 mL) was treated with trifluoroacetic acid (1 mL) and stirred under a nitrogen atmosphere at ambient temperature for 5 h. After this time, the reaction mixture was concentrated under reduced pressure. The residue was purified by reversed phase column chromatography (C18 column, 10-100% acetonitrile/water with 0.1% trifluoroacetic acid) and freeze dried to provide (S)-2-acetoxy-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt (164 mg, 76%) as a fluffy white solid: $^1$H NMR (300 MHz, DMSO-$d_6$) δ 13.37 (br s, 1H), 9.18 (br s, 1H), 6.85 (d, J=8.4 Hz, 1H), 6.75 (d, J=8.4 Hz, 1H), 6.30 (s, 1H), 5.59 (dd, J=5.7, 1.8 Hz, 1H), 5.27 (dd, J=7.8, 4.5 Hz, 1H), 5.18 (q, J=7.2 Hz, 1H), 5.00 (s, 1H), 3.75 (s, 3H), 3.65 (d, J=6.3 Hz, 1H), 3.43 (d, J=19.8 Hz, 1H, partially obscured by water peak), 3.16-3.07 (m, 2H), 3.05-2.90 (m, 2H), 2.84 (apparent d, J=3.0 Hz, 3H), 2.66-2.55 (m, 1H), 2.49-2.43 (m, 1H, partially obscured by solvent peak), 2.34-2.26 (m, 1H), 2.10-2.04 (m, 1H), 2.04 (s, 3H), 1.65 (d, J=11.1 Hz, 1H), 1.50 (d, J=7.2 Hz, 3H); ESI MS m/z 546 $[C_{27}H_{31}NO_{11}+H]^+$; HPLC (Method A) 99.0% (AUC), $t_R$=8.48 min.

Scheme 61: (2R,3R)-2,3-Diacetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

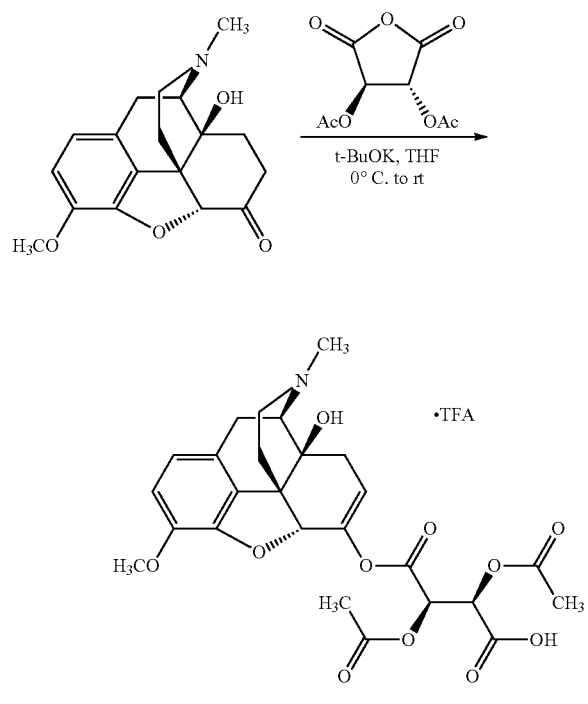

Preparation of (2R,3R)-2,3-Diacetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

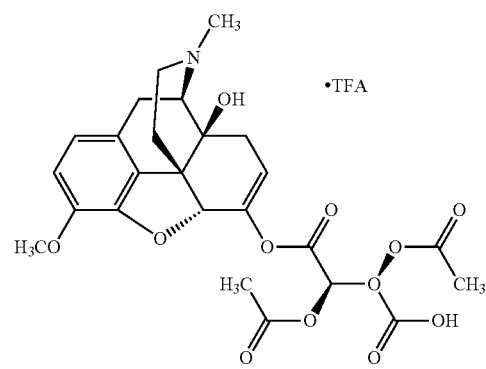

A suspension of oxycodone (252 mg, 0.799 mmol) in tetrahydrofuran (6 mL) was cooled in an ice bath and treated dropwise with a 1.0 M solution of potassium tert-butoxide in tetrahydrofuran (0.85 mL, 0.85 mmol). After stirring in the ice bath under a nitrogen atmosphere for 1 h, the mixture was treated with solid (3R,4R)-2,5-dioxotetrahydrofuran-3,4-diyl diacetate (268 mg, 1.24 mmol). After 30 min, the ice bath was removed, and the mixture was stirred at ambient temperature for 30 min. After this time, the reaction mixture was re-cooled in an ice bath, treated with a 1:1 mixture of trifluoroacetic acid/acetonitrile (0.5 mL), and concentrated under reduced pressure. The crude residue was purified by reversed phase column chromatography (50 g C18 column, 10-60% acetonitrile/water with 0.1% trifluoroacetic acid) and freeze dried to provide (2R,3R)-2,3-diacetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt (113 mg, 27%) as a white solid: $^1$H NMR (300 MHz, DMSO-$d_6$) δ 13.87 (br s, 1H), 9.17 (br s, 1H), 6.88 (d, J=8.4 Hz, 1H), 6.76 (d, J=8.4 Hz, 1H), 6.34 (s, 1H), 5.77 (d, J=3.0 Hz, 1H), 5.68 (d, J=3.0 Hz, 1H), 5.56 (dd, J=6.3, 2.1 Hz, 1H), 4.88 (s, 1H), 3.76 (s, 3H), 3.65 (d, J=6.3 Hz, 1H), 3.43 (d, J=20.1 Hz, 1H), 3.16-3.07 (m, 2H), 2.84 (apparent d, J=3.3 Hz, 3H), 2.64-2.57 (m, 1H), 2.49-2.43 (m, 1H, partially obscured by solvent peak), 2.33-2.25 (m, 1H), 2.18 (s, 3H), 2.14 (s, 3H), 2.11-2.05 (m, 1H), 1.65 (d, J=11.4 Hz, 1H); ESI MS m/z 532 $[C_{26}H_{29}NO_1+H]^+$; HPLC (Method A) 94.2% (AUC), $t_R$=7.90 min.

Scheme 62: (S)-3-Acetoxy-4-((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoroacetic acid salt
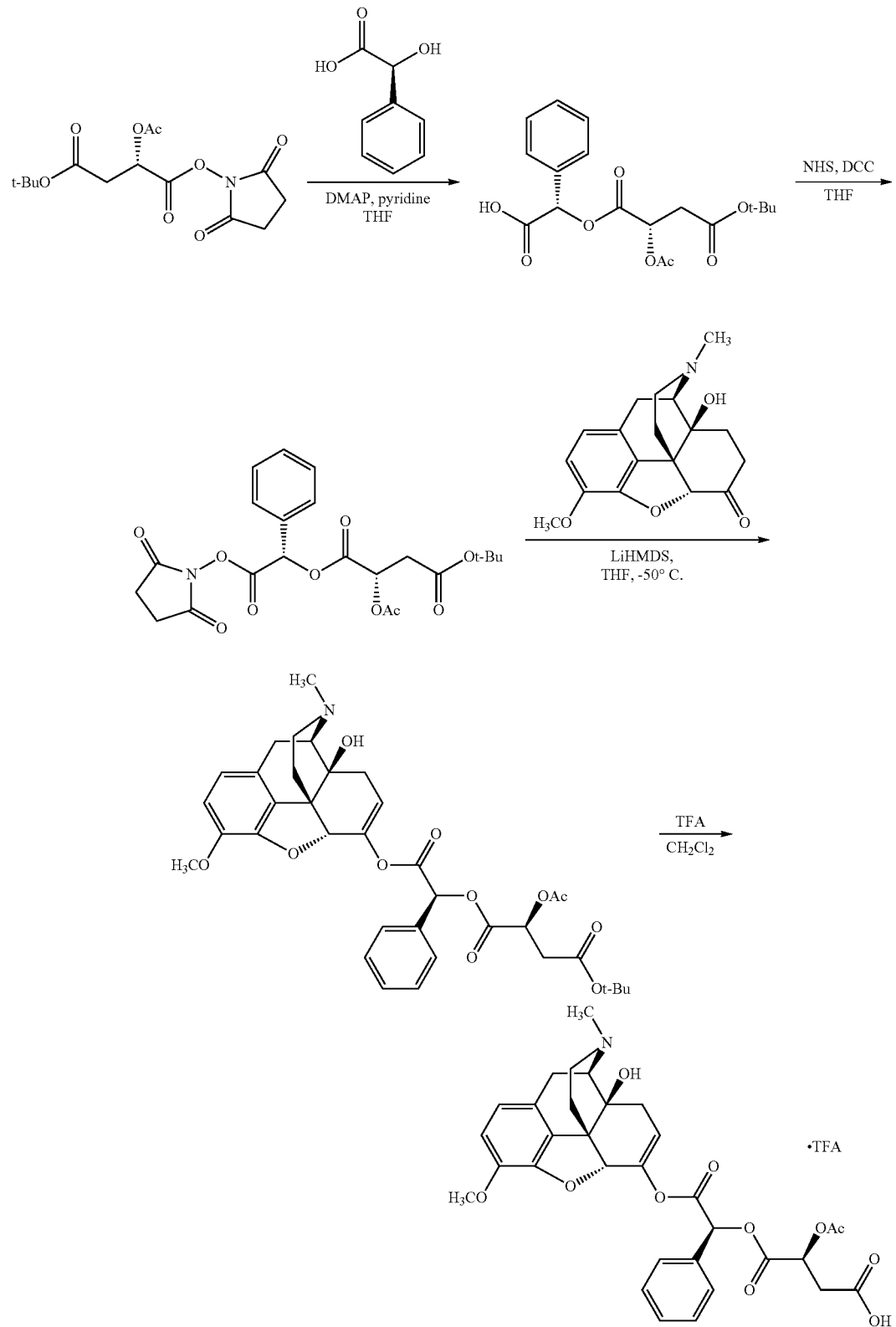

Preparation of (S)-2-(((S)-2-Acetoxy-4-(tert-butoxy)-4-oxobutanoyl)oxy)-2-phenylacetic acid

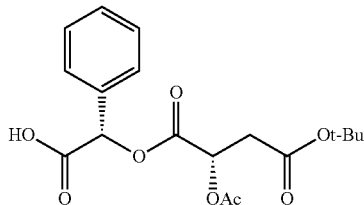 [SMILES: CC(=O)O[C@@H](CC(=O)OC(C)(C)C)C(=O)O[C@H](C(=O)O)c1ccccc1]

(S)-Mandelic acid (770 mg, 5.06 mmol), (S)-4-tert-butyl 1-(2,5-dioxopyrrolidin-1-yl) 2-acetoxysuccinate (2.00 g, 6.07 mmol), 4-(dimethylamino)pyridine (62 mg, 0.506 mmol), pyridine (480 mg, 6.07 mmol) and tetrahydrofuran (34 mL) were combined and heated at 60° C. under a nitrogen atmosphere for 24 h. After this time, the solvent was removed under reduced pressure, and the residue was participated between ethyl acetate (20 mL) and 10% aqueous citric acid. The organic layer was separated and extracted with saturated aqueous sodium bicarbonate (20 ml). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (S)-2-(((S)-2-acetoxy-4-(tert-butoxy)-4-oxobutanoyl)oxy)-2-phenylacetic acid (754 mg, 41%) as a colorless oil: $^1$H NMR (300 MHz, CDCl$_3$) δ 7.48-7.39 (m, 5H), 6.03 (s, 1H), 5.54 (m, 1H), 3.01-2.76 (m, 2H), 2.13 (s, 3H), 1.45 (s, 9H), CO$_2$H proton not observed.

Preparation of (S)-4-tert-Butyl 1-((S)-2-((2,5-dioxopyrrolidin-1-yl)oxy)-2-oxo-1-phenylethyl) 2-acetoxysuccinate

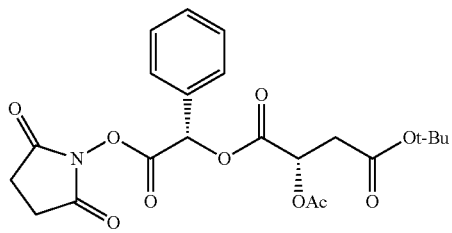 [SMILES: CC(=O)O[C@@H](CC(=O)OC(C)(C)C)C(=O)O[C@H](C(=O)ON1C(=O)CCC1=O)c1ccccc1]

A solution of (S)-2-(((S)-2-acetoxy-4-(tert-butoxy)-4-oxobutanoyl)oxy)-2-phenylacetic acid (754 mg, 2.06 mmol) in tetrahydrofuran (15 mL) was treated with N-hydroxysuccinimide (260 mg, 2.26 mmol) and N,N'-dicyclohexylcarbodiimide (466 mg, 2.26 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-4-tert-butyl 1-((S)-2-((2,5-dioxopyrrolidin-1-yl)oxy)-2-oxo-1-phenylethyl) 2-acetoxysuccinate (930 mg) as a yellow oil: $^1$H NMR (300 MHz, CDCl$_3$) δ 7.55-7.43 (m, 5H), 6.39 (s, 1H), 5.53 (m, 1H), 2.98-2.76 (m, 6H), 2.15 (s, 3H), 1.46 (s, 9H).

Preparation of (S)-4-tert-Butyl 1-((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl) 2-acetoxysuccinate

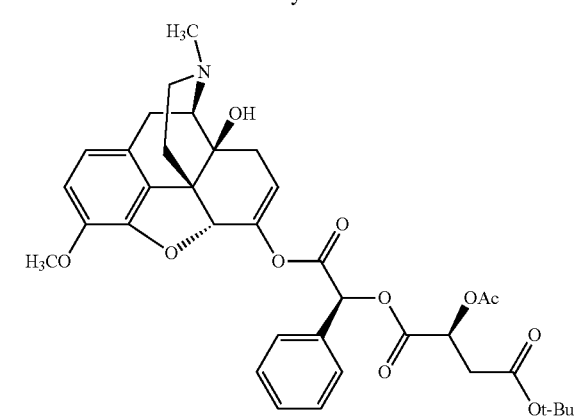

A suspension of oxycodone (286 mg, 1.59 mmol) in tetrahydrofuran (10 mL) was cooled to −50° C. and treated dropwise with a 1.0 M solution of potassium tert-butoxide in tetrahydrofuran (1.0 mL, 1.0 mmol). After addition was complete, the mixture was stirred at −50° C. for 45 min. The mixture was treated dropwise with a solution of (S)-4-tert-butyl 1-((S)-2-((2,5-dioxopyrrolidin-1-yl)oxy)-2-oxo-1-phenylethyl) 2-acetoxysuccinate (0.47 g, 1.0 mmol) in tetrahydrofuran (8 mL). After addition was complete, the mixture was stirred at −50° C. for 30 min. After this time, the reaction mixture was treated with saturated aqueous ammonium chloride (20 mL) and extracted with ethyl acetate (3×20 mL). The combined organics were dried over sodium sulfate, filtered, and concentrated under reduced pressure. The crude residue was purified by column chromatography (50 g C18 column, 10-100% acetonitrile/water) and freeze dried to provide (S)-4-tert-butyl 1-((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl) 2-acetoxysuccinate (89 mg, 15%) as a white solid: ESI MS m/z 602 [C36H$_{41}$NO$_{11}$+H]$^+$.

Preparation of (S)-3-Acetoxy-4-((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoroacetic acid salt

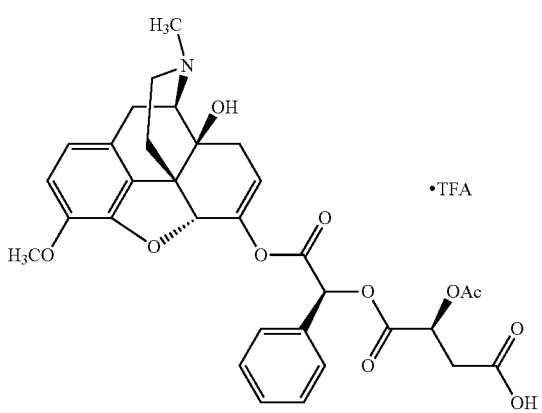 [SMILES: COc1ccc2c3c1O[C@H]1C(OC(=O)[C@@H](OC(=O)[C@H](CC(=O)O)OC(C)=O)c4ccccc4)=CC[C@@]4(O)[C@@H](C2)N(C)CC[C@]314]

A solution of (S)-4-tert-butyl 1-((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl) 2-acetoxysuccinate (89 mg, 0.13 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (S)-3-acetoxy-4-((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoroacetic acid salt (45 mg, 57%) as a white solid: $^1$H NMR (300 MHz, DMSO-d6; Mixture of diastereomers) δ 7.58-7.53 (m, 2H), 7.48-7.44 (m, 3H), 6.75-6.71 (m, 0.8H), 6.69-6.64 (m, 1.2H), 6.21 (s, 0.4H), 6.12 (s, 0.6H), 5.53-5.47 (m, 0.8H), 5.45-5.43 (m, 1.2H), 4.81 (s, 0.6H), 4.78 (s, 0.4H), 3.70 (s, 1.8H), 3.60 (s, 1.2H), 3.12 (d, J=18.3 Hz, 1H), 3.00-3.72 (m, 5H), 2.46-2.42 (m, 1H), 2.35 (s, 3H), 2.28-1.99 (m, 6H), 1.38 (d, J=12.6 Hz, 1H), CO$_2$H, CF$_3$CO$_2$H, and OH protons not observed; ESI MS m/z 608 [C$_{32}$H$_{33}$NO$_{11}$+H]$^+$; HPLC (Method A) 90.7% (AUC), $t_R$=9.40 min.

Scheme 63: (S)-2-(((S)-2-Acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt

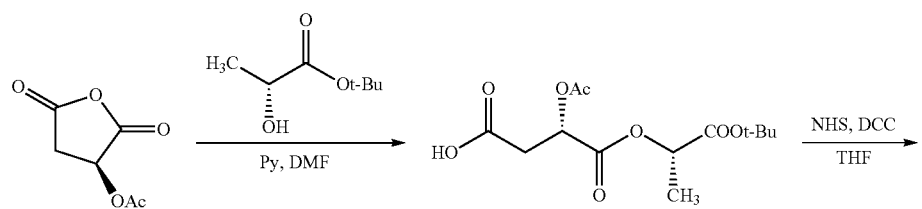

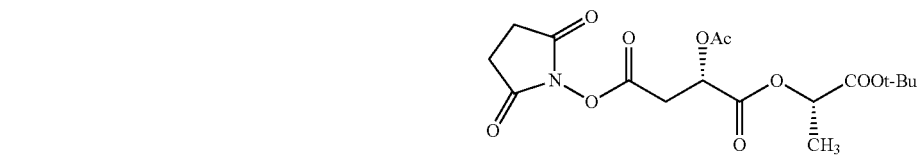

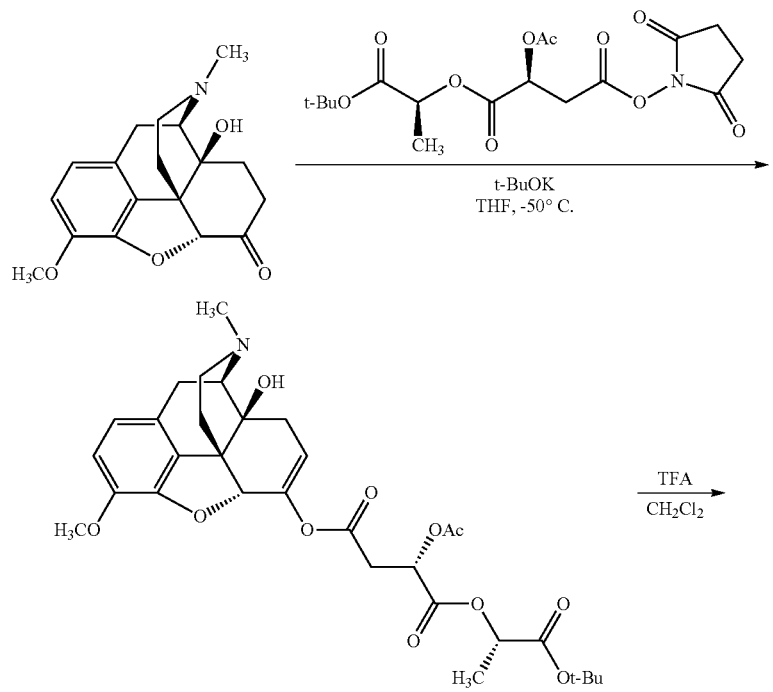

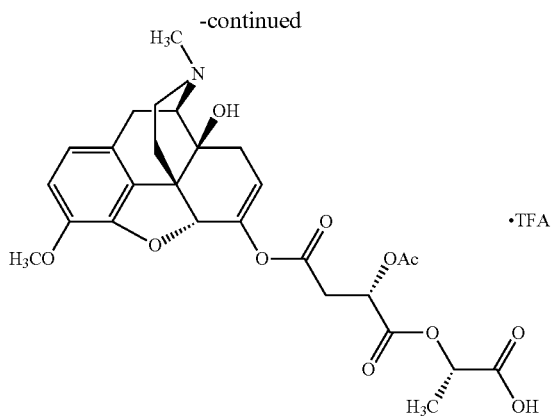

Preparation of (S)-3-acetoxy-4-(((S)-1-(tert-butoxy)-1-oxopropan-2-yl)oxy)-4-oxobutanoic acid

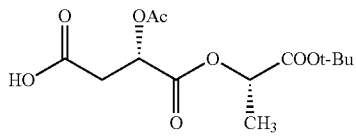

A solution of (S)-2,5-dioxotetrahydrofuran-3-yl acetate (0.70 g, 3.4 mmol) and (S)-tert-butyl 2-hydroxypropanoate (0.50 g, 3.4 mmol) in N,N-dimethylformamide (4 mL) was cooled in an ice bath and treated with pyridine (0.36 mL, 4.4 mmol). After addition was complete, the mixture was stirred at ambient temperature for 16 h. After this time, the mixture was diluted with water (20 mL) and extracted with ethyl acetate (2×20 mL). The combined organics were washed with brine (50 mL), dried over sodium sulfate, filtered, and concentrated under reduced pressure to provide (S)-3-acetoxy-4-(((S)-1-(tert-butoxy)-1-oxopropan-2-yl)oxy)-4-oxobutanoic acid (0.6 g, 58%) as a brown oil: $^1$H NMR (300 MHz, CDCl$_3$) $^1$H NMR (300 MHz, CDCl$_3$) δ 5.49 (dd, J=9.3, 3.3 Hz, 1H), 5.03 (dd, J=14.1, 6.9 Hz, 1H), 3.13 (dd, J=17.1, 3.3 Hz, 1H), 2.95 (dd, J=17.1, 9.3 Hz, 1H), 2.13 (s, 3H), 1.48 (d, J=7.2 Hz, 3H), 1.46 (s, 9H), CO$_2$H proton not observed.

Preparation of (S)-1-((S)-1-(tert-Butoxy)-1-oxopropan-2-yl) 4-(2,5-dioxopyrrolidin-1-yl) 2-acetoxsuccinate

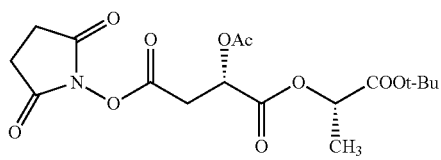

(S)-3-Acetoxy-4-(((S)-1-(tert-butoxy)-1-oxopropan-2-yl)oxy)-4-oxobutanoic acid (1.8 g, 6.01 mmol), 1-hydroxypyrrolidine-2,5-dione (0.81 g, 7.0 mmol) and dicyclohexylcarbodiimide (1.36 g, 6.61 mmol) were combined and stirred in tetrahydrofuran (40 mL) at ambient temperature for 4 h. After this time, the mixture was filtered and concentrated under reduced pressure to provide (S)-1-((S)-1-(tert-butoxy)-1-oxopropan-2-yl) 4-(2,5-dioxopyrrolidin-1-yl) 2-acetoxysuccinate (2.64 g, 99%) as a sticky solid: $^1$H NMR (300 MHz, DMSO-d$_6$) δ 5.50 (dd, J=8.7, 4.2 Hz, 1H), 5.00 (dd, J=14.1, 6.9 Hz, 1H), 3.40 (dd, J=17.1, 3.3 Hz, 1H), 3.30 (dd, J=17.1, 9.3 Hz, 1H), 2.77 (s, 4H), 2.10 (s, 3H), 1.46 (d, J=6.9 Hz, 3H), 1.41 (s, 9H).

Preparation of (S)-1-((S)-1-(tert-Butoxy)-1-oxopropan-2-yl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-acetoxysuccinate

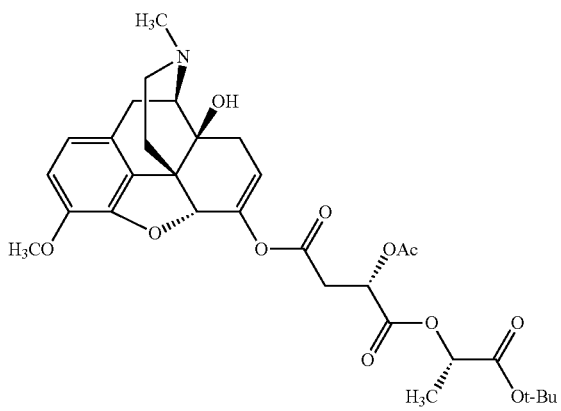 [SMILES: COc1ccc2c3c1O[C@H]1C(OC(=O)C[C@H](OC(C)=O)C(=O)O[C@@H](C)C(=O)OC(C)(C)C)=CC[C@@]4(O)[C@@H](C2)N(C)CC[C@]314]

A suspension of oxycodone (500 mg, 1.59 mmol) in tetrahydrofuran (10 mL) was cooled to −50° C. and treated dropwise with a 1.0 M solution of potassium tert-butoxide in tetrahydrofuran (1.8 mL, 1.8 mmol). After addition was complete, the mixture was stirred at −50° C. for 45 min. The mixture was treated dropwise with a solution of (S)-1-((S)-1-(tert-butoxy)-1-oxopropan-2-yl) 1-(2,5-dioxopyrrolidin-1-yl) 2-acetoxysuccinate (700 mg, 1.81 mmol) in tetrahydrofuran (8 mL). After addition was complete, the mixture was stirred at −50° C. for 30 min. After this time, the reaction mixture was treated with saturated aqueous ammonium chloride (20 mL) and extracted with ethyl acetate (3×20 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (S)-1-((S)-1-(tert-butoxy)-1-oxopropan-2-yl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-acetoxysuccinate (110 mg, 11%) as a white solid: ESI MS m/z 602 [C$_{31}$H$_{39}$NO$_{11}$+H]$^+$.

Preparation of (S)-2-(((S)-2-Acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy) propanoic acid trifluoroacetic acid salt

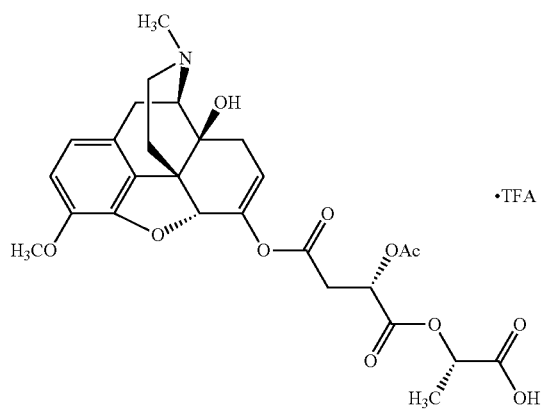 [SMILES: COc1ccc2c3c1O[C@H]1C(OC(=O)C[C@H](OC(C)=O)C(=O)O[C@@H](C)C(=O)O)=CC[C@@]4(O)[C@@H](C2)N(C)CC[C@]314]

A solution of (S)-1-((S)-1-(tert-butoxy)-1-oxopropan-2-yl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-acetoxysuccinate (110 mg, 0.171 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (S)-2-(((S)-2-acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt (66 mg, 71%) as a white solid: $^1$H NMR (300 MHz, DMSO-$d_6$) δ 6.81 (d, J=8.4 Hz, 1H), 6.71 (d, J=8.4 Hz, 1H), 5.57 (dd, J=5.7, 2.1 Hz, 1H), 5.39 (dd, J=9.6, 3.2 Hz, 1H), 5.04 (dd, J=14.1, 6.9 Hz, 1H), 4.95 (s, 1H), 3.73 (s, 3H), 3.29-3.26 (m, 1H), 3.17 (d, J=17.1 Hz, 1H), 3.00-2.72 (m, 3H), 2.64-2.62 (m, 3H), 2.39-2.37 (m, 3H), 2.22-2.00 (m, 2H), 2.11 (s, 3H), 1.53 (d, J=9.9 Hz, 1H), 1.43 (d, J=6.9 Hz, 3H), $CO_2H$, $CF_3CO_2H$, and OH protons not observed; ESI MS m/z 546 $[C_{27}H_{31}NO_{11}+H]^+$.

Scheme 64: (S)-2-(((S)-2-Acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt

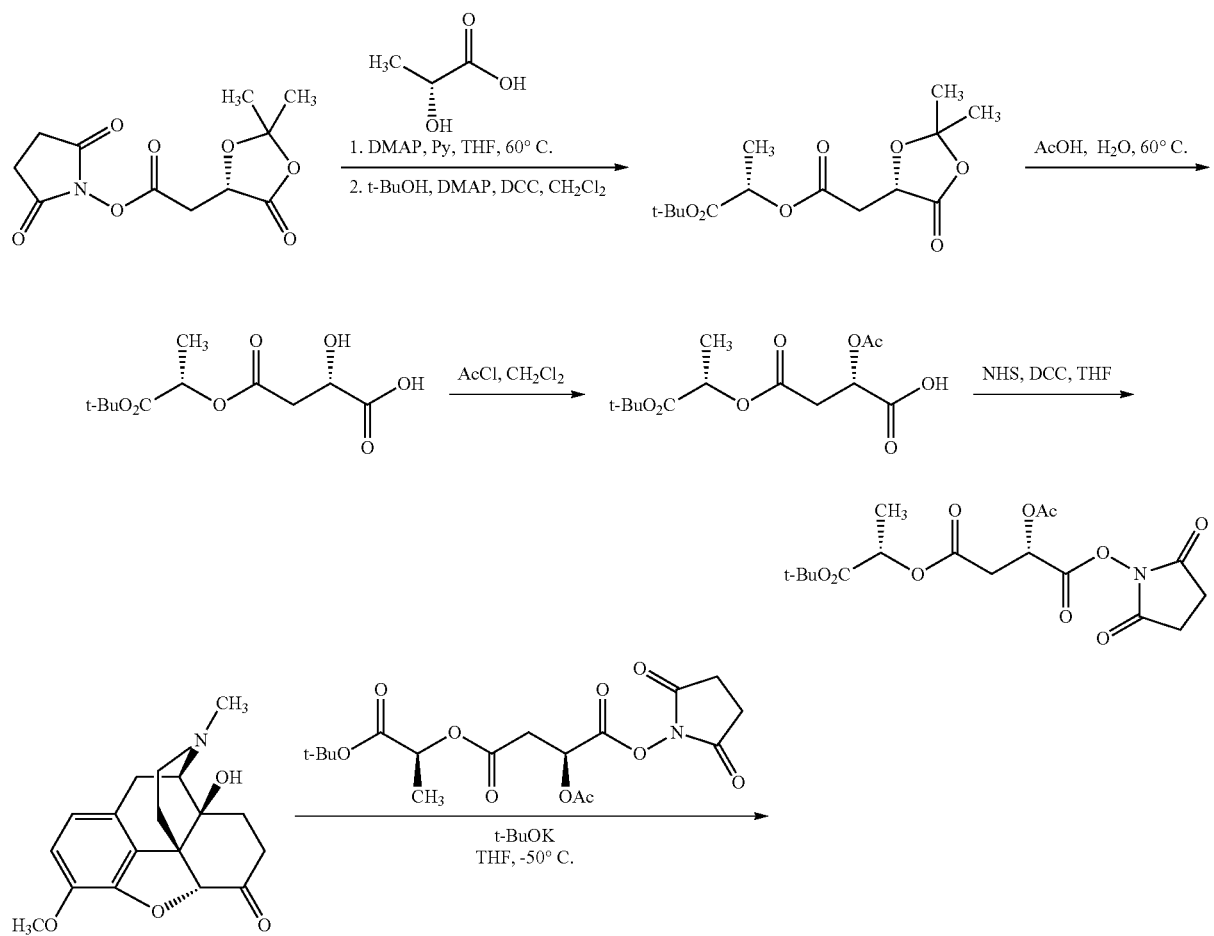

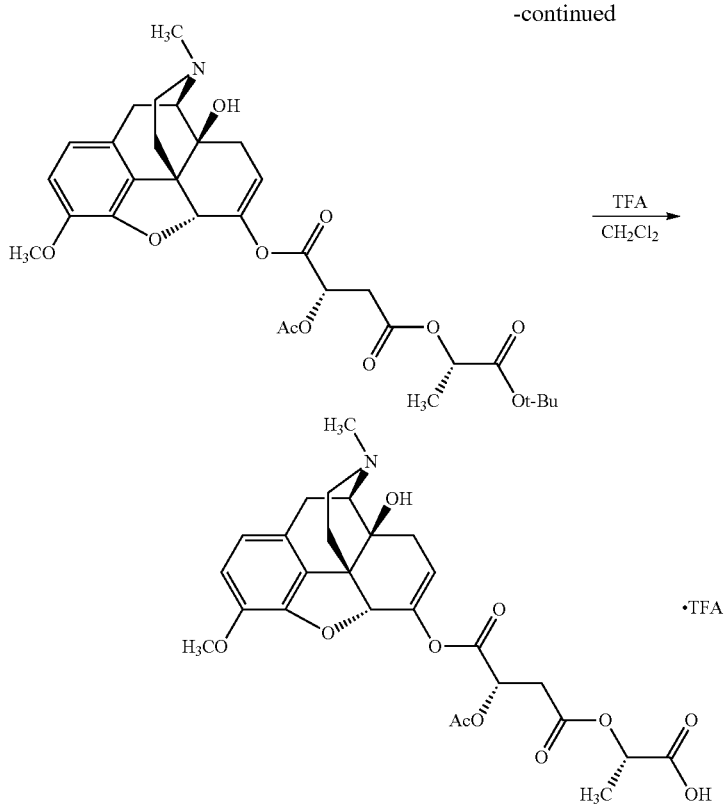

Preparation of (S)-tert-Butyl 2-(2-((S)-2,2-dimethyl-5-oxo-1,3-dioxolan-4-yl)acetoxy)propanoate

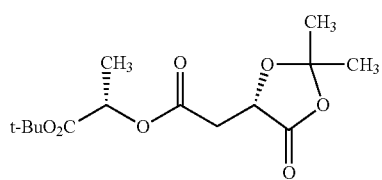

(S)-2,5-dioxopyrrolidin-1-yl 2-(2,2-dimethyl-5-oxo-1,3-dioxolan-4-yl)acetate (3.0 g, 11 mmol), (S)-lactic acid (1.0 g, 11 mmol), N,N-dimethylpyridin-4-amine (0.13 g, 0.11 mmol) and pyridine (1.16 mL, 12.5 mmol) were combined in tetrahydrofuran (50 mL) and heated at 60° C. for 72 h. After this time, the reaction mixture was treated with saturated aqueous ammonium chloride (10 mL) and extracted with ethyl acetate (2×25 mL). The combined organics were dried over sodium sulfate, filtered, and concentrated under reduced pressure to provide (S)-2-(2-((S)-2,2-dimethyl-5-oxo-1,3-dioxolan-4-yl)acetoxy)propanoic acid (2.0 g, 99%) as a yellow oil.

(S)-2-(2-((S)-2,2-Dimethyl-5-oxo-1,3-dioxolan-4-yl)acetoxy)propanoic acid (2.0 g, 8.1 mmol), tert-butyl alcohol (0.90 g, 12 mmol), N,N-dimethylpyridin-4-amine (0.30 g, 2.4 mmol) and dicyclohexylcarbodiimide (2.0 g, 9.7 mmol) were combined and stirred in methylene chloride (60 mL) at ambient temperature for 16 h. After this time, the mixture was concentrated under reduced pressure. The crude residue was purified by column chromatography (silica gel, 0-30% ethyl acetate/heptanes) to provide (S)-tert-butyl 2-(2-((S)-2,2-dimethyl-5-oxo-1,3-dioxolan-4-yl)acetoxy)propanoate (0.4 g, 16%) as a colorless oil: $^1$H NMR (300 MHz, CDCl$_3$) δ 4.99 (dd, J=14.1, 6.9 Hz, 1H), 4.74 (dd, J=6.6, 3.6 Hz, 1H), 3.04 (dd, J=17.4, 3.6 Hz, 1H), 2.84 (dd, J=14.1, 6.6 Hz, 1H), 1.62 (s, 3H), 1.56 (s, 3H), 1.47 (d, J=7.2 Hz, 3H), 1.46 (s, 9H).

Preparation of (S)-4-(((S)-1-(tert-Butoxy)-1-oxopropan-2-yl)oxy)-2-hydroxy-4-oxobutanoic acid

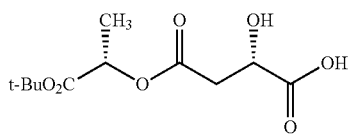

A solution of (S)-tert-butyl 2-(2-((S)-2,2-dimethyl-5-oxo-1,3-dioxolan-4-yl)acetoxy)propanoate (0.50 g, 1.7 mmol), acetic acid (3 mL) and water (1 mL) was heated at 60° C. for 1 h. After this time, the mixture was concentrated under reduced pressure. The residue was diluted with toluene and concentrated under reduced pressure to provide (S)-4-(((S)-1-(tert-butoxy)-1-oxopropan-2-yl)oxy)-2-hydroxy-4-oxobutanoic acid (0.5 g, 99%) as a colorless oil: $^1$H NMR (300 MHz, DMSO-d$_6$) δ 12.6 (s, 1H), 5.51 (s, 1H), 4.82 (dd, J=14.1, 6.9 Hz, 1H), 4.31-4.30 (m, 1H), 2.72 (dd, J=15.9, 4.5 Hz, 1H), 2.60 (dd, J=15.9, 7.8 Hz, 1H), 1.40 (s, 9H), 1.36 (d, J=7.2 Hz, 3H).

Preparation of (S)-2-Acetoxy-4-(((S)-1-(tert-butoxy)-1-oxopropan-2-yl)oxy)-4-oxobutanoic acid

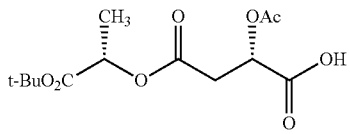

A solution of (S)-4-(((S)-1-(tert-butoxy)-1-oxopropan-2-yl)oxy)-2-hydroxy-4-oxobutanoic acid (0.43 g, 1.6 mmol) in methylene chloride (3 mL) in a cold bath was treated dropwise with acetyl chloride (0.13 mL, 1.8 mmol) and stirred at ambient temperature for 16 h. After this time, the mixture was concentrated under reduced pressure to provide (S)-2-acetoxy-4-(((S)-1-(tert-butoxy)-1-oxopropan-2-yl)oxy)-4-oxobutanoic acid (0.6 g, 99%) as a clear oil: $^1$H NMR (300 MHz, DMSO-$d_6$) δ 13.3 (s, 1H), 5.25 (dd, J=7.8, 4.8 Hz, 1H), 4.89 (dd, J=14.1, 7.2 Hz, 1H), 2.97-2.89 (m, 2H), 2.05 (s, 3H), 1.40 (s, 9H), 1.37 (d, J=6.9 Hz, 3H).

Preparation of (S)-4-((S)-1-(tert-Butoxy)-1-oxopropan-2-yl) 1-(2,5-dioxopyrrolidin-1-yl) 2-acetoxysuccinate

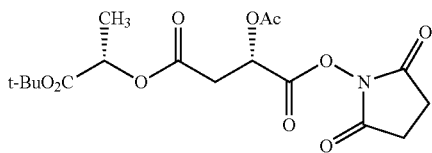

(S)-2-acetoxy-4-(((S)-1-(tert-butoxy)-1-oxopropan-2-yl)oxy)-4-oxobutanoic acid (0.50 g, 1.6 mmol), 1-hydroxypyrrolidine-2,5-dione (0.22 g, 1.9 mmol) and dicyclohexylcarbodiimide (0.37 g, 1.8 mmol) were combined and stirred in tetrahydrofuran (10 mL) at ambient temperature for 4 h. After this time, the mixture was filtered and concentrated under reduced pressure to provide (S)-1-((S)-1-(tert-butoxy)-1-oxopropan-2-yl) 4-(2,5-dioxopyrrolidin-1-yl) 2-((tert-butoxycarbonyl)oxy)succinate (0.3 g, 99%) as a sticky oil: $^1$H NMR (300 MHz, DMSO-$d_6$) δ 5.76 (dd, J=7.8, 4.8 Hz, 1H), 4.90 (dd, J=14.1, 7.2 Hz, 1H), 3.21-3.12 (m, 2H), 2.82 (s, 4H), 2.12 (s, 3H), 1.41 (s, 9H), 1.38 (d, J=6.9 Hz, 3H).

Preparation of (S)-4-((S)-1-(tert-Butoxy)-1-oxopropan-2-yl) 1-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-acetoxysuccinate

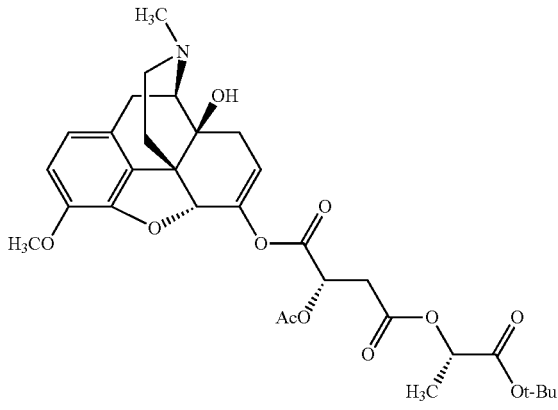 [SMILES: COc1ccc2c3c1O[C@H]1C(OC(=O)[C@H](CC(=O)O[C@@H](C)C(=O)OC(C)(C)C)OC(C)=O)=CC[C@@]4(O)[C@@H](C2)N(C)CC[C@]314]

A suspension of oxycodone (470 mg, 1.59 mmol) in tetrahydrofuran (10 mL) was cooled to −50° C. and treated dropwise with a 1.0 M solution of potassium tert-butoxide in tetrahydrofuran (1.7 mL, 1.7 mmol). After addition was complete, the mixture was stirred at −50° C. for 45 min. The mixture was treated dropwise with a solution of (S)-4-((S)-1-(tert-butoxy)-1-oxopropan-2-yl) 1-(2,5-dioxopyrrolidin-1-yl) 2-acetoxysuccinate (775 mg, 1.80 mmol) in tetrahydrofuran (8 mL). After addition was complete, the mixture was stirred at −50° C. for 30 min. After this time, the reaction mixture was treated with saturated aqueous ammonium chloride (20 mL) and extracted with ethyl acetate (3×20 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (S)-4-((S)-1-(tert-butoxy)-1-oxopropan-2-yl) 1-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-acetoxysuccinate (140 mg, 12%) as a white solid: ESI MS m/z 602 $[C_{31}H_{39}NO_{11}+H]^+$.

Preparation of (S)-2-(((S)-3-Acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt

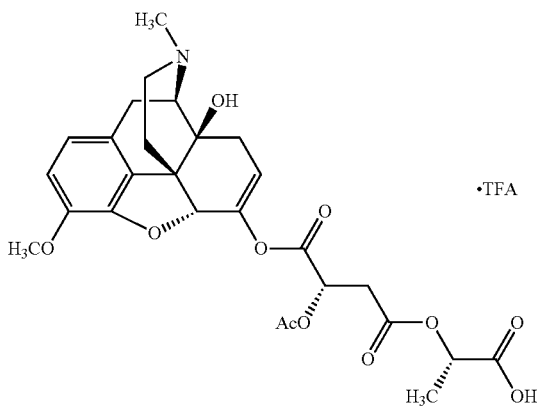 [SMILES: COc1ccc2c3c1O[C@H]1C(OC(=O)[C@H](CC(=O)O[C@@H](C)C(=O)O)OC(C)=O)=CC[C@@]4(O)[C@@H](C2)N(C)CC[C@]314]

A solution of (S)-4-((S)-1-(tert-butoxy)-1-oxopropan-2-yl) 1-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-acetoxysuccinate (0.14 g, 0.23 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (S)-2-(((S)-3-acetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt (79 mg, 63%) as a white solid: $^1$H NMR (300 MHz, DMSO-$d_6$) δ 6.77 (d, J=8.4 Hz, 1H), 6.68 (d, J=8.4 Hz, 1H), 5.61 (dd, J=5.7, 2.4 Hz, 1H), 5.45 (dd, J=6.9, 2.1 Hz, 1H), 4.99 (dd, J=14.1, 6.9 Hz, 1H), 4.87 (s, 1H), 3.74 (s, 3H), 3.19 (d, J=19.2 Hz, 1H), 3.12-2.99 (m, 5H), 2.79-2.59 (m, 2H), 2.47-2.46 (m, 1H), 2.37-1.97 (m, 7H), 1.45 (d, J=12.6 Hz, 1H), 1.40 (d, J=7.2 Hz, 3H), $CO_2H$, $CF_3CO_2H$, and OH protons not observed; ESI MS m/z 546 $[C_{27}H_{31}NO_{11}+H]^+$.

Scheme 65: (S)-3-Acetoxy-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt
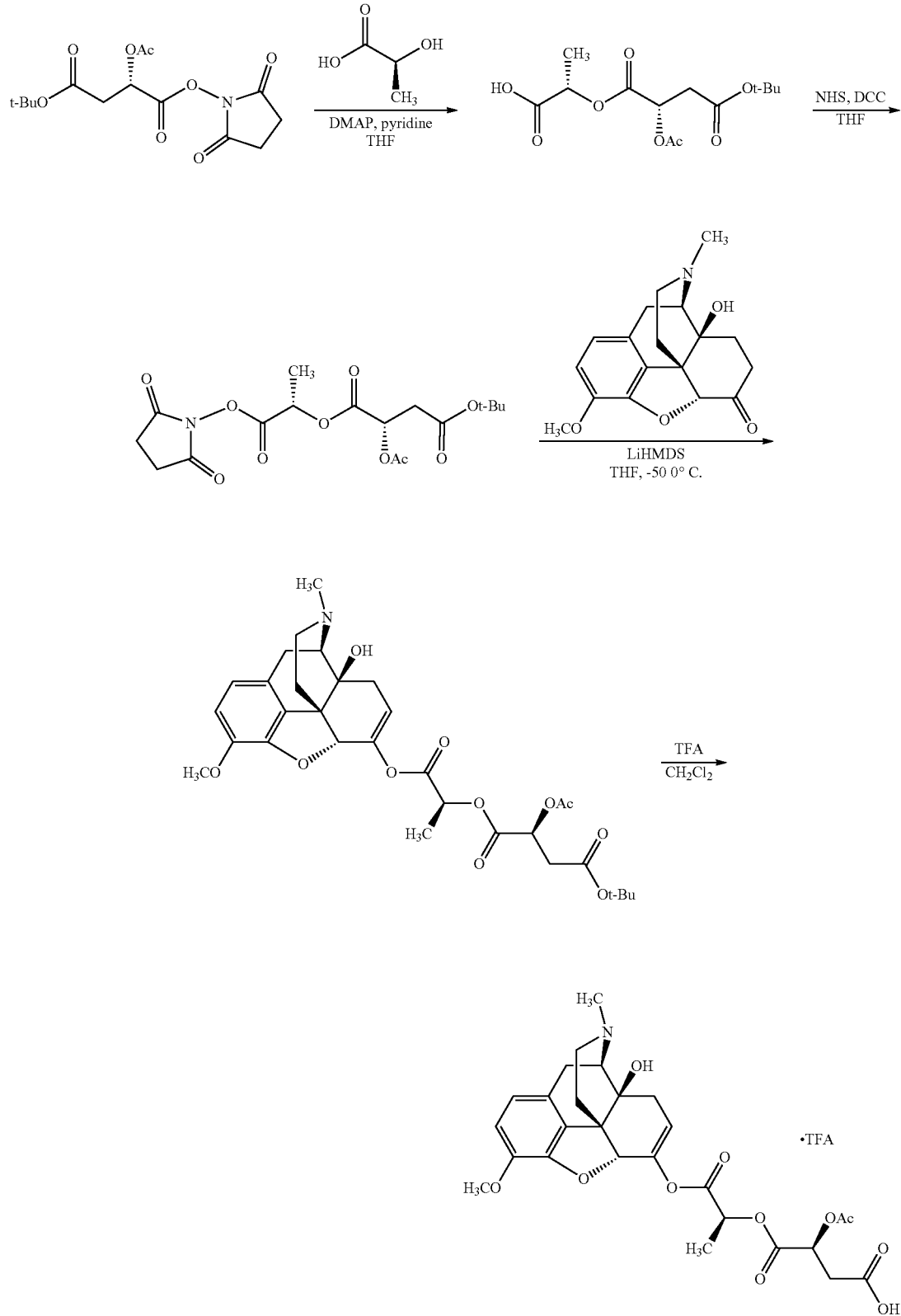

Preparation of (S)-2-(((S)-2-Acetoxy-4-(tert-butoxy)-4-oxobutanoyl)oxy)propanoic acid

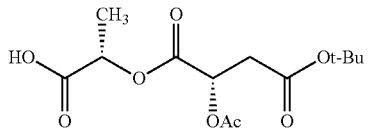

(S)-Lactic acid (109 mg, 1.21 mmol), (S)-4-tert-butyl 1-(2,5-dioxopyrrolidin-1-yl) 2-acetoxysuccinate (400 mg, 1.21 mmol), 4-(dimethylamino)pyridine (15 mg, 0.121 mmol), pyridine (115 mg, 1.45 mmol) and tetrahydrofuran (8 mL) were combined and heated at 60° C. under a nitrogen atmosphere for 24 h. After this time, the solvent was removed under reduced pressure, and the residue was partitioned between ethyl acetate (20 mL) and 10% aqueous citric acid. The organic layer was separated and extracted with saturated aqueous sodium bicarbonate (20 ml). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (S)-2-(((S)-2-acetoxy-4-(tert-butoxy)-4-oxobutanoyl)oxy)propanoic acid (247 mg, 67%) as a colorless oil: $^1$H NMR (300 MHz, CDCl$_3$) δ 5.47 (m, 1H), 5.21 (m, 1H), 2.95-2.77 (m, 2H), 2.13 (s, 3H), 1.56 (d, J=6.9 Hz, 3H), 1.45 (s, 9H), CO$_2$H proton not observed.

Preparation of (S)-4-tert-Butyl 1-((S)-1-((2,5-dioxopyrrolidin-1-yl)oxy)-1-oxopropan-2-yl) 2-acetoxysuccinate

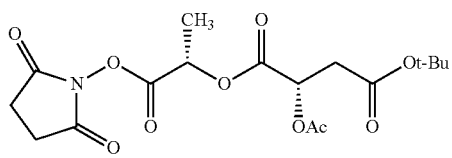 [SMILES: CC(=O)O[C@@H](CC(=O)OC(C)(C)C)C(=O)O[C@@H](C)C(=O)ON1C(=O)CCC1=O]

A solution of (S)-2-(((S)-2-acetoxy-4-(tert-butoxy)-4-oxobutanoyl)oxy)propanoic acid (247 mg, 0.812 mmol) in tetrahydrofuran (10 mL) was treated with N-hydroxysuccinimide (103 mg, 0.893 mmol) and N,N'-dicyclohexylcarbodiimide (184 mg, 0.893 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-4-tert-butyl 1-((S)-1-((2,5-dioxopyrrolidin-1-yl)oxy)-1-oxopropan-2-yl) 2-acetoxysuccinate (384 mg) as a white solid: $^1$H NMR (300 MHz, CDCl$_3$) δ 5.38-5.45 (m, 2H), 2.97-2.81 (m, 6H), 2.12 (s, 3H), 1.71 (q, J=6.9 Hz, 3H), 1.46 (s, 9H).

Preparation of (S)-4-tert-Butyl 1-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-acetoxysuccinate

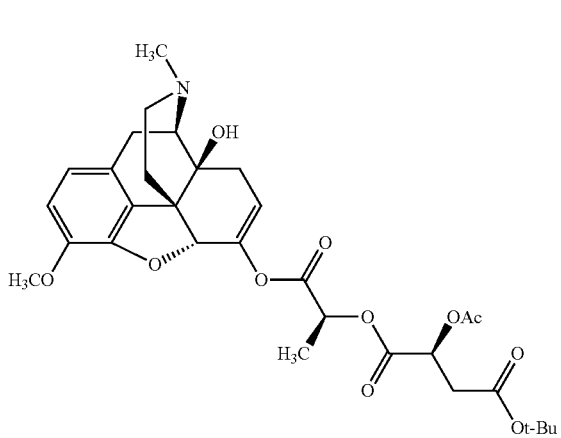 [SMILES: COc1ccc2c3c1O[C@H]1C(OC(=O)[C@H](C)OC(=O)[C@H](CC(=O)OC(C)(C)C)OC(C)=O)=CC[C@@]4(O)[C@@H](C2)N(C)CC[C@]314]

A suspension of oxycodone (500 mg, 1.59 mmol) in tetrahydrofuran (10 mL) was cooled to −50° C. and treated dropwise with a 1.0 M solution of lithium bis(trimethylsilyl)amide in tetrahydrofuran (1.8 mL, 1.8 mmol). After addition was complete, the mixture was stirred at −50° C. for 45 min. The mixture was treated dropwise with a solution of (S)-4-tert-butyl 1-((S)-1-((2,5-dioxopyrrolidin-1-yl)oxy)-1-oxopropan-2-yl) 2-acetoxysuccinate (1.0 g, 1.8 mmol) in tetrahydrofuran (8 mL). After addition was complete, the mixture was stirred at −50° C. for 30 min. After this time, the reaction mixture was treated with saturated aqueous ammonium chloride (20 mL) and extracted with ethyl acetate (3×20 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (S)-4-tert-butyl 1-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-acetoxysuccinate (420 mg, 45%) as a white solid: ESI MS m/z 602 [C$_{31}$H$_{39}$NO$_{11}$+H]$^+$.

Preparation of (S)-3-Acetoxy-4-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt

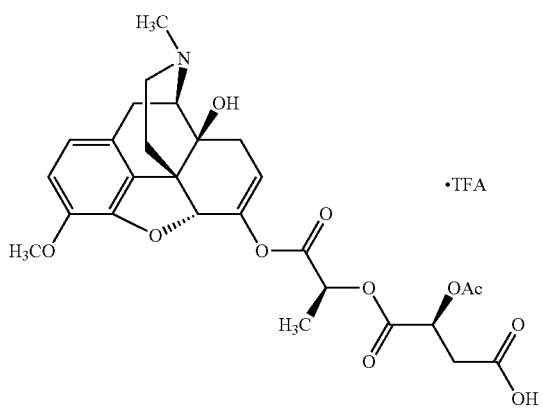 [SMILES: COc1ccc2c3c1O[C@H]1C(OC(=O)[C@H](C)OC(=O)[C@H](CC(=O)O)OC(C)=O)=CC[C@@]4(O)[C@@H](C2)N(C)CC[C@]314]

A solution of (S)-4-tert-butyl 1-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-acetoxysuccinate (120 mg, 0.2 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (S)-3-acetoxy-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt (69 mg, 63%) as a white solid: $^1$H NMR (300 MHz, DMSO-$d_6$) 512.8 (s, 1H), 9.19 (s, 1H), 6.86 (d, J=8.4 Hz, 1H), 6.76 (d, J=8.1 Hz, 1H), 6.31 (s, 1H), 5.59 (dd, J=6.0, 1.8 Hz, 1H), 5.36 (dd, J=9.0, 3.6 Hz, 1H), 5.26 (dd, J=14.1, 6.9 Hz, 1H), 5.00 (s, 1H), 3.75 (s, 3H), 3.65 (d, J=6.3 Hz, 1H), 3.43 (d, J=20.1 Hz, 1H), 3.16-3.07 (m, 2H), 2.96-2.72 (m, 5H), 2.62-2.52 (m, 1H), 2.46-2.42 (m, 1H), 2.34-2.26 (m, 1H), 2.09 (s, 3H), 2.06 (d, J=16.0 Hz, 1H), 1.64 (d, J=11.1 Hz, 1H), 1.52 (d, J=6.9 Hz, 3H); ESI MS m/z 546 $[C_{27}H_{31}NO_{11}+H]^+$.

Scheme 66: (S)-2-(((2R,3R)-2,3-Diacetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt

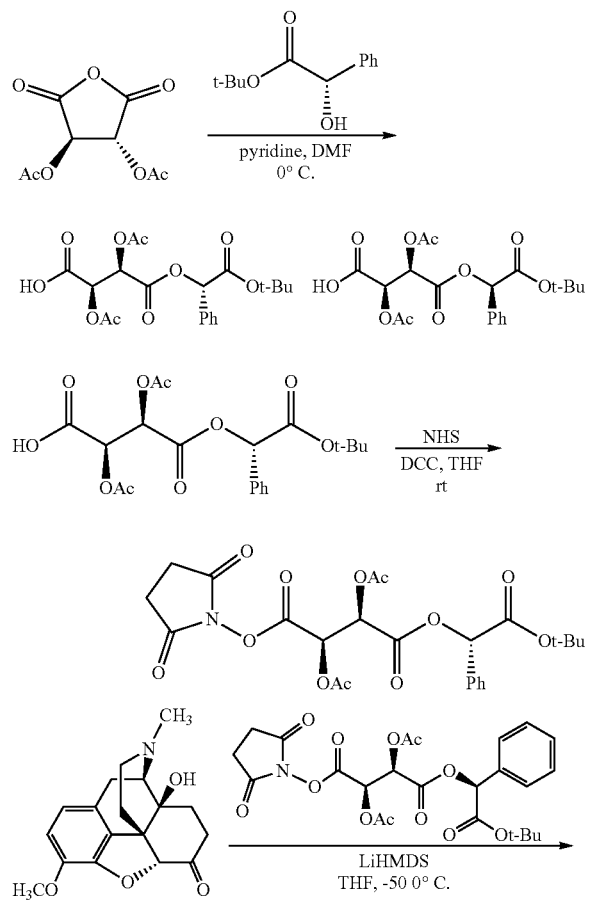

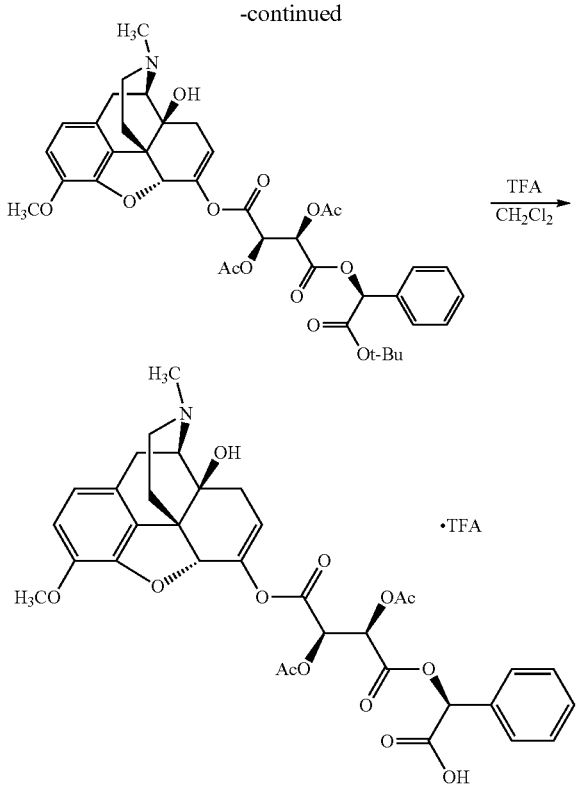

Preparation of (2R,3R)-2,3-Diacetoxy-4-((S)-2-(tert-butoxy)-2-oxo-1-phenylethoxy)-4-oxobutanoic acid and (2R,3R)-2,3-Diacetoxy-4-((R)-2-(tert-butoxy)-2-oxo-1-phenylethoxy)-4-oxobutanoic acid

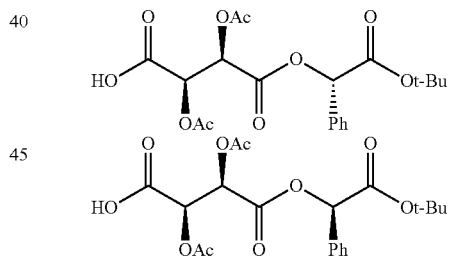

A solution of (3R,4R)-2,5-dioxotetrahydrofuran-3,4-diyl diacetate (1.35 g, 6.25 mmol) in N,N-dimethylformamide (1.5 mL) at 0° C. was treated with (S)-tert-butyl 2-hydroxy-2-phenylacetate (~7:3 S/R mixture, 1.02 g, 4.90 mmol) followed by pyridine (0.36 mL, 4.47 mmol), and the mixture was stirred at 0° C. for 1 h. After this time, the reaction mixture was diluted with ethyl acetate; washed with 10% citric acid, water, and brine; filtered; and concentrated. The residue was purified by reversed phase column chromatography (150 g C18 column, 3-20% acetonitrile/water) to provide (2R,3R)-2,3-diacetoxy-4-((S)-2-(tert-butoxy)-2-oxo-1-phenylethoxy)-4-oxobutanoic acid (dr 95:5, 1.47 g, 54%) and (2R,3R)-2,3-diacetoxy-4-((R)-2-(tert-butoxy)-2-oxo-1-phenylethoxy)-4-oxobutanoic acid (dr 85:15, 0.55 g, 18%).

(2R,3R)-2,3-Diacetoxy-4-((S)-2-(tert-butoxy)-2-oxo-1-phenylethoxy)-4-oxobutanoic acid: $^1$H NMR (300 MHz, CDCl$_3$) δ 7.26 (s, 5H), 5.94 (s, 1H), 5.90 (d, J=2.6 Hz, 1H), 5.81 (s, J=2.6 Hz, 1H), 2.17 (s, 3H), 1.92 (s, 3H), 1.40 (s, 9H), CO$_2$H proton not observed.

(2R,3R)-2,3-Diacetoxy-4-((R)-2-(tert-butoxy)-2-oxo-1-phenylethoxy)-4-oxobutanoic acid: $^1$H NMR (300 MHz, CDCl$_3$) δ 7.38 (s, 5H), 5.99 (d, J=2.6 Hz, 1H), 5.81 (d, J=2.6 Hz, 1H), 5.79 (s, 1H), 2.25 (s, 3H), 2.21 (s, 3H), 2.51 (s, 9H), CO$_2$H proton not observed.

Preparation of (2R,3R)-1-((S)-2-(tert-Butoxy)-2-oxo-1-phenylethyl) 4-(2,5-dioxopyrrolidin-1-yl) 2,3-diacetoxysuccinate

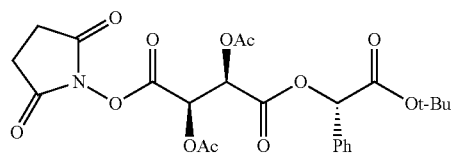 [SMILES: CC(=O)O[C@@H](C(=O)O[C@H](C(=O)OC(C)(C)C)c1ccccc1)[C@@H](OC(C)=O)C(=O)ON1C(=O)CCC1=O]

A mixture of (2R,3R)-2,3-diacetoxy-4-((S)-2-(tert-butoxy)-2-oxo-1-phenylethoxy)-4-oxobutanoic acid (1.07 g, 2.52 mmol) and N-hydroxysuccinimide (320 mg, 2.78 mmol) in tetrahydrofuran (14 mL) was treated with N,N'-dicyclohexylcarbodiimide (570 mg, 2.76 mmol), and the reaction mixture was stirred at ambient temperature for 4 h. After this time, diethyl ether (20 mL) was added, and the mixture was filtered. The filtrate was concentrated under reduced pressure to provide (2R,3R)-1-((S)-2-(tert-butoxy)-2-oxo-1-phenylethyl) 4-(2,5-dioxopyrrolidin-1-yl) 2,3-diacetoxysuccinate (1.41 g, 80%) that was used without purification: $^1$H NMR (300 MHz, CDCl$_3$) δ 7.38 (s, 5H), 6.14 (d, J=2.8 Hz, 1H), 6.02 (d, J=2.8 Hz, 1H), 5.92 (s, 1H), 2.83 (s, 4H), 2.24 (s, 3H), 1.97 (s, 3H), 1.41 (s, 9H).

Preparation of (2R,3R)-1-((S)-2-(tert-Butoxy)-2-oxo-1-phenylethyl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2,3-diacetoxysuccinate

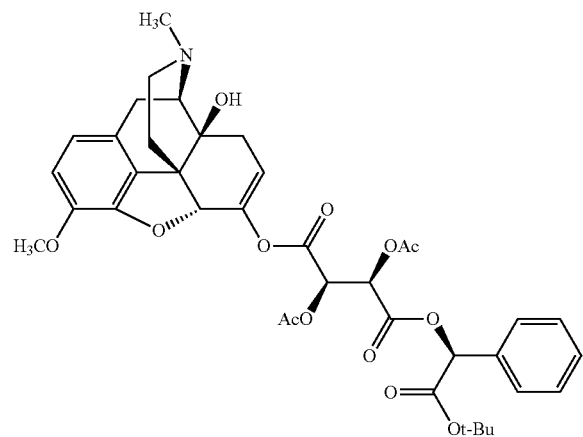 [SMILES: COc1ccc2c3c1O[C@H]1C(OC(=O)[C@H](OC(C)=O)[C@@H](OC(C)=O)C(=O)O[C@H](C(=O)OC(C)(C)C)c4ccccc4)=CC[C@@]4(O)[C@@H](C2)N(C)CC[C@]314]

A suspension of oxycodone (500 mg, 1.59 mmol) in tetrahydrofuran (10 mL) was cooled to −50° C. and treated dropwise with a 1.0 M solution of lithium bis(trimethylsilyl) amide in tetrahydrofuran (1.8 mL, 1.8 mmol). After addition was complete, the mixture was stirred at −50° C. for 45 min. The mixture was treated dropwise with a solution of (2R,3R)-1-((S)-2-(tert-butoxy)-2-oxo-1-phenylethyl) 4-(2,5-dioxopyrrolidin-1-yl) 2,3-diacetoxysuccinate (900 mg, 1.80 mmol) in tetrahydrofuran (8 mL). After addition was complete, the mixture was stirred at −50° C. for 30 min. After this time, the reaction mixture was treated with saturated aqueous ammonium chloride (15 mL) and extracted with ethyl acetate (3×15 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (2R,3R)-1-((S)-2-(tert-butoxy)-2-oxo-1-phenylethyl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2,3-diacetoxysuccinate (280 mg, 24%) as a white solid: ESI MS m/z 722 [C$_{38}$H$_{43}$NO$_{13}$+H]$^+$.

Preparation of (S)-2-(((2R,3R)-2,3-Diacetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt

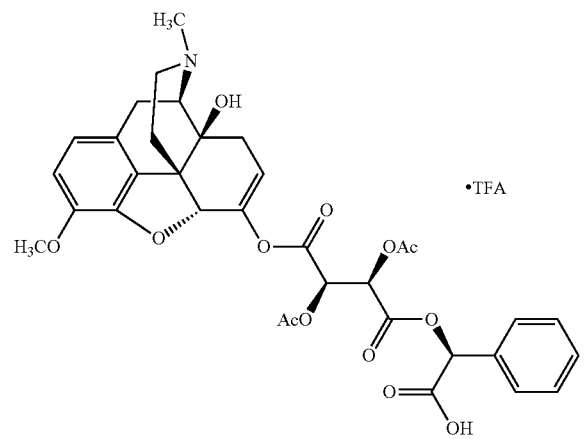 [SMILES: COc1ccc2c3c1O[C@H]1C(OC(=O)[C@H](OC(C)=O)[C@@H](OC(C)=O)C(=O)O[C@H](C(=O)O)c4ccccc4)=CC[C@@]4(O)[C@@H](C2)N(C)CC[C@]314]

A solution of (2R,3R)-1-((S)-2-(tert-butoxy)-2-oxo-1-phenylethyl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2,3-diacetoxysuccinate (0.15 g, 0.21 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (S)-2-(((2R,3R)-2,3-diacetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt (96 mg, 69%) as a white solid: $^1$H NMR (300 MHz, DMSO-d$_6$) δ 13.5 (s, 1H), 9.18 (s, 1H), 7.46-7.41 (m, 5H), 6.88 (d, J=8.4 Hz, 1H), 6.76 (d, J=8.4 Hz, 1H), 6.35 (s, 1H), 6.01 (s, 1H), 5.92 (dd, J=24.6, 2.7 Hz, 1H), 5.55 (dd, J=6.0, 2.1 Hz, 1H), 4.87 (s, 1H), 3.75 (s, 3H), 3.65 (d, J=6.0 Hz, 1H), 3.43 (d, J=20.1 Hz, 1H), 3.16-3.07

(m, 2H), 2.84 (d, J=3.6 Hz, 3H), 2.64-2.61 (m, 1H), 2.41-2.32 (m, 2H), 2.32-2.27 (m, 1H), 2.20 (s, 3H), 2.08 (d, J=18.3 Hz, 1H), 2.00 (s, 3H), 1.64 (d, J=11.7 Hz, 1H); ESI MS m/z 666 $[C_{34}H_{35}NO_{13}+H]^+$.

Scheme 67: (2S,3S)-2,3-Diacetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

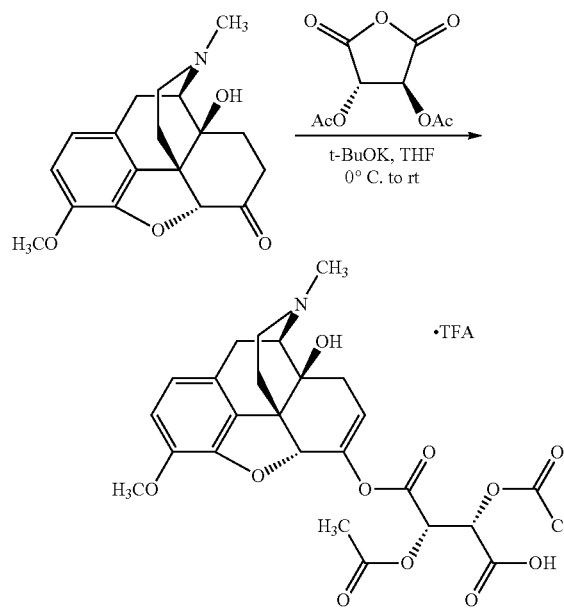

Preparation of (2S,3S)-2,3-Diacetoxy-4-(((4R,4aS, 7aR,12bS)-4a-hydroxy-9-methoxy-3-methyl-2,3,4, 4a,5,7a-hexahydro-1H-4,12-methanobenzofuro[3,2-e]isoquinolin-7-yl)oxy)-4-oxobutanoic acid trifluoroacetic acid salt

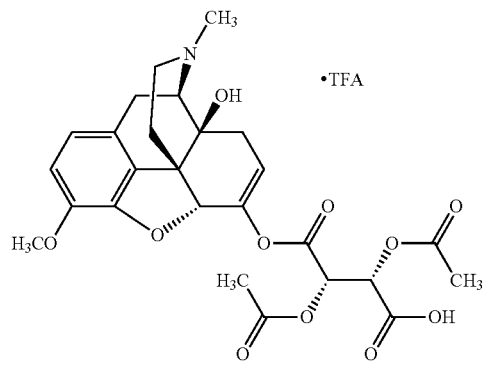 [SMILES: COc1ccc2c3c1O[C@H]1C(OC(=O)[C@@H](OC(C)=O)[C@H](OC(C)=O)C(=O)O)=CC[C@@]4(O)[C@@H](C2)N(C)CC[C@]314]

A suspension of oxycodone (270 mg, 0.856 mmol) in tetrahydrofuran (7 mL) was cooled in an ice bath and treated dropwise with a 1.0 M solution of potassium tert-butoxide in tetrahydrofuran (0.90 mL, 0.90 mmol). After 30 min, the mixture was treated with solid (3S,4S)-2,5-dioxotetrahydrofuran-3,4-diyl diacetate (338 mg, 1.56 mmol) and stirred in the ice bath under a nitrogen atmosphere for 2.5 h. After this time, the reaction mixture was treated with trifluoroacetic acid (0.3 mL) and concentrated under reduced pressure. The crude residue was purified by reversed phase column chromatography (50 g C18 column, 10-60% acetonitrile/water with 0.1% trifluoroacetic acid) and freeze dried to provide (2S,3S)-2,3-diacetoxy-4-(((4R,4aS,7aR,12bS)-4a-hydroxy-9-methoxy-3-methyl-2,3,4,4a,5, 7a-hexahydro-1H-4,12-methanobenzofuro[3,2-e]isoquinolin-7-yl)oxy)-4-oxobutanoic acid trifluoroacetic acid salt (219 mg, 40%) as a white solid: $^1$H NMR (300 MHz, DMSO-$d_6$) δ 13.87 (br s, 1H), 9.18 (br s, 1H), 6.84 (d, J=8.4 Hz, 1H), 6.75 (d, J=8.1 Hz, 1H), 6.33 (s, 1H), 5.80 (d, J=3.0 Hz, 1H), 5.59 (dd, J=5.7, 1.8 Hz, 1H), 5.56 (d, J=3.0 Hz, 1H), 5.00 (s, 1H), 3.72 (s, 3H), 3.65 (d, J=6.3 Hz, 1H), 3.43 (d, J=19.8 Hz, 1H), 3.16-3.07 (m, 2H), 2.84 (apparent d, J=2.7 Hz, 3H), 2.65-2.58 (m, 1H), 2.49-2.43 (m, 1H, partially obscured by solvent peak), 2.34-2.25 (m, 1H), 2.17 (s, 3H), 2.15 (s, 3H), 2.11-2.05 (m, 1H), 1.66 (d, J=10.8 Hz, 1H); ESI MS m/z 532 $[C_{26}H_{29}NO_{11}+H]^+$; HPLC (Method A) 98.3% (AUC), $t_R$=7.91 min.

Scheme 68: (S)-4-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-(((S)-2-hydroxypropanoyl)oxy)-4-oxobutanoic acid trifluoroacetic acid salt and (S)-1-tert-Butyl 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-(((S)-2-hydroxypropanoyl)oxy)succinate trifluoroacetic acid salt

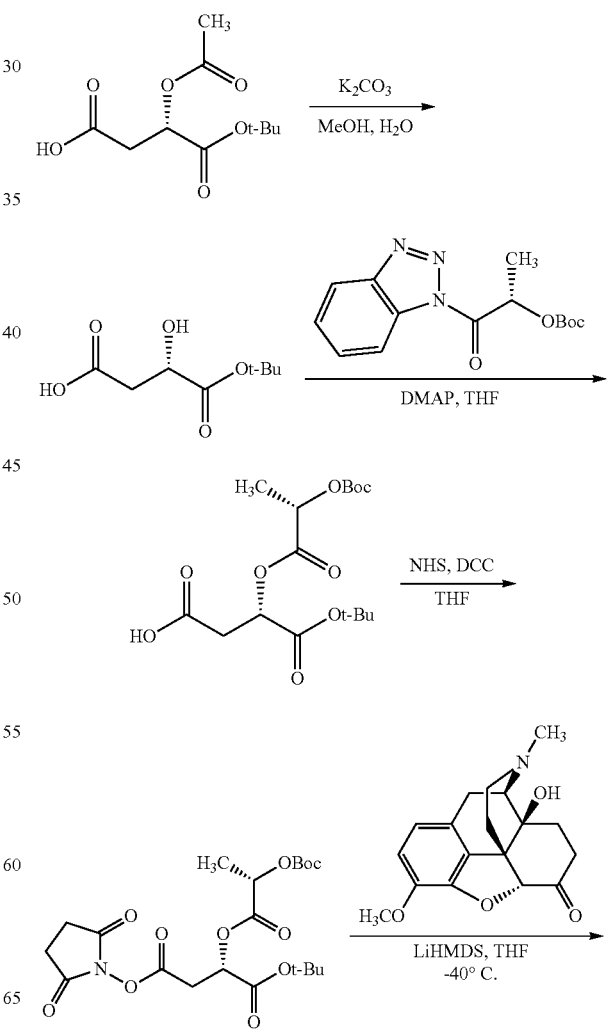

-continued

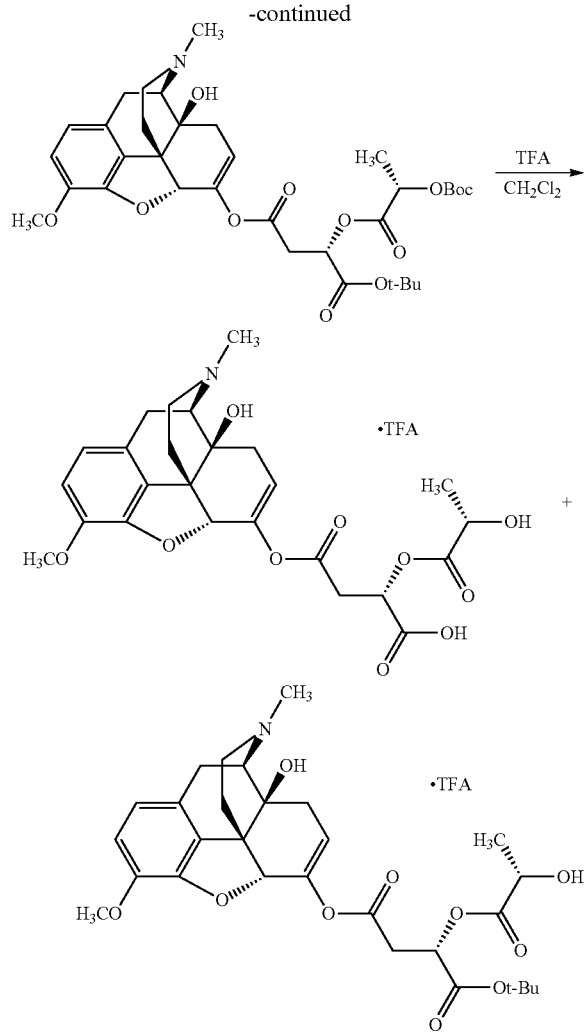

Preparation of (S)-4-(tert-Butoxy)-3-hydroxy-4-oxobutanoic acid

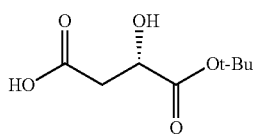

A solution of (S)-3-acetoxy-4-(tert-butoxy)-4-oxobutanoic acid (3.58 g, 15.4 mmol) in methanol (80 mL) was cooled in an ice bath and treated with a chilled solution potassium carbonate (4.71 g, 34.1 mmol) in water (40 mL). The mixture was stirred in the ice bath for 6 h. After this time, the reaction mixture was treated with aqueous 10% citric acid (200 mL) to a pH of approximately 3-4 and concentrated under reduced pressure to remove the volatiles. The aqueous mixture was extracted with methylene chloride (4×100 mL). The aqueous mixture was then further acidified to pH ~2 with 6 N hydrochloric acid and extracted again with methylene chloride (8×100 mL). The combined organics from all extractions were dried over sodium sulfate, filtered, and concentrated under reduced pressure to provide (S)-4-(tert-butoxy)-3-hydroxy-4-oxobutanoic acid (2.44 g, 84%) as a white solid: $^1$H NMR (300 MHz, DMSO-$d_6$) δ 12.27 (br s, 1H), 5.46 (br s, 1H), 4.19 (dd, J=7.5, 5.4 Hz, 1H), 2.57 (dd, J=15.6, 5.4 Hz, 1H), 2.43 (dd, J=15.6, 7.5 Hz, 1H), 1.41 (s, 9H).

Preparation of (S)-4-(tert-Butoxy)-3-(((S)-2-((tert-butoxycarbonyl)oxy)propanoyl)oxy)-4-oxobutanoic acid

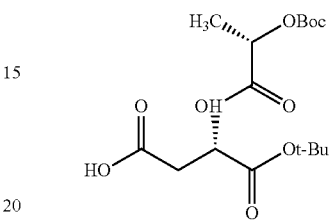

A solution of (S)-4-(tert-butoxy)-3-hydroxy-4-oxobutanoic acid (955 mg, 5.02 mmol) in tetrahydrofuran (12 mL) was cooled in an ice bath under a nitrogen atmosphere and treated with a solution of (S)-1-(1H-benzo[d][1,2,3]triazol-1-yl)-1-oxopropan-2-yl tert-butyl carbonate (1.51 g, 5.20 mmol) in tetrahydrofuran (13 mL) followed by 4-dimethylaminopyridine (617 mg, 5.05 mmol). After 5 min, the ice bath was removed, and the mixture was stirred at ambient temperature for 48 h. After this time, the reaction mixture was concentrated under reduced pressure. The residue was dissolved in ethyl acetate (50 mL) and washed with aqueous 10% citric acid (2×25 mL), water (25 mL), and brine (25 mL). The organic layer was extracted with saturated aqueous sodium bicarbonate (2×25 mL). The combined aqueous bicarbonate layers were acidified to pH ~3 with 6 N hydrochloric acid and extracted with ethyl acetate (4×25 mL). The combined organics were dried over sodium sulfate, filtered, and concentrated under reduced pressure. The crude residue was purified by column chromatography (silica gel, 0-10% methanol/methylene chloride) to provide (S)-4-(tert-butoxy)-3-(((S)-2-((tert-butoxycarbonyl)oxy)propanoyl)oxy)-4-oxobutanoic acid (507 mg, 28%) as a colorless oil: $^1$H NMR (300 MHz, DMSO-$d_6$) δ 12.79 (br s, 1H), 5.20 (dd, J=7.2, 4.8 Hz, 1H), 4.95 (q, J=7.2 Hz, 1H), 2.86-2.70 (m, 2H), 1.46-1.39 (m, 21H).

Preparation of (S)-1-tert-Butyl 4-(2,5-dioxopyrrolidin-1-yl) 2-(((S)-2-((tert-butoxycarbonyl)oxy)propanoyl)oxy)succinate

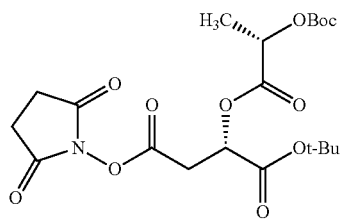

A solution of (S)-4-(tert-butoxy)-3-(((S)-2-((tert-butoxycarbonyl)oxy)propanoyl)oxy)-4-oxobutanoic acid (620 mg, 1.71 mmol) in tetrahydrofuran (15 mL) was treated with N-hydroxysuccinimide (213 mg, 1.85 mmol) and N,N'- dicyclohexylcarbodiimide (385 mg, 1.87 mmol) and stirred under a nitrogen atmosphere for 6.5 h. After this time, the reaction mixture was filtered to remove the solid dicyclohexylurea byproduct. The solid was washed with diethyl ether, and the combined filtrate and washings were concentrated under reduced pressure to provide (S)-1-tert-butyl 4-(2,5-dioxopyrrolidin-1-yl) 2-(((S)-2-((tert-butoxycarbonyl)oxy)propanoyl)oxy)succinate (813 mg, quantitative) as a white semi-solid: $^1$H NMR (300 MHz, DMSO-d$_6$) δ 5.40-5.29 (m, 1H), 4.98 (q, J=7.2 Hz, 1H), 3.36-3.32 (m, 2H, partially obscured by solvent peak), 2.82 (br s, 4H), 1.43-1.40 (m, 21H).

Preparation of (S)-1-tert-Butyl 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-(((S)-2-((tert-butoxycarbonyl)oxy)propanoyl)oxy)succinate

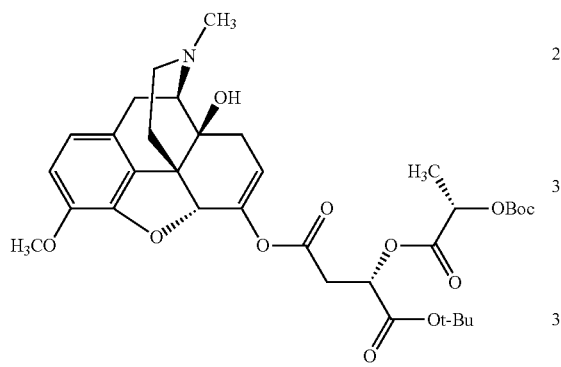

A suspension of oxycodone (253 mg, 0.802 mmol) in tetrahydrofuran (4 mL) was cooled in an ice bath and treated dropwise with a 1.0 M solution of lithium bis(trimethylsilyl)amide in tetrahydrofuran (0.9 mL, 0.9 mmol). After stirring at 0° C. for 45 min, the ice bath was replaced with a dry ice/acetonitrile bath (−45° C.). The mixture was treated dropwise with a solution of (S)-1-tert-butyl 4-(2,5-dioxopyrrolidin-1-yl) 2-(((S)-2-((tert-butoxycarbonyl)oxy)propanoyl)oxy)succinate (401 mg, 0.873 mmol) in tetrahydrofuran (4 mL) and stirred for 30 min. After this time, the dry ice/acetonitrile bath was replaced with a wet ice bath, and the reaction mixture was treated with chilled saturated aqueous ammonium chloride (25 mL) and extracted with ethyl acetate (2×25 mL). The combined organics were washed with water (25 mL) and brine (25 mL), dried over sodium sulfate, filtered, and concentrated under reduced pressure. The crude residue was purified by reversed phase column chromatography (50 g C18 column, 20-100% acetonitrile/water) and freeze dried to provide (S)-1-tert-butyl 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-(((S)-2-((tert-butoxycarbonyl)oxy)propanoyl)oxy)succinate (63 mg, 12%) as a fluffy white solid: ESI MS m/z 660 [C$_{34}$H$_{45}$NO$_{12}$+H]$^+$.

Preparation of (S)-4-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-2-(((S)-2-hydroxypropanoyl)oxy)-4-oxobutanoic acid trifluoroacetic acid salt and (S)-1-tert-Butyl 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-(((S)-2-hydroxypropanoyl)oxy)succinate trifluoroacetic acid salt

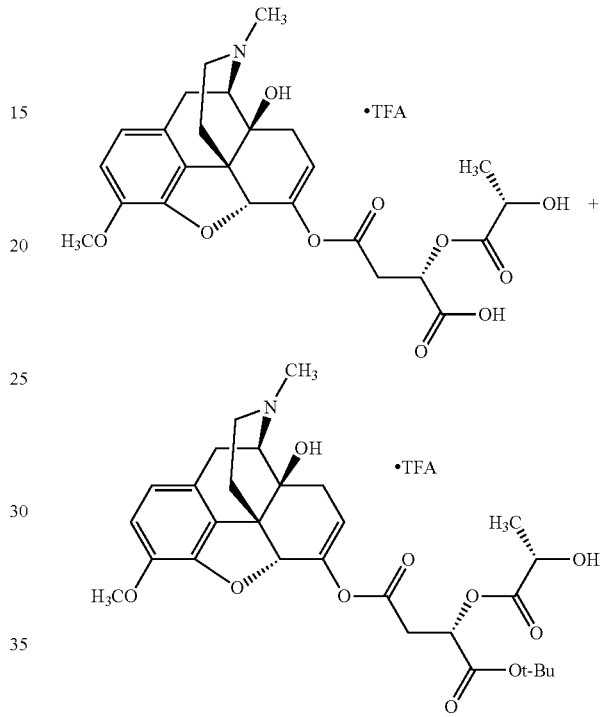

A solution of (S)-1-tert-butyl 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-(((S)-2-((tert-butoxycarbonyl)oxy)propanoyl)oxy)succinate (61 mg, 0.092 mmol) in methylene chloride (2 mL) was treated with trifluoroacetic acid (0.5 mL) and stirred under a nitrogen atmosphere at ambient temperature for 2 h. After this time, the reaction mixture was concentrated under reduced pressure. The residue was purified by reversed phase column chromatography (50 g C18 column, 10-70% acetonitrile/water with 0.1% trifluoroacetic acid) to provide two compounds. Each compound was freeze dried to afford (S)-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-(((S)-2-hydroxypropanoyl)oxy)-4-oxobutanoic acid trifluoroacetic acid salt (20 mg, 35%) as a fluffy white solid: $^1$H NMR (300 MHz, DMSO-d$_6$) δ 13.42 (br s, 1H), 9.18 (br s, 1H), 6.86 (d, J=8.4 Hz, 1H), 6.75 (d, J=8.4 Hz, 1H), 6.29 (s, 1H), 5.56-5.55 (m, 1H), 5.46 (br s, 1H), 5.31 (dd, J=8.1, 4.2 Hz, 1H), 4.99 (s, 1H), 4.21 (q, J=6.9 Hz, 1H), 3.75 (s, 3H), 3.64 (d, J=6.3 Hz, 1H), 3.48-3.40 (m, 1H, partially obscured by water peak), 3.15-2.96 (m, 4H), 2.84 (apparent d, J=4.2 Hz, 3H), 2.66-2.58 (m, 1H), 2.49-2.42 (m, 1H, partially obscured by solvent peak), 2.32-2.24 (m, 1H), 2.07 (apparent d, J=18.0 Hz, 1H), 1.64 (d, J=11.7 Hz, 1H), 1.31 (d, J=6.9 Hz, 3H); ESI MS m/z 504 [C$_{25}$H$_{29}$NO$_{10}$+H]$^+$; HPLC (Method A) 95.0% (AUC), t$_R$=7.36 min; and (S)-1-tert-butyl 4-((4R,4aS,7aR,12bS)-4a-hydroxy-9-methoxy-3-methyl-2,3,4,4a,5,7a-hexahydro-1H-

4,12-methanobenzofuro[3,2-e]isoquinolin-7-yl) 2-(((S)-2-hydroxypropanoyl)oxy)succinate trifluoroacetic acid salt (10 mg, 15%) as a fluffy white solid: $^1$H NMR (300 MHz, CDCl$_3$) δ 9.18 (br s, 1H), 6.86 (d, J=8.4 Hz, 1H), 6.75 (d, J=8.4 Hz, 1H), 6.27 (s, 1H), 5.56-5.54 (m, 1H), 5.48 (br s, 1H), 5.24 (dd, J=7.5, 4.8 Hz, 1H), 4.99 (s, 1H), 4.21 (q, J=6.6 Hz, 1H), 3.74 (s, 3H), 3.64 (d, J=6.0 Hz, 1H), 3.46-3.40 (m, 1H, partially obscured by water peak), 3.15-2.97 (m, 4H), 2.85 (apparent d, J=4.8 Hz, 3H), 2.66-2.57 (m, 1H), 2.49-2.42 (m, 1H, partially obscured by solvent peak), 2.33-2.24 (m, 1H), 2.07 (apparent d, J=18.3 Hz, 1H), 1.64 (d, J=12.0 Hz, 1H), 1.41 (s, 9H), 1.32 (d, J=6.9 Hz, 3H); ESI MS m/z 560 [C$_{29}$H$_{37}$NO$_{10}$+H]$^+$; HPLC (Method A) 97.7% (AUC), t$_R$=9.28 min.

Scheme 69: (R)-2-Hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

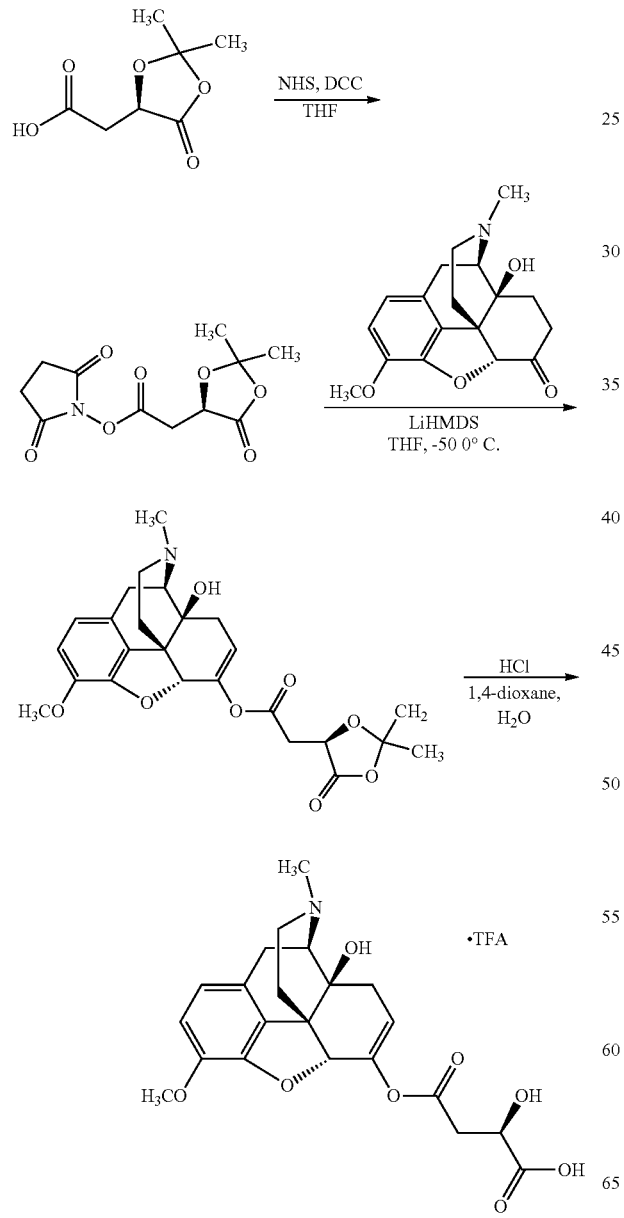

Preparation of (R)-2,5-Dioxopyrrolidin-1-yl 2-(2,2-dimethyl-5-oxo-1,3-dioxolan-4-yl)acetate

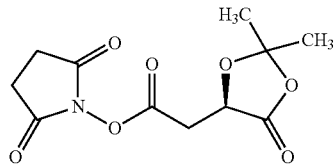 [SMILES: CC1(C)OC(=O)[C@@H](CC(=O)ON2C(=O)CCC2=O)O1]

A solution of (R)-2-(2,2-dimethyl-5-oxo-1,3-dioxolan-4-yl)acetic acid (696 mg, 4.00 mmol) in tetrahydrofuran (40 mL) was treated with N-hydroxysuccinimide (506 mg, 4.40 mmol) and N,N'-dicyclohexylcarbodiimide (906 mg, 4.40 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (R)-2,5-dioxopyrrolidin-1-yl 2-(2,2-dimethyl-5-oxo-1,3-dioxolan-4-yl)acetate (1.40 g, quantitative) as a yellow solid: $^1$H NMR (300 MHz, CDCl$_3$) δ 4.77 (dd, J=6.3, 3.6 Hz, 1H), 3.28 (dd, J=17.4, 3.9 Hz, 1H), 3.10 (dd, J=17.1, 6.3 Hz, 1H), 2.85 (s, 4H), 1.63 (s, 3H), 1.58 (s, 3H).

Preparation of (4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((R)-2,2-dimethyl-5-oxo-1,3-dioxolan-4-yl)acetate

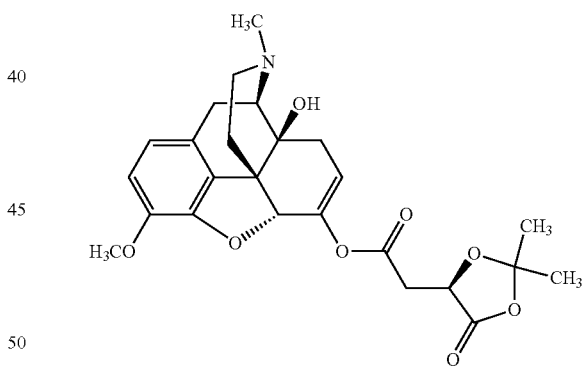

A suspension of oxycodone (500 mg, 1.59 mmol) in tetrahydrofuran (10 mL) was cooled to −50° C. and treated dropwise with a 1.0 M solution of lithium bis(trimethylsilyl)amide in tetrahydrofuran (1.8 mL, 1.8 mmol). After addition was complete, the mixture was stirred at −50° C. for 45 min. The mixture was treated dropwise with a solution of (R)-2,5-dioxopyrrolidin-1-yl 2-(2,2-dimethyl-5-oxo-1,3-dioxolan-4-yl)acetate (640 mg, 2.40 mmol) in tetrahydrofuran (8 mL). After addition was complete, the mixture was stirred at −50° C. for 30 min. After this time, the reaction mixture was treated with saturated aqueous ammonium chloride (15 mL) and extracted with ethyl acetate (3×15 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((R)-2,2-dimethyl-5-oxo-1,3-dioxolan-4-yl)acetate (43 mg, 6%) as a white solid: ESI MS m/z 472 [$C_{25}H_{29}NO_8$+H]$^+$.

Preparation of (R)-2-Hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

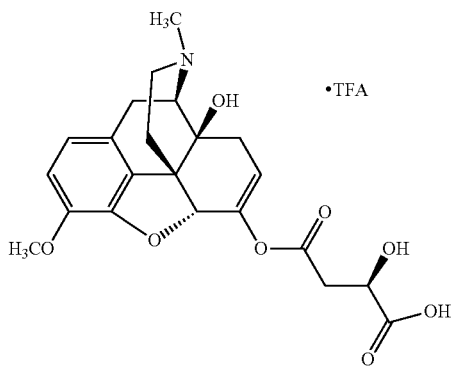 [SMILES: COc1ccc2c3c1O[C@H]1C(OC(=O)C[C@@H](O)C(=O)O)=CC[C@@]4(O)[C@@H](C2)N(C)CC[C@]314]

A solution of (4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((R)-2,2-dimethyl-5-oxo-1,3-dioxolan-4-yl)acetate (43 mg, 0.090 mmol) was treated with 1 M hydrogen chloride solution in 1,4-dioxanes (1 mL) and water (a few drops) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (R)-2-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt (28 mg, 71%) as a white solid: $^1$H NMR (300 MHz, DMSO-$d_6$) δ 12.7 (s, 1H), 9.19 (s, 1H), 6.86 (d, J=8.4 Hz, 1H), 6.75 (d, J=8.4 Hz, 1H), 6.28 (s, 1H), 5.63 (s, 1H), 5.53-5.51 (m, 1H), 4.98 (s, 1H), 4.34 (dd, J=7.8, 2.1 Hz, 1H), 3.76 (s, 3H), 3.64 (d, J=6.3 Hz, 1H), 3.43 (d, J=20.1 Hz, 1H), 3.15-3.07 (m, 2H), 2.89-2.82 (m, 4H), 2.72-2.61 (m, 2H), 2.46-2.42 (m, 1H), 2.33-2.26 (m, 1H), 2.05 (d, J=18.0 Hz, 1H), 1.64 (d, J=11.5 Hz, 1H); ESI MS m/z 432 [$C_{22}H_{25}NO_8$+H]$^+$, HPLC (Method A) 97.2% (AUC), $t_R$=7.04 min.

Scheme 70: (S)-2-Amino-5-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid bis(trifluoroacetic acid salt)

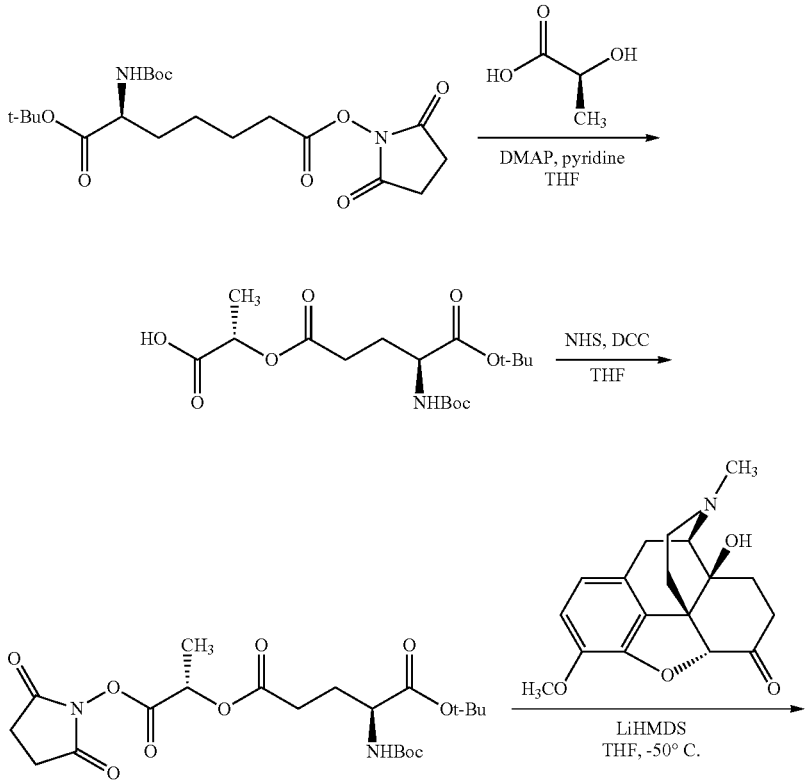

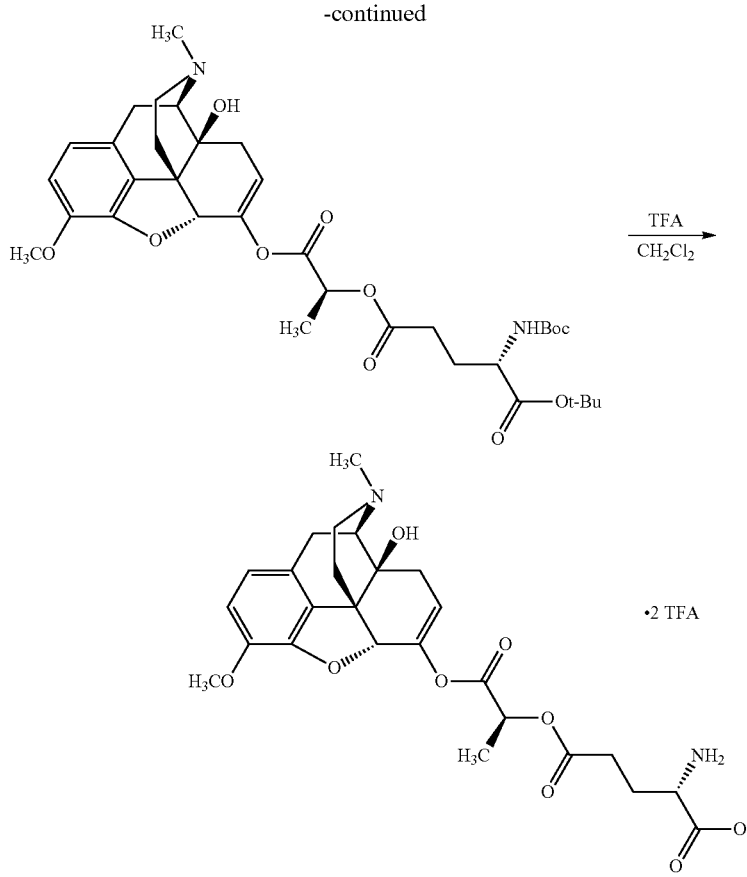

Preparation of (S)-2-(((S)-5-(tert-Butoxy)-4-((tert-butoxycarbonyl)amino)-5-oxopentanoyl)oxy)propanoic acid

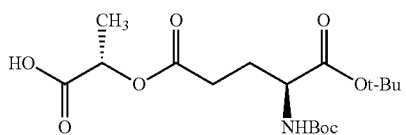 [SMILES: C[C@H](OC(=O)CC[C@H](NC(=O)OC(C)(C)C)C(=O)OC(C)(C)C)C(=O)O]

(S)-Lactic acid (270 mg, 3.00 mmol), (S)-1-tert-butyl 5-(2,5-dioxopyrrolidin-1-yl) 2-((tert-butoxycarbonyl)amino)pentanedioate (1.00 g, 2.50 mmol), 4-(dimethylamino)pyridine (31 mg, 0.250 mmol), and pyridine (237 mg, 3.00 mmol) were combined and heated at 60° C. under a nitrogen atmosphere for 48 h. After this time, the solvent was removed under reduced pressure, and the residue was participated between ethyl acetate (20 mL) and 10% aqueous citric acid. The organic layer was separated and extracted with saturated aqueous sodium bicarbonate (20 ml). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (S)-2-(((S)-5-(tert-butoxy)-4-((tert-butoxycarbonyl)amino)-5-oxopentanoyl)oxy)propanoic acid (726 mg, 77%) as a colorless oil: $^1$H NMR (300 MHz, CDCl$_3$) δ 5.19-5.12 (m, 2H), 2.51-2.42 (m, 2H), 2.18 (m, 1H), 1.91 (m, 1H), 1.54 (d, J=7.2 Hz, 3H), 1.47 (s, 9H), 1.45 (s, 9H), CO$_2$H and NH protons not observed.

Preparation of (S)-1-tert-Butyl 5-((S)-1-((2,5-dioxopyrrolidin-1-yl)oxy)-1-oxopropan-2-yl) 2-((tert-butoxycarbonyl)amino)pentanedioate

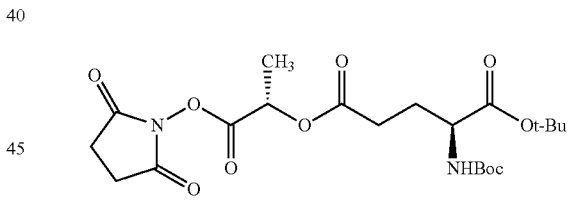

A solution of (S)-2-(((S)-5-(tert-butoxy)-4-((tert-butoxycarbonyl)amino)-5-oxopentanoyl)oxy)propanoic acid (726 mg, 1.93 mmol) in tetrahydrofuran (15 mL) was treated with N-hydroxysuccinimide (245 mg, 2.13 mmol) and N,N'-dicyclohexylcarbodiimide (439 mg, 2.13 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-1-tert-butyl 5-((S)-1-((2,5-dioxopyrrolidin-1-yl)oxy)-1-oxopropan-2-yl) 2-((tert-butoxycarbonyl)amino)pentanedioate (1.03 g, quantitative) as a white solid: $^1$H NMR (300 MHz, CDCl$_3$) δ 5.42 (dd, J=14.1, 7.2 Hz, 1H), 5.08 (m, 1H), 2.84 (s, 4H), 2.53-2.46 (m, 2H), 2.20 (m, 1H), 1.91 (m, 1H), 1.67 (d, J=7.2 Hz, 3H), 1.47 (s, 9H), 1.45 (s, 9H), NH proton not observed.

531

Preparation of (S)-1-tert-Butyl 5-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-((tert-butoxycarbonyl)amino)pentanedioate

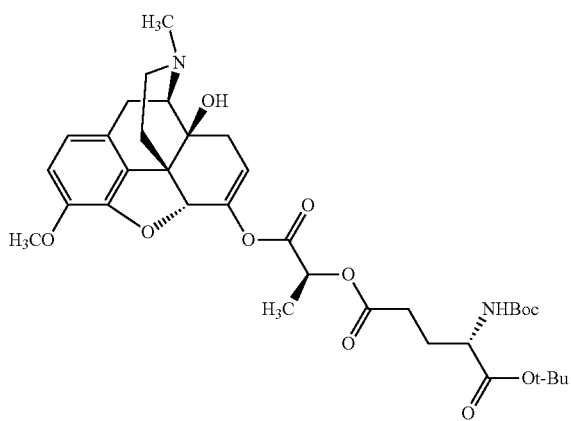 [SMILES: COc1ccc2c3c1O[C@H]1C(OC(=O)[C@H](C)OC(=O)CC[C@H](NC(=O)OC(C)(C)C)C(=O)OC(C)(C)C)=CC[C@@]4(O)[C@@H](C2)N(C)CC[C@]314]

A suspension of oxycodone (400 mg, 1.27 mmol) in tetrahydrofuran (10 mL) was cooled to −50° C. and treated dropwise with a 1.0 M solution of lithium bis(trimethylsilyl)amide in tetrahydrofuran (1.4 mL, 1.4 mmol). After addition was complete, the mixture was stirred at −50° C. for 45 min. The mixture was treated dropwise with a solution of (S)-1-tert-butyl 5-((S)-1-((2,5-dioxopyrrolidin-1-yl)oxy)-1-oxopropan-2-yl) 2-((tert-butoxycarbonyl)amino)pentanedioate (640 mg, 1.40 mmol) in tetrahydrofuran (8 mL). After addition was complete, the mixture was stirred at −50° C. for 30 min. After this time, the reaction mixture was treated with saturated aqueous ammonium chloride (15 mL) and extracted with ethyl acetate (3×15 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (S)-1-tert-butyl 5-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-((tert-butoxycarbonyl)amino)pentanedioate (240 mg, 28%) as a white solid: ESI MS m/z 673 $[C_{35}H_{48}N_2O_{11}+H]^+$.

532

Preparation of (S)-2-Amino-5-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid bis(trifluoroacetic acid salt)

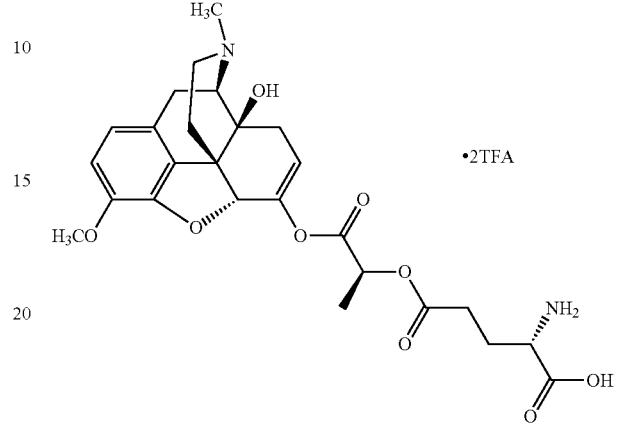

A solution of (S)-1-tert-butyl 5-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-((tert-butoxycarbonyl)amino)pentanedioate (0.18 g, 0.27 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (S)-2-amino-5-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid bis(trifluoroacetic acid salt) (100 mg, 72%) as a white solid: $^1$H NMR (300 MHz, DMSO-$d_6$) δ 9.20 (s, 1H), 8.29 (s, 3H), 6.86 (d, J=8.4 Hz, 1H), 6.76 (d, J=8.1 Hz, 1H), 6.34 (s, 1H), 5.60-5.58 (m, 1H), 5.14 (dd, J=13.8, 7.2 Hz, 1H), 5.00 (s, 1H), 3.76 (s, 3H), 3.66 (d, J=6.3 Hz, 1H), 3.43 (d, J=20.1 Hz, 1H), 3.16-3.07 (m, 2H), 2.85 (s, 3H), 2.72-2.61 (m, 3H), 2.46-2.42 (m, 1H), 2.33-2.26 (m, 1H), 2.15-1.99 (m, 3H), 2.07 (d, J=18.0 Hz, 1H), 1.64 (d, J=11.5 Hz, 1H), 1.51 (d, J=7.2 Hz, 3H), CO$_2$H proton not observed; ESI MS m/z 517 $[C_{26}H_{32}N_2O_9+H]$, HPLC (Method A) 97.8% (AUC), $t_R$=7.13 min.

Scheme 71: (S)-2-Acetoxy-4-((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoroacetic acid salt

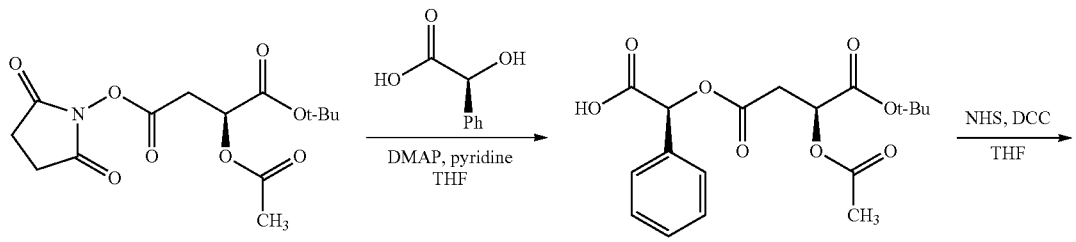

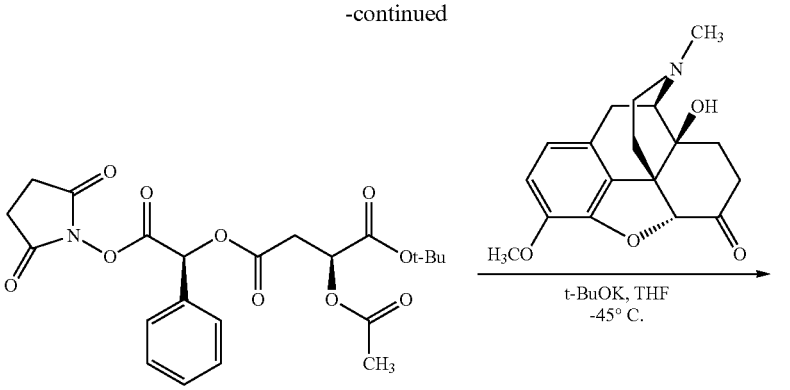

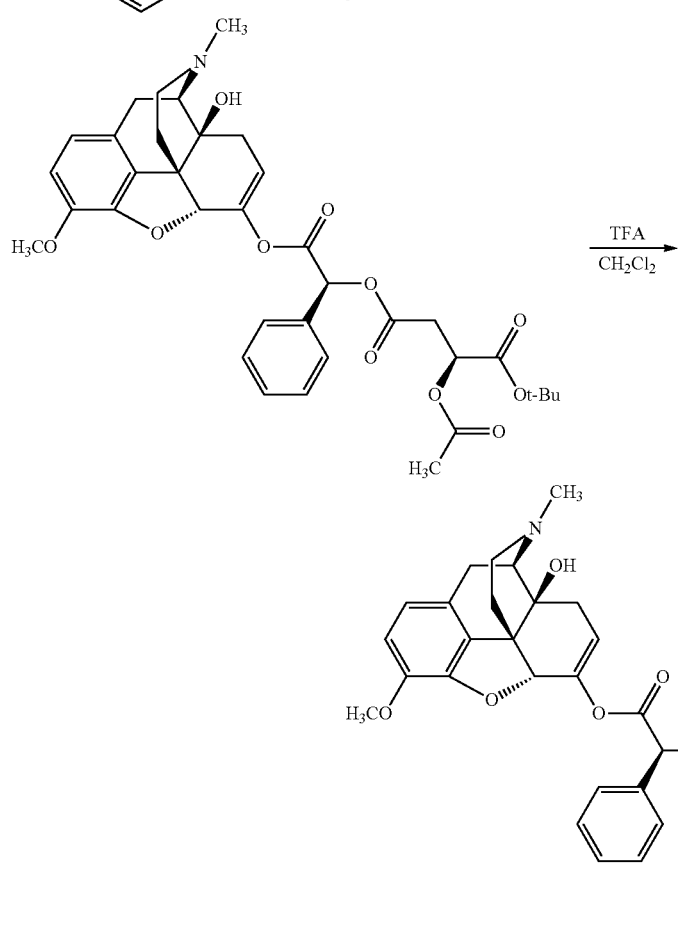

Preparation of (S)-2-(((S)-3-Acetoxy-4-(tert-butoxy)-4-oxobutanoyl)oxy)-2-phenylacetic acid

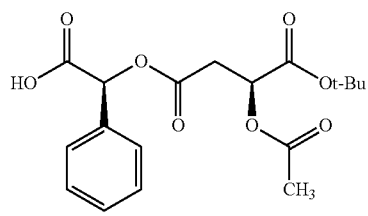 [SMILES: CC(=O)O[C@@H](CC(=O)O[C@H](C(=O)O)c1ccccc1)C(=O)OC(C)(C)C]

A solution of (S)-1-tert-butyl 4-(2,5-dioxopyrrolidin-1-yl) 2-acetoxysuccinate (1.66 g, 5.05 mmol), (S)-mandelic acid (861 mg, 5.66 mmol), and 4-dimethylaminopyridine (68 mg, 0.56 mmol) in tetrahydrofuran (30 mL) was treated with pyridine (0.82 mL, 10 mmol) and heated at 50° C. under a nitrogen atmosphere for 64 h. After this time, the reaction mixture was cooled to room temperature and concentrated under reduced pressure. The residue was dissolved in ethyl acetate (50 mL); washed with aqueous 10% citric acid (2×25 mL), water (25 mL), and brine (25 mL); dried over sodium sulfate; filtered; and concentrated under reduced pressure. The crude residue was purified by column chromatography (silica gel, 0-10% methanol/methylene chloride) to provide (S)-2-(((S)-3-acetoxy-4-(tert-butoxy)-4-oxobutanoyl)oxy)-2-phenylacetic acid (849 mg, 46%) as a colorless oil: $^1$H NMR (300 MHz, DMSO-$d_6$) δ 13.31 (s, 1H), 7.47-7.40 (m, 5H), 5.88 (s, 1H), 5.23 (dd, J=8.7, 4.2 Hz, 1H), 3.05 (dd, J=16.8, 4.2 Hz, 1H), 2.94 (dd, J=16.8, 8.7 Hz, 1H), 2.05 (s, 3H), 1.38 (s, 9H); ESI MS m/z 731 [(2×$C_{18}H_{22}O_8$)−H]$^-$.

Preparation of (S)-1-tert-Butyl 4-((S)-2-((2,5-dioxopyrrolidin-1-yl)oxy)-2-oxo-1-phenylethyl) 2-acetoxysuccinate

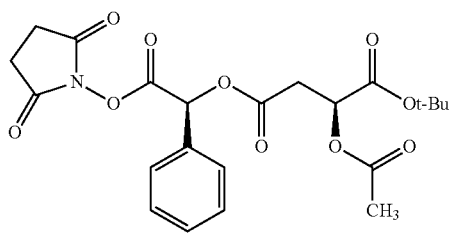 [SMILES: CC(=O)O[C@@H](CC(=O)O[C@H](C(=O)ON1C(=O)CCC1=O)c1ccccc1)C(=O)OC(C)(C)C]

A solution of (S)-2-(((S)-3-acetoxy-4-(tert-butoxy)-2-phenylacetic acid (845 mg, 2.31 mmol) in tetrahydrofuran (23 mL) was treated with N-hydroxysuccinimide (292 mg, 2.54 mmol) and N,N'-dicyclohexylcarbodiimide (541 mg, 2.62 mmol) and stirred under a nitrogen atmosphere for 16 h. After this time, the reaction mixture was filtered to remove the solid dicyclohexylurea byproduct. The solid was washed with diethyl ether, and the combined filtrate and washings were concentrated under reduced pressure to provide (S)-1-tert-butyl 4-((S)-2-((2,5-dioxopyrrolidin-1-yl)oxy)-2-oxo-1-phenylethyl) 2-acetoxysuccinate (1.20 g, quantitative) as a white semi-solid: $^1$H NMR (300 MHz, DMSO-$d_6$) δ 7.59-7.56 (m, 2H), 7.50-7.47 (m, 3H), 6.57 (s, 1H), 5.22 (dd, J=8.1, 4.5 Hz, 1H), 3.10 (dd, J=16.8, 4.5 Hz, 1H), 3.00 (dd, J=16.8, 8.4 Hz, 1H), 2.78 (br s, 4H), 2.04 (s, 3H), 1.37 (s, 9H).

Preparation of (S)-1-tert-Butyl 4-((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl) 2-acetoxysuccinate

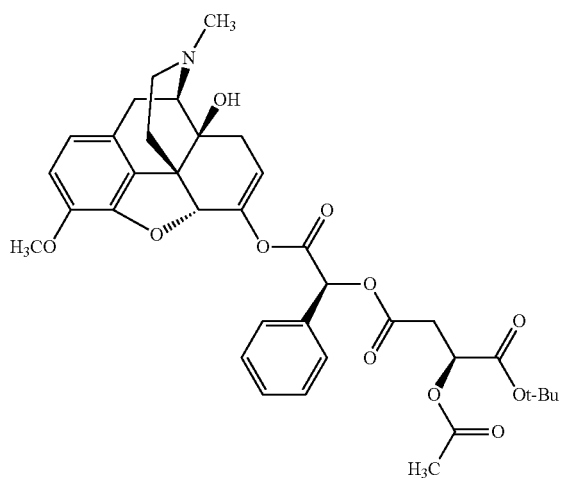 [SMILES: COc1ccc2c3c1O[C@H]1C(OC(=O)[C@@H](OC(=O)C[C@H](OC(C)=O)C(=O)OC(C)(C)C)c4ccccc4)=CC[C@@]4(O)[C@@H](C2)N(C)CC[C@]314]

A suspension of oxycodone (335 mg, 1.06 mmol) in tetrahydrofuran (5 mL) was cooled in an ice bath and treated dropwise with a 1.0 M solution of potassium tert-butoxide in tetrahydrofuran (1.2 mL, 1.2 mmol). After stirring at 0° C. for 1 h, the ice bath was replaced with a dry ice/acetonitrile bath (−45° C.). The mixture was treated dropwise with a solution of (S)-1-tert-butyl 4-((S)-2-((2,5-dioxopyrrolidin-1-yl)oxy)-2-oxo-1-phenylethyl) 2-acetoxysuccinate (533 mg, 1.15 mmol) in tetrahydrofuran (5 mL). The dry ice was removed from the acetonitrile bath, and the bath temperature increased to −10° C. over 30 min. After this time, the reaction mixture was treated with saturated aqueous ammonium chloride (25 mL) and extracted with ethyl acetate (2×25 mL). The combined organics were washed with brine (25 mL), dried over sodium sulfate, filtered, and concentrated under reduced pressure. The crude residue was purified by reversed phase column chromatography (50 g C18 column, 10-100% acetonitrile/water) and freeze dried to provide (S)-1-tert-butyl 4-((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl) 2-acetoxysuccinate (71 mg, 10%) as a fluffy white solid: ESI MS m/z 664 [$C_{36}H_{41}NO_{11}$+H]$^+$.

Preparation of (S)-2-Acetoxy-4-((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoroacetic acid salt

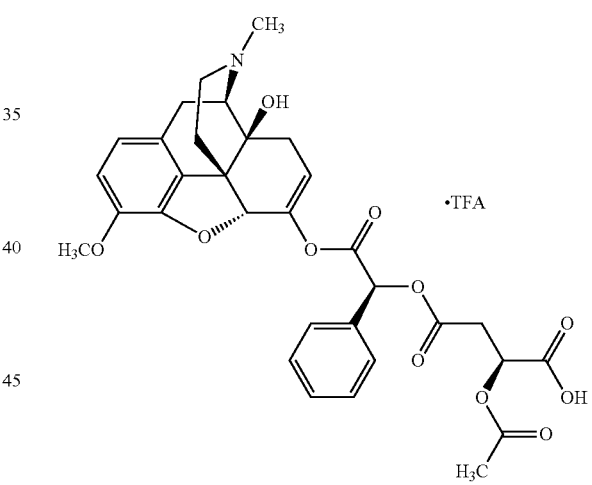

A solution of (S)-1-tert-butyl 4-((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethyl) 2-acetoxysuccinate (70 mg, 0.11 mmol) in methylene chloride (2 mL) was treated with trifluoroacetic acid (0.5 mL) and stirred under a nitrogen atmosphere at ambient temperature for 3 h. After this time, the reaction mixture was concentrated under reduced pressure. The residue was purified by reversed phase column chromatography (50 g C18 column, 10-80% acetonitrile/water with 0.1% trifluoroacetic acid) and freeze dried to provide (S)-2-acetoxy-4-((S)-2-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoroacetic acid salt (25 mg, 33%) as a fluffy white solid: $^1$H NMR (300 MHz, DMSO-$d_6$) δ 13.40 (br s, 1H), 9.16 (br s, 1H), 7.57-7.54 (m, 2H), 7.48-7.46 (m, 3H), 6.81 (d, J=8.4 Hz, 1H), 6.73 (d, J=8.4 Hz, 1H), 6.29 (s, 1H), 6.17 (s, 1H), 5.55 (dd, J=6.0, 2.1 Hz, 1H), 5.33 (dd, J=8.7, 3.9 Hz, 1H), 4.95 (s, 1H), 3.75 (br s, 4H), 3.44-3.38 (m, 1H, partially obscured by water peak), 3.14-2.97 (m, 4H), 2.83 (apparent d, J=4.2 Hz, 3H), 2.68-2.57 (m, 1H), 2.49-2.40 (m, 1H, partially obscured by solvent peak), 2.31-2.22 (m, 1H), 2.09-2.04 (m, 1H), 2.04 (s, 3H), 1.63 (d, J=12.0 Hz, 3H); ESI MS m/z 608 $[C_{32}H_{33}NO_{11}+H]^+$; HPLC (Method A) 98.0% (AUC), $t_R$=9.62 min.

Scheme 72: (S)-2-(((2R,3R)-2,3-Diacetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl acid trifluoroacetic acid salt

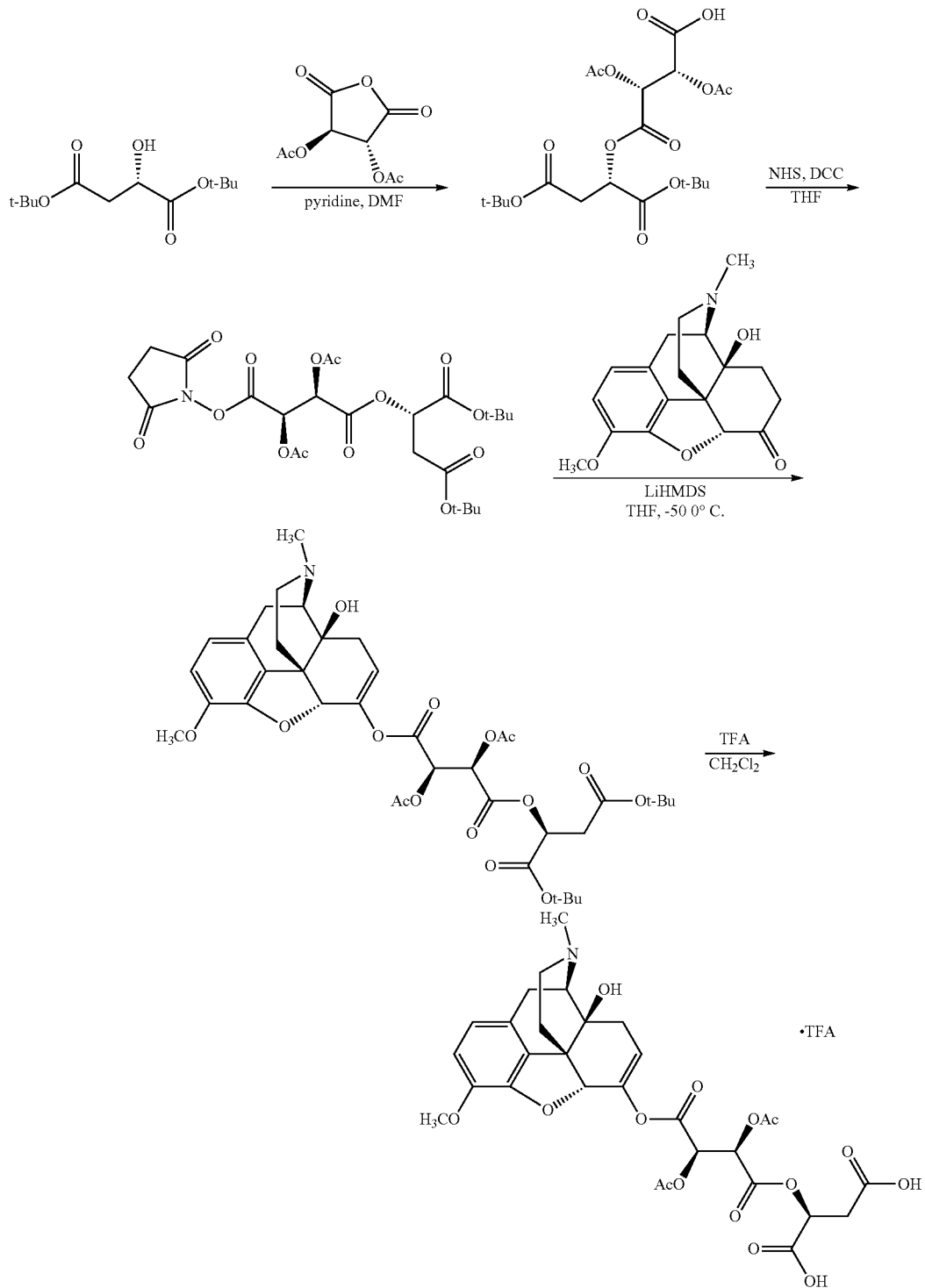

Preparation of (2R,3R)-2,3-Diacetoxy-4-(((S)-1,4-di-tert-butoxy-1,4-dioxobutan-2-yl)oxy)-4-oxobutanoic acid

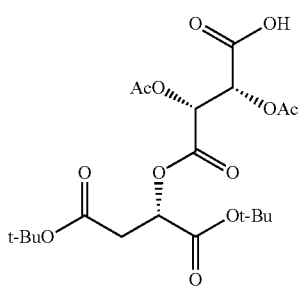 [SMILES: CC(=O)O[C@@H](C(=O)O)[C@@H](OC(C)=O)C(=O)O[C@@H](CC(=O)OC(C)(C)C)C(=O)OC(C)(C)C]

(S)-Di-tert-butyl 2-hydroxysuccinate (968 mg, 3.93 mmol), (3R,4R)-2,5-dioxotetrahydrofuran-3,4-diyl diacetate (1.06 g, 4.91 mmol), pyridine (279 mg, 3.54 mmol), and N,N-dimethylformamide (2 mL) were combined and stirred at 0° C. under a nitrogen atmosphere for 2 h. After this time, saturated sodium bicarbonate (15 mL) was added, and the resulting aqueous solution was washed with ethyl acetate (10 mL). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (2R,3R)-2,3-diacetoxy-4-(((S)-1,4-di-tert-butoxy-1,4-dioxobutan-2-yl)oxy)-4-oxobutanoic acid (1.74 g, 95%) as a yellow oil: $^1$H NMR (300 MHz, CDCl$_3$) δ 5.80 (d, J=3.0 Hz, 1H), 5.68 (d, J=3.0 Hz, 1H), 5.30 (dd, J=7.2, 5.1 Hz, 1H), 2.77-2.74 (m, 2H), 2.20 (s, 3H), 2.18 (s, 3H), 1.46 (s, 9H), 1.44 (s, 9H), CO$_2$H proton not observed.

Preparation of (2R,3R)-1-((S)-1,4-Di-tert-butoxy-1,4-dioxobutan-2-yl) 4-(2,5-dioxopyrrolidin-1-yl) 2,3-diacetoxysuccinate

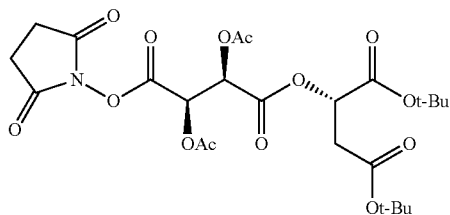 [SMILES: CC(=O)O[C@@H](C(=O)O[C@@H](CC(=O)OC(C)(C)C)C(=O)OC(C)(C)C)[C@@H](OC(C)=O)C(=O)ON1C(=O)CCC1=O]

A solution of (2R,3R)-2,3-diacetoxy-4-(((S)-1,4-di-tert-butoxy-1,4-dioxobutan-2-yl)oxy)-4-oxobutanoic acid (1.74 g, 3.76 mmol) in tetrahydrofuran (25 mL) was treated with N-hydroxysuccinimide (476 mg, 4.14 mmol) and N,N'-dicyclohexylcarbodiimide (929 mg, 4.51 mmol) and stirred under a nitrogen atmosphere for 4 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (2R,3R)-1-((S)-1,4-di-tert-butoxy-1,4-dioxobutan-2-yl) 4-(2,5-dioxopyrrolidin-1-yl) 2,3-diacetoxysuccinate (2.06 g) as a yellow solid: $^1$H NMR (300 MHz, CDCl$_3$) δ 6.04 (d, J=3.0 Hz, 1H), 5.95 (d, J=2.7 Hz, 1H), 5.32 (dd, J=8.1, 4.2 Hz, 1H), 2.85-2.74 (m, 6H), 2.25 (s, 3H), 2.23 (s, 3H), 1.46 (s, 9H), 1.44 (s, 9H).

Preparation of (2R,3R)-1-((S)-1,4-di-tert-Dutoxy-1,4-dioxobutan-2-yl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2,3-diacetoxysuccinate

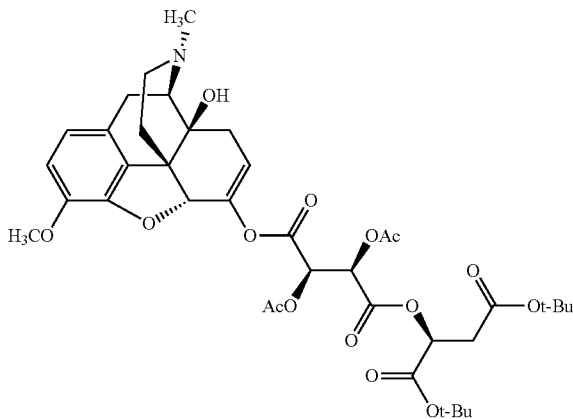

A suspension of oxycodone (380 mg, 1.22 mmol) in tetrahydrofuran (10 mL) was cooled to −50° C. and treated dropwise with a 1.0 M solution of lithium bis(trimethylsilyl)amide in tetrahydrofuran (1.3 mL, 1.3 mmol). After addition was complete, the mixture was stirred at −50° C. for 45 min. The mixture was treated dropwise with a solution of (2R,3R)-1-((S)-1,4-di-tert-butoxy-1,4-dioxobutan-2-yl) 4-(2,5-dioxopyrrolidin-1-yl) 2,3-diacetoxysuccinate (750 mg, 1.30 mmol) in tetrahydrofuran (8 mL). After addition was complete, the mixture was stirred at −50° C. for 30 min. After this time, the reaction mixture was treated with saturated aqueous ammonium chloride (15 mL) and extracted with ethyl acetate (3×15 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (2R,3R)-1-((S)-1,4-di-tert-butoxy-1,4-dioxobutan-2-yl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2,3-diacetoxysuccinate (120 mg, 11%) as a white solid: ESI MS m/z 760 [C$_{37}$H$_{49}$NO$_{15}$+H]$^+$.

541

Preparation of (S)-2-(((2R,3R)-2,3-Diacetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid trifluoroacetic acid salt

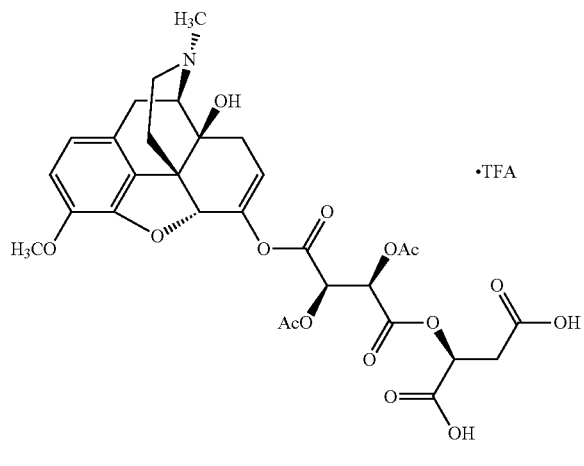

542

A solution of (2R,3R)-1-((S)-1,4-di-tert-butoxy-1,4-dioxobutan-2-yl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2,3-diacetoxysuccinate (0.12 g, 0.16 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (S)-2-(((2R,3R)-2,3-diacetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid trifluoroacetic acid salt (66 mg, 65%) as a white solid: $^1$H NMR (300 MHz, DMSO-$d_6$) δ 13.5 (s, 1H), 12.6 (s, 1H), 9.18 (s, 1H), 6.88 (d, J=8.1 Hz, 1H), 6.77 (d, J=8.1 Hz, 1H), 6.34 (s, 1H), 5.85 (d, J=2.7 Hz, 1H), 5.78 (d, J=2.7 Hz, 1H), 5.55 (dd, J=6.0, 2.1 Hz, 1H), 5.30 (dd, J=8.4, 3.6 Hz, 1H), 4.88 (s, 1H), 3.75 (s, 3H), 3.65 (d, J=6.0 Hz, 1H), 3.43 (d, J=20.1 Hz, 1H), 3.16-3.07 (m, 2H), 2.90-2.80 (m, 5H), 2.64-2.61 (m, 1H), 2.41-2.32 (m, 1H), 2.32-2.27 (m, 1H), 2.20 (s, 3H), 2.12 (s, 3H), 2.08 (d, J=18.3 Hz, 1H), 1.64 (d, J=11.7 Hz, 1H); ESI MS m/z 648 [$C_{30}H_{33}NO_{15}$+H]*, HPLC (Method A) 96.7% (AUC), $t_R$=8.23 min.

Scheme 73: (S)-4-((S)-1-Carboxy-3-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-2-oxopropoxy)-2-hydroxy-4-oxobutanoic acid trifluoroacetic acid salt

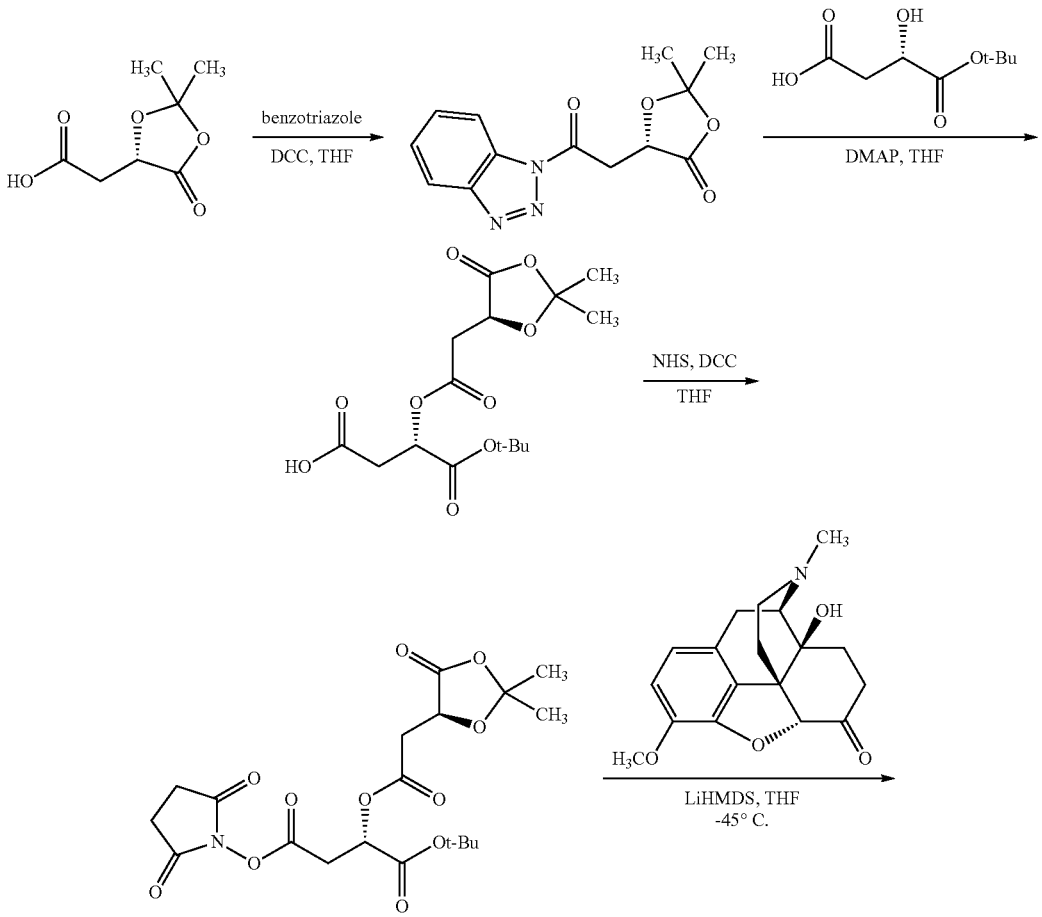

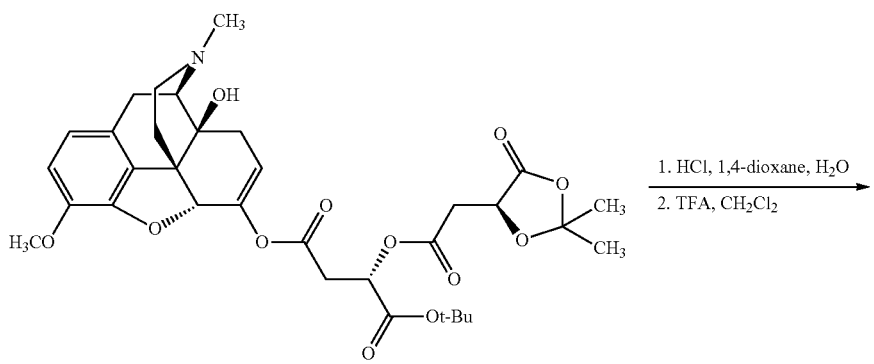

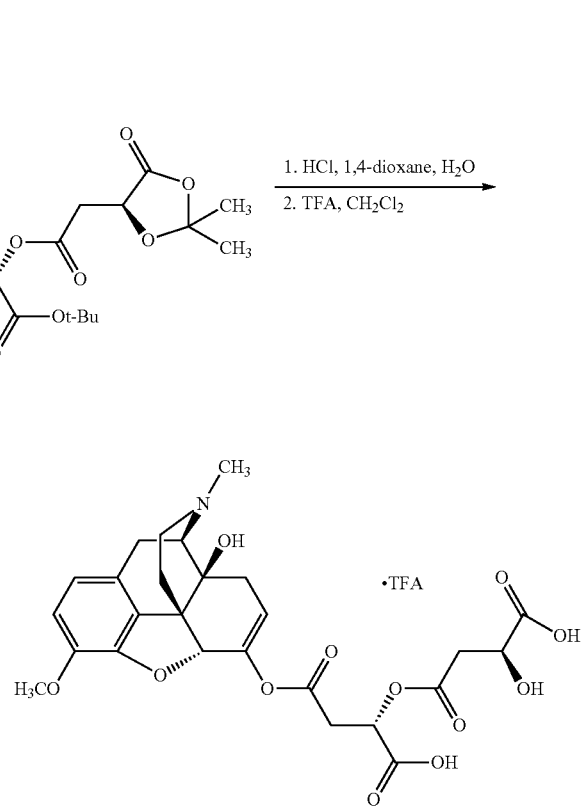

Preparation of (S)-5-(2-(1H-Benzo[d][1,2,3]triazol-1-yl)-2-oxoethyl)-2,2-dimethyl-1,3-dioxolan-4-one

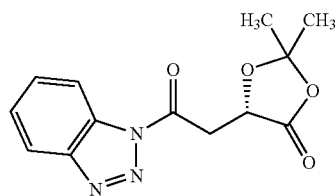 [SMILES: CC1(C)OC(=O)[C@H](CC(=O)n2nnc3ccccc32)O1]

A solution of (S)-2-(2,2-dimethyl-5-oxo-1,3-dioxolan-4-yl)acetic acid (1.51 g, 8.66 mmol) in tetrahydrofuran (40 mL) was treated with benzotriazole (1.14 g, 9.60 mmol) and N,N'-dicyclohexylcarbodiimide (2.00 g, 9.69 mmol) and stirred under a nitrogen atmosphere for 16 h. After this time, the reaction mixture was filtered to remove the solid dicyclohexylurea byproduct. The solid was washed with diethyl ether, and the combined filtrate and washings were concentrated under reduced pressure to provide (S)-5-(2-(1H-benzo[d][1,2,3]triazol-1-yl)-2-oxoethyl)-2,2-dimethyl-1,3-dioxolan-4-one (2.99 g, quantitative) as a white solid: $^1$H NMR (300 MHz, DMSO-$d_6$) δ 8.30-8.23 (m, 2H), 7.84-7.79 (m, 1H), 7.67-7.61 (m, 1H), 5.19 (dd, J=6.0, 3.9 Hz, 1H), 4.17 (dd, J=18.0, 3.9 Hz, 1H), 3.91 (dd, J=18.0, 6.0 Hz, 1H), 1.59 (s, 6H).

Preparation of (S)-4-(tert-Butoxy)-3-(2-((S)-2,2-dimethyl-5-oxo-1,3-dioxolan-4-yl)acetoxy)-4-oxobutanoic acid

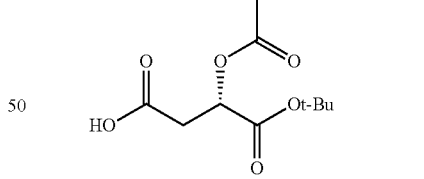

A solution of (S)-4-(tert-butoxy)-3-hydroxy-4-oxobutanoic acid (1.46 g, 7.69 mmol) in tetrahydrofuran (15 mL) was cooled in an ice bath under a nitrogen atmosphere and treated with a solution of (S)-5-(2-(1H-benzo[d][1,2,3]triazol-1-yl)-2-oxoethyl)-2,2-dimethyl-1,3-dioxolan-4-one (2.38 g, 8.66 mmol) in tetrahydrofuran (15 mL) followed by 4-dimethylaminopyridine (953 mg, 7.80 mmol). After 10 min, the ice bath was removed, and the mixture was stirred at ambient temperature for 48 h. After this time, the reaction mixture was diluted with ethyl acetate (100 mL), washed with aqueous 10% citric acid (50 mL) and brine (25 mL), dried over sodium sulfate, filtered, and concentrated under reduced pressure. The crude residue was purified by column chromatography (silica gel, 0-10% methanol/methylene chloride) to provide (S)-4-(tert-butoxy)-3-(2-((S)-2,2-dimethyl-5-oxo-1,3-dioxolan-4-yl)acetoxy)-4-oxobutanoic acid (1.09 g, 41%) as a colorless oil: $^1$H NMR (300 MHz, DMSO-$d_6$) δ 12.62 (s, 1H), 5.14 (dd, J=7.8, 4.8 Hz, 1H), 4.85 (overlapping dd, J=4.5, 4.5 Hz, 1H), 2.84-2.67 (m, 4H), 1.53 (s, 6H), 1.40 (s, 9H).

Preparation of (S)-1-tert-Butyl 4-(2,5-dioxopyrrolidin-1-yl) 2-(2-((S)-2,2-dimethyl-5-oxo-1,3-dioxolan-4-yl)acetoxy)succinate

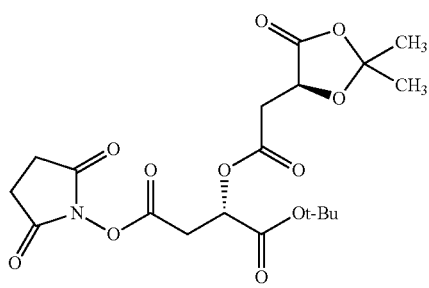 [SMILES: CC(C)(C)OC(=O)[C@H](CC(=O)ON1C(=O)CCC1=O)OC(=O)C[C@@H]1OC(C)(C)OC1=O]

A solution of (S)-4-(tert-butoxy)-3-(2-((S)-2,2-dimethyl-5-oxo-1,3-dioxolan-4-yl)acetoxy)-4-oxobutanoic acid (1.04 g, 3.01 mmol) in tetrahydrofuran (30 mL) was treated with N-hydroxysuccinimide (383 mg, 3.33 mmol) and N,N'-dicyclohexylcarbodiimide (687 mg, 3.33 mmol) and stirred under a nitrogen atmosphere for 16 h. After this time, the reaction mixture was filtered to remove the solid dicyclohexylurea byproduct. The solid was washed with diethyl ether, and the combined filtrate and washings were concentrated under reduced pressure to provide (S)-1-tert-butyl 4-(2,5-dioxopyrrolidin-1-yl) 2-(2-((S)-2,2-dimethyl-5-oxo-1,3-dioxolan-4-yl)acetoxy)succinate (1.46 g, quantitative) as a white semi-solid. The material used without further purification.

Preparation of (S)-1-tert-Butyl 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-(2-((S)-2,2-dimethyl-5-oxo-1,3-dioxolan-4-yl)acetoxy)succinate

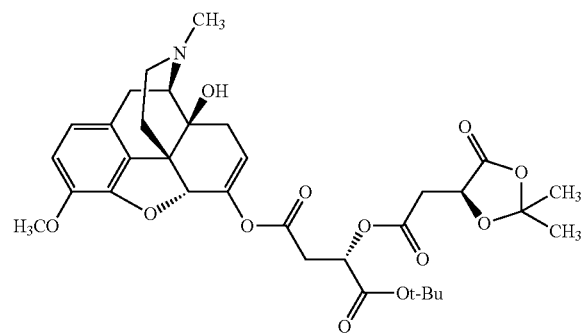 [SMILES: COc1ccc2c3c1O[C@H]1C(OC(=O)C[C@H](OC(=O)C[C@@H]4OC(C)(C)OC4=O)C(=O)OC(C)(C)C)=CC[C@@]4(O)[C@@H](C2)N(C)CC[C@]314]

A suspension of oxycodone (493 mg, 1.56 mmol) in tetrahydrofuran (7 mL) was cooled in an ice bath and treated dropwise with a 1.0 M solution of lithium bis(trimethylsilyl) amide in tetrahydrofuran (1.8 mL, 1.8 mmol). After stirring at 0° C. for 30 min, the ice bath was replaced with a dry ice/acetonitrile bath (−45° C.). The mixture was treated dropwise with a solution of (S)-1-tert-butyl 4-(2,5-dioxopyrrolidin-1-yl) 2-(2-((S)-2,2-dimethyl-5-oxo-1,3-dioxolan-4-yl)acetoxy)succinate (745 mg, 1.68 mmol) in tetrahydrofuran (8 mL). The dry ice was removed from the acetonitrile bath, and the bath temperature increased to −10° C. over 30 min. After this time, the reaction mixture was treated with chilled saturated aqueous ammonium chloride (25 mL) and extracted with ethyl acetate (2×25 mL). The combined organics were washed with brine (25 mL), dried over sodium sulfate, filtered, and concentrated under reduced pressure. The crude residue was purified by reversed phase column chromatography (150 g C18 column, 10-100% acetonitrile/water) and freeze dried to provide (S)-1-tert-butyl 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-(2-((S)-2,2-dimethyl-5-oxo-1,3-dioxolan-4-yl)acetoxy)succinate (146 mg, 15%) as a fluffy white solid: ESI MS m/z 644 [$C_{33}H_{41}NO_{12}$+H]$^+$.

Preparation of (S)-4-((S)-1-Carboxy-3-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-3-oxopropoxy)-2-hydroxy-4-butanoic acid trifluoroacetic acid salt

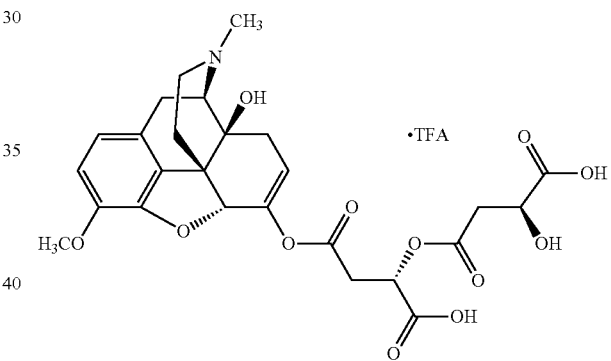

A solution of (S)-1-tert-butyl 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-(2-((S)-2,2-dimethyl-5-oxo-1,3-dioxolan-4-yl)acetoxy)succinate (145 mg, 0.225 mmol) in 1,4-dioxane (4 mL) was treated with a 4.0 M solution of hydrogen chloride in 1,4-dioxane (0.4 mL) followed by water (4 drops) and stirred under a nitrogen atmosphere at ambient temperature for 2 h. Additional hydrogen chloride solution (0.4 mL) was added, and the mixture was stirred for 1 h. After this time, the reaction mixture was partially concentrated under reduced pressure, diluted with acetonitrile and water, and freeze-dried. The residue was suspended in methylene chloride (3 mL) was treated with trifluoroacetic acid (1 mL) and stirred under a nitrogen atmosphere at ambient temperature for 2 h. After this time, the reaction mixture was concentrated under reduced pressure. The residue was purified by reversed phase column chromatography (50 g C18 column, 10-30% acetonitrile/water with 0.1% trifluoroacetic acid) and freeze dried to provide (S)-4-((S)-1-carboxy-3-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-3-oxopropoxy)-2-hydroxy-4-oxobutanoic acid trifluoroacetic acid salt (88 mg, 59%) as a fluffy white solid: $^1$H NMR (300 MHz, DMSO-$d_6$) δ 13.41 (br s, 1H), 12.69 (br s, 1H), 9.19 (br s, 1H), 6.86 (d, J=8.4 Hz, 1H), 6.75 (d, J=8.1 Hz, 1H), 6.31 (br s, 1H), 5.57 (dd, J=5.7, 1.5 Hz, 1H), 5.55 (br s, 1H), 5.30 (dd, J=7.8, 4.5 Hz, 1H), 4.99 (s, 1H), 4.32 (dd, J=7.8, 4.2 Hz, 1H), 3.75 (s, 3H), 3.65 (d, J=6.3 Hz, 1H), 3.43 (d, J=20.1 Hz, 1H), 3.16-2.95 (m, 4H), 2.84 (s, 3H), 2.81-2.58 (m, 3H), 2.49-2.43 (m, 1H, partially obscured by solvent peak), 2.32-2.24 (m, 1H), 2.07 (apparent d, J=18.0 Hz, 1H), 1.64 (d, J=11.1 Hz, 1H); ESI MS m/z 548 $[C_{26}H_{29}NO_{12}+H]^+$; HPLC (Method A) 92.0% (AUC), $t_R$=7.23 min.

Scheme 74: (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((3-((S)-pyrrolidine-2-carboxamido)propanoyl)oxy)propanoate bis(trifluoroacetic acid salt)

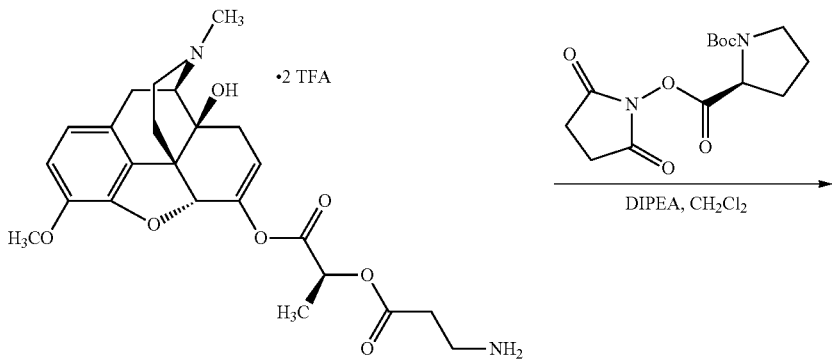

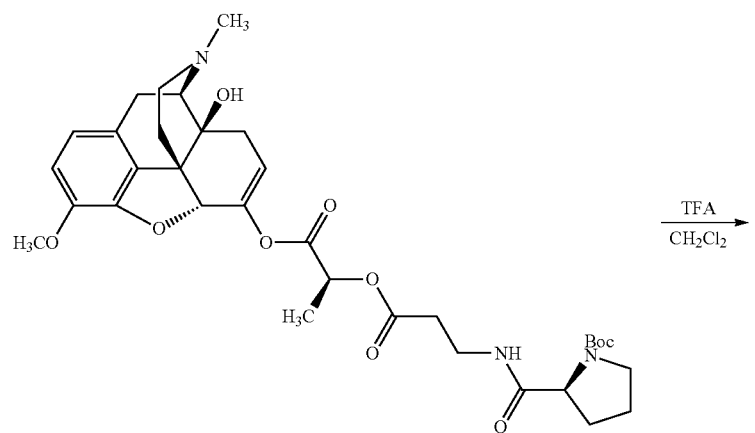

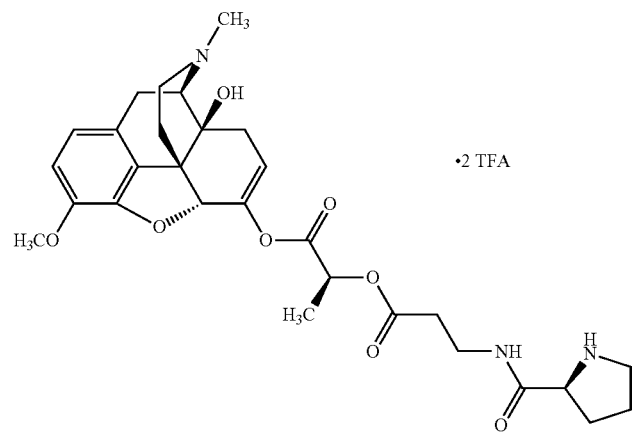

549

Preparation of (S)-tert-Butyl 2-((3-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)carbamoyl)pyrrolidine-1-carboxylate

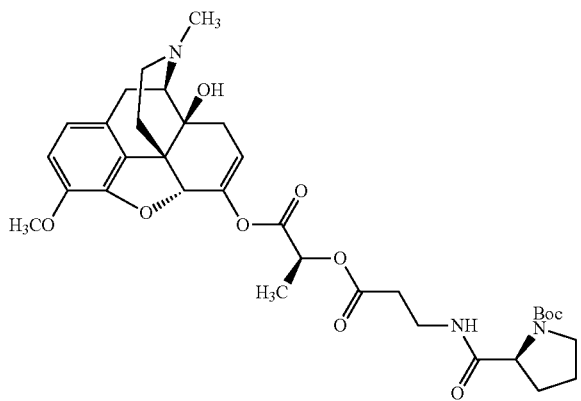 [SMILES: COc1ccc2c3c1O[C@H]1C(OC(=O)[C@H](C)OC(=O)CCNC(=O)[C@@H]4CCCN4C(=O)OC(C)(C)C)=CC[C@@]4(O)[C@@H](C2)N(C)CC[C@]314]

A suspension (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-aminopropanoyl)oxy)propanoate bis(2,2,2-trifluoroacetate) (125 mg, 0.182 mmol) and (S)-1-tert-butyl 2-(2,5-dioxopyrrolidin-1-yl) pyrrolidine-1,2-dicarboxylate (86 mg, 0.275 mmol) in methylene chloride (3 mL) was treated with N,N-diisopropylethylamine (0.13 mL, 0.75 mmol) and stirred under a nitrogen atmosphere for 30 min. After this time, the reaction mixture was diluted with methylene chloride (15 mL) and washed with saturated aqueous ammonium chloride (10 mL). The organic layer was dried over sodium sulfate, filtered, and concentrated under reduced pressure to provide (S)-tert-butyl 2-((3-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)carbamoyl)pyrrolidine-1-carboxylate (127 mg, quantitative) as a colorless semi-solid: ESI MS m/z 656 $[C_{34}H_{45}N_3O_{10}+H]^+$.

550

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((3-((S)-pyrrolidine-2-carboxamido)propanoyl)oxy) propanoate bis(trifluoroacetic acid salt)

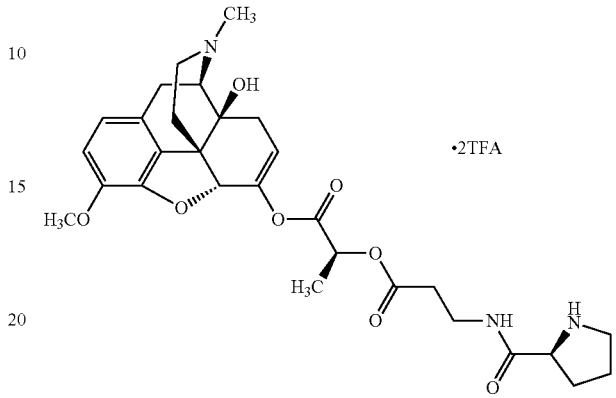

A solution of (S)-tert-butyl 2-((3-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)carbamoyl)pyrrolidine-1-carboxylate (119 mg, 0.182 mmol) in methylene chloride (2 mL) was treated with trifluoroacetic acid (1 mL) and stirred under a nitrogen atmosphere at ambient temperature for 30 min. After this time, the reaction mixture was concentrated under reduced pressure. The residue was purified by reversed phase column chromatography (50 g C18 column, 5-70% acetonitrile/water with 0.1% trifluoroacetic acid) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-((S)-pyrrolidine-2-carboxamido)propanoyl)oxy) propanoate bis(trifluoroacetic acid salt)(67 mg, 47%) as a white solid: $^1$H NMR (300 MHz, DMSO-$d_6$) δ 9.20 (br s, 2H), 8.61 (t, J=5.7 Hz, 1H), 8.54 (br s, 1H), 6.86 (d, J=8.4 Hz, 1H), 6.76 (d, J=8.1 Hz, 1H), 6.31 (br s, 1H), 5.59 (dd, J=6.0, 2.1 Hz, 1H), 5.12 (q, J=7.2 Hz, 1H), 5.00 (s, 1H), 4.13-4.09 (m, 1H), 3.76 (s, 3H), 3.66 (d, J=6.0 Hz, 1H), 3.51-3.29 (m, 4H), 3.22-3.07 (m, 4H), 2.85 (apparent d, J=4.5 Hz, 3H), 2.70-2.58 (m, 2H), 2.49-2.41 (m, 1H, partially obscured by solvent peak), 2.34-2.19 (m, 2H), 2.06 (apparent d, J=18.0 Hz, 1H), 1.92-1.77 (m, 3H), 1.64 (d, J=11.1 Hz, 1H), 1.51 (d, J=6.9 Hz, 3H); ESI MS m/z 556 $[C_{29}H_{37}N_3O_8+H]^+$; HPLC (Method A) 97.4% (AUC), $t_R$=7.32 min.

Scheme 75: (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((3-((S)-2-acetamido-6-aminohexanamido)propanoyl)oxy)propanoate bis(trifluoroacetic acid salt)

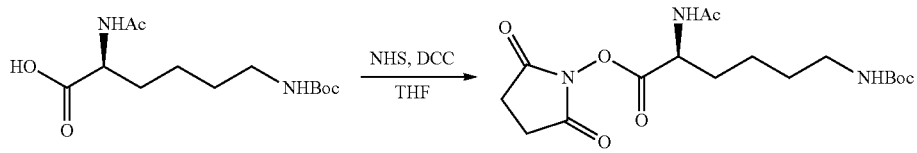

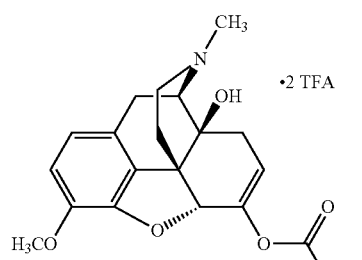
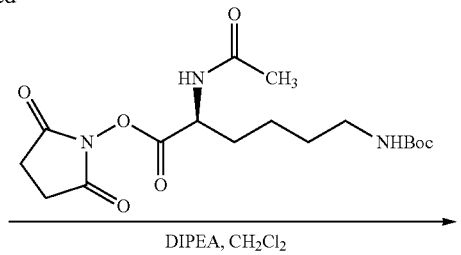

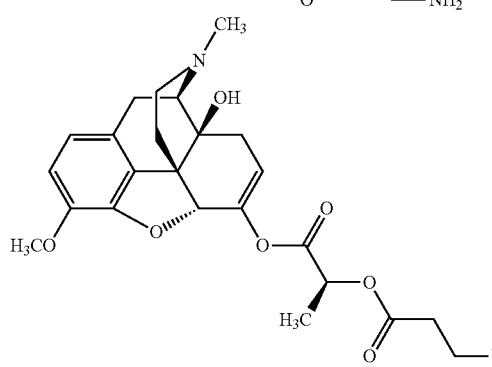

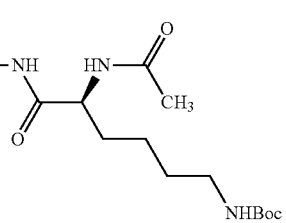

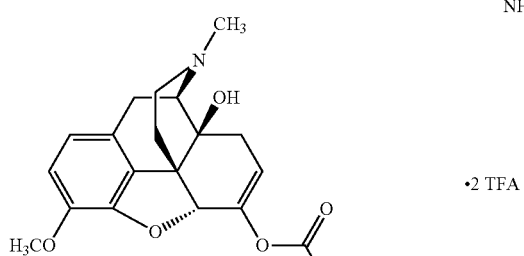

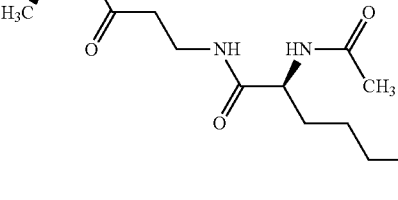

Preparation of (S)-2,5-Dioxopyrrolidin-1-yl 2-acetamido-6-((tert-butoxycarbonyl)amino)hexanoate

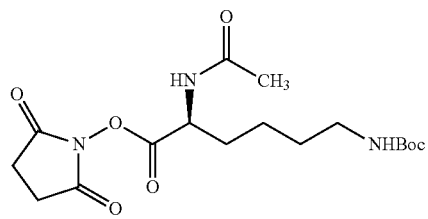 [SMILES: CC(=O)N[C@@H](CCCCNC(=O)OC(C)(C)C)C(=O)ON1C(=O)CCC1=O]

A solution of (S)-2-acetamido-6-((tert-butoxycarbonyl)amino)hexanoic acid (1.00 g, 3.47 mmol) in tetrahydrofuran (20 mL) was treated with N-hydroxysuccinimide (439 mg, 3.81 mmol) and N,N'-dicyclohexylcarbodiimide (785 mg, 3.81 mmol) and stirred under a nitrogen atmosphere for 2 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-2,5-dioxopyrrolidin-1-yl 2-acetamido-6-((tert-butoxycarbonyl)amino)hexanoate (1.49 mg) as a white solid: $^1$H NMR (300

MHz, CDCl$_3$) δ 6.27 (m, 1H), 4.94 (m, 1H), 4.69 (m, 1H), 3.15-3.13 (m, 2H), 2.87 (s, 4H), 2.08 (s, 3H), 2.02-1.83 (m, 2H), 1.55-1.22 (m, 4H), 1.45 (s, 9H).

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((3-((S)-2-acetamido-6-((tert-butoxycarbonyl)amino)hexanamido)propanoyl)oxy)propanoate

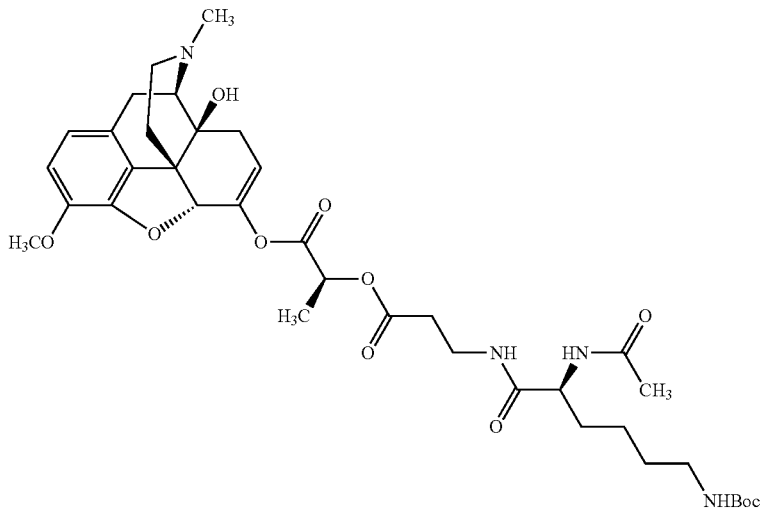 [SMILES: COc1ccc2c3c1O[C@H]1C(OC(=O)[C@H](C)OC(=O)CCNC(=O)[C@H](CCCCNC(=O)OC(C)(C)C)NC(C)=O)=CC[C@@]4(O)[C@@H](C2)N(C)CC[C@]314]

A suspension (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-aminopropanoyl)oxy)propanoate bis(2,2,2-trifluoroacetate) (166 mg, 0.242 mmol) and (S)-2,5-dioxopyrrolidin-1-yl 2-acetamido-6-((tert-butoxycarbonyl)amino)hexanoate (141 mg, 0.366 mmol) in methylene chloride (3 mL) was treated with N,N-diisopropylethylamine (0.17 mL, 0.98 mmol) and stirred under a nitrogen atmosphere for 30 min. After this time, the reaction mixture was diluted with methylene chloride (15 mL) and washed with saturated aqueous ammonium chloride (10 mL). The organic layer was dried over sodium sulfate, filtered, and concentrated under reduced pressure to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-((S)-2-acetamido-6-((tert-butoxycarbonyl)amino)hexanamido)propanoyl)oxy)propanoate (181 mg, quantitative) as a colorless semi-solid: ESI MS m/z 729 [C$_{37}$H$_{52}$N$_4$O$_{11}$+H]$^+$.

Preparation of (S)-(4R,4aS,7aR,12bS)-4a-Hydroxy-9-methoxy-3-methyl-2,3,4,4a,5,7a-hexahydro-H-4,12-methanobenzofuro[3,2-e]isoquinolin-7-yl 2-((3-((S)-2-acetamido-6-aminohexanamido)propanoyl)oxy)propanoate bis(trifluoroacetic acid salt)

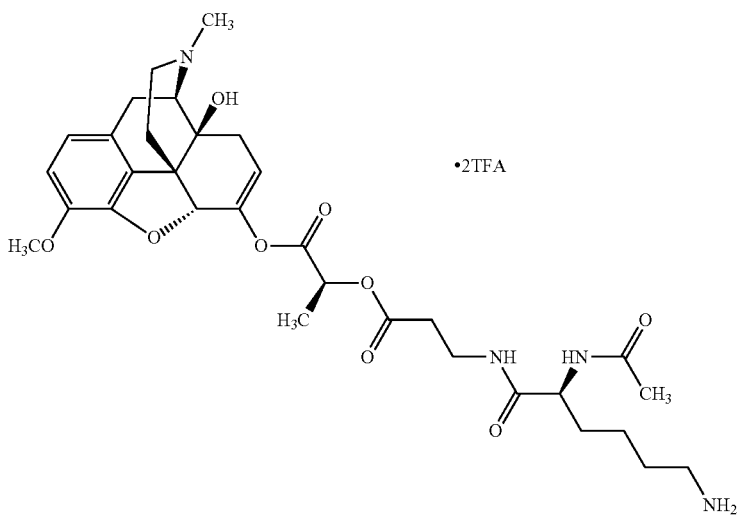 [SMILES: COc1ccc2c3c1O[C@H]1C(OC(=O)[C@H](C)OC(=O)CCNC(=O)[C@H](CCCCN)NC(C)=O)=CC[C@@]4(O)[C@@H](C2)N(C)CC[C@]314]

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-((S)-2-acetamido-6-((tert-butoxycarbonyl)amino)hexanamido)propanoyl)oxy)propanoate (176 mg, 0.242 mmol) in methylene chloride (2 mL) was treated with trifluoroacetic acid (1 mL) and stirred under a nitrogen atmosphere at ambient temperature for 30 min. After this time, the reaction mixture was concentrated under reduced pressure. The residue was purified by reversed phase column chromatography (50 g C18 column, 5-70% acetonitrile/water with 0.1% trifluoroacetic acid) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-((S)-2-acetamido-6-aminohexanamido)propanoyl)oxy)propanoate bis(trifluoroacetic acid salt)(94 mg, 44%) as a white solid: $^1$H NMR (300 MHz, DMSO-$d_6$) δ 9.19 (br s, 1H), 8.05-7.98 (m, 2H), 7.65 (br s, 3H), 6.86 (d, J=8.4 Hz, 1H), 6.76 (d, J=8.4 Hz, 1H), 6.32 (s, 1H), 5.59 (dd, J=5.7, 1.8 Hz, 1H), 5.10 (q, J=6.9 Hz, 1H), 5.00 (s, 1H), 4.19-4.12 (m, 1H), 3.75 (s, 3H), 3.66 (d, J=6.0 Hz, 1H), 3.43 (d, J=19.8 Hz, 1H), 3.35-3.25 (m, 2H), 3.16-3.07 (m, 2H), 2.85 (apparent d, J=4.5 Hz, 3H), 2.79-2.70 (m, 2H), 2.65-2.53 (m, 3H, partially obscured by solvent peak), 2.49-2.43 (m, 1H, partially obscured by solvent peak), 2.34-2.26 (m, 1H), 2.06 (apparent d, J=18.3 Hz, 1H), 1.84 (s, 3H), 1.67-1.40 (m, 8H), 1.33-1.20 (m, 2H);ESI MS m/z 629 $[C_{32}H_{44}N_4O_9+H]^+$; HPLC (Method A)>99% (AUC), $t_R$=7.16 min.

Scheme 76: 4-(((S)-4-Ethoxy-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1,4-dioxobutan-2-yl)oxy)-4-oxobutanoic acid trifluoroacetic acid salt

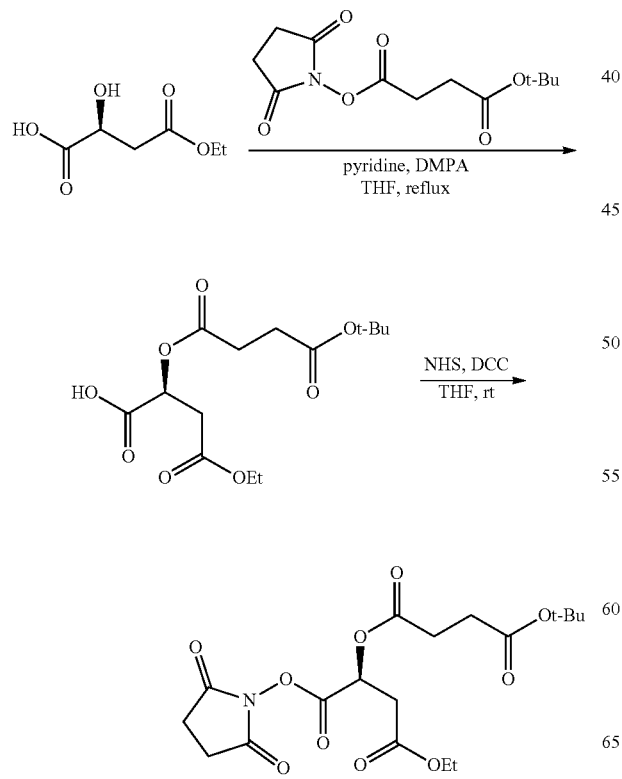

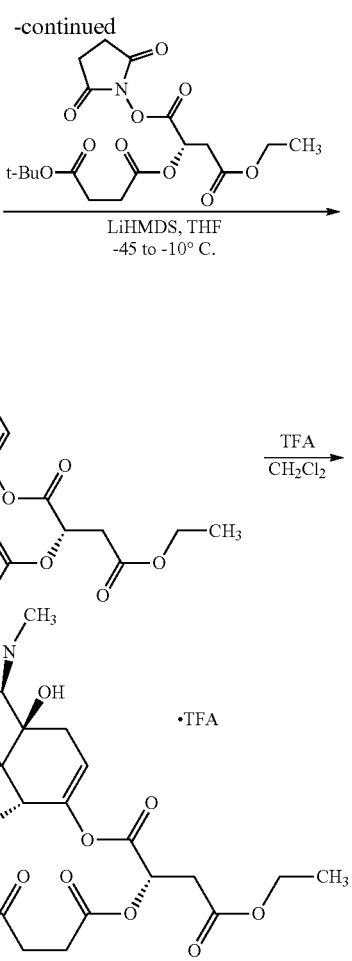

Preparation of (S)-2-((4-(tert-Butoxy)-4-oxobutanoyl)oxy)-4-ethoxy-4-oxobutanoic acid A mixture of (S)-4-ethoxy-2-hydroxy-4-oxobutanoic acid (1.51 g, 9.32 mmol), tert-butyl (2,5-dioxopyrrolidin-1-yl) succinate (2.65 g, 9.78 mmol), pyridine (1.0 mL, 12 mmol), and 4-dimethylaminopyridine (150 mg, 1.23 mmol) in tetrahydrofuran (40 mL) was stirred at reflux for 24 h. After this time, the mixture was cooled to room temperature and concentrated under reduced pressure. The residue was dissolved in ethyl acetate, washed with 10% citric acid, and extracted with saturated sodium bicarbonate. The aqueous layer was collected, carefully treated with 6N hydrochloric acid until acidic by pH paper analysis, and then extracted with ethyl acetate. The organic extracts were dried over sodium sulfate, filtered, and concentrated to provide (S)-2-((4-(tert-butoxy)-4-oxobutanoyl)oxy)-4-ethoxy-4-oxobutanoic acid (1.47 g, 49%): $^1$H NMR (300 MHz, CDCl$_3$) δ 5.56 (t, J=6.0 Hz, 1H), 4.19 (q, J=7.1 Hz, 2H), 2.93 (d, J=6.0 Hz, 2H), 2.71-2.52 (m, 4H), 1.44 (s, 9H), 1.27 (t, J=7.1 Hz, 3H), CO$_2$H proton not observed.

Preparation of (S)-1-(2,5-Dioxopyrrolidin-1-yl) 4-ethyl 2-((4-(tert-butoxy)-4-oxobutanoyl)oxy)succinate

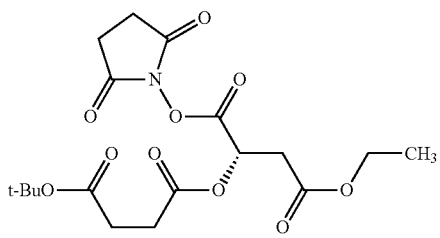 [SMILES: CCOC(=O)C[C@H](OC(=O)CCC(=O)OC(C)(C)C)C(=O)ON1C(=O)CCC1=O]

A mixture of (S)-2-((4-(tert-butoxy)-4-oxobutanoyl)oxy)-4-ethoxy-4-oxobutanoic acid (1.40 g, 4.40 mmol) and N-hydroxysuccinimide (560 mg, 4.87 mmol) in tetrahydrofuran (25 mL) was treated with N,N'-dicyclohexylcarbodiimide (1.00 g, 4.85 mmol), and the reaction mixture was stirred at ambient temperature for 4 h. After this time, diethyl ether (20 mL) was added, and the mixture was filtered. The filtrate was concentrated under reduced pressure to provide (S)-1-(2,5-dioxopyrrolidin-1-yl) 4-ethyl 2-((4-(tert-butoxy)-4-oxobutanoyl)oxy)succinate (1.9 g) that was used without purification: $^1$H NMR (300 MHz, CDCl$_3$) δ 5.82 (dd, J=7.1, 5.2 Hz, 1H), 4.22 (dd, J=7.1 Hz, 2H), 3.05-3.03 (m, 2H), 2.84 (s, 4H), 2.72-2.65 (m, 2H), 2.60-2.53 (m, 2H), 1.44 (s, 9H), 2.28 (t, J=7.1 Hz, 3H).

Preparation of (S)-4-Ethyl 1-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-((4-(tert-butoxy)-4-oxobutanoyl)oxy)succinate

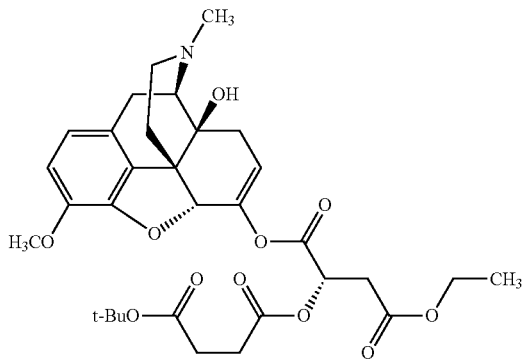 [SMILES: CCOC(=O)C[C@H](OC(=O)CCC(=O)OC(C)(C)C)C(=O)OC1=CC[C@@]2(O)[C@H]3Cc4ccc(OC)c5c4[C@@]2(CCN3C)[C@H]1O5]

A suspension of oxycodone (984 mg, 3.12 mmol) in tetrahydrofuran (15 mL) was cooled in an ice bath and treated dropwise with a 1.0 M solution of lithium bis(trimethylsilyl)amide in tetrahydrofuran (3.7 mL, 3.7 mmol). After stirring at 0° C. for 30 min, the ice bath was replaced with a dry ice/acetonitrile bath (−45° C.). The mixture was treated dropwise with a solution of (S)-1-(2,5-dioxopyrrolidin-1-yl) 4-ethyl 2-((4-(tert-butoxy)-4-oxobu- tanoyl)oxy)succinate (1.55 g, 3.74 mmol) in tetrahydrofuran (15 mL). The dry ice was removed from the acetonitrile bath, and the bath temperature increased to −10° C. over 30 min. After this time, the reaction mixture was treated with chilled saturated aqueous ammonium chloride (50 mL) and extracted with ethyl acetate (2×50 mL). The combined organics were washed with brine (50 mL), dried over sodium sulfate, filtered, and concentrated under reduced pressure. The crude residue was purified by reversed phase column chromatography (150 g C18 column, 10-100% acetonitrile/water) and freeze dried to provide (S)-4-ethyl 1-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-((4-(tert-butoxy)-4-oxobutanoyl)oxy)succinate (177 mg, 9%) as a white solid: ESI MS m/z 616 [C$_{32}$H$_{41}$NO$_{11}$+H]$^+$.

Preparation of 4-(((S)-4-Ethoxy-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1,4-dioxobutan-2-yl)oxy)-4-oxobutanoic acid trifluoroacetic acid salt

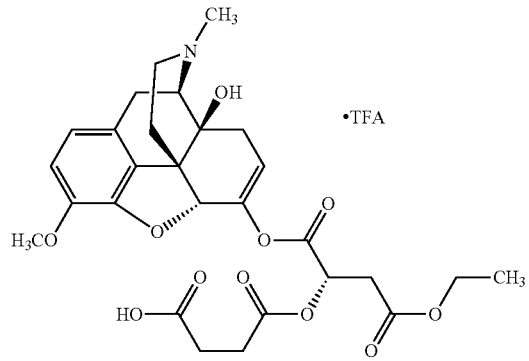 [SMILES: CCOC(=O)C[C@H](OC(=O)CCC(=O)O)C(=O)OC1=CC[C@@]2(O)[C@H]3Cc4ccc(OC)c5c4[C@@]2(CCN3C)[C@H]1O5]

A solution of (S)-4-ethyl 1-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-((4-(tert-butoxy)-4-oxobutanoyl)oxy)succinate (175 mg, 0.284 mmol) in methylene chloride (3 mL) was treated with trifluoroacetic acid (1 mL) and stirred under a nitrogen atmosphere at ambient temperature for 4 h. After this time, the reaction mixture was concentrated under reduced pressure. The residue was purified by reversed phase column chromatography (50 g C18 column, 10-80% acetonitrile/water with 0.1% trifluoroacetic acid) and freeze dried to provide 4-(((S)-4-ethoxy-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1,4-dioxobutan-2-yl)oxy)-4-oxobutanoic acid trifluoroacetic acid salt (124 mg, 65%) as a white solid: $^1$H NMR (300 MHz, DMSO-d$_6$) δ 12.28 (br s, 1H), 9.19 (br s, 1H), 6.85 (d, J=8.4 Hz, 1H), 6.75 (d, J=8.4 Hz, 1H), 6.31 (s, 1H), 5.61 (dd, J=5.7, 1.8 Hz, 1H), 5.47 (t, J=5.4 Hz, 1H), 4.96 (s, 1H), 4.13 (q, J=6.9 Hz, 2H), 3.74 (s, 3H), 3.65 (d, J=6.0 Hz, 1H), 3.43 (d, J=19.8 Hz, 1H), 3.16-3.07 (m, 2H), 2.98 (d, J=6.6 Hz, 2H), 2.84 (apparent d, J=4.8 Hz, 3H), 2.69-2.58 (m, 3H), 2.49-2.43 (m, 1H, partially obscured by solvent peak), 2.34-2.26 (m, 1H), 2.07 (apparent d, J=18.3 Hz, 1H), 1.65 (d, J=10.8 Hz, 1H), 1.21 (t, J=6.9 Hz, 3H), two protons obscured by the solvent peaks; ESI MS m/z 560 [C$_{28}$H$_{33}$NO$_{11}$+H]$^+$; HPLC (Method A)>99% (AUC), t$_R$=8.78 min.

Scheme 77: (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((3-((S)-2-amino-4-methylpentanamido)propanoyl)oxy)propanoate bis(trifluoroacetic acid salt)
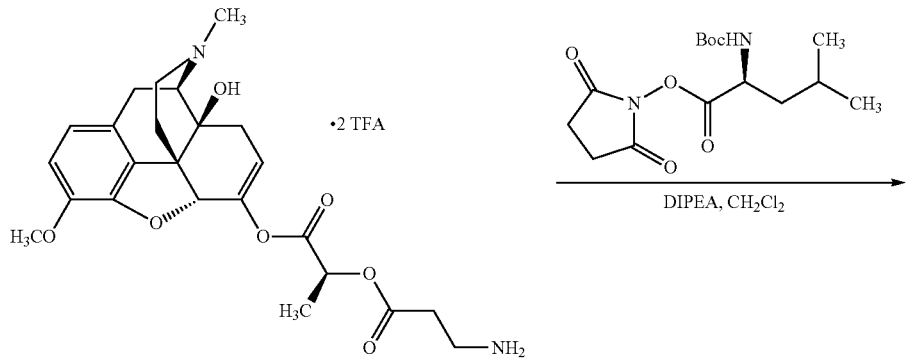
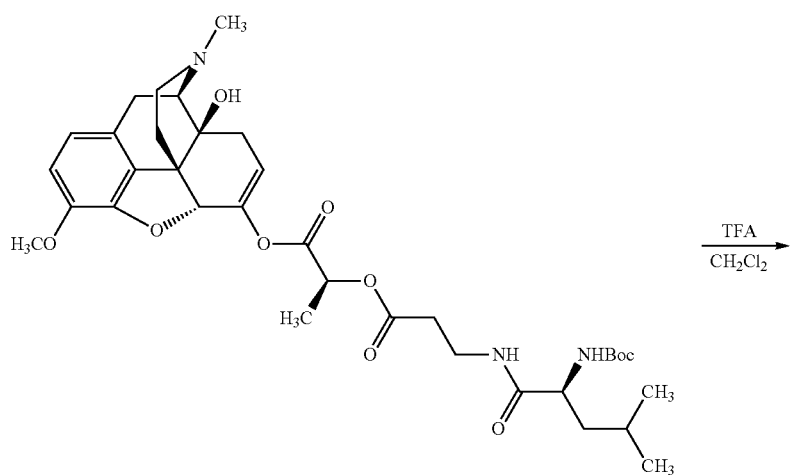
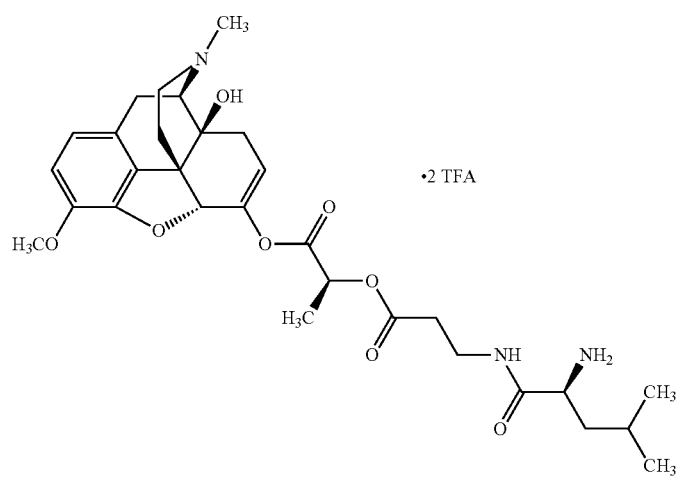

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((3-((S)-2-((tert-butoxycarbonyl)amino)-4-methylpentanamido)propanoyl)oxy)propanoate

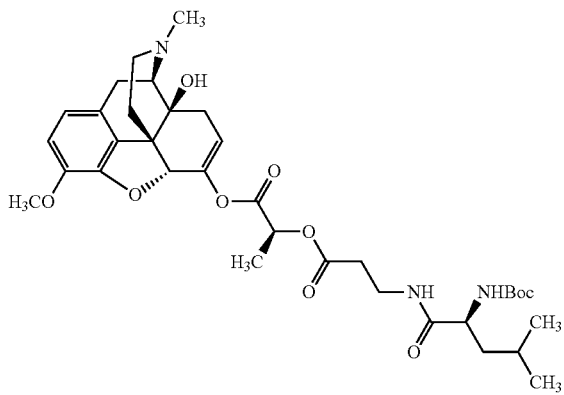 [SMILES: COc1ccc2c3c1O[C@H]1C(OC(=O)[C@H](C)OC(=O)CCNC(=O)[C@H](CC(C)C)NC(=O)OC(C)(C)C)=CC[C@@]4(O)[C@@H](C2)N(C)CC[C@]314]

A suspension (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-aminopropanoyl)oxy)propanoate bis(2,2,2-trifluoroacetate) (104 mg, 0.152 mmol) and (S)-2,5-dioxopyrrolidin-1-yl 2-((tert-butoxycarbonyl)amino)-4-methylpentanoate (75 mg, 0.23 mmol) in methylene chloride (2 mL) was treated with N,N-diisopropylethylamine (0.11 mL, 0.63 mmol) and stirred under a nitrogen atmosphere for 30 min. After this time, the reaction mixture was diluted with methylene chloride (15 mL) and washed with saturated aqueous ammonium chloride (10 mL). The organic layer was dried over sodium sulfate, filtered, and concentrated under reduced pressure to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-((S)-2-((tert-butoxycarbonyl)amino)-4-methylpentanamido)propanoyl)oxy)propanoate (100 mg, 98%) as a colorless semi-solid: ESI MS m/z 672 $[C_{35}H_{49}N_3O_{10}+H]^+$.

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((3-((S)-2-amino-4-methylpentanamido)propanoyl)oxy)propanoate bis(trifluoroacetic acid salt)

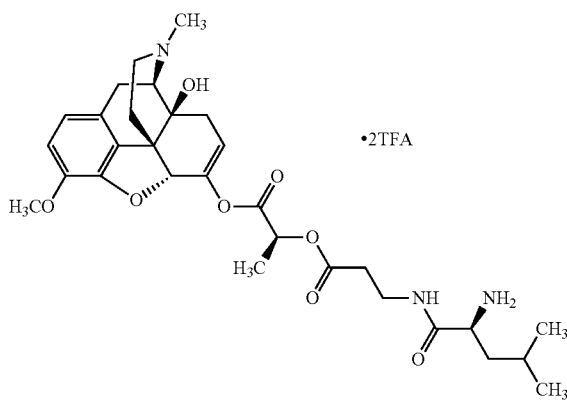 [SMILES: COc1ccc2c3c1O[C@H]1C(OC(=O)[C@H](C)OC(=O)CCNC(=O)[C@@H](N)CC(C)C)=CC[C@@]4(O)[C@@H](C2)N(C)CC[C@]314]

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-((S)-2-((tert-butoxycarbonyl)amino)-4-methylpentanamido)propanoyl)oxy)propanoate (100 mg, 0.149 mmol) in methylene chloride (2 mL) was treated with trifluoroacetic acid (1 mL) and stirred under a nitrogen atmosphere at ambient temperature for 45 min. After this time, the reaction mixture was concentrated under reduced pressure. The residue was purified by reversed phase column chromatography (50 g C18 column, 10-80% acetonitrile/water with 0.1% trifluoroacetic acid) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-((S)-2-amino-4-methylpentanamido)propanoyl)oxy)propanoate bis(trifluoroacetic acid salt)(57 mg, 48%) as a white solid: $^1$H NMR (300 MHz, DMSO-$d_6$) δ 9.19 (br s, 1H), 8.63 (t, J=5.4 Hz, 1H), 8.11 (br s, 3H), 6.86 (d, J=8.4 Hz, 1H), 6.76 (d, J=8.4 Hz, 1H), 6.32 (br s, 1H), 5.59 (dd, J=5.7, 1.8 Hz, 1H), 5.13 (q, J=6.9 Hz, 1H), 5.00 (s, 1H), 3.76 (s, 3H), 3.67-3.65 (m, 2H), 3.53-3.40 (m, 2H), 3.35-3.24 (m, 1H), 3.16-3.07 (m, 2H), 2.85 (apparent d, J=4.5 Hz, 3H), 2.73-2.59 (m, 3H), 2.49-2.43 (m, 1H, partially obscured by solvent peak), 2.34-2.26 (m, 1H), 2.06 (apparent d, J=18.3 Hz, 1H), 1.66-1.50 (m, 7H), 0.90-0.87 (m, 6H); ESI MS m/z 572 $[C_{30}H_{41}N_3O_8+H]^+$; HPLC (Method A) 95.1% (AUC), $t_R$=7.76 min.

Scheme 78: (2R,3R)-2,3-Dihydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

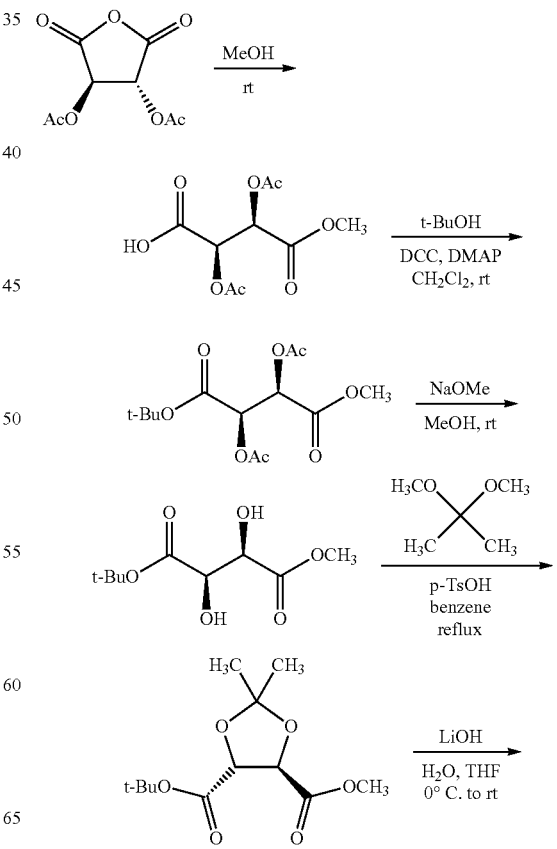

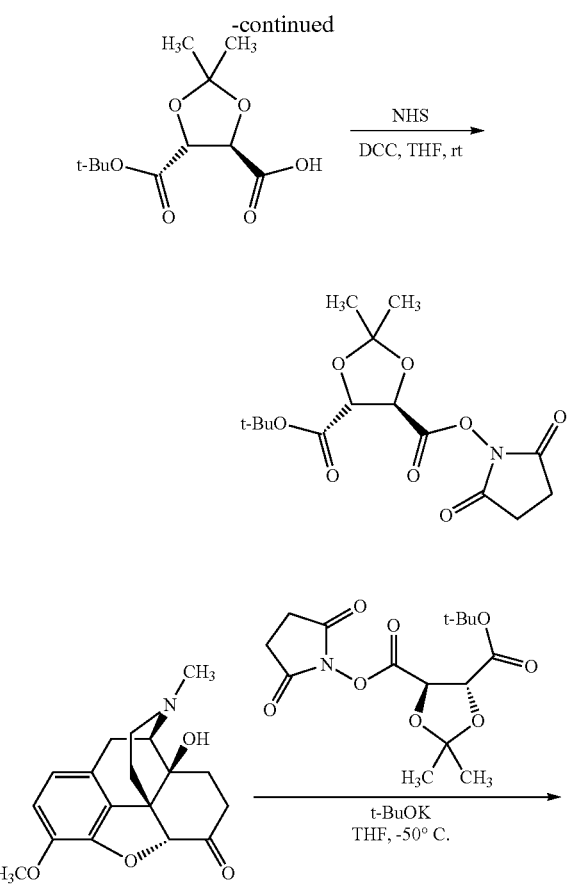

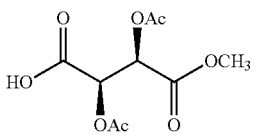 [SMILES: COC(=O)[C@H](OC(C)=O)[C@@H](OC(C)=O)C(=O)O]

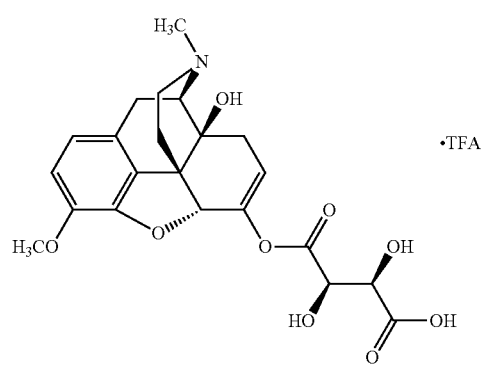

Preparation of (2R,3R)-2,3-Diacetoxy-4-methoxy-4-oxobutanoic acid

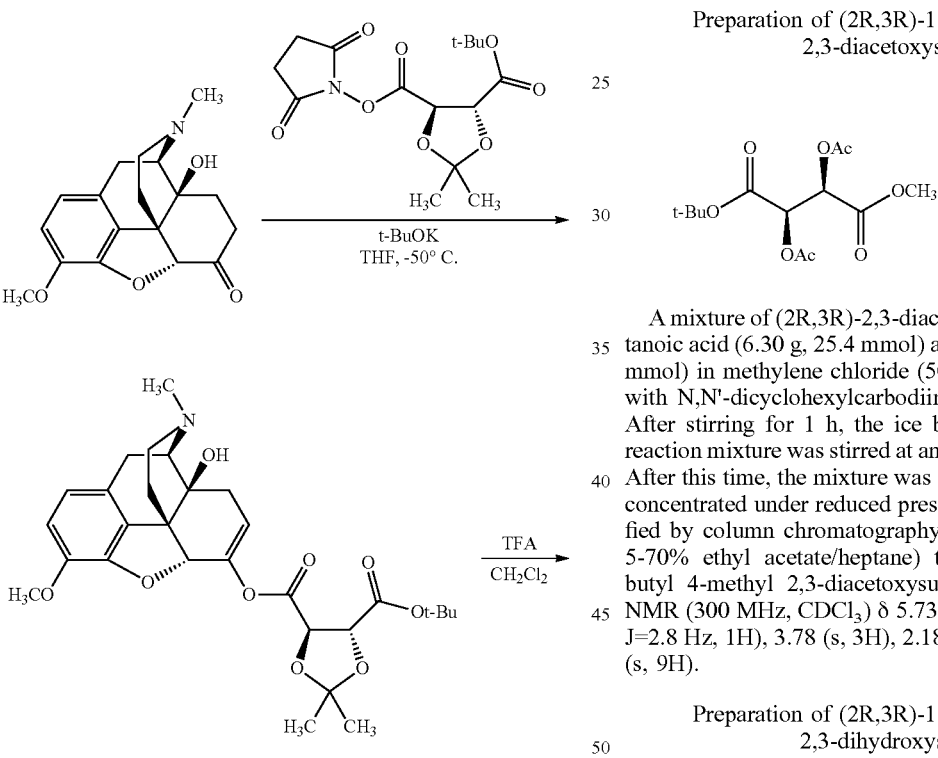

A mixture of (3R,4R)-2,5-dioxotetrahydrofuran-3,4-diyl diacetate (5.66 g, 26.2 mmol) in methanol (26 mL) was stirred at room temperature for 30 min. After this time, the mixture was concentrated to dryness to provide (2R,3R)-2,3-diacetoxy-4-methoxy-4-oxobutanoic acid (6.30 g, 97%): $^1$H NMR (300 MHz, DMSO-$d_6$) δ 5.63 (d, J=2.9 Hz, 1H), 5.52 (d, J=2.9 Hz, 1H), 3.70 (s, 3H), 2.12 (s, 3H), 2.10 (s, 3H), $CO_2H$ proton not observed.

Preparation of (2R,3R)-1-tert-Butyl 4-methyl 2,3-diacetoxysuccinate

A mixture of (2R,3R)-2,3-diacetoxy-4-methoxy-4-oxobutanoic acid (6.30 g, 25.4 mmol) and tert-butanol (6.5 mL, 68 mmol) in methylene chloride (50 mL) at 0° C. was treated with N,N'-dicyclohexylcarbodiimide (6.70 g, 32.5 mmol). After stirring for 1 h, the ice bath was removed and the reaction mixture was stirred at ambient temperature for 18 h. After this time, the mixture was filtered, and the filtrate was concentrated under reduced pressure. The residue was purified by column chromatography (120 g silica gel column, 5-70% ethyl acetate/heptane) to provide (2R,3R)-1-tert-butyl 4-methyl 2,3-diacetoxysuccinate (4.2 g, 54%): $^1$H NMR (300 MHz, CDCl$_3$) δ 5.73 (d, J=2.8 Hz, 1H), 5.60 (d, J=2.8 Hz, 1H), 3.78 (s, 3H), 2.18 (s, 3H), 2.16 (s, 3H), 1.45 (s, 9H).

Preparation of (2R,3R)-1-tert-Butyl 4-methyl 2,3-dihydroxysuccinate

A solution of (2R,3R)-1-tert-butyl 4-methyl 2,3-diacetoxysuccinate (4.15 g, 13.7 mmol) in methanol (28 mL) was treated with sodium methoxide (25% in methanol, 0.30 mL, 1.3 mmol), and the mixture was stirred at room temperature for 19 h. After this time, the reaction mixture was treated with a few drops of 2N hydrochloric acid, until neutral by pH paper analysis. The mixture was partially concentrated, and the residue was dissolved in ethyl acetate, washed with saturated ammonium chloride and brine, dried over sodium sulfate, filtered, and concentrated under reduced pressure to provide (2R,3R)-1-tert-butyl 4-methyl 2,3-dihydroxysuccinate (2.62 g, 87%): $^1$H NMR (300 MHz, CDCl$_3$) δ 4.51 (dd, J=7.5, 1.7 Hz, 1H), 4.41 (d, J=6.3, 1.7 Hz, 1H), 3.86 (s, 3H), 3.19 (d, J=6.3 Hz, 1H), 3.05 (d, J=7.5 Hz, 1H), 1.52 (s, 9H).

Preparation of (4R,5R)-4-tert-Butyl 5-methyl 2,2-dimethyl-1,3-dioxolane-4,5-dicarboxylate

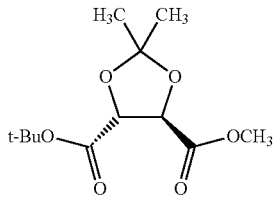

A mixture of (2R,3R)-1-tert-butyl 4-methyl 2,3-dihydroxysuccinate (2.62 g, 11.9 mmol), 2,2-dimethoxypropane (2.2 mL, 18 mmol), and p-toluenesulfonic acid (50 mg, 0.26 mmol) in benzene (30 mL) was stirred at reflux for 20 h. After this time, the mixture was cooled to room temperature, and saturated sodium bicarbonate was added. The mixture was stirred for 5 min and then extracted with ethyl acetate. The organic extracts were washed with water and brine and then concentrated. The residue was purified by column chromatography (80 g silica gel column, 5-70% ethyl acetate/heptane) to provide (4R,5R)-4-tert-butyl 5-methyl 2,2-dimethyl-1,3-dioxolane-4,5-dicarboxylate (1.63 g, 53%): $^1$H NMR (300 MHz, CDCl$_3$) δ 4.71 (d, J=5.9 Hz, 1H), 4.64 (d, J=5.9 Hz, 1H), 3.82 (s, 3H), 1.50 (s, 15H).

Preparation of (4R,5R)-5-(tert-Butoxycarbonyl)-2,2-dimethyl-1,3-dioxolane-4-carboxylic acid

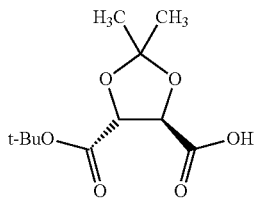

A solution of (4R,5R)-4-tert-butyl 5-methyl 2,2-dimethyl-1,3-dioxolane-4,5-dicarboxylate (4.96 g, 19.1 mmol) in tetrahydrofuran (35 mL) was treated with a solution of lithium hydroxide (940 mg, 22.4 mmol) in water (15 mL), and the mixture was stirred at room temperature for 1 h. After this time, 2N hydrochloric acid was added until the mixture tested neutral by pH paper analysis. The mixture was partially concentrated and then extracted with ethyl acetate. The organic extracts were washed with 10% citric acid and brine, dried over sodium sulfate, filtered and concentrated to provide (4R,5R)-5-(tert-butoxycarbonyl)-2,2-dimethyl-1,3-dioxolane-4-carboxylic acid (2.00 g, 43%): $^1$H NMR (300 MHz, CDCl$_3$) δ 4.80 (d, J=5.7 Hz, 1H), 4.66 (d, J=5.7 Hz, 1H), 1.53 (s, 3H), 1.52 (s, 9H), 1.50 (s, 3H), CO$_2$H proton not observed.

Preparation of (4R,5R)-4-tert-Butyl 5-(2,5-dioxopyrrolidin-1-yl) 2,2-dimethyl-1,3-dioxolane-4,5-dicarboxylate

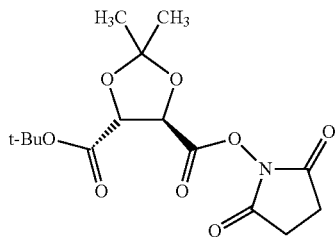

A mixture of (4R,5R)-5-(tert-butoxycarbonyl)-2,2-dimethyl-1,3-dioxolane-4-carboxylic acid (410 mg, 1.67 mmol) and N-hydroxysuccinimide (210 mg, 1.82 mmol) in tetrahydrofuran (10 mL) was treated with N,N'-dicyclohexylcarbodiimide (380 mg, 1.84 mmol), and the reaction mixture was stirred at ambient temperature for 4 h. After this time, diethyl ether (20 mL) was added, and the mixture was filtered. The filtrate was concentrated under reduced pressure to provide (4R,5R)-4-tert-butyl 5-(2,5-dioxopyrrolidin-1-yl) 2,2-dimethyl-1,3-dioxolane-4,5-dicarboxylate (650 mg) that was used without purification: $^1$H NMR (300 MHz, CDCl$_3$) δ 5.09 (d, J=4.9 Hz, 1H), 4.87 (d, J=4.9 Hz, 1H), 2.87 (s, 4H), 1.54 (s, 3H), 1.52 (s, 3H), 1.51 (s, 9H).

Preparation of (4R,5R)-4-tert-Butyl 5-((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl) 2,2-dimethyl-1,3-dioxolane-4,5-dicarboxylate

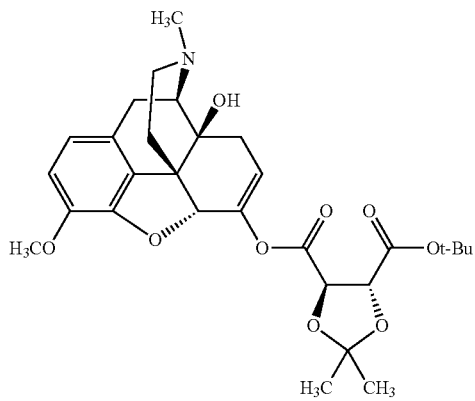 [SMILES: COc1ccc2c3c1O[C@H]1C(OC(=O)[C@@H]4OC(C)(C)O[C@H]4C(=O)OC(C)(C)C)=CC[C@@]4(O)[C@@H](C2)N(C)CC[C@]314]

A suspension of oxycodone (280 mg, 0.901 mmol) in tetrahydrofuran (8 mL) was cooled to −50° C. and treated dropwise with a 1.0 M solution of potassium tert-butoxide in tetrahydrofuran (1.0 mL, 1.0 mmol). After addition was complete, the mixture was stirred at −50° C. for 45 min. The mixture was treated dropwise with a solution of (4R,5R)-4-tert-butyl 5-(2,5-dioxopyrrolidin-1-yl) 2,2-dimethyl-1,3-dioxolane-4,5-dicarboxylate (330 mg, 1.0 mmol) in tetrahydrofuran (8 mL). After addition was complete, the mixture was stirred at −50° C. for 30 min. After this time, the reaction mixture was treated with saturated aqueous ammonium chloride (10 mL) and extracted with ethyl acetate (3×15 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (4R,5R)-4-tert-butyl 5-((4R,4aS,7aR,12bS)-4a-hydroxy-9-methoxy-3-methyl-2,3,4,4a,5,7a-hexahydro-1H-4,12-methanobenzofuro[3,2-e]

isoquinolin-7-yl) 2,2-dimethyl-1,3-dioxolane-4,5-dicarboxylate (120 mg, 25%) as a white solid: ESI MS m/z 544 $[C_{29}H_{37}NO_9+H]^+$.

Preparation of (2R,3R)-2,3-Dihydroxy-4-(((4R,4aS, 7aR,12bS)-4a-hydroxy-9-methoxy-3-methyl-2,3,4, 4a,5,7a-hexahydro-1H-4,12-methanobenzofuro[3,2-e]isoquinolin-7-yl)oxy)-4-oxobutanoic acid trifluoroacetic acid salt

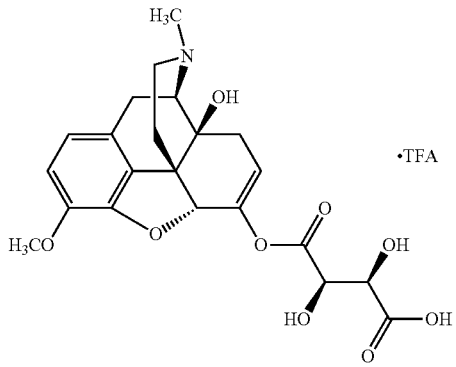 [SMILES: COc1ccc2c3c1O[C@H]1C(OC(=O)[C@H](O)[C@@H](O)C(=O)O)=CC[C@@]4(O)[C@@H](C2)N(C)CC[C@]314]

A solution of (4R,5R)-4-tert-butyl 5-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2,2-dimethyl-1,3-dioxolane-4,5-dicarboxylate (120 mg, 0.221 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (2R,3R)-2,3-dihydroxy-4-(((4R,4aS,7aR,12bS)-4α-hydroxy-9-methoxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt (70 mg, 71%) as a fluffy white solid: $^1$H NMR (300 MHz, DMSO-$d_6$) δ 12.8 (s, 1H), 9.20 (s, 1H), 6.86 (d, J=8.4 Hz, 1H), 6.75 (d, J=8.4 Hz, 1H), 6.30 (s, 1H), 5.71 (s, 1H), 5.54 (dd, J=6.0, 2.1 Hz, 1H), 5.31 (s, 1H), 5.04 (s, 1H), 4.55 (s, 1H), 4.41 (s, 1H), 3.75 (s, 3H), 3.64 (d, J=6.3 Hz, 1H), 3.43 (d, J=19.8 Hz, 1H), 3.15-3.07 (m, 2H), 2.85 (d, J=3.3 Hz, 3H), 2.69-2.62 (m, 1H), 2.49-2.43 (m, 1H), 2.32-2.26 (m, 1H), 2.07 (d, J=18.3 Hz, 1H), 1.65 (d, J=11.1 Hz, 1H); ESI MS m/z 448 $[C_{22}H_{25}NO_9+H]^+$.

Scheme 79: (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(((S)-2-((S)-pyrrolidine-2-carboxamido)propanoyl)oxy)propanoate bis(trifluoroacetic acid salt)

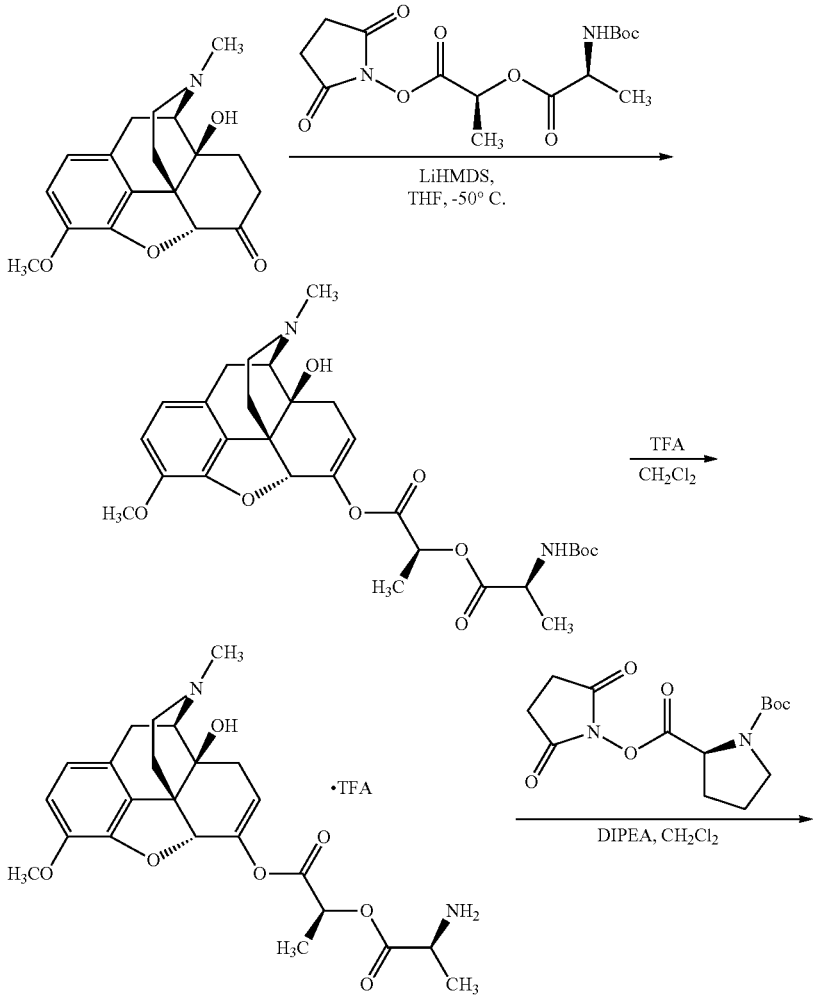

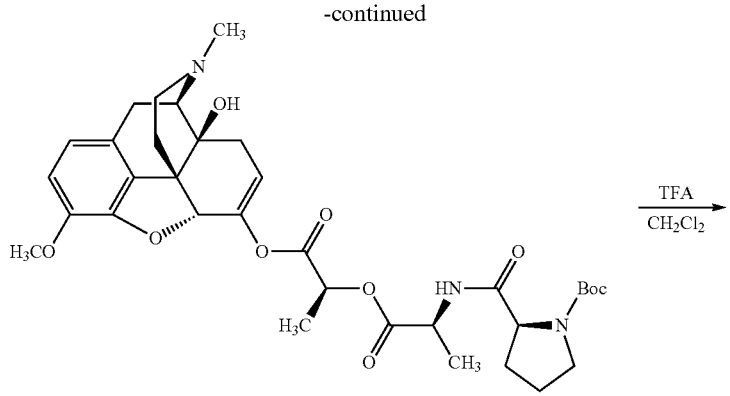

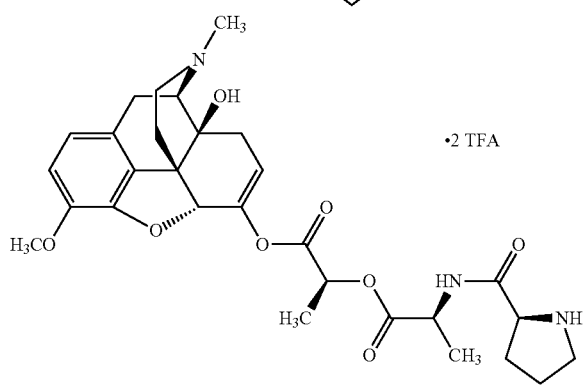

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(((S)-2-((tert-butoxycarbonyl)amino)propanoyl)oxy)propanoate

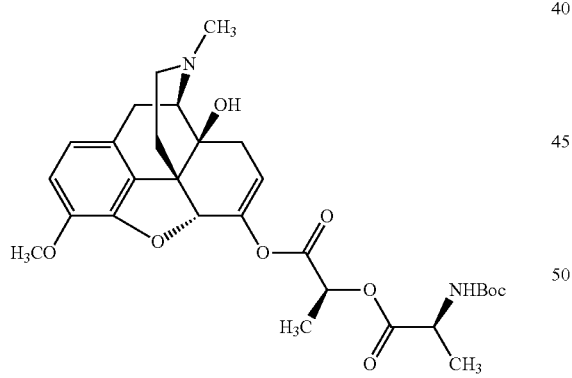

A suspension of oxycodone (810 mg, 2.54 mmol) in tetrahydrofuran (20 mL) was cooled to −50° C. and treated dropwise with a 1.0 M solution of lithium bis(trimethylsilyl)amide in tetrahydrofuran (2.8 mL, 2.8 mmol). After addition was complete, the mixture was stirred at −50° C. for 45 min. The mixture was treated dropwise with a solution of (S)-2,5-dioxopyrrolidin-1-yl 2-(((S)-2-((tert-butoxycarbonyl)amino)propanoyl)oxy)propanoate (1.0 g, 2.8 mmol) in tetrahydrofuran (15 mL). After addition was complete, the mixture was stirred at −50° C. for 30 min. After this time, the reaction mixture was treated with saturated aqueous ammonium chloride (30 mL) and extracted with ethyl acetate (3×30 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(((S)-2-((tert-butoxycarbonyl)amino)propanoyl)oxy)propanoate (270 mg, 19%) as a white solid: ESI MS m/z 559 $[C_{29}H_{38}N_2O_9+H]^+$.

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(((S)-2-aminopropanoyl)oxy)propanoatetrifluoroacetic acid salt

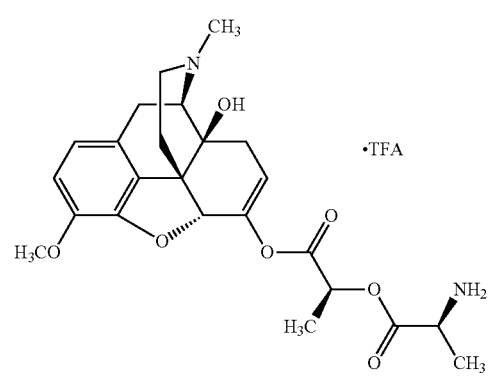 [SMILES: COc1ccc2c3c1O[C@H]1C(OC(=O)[C@H](C)OC(=O)[C@H](C)N)=CC[C@@]4(O)[C@@H](C2)N(C)CC[C@]314]

A solution of (S)-(4R,4aS,7aR,12bS)-4a-hydroxy-9-methoxy-3-methyl-2,3,4,4a,5,7a-hexahydro-1H-4,12- methanobenzofuro[3,2-e]isoquinolin-7-yl 2-(((S)-2-((tert-butoxycarbonyl)amino)propanoyl)oxy)propanoate (100 mg, 0.181 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(((S)-2-aminopropanoyl)oxy)propanoatetrifluoroacetic acid salt (100 mg, quantitative) as a clear oil: ESI MS m/z 459 $[C_{24}H_{30}N_2O_7+H]^+$.

Preparation of provide (S)-tert-Butyl 2-(((S)-1-(((S)-1-(((4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl)carbamoyl)pyrrolidine-1-carboxylate

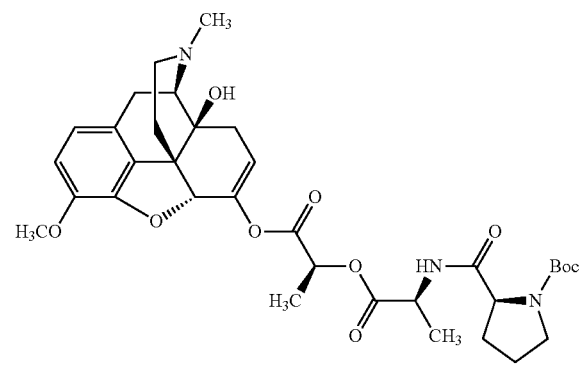 [SMILES: COc1ccc2c3c1O[C@H]1C(OC(=O)[C@H](C)OC(=O)[C@H](C)NC(=O)[C@@H]4CCCN4C(=O)OC(C)(C)C)=CC[C@@]4(O)[C@@H](C2)N(C)CC[C@]314]

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(((S)-2-aminopropanoyl)oxy)propanoate (85 mg, 0.15 mmol) in methylene chloride (1 mL) was treated with (S)-1-tert-butyl 2-(2,5-dioxopyrrolidin-1-yl) pyrrolidine-1,2-dicarboxylate (51 mg, 0.17 mmol) and N,N-diisopropylethylamine (0.1 mL, 0.6 mmol) and stirred under a nitrogen atmosphere at ambient temperature for 15 min. After this time, the reaction mixture was concentrated under reduced pressure. This material was purified by reversed phase column chromatography (50 g C18 column, 5-40% acetonitrile/water) and freeze dried to provide (S)-tert-butyl 2-(((S)-1-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoqui-nolin-7-yl)oxy)-1-oxopropan-2-yl)oxy)-1-oxopropan-2-yl)carbamoyl)pyrrolidine-1-carboxylate (84 mg, 85%) as a white solid: ESI MS m/z 656 $[C_{34}H_{45}N_3O_{10}+H]^+$.

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(((S)-2-((S)-pyrrolidine-2-carboxamido)propanoyl)oxy)propanoate bis(trifluoroacetic acid salt)

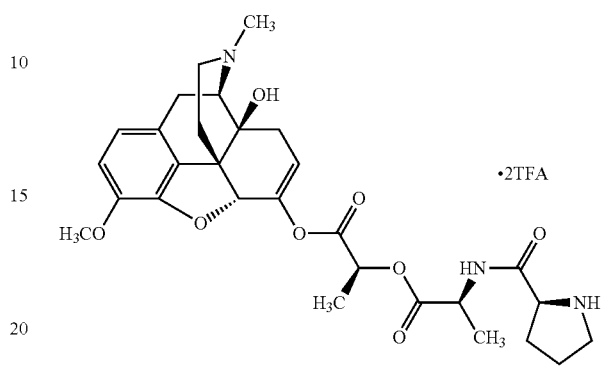

A solution of (S)-tert-butyl 2-(((S)-1-(((S)-1-(((4R,4aS,7aR,12bS)-4α-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl)carbamoyl)pyrrolidine-1-carboxylate (84 mg, 0.13 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(((S)-2-((S)-pyrrolidine-2-carboxamido)propanoyl)oxy)propanoatebis (trifluoroacetic acid salt) (41 mg, 58%) as a white solid: $^1$H NMR (300 MHz, DMSO-$d_6$) δ 9.21 (s, 2H), 8.96 (d, J=6.6 Hz, 1H), 8.55 (s, 1H), 6.86 (d, J=8.1 Hz, 1H), 6.75 (d, J=8.1 Hz, 1H), 6.30 (s, 1H), 5.59 (dd, J=6.0, 2.1 Hz, 1H), 5.19 (dd, J=14, 7.2 Hz, 1H), 4.99 (s, 1H), 4.48-4.39 (m, 1H), 4.25-4.18 (m, 1H), 3.76 (s, 3H), 3.66 (d, J=6.0 Hz, 1H), 3.43 (d, J=19.8 Hz, 1H), 3.23-3.07 (m, 4H), 2.85 (d, J=4.5 Hz, 3H), 2.69-2.57 (m, 1H), 2.49-2.41 (m, 1H), 2.33-2.26 (m, 2H), 2.06 (d, J=18 Hz, 1H), 1.93-1.84 (m, 3H), 1.64 (d, J=11.1 Hz, 1H), 1.52 (d, J=6.9 Hz, 3H), 1.41 (d, J=7.2 Hz, 3H); ESI MS m/z 556 $[C_{29}H_{37}N_3O_8+H]^+$.

Scheme 80: (S)-2-(((2R,3R)-2,3-Diacetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt

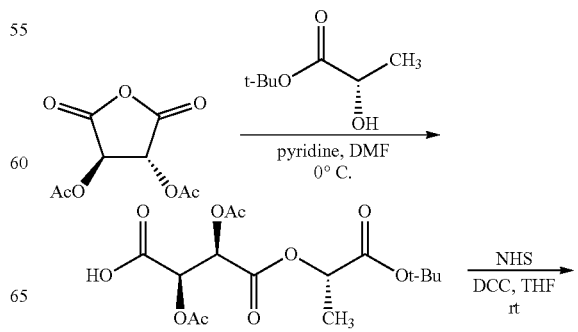

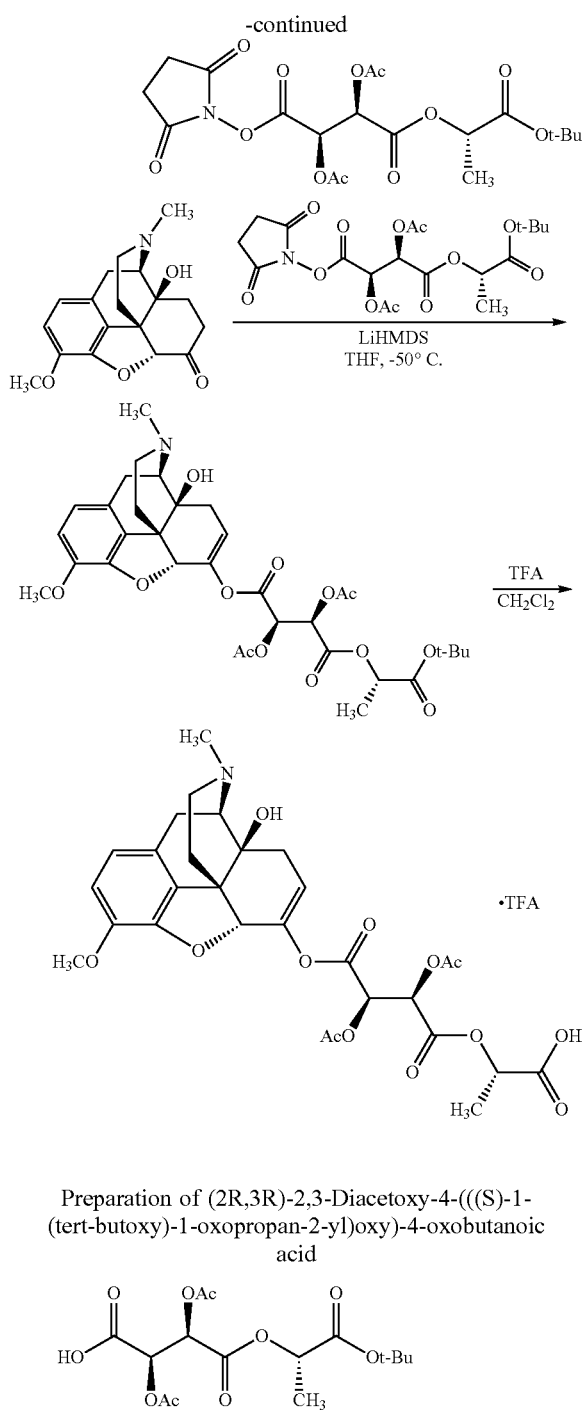

Preparation of (2R,3R)-2,3-Diacetoxy-4-(((S)-1-(tert-butoxy)-1-oxopropan-2-yl)oxy)-4-oxobutanoic acid A solution of (3R,4R)-2,5-dioxotetrahydrofuran-3,4-diyl diacetate (1.25 g, 5.78 mmol) in N,N-dimethylformamide (1.5 mL) at 0° C. was treated with (S)-tert-butyl 2-hydroxypropanoate (675 mg, 4.62 mmol) followed by pyridine (0.36 mL, 4.47 mmol), and the mixture was stirred at 0° C. for 1 h. After this time, the reaction mixture was diluted with ethyl acetate and extracted with saturated sodium bicarbonate. The aqueous extracts were acidified with 6N hydrochloric acid and then extracted with ethyl acetate. The organic extracts were dried over sodium sulfate, filtered, and concentrated to provide (2R,3R)-2,3-diacetoxy-4-(((S)-1-(tert-butoxy)-1-oxopropan-2-yl)oxy)-4-oxobutanoic acid (1.66 g, quantitative): $^1$H NMR (300 MHz, CDCl$_3$) δ 5.85 (d, J=2.6 Hz, 1H), 5.83 (d, J=2.6 Hz, 1H), 5.02 (q, J=7.0 Hz, 1H), 2.19 (s, 3H), 2.19 (s, 3H), 1.47-1.43 (m, 12H), CO$_2$H proton not observed.

Preparation of (2R,3R)-1-((S)-1-(tert-Butoxy)-1-oxopropan-2-yl) 4-(2,5-dioxopyrrolidin-1-yl) 2,3-diacetoxysuccinate

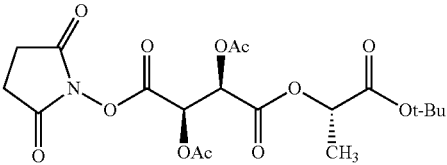 [SMILES: CC(=O)O[C@@H](C(=O)O[C@@H](C)C(=O)OC(C)(C)C)[C@@H](OC(C)=O)C(=O)ON1C(=O)CCC1=O]

A mixture of (2R,3R)-2,3-diacetoxy-4-(((S)-1-(tert-butoxy)-1-oxopropan-2-yl)oxy)-4-oxobutanoic acid (1.20 g, 3.31 mmol) and N-hydroxysuccinimide (410 mg, 3.56 mmol) in tetrahydrofuran (20 mL) was treated with N,N'-dicyclohexylcarbodiimide (740 mg, 3.58 mmol), and the reaction mixture was stirred at ambient temperature for 4 h. After this time, diethyl ether (20 mL) was added, and the mixture was filtered. The filtrate was concentrated under reduced pressure to provide (2R,3R)-1-((S)-1-(tert-butoxy)-1-oxopropan-2-yl) 4-(2,5-dioxopyrrolidin-1-yl) 2,3-diacetoxysuccinate (1.60 g) that was used without purification: $^1$H NMR (300 MHz, CDCl$_3$) δ 6.20 (d, J=2.7 Hz, 1H), 5.95 (d, J=2.7 Hz, 1H), 5.01 (q, J=7.0 Hz, 1H), 2.84 (s, 4H), 2.26 (s, 3H), 2.22 (s, 3H), 1.47-1.43 (m, 12H).

Preparation of (2R,3R)-1-((S)-1-(tert-Butoxy)-1-oxopropan-2-yl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2,3-diacetoxysuccinate

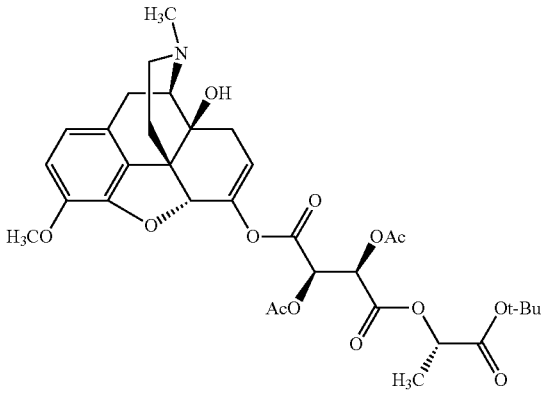 [SMILES: COc1ccc2c3c1O[C@H]1C(OC(=O)[C@H](OC(C)=O)[C@@H](OC(C)=O)C(=O)O[C@@H](C)C(=O)OC(C)(C)C)=CC[C@@]4(O)[C@@H](C2)N(C)CC[C@]314]

A suspension of oxycodone (380 mg, 1.21 mmol) in tetrahydrofuran (10 mL) was cooled to −50° C. and treated dropwise with a 1.0 M solution of lithium bis(trimethylsilyl)amide in tetrahydrofuran (1.3 mL, 1.3 mmol). After addition was complete, the mixture was stirred at −50° C. for 45 min. The mixture was treated dropwise with a solution of (2S,3S)-1-((S)-1-(tert-butoxy)-1-oxopropan-2-yl) 4-(2,5-dioxopyrrolidin-1-yl) 2,3-diacetoxysuccinate (560 mg, 1.31 mmol) in tetrahydrofuran (8 mL). After addition was complete, the mixture was stirred at −50° C. for 30 min. After this time, the reaction mixture was treated with saturated aqueous ammonium chloride (15 mL) and extracted with ethyl acetate (3×15 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (2R,3R)-1-((S)-1-(tert-butoxy)-1-oxopropan-2-yl) 4-((4R, 4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2,3-diacetoxysuccinate (57 mg, 7%) as a white solid: ESI MS m/z 660 [$C_{33}H_{41}NO_{13}$+H]$^+$.

Preparation of (S)-2-(((2R,3R)-2,3-Diacetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt

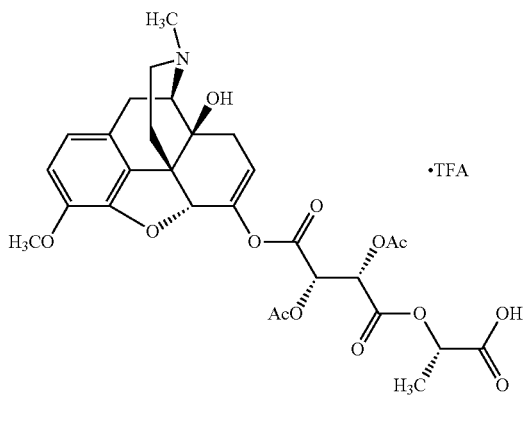 [SMILES: COc1ccc2c3c1O[C@H]1C(OC(=O)[C@@H](OC(C)=O)[C@H](OC(C)=O)C(=O)O[C@@H](C)C(=O)O)=CC[C@@]4(O)[C@@H](C2)N(C)CC[C@]314]

A solution of (2S,3S)-1-((S)-1-(tert-butoxy)-1-oxopropan-2-yl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2,3-diacetoxysuccinate (57 mg, 0.086 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (S)-2-(((2R,3R)-2,3-diacetoxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt (45 mg, 86%) as a white solid: $^1$H NMR (300 MHz, DMSO-$d_6$) δ 13.2 (s, 1H), 9.17 (s, 1H), 6.88 (d, J=8.4 Hz, 1H), 6.77 (d, J=8.4 Hz, 1H), 6.35 (s, 1H), 5.87 (dd, J=13.5, 2.7 Hz, 2H), 5.57 (dd, J=6.3, 2.1 Hz, 1H), 5.04 (dd, J=13.8, 1.2 Hz, 1H), 4.88 (s, 1H), 3.76 (s, 3H), 3.65 (d, J=6.3 Hz, 1H), 3.41 (d, J=20.1 Hz, 1H), 3.16-3.07 (m, 2H), 2.84 (d, J=3.6 Hz, 3H), 2.64-2.61 (m, 1H), 2.46-2.42 (m, 1H), 2.33-2.26 (m, 1H), 2.21 (s, 3H), 2.15 (s, 3H), 2.08 (d, J=18.0 Hz, 1H), 1.64 (d, J=11.1 Hz, 1H), 1.38 (d, J=7.2 Hz, 3H); ESI MS m/z 604 [$C_{29}H_{33}NO_{13}$+H]$^+$.

Scheme 81: (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(((S)-2-((S)-2-acetamido-6-aminohexanamido)propanoyl)oxy)propanoate bis(trifluoroacetic acid salt)

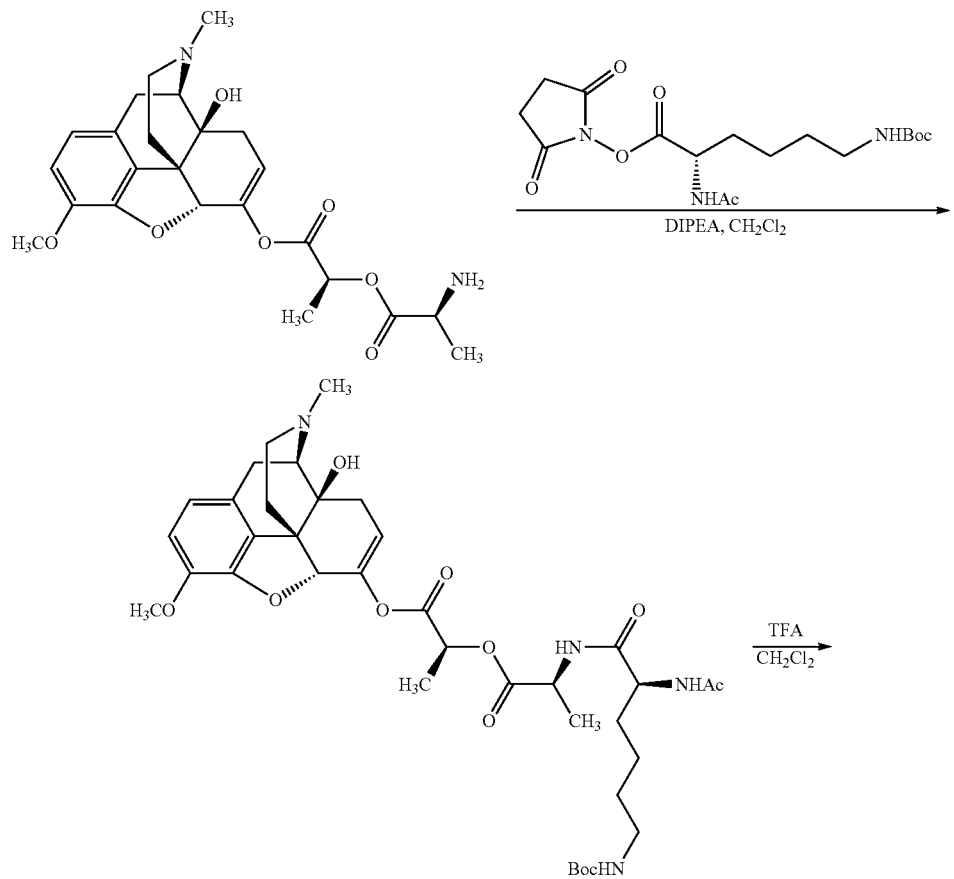

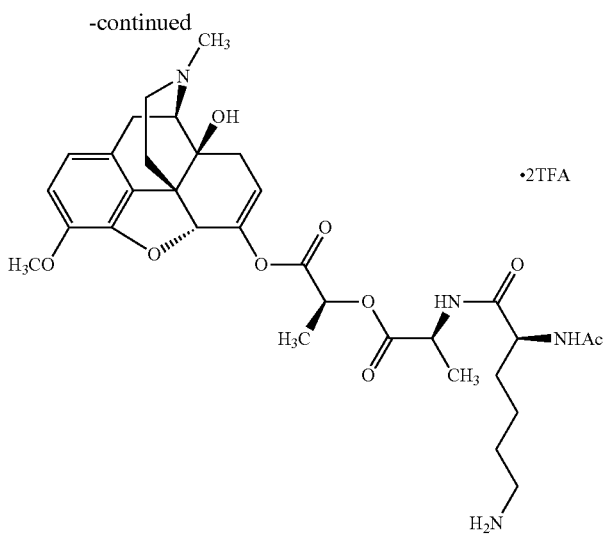

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-(((S)-2-((S)-2-acetamido-6-((tert-butoxycarbonyl)amino)hexanamido)propanoyl)oxy)propanoate

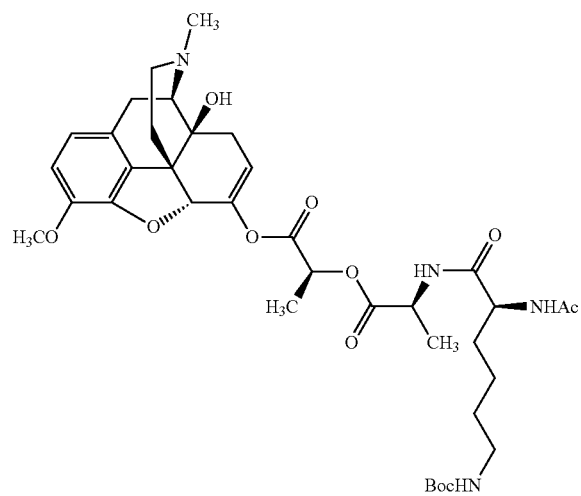 [SMILES: COc1ccc2c3c1O[C@H]1C(OC(=O)[C@H](C)OC(=O)[C@H](C)NC(=O)[C@H](CCCCNC(=O)OC(C)(C)C)NC(C)=O)=CC[C@@]4(O)[C@@H](C2)N(C)CC[C@]314]

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(((S)-2-aminopropanoyl)oxy)propanoate (82 mg, 0.18 mmol) in methylene chloride (1 mL) was treated with (S)-2,5-dioxopyrrolidin-1-yl 2-acetamido-6-((tert-butoxycarbonyl)amino)hexanoate (76 mg, 0.20 mmol) and N-ethyl-N-isopropylpropan-2-amine (0.12 mL, 0.72 mmol) and stirred under a nitrogen atmosphere at ambient temperature for 15 min. After this time, the reaction mixture was concentrated under reduced pressure. This material was purified by reversed phase column chromatography (50 g C18 column, 5-40% acetonitrile/water) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(((S)-2-((S)-2-acetamido-6-((tert-butoxycarbonyl)amino)hexanamido)propanoyl)oxy)propanoate (64 mg, 49%) as a white solid: ESI MS m/z 729 $[C_{37}H_{52}N_4O_{11}+H]^+$.

Preparation of (S)-(4R,4aS,7aR,12bS)-4a-Hydroxy-9-methoxy-3-methyl-2,3,4,4a,5,7a-hexahydro-H-4,12-methanobenzofuro[3,2-e]isoquinolin-7-yl 2-(((S)-2-((S)-2-acetamido-6-aminohexanamido)propanoyl)oxy)propanoatebis(trifluoroacetic acid salt)

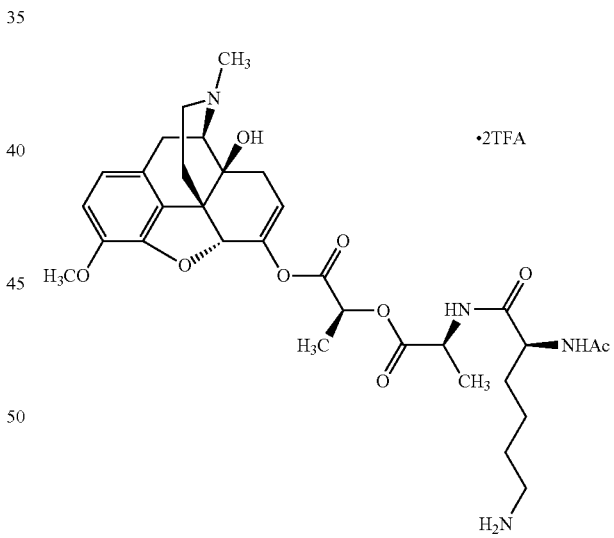

A solution of (S)-tert-butyl 2-(((S)-1-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl)carbamoyl)pyrrolidine-1-carboxylate (84 mg, 0.13 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-(((S)-2-((S)-2-acetamido-6-aminohexanamido)propanoyl)oxy)propanoatebis(trifluoroacetic acid salt)(32 mg, 58%) as a white solid: $^1$H NMR (300 MHz, DMSO-$d_6$) δ 9.19 (s, 1H), 8.42 (d, J=6.6 Hz, 1H), 8.00 (d, J=8.4 Hz, 1H), 7.64 (s, 3H), 6.86 (d, J=8.4 Hz, 1H), 6.76 (d, J=8.4 Hz, 1H), 6.30 (s, 1H), 5.57 (dd, J=6.0, 2.1 Hz, 1H), 5.15 (dd, J=14, 6.9 Hz, 1H), 4.99 (s, 1H), 4.34-4.25 (m, 2H), 3.75 (s, 3H), 3.66 (d, J=6.0 Hz, 1H), 3.43 (d, J=19.8 Hz, 1H), 3.16-3.07 (m, 2H), 2.85 (d, J=4.5 Hz, 3H), 2.76-2.62 (m, 2H), 2.33-2.26 (m, 2H), 2.06 (d, J=18 Hz, 1H), 1.84 (s, 3H), 1.66-1.34 (m, 14H); ESI MS m/z 629 $[C_{32}H_{44}N_4O_9+H]^+$.

Scheme 82: (S)-2-(((S)-3-Hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt

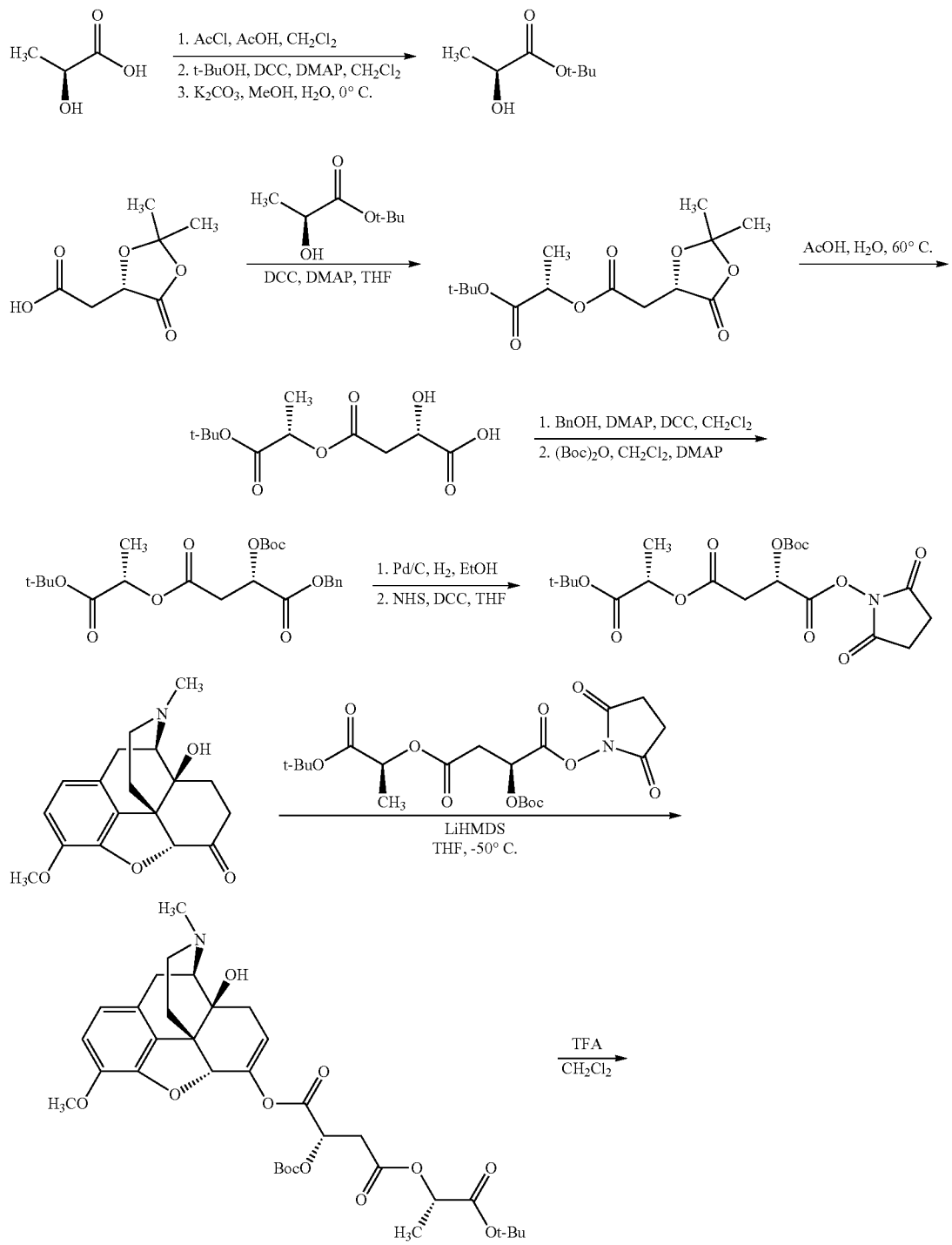

-continued

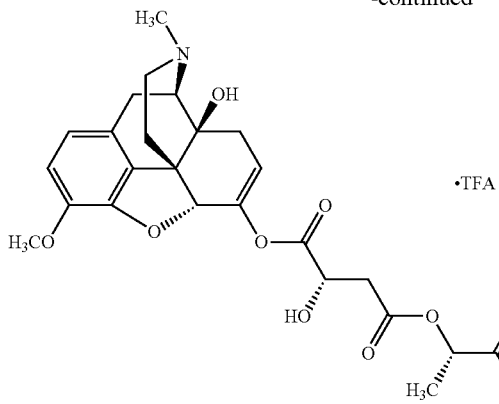

Preparation of (S)-tert-Butyl 2-hydroxypropanoate

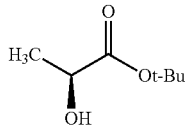

A solution of (S)-2-hydroxypropanoic acid (5.0 g, 55 mmol) and acetic acid (1 mL) in dichloromethane (40 mL) was cooled in an ice bath and treated dropwise with acetyl chloride (4.5 mL, 61 mmol). After addition was complete, the mixture was stirred at ambient temperature for 16 h. After this time, the mixture was diluted with water (50 mL) and extracted with methylene chloride (2×50 mL). The combined organics were washed with brine (50 mL), dried over sodium sulfate, filtered, and concentrated under reduced pressure to provide (S)-2-acetoxypropanoic acid (6.0 g) as a colorless oil.

(S)-2-acetoxypropanoic acid (6.0 g, 55 mmol), tert-butyl alcohol (8.10 g, 110 mmol),N,N-dimethylpyridin-4-amine (2.0 g, 16 mmol) and N,N'-dicyclohexylcarbodiimide (14.7 g, 71.5 mmol) were combined and stirred at ambient temperature for 16 h. After this time, the mixture was filtered and concentrated under reduced pressure to provide (S)-tert-butyl 2-acetoxypropanoate (12 g) as a colorless oil.

A solution of (S)-tert-butyl 2-acetoxypropanoate (12 g, 55 mmol) in methanol (40 mL) was cooled in an ice bath and treated with a solution of potassium carbonate (22.8 g, 165 mmol) in water (40 mL). After addition was complete, the mixture was stirred in an ice bath for 5 h. After this time, the mixture was diluted with water (50 mL) and extracted with ethyl acetate (3×50 mL). The combined organics were washed with brine (50 mL), dried over sodium sulfate, filtered, and concentrated under reduced pressure. The crude residue was purified by column chromatography (silica gel, 0-30% ethyl acetate/heptanes) to provide (S)-tert-butyl 2-hydroxypropanoate (1.14 g, 15% in three steps) as a white solid: $^1$H NMR (300 MHz, CDCl$_3$) δ 4.13 (dd, J=6.9, 5.4 Hz, 1H), 2.82 (d, J=5.4 Hz, 1H), 1.49 (s, 9H), 1.37 (d, J=6.9 Hz, 3H).

Preparation of (S)-tert-Butyl 2-(2-((S)-2,2-dimethyl-5-oxo-1,3-dioxolan-4-yl)acetoxy)propanoate

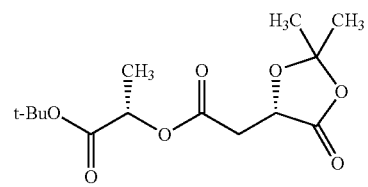 [SMILES: C[C@H](OC(=O)C[C@@H]1OC(C)(C)OC1=O)C(=O)OC(C)(C)C]

A solution of (S)-2-(2,2-dimethyl-5-oxo-1,3-dioxolan-4-yl)acetic acid (0.66 g, 3.8 mmol) in dichloromethane (20 mL) was treated with (S)-tert-butyl 2-hydroxypropanoate (0.50 g, 3.4 mmol),N,N-dimethylpyridin-4-amine (0.13 g, 1.0 mmol) and N,N'-dicyclohexylcarbodiimide (0.85 g, 4.1 mmol). The mixture was stirred at ambient temperature for 16 h. After this time, the mixture was filtered and concentrated under reduced pressure. The crude residue was purified by column chromatography (silica gel, 0-30% ethyl acetate/heptanes) to provide (S)-tert-butyl 2-(2-((S)-2,2-dimethyl-5-oxo-1,3-dioxolan-4-yl)acetoxy)propanoate (0.22 g, 21%) as a colorless oil: $^1$H NMR (300 MHz, CDCl$_3$) δ 4.99 (dd, J=14.1, 8.4 Hz, 1H), 4.74 (dd, J=6.6, 3.6 Hz, 1H), 3.04 (dd, J=14.1, 3.6 Hz, 1H), 2.85 (dd, J=17.4, 8.4 Hz, 1H), 1.62 (s, 3H), 1.55 (s, 3H), 1.47 (d, J=6.2 Hz, 3H), 1.46 (s, 9H).

Preparation of (S)-4-(((S)-1-(tert-Butoxy)-1-oxopropan-2-yl)oxy)-2-hydroxy-4-oxobutanoic acid

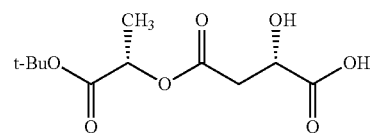 [SMILES: C[C@H](OC(=O)C[C@H](O)C(=O)O)C(=O)OC(C)(C)C]

A solution of (S)-tert-butyl 2-(2-((S)-2,2-dimethyl-5-oxo-1,3-dioxolan-4-yl)acetoxy)propanoate (3.07 g, 10.2 mmol), acetic acid (35 mL), and water (15 mL) was heated at 60° C. for 1 h. After this time, the mixture was concentrated under reduced pressure. The residue was diluted with toluene and concentrated under reduced pressure to provide of (S)-4-(((S)-1-(tert-butoxy)-1-oxopropan-2-yl)oxy)-2-hydroxy-4- oxobutanoic acid (2.99 g, 99%) as a colorless oil: ¹H NMR (300 MHz, DMSO-d₆) δ 12.6 (s, 1H), 5.51 (s, 1H), 4.82 (dd, J=14.1, 6.9 Hz, 1H), 4.31-4.30 (m, 1H), 2.72 (dd, J=15.9, 4.5 Hz, 1H), 2.60 (dd, J=15.9, 7.8 Hz, 1H), 1.40 (s, 9H), 1.36 (d, J=7.2 Hz, 3H).

Preparation of (S)-1-Benzyl 4-((S)-1-(tert-butoxy)-1-oxopropan-2-yl) 2-((tert-butoxycarbonyl)oxy)succinate

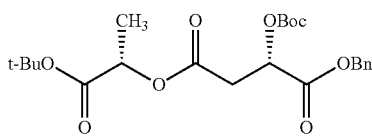

(S)-4-(((S)-1-(tert-Butoxy)-1-oxopropan-2-yl)oxy)-2-hydroxy-4-oxobutanoic acid (0.26 g, 1.0 mmol), benzylalcohol (0.15 g, 1.2 mmol), N,N-dimethylpyridin-4-amine (44 mg, 0.30 mmol), and N,N'-dicyclohexylcarbodiimide (0.30 g, 1.2 mmol) were combined and stirred in methylene chloride (10 mL) at ambient temperature for 16 h. After this time, the mixture was filtered and concentrated under reduced pressure to provide to provide (S)-1-benzyl 4-((S)-1-(tert-butoxy)-1-oxopropan-2-yl) 2-hydroxysuccinate (0.32 g) as a colorless oil.

(S)-1-Benzyl 4-((S)-1-(tert-butoxy)-1-oxopropan-2-yl) 2-hydroxysuccinate (0.32 g, 0.91 mmol), di-tert-butyl dicarbonate (0.22 g, 1.0 mmol), and 4-dimethylaminopyridine (12 mg, 0.098 mmol) were combined and stirred in methylene chloride (10 mL) at ambient temperature for 3 h. After this time, the mixture was concentrated under reduced pressure. The crude residue was purified by column chromatography (silica gel, 0-30% ethyl acetate/heptanes) to provide (S)-1-benzyl 4-((S)-1-(tert-butoxy)-1-oxopropan-2-yl) 2-((tert-butoxycarbonyl)oxy)succinate (0.21 g, 46% in two steps) as a colorless oil: ¹H NMR (300 MHz, CDCl₃) δ 7.34-7.32 (m, 5H), 5.41 (dd, J=8.1, 4.5 Hz, 1H), 5.26 (d, J=12 Hz, 1H), 5.14 (d, J=12 Hz, 1H), 4.96 (dd, J=14.1, 7.2 Hz, 1H), 2.98-2.94 (m, 2H), 1.46 (s, 9H), 1.45 (s, 9H), 1.42 (d, J=7.2 Hz, 3H).

Preparation of (S)-4-((S)-1-(tert-Butoxy)-1-oxopropan-2-yl) 1-(2,5-dioxopyrrolidin-1-yl) 2-((tert-butoxycarbonyl)oxy)succinate

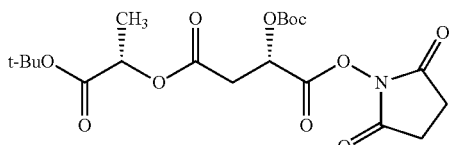

A solution of (S)-1-benzyl 4-((S)-1-(tert-butoxy)-1-oxopropan-2-yl) 2-((tert-butoxycarbonyl)oxy)succinate (0.54 g, 1.2 mmol) in ethyl alcohol (8 mL) was treated with palladium on carbon (10%, 0.1 g). The mixture was stirred under a hydrogen atmosphere at ambient temperature for 2 h. After this time, the reaction mixture was filtered and concentrated under reduced pressure to provide (S)-4-(((S)-1-(tert-butoxy)-1-oxopropan-2-yl)oxy)-2-((tert-butoxycarbonyl)oxy)-4-oxobutanoic acid (0.5 g) as a colorless oil.

(S)-4-(((S)-1-(tert-Butoxy)-1-oxopropan-2-yl)oxy)-2-((tert-butoxycarbonyl)oxy)-4-oxobutanoic acid (0.50 g, 1.2 mmol), 1-hydroxypyrrolidine-2,5-dione (0.16 g, 1.4 mmol) and N,N'-dicyclohexylcarbodiimide (0.27 g, 1.3 mmol) were combined and stirred in tetrahydrofuran (10 mL) at ambient temperature for 4 h. After this time, the mixture was filtered and concentrated under reduced pressure to provide (S)-4-((S)-1-(tert-butoxy)-1-oxopropan-2-yl) 1-(2,5-dioxopyrrolidin-1-yl) 2-((tert-butoxycarbonyl)oxy)succinate (0.8 g) as a sticky solid, which was used without purification.

Preparation of (S)-4-((S)-1-(tert-Butoxy)-1-oxopropan-2-yl) 1-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-((tert-butoxycarbonyl)oxy)succinate

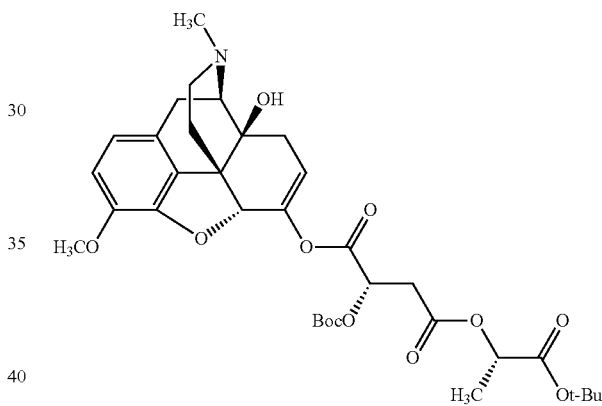

A suspension of oxycodone (380 mg, 1.21 mmol) in tetrahydrofuran (10 mL) was cooled to −50° C. and treated dropwise with a 1.0 M solution of lithium bis(trimethylsilyl) amide in tetrahydrofuran (1.4 mL, 1.4 mmol). After addition was complete, the mixture was stirred at −50° C. for 45 min. The mixture was treated dropwise with a solution of (S)-4-((S)-1-(tert-butoxy)-1-oxopropan-2-yl) 1-(2,5-dioxopyrrolidin-1-yl) 2-((tert-butoxycarbonyl)oxy)succinate (610 mg, 1.4 mmol) in tetrahydrofuran (8 mL). After addition was complete, the mixture was stirred at −50° C. for 30 min. After this time, the reaction mixture was treated with saturated aqueous ammonium chloride (20 mL) and extracted with ethyl acetate (3×20 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (S)-4-((S)-1-(tert-butoxy)-1-oxopropan-2-yl) 1-((4R,4aS,7aR,12bS)-4α-hydroxy-9-methoxy-3-methyl-2,3,4,4a,5,7a-hexahydro-1H-4,12-methanobenzofuro[3,2-e]isoquinolin-7-yl) 2-((tert-butoxycarbonyl)oxy)succinate (48 mg, 6%) as a white solid: ESI MS m/z 660 [C₃₄H₄₅NO₁₂+H]⁺.

Preparation of (S)-2-(((S)-3-Hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy) propanoic acid trifluoroacetic acid salt

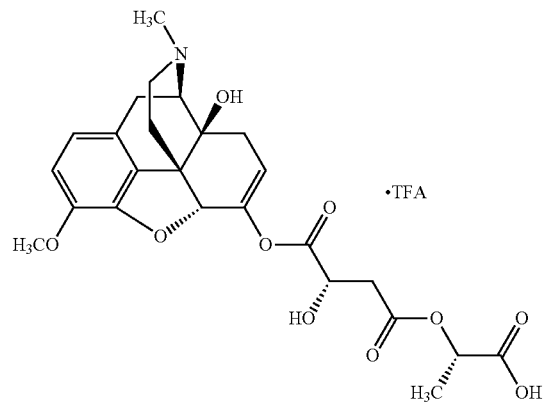 [SMILES: COc1ccc2c3c1O[C@H]1C(OC(=O)[C@@H](O)CC(=O)O[C@@H](C)C(=O)O)=CC[C@@]4(O)[C@@H](C2)N(C)CC[C@]314]

A solution of (S)-4-((S)-1-(tert-butoxy)-1-oxopropan-2-yl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2-((tert-butoxycarbonyl)oxy) succinate (48 mg, 0.071 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (S)-2-(((S)-3-hydroxy-4-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy) propanoic acid trifluoroacetic acid salt (28 mg, 76%) as a white solid: $^1$H NMR (300 MHz, DMSO-$d_6$) δ 13.1 (s, 1H), 9.17 (s, 1H), 6.87 (d, J=8.4 Hz, 1H), 6.76 (d, J=8.4 Hz, 1H), 6.29 (s, 1H), 6.00 (s, 1H), 5.57 (dd, J=6.0, 1.8 Hz, 1H), 4.98 (d, J=4.5 Hz, 1H), 4.96 (dd, J=14.1, 6.9 Hz, 1H), 4.54-4.50 (m, 1H), 3.76 (s, 3H), 3.64 (d, J=5.7 Hz, 1H), 3.43 (d, J=20.1 Hz, 1H), 3.16-3.07 (m, 2H), 2.85-2.78 (m, 5H), 2.65-2.61 (m, 1H), 2.46-2.42 (m, 1H), 2.33-2.25 (m, 1H), 2.07 (d, J=18.0 Hz, 1H), 1.64 (d, J=11.1 Hz, 1H), 1.40 (d, J=6.9 Hz, 3H); ESI MS m/z 504 $[C_{25}H_{29}NO_{10}+H]^+$.

Scheme 83: (2R,3R)-2,3-Diacetoxy-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt)

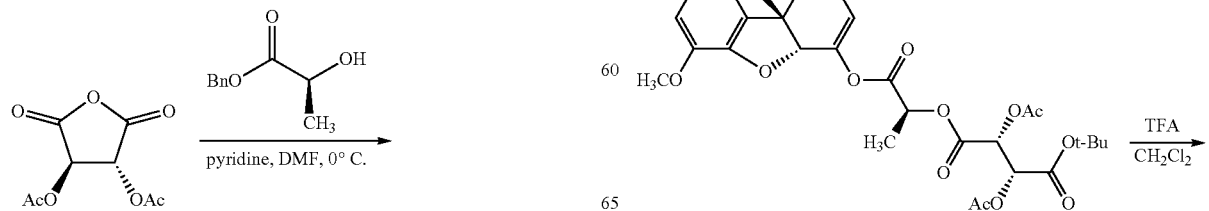

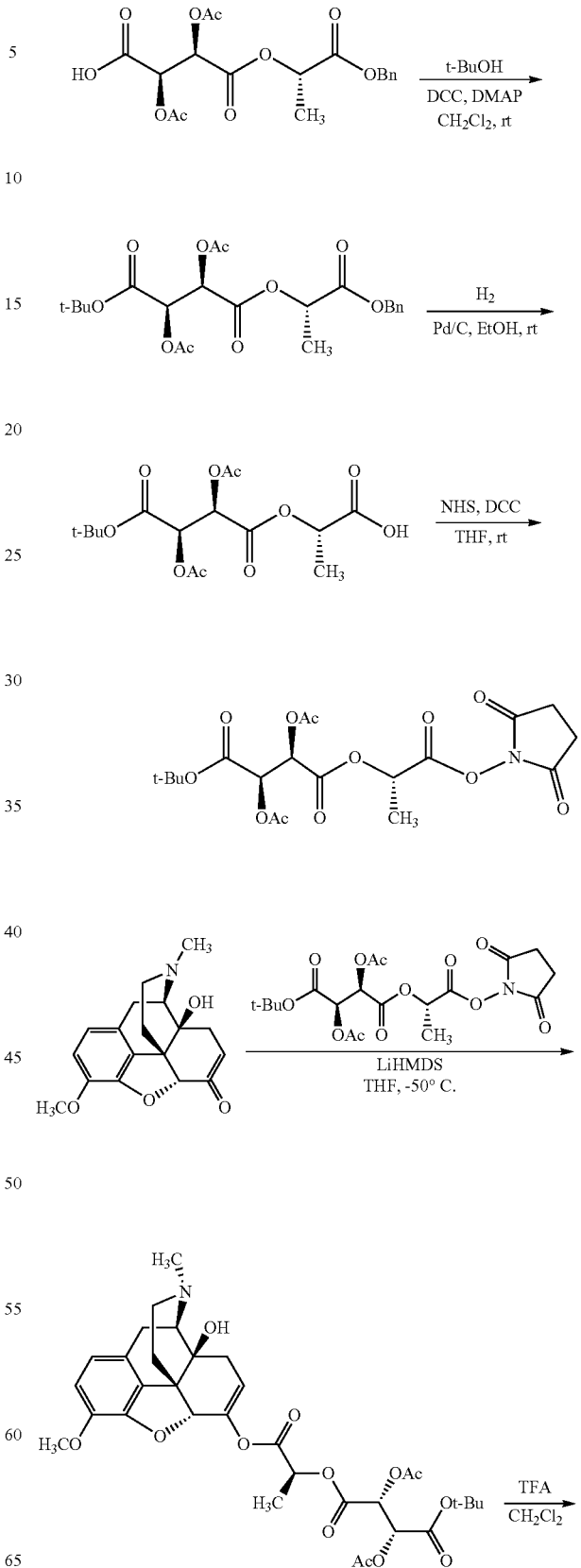

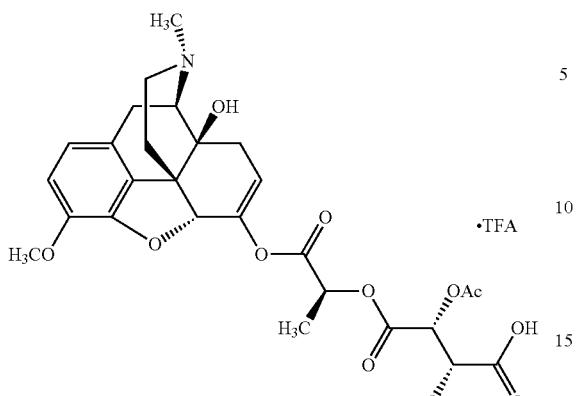

Preparation of (2R,3R)-2,3-Diacetoxy-4-(((S)-1-(benzyloxy)-1-oxopropan-2-yl)oxy)-4-oxobutanoic acid

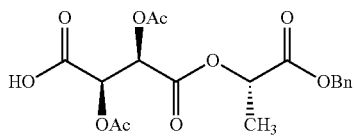 [SMILES: CC(=O)O[C@@H](C(=O)O)[C@@H](OC(C)=O)C(=O)O[C@@H](C)C(=O)OCc1ccccc1]

A solution of (3R,4R)-2,5-dioxotetrahydrofuran-3,4-diyl diacetate (1.85 g, 8.56 mmol) in N,N-dimethylformamide (2.2 mL) at 0° C. was treated with (S)-benzyl 2-hydroxypropanoate (1.30 g, 7.21 mmol) followed by pyridine (0.53 mL, 6.58 mmol), and the mixture was stirred at 0° C. for 1 h. After this time, the reaction mixture was diluted with ethyl acetate and extracted with saturated sodium bicarbonate. The aqueous layer was collected, carefully treated with 6N hydrochloric acid until acidic by pH paper analysis, and then extracted with ethyl acetate. The organic extracts were dried over sodium sulfate, filtered and concentrated to give (2R,3R)-2,3-diacetoxy-4-(((S)-1-(benzyloxy)-1-oxopropan-2-yl)oxy)-4-oxobutanoic acid (2.80 g, 98%): $^1$H NMR (300 MHz, CDCl$_3$) δ 7.38-7.33 (m, 5H), 5.84-5.83 (m, 2H), 5.23-5.13 (m, 3H), 2.18 (s, 3H), 2.17 (s, 3H), 1.49 (d, J=7.1 Hz, 3H), CO$_2$H proton not observed.

Preparation of (2R,3R)-1-((S)-1-(Benzyloxy)-1-oxopropan-2-yl) 4-tert-butyl 2,3-diacetoxysuccinate

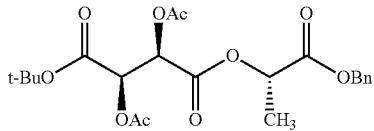 [SMILES: CC(=O)O[C@@H](C(=O)O[C@@H](C)C(=O)OCc1ccccc1)[C@@H](OC(C)=O)C(=O)OC(C)(C)C]

A mixture of (2R,3R)-2,3-diacetoxy-4-(((S)-1-(benzyloxy)-1-oxopropan-2-yl)oxy)-4-oxobutanoic acid (2.80 g, 7.07 mmol), tert-butanol (1.8 mL, 19 mmol), and 4-dimethylaminopyridine (280 mg, 2.29 mmol) in methylene chloride (16 mL) at 0° C. was treated with N,N'-dicyclohexylcarbodiimide (1.70 g, 8.24 mmol). The ice bath was removed, and the reaction mixture was stirred at ambient temperature for 4 h. After this time, the mixture was filtered, and the filtrate was concentrated under reduced pressure. The residue was purified by column chromatography (80 g silica gel column, 0-70% ethyl acetate/heptane) to provide (2R,3R)-1-((S)-1-(benzyloxy)-1-oxopropan-2-yl) 4-tert-butyl 2,3-diacetoxysuccinate (1.38 g, 43%): $^1$H NMR (300 MHz, CDCl$_3$) δ 7.38-7.31 (m, 5H), 5.85 (d, J=2.7 Hz, 1H), 5.69 (d, J=2.7 Hz, 1H), 5.23-5.13 (m, 3H), 2.17 (s, 3H), 2.16 (s, 3H), 1.49 (d, J=7.1 Hz, 3H), 1.45 (s, 9H).

Preparation of (S)-2-(((2R,3R)-2,3-Diacetoxy-4-(tert-butoxy)-4-oxobutanoyl)oxy)propanoic acid

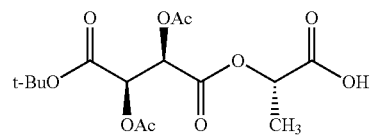

A mixture of (2R,3R)-1-((S)-1-(benzyloxy)-1-oxopropan-2-yl) 4-tert-butyl 2,3-diacetoxysuccinate (1.35 g, 2.99 mmol) and palladium (5% on carbon, 180 mg) in ethanol (15 mL) was stirred at room temperature under balloon pressure hydrogen for 2 h. After this time, the reaction mixture was purged with nitrogen and filtered through diatomaceous earth. The filtrate was concentrated under reduced pressure to provide (S)-2-(((2R,3R)-2,3-diacetoxy-4-(tert-butoxy)-4-oxobutanoyl)oxy)propanoic acid (1.01 g, 93%): $^1$H NMR (300 MHz, CDCl$_3$) δ 5.80 (d, J=2.7 Hz, 1H), 5.69 (d, J=2.7 Hz, 1H), 5.16 (q, J=7.1 Hz, 1H), 2.18 (s, 3H), 2.17 (s, 3H), 1.53 (d, J=7.1 Hz, 3H), 1.46 (s, 9H), CO$_2$H proton not observed.

Preparation of (2R,3R)-1-tert-Butyl 4-((S)-1-((2,5-dioxopyrrolidin-1-yl)oxy)-1-oxopropan-2-yl) 2,3-diacetoxysuccinate

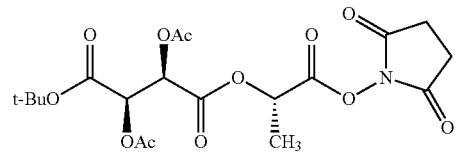 [SMILES: CC(=O)O[C@@H](C(=O)O[C@@H](C)C(=O)ON1C(=O)CCC1=O)[C@@H](OC(C)=O)C(=O)OC(C)(C)C]

A mixture of (S)-2-(((2R,3R)-2,3-diacetoxy-4-(tert-butoxy)-4-oxobutanoyl)oxy)propanoic acid (1.00 g, 2.76 mmol) and N-hydroxysuccinimide (350 mg, 3.04 mmol) in tetrahydrofuran (20 mL) was treated with N,N'-dicyclohexylcarbodiimide (627 mg, 3.04 mmol), and the reaction mixture was stirred at ambient temperature for 4 h. After this time, diethyl ether (20 mL) was added, and the mixture was filtered. The filtrate was concentrated under reduced pressure to provide (2R,3R)-1-tert-butyl 4-((S)-1-((2,5-dioxopyrrolidin-1-yl)oxy)-1-oxopropan-2-yl) 2,3-diacetoxysuccinate (960 mg, 76%) that was used without purification: $^1$H NMR (300 MHz, CDCl$_3$) δ 5.82 (d, J=2.7 Hz, 1H), 5.66 (d, J=2.7 Hz, 1H), 5.49 (q, J=7.1 Hz, 1H), 2.85 (s, 4H), 2.18 (s, 3H), 2.16 (s, 3H), 1.67 (d, J=7.1 Hz, 3H), 1.46 (s, 9H).

Preparation of (2R,3R)-1-tert-Butyl 4-((S)-1-(((4R, 4aS,7aR,12bS)-4a-hydroxy-9-methoxy-3-methyl-2, 3,4,4a,5,7a-hexahydro-1H-4,12-methanobenzofuro [3,2-e]isoquinolin-7-yl)oxy)-1-oxopropan-2-yl) 2,3-diacetoxysuccinate Preparation of (2R,3R)-2,3-Diacetoxy-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt

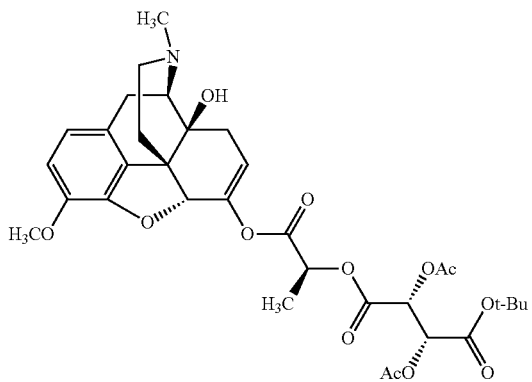 [SMILES: COc1ccc2c3c1O[C@H]1C(OC(=O)[C@H](C)OC(=O)[C@H](OC(C)=O)[C@@H](OC(C)=O)C(=O)OC(C)(C)C)=CC[C@@]4(O)[C@@H](C2)N(C)CC[C@]314]

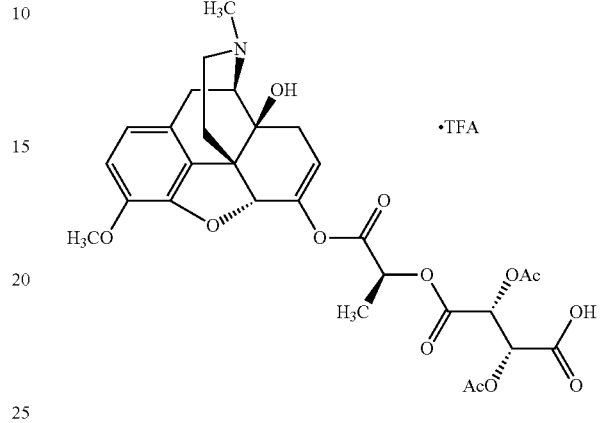

A suspension of oxycodone (380 mg, 1.21 mmol) in tetrahydrofuran (10 mL) was cooled to −50° C. and treated dropwise with a 1.0 M solution of lithium bis(trimethylsilyl) amide in tetrahydrofuran (1.3 mL, 1.3 mmol). After addition was complete, the mixture was stirred at −50° C. for 45 min. The mixture was treated dropwise with a solution of (2R, 3R)-1-tert-butyl 4-((S)-1-((2,5-dioxopyrrolidin-1-yl)oxy)-1-oxopropan-2-yl) 2,3-diacetoxysuccinate (560 mg, 1.32 mmol) in tetrahydrofuran (8 mL). After addition was complete, the mixture was stirred at −50° C. for 30 min. After this time, the reaction mixture was treated with saturated aqueous ammonium chloride (15 mL) and extracted with ethyl acetate (3×15 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (2R,3R)-1-tert-butyl 4-((S)-1-(((4R,4aS,7aR,12bS)-4a-hydroxy-9-methoxy-3-methyl-2,3,4,4a,5,7a-hexahydro-1H-4, 12-methanobenzofuro[3,2-e]isoquinolin-7-yl)oxy)-1-oxopropan-2-yl) 2,3-diacetoxysuccinate (103 mg, 13%) as a white solid: ESI MS m/z 660 $[C_{33}H_{41}NO_{13}+H]^+$.

A solution of (2S,3S)-1-((S)-1-(tert-butoxy)-1-oxopropan-2-yl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2,3-diacetoxysuccinate (57 mg, 0.091 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (2R,3R)-2,3-diacetoxy-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt (68 mg, 72%) as a white solid: $^1$H NMR (300 MHz, DMSO-$d_6$) δ 13.9 (s, 1H), 9.19 (s, 1H), 6.85 (d, J=8.1 Hz, 1H), 6.75 (d, J=8.1 Hz, 1H), 6.32 (s, 1H), 5.72 (d, J=3.0 Hz, 1H), 5.66-5.60 (m, 2H), 5.29 (dd, J=13.8, 6.9 Hz, 1H), 5.03 (s, 1H), 3.74 (s, 3H), 3.65 (d, J=6.3 Hz, 1H), 3.41 (d, J=20.1 Hz, 1H), 3.16-3.07 (m, 2H), 2.84 (d, J=3.6 Hz, 3H), 2.64-2.61 (m, 1H), 2.46-2.42 (m, 1H), 2.33-2.26 (m, 1H), 2.13 (s, 3H), 2.11 (s, 3H), 2.06 (d, J=18.0 Hz, 1H), 1.65 (d, J=11.1 Hz, 1H), 1.48 (d, J=6.9 Hz, 3H); ESI MS m/z 604 $[C_{29}H_{33}NO_{13}+H]^+$.

Scheme 84: (R)-2-(((2R,3R)-2,3-Diacetoxy-4-((4R,4aS,7aR,12bS)-4a-hydroxy-9-methoxy-3-methyl-2,3,4,4a,5,7a-hexahydro-1H-4, 12-methanobenzofuro[3,2-e]isoquinolin-7-yl)oxy)-4-oxobutanoyl)oxy)succinic acid trifluoroacetic acid salt

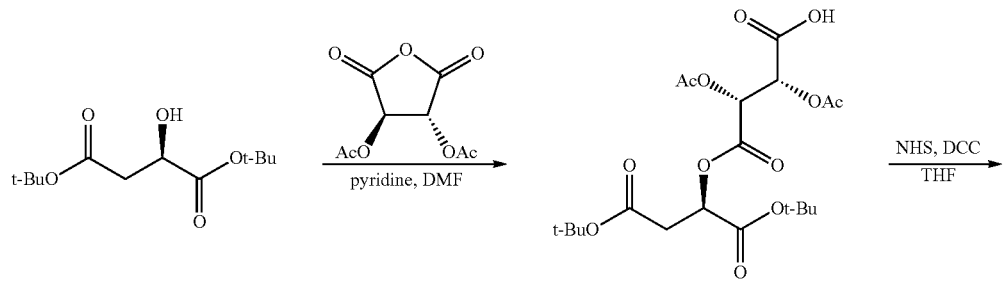

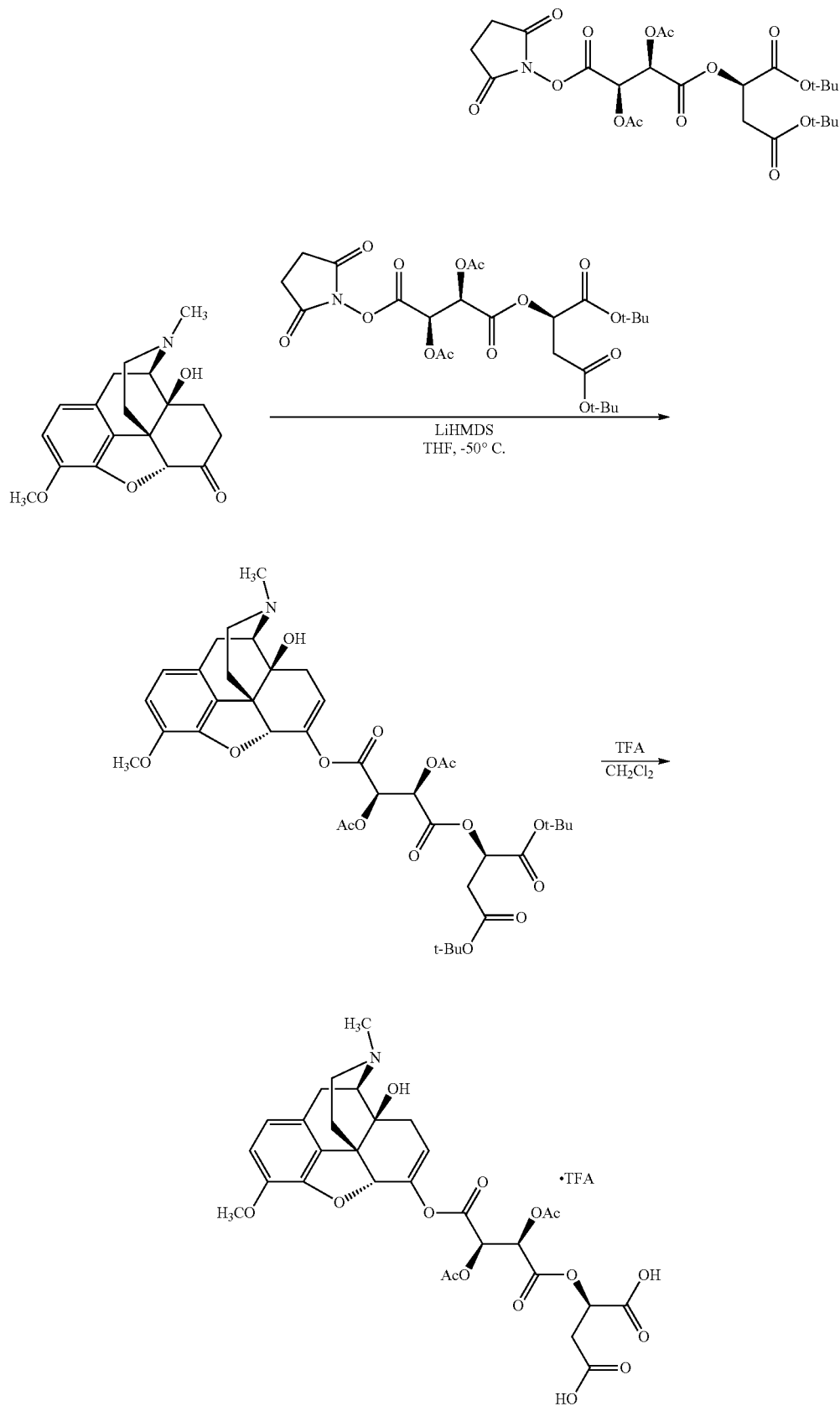

Preparation of (2R,3R)-2,3-Diacetoxy-4-(((R)-1,4-di-tert-butoxy-1,4-dioxobutan-2-yl)oxy)-4-oxobutanoic acid

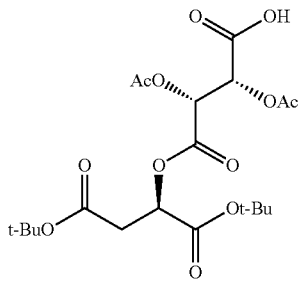 [SMILES: CC(=O)O[C@@H](C(=O)O)[C@@H](OC(C)=O)C(=O)O[C@H](CC(=O)OC(C)(C)C)C(=O)OC(C)(C)C]

(R)-Di-tert-butyl 2-hydroxysuccinate (1.60 g, 6.50 mmol), (3R,4R)-2,5-dioxotetrahydrofuran-3,4-diyl diacetate (1.76 g, 8.12 mmol), pyridine (462 mg, 5.85 mmol), and N,N-dimethylformamide (4 mL) were combined and stirred at 0° C. under a nitrogen atmosphere for 3 h. After this time, saturated sodium bicarbonate (15 mL) was added, and the resulting aqueous solution was washed with ethyl acetate (10 mL). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (2R,3R)-2,3-diacetoxy-4-(((R)-1,4-di-tert-butoxy-1,4-dioxobutan-2-yl)oxy)-4-oxobutanoic acid (2.28 g, 75%) as a yellow oil: $^1$H NMR (300 MHz, CDCl$_3$) δ 5.80 (d, J=2.7 Hz, 1H), 5.75 (d, J=2.4 Hz, 1H), 5.36 (dd, J=7.8, 5.1 Hz, 1H), 2.78-2.74 (m, 2H), 2.21 (s, 3H), 2.19 (s, 3H), 1.46 (s, 9H), 1.44 (s, 9H), CO$_2$H proton not observed.

Preparation of (2R,3R)-1-((R)-1,4-Di-tert-butoxy-1,4-dioxobutan-2-yl) 4-(2,5-dioxopyrrolidin-1-yl) 2,3-diacetoxysuccinate

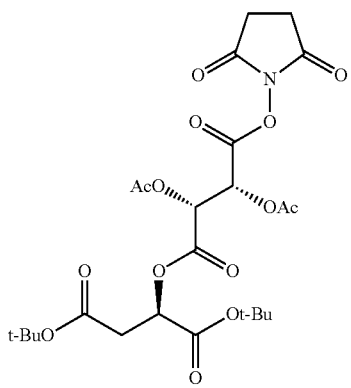 [SMILES: CC(=O)O[C@@H](C(=O)O[C@H](CC(=O)OC(C)(C)C)C(=O)OC(C)(C)C)[C@@H](OC(C)=O)C(=O)ON1C(=O)CCC1=O]

A solution of (2R,3R)-2,3-diacetoxy-4-(((R)-1,4-di-tert-butoxy-1,4-dioxobutan-2-yl)oxy)-4-oxobutanoic acid (2.28 g, 4.93 mmol) in tetrahydrofuran (40 mL) was treated with N-hydroxysuccinimide (624 mg, 5.42 mmol) and N,N'-dicyclohexylcarbodiimide (1.12 g, 5.42 mmol) and stirred under a nitrogen atmosphere for 4 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (2R,3R)-1-((R)-1,4-di-tert-butoxy-1,4-dioxobutan-2-yl) 4-(2,5-dioxopyrrolidin-1-yl) 2,3-diacetoxysuccinate (3.39 g, quantitative) as a yellow solid: $^1$H NMR (300 MHz, CDCl$_3$) δ 6.14 (d, J=3.0 Hz, 1H), 5.88 (d, J=3.0 Hz, 1H), 5.38 (dd, J=8.1, 3.3 Hz, 1H), 2.88-2.68 (m, 6H), 2.24 (s, 3H), 2.23 (s, 3H), 1.46 (s, 9H), 1.44 (s, 9H).

Preparation of (2R,3R)-1-((R)-1,4-Di-tert-butoxy-1,4-dioxobutan-2-yl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2,3-diacetoxysuccinate

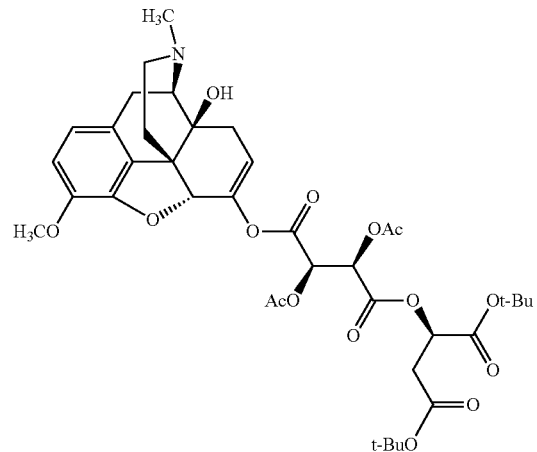 [SMILES: COc1ccc2c3c1O[C@H]1C(OC(=O)[C@H](OC(C)=O)[C@@H](OC(C)=O)C(=O)O[C@H](CC(=O)OC(C)(C)C)C(=O)OC(C)(C)C)=CC[C@@]4(O)[C@@H](C2)N(C)CC[C@]314]

A suspension of oxycodone (400 mg, 1.27 mmol) in tetrahydrofuran (10 mL) was cooled to −50° C. and treated dropwise with a 1.0 M solution of lithium bis(trimethylsilyl)amide in tetrahydrofuran (1.4 mL, 1.4 mmol). After addition was complete, the mixture was stirred at −50° C. for 45 min. The mixture was treated dropwise with a solution of (2R,3R)-1-((R)-1,4-di-tert-butoxy-1,4-dioxobutan-2-yl) 4-(2,5-dioxopyrrolidin-1-yl) 2,3-diacetoxysuccinate (800 mg, 1.4 mmol) in tetrahydrofuran (8 mL). After addition was complete, the mixture was stirred at −50° C. for 30 min. After this time, the reaction mixture was treated with saturated aqueous ammonium chloride (15 mL) and extracted with ethyl acetate (3×15 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (2R,3R)-1-((R)-1,4-di-tert-butoxy-1,4-dioxobutan-2-yl) 4-((4R,4aS,7aR,12bS)-4a-hydroxy-9-methoxy-3-methyl-2,3,4a,5,7a-hexahydro-1H-4,12-methanobenzofuro[3,2-e]isoquinolin-7-yl) 2,3-diacetoxysuccinate (128 mg, 13%) as a white solid: ESI MS m/z 760 [C$_{38}$H$_{49}$NO$_{15}$+H]$^+$.

Preparation of (R)-2-(((2R,3R)-2,3-Diacetoxy-4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid trifluoroacetic acid salt

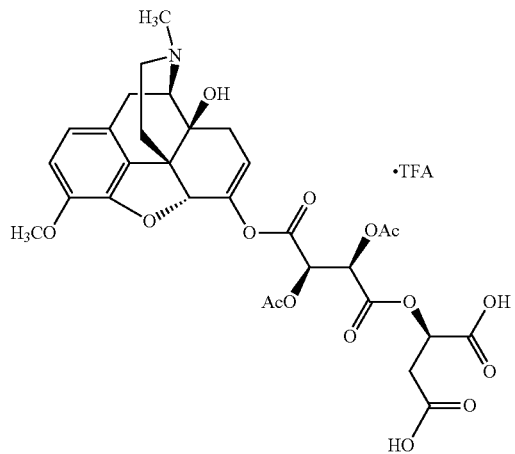 [SMILES: COc1ccc2c3c1O[C@H]1C(OC(=O)[C@H](OC(C)=O)[C@@H](OC(C)=O)C(=O)O[C@H](CC(=O)O)C(=O)O)=CC[C@@]4(O)[C@@H](C2)N(C)CC[C@]314]

A solution of (2R,3R)-1-((R)-1,4-di-tert-butoxy-1,4-dioxobutan-2-yl) 4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) 2,3-diacetoxysuccinate (128 mg, 0.171 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (R)-2-(((2R,3R)-2,3-diacetoxy-4-((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-4-oxobutanoyl)oxy)succinic acid trifluoroacetic acid salt (65 mg, 59%) as a white solid: $^1$H NMR (300 MHz, DMSO-$d_6$) δ 13.5 (s, 1H), 12.7 (s, 1H), 9.17 (s, 1H), 6.88 (d, J=8.4 Hz, 1H), 6.77 (d, J=8.4 Hz, 1H), 6.33 (s, 1H), 5.80 (dd, J=9.6, 2.7 Hz, 2H), 5.57 (dd, J=6.0, 2.1 Hz, 1H), 5.35 (dd, J=7.8, 1.2 Hz, 1H), 4.89 (s, 1H), 3.75 (s, 3H), 3.65 (d, J=6.3 Hz, 1H), 3.41 (d, J=20.1 Hz, 1H), 3.15-3.07 (m, 2H), 2.93-2.80 (m, 5H), 2.64-2.61 (m, 1H), 2.41-2.32 (m, 1H), 2.32-2.26 (m, 1H), 2.27 (s, 3H), 2.07 (s, 3H), 2.06 (d, J=18.3 Hz, 1H), 1.64 (d, J=11.4 Hz, 1H); ESI MS m/z 648 $[C_{30}H_{33}NO_{15}+H]^+$.

Scheme 85: (S)-3-Amino-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid bis(trifluoroacetic acid salt)

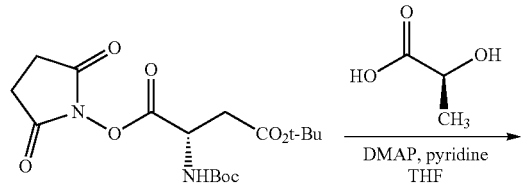

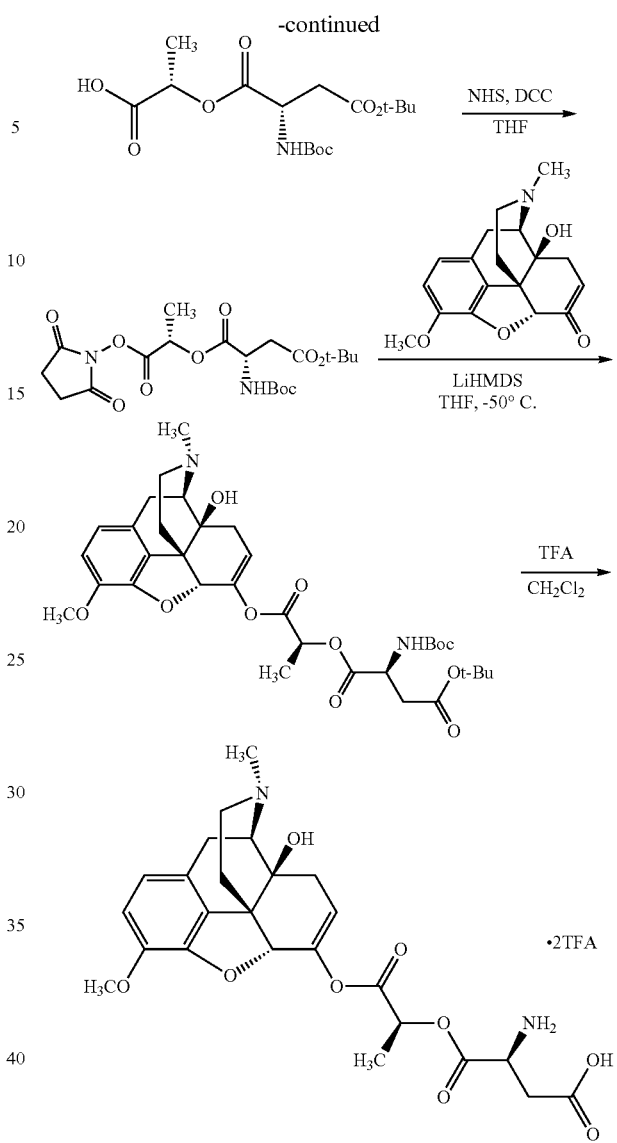

Preparation of (S)-2-(((S)-4-(tert-Butoxy)-2-((tert-butoxycarbonyl)amino)-4-oxobutanoyl)oxy)propanoic acid

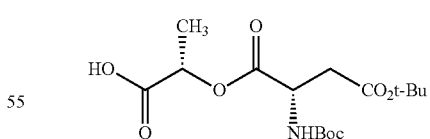

(S)-Lactic acid (280 mg, 3.11 mmol), (S)-4-tert-butyl 1-(2,5-dioxopyrrolidin-1-yl) 2-((tert-butoxycarbonyl)amino)succinate (1.00 g, 2.59 mmol), 4-(dimethylamino)pyridine (32 mg, 0.259 mmol), pyridine (248 mg, 3.11 mmol), and tetrahydrofuran (17 mL) were combined and heated at 60° C. under a nitrogen atmosphere for 24 h. After this time, the solvent was removed under reduced pressure, and the residue was participated between ethyl acetate (30 mL) and 10% aqueous citric acid. The organic layer was separated and washed with water (50 mL), dried over sodium sulfate, filtered, and concentrated under reduced pressure to provide (S)-2-(((S)-4-(tert-butoxy)-2-((tert-butoxycarbonyl)amino)-4-oxobutanoyl)oxy)propanoic acid (858 mg, 91%) as a colorless oil: $^1$H NMR (300 MHz, CDCl$_3$) δ 5.51 (m, 1H), 4.58 (m, 1H), 2.96-2.69 (m, 2H), 1.55 (m, 3H), 1.45 (s, 18H), CO$_2$H and NH protons not observed.

Preparation of (S)-4-tert-Butyl 1-((S)-1-((2,5-dioxopyrrolidin-1-yl)oxy)-1-oxopropan-2-yl) 2-((tert-butoxycarbonyl)amino)succinate

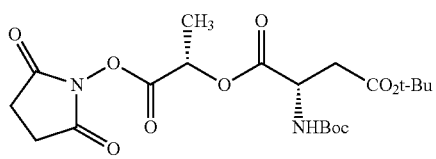 [SMILES: C[C@H](OC(=O)[C@H](CC(=O)OC(C)(C)C)NC(=O)OC(C)(C)C)C(=O)ON1C(=O)CCC1=O]

A solution of (S)-2-(((S)-4-(tert-butoxy)-2-((tert-butoxycarbonyl)amino)-4-oxobutanoyl)oxy)propanoic acid (858 mg, 2.37 mmol) in tetrahydrofuran (30 mL) was treated with N-hydroxysuccinimide (300 mg, 2.61 mmol) and N,N'-dicyclohexylcarbodiimide (538 mg, 2.61 mmol) and stirred at room temperature under a nitrogen atmosphere for 5 h. After this time, the reaction mixture was filtered to remove the solid dicyclohexylurea byproduct. The solid was washed with diethyl ether (50 mL), and the combined filtrate and washings were concentrated under reduced pressure. The residue was triturated with diethyl ether to provide (S)-4-tert-butyl 1-((S)-1-((2,5-dioxopyrrolidin-1-yl)oxy)-1-oxopropan-2-yl) 2-((tert-butoxycarbonyl)amino)succinate (1.24 g, quantitative) as a white solid: $^1$H NMR (300 MHz, CDCl$_3$) δ 5.52 (m, 1H), 4.63 (m, 1H), 2.97-2.73 (m, 6H), 1.68 (m, 3H), 1.45 (s, 18H), NH proton not observed.

Preparation of (S)-4-tert-Butyl 1-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-((tert-butoxycarbonyl)amino)succinate

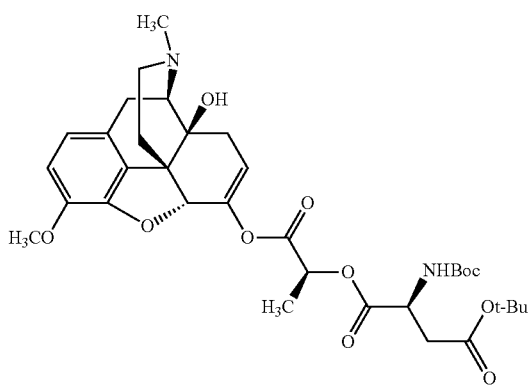 [SMILES: COc1ccc2c3c1O[C@H]1C(OC(=O)[C@H](C)OC(=O)[C@H](CC(=O)OC(C)(C)C)NC(=O)OC(C)(C)C)=CC[C@@]4(O)[C@@H](C2)N(C)CC[C@]314]

A suspension of oxycodone (380 mg, 1.21 mmol) in tetrahydrofuran (10 mL) was cooled to −50° C. and treated dropwise with a 1.0 M solution of lithium bis(trimethylsilyl)amide in tetrahydrofuran (1.3 mL, 1.3 mmol). After addition was complete, the mixture was stirred at −50° C. for 45 min. The mixture was treated dropwise with a solution of (S)-4-tert-butyl 1-((S)-1-((2,5-dioxopyrrolidin-1-yl)oxy)-1-oxopropan-2-yl) 2-((tert-butoxycarbonyl)amino)succinate (560 mg, 1.31 mmol) in tetrahydrofuran (8 mL). After addition was complete, the mixture was stirred at −50° C. for 30 min. After this time, the reaction mixture was treated with saturated aqueous ammonium chloride (15 mL) and extracted with ethyl acetate (3×15 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (S)-4-tert-butyl 1-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-((tert-butoxycarbonyl)amino)succinate (65 mg, 8%) as a white solid: ESI MS m/z 659 [C$_{34}$H$_{46}$N$_2$O$_{11}$+H]$^+$.

Preparation of (S)-3-Amino-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid bis(trifluoroacetic acid salt)

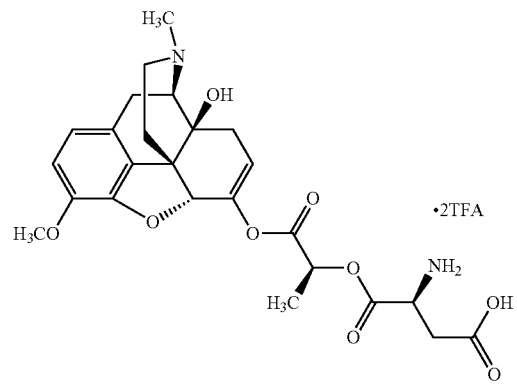 [SMILES: COc1ccc2c3c1O[C@H]1C(OC(=O)[C@H](C)OC(=O)[C@@H](N)CC(=O)O)=CC[C@@]4(O)[C@@H](C2)N(C)CC[C@]314]

A solution of (S)-4-tert-butyl 1-((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl) 2-((tert-butoxycarbonyl)amino)succinate (65 mg, 0.10 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. This material was purified by reversed phase column chromatography (50 g C18 column, 5-40% acetonitrile/water) and freeze dried to provide (S)-3-amino-4-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid bis(trifluoroacetic acid salt)(46 mg, 90%) as a white solid: $^1$H NMR (300 MHz, DMSO-d$_6$) δ 13.2 (s, 1H), 9.20 (s, 1H), 8.48 (s, 3H), 6.87 (d, J=8.4 Hz, 1H), 6.76 (d, J=8.4 Hz, 1H), 6.32 (s, 1H), 5.62-5.59 (m, 1H), 5.39-5.30 (m, 1H), 5.00 (d, J=7.5 Hz, 1H), 4.48-4.45 (m, 1H), 3.76 (s, 3H), 3.66 (d, J=6.3 Hz, 1H), 3.44 (d, J=20.1 Hz, 1H), 3.16-3.07 (m, 2H), 2.96-2.85 (m, 5H), 2.64-2.61 (m, 1H), 2.46-2.42 (m, 1H), 2.33-2.26 (m, 1H), 2.07 (d, J=18.0 Hz, 1H), 1.64 (d, J=12.6 Hz, 1H), 1.55 (d, J=7.2 Hz, 3H); ESI MS m/z 503 [C$_{25}$H$_{30}$N$_2$O$_9$+H]$^+$.

Scheme 86: (S)-4-Amino-5-((3-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoic acid bis (trifluoroacetic acid salt)
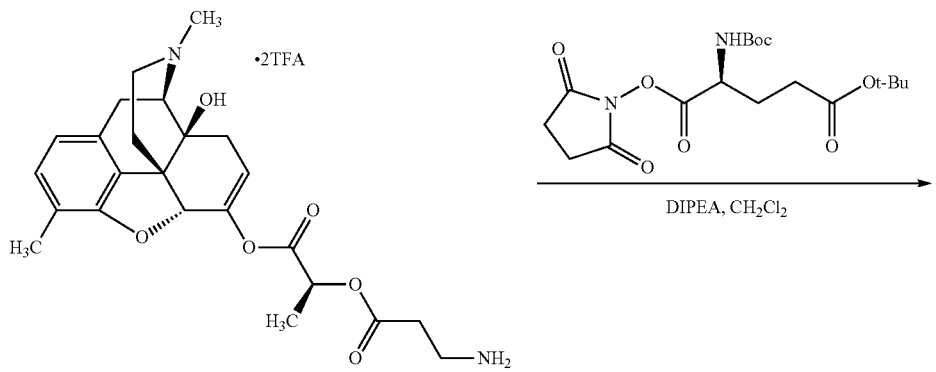
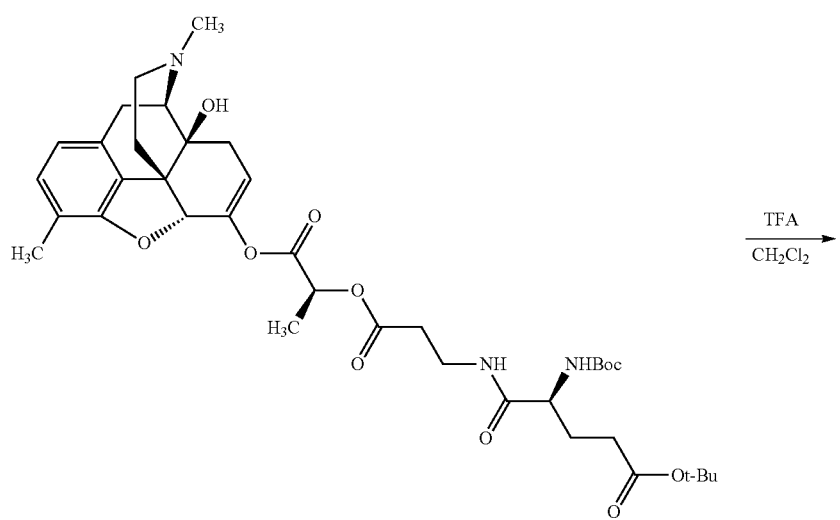
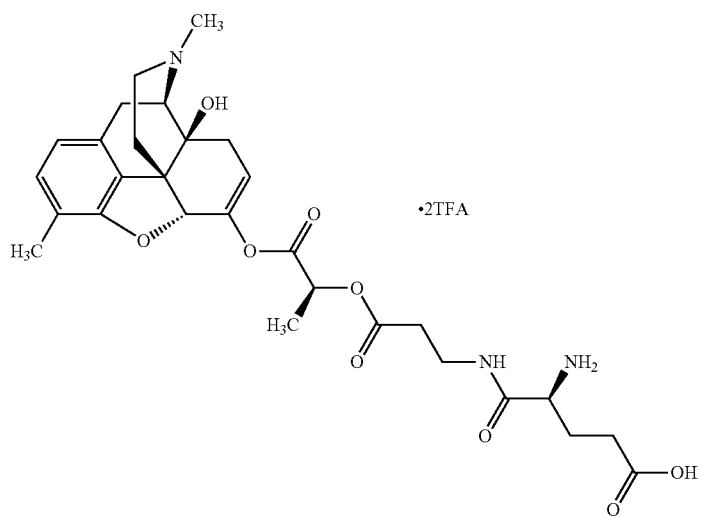

601

Preparation of (S)-tert-Butyl 4-((tert-butoxycarbonyl)amino)-5-[(3-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoate

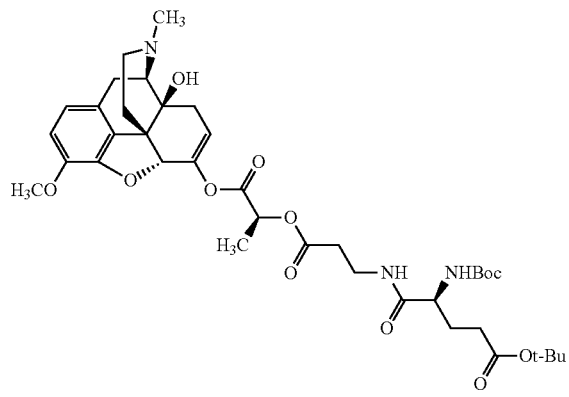 [SMILES: COc1ccc2c3c1O[C@H]1C(OC(=O)[C@H](C)OC(=O)CCNC(=O)[C@H](CCC(=O)OC(C)(C)C)NC(=O)OC(C)(C)C)=CC[C@@]4(O)[C@@H](C2)N(C)CC[C@]314]

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-aminopropanoyl)oxy)propanoate bis(2,2,2-trifluoroacetate) (121 mg, 0.176 mmol) and (S)-5-tert-butyl 1-(2,5-dioxopyrrolidin-1-yl) 2-((tert-butoxycarbonyl)amino)pentanedioate (108 mg, 0.269 mmol) in methylene chloride (3 mL) was treated with N,N-diisopropylethylamine (0.13 mL, 0.75 mmol) and stirred under a nitrogen atmosphere for 45 min. After this time, the reaction mixture was diluted with methylene chloride (15 mL) and washed with saturated aqueous ammonium chloride (10 mL). The organic layer was dried over sodium sulfate, filtered, and concentrated under reduced pressure to provide (S)-tert-butyl 4-((tert-butoxycarbonyl)amino)-5-((3-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoate (155 mg, quantitative) as a colorless semi-solid: ESI MS m/z 744 $[C_{38}H_{53}N_3O_{12}+H]^+$.

602

Preparation of (S)-4-Amino-5-((3-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoic acid bis (trifluoroacetic acid salt)

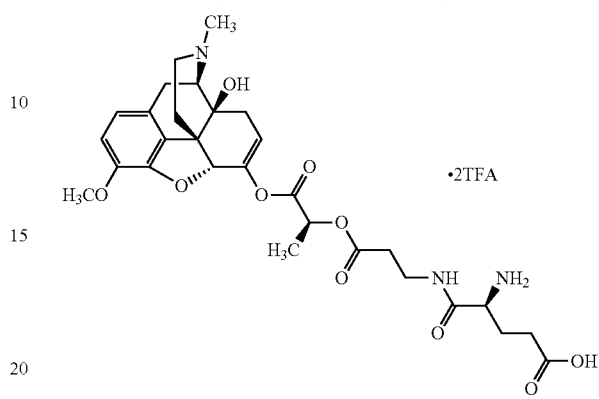

A solution of (S)-tert-butyl 4-((tert-butoxycarbonyl)amino)-5-((3-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoate (130 mg, 0.176 mmol) in methylene chloride (2 mL) was treated with trifluoroacetic acid (1 mL) and stirred under a nitrogen atmosphere at ambient temperature for 30 min. After this time, the reaction mixture was concentrated under reduced pressure. The residue was purified by reversed phase column chromatography (50 g C18 column, 5-70% acetonitrile/water with 0.1% trifluoroacetic acid) and freeze dried to provide (S)-4-Amino-5-((3-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoic acid bis(trifluoroacetic acid salt)(73 mg, 51%) as a white solid: $^1$H NMR (300 MHz, DMSO-$d_6$) δ 12.35 (br s, 1H), 9.19 (br s, 1H), 8.61 (t, J=5.4 Hz, 1H), 8.13 (br s, 3H), 6.86 (d, J=8.4 Hz, 1H), 6.76 (d, J=8.4 Hz, 1H), 6.31 (br s, 1H), 5.59 (dd, J=5.7, 1.8 Hz, 1H), 5.12 (q, J=7.2 Hz, 1H), 5.00 (s, 1H), 3.76 (s, 3H), 3.75-3.71 (m, 1H), 3.66 (d, J=6.3 Hz, 1H), 3.53-3.40 (m, 3H), 3.35-3.25 (m, 1H), 3.16-3.07 (m, 2H), 2.85 (apparent d, J=3.6 Hz, 3H), 2.67-2.55 (m, 2H), 2.49-2.42 (m, 1H, partially obscured by solvent peak), 2.35-2.26 (m, 3H), 2.09-2.03 (m, 1H), 1.95-1.89 (m, 2H), 1.64 (d, J=11.1 Hz, 1H), 1.51 (d, J=7.2 Hz, 3H); ESI MS m/z 588 $[C_{29}H_{37}N_3O_{10}+H]^+$; HPLC (Method A)>99% (AUC), $t_R$=7.16 min.

Scheme 87: (S)-1-Amino-5-((3-(((S)-1-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoic acid bis(trifluoroacetic acid salt)

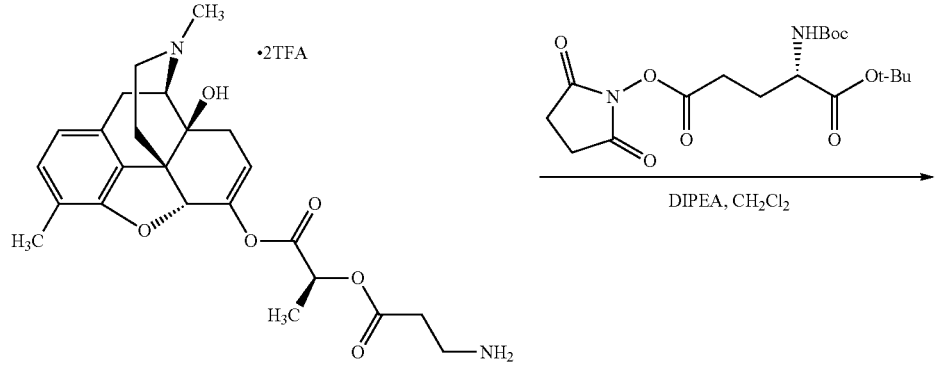

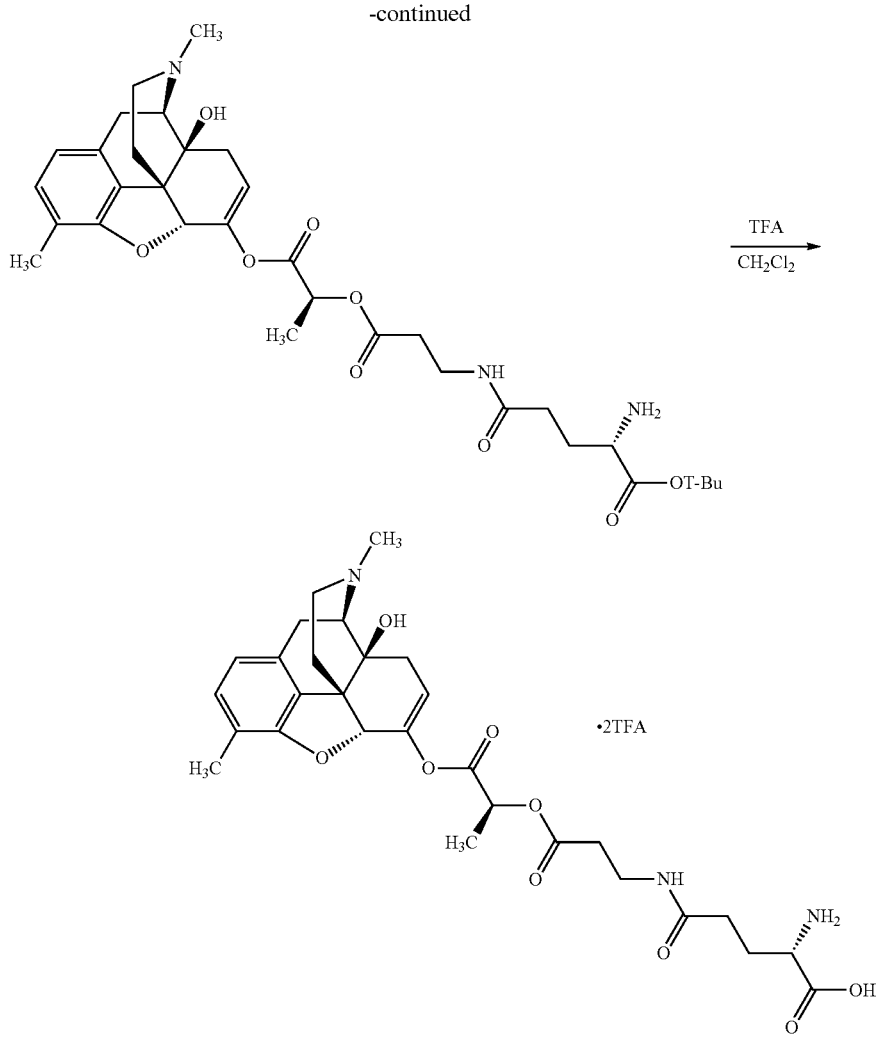

Preparation of (S)-tert-Butyl 2-((tert-butoxycarbonyl)amino)-5-((3-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoate

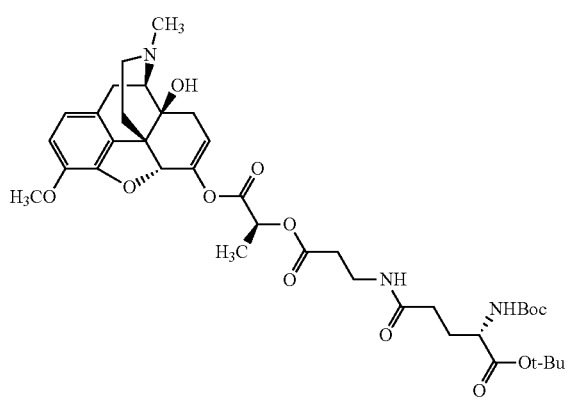 [SMILES: COc1ccc2c3c1O[C@H]1C(OC(=O)[C@H](C)OC(=O)CCNC(=O)CC[C@H](NC(=O)OC(C)(C)C)C(=O)OC(C)(C)C)=CC[C@@]4(O)[C@@H](C2)N(C)CC[C@]314]

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-aminopropanoyl)oxy)propanoate bis(2,2,2-trifluoroacetate) (123 mg, 0.179 mmol) and (S)-1-tert-butyl 5-(2,5-dioxopyrrolidin-1-yl) 2-((tert-butoxycarbonyl)amino)pentanedioate (108 mg, 0.269 mmol) in methylene chloride (3 mL) was treated with N,N-diisopropylethylamine (0.13 mL, 0.75 mmol) and stirred under a nitrogen atmosphere for 30 min. After this time, the reaction mixture was diluted with methylene chloride (15 mL) and washed with saturated aqueous ammonium chloride (10 mL). The organic layer was dried over sodium sulfate, filtered, and concentrated under reduced pressure to provide (S)-tert-butyl 2-((tert-butoxycarbonyl)amino)-5-((3-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoate (151 mg, quantitative) as a colorless semi-solid: ESI MS m/z 744 $[C_{38}H_{53}N_3O_{12}+H]^+$.

Preparation of (S)-2-Amino-5-((3-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoic acid bis (trifluoroacetic acid salt)

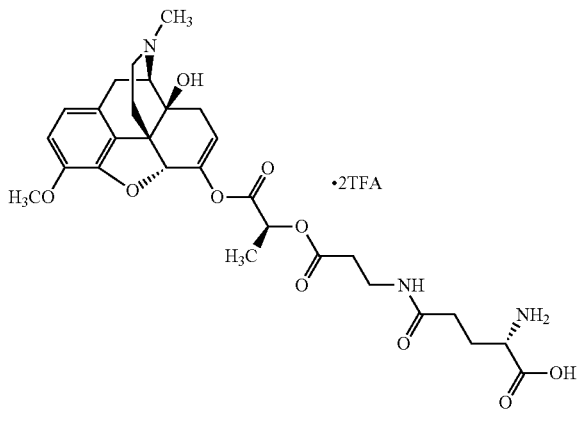 [SMILES: COc1ccc2c3c1O[C@H]1C(OC(=O)[C@H](C)OC(=O)CCNC(=O)CC[C@H](N)C(=O)O)=CC[C@@]4(O)[C@@H](C2)N(C)CC[C@]314]

A solution of (S)-tert-butyl 2-((tert-butoxycarbonyl)amino)-5-((3-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoate (133 mg, 0.179 mmol) in methylene chloride (2 mL) was treated with trifluoroacetic acid (1 mL) and stirred under a nitrogen atmosphere at ambient temperature for 30 min. After this time, the reaction mixture was concentrated under reduced pressure. The residue was purified by reversed phase column chromatography (50 g C18 column, 5-70% acetonitrile/water with 0.1% trifluoroacetic acid) and freeze dried to provide (S)-2-amino-5-((3-(((S)-1-(((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoic acid bis(trifluoroacetic acid salt)(77 mg, 53%) as a white solid: $^1$H NMR (300 MHz, DMSO-$d_6$) δ 9.19 (br s, 1H), 8.26 (br s, 3H), 8.10 (t, J=5.7 Hz, 1H), 6.86 (d, J=8.4 Hz, 1H), 6.76 (d, J=8.4 Hz, 1H), 6.32 (br s, 1H), 5.58 (dd, J=5.7, 1.8 Hz, 1H), 5.11 (q, J=7.2 Hz, 1H), 5.00 (s, 1H), 3.93 (br s, 1H), 3.75 (s, 3H), 3.66 (d, J=6.3 Hz, 1H), 3.47-3.40 (m, 2H, partially obscured by water peak), 3.36-3.27 (m, 2H), 3.16-3.07 (m, 2H), 2.85 (s, 3H), 2.63-2.55 (m, 2H), 2.49-2.43 (m, 1H, partially obscured by solvent peak), 2.34-2.17 (m, 3H), 2.09-1.93 (m, 3H), 1.64 (d, J=11.1 Hz, 1H), 1.50 (d, J=7.2 Hz, 3H), $CO_2H$ proton not observed; ESI MS m/z 588 $[C_{29}H_{37}N_3O_{10}+H]^+$; HPLC (Method A)>99% (AUC), $t_R$=7.23 min.

Scheme 88: (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((3-((S)-2-amino-3-phenylpropanamido)propanoyl)oxy)propanoate bis(trifluoroacetic acid salt)

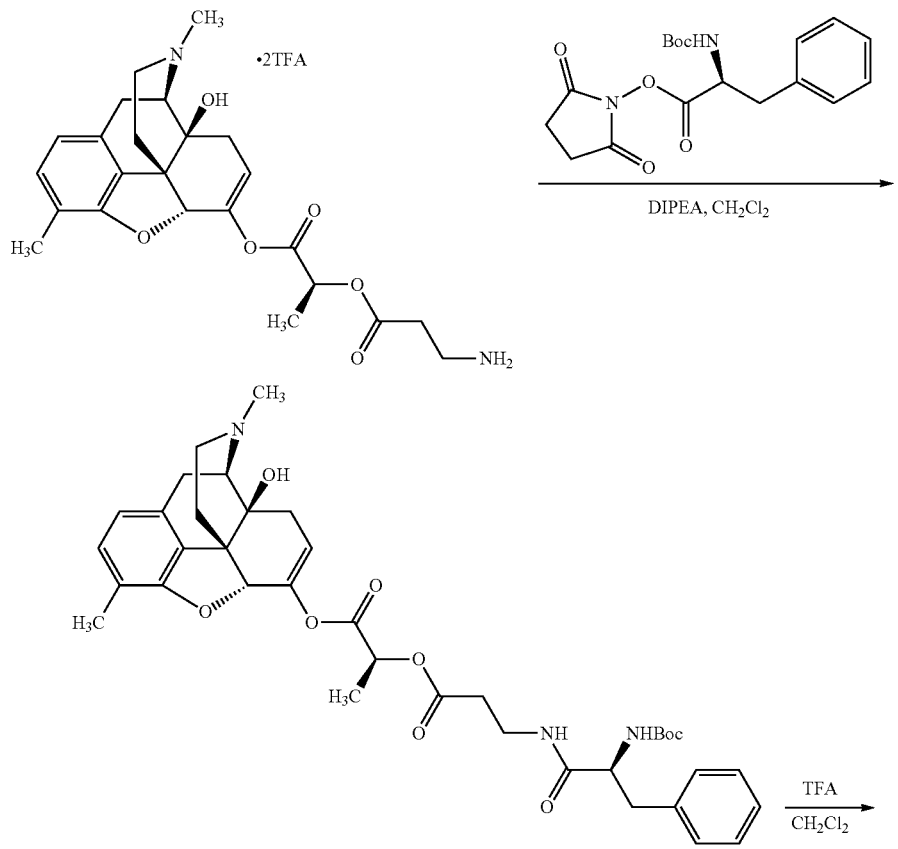

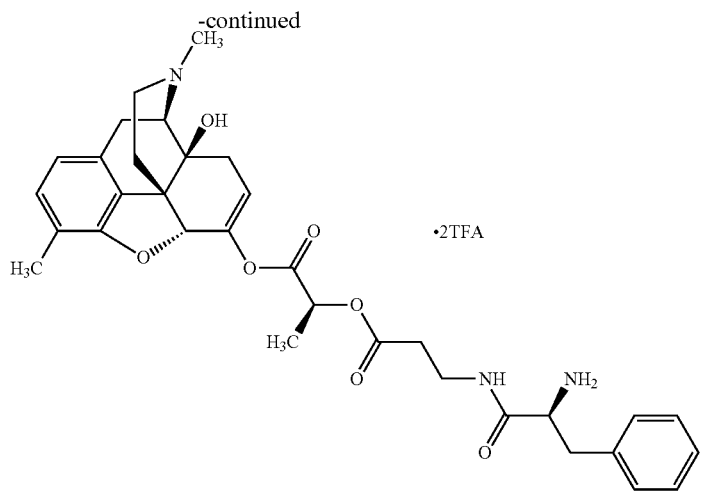

Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((3-((S)-2-((tert-butoxycarbonyl)amino)-3-phenylpropanamido)propanoyl)oxy)propanoate Preparation of (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((3-((S)-2-amino-3-phenylpropanamido)propanoyl)oxy)propanoate bis(trifluoroacetic acid salt)

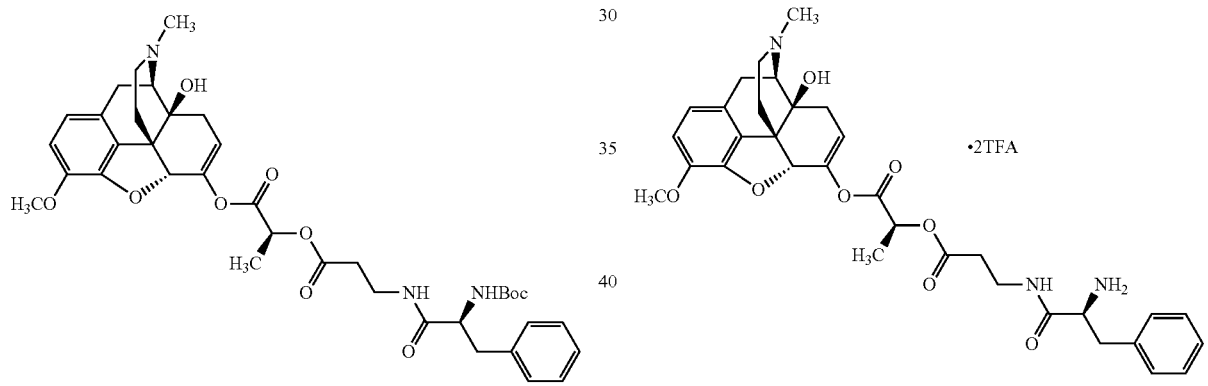

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-aminopropanoyl)oxy)propanoate bis(2,2,2-trifluoroacetate) (134 mg, 0.195 mmol) and (S)-2,5-dioxopyrrolidin-1-yl 2-((tert-butoxycarbonyl)amino)-3-phenylpropanoate (109 mg, 0.301 mmol) in methylene chloride (3 mL) was treated with N,N-diisopropylethylamine (0.14 mL, 0.80 mmol) and stirred under a nitrogen atmosphere for 15 min. After this time, the reaction mixture was diluted with methylene chloride (15 mL) and washed with saturated aqueous ammonium chloride (10 mL). The organic layer was dried over sodium sulfate, filtered, and concentrated under reduced pressure to provide (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-((S)-2-((tert-butoxycarbonyl)amino)-3-phenylpropanamido)propanoyl)oxy)propanoate (156 mg, quantitative) as a colorless semi-solid: ESI MS m/z 706 $[C38H_{47}N_3O_{10}+H]^+$.

A solution of (S)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((3-((S)-2-((tert-butoxycarbonyl)amino)-3-phenylpropanamido)propanoyl)oxy)propanoate (137 mg, 0.195 mmol) in methylene chloride (2 mL) was treated with trifluoroacetic acid (1 mL) and stirred under a nitrogen atmosphere at ambient temperature for 30 min. After this time, the reaction mixture was concentrated under reduced pressure. The residue was purified by reversed phase column chromatography (50 g C18 column, 5-70% acetonitrile/water with 0.1% trifluoroacetic acid) and freeze dried to provide (S)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((3-((S)-2-amino-3-phenylpropanamido)propanoyl)oxy)propanoate bis(trifluoroacetic acid salt)(80 mg, 49%) as a white solid: $^1$H NMR (300 MHz, DMSO-$d_6$) δ 9.18 (br s, 1H), 8.48 (t, J=5.7 Hz, 1H), 8.17 (br s, 3H), 7.37-7.26 (m, 3H), 7.23-7.20 (m, 2H), 6.86 (d, J=8.4 Hz, 1H), 6.76 (d, J=8.4 Hz, 1H), 6.29 (br s, 1H), 5.58 (dd, J=6.0, 2.1 Hz, 1H), 5.09 (q, J=7.2 Hz, 1H), 4.99 (s, 1H), 3.94 (br s, 1H), 3.75 (s, 3H), 3.65 (d, J=6.3 Hz, 1H), 3.45-3.40 (m, 3H, partially obscured by water peak), 3.24-3.07 (m, 4H), 2.99-2.96 (m, 2H), 2.85 (apparent d, J=4.2 Hz, 3H), 2.68-2.55 (m, 1H), 2.49-2.41 (m, 1H, partially obscured by solvent peak), 2.37-2.25 (m, 1H), 2.05 (apparent d, J=17.7 Hz, 1H), 1.64 (d, J=13.2 Hz, 1H), 1.52 (d, J=6.9 Hz, 3H);ESI MS m/z 606 [C$_{33}$H$_{39}$N$_3$O$_8$+H]$^+$; HPLC (Method A) 99.0% (AUC), t$_R$=7.94 min.

Scheme 89: (S)-(4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 2-((tert-butoxycarbonyl)oxy)-2-phenylacetate and (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-hydroxy-2-phenylacetate hydrochloride

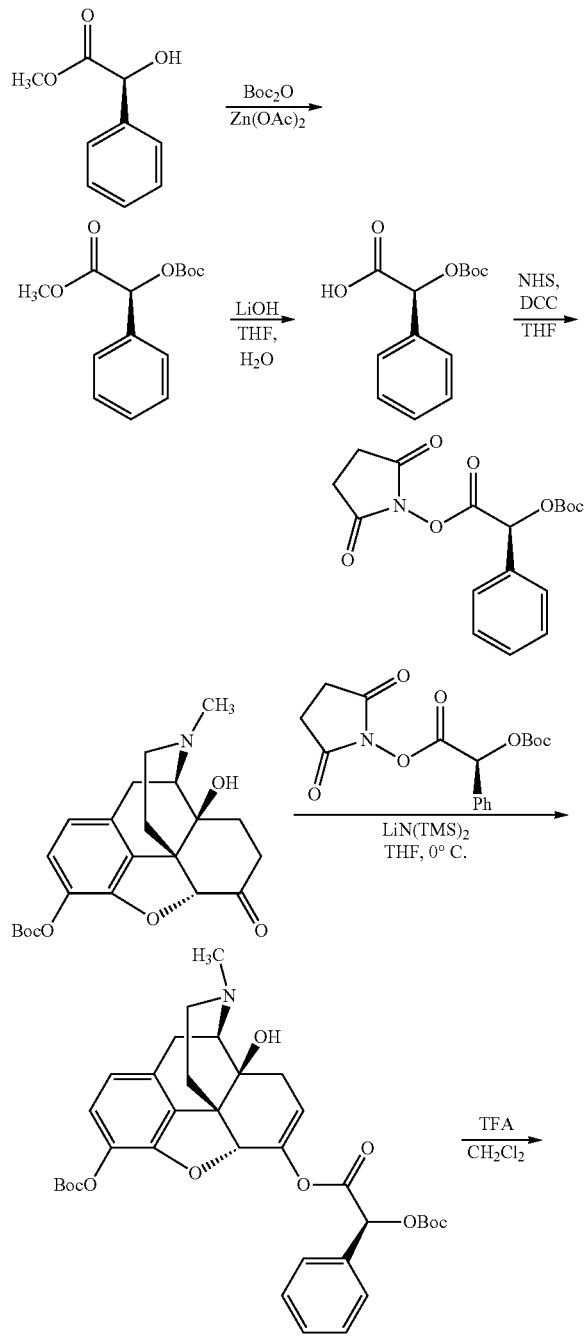

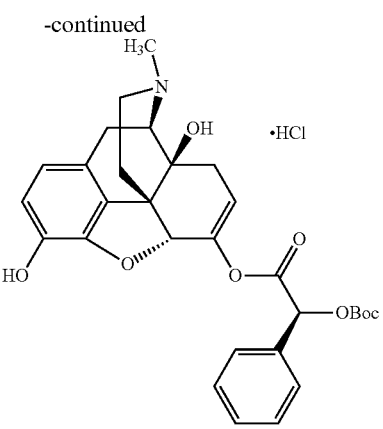

Preparation of (S)-Methyl 2-((tert-butoxycarbonyl)oxy)-2-phenylacetate (S)-Methyl 2-hydroxy-2-phenylacetate (30.0 g, 180 mmol), di-tert-butyl dicarbonate (43.3 g, 198 mmol), and zinc acetate (3.96 g, 18.0 mmol) were combined and heated at 55° C. under a nitrogen atmosphere for 48 h. After this time, the reaction mixture was cooled to ambient temperature. The mixture was diluted with water (400 mL) and extracted with methylene chloride (3×200 mL). The combined organics were washed with brine (200 mL), dried over sodium sulfate, filtered, and concentrated under reduced pressure to provide (S)-methyl 2-((tert-butoxycarbonyl)oxy)-2-phenylacetate (39.2 g, 82%) as a colorless oil: $^1$H NMR (500 MHz, CDCl$_3$) δ 7.37-7.32 (m, 5H), 5.80 (s, 1H), 3.74 (s, 3H), 1.51 (s, 9H).

Preparation of (S)-2-((tert-Butoxycarbonyl)oxy)-2-phenylacetic acid

A solution of (S)-methyl 2-((tert-butoxycarbonyl)oxy)-2-phenylacetate (9.06 g, 34.0 mmol) in a mixture of tetrahydrofuran (106 mL) and water (53 mL) was treated with lithium hydroxide hydrate (4.30 g, 102 mmol) and stirred at ambient temperature for 3 h. After this time, the volatiles were removed under reduced pressure. The aqueous mixture was diluted with water (50 mL) and extracted with diethyl ether (100 mL). The aqueous layer was cooled in an ice bath, acidified to pH ~3 with 1 M hydrochloric acid, and extracted with ethyl acetate (3×100 mL). The combined organics were dried over sodium sulfate, filtered, and concentrated under reduced pressure to provide (S)-2-((tert-butoxycarbonyl)

oxy)-2-phenylacetic acid (8.40 g, 98%) as a white solid: $^1$H NMR (500 MHz, CDCl$_3$) δ 7.50 (7.47 (m, 2H), 7.48-7.37 (m, 3H), 5.82 (s, 1H), 1.50 (s, 9H), CO$_2$H proton not observed.

Preparation of (S)-2,5-Dioxopyrrolidin-1-yl 2-((tert-butoxycarbonyl)oxy)-2-phenylacetate

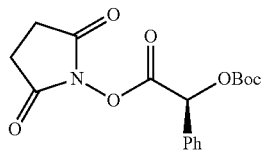

A solution of (S)-2-((tert-butoxycarbonyl)oxy)-2-phenylacetic acid (8.02 g, 31.8 mmol) in tetrahydrofuran (107 mL) was treated with N-hydroxysuccinimide (4.03 g, 35.0 mmol) and N,N'-dicyclohexylcarbodiimide (7.22 g, 16.4 mmol) and stirred under a nitrogen atmosphere for 3 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-2,5-dioxopyrrolidin-1-yl 2-((tert-butoxycarbonyl)oxy)-2-phenylacetate (8.20 g, 74%) as a white powder: $^1$H NMR (500 MHz, DMSO) δ 7.58-7.56 (m, 2H), 7.49-7.45 (m, 3H), 6.39 (s, 1H), 2.93-2.76 (m, 4H), 1.45 (s, 9H).

Preparation of (S)-(4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 2-((tert-butoxycarbonyl)oxy)-2-phenylacetate

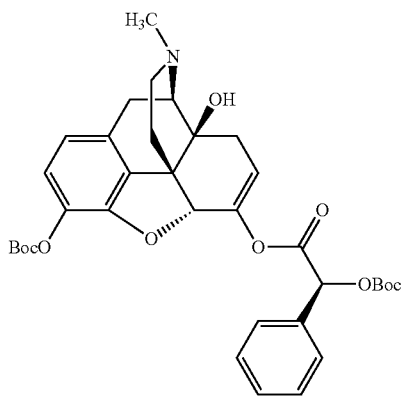

A suspension of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (340 mg, 0.85 mmol) in tetrahydrofuran (10 mL) was cooled in an ice bath and treated dropwise with a 1.0 M solution of lithium bis(trimethylsilyl)amide in tetrahydrofuran (1.7 mL, 1.7 mmol). After 30 min, the mixture was treated dropwise with a solution of (S)-2,5-dioxopyrrolidin-1-yl 2-((tert-butoxycarbonyl)oxy)-2-phenylacetate (592 mg, 1.69 mmol) in tetrahydrofuran (5 mL) and stirred at 0° C. for 16 h. After this time, the reaction mixture was poured into cold saturated aqueous ammonium chloride (50 mL) and extracted with ethyl acetate (2x). The combined organics were washed with saturated aqueous sodium bicarbonate and brine, dried over sodium sulfate, filtered, and concentrated under reduced pressure. The crude residue was purified by reversed phase column chromatography (50 g C18 column, 0-100% acetonitrile/water) and freeze dried to provide (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-((tert-butoxycarbonyl)oxy)-2-phenylacetate (173 mg, 32%) as a white solid and as a mixture of diastereomers: $^1$H NMR (300 MHz, DMSO-d$_6$) δ 7.54-7.51 (m, 2H), 7.46-7.44 (m, 3H), 6.90 (d, J=8.1 Hz, 0.14H), 6.87 (d, J=8.1 Hz, 0.86H), 6.72 (d, J=8.4 Hz, 0.14H), 6.71 (d, J=8.1 Hz, 0.86H), 5.98 (s, 0.14H), 5.97 (s, 0.86H), 5.57 (dd, J=5.4, 2.1 Hz, 0.86H), 5.42-5.41 (m, 0.14H), 4.86 (s, 0.86H), 4.83 (s, 0.14H), 4.76 (br s, 1H), 3.14 (d, J=19.2 Hz, 1H), 2.86-2.84 (m, 1H), 2.69-2.61 (m, 1H), 2.43-2.41 (m, 1H), 2.31 (s, 3H), 2.27-2.23 (m, 1H), 2.11-1.94 (m, 3H), 1.47 (s, 1.26H), 1.46 (s, 7.74H), 1.43 (s, 9H), 1.39-1.33 (m, 1H); ESI MS m/z 636 [C$_{35}$H$_{41}$NO$_{10}$+H]$^+$.

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-hydroxy-2-phenylacetate hydrochloride

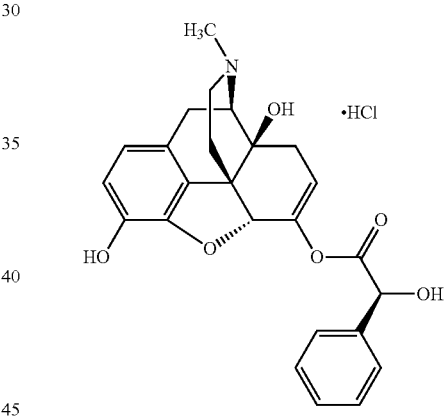

A solution of (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-((tert-butoxycarbonyl)oxy)-2-phenylacetate (250 mg, 0.574 mmol) in methylene chloride (1 mL) was treated with trifluoroacetic acid (1 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water) and freeze dried. The product was converted to the hydrochloride salt by dissolving in ethyl acetate and treating with an excess of a 4 M solution of hydrogen chloride in 1,4-dioxane. The resulting solid was collected by filtration to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-hydroxy-2-phenylacetate hydrochloride (15 mg, 6%) as a white solid: $^1$H NMR (300 MHz, DMSO-d$_6$) δ 9.30 (s, 1H), 9.12 (br s, 1H), 7.50-7.47 (m, 2H), 7.42-7.31 (m, 3H), 6.68 (d, J=8.1 Hz, 1H), 6.62 (d, J=8.1 Hz, 1H), 6.26 (d, J=5.7 Hz, 1H), 6.24 (s, 1H), 5.48-5.45 (m, 1H), 5.27 (d, J=5.4 Hz, 1H), 4.87 (s, 1H), 3.61-3.60 (m, 1H), 3.40-3.34 (m, 1H), 3.07-3.01 (m, 2H), 2.82 (d, J=4.5 Hz, 3H), 2.64-2.57 (m, 1H), 2.43-2.38 (m, 1H), 2.28-2.18 (m, 1H), 2.09-2.03 (m, 1H), 1.62-1.58 (m, 1H); ESI MS m/z 436 $[C_{25}H_{25}NO_6+H]^+$.

Scheme 90: (S)-(4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 2-((tert-butoxycarbonyl)oxy)propanoate and (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-hydroxypropanoate trifluoroacetic acid salt

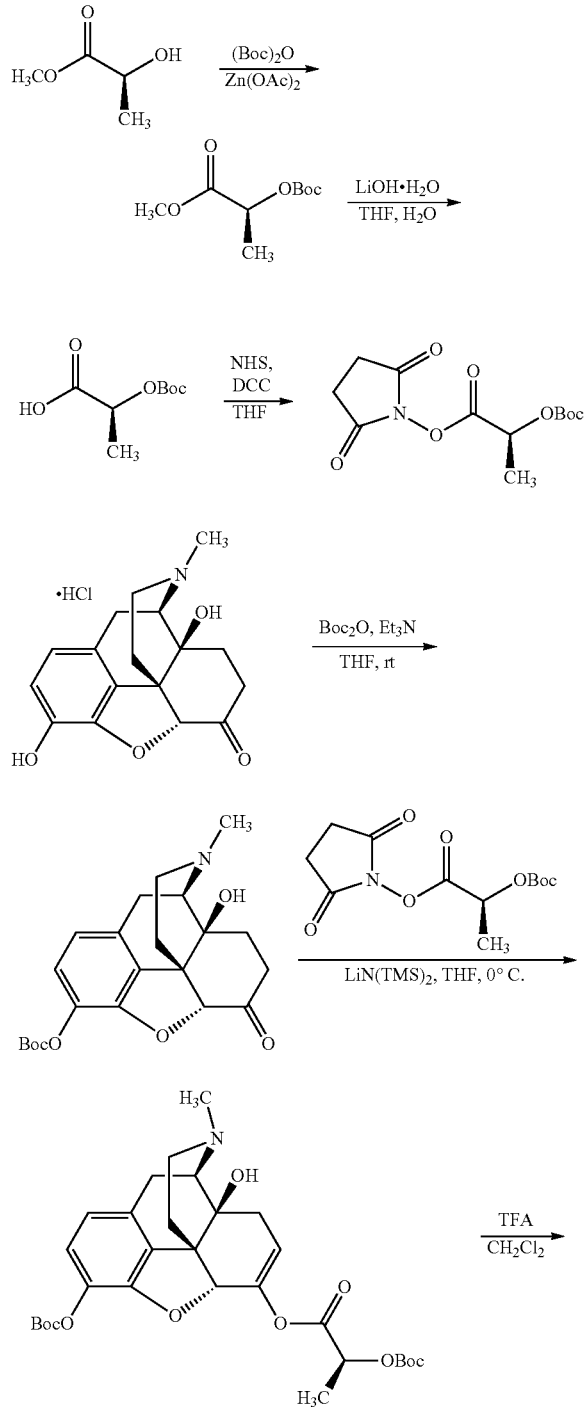

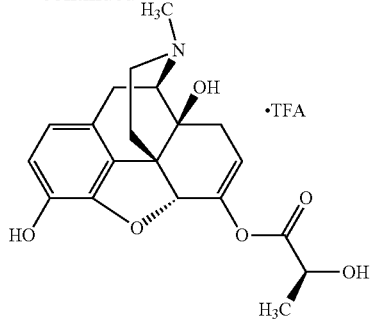

Preparation of (S)-Methyl 2-((tert-butoxycarbonyl)oxy)propanoate

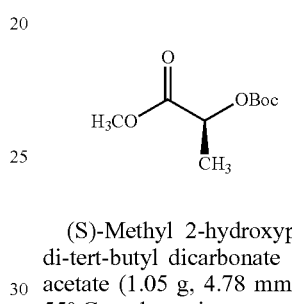

(S)-Methyl 2-hydroxypropanoate (5.01 g, 48.2 mmol), di-tert-butyl dicarbonate (11.63 g, 53.29 mmol), and zinc acetate (1.05 g, 4.78 mmol) were combined and heated at 55° C. under a nitrogen atmosphere for 48 h. After this time, the reaction mixture was cooled to room temperature. The mixture was diluted with water (50 mL) and extracted with methylene chloride (2×50 mL). The combined organics were washed with brine (50 mL), dried over sodium sulfate, filtered, and concentrated under reduced pressure to provide (S)-methyl 2-((tert-butoxycarbonyl)oxy)propanoate (8.03 g, 82%) as a colorless oil: $^1$H NMR (500 MHz, CDCl$_3$) δ 4.96 (q, J=7.0 Hz, 1H), 3.77 (s, 3H), 1.52 (d, J=6.5 Hz, 3H), 1.50 (s, 9H).

Preparation of (S)-2-((tert-Butoxycarbonyl)oxy)propanoic acid

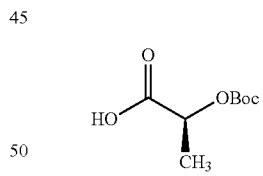

A solution of (S)-methyl 2-((tert-butoxycarbonyl)oxy)propanoate (7.00 g, 34.3 mmol) in tetrahydrofuran (100 mL) and water (50 mL) was treated with lithium hydroxide hydrate (1.45 g, 34.5 mmol) and stirred at ambient temperature for 16 h. After this time, the volatiles were removed under reduced pressure. The aqueous mixture was diluted with water (50 mL) and extracted with diethyl ether (100 mL). The aqueous layer was cooled in an ice bath, acidified to pH ~3 with 0.5 M hydrochloric acid, and extracted with diethyl ether (3×100 mL). The combined organics were dried over sodium sulfate, filtered, and concentrated under reduced pressure to provide of (S)-2-((tert-butoxycarbonyl)oxy)propanoic acid (2.83 g, 43%) as a white solid: $^1$H NMR (500 MHz, CDCl$_3$) δ 4.99 (q, J=7.0 Hz, 1H), 1.56 (d, J=7.5 Hz, 3H), 1.50 (s, 9H).

Preparation of (S)-2,5-Dioxopyrrolidin-1-yl 2-((tert-butoxycarbonyl)oxy)propanoate

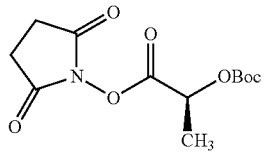

A solution of (S)-2-((tert-butoxycarbonyl)oxy)propanoic acid (2.83 g, 14.9 mmol) in tetrahydrofuran (50 mL) was treated with N-hydroxysuccinimide (1.88 g, 16.3 mmol) and N,N'-dicyclohexylcarbodiimide (3.38 g, 16.4 mmol) and stirred under a nitrogen atmosphere for 3 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-2,5-dioxopyrrolidin-1-yl 2-((tert-butoxycarbonyl)oxy)propanoate (3.54 g, 83%) as a white powder: $^1$H NMR (500 MHz, CDCl$_3$) δ 5.24 (q, J=7.0 Hz, 1H), 2.84 (s, 4H), 1.69 (d, J=7.0 Hz, 3H), 1.51 (s, 9H).

Preparation of tert-Butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate

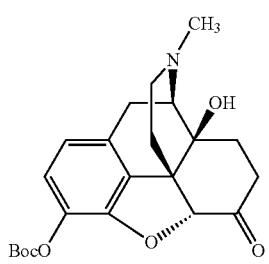

A mixture of oxymorphone hydrochloride (10.0 g, 29.6 mmol), triethylamine (15.0 g, 148 mmol), and pyridine (2.34 g, 29.6 mmol) in tetrahydrofuran (100 mL) was treated with di-tert-butyl dicarbonate (12.9 g, 59.2 mmol) and stirred under nitrogen for 16 h. After this time, the reaction mixture was concentrated under reduced pressure. The crude residue was purified by column chromatography (330 g silica column, 20% methanol/methylene chloride) to provide tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (8.00 g, 67%) as a white solid: ESI MS m/z 402 [C$_{22}$H$_{27}$NO$_6$+H]$^+$.

Preparation of (S)-(4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 2-((tert-butoxycarbonyl)oxy)propanoate

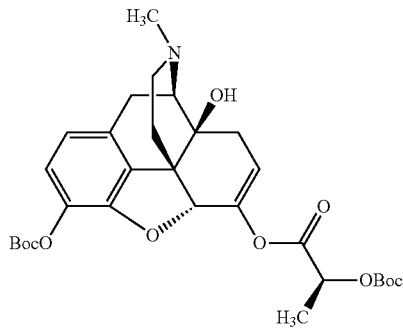

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (2.49 mL, 2.49 mmol). After 30 min, the mixture was treated dropwise with a solution of (S)-2,5-dioxopyrrolidin-1-yl 2-((tert-butoxycarbonyl)oxy)propanoate (716 mg, 2.49 mmol) in tetrahydrofuran (5 mL) and stirred at 0° C. for 1 h. After this time, the reaction mixture was poured into cold saturated aqueous ammonium chloride (10 mL) and extracted with ethyl acetate (2×25 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-((tert-butoxycarbonyl)oxy)propanoate (199 mg, 28%) as a white solid: $^1$H NMR (300 MHz, DMSO-d$_6$) δ 6.88 (d, J=8.4 Hz, 1H), 6.72 (d, J=8.4 Hz, 1H), 5.58 (dd, J=5.7, 2.4 Hz, 1H), 4.99-4.92 (m, 2H), 4.78 (s, 1H), 3.15 (d, J=18.9 Hz, 1H), 2.87-2.86 (m, 1H), 2.73-2.62 (m, 1H), 2.49-2.41 (m, 1H), 2.32 (s, 3H), 2.29-2.23 (m, 1H), 2.12-1.95 (m, 2H), 1.47-1.22 (m, 23H); ESI MS m/z 574 [C$_{30}$H$_{39}$NO$_{10}$+H]$^+$.

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-hydroxypropanoate trifluoroacetic acid salt

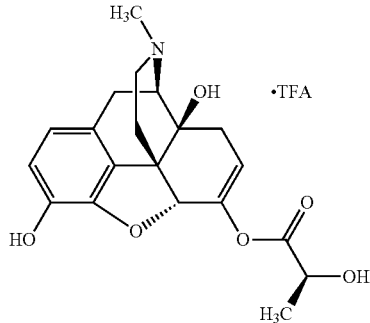 [SMILES: C[C@H](O)C(=O)OC1=CC[C@@]2(O)[C@H]3Cc4ccc(O)c5c4[C@@]2(CCN3C)[C@H]1O5]

A solution of (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-((tert-butoxycarbonyl)oxy)propanoate (110 mg, 0.192 mmol) in methylene chloride (2 mL) was treated with trifluoroacetic acid (1 mL) and stirred under a nitrogen atmosphere at ambient temperature for 1 h. After this time, the reaction mixture was concentrated under reduced pressure. The residue was purified by column chromatography (24 g silica column, 0-20% methanol/ethyl acetate) to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-hydroxypropanoate trifluoroacetic acid salt (9 mg, 10%) as an off-white solid: $^1$H NMR (300 MHz, DMSO-$d_6$) δ 9.29 (s, 1H), 9.19 (br s, 1H), 6.67 (d, J=8.1 Hz, 1H), 6.61 (d, J=8.1 Hz, 1H), 6.21 (br s, 1H), 5.60-5.53 (m, 2H), 4.94 (s, 1H), 4.30-4.25 (m, 1H), 3.57 (br s, 1H), 3.04-2.99 (m, 2H), 2.79 (s, 3H), 2.65-2.35 (m, 2H), 2.29-2.22 (m, 1H), 2.09-2.02 (m, 1H), 1.62-1.57 (m, 1H), 1.36 (d, J=6.9 Hz, 3H), one proton obscured by solvent peaks; ESI MS m/z 374 $[C_{20}H_{23}NO_6+H]^+$.

Preparation 2,5-Dioxopyrrolidin-1-yl oleate

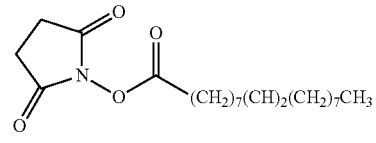

A solution of oleic acid (1.00 g, 3.54 mmol) and N-hydroxysuccinimide (407 mg, 3.54 mmol) in tetrahydrofuran (10 mL) was treated dropwise with a solution of N,N'-dicyclohexylcarbodiimide (730 mg, 3.54 mmol) in tetrahydrofuran (10 mL). The mixture was heated at 50° C. under a nitrogen atmosphere for 2 h. After this time, the reaction Scheme 91: (4R,4aS,7aR,12bS)-4a,9-Dihydroxy-3-methyl-2,3,4,4a,5,7a-hexahydro-1H-4,12-methanobenzofuro[3,2-e]isoquinolin-7-yl oleate trifluoroacetic acid salt

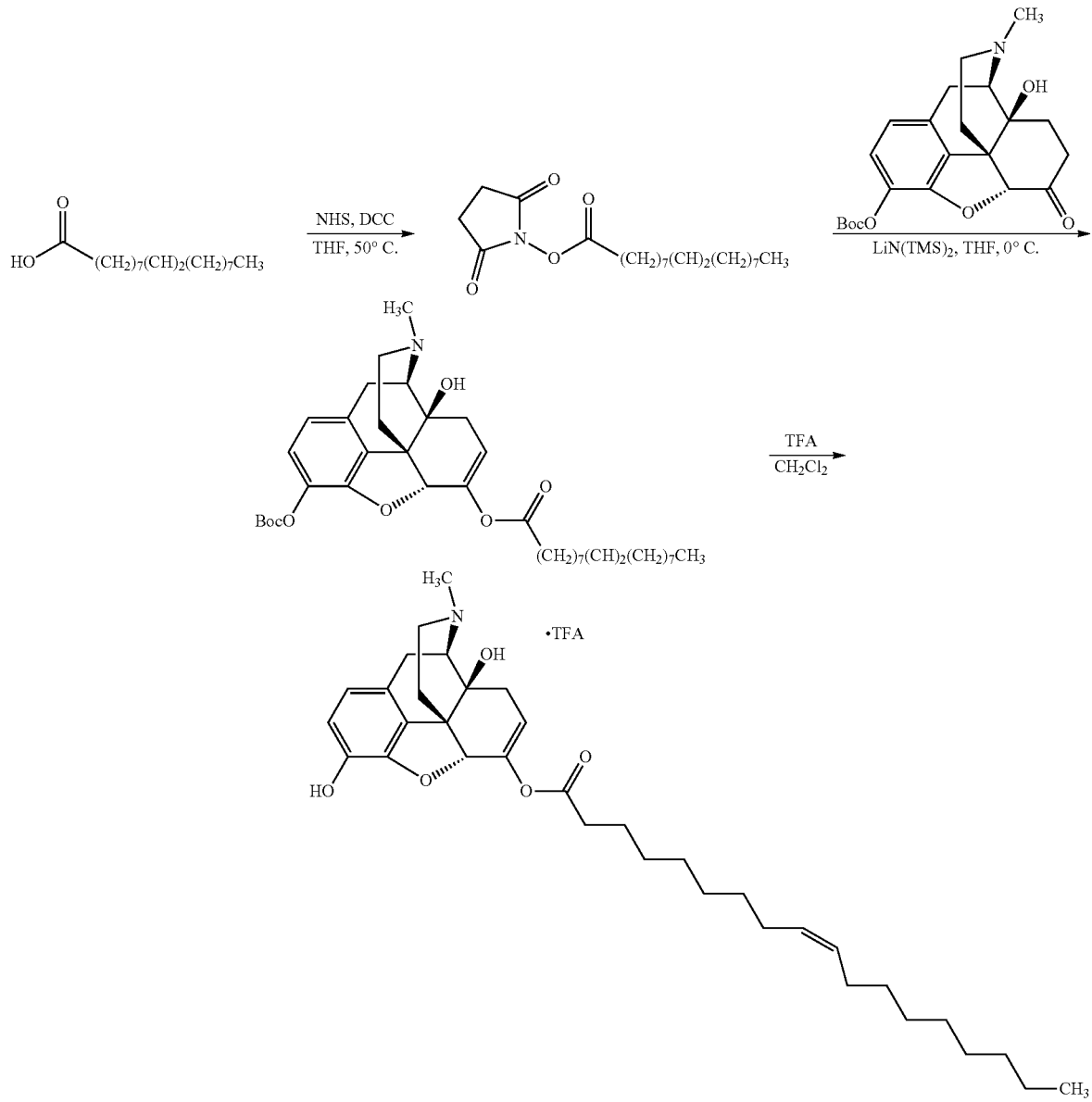

mixture was cooled to room temperature and filtered to remove the solid dicyclohexylurea byproduct. The filtrate was concentrated under reduced pressure and dried under vacuum overnight to provide 2,5-dioxopyrrolidin-1-yl oleate (3.54 g, 83%) as a white semi-solid: $^1$H NMR (300 MHz, DMSO-$d_6$) δ 5.32 (m, 2H), 2.81 (s, 4H), 2.65 (t, J=7.2 Hz, 2H), 1.99-1.95 (m, 4H), 1.63-1.95 (m, 3H), 1.24-1.18 (m, 19H), 0.85 (t, J=6.3 Hz, 3H).

Preparation of (4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl oleate

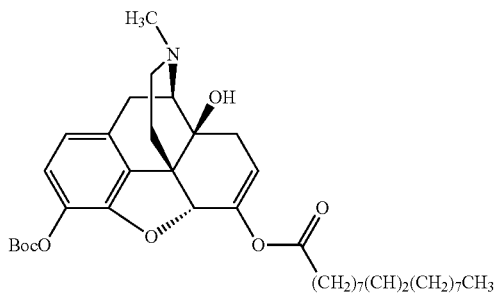

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (300 mg, 0.747 mmol) in tetrahydrofuran (10 mL) was cooled in an ice bath and treated dropwise with a 1.0 M solution of lithium bis(trimethylsilyl)amide in tetrahydrofuran (2.24 mL, 2.24 mmol). After 30 min, the mixture was treated dropwise with a solution of 2,5-dioxopyrrolidin-1-yl oleate (312 mg, 0.821 mmol) in tetrahydrofuran (5 mL) and stirred at 0° C. for 1 h. After this time, the reaction mixture was poured into cold saturated aqueous ammonium chloride (10 mL) and extracted with ethyl acetate (2×25 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl oleate (50 mg, 10%) as a white solid: ESI LC/MS m/z 666 [$C_{40}H_{59}NO_7$+H]$^+$.

Preparation of (4R,4aS,7aR,12bS)-4a,9-Dihydroxy-3-methyl-2,3,4,4a,5,7a-hexahydro-1H-4,12-methanobenzofuro[3,2-e]isoquinolin-7-yl oleate trifluoroacetic acid salt

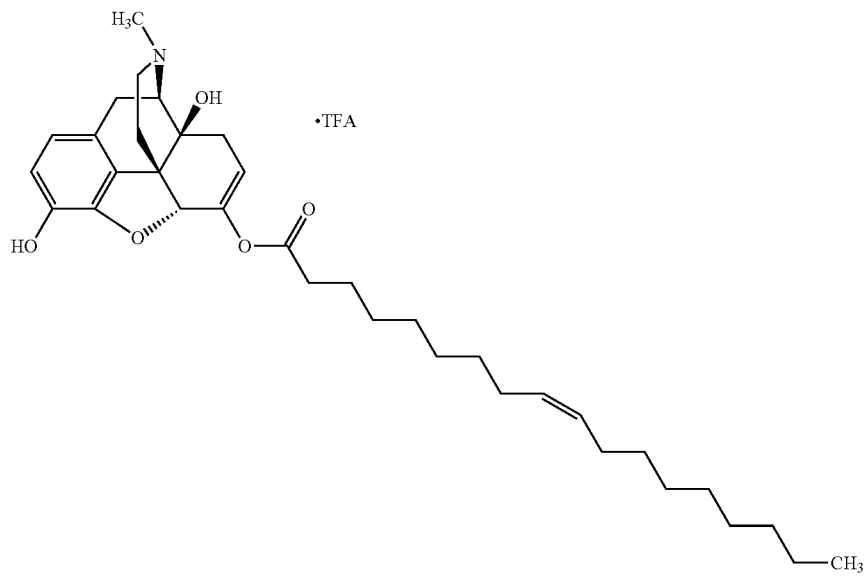 [SMILES: CCCCCCCC/C=C\CCCCCCCC(=O)OC1=CC[C@@]2(O)[C@H]3Cc4ccc(O)c5c4[C@@]2(CCN3C)[C@H]1O5]

A solution of (4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl oleate (50 mg, 0.075 mmol) in methylene chloride (1 mL) was treated with trifluoroacetic acid (0.5 mL) and stirred under a nitrogen atmosphere at ambient temperature for 75 min. After this time, the reaction mixture was concentrated under reduced pressure. The residue was dissolved in acetonitrile/water and freeze-dried to provide (4R,4aS,7aR,12bS)-4a,9-dihydroxy-3-methyl-2,3,4,4a,5,7a-hexahydro-1H-4,12-methanobenzofuro[3,2-e]isoquinolin-7-yl oleate trifluoroacetic acid salt (61 mg, quantitative) as an off-white, sticky solid: $^1$H NMR (300 MHz, DMSO-$d_6$) δ 9.29 (s, 1H), 9.15 (br s, 1H), 6.67 (d, J=8.1 Hz, 1H), 6.62 (d, J=8.1 Hz, 1H), 6.22 (s, 1H), 5.51-5.49 (m, 1H), 5.34-5.31 (m, 2H), 4.95 (s, 1H), 3.62-3.60 (m, 1H), 3.37 (d, J=19.8 Hz, 1H), 3.11-3.02 (m, 2H), 2.84 (d, J=4.8 Hz, 3H), 2.78-2.56 (m, 1H), 2.45-2.40 (m, 3H), 3.37 (dd, J=18.0, 6.0 Hz, 1H), 2.08-1.98 (m, 5H), 1.63-1.52 (m, 3H), 1.28-1.24 (br m, 20H), 0.85 (t, J=6.3 Hz, 3H); ESI MS m/z 566 [$C_{35}H_{51}NO_5$+H]$^+$.

Scheme 92: (4R,4aS,7aR,12bS)-4a,9-Dihydroxy-3-methyl-2,3,4,4a,5,7a-hexahyro-1H-4,12-methanobenzofuro[3,2-e]isoquinolin-7-yl stearate trifluoroacetic acid salt

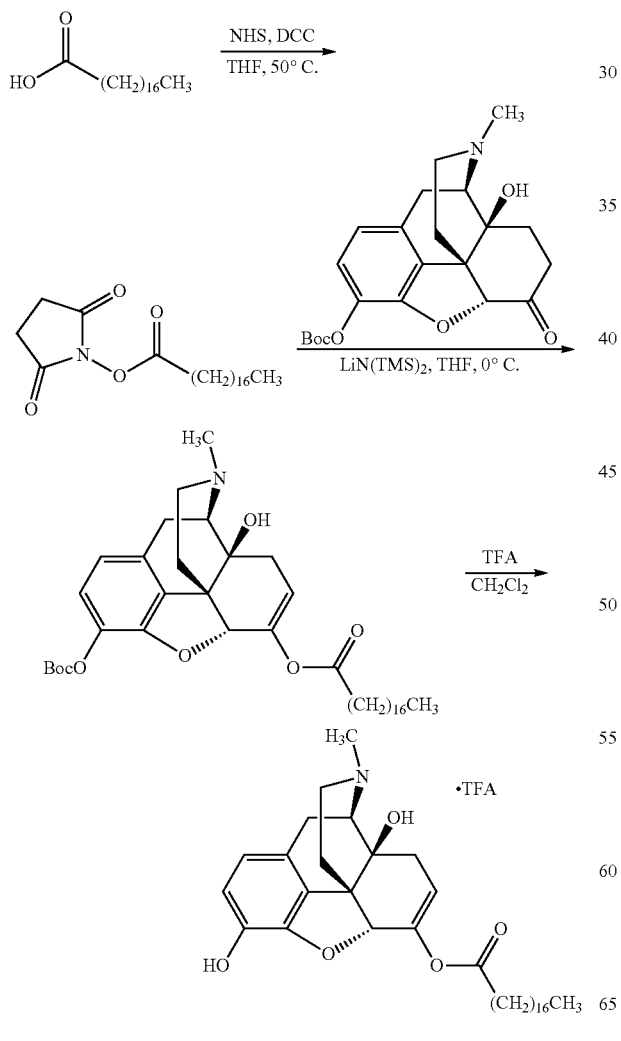

Preparation 2,5-Dioxopyrrolidin-1-yl stearate

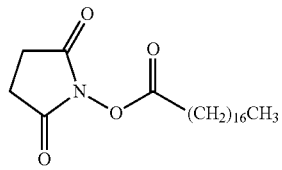

A solution of stearic acid (1.00 g, 3.52 mmol) and N-hydroxysuccinimide (405 mg, 3.52 mmol) in tetrahydrofuran (15 mL) was treated dropwise with a solution of N,N'-dicyclohexylcarbodiimide (725 mg, 3.52 mmol) in tetrahydrofuran (10 mL). The mixture was heated at 50° C. under a nitrogen atmosphere for 2 h. After this time, the reaction mixture was cooled to room temperature and filtered to remove the solid dicyclohexylurea byproduct. The filtrate was concentrated under reduced pressure and dried under vacuum overnight to provide 2,5-dioxopyrrolidin-1-yl stearate (1.45 g) as a white solid: $^1$H NMR (300 MHz, CDCl$_3$) δ 2.84 (s, 4H), 2.60 (t, J=7.5 Hz, 2H), 1.79-1.08 (m, 30H), 0.88 (t, J=6.6 Hz, 3H).

Preparation of (4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl stearate

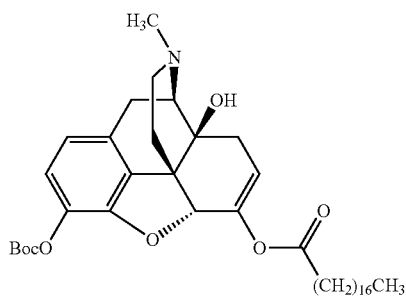

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (300 mg, 0.748 mmol) in tetrahydrofuran (10 mL) was cooled in an ice bath and treated dropwise with a 1.0 M solution of lithium bis(trimethylsilyl)amide in tetrahydrofuran (1.90 mL, 1.90 mmol). After 30 min, the mixture was treated dropwise with a solution of 2,5-dioxopyrrolidin-1-yl stearate (314 mg, 0.822 mmol) in tetrahydrofuran (5 mL) and stirred at 0° C. for 1 h. After this time, the reaction mixture was poured into cold saturated aqueous ammonium chloride (10 mL) and extracted with ethyl acetate (2×25 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl stearate (42 mg, 8%) as a white solid: ESI LC/MS m/z 668 [$C_{40}H_{61}NO_7$+H]$^+$.

623

Preparation of (4R,4aS,7aR,12bS)-4a,9-Dihydroxy-3-methyl-2,3,4,4a,5,7a-hexahydro-1H-4,12-methanobenzofuro[3,2-e]isoquinolin-7-yl stearate trifluoroacetic acid salt

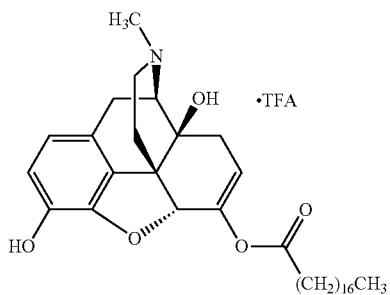

624

A solution of (4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl stearate (42 mg, 0.063 mmol) in methylene chloride (1 mL) was treated with trifluoroacetic acid (0.5 mL) and stirred under a nitrogen atmosphere at ambient temperature for 45 min. After this time, the reaction mixture was concentrated under reduced pressure. The residue was dissolved in acetonitrile/water and freeze-dried to provide (4R,4aS,7aR,12bS)-4a,9-dihydroxy-3-methyl-2,3,4,4a,5,7a-hexahydro-1H-4,12-methanobenzofuro[3,2-e]isoquinolin-7-yl stearate trifluoroacetic acid salt (41 mg, 92%) as a white solid: $^1$H NMR (300 MHz, DMSO-$d_6$) δ 9.28 (s, 1H), 9.14 (br s, 1H), 6.67 (d, J=8.1 Hz, 1H), 6.61 (d, J=8.1 Hz, 1H), 6.21 (s, 1H), 5.52-5.49 (m, 1H), 4.95 (s, 1H), 3.62-3.60 (m, 1H), 3.41-3.33 (m, 1H), 3.11-3.02 (m, 2H), 2.84 (d, J=4.8 Hz, 3H), 2.73-2.63 (m, 1H), 2.45-2.40 (m, 3H), 2.30-2.22 (m, 1H), 2.08-2.03 (m, 1H), 1.63-1.54 (m, 3H), 1.33-1.24 (br m, 28H), 0.85 (t, J=6.3 Hz, 3H); ESI MS m/z 568 [$C_{35}H_{53}NO_5$+H]$^+$.

Scheme 93: (S)-4-(((4R,4aS,7aR,12bS)-4a,9-Dihydroxy-3-methyl-2,3,4,4a,5,7a-hexahydro-1H-4, 12-methanobenzofuro[3,2-e]isoquinolin-7-yl)oxy)-2-hydroxy-4-oxobutanoic acid trifluoroacetic acid salt

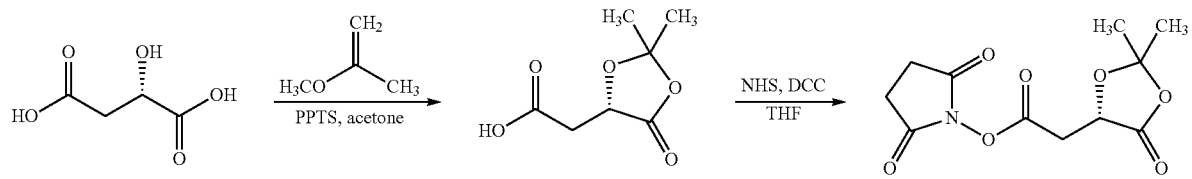

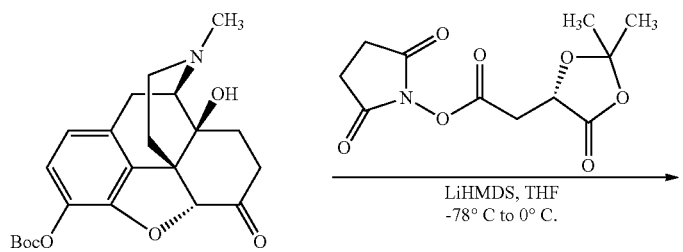

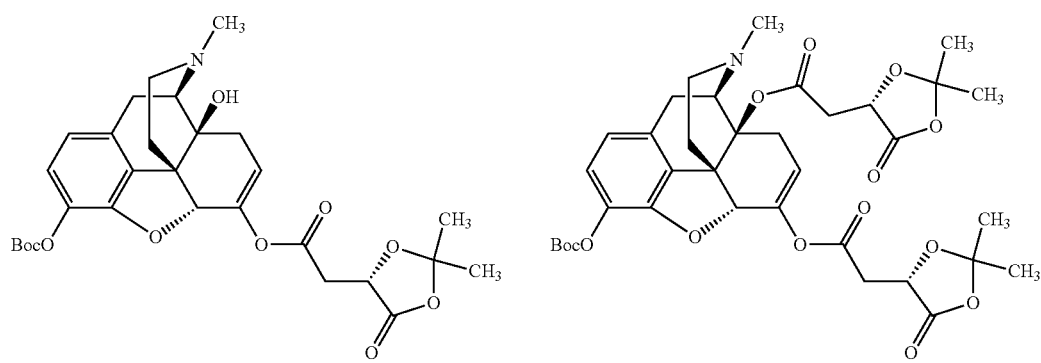

625

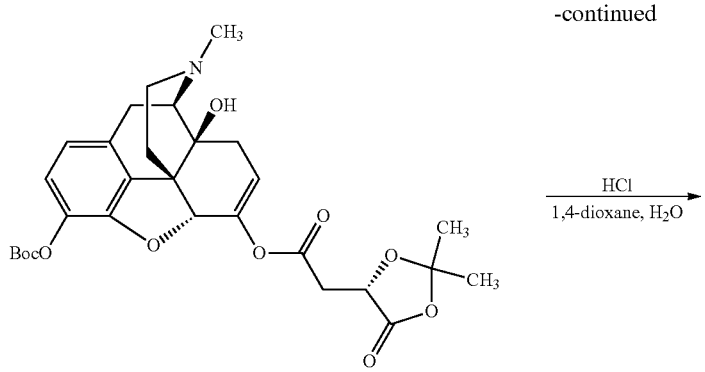

626

-continued

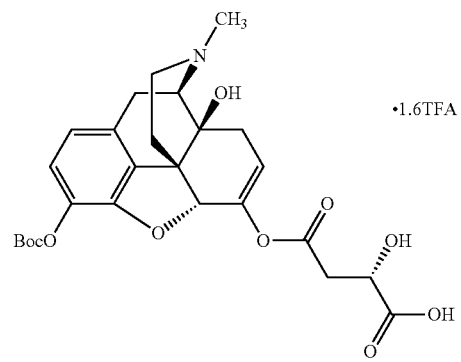

Preparation of (S)-2-(2,2-Dimethyl-5-oxo-1,3-dioxolan-4-yl)acetic acid

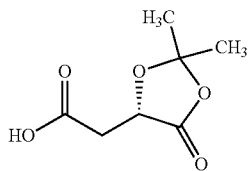

A solution of (S)-2-hydroxysuccinic acid (25.0 g, 186 mmol) and 2-methoxypropene (71.4 mL, 746 mmol) in acetone (400 mL) at 0° C. was slowly treated with pyridinium p-toluenesulfonate (4.68 g, 18.6 mmol). The reaction mixture was warmed to ambient temperature then heated at 35° C. for overnight. After this time, the volatiles were removed under reduced pressure. The residue was triturated in heptane/ethyl acetate (150 mL, 1:1) and filtered. The filtrate was diluted with ethyl acetate (300 mL) and washed with water (150 mL). The organic layer was dried over sodium sulfate, filtered and concentrated at reduced pressure to give (S)-2-(2,2-dimethyl-5-oxo-1,3-dioxolan-4-yl)acetic acid (27.9 g, 86%) as a light brown solid: $^1$H NMR (500 MHz, CDCl$_3$) δ 4.72 (apparent t, J=3.5 Hz, 1H), 3.00 (dd, J=17.0, 3.5 Hz, 1H), 2.56 (dd, J=17.0, 6.5 Hz, 1H), 1.57 (s, 3H), 1.50 (s, 3H).

Preparation of (S)-2,5-Dioxopyrrolidin-1-yl 2-(2,2-dimethyl-5-oxo-1,3-dioxolan-4-yl)aceate

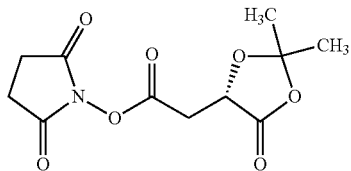 [SMILES: CC1(C)OC(=O)[C@H](CC(=O)ON2C(=O)CCC2=O)O1]

The combined organics were washed with brine (50 mL), dried over sodium sulfate, filtered, and concentrated under reduced pressure to provide (S)-methyl 2-((tert-butoxycarbonyl)oxy)propanoate (18.5 g, quantitative) as a colorless oil: $^1$H NMR (300 MHz, DMSO-d$_6$) δ 4.98 (apparent t, J=4.5 Hz, 1H), 3.34-3.32 (m, 2H), 2.81 (s, 4H), 1.55 (s, 3H), 1.53 (s, 3H).

Preparation of (4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 2-((S)-2,2-dimethyl-5-oxo-1,3-dioxolan-4-yl)acetate and (S)-(4R,4aS,7aR,12bS)-9-((tert-Butoxycarbonyl)oxy)-3-methyl-2,3,4,4a,5,7a-hexahydro-1H-4,12-methanobenzofuro[3,2-e]isoquinoline-4a,7-diyl bis(2-((S)-2,2-dimethyl-5-oxo-1,3-dioxolan-4-yl)acetate)

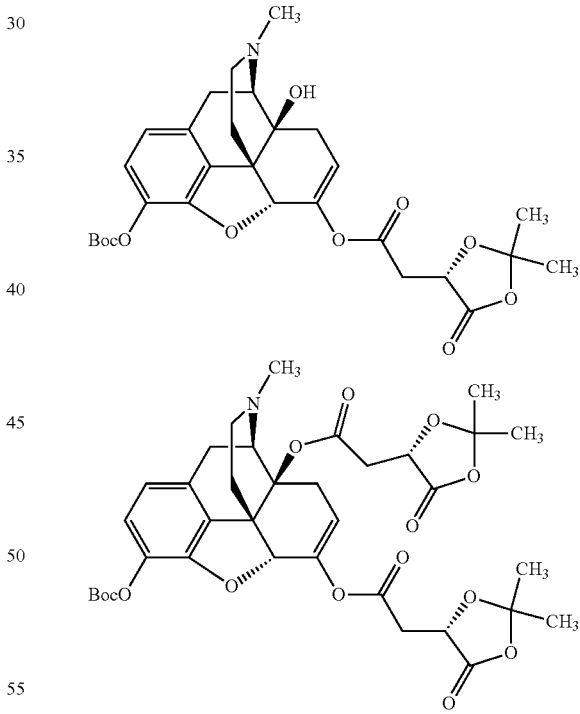

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (1.00 g, 2.49 mmol) in tetrahydrofuran (15 mL) was cooled to 0° C. and treated dropwise with a 1.0 M solution of lithium bis(trimethylsilyl)amidein tetrahydrofuran (2.75 mL, 2.75 mmol). After addition was complete, the mixture was stirred at 0° C. for 25 min and then at ambient temperature for 25 min. The mixture was re-cooled to −78° C. and (S)-2,5-dioxopyrrolidin-1-yl 2-(2,2-dimethyl-5-oxo-1,3-dioxolan-4- yl)acetate (900 mg, 3.32 mmol) was added. The mixture was allowed to warm to 0° C. over 2 h. After this time, the mixture was treated with saturated aqueous ammonium chloride, and extracted with ethyl acetate. The combined organics were dried over sodium sulfate, filtered, and concentrated under reduced pressure. The residue was purified by reversed phase column chromatography (150 g C18 column, 5-100% acetonitrile/water) to provide (4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-((S)-2,2-dimethyl-5-oxo-1,3-dioxolan-4-yl)acetate (425 mg, 31%): ESI MS m/z 558 [$C_{29}H_{35}NO_{10}$+H]+ and (S)-(4R,4aS,7aR,12bS)-9-((tert-butoxycarbonyl)oxy)-3-methyl-2,3,4,4a,5,7a-hexahydro-1H-4,12-methanobenzofuro[3,2-e]isoquinoline-4a,7-diyl bis(2-((S)-2,2-dimethyl-5-oxo-1,3-dioxolan-4-yl)acetate) (197 mg, 11%): ESI MS m/z 714 [$C_{36}H_{43}NO_{14}$+H]+.

Preparation of (S)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-hydroxy-4-oxobutanoic acid trifluoroacetic acid salt

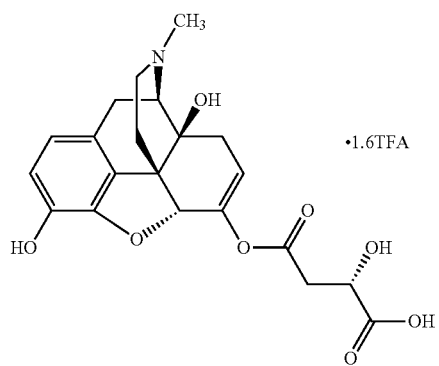 [SMILES: CN1CC[C@]23c4c5ccc(O)c4O[C@H]2C(OC(=O)C[C@H](O)C(=O)O)=CC[C@@]3(O)[C@H]1C5]

A solution of (4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-((S)-2,2-dimethyl-5-oxo-1,3-dioxolan-4-yl)acetate (100 mg, 0.18 mmol) in 1,4-dioxane (2.5 mL) and water (0.1 mL) was treated with hydrogen chloride (4N in 1,4-dioxane, 0.4 mL, 1.6 mmol) and stirred at ambient temperature for 2.5 h. After this time, the reaction mixture was concentrated under reduced pressure. The residue was purified by reversed phase column chromatography (15.5 g C18 column, 3-25% acetonitrile/water, with 0.1% trifluoracetic acid) and freeze dried to provide (S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-hydroxy-4-oxobutanoic acid trifluoroacetic acid salt (50 mg, 46%): $^1$H NMR (300 MHz, DMSO-$d_6$) δ 12.7 (br s, 1H), 9.32 (s, 1H), 9.16 (s, 1H), 6.67 (d, J=8.1 Hz, 1H), 6.62 (d, J=8.1 Hz, 1H), 6.24 (s, 1H), 5.52 (dd, J=5.9, 1.9 Hz, 1H), 4.95 (s, 1H), 4.35 (dd, J=7.4, 5.0 Hz, 1H), 3.61 (d, J=8.4 Hz, 1H), 3.13-3.00 (m, 2H), 2.90-2.80 (m, 4H), 2.74-2.59 (m, 2H), 2.50-2.40 (m, 1H), 2.27 (dd, J=17.9, 6.1 Hz, 1H), 2.05 (d, J=17.9 Hz, 1H), 1.62 (d, J=10.9 Hz, 1H), one proton obscured by solvent peaks; ESI MS m/z 418 [$C_{21}H_{23}NO_8$+H]+; HPLC (Method A) 98.4% (AUC), $t_R$=6.13 min.

Scheme 94: (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((S)-2-hydroxypropanamido)propanoate trifluoroacetic acid salt

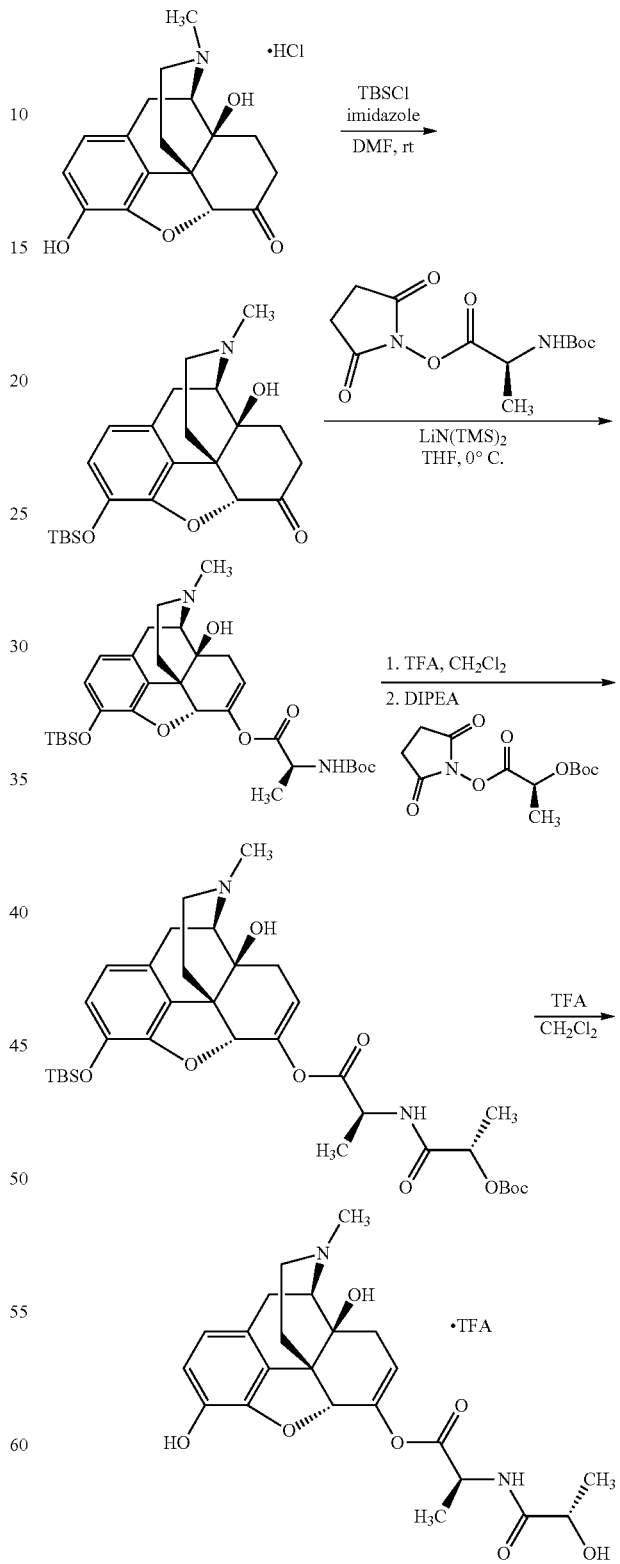

Preparation (4R,4aS,7aR,12bS)-9-((tert-Butyldimethylsilyl)oxy)-4a-hydroxy-3-methyl-2,3,4,4a,5,6-hexahydro-1H-4,12-methanobenzofuro[3,2-e]isoquinolin-7(7aH)-one

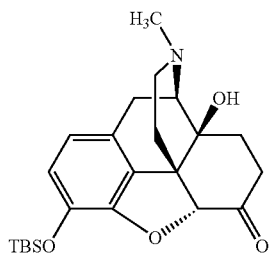 [SMILES: CN1CC[C@]23c4c5ccc(O[Si](C)(C)C(C)(C)C)c4O[C@H]2C(=O)CC[C@@]3(O)[C@H]1C5]

A solution of (4R,4aS,7aR,12bS)-4a,9-dihydroxy-3-methyl-2,3,4,4a,5,6-hexahydro-1H-4,12-methanobenzofuro[3,2-e]isoquinolin-7(7aH)-one hydrochloride (10.0 g, 29.6 mmol) in N,N-dimethylformamide (15 mL) was treated with imidazole (11.0 g, 163 mmol) and tert-butyldimethylsilyl chloride (11.0 g, 74.0 mmol) at room temperature. After 30 min, the mixture was partitioned between diethyl ether and water. The organic phase was separated and the aqueous phase was extracted with diethyl ether. The combined organics were dried over sodium sulfate, filtered, and concentrated under reduced pressure. The crude residue was purified by recrystallization in ethanol to provide (4R,4aS,7aR,12bS)-9-((tert-butyldimethylsilyl)oxy)-4a-hydroxy-3-methyl-2,3,4,4a,5,6-hexahydro-1H-4,12-methanobenzofuro[3,2-e]isoquinolin-7(7aH)-one (9.81 g, 79%) as a white solid: ESI MS m/z 416 $[C_{23}H_{33}NO_4Si+H]^+$.

Preparation of (S)-(4R,4aS,7aR,12bS)-9-((tert-Butyldimethylsilyl)oxy)-4a-hydroxy-3-methyl-2,3,4,4a,5,7a-hexahydro-1H-4,12-methanobenzofuro[3,2-e]isoquinolin-7-yl 2-((tert-butoxycarbonyl)amino)propanoate

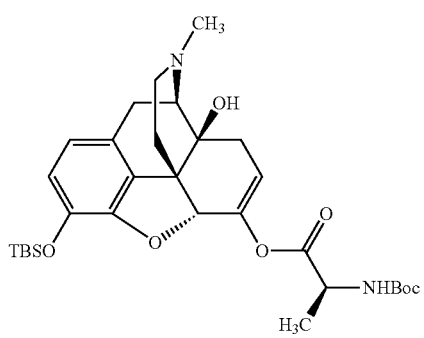 [SMILES: C[C@H](NC(=O)OC(C)(C)C)C(=O)OC1=CC[C@@]2(O)[C@H]3Cc4ccc(O[Si](C)(C)C(C)(C)C)c5c4[C@@]2(CCN3C)[C@H]1O5]

A suspension of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (5.09 g, 12.2 mmol) in tetrahydrofuran (60 mL) was cooled in an ice bath and treated dropwise with a 1.0 M solution of lithium bis(trimethylsilyl)amide in tetrahydrofuran (24.5 mL, 24.5 mmol). After 30 min, the mixture was treated dropwise with a solution of (S)-2,5-dioxopyrrolidin-1-yl 2-((tert-butoxycarbonyl)amino)propanoate (7.00 g, 24.5 mmol) in tetrahydrofuran (25 mL) and stirred at 0° C. for 16 h. After this time, the reaction mixture was poured into cold saturated aqueous ammonium chloride and extracted with ethyl acetate. The combined organics were washed with saturated aqueous sodium bicarbonate and brine, dried over sodium sulfate, filtered, and concentrated under reduced pressure. The crude residue was purified by reversed phase column chromatography (50 g C18 column, 0-100% acetonitrile/water) and freeze dried to provide (S)-(4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 2-((tert-butoxycarbonyl)amino)propanoate (3.52 g, 49%): ESI MS m/z 587 $[C_{31}H_{46}N_2O_7Si+H]^+$.

Preparation of (S)-(4R,4aS,7aR,12bS)-9-((tert-Butyldimethylsilyl)oxy)-4a-hydroxy-3-methyl-2,3,4,4a,5,7a-hexahydro-1H-4,12-methanobenzofuro[3,2-e]isoquinolin-7-yl 2-((S)-2-((tert-butoxycarbonyl)oxy)propanamido)propanoate

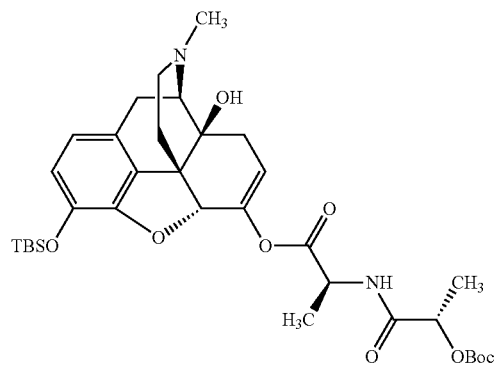

A solution (S)-(4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 2-((tert-butoxycarbonyl)amino)propanoate (300 mg, 0.51 mmol), in methylene chloride (5 mL) was treated with trifluoroacetic acid (1.5 mL) and the mixture was stirred at room temperature for 1 h. After this time, N,N-diisopropylethylamine was added slowly until the reaction mixture tested basic by pH paper analysis. The mixture was treated with a solution of (S)-2,5-dioxopyrrolidin-1-yl 2-((tert-butoxycarbonyl)amino)propanoate (220 mg, 0.76 mmol) in methylene chloride (1.5 mL) and stirred at room temperature for 1 h. After this time, the mixture was concentrated under reduced pressure. The residue was diluted with ethyl acetate and washed with 10% citric acid, saturated aqueous sodium bicarbonate, and brine. The organic extracts were dried over sodium sulfate, filtered and concentrated to provide (S)-(4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 2-((S)-2-((tert-butoxycarbonyl)oxy)propanamido)propanoate (330 mg, 98%): ESI MS m/z 659 $[C_{34}H_{50}N_2O_9Si+H]^+$.

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((S)-2-hydroxypropanamido)propanoate trifluoroacetic acid salt

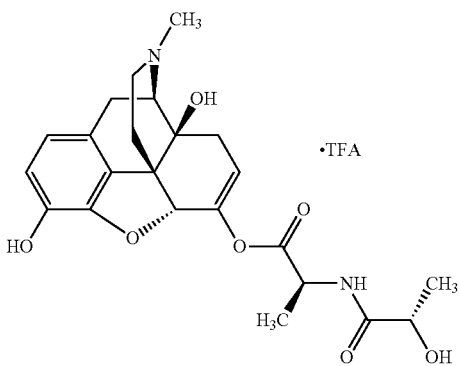 [SMILES: C[C@H](O)C(=O)N[C@@H](C)C(=O)OC1=CC[C@@]2(O)[C@H]3Cc4ccc(O)c5c4[C@@]2(CCN3C)[C@H]1O5]

A solution of (S)-(4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 2-((S)-2-((tert-butoxycarbonyl)oxy)propanamido)propanoate (150 mg) in methylene chloride (1 mL) was treated with trifluoroacetic acid (0.5 mL) and stirred at ambient temperature for 30 min. After this time, the reaction mixture was concentrated under reduced pressure. The residue was dissolved in water (3 mL), treated with trifluoroacetic acid (0.5 mL) for 1 h and then freeze dried. The crude product was purified by reversed phase column chromatography (15.5 g C18 column, 5-100% acetonitrile/water) and freeze dried to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((S)-2-hydroxypropanamido)propanoate trifluoroacetic acid salt (31 mg, 24%): $^1$H NMR (300 MHz, DMSO-$d_6$) δ 9.28 (s, 1H), 9.16 (br s, 1H), 8.10 (d, J=7.1 Hz, 1H), 6.68 (d, J=8.1 Hz, 1H), 6.62 (d, J=8.1 Hz, 1H), 6.24 (s, 1H), 5.57-5.49 (m, 2H), 4.96 (s, 1H), 4.41-4.31 (m, 1H), 4.06-4.97 (m, 1H), 3.61 (d, J=6.1 Hz, 1H), 3.36 (d, partially obscured by solvent peak, 1H), 3.11-3.01 (m, 2H), 2.84 (apparent d, J=3.9 Hz, 3H), 2.69-2.60 (m, 1H), 2.43 (dd, J=13.1, 5.0 Hz, 1H), 2.27 (dd, J=18.0, 6.0 Hz, 1H), 2.05 (d, J=18.0 Hz, 1H), 1.62 (d, J=10.7 Hz, 1H), 1.41 (d, J=7.2 Hz, 3H), 1.22 (d, J=6.8 Hz, 3H); ESI MS m/z 445 $[C_{23}H_{28}N_2O_7+H]^+$; HPLC (Method B) 97.7% (AUC), $t_R$=11.6 min.

Scheme 95: (S)-4-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl)amino)-2-hydroxy-4-oxobutanoic acid

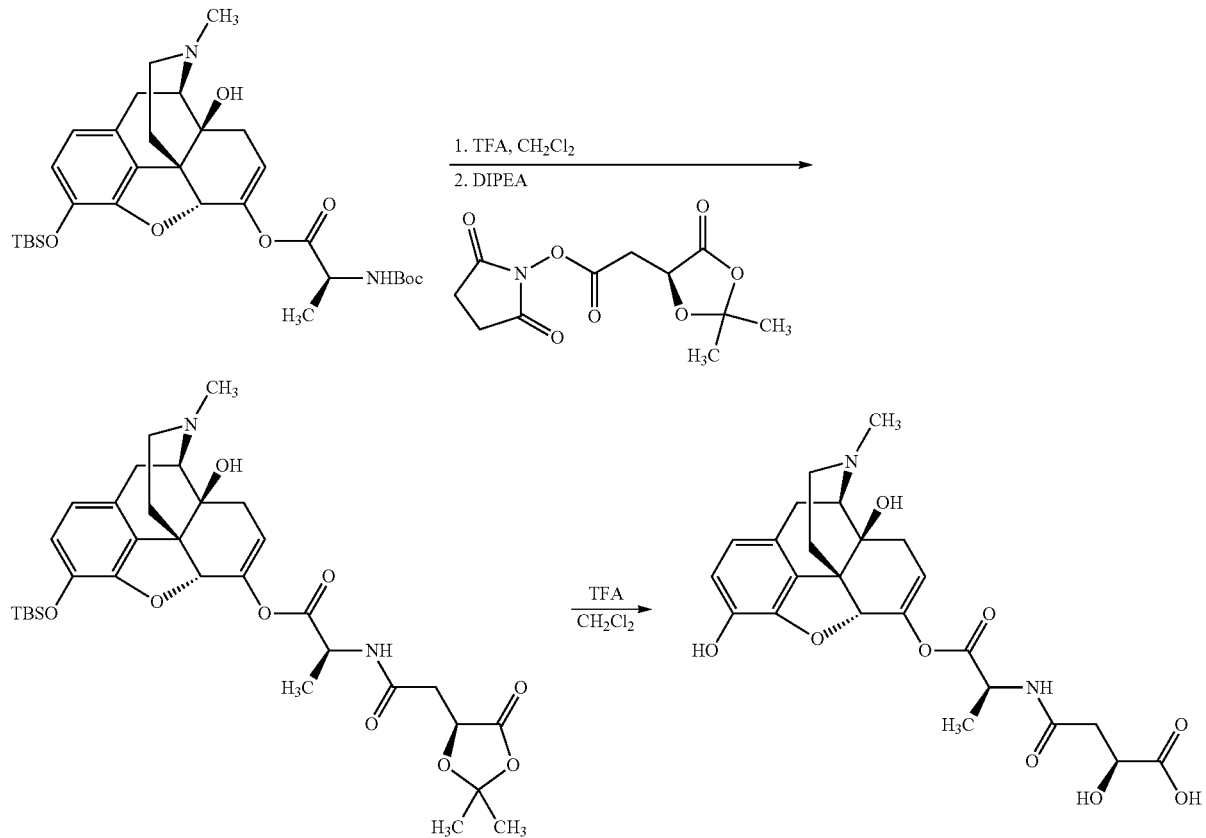

633

Preparation of (S)-(4R,4aS,7aR,12bS)-9-((tert-Butyldimethylsilyl)oxy)-4a-hydroxy-3-methyl-2,3,4,4a,5,7a-hexahydro-1H-4,12-methanobenzofuro[3,2-e]isoquinolin-7-yl 2-(2-((S)-2,2-dimethyl-5-oxo-1,3-dioxolan-4-yl)acetamido)propanoate

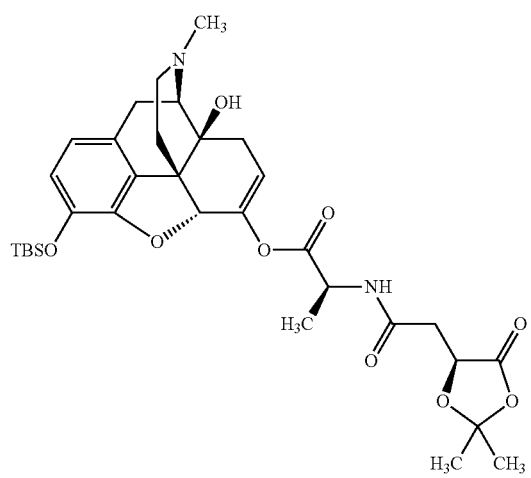 [SMILES: C[C@H](NC(=O)C[C@@H]1OC(C)(C)OC1=O)C(=O)OC1=CC[C@@]2(O)[C@H]3Cc4ccc(O[Si](C)(C)C(C)(C)C)c5c4[C@@]2(CCN3C)[C@H]1O5]

A solution (S)-(4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 2-((tert-butoxycarbonyl)amino)propanoate (300 mg, 0.51 mmol), in methylene chloride (5 mL) was treated with trifluoroacetic acid (1.5 mL) and the mixture was stirred at room temperature for 1 h. After this time, N,N-diisopropylethylamine was added slowly until the reaction mixture tested basic by pH paper analysis. The mixture was treated with a solution of (S)-2,5-dioxopyrrolidin-1-yl 2-(2,2-dimethyl-5-oxo-1,3-dioxolan-4-yl)acetate (208 mg, 0.77 mmol) in methylene chloride (1.5 mL) and stirred at room temperature for 1 h. After this time, the mixture was concentrated under reduced pressure. The residue was diluted with ethyl acetate and washed with 10% citric acid, saturated aqueous sodium bicarbonate, and brine, dried over sodium sulfate, filtered and concentrated. The crude product was purified by column chromatography (12 g silica, 0-100% ethyl acetate/methylene chloride) to provide (S)-(4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 2-(2-((S)-2,2-dimethyl-5-oxo-1,3-dioxolan-4-yl)acetamido)propanoate (184 mg, 56%): ESI MS m/z 643 $[C_{33}H_{46}N_2O_9Si+H]^+$.

634

Preparation of (S)-4-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl)amino)-2-hydroxy-4-oxobutanoic acid

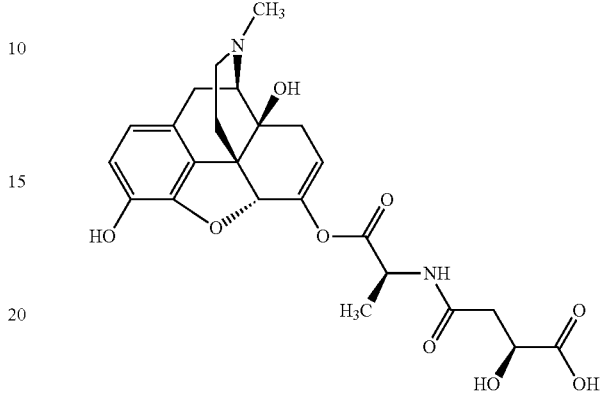

A mixture of (S)-(4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 2-(2-((S)-2,2-dimethyl-5-oxo-1,3-dioxolan-4-yl)acetamido)propanoate (183 mg, 0.285 mmol), trifluoroacetic acid (0.8 mL), water (0.8 mL) and methylene chloride (0.8 mL) was vigorously stirred at ambient temperature for 2 h. After this time, the reaction mixture was concentrated under reduced pressure. The residue was purified by reversed phase column chromatography (50 g C18 column, 5-30% acetonitrile/water) and freeze dried to provide (S)-4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)amino)-2-hydroxy-4-oxobutanoic acid (33 mg, 24%): $^1$H NMR (300 MHz, DMSO-$d_6$) δ 8.54 (d, J=6.8 Hz, 1H), 6.58 (d, J=8.1 Hz, 1H), 6.53 (d, J=8.1 Hz, 1H), 5.51 (dd, J=5.6, 2.5 Hz, 1H), 4.83 (s, 1H), 4.37-4.27 (m, 1H), 4.22 (dd, J=8.4, 4.3 Hz, 1H), 3.10 (d, J=18.9 Hz, 1H), 2.93 (d, J=5.6 Hz, 1H), 2.64 (dd, J=18.9, 5.9 Hz, 1H), 2.48-2.40 (m, 2H), 2.39 (s, 3H), 2.34-1.93 (m, 5H), 1.45-1.33 (m, 4H), CO$_2$H and three OH protons not observed; ESI MS m/z 489 $[C_{24}H_{28}N_2O_9+H]^+$; HPLC (Method B) 95.3% (AUC), $t_R$=10.96 min.

Scheme 96: (R)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-hydroxy-2-phenylacetate trifluoroacetic acid salt

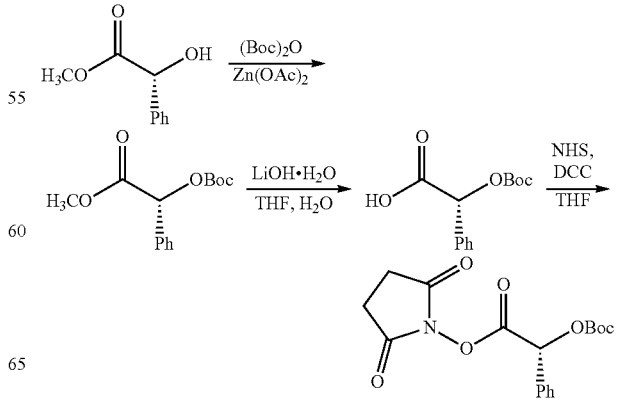

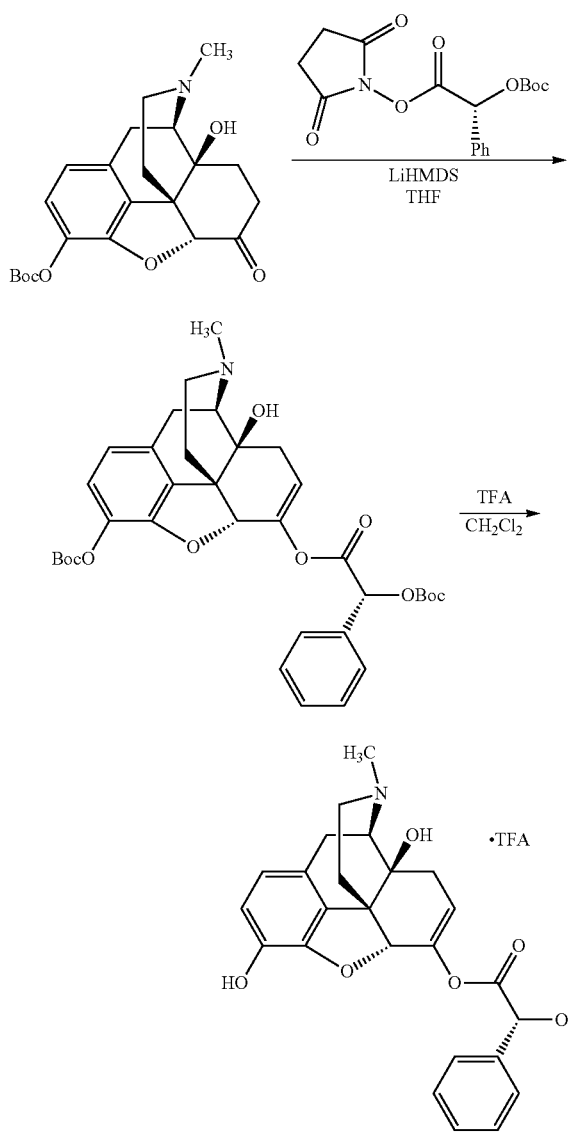

Preparation of (R)-Methyl 2-((tert-butoxycarbonyl)oxy)-2-phenylacetate

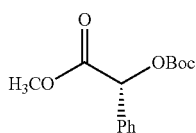

(R)-Methyl 2-hydroxy-2-phenylacetate (20.0 g, 120 mmol), di-tert-butyl dicarbonate (34.1 g, 156 mmol), and zinc acetate (3.96 g, 18.0 mmol) were combined and heated at 55° C. overnight under a nitrogen atmosphere. After this time, the reaction mixture was cooled to room temperature. The mixture was diluted with water (300 mL) and extracted with methylene chloride (3×150 mL). The combined organics were washed with brine (150 mL), dried over sodium sulfate, filtered, and concentrated under reduced pressure to provide (R)-methyl 2-((tert-butoxycarbonyl)oxy)-2-phenylacetate (31.4 g, 98%) as a colorless oil: $^1$H NMR (500 MHz, CDCl$_3$) δ 7.49-7.46 (m, 2H), 7.40-7.36 (m, 3H), 5.80 (s, 1H), 3.74 (s, 3H), 1.51 (s, 9H).

Preparation of (R)-2-((tert-Butoxycarbonyl)oxy)-2-phenylacetic acid

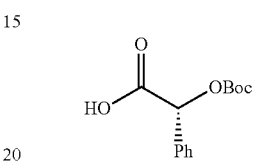

A solution of (R)-methyl 2-((tert-butoxycarbonyl)oxy)-2-phenylacetate (30.0 g, 110 mmol) in a mixture of tetrahydrofuran (300 mL) and water (150 mL) was treated with lithium hydroxide hydrate (9.45 g, 220 mmol) and stirred at ambient temperature for 3 h. After this time, the volatiles were removed under reduced pressure. The aqueous mixture was diluted with water (50 mL) and extracted with diethyl ether (150 mL). The aqueous layer was cooled in an ice bath, acidified to pH ~3 with 1.0 M hydrochloric acid, and extracted with ethyl acetate (3×150 mL). The combined organics were dried over sodium sulfate, filtered, and concentrated under reduced pressure to provide (R)-2-((tert-butoxycarbonyl)oxy)-2-phenylacetic acid (16.8 g, 61%) as a white solid: $^1$H NMR (300 MHz, CDCl$_3$) δ 7.51-7.44 (m, 2H), 7.41-7.36 (m, 3H), 5.25 (s, 1H), 1.51 (s, 9H), CO$_2$H proton not observed.

Preparation of (R)-2,5-Dioxopyrrolidin-1-yl 2-((tert-butoxycarbonyl)oxy)-2-phenylacetate

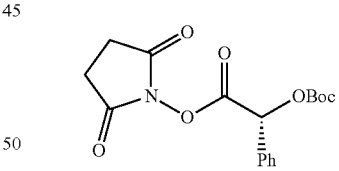

A solution of (R)-2-((tert-butoxycarbonyl)oxy)-2-phenylacetic acid (7.78 g, 30.8 mmol) in tetrahydrofuran (110 mL) was treated with N-hydroxysuccinimide (3.90 g, 34.0 mmol) and N,N'-dicyclohexylcarbodiimide (7.00 g, 34.0 mmol) and stirred under a nitrogen atmosphere for 3 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (R)-2,5-dioxopyrrolidin-1-yl 2-((tert-butoxycarbonyl)oxy)-2-phenylacetate (8.50 g, 79%) as a white solid: $^1$H NMR (300 MHz, CDCl$_3$) δ 7.57-7.55 (m, 2H), 7.44-7.42 (m, 3H), 6.15 (s, 1H), 2.80 (m, 4H), 1.52 (s, 9H).

Preparation of (R)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((tert-butoxycarbonyl)oxy)-2-phenylacetate

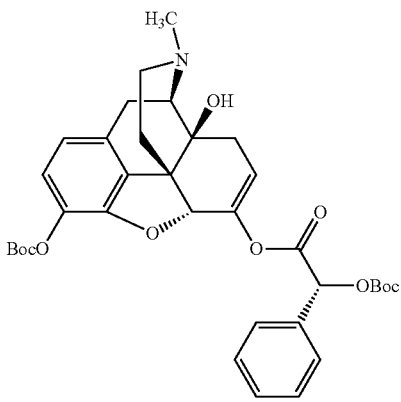

A suspension of oxycodone (0.500 g, 1.24 mmol) in tetrahydrofuran (10 mL) was cooled in an ice bath and treated dropwise with a 1.0 M solution of lithium bis(trimethylsilyl)amide in tetrahydrofuran (1.50 mL, 1.50 mmol). The mixture was stirred at 0° C. for 15 min and then treated dropwise with a solution of (S)-2,5-dioxopyrrolidin-1-yl 2-((tert-butoxycarbonyl)oxy)-2-phenylacetate (0.522 g, 1.49 mmol) in tetrahydrofuran (10 mL). The mixture was stirred at 0° C. for 1 h. After this time, the reaction mixture was treated with saturated aqueous ammonium chloride (50 mL) and extracted with ethyl acetate (3×75 mL). The combined organics were dried over sodium sulfate, filtered, and concentrated under reduced pressure. The crude residue was purified by column chromatography (silica gel, 0-6% methanol/methylene chloride) to provide (R)-(4R,4aS,7aR,12bS)-4a-Hydroxy-9-methoxy-3-methyl-2,3,4,4a,5,7a-hexahydro-1H-4,12-methanobenzofuro[3,2-e]isoquinolin-7-yl 2-((tert-butoxycarbonyl)oxy)-2-phenylacetate (0.290 g, 37%) as a colorless oil: ESI MS m/z 636 $[C_{35}H_{41}NO_{10}+H]^+$.

Preparation of (R)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-hydroxy-2-phenylacetate trifluoroacetic acid salt

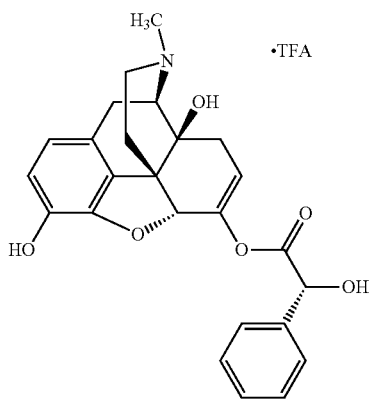 [SMILES: CN1CC[C@]23c4c5ccc(O)c4O[C@H]2C(OC(=O)[C@H](O)c2ccccc2)=CC[C@@]3(O)[C@H]1C5]

A solution of (R)-(4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl 2-((tert-butoxycarbonyl)oxy)-2-phenylacetate (0.100 g, 0.157 mmol) in methylene chloride (4 mL) was treated with trifluoroacetic acid (2 mL) and stirred under a nitrogen atmosphere at ambient temperature for 1 h. After this time, the reaction mixture was concentrated under reduced pressure. The residue was triturated with diethyl ether and then freeze dried from water to give (R)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-hydroxy-2-phenylacetate trifluoroacetic acid salt (0.066 g, 96%) as a white powder: $^1$H NMR (300 MHz, DMSO-$d_6$) δ 9.34 (s, 1H), 9.14 (br s, 1H), 7.50-7.41 9 m, 2H), 7.40-7.30 9 m, 3H), 6.68 (d, J=8.1 Hz, 1H), 6.61 (d, J=8.1 Hz, 1H), 6.25 (d, J=5.4 Hz 1H), 6.21 (s, 1H), 5.32 (dd, J=23.7, 3.9 Hz, 1H), 4.97 (s, 1H), 3.60 (d, J=6.0 Hz, 1H), 3.09-3.00 (m, 2H), 2.83 (d, J=4.2 Hz, 3H), 2.72-2.52 (m, 1H), 2.22 (dd, J=18.3, 6.3 Hz, 1H), 2.01 (d, J=17.7 Hz, 1H), 1.62 (d, J=11.1 Hz, 1H); ESI MS m/z 436 $[C_{25}H_{25}NO_6+H]^+$; HPLC (Method A) 96.6% (AUC), $t_R$=7.84 min.

Scheme 897: (S)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-3-hydroxy-4-oxobutanoic acid trifluoroacetic acid salt

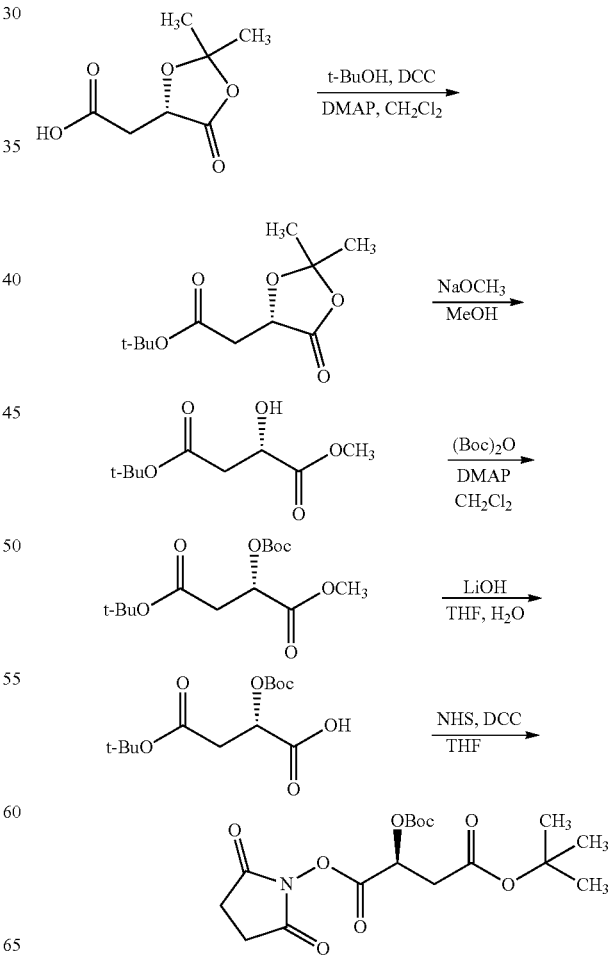

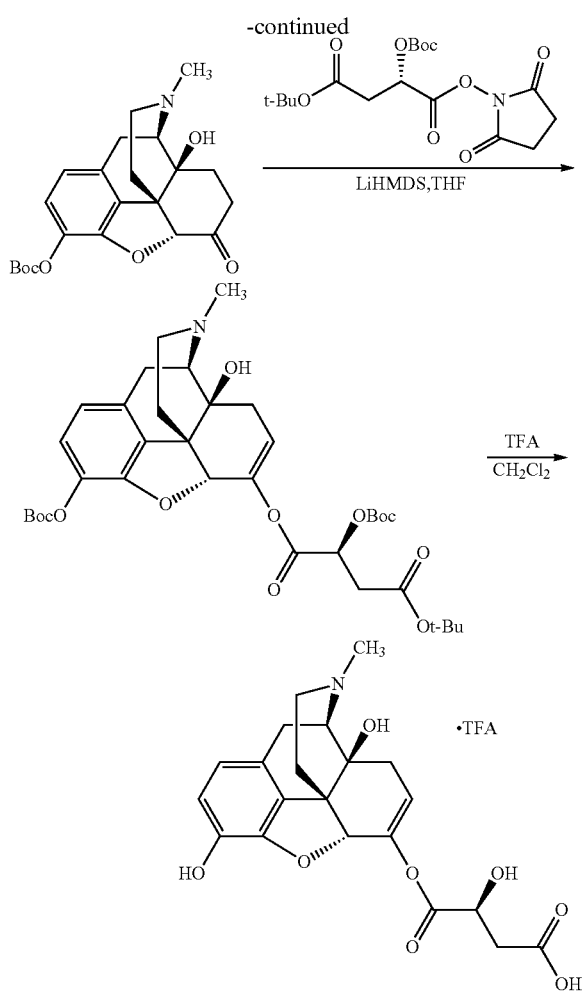

Preparation of (S)-tert-Butyl 2-(2,2-dimethyl-5-oxo-1,3-dioxolan-4-yl)acetate

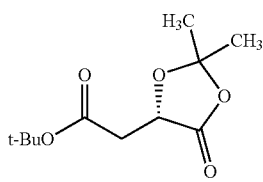 [SMILES: CC(C)(C)OC(=O)C[C@@H]1OC(C)(C)OC1=O]

A solution of (S)-2-(2,2-dimethyl-5-oxo-1,3-dioxolan-4-yl)acetic acid (7.50 g, 43.1 mmol) in methylene chloride (150 mL) was treated with N,N'-dicyclohexylcarbodiimide (10.7 g, 51.7 mmol), 4-dimethylaminopyridine (1.60 g, 12.9 mmol), and tert-butyl alcohol (6.2 mL, 64.7 mmol) and stirred under a nitrogen atmosphere for 2 h. After this time, the reaction mixture was filtered to remove the solid dicyclohexylurea byproduct. The filtrate was concentrated under reduced pressure. The crude residue was purified by column chromatography (silica gel, 0-10% ethyl acetate/heptanes) to provide (S)-tert-butyl 2-(2,2-dimethyl-5-oxo-1,3-dioxolan-4-yl)acetate (7.2 g, 73%) as an off-white solid: $^1$H NMR (300 MHz, CDCl$_3$) δ 4.66 (dd, J=6.3, 3.9 Hz, 1H), 2.84 (dd, J=16.8, 3.9 Hz, 1H), 2.72 (dd, J=16.8, 6.3 Hz, 1H), 1.63 (s, 3H), 1.56 (s, 3H), 1.47 (s, 9H).

Preparation of (S)-4-tert-Butyl 1-methyl 2-hydroxysuccinate

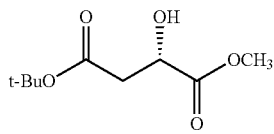 [SMILES: COC(=O)[C@@H](O)CC(=O)OC(C)(C)C]

A solution of (S)-tert-butyl 2-(2,2-dimethyl-5-oxo-1,3-dioxolan-4-yl)acetate (6.80 g, 29.6 mmol) in methanol (100 mL) was cooled in an ice bath and treated portion-wise over 10 min with anhydrous sodium methoxide (1.76 g, 32.5 mmol). After addition was complete, the mixture was stirred at 0° C. for 1.5 h. After this time, the reaction mixture was treated with saturated aqueous ammonium chloride (100 mL) and extracted with ethyl acetate (3×100 mL). The combined organics were dried over sodium sulfate, filtered, concentrated under reduced pressure, and dried under vacuum to provide (S)-4-tert-butyl 1-methyl 2-hydroxysuccinate (5.2 g, 86%) as a yellow oil: $^1$H NMR (300 MHz, CDCl$_3$) δ 4.44 (dd, J=10.5, 5.4 Hz, 1H), 3.81 (s, 3H), 3.22 (d, J=5.4 Hz, 1H), 2.87-2.64 (m, 2H), 1.45 (s, 9H).

Preparation of (S)-4-tert-Butyl 1-methyl 2-((tert-butoxycarbonyl)oxy)succinate

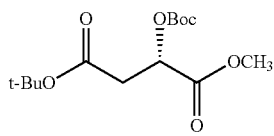

A solution of (S)-4-tert-butyl 1-methyl 2-hydroxysuccinate (5.30 g, 26.0 mmol) in methylene chloride (150 mL) was cooled in an ice bath under a nitrogen atmosphere and treated with 4-dimethylaminopyridine (0.317 g, 2.60 mmol) followed by di-tert-butyl dicarbonate (8.50 g, 40.0 mmol). After 2-3 min, the ice bath was removed, and the mixture was stirred at ambient temperature for 2 h. After this time, the reaction mixture was concentrated under reduced pressure and purified by column chromatography (silica gel, 0-5% ethyl acetate/heptanes) to provide (S)-4-tert-butyl 1-methyl 2-((tert-butoxycarbonyl)oxy)succinate (6.6 g, 83%) as a light yellow oil: $^1$H NMR (300 MHz, CDCl$_3$) δ 5.32 (dd, J=6.9, 6.0 Hz, 1H), 3.78 (s, 3H), 2.81-2.79 (m, 2H), 1.50 (s, 9H), 1.45 (s, 9H).

Preparation of (S)-4-(tert-Butoxy)-2-((tert-butoxycarbonyl)oxy)-4-oxobutanoic acid

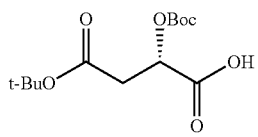

A solution of (S)-4-tert-butyl 1-methyl 2-((tert-butoxycarbonyl)oxy)succinate (6.60 g, 21.7 mmol) in tetrahydrofuran (74 mL) and water (37 mL) was cooled in an ice bath, treated with lithium hydroxide hydrate (1.09 g, 26.1 mmol), and stirred at 0° C. for 3 h. After this time, the reaction mixture was concentrated to remove the volatiles, acidified at 0° C. to pH ~3, and extracted with ethyl acetate (3×100 mL). The combined organics were dried over sodium sulfate, filtered, concentrated under reduced pressure, and dried under vacuum to provide (S)-4-(tert-butoxy)-2-((tert-butoxycarbonyl)oxy)-4-oxobutanoic acid (5.7 g, 90%): $^1$H NMR (300 MHz, CDCl$_3$) δ 5.32 (apparent t, J=6.0 Hz, 1H), 2.85 (apparent d, J=6.0 Hz, 2H), 1.50 (s, 9H), 1.46 (s, 9H), CO$_2$H proton not observed.

Preparation of (S)-4-tert-Butyl 1-(2,5-dioxopyrrolidin-1-yl) 2-((tert-butoxycarbonyl)oxy)succinate

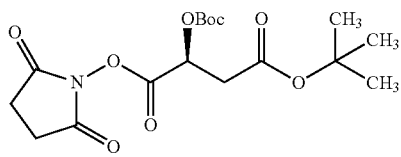

A solution of (S)-4-(tert-butoxy)-2-((tert-butoxycarbonyl)oxy)-4-oxobutanoic acid (525 mg, 1.81 mmol) in tetrahydrofuran (10 mL) was treated with N-hydroxysuccinimide (292 mg, 2.53 mmol) and N,N'-dicyclohexylcarbodiimide (523 mg, 2.53 mmol) and stirred under a nitrogen atmosphere for 1 h. After this time, the reaction mixture was filtered to remove the solid dicyclohexylurea byproduct. The solid was washed with tetrahydrofuran (25 mL), and the combined filtrate and washings were concentrated under reduced pressure. The residue was triturated with tetrahydrofuran (25 mL) and filtered to remove the solids. The filtrate was concentrated under reduced pressure. The residue was triturated with diethyl ether and filtered to remove the solids. The filtrate was concentrated under reduced pressure and dried under vacuum to provide (S)-4-tert-butyl 1-(2,5-dioxopyrrolidin-1-yl) 2-((tert-butoxycarbonyl)oxy)succinate (702 mg, quantitative) as a light yellow oil: $^1$H NMR (300 MHz, CDCl$_3$) δ 5.61 (dd, J=8.1, 4.8 Hz, 1H), 2.98-2.94 (m, 2H), 2.84 (s, 4H), 1.51 (s, 9H), 1.47 (s, 9H).

Preparation of (S)-1-((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2-((tert-butoxycarbonyl)oxy)succinate

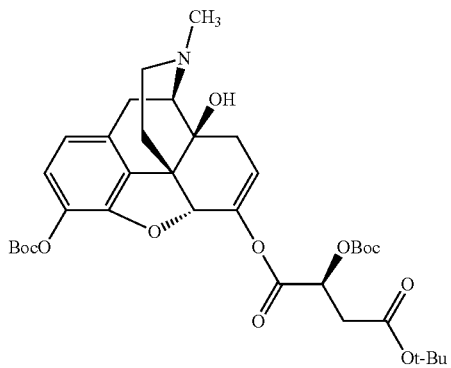

A suspension of oxycodone (0.402 g, 1.00 mmol) in tetrahydrofuran (8 mL) was cooled in an ice bath and treated dropwise with a 1.0 M solution of lithium bis(trimethylsilyl)amide in tetrahydrofuran (2.00 mL, 2.00 mmol). The mixture was stirred at 0° C. for 15 min and then treated dropwise with a solution of (S)-4-tert-butyl 1-(2,5-dioxopyrrolidin-1-yl) 2-((tert-butoxycarbonyl)oxy)succinate (0.465 g, 1.20 mmol) in tetrahydrofuran (8 mL). The reaction mixture was stirred at 0° C. for 1 h. After this time, the mixture was poured into saturated aqueous ammonium chloride (100 mL) and extracted with ethyl acetate (2×100 mL). The combined organics were dried over sodium sulfate, filtered, and concentrated under reduced pressure. The crude residue was purified by reversed phase chromatography (150 g C18 column, 10-100% acetonitrile/water) and freeze dried to provide (S)-1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2-((tert-butoxycarbonyl)oxy)succinate (0.078 g, 11%) as a white solid: ESI MS m/z 674[C$_{35}$H$_{47}$NO$_{12}$+H]$^+$.

Preparation of (S)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-3-hydroxy-4-oxobutanoic acid trifluoroacetic acid salt

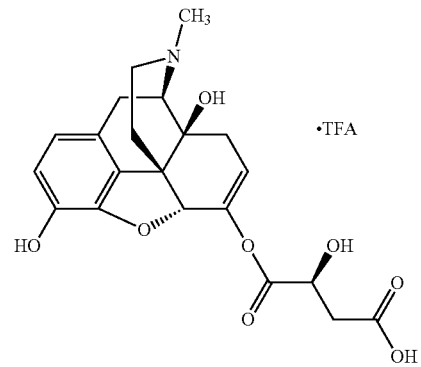 [SMILES: CN1CC[C@]23c4c5ccc(O)c4O[C@H]2C(OC(=O)[C@@H](O)CC(=O)O)=CC[C@@]3(O)[C@H]1C5]

A solution of (S)-1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2-((tert-butoxycarbonyl)oxy)succinate (0.060 g, 0.089 mmol) in methylene chloride (8 mL) was treated with trifluoroacetic acid (2.5 mL) and stirred under a nitrogen atmosphere at ambient temperature for 1 h. After this time, the reaction mixture was concentrated under reduced pressure. The residue obtained was triturated with diethyl ether then freeze dried from water to provide (S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-hydroxy-4-oxobutanoic acid trifluoroacetic acid salt (0.044 g, quantitative) as a white solid: $^1$H NMR (300 MHz, DMSO-d$_6$) δ 12.43 (br s, 1H), 9.30 (s, 1H), 9.16 (br s, 1H), 6.69-6.64 (m, 2H), 6.25 (s, 1H), 5.90 (s, 1H), 5.55 (s, 1H), 4.93 (s, 1H), 4.49 (s, 1H), 3.62 (s, 1H), 3.18-3.00 (m, 2H), 2.83 (s, 3H), 2.80-2.58 (m, 3H), 2.29-2.26 (m, 1H), 2.07 (d, J=18.0 Hz, 1H), 1.62 (d, J=13.2 Hz, 1H), two protons obscured by solvent peaks; ESI MS m/z 418[C$_{21}$H$_{23}$NO$_8$+H]$^+$.

Scheme 98: (S)-4-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2yl)amino)-3-hydroxy-4-oxobutanoic acid trifluoroacetic acid salt
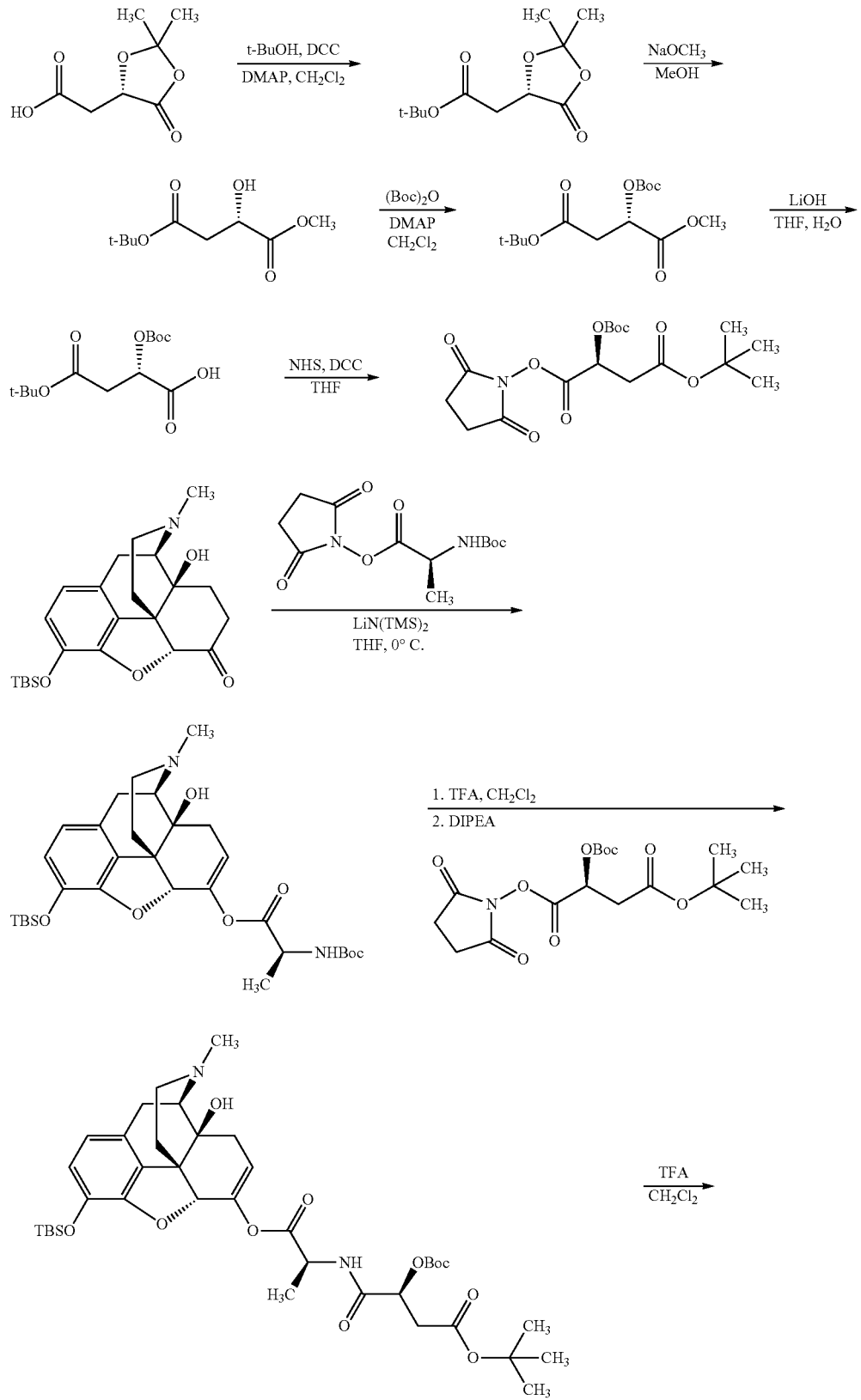

-continued

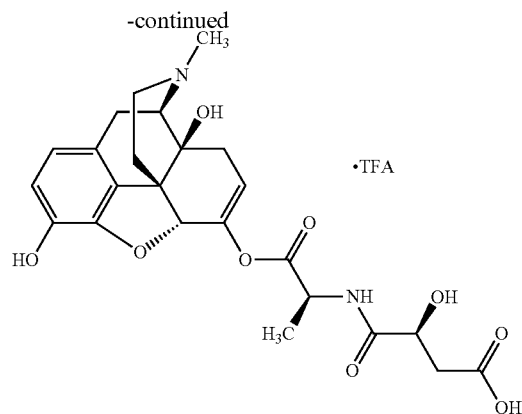

Preparation of (S)-tert-Butyl 2-(2,2-dimethyl-5-oxo-1,3-dioxolan-4-yl)acetate

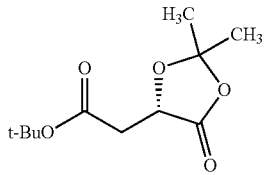 [SMILES: CC(C)(C)OC(=O)C[C@@H]1OC(C)(C)OC1=O]

A solution of (S)-2-(2,2-dimethyl-5-oxo-1,3-dioxolan-4-yl)acetic acid (7.50 g, 43.1 mmol) in methylene chloride (150 mL) was treated with N,N'-dicyclohexylcarbodiimide (10.7 g, 51.7 mmol), 4-dimethylaminopyridine (1.60 g, 12.9 mmol), and tert-butyl alcohol (6.2 mL, 64.7 mmol) and stirred under a nitrogen atmosphere for 2 h. After this time, the reaction mixture was filtered to remove the solid dicyclohexylurea byproduct. The filtrate was concentrated under reduced pressure. The crude residue was purified by column chromatography (silica gel, 0-10% ethyl acetate/heptanes) to provide (S)-tert-butyl 2-(2,2-dimethyl-5-oxo-1,3-dioxolan-4-yl)acetate (7.2 g, 73%) as an off-white solid: $^1$H NMR (300 MHz, CDCl$_3$) δ 4.66 (dd, J=6.3, 3.9 Hz, 1H), 2.84 (dd, J=16.8, 3.9 Hz, 1H), 2.72 (dd, J=16.8, 6.3 Hz, 1H), 1.63 (s, 3H), 1.56 (s, 3H), 1.47 (s, 9H).

Preparation of (S)-4-tert-Butyl 1-methyl 2-hydroxysuccinate

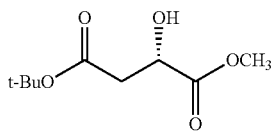

A solution of (S)-tert-butyl 2-(2,2-dimethyl-5-oxo-1,3-dioxolan-4-yl)acetate (6.80 g, 29.6 mmol) in methanol (100 mL) was cooled in an ice bath and treated portion-wise over 10 min with anhydrous sodium methoxide (1.76 g, 32.5 mmol). After addition was complete, the mixture was stirred at 0° C. for 1.5 h. After this time, the reaction mixture was treated with saturated aqueous ammonium chloride (100 mL) and extracted with ethyl acetate (3×100 mL). The combined organics were dried over sodium sulfate, filtered, concentrated under reduced pressure, and dried under vacuum to provide (S)-4-tert-butyl 1-methyl 2-hydroxysuccinate (5.2 g, 86%) as a yellow oil: $^1$H NMR (300 MHz, CDCl$_3$) δ 4.44 (dd, J=10.5, 5.4 Hz, 1H), 3.81 (s, 3H), 3.22 (d, J=5.4 Hz, 1H), 2.87-2.64 (m, 2H), 1.45 (s, 9H).

Preparation of (S)-4-tert-Butyl 1-methyl 2-((tert-butoxycarbonyl)oxy)succinate

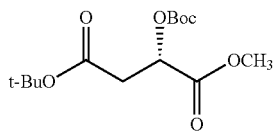

A solution of (S)-4-tert-butyl 1-methyl 2-hydroxysuccinate (5.30 g, 26.0 mmol) in methylene chloride (150 mL) was cooled in an ice bath under a nitrogen atmosphere and treated with 4-dimethylaminopyridine (0.317 g, 2.60 mmol) followed by di-tert-butyl dicarbonate (8.50 g, 40.0 mmol). After 2-3 min, the ice bath was removed, and the mixture was stirred at ambient temperature for 2 h. After this time, the reaction mixture was concentrated under reduced pressure and purified by column chromatography (silica gel, 0-5% ethyl acetate/heptanes) to provide (S)-4-tert-butyl 1-methyl 2-((tert-butoxycarbonyl)oxy)succinate (6.6 g, 83%) as a light yellow oil: $^1$H NMR (300 MHz, CDCl$_3$) δ 5.32 (dd, J=6.9, 6.0 Hz, 1H), 3.78 (s, 3H), 2.81-2.79 (m, 2H), 1.50 (s, 9H), 1.45 (s, 9H).

Preparation of (S)-4-(tert-Butoxy)-2-((tert-butoxycarbonyl)oxy)-4-oxobutanoic acid

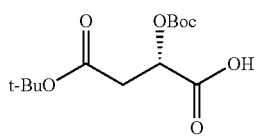

A solution of (S)-4-tert-butyl 1-methyl 2-((tert-butoxycarbonyl)oxy)succinate (6.60 g, 21.7 mmol) in tetrahydrofuran (74 mL) and water (37 mL) was cooled in an ice bath, treated with lithium hydroxide hydrate (1.09 g, 26.1 mmol), and stirred at 0° C. for 3 h. After this time, the reaction mixture was concentrated to remove the volatiles, acidified at 0° C. to pH ~3, and extracted with ethyl acetate (3×100 mL). The combined organics were dried over sodium sulfate, filtered, concentrated under reduced pressure, and dried under vacuum to provide (S)-4-(tert-butoxy)-2-((tert-butoxycarbonyl)oxy)-4-oxobutanoic acid (5.7 g, 90%): $^1$H NMR (300 MHz, CDCl$_3$) δ 5.32 (apparent t, J=6.0 Hz, 1H), 2.85 (apparent d, J=6.0 Hz, 2H), 1.50 (s, 9H), 1.46 (s, 9H), CO$_2$H proton not observed.

Preparation of (S)-4-tert-Butyl 1-(2,5-dioxopyrrolidin-1-yl) 2-((tert-butoxycarbonyl)oxy)succinate

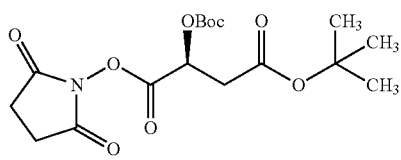

A solution of (S)-4-(tert-butoxy)-2-((tert-butoxycarbonyl)oxy)-4-oxobutanoic acid (525 mg, 1.81 mmol) in tetrahydrofuran (10 mL) was treated with N-hydroxysuccinimide (292 mg, 2.53 mmol) and N,N'-dicyclohexylcarbodiimide (523 mg, 2.53 mmol) and stirred under a nitrogen atmosphere for 1 h. After this time, the reaction mixture was filtered to remove the solid dicyclohexylurea byproduct. The solid was washed with tetrahydrofuran (25 mL), and the combined filtrate and washings were concentrated under reduced pressure. The residue was triturated with tetrahydrofuran (25 mL) and filtered to remove the solids. The filtrate was concentrated under reduced pressure. The residue was triturated with diethyl ether and filtered to remove the solids. The filtrate was concentrated under reduced pressure and dried under vacuum to provide (S)-4-tert-butyl 1-(2,5-dioxopyrrolidin-1-yl) 2-((tert-butoxycarbonyl)oxy)succinate (702 mg, quantitative) as a light yellow oil: $^1$H NMR (300 MHz, CDCl$_3$) δ 5.61 (dd, J=8.1, 4.8 Hz, 1H), 2.98-2.94 (m, 2H), 2.84 (s, 4H), 1.51 (s, 9H), 1.47 (s, 9H).

Preparation of (S)-tert-Butyl 3-((tert-butoxycarbonyl)oxy)-4-(((S)-1-(((4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl)amino)-4-oxobutanoate

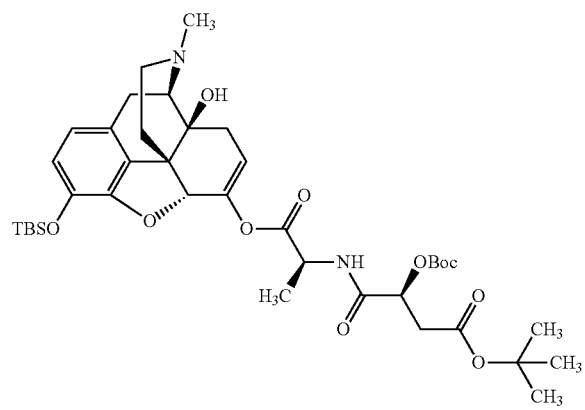

A solution (S)-(4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 2-((tert-butoxycarbonyl)amino)propanoate (500 mg, 0.85 mmol) in methylene chloride (8 mL) was treated with trifluoroacetic acid (1.5 mL), and the mixture was stirred at room temperature for 1 h. After this time, N,N-diisopropylethylamine was added slowly until the reaction mixture tested basic by pH paper analysis. The mixture was treated with a solution of (S)-4-tert-butyl 1-(2,5-dioxopyrrolidin-1-yl) 2-((tert-butoxycarbonyl)oxy)succinate (495 mg, 1.28 mmol) in methylene chloride (3 mL) and stirred at room temperature for 1 h. After this time, the mixture was concentrated under reduced pressure. The residue was diluted with ethyl acetate and washed with 10% citric acid, saturated aqueous sodium bicarbonate, and brine, dried over sodium sulfate, filtered, and concentrated. The crude product was purified by column chromatography (24 g silica, 0-100% ethyl acetate/methylene chloride) to provide (S)-tert-butyl 3-((tert-butoxycarbonyl)oxy)-4-(((S)-1-(((4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl)amino)-4-oxobutanoate (410 mg, 63%): ESI MS m/z 759 [C$_{39}$H$_{58}$N$_2$O$_{11}$Si+H]$^+$.

Preparation of (S)-4-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl)amino)-3-hydroxy-4-oxobutanoic acid trifluoroacetic acid salt

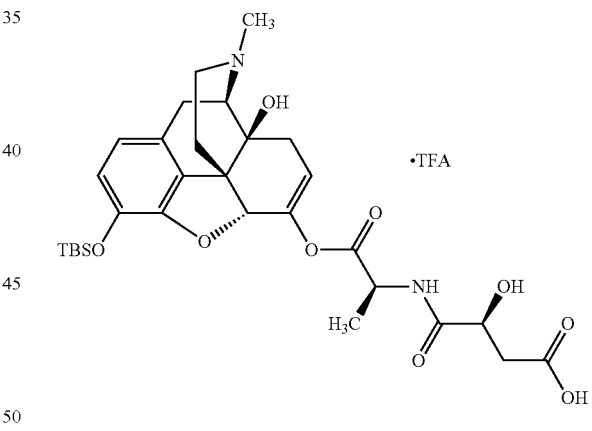

A mixture of (S)-tert-butyl 3-((tert-butoxycarbonyl)oxy)-4-(((S)-1-(((4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl)amino)-4-oxobutanoate (250 mg, 0.33 mmol), trifluoroacetic acid (0.8 mL), water (0.8 mL) and methylene chloride (0.8 mL) was vigorously stirred at ambient temperature for 3 h. After this time, the reaction mixture was concentrated under reduced pressure. The residue was purified by reversed phase column chromatography (50 g C18 column, 5-30% acetonitrile/water) and freeze dried to provide (S)-4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)amino)-3-hydroxy-4-oxobutanoic acid trifluoroacetic acid salt (44 mg, 27%): $^1$H NMR (300 MHz, DMSO-$d_6$) δ 8.21 (d, J=7.3 Hz, 1H), 6.57 (d, J=8.1 Hz, 1H), 6.52 (d, J=8.1 Hz, 1H), 5.51 (dd, J=4.4, 2.8 Hz, 1H), 4.83 (s, 1H), 4.43-4.32 (m, 1H), 4.27 (dd, J=8.8, 3.7 Hz, 1H), 3.08 (d, J=18.6 Hz, 1H), 2.85 (d, J=5.8 Hz, 1H), 2.65-2.54 (m, 2H), 2.48-2.38 (m, 1H), 2.34 (s, 3H), 2.30-2.17 (m, 2H), 2.10 (d, J=8.7 Hz, 1H), 2.07-1.98 (m, 2H), 1.43-1.34 (m, 4H), $CO_2H$, $CF_3CO_2H$, and three OH protons not observed; ESI MS m/z 489 $[C_{24}H_{28}N_2O_9+H]^+$.
Scheme 99: (S)-4-((3-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-3-oxopropyl)amino)-2-hydroxy-4-oxobutanoic acid trifluoroacetic acid salt
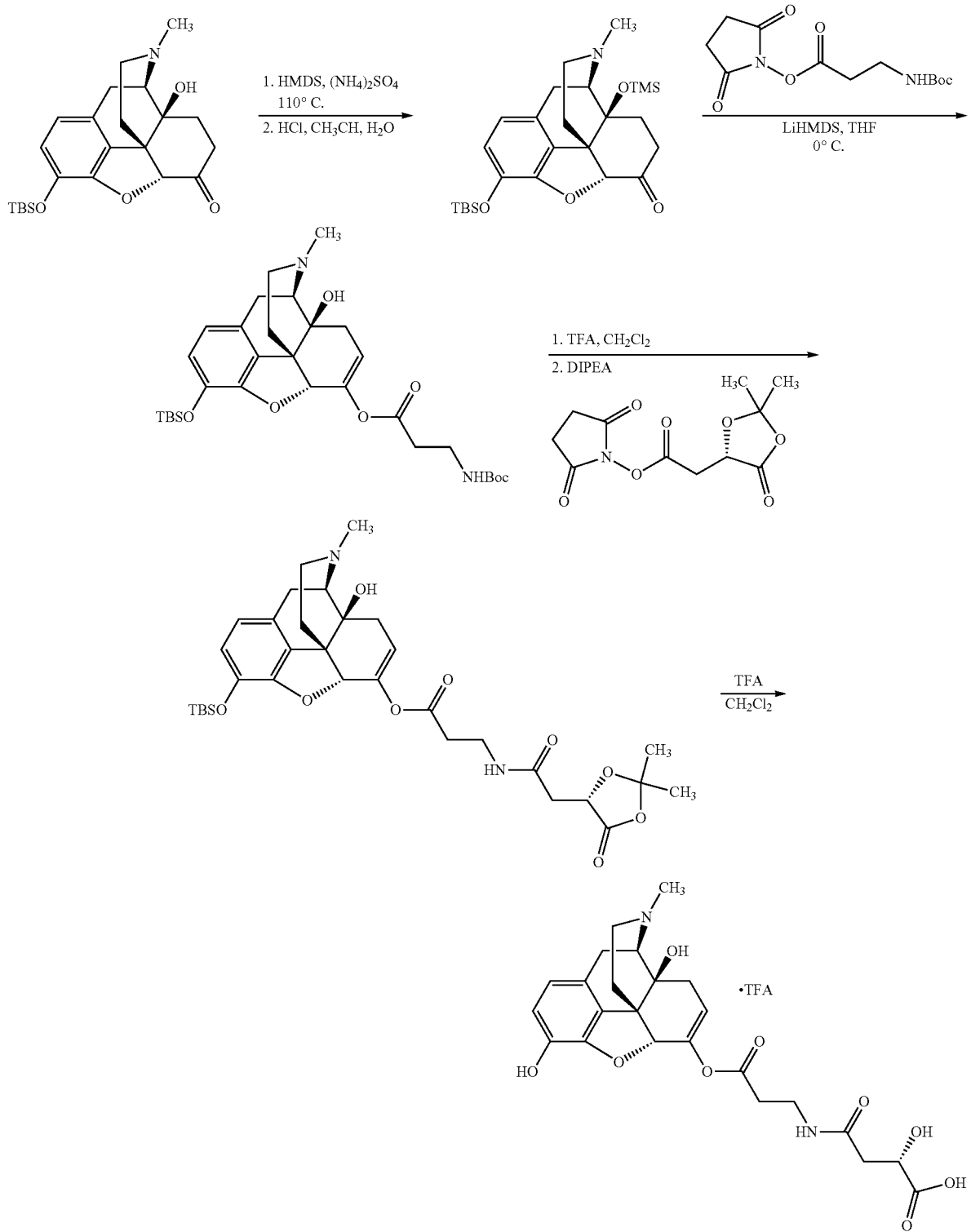

Preparation of (4R,4aS,7aR,12bS)-9-((tert-Butyldimethyisilyl)oxy)-3-methyl-4a-((trimethylsilyl)oxy)-2,3,4,4a,5,6-hexahydro-1H-4,12-methanobenzofuro[3,2-e]isoquinolin-7(7aH)-one

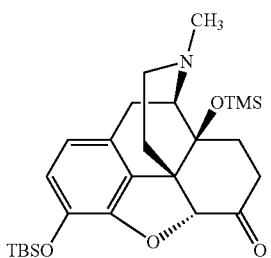

A suspension of (4R,4aS,7aR,12bS)-9-((tert-butyldimethylsilyl)oxy)-4a-hydroxy-3-methyl-2,3,4,4a, 5,6-hexahydro-1H-4,12-methanobenzofuro[3,2-e]isoquinolin-7(7aH)-one (1.20 g, 2.89 mmol) and ammonium sulfate (8 mg, 0.06 mmol) in bis(trimethylsilyl)amine (4 mL) was heated to 110° C. to obtain a clear solution that was stirred for 6 h. After this time, the mixture was cooled to room temperature and concentrated under reduced pressure. The residue was suspended in 1:1 acetonitrile/water (10 mL) and acidified by dropwise addition of 2 N hydrochloric acid to obtain a clear solution that was stirred at room temperature for 10 min. The mixture was diluted with ethyl acetate and washed with a saturated solution of sodium bicarbonate and brine. The organic layer was dried over sodium sulfate, filtered, and concentrated under reduced pressure to provide (4R,4aS,7aR,12bS)-9-((tert-butyldimethylsilyl)oxy)-3-methyl-4a-((trimethylsilyl)oxy)-2,3,4,4a,5,6-hexahydro-1H-4,12-methanobenzofuro[3,2-e]isoquinolin-7(7aH)-one (1.23 g, 87%): $^1$H NMR (300 MHz, CDCl$_3$) δ 6.61 (d, J=8.1 Hz, 1H), 6.52 (d, J=8.1 Hz, 1H), 4.50 (s, 1H), 3.17 (d, J 18.4 Hz, 1H), 3.02-2.89 (m, 2H), 2.46-2.35 (m, 3H), 2.31 (s, 3H), 2.23-2.05 (m, 2H), 1.75-1.69 (m, 2H), 1.41-1.35 (m, 1H), 0.99 (s, 9H), 0.27 (s, 3H), 0.18 (s, 12H).

Preparation of (4R,4aS,7aR,12bS)-9-((tert-Butyldimethylsilyl)oxy)-4a-hydroxy-3-methyl-2,3,4,4a,5,7a-hexahydro-1H-4,12-methanobenzofuro[3,2-e]isoquinolin-7-yl 3-((tert-butoxycarbonyl)amino)propanoate

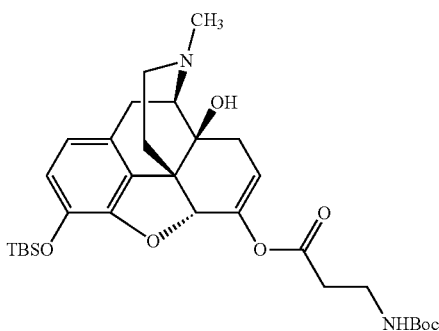 [SMILES: CN1CC[C@]23c4c5ccc(O[Si](C)(C)C(C)(C)C)c4O[C@H]2C(OC(=O)CCNC(=O)OC(C)(C)C)=CC[C@@]3(O)[C@H]1C5]

A suspension of (4R,4aS,7aR,12bS)-9-((tert-butyldimethylsilyl)oxy)-3-methyl-4a-((trimethylsilyl)oxy)-2,3,4,4a,5,6-hexahydro-1H-4,12-methanobenzofuro[3,2-e]isoquinolin-7 (7aH)-one (0.26 g, 0.53 mmol) in tetrahydrofuran (8 mL) was cooled in an ice bath and treated dropwise with a 1.0 M solution of lithium bis(trimethylsilyl)amidein tetrahydrofuran (0.7 mL, 0.7 mmol). After addition was complete, the mixture was stirred at ambient temperature for 10 min. The mixture was re-cooled in the ice bath and treated dropwise with a solution of 2,5-dioxopyrrolidin-1-yl 3-((tert-butoxycarbonyl)amino)propanoate (0.26 g, 0.91 mmol) in tetrahydrofuran (4 mL). After addition was complete, the mixture was stirred at ambient temperature for 45 min. After this time, the reaction mixture was cooled in an ice bath, treated with saturated aqueous ammonium chloride, and extracted with ethyl acetate. The combined organics were dried over sodium sulfate, filtered, and concentrated under reduced pressure. The residue was purified by column chromatography (silica gel, 0-10% methanol/methylene chloride) to provide (4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 3-((tert-butoxycarbonyl)amino)propanoate (0.20 g, 57%): $^1$H NMR (300 MHz, CDCl$_3$) δ 6.65 (d, J=8.1 Hz, 1H), 6.55 (d, J=8.1 Hz, 1H), 5.61 (dd, J=5.6, 2.8 Hz, 1H), 5.02 (s, 1H), 3.42-3.39 (m, 2H), 3.16 (d, J=18.7 Hz, 1H), 2.72-2.60 (m, 6H), 2.43 (s. 3H), 2.42-2.15 (m, 4H), 1.65-1.55 (m, 1H), 1.44 (s, 9H), 9.67 (s, 9H), 0.17 (s, 3H), 0.14 (s, 3H), NH proton not observed.

Preparation of (4R,4aS,7aR,12bS)-9-((tert-Butyldimethylsilyl)oxy)-4a-hydroxy-3-methyl-2,3,4,4a,5,7a-hexahydro-1H-4,12-methanobenzofuro[3,2-e]isoquinolin-7-yl 3-(2-((S)-2,2-dimethyl-5-oxo-1,3-dioxolan-4-yl)acetamido)propanoate

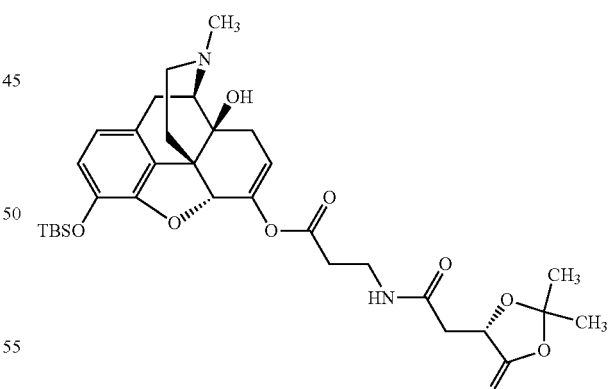

A solution (4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 3-((tert-butoxycarbonyl)amino)propanoate (300 mg, 0.51 mmol), in methylene chloride (5 mL) was treated with trifluoroacetic acid (1.5 mL) and the mixture was stirred at room temperature for 1 h. After this time, N,N-diisopropylethylamine was added slowly until the reaction mixture tested basic by pH paper analysis. The mixture was treated with a solution of (S)-2,5-dioxopyrrolidin-1-yl 2-(2,2-dimethyl-5-oxo-1,3-dioxolan-4-yl)acetate (208 mg, 0.767 mmol) in methylene chloride (1.5 mL) and stirred at room temperature for 1 h. After this time, the mixture was concentrated under reduced pressure. The residue was diluted with ethyl acetate and washed with 10% citric acid, saturated aqueous sodium bicarbonate, and brine, dried over sodium sulfate, filtered and concentrated to provide (4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 3-(2-((S)-2,2-dimethyl-5-oxo-1,3-dioxolan-4-yl)acetamido)propanoate (372 mg): ESI MS m/z 643 $[C_{33}H_{46}N_2O_9Si+H]^+$.

Preparation of (S)-4-((3-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-3-oxopropyl)amino)-2-hydroxy-4-oxobutanoic acid trifluoroacetic acid salt

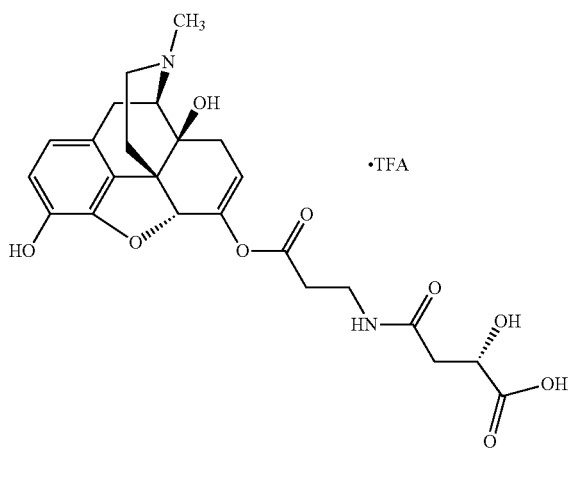 [SMILES: CN1CC[C@]23c4c5ccc(O)c4O[C@H]2C(OC(=O)CCNC(=O)C[C@H](O)C(=O)O)=CC[C@@]3(O)[C@H]1C5]

A mixture of (4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 3-(2-((S)-2,2-dimethyl-5-oxo-1,3-dioxolan-4-yl)acetamido)propanoate (365 mg, 0.568 mmol), trifluoroacetic acid (1 mL), water (1 mL) and methylene chloride (1 mL) was vigorously stirred at ambient temperature for 3 h. After this time, the reaction mixture was concentrated under reduced pressure. The residue was purified by reversed phase column chromatography (150 g C18 column, 5-30% acetonitrile/water) and freeze dried to provide (S)-4-((3-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-oxopropyl)amino)-2-hydroxy-4-oxobutanoic acid trifluoroacetic acid salt (120 mg, 48%): $^1$H NMR (300 MHz, DMSO-$d_6$) δ 8.08 (t, J=5.6 Hz, 1H), 6.58 (d, J=8.1 Hz, 1H), 6.53 (d, J=8.1 Hz, 1H), 5.53 (dd, J=5.5, 2.6 Hz, 1H), 4.85 (s, 1H), 4.22 (dd, J=8.1, 4.5 Hz, 1H), 3.41-3.24 (m, 2H), 3.12 (d, J=18.8 Hz, 1H), 2.95 (d, J=6.0 Hz, 1H), 2.70-2.51 (m, 4H), 2.49-4.22 (m, 1H), 2.40 (s, 3H), 2.35-1.95 (m, 5H), 1.41 (d, J=12.2 Hz, 1H), $CO_2H$ and three OH protons not observed; ESI MS m/z 489 $[C_{24}H_{28}N_2O_9+H]^+$; HPLC (Method B) 97.6% (AUC), $t_R$=10.71 min.

Scheme 100: (S)-4-((S)-2-(((((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)carbonyl)pyrrolidin-1-yl)-2-hydroxy-4-oxobutanoic acid trifluoroacetic acid salt

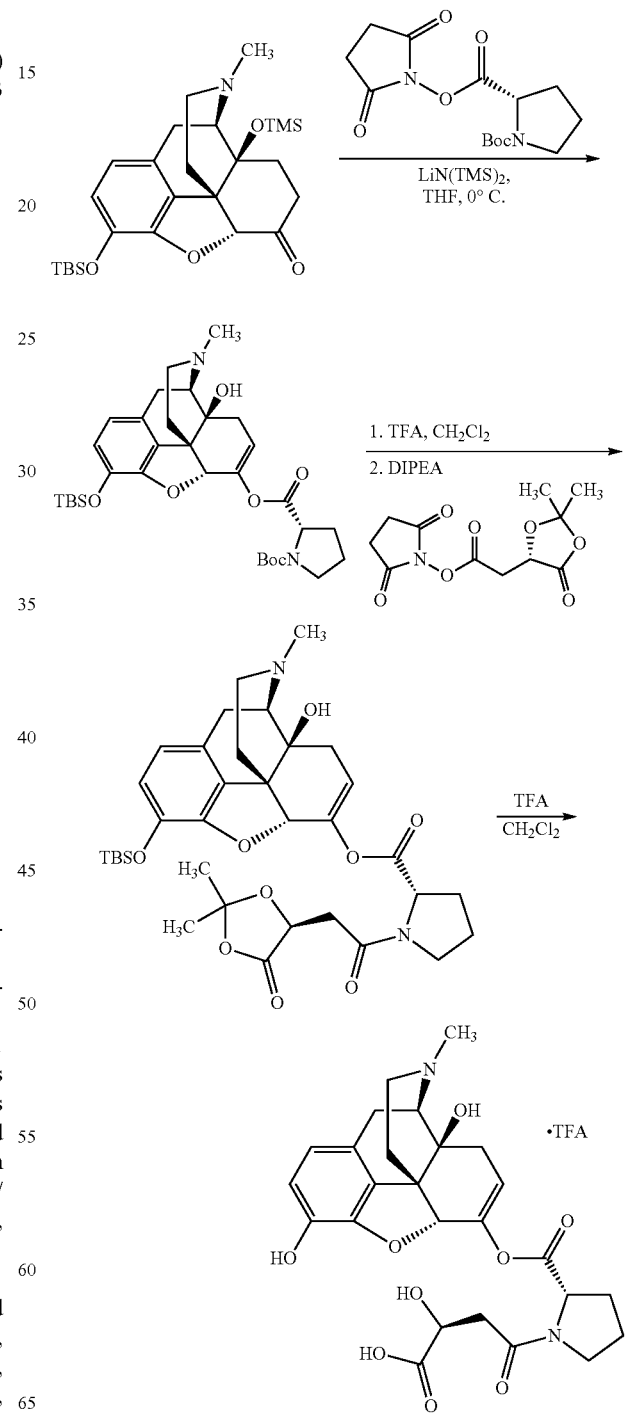

Preparation of (S)-1-tert-Butyl 2-((4R,4aS,7aR, 12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl) pyrrolidine-1,2-dicarboxylate

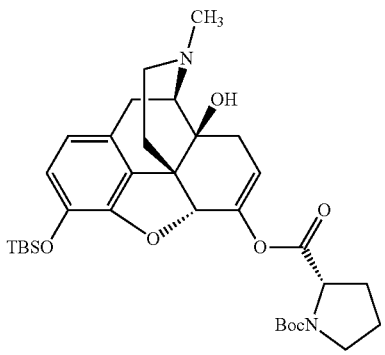 [SMILES: CN1CC[C@]23c4c5ccc(O[Si](C)(C)C(C)(C)C)c4O[C@H]2C(OC(=O)[C@@H]2CCCN2C(=O)OC(C)(C)C)=CC[C@@]3(O)[C@H]1C5]

A suspension of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (1.02 g, 2.45 mmol) in tetrahydrofuran (12 mL) was cooled in an ice bath and treated dropwise with a 1.0 M solution of lithium bis(trimethylsilyl)amide in tetrahydrofuran (4.9 mL, 4.9 mmol). After 30 min, the mixture was treated dropwise with a solution of (S)-1-tert-butyl 2-(2,5-dioxopyrrolidin-1-yl) pyrrolidine-1,2-dicarboxylate (1.5 g, 4.9 mmol) in tetrahydrofuran (6 mL) and stirred at 0° C. for 16 h. After this time, the reaction mixture was poured into cold saturated aqueous ammonium chloride and extracted with ethyl acetate. The combined organics were washed with saturated aqueous sodium bicarbonate and brine, dried over sodium sulfate, filtered, and concentrated under reduced pressure. The crude residue was purified by reversed phase column chromatography (50 g C18 column, 0-100% acetonitrile/water) and freeze dried to provide (S)-1-tert-butyl 2-((4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl) pyrrolidine-1,2-dicarboxylate (294 mg, 20%): ESI MS m/z 613 $[C_{33}H_{48}N_2O_7Si+H]^+$.

Preparation of (S)-(4R,4aS,7aR,12bS)-9-((tert-Butyldimethylsilyl)oxy)-4a-hydroxy-3-methyl-2,3,4,4a,5,7a-hexahydro-1H-4,12-methanobenzofuro[3,2-e]isoquinolin-7-yl 1-(2-((S)-2,2-dimethyl-5-oxo-1,3-dioxolan-4-yl)acetyl)pyrrolidine-2-carboxylate

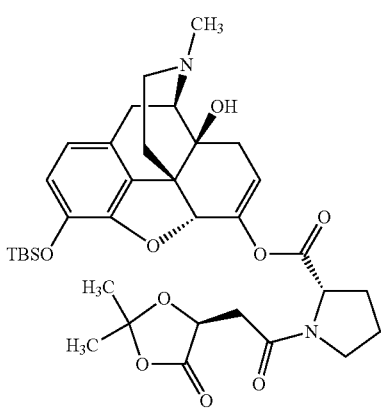 [SMILES: CN1CC[C@]23c4c5ccc(O[Si](C)(C)C(C)(C)C)c4O[C@H]2C(OC(=O)[C@@H]2CCCN2C(=O)C[C@@H]2OC(C)(C)OC2=O)=CC[C@@]3(O)[C@H]1C5]

A solution (S)-1-tert-butyl 2-((4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl) pyrrolidine-1,2-dicarboxylate (280 mg, 0.46 mmol) in methylene chloride (5 mL) was treated with trifluoroacetic acid (1.5 mL), and the mixture was stirred at room temperature for 1 h. After this time, N,N-diisopropylethylamine was added slowly until the reaction mixture tested basic by pH paper analysis. The mixture was treated with a solution of (S)-2,5-dioxopyrrolidin-1-yl 2-(2,2-dimethyl-5-oxo-1,3-dioxolan-4-yl)acetate (186 mg, 0.69 mmol) in methylene chloride (1.5 mL) and stirred at room temperature for 1 h. After this time, the mixture was concentrated under reduced pressure. The residue was diluted with ethyl acetate and washed with 10% citric acid, saturated aqueous sodium bicarbonate, and brine, dried over sodium sulfate, filtered and concentrated to provide (S)-(4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 1-(2-((S)-2,2-dimethyl-5-oxo-1,3-dioxolan-4-yl)acetyl)pyrrolidine-2-carboxylate (430 mg): ESI MS m/z 669 $[C_{35}H_{48}N_2O_9Si+H]^+$.

Preparation of (S)-4-((S)-2-((((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)carbonyl)pyrrol din-1-yl)-2-hydroxy-4-oxobutanoic acid trifluoroacetic acid salt

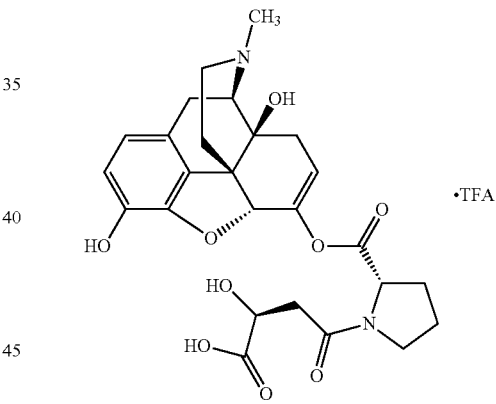

A mixture of (S)-(4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 1-(2-((S)-2,2-dimethyl-5-oxo-1,3-dioxolan-4-yl)acetyl)pyrrolidine-2-carboxylate (200 mg, 0.30 mmol), trifluoroacetic acid (0.5 mL), water (0.5 mL) and methylene chloride (0.5 mL) was vigorously stirred at ambient temperature for 3 h. After this time, the reaction mixture was concentrated under reduced pressure. The residue was purified by reversed phase column chromatography (150 g C18 column, 5-30% acetonitrile/water) and freeze dried to provide (S)-4-((S)-2-((((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)carbonyl)pyrrolidin-1-yl)-2-hydroxy-4-oxobutanoic acid trifluoroacetic acid salt (69 mg, 36%): $^1$H NMR (300 MHz, DMSO-$d_6$) δ 6.58 (d, J=8.1 Hz, 1H), 6.53 (d, J=8.1 Hz, 1H), 5.51 (dd, J=5.5, 2.5 Hz, 1H), 4.86-4.83 (m, 1H), 4.39 (dd, J=8.7, 3.5 Hz, 1H), 4.29-4.24 (m, 1H), 3.65-3.54 (m, 2H), 3.10 (d, J=18.8 Hz, 1H), 2.93 (d, J=5.9

Hz, 1H), 2.69-2.60 (m, 3H), 2.39 (s, 3H), 2.30-2.20 (m, 2H), 2.15 (d, J=13.4 Hz, 1H), 2.10-1.92 (m, 5H), 1.40 (d, J=11.1 Hz, 1H), five protons not observed; ESI MS m/z 515 $[C_{26}H_{30}N_2O_9+H]^+$; HPLC (Method B) 95.0% (AUC), $t_R$=11.86 min.

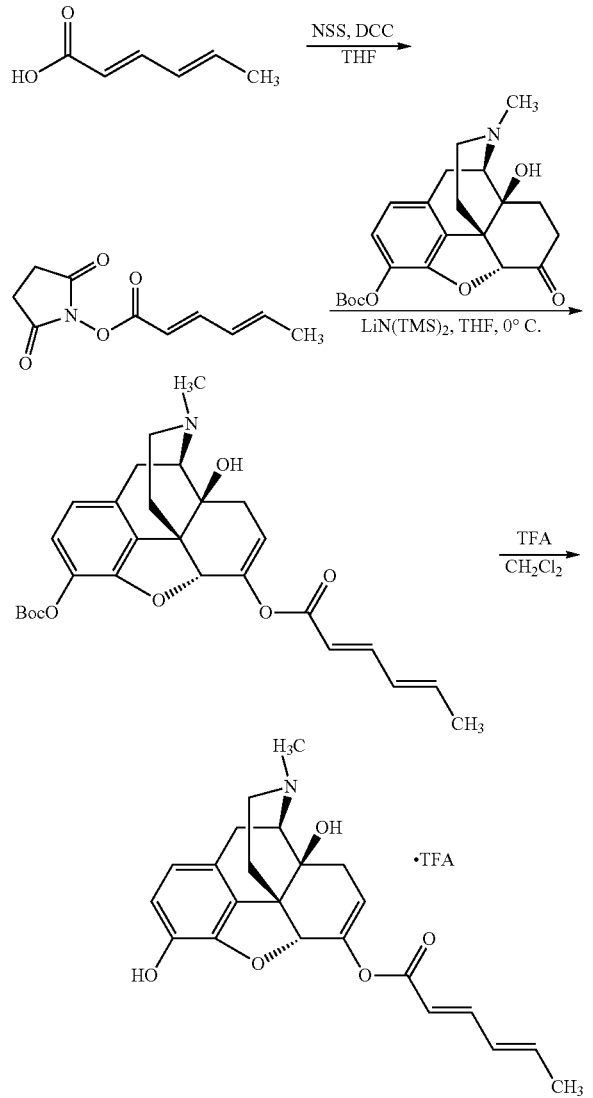

Scheme 101: (2E,4E)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl hexa-2,4-dienoate trifluoroacetic acid salt Preparation of (2E,4E)-2,5-Dioxopyrrolidin-1-yl hexa-2,4-dienoate

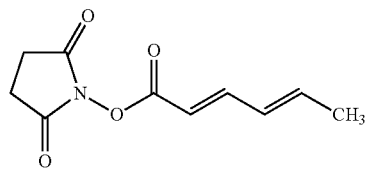

A solution of (2E,4E)-hexa-2,4-dienoic acid (2.00 g, 17.8 mmol) in tetrahydrofuran (50 mL) was treated with N-hydroxysuccinimide (2.26 g, 19.6 mmol) and N,N'-dicyclohexylcarbodiimide (4.04 g, 19.6 mmol) and stirred under a nitrogen atmosphere for 2.5 h. After this time, the reaction mixture was filtered to remove the solid dicyclohexylurea byproduct. The solid was washed with diethyl ether, and the combined filtrate and washings were concentrated under reduced pressure to provide (2E,4E)-2,5-dioxopyrrolidin-1-yl hexa-2,4-dienoate (5.14 g, quantitative) as a white solid: $^1$H NMR (300 MHz, CDCl$_3$) δ 7.53-5.44 (m, 1H), 6.31-6.27 (m, 2H), 5.93 (d, J=15.3 Hz, 1H), 2.85 (s, 4H), 1.91 (d, J=5.4 Hz, 3H).

Preparation of (2E,4E)-(4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl hexa-2,4-dienoate

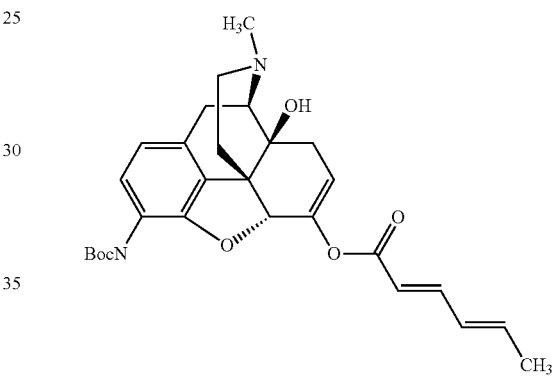

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.50 mL, 1.50 mmol). After 30 min, the mixture was treated dropwise with a solution of (2E,4E)-2,5-dioxopyrrolidin-1-yl hexa-2,4-dienoate (313 mg, 1.50 mmol) in tetrahydrofuran (5 mL) and stirred at 0° C. for 1 h. After this time, the reaction mixture was poured into cold saturated aqueous ammonium chloride (10 mL) and extracted with ethyl acetate (2×25 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (2E,4E)-(4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl hexa-2,4-dienoate (93 mg, 15%) as a white solid: ESI LC/MS m/z 496 $[C_{28}H_3NO_7+H]^+$.

Preparation of (2E,4E)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl hexa-2,4-dienoate trifluoroacetic acid salt

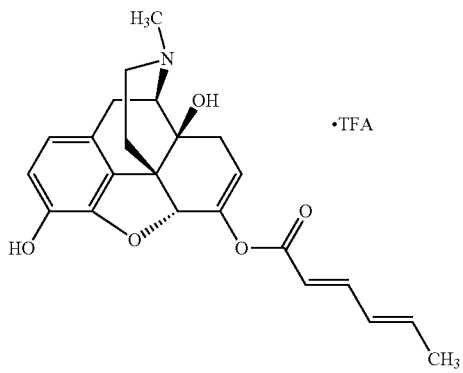 [SMILES: C/C=C/C=C/C(=O)OC1=CC[C@@]2(O)[C@H]3Cc4ccc(O)c5c4[C@@]2(CCN3C)[C@H]1O5]

A solution of (2E,4E)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl hexa-2,4-dienoate (90 mg, 0.18 mmol) in methylene chloride (0.25 mL) was treated with trifluoroacetic acid (0.25 mL) and stirred under a nitrogen atmosphere at ambient temperature for 1 h. After this time, the reaction mixture was concentrated under reduced pressure. The residue was purified by reversed phase column chromatography (15 g C18 column, 10-100% acetonitrile/water) and freeze dried to provide (2E,4E)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl hexa-2,4-dienoate trifluoroacetic acid salt (51 mg, 55%) as an off-white solid: $^1$H NMR (300 MHz, DMSO-$d_6$) δ 9.32 (s, 1H), 9.15 (br s, 1H), 7.37-7.28 (m, 1H), 6.67 (d, J=8.1 Hz, 1H), 6.62 (d, J=8.1 Hz, 1H), 6.38-6.35 (m, 2H), 6.24 (s, 1H), 5.98 (d, J=15.0 Hz, 1H), 5.59-5.57 (m, 1H), 5.03 (s, 1H), 3.63-3.61 (m, 1H), 3.41-3.33 (m, 1H), 3.09-3.05 (m, 2H), 2.84 (d, J=4.5 Hz, 3H), 2.67-2.60 (m, 1H), 2.49-2.41 (m, 1H), 2.31-2.23 (m, 1H), 2.11-2.05 (m, 1H), 1.85 (d, J=4.5 Hz, 3H), 1.65-1.60 (m, 1H); ESI MS m/z 396 [$C_{23}H_{25}NO_5$+H]$^+$.

Scheme 102: (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-(((S)-2-hydroxypropanoyl)oxy)propanoate trifluoroacetic acid salt

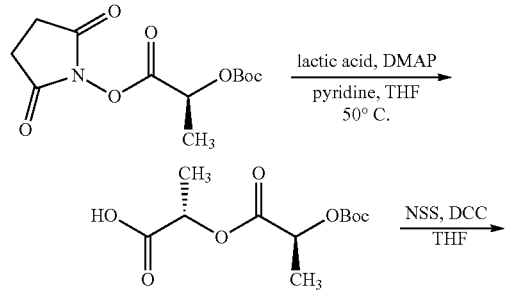

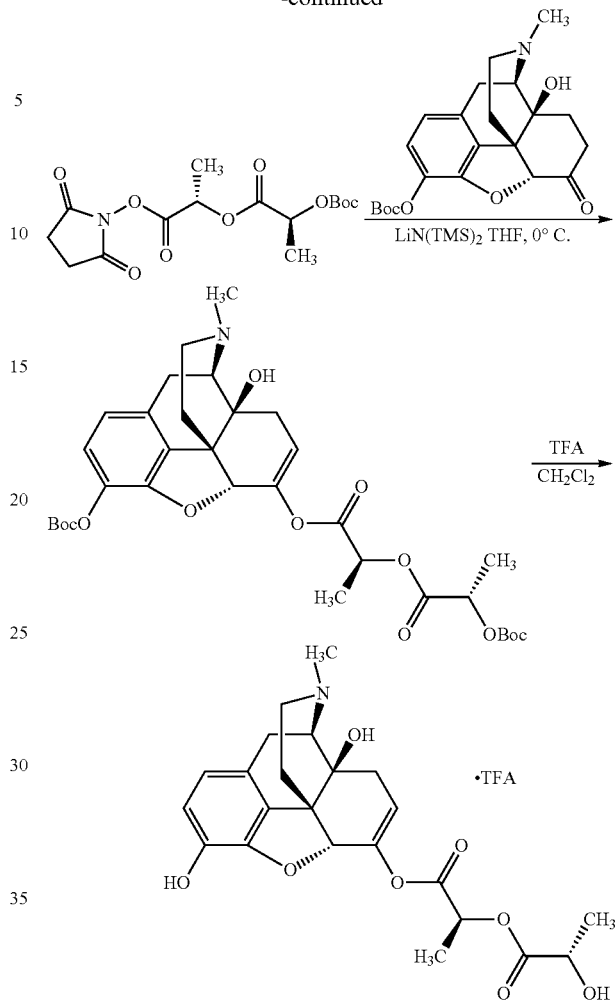

Preparation (S)-2-(((S)-2-((tert-Butoxycarbonyl)oxy)propanoyl)oxy)propanoic acid

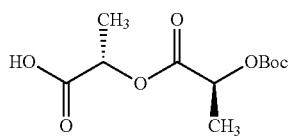

A solution of (S)-2,5-dioxopyrrolidin-1-yl 2-((tert-butoxycarbonyl)oxy)propanoate (1.00 g, 3.48 mmol), lactic acid (376 mg, 4.17 mmol), and 4-dimethylaminopyridine (53 mg, 0.43 mmol) in tetrahydrofuran (17 mL) was treated with pyridine (0.33 g, 4.2 mmol) and heated at 50° C. under a nitrogen atmosphere for 48 h. After this time, the reaction mixture was cooled to room temperature and concentrated under reduced pressure. The residue was dissolved in ethyl acetate (50 mL) and washed with aqueous 10% citric acid (2×25 mL) and water (25 mL). The organic layer was extracted with saturated aqueous sodium bicarbonate (2×25 mL). The combined aqueous bicarbonate layers were acidified to pH ~2 with 6 N hydrochloric acid and extracted with ethyl acetate (4×25 mL). The combined organics were dried over sodium sulfate, filtered, and concentrated under reduced pressure to provide (S)-2-(((S)-2-((tert-butoxycarbonyl)oxy)propanoyl)oxy)propanoic acid (659 mg, 72%) as a colorless oil: $^1$H NMR (300 MHz, CDCl$_3$) δ 5.27-5.17 (m, 1H), 4.98 (q, J=7.2 Hz, 1H), 1.60-1.55 (m, 6H), 1.50 (s, 9H), CO$_2$H proton not observed; ESI MS m/z 261 [C$_{11}$H$_{18}$O$_7$–H]$^-$.

Preparation of (S)-2,5-Dioxopyrrolidin-1-yl 2-(((S)-2-((tert-butoxycarbonyl)oxy)propanoyl)oxy)propanoate

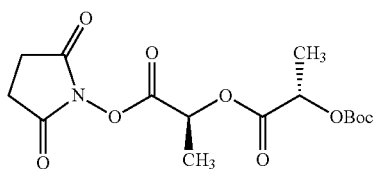

A solution of (S)-2-(((S)-2-((tert-butoxycarbonyl)oxy)propanoyl)oxy)propanoic acid (659 mg, 2.51 mmol) in tetrahydrofuran (10 mL) was treated with N-hydroxysuccinimide (323 mg, 2.81 mmol) and N,N'-dicyclohexylcarbodiimide (573 mg, 2.78 mmol) and stirred under a nitrogen atmosphere for 3 h. After this time, the reaction mixture was filtered to remove the solid dicyclohexylurea byproduct. The solid was washed with diethyl ether, and the combined filtrate and washings were concentrated under reduced pressure to provide (S)-2,5-dioxopyrrolidin-1-yl 2-(((S)-2-((tert-butoxycarbonyl)oxy)propanoyl)oxy)propanoate (813 g, 90%) as an off-white solid: $^1$H NMR (300 MHz, CDCl$_3$) δ 5.54 (q, J=6.9 Hz, 1H), 4.99 (q, J=7.2 Hz, 1H), 2.84 (s, 4H), 1.72 (d, J=7.2 Hz, 3H), 1.56 (d, J=6.9 Hz, 3H), 1.48 (s, 9H).

Preparation of (S)-(4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 2-(((S)-2-((tert-butoxycarbonyl)oxy)propanoyl)oxy)propanoate

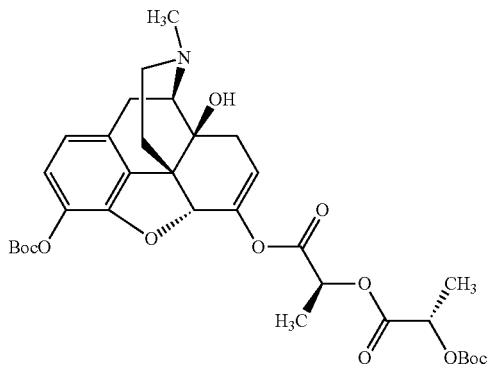

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (1.50 g, 3.79 mmol) in tetrahydrofuran (30 mL) was cooled in an ice bath and treated dropwise with a 1.0 M solution of lithium bis(trimethylsilyl)amide in tetrahydrofuran (7.60 mL, 7.60 mmol). After 30 min, the mixture was treated dropwise with a solution of 2(S)-2,5-dioxopyrrolidin-1-yl 2-(((S)-2-((tert-butoxycarbonyl)oxy)propanoyl)oxy)propanoate (1.50 g, 4.17 mmol) in tetrahydrofuran (15 mL) and stirred at 0° C. for 25 min. After this time, the reaction mixture was poured into cold saturated aqueous ammonium chloride (10 mL) and extracted with ethyl acetate (2×25 mL). The combined organics were dried over sodium sulfate, filtered, and concentrated under reduced pressure. The crude residue was purified by reversed phase column chromatography (50 g C18 column, 10-100% acetonitrile/water) and freeze dried to provide (S)-(4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 2-(((S)-2-((tert-butoxycarbonyl)oxy)propanoyl)oxy)propanoate (55 mg, 2%) as a white solid: ESI LC/MS m/z 646 [C$_{33}$H$_{43}$NO$_{12}$+H]$^+$.

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-(((S)-2-hydroxypropanoyl)oxy)propanoate trifluoroacetic acid salt

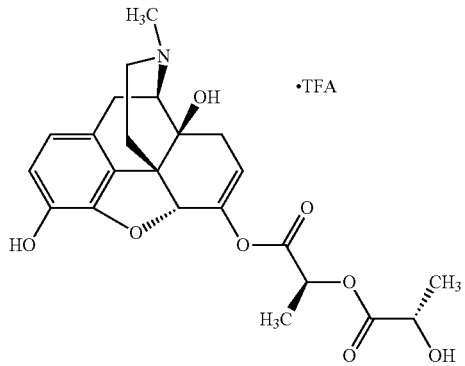 [SMILES: C[C@H](O)C(=O)O[C@@H](C)C(=O)OC1=CC[C@@]2(O)[C@H]3Cc4ccc(O)c5c4[C@@]2(CCN3C)[C@H]1O5]

A solution of (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-(((S)-2-((tert-butoxycarbonyl)oxy)propanoyl)oxy)propanoate (55 mg, 0.085 mmol) in methylene chloride (0.25 mL) was treated with trifluoroacetic acid (0.25 mL) and stirred under a nitrogen atmosphere at ambient temperature for 30 min. After this time, the reaction mixture was concentrated under reduced pressure. The residue was purified by reversed phase column chromatography (15.5 g C18 column, 10-100% acetonitrile/water) and freeze dried to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-(((S)-2-hydroxypropanoyl)oxy)propanoate trifluoroacetic acid salt (47 mg, 99%) as an off-white solid: $^1$H NMR (300 MHz, DMSO-d$_6$) δ 9.29 (s, 1H), 9.15 (br s, 1H), 6.68 (d, J=8.4 Hz, 1H), 6.62 (d, J=8.1 Hz, 1H), 6.25 (br s, 1H), 5.59-5.55 (m, 1H), 5.50 (d, J=5.7 Hz, 1H), 5.15 (q, J=6.9 Hz, 1H), 4.96 (s, 1H), 4.29-4.20 (m, 1H), 3.62 (br s, 1H), 3.41-3.33 (m, 1H), 3.10-3.03 (m, 2H), 2.83 (s, 3H), 2.68-2.56 (m, 1H), 2.46-2.41 (m, 1H), 2.33-2.25 (m, 1H), 2.09-2.03 (m, 1H), 1.64-1.60 (m, 1H), 1.53 (d, J=6.9 Hz, 3H), 1.32 (d, J=6.6 Hz, 3H); ESI MS m/z 446 [C$_{23}$H$_{27}$NO$_8$+H]$^+$.

Scheme 103: (S)-(4R,4aS,7aR,12bS)-4a,9-Dihydroxy-3-methyl-2,3,4,4a,5,7a-hexahydro-1H-4, 12-methanobenzofuro[3,2-e]isoquinolin-7-yl 2-(3-aminopropanamido)-3-(1H-imidazol-4-yl)propanoate trifluoroacetic acid salt

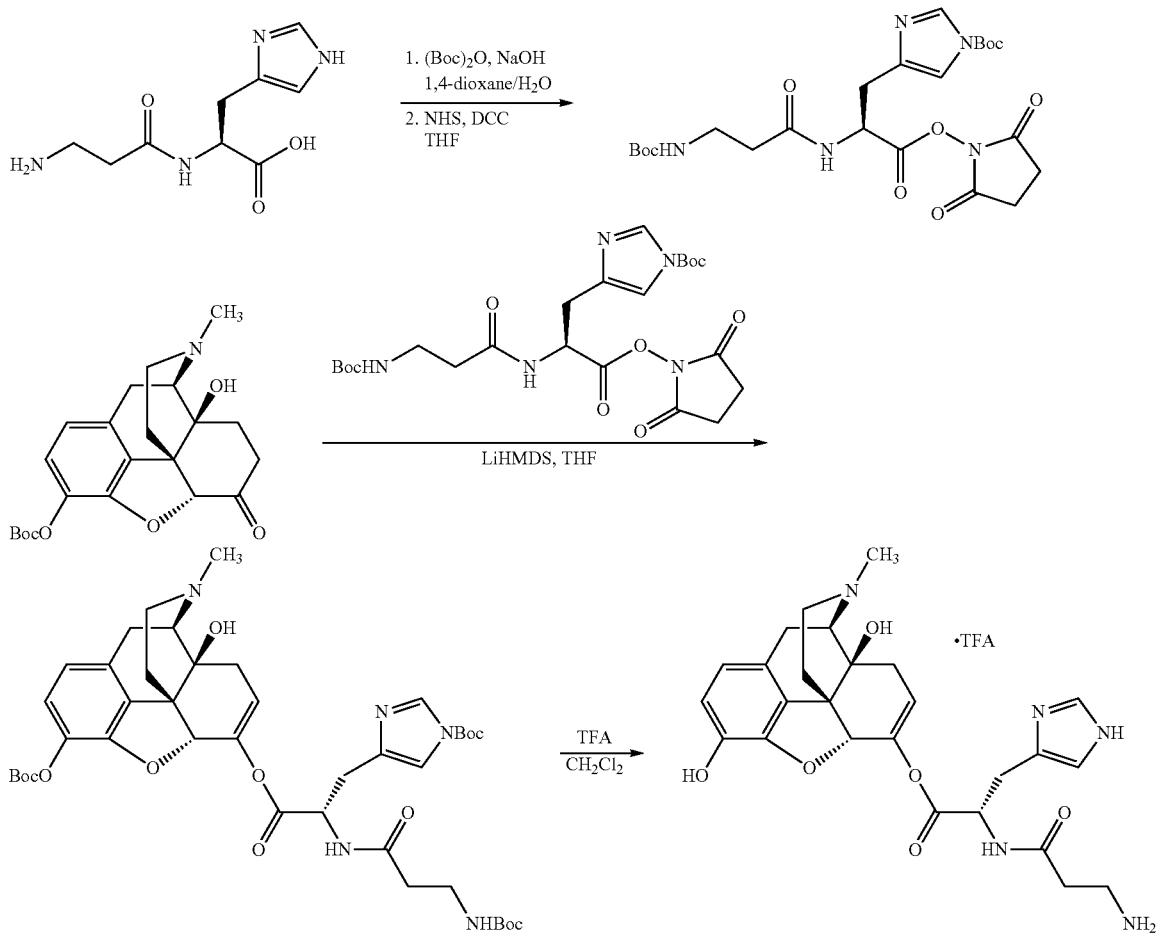

Preparation of (S)-3-(1-(tert-Butoxycarboyl)-1H-imidazol-4-yl)-2-(3-((tert-butoxycarbonyl)amino)propanamido)propanoic acid

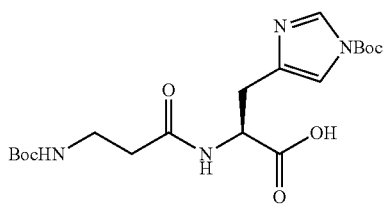 [SMILES: CC(C)(C)OC(=O)NCCC(=O)N[C@@H](Cc1cn(C(=O)OC(C)(C)C)cn1)C(=O)O]

A suspension of (S)-2-(3-aminopropanamido)-3-(1H-imidazol-4-yl)propanoic acid (3.00 g, 13.3 mmol) in a mixture of 1,4-dioxane/water (13.5 mL, 2:1) was stirred at ambient temperature until a clear solution was obtained (~10 minutes). The mixture was treated dropwise with a solution of 1 M aqueous NaOH (4.40 mL, 4.42 mmol). The reaction mixture was cooled to 0° C. and treated with di-tert-butyl dicarbonate (2.12 g, 9.72 mmol). The ice bath was removed and stirring continued at ambient temperature for 2 h. After this time, the volatiles were removed under reduced pressure. The residue was diluted with water (40 mL) and ethyl acetate (60 mL), acidified to pH ~3 with 1.0 M potassium bisulfate and extracted with ethyl acetate (3×100 mL). The combined organics were dried over sodium sulfate, filtered, and concentrated under reduced pressure to provide (S)-3-(1-(tert-butoxycarboyl)-1H-imidazol-4-yl)-2-(3-((tert-butoxycarbonyl)amino)propanamido)propanoic acid (1.70 g, 90%) as a white solid: $^1$H NMR (300 MHz, CDCl$_3$) δ 8.15 (s, 1H), 7.21 (s, 1H), 6.69-6.67 (br s, 1H), 5.28 (s, 1H), 4.72-4.66 (m, 1H), 3.46-3.40 (m, 2H), 3.26 (dd, J=11.7, 5.7 Hz, 1H), 3.13 (dd, J=15.0, 6.3 Hz, 1H), 2.46 (t, J=26.3 Hz, 2H), 1.61 (s, 9H), 1.44 (s, 9H), CO$_2$H proton not observed.

Preparation of (S)-tert-Butyl 4-(2-(3-((tert-butoxycarbonyl)amino)propanamido)-3-((2,5-dioxopyrrolidin-1-yl)oxy)-3-oxopropyl)-1H-imidazole-1-carboxylate

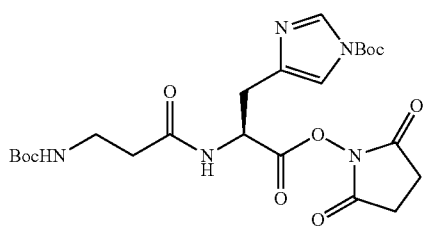 [SMILES: CC(C)(C)OC(=O)NCCC(=O)N[C@@H](Cc1cn(C(=O)OC(C)(C)C)cn1)C(=O)ON1C(=O)CCC1=O]

A solution of (S)-3-(1-(tert-butoxycarboyl)-1H-imidazol-4-yl)-2-(3-((tert-butoxycarbonyl)amino)propanamido)propanoic acid (4.90 g, 11.5 mmol) in tetrahydrofuran (60 mL) was treated with N-hydroxysuccinimide (1.70 g, 14.9 mmol) and N,N'-dicyclohexylcarbodiimide (3.08 g, 14.9 mmol) and stirred under a nitrogen atmosphere for 3 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-tert-butyl 4-(2-(3-((tert-butoxycarbonyl)amino)propanamido)-3-((2,5-dioxopyrrolidin-1-yl)oxy)-3-oxopropyl)-1H-imidazole-1-carboxylate (7.20 g, quantitative) as a white foam: $^1$H NMR (300 MHz, CDCl$_3$) δ 8.02 (s, 1H), 7.41 (s, 1H), 5.72 (br s, 1H), 5.17-5.11 (m, 1H), 3.51-3.3.41 (m, 2H), 3.21 (d, J=4.8 Hz, 2H), 2.82 (m, 5H), 2.49-2.44 (m, 2H), 1.61 (s, 9H), 1.42 (s, 9H).

Preparation of tert-Butyl 4-((S)-2-(3-((tert-butoxycarbonyl)amino)propanamido)-3-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-3-oxopropyl)-1H-imidazole-1-carboxylate

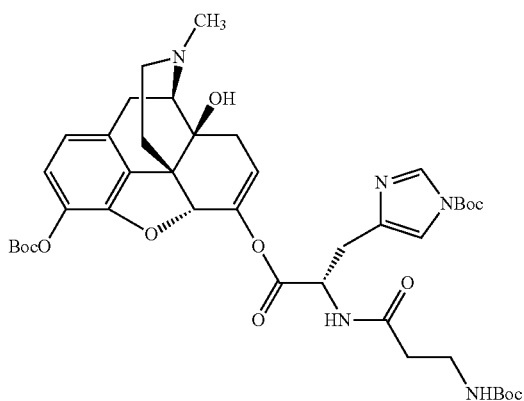

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (0.400 g, 0.996 mmol) in tetrahydrofuran (8 mL) was cooled in an ice bath and treated dropwise with a 1.0 M solution of lithium bis(trimethylsilyl)amide in tetrahydrofuran (2.0 mL, 2.0 mmol). The mixture was stirred at 0° C. for 20 min and then treated dropwise with a solution of (S)-tert-butyl 4-(2-(3-((tert-butoxycarbonyl)amino)propanamido)-3-((2,5-dioxopyrrolidin-1-yl)oxy)-3-oxopropyl)-1H-imidazole-1-carboxylate (1.04 g, 1.99 mmol) in tetrahydrofuran (8 mL). The reaction mixture was stirred at 0° C. for 1.5 h. After this time, the mixture was poured into saturated aqueous ammonium chloride (75 mL) and extracted with ethyl acetate (2×100 mL). The combined organics were dried over sodium sulfate, filtered, and concentrated under reduced pressure. The crude residue was purified by reversed phase chromatography (150 g C18 column, 10-75% acetonitrile/water) followed by regular phase chromatography (silica, 0-4% methanol/methylene chloride) to provide tert-butyl 4-((S)-2-(3-((tert-butoxycarbonyl)amino)propanamido)-3-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-3-oxopropyl)-1H-imidazole-1-carboxylate (0.025 g, 3%) as a white solid. This material was used without further purification.

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-(3-aminopropanamido)-3-(1H-imidazol-4-yl)propanoate trifluoroacetic acid salt

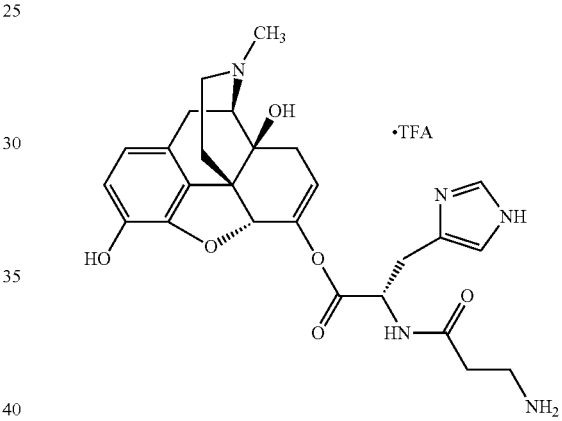

A solution of tert-butyl 4-((S)-2-(3-((tert-butoxycarbonyl)amino)propanamido)-3-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-3-oxopropyl)-1H-imidazole-1-carboxylate (0.025 g, 0.03 mmol) in methylene chloride (3 mL) was treated with trifluoroacetic acid (1.5 mL) and stirred under a nitrogen atmosphere at ambient temperature for 1 h. After this time, the reaction mixture was concentrated under reduced pressure. The residue was triturated with diethyl ether then freeze dried from water to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-(3-aminopropanamido)-3-(1H-imidazol-4-yl)propanoate trifluoroacetic acid salt (0.026 g, quantitative) as an off-white solid: $^1$H NMR (300 MHz, DMSO-d$_6$) δ 9.40 (br s, 1H), 9.18 (br s, 1H), 8.94 (br s, 1H), 8.82 (d, J=7.2 Hz, 1H), 7.73 (br s, 3H), 7.47 (s, 1H), 6.70 (d, J=8.1 Hz, 1H), 6.63 (d, J=8.1 Hz, 1H), 6.27 (s, 1H), 5.53-5.51 (m, 1H), 4.91 (s, 1H), 4.69 (q, J=7.2 Hz, 1H), 3.63 (d, J=4.8 Hz, 1H), 3.39 (d, J=19.8 Hz, 1H), 3.28-2.93 (m, 7H), 2.85 (s, 3H), 2.74-2.55 (m, 1H), 2.29 (dd, J=17.7, 6.0 Hz, 1H), 2.04 (d, J=18.0 Hz, 1H), three protons not observed; ESI MS m/z 510 [$C_{26}H_{31}N_5O_6$+H]$^+$.

Scheme 104: (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((S)-2-hydroxy-2-phenylacetamido)propanoate trifluoroacetic acid salt

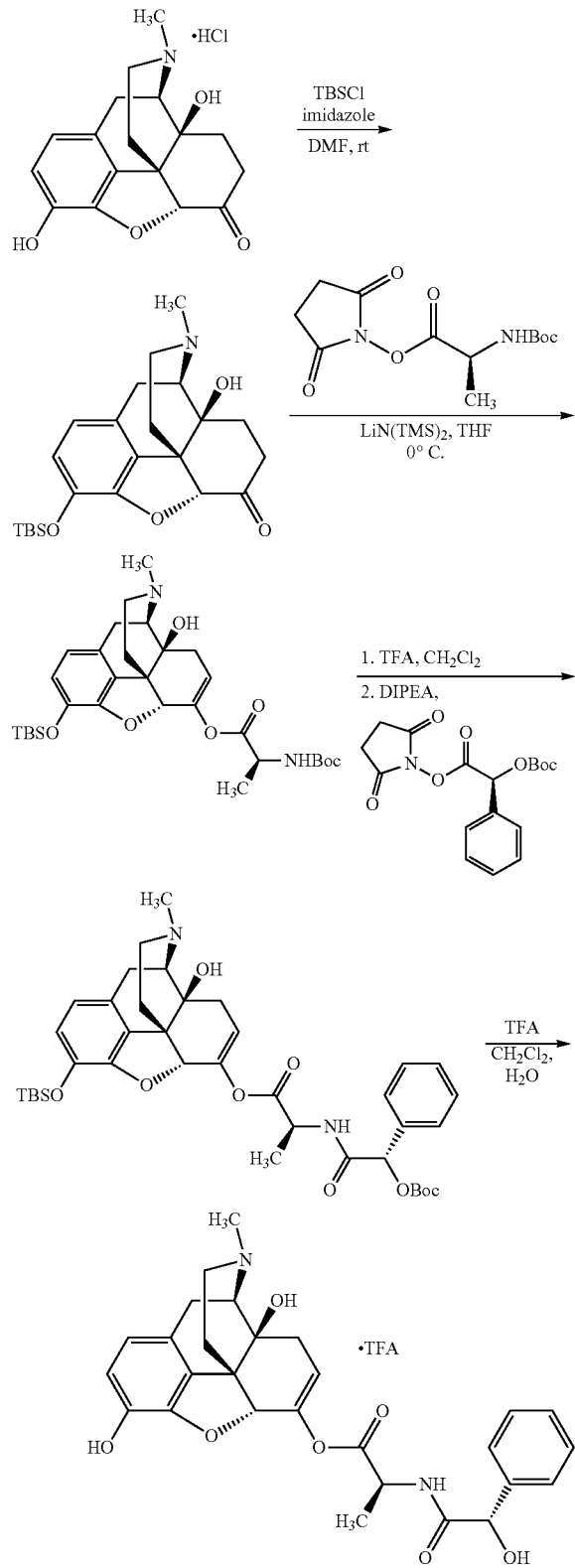

Preparation (4R,4aS,7aR,12bS)-9-((tert-Butyldimethylsilyl)oxy)-4a-hydroxy-3-methyl-2,3,4,4a,5,6-hexahydro-1H-4,12-methanobenzofuro[3,2-e]isoquinolin-7(7aH)-one

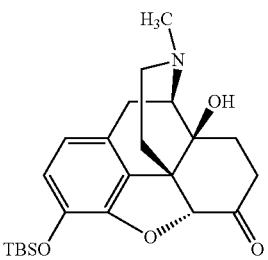 [SMILES: CN1CC[C@]23c4c5ccc(O[Si](C)(C)C(C)(C)C)c4O[C@H]2C(=O)CC[C@@]3(O)[C@H]1C5]

A solution of oxymorphone hydrochloride (10.0 g, 29.6 mmol) in N,N-dimethylformamide (15 mL) was treated with imidazole (11.0 g, 163 mmol) and tert-butyldimethylsilyl chloride (11.0 g, 74.0 mmol) at room temperature. After 30 min, the mixture was partitioned between diethyl ether and water. The organic phase was separated and the aqueous phase was extracted with diethyl ether. The combined organics were dried over sodium sulfate, filtered, and concentrated under reduced pressure. The crude residue was purified by recrystallization in ethanol to provide (4R,4aS,7aR,12bS)-9-((tert-butyldimethylsilyl)oxy)-4a-hydroxy-3-methyl-2,3,4,4a,5,6-hexahydro-1H-4,12-methanobenzofuro[3,2-e]isoquinolin-7(7aH)-one (9.81 g, 79%) as a white solid: ESI MS m/z 416 $[C_{23}H_{33}NO_4Si+H]^+$.

Preparation (S)-(4R,4aS,7aR,12bS)-9-((tert-Butyldimethylsilyl)oxy)-4a-hydroxy-3-methyl-2,3,4,4a,5,7a-hexahydro-1H-4,12-methanobenzofuro[3,2-e]isoquinolin-7-yl 2-((tert-butoxycarbonyl)amino)propanoate

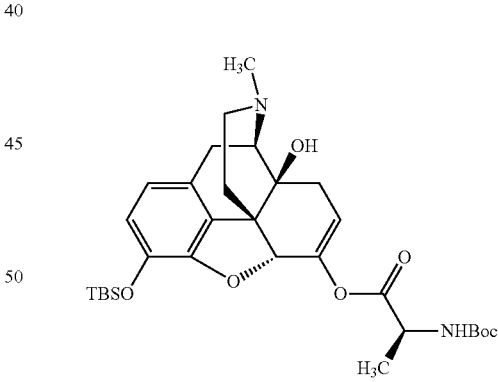

A solution of (4R,4aS,7aR,12bS)-9-((tert-butyldimethylsilyl)oxy)-4a-hydroxy-3-methyl-2,3,4,4a,5,6-hexahydro-1H-4,12-methanobenzofuro[3,2-e]isoquinolin-7(7aH)-one (5.09 g, 12.2 mmol) in tetrahydrofuran (60 mL) was cooled in an ice bath and treated dropwise with a 1.0 M solution of lithium bis(trimethylsilyl)amide in tetrahydrofuran (24.5 mL, 24.5 mmol). After 30 min, the mixture was treated dropwise with a solution of (S)-2,5-dioxopyrrolidin-1-yl 2-((tert-butoxycarbonyl)amino)propanoate (7.00 g, 24.5 mmol) in tetrahydrofuran (25 mL) and stirred at 0° C. for 16 h. After this time, the reaction mixture was poured into cold saturated aqueous ammonium chloride and extracted with ethyl acetate. The combined organics were dried over sodium sulfate, filtered, and concentrated under reduced pressure. The crude residue was purified by reversed phase column chromatography (50 g C18 column, 0-100% acetonitrile/water) and freeze dried to provide (S)-(4R,4aS,7aR,12bS)-9-((tert-Butyldimethylsilyl)oxy)-4a-hydroxy-3-methyl-2,3,4,4a,5,7a-hexahydro-1H-4,12-methanobenzofuro[3,2-e]isoquinolin-7-yl 2-((tert-butoxycarbonyl)amino)propanoate (3.52 g, 49%) as a white solid: $^1$H NMR (300 MHz, CDCl$_3$) δ 6.65 (d, J=8.1 Hz, 1H), 6.56 (d, J=7.8 Hz, 1H), 5.64 (dd, J=5.7, 2.4 Hz, 1H), 5.08 (m, 1H), 4.98 (s, 1H), 4.43 (m, 1H), 3.49 (m, 1H), 3.17 (d, J=19.2 Hz, 1H), 2.73-2.10 (m, 9H), 1.67-1.58 (m, 2H), 1.48 (d, J=7.2 Hz, 3H), 1.45 (s, 9H), 0.97 (s, 9H), 0.16 (s, 3H), 0.14 (s, 3H).

Preparation of (S)-(4R,4aS,7aR,12bS)-9-((tert-Butyldimethylsilyl)oxy)-4a-hydroxy-3-methyl-2,3,4,4a,5,7a-hexahydro-1H-4,12-methanobenzofuro[3,2-e]isoquinolin-7-yl 2-((S)-2-((tert-butoxycarbonyl)oxy)-2-phenylacetamido)propanoate

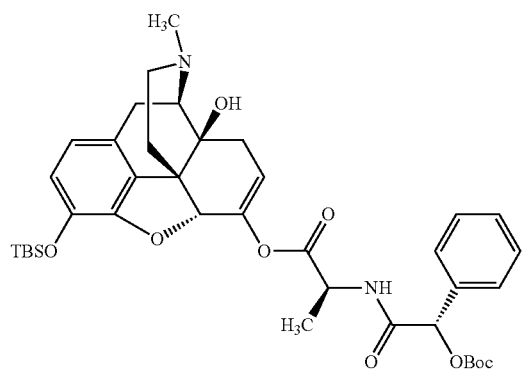

A solution of (S)-(4R,4aS,7aR,12bS)-9-((tert-Butyldimethylsilyl)oxy)-4a-hydroxy-3-methyl-2,3,4,4a,5,7a-hexahydro-1H-4,12-methanobenzofuro[3,2-e]isoquinolin-7-yl 2-((tert-butoxycarbonyl)amino)propanoate (300 mg, 0.511 mmol) in methylene chloride (2 mL) was treated with trifluoroacetic acid (0.5 mL) and stirred under a nitrogen atmosphere at ambient temperature for 1 h. The reaction mixture was then basified to pH 8-9 with N,N-diisopropylethylamine and treated with a solution of (S)-2,5-dioxopyrrolidin-1-yl 2-((tert-butoxycarbonyl)oxy)-2-phenylacetate (268 mg, 0.767 mmol) in methylene chloride (1 mL). After stirring at room temperature for 2 h, the reaction mixture was washed with 10% aqueous citric acid and saturated sodium bicarbonate. The organic phase were separated, dried over sodium sulfate, filtered, and concentrated under reduced pressure. The crude residue was purified by chromatography to provide (S)-(4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 2-((S)-2-((tert-butoxycarbonyl)oxy)-2-phenylacetamido)propanoate (100 mg, 27%) as a white solid: $^1$H NMR (300 MHz, CDCl$_3$) δ 7.48-7.43 (m, 2H), 7.40-7.34 (m, 3H), 6.64 (d, J=8.1 Hz, 1H), 6.55 (d, J=8.1 Hz, 1H), 5.89 (s, 1H), 5.64 (m, 1H), 4.96 (s, 1H), 4.72 (m, 1H), 3.19-3.13 (m, 1H), 2.85 (d, J=6.3 Hz, 1H), 2.65-2.57 (m, 1H), 2.46-2.15 (m, 8H), 1.60-1.47 (m, 13H), 0.96 (s, 9H), 0.13 (s, 3H), 0.10 (s, 3H), NH and OH protons not observed.

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((S)-2-hydroxy-2-phenylacetamido)propanoate trifluoroacetic acid salt

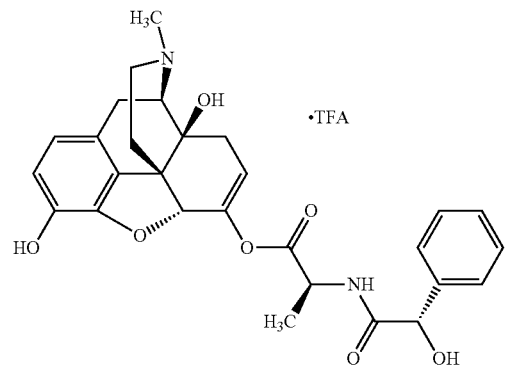 [SMILES: C[C@H](NC(=O)[C@@H](O)c1ccccc1)C(=O)OC1=CC[C@@]2(O)[C@H]3Cc4ccc(O)c5c4[C@@]2(CCN3C)[C@H]1O5]

A solution of (S)-(4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 2-((S)-2-((tert-butoxycarbonyl)oxy)-2-phenylacetamido)propanoate (100 mg, 0.139 mmol) in methylene chloride (400 μL) was treated with trifluoroacetic acid (400 μL) and stirred under a nitrogen atmosphere at ambient temperature for 10 min. Water (400 μL) was added, and the mixture was stirred for 21 h. After this time, the reaction mixture was directly purified by reversed phase column chromatography (50 g C18 column, 10-100% acetonitrile/water) and freeze dried to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((S)-2-hydroxy-2-phenylacetamido)propanoate trifluoroacetic acid salt (18 mg, 21%) as an off-white solid: $^1$H NMR (300 MHz, DMSO-d$_6$) δ 9.29 (s, 1H), 9.17 (br s, 1H), 8.43 (d, J=7.2 Hz, 1H), 7.47-7.10 (m, 5H), 6.65 (q, J=8.1 Hz, 2H), 6.27-6.23 (m, 2H), 5.48 (dd, J=6.0, 2.1 Hz, 1H), 4.95 (d, J=4.5 Hz, 1H), 4.91 (s, 1H), 4.36 (m, 1H), 3.59 (m, 1H), 3.09-3.00 (m, 2H), 2.82 (s, 3H), 2.72-2.38 (m, 3H), 2.28-2.20 (m, 1H), 2.06-2.00 (m, 1H), 1.63-1.60 (m, 1H), 1.41 (d, J=7.2 Hz, 3H); ESI MS m/z 507 [C$_{28}$H$_{30}$N$_2$O$_7$+H]$^+$.

Scheme 105: (4R,4aS,7aR,12bS)-4a,9-Dihydroxy-3-methyl-2,3,4,4a,5,7a-hexahydro-1H-4,12-methanobenzofuro[3,2-e]isoquinolin-7-yl 3-((S)-2-hydroxy-2-phenylacetamido)propanoate trifluoroacetic acid salt

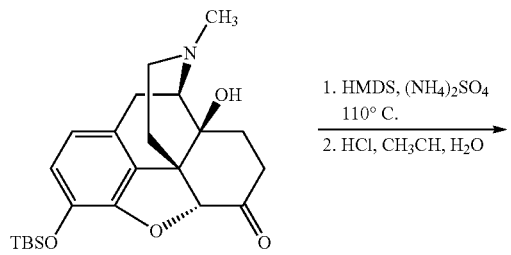

-continued

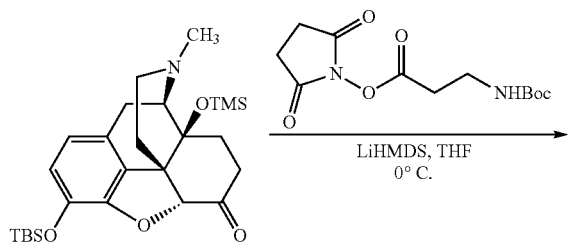

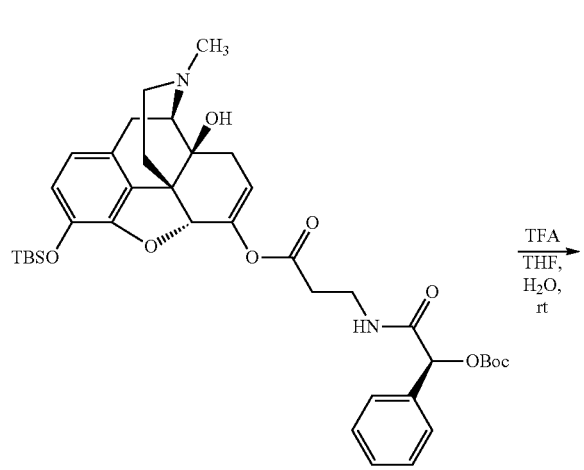

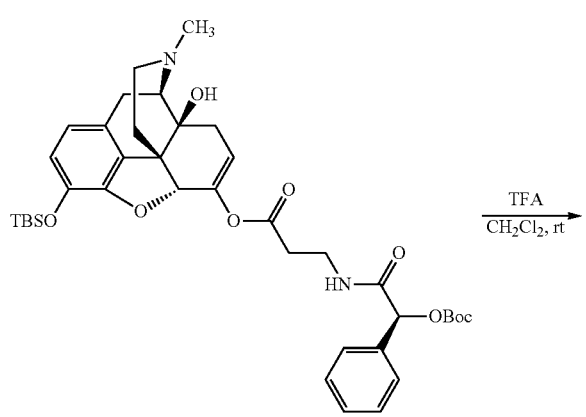

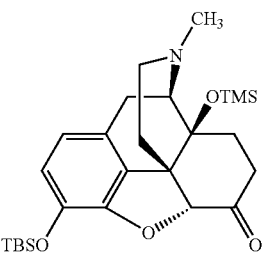

-continued

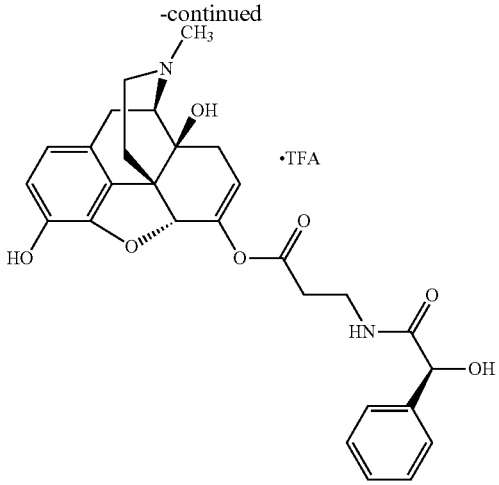

Preparation of (4R,4aS,7aR,12bS)-9-((tert-Butyldimethylsilyl)oxy)-3-methyl-4a-((trimethylsilyl)oxy)-2,3,4,4a,5,6-hexahydro-1H-4, 12-methanobenzofuro[3,2-e]isoquinolin-7(7aH)-one A suspension of (4R,4aS,7aR,12bS)-9-((tert-butyldimethylsilyl)oxy)-4a-hydroxy-3-methyl-2,3,4,4a,5,6-hexahydro-1H-4,12-methanobenzofuro[3,2-e]isoquinolin-7(7aH)-one (1.20 g, 2.89 mmol) and ammonium sulfate (8 mg, 0.06 mmol) in bis(trimethylsilyl)amine (4 mL) was heated to 110° C. to obtain a clear solution that was stirred for 6 h. After this time, the mixture was cooled to room temperature and concentrated under reduced pressure. The residue was suspended in 1:1 acetonitrile/water (10 mL) and acidified by dropwise addition of 2 N hydrochloric acid to obtain a clear solution that was stirred at room temperature for 10 min. The mixture was diluted with ethyl acetate and washed with a saturated solution of sodium bicarbonate and brine. The organic layer was dried over sodium sulfate, filtered, and concentrated under reduced pressure to provide (4R,4aS,7aR,12bS)-9-((tert-butyldimethylsilyl)oxy)-3-methyl-4a-((trimethylsilyl)oxy)-2,3,4,4a,5,6-hexahydro-1H-4,12-methanobenzofuro[3,2-e]isoquinolin-7(7aH)-one (1.23 g, 87%): $^1$H NMR (300 MHz, CDCl$_3$) δ 6.61 (d, J=8.1 Hz, 1H), 6.52 (d, J=8.1 Hz, 1H), 4.50 (s, 1H), 3.17 (d, J 18.4 Hz, 1H), 3.02-2.89 (m, 2H), 2.46-2.35 (m, 3H), 2.31 (s, 3H), 2.23-2.05 (m, 2H), 1.75-1.69 (m, 2H), 1.41-1.35 (m, 1H), 0.99 (s, 9H), 0.27 (s, 3H), 0.18 (s, 12H).

673

Preparation of (4R,4aS,7aR,12bS)-9-((tert-Butyldimethylsilyl)oxy)-4a-hydroxy-3-methyl-2,3,4,4a,5,7a-hexahydro-1H-4,12-methanobenzofuro[3,2-e]isoquinolin-7-yl 3-((tert-butoxycarbonyl)amino)propanoate

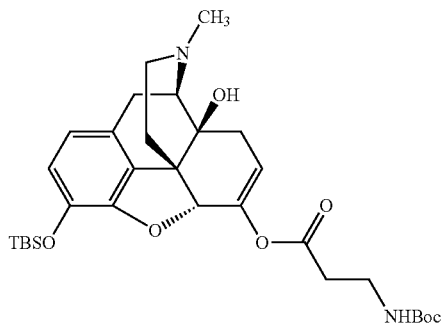 [SMILES: CN1CC[C@]23c4c5ccc(O[Si](C)(C)C(C)(C)C)c4O[C@H]2C(OC(=O)CCNC(=O)OC(C)(C)C)=CC[C@@]3(O)[C@H]1C5]

A suspension of (4R,4aS,7aR,12bS)-9-((tert-butyldimethylsilyl)oxy)-3-methyl-4a-((trimethylsilyl)oxy)-2,3,4,4a,5,6-hexahydro-1H-4,12-methanobenzofuro[3,2-e]isoquinolin-7 (7aH)-one (0.26 g, 0.53 mmol) in tetrahydrofuran (8 mL) was cooled in an ice bath and treated dropwise with a 1.0 M solution of lithium bis(trimethylsilyl)amidein tetrahydrofuran (0.7 mL, 0.7 mmol). After addition was complete, the mixture was stirred at ambient temperature for 10 min. The mixture was re-cooled in the ice bath and treated dropwise with a solution of 2,5-dioxopyrrolidin-1-yl 3-((tert-butoxycarbonyl)amino)propanoate (0.26 g, 0.91 mmol) in tetrahydrofuran (4 mL). After addition was complete, the mixture was stirred at ambient temperature for 45 min. After this time, the reaction mixture was cooled in an ice bath, treated with saturated aqueous ammonium chloride, and extracted with ethyl acetate. The combined organics were dried over sodium sulfate, filtered, and concentrated under reduced pressure. The residue was purified by column chromatography (silica gel, 0-10% methanol/methylene chloride) to provide (4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 3-((tert-butoxycarbonyl)amino)propanoate (0.20 g, 57%): $^1$H NMR (300 MHz, CDCl$_3$) δ 6.65 (d, J=8.1 Hz, 1H), 6.55 (d, J=8.1 Hz, 1H), 5.61 (dd, J=5.6, 2.8 Hz, 1H), 5.02 (s, 1H), 3.42-3.39 (m, 2H), 3.16 (d, J=18.7 Hz, 1H), 2.72-2.60 (m, 6H), 2.43 (s, 3H), 2.42-2.15 (m, 4H), 1.65-1.55 (m, 1H), 1.44 (s, 9H), 9.67 (s, 9H), 0.17 (s, 3H), 0.14 (s, 3H), NH proton not observed.

674

Preparation of (4R,4aS,7aR,12bS)-9-((tert-Butyldimethylsilyl)oxy)-4a-hydroxy-3-methyl-2,3,4,4a,5,7a-hexahydro-1H-4,12-methanobenzofuro[3,2-e]isoquinolin-7-yl 3-((S)-2-((tert-butoxycarbonyl)oxy)-2-phenylacetamido)propanoate

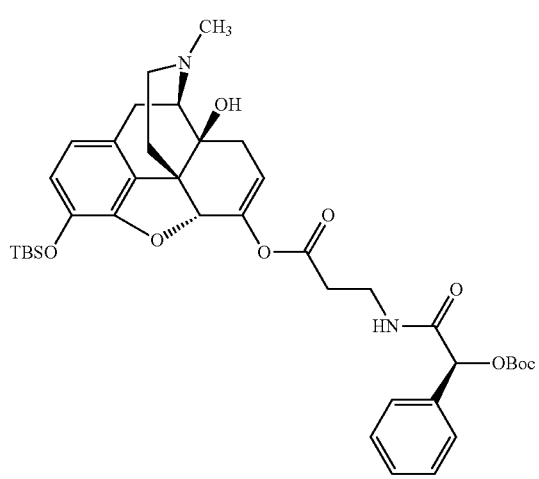

A solution of (4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 3-((tert-butoxycarbonyl)amino)propanoate (115 mg, 0.196 mmol) in methylene chloride (2.5 mL) was treated with trifluoroacetic acid (0.3 mL), and the mixture was stirred at room temperature for 10 min. After this time, LC-MS analysis of the reaction mixture showed cleavage of the Boc protecting group. N,N-Diisopropylethylamine was added slowly until the reaction mixture tested basic by pH paper analysis (0.4 mL of base added), followed by addition of (S)-2,5-dioxopyrrolidin-1-yl 2-((tert-butoxycarbonyl)oxy)-2-phenylacetate (80 mg, 0.23 mmol) in one portion. The reaction mixture was stirred at room temperature for 1.5 h, and then diluted with ethyl acetate; washed successively with 10% citric acid, saturated sodium bicarbonate, and brine; dried over sodium sulfate; filtered; and concentrated. The residue was purified by column chromatography (12 g silica, 0-10% methanol/methylene chloride) to provide (4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 3-((S)-2-((tert-butoxycarbonyl)oxy)-2-phenylacetamido)propanoate (50 mg, 35%): ESI MS m/z 721 [C$_{39}$H$_{52}$N$_2$O$_9$Si+H]$^+$.

Preparation of (4R,4aS,7aR,12bS)-4a,9-Dihydroxy-3-methyl-2,3,4,4a,5,7a-hexahydro-1H-4,12-methanobenzofuro[3,2-e]isoquinolin-7-yl 3-((S)-2-((tert-butoxycarbonyl)oxy)-2-phenylacetamido)propanoate

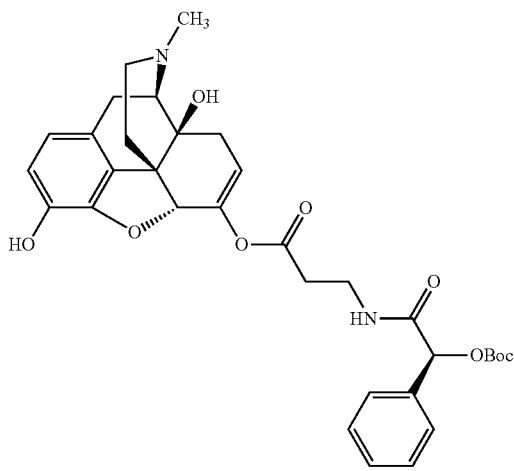

A solution of (4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 3-((S)-2-((tert-butoxycarbonyl)oxy)-2-phenylacetamido)propanoate (50 mg, 0.07 mmol) in tetrahydrofuran (2 mL) was treated with water (1 mL), followed by trifluoroacetic acid (1 mL), and the mixture was stirred at room temperature for 4 h. After this time, the mixture was concentrated, and the residue was azeotroped with toluene to provide (4R,4aS,7aR,12bS)-4a,9-dihydroxy-3-methyl-2,3,4,4a,5,7a-hexahydro-1H-4,12-methanobenzofuro[3,2-e]isoquinolin-7-yl 3-((S)-2-((tert-butoxycarbonyl)oxy)-2-phenylacetamido)propanoate (50 mg, crude) that was used without purification: ESI MS m/z 607 $[C_{33}H_{38}N_2O_9+H]^+$.

Preparation of (4R,4aS,7aR,12bS)-4a,9-Dihydroxy-3-methyl-2,3,4,4a,5,7a-hexahydro-1H-4,12-methanobenzofuro[3,2-e]isoquinolin-7-yl 3-((S)-2-hydroxy-2-phenylacetamido)propanoate trifluoroacetic acid salt

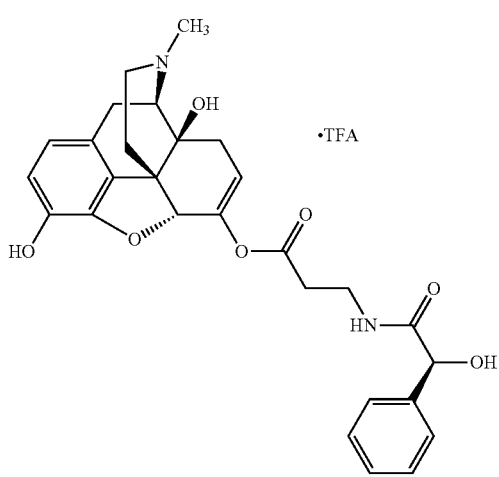 [SMILES: CN1CC[C@]23c4c5ccc(O)c4O[C@H]2C(OC(=O)CCNC(=O)[C@@H](O)c2ccccc2)=CC[C@@]3(O)[C@H]1C5]

A solution of (4R,4aS,7aR,12bS)-4a,9-dihydroxy-3-methyl-2,3,4,4a,5,7a-hexahydro-1H-4,12-methanobenzofuro[3,2-e]isoquinolin-7-yl 3-((S)-2-((tert-butoxycarbonyl)oxy)-2-phenylacetamido)propanoate (50 mg) in methylene chloride (1.5 mL) was treated with trifluoroacetic acid (1 mL) and stirred at ambient temperature for 1 h. After this time, the reaction mixture was concentrated under reduced pressure. The residue was purified by reversed phase column chromatography (15.5 g C18 column, 5-50% acetonitrile/water) and freeze dried to provide (4R,4aS,7aR,12bS)-4a,9-dihydroxy-3-methyl-2,3,4,4a,5,7a-hexahydro-1H-4,12-methanobenzofuro[3,2-e]isoquinolin-7-yl 3-((S)-2-hydroxy-2-phenylacetamido)propanoate trifluoroacetic acid salt (21 mg, 58% over two steps) as a fluffy white solid: $^1$H NMR (300 MHz, DMSO-$d_6$) δ 9.31 (s, 1H), 9.15 (s, 1H), 8.15 (t, J=5.8 Hz, 1H), 7.41-7.37 (m, 2H), 7.33-7.23 (m, 3H), 6.65 (q, J=7.9 Hz, 2H), 6.22-6.20 (m, 2H), 5.46 (dd, J=5.8, 1.9 Hz, 1H), 4.94 (s, 1H), 4.90 (d, J=4.5 Hz, 1H), 3.60 (s, 1H), 3.40-3.32 (m, 2H), 3.13-3.00 (m, 2H), 2.83 (s, 3H), 2.62 (t, J=7.0 Hz, 3H), 2.50-2.38 (m, 1H), 2.28-2.19 (m, 1H), 2.03 (d, J=18.0 Hz, 1H), 1.61 (d, J=12.3 Hz, 1H); ESI MS m/z 507 $[C_{30}H_{30}F_3N_2O_8+H]^+$; HPLC (Method A) 94.9% (AUC), $t_R$=7.47 min.

Scheme 106: (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((3-aminopropanoyl)oxy)propanoate bis(trifluoroacetic acid salt)

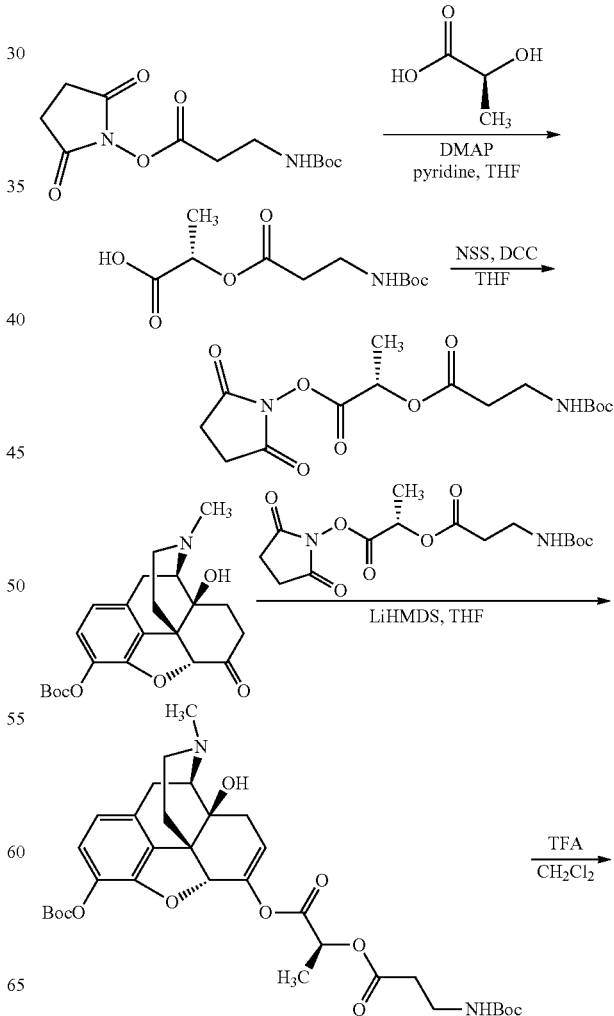

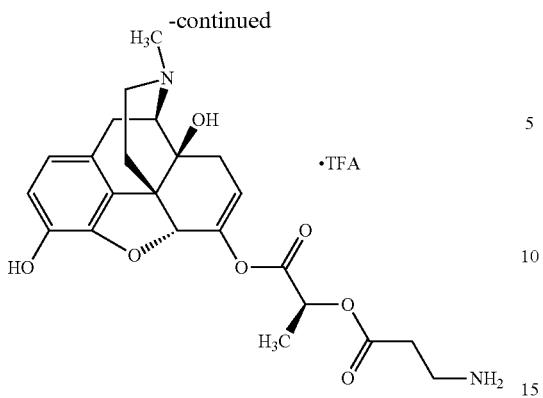

Preparation of (S)-2-((3-((tert-Butoxycarbonyl)amino)propanoyl)oxy)propanoic acid

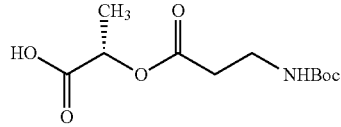

(S)-Lactic acid (755 mg, 8.38 mmol), 2,5-dioxopyrrolidin-1-yl 3-((tert-butoxycarbonyl)amino)propanoate (2.00 g, 6.99 mmol), 4-(dimethylamino)pyridine (85 mg, 0.70 mmol), pyridine (663 mg, 8.38 mmol) and tetrahydrofuran (34 mL) were combined and heated at 80° C. under a nitrogen atmosphere for 24 h. After this time, the solvent was removed under reduced pressure, and the residue was partitioned between ethyl acetate (20 mL) and 10% aqueous citric acid. The organic layer was separated and extracted with saturated aqueous sodium bicarbonate (20 ml). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (S)-2-((3-((tert-butoxycarbonyl)amino)propanoyl)oxy)propanoic acid (1.67 g, 91%) as a white solid: $^1$H NMR (300 MHz, CDCl$_3$) δ 5.17 (q, J=6.9 Hz, 1H), 3.45 (m, 2H), 2.60 (m, 2H), 1.54 (d, J=6.9 Hz, 3H), 1.44 (s, 9H).

Preparation of (S)-2,5-Dioxopyrrolidin-1-yl 2-((3-((tert-butoxycarbonyl)amino)propanoyl)oxy)propanoate

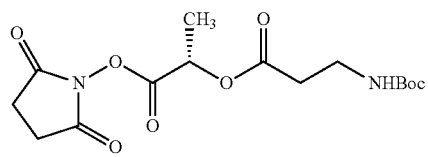 [SMILES: C[C@H](OC(=O)CCNC(=O)OC(C)(C)C)C(=O)ON1C(=O)CCC1=O]

A solution of (S)-2-((3-((tert-butoxycarbonyl)amino)propanoyl)oxy)propanoic acid (1.67 g, 6.40 mmol) in tetrahydrofuran (30 mL) was treated with N-hydroxysuccinimide (810 mg, 7.04 mmol) and N,N'-dicyclohexylcarbodiimide (1.45 g, 7.04 mmol) and stirred under a nitrogen atmosphere for 16 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-2,5-dioxopyrrolidin-1-yl 2-((3-((tert-butoxycarbonyl)amino)propanoyl)oxy)propanoate (2.73 g) as a white powder: $^1$H NMR (300 MHz, CDCl$_3$) δ 5.41 (q, J=6.9 Hz, 1H), 3.46 (m, 2H), 2.85 (s, 4H), 2.64 (m, 2H), 1.69 (d, J=6.9 Hz, 3H), 1.43 (s, 9H).

Preparation of (S)-(4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 2-((3-((tert-butoxycarbonyl)amino)propanoyl)oxy)propanoate

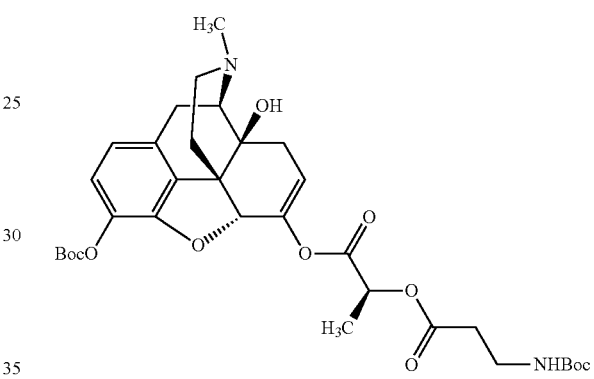

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled to 0° C. and treated dropwise with a 1.0 M solution of lithium bis(trimethylsilyl)amide in tetrahydrofuran (1.5 mL, 1.5 mmol). After addition was complete, the mixture was stirred at 0° C. for 25 min and then at ambient temperature for 25 min. The mixture was re-cooled to −78° C. and a solution of (S)-2,5-dioxopyrrolidin-1-yl 2-((3-((tert-butoxycarbonyl)amino)propanoyl)oxy)propanoate (490 mg, 1.37 mmol) in tetrahydrofuran (5 mL) was added. The mixture was allowed to warm to 0° C. over 2 h and then treated with saturated aqueous ammonium chloride (10 mL), and extracted with ethyl acetate (2×25 mL). The combined organics were dried over sodium sulfate, filtered, and concentrated under reduced pressure. The crude residue was purified by column chromatography (40 g, silica gel, 0-20% methanol/methylene chloride, then 50 g, C18, 10-100% acetonitrile/water) to provide (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-((3-((tert-butoxycarbonyl)amino)propanoyl)oxy)propanoate (188 mg, 23%) as a white solid: $^1$H NMR (300 MHz, CDCl$_3$) δ 6.91 (d, J=8.1 Hz, 1H), 6.66 (d, J=8.4 Hz, 1H), 5.63 (dd, J=5.7, 2.7 Hz, 1H), 5.17 (q, J=7.2 Hz, 1H), 5.05 (s, 1H), 3.45 (m, 2H), 3.18 (d, J=18.9 Hz, 1H), 2.87 (d, J=6.3 Hz, 1H), 2.59-2.69 (m, 3H), 2.47-2.01 (m, 5H), 2.38 (s, 3H), 1.53-1.67 (m, 13H), 1.42 (s, 9H).

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((3-aminopropanoyl)oxy)propanoate bis(trifluoroacetic acid salt)

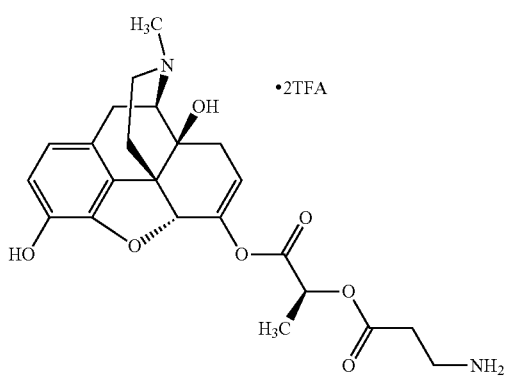 [SMILES: C[C@H](OC(=O)CCN)C(=O)OC1=CC[C@@]2(O)[C@H]3Cc4ccc(O)c5c4[C@@]2(CCN3C)[C@H]1O5]

A solution of (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-((3-((tert-butoxycarbonyl)amino)propanoyl)oxy)propanoate (45 mg, 0.070 mmol) in methylene chloride (0.8 mL) was treated with trifluoroacetic acid (0.8 mL) and stirred under a nitrogen atmosphere at ambient temperature for 15 min. After this time, the reaction mixture was concentrated under reduced pressure. The residue was purified by reversed phase column chromatography (50 g C18 column, 0-100% acetonitrile/water) and freeze dried to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-aminopropanoyl)oxy)propanoate bis(trifluoroacetic acid salt) (32.2 mg, 68%) as a fluffy white solid: $^1$H NMR (300 MHz, DMSO-$d_6$) δ 9.32 (s, 1H), 9.16 (s, 1H), 7.78 (s, 3H), 6.66 (q, J=10.5 Hz, 2H), 6.23 (s, 1H), 5.59 (dd, J=6.0, 4.2 Hz, 1H), 5.17 (q, J=6.9 Hz, 1H), 3.62 (m, 1H), 3.08 (m, 4H), 2.63-2.84 (m, 6H), 2.45-2.49 (m, 4H), 2.05 (d, J=18.3 Hz, 1H), 1.61 (d, J=12.3 Hz, 1H), 1.54 (d, J=6.9 Hz, 3H); ESI MS m/z 459 $[C_{23}H_{28}N_2O_7+H]^+$.

Scheme 107: (S)-(S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl 2-amino-4-methylpentanoate bis(trifluoroacetic acid salt)

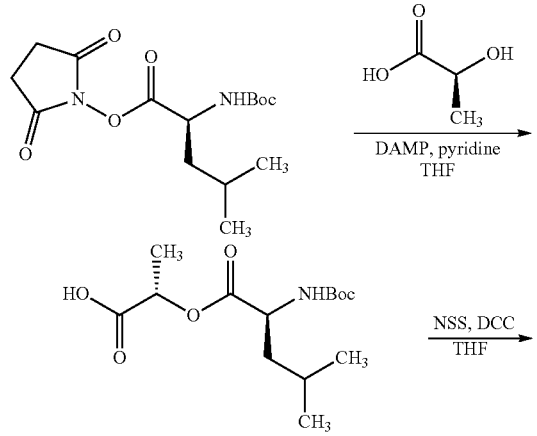

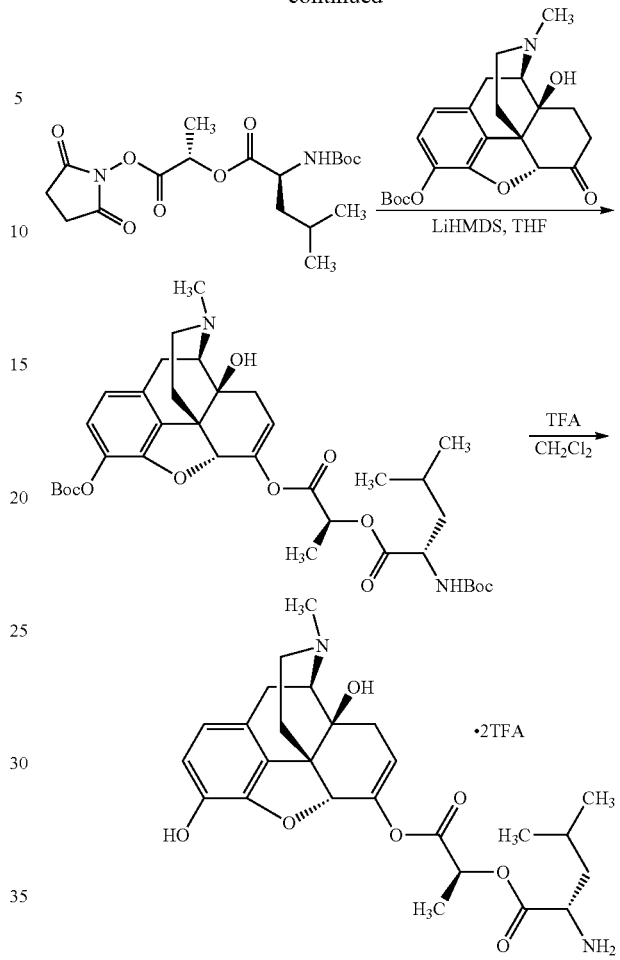

Preparation of (S)-2-(((S)-2-((tert-Butoxycarbonyl)amino)-4-methylpentanoyl)oxy)propanoic acid

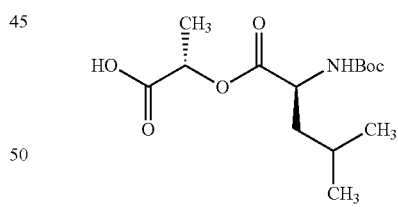

(S)-Lactic acid (658 mg, 7.31 mmol), (S)-2,5-dioxopyrrolidin-1-yl 2-((tert-butoxycarbonyl)amino)-4-methylpentanoate (2.00 g, 6.09 mmol), 4-(dimethylamino)pyridine (74 mg, 0.61 mmol), pyridine (578 mg, 7.31 mmol), and tetrahydrofuran (35 mL) were combined and heated at 80° C. under a nitrogen atmosphere for 24 h. After this time, the solvent was removed under reduced pressure, and the residue was partitioned between ethyl acetate (20 mL) and 10% aqueous citric acid. The organic layer was separated and extracted with saturated aqueous sodium bicarbonate (20 ml). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (S)-2-(((S)-2-((tert-butoxycarbonyl)amino)-4-methylpentanoyl)oxy)propanoic acid (1.83 g, 99%) as a white solid: ¹H NMR (300 MHz, CDCl₃) δ 5.20-5.14 (m, 1H), 4.88 (m, 1H), 4.32 (m, 1H), 1.81-1.65 (m, 2H), 1.59-1.51 (m, 4H), 1.45 (s, 9H), 0.96 (d, J=6.3 Hz, 6H), CO₂H proton not observed.

Preparation of (S)-(S)-1-((2,5-Dioxopyrrolidin-1-yl)oxy)-1-oxopropan-2-yl 2-((tert-butoxycarbonyl)amino)-4-methylpentanoate

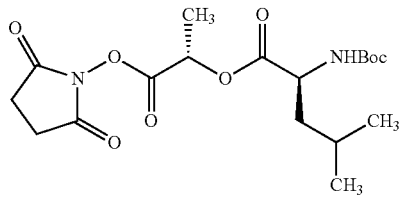 [SMILES: CC(C)C[C@H](NC(=O)OC(C)(C)C)C(=O)O[C@@H](C)C(=O)ON1C(=O)CCC1=O]

A solution of (S)-2-(((S)-2-((tert-butoxycarbonyl)amino)-4-methylpentanoyl)oxy)propanoic acid (1.83 g, 6.04 mmol) in tetrahydrofuran (40 mL) was treated with N-hydroxysuccinimide (765 mg, 6.64 mmol) and N,N'-dicyclohexylcarbodiimide (1.37 g, 6.64 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-(S)-1-((2,5-dioxopyrrolidin-1-yl)oxy)-1-oxopropan-2-yl 2-((tert-butoxycarbonyl)amino)-4-methylpentanoate (3.03 g) as a white semi-solid: ¹H NMR (300 MHz, CDCl₃) δ 5.48-5.43 (m, 1H), 4.86 (m, 1H), 4.38-4.33 (m, 1H), 2.84 (s, 4H), 1.91-1.48 (m, 2H), 1.72-1.70 (m, 4H), 1.44 (s, 9H), 0.95 (m, 6H).

Preparation of (S)-(S)-1-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl 2-((tert-butoxycarbonyl)amino)-4-methylpentanoate

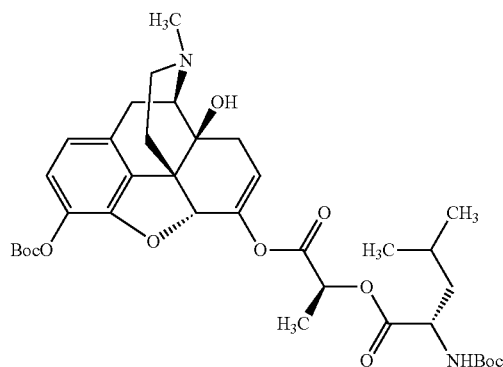

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled to 0° C. and treated dropwise with a 1.0 M solution of lithium bis(trimethylsilyl)amide in tetrahydrofuran (1.5 mL, 1.5 mmol). After addition was complete, the mixture was stirred at 0° C. for 25 min and then at ambient temperature for 25 min. The mixture was re-cooled to -78° C., and a solution of (S)-(S)-1-((2,5-dioxopyrrolidin-1-yl)oxy)-1-oxopropan-2-yl 2-((tert-butoxycarbonyl)amino)-4-methylpentanoate (550 mg, 1.37 mmol) in tetrahydrofuran (5 mL) was added. The mixture was allowed to warm to 0° C. over 2 h. After this time, the mixture was treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-(S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl 2-((tert-butoxycarbonyl)amino)-4-methylpentanoate (338 mg, 39%) as a white solid: ¹H NMR (300 MHz, CDCl₃) δ 6.89 (d, J=8.1 Hz, 1H), 6.65 (d, J=8.4 Hz, 1H), 5.61-5.60 (m, 1H), 5.20-5.16 (m, 1H), 3.19 (d, J=18.9 Hz, 1H), 2.86 (d, J=6.3 Hz, 1H), 2.64 (dd, J=18.9, 6.3 Hz, 1H), 2.48-2.07 (m, 5H), 2.38 (s, 3H), 1.83-1.53 (m, 6H), 1.59 (d, J=7.2 Hz, 3H), 1.54 (s, 9H), 1.44 (s, 9H), 0.99-0.94 (m, 6H), OH, NH protons not observed.

Preparation of (S)-(S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl 2-amino-4-methylpentanoate bis(trifluoroacetic acid salt)

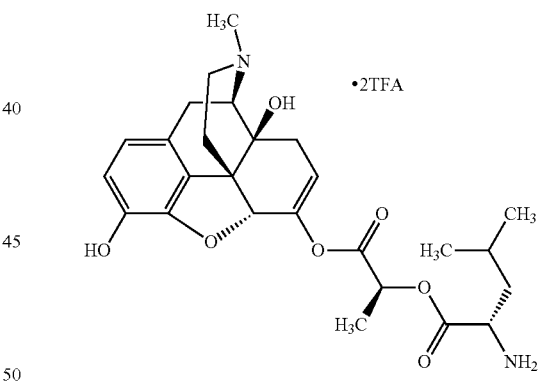

A solution of (S)-(S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl 2-((tert-butoxycarbonyl)amino)-4-methylpentanoate (45 mg, 0.066 mmol) in methylene chloride (0.8 mL) was treated with trifluoroacetic acid (0.8 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water) and freeze dried to provide (S)-(S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl 2-amino-4-methylpentanoate bis(trifluoroacetic acid salt) (27 mg, 58%) as a fluffy white solid: ¹H NMR (300 MHz, DMSO-d$_6$) δ 9.31 (s, 1H), 9.13 (br s, 1H), 8.32 (br s, 3H), 6.66 (apparent q, J=9.6 Hz, 2H), 6.21 (br s, 1H), 5.60 (dd, J=6.0, 2.1 Hz, 1H), 5.34 (q, J=7.2 Hz, 1H), 4.96 (s, 1H), 4.11 (t, J=6.6 Hz, 1H), 3.71-3.53 (m, 1H, partially obscured by water peak), 3.07-3.04 (m, 2H), 2.83 (s, 3H), 2.63-2.41 (m, 3H), 2.33-2.25 (m, 1H), 2.06 (d, J=18.0 Hz, 1H), 1.91-1.57 (m, 4H), 1.58 (d, J=7.2 Hz, 3H), 0.93 (t, J=6.3 Hz, 6H); ESI MS m/z 487 [C$_{26}$H$_{34}$N$_2$O$_7$+H]$^+$.
Scheme 108: (4R,4aS,7aR,12bS)-4a,9-Dihydroxy-3-methyl-2,3,4,4a,5,7a-hexahydro-1H-4,12-methanobenzofuro[3,2-e]isoquinolin-7-yl 3-((S)-2-hydroxypropanamido)propanoate trifluoroacetic acid salt
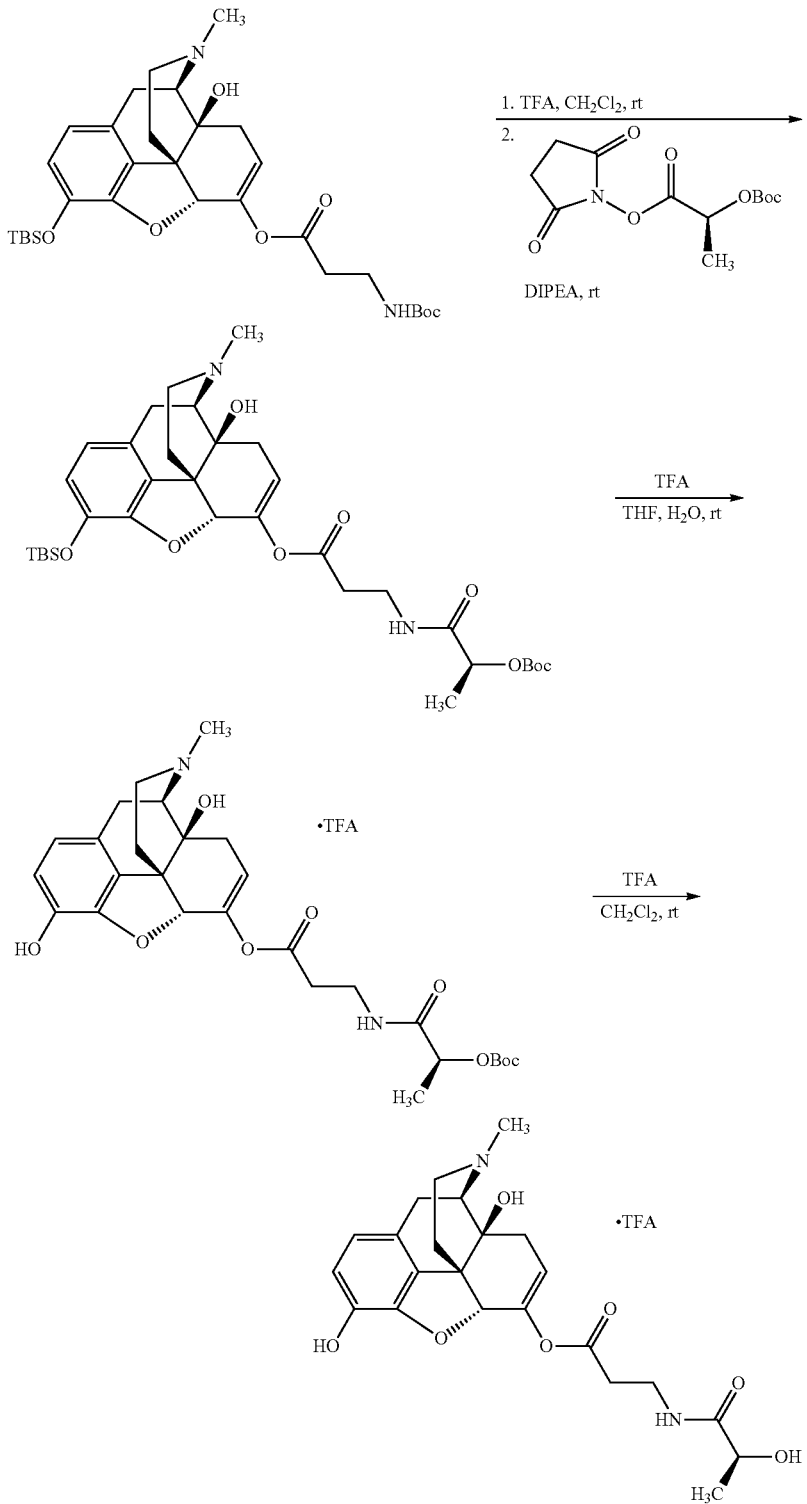

Preparation of (4R,4aS,7aR,12bS)-9-((tert-Butyldimethylsilyl)oxy)-4a-hydroxy-3-methyl-2,3,4,4a,5,7a-hexahydro-1H-4,12-methanobenzofuro[3,2-e]isoquinolin-7-yl 3-((S)-2-((tert-butoxycarbonyl)oxy)propanamido)propanoate

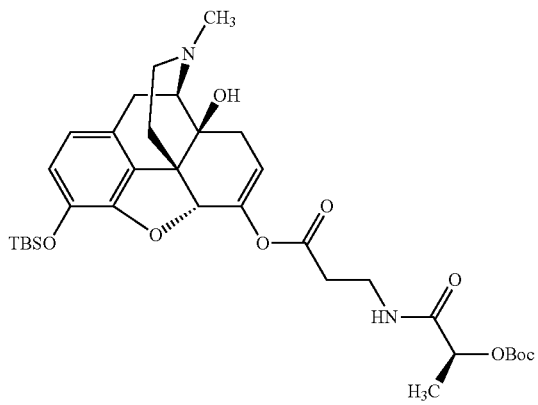

A solution of (4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 3-((tert-butoxycarbonyl)amino)propanoate (120 mg, 0.20 mmol) in methylene chloride (2.5 mL) was treated with trifluoroacetic acid (0.3 mL), and the mixture was stirred at room temperature for 15 min. After this time, LC-MS analysis of the reaction mixture showed cleavage of the Boc protecting group. N,N-Diisopropylethylamine was added slowly until the reaction mixture tested basic by pH paper analysis (0.4 mL of base added). The mixture was treated with (S)-2,5-dioxopyrrolidin-1-yl 2-((tert-butoxycarbonyl)oxy)propanoate (60 mg, 0.21 mmol) in one portion and stirred at room temperature for 2.5 h. After this time, the mixture was diluted with ethyl acetate and washed successively with 10% citric acid, saturated sodium bicarbonate, and brine. The organic extracts were dried over sodium sulfate, filtered and concentrated. The residue was purified by column chromatography (12 g silica, 0-10% methanol/methylene chloride) to provide (4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 3-((S)-2-((tert-butoxycarbonyl)oxy)propanamido)propanoate (60 mg, 46%): ESI MS m/z 659 $[C_{34}H_{50}N_2O_9Si+H]^+$.

Preparation of (4R,4aS,7aR,12bS)-4a,9-Dihydroxy-3-methyl-2,3,4,4a,5,7a-hexahydro-1H-4,12-methanobenzofuro[3,2-e]isoquinolin-7-yl 3-((S)-2-((tert-butoxycarbonyl)oxy)propanamido)propanoate trifluoroacetic acid salt

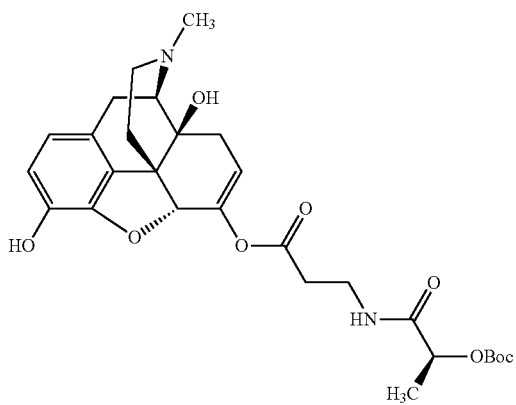

A solution of (4R,4aS,7aR,12bS)-9-((tert-butyldimethylsilyl)oxy)-4a-hydroxy-3-methyl-2,3,4,4a,5,7a-hexahydro-1H-4,12-methanobenzofuro[3,2-e]isoquinolin-7-yl 3-((S)-2-((tert-butoxycarbonyl)oxy)propanamido)propanoate (58 mg, 0.088 mmol) in tetrahydrofuran (2 mL) was treated with water (1 mL) followed by trifluoroacetic acid (1 mL), and the mixture was stirred at room temperature for 3 h. After this time, the mixture was concentrated, and the residue was azeotroped with toluene to provide (4R,4aS,7aR,12bS)-4a,9-dihydroxy-3-methyl-2,3,4,4a,5,7a-hexahydro-1H-4,12-methanobenzofuro[3,2-e]isoquinolin-7-yl 3-((S)-2-((tert-butoxycarbonyl)oxy)propanamido)propanoate trifluoroacetic acid salt (60 mg, crude) that was used without purification: ESI MS m/z 445 $[C_{28}H_{36}N_2O_9+H]^+$.

Preparation of (4R,4aS,7aR,12bS)-4a,9-Dihydroxy-3-methyl-2,3,4,4a,5,7a-hexahydro-1H-4,12-methanobenzofuro[3,2-e]isoquinolin-7-yl 3-((S)-2-hydroxypropanamido)propanoate trifluoroacetic acid salt

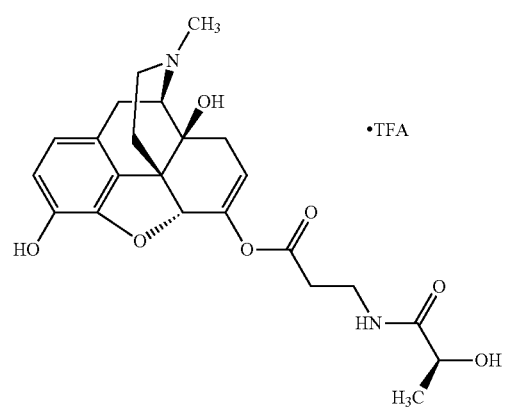 [SMILES: C[C@H](O)C(=O)NCCC(=O)OC1=CC[C@@]2(O)[C@H]3Cc4ccc(O)c5c4[C@@]2(CCN3C)[C@H]1O5]

A solution of (4R,4aS,7aR,12bS)-4a,9-dihydroxy-3-methyl-2,3,4,4a,5,7a-hexahydro-1H-4,12-methanobenzofuro[3,2-e]isoquinolin-7-yl 3-((S)-2-((tert-butoxycarbonyl)oxy)propanamido)propanoate (60 mg) in methylene chloride (2 mL) was treated with trifluoroacetic acid (1 mL) and stirred at ambient temperature for 0.5 h. After this time, the reaction mixture was concentrated under reduced pressure. The residue was purified by reversed phase column chromatography (15.5 g C18 column, 5-40% acetonitrile/water) and freeze dried to provide (4R,4aS,7aR,12bS)-4a,9-dihydroxy-3-methyl-2,3,4,4a,5,7a-hexahydro-1H-4,12-methanobenzofuro[3,2-e]isoquinolin-7-yl 3-((S)-2-hydroxypropanamido)propanoate trifluoroacetic acid salt (26 mg, 53% over two steps) as a fluffy white solid: $^1$H NMR (300 MHz, DMSO-$d_6$) δ 9.30 (s, 1H), 9.15 (s, 1H), 7.84 (t, J=5.9 Hz, 1H), 6.67 (d, J=8.1 Hz, 1H), 6.62 (d, J=8.1 Hz, 1H), 6.23 (s, 1H), 5.56-5.51 (m, 2H), 4.96 (s, 1H), 4.00-3.91 (m, 1H), 3.61 (d, J=5.4 Hz, 1H), 3.42-3.31 (m, 3H), 3.12-3.00 (m, 2H), 2.83 (s, 3H), 2.62 (t, J=6.9 Hz, 3H), 2.50-2.39 (m, 1H), 2.26 (dd, J=17.7, 6.0 Hz, 1H), 2.06 (d, J=17.7 Hz, 1H), 1.62 (d, J=11.6 Hz, 1H), 1.20 (d, J 6.8 Hz, 3H); ESI MS m/z 445 $[C_{23}H_{28}N_2O_7+H]^+$; HPLC (Method A) 97.7% (AUC), $t_R$=6.33 min.

Scheme 90: (S)-2-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-oxo-1-phenylethyl 3-aminopropanoate bis(trifluoroacetic acid salt)

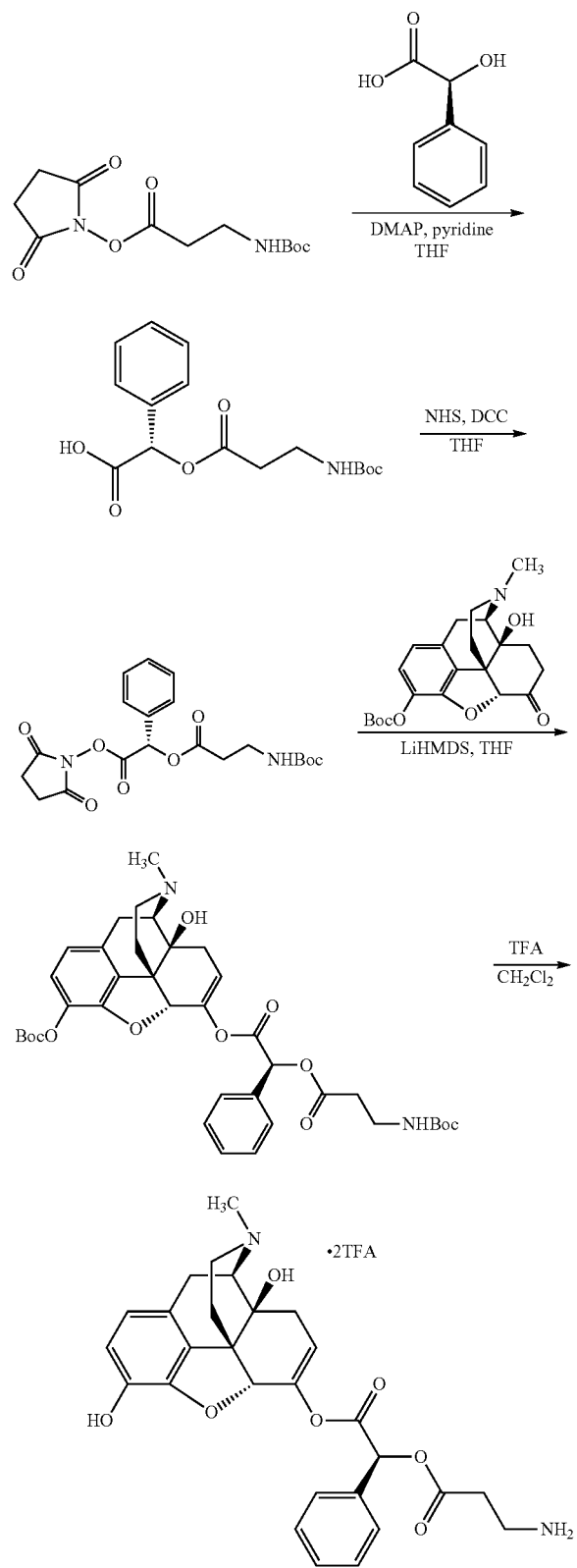

Preparation of (S)-2-((3-((tert-Butoxycarbonyl)amino)propanoyl)oxy)-2-phenylacetic acid

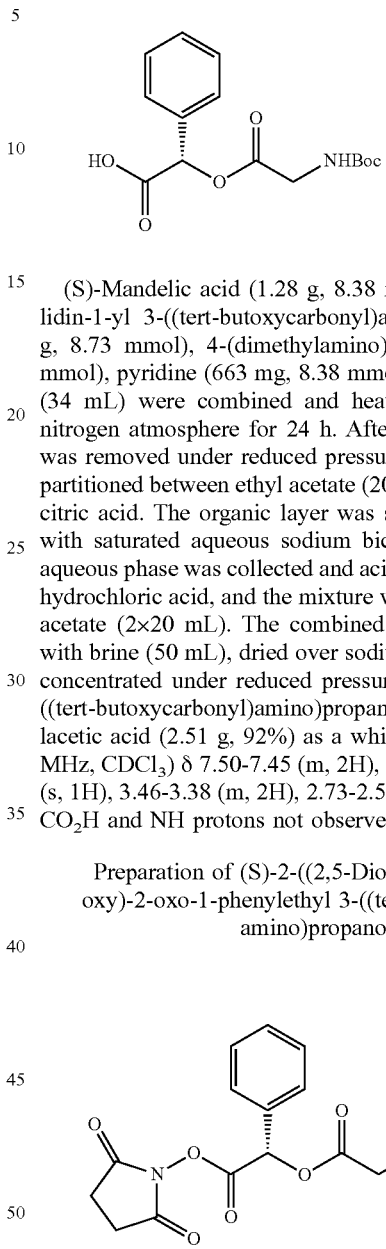

(S)-Mandelic acid (1.28 g, 8.38 mmol), 2,5-dioxopyrrolidin-1-yl 3-((tert-butoxycarbonyl)amino)propanoate (2.50 g, 8.73 mmol), 4-(dimethylamino)pyridine (85 mg, 0.70 mmol), pyridine (663 mg, 8.38 mmol), and tetrahydrofuran (34 mL) were combined and heated at 80° C. under a nitrogen atmosphere for 24 h. After this time, the solvent was removed under reduced pressure, and the residue was partitioned between ethyl acetate (20 mL) and 10% aqueous citric acid. The organic layer was separated and extracted with saturated aqueous sodium bicarbonate (20 ml). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (S)-2-((3-((tert-butoxycarbonyl)amino)propanoyl)oxy)-2-phenylacetic acid (2.51 g, 92%) as a white solid: $^1$H NMR (300 MHz, CDCl$_3$) δ 7.50-7.45 (m, 2H), 7.40-7.33 (m, 3H), 6.00 (s, 1H), 3.46-3.38 (m, 2H), 2.73-2.59 (m, 2H), 1.43 (s, 9H); CO$_2$H and NH protons not observed.

Preparation of (S)-2-((2,5-Dioxopyrrolidin-1-yl)oxy)-2-oxo-1-phenylethyl 3-((tert-butoxycarbonyl)amino)propanoate A solution of (S)-2-((3-((tert-butoxycarbonyl)amino)propanoyl)oxy)-2-phenylacetic acid (2.51 g, 7.77 mmol) in tetrahydrofuran (40 mL) was treated with N-hydroxysuccinimide (984 mg, 8.55 mmol) and N,N'-dicyclohexylcarbodiimide (1.76 g, 8.55 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-2-((2,5-dioxopyrrolidin-1-yl)oxy)-2-oxo-1-phenylethyl 3-((tert-butoxycarbonyl)amino)propanoate (3.51 g) as a white powder: $^1$H NMR (300 MHz, CDCl$_3$) δ 7.54-7.53 (m, 2H), 7.46-7.44 (m, 3H), 6.32 (s, 1H), 3.49-3.42 (m, 2H), 2.82 (s, 4H), 2.74-2.68 (m, 2H), 1.43 (s, 9H); NH proton not observed.

Preparation of (S)-2-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl 3-((tert-butoxycarbonyl)amino)propanoate

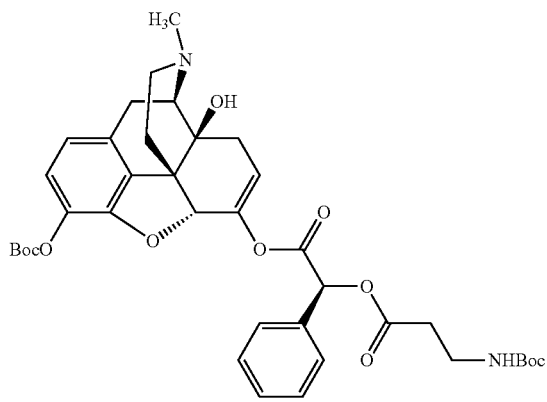

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled to 0° C. and treated dropwise with a 1.0 M solution of lithium bis(trimethylsilyl)amide in tetrahydrofuran (1.5 mL, 1.5 mmol). After addition was complete, the mixture was stirred at 0° C. for 25 min and then at ambient temperature for 25 min. The mixture was re-cooled to −78° C., and a solution of (S)-2-((2,5-dioxopyrrolidin-1-yl)oxy)-2-oxo-1-phenylethyl 3-((tert-butoxycarbonyl)amino)propanoate (580 mg, 1.37 mmol) in tetrahydrofuran (5 mL) was added. The mixture was allowed to warm to 0° C. over 2 h. After this time, the mixture was treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl 3-((tert-butoxycarbonyl)amino)propanoate (176 mg, 20%) as a white solid: $^1$H NMR (300 MHz, CDCl$_3$) δ 7.54-7.51 (m, 2H), 7.45-7.36 (m, 3H), 6.91 (d, J=8.4 Hz, 1H), 6.65 (d, J=8.1 Hz, 1H), 6.04 (s, 1H), 5.60 (dd, J=5.7, 2.7 Hz, 1H), 4.96 (s, 1H), 3.51-3.46 (m, 2H), 3.17 (d, J=18.9 Hz, 1H), 2.86-2.59 (m, 4H), 2.46-2.05 (m, 5H), 2.37 (s, 3H), 1.64-1.56 (m, 3H), 1.55 (s, 9H), 1.42 (s, 9H).

Preparation of (S)-2-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-oxo-1-phenylethyl 3-aminopropanoate bis (trifluoroacetic acid salt)

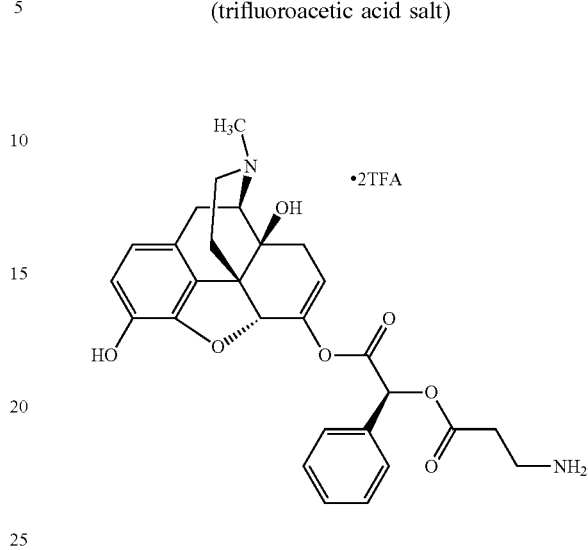

A solution of (S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl 3-((tert-butoxycarbonyl)amino)propanoate (45 mg, 0.064 mmol) in methylene chloride (0.8 mL) was treated with trifluoroacetic acid (0.8 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water) and freeze dried to provide (S)-2-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-oxo-1-phenylethyl 3-aminopropanoate bis(trifluoroacetic acid salt) (33 mg, 71%) as a fluffy white solid: $^1$H NMR (300 MHz, DMSO-d$_6$) δ 9.31 (s, 1H), 9.13 (s, 1H), 7.79 (s, 3H), 7.59-7.56 (m, 2H), 7.49-7.47 (m, 3H), 6.64 (q, J=11.4 Hz, 2H), 6.23 (s, 1H), 6.15 (s, 1H), 5.59 (dd, J=6.0, 2.1 Hz, 1H), 4.87 (s, 1H), 3.61 (m, 1H), 3.10 (m, 4H), 2.85-2.83 (m, 5H), 2.65-2.43 (m, 3H), 2.29-2.21 (m, 1H), 2.06 (d, J=18.3 Hz, 1H), 1.62-1.58 (m, 1H); ESI MS m/z 507 [C$_{28}$H$_{30}$N$_2$O$_7$+H]$^+$; HPLC (Method A) 98.2% (AUC), t$_R$=7.30 min.

Scheme 110: (S)-(S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl 2-amino-3-phenylpropanoate bis(trifluoroacetic acid salt)

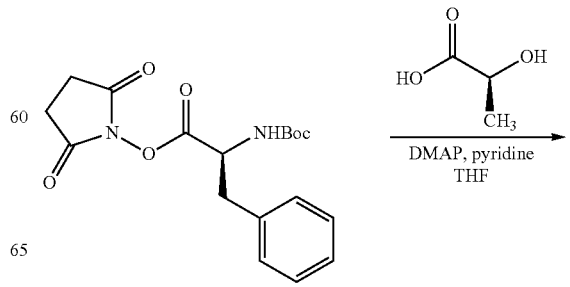

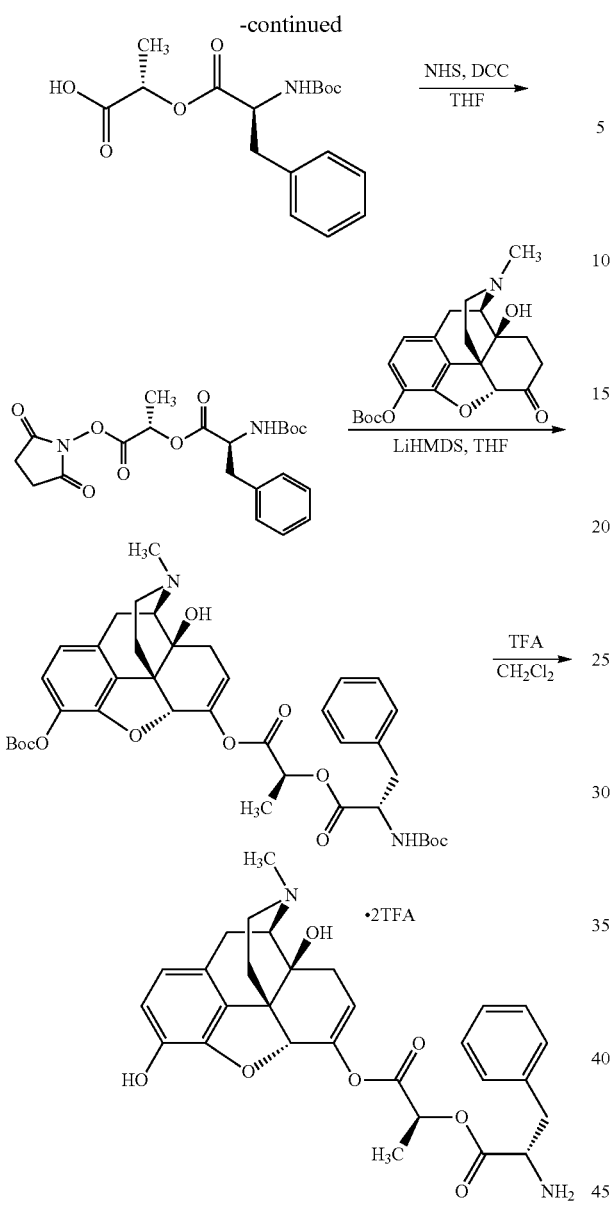

Preparation of (S)-2-(((S)-2-((tert-Butoxycarbonyl)amino)-3-phenylpropanoyl)oxy)propanoic acid

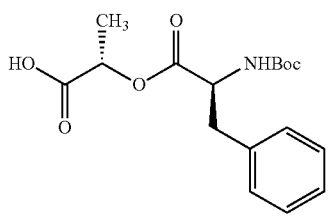 [SMILES: C[C@H](OC(=O)[C@H](Cc1ccccc1)NC(=O)OC(C)(C)C)C(=O)O]

(S)-Lactic acid (597 mg, 6.62 mmol), (S)-2,5-dioxopyrrolidin-1-yl 2-((tert-butoxycarbonyl)amino)-3-phenylpropanoate (2.00 g, 5.52 mmol), 4-(dimethylamino)pyridine (67 mg, 0.552 mmol), pyridine (437 mg, 5.52 mmol), and tetrahydrofuran (35 mL) were combined and heated at 80° C. under a nitrogen atmosphere for 24 h. After this time, the solvent was removed under reduced pressure, and the residue was partitioned between ethyl acetate (20 mL) and 10% aqueous citric acid. The organic layer was separated and extracted with saturated aqueous sodium bicarbonate (20 ml). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (S)-2-(((S)-2-((tert-butoxycarbonyl)amino)-3-phenylpropanoyl)oxy)propanoic acid (2.02 g, quantitative) as a colorless semi-solid: $^1$H NMR (300 MHz, CDCl$_3$) δ 7.34-7.18 (m, 5H), 5.24-5.19 (m, 1H), 4.90 (m, 1H), 4.61 (m, 1H), 3.25 (dd, J=14.1, 8.7 Hz, 1H), 3.07 (m, 1H), 1.55 (d, J=8.7 Hz, 3H), 1.39 (s, 9H), CO$_2$H proton not observed.

Preparation of (S)-(S)-1-((2,5-Dioxopyrrolidin-1-yl)oxy)-1-oxopropan-2-yl 2-((tert-butoxycarbonyl)amino)-3-phenylpropanoate

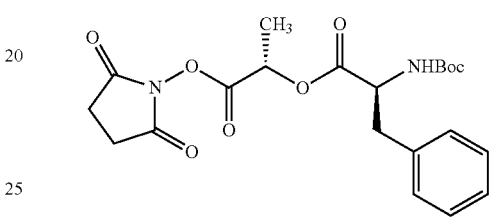

A solution of (S)-2-(((S)-2-((tert-butoxycarbonyl)amino)-3-phenylpropanoyl)oxy)propanoic acid (2.02 g, 5.99 mmol) in tetrahydrofuran (40 mL) was treated with N-hydroxysuccinimide (759 mg, 6.59 mmol) and N,N'-dicyclohexylcarbodiimide (1.36 g, 6.59 mmol) and stirred under a nitrogen atmosphere for 6 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-(S)-1-((2,5-dioxopyrrolidin-1-yl)oxy)-1-oxopropan-2-yl 2-((tert-butoxycarbonyl)amino)-3-phenylpropanoate (2.36 g) as a white powder: $^1$H NMR (300 MHz, CDCl$_3$) δ 7.33-7.18 (m, 5H), 5.50 (q, J=6.9 Hz, 1H), 4.89 (m, 1H), 4.74 (m, 1H), 3.25 (dd, J=14.4, 5.4 Hz, 1H), 3.03 (m, 1H), 2.84 (s, 4H), 1.69 (d, J=7.2 Hz, 3H), 1.41 (s, 9H).

Preparation of (S)-(S)-1-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl 2-((tert-butoxycarbonyl)amino)-3-phenylpropanoate

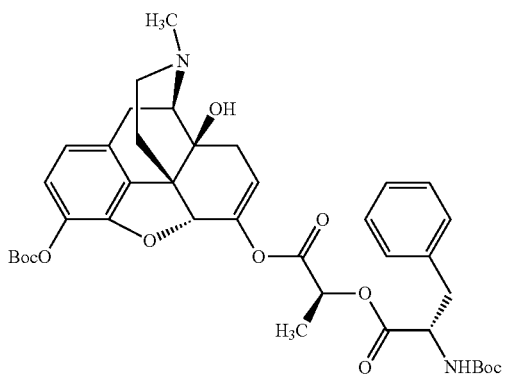

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at ambient temperature for 15 min. The mixture was re-cooled to −45° C. and treated dropwise with a solution of (S)-(S)-1-((2,5-dioxopyrrolidin-1-yl)oxy)-1-oxopropan-2-yl 2-((tert-butoxycarbonyl)amino)-3-phenylpropanoate (543 mg, 1.37 mmol) in tetrahydrofuran (5 mL). After addition was complete, the mixture was warmed to 0° C. After this time, the reaction mixture was treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-(S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl 2-((tert-butoxycarbonyl)amino)-3-phenylpropanoate (223 mg, 24%) as a white solid: $^1$H NMR (300 MHz, CDCl$_3$) δ 7.33-7.24 (m, 5H), 6.91 (d, J=8.1 Hz, 1H), 6.66 (d, J=8.4 Hz, 1H), 5.62 (m, 1H), 5.60 (q, J=6.9 Hz, 1H), 5.10 (s, 1H), 5.05-4.96 (m, 1H), 4.62 (m, 1H), 3.32-3.23 (m, 1H), 3.19 (d, J=19.2 Hz, 1H), 3.01 (m, 1H), 2.87 (d, J=6.3 Hz, 1H), 2.65 (dd, J=18.9, 6.0 Hz, 1H), 2.47-2.09 (m, 4H), 2.38 (s, 3H), 1.74-1.58 (m, 4H), 1.53 (s, 9H), 1.38 (s, 9H), OH, NH protons not observed.

Preparation of (S)-(S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl 2-amino-3-phenylpropanoate bis (trifluoroacetic acid salt)

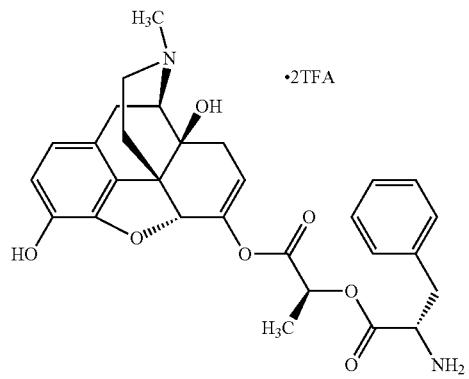 [SMILES: C[C@H](OC(=O)[C@@H](N)Cc1ccccc1)C(=O)OC1=CC[C@@]2(O)[C@H]3Cc4ccc(O)c5c4[C@@]2(CCN3C)[C@H]1O5]

A solution of (S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl 3-((tert-butoxycarbonyl)amino)propanoate (50 mg, 0.069 mmol) in methylene chloride (0.8 mL) was treated with trifluoroacetic acid (0.8 mL) and stirred under a nitrogen atmosphere at ambient temperature for 2 h. After this time, the reaction mixture was concentrated under reduced pressure. The residue was purified by reversed phase column chromatography (50 g C18 column, 0-100% acetonitrile/water) and freeze dried to provide (S)-(S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl 2-amino-3-phenylpropanoate bis(trifluoroacetic acid salt) (27 mg, 48%) as a fluffy white solid: $^1$H NMR (300 MHz, DMSO-d$_6$) δ 9.31 (s, 1H), 9.15 (s, 1H), 8.35 (s, 3H), 7.35-7.27 (m, 5H), 6.66 (apparent q, J=9.6 Hz, 2H), 6.24 (s, 1H), 5.59 (dd, J=6.0, 2.1 Hz, 1H), 5.30 (q, J=7.2 Hz, 1H), 4.97 (s, 1H), 4.44 (t, J=6.6 Hz, 1H), 3.62 (m, 1H), 3.25-3.05 (m, 5H), 2.84 (s, 3H), 2.64 (m, 1H), 2.29-2.26 (m, 1H), 2.07 (d, J=18.3 Hz, 1H), 1.64-1.61 (m, 1H), 1.51 (d, J=6.9 Hz, 3H), one proton obscured by solvent peaks; ESI MS m/z 521 [C$_{29}$H$_{32}$N$_2$O$_7$+H]$^+$.

Scheme 111: (S)-(4R,4aS,7aR,12bS)-4a,9-Dihydroxy-3-methyl-2,3,4,4a,5,7a-hexahydro-1H-4, 12-methanolbenzofuro[3,2-e]isoquinolin-7-yl 2-((3-((S)-2-hydroxypropanamido)propanoyl)oxy)propanoate trifluoroacetic acid salt

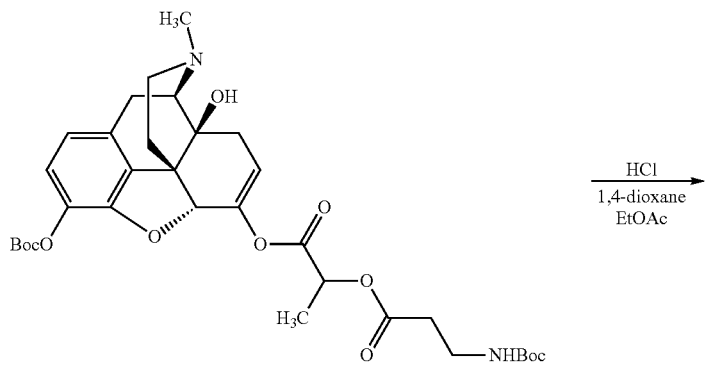

-continued
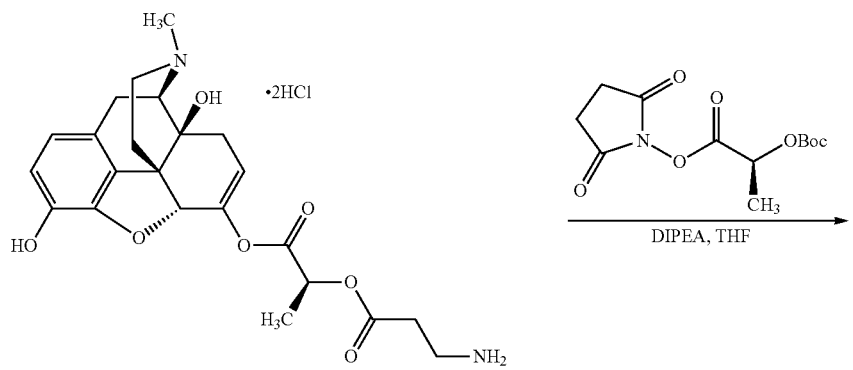
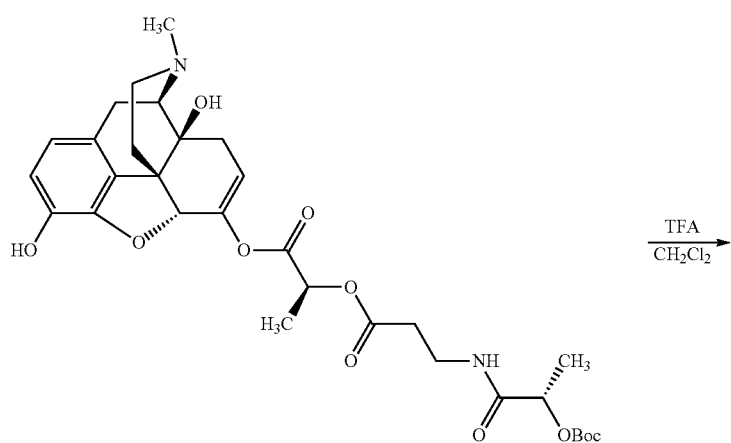
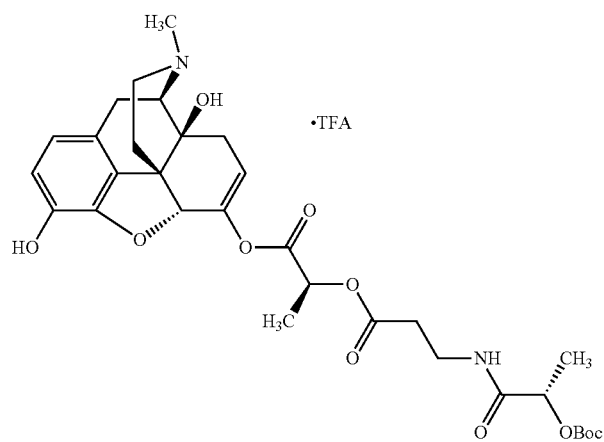

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((3-aminopropanoyl)oxy)propanoate dihydrochloride

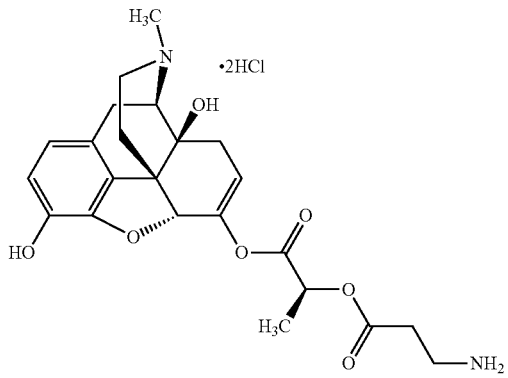 [SMILES: C[C@H](OC(=O)CCN)C(=O)OC1=CC[C@@]2(O)[C@H]3Cc4ccc(O)c5c4[C@@]2(CCN3C)[C@H]1O5]

A solution of (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-((3-((tert-butoxycarbonyl)amino)propanoyl)oxy)propanoate (45 mg, 0.070 mmol) in ethyl acetate (0.8 mL) was treated with a 4.0 M solution of hydrogen chloride in 1,4-dioxane (0.5 mL) and stirred under a nitrogen atmosphere at ambient temperature for 30 min. After this time, the reaction mixture was filtered and the filter cake was collected and dried under vacuum to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-aminopropanoyl)oxy)propanoate dihydrochloride (47 mg, 100%) as a white solid: $^1$H NMR (300 MHz, DMSO-$d_6$) δ 9.32 (s, 1H), 9.20 (s, 1H), 7.91 (s, 3H), 6.66 (apparent q, J=8.1 Hz, 2H), 6.27 (s, 1H), 5.59 (m, 1H), 5.17 (q, J=7.5 Hz, 1H), 4.96 (s, 1H), 3.11-3.03 (m, 2H), 2.85-2.76 (m, 6H), 2.46-2.27 (m, 2H), 2.06 (m, 1H), 1.60-1.46 (m, 8H).

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((3-((S)-2-((tert-butoxycarbonyl)oxy)propanamido)propanoyl)oxy)propanoate

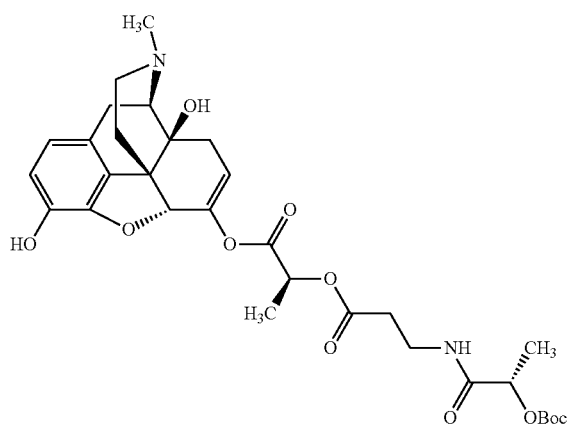

A solution of (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-aminopropanoyl)oxy)propanoate dihydrochloride (47 mg, 0.070 mmol) in tetrahydrofuran (2 mL) was treated with (S)-2,5-dioxopyrrolidin-1-yl 2-((tert-butoxycarbonyl)oxy)propanoate (20 mg, 0.070 mmol) and N,N-diisopropylethylamine (18 mg, 0.024 mmol) at 0° C. and stirred under a nitrogen atmosphere for 1 h. After this time the reaction mixture was concentrated under reduced pressure. The residue was purified by column chromatography (40 g silica gel column, 0-20% methanol/methylene chloride) to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-((S)-2-((tert-butoxycarbonyl)oxy)propanamido)propanoyl)oxy)propanoate (52 mg) as a white solid. ESI MS m/z 617 [$C_{31}H_{40}N_2O_{11}$+H]$^+$.

Preparation of (S)-(4R,4aS,7aR,12bS)-4a,9-Dihydroxy-3-methyl-2,3,4,4a,5,7a-hexahydro-H-4,12-methanobenzofuro[3,2-e]isoquinolin-7-yl 2-((3-((S)-2-hydroxypropanamido)propanoyl)oxy)propanoate trifluoroacetic acid salt

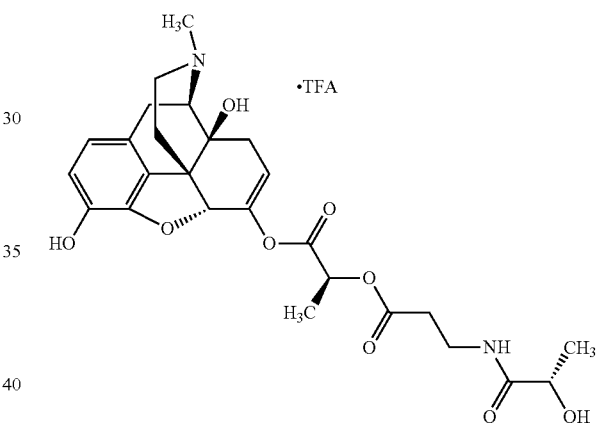

A solution of (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-((S)-2-((tert-butoxycarbonyl)oxy)propanamido)propanoyl)oxy)propanoate (52 mg, 0.084 mmol) in methylene chloride (0.8 mL) was treated with trifluoroacetic acid (0.8 mL) and stirred under a nitrogen atmosphere at ambient temperature for 2 h. After this time, the reaction mixture was concentrated under reduced pressure. The residue was purified by reversed phase column chromatography (50 g C18 column, 0-100% acetonitrile/water) and freeze dried to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-((S)-2-hydroxypropanamido)propanoyl)oxy)propanoate trifluoroacetic acid salt (22 mg, 49%) as a fluffy white solid: $^1$H NMR (300 MHz, DMSO-$d_6$) δ 9.28 (s, 1H), 9.15 (s, 1H), 7.79 (t, J=6.0 Hz, 1H), 6.65 (apparent q, J=8.4 Hz, 1H), 6.25 (s, 1H), 5.58 (dd, J=6.0, 2.1 Hz, 1H), 5.11 (q, J=7.2 Hz, 1H), 4.96 (s, 1H), 3.94 (m, 1H), 3.62 (m, 1H), 3.38 (m, 4H), 3.05 (m, 2H), 2.83 (s, 3H), 2.64 (m, 1H), 2.57 (t, J=6.9 Hz, 2H), 2.42 (m, 2H), 2.29 (m, 1H), 2.06 (d, J=18.0 Hz, 1H), 1.63 (d, J=11.4 Hz, 1H), 1.52 (d, J=9.6 Hz, 3H), 1.19 (d, J=9.6 Hz, 3H); ESI MS m/z 517 [$C_{26}H_{32}N_2O_9$+H]$^+$.

Scheme 112: (S)-(4R,4aS,7aR,12bS)-9-Hydroxy-3-methyl-2,3,4,4a,5,7a-hexahydro-1H-4,12-methanobenzofuro[3,2-e]isoquinoline-4a,7-diyl bis(3-((S)-2-hydroxy-2-phenylacetamido)propanoate) trifluoroacetic acid salt
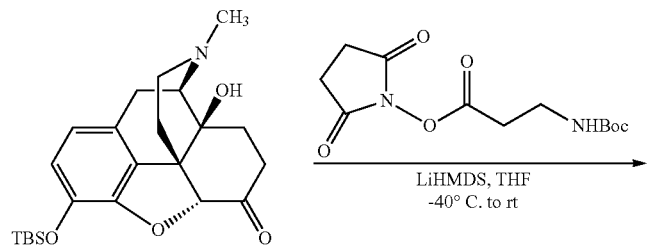
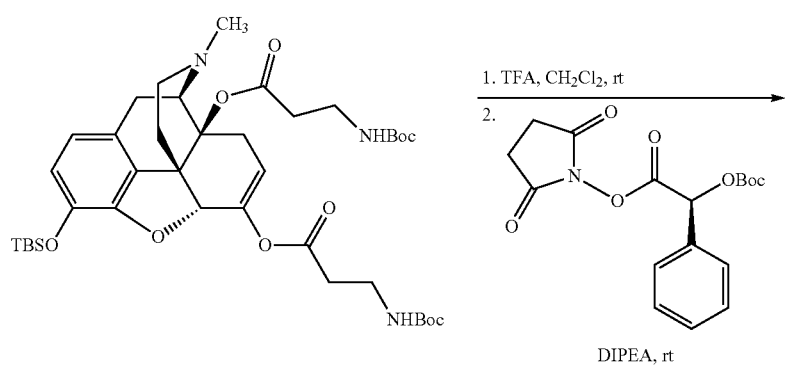
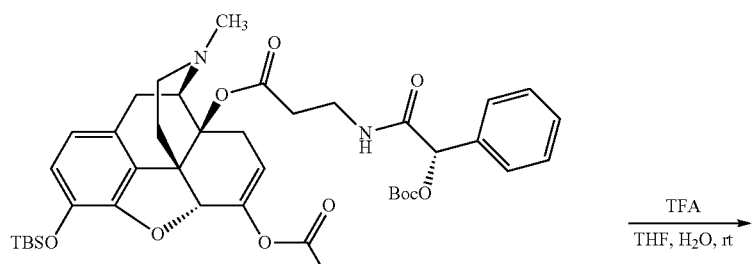
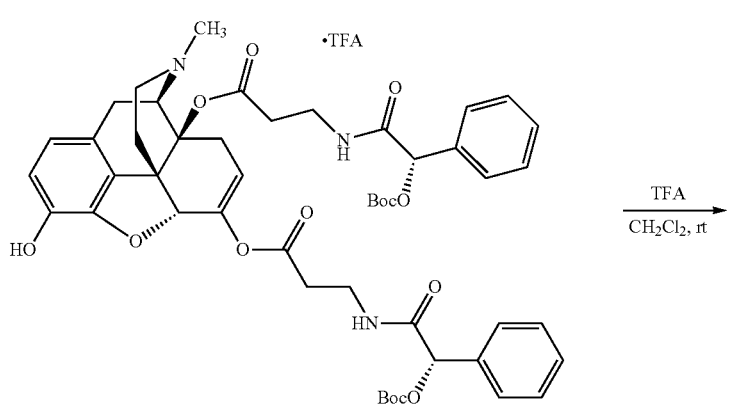

-continued

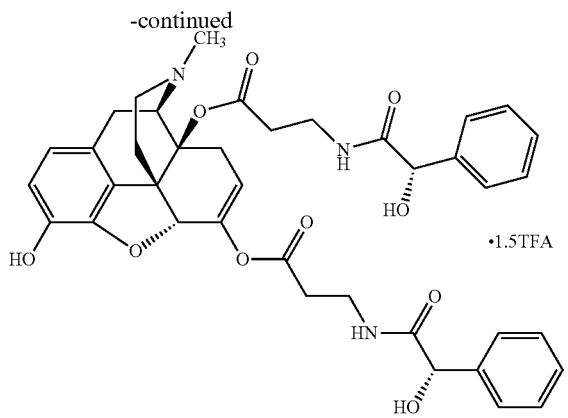

Preparation of (4R,4aS,7aR,12bS)-9-((tert-Butyldimethylsilyl)oxy)-3-methyl-2,3,4,4a,5,7a-hexahydro-1H-4,12-methanobenzofuro[3,2-e]isoquinoline-4a,7-diyl bis(3-((tert-butoxycarbonyl)amino)propanoate)

Preparation of (S)-(4R,4aS,7aR,12bS)-9-((tert-Butyldimethylsilyl)oxy)-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)-2-phenylacetamido)propanoate)

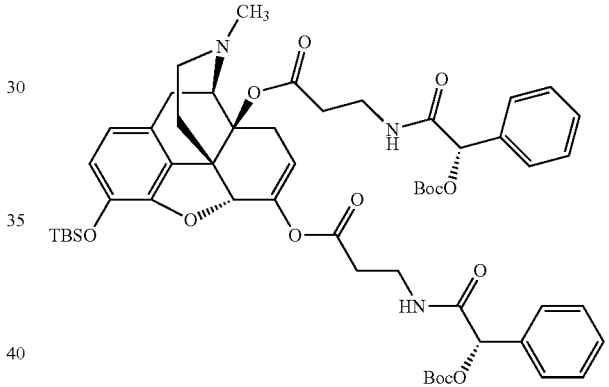

A solution of (4R,4aS,7aR,12bS)-9-((tert-butyldimethylsilyl)oxy)-4a-hydroxy-3-methyl-2,3,4,4a,5,6-hexahydro-1H-4,12-methanobenzofuro[3,2-e]isoquinolin-7(7aH)-one (1.07 g, 2.57 mmol) in tetrahydrofuran (15 mL) was cooled in an ice bath and treated dropwise with a 1.0 M solution of lithium bis(trimethylsilyl)amide in tetrahydrofuran (4.6 mL, 4.6 mmol). After addition was complete, the mixture was stirred at ambient temperature for 10 min. The mixture was re-cooled to −40° C. and treated dropwise with a solution of 2,5-dioxopyrrolidin-1-yl 3-((tert-butoxycarbonyl)amino)propanoate (1.30 g, 4.54 mmol) in tetrahydrofuran (6 mL). After addition was complete, the mixture was stirred at −40° C. for 20 min and then at ambient temperature for 40 min. After this time, the reaction mixture was cooled in an ice bath, treated with saturated aqueous ammonium chloride, and extracted with ethyl acetate. The combined organics were dried over sodium sulfate, filtered, and concentrated under reduced pressure. The residue was purified by column chromatography (silica gel, 0-10% methanol/methylene chloride) to provide (4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl bis(3-((tert-butoxycarbonyl)amino)propanoate) (1.0 g, 66%): ESI MS m/z 758 $[C_{39}H_{59}N_3O_{10}Si+H]^+$.

A solution of (4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl bis(3-((tert-butoxycarbonyl)amino)propanoate) (255 mg, 0.336 mmol) in methylene chloride (5 mL) was treated with trifluoroacetic acid (0.5 mL), and the mixture was stirred at room temperature for 30 min. After this time, LC-MS analysis of the reaction mixture showed cleavage of the Boc protecting groups. N,N-Diisopropylethylamine was added slowly until the reaction mixture tested basic by pH paper analysis (1 mL of base added). The mixture was treated with (S)-2,5-dioxopyrrolidin-1-yl 2-((tert-butoxycarbonyl)oxy)-2-phenylacetate (330 mg, 1.32 mmol) in one portion and stirred at room temperature for 2 h. After this time, the mixture was diluted with ethyl acetate and washed water. The organic extracts were dried over sodium sulfate, filtered, and concentrated. The residue was purified by reversed phase column chromatography (50 g C18 column, 5-100% acetonitrile/water) to provide (S)-(4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)-2-phenylacetamido)propanoate) (254 mg, 73%): ESI MS m/z 1026 $[C_{55}H_{71}N_3O_{14}Si+H]^+$.

Preparation of (S)-(4R,4aS,7aR,12bS)-9-Hydroxy-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)-2-phenylacetamido)propanoate) trifluoroacetic acid salt

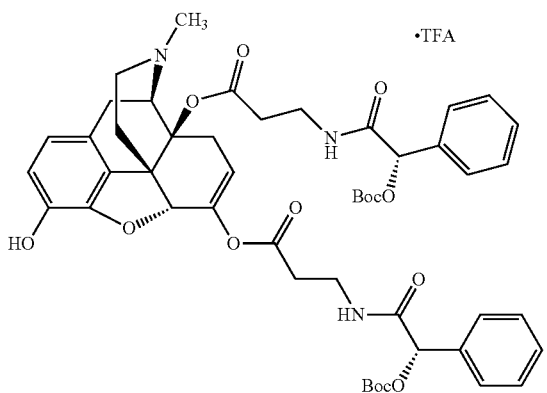

A solution of (S)-(4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)-2-phenylacetamido)propanoate) (250 mg, 0.24 mmol) in tetrahydrofuran (6 mL) was treated with water (4 mL) followed by trifluoroacetic acid (3 mL), and the mixture was stirred at room temperature for 3 h. After this time, the mixture was concentrated, and the residue was azeotroped with toluene to provide (S)-(4R,4aS,7aR,12bS)-9-hydroxy-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)-2-phenylacetamido)propanoate) trifluoroacetic acid salt (270 mg, crude) that was used without purification: ESI MS m/z 912 $[C_{49}H_{57}N_3O_{14}+H]^+$.

Preparation of (S)-(4R,4aS,7aR,12bS)-9-Hydroxy-3-methyl-2,3,4,4a,5,7a-hexahydro-1H-4,12-methanobenzofuro[3,2-e]isoquinoline-4a,7-diyl bis(3-((S)-2-hydroxy-2-phenylacetamido)propanoate) trifluoroacetic acid salt

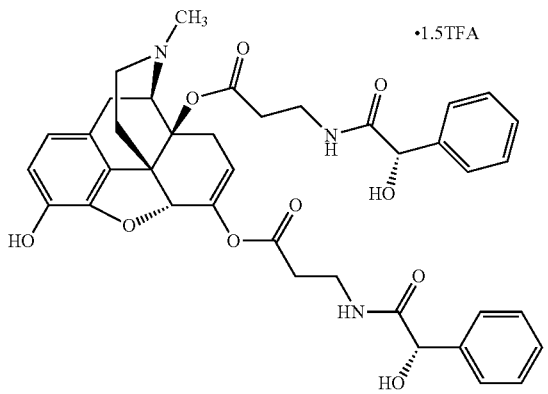 [SMILES: CN1CC[C@]23c4c5ccc(O)c4O[C@H]2C(OC(=O)CCNC(=O)[C@@H](O)c2ccccc2)=CC[C@@]3(OC(=O)CCNC(=O)[C@@H](O)c2ccccc2)[C@H]1C5]

A solution of (S)-(4R,4aS,7aR,12bS)-9-hydroxy-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)-2-phenylacetamido)propanoate) (270 mg) in methylene chloride (6 mL) was treated with trifluoroacetic acid (2 mL) and stirred at ambient temperature for 40 min. After this time, the reaction mixture was concentrated under reduced pressure. The residue was purified by reversed phase column chromatography (50 g C18 column, 5-30% acetonitrile/water, with 0.1% trifluoroacetic acid) and freeze dried to provide (S)-(4R,4aS,7aR,12bS)-9-hydroxy-3-methyl-2,3,4,4a,5,7a-hexahydro-1H-4,12-methanobenzofuro[3,2-e]isoquinoline-4a,7-diyl bis(3-((S)-2-hydroxy-2-phenylacetamido)propanoate) trifluoroacetic acid salt (147 mg, 69% over two steps) as a fluffy white solid: $^1$H NMR (300 MHz, DMSO-$d_6$) δ 9.46 (broad s, 1.5H), 8.24-8.15 (m, 2H), 7.41-7.20 (m, 10H), 6.72 (d, J=8.2 Hz, 1H), 6.66 (d, J=8.2 Hz, 1H), 5.36 (dd, J=6.3, 1.8 Hz, 1H), 5.03 (s, 1H), 4.92-4.90 (m, 2H), 4.68 (d, J=6.3 Hz, 1H), 3.46-3.10 (m, 8H), 3.00-2.71 (m, 5H), 2.69-2.51 (m, 4H), 2.43-2.35 (m, 1H), 2.05 (d, J=18.6 Hz, 1H), 1.76 (d, J=12.6 Hz, 1H); ESI MS m/z 712 $[C_{39}H_{41}N_3O_{10}+H]^+$; HPLC (Method A) 98.9% (AUC), $t_R$=8.66 min.

Scheme 113: (S)-2-Amino-4-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid bis(trifluoroacetic acid salt)

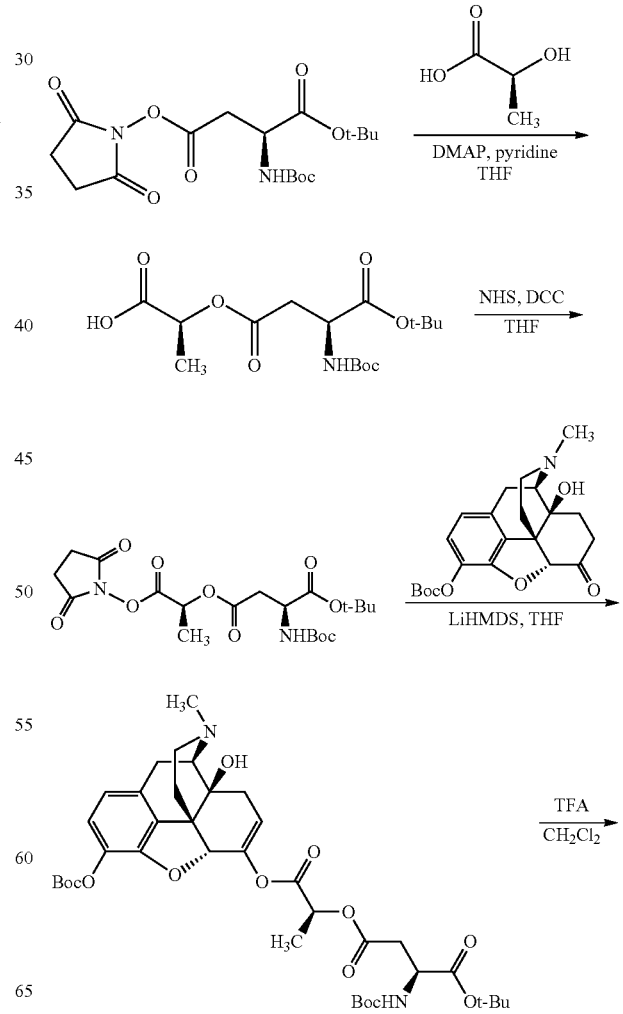

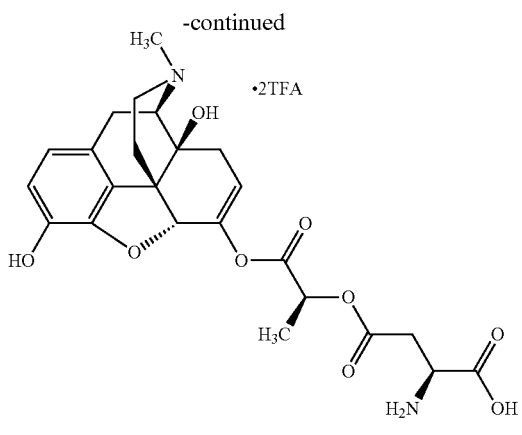
·2TFA

Preparation of (S)-2-(((S)-4-(tert-Butoxy)-3-((tert-butoxycarbonyl)amino)-4-oxobutanoyl)oxy)propanoic acid

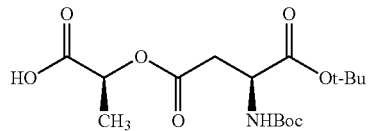

A solution of (S)-1-tert-butyl 4-(2,5-dioxopyrrolidin-1-yl) 2-((tert-butoxycarbonyl)amino)succinate (3.42 g, 8.84 mmol), (S)-lactic acid (963 mg, 10.7 mmol), and 4-dimethylaminopyridine (104 mg, 0.85 mmol) in tetrahydrofuran (40 mL) was treated with pyridine (0.85 mL, 10.6 mmol) and heated at 50° C. under a nitrogen atmosphere for 16 h. After this time, the reaction mixture was cooled to room temperature and concentrated under reduced pressure. The residue was dissolved in ethyl acetate (100 mL) and washed with aqueous 10% citric acid (2×50 mL) and water (50 mL). The organic layer was extracted with saturated aqueous sodium bicarbonate (2×50 mL). The combined aqueous bicarbonate layers were acidified to pH ~2 with 6 N hydrochloric acid and extracted with ethyl acetate (4×50 mL). The combined organics were dried over sodium sulfate, filtered, and concentrated under reduced pressure to provide (S)-2-(((S)-4-(tert-butoxy)-3-((tert-butoxycarbonyl)amino)-4-oxobutanoyl)oxy)propanoic acid (1.47 mg, 46%) as a white semi-solid: $^1$H NMR (300 MHz, CDCl$_3$) δ 5.51-5.48 (m, 1H), 5.17 (q, J=7.2 Hz, 1H), 4.55-4.45 (br m, 1H), 2.92-2.89 (m, 2H), 1.54 (d, J=7.2 Hz, 3H), 1.46 (s, 9H), 1.44 (s, 9H), CO$_2$H proton not observed.

Preparation of (S)-1-tert-Butyl 4-((S)-1-((2,5-dioxopyrrolidin-1-yl)oxy)-1-oxopropan-2-yl) 2-((tert-butoxycarbonyl)amino)succinate

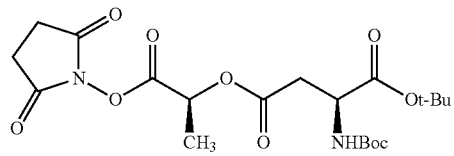 [SMILES: C[C@H](OC(=O)C[C@H](NC(=O)OC(C)(C)C)C(=O)OC(C)(C)C)C(=O)ON1C(=O)CCC1=O]

A solution of (S)-2-(((S)-4-(tert-butoxy)-3-((tert-butoxycarbonyl)amino)-4-oxobutanoyl)oxy)propanoic acid (1.47 g, 4.05 mmol) in tetrahydrofuran (20 mL) was treated with N-hydroxysuccinimide (513 mg, 4.46 mmol) and N,N'-dicyclohexylcarbodiimide (921 mg, 4.46 mmol) and stirred under a nitrogen atmosphere for 4 h. After this time, the reaction mixture was filtered to remove the solid dicyclohexylurea byproduct. The solid was washed with diethyl ether, and the combined filtrate and washings were concentrated under reduced pressure to provide (S)-1-tert-butyl 4-((S)-1-((2,5-dioxopyrrolidin-1-yl)oxy)-1-oxopropan-2-yl) 2-((tert-butoxycarbonyl)amino)succinate (2.04 g, quantitative) as a white foam: $^1$H NMR (300 MHz, CDCl$_3$) δ 5.54-5.48 (m, 1H), 5.42 (q, J=7.2 Hz, 1H), 4.51-4.45 (m, 1H), 3.08-2.82 (m, 6H), 1.68 (d, J=7.2 Hz, 3H), 1.46 (s, 9H), 1.44 (s, 9H).

Preparation of (S)-4-((S)-1-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 1-tert-butyl 2-((tert-butoxycarbonyl)amino)succinate

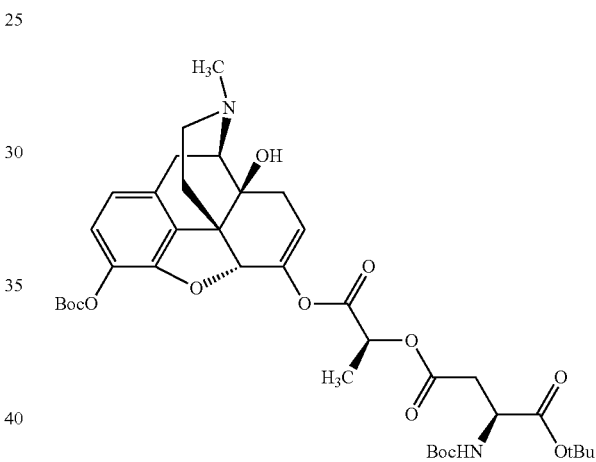

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at ambient temperature for 15 min. The mixture was re-cooled to −45° C. and treated dropwise with a solution of (S)-1-tert-butyl 4-((S)-1-((2,5-dioxopyrrolidin-1-yl)oxy)-1-oxopropan-2-yl) 2-((tert-butoxycarbonyl)amino)succinate (630 mg, 1.37 mmol) in tetrahydrofuran (5 mL). After addition was complete, the mixture was warmed to 0° C. After this time, the reaction mixture was treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-4-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 1-tert-butyl 2-((tert-butoxycarbonyl)amino)succinate (235 mg, 25%) as a white solid: ESI MS m/z 745 $[C_{36}H_{52}N_2O_{13}+H]^+$.

Preparation of (S)-2-Amino-4-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid bis(trifluoroacetic acid salt)

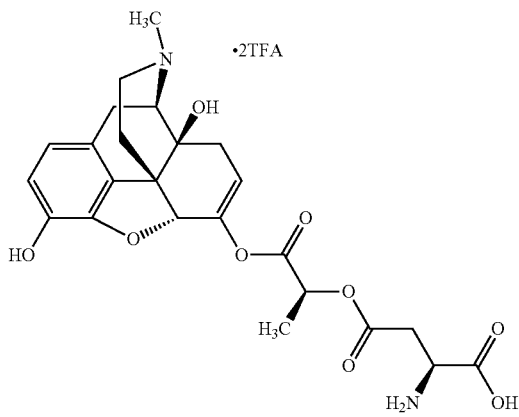 [SMILES: C[C@H](OC(=O)C[C@H](N)C(=O)O)C(=O)OC1=CC[C@@]2(O)[C@H]3Cc4ccc(O)c5c4[C@@]2(CCN3C)[C@H]1O5]

A solution of (S)-4-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 1-tert-butyl 2-((tert-butoxycarbonyl)amino)succinate (90 mg, 0.12 mmol) in methylene chloride (0.8 mL) was treated with trifluoroacetic acid (0.8 mL) and stirred under a nitrogen atmosphere at ambient temperature for 2 h. After this time, the reaction mixture was concentrated under reduced pressure. The residue was purified by reversed phase column chromatography (50 g C18 column, 0-100% acetonitrile/water) and freeze dried to provide (S)-2-amino-4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid bis(trifluoroacetic acid salt) (30.2 mg, 41%) as a fluffy white solid: $^1$H NMR (300 MHz, DMSO-$d_6$) δ 8.33 (br s, 3H), 6.63 (apparent q, J=8.1 Hz, 2H), 5.58 (dd, J=6.0, 2.1 Hz, 1H), 5.01 (q, J=6.9 Hz, 1H), 4.88 (s, 1H), 3.71 (m, 1H), 3.55 (m, 1H), 3.04-2.97 (m, 4H), 2.79-2.72 (m, 4H), 2.63-2.40 (m, 2H), 2.28-2.22 (m, 1H), 2.04 (d, J=18.3 Hz, 1H), 1.60 (d, J=12.6 Hz, 1H), 1.52 (d, J=6.9 Hz, 3H), $CO_2H$ and two OH protons not observed; ESI MS m/z 489 $[C_{24}H_{28}N_2O_9+H]^+$.

Scheme 114: (S)-(4R,4aS,7aR,12bS)-9-Hydroxy-3-methyl-2,3,4,4a,5,7a-hexahydro-1H-4,12-methanobenzofuro[3,2-e]isoquinoline-4a,7-diyl bis(3-((S)-2-hydroxypropanamido)propanoate) trifluoroacetic acid salt

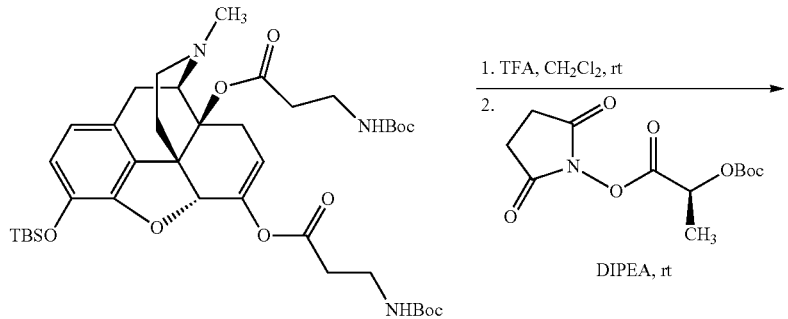

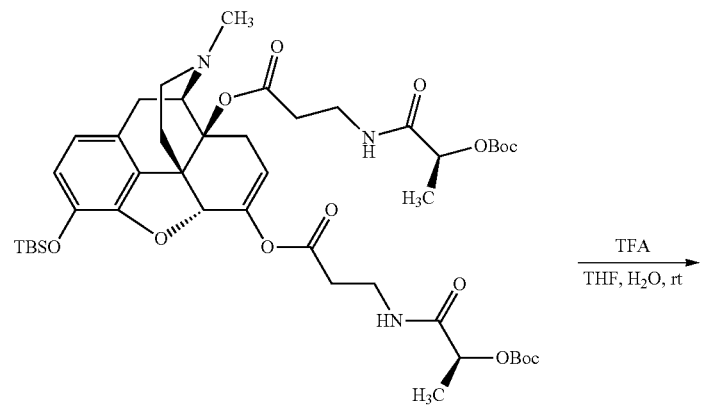

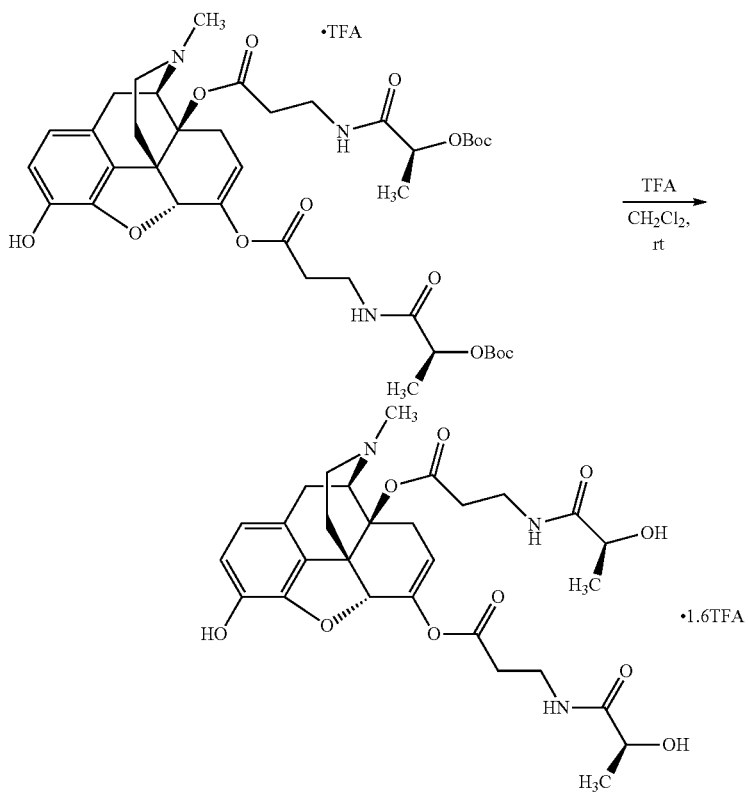

Preparation of (S)-(4R,4aS,7aR,12bS)-9-((tert-Butyldimethylsilyl)oxy)-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)propanamido)propanoate)

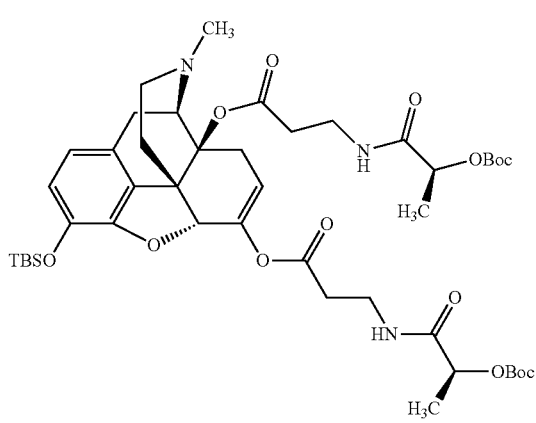

A solution of (4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl bis(3-((tert-butoxycarbonyl)amino)propanoate) (233 mg, 0.307 mmol) in methylene chloride (5 mL) was treated with trifluoroacetic acid (0.5 mL), and the mixture was stirred at room temperature for 40 min. After this time, LC-MS analysis of the reaction mixture showed cleavage of the Boc protecting groups. N,N-Diisopropylethylamine was added slowly until the reaction mixture tested basic by pH paper analysis (1.4 mL of base added). The mixture was treated with (S)-2,5-dioxopyrrolidin-1-yl 2-((tert-butoxycarbonyl)oxy)propanoate (270 mg, 0.94 mmol) in one portion and stirred at room temperature for 30 min. After this time, the mixture was diluted with ethyl acetate and washed water and brine. The organic extracts were dried over sodium sulfate, filtered, and concentrated. The residue was purified by reversed phase column chromatography (50 g C18 column, 10-100% acetonitrile/water) to provide (S)-(4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)propanamido)propanoate) (236 mg, 84%): ESI MS m/z 902 $[C_{45}H_{67}N_3O_{14}Si+H]^+$.

Preparation of (S)-(4R,4aS,7aR,12bS)-9-Hydroxy-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)propanamido)propanoate) trifluoroacetic acid salt

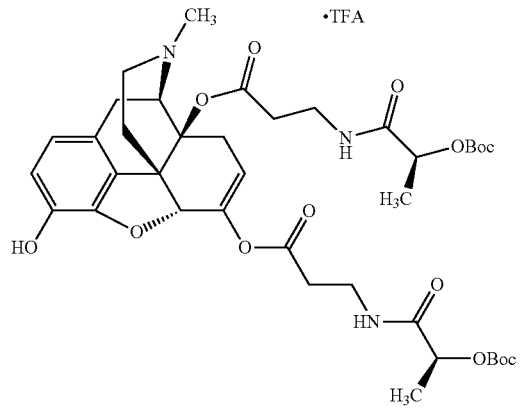

A solution of (S)-(4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)propanamido)propanoate) (235 mg, 0.26 mmol) in tetrahydrofuran (5 mL) was treated with water (4 mL) followed by trifluoroacetic acid (3 mL), and the mixture was stirred at room temperature for 2 h. After this time, the mixture was concentrated, and the residue was azeotroped with toluene to provide (S)-(4R,4aS,7aR,12bS)-9-Hydroxy-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)propanamido)propanoate) trifluoroacetic acid salt (240 mg, crude) that was used without purification: ESI MS m/z 788 $[C_{36}H_{53}N_3O_{14}+H]^+$.

Preparation of (S)-(4R,4aS,7aR,12bS)-9-Hydroxy-3-methyl-2,3,4,4a,5,7a-hexahydro-1H-4,12-methanobenzofuro[3,2-e]isoquinoline-4a,7-diyl bis(3-((S)-2-hydroxypropanamido)propanoate) trifluoroacetic acid salt

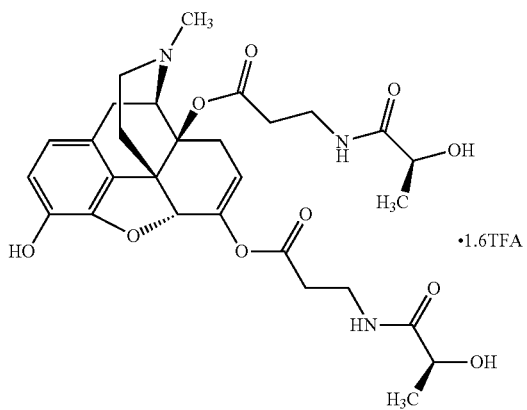 [SMILES: C[C@H](O)C(=O)NCCC(=O)OC1=CC[C@@]2(OC(=O)CCNC(=O)[C@H](C)O)[C@H]3Cc4ccc(O)c5c4[C@@]2(CCN3C)[C@H]1O5]

A solution of (S)-(4R,4aS,7aR,12bS)-9-hydroxy-3-methyl-2,3,4,4a,5,7a-hexahydro-1H-4,12-methanobenzofuro[3,2-e]isoquinoline-4a,7-diyl bis(3-((S)-2-((tert-butoxycarbonyl)oxy)propanamido)propanoate) (240 mg) in methylene chloride (5 mL) was treated with trifluoroacetic acid (0.5 mL) and stirred at ambient temperature for 1 h. After this time, the reaction mixture was concentrated under reduced pressure. The residue was purified by reversed phase column chromatography (50 g C18 column, 5-30% acetonitrile/water, with 0.1% trifluoroacetic acid) and freeze dried to provide (S)-(4R,4aS,7aR,12bS)-9-hydroxy-3-methyl-2,3,4,4a,5,7a-hexahydro-1H-4,12-methanobenzofuro[3,2-e]isoquinoline-4a,7-diyl bis(3-((S)-2-hydroxypropanamido)propanoate) trifluoroacetic acid salt (81 mg, 39% over two steps) as a fluffy white solid: $^1$H NMR (300 MHz, DMSO-$d_6$) δ 9.70-9.40 (m, 1.6H), 7.92-7.84 (m, 2H), 6.73 (d, J=8.2 Hz, 1H), 6.67 (d, J=8.2 Hz, 1H), 5.50 (dd, J=6.3, 1.6 Hz, 1H), 5.06 (s, 1H), 4.73 (d, J=5.7 Hz, 1H), 4.01-3.91 (m, 2H), 3.45-3.13 (m, 10H), 3.17-2.89 (m, 4H), 2.87-2.70 (m, 1H), 2.69-2.52 (m, 4H), 2.47-2.36 (m, 1H), 2.09 (d, J=18.6 Hz, 1H), 1.78 (d, J=12.7 Hz, 1H), 1.21 (d, J=2.7 Hz, 3H), 1.19 (d, J=2.7 Hz, 3H); ESI MS m/z 588 $[C_{29}H_{37}N_3O_{10}+H]^+$; HPLC (Method A)>99% (AUC), $t_R$=6.65 min.

Scheme 115: (S)-(S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl 2-((S)-2-hydroxypropanamido)-4-methylpentanoate trifluoroacetic acid salt

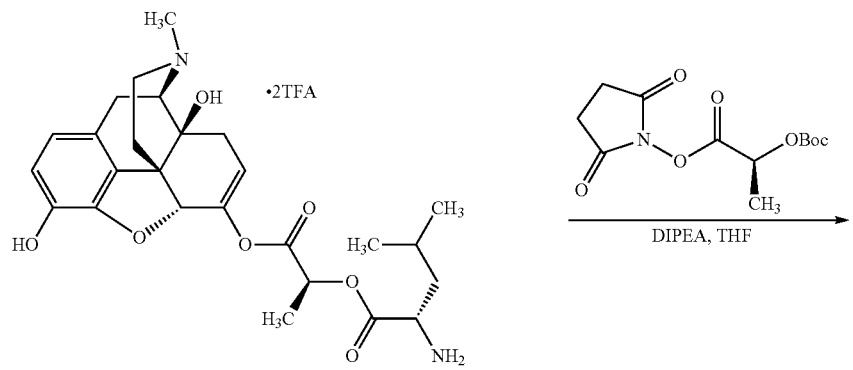

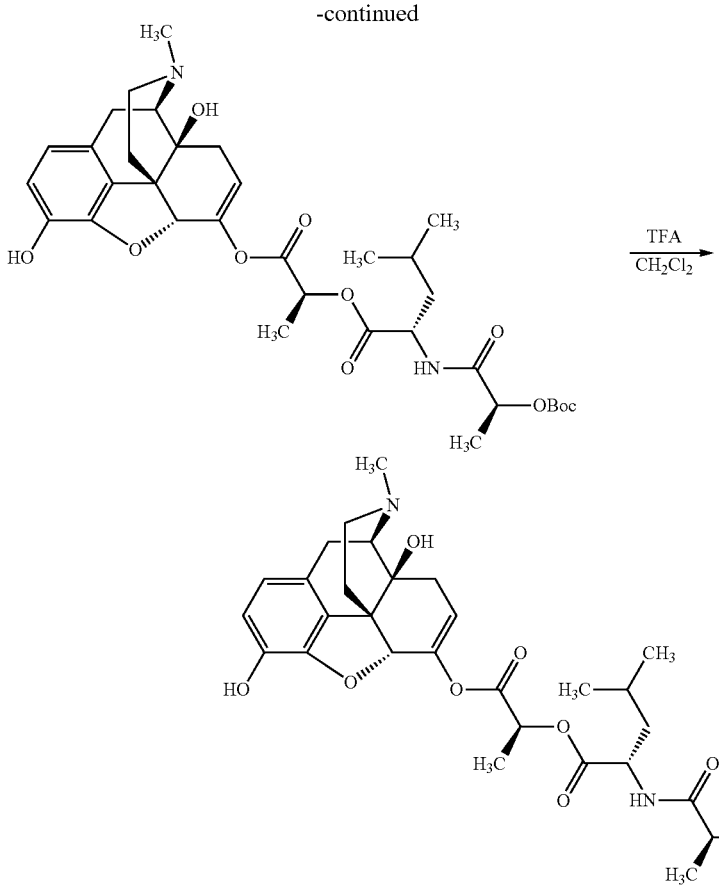

Preparation of (S)-(S)-1-(((4R,4aS,7aR,12bS)-4a,9-Dihydroxy-3-methyl-2,3,4,4a,5,7a-hexahydro-1H-4,12-methanobonzofuro[3,2-e]isoquinolin-7-yl)oxy)-1-oxopropan-2-yl 2-((S)-2-((tert-butoxycarbonyl)oxy)propanamido)-4-methylpentanoate

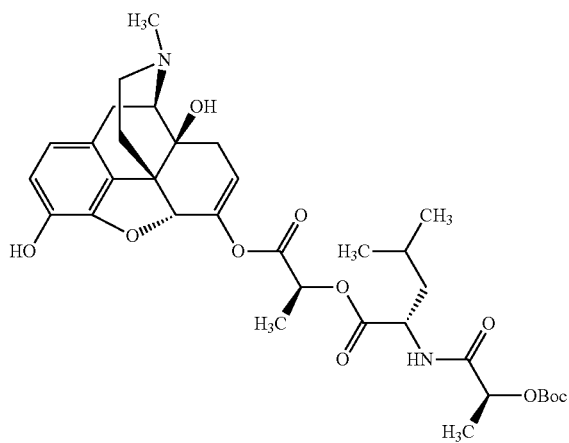

A solution of (S)-(S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-y)oxy)-1-oxopropan-2-yl 2-amino-4-methylpentanoate bis(trifluoroacetic acid salt) (83 mg, 0.12 mmol) in tetrahydrofuran (2 mL) was treated with (S)-2,5-dioxopyrrolidin-1-yl 2-((tert-butoxycarbonyl)oxy)propanoate (22 mg, 0.12 mmol) and N, N-diisopropylethylamine (30 mg, 0.039 mmol) at 0° C. and stirred under a nitrogen atmosphere for 1 h. After this time the reaction mixture was concentrated under reduced pressure. The residue was purified by column chromatography (40 g silica gel column, 0-20% methanol/methylene chloride) to provide (S)-(S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl 2-((S)-2-((tert-butoxycarbonyl)oxy)propanamido)-4-methylpentanoate (54 mg, 70%) as a white solid: ESI MS m/z 659 $[C_{34}H_{46}N_2O_{11}+H]^+$.

Preparation of (S)-(S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl 2-((S)-2-hydroxypropanamido)-4-methylpentanoate trifluoroacetic acid salt

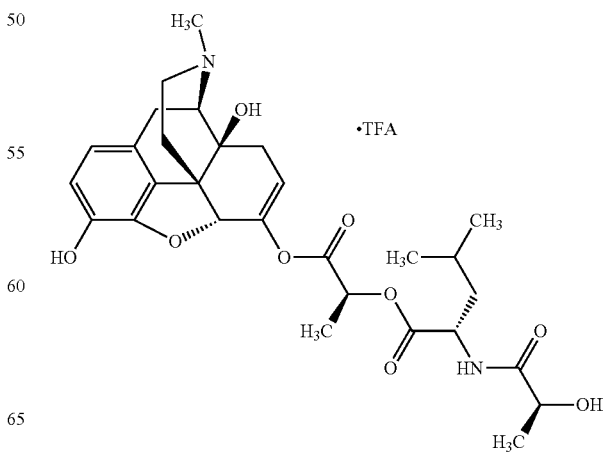

A solution of (S)-(S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl 2-((S)-2-((tert-butoxycarbonyl)oxy)propanamido)-4-methylpentanoate (54 mg, 0.082 mmol) in methylene chloride (1.0 mL) was treated with trifluoroacetic acid (1.0 mL) and stirred under a nitrogen atmosphere at ambient temperature for 2 h. After this time, the reaction mixture was concentrated under reduced pressure. The residue was purified by reversed phase column chromatography (50 g C18 column, 0-100% acetonitrile/water) and freeze dried to provide (S)-(S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl 2-((S)-2-hydroxypropanamido)-4-methylpentanoate trifluoroacetic acid salt (19 mg, 32%) as a fluffy white solid: $^1$H NMR (300 MHz, DMSO-$d_6$) δ 9.30 (s, 1H), 9.14 (br s, 1H), 7.89 (d, J=8.1 Hz, 1H), 6.66 (apparent q, J=8.1 Hz, 1H), 6.23 (s, 1H), 5.58 (dd, J=6.0, 2.1 Hz, 1H), 5.53 (br s, 1H), 5.15 (q, J=6.9 Hz, 1H), 4.96 (s, 1H), 4.40 (m, 1H), 4.01 (m, 1H), 3.62 (m, 1H), 3.11-3.03 (m, 2H), 2.84 (d, J=4.5 Hz, 3H), 2.65 (m, 1H), 2.43 (m, 2H), 2.27 (m, 1H), 2.06 (d, J=17.7 Hz, 1H), 1.75-1.61 (m, 4H), 1.53 (d, J=6.9 Hz, 3H), 1.21 (d, J=6.9 Hz, 3H), 0.91 (d, J=6.0 Hz, 3H), 0.86 (d, J=5.7 Hz, 3H), one proton obscured by solvent peaks; ESI MS m/z 559 $[C_{29}H_{38}N_2O_9+H]^+$.

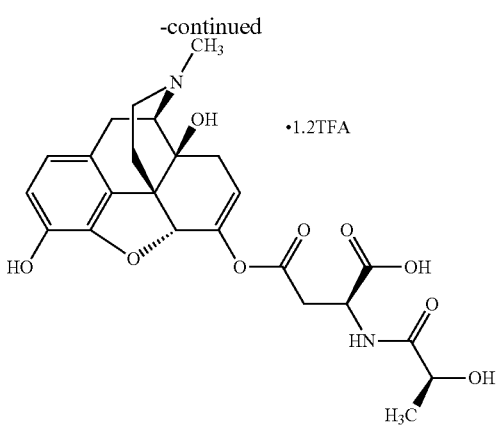

Preparation of (S)-1-tert-Butyl 4-((4R,4aS,7aR,12bS)-4a,9-dihydroxy-3-methyl-2,3,4,4a,5,7a-hexahydro-1H-4,12-methanobenzofuro[3,2-e]isoquinolin-7-yl) 2-((S)-2-((tert-butoxycarbonyl)oxy)propanamido)succinate Scheme 116: (S)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-((S)-2-hydroxypropanamido)-4-oxobutanoic acid trifluoroacetic acid salt

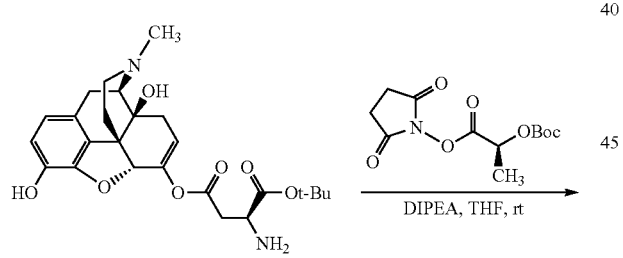

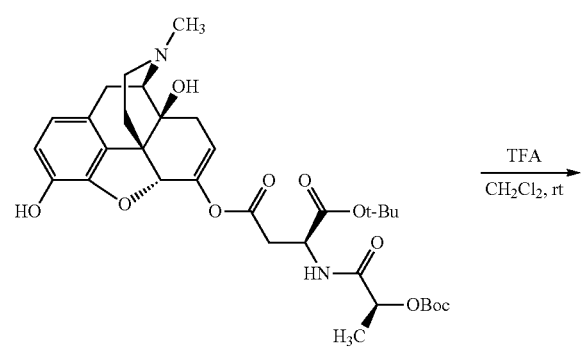

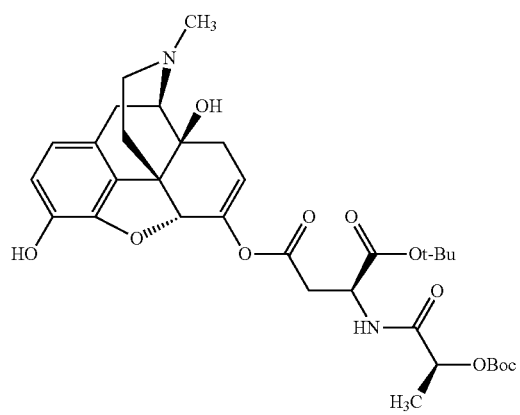

A mixture of (S)-1-tert-butyl 4-((4R,4aS,7aR,12bS)-4a,9-dihydroxy-3-methyl-2,3,4,4a,5,7a-hexahydro-1H-4,12-methanobenzofuro[3,2-e]isoquinolin-7-yl) 2-aminosuccinate trifluoroacetic acid salt (530 mg, 0.90 mmol) and (S)-2,5-dioxopyrrolidin-1-yl 2-((tert-butoxycarbonyl)oxy)propanoate (300 mg, 1.05 mmol) in tetrahydrofuran (6 mL) was treated with N,N-diisopropylethylamine (0.60 mL, 3.4 mmol) and stirred at room temperature for 1 h. After this time, the mixture was diluted with ethyl acetate and washed with water and brine. The organic extracts were dried over sodium sulfate, filtered, and concentrated. The residue was purified by reversed phase column chromatography (50 g C18 column, 5-100% acetonitrile/water) to provide (S)-1-tert-butyl 4-((4R,4aS,7aR,12bS)-4a,9-dihydroxy-3-methyl-2,3,4,4a,5,7a-hexahydro-1H-4,12-methanobenzofuro[3,2-e]isoquinolin-7-yl) 2-((S)-2-((tert-butoxycarbonyl)oxy)propanamido)succinate (120 mg, 19%): ESI MS m/z 645 $[C_{33}H_{44}N_2O_{11}+H]^+$.

717

Preparation of (S)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-((S)-2-hydroxypropanamido)-4-oxobutanoic acid trifluoroacetic acid salt

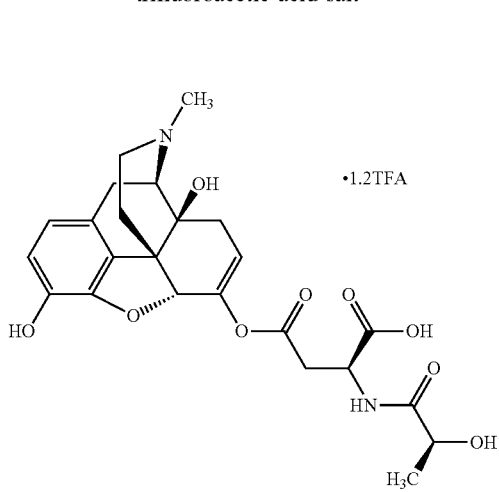

A solution of (S)-1-tert-butyl 4-((4R,4aS,7aR,12bS)-4a,9-dihydroxy-3-methyl-2,3,4,4a,5,7a-hexahydro-1H-4,12-methanobenzofuro[3,2-e]isoquinolin-7-yl) 2-((S)-2-((tert-butoxycarbonyl)oxy)propanamido)succinate (312 mg, 0.484 mmol) in methylene chloride (5 mL) was treated with trifluoroacetic acid (0.8 mL) and stirred at ambient temperature for 1 h. After this time, the reaction mixture was concentrated under reduced pressure. The residue was purified by reversed phase column chromatography (50 g C18 column, 3-20% acetonitrile/water, with 0.1% trifluoroacetic acid) and freeze dried to provide (S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-((S)-2-hydroxypropanamido)-4-oxobutanoic acid trifluoroacetic acid salt (29 mg, 10% over three steps) as a fluffy white solid: $^1$H NMR (300 MHz, DMSO-$d_6$) δ 12.99 (br s, 1H), 9.29 (s, 1H), 9.16 (s, 1H), 8.05 (d, J=8.4 Hz, 1H), 6.67 (d, J=8.2 Hz, 1H), 6.63 (d, J=8.2 Hz, 1H), 6.23 (s, 1H), 5.69 (br s, 1H), 5.52-5.49 (m, 1H), 4.94 (s, 1H), 4.72-4.64 (m, 1H), 4.02 (q, J=6.8 Hz, 1H), 3.61 (d, J=6.1 Hz, 1H), 3.13-3.00 (m, 3H), 3.00-2.87 (m, 2H), 2.87-2.78 (m, 3H), 2.78-2.55 (m, 1H), 2.48-2.38 (m, 1H), 2.27 (dd, J=17.8, 6.1 Hz, 1H), 2.05 (d, J=17.8 Hz, 1H), 1.62 (d, J=12.0 Hz, 1H), 1.22 (d, J=6.8 Hz, 1H), two protons obscured by solvent peaks; ESI MS m/z 489 $[C_{24}H_{28}N_2O_9+H]^+$; HPLC (Method A) 94.8% (AUC), $t_R$=6.33 min.

Scheme 117: (S)-4-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-2-hydroxy-4-oxobutanoic acid hydrochloride

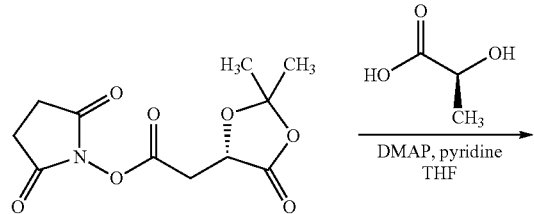

718

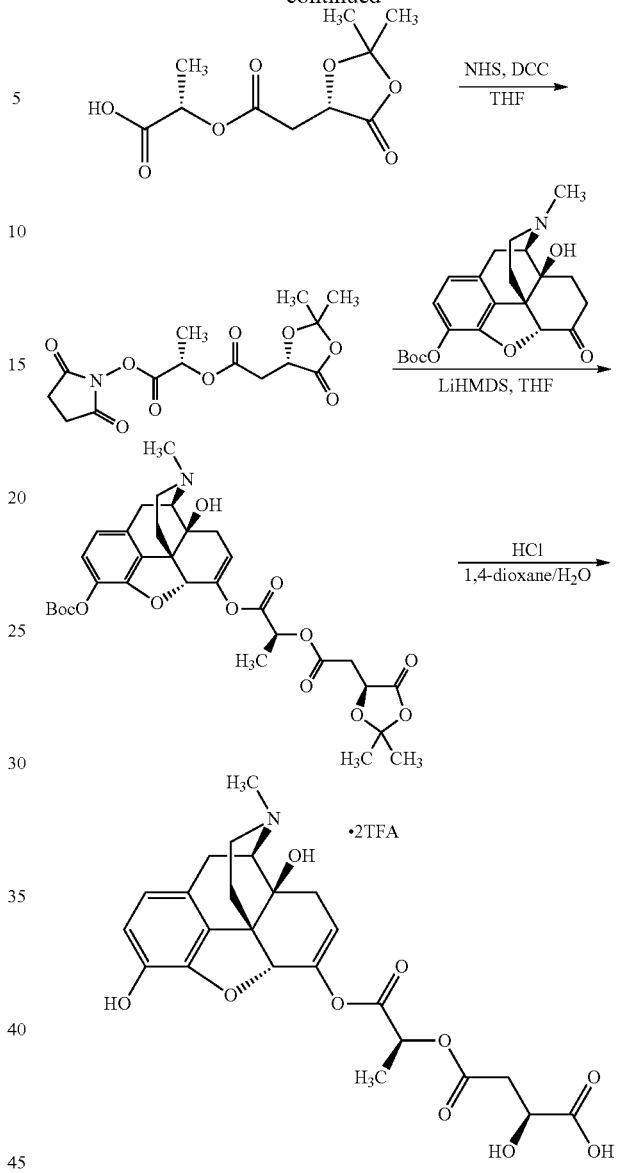

Preparation of (S)-2-(2-((S)-2,2-Dimethyl-5-oxo-1,3-dioxolan-4-yl)acetoxy)propanoic acid

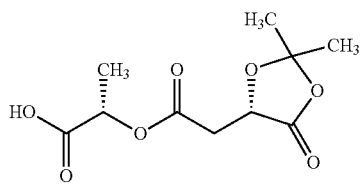

(S)-Lactic acid (399 mg, 4.43 mmol), (S)-2,5-dioxopyrrolidin-1-yl 2-(2,2-dimethyl-5-oxo-1,3-dioxolan-4-yl)acetate (1.00 g, 3.69 mmol), 4-(dimethylamino)pyridine (45 mg, 0.37 mmol), pyridine (350 mg, 4.43 mmol), and tetrahydrofuran (15 mL) were combined and heated at 50° C. under a nitrogen atmosphere for 48 h. After this time, the solvent was removed under reduced pressure, and the residue was partitioned between ethyl acetate (20 mL) and 10% aqueous citric acid. The organic layer was separated and washed with water (50 mL), dried over sodium sulfate, filtered, and concentrated under reduced pressure to provide (S)-2-(2-((S)-2,2-dimethyl-5-oxo-1,3-dioxolan-4-yl)acetoxy)propanoic acid (810 mg, 89%) as a yellow oil: $^1$H NMR (300 MHz, CDCl$_3$) δ 5.19 (m, 1H), 4.74 (m, 1H), 3.03 (td, J=17.1, 3.6 Hz, 1H), 2.88 (m, 1H), 1.69-1.55 (m, 9H), CO$_2$H proton not observed.

Preparation of (S)-2,5-Dioxopyrrolidin-1-yl 2-(2-((S)-2,2-dimethyl-5-oxo-1,3-dioxolan-4-yl)acetoxy)propanoate

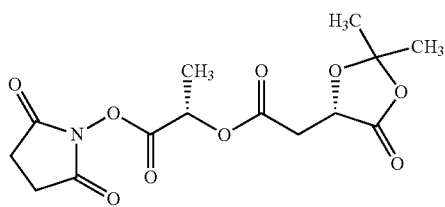 [SMILES: C[C@H](OC(=O)C[C@@H]1OC(C)(C)OC1=O)C(=O)ON1C(=O)CCC1=O]

A solution of (S)-2-(2-((S)-2,2-dimethyl-5-oxo-1,3-dioxolan-4-yl)acetoxy)propanoic acid (810 mg, 3.29 mmol) in tetrahydrofuran (12 mL) was treated with N-hydroxysuccinimide (417 mg, 3.62 mmol) and N,N'-dicyclohexylcarbodiimide (746 mg, 3.62 mmol) and stirred under a nitrogen atmosphere for 5 h. After this time, the reaction mixture was filtered to remove the solid dicyclohexylurea byproduct. The solid was washed with diethyl ether (50 mL), and the combined filtrate and washings were concentrated under reduced pressure. The residue was triturated with diethyl ether to provide (S)-2,5-dioxopyrrolidin-1-yl 2-(2-((S)-2,2-dimethyl-5-oxo-1,3-dioxolan-4-yl)acetoxy)propanoate (1.20 g) as a yellow solid: $^1$H NMR (300 MHz, CDCl$_3$) δ 5.49 (q, J=6.6 Hz, 1H), 4.76 (m, 1H), 3.11 (m, 1H), 3.05 (q, J=3.0 Hz, 1H), 2.85 (s, 4H), 1.73-1.57 (m, 9H).

Preparation of (S)-(4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 2-(2-((S)-2,2-dimethyl-5-oxo-1,3-dioxolan-4-yl)acetoxy)propanoate

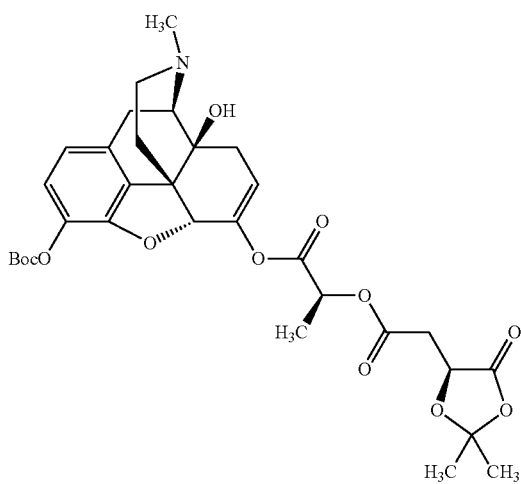

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (425 mg, 1.06 mmol) in tetrahydrofuran (10 mL) was cooled in an ice bath and treated dropwise with a 1.0 M solution of lithium bis(trimethylsilyl)amide in tetrahydrofuran (1.3 mL, 1.3 mmol). After addition was complete, the mixture was stirred at ambient temperature for 15 min. The mixture was re-cooled to −45° C. and treated dropwise with a solution of (S)-2,5-dioxopyrrolidin-1-yl 2-(2-((S)-2,2-dimethyl-5-oxo-1,3-dioxolan-4-yl)acetoxy)propanoate (400 mg, 1.17 mmol) in tetrahydrofuran (5 mL). After addition was complete, the mixture was warmed to 0° C. After this time, the reaction mixture was treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-(2-((S)-2,2-dimethyl-5-oxo-1,3-dioxolan-4-yl)acetoxy)propanoate (159 mg, 23%) as a white solid: $^1$H NMR (300 MHz, CDCl$_3$) δ 6.90 (d, J=8.1 Hz, 1H), 6.66 (d, J=8.4 Hz, 1H), 5.63 (m, 1H), 5.22 (m, 1H), 5.04 (d, J=9.9 Hz, 1H), 4.75 (dd, J=6.9, 3.3 Hz, 1H), 3.19 (d, J=18.6 Hz, 1H), 3.06 (m, 1H), 2.89 (m, 2H), 2.65 (dd, J=18.9, 6.3 Hz, 1H), 2.48-2.08 (m, 4H), 2.39 (s, 3H), 1.62-1.51 (m, 20H), OH proton not observed.

Preparation of (S)-4-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-2-hydroxy-4-oxobutanoic acid hydrochloride

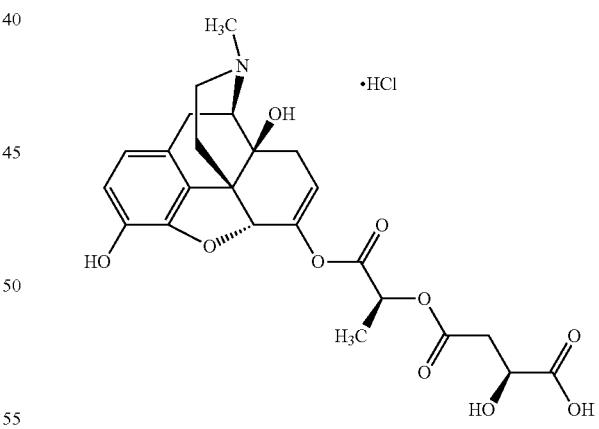

A solution of (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-(2-((S)-2,2-dimethyl-5-oxo-1,3-dioxolan-4-yl)acetoxy)propanoate (159 mg, 0.253 mmol) was treated with a 4.0 M solution of hydrochloric acid in 1,4-dioxane (5 mL, 20.0 mmol) and water (0.2 mL). The reaction mixture was stirred under a nitrogen atmosphere at ambient temperature for 2 h. After this time, the reaction mixture was concentrated under reduced pressure. The residue was purified by reversed phase column chromatography (50 g C18 column, 0-100% acetonitrile/water) and freeze dried to provide (S)-4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-2-hydroxy-4-oxobutanoic acid hydrochloride (52.3 mg, 39%) as a fluffy white solid: $^1$H NMR (300 MHz, DMSO-$d_6$) δ 6.57 (apparent q, J=7.8 Hz, 2H), 5.56 (dd, J=5.7, 2.4 Hz, 1H), 5.10 (q, J=6.9 Hz, 1H), 4.84 (s, 1H), 4.24 (dd, J=8.1, 4.2 Hz, 1H), 3.14 (d, J=18.9 Hz, 1H), 3.01 (m, 1H), 2.79 (dd, J=15.6, 4.2 Hz, 1H), 2.75-2.54 (m, 3H), 2.44 (s, 3H), 2.33-2.13 (m, 2H), 2.09-1.96 (m, 2H), 1.50 (d, J=6.9 Hz, 3H), 1.42 (m, 1H), CO$_2$H, HCl, and OH protons not observed; ESI MS m/z 490 [C$_{24}$H$_{27}$NO$_{10}$+H]$^+$.

Scheme 118: (S)-(S)-2-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-oxo-1-phenylethyl 2-hydroxypropanoate trifluoroaceatic acid salt

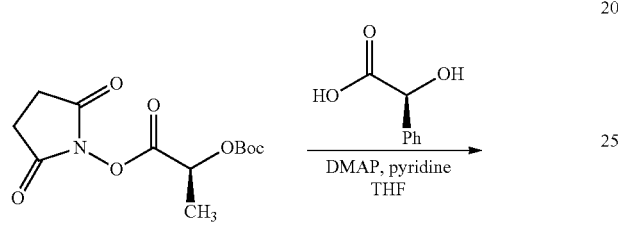

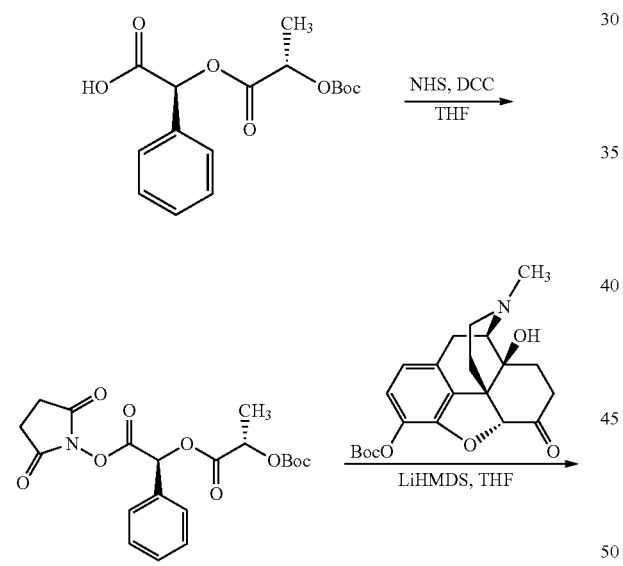

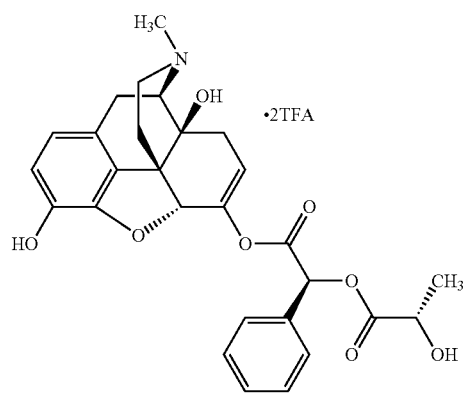

Preparation of (S)-2-(((S)-2-((tert-Butoxycarbonyl)oxy)propanoyl)oxy)-2-phenylacetic acid

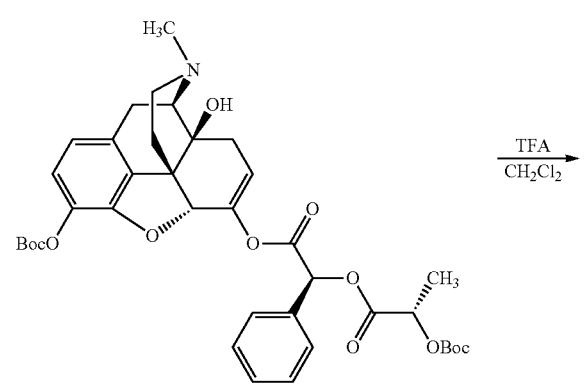

A solution of (S)-2,5-dioxopyrrolidin-1-yl 2-((tert-butoxycarbonyl)oxy)propanoate (2.00 g, 6.96 mmol), mandelic acid (1.28 g, 8.41 mmol), and 4-dimethylaminopyridine (87 mg, 0.71 mmol) in tetrahydrofuran (30 mL) was treated with pyridine (0.67 mL, 8.3 mmol) and heated at 50° C. under a nitrogen atmosphere for 20 h. After this time, the reaction mixture was cooled to room temperature and concentrated under reduced pressure. The residue was dissolved in ethyl acetate (50 mL) and washed with aqueous 10% citric acid (2×25 mL) and water (25 mL). The organic layer was extracted with saturated aqueous sodium bicarbonate (2×25 mL). The combined aqueous bicarbonate layers were acidified to pH ~2 with 6 N hydrochloric acid and extracted with ethyl acetate (4×25 mL). The combined organics were dried over sodium sulfate, filtered, and concentrated under reduced pressure to provide (S)-2-(((S)-2-((tert-butoxycarbonyl)oxy)propanoyl)oxy)-2-phenylacetic acid (1.71 g, 76%) as a colorless oil: $^1$H NMR (300 MHz, CDCl$_3$) δ 7.48-7.36 (m, 5H), 6.00 (s, 1H), 5.06 (q, J=6.9 Hz, 1H), 1.62 (d, J=6.9 Hz, 3H), 1.48 (s, 9H), CO$_2$H proton not observed; ESI MS m/z 647 [(2×C$_{16}$H$_{20}$O$_7$)−H]$^-$.

Preparation of (S)-(S)-2-((2,5-Dioxopyrrolidin-1-yl)oxy)-2-oxo-1-phenylethyl 2-((tert-butoxycarbonyl)oxy)propanoate

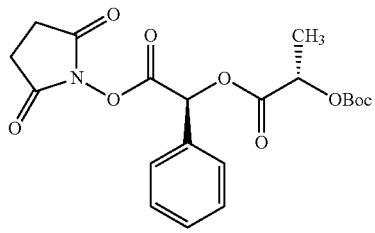

A solution of (S)-2-(((S)-2-((tert-butoxycarbonyl)oxy)propanoyl)oxy)-2-phenylacetic acid (1.71 g, 5.27 mmol) in tetrahydrofuran (20 mL) was treated with N-hydroxysuccinimide (667 mg, 5.80 mmol) and N,N'-dicyclohexylcarbodiimide (1.21 g, 5.86 mmol) and stirred under a nitrogen atmosphere for 2.5 h. After this time, the reaction mixture was filtered to remove the solid dicyclohexylurea byproduct. The solid was washed with diethyl ether, and the combined filtrate and washings were concentrated under reduced pressure to provide (S)-(S)-2-((2,5-dioxopyrrolidin-1-yl)oxy)-2-oxo-1-phenylethyl 2-((tert-butoxycarbonyl)oxy)propanoate (2.21 g, 99%) as an white crushable foam: $^1$H NMR (300 MHz, CDCl$_3$) δ 7.55-7.51 (m, 2H), 7.47-7.42 (m, 3H), 6.39 (s, 1H), 5.05 (q, J=7.2 Hz, 1H), 2.80 (s, 4H), 1.61 (d, J=7.2 Hz, 3H), 1.48 (s, 9H).

Preparation of (S)-(S)-2-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl 2-((tert-butoxycarbonyl)oxy)propanoate

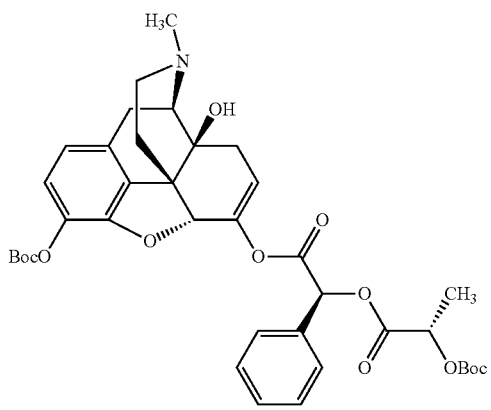

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (800 mg, 1.99 mmol) in tetrahydrofuran (8 mL) was cooled to 0° C. and treated dropwise with a 1.0 M solution of lithium bis(trimethylsilyl)amide in tetrahydrofuran (2.4 mL, 2.4 mmol). After addition was complete, the mixture was stirred at 0° C. for 25 min and then at ambient temperature for 25 min. The mixture was re-cooled to −78° C., and a solution of (S)-(S)-2-((2,5-dioxopyrrolidin-1-yl)oxy)-2-oxo-1-phenylethyl 2-((tert-butoxycarbonyl)oxy)propanoate (1.10 g, 2.59 mmol) in tetrahydrofuran (10 mL) was added. The mixture was allowed to warm to 0° C. over 2 h. After this time, the mixture was treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-(S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl 2-((tert-butoxycarbonyl)oxy)propanoate (685 mg, 56%) as a white solid: ESI MS m/z 708 [C$_{38}$H$_{45}$NO$_{12}$+H]$^+$.

Preparation of (S)-(S)-2-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-oxo-1-phenylethyl 2-hydroxypropanoate trifluoroacetic acid salt

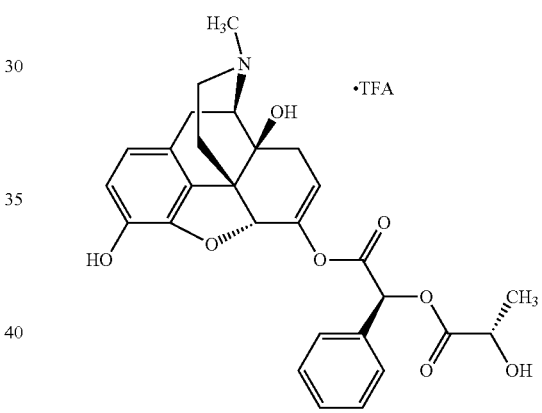

A solution of (S)-(S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl 2-((tert-butoxycarbonyl)oxy)propanoate (100 mg, 0.141 mmol) in methylene chloride (2 mL) was treated with trifluoroacetic acid (2 mL) and stirred under a nitrogen atmosphere at ambient temperature for 2 h. After this time, the reaction mixture was concentrated under reduced pressure. The residue was purified by reversed phase column chromatography (50 g C18 column, 0-100% acetonitrile/water) and freeze dried to provide (S)-(S)-2-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-oxo-1-phenylethyl 2-hydroxypropanoate trifluoroacetic acid salt (52 mg, 59%) as a fluffy white solid: $^1$H NMR (300 MHz, DMSO-d$_6$) δ 9.26 (s, 1H), 9.13 (s, 1H), 7.60-7.56 (m, 2H), 7.49-7.46 (m, 3H), 6.64 (apparent q, J=8.1 Hz, 2H), 6.24 (s, 1H), 6.14 (s, 1H), 5.60-5.54 (m, 2H), 4.87 (t, 1H), 4.31 (m, 1H), 3.03 (m, 1H), 2.82 (m, 3H), 2.64-2.39 (m, 3H), 2.30-2.22 (m, 1H), 2.05 (d, J=18.0 Hz, 1H), 1.59 (d, J=11.4 Hz, 3H), 1.38 (d, J=6.9 Hz, 3H); ESI MS m/z 508 [C$_{28}$H$_{29}$NO$_8$+H]$^+$.

Scheme 119: (S)-2-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-oxo-1-phenylethyl stearate trifluoroacetic acid salt

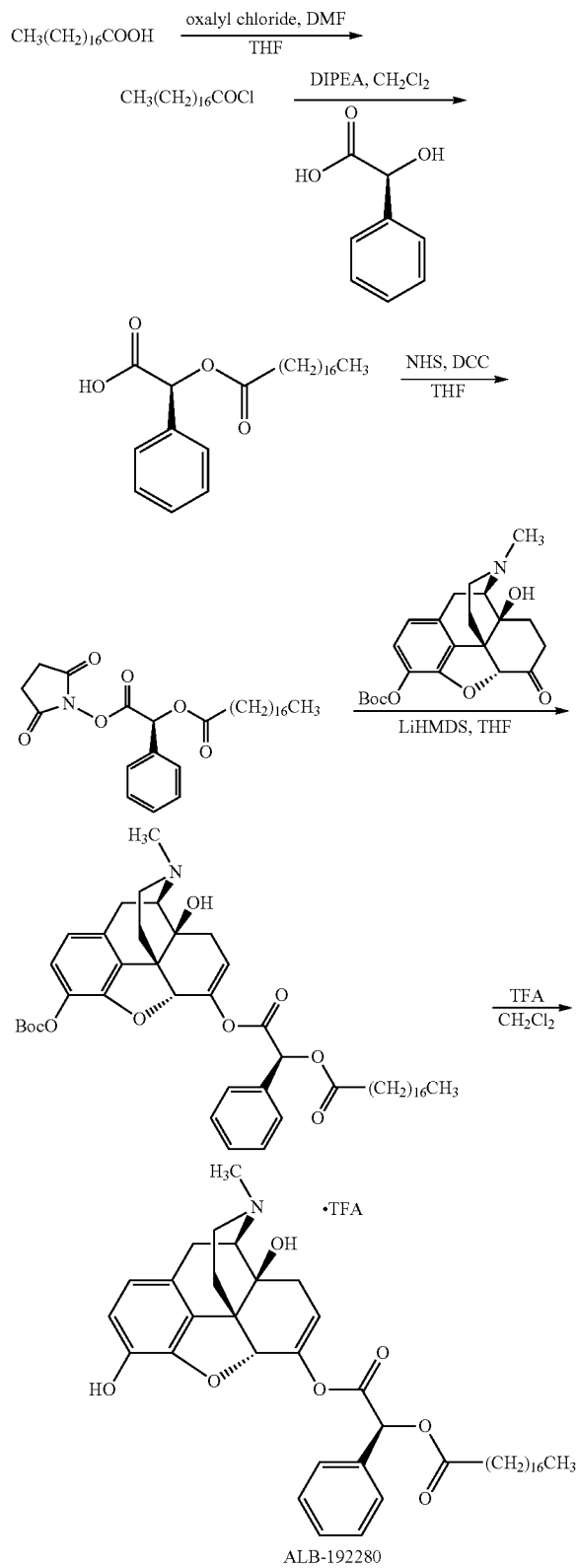

ALB-192280

Preparation of (S)-2-Phenyl-2-(stearoyloxy)acetic acid

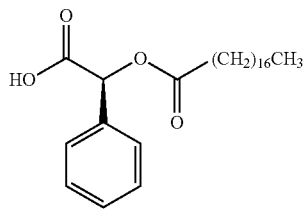

A solution of stearoyl chloride (364 mg, 1.20 mmol) in methylene chloride (5 mL) was cooled in an ice bath and treated with (S)-mandelic acid (182 mg, 1.20 mmol) and N,N-diisopropylethylamine (465 mg, 3.60 mmol) and stirred under a nitrogen atmosphere for 16 h. After this time, 10% aqueous citric acid (10 mL) was added, and the resulting mixture was extracted with ethyl acetate (2×20 mL). The combined organics were washed with brine (50 mL), dried over sodium sulfate, filtered, and concentrated under reduced pressure. The residue was purified by column chromatography (40 g silica gel column, 0-100% ethyl acetate/heptane) to provide of (S)-2-phenyl-2-(stearoyloxy)acetic acid (140 mg, 28%) as a white solid: $^1$H NMR (300 MHz, DMSO-$d_6$) δ 7.51-7.47 (m, 2H), 7.42-7.39 (m, 3H), 5.97 (s, 1H), 2.45 (m, 2H), 1.68 (m, 3H), 1.27 (m, 28H), 0.88 (t, J=6.6 Hz, 3H).

Preparation of (S)-2-((2,5-Dioxopyrrolidin-1-yl)oxy)-2-oxo-1-phenylethyl stearate

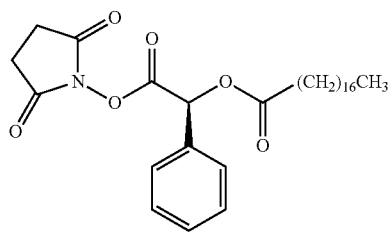

A solution of (S)-2-phenyl-2-(stearoyloxy)acetic acid (140 mg, 0.334 mmol) in tetrahydrofuran (3 mL) was treated with N-hydroxysuccinimide (42 mg, 0.368 mmol) and N,N'-dicyclohexylcarbodiimide (76 mg, 0.368 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-2-((2,5-dioxopyrrolidin-1-yl)oxy)-2-oxo-1-phenylethyl stearate (191 mg) as a white powder: $^1$H NMR (300 MHz, CDCl$_3$) δ 7.56-7.53 (m, 2H), 7.46-7.43 (m, 3H), 6.34 (s, 1H), 2.81 (s, 4H), 2.46 (m, 2H), 1.68 (m, 2H), 1.24 (m, 28H), 0.88 (t, J=6.6 Hz, 3H).

Preparation of (S)-2-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl stearate

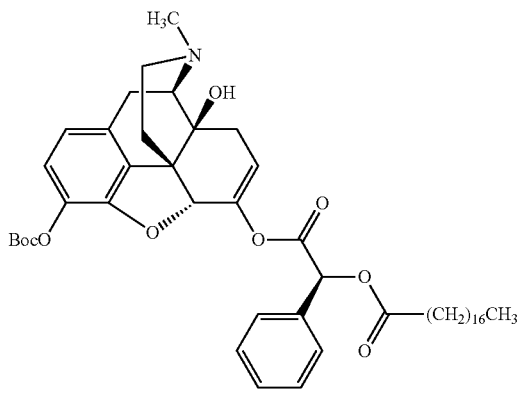

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (122 mg, 0.304 mmol) in tetrahydrofuran (5 mL) was cooled in an ice bath and treated dropwise with a 1.0 M solution of lithium bis(trimethylsilyl)amide in tetrahydrofuran (0.37 mL, 0.37 mmol). After addition was complete, the mixture was stirred at ambient temperature for 15 min. The mixture was re-cooled to −45° C. and treated dropwise with a solution of (S)-2-((2,5-dioxopyrrolidin-1-yl)oxy)-2-oxo-1-phenylethyl stearate (172 mg, 0.334 mmol) in tetrahydrofuran (2 mL). After addition was complete, the mixture was warmed to 0° C. After this time, the reaction mixture was treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (40 g, silica gel, 0-20% methanol/methylene chloride) to provide (S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl stearate (101 mg, 41%) as a white solid: ESI MS m/z 802 [C$_4$H$_{67}$NO$_9$+H]$^+$.

Preparation of (S)-2-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-oxo-1-phenylethyl stearate trifluoroacetic acid salt

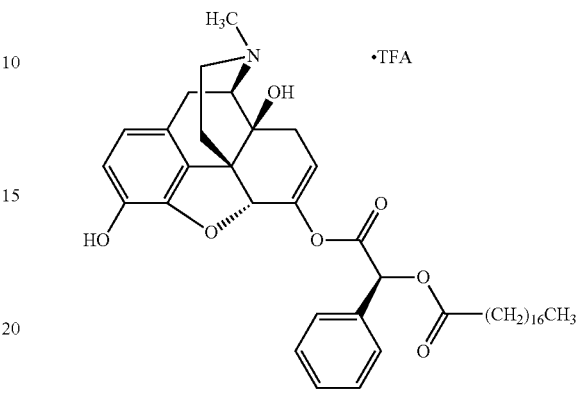

A solution of (S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl stearate (100 mg, 0.126 mmol) in methylene chloride (0.8 mL) was treated with trifluoroacetic acid (0.8 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water) and freeze dried to provide (S)-2-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-oxo-1-phenylethyl stearate trifluoroacetic acid salt (37 mg, 34%) as a fluffy white solid: $^1$H NMR (300 MHz, DMSO-d$_6$) δ 9.25 (s, 1H), 9.13 (s, 1H), 7.58-7.55 (m, 2H), 7.47-7.44 (m, 3H), 6.63 (q, J=8.1 Hz, 2H), 6.23 (s, 1H), 6.09 (s, 1H), 5.58 (dd, J=6.3, 2.1 Hz, 1H), 4.86 (s, 1H), 3.06 (m, 1H), 2.82 (d, J=4.8 Hz, 3H), 2.64-2.22 (m, 6H), 2.05 (m, 1H), 2.58 (m, 3H), 1.23 (m, 30H), 0.85 (t, J=6.9 Hz, 3H); ESI MS m/z 702 [C$_{43}$H$_{59}$NO$_7$+H]$^+$; HPLC (Method A) 98.7% (AUC), t$_R$=16.14 min.

Scheme 120: (S,2S,2'S)-4,4'-(((4R,4aS,7aR,12bS)-9-Hydroxy-3-methyl-2,3,4,4a,5,7a-hexahydro-1H-4,12-methanobenzofuro[3,2-e]isoquinolin-4a,7-diyl)bis(oxy))bis(2-((S)-2-hydroxypropanamido)-4-oxobutanoic acid trifluoroacetic acid salt

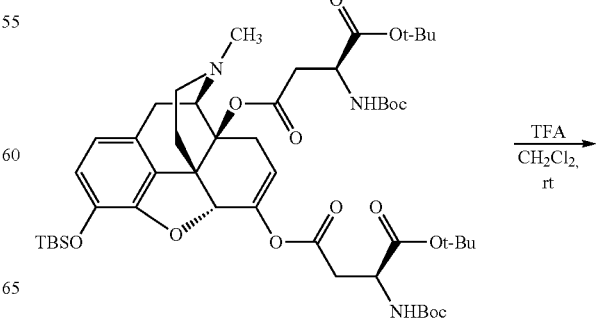

729
-continued

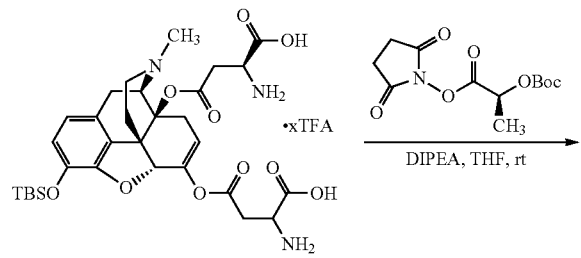

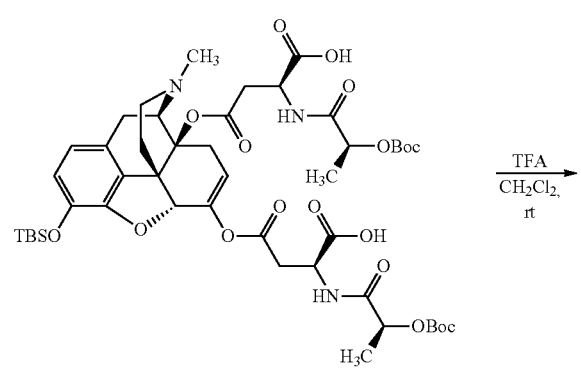

TFA
CH₂Cl₂,
rt

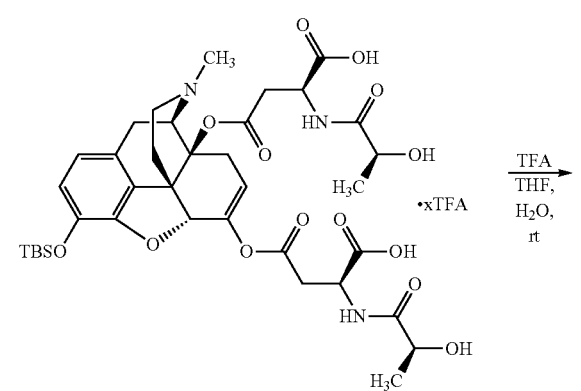

TFA
THF,
H₂O,
rt

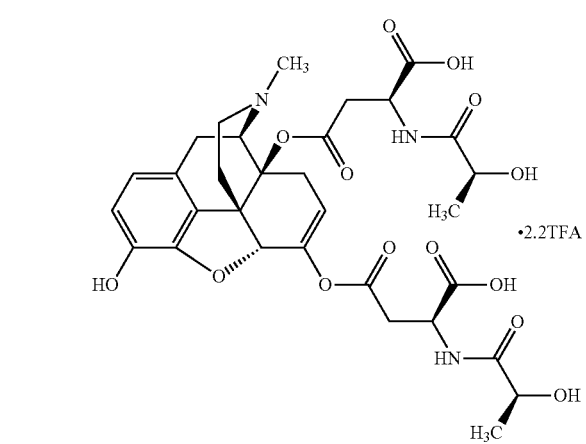

730

Preparation of (2S,2'S)-4,4'-(((4R,4aS,7aR,12bS)-9-((tert-Butyldimethylsilyl)oxy)-3-methyl-2,3,4,4a,5,7a-hexahydro-1H-4,12-methanobenzofuro[3,2-e]isoquinoline-4a,7-diyl)bis(oxy))bis(2-amino-4-oxobutanoic acid) trifluoroacetic acid salt

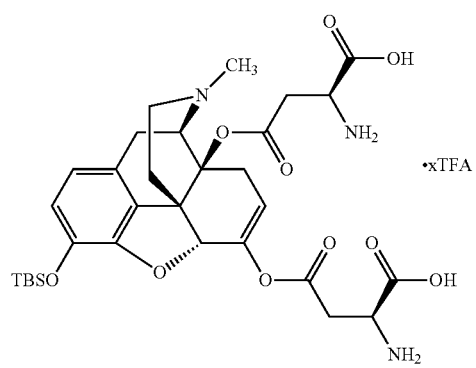 [SMILES: CN1CC[C@]23c4c5ccc(O[Si](C)(C)C(C)(C)C)c4O[C@H]2C(OC(=O)C[C@H](N)C(=O)O)=CC[C@@]3(OC(=O)C[C@H](N)C(=O)O)[C@H]1C5]

A solution of (2S,2'S)-1-di-tert-butyl O'⁴, O⁴-((4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl) bis(2-((tert-butoxycarbonyl)amino)succinate)(155 mg, 0.162 mmol) in methylene chloride (6 mL) was treated with trifluoroacetic acid (0.6 mL) and stirred at ambient temperature for 18 h. After this time, the reaction mixture was concentrated under reduced pressure to obtain (2S,2'S)-4,4'-(((4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl)bis(oxy)) bis(2-amino-4-oxobutanoic acid) trifluoroacetic acid salt (150 mg, quantitative) that was used without purification: ESI MS m/z 646 $[C_{31}H_{43}N_3O_{10}Si+H]^+$.

Preparation of (S,2S,2'S)-4,4'-(((4R,4aS,7aR,12bS)-9-((tert-Butyldimethylsilyl)oxy)-3-methyl-2,3,4,4a,5,7a-hexahydro-1H-4,12-methanobenzofuro[3,2-e]isoquinoline-4a,7-diyl)bis(oxy))bis(2-((S)-2-((tert-butoxycarbonyl)oxy)propanamido)-4-oxobutanoic acid)

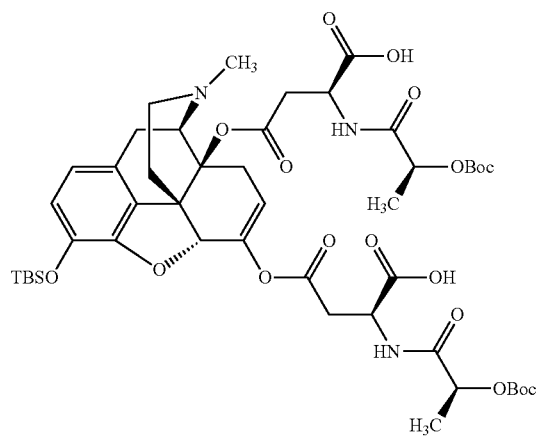

A mixture of (2S,2'S)-4,4'-(((4R,4aS,7aR,12bS)-9-((tert-butyldimethylsilyl)oxy)-3-methyl-2,3,4,4a,5,7a-hexahydro- 1H-4,12-methanobenzofuro[3,2-e]isoquinoline-4a,7-diyl)bis(oxy))bis(2-amino-4-oxobutanoic acid) trifluoroacetic acid salt (150 mg, 0.16 mmol) and (S)-2,5-dioxopyrrolidin-1-yl 2-((tert-butoxycarbonyl)oxy)propanoate (105 mg, 0.366 mmol) in methylene chloride (6 mL) was treated with N,N-diisopropylethylamine (0.20 mL, 1.2 mmol) and stirred at room temperature for 1 h. After this time, the reaction mixture was diluted with ethyl acetate and washed with water and brine. The organic extracts were dried over sodium sulfate, filtered, and concentrated to provide (S,2S,2'S)-4,4'-(((4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl)bis(oxy))bis(2-((S)-2-((tert-butoxycarbonyl)oxy)propanamido)-4-oxobutanoic acid) (130 mg) that was used without purification: ESI MS m/z 990 $[C_{47}H_{67}N_3O_{18}Si+H]^+$.

Preparation of (S,2S,2'S)-4,4'-(((4R,4aS,7aR,12bS)-9-((tert-Butyldimethylsilyl)oxy)-3-methyl-2,3,4,4a,5,7a-hexahydro-1H-4,12-methanobenzofuro[3,2-e]isoquinoline-4a,7-diyl)bis(oxy))bis(2-((S)-2-hydroxypropanamido)-4-oxobutanoic acid) trifluoroacetic acid salt

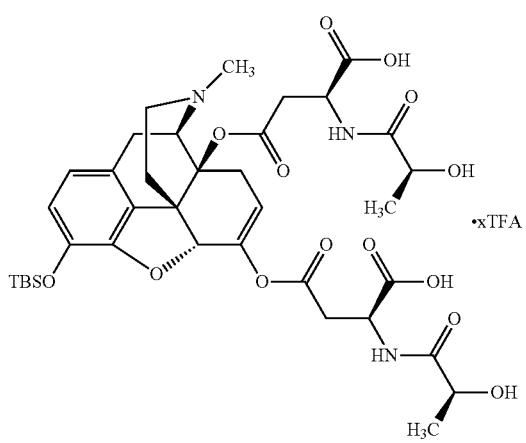 [SMILES: C[C@H](O)C(=O)N[C@@H](CC(=O)OC1=CC[C@@]2(OC(=O)C[C@H](NC(=O)[C@H](C)O)C(=O)O)[C@H]3Cc4ccc(O[Si](C)(C)C(C)(C)C)c5c4[C@@]2(CCN3C)[C@H]1O5)C(=O)O]

A solution of (S,2S,2'S)-4,4'-(((4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl)bis(oxy))bis(2-((S)-2-((tert-butoxycarbonyl)oxy)propanamido)-4-oxobutanoic acid) (130 mg) in methylene chloride (6 mL) was treated with trifluoroacetic acid (2 mL) and stirred at ambient temperature for 30 min. After this time, the reaction mixture was concentrated under reduced pressure to provide (S,2S,2'S)-4,4'-(((4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl)bis(oxy))bis(2-((S)-2-hydroxypropanamido)-4-oxobutanoic acid) trifluoroacetic acid salt (130 mg) that was used without purification: ESI MS m/z 790 $[C_{37}H_{51}N_3O_{14}Si+H]^+$.

Preparation of (S,2S,2'S)-4,4'-(((4R,4aS,7aR,12bS)-9-Hydroxy-3-methyl-2,3,4,4a,5,7a-hexahydro-1H-4,12-methanobenzofuro[3,2-e]isoquinoline-4a,7-diyl)bis(oxy))bis(2-((S)-2-hydroxypropanamido)-4-oxobutanoic acid) trifluoroacetic acid salt

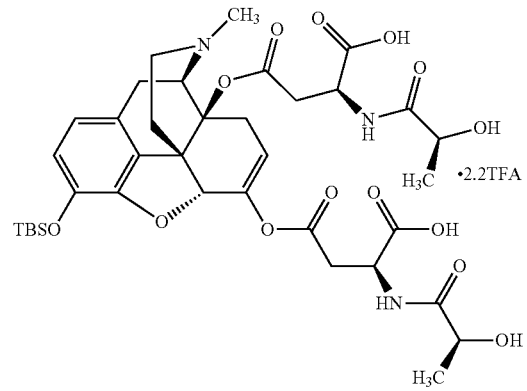 [SMILES: C[C@H](O)C(=O)N[C@@H](CC(=O)OC1=CC[C@@]2(OC(=O)C[C@H](NC(=O)[C@H](C)O)C(=O)O)[C@H]3Cc4ccc(O[Si](C)(C)C(C)(C)C)c5c4[C@@]2(CCN3C)[C@H]1O5)C(=O)O]

A solution of (S,2S,2'S)-4,4'-(((4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl)bis(oxy))bis(2-((S)-2-hydroxypropanamido)-4-oxobutanoic acid) (130 mg) in tetrahydrofuran (4 mL) and water (3 mL) was treated with trifluoroacetic acid (3 mL) and stirred at room temperature for 1.5 h. After this time, the mixture was concentrated. The residue was purified by reversed phase column chromatography (50 g C18 column, 3-20% acetonitrile/water, with 0.1% trifluoracetic acid) and freeze dried to provide (S,2S,2'S)-4,4'-(((4R,4aS,7aR,12bS)-9-hydroxy-3-methyl-2,3,4,4a,5,7a-hexahydro-1H-4,12-methanobenzofuro[3,2-e]isoquinoline-4a,7-diyl)bis(oxy))bis(2-((S)-2-hydroxypropanamido)-4-oxobutanoic acid) trifluoroacetic acid salt (40 mg, 27% over three steps) as a fluffy white solid: $^1H$ NMR (300 MHz, DMSO-$d_6$) δ 12.97 (br s, 1H), 9.40 (br s, 2H), 8.10 (d, J=8.4 Hz, 1H), 7.95 (d, J=8.0 Hz, 1H), 6.72 (d, J=8.2 Hz, 1H), 6.66 (d, J=8.2 Hz, 1H), 5.42 (dd, J=6.1, 1.7 Hz, 1H), 5.01 (s, 1H), 4.76-4.60 (m, 3H), 4.06-3.98 (m, 2H), 2.30-3.10 (m, 4H), 3.09-2.56 (m, 10H), 2.48-2.33 (m, 2H), 2.11 (d, J=19.0 Hz, 1H), 1.78 (d, J=12.8 Hz, 1H), 1.21 (d, J=6.8 Hz, 6H); ESI MS m/z 676 $[C_{31}H_{37}N_3O_{14}+H]^+$.

Scheme 121: (S)-(4R,4aS,7aR,12bS)-4a,9-Dihydroxy-3-methyl-2,3,4,4a,5,7a-hexahydro-1H-4, 12-methanobenzofuro[3,2-e]isoquinolin-7-yl 2-((S)-2-hydroxy-2-phenylacetoxy)propanoate trifluoroacetic acid salt

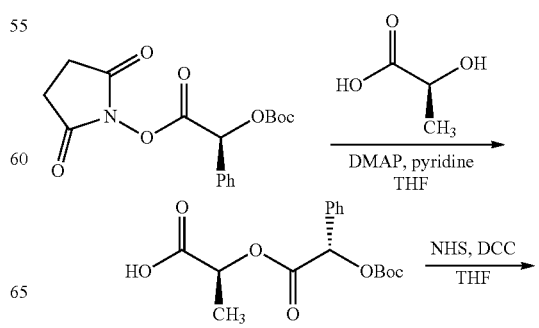

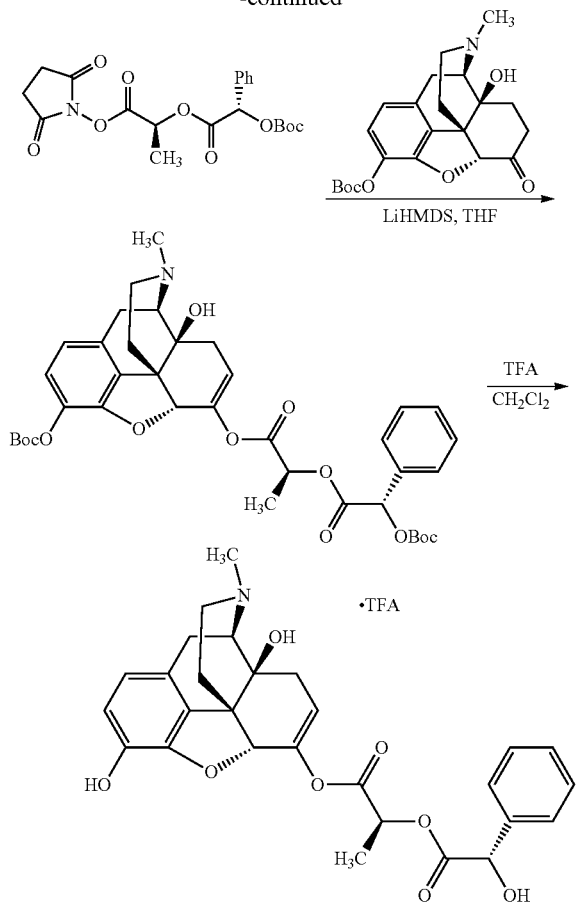

Preparation of (S)-2-((S)-2-((tert-Butoxycarbonyl)oxy)-2-phenylacetoxy)propanoic acid

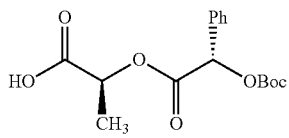

A solution of (S)-2,5-dioxopyrrolidin-1-yl 2-((tert-butoxycarbonyl)oxy)-2-phenylacetate (2.00 g, 5.73 mmol), lactic acid (627 mg, 6.96 mmol), and 4-dimethylaminopyridine (68 mg, 0.56 mmol) in tetrahydrofuran (25 mL) was treated with pyridine (0.56 g, 7.0 mmol) and heated at 50° C. under a nitrogen atmosphere for 16 h. After this time, the reaction mixture was cooled to room temperature and concentrated under reduced pressure. The residue was dissolved in ethyl acetate (50 mL) and washed with aqueous 10% citric acid (2×25 mL) and water (25 mL). The organic layer was extracted with saturated aqueous sodium bicarbonate (2×25 mL). The combined aqueous bicarbonate layers were acidified to pH ~2 with 6 N hydrochloric acid and extracted with ethyl acetate (4×25 mL). The combined organics were dried over sodium sulfate, filtered, and concentrated under reduced pressure to provide (S)-2-((S)-2-((tert-butoxycarbonyl)oxy)-2-phenylacetoxy)propanoic acid (1.42 g, 76%) as a colorless oil: $^1$H NMR (300 MHz, CDCl$_3$) δ 7.52-7.48 (m, 2H), 7.40-7.37 (m, 3H), 5.85 (s, 1H), 5.23 (q, J=6.9 Hz, 1H), 1.56-1.44 (m, 12H), CO$_2$H proton not observed; ESI MS m/z 647 [(2×C$_{16}$H$_{20}$O$_7$)–H]$^-$.

Preparation of (S)-2,5-Dioxopyrrolidin-1-yl 2-((S)-2-((tert-butoxycarbonyl)oxy)-2-phenylacetoxy)propanoate

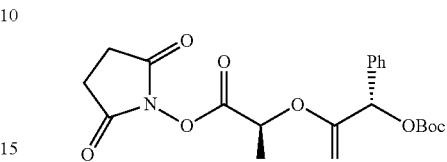

A solution of (S)-2-((S)-2-((tert-butoxycarbonyl)oxy)-2-phenylacetoxy)propanoic acid (1.42 g, 4.36 mmol) in tetrahydrofuran (20 mL) was treated with N-hydroxysuccinimide (558 mg, 4.85 mmol) and N,N'-dicyclohexylcarbodiimide (997 mg, 4.83 mmol) and stirred under a nitrogen atmosphere for 2.5 h. After this time, the reaction mixture was filtered to remove the solid dicyclohexylurea byproduct. The solid was washed with diethyl ether, and the combined filtrate and washings were concentrated under reduced pressure to provide (S)-2,5-dioxopyrrolidin-1-yl 2-((S)-2-((tert-butoxycarbonyl)oxy)-2-phenylacetoxy)propanoate (2.02 g, quantitative) as a white crushable foam: $^1$H NMR (300 MHz, CDCl$_3$) δ 7.51-7.45 (m, 2H), 7.40-7.34 (m, 3H), 5.85 (s, 1H), 5.53 (q, J=6.9 Hz, 1H), 2.82 (br s, 4H), 1.69 (d, J=6.9 Hz, 3H), 1.51 (s, 9H).

Preparation of (S)-(4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 2-((S)-2-((tert-butoxycarbonyl)oxy)-2-phenylacetoxy)propanoate

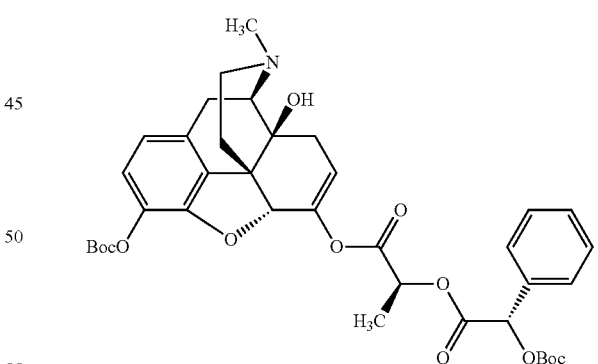

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at ambient temperature for 15 min. The mixture was re-cooled to −45° C. and treated dropwise with a solution of (S)-2,5-dioxopyrrolidin-1-yl 2-((S)-2-((tert-butoxycarbonyl)oxy)-2-phenylacetoxy)propanoate (577 mg, 1.37 mmol)

in tetrahydrofuran (2 mL). After addition was complete, the mixture was warmed to 0° C. After this time, the reaction mixture was treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-((S)-2-((tert-butoxycarbonyl)oxy)-2-phenylacetoxy)propanoate (301 mg, 34%) as a white solid: ESI MS m/z 708 [C38H$_{45}$NO$_{12}$+H]$^+$.

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((S)-2-hydroxy-2-phenylacetoxy)propanoate trifluoroacetic acid salt

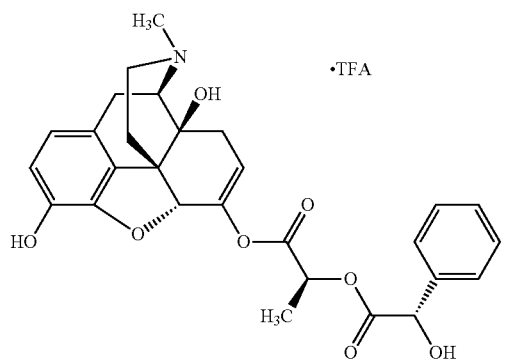 [SMILES: C[C@H](OC(=O)[C@@H](O)c1ccccc1)C(=O)OC1=CC[C@@]2(O)[C@H]3Cc4ccc(O)c5c4[C@@]2(CCN3C)[C@H]1O5]

A solution of (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-((S)-2-((tert-butoxycarbonyl)oxy)-2-phenylacetoxy)propanoate (150 mg, 0.212 mmol) in methylene chloride (2.0 mL) was treated with trifluoroacetic acid (2.0 mL) and stirred under a nitrogen atmosphere at ambient temperature for 2 h. After this time, the reaction mixture was concentrated under reduced pressure. The residue was purified by reversed phase column chromatography (50 g C18 column, 0-100% acetonitrile/water) and freeze dried to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((S)-2-hydroxy-2-phenylacetoxy)propanoate trifluoroacetic acid salt (49.6 mg, 37%) as a fluffy white solid: $^1$H NMR (300 MHz, DMSO-d$_6$) δ 9.29 (s, 1H), 9.14 (s, 1H), 7.46-7.43 (m, 2H), 7.38-7.27 (m, 3H), 6.64 (apparent q, J=8.1 Hz, 2H), 6.21 (s, 1H), 6.16 (d, J=5.7 Hz, 1H), 5.49 (dd, J=5.7, 2.1 Hz, 1H), 5.24-5.15 (m, 2H), 4.82 (s, 1H), 3.06 (m, 1H), 2.83 (d, J=4.2 Hz, 3H), 2.63-2.22 (m, 6H), 2.03 (d, J=18.0 Hz, 1H), 1.60 (d, J=10.2 Hz, 1H), 1.50 (d, J=6.9 Hz, 3H); ESI MS m/z 508 [C$_{28}$H$_{29}$NO$_8$+H]$^+$.

Scheme 122: 4-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt

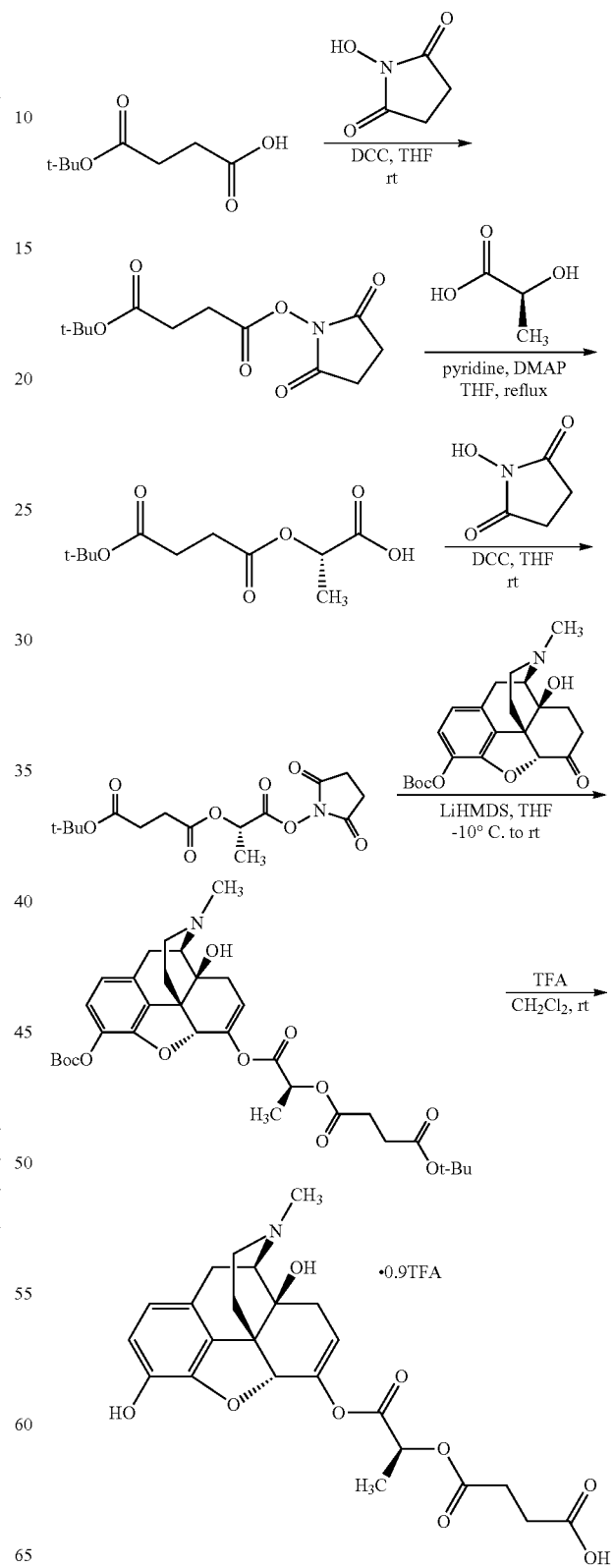

Preparation of tert-Butyl (2,5-dioxopyrrolidin-1-yl) succinate

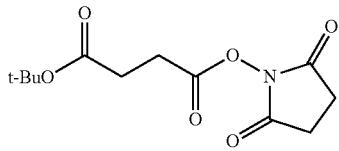 [SMILES: CC(C)(C)OC(=O)CCC(=O)ON1C(=O)CCC1=O]

A mixture of 4-(tert-butoxy)-4-oxobutanoic acid (9.75 g, 56.0 mmol) and N-hydroxysuccinimide (7.00 g, 60.8 mmol) in tetrahydrofuran (280 mL) at 0° C. was treated with N,N'-dicyclohexylcarbodiimide (12.5 g, 60.8 mmol). The ice bath was removed, and the reaction mixture was stirred at ambient temperature for 4 h. After this time, diethyl ether (100 mL) was added, and the mixture was filtered. The filtrate was concentrated under reduced pressure to provide tert-butyl (2,5-dioxopyrrolidin-1-yl) succinate (15.0 g) that was used without purification: $^1$H NMR (300 MHz, CDCl$_3$) δ 2.91 (t, J=7.2 Hz, 2H), 2.83 (s, 4H), 2.66 (t, J=7.2 Hz, 2H), 1.46 (s, 9H).

Preparation of (S)-2-((4-(tert-Butoxy)-4-oxobutanoyl)oxy)propanoic acid

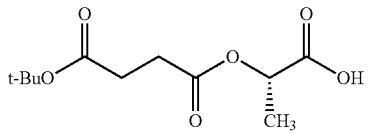

A mixture of tert-butyl (2,5-dioxopyrrolidin-1-yl) succinate (7.60 g, 28.0 mmol), (S)-2-hydroxypropanoic acid (3.00 g, 33.3 mmol), pyridine (2.7 mL, 33.5 mmol), and 4-dimethylaminopyridine (200 mg, 1.6 mmol) in tetrahydrofuran (120 mL) was stirred at reflux for 24 h. After this time, the mixture was cooled to room temperature, partially concentrated under reduced pressure, diluted with ethyl acetate, and washed with 10% citric acid. The organic layer was extracted with saturated sodium bicarbonate. The aqueous extract was carefully treated with 2 N hydrochloric acid until acidic by pH paper analysis, and then extracted with ethyl acetate. The organic extracts were dried over sodium sulfate, filtered, and concentrated to give (S)-2-((4-(tert-butoxy)-4-oxobutanoyl)oxy)propanoic acid (4.84 g, 70%): ESI MS m/z 245 [C$_{11}$H$_{18}$O$_6$–H]$^-$

Preparation of (S)-tert-Butyl (1-((2,5-dioxopyrrolidin-1-yl)oxy)-1-oxopropan-2-yl) succinate

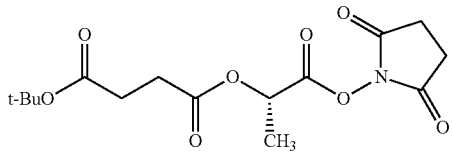 [SMILES: C[C@H](OC(=O)CCC(=O)OC(C)(C)C)C(=O)ON1C(=O)CCC1=O]

A mixture of (S)-2-((4-(tert-butoxy)-4-oxobutanoyl)oxy) propanoic acid (4.80 g, 19.5 mmol) and N-hydroxysuccinimide (2.50 g, 21.7 mmol) in tetrahydrofuran (100 mL) at 0° C. was treated with N,N'-dicyclohexylcarbodiimide (4.45 g, 21.6 mmol). The ice bath was removed, and the reaction mixture was stirred at ambient temperature for 4 h. After this time, diethyl ether (100 mL) was added, and the mixture was filtered. The filtrate was concentrated under reduced pressure to provide (S)-tert-butyl (1-((2,5-dioxopyrrolidin-1-yl) oxy)-1-oxopropan-2-yl) succinate (6.85 g) that was used without purification: $^1$H NMR (300 MHz, CDCl$_3$) δ 5.44 (q, J=7.1 Hz, 1H), 2.84 (s, 4H), 2.72-2.52 (m, 4H), 1.68 (d, J=7.1 Hz, 3H), 1.44 (s, 9H).

Preparation of (S)-1-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e] isoquinolin-7-yl)oxy)-1-oxopropan-2-yl tert-butyl succinate

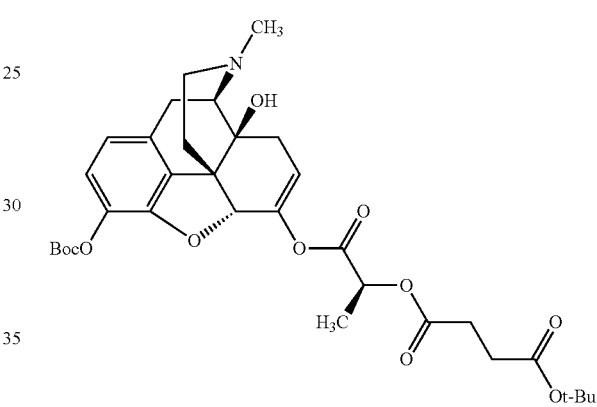

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.24 mmol) in tetrahydrofuran (10 mL) was cooled to −10° C. and treated dropwise with a 1.0 M solution of lithium bis(trimethylsilyl)amide in tetrahydrofuran (1.4 mL, 1.4 mmol). After addition was complete, the mixture was stirred at ambient temperature for 10 min. The mixture was re-cooled to −10° C., and a solution of (S)-tert-butyl (1-((2, 5-dioxopyrrolidin-1-yl)oxy)-1-oxopropan-2-yl) succinate (480 mg, 1.4 mmol) in tetrahydrofuran (5 mL) was added. The mixture was stirred at −10° C. to ambient temperature over 1 h. After this time, the reaction mixture was cooled in an ice bath, treated with saturated aqueous ammonium chloride, and extracted with ethyl acetate. The combined organics were dried over sodium sulfate, filtered, and concentrated under reduced pressure. The residue was purified by reverse phase column chromatography (50 g C18 column, 5-100% acetonitrile/water) to provide (S)-1-(((4R,4aS, 7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl tert-butyl succinate (420 mg, 53%): ESI MS m/z 630 [C$_{33}$H$_{43}$NO$_{11}$+H]$^+$.

739

Preparation of 4-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt

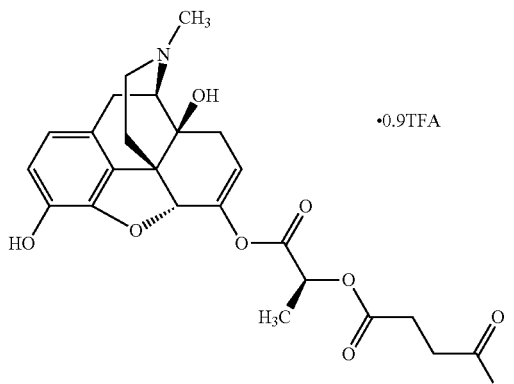

A solution of (S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl tert-butyl succinate (420 mg, 0.67 mmol) in methylene chloride (10 mL) was treated with trifluoroacetic acid (4 mL) and stirred at ambient temperature for 2 h. After this time, the reaction mixture was concentrated under reduced pressure. The residue was purified by reversed phase column chromatography (50 g C18 column, 5-25% acetonitrile/water) and freeze dried to provide 4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt (210 mg, 54%) as a fluffy white solid: $^1$H NMR (300 MHz, DMSO-$d_6$) δ 9.26 (br s, 1H), 6.66 (d, J=8.2 Hz, 1H), 6.60 (d, J=8.2 Hz, 1H), 5.57 (dd, J=5.8, 2.0 Hz, 1H), 5.11 (q, J=7.0 Hz, 1H), 4.92 (s, 1H), 3.02-2.78 (m, 2H), 2.8-2.58 (m, 5H), 2.50-2.31 (m, 1H), 2.24 (dd, J=17.8, 5.4 Hz, 1H), 2.04 (d, J=19.9 Hz, 1H), 1.57 (d, J=11.3 Hz, 1H), 1.51 (d, J=7.0 Hz, 3H), $CO_2H$ and OH protons not observed, five protons obscured by solvent peaks; ESI MS m/z 474 $[C_{24}H_{27}NO_9+H]^+$; HPLC (Method A) 96.8% (AUC), $t_R$=7.36 min.

Scheme 123: 4-((S)-2-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoroacetic acid salt

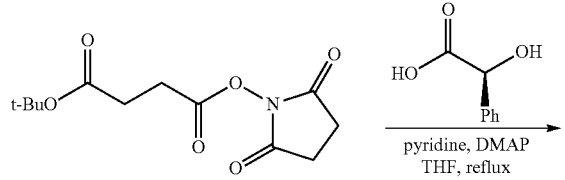

740

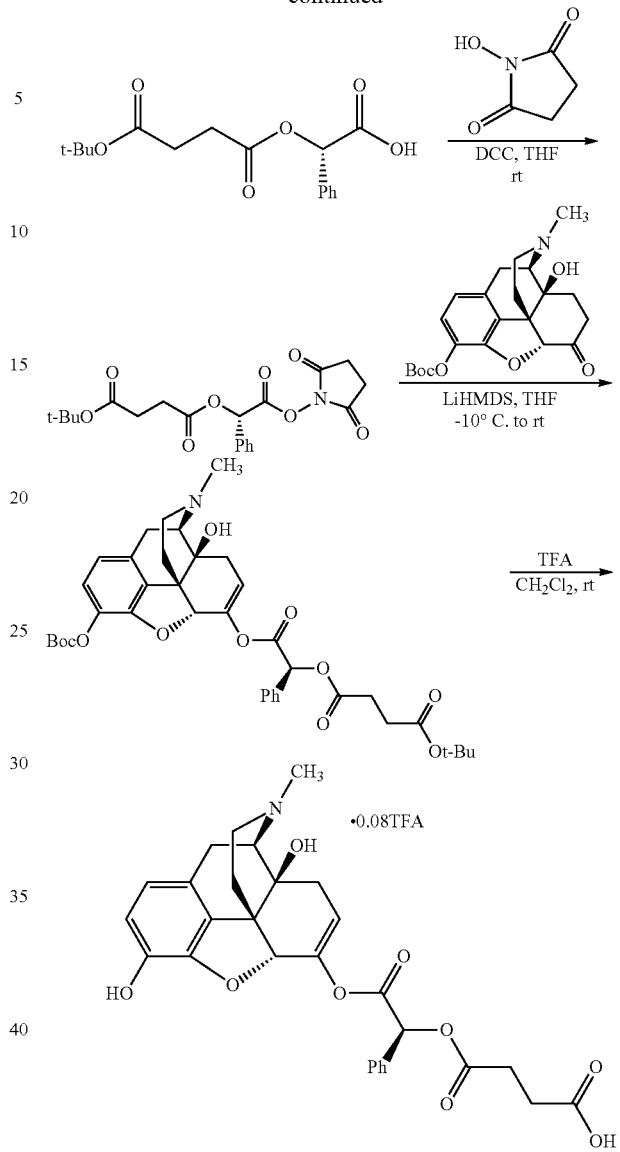

Preparation of (S)-2-((4-(tert-Butoxy)-4-oxobutanoyl)oxy)-2-phenylacetic acid

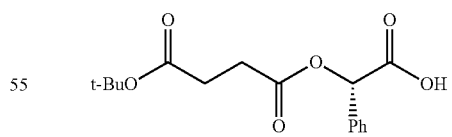

A mixture of tert-butyl (2,5-dioxopyrrolidin-1-yl) succinate (7.60 g, 28.0 mmol), (S)-2-hydroxy-2-phenylacetic acid (4.26 g, 28.0 mmol), pyridine (2.7 mL, 33.5 mmol), and 4-dimethylaminopyridine (200 mg, 1.6 mmol) in tetrahydrofuran (120 mL) was stirred at reflux for 48 h. After this time, the mixture was cooled to room temperature, partially concentrated under reduced pressure, diluted with ethyl acetate, and washed with 10% citric acid. The organic layer was extracted with saturated sodium bicarbonate. The aqueous extract was carefully treated with 2 N hydrochloric acid until acidic by pH paper analysis, and then extracted with ethyl acetate. The organic extracts were dried over sodium sulfate, filtered, and concentrated to give (S)-2-((4-(tert-butoxy)-4-oxobutanoyl)oxy)-2-phenylacetic acid (6.00 g, 70%): $^1$H NMR (300 MHz, CDCl$_3$) δ 7.51-7.45 (m, 2H), 7.42-7.35 (m, 3H), 5.97 (s, 1H), 2.76-2.69 (m, 2H), 2.63-2.55 (m, 2H), 1.41 (s, 9H), CO$_2$H proton not observed.

Preparation of (S)-tert-Butyl (2-((2,5-dioxopyrrolidin-1-yl)oxy)-2-oxo-1-phenylethyl) succinate

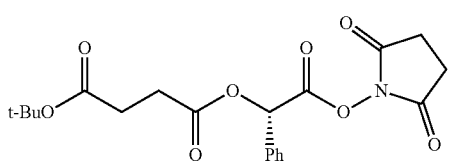 [SMILES: CC(C)(C)OC(=O)CCC(=O)O[C@H](C(=O)ON1C(=O)CCC1=O)c1ccccc1]

A mixture of (S)-2-((4-(tert-butoxy)-4-oxobutanoyl)oxy)-2-phenylacetic acid (6.00 g, 19.5 mmol) and N-hydroxysuccinimide (2.50 g, 21.7 mmol) in tetrahydrofuran (100 mL) at 0° C. was treated with N,N'-dicyclohexylcarbodiimide (4.45 g, 21.6 mmol). The ice bath was removed, and the reaction mixture was stirred at ambient temperature for 4 h. After this time, diethyl ether (100 mL) was added, and the mixture was filtered. The filtrate was concentrated under reduced pressure to provide (S)-tert-butyl (2-((2,5-dioxopyrrolidin-1-yl)oxy)-2-oxo-1-phenylethyl) succinate (8.33 g) that was used without purification: $^1$H NMR (300 MHz, CDCl$_3$) δ 7.57-7.51 (m, 2H), 7.46-7.40 (m, 3H), 6.35 (s, 1H), 2.80 (s, 4H), 2.77-2.71 (m, 2H), 2.63-2.56 (m, 2H), 1.41 (s, 9H).

Preparation of (S)-2-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl tert-butyl succinate

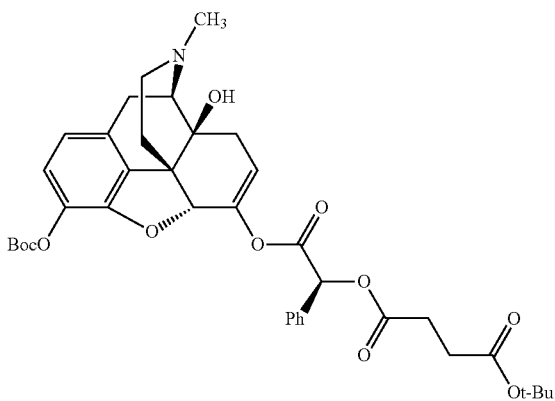

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (505 mg, 1.26 mmol) in tetrahydrofuran (10 mL) was cooled to −10° C. and treated dropwise with a 1.0 M solution of lithium bis(trimethylsilyl)amide in tetrahydrofuran (1.4 mL, 1.4 mmol). After addition was complete, the mixture was stirred at ambient temperature for 10 min. The mixture was re-cooled to −10° C., and (S)-tert-butyl (2-((2,5-dioxopyrrolidin-1-yl)oxy)-2-oxo-1-phenylethyl) succinate (670 mg, 1.65 mmol) was added in one portion. The mixture was stirred at −10° C. to ambient temperature over 1 h. After this time, the reaction mixture was cooled in an ice bath, treated with saturated aqueous ammonium chloride, and extracted with ethyl acetate. The combined organics were dried over sodium sulfate, filtered, and concentrated under reduced pressure. The residue was purified by reversed phase column chromatography (50 g C18 column, 5-100% acetonitrile/water) to provide (S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl tert-butyl succinate (420 mg, 48%): ESI MS m/z 692 [C$_{38}$H$_{45}$NO$_{11}$+H]$^+$.

Preparation of 4-((S)-2-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoracetic acid salt

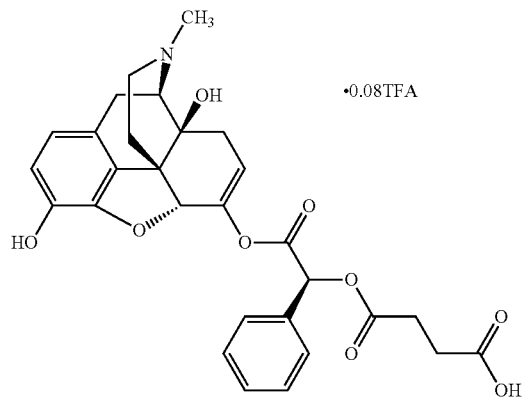 [SMILES: CN1CC[C@]23c4c5ccc(O)c4O[C@H]2C(OC(=O)[C@@H](OC(=O)CCC(=O)O)c2ccccc2)=CC[C@@]3(O)[C@H]1C5]

A solution of (S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl tert-butyl succinate (420 mg, 0.60 mmol) in methylene chloride (10 mL) was treated with trifluoroacetic acid (4 mL) and stirred at ambient temperature for 2 h. After this time, the reaction mixture was concentrated under reduced pressure. The residue was purified by reversed phase column chromatography (50 g C18 column, 5-30% acetonitrile/water) and freeze dried to provide 4-((S)-2-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoracetic acid salt (210 mg, 54%) as a fluffy white solid: $^1$H NMR (300 MHz, DMSO-d$_6$) δ 7.59-7.51 (m, 2H), 7.50-7.40 (m, 3H), 6.57 (d, J=8.1 Hz, 1H), 6.51 (d, J=8.1 Hz, 1H), 6.07 (s, 1H), 5.55 (dd, J=5.5, 2.6 Hz, 1H), 4.70 (s, 1H), 3.20-3.03 (m, 2H), 3.84 (d, J=6.0 Hz, 1H), 2.74-2.63 (m, 2H), 2.62-2.54 (m, 3H), 2.43 (dd, J=10.9, 3.6 Hz, 1H), 2.32 (s, 3H), 2.19 (dd, J=12.3, 4.5 Hz, 1H), 2.13-1.93 (m, 3H), 1.36 (d, J=10.8 Hz, 1H), CO$_2$H and OH protons not observed; ESI MS m/z 536 [C$_{29}$H$_{29}$NO$_9$+H]$^+$; HPLC (Method A) 96.7% (AUC), t$_R$=8.58 min.

Scheme 124: (2S,2'S)-4,4'-(((4R,4aS,7aR,12bS)-9-Hydroxy-3-methyl-2,3,4,4a,5,7a-hexahydro-1H-4,12-methanobenzofuro[3,2-e]isoquinoline-4a,7-diyl)bis(oxy))bis(2-hdroxy-4-oxobutanoic acid)

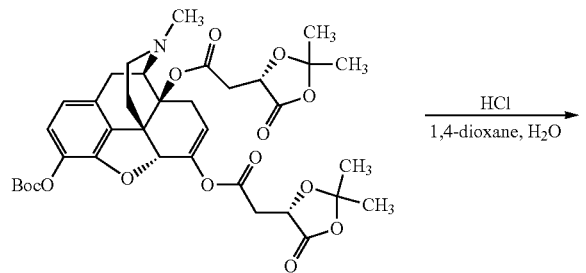

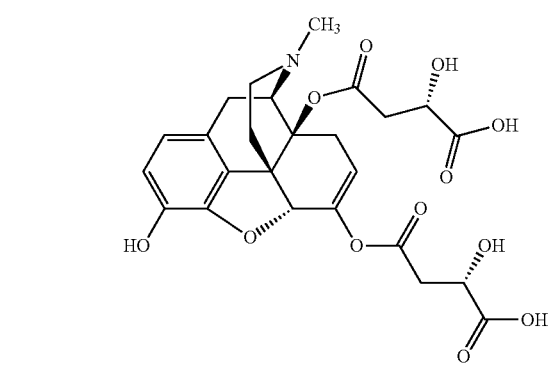

Preparation of (2S,2'S)-4,4'-(((4R,4aS,7aR,12bS)-9-Hydroxy-3-methyl-2,3,4,4a,5,7a-hexahydro-1H-4,12-methanobenzofuro[3,2-e]isoquinoline-4a,7-diyl)bis(oxy))bis(2-hydroxy-4-oxobutanoic acid)

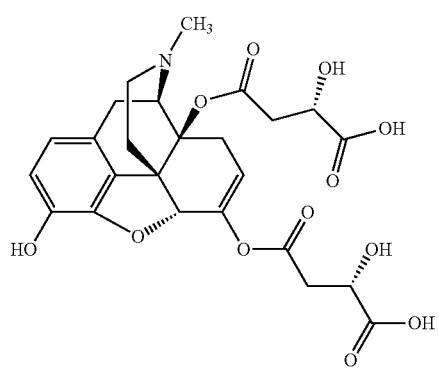 [SMILES: CN1CC[C@]23c4c5ccc(O)c4O[C@H]2C(OC(=O)C[C@H](O)C(=O)O)=CC[C@@]3(OC(=O)C[C@H](O)C(=O)O)[C@H]1C5]

A solution of (S)-(4R,4aS,7aR,12bS)-9-((tert-butoxycarbonyl)oxy)-3-methyl-2,3,4,4a,5,7a-hexahydro-1H-4,12-methanobenzofuro[3,2-e]isoquinoline-4a,7-diyl bis(2-((S)-2,2-dimethyl-5-oxo-1,3-dioxolan-4-yl)acetate) (93 mg, 0.13 mmol) in 1,4-dioxane (2.5 mL) and water (0.1 mL) was treated with a 4 N solution of hydrogen chloride in 1,4-dioxane (0.4 mL, 1.6 mmol) and stirred at ambient temperature for 2.5 h. After this time, the reaction mixture was concentrated under reduced pressure. The residue was purified by reversed phase column chromatography (50 g C18 column, 0-10% acetonitrile/water, with 0.1% trifluoracetic acid) and freeze dried to provide (2S,2'S)-4,4'-(((4R,4aS,7aR,12bS)-9-hydroxy-3-methyl-2,3,4,4a,5,7a-hexahydro-1H-4,12-methanobenzofuro[3,2-e]isoquinoline-4a,7-diyl) bis(oxy))bis(2-hydroxy-4-oxobutanoic acid) (26 mg, 38%): $^1$H NMR (300 MHz, DMSO-$d_6$) δ 9.44 (br s, 1H), 9.31 (br s, 1H), 9.15 (br s, 1H), 6.75-6.58 (m, 3H), 5.46-5.41 (m, 2H), 5.02 (s, 1H), 4.69 (d, J=5.9 Hz, 1H), 4.25-4.33 (m, 3H), 3.60-2.60 (m, 11H), 2.47-2.37 (m, 1H), 2.10 (d, J=19.3 Hz, 1H), 1.77 (d, J=11.4 Hz, 1H); ESI MS m/z 534 $[C_{25}H_{27}NO_{12}+H]^+$.

Scheme 125: (S)-4-((S)-2-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-oxo-1-phenylethoxy)-2-hydroxy-4-oxobutanoic acid hydrochloride

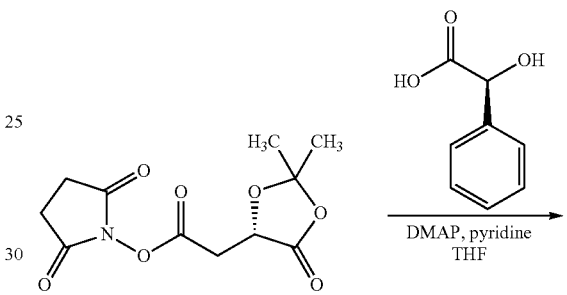

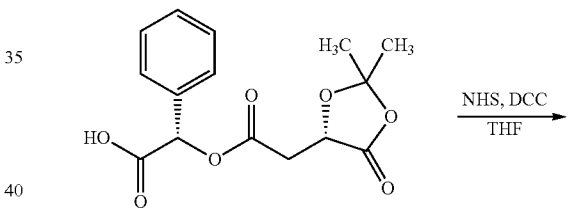

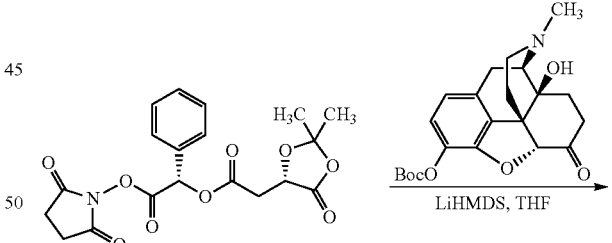

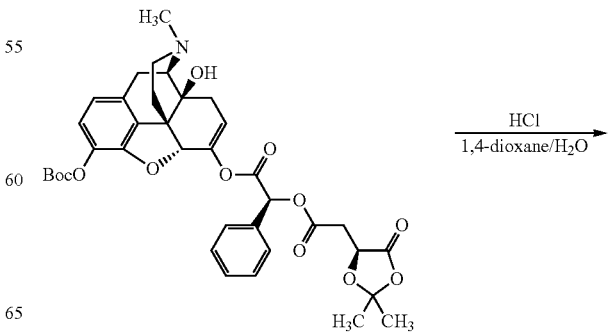

-continued

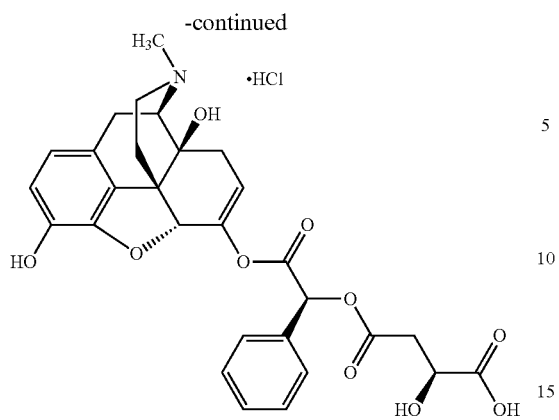

Preparation of (S)-2-(2-((S)-2,2-Dimethyl-5-oxo-1,3-dioxolan-4-yl)acetoxy)-2-phenylacetic acid

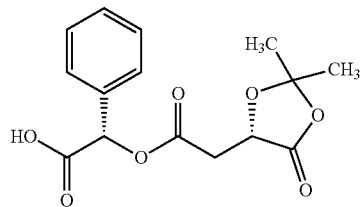 [SMILES: CC1(C)OC(=O)[C@H](CC(=O)O[C@H](C(=O)O)c2ccccc2)O1]

(S)-Mandelic acid (935 mg, 6.15 mmol), (S)-2,5-dioxopyrrolidin-1-yl 2-(2,2-dimethyl-5-oxo-1,3-dioxolan-4-yl)acetate (2.00 g, 7.37 mmol), 4-(dimethylamino)pyridine (75 mg, 0.62 mmol), pyridine (582 mg, 7.37 mmol), and tetrahydrofuran (30 mL) were combined and heated at 50° C. under a nitrogen atmosphere for 48 h. After this time, the solvent was removed under reduced pressure, and the residue was partitioned between ethyl acetate (30 mL) and 10% aqueous citric acid. The organic layer was separated and washed with water (50 mL), dried over sodium sulfate, filtered, and concentrated under reduced pressure to provide (S)-2-(2-((S)-2,2-dimethyl-5-oxo-1,3-dioxolan-4-yl)acetoxy)-2-phenylacetic acid (2.54 g, quantitative) as a yellow oil: $^1$H NMR (300 MHz, CDCl$_3$) δ 7.50-7.32 (m, 5H), 6.01 (s, 1H), 4.77 (m, 1H), 3.14 (dd, J=17.1, 3.9 Hz, 1H), 2.88 (m, 1H), 1.54 (m, 6H), CO$_2$H proton not observed.

Preparation of (S)-2,5-Dioxopyrrolidin-1-yl 2-(2-((S)-2,2-dimethyl-5-oxo-1,3-dioxolan-4-yl)acetoxy)-2-phenylacetate

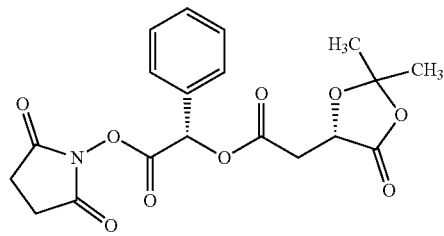 [SMILES: CC1(C)OC(=O)[C@H](CC(=O)O[C@H](C(=O)ON2C(=O)CCC2=O)c2ccccc2)O1]

A solution of (S)-2-(2-((S)-2,2-dimethyl-5-oxo-1,3-dioxolan-4-yl)acetoxy)-2-phenylacetic acid (2.27 g, 7.37 mmol) in tetrahydrofuran (60 mL) was treated with N-hydroxysuccinimide (932 mg, 8.11 mmol) and N,N'-dicyclohexylcarbodiimide (1.67 g, 8.11 mmol) and stirred under a nitrogen atmosphere for 4 h. After this time, the reaction mixture was filtered to remove the solid dicyclohexylurea byproduct. The solid was washed with diethyl ether (50 mL), and the combined filtrate and washings were concentrated under reduced pressure. The residue was triturated with diethyl ether to provide (S)-2,5-dioxopyrrolidin-1-yl 2-(2-((S)-2,2-dimethyl-5-oxo-1,3-dioxolan-4-yl)acetoxy)-2-phenylacetate (3.52 g) as a yellow solid that was used without purification.

Preparation of (S)-(4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 2-(2-((S)-2,2-dimethyl-5-oxo-1,3-dioxolan-4-yl)acetoxy)-2-phenylacetate

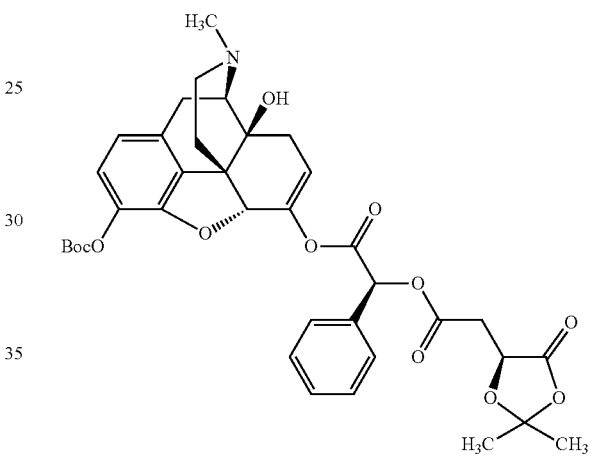

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at ambient temperature for 15 min. The mixture was re-cooled to −45° C. and treated dropwise with a solution of (S)-2,5-dioxopyrrolidin-1-yl 2-(2-((S)-2,2-dimethyl-5-oxo-1,3-dioxolan-4-yl)acetoxy)-2-phenylacetate (555 mg, 1.37 mmol) in tetrahydrofuran (5 mL). After addition was complete, the mixture was warmed to 0° C. After this time, the reaction mixture was treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-(2-((S)-2,2-dimethyl-5-oxo-1,3-dioxolan-4-yl)acetoxy)-2-phenylacetate (160 mg, 18%) as a white solid: ESI MS m/z 692 [C$_{37}$H$_{41}$NO$_{12}$+H]$^+$.

Preparation of (S)-4-((S)-2-(((4R,4aS,7aR,12bS)-4a, 9-Dihydroxy-3-methyl-2,3,4,4a,5,7a-hexahydro-1H-4,12-methanobenzofuro[3,2-e]isoquinolin-7-yl)oxy)-2-oxo-1-phenylethoxy)-2-hydroxy-4-oxobutanoic acid hydrochloride

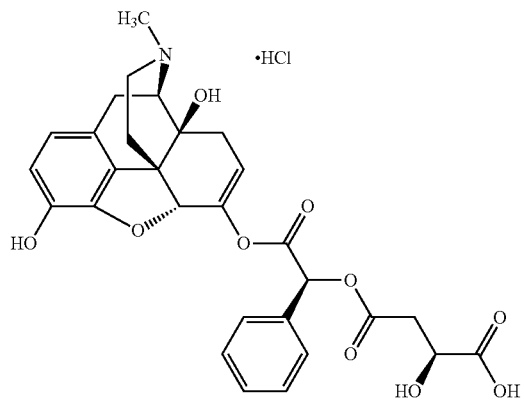 [SMILES: CN1CC[C@]23c4c5ccc(O)c4O[C@H]2C(OC(=O)[C@@H](OC(=O)C[C@H](O)C(=O)O)c2ccccc2)=CC[C@@]3(O)[C@H]1C5 ; Cl]

A solution of (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-(2-((S)-2,2-dimethyl-5-oxo-1,3-dioxolan-4-yl)acetoxy)-2-phenylacetate (160 mg, 0.231 mmol) was treated with a 4.0 M solution of hydrochloric acid in 1,4-dioxane (5 mL) and water (0.2 mL). The reaction mixture was stirred under a nitrogen atmosphere at ambient temperature for 2 h. After this time, the reaction mixture was concentrated under reduced pressure. The residue was purified by reversed phase column chromatography (50 g C18 column, 0-100% acetonitrile/water) and freeze dried to provide (S)-4-((S)-2-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-oxo-1-phenylethoxy)-2-hydroxy-4-oxobutanoic acid hydrochloride (63.2 mg, 46%) as a fluffy white solid: $^1$H NMR (300 MHz, DMSO-$d_6$) δ 7.59-7.54 (m, 2H), 7.48-7.44 (m, 3H), 6.55 (apparent q, J=7.8 Hz, 2H), 6.08 (s, 1H), 5.56 (dd, J=5.7, 2.4 Hz, 1H), 4.74 (s, 1H), 4.26 (dd, J=8.4, 4.2 Hz, 1H), 3.15 (s, 1H), 3.09 (s, 1H), 2.97 (d, J=5.7 Hz, 1H), 2.88 (dd, J=15.9, 4.2 Hz, 1H), 2.73-1.95 (m, 6H), 2.41 (s, 3H), 1.40 (d, J=11.1 Hz, 1H), $CO_2H$, HCl, and three OH protons not observed; ESI MS m/z 552 $[C_{29}H_{29}NO_{10}+H]^+$.

Scheme 126: (S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl stearate trifluoroacetic acid salt

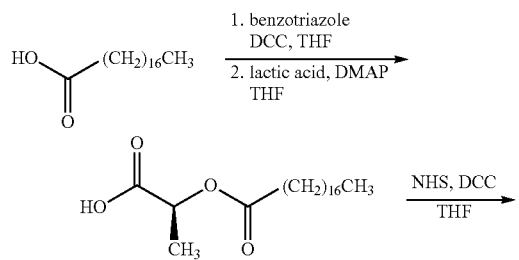

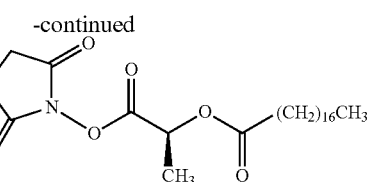

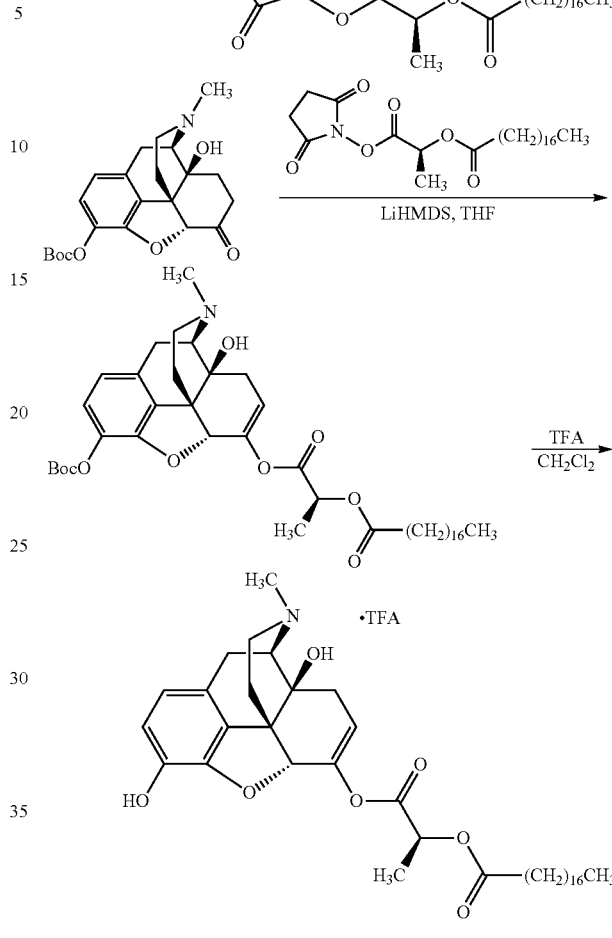

Preparation of (S)-2-(Stearoyloxy)propanoic acid

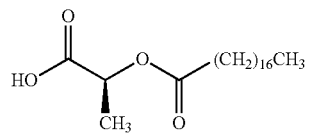

A solution of stearic acid (5.02 g, 17.6 mmol) and benzotriazole (2.31 g, 19.4 mmol) in tetrahydrofuran (80 mL) was treated with N,N'-dicyclohexylcarbodiimide (4.00 g, 19.4 mmol) and stirred under a nitrogen atmosphere for 5.5 h. After this time, the reaction mixture was filtered to remove the solid dicyclohexylurea byproduct, and the solids were washed with diethyl ether. The combined filtrate and washings were concentrated. The residue was dissolved in tetrahydrofuran (90 mL) and cooled in an ice bath. The mixture was treated with lactic acid (1.61 g, 17.9 mmol) and 4-dimethylaminopyridine (2.18 g, 17.8 mmol), and the ice bath was removed. The mixture was stirred at ambient temperature under a nitrogen atmosphere for 40 h. After this time, the reaction mixture was concentrated under reduced pressure. The residue was dissolved in ethyl acetate (250 mL) and washed with aqueous 10% citric acid (2×100 mL) and water (100 mL). The organic layer was extracted with saturated aqueous sodium bicarbonate (2×100 mL). The combined aqueous bicarbonate layers were acidified to pH ~1 with 6 N hydrochloric acid and extracted with ethyl acetate (2×100 mL). The combined organics were dried over sodium sulfate, filtered, and concentrated under reduced pressure. The residue was dissolved/suspended in heptanes (100 mL), filtered to remove undissolved solids, washed with aqueous 10% citric acid (50 mL), dried over sodium sulfate, filtered, and concentrated under reduced pressure to provide (S)-2-(stearoyloxy)propanoic acid (4.86 g, 77%) as a colorless oil: $^1$H NMR (300 MHz, CDCl$_3$) δ 5.12 (q, J=7.2 Hz, 1H), 2.41-2.32 (m, 2H), 1.67-1.52 (m, 5H), 1.31-1.27 (m, 28H), 0.88 (t, J=6.3 Hz, 3H), CO$_2$H proton not observed.

Preparation of (S)-1-((2,5-Dioxopyrrolidin-1-yl) oxy)-1-oxopropan-2-yl stearate

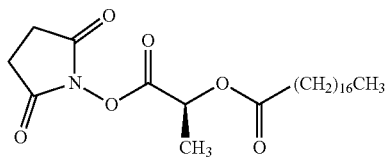

A solution of (S)-2-(stearoyloxy)propanoic acid (4.85 g, 13.6 mmol) in tetrahydrofuran (80 mL) was treated with N-hydroxysuccinimide (1.57 mg, 13.6 mmol) and N,N'-dicyclohexylcarbodiimide (2.80 g, 13.6 mmol) and stirred under a nitrogen atmosphere for 1.5 h. After this time, the reaction mixture was filtered to remove the solid dicyclohexylurea byproduct. The solid was washed with diethyl ether, and the combined filtrate and washings were concentrated under reduced pressure to provide (S)-1-((2,5-dioxopyrrolidin-1-yl)oxy)-1-oxopropan-2-yl stearate (6.69 g, quantitative) as a white crushable foam: $^1$H NMR (300 MHz, CDCl$_3$) δ 5.42 (q, J=7.2 Hz, 1H), 2.84 (br s, 4H), 2.42-2.37 (m, 2H), 1.73-1.53 (m, 5H), 1.31-1.27 (m, 28H), 0.88 (t, J=6.3 Hz, 3H).

Preparation of (S)-1-(((4R,4aS,7aR,12bS)-9-((tert-Butoxycarbonyl)oxy)-4a-hydroxy-3-methyl-2,3,4,4a, 5,7a-hexahydro-1H-4,12-methanobenzofuro[3,2-e] isoquinolin-7-yl)oxy)-1-oxopropan-2-yl stearate

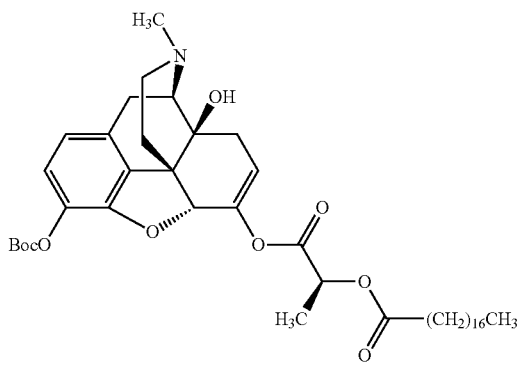

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at ambient temperature for 15 min. The mixture was re-cooled to −45° C. and treated dropwise with a solution of (S)-1-((2,5-dioxopyrrolidin-1-yl)oxy)-1-oxopropan-2-yl stearate (621 mg, 1.37 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride) to provide (S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl stearate (600 mg, 25%) as a white solid: ESI MS m/z 740 [C$_{43}$H$_{65}$NO$_9$+H]$^+$.

Preparation of (S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl stearate trifluoroacetic acid salt

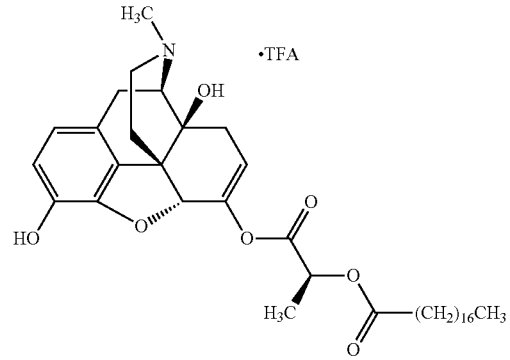

A solution of (S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) oxy)-1-oxopropan-2-yl stearate (300 mg, 0.405 mmol) in methylene chloride (3.0 mL) was treated with trifluoroacetic acid (3.0 mL) and stirred under a nitrogen atmosphere at ambient temperature for 1 h. After this time, the reaction mixture was concentrated under reduced pressure. The residue was purified by reversed phase column chromatography (150 g C18 column, 0-100% acetonitrile/water) and freeze dried to provide (S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl stearate trifluoroacetic acid salt (47.5 mg, 15%) as a fluffy white solid: $^1$H NMR (300 MHz, DMSO-d$_6$) δ 9.27 (s, 1H), 9.13 (s, 1H), 6.65 (apparent q, J=8.1 Hz, 2H), 6.23 (s, 1H), 5.57 (dd, J=6.3, 2.1 Hz, 1H), 5.09 (q, J=6.9 Hz, 1H), 4.95 (s, 1H), 3.09 (m, 1H), 2.84 (d, J=3.9 Hz, 3H), 2.63-2.26 (m, 5H), 2.05 (d, J=18.0 Hz, 1H), 1.64-1.49 (m, 7H), 1.23 (m, 30H), 0.85 (t, J=6.6 Hz, 3H); ESI MS m/z 640 [C$_{36}$H$_{57}$NO$_7$+H]$^+$.

Scheme 127: (S)-2-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-oxo-1-phenylethyl oleate trifluoroacetic acid salt
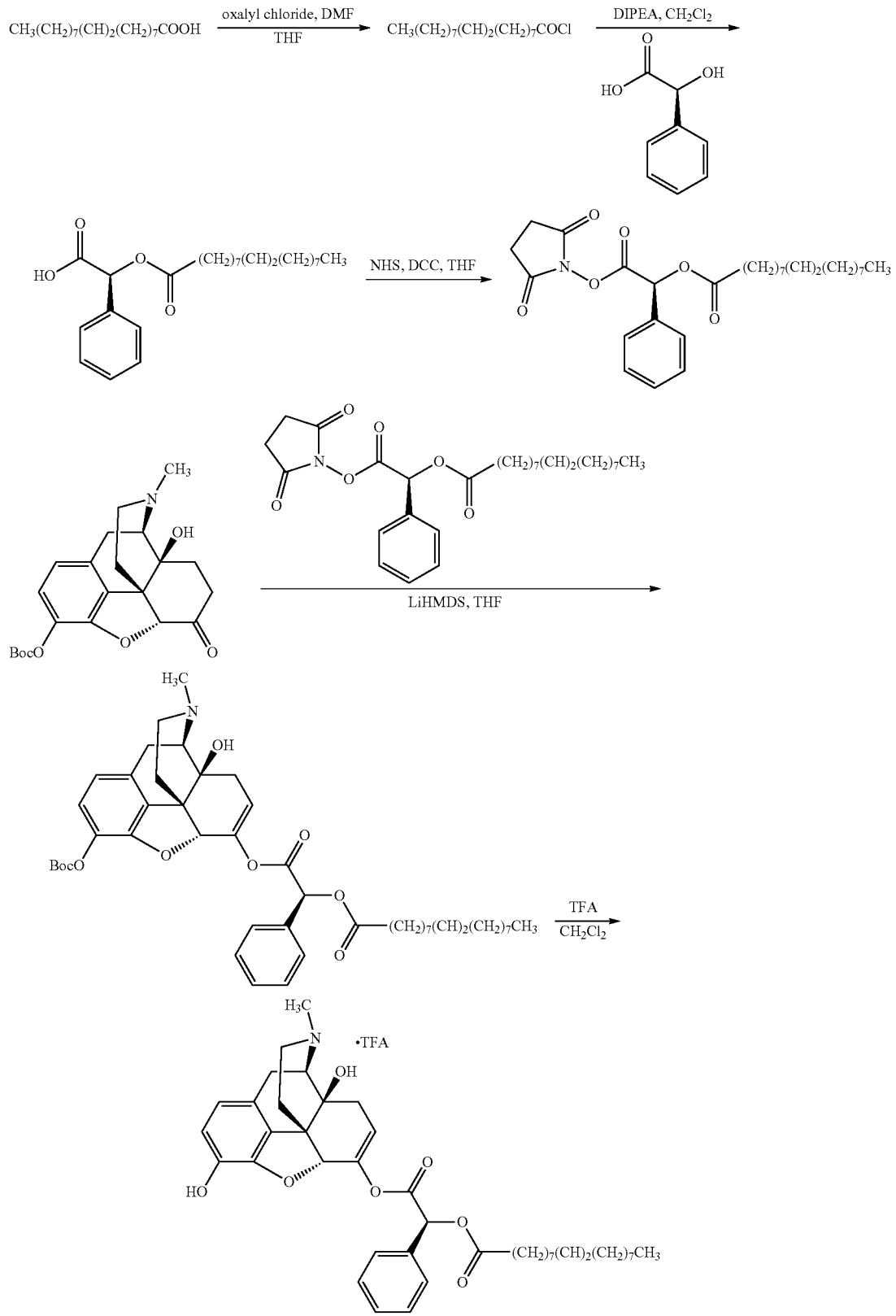

Preparation of (S,Z)-2-(Oleoyloxy)-2-phenylacetic acid

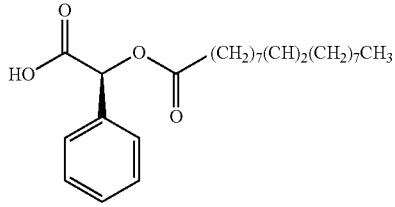

A solution of oleoyl chloride (2.13 g, 7.08 mmol) in methylene chloride (35 mL) was cooled in an ice bath and treated with (S)-mandelic acid (1.08 g, 7.08 mmol) and N,N-diisopropylethylamine (2.75 g, 21.2 mmol) and stirred under a nitrogen for 5 h. After this time, 10% aqueous citric acid (100 mL) was added, and the resulting mixture was extracted with ethyl acetate (2×100 mL). The combined organics were washed with brine (100 mL), dried over sodium sulfate, filtered, and concentrated under reduced pressure. The residue was purified by column chromatography (80 g silica gel column, 0-50% ethyl acetate/heptane) to provide of (S,Z)-2-(oleoyloxy)-2-phenylacetic acid (1.26 g, 42%) as a white solid: $^1$H NMR (300 MHz, DMSO-$d_6$) δ 7.50-7.46 (m, 2H), 7.41-7.37 (m, 3H), 5.95 (s, 1H), 5.36-5.32 (m, 2H), 2.47 (m, 2H), 1.99 (m, 4H), 1.66 (m, 2H), 1.27 (m, 20H), 0.87 (t, J=6.6 Hz, 3H), CO$_2$H proton not observed.

Preparation of (S)-2-((2,5-Dioxopyrrolidin-1-yl)oxy)-2-oxo-1-phenylethyl oleate

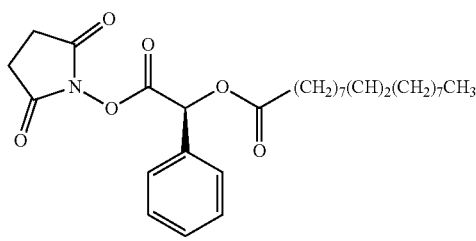

A solution of (S,Z)-2-(oleoyloxy)-2-phenylacetic acid (1.26 g, 3.02 mmol) in tetrahydrofuran (30 mL) was treated with N-hydroxysuccinimide (383 mg, 3.33 mmol) and N,N'-dicyclohexylcarbodiimide (686 mg, 3.33 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-2-((2,5-dioxopyrrolidin-1-yl)oxy)-2-oxo-1-phenylethyl oleate (1.68 g) as a white solid: $^1$H NMR (300 MHz, CDCl$_3$) δ 7.61-7.53 (m, 2H), 7.46-7.42 (m, 3H), 6.34 (s, 1H), 5.36-5.32 (m, 2H), 2.87 (s, 4H), 2.45 (m, 2H), 1.99 (m, 4H), 1.66 (m, 2H), 1.27 (m, 20H), 0.88 (t, J=6.6 Hz, 3H).

Preparation of (S)-2-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl oleate

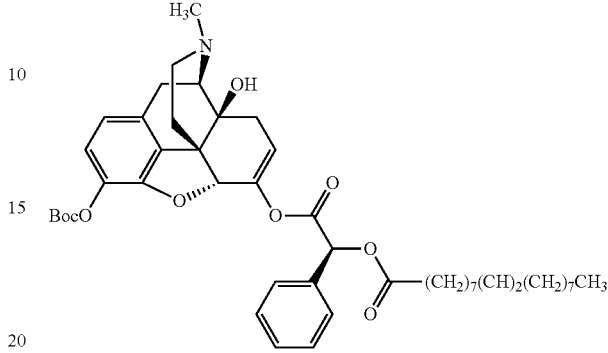

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at 0° C. for 1 h. The mixture was re-cooled to −45° C. and treated dropwise with a solution of (S)-2-((2,5-dioxopyrrolidin-1-yl)oxy)-2-oxo-1-phenylethyl oleate (703 mg, 1.37 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g, silica gel, 0-20% methanol/methylene chloride) to provide (S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl oleate (900 mg, 90%) as a white solid: ESI MS m/z 800 [C48H$_{65}$NO$_9$+H]$^+$.

Preparation of (S)-2-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-oxo-1-phenylethyl oleate trifluoroacetic acid salt

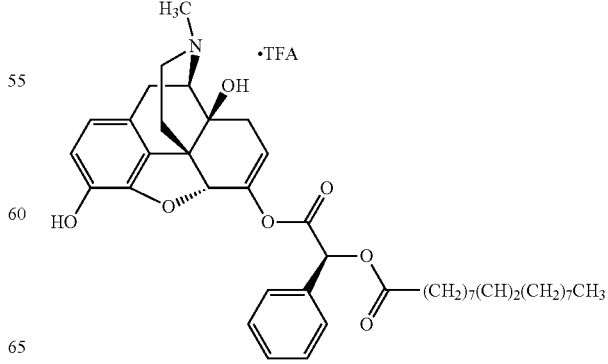

A solution of (S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl oleate (450 mg, 0.625 mmol) in methylene chloride (3.0 mL) was treated with trifluoroacetic acid (3.0 mL) and stirred under a nitrogen atmosphere at ambient temperature for 2 h. After this time, the reaction mixture was concentrated under reduced pressure. The residue was purified by reversed phase column chromatography (150 g C18 column, 0-100% acetonitrile/water) and freeze dried to provide (S)-2-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-oxo-1-phenylethyl oleate trifluoroacetic acid salt (31 mg, 6%) as a fluffy white solid: $^1$H NMR (300 MHz, DMSO-$d_6$) δ 9.25 (s, 1H), 9.12 (s, 1H), 7.58-7.54 (m, 2H), 7.48-7.45 (m, 3H), 6.64 (q, J=8.1 Hz, 2H), 6.23 (s, 1H), 6.09 (s, 1H), 5.58 (dd, J=6.3, 2.1 Hz, 1H), 5.32 (t, J=4.8 Hz, 2H), 4.86 (s, 1H), 3.04 (m, 1H), 2.82 (d, J=4.8 Hz, 3H), 2.64-2.22 (m, 3H), 2.08-1.96 (m, 5H), 1.60-1.40 (m, 4H), 1.23 (m, 24H), 0.85 (t, J=6.9 Hz, 3H); ESI MS m/z 700 $[C_{43}H_{57}NO_7+H]^+$; HPLC (Method A) 95.1% (AUC), $t_R$=15.51 min.

Scheme 128: (S)-4-(((S)-1-(((4R,4aS,7aR,12bS)-4a,9-Dihydroxy-3-methyl-2,3,4,4a,5,7a-hexahydro-1H-4, 12-methanobenzofuro[3,2-e]isoquinolin-7-yl)oxy)-1-oxopropan-2-yl)oxy)-3-hydroxy-4-oxobutanoic acid trifluoroacetic acid salt

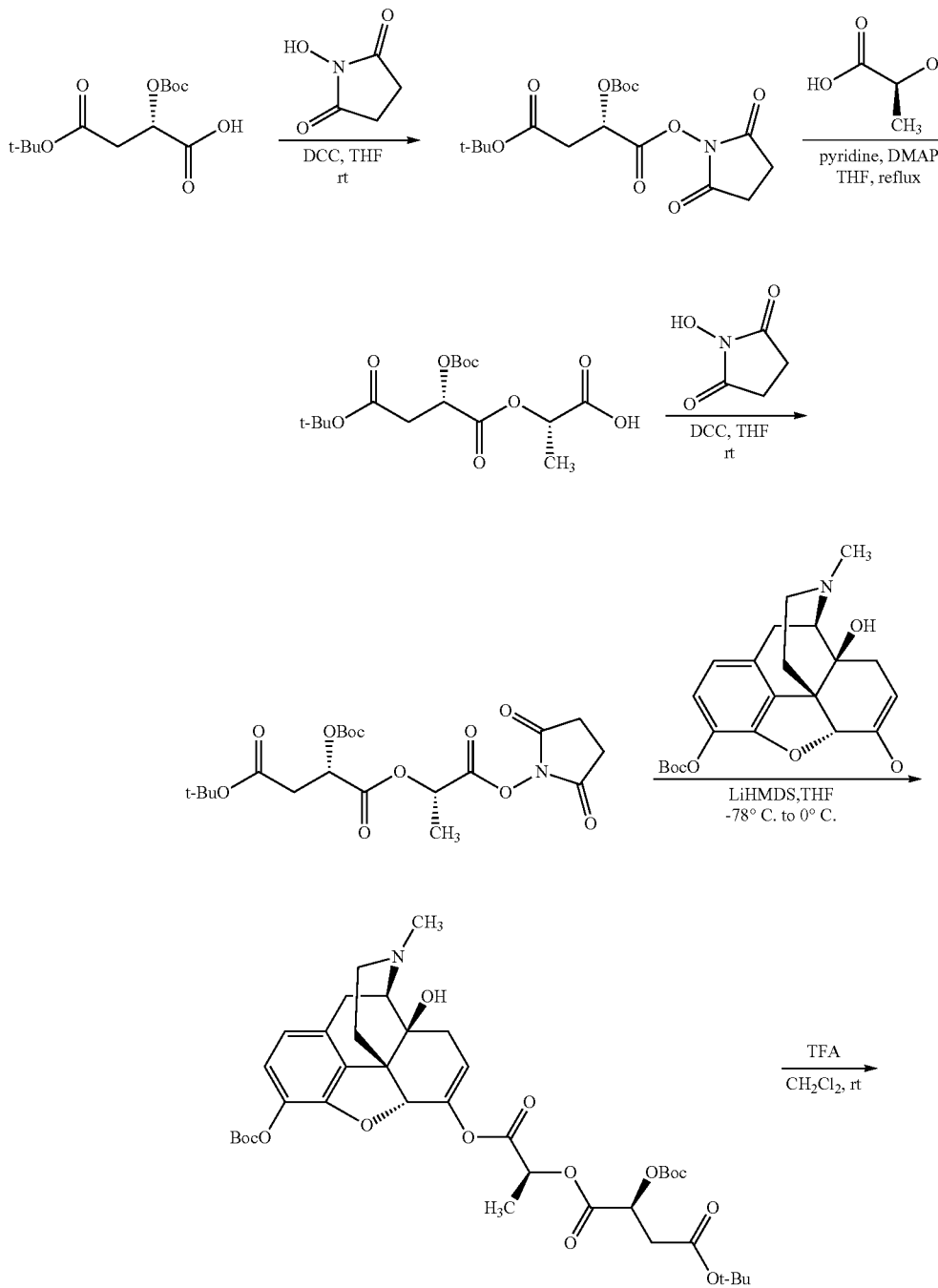

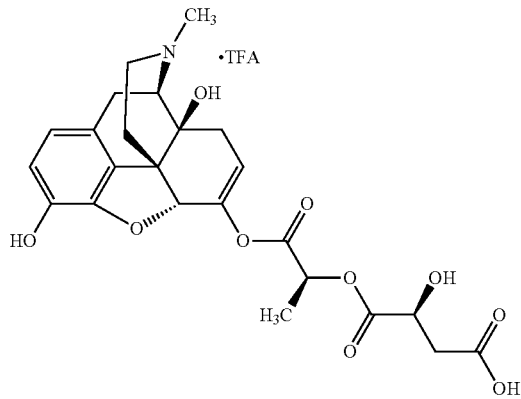

Preparation of (S)-4-tert-Butyl 1-(2,5-dioxopyrrolidin-1-yl) 2-((tert-butoxycarbonyl)oxy)succinate

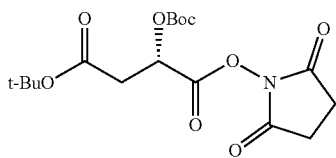

A mixture of (S)-4-(tert-butoxy)-2-((tert-butoxycarbonyl)oxy)-4-oxobutanoic acid (2.70 g, 9.31 mmol) and N-hydroxysuccinimide (1.25 g, 10.9 mmol) in tetrahydrofuran (50 mL) at 0° C. was treated with N,N'-dicyclohexylcarbodiimide (2.20 g, 10.7 mmol). The ice bath was removed, and the reaction mixture was stirred at ambient temperature for 4 h. After this time, diethyl ether (100 mL) was added, and the mixture was filtered. The filtrate was concentrated under reduced pressure to provide (S)-4-tert-butyl 1-(2,5-dioxopyrrolidin-1-yl) 2-((tert-butoxycarbonyl)oxy)succinate (3.78 g) that was used without purification: $^1$H NMR (300 MHz, CDCl$_3$) δ 5.61 (dd, J=8.0, 4.8 Hz, 1H), 2.98-2.93 (m, 2H), 2.84 (s, 4H), 1.51 (s, 9H), 1.47 (s, 9H).

Preparation of (S)-2-(((S)-4-(tert-Butoxy)-2-((tert-butoxycarbonyl)oxy)-4-oxobutanoyl)oxy)propanoic acid

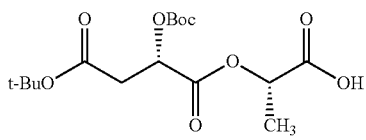

A mixture of (S)-4-tert-butyl 1-(2,5-dioxopyrrolidin-1-yl) 2-((tert-butoxycarbonyl)oxy)succinate (3.38 g, 8.73 mmol), (S)-2-hydroxypropanoic acid (1.20 g, 13.3 mmol), pyridine (1.1 mL, 14 mmol), and 4-dimethylaminopyridine (100 mg, 0.8 mmol) in tetrahydrofuran (40 mL) was stirred at reflux for 18 h. After this time, the mixture was cooled to room temperature, partially concentrated under reduced pressure, diluted with ethyl acetate, and washed with 10% citric acid. The organic layer was extracted with saturated sodium bicarbonate. The aqueous extract was carefully treated with 2 N hydrochloric acid until acidic by pH paper analysis, and then extracted with ethyl acetate. The organic extracts were dried over sodium sulfate, filtered, and concentrated under reduced pressure to give (S)-2-(((S)-4-(tert-butoxy)-2-((tert-butoxycarbonyl)oxy)-4-oxobutanoyl)oxy)propanoic acid (1.58 g, 50%): $^1$H NMR (300 MHz, CDCl$_3$) δ 5.37-5.22 (m, 2H), 2.96-2.82 (m, 2H), 1.57 (d, J=7.1 Hz, 3H), 1.49 (s, 9H), 1.46 (s, 9H), CO$_2$H proton not observed.

Preparation of (S)-4-tert-Butyl 1-((S)-1-((2,5-dioxopyrrolidin-1-yl)oxy)-1-oxopropan-2-yl) 2-((tert-butoxycarbonyl)oxy)succinate

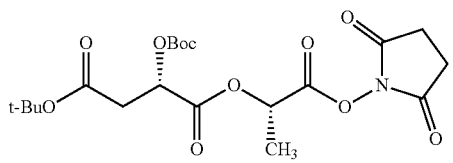

A mixture of (S)-2-(((S)-4-(tert-butoxy)-2-((tert-butoxycarbonyl)oxy)-4-oxobutanoyl)oxy)propanoic acid (1.58 g, 4.36 mmol) and N-hydroxysuccinimide (550 mg, 4.78 mmol) in tetrahydrofuran (30 mL) at 0° C. was treated with N,N'-dicyclohexylcarbodiimide (990 mg, 4.80 mmol). The ice bath was removed, and the reaction mixture was stirred at ambient temperature for 4 h. After this time, diethyl ether (30 mL) was added, and the mixture was filtered. The filtrate was concentrated under reduced pressure to provide (S)-4-tert-butyl 1-((S)-1-((2,5-dioxopyrrolidin-1-yl)oxy)-1-oxopropan-2-yl) 2-((tert-butoxycarbonyl)oxy)succinate (2.2 g) that was used without purification: $^1$H NMR (300 MHz, CDCl$_3$) δ 5.56 (q, J=7.1 Hz, 1H), 3.37 (dd, J=8.8, 3.9 Hz, 1H), 2.98-2.93 (m, 2H), 2.84 (s, 4H), 1.72 (d, J=7.1 Hz, 3H), 1.50 (s, 9H), 1.46 (s, 9H).

Preparation of (S)-1-((S)-1-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 4-tert-butyl 2-((tert-butoxycarbonyl)oxy)succinate

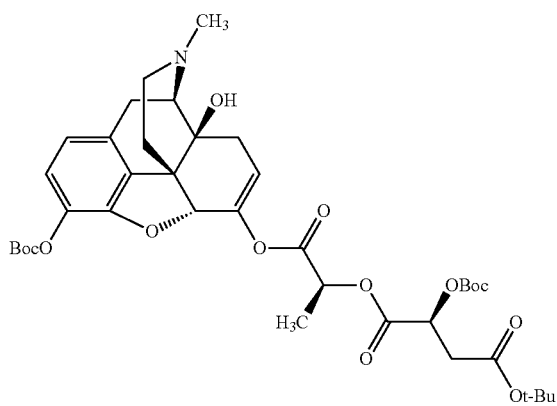

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (700 mg, 1.74 mmol) in tetrahydrofuran (15 mL) was cooled to 0° C. and treated dropwise with a 1.0 M solution of lithium bis(trimethylsilyl)amide in tetrahydrofuran (1.95 mL, 1.95 mmol). After addition was complete, the mixture was stirred at 0° C. for 25 min and then at ambient temperature for 25 min. The mixture was re-cooled to −78° C., and (S)-4-tert-butyl 1-((S)-1-((2,5-dioxopyrrolidin-1-yl)oxy)-1-oxopropan-2-yl) 2-((tert-butoxycarbonyl)oxy)succinate (900 mg, 1.96 mmol) was added. The mixture was allowed to warm to 0° C. over 2 h. After this time, the mixture was treated with saturated aqueous ammonium chloride, and extracted with ethyl acetate. The combined organics were dried over sodium sulfate, filtered, and concentrated under reduced pressure. The residue was purified by reversed phase column chromatography (150 g C18 column, 5-100% acetonitrile/water) to provide (S)-1-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 4-tert-butyl 2-((tert-butoxycarbonyl)oxy)succinate (260 mg, 20%): ESI MS m/z 746 [C38H51NO14+H]+.

Preparation of (S)-4-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-3-hydroxy-4-oxobutanoic acid trifluoroacetic acid salt

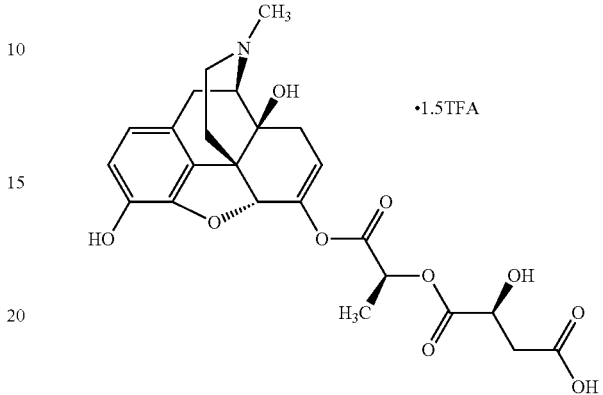

A solution of (S)-1-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 4-tert-butyl 2-((tert-butoxycarbonyl)oxy)succinate (260 mg, 0.35 mmol) in methylene chloride (6 mL) was treated with trifluoroacetic acid (3 mL) and stirred at ambient temperature for 1.5 h. After this time, the reaction mixture was concentrated under reduced pressure. The residue was purified by reversed phase column chromatography (50 g C18 column, 3-20% acetonitrile/water, with 0.1% trifluoroacetic acid) and freeze dried to provide (S)-4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-3-hydroxy-4-oxobutanoic acid trifluoroacetic acid salt (89 mg, 39%) as a fluffy white solid: $^1$H NMR (300 MHz, DMSO-d$_6$) δ 12.39 (br s, 1H), 9.30 (s, 1H), 9.17 (s, 1H), 6.69 (d, J=8.1 Hz, 1H), 6.62 (d, J=8.1 Hz, 1H), 6.28 (s, 1H), 5.84 (br s, 1H), 5.59 (dd, J=5.9, 2.0 Hz, 1H), 5.17 (q, J=7.0 Hz, 1H), 4.97 (s, 1H), 4.47 (dd, J=8.6, 4.0 Hz, 1H), 3.63 (d, J=6.2 Hz, 1H), 3.13-3.00 (m, 2H), 2.84 (d, J=3.3 Hz, 3H), 2.72 (dd, J=16.0, 4.2 Hz, 1H), 2.69-2.57 (m, 1H), 2.50-2.40 (m, 1H), 2.29 (dd, J=18.0, 6.0 Hz, 1H), 2.06 (d, J=18.0 Hz, 1H), 1.62 (d, J=11.2 Hz, 1H), 1.53 (d, J=7.0 Hz, 3H), two protons obscured by solvent peaks; ESI MS m/z 490 [C$_{24}$H$_{27}$NO$_{10}$+H]$^+$; HPLC (Method A) 97.9% (AUC), t$_R$=6.68 min.

Scheme 129: (S)-1-(((S)-1(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl stearate trifluoroacetic acid salt

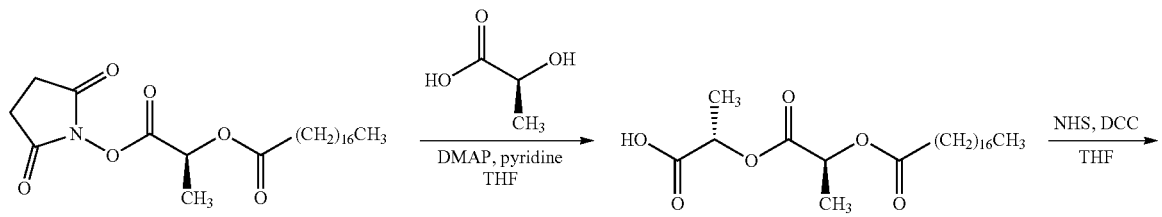

-continued

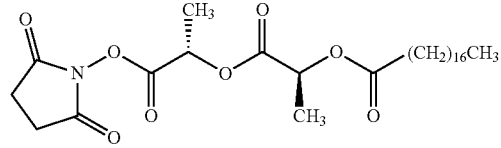
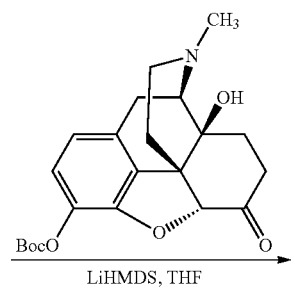

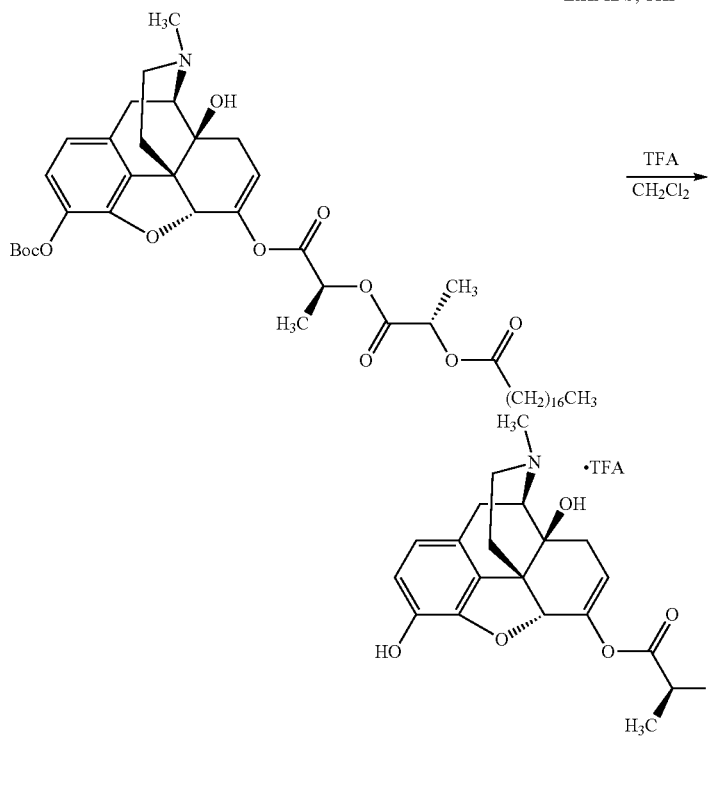

Preparation of (S)-2-(((S)-2-(Stearoyloxy)propanoyl)oxy)propanoic acid

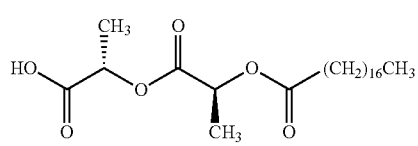

(S)-Lactic acid (238 mg, 2.65 mmol), (S)-1-((2,5-dioxopyrrolidin-1-yl)oxy)-1-oxopropan-2-yl stearate (1.00 g, 2.20 mmol), 4-(dimethylamino)pyridine (27 mg, 0.220 mmol), pyridine (210 mg, 7.65 mmol), and tetrahydrofuran (10 mL) were combined and heated at 60° C. under a nitrogen atmosphere for 24 h. After this time, the solvent was removed under reduced pressure, and the residue was participated between ethyl acetate (30 mL) and 10% aqueous citric acid. The organic layer was separated and washed with water (50 mL), dried over sodium sulfate, filtered, and concentrated under reduced pressure to provide (S)-2-(((S)-2-(stearoyloxy)propanoyl)oxy)propanoic acid (608 mg, 64%) as a white solid: $^1$H NMR (300 MHz, CDCl$_3$) δ 5.22 (dd, J=14.4, 7.2 Hz, 1H), 5.11 (dd, J=14.4, 7.2 Hz, 1H), 2.38 (m, 2H), 1.58-1.54 (m, 6H), 1.28 (m, 30H), 0.86 (t, J=11.4 Hz, 3H), CO$_2$H proton not observed.

Preparation of (S)-1-(((S)-1-((2,5-Dioxopyrrolidin-1-yl)oxy)-1-oxopropan-2-yl)oxy)-1-oxopropan-2-yl stearate

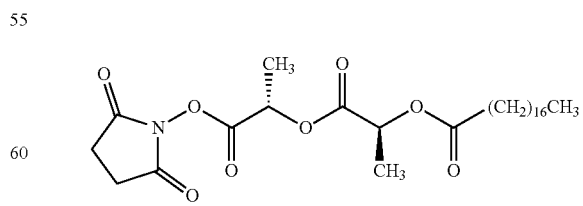

A solution of (S)-2-(((S)-2-(stearoyloxy)propanoyl)oxy) propanoic acid (608 mg, 1.42 mmol) in tetrahydrofuran (15 mL) was treated with N-hydroxysuccinimide (179 mg, 1.56 mmol) and N,N'-dicyclohexylcarbodiimide (321 mg, 1.56 mmol) and stirred at room temperature under a nitrogen atmosphere for 4 h. After this time, the reaction mixture was filtered to remove the solid dicyclohexylurea byproduct. The solid was washed with diethyl ether (50 mL), and the combined filtrate and washings were concentrated under reduced pressure. The residue was triturated with diethyl ether to provide (S)-1-(((S)-1-((2,5-dioxopyrrolidin-1-yl)oxy)-1-oxopropan-2-yl)oxy)-1-oxopropan-2-yl stearate (803 mg) as a white solid that was used without purification.

Preparation of (S)-1-(((S)-1-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl stearate

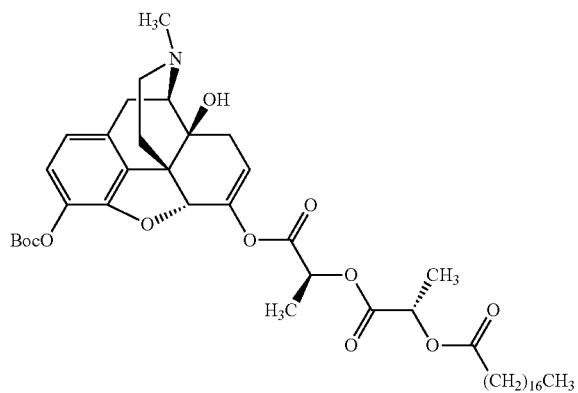

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (208 mg, 0.519 mmol) in tetrahydrofuran (5 mL) was cooled in an ice bath and treated dropwise with a 1.0 M solution of lithium bis(trimethylsilyl)amide in tetrahydrofuran (0.62 mL, 0.62 mmol). After addition was complete, the mixture was stirred at 0° C. for 1 h. The mixture was re-cooled to −45° C. and treated dropwise with a solution of (S)-1-(((S)-1-((2,5-dioxopyrrolidin-1-yl)oxy)-1-oxopropan-2-yl)oxy)-1-oxopropan-2-yl stearate (300 mg, 0.571 mmol) in tetrahydrofuran (2.5 mL). After addition was complete, the mixture was warmed to 0° C. After this time, the reaction mixture was treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride) to provide (S)-1-(((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl stearate (320 mg, 75%) as a white solid: ESI MS m/z 812 $[C_{46}H_{69}NO_{11}+H]^+$.

Preparation of (S)-1-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl stearate trifluoroacetic acid salt

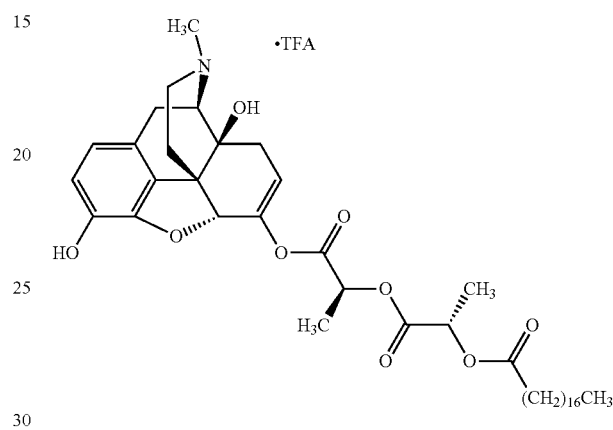

A solution of (S)-1-(((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl stearate (320 mg, 0.394 mmol) in methylene chloride (3 mL) was treated with trifluoroacetic acid (3 mL) and stirred under a nitrogen atmosphere at ambient temperature for 2 h. After this time, the reaction mixture was concentrated under reduced pressure. The residue was purified by reversed phase column chromatography (150 g C18 column, 0-100% acetonitrile/water) and freeze dried to provide (S)-1-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl stearate trifluoroacetic acid salt (70.3 mg, 20%) as a fluffy white solid: $^1$H NMR (300 MHz, DMSO-d$_6$) δ 9.27 (s, 1H), 9.13 (s, 1H), 6.65 (apparent q, J=8.1 Hz, 2H), 6.23 (s, 1H), 5.58 (dd, J=6.3, 2.1 Hz, 1H), 5.23 (q, J=6.9 Hz, 1H), 5.08 (q, J=7.2 Hz, 1H), 4.95 (s, 1H), 3.06 (m, 1H), 2.83 (d, J=4.8 Hz, 3H), 2.63-2.25 (m, 5H), 2.06 (d, J=17.4 Hz, 1H), 1.64-1.46 (m, 10H), 1.23 (m, 30H), 0.85 (t, J=6.9 Hz, 3H); ESI MS m/z 712 $[C_{41}H_{61}NO_9+H]^+$.

Scheme 130: (S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl oleate trifluoroacetic acid salt

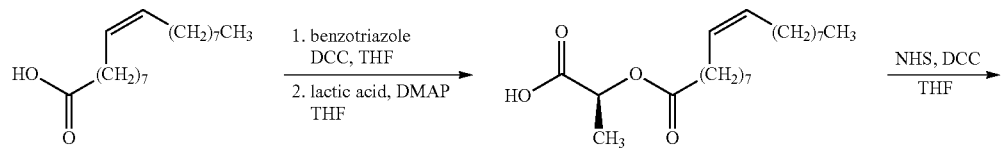

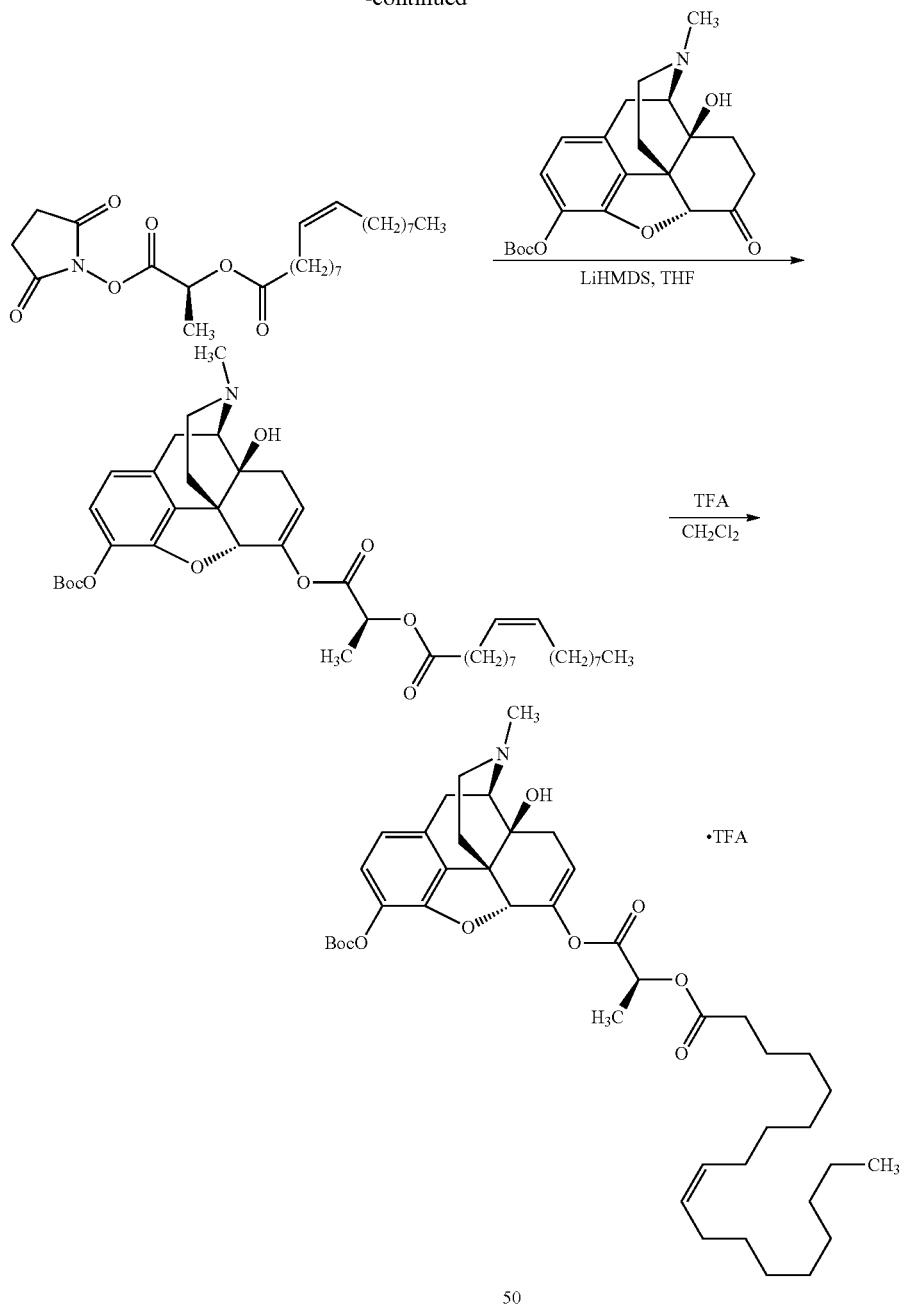

Preparation of (S,Z)-2-(Oleoyloxy)propanoic acid

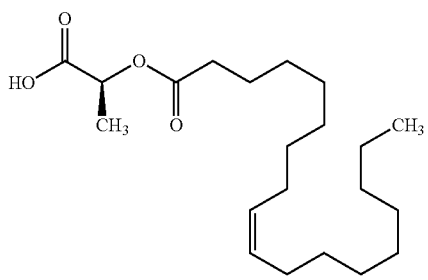 [SMILES: CCCCCCCC/C=C\CCCCCCCC(=O)O[C@@H](C)C(=O)O]

A solution of oleic acid (5.04 g, 17.9 mmol) and 1H-benzo[d][1,2,3]triazole (2.35 g, 19.8 mmol) in tetrahydrofuran (80 mL) was treated with N,N'-dicyclohexylcarbodiimide (4.13 g, 20.0 mmol) and stirred under a nitrogen atmosphere for 16 h. After this time, the reaction mixture was filtered to remove the solid dicyclohexylurea byproduct, and the solids were washed with diethyl ether. The combined filtrate and washings were concentrated. The residue was dissolved in tetrahydrofuran (75 mL) and cooled in an ice bath. The mixture was treated with (S)-lactic acid (1.62 g, 18.0 mmol) and 4-dimethylaminopyridine (2.20 g, 18.0 mmol), and the ice bath was removed. The mixture was stirred at ambient temperature under a nitrogen atmosphere for 40 h. After this time, the reaction mixture was concentrated under reduced pressure. The residue was dissolved in ethyl acetate (250 mL) and washed with aqueous 10% citric acid (2×100 mL), water (100 mL), and brine (100 mL). The organic layer was extracted with saturated aqueous sodium bicarbonate (2×100 mL). The combined aqueous bicarbonate layers were acidified to pH ~1 with 6 N hydrochloric acid and extracted with ethyl acetate (2×100 mL). The combined organics were dried over sodium sulfate, filtered, and concentrated under reduced pressure. The residue was dissolved/suspended in heptanes (100 mL), washed with aqueous 10% citric acid (50 mL) and brine (50 mL), dried over sodium sulfate, filtered, and concentrated under reduced pressure to provide (S,Z)-2-(oleoyloxy)propanoic acid (4.50 g, 71%) as a colorless oil: $^1$H NMR (300 MHz, CDCl$_3$) δ 5.36-5.30 (m, 2H), 5.10 (q, J=5.4 Hz, 1H), 2.41-2.32 (m, 2H), 2.02-1.98 (m, 4H), 1.67-1.52 (m, 5H), 1.31-1.27 (m, 20H), 0.88 (t, J=6.3 Hz, 3H), CO$_2$H proton not observed.

Preparation of (S)-1-((2,5-Dioxopyrrolidin-1-yl)oxy)-1-oxopropan-2-yl oleate

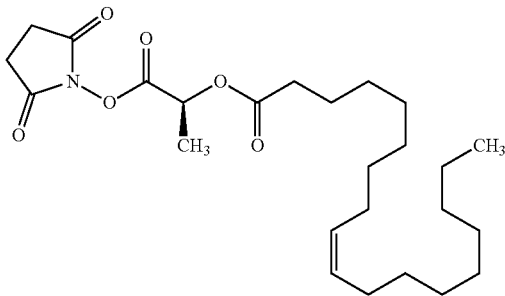 [SMILES: CCCCCCCC/C=C\CCCCCCCC(=O)O[C@@H](C)C(=O)ON1C(=O)CCC1=O]

A solution of (S,Z)-2-(oleoyloxy)propanoic acid (4.50 g, 12.7 mmol) in tetrahydrofuran (60 mL) was treated with N-hydroxysuccinimide (1.58 mg, 13.8 mmol) and N,N'-dicyclohexylcarbodiimide (2.91 g, 14.1 mmol) and stirred under a nitrogen atmosphere for 1.5 h. After this time, the reaction mixture was filtered to remove the solid dicyclohexylurea byproduct. The solid was washed with diethyl ether, and the combined filtrate and washings were concentrated under reduced pressure to provide (S)-1-((2,5-dioxopyrrolidin-1-yl)oxy)-1-oxopropan-2-yl oleate (6.20 g, quantitative) as an amber semi-solid: $^1$H NMR (300 MHz, CDCl$_3$) δ 5.42 (q, J=7.2 Hz, 1H), 5.36-5.32 (m, 2H), 2.84 (br s, 4H), 2.42-2.37 (m, 2H), 2.02-1.98 (m, 4H), 1.72-1.53 (m, 5H), 1.30-1.27 (m, 20H), 0.88 (t, J=6.3 Hz, 3H).

Preparation of (S)-1-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl oleate

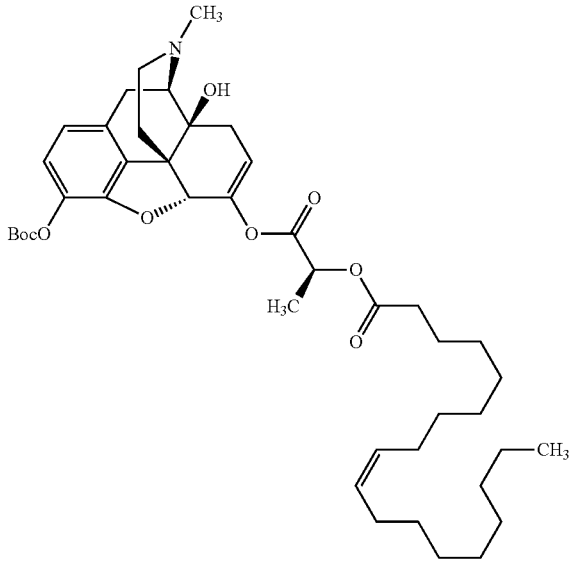

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (640 mg, 1.59 mmol) in tetrahydrofuran (10 mL) was cooled to 0° C. and treated dropwise with a 1.0 M solution of lithium bis(trimethylsilyl)amide in tetrahydrofuran (1.75 mL, 1.75 mmol). After addition was complete, the mixture was stirred at 0° C. for 25 min and then at ambient temperature for 25 min. The mixture was re-cooled to −78° C., and a solution of (S)-1-((2,5-dioxopyrrolidin-1-yl)oxy)-1-oxopropan-2-yl oleate (830 mg, 1.83 mmol) in tetrahydrofuran (5 mL) was added. The mixture was allowed to warm to 0° C. over 2 h. After this time, the mixture was treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride) to provide (S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl oleate (820 mg, 69%) as a yellow solid: ESI MS m/z 738 [C$_{43}$H$_{63}$NO$_9$+H]$^+$.

Preparation of (S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl oleate trifluoroacetic acid salt

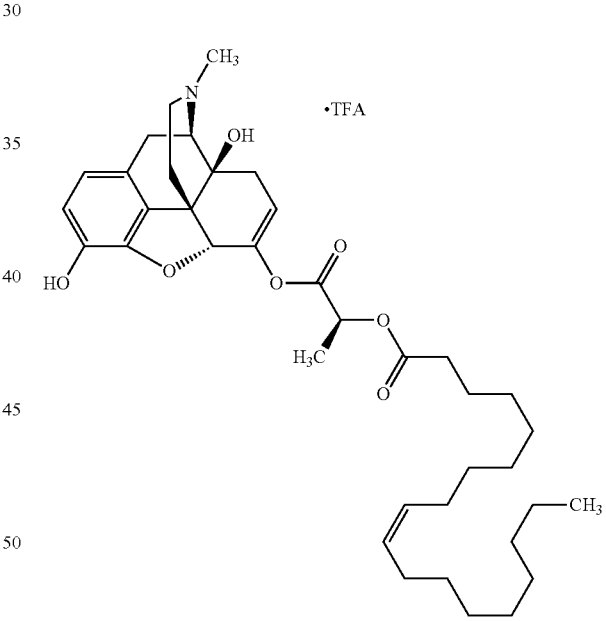

A solution of (S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl oleate (410 mg, 0.556 mmol) in methylene chloride (3 mL) was treated with trifluoroacetic acid (3 mL) and stirred under a nitrogen atmosphere at ambient temperature for 1 h. After this time, the reaction mixture was concentrated under reduced pressure. The residue was purified by reversed phase column chromatography (150 g C18 column, 0-100% acetonitrile/water) and freeze dried to provide (S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl oleate trifluoroacetic acid salt (121 mg, 28%) as a fluffy white solid: $^1$H NMR (300 MHz, DMSO-$d_6$) δ 9.27 (s, 1H), 9.14 (s, 1H), 6.65 (apparent q, J=8.1 Hz, 2H), 6.23 (s, 1H), 5.57 (dd, J=5.7, 2.1 Hz, 1H), 5.32 (t, J=4.5 Hz, 2H), 5.09 (q, J=7.2 Hz, 1H), 4.95 (s, 1H), 3.09 (m, 1H), 2.83 (d, J=4.5 Hz, 3H), 2.67-2.24 (m, 7H), 2.09-1.95 (m, 5H), 1.64-1.49 (m, 6H), 1.25 (m, 21H), 0.85 (t, J=6.3 Hz, 3H); ESI MS m/z 638 $[C_{38}H_{53}NO_7+H]^+$.

Scheme 131: (S)-4-((3-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-3-oxopropyl)amino)-3-hydroxy-4-oxobutanoic acid trifluoroacetic acid salt and (E)-4-((3-(((4R,4aS,7aR,12bS)-4a,9-Dihydroxy-3-methyl-2,3,4,4a,5,7a-hexahydro-1H-4,12-methanobenzofura[3,2-e]isoquinolin-7-yl)oxy)-3-oxopropyl)amino)-4-oxobut-2-enoic acid trifluoroacetic acid salt

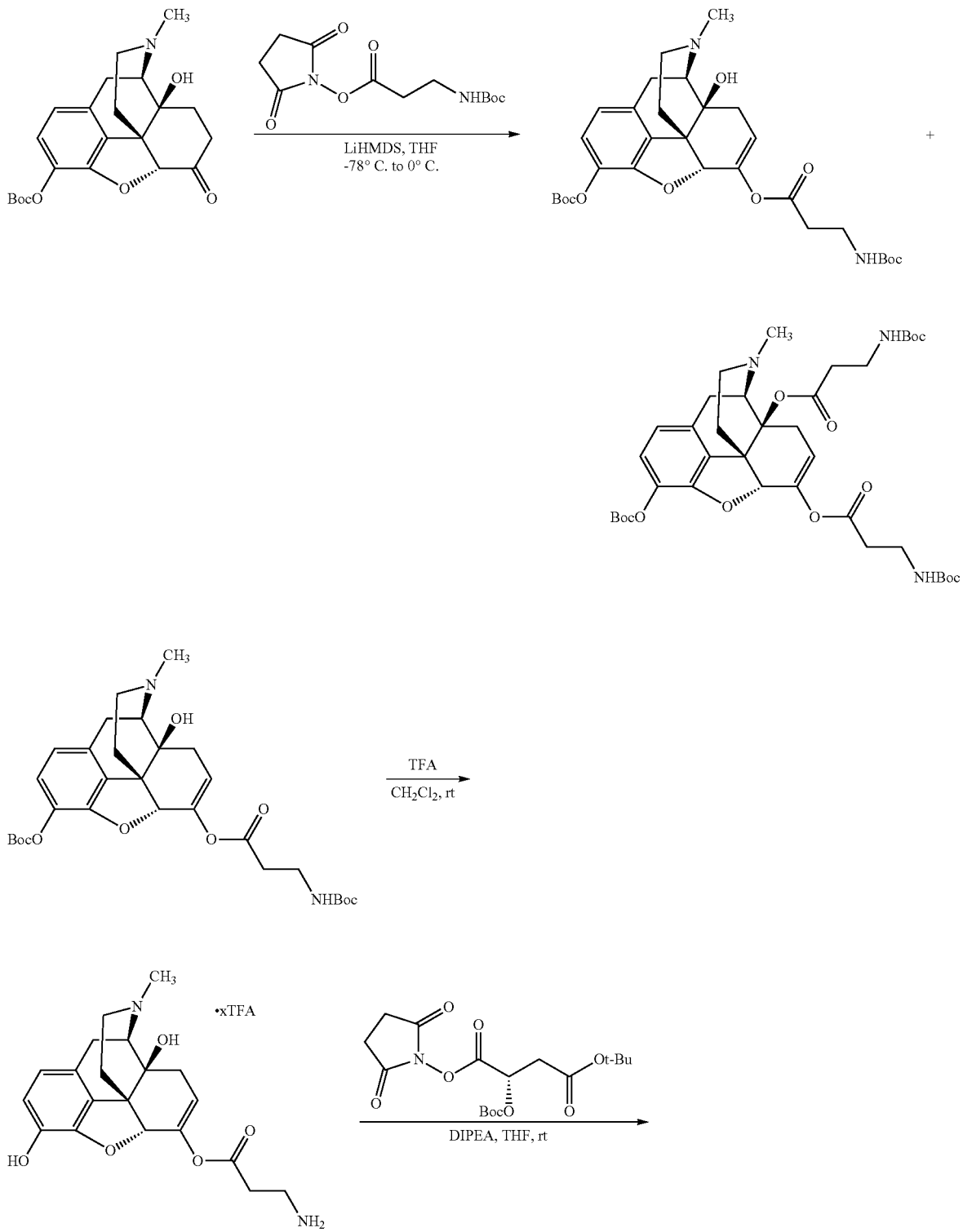

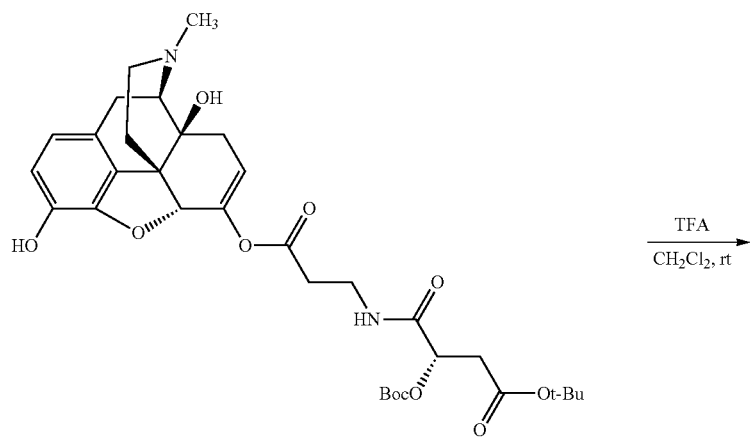
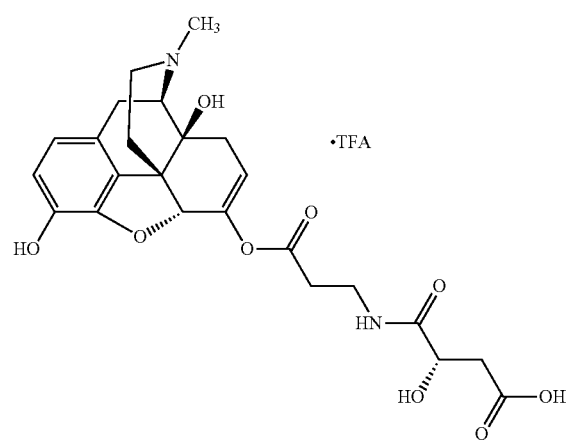
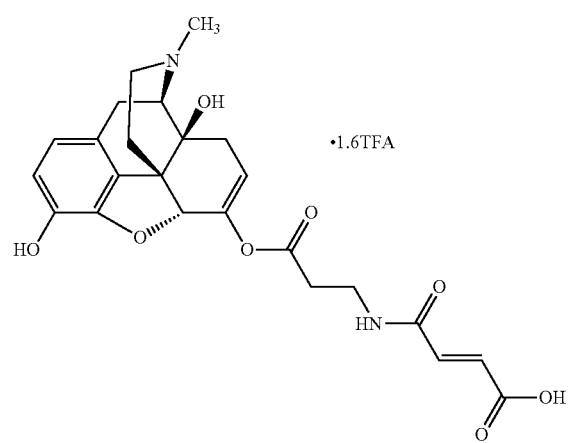 [SMILES: CN1CC[C@]23c4c5ccc(O)c4O[C@H]2C(OC(=O)CCNC(=O)/C=C/C(=O)O)=CC[C@@]3(O)[C@H]1C5]

Preparation of (4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 3-((tert-butoxycarbonyl)amino)propanoate and (4R,4aS,7aR,12bS)-9-((tert-Butoxycarbonyl)oxy)-3-methyl-2,3,4,4a,5,7a-hexahydro-1H-4,12-methanobenzofuro[3,2-e]isoquinoline-4a,7-diyl bis(3-((tert-butoxycarbonyl)amino)propanoate)

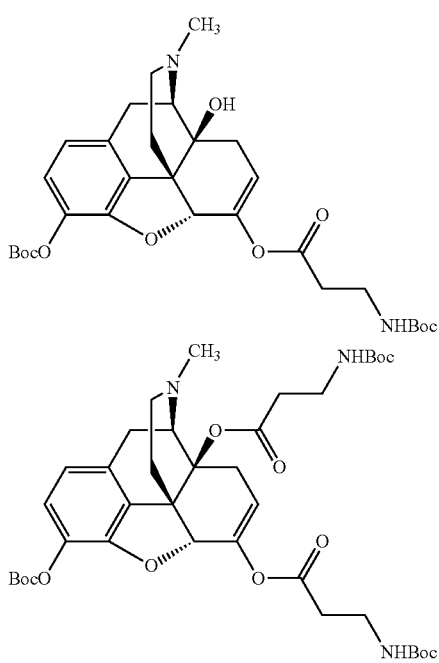

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (1.00 g, 2.49 mmol) in tetrahydrofuran (15 mL) was cooled to 0° C. and treated dropwise with a 3.1 M solution of lithium tert-amylate in heptanes (0.90 mL, 2.80 mmol). After addition was complete, the mixture was stirred at 0° C. for 25 min and then at ambient temperature for 25 min. The mixture was re-cooled to −78° C., and 2,5-dioxopyrrolidin-1-yl 3-((tert-butoxycarbonyl)amino)propanoate (900 mg, 3.32 mmol) was added. The mixture was allowed to warm to 0° C. over 2 h. After this time, the mixture was treated with saturated aqueous ammonium chloride and extracted with ethyl acetate. The combined organics were dried over sodium sulfate, filtered, and concentrated under reduced pressure. The residue was purified by reversed phase column chromatography (150 g C18 column, 5-100% acetonitrile/water) to provide (4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 3-((tert-butoxycarbonyl)amino)propanoate (520 mg, 36%): ESI MS m/z 573 $[C_{30}H_{40}N_2O_9+H]^+$ and (4R,4aS,7aR,12bS)-9-((tert-butoxycarbonyl)oxy)-3-methyl-2,3,4,4a,5,7a-hexahydro-1H-4,12-methanobenzofuro[3,2-e]isoquinoline-4a,7-diyl bis(3-((tert-butoxycarbonyl)amino)propanoate): ESI MS m/z 744 $[C_{38}H_{53}N_3O_{12}+H]^+$.

Preparation of (4R,4aS,7aR,12bS)-4a,9-Dihydroxy-3-methyl-2,3,4,4a,5,7a-hexahydro-1H-4,12-methanobenzofuro[3,2-e]isoquinolin-7-yl 3-aminopropanoate trifluoroacetic acid salt

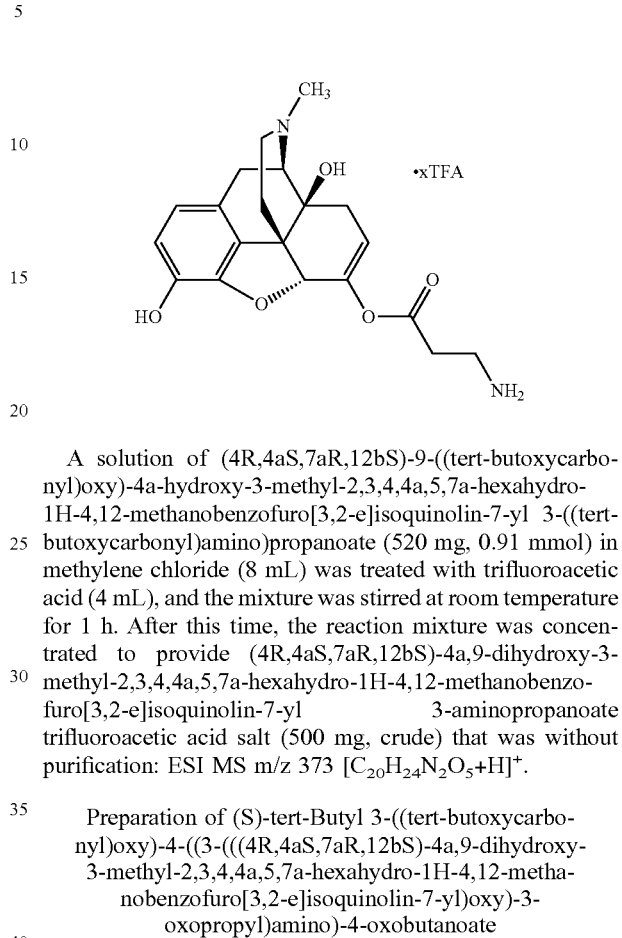

A solution of (4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 3-((tert-butoxycarbonyl)amino)propanoate (520 mg, 0.91 mmol) in methylene chloride (8 mL) was treated with trifluoroacetic acid (4 mL), and the mixture was stirred at room temperature for 1 h. After this time, the reaction mixture was concentrated to provide (4R,4aS,7aR,12bS)-4a,9-dihydroxy-3-methyl-2,3,4,4a,5,7a-hexahydro-1H-4,12-methanobenzofuro[3,2-e]isoquinolin-7-yl 3-aminopropanoate trifluoroacetic acid salt (500 mg, crude) that was without purification: ESI MS m/z 373 $[C_{20}H_{24}N_2O_5+H]^+$.

Preparation of (S)-tert-Butyl 3-((tert-butoxycarbonyl)oxy)-4-((3-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-oxopropyl)amino)-4-oxobutanoate

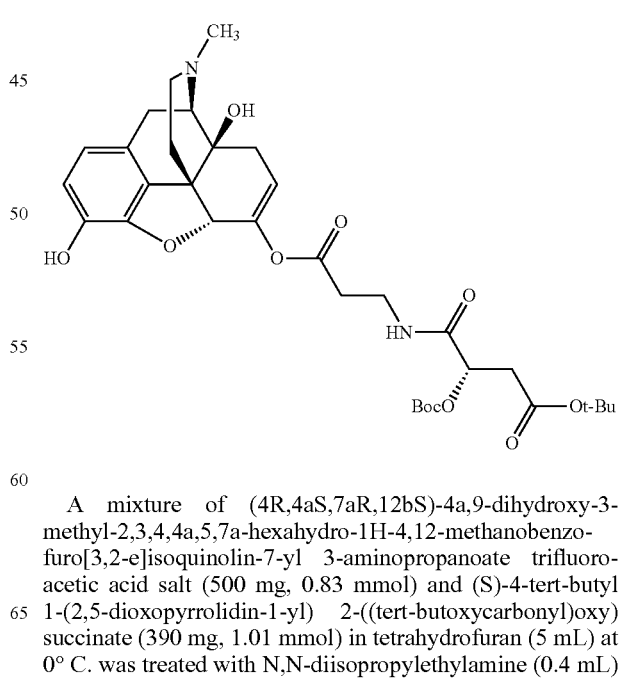

A mixture of (4R,4aS,7aR,12bS)-4a,9-dihydroxy-3-methyl-2,3,4,4a,5,7a-hexahydro-1H-4,12-methanobenzofuro[3,2-e]isoquinolin-7-yl 3-aminopropanoate trifluoroacetic acid salt (500 mg, 0.83 mmol) and (S)-4-tert-butyl 1-(2,5-dioxopyrrolidin-1-yl) 2-((tert-butoxycarbonyl)oxy)succinate (390 mg, 1.01 mmol) in tetrahydrofuran (5 mL) at 0° C. was treated with N,N-diisopropylethylamine (0.4 mL)

and stirred for 1.5 h. After this time, the mixture was diluted with ethyl acetate and washed with water and brine. The organic extracts were dried over sodium sulfate, filtered, and concentrated under reduced pressure. The residue was purified by column chromatography (50 g C18 column, 5-100% acetonitrile/water) to provide (S)-tert-butyl 3-((tert-butoxycarbonyl)oxy)-4-((3-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-oxopropyl)amino)-4-oxobutanoate (240 mg, 41% over two steps): ESI MS m/z 645 $[C_{33}H_{44}N_2O_{11}+H]^+$.

Preparation of (S)-4-((3-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-3-oxopropyl)amino)-3-hydroxy-4-oxobutanoic acid trifluoroacetic acid salt

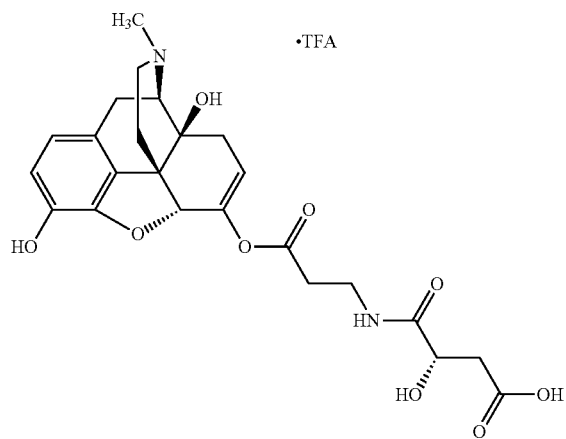 [SMILES: CN1CC[C@]23c4c5ccc(O)c4O[C@H]2C(OC(=O)CCNC(=O)[C@@H](O)CC(=O)O)=CC[C@@]3(O)[C@H]1C5]

A solution of (S)-tert-butyl 3-((tert-butoxycarbonyl)oxy)-4-((3-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-oxopropyl)amino)-4-oxobutanoate (240 mg, 0.37 mmol) in methylene chloride (6 mL) was treated with trifluoroacetic acid (3 mL) and stirred at ambient temperature for 1 h. After this time, the reaction mixture was concentrated under reduced pressure. The residue was purified by reversed phase column chromatography (50 g C18 column, 3-20% acetonitrile/water, with 0.1% trifluoroacetic acid) and freeze dried to provide (S)-4-((3-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-oxopropyl)amino)-3-hydroxy-4-oxobutanoic acid trifluoroacetic acid salt (118 mg, 53%): $^1$H NMR (300 MHz, DMSO-$d_6$) δ 12.23 (br s, 1H), 9.30 (s, 1H), 9.15 (s, 1H), 7.97 (t, J=6.0 Hz, 1H), 6.64 (apparent q, J=8.1 Hz, 2H), 6.22 (s, 1H), 5.85 (s, 1H), 5.55 (dd, J=6.0, 2.1 Hz, 1H), 4.96 (s, 1H), 4.22 (dd, J=8.7, 3.6 Hz, 1H), 3.62-3.43 (m, 5H), 3.11-3.02 (m, 1H), 2.84 (d, J=4.8 Hz, 3H), 2.66-2.60 (m, 4H), 2.49-2.23 (m, 3H), 2.05 (d, J=17.7 Hz, 1H), 1.62 (d, J=10.5 Hz, 1H); ESI MS m/z 508 $[C_{24}H_{28}N_2O_9+H]^+$.

Preparation of (E)-4-((3-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-3-oxopropyl)amino)-4-oxobut-2-enoic acid trifluoroacetic acid salt

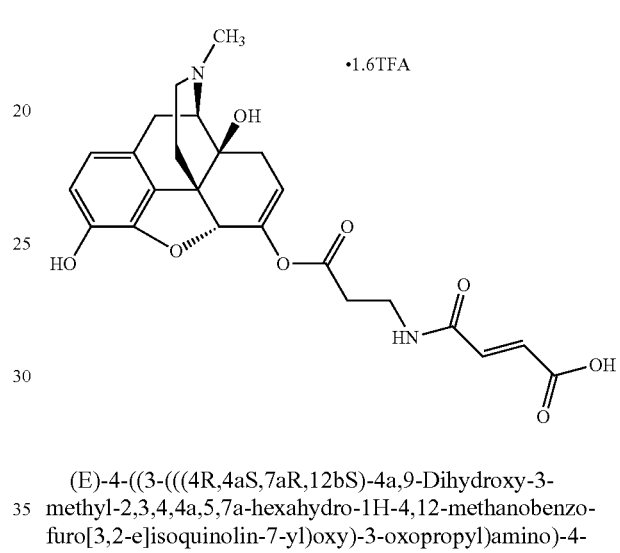

(E)-4-((3-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-3-oxopropyl)amino)-4-oxobut-2-enoic acid trifluoroacetic acid salt (10 mg, 4%) was isolated as a byproduct from the deprotection step of (S)-tert-butyl 3-((tert-butoxycarbonyl)oxy)-4-((3-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-oxopropyl)amino)-4-oxobutanoate with trifluoroacetic acid in methylene chloride: $^1$H NMR (300 MHz, DMSO-$d_6$) δ 12.86 (br s, 1H), 9.30 (s, 1H), 9.15 (s, 1H), 8.65 (t, J=5.5 Hz, 1H), 6.92 (d, J=15.5 Hz, 1H), 6.68 (d, J=8.1 Hz, 1H), 6.62 (d, J=8.1 Hz, 1H), 6.53 (d, J=15.5 Hz, 1H), 6.21 (s, 1H), 5.55 (dd, J=6.0, 2.0 Hz, 1H), 4.96 (s, 1H), 3.61 (d, J=6.3 Hz, 1H), 3.50-3.42 (m, 2H), 3.13-3.01 (m, 3H), 2.84 (d, J=4.7 Hz, 3H), 2.70-2.62 (m, 3H), 2.50-2.40 (m, 1H), 2.32-2.22 (m, 1H), 2.06 (d, J=17.5 Hz, 1H), 1.62 (d, J=11.3 Hz, 1H); ESI MS m/z 471 $[C_{24}H_{26}N_2O_8+H]^+$; HPLC (Method A) 98.9% (AUC), $t_R$=6.64 min.

Scheme 132: (S,Z)-3-((((4R,4aS,7aR,12bS)-4a,9-Dihydroxy-3-methyl-2,3,4,4a,5,7a-hexahydro-1H-4, 12-methanobenzofuro[3,2-e]isoquinolin-7-yl)oxy) carbonyl)-5-oxodocos-13-enoic acid trifluoroacetic acid salt

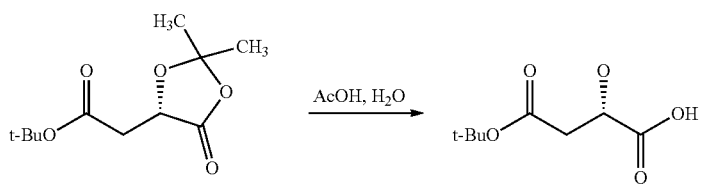

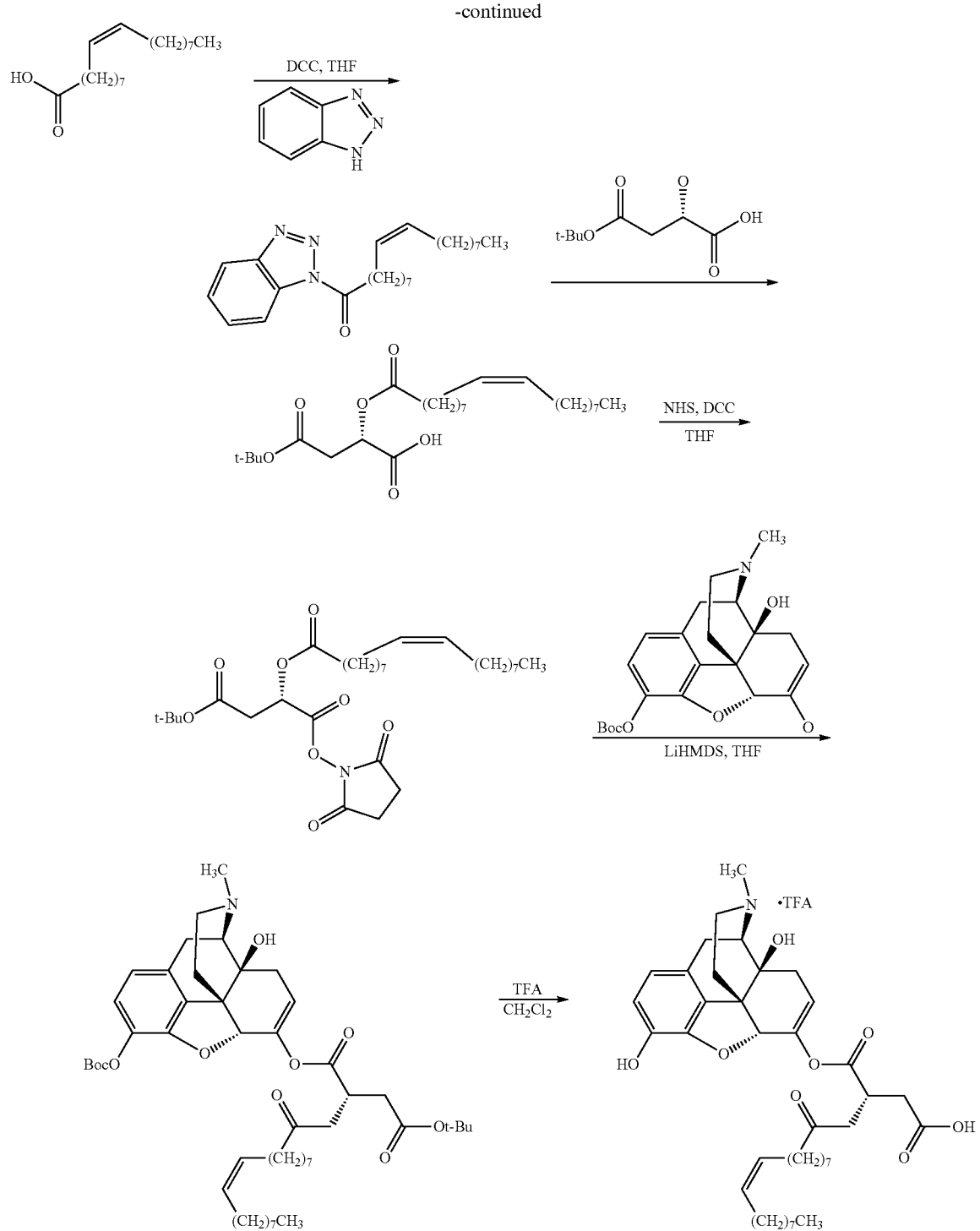

Preparation of (S)-4-(tert-Butoxy)-2-hydroxy-4-oxobutanoic acid

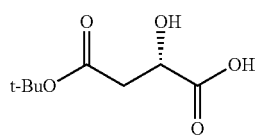 [SMILES: CC(C)(C)OC(=O)C[C@H](O)C(=O)O]

A solution of (S)-tert-butyl 2-(2,2-dimethyl-5-oxo-1,3-dioxolan-4-yl)acetate (4.58 g, 19.9 mmol) in acetic acid (31.5 mL) and water (13.5, mL) was stirred at 60° C. for 4 h. After this time, the solvent was removed under reduced pressure. The residue was dried under vacuum to provide (S)-4-(tert-butoxy)-2-hydroxy-4-oxobutanoic acid (3.37 g, 89%) as a white solid: $^1$H NMR (300 MHz, DMSO-d$_6$) δ 4.48 (t, J=5.7 Hz, 1H), 3.72 (br s, 1H), 2.83 (m, 2H), 1.48 (m, 9H), CO$_2$H proton not observed.

Preparation of (Z)-1-(1H-Benzo[d][1,2,3]triazol-1-yl)octadec-9-en-1-one

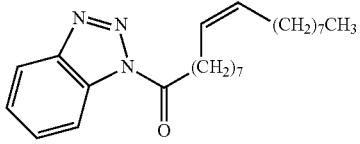

A solution of oleic acid (2.00 g, 7.08 mmol) in tetrahydrofuran (30 mL) was treated with 1H-benzo[d][1,2,3]triazole (928 mg, 7.79 mmol) and N,N'-dicyclohexylcarbodiimide (1.61 g, 7.79 mmol) and stirred under a nitrogen atmosphere for 3 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (Z)-1-(1H-benzo[d][1,2,3]triazol-1-yl)octadec-9-en-1-one (3.13 g) as a white solid that was used without purification.

Preparation of (S,Z)-4-(tert-Butoxy)-2-(oleoyloxy)-4-oxobutanoic acid

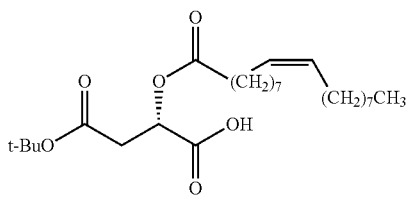

(S)-4-(tert-Butoxy)-2-hydroxy-4-oxobutanoic acid (992 mg, 5.22 mmol), (Z)-1-(1H-benzo[d][1,2,3]triazol-1-yl)octadec-9-en-1-one (2.00 g, 5.22 mmol), 4-(dimethylamino)pyridine (638 mg, 5.22 mmol), and tetrahydrofuran (40 mL) were combined and stirred at room temperature under a nitrogen atmosphere for 48 h. After this time, the solvent was removed under reduced pressure, and the residue was partitioned between ethyl acetate (30 mL) and 10% aqueous citric acid. The organic layer was separated and washed with water (50 mL), dried over sodium sulfate, filtered, and concentrated under reduced pressure. The crude residue was purified by column chromatography (40 g silica gel column, 0-50% ethyl acetate/heptane) to provide (S,Z)-4-(tert-butoxy)-2-(oleoyloxy)-4-oxobutanoic acid (850 mg, 36%) as a colorless oil: $^1$H NMR (300 MHz, CDCl$_3$) δ 5.47 (t, J=5.7 Hz, 1H), 5.36-5.32 (m, 2H), 2.84 (d, J=0.9 Hz, 2H), 2.38 (m, 2H), 2.00 (m, 4H), 1.64 (m, 2H), 1.45 (s, 9H), 1.35-1.27 (m, 20H), 0.85 (m, 3H), CO$_2$H proton not observed.

Preparation of (S,Z)-4-tert-Butyl 1-(2,5-dioxopyrrolidin-1-yl) 2-(oleoyloxy)succinate

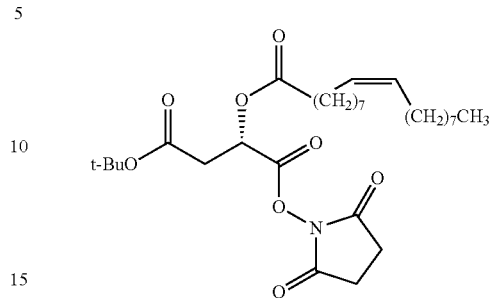

A solution of (S,Z)-4-(tert-butoxy)-2-(oleoyloxy)-4-oxobutanoic acid (820 mg, 1.80 mmol) in tetrahydrofuran (20 mL) was treated with N-hydroxysuccinimide (228 mg, 1.98 mmol) and N,N'-dicyclohexylcarbodiimide (408 mg, 1.98 mmol) and stirred under a nitrogen atmosphere for 4 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S,Z)-4-tert-butyl 1-(2,5-dioxopyrrolidin-1-yl) 2-(oleoyloxy)succinate (1.06 g) as a white solid: $^1$H NMR (300 MHz, CDCl$_3$) δ 5.76 (dd, J=8.1, 1.8 Hz, 1H), 5.36-5.32 (m, 2H), 2.97 (m, 2H), 2.84 (s, 4H), 2.38 (m, 2H), 2.00 (m, 4H), 2.48 (m, 2H), 1.44 (s, 9H), 1.29-1.27 (m, 20H), 0.88 (t, J=6.3 Hz, 3H).

Preparation of (S)-1-((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2-((Z)-2-oxononadec-10-en-1-yl)succinate

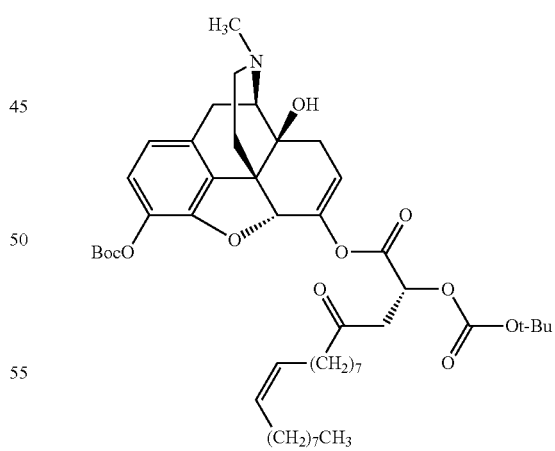

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (328 mg, 0.818 mmol) in tetrahydrofuran (10 mL) was cooled in an ice bath and treated dropwise with a 1.0 M solution of lithium bis(trimethylsilyl)amide in tetrahydrofuran (0.98 mL, 0.98 mmol). After addition was complete, the mixture was stirred at 0° C. for 1 h. The mixture was re-cooled to −45° C. and treated dropwise with a solution of (S,Z)-4-tert-butyl 1-(2,5-dioxopyrrolidin-1-yl) 2-(oleoyloxy)succinate (496 mg, 0.900 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g silica gel column, 0-20% methanol/methylene chloride) to provide (S)-1-((4R,4aS,7aR,12bS)-9-((tert butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2-((Z)-2-oxononadec-10-en-1-yl)succinate (548 mg, 80%) as a white solid: ESI MS m/z 838 $[C_{48}H_{71}NO_{11}+H]^+$.

Preparation of (S,Z)-3-((((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)carbonyl)-5-oxodocos-13-enoic acid trifluoroacetic acid salt

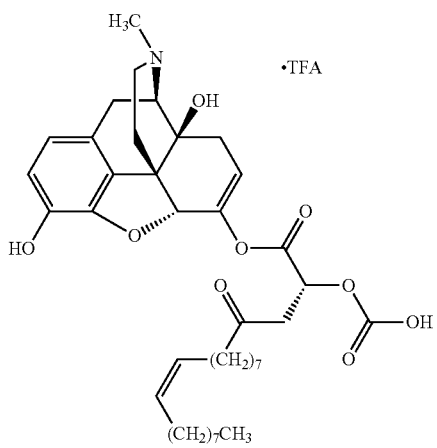

A solution of (S)-1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2-((Z)-2-oxononadec-10-en-1-yl)succinate (270 mg, 0.396 mmol) in methylene chloride (3 mL) was treated with trifluoroacetic acid (3 mL) and stirred under a nitrogen atmosphere at ambient temperature for 1 h. After this time, the reaction mixture was concentrated under reduced pressure. The residue was purified by reversed phase column chromatography (150 g C18 column, 0-100% acetonitrile/water) and freeze dried to provide (S,Z)-3-((((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)carbonyl)-5-oxodocos-13-enoic acid trifluoroacetic acid salt (52.2 mg, 16%) as a fluffy white solid: $^1$H NMR (300 MHz, DMSO-$d_6$) δ 12.75 (br s, 1H), 9.26 (s, 1H), 9.13 (s, 1H), 6.64 (apparent q, J=8.1 Hz, 2H), 6.23 (s, 1H), 5.59 (dd, J=6.0, 2.1 Hz, 1H), 5.40 (dd, J=7.8, 4.2 Hz, 1H), 5.32 (t, J=4.5 Hz, 2H), 4.93 (s, 1H), 3.62-3.41 (m, 1H), 3.04-2.88 (m, 4H), 2.84 (d, J=4.5 Hz, 3H), 2.66-2.24 (m, 6H), 2.09-1.97 (m, 4H), 1.64-1.52 (m, 3H), 1.25 (m, 23H), 0.85 (t, J=6.9 Hz, 3H); ESI MS m/z 680 $[C_{40}H_{57}NO_8+H]^+$.

Scheme 133: (S)-3-((((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)carbonyl)-5-oxodocosanoic acid trifluoroacetic acid salt

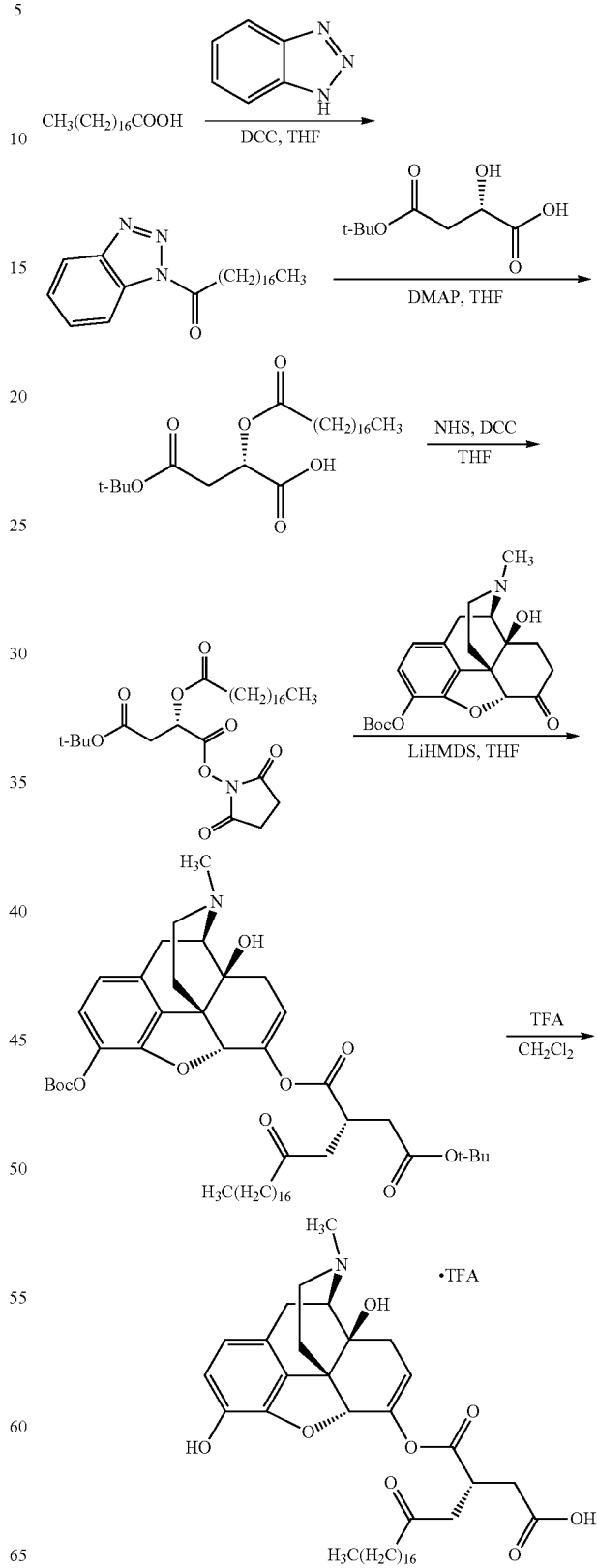

Preparation of 1-(1H-Benzo[d][1,2,3]triazol-1-yl)octadecan-1-one

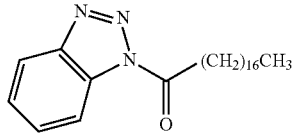

A solution of stearic acid (2.00 g, 7.03 mmol) in tetrahydrofuran (30 mL) was treated with 1H-benzo[d][1,2,3]triazole (921 mg, 7.73 mmol) and N,N'-dicyclohexylcarbodiimide (1.59 g, 7.73 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide 1-(1H-benzo[d][1,2,3]triazol-1-yl)octadecan-1-one (3.02 g) as a white solid, which was used without purification.

Preparation of (S)-4-(tert-Butoxy)-4-oxo-2-(stearoyloxy)butanoic acid

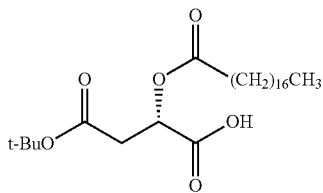

(S)-4-(tert-Butoxy)-2-hydroxy-4-oxobutanoic acid (247 mg, 1.30 mmol), 1-(1H-benzo[d][1,2,3]triazol-1-yl)octadecan-1-one (500 mg, 1.30 mmol), 4-(dimethylamino)pyridine (159 mg, 1.30 mmol), and tetrahydrofuran (10 mL) were combined and stirred at room temperature under a nitrogen atmosphere for 48 h. After this time, the solvent was removed under reduced pressure, and the residue was partitioned between ethyl acetate (30 mL) and 10% aqueous citric acid. The organic layer was separated and washed with water (50 mL), dried over sodium sulfate, filtered, and concentrated under reduced pressure. The crude residue was purified by column chromatography (40 g silica gel column, 0-50% ethyl acetate/heptane) to provide of (S)-4-(tert-butoxy)-4-oxo-2-(stearoyloxy)butanoic acid (430 mg, 72%) as a white solid: $^1$H NMR (300 MHz, CDCl$_3$) δ 5.47 (t, J=5.7 Hz, 1H), 2.84 (d, J=0.9 Hz, 2H), 2.38 (m, 2H), 1.62 (m, 2H), 1.45 (s, 9H), 1.25 (m, 28H), 0.88 (t, J=6.6 Hz, 3H), CO$_2$H proton not observed.

Preparation of (S)-4-tert-Butyl 1-(2,5-dioxopyrrolidin-1-yl) 2-(stearoyloxy)succinate

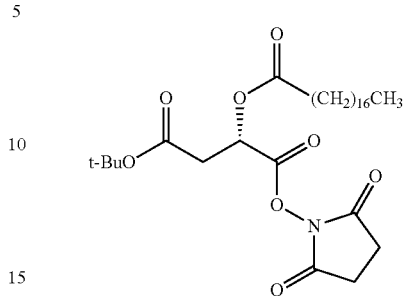

A solution of (S)-4-(tert-butoxy)-4-oxo-2-(stearoyloxy)butanoic acid (430 mg, 0.942 mmol) in tetrahydrofuran (10 mL) was treated with N-hydroxysuccinimide (119 mg, 1.04 mmol) and N,N'-dicyclohexylcarbodiimide (214 mg, 1.04 mmol) and stirred under a nitrogen atmosphere for 4 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-4-tert-butyl 1-(2,5-dioxopyrrolidin-1-yl) 2-(stearoyloxy)succinate (610 mg) as a white solid: $^1$H NMR (300 MHz, CDCl$_3$) δ 5.76 (dd, J=8.1, 1.8 Hz, 1H), 2.96 (m, 2H), 2.84 (s, 4H), 2.38 (m, 2H), 1.67 (m, 2H), 1.46 (s, 9H), 1.25 (m, 28H), 0.88 (t, J=6.3 Hz, 3H).

Preparation of (S)-1-((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2-(2-oxononadecyl)succinate

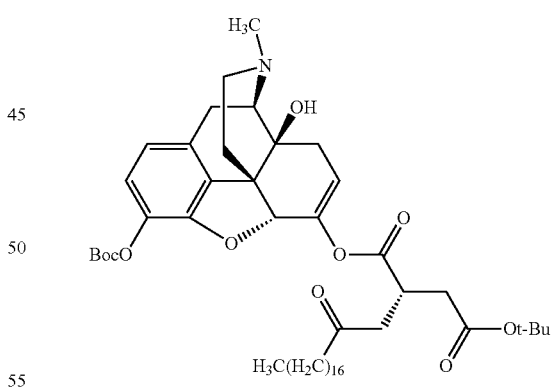

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (20 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at 0° C. for 1 h. The mixture was re-cooled to −45° C. and treated dropwise with a solution of (S)-4-tert-butyl 1-(2,5-dioxopyrrolidin-1-yl) 2-(stearoyloxy)succinate (759 mg, 1.37 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g silica gel column, 0-20% methanol/methylene chloride) to provide (S)-1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2-(2-oxononadecyl)succinate (782 mg, 74%) as a white solid: ESI MS m/z 840 $[C_{48}H_{73}NO_{11}+H]^+$.

Preparation of (S)-3-((((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)carbonyl)-5-oxodocosanoic acid trifluoroacetic acid salt

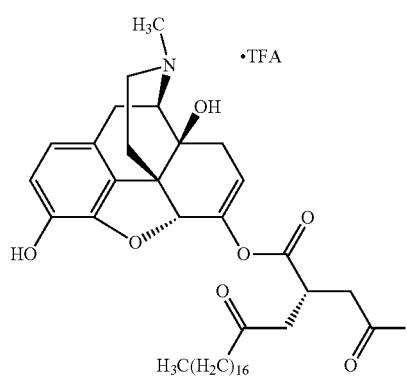

A solution of (S)-1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2-(2-oxononadecyl)succinate (390 mg, 0.464 mmol) in methylene chloride (3 mL) was treated with trifluoroacetic acid (3 mL) and stirred under a nitrogen atmosphere at ambient temperature for 1 h. After this time, the reaction mixture was concentrated under reduced pressure. The residue was purified by reversed phase column chromatography (150 g C18 column, 0-100% acetonitrile/water) and freeze dried to provide (S)-3-((((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)carbonyl)-5-oxodocosanoic acid trifluoroacetic acid salt (69 mg, 13%) as a fluffy white solid: $^1$H NMR (300 MHz, DMSO-$d_6$) δ 12.77 (s, 1H), 9.26 (s, 1H), 9.14 (s, 1H), 6.65 (q, J=8.1 Hz, 2H), 6.24 (s, 1H), 5.59 (dd, J=6.0, 2.1 Hz, 1H), 5.40 (dd, J=7.8, 4.2 Hz, 1H), 4.92 (s, 1H), 3.04-2.83 (m, 6H), 2.63-2.24 (m, 6H), 2.06 (d, J=18.0 Hz, 1H), 1.64-1.52 (m, 3H), 1.25 (m, 31H), 0.85 (t, J=6.9 Hz, 3H); ESI MS m/z 682 $[C_{40}H_{59}NO_8+H]^+$.

Scheme 134: (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-acetoxypropanoate trifluoroacetic acid salt

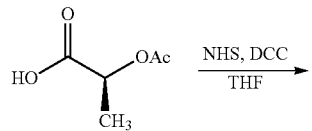

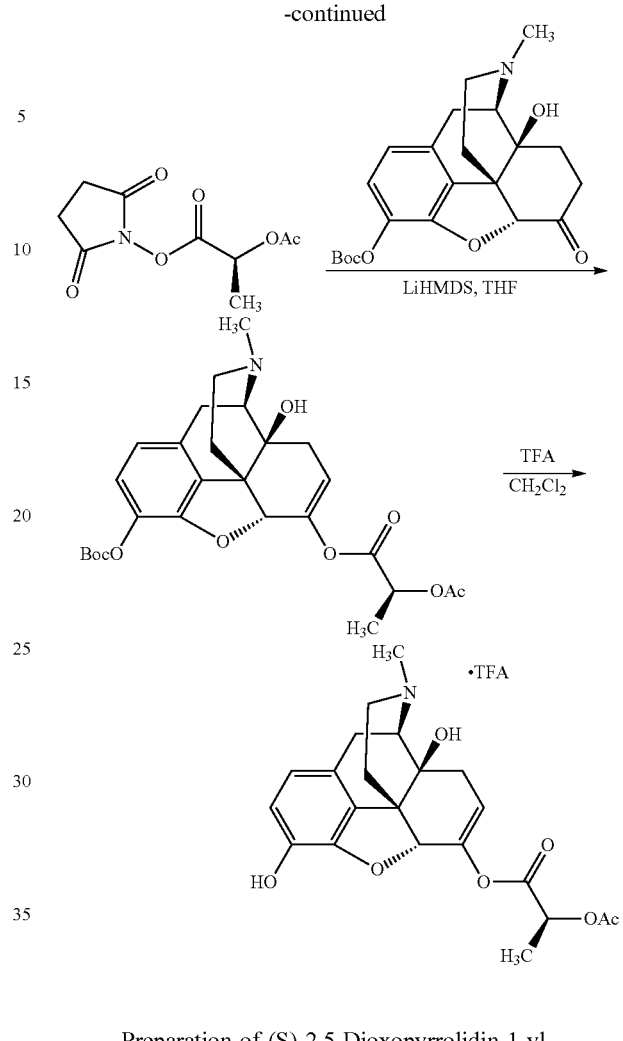

Preparation of (S)-2,5-Dioxopyrrolidin-1-yl 2-acetoxypropanoate

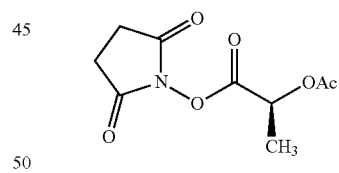

A solution of (S)-2-acetoxypropanoic acid (10.06 g, 76.15 mmol) in tetrahydrofuran (300 mL) was treated with N-hydroxysuccinimide (9.71 g, 84.4 mmol) and N,N'-dicyclohexylcarbodiimide (17.36 g, 84.14 mmol) and stirred under a nitrogen atmosphere for 4.5 h. After this time, the reaction mixture was filtered to remove the solid dicyclohexylurea byproduct. The solid was washed with diethyl ether, and the combined filtrate and washings were concentrated under reduced pressure. The crude residue was triturated with 5:1 diethyl ether/methylene chloride (120 mL). The resulting solid was isolated by filtration and washed with diethyl ether. The combined filtrate and washings were concentrated under reduced pressure to provide (S)-2,5-dioxopyrrolidin-1-yl 2-acetoxypropanoate (18.24 g, quantitative) as an off-white foam: $^1$H NMR (300 MHz, CDCl$_3$) δ 5.41 (t, J=7.2 Hz, 1H), 2.81 (s, 4H), 2.16 (s, 3H), 1.67 (d, J=7.2 Hz, 3H).

Preparation of (S)-(4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 2-acetoxypropanoate

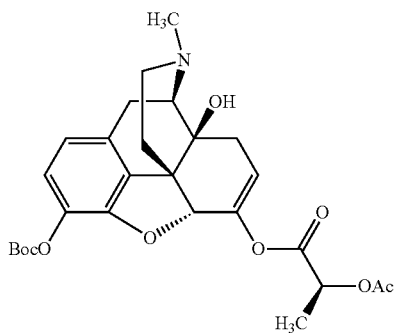

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at 0° C. for 1 h. The mixture was re-cooled to −45° C. and treated dropwise with a solution of (S)-2,5-dioxopyrrolidin-1-yl 2-acetoxypropanoate (314 mg, 1.37 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-acetoxypropanoate (131 mg, 20%) as a white solid: ESI MS m/z 516 $[C_{27}H_{33}NO_9+H]^+$.

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-acetoxypropanoate trifluoroacetic acid salt

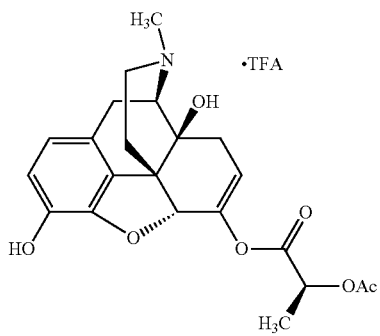 [SMILES: CC(=O)O[C@@H](C)C(=O)OC1=CC[C@@]2(O)[C@H]3Cc4ccc(O)c5c4[C@@]2(CCN3C)[C@H]1O5]

A solution of (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-acetoxypropanoate (131 mg, 0.254 mmol) in methylene chloride (5.0 mL) was treated with trifluoroacetic acid (3.0 mL) and stirred under a nitrogen atmosphere at ambient temperature for 2 h. After this time, the reaction mixture was concentrated under reduced pressure. The residue was purified by reversed phase column chromatography (50 g C18 column, 0-100% acetonitrile/water) and freeze dried to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-acetoxypropanoate trifluoroacetic acid salt (99 mg, 67%) as a fluffy white solid: $^1$H NMR (300 MHz, DMSO-$d_6$) δ 9.28 (s, 1H), 9.14 (s, 1H), 6.65 (q, J=8.1 Hz, 2H), 6.25 (s, 1H), 5.58 (dd, J=6.0, 2.1 Hz, 1H), 5.08 (q, J=6.9 Hz, 1H), 4.95 (s, 1H), 3.05 (m, 1H), 2.83 (d, J=4.2 Hz, 3H), 2.67-2.24 (m, 6H), 2.11-2.03 (m, 4H), 1.62 (d, J=12.6 Hz, 1H), 1.51 (d, J=7.2 Hz, 3H); ESI MS m/z 416 $[C_{22}H_{25}NO_7+H]^+$.

Scheme 135: (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-(((S)-2-acetoxypropanoyl)oxy)propanoate trifluoroacetic acid salt

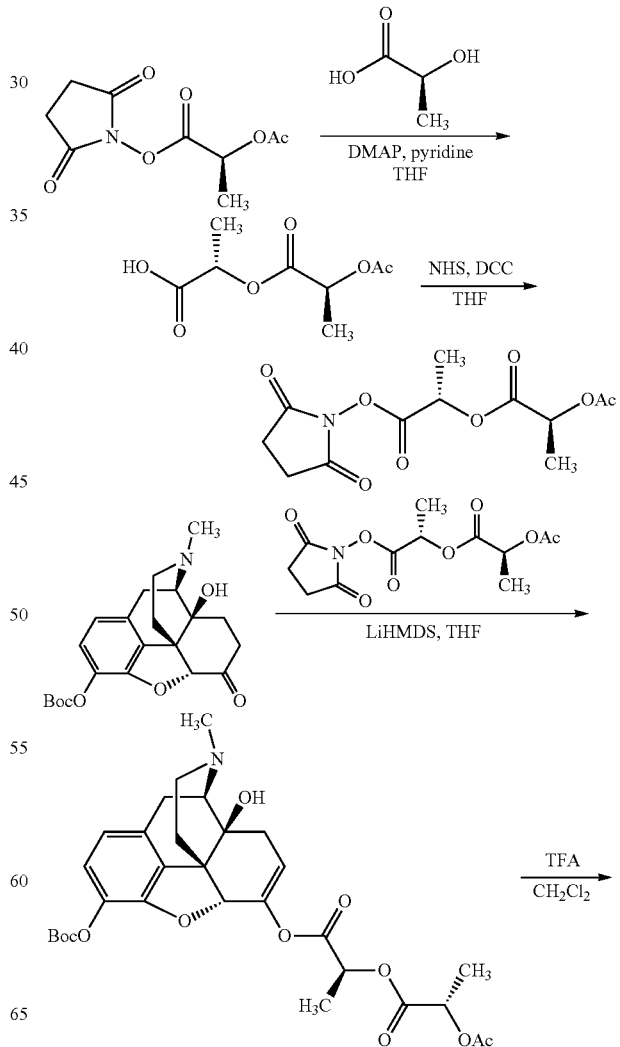

-continued

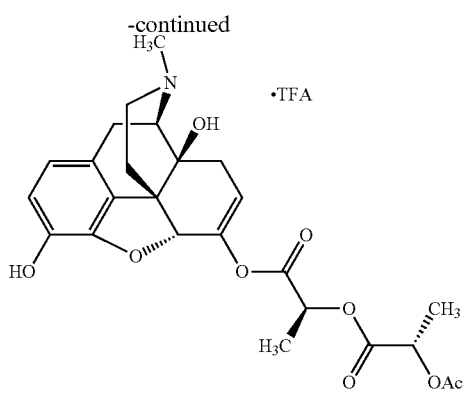

Preparation of (S)-2-(((S)-2-Acetoxypropanoyl)oxy)propanoic acid

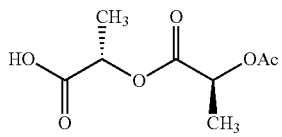

(S)-Lactic acid (472 mg, 5.24 mmol), (S)-2,5-dioxopyrrolidin-1-yl 2-acetoxypropanoate (1.00 g, 4.36 mmol), 4-(dimethylamino)pyridine (53 mg, 0.44 mmol), pyridine (414 mg, 5.24 mmol) and tetrahydrofuran (17 mL) were combined and heated at 80° C. under a nitrogen atmosphere for 24 h. After this time, the solvent was removed under reduced pressure, and the residue was partitioned between ethyl acetate (20 mL) and 10% aqueous citric acid. The organic layer was separated and extracted with saturated aqueous sodium bicarbonate (20 ml). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (S)-2-(((S)-2-acetoxypropanoyl)oxy)propanoic acid (323 mg, 36%) as a colorless oil: $^1$H NMR (300 MHz, CDCl$_3$) δ 5.23-5.08 (m, 2H), 2.14 (s, 3H), 1.60-1.48 (m, 6H), CO$_2$H proton not observed.

Preparation of (S)-2,5-Dioxopyrrolidin-1-yl 2-(((S)-2-acetoxypropanoyl)oxy)propanoate

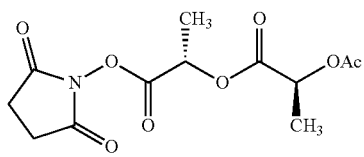 [SMILES: CC(=O)O[C@@H](C)C(=O)O[C@@H](C)C(=O)ON1C(=O)CCC1=O]

A solution of (S)-2-(((S)-2-acetoxypropanoyl)oxy)propanoic acid (323 mg, 1.58 mmol) in tetrahydrofuran (15 mL) was treated with N-hydroxysuccinimide (200 mg, 1.74 mmol) and N,N'-dicyclohexylcarbodiimide (358 mg, 1.74 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-2,5-dioxopyrrolidin-1-yl 2-(((S)-2-acetoxypropanoyl)oxy)propanoate (543 mg) as a colorless oil: $^1$H NMR (300 MHz, CDCl$_3$) δ 5.53 (q, J=5.4 Hz, 1H), 5.13 (q, J=5.4 Hz, 1H), 2.85 (s, 4H), 2.13 (s, 3H), 1.72 (m, 3H), 1.57 (m, 3H).

Preparation of (S)-(4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 2-(((S)-2-acetoxypropanoyl)oxy)propanoate

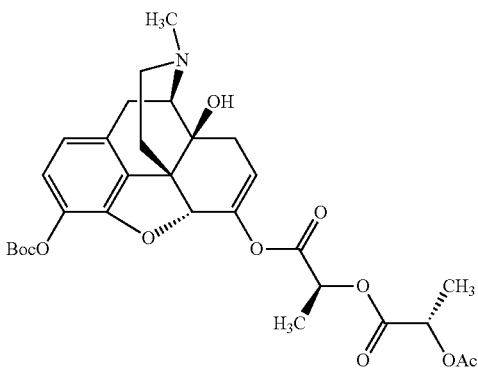

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (577 mg, 1.44 mmol) in tetrahydrofuran (10 mL) was cooled in an ice bath and treated dropwise with a 1.0 M solution of lithium bis(trimethylsilyl)amide in tetrahydrofuran (1.7 mL, 1.7 mmol). After addition was complete, the mixture was stirred at 0° C. for 1 h. The mixture was re-cooled to −45° C. and treated dropwise with a solution of (S)-2,5-dioxopyrrolidin-1-yl 2-(((S)-2-acetoxypropanoyl)oxy)propanoate (476 mg, 1.58 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-(((S)-2-acetoxypropanoyl)oxy)propanoate (236 mg, 28%) as a white solid: ESI MS m/z 588 [C$_{30}$H$_{37}$NO$_{11}$+H]$^+$.

791

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-(((S)-2-acetoxypropanoyl)oxy)propanoate trifluoroacetic acid salt

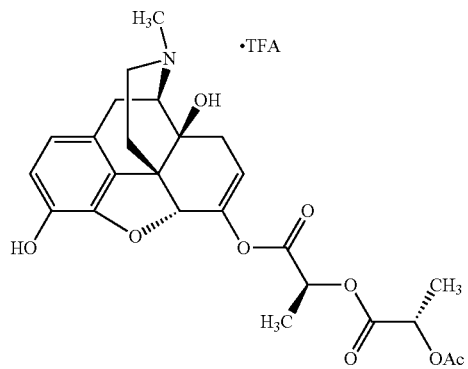 [SMILES: CC(=O)O[C@@H](C)C(=O)O[C@@H](C)C(=O)OC1=CC[C@@]2(O)[C@H]3Cc4ccc(O)c5c4[C@@]2(CCN3C)[C@H]1O5]

A solution of (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-(((S)-2-acetoxypropanoyl)oxy)propanoate (118 mg, 0.201 mmol) in methylene chloride (3.0 mL) was treated with trifluoroacetic acid (3.0 mL) and stirred under a nitrogen atmosphere at ambient temperature for 2 h. After this time, the reaction mixture was concentrated under reduced pressure. The residue was purified by reversed phase column chromatography (50 g C18 column, 0-100% acetonitrile/water) and freeze dried to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-(((S)-2-acetoxypropanoyl)oxy)propanoate trifluoroacetic acid salt (68.4 mg, 54%) as a fluffy white solid: $^1$H NMR (300 MHz, DMSO-d$_6$) δ 9.27 (s, 1H), 9.14 (s, 1H), 6.65 (q, J=8.1 Hz, 2H), 6.24 (s, 1H), 5.58 (dd, J=5.7, 1.8 Hz, 1H), 5.23 (q, J=6.9 Hz, 1H), 5.07 (q, J=7.2 Hz, 1H), 4.95 (s, 1H), 3.05 (m, 1H), 2.82 (s, 3H), 2.63-2.24 (m, 6H), 2.08-2.03 (m, 4H), 1.62 (d, J=12.3 Hz, 1H), 1.54 (d, J=7.2 Hz, 3H), 1.47 (d, J=7.2 Hz, 3H); ESI MS m/z 488 [C$_{25}$H$_{29}$NO$_9$+H]$^+$.

Scheme 136: (S)-(S)-2-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-oxo-1-phenylethyl 2-acetoxypropanoate trifluoroacetic acid salt

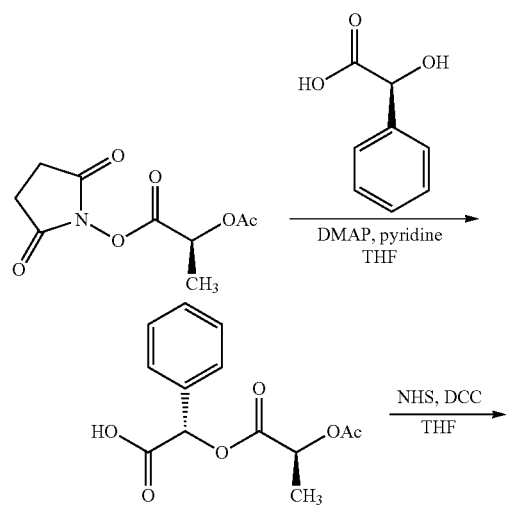

792

-continued

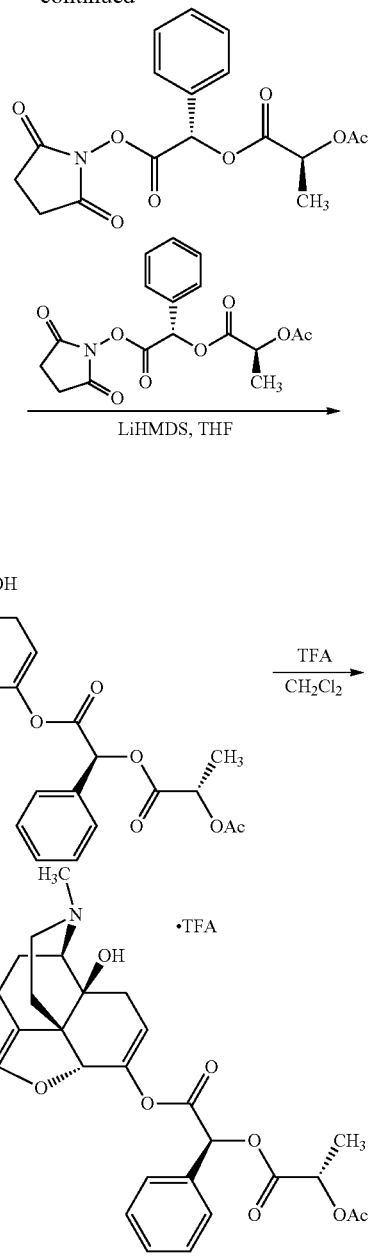

Preparation of (S)-2-(((S)-2-Acetoxypropanoyl)oxy)-2-phenylacetic acid (S)-Mandelic acid (553 mg, 3.63 mmol), (S)-2,5-dioxopyrrolidin-1-yl 2-acetoxypropanoate (1.00 g, 4.36 mmol), 4-(dimethylamino)pyridine (44 mg, 0.363 mmol), pyridine (345 mg, 4.36 mmol) and tetrahydrofuran (15 mL) were combined and heated at 60° C. under a nitrogen atmosphere for 48 h. After this time, the solvent was removed under reduced pressure, and the residue was partitioned between ethyl acetate (20 mL) and 10% aqueous citric acid. The organic layer was separated and extracted with saturated aqueous sodium bicarbonate (20 ml). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (S)-2-(((S)-2-acetoxypropanoyl)oxy)-2-phenylacetic acid (1.02 g, 87%) as a colorless oil: $^1$H NMR (300 MHz, CDCl$_3$) δ 7.46-7.37 (m, 5H), 5.99 (s, 1H), 5.19 (q, J=7.2 Hz, 1H), 2.12 (s, 3H), 1.61 (d, J=6.9 Hz, 3H), CO$_2$H proton not observed.

Preparation of (S)-(S)-2-((2,5-Dioxopyrrolidin-1-yl)oxy)-2-oxo-1-phenylethyl 2-acetoxypropanoate

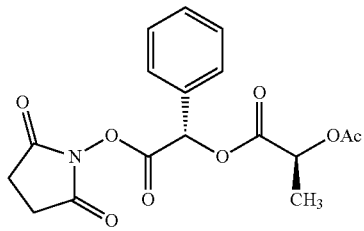 [SMILES: CC(=O)O[C@@H](C)C(=O)O[C@H](C(=O)ON1C(=O)CCC1=O)c1ccccc1]

A solution of (S)-2-(((S)-2-acetoxypropanoyl)oxy)-2-phenylacetic acid (1.02 g, 3.83 mmol) in tetrahydrofuran (40 mL) was treated with N-hydroxysuccinimide (485 mg, 4.21 mmol) and N,N'-dicyclohexylcarbodiimide (867 mg, 4.21 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-(S)-2-((2,5-dioxopyrrolidin-1-yl)oxy)-2-oxo-1-phenylethyl 2-acetoxypropanoate (1.65 g) as a white solid: $^1$H NMR (300 MHz, CDCl$_3$) δ 7.56-7.51 (m, 5H), 6.38 (s, 1H), 5.17 (q, J=7.2 Hz, 1H), 2.82 (s, 4H), 2.12 (s, 3H), 1.59 (d, J=6.9 Hz, 3H).

Preparation of (S)-(S)-2-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl 2-acetoxypropanoate

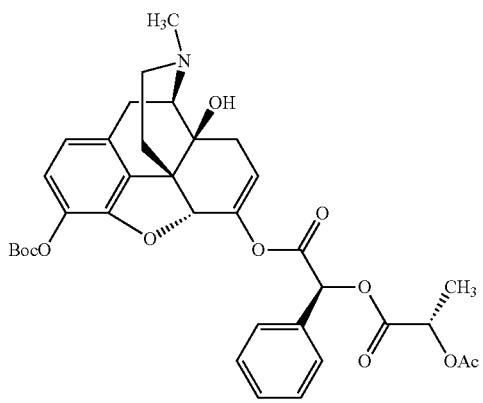

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at 0° C. for 1 h. The mixture was re-cooled to −45° C. and treated dropwise with a solution of (S)-(S)-2-((2,5-dioxopyrrolidin-1-yl)oxy)-2-oxo-1-phenylethyl 2-acetoxypropanoate (498 mg, 1.37 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-(S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl 2-acetoxypropanoate (318 mg, 39%) as a white solid: ESI MS m/z 650 [C$_{35}$H$_{39}$NO$_{11}$+H]$^+$.

Preparation of (S)-(S)-2-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-oxo-1-phenylethyl 2-acetoxypropanoate trifluoroacetic acid salt

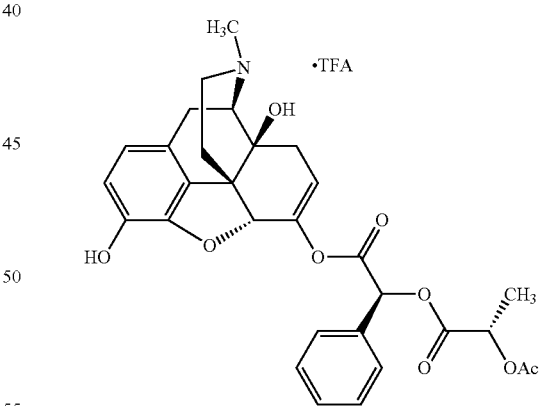

A solution of (S)-(S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl 2-acetoxypropanoate (159 mg, 0.245 mmol) in methylene chloride (5.0 mL) was treated with trifluoroacetic acid (3.0 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water) and freeze dried to provide (S)-(S)-2-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-oxo-1-phenylethyl 2-acetoxypropanoate trifluoroacetic acid salt (90 mg, 52%) as a fluffy white solid: $^1$H NMR (300 MHz, DMSO-$d_6$) δ 9.25 (s, 1H), 9.12 (s, 1H), 7.60-7.55 (m, 2H), 7.52-7.46 (m, 3H), 6.65 (q, J=8.1 Hz, 2H), 6.24 (s, 1H), 6.21 (s, 1H), 5.58 (dd, J=6.0, 2.1 Hz, 1H), 5.15 (q, J=6.9 Hz, 1H), 4.86 (s, 1H), 3.03 (m, 1H), 2.82 (s, 3H), 2.63-2.22 (m, 6H), 2.08-2.02 (m, 4H), 1.62 (d, J=13.5 Hz, 1H), 1.54 (d, J=7.2 Hz, 3H); ESI MS m/z 550 [$C_{30}H_{31}NO_9$+H]$^+$.

Scheme 137: (3S,6S)-6-Acetoxy-3-((((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)carbonyl)-5-oxoheptanoic acid trifluoroacetic acid salt

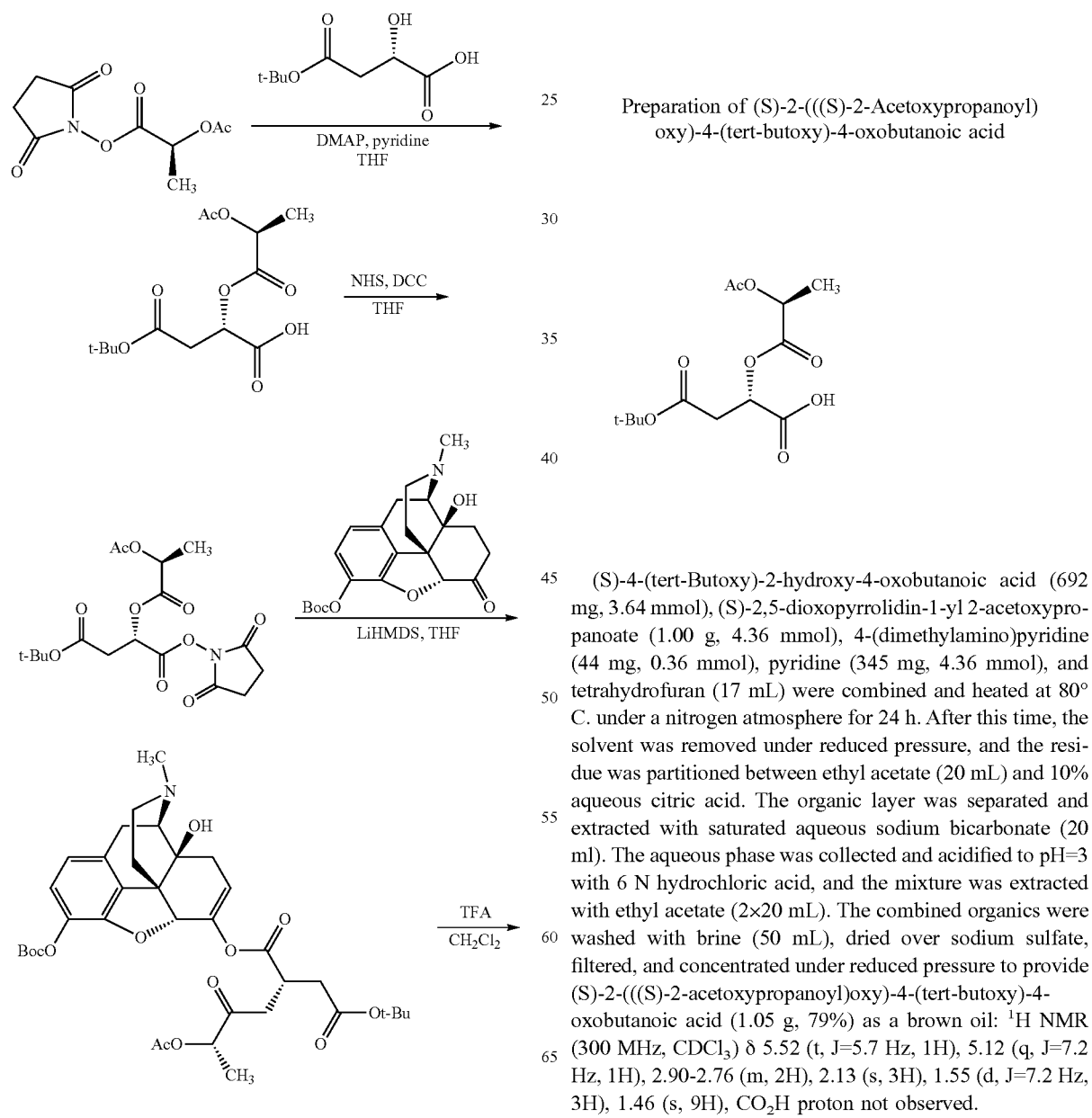

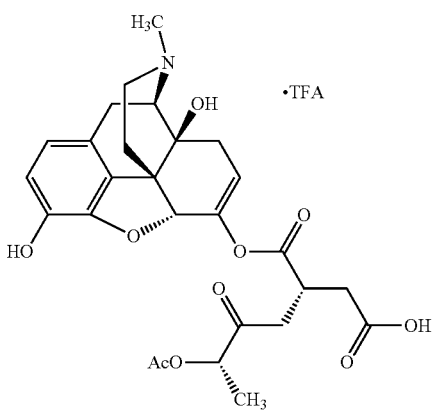

Preparation of (S)-2-(((S)-2-Acetoxypropanoyl)oxy)-4-(tert-butoxy)-4-oxobutanoic acid (S)-4-(tert-Butoxy)-2-hydroxy-4-oxobutanoic acid (692 mg, 3.64 mmol), (S)-2,5-dioxopyrrolidin-1-yl 2-acetoxypropanoate (1.00 g, 4.36 mmol), 4-(dimethylamino)pyridine (44 mg, 0.36 mmol), pyridine (345 mg, 4.36 mmol), and tetrahydrofuran (17 mL) were combined and heated at 80° C. under a nitrogen atmosphere for 24 h. After this time, the solvent was removed under reduced pressure, and the residue was partitioned between ethyl acetate (20 mL) and 10% aqueous citric acid. The organic layer was separated and extracted with saturated aqueous sodium bicarbonate (20 ml). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (S)-2-(((S)-2-acetoxypropanoyl)oxy)-4-(tert-butoxy)-4-oxobutanoic acid (1.05 g, 79%) as a brown oil: $^1$H NMR (300 MHz, CDCl$_3$) δ 5.52 (t, J=5.7 Hz, 1H), 5.12 (q, J=7.2 Hz, 1H), 2.90-2.76 (m, 2H), 2.13 (s, 3H), 1.55 (d, J=7.2 Hz, 3H), 1.46 (s, 9H), CO$_2$H proton not observed.

Preparation of (S)-4-tert-Butyl 1-(2,5-dioxopyrrolidin-1-yl) 2-(((S)-2-acetoxypropanoyl)oxy)succinate

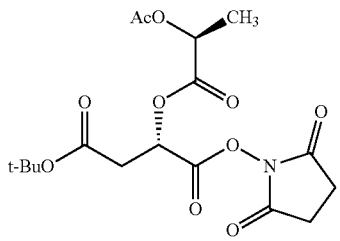 [SMILES: CC(=O)O[C@@H](C)C(=O)O[C@@H](CC(=O)OC(C)(C)C)C(=O)ON1C(=O)CCC1=O]

A solution of (S)-2-(((S)-2-acetoxypropanoyl)oxy)-4-(tert-butoxy)-4-oxobutanoic acid (1.05 g, 3.45 mmol) in tetrahydrofuran (40 mL) was treated with N-hydroxysuccinimide (436 mg, 3.80 mmol) and N,N'-dicyclohexylcarbodiimide (783 mg, 3.80 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-4-tert-butyl 1-(2,5-dioxopyrrolidin-1-yl) 2-(((S)-2-acetoxypropanoyl)oxy)succinate (1.80 g) as a white solid: $^1$H NMR (300 MHz, CDCl$_3$) δ 5.84 (dd, J=7.2, 5.1 Hz, 1H), 5.12 (q, J=7.2 Hz, 1H), 3.02-2.92 (m, 2H), 2.84 (s, 4H), 2.13 (s, 3H), 1.54 (d, J=7.2 Hz, 3H), 1.45 (s, 9H).

Preparation of (S)-1-((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2-((S)-3-acetoxy-2-oxobutyl)succinate

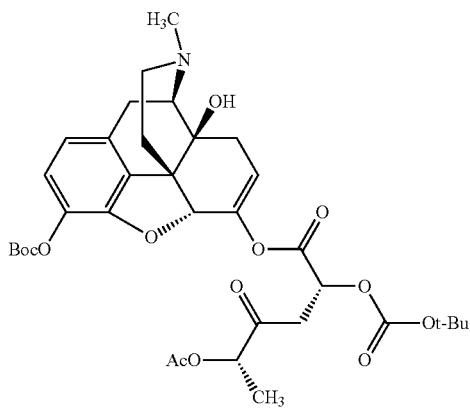

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at 0° C. for 1 h. The mixture was re-cooled to −45° C. and treated dropwise with a solution of (S)-4-tert-butyl 1-(2,5-dioxopyrrolidin-1-yl) 2-(((S)-2-acetoxypropanoyl) oxy)succinate (550 mg, 1.37 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2-((S)-3-acetoxy-2-oxobutyl)succinate (318 mg, 39%) as a white solid: ESI MS m/z 688 $[C_{35}H_{45}NO_{13}+H]^+$.

Preparation of (3S,6S)-6-Acetoxy-3-((((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)carbonyl)-5-oxoheptanoic acid trifluoroacetic acid salt

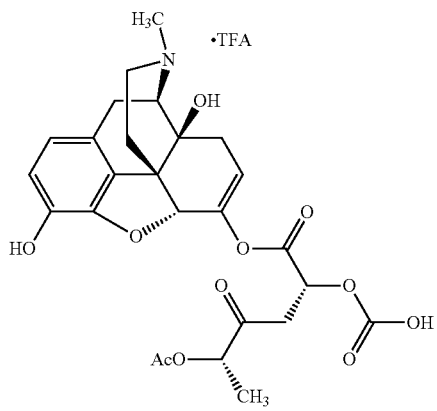 [SMILES: CC(=O)O[C@@H](C)C(=O)C[C@@H](OC(=O)O)C(=O)OC1=CC[C@@]2(O)[C@H]3Cc4ccc(O)c5c4[C@@]2(CCN3C)[C@H]1O5]

A solution of (S)-1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2-((S)-3-acetoxy-2-oxobutyl)succinate (126 mg, 0.183 mmol) in methylene chloride (3 mL) was treated with trifluoroacetic acid (3 mL) and stirred under a nitrogen atmosphere at ambient temperature for 3 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (3S,6S)-6-acetoxy-3-((((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)carbonyl)-5-oxoheptanoic acid trifluoroacetic acid salt (73 mg, 56%) as a fluffy white solid: $^1$H NMR (300 MHz, DMSO-d$_6$) δ 12.82 (s, 1H), 9.27 (s, 1H), 9.15 (s, 1H), 6.65 (apparent q, J=8.1 Hz, 2H), 6.25 (s, 1H), 5.59 (dd, J=6.0, 2.1 Hz, 1H), 5.50 (t, J=5.4 Hz, 1H), 5.08 (q, J=7.2 Hz, 1H), 4.91 (s, 1H), 3.04 (m, 1H), 2.95 (d, J=6.0 Hz, 2H), 2.84 (d, J=4.5 Hz, 3H), 2.67-2.25 (m, 8H), 2.08-2.03 (m, 4H), 1.62 (d, J=11.7 Hz, 1H), 1.46 (d, J=6.9 Hz, 3H); ESI MS m/z 530 $[C_{27}H_{31}NO_{10}+H]^+$.

Scheme 138: (S)-1-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl oleate trifluoroacetic acid salt
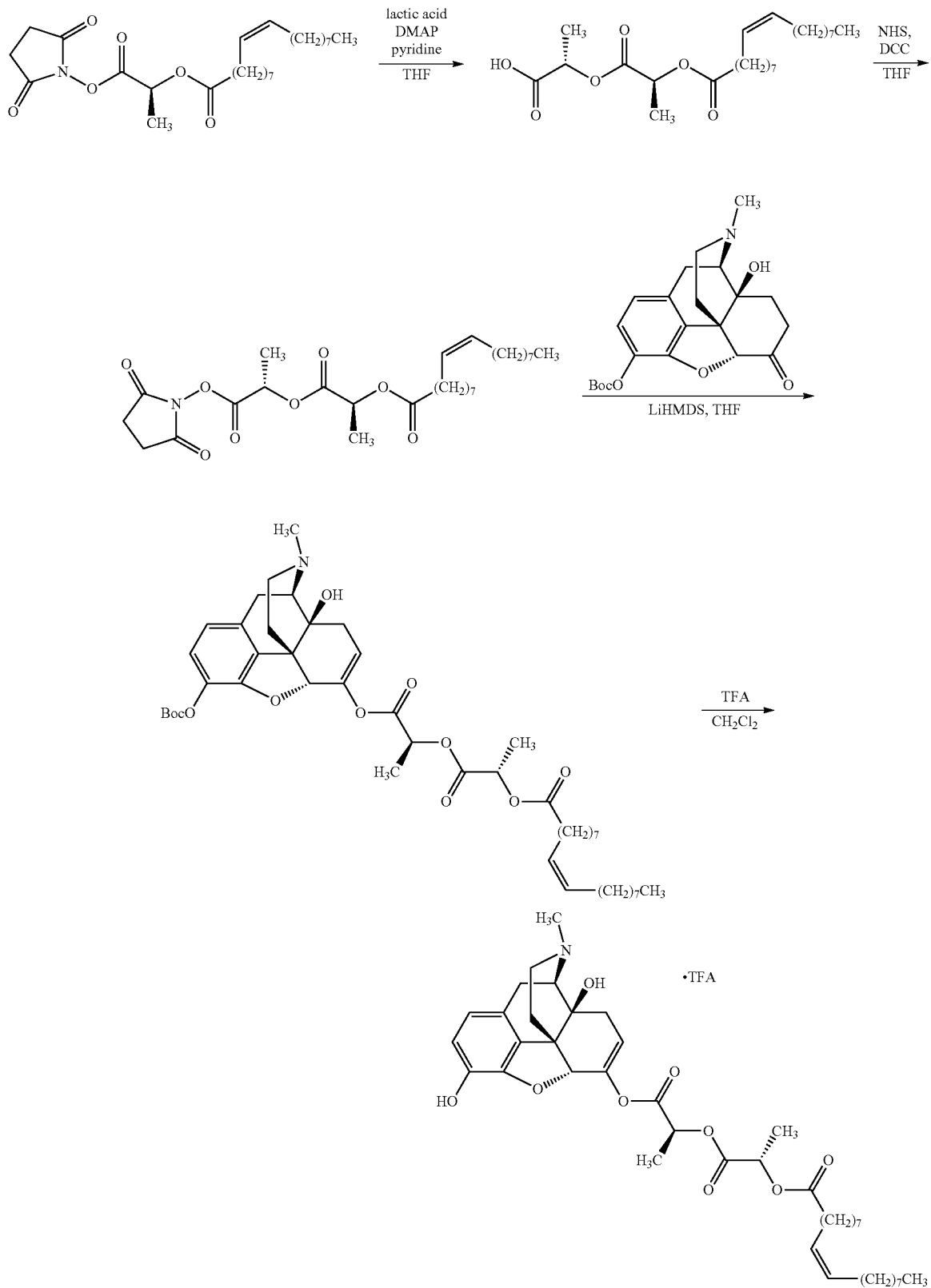

Preparation of (S)-2-(((S)-2-(Oleoyloxy)propanoyl)oxy)propanoic acid

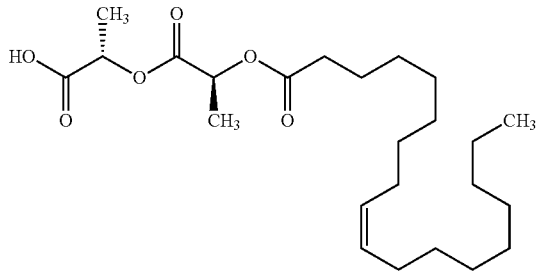 [SMILES: CCCCCCCC/C=C\CCCCCCCC(=O)O[C@@H](C)C(=O)O[C@@H](C)C(=O)O]

A solution of (S)-1-((2,5-dioxopyrrolidin-1-yl)oxy)-1-oxopropan-2-yl oleate (3.49 g, 7.73 mmol), (S)-lactic acid (764 mg, 8.48 mmol), and 4-dimethylaminopyridine (100 mg, 0.819 mmol) in tetrahydrofuran (35 mL) was treated with pyridine (0.69 g, 8.6 mmol) and heated at 50° C. under a nitrogen atmosphere for 64 h. After this time, the reaction mixture was cooled to room temperature and concentrated under reduced pressure. The residue was dissolved in methylene chloride (100 mL) and washed with aqueous 10% citric acid (2×50 mL). The organic layer was dried over sodium sulfate, filtered, and concentrated. The crude residue was purified by column chromatography (silica gel, 0-10% methanol/methylene chloride) to provide (S)-2-(((S)-2-(oleoyloxy)propanoyl)oxy)propanoic acid (835 mg, 25%) as a colorless oil: $^1$H NMR (300 MHz, CDCl$_3$) δ 5.36-5.29 (m, 2H), 5.24-5.08 (m, 2H), 2.41-2.35 (m, 2H), 2.02-1.98 (m, 4H), 1.67-1.60 (m, 2H), 1.58-1.52 (m, 6H), 1.30-1.27 (m, 20H), 0.88 (t, J=6.6 Hz, 3H), CO$_2$H proton not observed.

Preparation of (S)-1-(((S)-1-((2,5-Dioxopyrrolidin-1-yl)oxy)-1-oxopropan-2-yl)oxy)-1-oxopropan-2-yl oleate

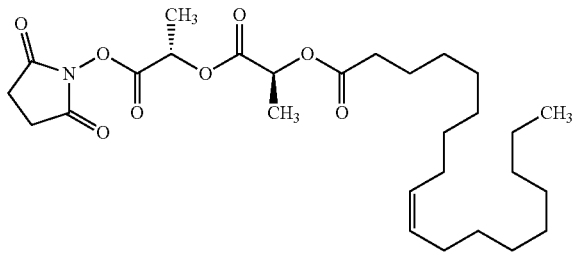 [SMILES: CCCCCCCC/C=C\CCCCCCCC(=O)O[C@@H](C)C(=O)O[C@@H](C)C(=O)ON1C(=O)CCC1=O]

A solution of (S)-2-(((S)-2-(oleoyloxy)propanoyl)oxy)propanoic acid (0.83 g, 2.0 mmol) in tetrahydrofuran (10 mL) was treated with N-hydroxysuccinimide (262 mg, 2.28 mmol) and N,N'-dicyclohexylcarbodiimide (446 mg, 2.16 mmol) and stirred under a nitrogen atmosphere for 3 h. After this time, the reaction mixture was filtered to remove the solid dicyclohexylurea byproduct. The solid was washed with diethyl ether, and the combined filtrate and washings were concentrated under reduced pressure to provide (S)-1-(((S)-1-((2,5-dioxopyrrolidin-1-yl)oxy)-1-oxopropan-2-yl)oxy)-1-oxopropan-2-yl oleate (1.07 g, quantitative) as a white semi-solid: $^1$H NMR (300 MHz, CDCl$_3$) δ 5.52 (q, J=7.2 Hz, 1H), 5.38-5.33 (m, 2H), 5.11 (q, J=7.2 Hz, 1H), 2.84 (br s, 4H), 2.42-2.35 (m, 2H), 2.02-1.98 (m, 4H), 1.72-1.53 (m, 8H), 1.30-1.27 (m, 20H), 0.88 (t, J=6.6 Hz, 3H).

Preparation of (S)-1-(((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl oleate

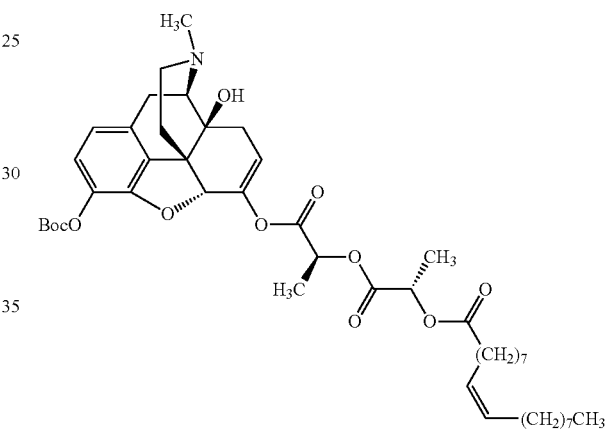

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (350 mg, 0.872 mmol) in tetrahydrofuran (10 mL) was cooled to 0° C. and treated dropwise with a 1.0 M solution of lithium bis(trimethylsilyl)amide in tetrahydrofuran (0.95 mL, 0.95 mmol). After addition was complete, the mixture was stirred at 0° C. for 25 min and then at ambient temperature for 25 min. The mixture was re-cooled to −78° C., and a solution of (S)-1-(((S)-1-((2,5-dioxopyrrolidin-1-yl)oxy)-1-oxopropan-2-yl)oxy)-1-oxopropan-2-yl oleate (500 mg, 0.956 mmol) in tetrahydrofuran (5 mL) was added. The mixture was allowed to warm to 0° C. over 2 h. After this time, the mixture was treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride) to provide (S)-1-(((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl oleate (628 mg, 88%) as a white solid: ESI MS m/z 810 [C$_{46}$H$_{67}$NO$_{11}$+H]$^+$.

803

Preparation of (S)-1-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl oleate trifluoroacetic acid salt

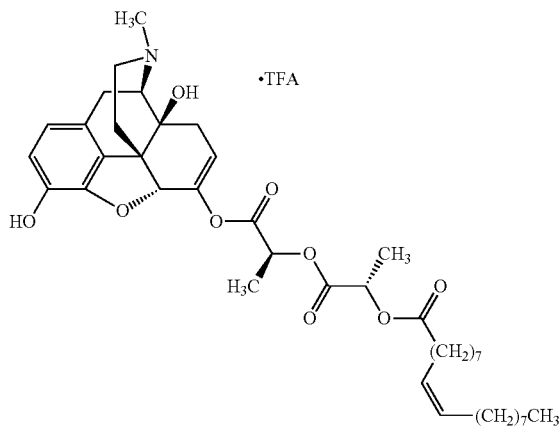

804

A solution of (S)-1-(((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl oleate (314 mg, 0.388 mmol) in methylene chloride (5.0 mL) was treated with trifluoroacetic acid (5.0 mL) and stirred under a nitrogen atmosphere at ambient temperature for 3 h. After this time, the reaction mixture was concentrated under reduced pressure. The residue was purified by reversed phase column chromatography (150 g C18 column, 0-100% acetonitrile/water with 0.1% trifluoroacetic acid) and freeze dried to provide (S)-1-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl oleate trifluoroacetic acid salt (63 mg, 18%) as a fluffy white solid: $^1$H NMR (300 MHz, DMSO-$d_6$) δ 9.27 (s, 1H), 9.14 (s, 1H), 6.65 (apparent q, J=8.1 Hz, 2H), 6.23 (s, 1H), 5.57 (dd, J=6.3, 2.1 Hz, 1H), 5.32 (t, J=4.5 Hz, 1H), 5.22 (q, J=6.9 Hz, 1H), 5.08 (q, J=7.2 Hz, 1H), 4.95 (s, 1H), 3.06 (m, 1H), 2.84 (d, J=4.5 Hz, 3H), 2.63-2.25 (m, 8H), 2.09-1.95 (m, 4H), 1.64-1.46 (m, 10H), 1.23 (m, 21H), 0.85 (t, J=6.6 Hz, 3H); ESI MS m/z 710 $[C_{41}H_{59}NO_9+H]^+$.

Scheme 139: (S)-2-((4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic salt

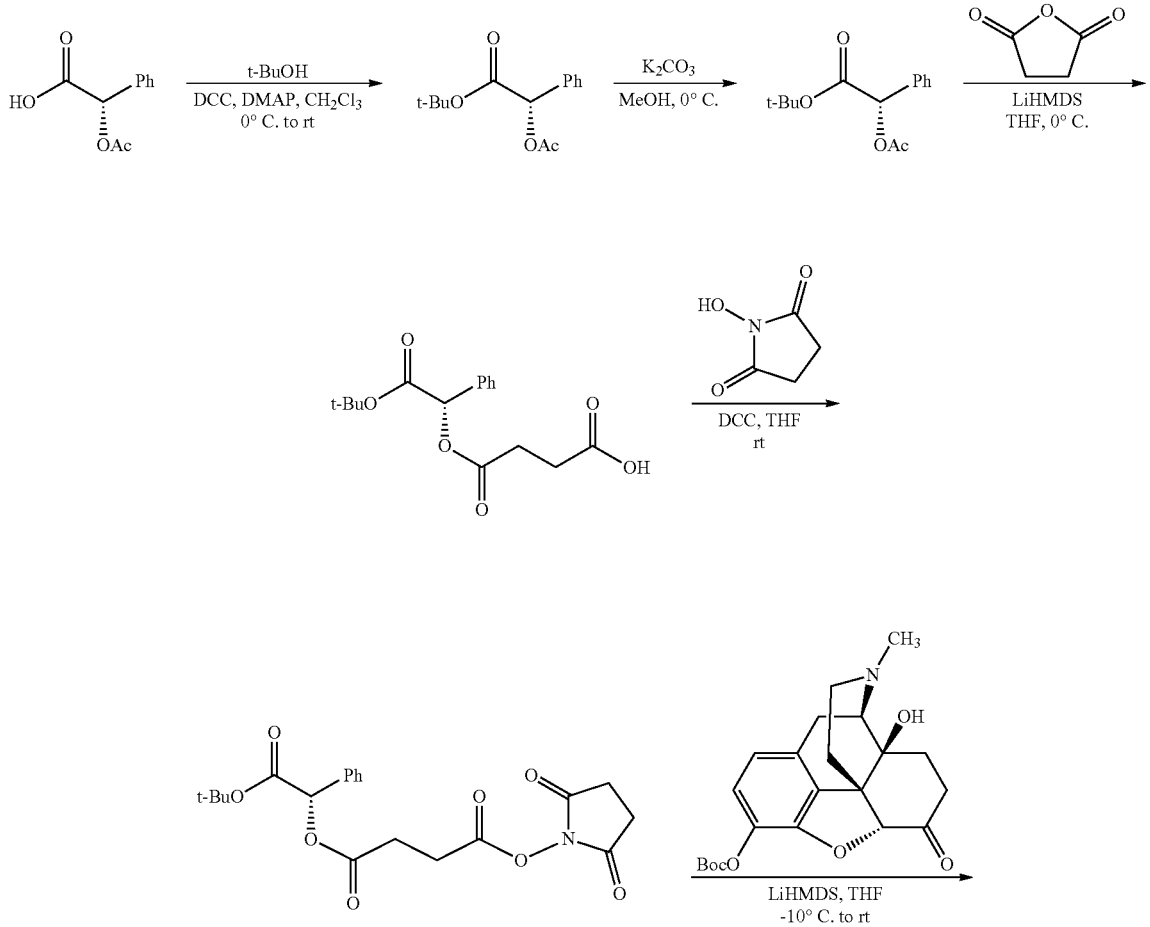

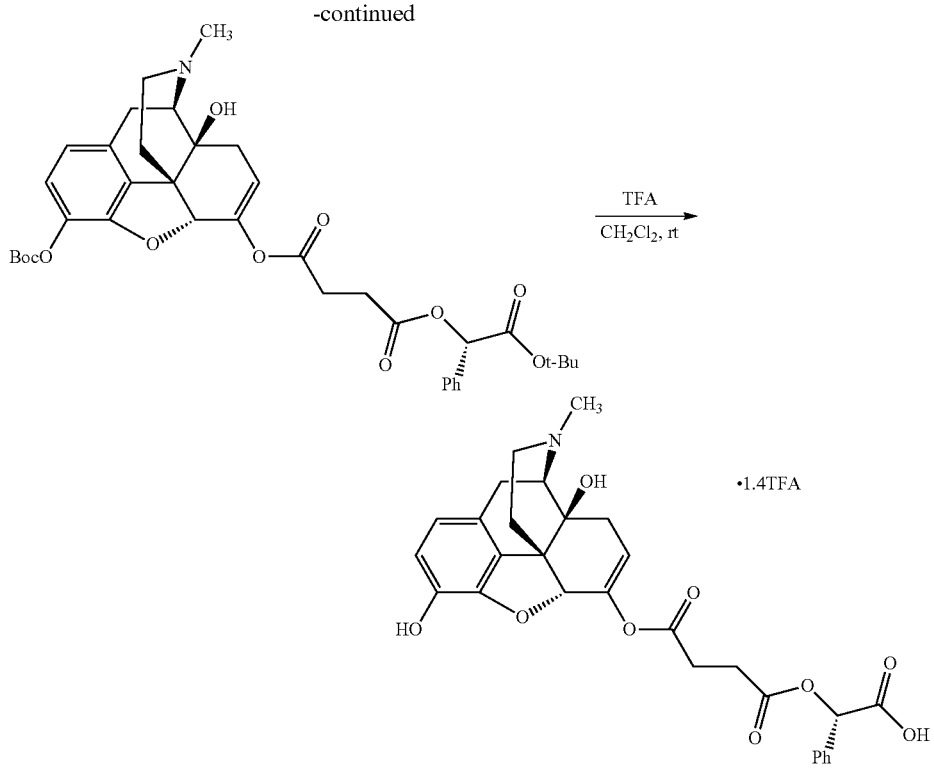

Preparation of (S)-tert-Butyl 2-acetoxy-2-phenylacetate

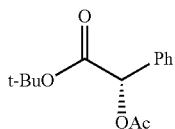

A mixture of (S)-2-acetoxy-2-phenylacetic acid (22.0 g, 104 mmol) and tert-butanol (19.0 g, 257 mmol) in methylene chloride (150 mL) at 0° C. was treated with N,N'-dicyclohexylcarbodiimide (28.0 g, 136 mmol). After stirring for 1 h, the ice bath was removed and the reaction mixture was stirred at ambient temperature for 18 h. After this time, the mixture was filtered and the filtrate was concentrated under reduced pressure. The residue was purified by column chromatography (330 g silica gel column, 5-20% ethyl acetate/heptane) to provide (S)-tert-butyl 2-acetoxy-2-phenylacetate (14.4 g, 52%): $^1$H NMR (300 MHz, CDCl$_3$) δ 7.48-7.43 (m, 2H), 7.40-7.35 (m, 3H), 5.80 (s, 1H), 2.18 (s, 3H), 1.40 (s, 9H).

Preparation of (S)-tert-Butyl 2-hydroxy-2-phenylacetate

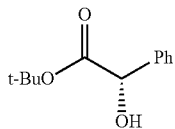

A solution of (S)-tert-butyl 2-acetoxy-2-phenylacetate (14.4 g, 54.1 mmol) in methanol (15 mL) was cooled to 0° C. and treated with a solution of sodium bicarbonate (22.5 g, 163 mmol) in water/methanol (3:2, 145 mL). The reaction mixture was stirred at 0° C. for 2 h, and then neutralized by addition of citric acid (10 g, 52 mmol). The mixture was partially concentrated under reduced pressure and then extracted with methylene chloride. The organic layer was washed with water and brine, dried over sodium sulfate, filtered, and concentrated under reduced pressure to provide (S)-tert-butyl 2-hydroxy-2-phenylacetate (11.2 g), which was used without purification: $^1$H NMR (300 MHz, CDCl$_3$) δ 7.43-7.29 (m, 5H), 5.03 (d, J=6.0 Hz, 1H), 3.50 (d, J=6.0 Hz, 1H), 1.41 (s, 9H).

Preparation of (S)-4-(2-(tert-Butoxy)-2-oxo-1-phenylethoxy)-4-oxobutanoic acid

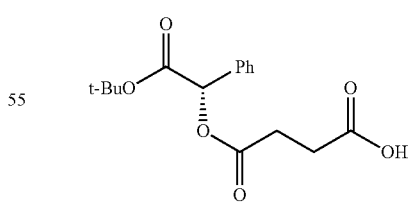

A solution of (S)-tert-butyl 2-hydroxy-2-phenylacetate (3.15 g, 15.1 mmol) in tetrahydrofuran (35 mL) at 0° C. was treated with a 1.0 M solution of lithium bis(trimethylsilyl)amide in tetrahydrofuran (16 mL, 16 mmol), and the mixture was stirred for 10 min. After this time, a solution of succinic anhydride (1.33 g, 16.6 mmol) in tetrahydrofuran (25 mL) was added, and the mixture was stirred at 0° C. for 1.5 h.

After this time, the mixture was poured into a saturated solution of ammonium chloride and extracted with ethyl acetate. The organic extract was dried over sodium sulfate, filtered, and concentrated under reduced pressure to provide (S)-4-(2-(tert-butoxy)-2-oxo-1-phenylethoxy)-4-oxobutanoic acid (4.60 g): ESI MS m/z 634 $[C_{16}H_{20}O_6+NH_4]^+$.

Preparation of (S)-2-(tert-Butoxy)-2-oxo-1-phenylethyl (2,5-dioxopyrrolidin-1-yl) succinate

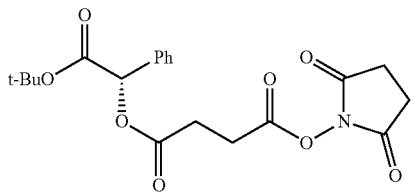 [SMILES: CC(C)(C)OC(=O)[C@@H](OC(=O)CCC(=O)ON1C(=O)CCC1=O)c1ccccc1]

A mixture of (S)-4-(2-(tert-butoxy)-2-oxo-1-phenylethoxy)-4-oxobutanoic acid (4.60 g, 15.0 mmol) and N-hydroxysuccinimide (1.90 g, 16.5 mmol) in tetrahydrofuran (75 mL) at 0° C. was treated with N,N'-dicyclohexylcarbodiimide (3.40 g, 16.5 mmol). The ice bath was removed, and the reaction mixture was stirred at ambient temperature for 4 h. After this time, diethyl ether (75 mL) was added, and the mixture was filtered. The filtrate was concentrated under reduced pressure to provide (S)-2-(tert-butoxy)-2-oxo-1-phenylethyl (2,5-dioxopyrrolidin-1-yl) succinate (10.0 g) that was used without purification: $^1$H NMR (300 MHz, CDCl$_3$) δ 7.47-7.42 (m, 2H), 7.42-7.35 (m, 3H), 5.84 (s, 1H), 3.06-2.98 (m, 2H), 2.93-2.88 (m, 2H), 2.83 (s, 4H), 1.39 (s, 9H).

Preparation of (S)-2-(tert-Butoxy)-2-oxo-1-phenylethyl ((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) succinate

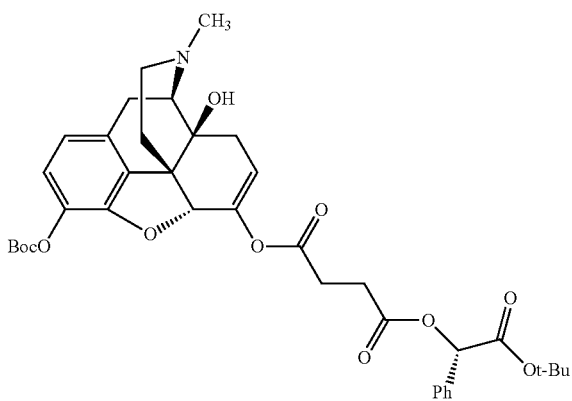

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (490 mg, 1.22 mmol) in tetrahydrofuran (10 mL) was cooled to −10° C. and treated dropwise with a 1.0 M solution of lithium bis(trimethylsilyl)amidein tetrahydrofuran (1.4 mL, 1.4 mmol). After addition was complete, the mixture was stirred at ambient temperature for 10 min. The mixture was re-cooled to −10° C. and (S)-2-(tert-butoxy)-2-oxo-1-phenylethyl (2,5-dioxopyrrolidin-1-yl) succinate (650 mg, 1.6 mmol) was added in one portion. The mixture was stirred at −10° C. to ambient temperature over 1.5 h. After this time, the reaction mixture was cooled in an ice bath, treated with saturated aqueous ammonium chloride, and extracted with ethyl acetate. The combined organics were dried over sodium sulfate, filtered, and concentrated under reduced pressure. The residue was purified by reversed phase column chromatography (50 g C18 column, 5-100% acetonitrile/water) to provide (S)-2-(tert-butoxy)-2-oxo-1-phenylethyl ((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) succinate (530 mg, 62%): ESI MS m/z 692 $[C_3H_{45}NO_{11}+H]^+$.

Preparation of (S)-2-((4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt

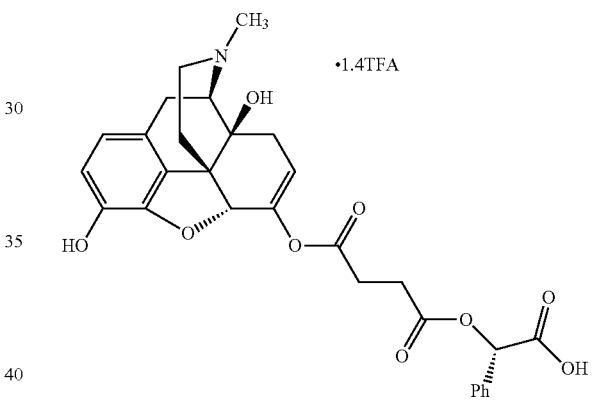

A solution of (S)-2-(tert-butoxy)-2-oxo-1-phenylethyl ((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) succinate (530 mg, 0.77 mmol) in methylene chloride (10 mL) was treated with trifluoroacetic acid (4 mL) and stirred at ambient temperature for 2.5 h. After this time, the reaction mixture was concentrated under reduced pressure. The residue was purified by reversed phase column chromatography (50 g C18 column, 3-20% acetonitrile/water, with 0.1% trifluoracetic acid) and freeze dried to provide (S)-2-((4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt (121 mg, 23%) as a fluffy white solid: $^1$H NMR (300 MHz, DMSO-d$_6$) δ 9.30 (s, 1H), 9.15 (br s, 1H), 7.50-7.44 (m, 2H), 7.44-7.40 (m, 3H), 6.68 (d, J=8.2 Hz, 1H), 6.62 (d, J=8.2 Hz, 1H), 6.22 (s, 1H), 5.85 (s, 1H), 5.49 (dd, J=6.0, 1.9 Hz, 1H), 4.93 (s, 1H), 3.61 (d, J=6.3 Hz, 1H), 3.12-3.01 (m, 2H), 2.84 (s, 3H), 2.79-2.70 (m, 4H), 2.70-2.58 (m, 1H), 2.42 (dd, J=13.3, 4.7 Hz, 1H), 2.25 (dd, J=17.1, 7.1 Hz, 1H), 2.04 (d, J=17.1 Hz, 1H), 1.61 (d, J=11.2 Hz, 1H), CO$_2$H proton not observed, one proton obscured by solvent peaks; ESI MS m/z 536 $[C_{29}H_{29}NO_9+H]^+$; HPLC (Method A) 98.9% (AUC), $t_R$=8.55 min.

Scheme 140: (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-acetoxy-2-phenylacetate trifluoroacetic acid salt

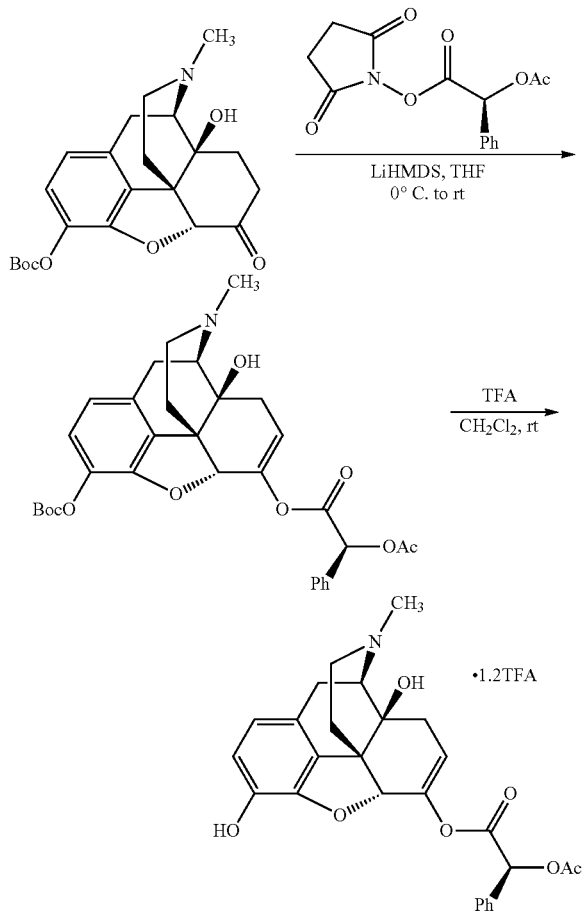

Preparation of (S)-(4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 2-acetoxy-2-phenylacetate

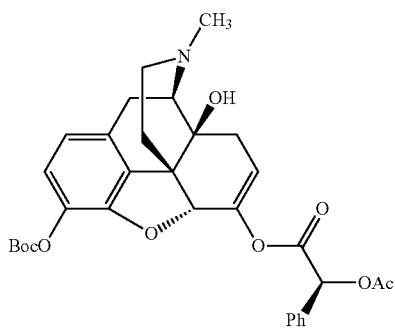

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (360 mg, 0.90 mmol) in tetrahydrofuran (8 mL) was cooled to 0° C. and treated dropwise with a 1.0 M solution of lithium bis(trimethylsilyl)amide in tetrahydrofuran (1.0 mL, 1.0 mmol). After addition was complete, the mixture was stirred at ambient temperature for 10 min. The mixture was re-cooled to 0° C., and (S)-2,5-dioxopyrrolidin-1-yl 2-acetoxy-2-phenylacetate (340 mg, 1.1 mmol) was added in one portion. The mixture was stirred at 0° C. to ambient temperature over 1 h. After this time, the reaction mixture was cooled in an ice bath, treated with saturated aqueous ammonium chloride, and extracted with ethyl acetate. The combined organics were dried over sodium sulfate, filtered, and concentrated under reduced pressure. The residue was purified by reversed phase column chromatography (50 g C18 column, 5-100% acetonitrile/water) to provide (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-acetoxy-2-phenylacetate (235 mg, 45%): ESI MS m/z 578 $[C_{32}H_{35}NO_9+H]^+$.

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-acetoxy-2-phenylacetate trifluoroacetic acid salt

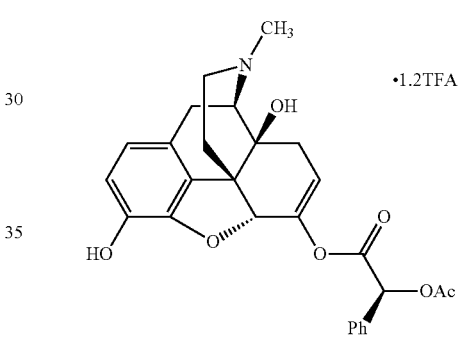

A solution of (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-acetoxy-2-phenylacetate (230 mg, 0.40 mmol) in methylene chloride (6 mL) was treated with trifluoroacetic acid (2.5 mL) and stirred at ambient temperature for 2 h. After this time, the reaction mixture was concentrated under reduced pressure. The residue was purified by reversed phase column chromatography (50 g C18 column, 5-20% acetonitrile/water, with 0.1% trifluoroacetic acid) and freeze dried to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-acetoxy-2-phenylacetate trifluoroacetic acid salt (121 mg, 23%) as a fluffy white solid: $^1$H NMR (300 MHz, DMSO-$d_6$) δ 9.29 (s, 1H), 9.15 (br s, 1H), 7.60-7.51 (m, 2H), 7.51-7.43 (m, 3H), 6.68 (d, J=8.1 Hz, 1H), 6.61 (d, J=8.1 Hz, 1H), 6.27 (s, 1H), 6.08 (s, 1H), 5.58 (dd, J=6.0, 1.9 Hz, 1H), 4.87 (s, 1H), 3.61 (d, J=6.1 Hz, 1H), 3.11-3.00 (m, 2H), 2.83 (d, J=4.6 Hz, 3H), 2.70-2.55 (m, 1H), 2.42 (dd, J=12.8, 4.2 Hz, 1H), 2.26 (dd, J=18.0, 6.1 Hz, 1H), 2.17 (s, 3H), 2.05 (d, J=18.0 Hz, 1H), 1.60 (d, J=11.1 Hz, 1H), one proton obscured by solvent peaks; ESI MS m/z 478 $[C_{27}H_{27}NO_7+H]^+$; HPLC (Method A) 98.7% (AUC), $t_R$=9.03 min.

Scheme 141: (3S,3'S)-4,4'-(((((4R,4aS,7aR,12bS)-9-Hydroxy-3-methyl-2,3,4,4a,5,7a-hexahydro-1H-4,12-methanobenzofuro[3,2-e]isoquinoline-4a,7-diyl)bis(oxy))bis(3-oxopropane-3,1-diyl))bis(azanediyl))bis(3-hydroxy-4-oxobutanoic acid) trifluoroacetic acid salt
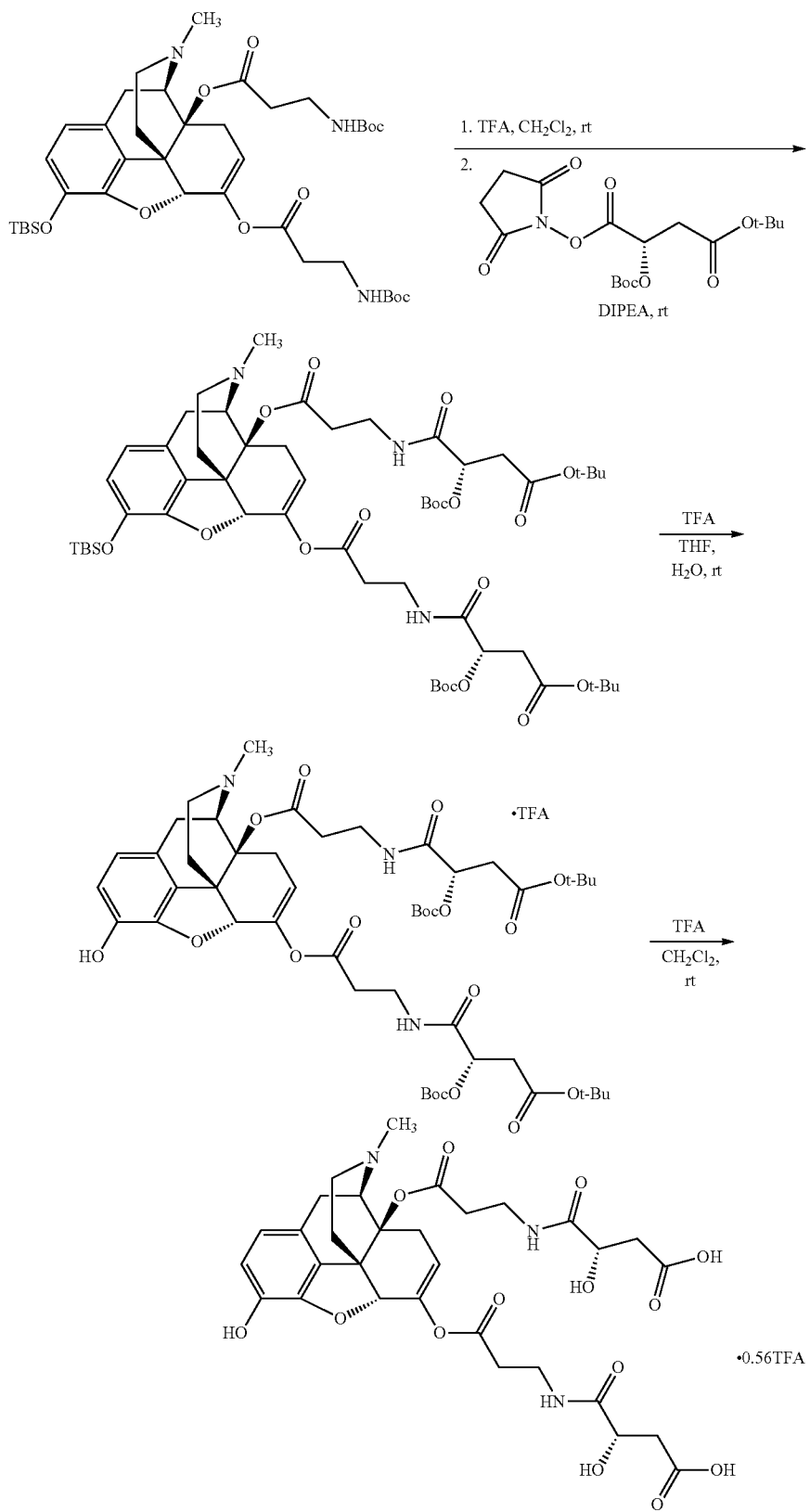

813

Preparation of (3S,3'S)-Di-tert-butyl 4,4'-(((((4R,4aS,7aR,12bS) H-9-((tert-butyldimethylsilyl)oxy)-3-methyl-2,3,4,4a,5,7a-hexahydro-1H-4,12-methanobenzofuro[3,2-e]isoquinoline-4a,7-diyl)bis(oxy))bis(3-oxopropane-3,1-diyl))bis(azanediyl))bis(3-((tert-butoxycarbonyl)oxy)-4-oxobutanoate)

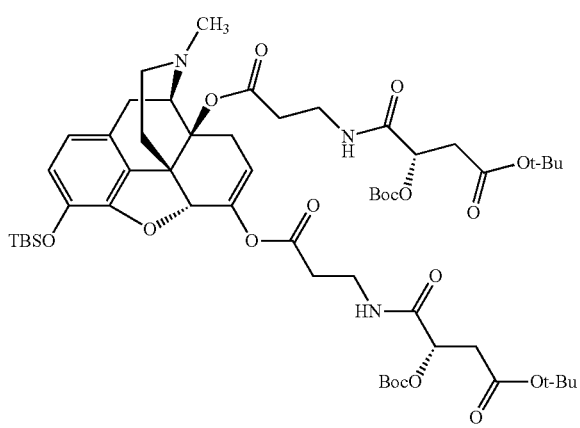

A solution of (4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl bis(3-((tert-butoxycarbonyl)amino)propanoate) (800 mg, 1.06 mmol) in methylene chloride (12 mL) was treated with trifluoroacetic acid (1.2 mL), and the mixture was stirred at room temperature for 2 h. After this time, LC-MS analysis of the reaction mixture showed cleavage of the Boc protecting groups. N,N-Diisopropylethylamine was added slowly until the reaction mixture tested basic by pH paper analysis (3 mL of base added). The mixture was treated with (S)-4-tert-butyl 1-(2,5-dioxopyrrolidin-1-yl) 2-((tert-butoxycarbonyl)oxy) succinate (900 mg, 2.32 mmol) in one portion and stirred at room temperature for 2 h. After this time, the mixture was diluted with ethyl acetate and washed water and brine. The organic extracts were dried over sodium sulfate, filtered, and concentrated. The residue was purified by reversed phase column chromatography (50 g C18 column, 5-100% acetonitrile/water) to provide (3S,3'S)-di-tert-butyl 4,4'-(((((4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl)bis(oxy))bis(3-oxopropane-3,1-diyl))bis(azanediyl))bis(3-((tert-butoxycarbonyl)oxy)-4-oxobutanoate) (470 mg, 40%): ESI MS m/z 1102 [$C_{55}H_{83}N_3O_{18}Si$+H]$^+$.

814

Preparation of (3S,3'S)-Di-tert-butyl 4,4'-(((((4R,4aS,7aR,12bS)-9-hydroxy-3-methyl-2,3,4,4a,5,7a-hexahydro-1H-4,12-methanobenzofuro[3,2-e]isoquinoline-4a,7-diyl)bis(oxy))bis(3-oxopropane-3,1-diyl))bis(azanediyl))bis(3-((tert-butoxycarbonyl)oxy)-4-oxobutanoate) trifluoroacetic acid salt

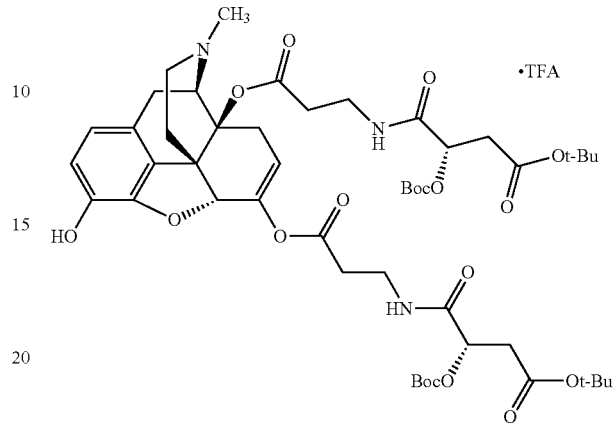

A solution of (3S,3'S)-di-tert-butyl 4,4'-(((((4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl)bis(oxy))bis(3-oxopropane-3,1-diyl))bis(azanediyl))bis(3-((tert-butoxycarbonyl)oxy)-4-oxobutanoate) (470 mg, 0.43 mmol) in tetrahydrofuran (8 mL) was treated with water (5 mL) followed by trifluoroacetic acid (3 mL), and the mixture was stirred at room temperature for 3 h. After this time, the mixture was concentrated, and the residue was azeotroped with toluene to provide (3S,3'S)-di-tert-butyl 4,4'-(((((4R,4aS,7aR,12bS)-9-hydroxy-3-methyl-2,3,4,4a,5,7a-hexahydro-1H-4,12-methanobenzofuro[3,2-e]isoquinoline-4a,7-diyl)bis(oxy))bis(3-oxopropane-3,1-diyl))bis(azanediyl))bis(3-((tert-butoxycarbonyl)oxy)-4-oxobutanoate) trifluoroacetic acid salt (440 mg, crude) that was used without purification: ESI MS m/z 988 [$C_{49}H_{69}N_3O_{18}$+H]$^+$.

Preparation of (3S,3'S)-4,4'-(((((4R,4aS,7aR,12bS)-9-Hydroxy-3-methyl-2,3,4,4a,5,7a-hexahydro-1H-4,12-methanobenzofuro[3,2-e]isoquinoline-4a,7-diyl)bis(oxy))bis(3-oxopropane-3,1-diyl))bis(azanediyl))bis(3-hydroxy-4-oxobutanoic acid) trifluoroacetic acid salt

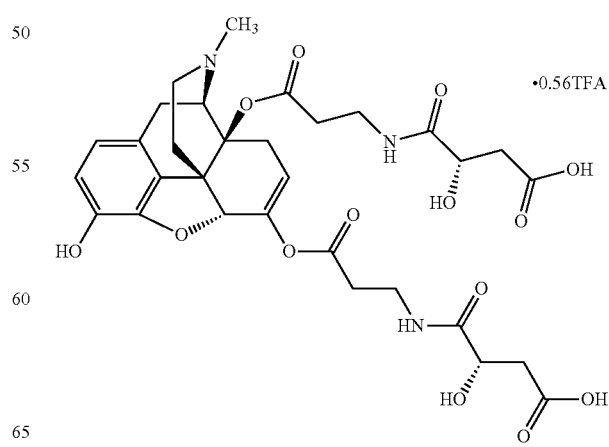

A solution of (3S,3'S)-di-tert-butyl 4,4'-(((((4R,4aS,7aR,12bS)-9-hydroxy-3-methyl-2,3,4,4a,5,7a-hexahydro-1H-4,12-methanobenzofuro[3,2-e]isoquinoline-4a,7-diyl)bis(oxy))bis(3-oxopropane-3,1-diyl))bis(azanediyl))bis(3-((tert-butoxycarbonyl)oxy)-4-oxobutanoate) (440 mg) in methylene chloride (6 mL) was treated with trifluoroacetic acid (2.5 mL) and stirred at ambient temperature for 2 h. After this time, the reaction mixture was concentrated under reduced pressure. The residue was purified by reversed phase column chromatography (50 g C18 column, 5-20% acetonitrile/water, with 0.1% trifluoroacetic acid) and freeze dried to provide (3S,3'S)-4,4'-(((((4R,4aS,7aR,12bS)-9-hydroxy-3-methyl-2,3,4,4a,5,7a-hexahydro-1H-4,12-methanobenzofuro[3,2-e]isoquinoline-4a,7-diyl)bis(oxy))bis(3-oxopropane-3,1-diyl))bis(azanediyl))bis(3-hydroxy-4-oxobutanoic acid) trifluoroacetic acid salt (167 mg, 53% over two steps) as a fluffy white solid: $^1$H NMR (300 MHz, DMSO-$d_6$) δ 9.55 (br s, 2H), 8.03-7.97 (m, 2H), 6.73 (d, J=8.2 Hz, 1H), 6.66 (d, J=8.2 Hz, 1H), 5.50 (dd, J=6.7, 1.8 Hz, 1H), 5.06 (s, 1H), 4.73 (d, J=6.0 Hz, 1H), 4.26-4.21 (m, 2H), 3.45-3.13 (m, 10H), 3.08-2.90 (m, 4H), 2.86-2.70 (m, 1H), 2.70-2.53 (m, 5H), 2.45-2.25 (m, 3H), 2.09 (d, J=18.6 Hz, 1H), 1.78 (d, J=13.5 Hz, 1H), CO$_2$H protons not observed; ESI MS m/z 676 [$C_{31}H_{37}N_3O_{14}$+H]$^+$; HPLC (Method A) 98.6% (AUC), $t_R$=6.42 min.

Scheme 142: (S)-2-((4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-4-oxobutanoyl)oxy)succinic acid trifluoroacetic acid salt

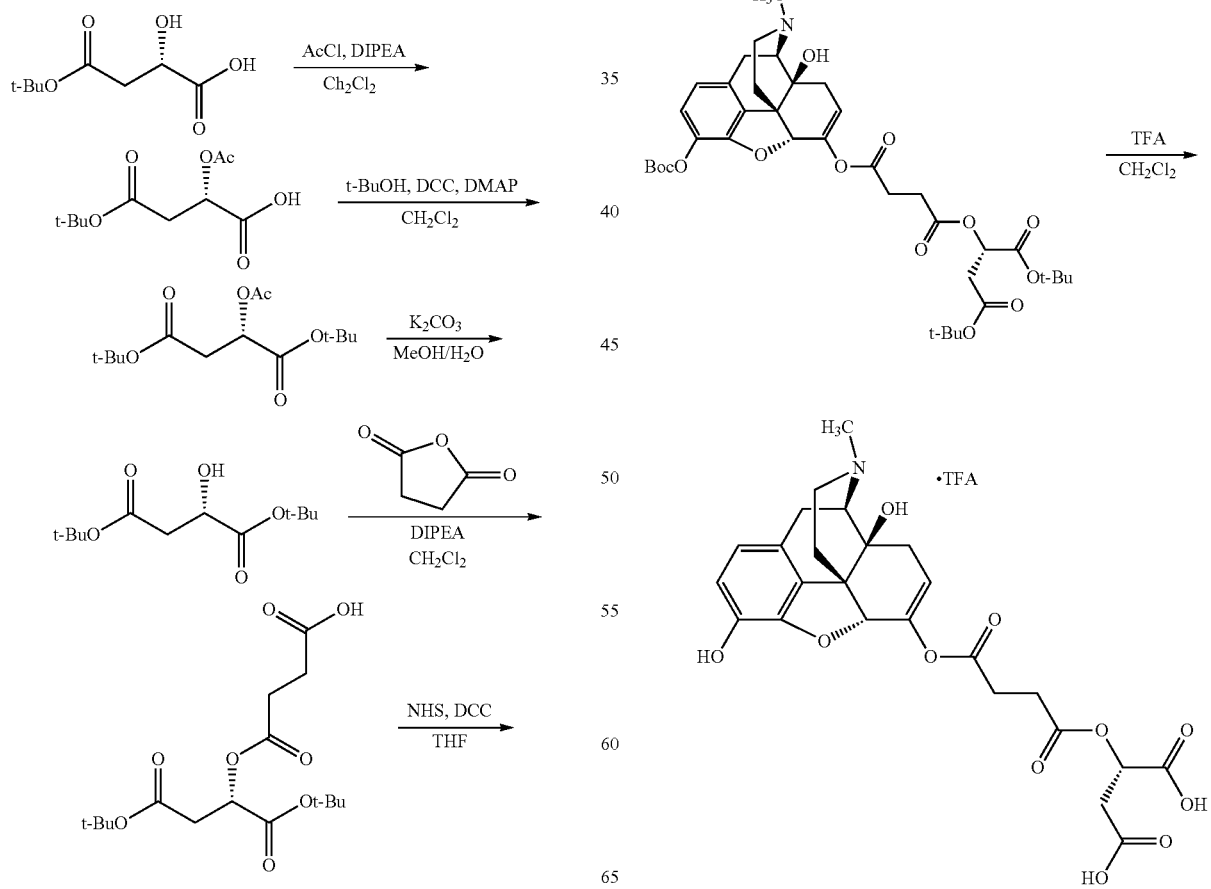

Preparation of (S)-2-Acetoxy-4-(tert-butoxy)-4-oxobutanoic acid

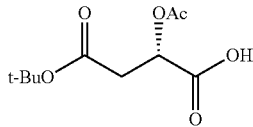 [SMILES: CC(=O)O[C@@H](CC(=O)OC(C)(C)C)C(=O)O]

(S)-4-(tert-Butoxy)-2-hydroxy-4-oxobutanoic acid (4.88 g, 25.7 mmol), acetyl chloride (2.22 g, 28.2 mmol), N,N-diisopropylethylamine (3.99 g, 30.8 mmol), and methylene chloride (200 mL) were combined at 0° C. and stirred at room temperature under a nitrogen atmosphere for 16 h. After this time, 10% aqueous citric acid (100 mL) was added. The organic layer was separated and extracted with methylene chloride (2×100 mL). The combined organics were washed with brine (50 mL), dried over sodium sulfate, filtered, and concentrated under reduced pressure to provide (S)-2-acetoxy-4-(tert-butoxy)-4-oxobutanoic acid (4.59 g, 76%) as a light yellow oil: $^1$H NMR (300 MHz, CDCl$_3$) δ 5.46 (m, 1H), 2.83 (m, 2H), 2.14 (s, 3H), 1.46 (s, 9H), CO$_2$H proton not observed.

Preparation of (S)-Di-tert-butyl 2-acetoxysuccinate

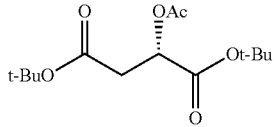 [SMILES: CC(=O)O[C@@H](CC(=O)OC(C)(C)C)C(=O)OC(C)(C)C]

A solution of (S)-2-acetoxy-4-(tert-butoxy)-4-oxobutanoic acid (4.59 g, 19.8 mmol) and tert-butanol (3.22 g, 43.5 mmol) in methylene chloride (70 mL) was treated with N,N'-dicyclohexylcarbodiimide (5.31 g, 25.7 mmol) and 4-(dimethylamino)pyridine (798 mg, 6.53 mmol) at 0° C. and stirred at room temperature under a nitrogen atmosphere for 16 h. After this time, the reaction mixture was filtered to remove the solid dicyclohexylurea byproduct. The solid was washed with diethyl ether (100 mL), and the combined filtrate and washings were concentrated under reduced pressure. The crude residue was purified by column chromatography (80 g silica gel column, 0-30% ethyl acetate/heptane) to provide (S)-di-tert-butyl 2-acetoxysuccinate (3.44 g, 60%) as a colorless oil: $^1$H NMR (300 MHz, CDCl$_3$) δ 5.30 (dd, J=7.5, 5.4 Hz, 1H), 2.75 (m, 2H), 2.13 (s, 3H), 1.46 (s, 18H).

Preparation of (S)-Di-tert-butyl 2-hydroxysuccinate

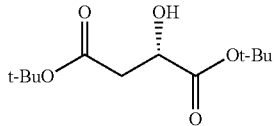 [SMILES: CC(C)(C)OC(=O)C[C@H](O)C(=O)OC(C)(C)C]

(S)-Di-tert-butyl 2-acetoxysuccinate (3.44 g, 11.9 mmol), potassium carbonate (4.94 g, 35.8 mmol), methanol (240 mL) and water (40 mL) were combined and stirred at 0° C. for 4 h. After this time, water (200 mL) was added, and the aqueous solution was extracted with methylene chloride (2×200 mL). The combined organics were washed with brine (50 mL), dried over sodium sulfate, filtered, and concentrated under reduced pressure to provide (S)-di-tert-butyl 2-hydroxysuccinate (2.71 g, 92%) as a colorless oil: $^1$H NMR (300 MHz, CDCl$_3$) δ 4.30 (dd, J=10.2, 5.7 Hz, 1H), 3.21 (d, J=5.4 Hz, 1H), 2.77-2.60 (m, 2H), 1.45 (s, 9H), 1.42 (s, 9H).

Preparation of (S)-4-((1,4-Di-tert-butoxy-1,4-dioxobutan-2-yl)oxy)-4-oxobutanoic acid

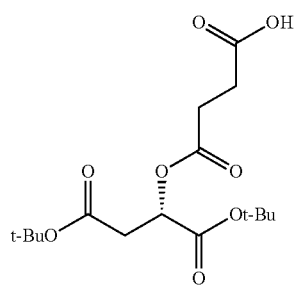 [SMILES: CC(C)(C)OC(=O)C[C@H](OC(=O)CCC(=O)O)C(=O)OC(C)(C)C]

(S)-Di-tert-butyl 2-hydroxysuccinate (428 mg, 1.74 mmol), dihydrofuran-2,5-dione (414 mg, 4.14 mmol), N,N-diisopropylethylamine (535 mg, 4.14 mmol), and methylene chloride (10 mL) were combined and stirred at room temperature under a nitrogen atmosphere for 16 h. After this time, 10% aqueous citric acid (100 mL) was added. The organic layer was separated and extracted with methylene chloride (2×50 mL). The combined organics were washed with brine (50 mL), dried over sodium sulfate, filtered, and concentrated under reduced pressure to provide (S)-4-((1,4-di-tert-butoxy-1,4-dioxobutan-2-yl)oxy)-4-oxobutanoic acid (534 mg, 95%) as a brown oil: $^1$H NMR (300 MHz, CDCl$_3$) δ 5.32 (dd, J=7.5, 5.1 Hz, 1H), 2.77-2.66 (m, 6H), 1.46 (s, 18H), CO$_2$H proton not observed.

Preparation of (S)-Di-tert-butyl 2-((4-((2,5-dioxopyrrolidin-1-yl)oxy)-4-oxobutanoyl)oxy)succinate

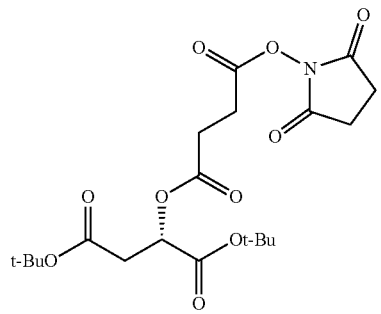 [SMILES: CC(C)(C)OC(=O)C[C@H](OC(=O)CCC(=O)ON1C(=O)CCC1=O)C(=O)OC(C)(C)C]

A solution of (S)-4-((1,4-di-tert-butoxy-1,4-dioxobutan-2-yl)oxy)-4-oxobutanoic acid (534 mg, 1.38 mmol) in tetrahydrofuran (15 mL) was treated with N-hydroxysuccinimide (159 mg, 1.38 mmol) and N,N'-dicyclohexylcarbodiimide (284 mg, 1.38 mmol) and stirred under a nitrogen atmosphere for 3 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-di-tert-butyl 2-((4-((2,5-dioxopyrrolidin-1-yl)oxy)-4-oxobutanoyl)oxy)succinate (684 mg) as a brown oil: $^1$H NMR (300 MHz, CDCl$_3$) δ 5.34 (dd, J=6.9, 5.7 Hz, 1H), 3.01-2.96 (m, 2H), 2.87-2.70 (m, 8H), 1.44 (s, 18H).

Preparation (S)-Di-tert-butyl 2-((4-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-4-oxobutanoyl)oxy)succinate

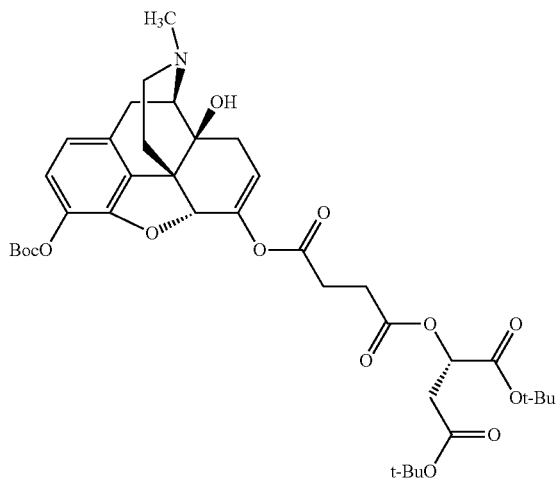

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (280 mg, 0.698 mmol) in tetrahydrofuran (5 mL) was cooled to 0° C. and treated dropwise with a 1.0 M solution of lithium bis(trimethylsilyl)amide in tetrahydrofuran (0.78 mL, 0.78 mmol). After addition was complete, the mixture was stirred at 0° C. for 25 min and then at ambient temperature for 25 min. The mixture was re-cooled to −78° C. and a solution of (S)-di-tert-butyl 2-((4-((2,5-dioxopyrrolidin-1-yl)oxy)-4-oxobutanoyl)oxy)succinate (340 mg, 0.767 mmol) in tetrahydrofuran (3 mL) was added. The mixture was allowed to warm to 0° C. over 2 h and then treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (40 g, silica gel, 0-20% methanol/methylene chloride, then 50 g, C18, 10-100% acetonitrile/water) to provide (S)-di-tert-butyl 2-((4-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-4-oxobutanoyl)oxy)succinate (137 mg, 26%) as a colorless oil: ESI MS m/z 730 [C38H51NO13+H]$^+$.

Preparation of (S)-2-((4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-4-oxobutanoyl)oxy)succinic acid trifluoroacetic acid salt

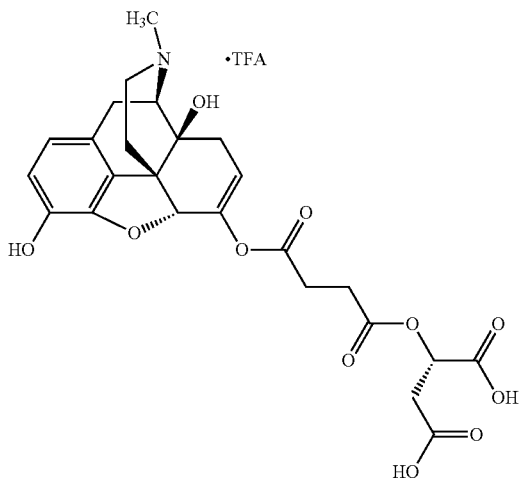 [SMILES: CN1CC[C@]23c4c5ccc(O)c4O[C@H]2C(OC(=O)CCC(=O)O[C@@H](CC(=O)O)C(=O)O)=CC[C@@]3(O)[C@H]1C5]

A solution of (S)-di-tert-butyl 2-((4-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-4-oxobutanoyl)oxy)succinate (137 mg, 0.188 mmol) in methylene chloride (3 mL) was treated with trifluoroacetic acid (3 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-2-((4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)succinic acid trifluoroacetic acid salt (85 mg, 76%) as a fluffy white solid: $^1$H NMR (300 MHz, DMSO-d$_6$) δ 12.3 (s, 1H), 12.6 (s, 1H), 9.30 (s, 1H), 9.14 (s, 1H), 6.65 (apparent q, J=8.1 Hz, 2H), 6.22 (s, 1H), 5.53 (dd, J=6.3, 2.1 Hz, 1H), 5.23 (dd, J=7.8, 4.5 Hz, 1H), 4.95 (s, 1H), 3.06 (m, 1H), 2.91-2.66 (m, 11H), 2.47 (m, 3H), 2.27 (m, 1H), 2.06 (d, J=18.0 Hz, 1H), 1.63 (d, J=11.7 Hz, 1H); ESI MS m/z 518 [C$_{25}$H$_{27}$NO$_{11}$+H]$^+$; HPLC (Method A)>99% (AUC), t$_R$=6.80 min.

Scheme 143: (S)-2-Acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

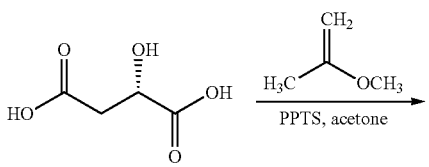

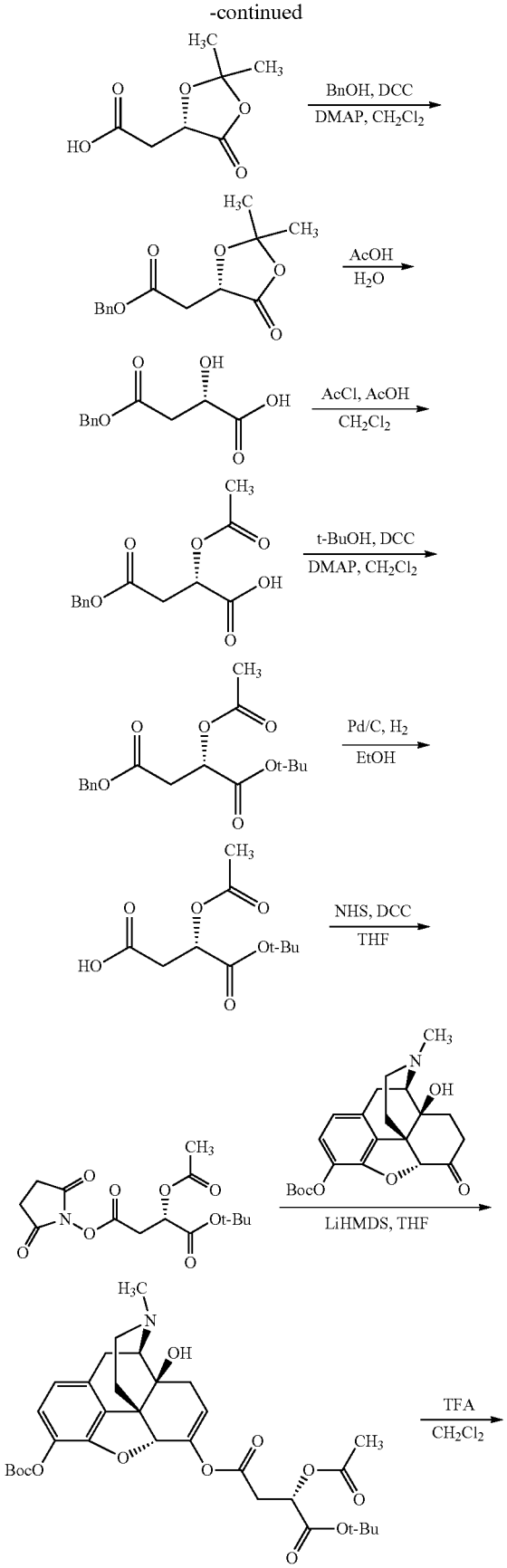

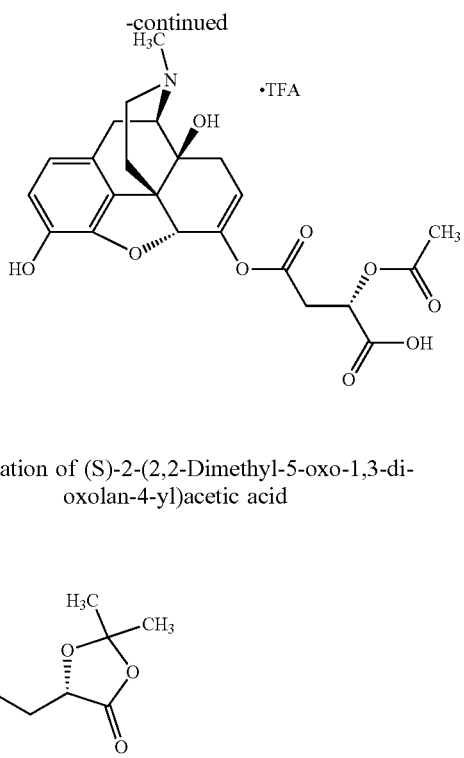

Preparation of (S)-2-(2,2-Dimethyl-5-oxo-1,3-dioxolan-4-yl)acetic acid

A solution of (S)-malic acid (30.28 g, 225.8 mmol) and pyridinium p-toluenesulfonate (5.16 g, 20.5 mmol) in acetone (17 mL) was cooled in an ice bath and treated with 2-methoxyprop-1-ene (85.0 mL, 888 mmol) under a nitrogen atmosphere. After 30 min, the ice bath was removed, and the mixture was heated at 35° C. for 16 h. After this time, the reaction mixture was cooled to room temperature and concentrated under reduced pressure. The residue was dissolved in ethyl acetate (500 mL), washed with 1:1 brine/water (4×200 mL), dried over sodium sulfate, filtered, and partially concentrated under reduced pressure to a volume of approximately 200 mL. The solution was treated with heptanes (200 mL) and cooled in an ice bath for 1 h. The resulting solids were isolated by filtration and washed with heptanes to provide (S)-2-(2,2-dimethyl-5-oxo-1,3-dioxolan-4-yl)acetic acid (23.14 g, 59%) as a white solid: $^1$H NMR (300 MHz, DMSO-$d_6$) δ 12.61 (s, 1H), 4.79 (dd, J=5.1, 4.8 Hz, 1H), 2.83-2.68 (m, 2H), 1.53 (s, 3H), 1.52 (s, 3H).

Preparation of (S)-Benzyl 2-(2,2-dimethyl-5-oxo-1,3-dioxolan-4-yl)acetate

A solution of (S)-2-(2,2-dimethyl-5-oxo-1,3-dioxolan-4-yl)acetic acid (10.08 g, 57.88 mmol) in methylene chloride (290 mL) was treated with benzyl alcohol (9.0 mL, 87 mmol), N,N'-dicyclohexylcarbodiimide (14.3 g, 69.2 mmol), and 4-dimethylaminopyridine (2.12 g, 17.4 mmol) and stirred under a nitrogen atmosphere for 1.5 h. After this time, the reaction mixture was filtered to remove the solid dicyclohexylurea byproduct. The solid was washed with methylene chloride, and the combined filtrate and washings were concentrated under reduced pressure. The crude residue was purified by column chromatography (silica gel, 0-20% ethyl acetate/heptanes) to provide (S)-benzyl 2-(2,2-dimethyl-5-oxo-1,3-dioxolan-4-yl)acetate (8.63 g, 56%) as a white solid: $^1$H NMR (300 MHz, DMSO-$d_6$) δ 7.41-7.30 (m, 5H), 5.13 (dd, J=14.4, 12.3 Hz, 2H), 4.87 (t, J=4.8 Hz, 1H), 3.02-2.89 (m, 2H), 1.52 (s, 3H), 1.49 (s, 3H).

Preparation of (S)-4-(Benzyloxy)-2-hydroxy-4-oxobutanoic acid

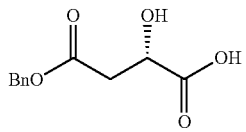

A solution of (S)-benzyl 2-(2,2-dimethyl-5-oxo-1,3-dioxolan-4-yl)acetate (8.63 g, 32.7 mmol) in acetic acid (50 mL) and water (25 mL) was heated at 60° C. for 1.5 h. After this time, the reaction mixture was concentrated under reduced pressure. The residue was dissolved in water and freeze dried to provide (S)-4-(benzyloxy)-2-hydroxy-4-oxobutanoic acid (7.32 g, quantitative) as a white solid: $^1$H NMR (300 MHz, DMSO-$d_6$) δ 12.57 (br s, 1H), 7.40-7.29 (m, 5H), 5.57 (br s, 1H), 5.11 (s, 2H), 4.33 (dd, J=7.8, 4.8 Hz, 1H), 2.77 (dd, J=15.6, 4.8 Hz, 1H), 2.61 (dd, J=15.6, 7.8 Hz, 1H); ESI MS m/z 223 $[C_{11}H_{12}O_5–H]^-$.

Preparation of (S)-2-Acetoxy-4-(benzyloxy)-4-oxobutanoic acid

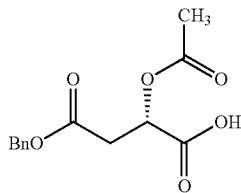 [SMILES: CC(=O)O[C@@H](CC(=O)OCc1ccccc1)C(=O)O]

A solution of (S)-4-(benzyloxy)-2-hydroxy-4-oxobutanoic acid (3.00 g, 13.4 mmol) in methylene chloride (15 mL) was treated with acetic acid (3 mL) and cooled in an ice bath under a nitrogen atmosphere. The solution was treated dropwise with acetyl chloride (1.05 mL, 14.8 mmol). After 15 min, the ice bath was removed, and the mixture was stirred at ambient temperature for 16 h. After this time, the reaction mixture was concentrated under reduced pressure and dried under vacuum to provide (S)-2-acetoxy-4-(benzyloxy)-4-oxobutanoic acid (4.12 g, quantitative) as a colorless oil: $^1$H NMR (300 MHz, DMSO-$d_6$) δ 7.39-7.33 (m, 5H), 5.25 (dd, J=8.1, 4.5 Hz, 1H), 5.14 (dd, J=14.4, 12.6 Hz, 2H), 3.00 (dd, J=16.5, 4.5 Hz, 1H), 2.89 (dd, J=16.5, 8.1 Hz, 1H), 2.02 (s, 3H), $CO_2H$ proton not observed.

Preparation of (S)-4-Benzyl 1-tert-butyl 2-acetoxysuccinate

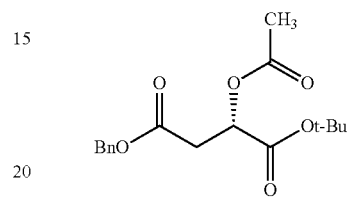

A solution of (S)-2-acetoxy-4-(benzyloxy)-4-oxobutanoic acid (3.57 g, 13.4 mmol) in methylene chloride (60 mL) was treated with tert-butanol (4.5 mL, 47 mmol), N,N'-dicyclohexylcarbodiimide (4.30 g, 20.8 mmol), and 4-dimethylaminopyridine (462 mg, 3.78 mmol) and stirred under a nitrogen atmosphere for 5 h. After this time, the reaction mixture was filtered to remove the solid dicyclohexylurea byproduct. The solid was washed with diethyl ether, and the combined filtrate and washings were concentrated under reduced pressure. The crude residue was purified by column chromatography (silica gel, 0-20% ethyl acetate/heptanes) to provide (S)-4-benzyl 1-tert-butyl 2-acetoxysuccinate (2.78 g, 64%) as a colorless oil: $^1$H NMR (300 MHz, DMSO-$d_6$) δ 7.42-7.30 (m, 5H), 5.19-5.14 (m, 3H), 3.00-2.85 (m, 2H), 2.03 (s, 3H), 1.37 (s, 9H).

Preparation of (S)-3-Acetoxy-4-(tert-butoxy)-4-oxobutanoic acid

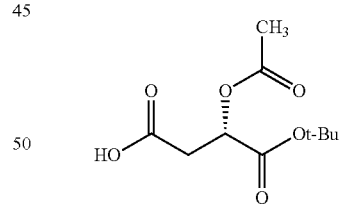

A solution of (S)-4-benzyl 1-tert-butyl 2-acetoxysuccinate (1.02 g, 3.16 mmol) in ethanol (30 mL) was sparged with nitrogen gas for 30 min. The solution was treated with 5% palladium on carbon (214 mg) and sparged with hydrogen gas for 5 min. The mixture was stirred under a hydrogen atmosphere for 2 h. After this time, the reaction mixture was sparged with nitrogen gas for 5 min and filtered through diatomaceous earth. The filtrate was concentrated under reduced pressure to provide (S)-3-acetoxy-4-(tert-butoxy)-4-oxobutanoic acid (731 mg, 99%) as a colorless oil: $^1$H NMR (300 MHz, DMSO-$d_6$) δ 12.74 (br s, 1H), 5.10 (dd, J=8.1, 4.8 Hz, 1H), 2.81-2.64 (m, 2H), 2.06 (s, 3H), 1.40 (s, 9H).

Preparation of (S)-1-tert-Butyl 4-(2,5-dioxopyrrolidin-1-yl) 2-acetoxysuccinate

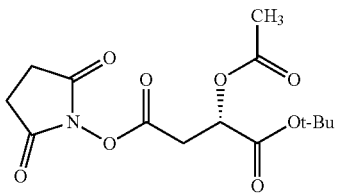 [SMILES: CC(=O)O[C@@H](CC(=O)ON1C(=O)CCC1=O)C(=O)OC(C)(C)C]

A solution of (S)-3-acetoxy-4-(tert-butoxy)-4-oxobutanoic acid (725 mg, 3.12 mmol) in tetrahydrofuran (15 mL) was treated with N-hydroxysuccinimide (396 mg, 3.44 mmol) and N,N'-dicyclohexylcarbodiimide (709 mg, 3.44 mmol) and stirred under a nitrogen atmosphere for 6 h. After this time, the reaction mixture was filtered to remove the solid dicyclohexylurea byproduct. The solid was washed with diethyl ether, and the combined filtrate and washings were concentrated under reduced pressure to provide (S)-1-tert-butyl 4-(2,5-dioxopyrrolidin-1-yl) 2-acetoxysuccinate (1.25 g, quantitative) as an off-white solid: $^1$H NMR (300 MHz, DMSO-$d_6$) δ 5.28 (dd, J=7.5, 4.8 Hz, 1H), 3.39-3.22 (m, 2H), 2.82 (s, 4H), 2.08 (s, 3H), 1.41 (s, 9H).

Preparation of (S)-4-((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl) 1-tert-butyl 2-acetoxysuccinate

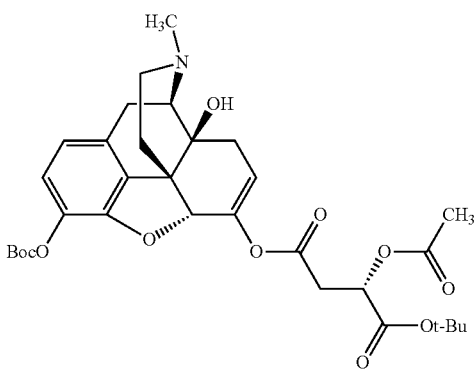

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (660 mg, 1.64 mmol) in tetrahydrofuran (10 mL) was cooled to 0° C. and treated dropwise with a 1.0 M solution of lithium bis(trimethylsilyl)amide in tetrahydrofuran (1.8 mL, 1.8 mmol). After addition was complete, the mixture was stirred at 0° C. for 25 min and then at ambient temperature for 25 min. The mixture was re-cooled to −78° C., and a solution of (S)-1-tert-butyl 4-(2,5-dioxopyrrolidin-1-yl) 2-acetoxysuccinate (600 mg, 1.82 mmol) in tetrahydrofuran (5 mL) was added. The mixture was allowed to warm to 0° C. over 2 h. After this time, the mixture was treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-4-((4R,4aS,7aR,12bS)-9-((tert-butoxycarbonyl)oxy)-4a-hydroxy-3-methyl-2,3,4,4a, 5,7a-hexahydro-1H-4,12-methanobenzofuro[3,2-e]isoquinolin-7-yl) 1-tert-butyl 2-acetoxysuccinate (332 mg, 32%) as a white solid: ESI MS m/z 616 $[C_{32}H_{41}NO_{11}+H]^+$.

Preparation of (S)-2-Acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

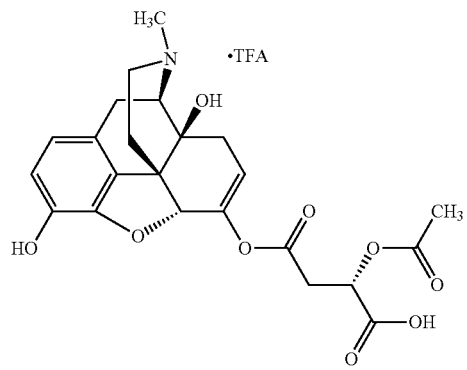 [SMILES: CC(=O)O[C@@H](CC(=O)OC1=CC[C@@]2(O)[C@H]3Cc4ccc(O)c5c4[C@@]2(CCN3C)[C@H]1O5)C(=O)O]

A solution of (S)-4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 1-tert-butyl 2-acetoxysuccinate (166 mg, 0.270 mmol) in methylene chloride (3 mL) was treated with trifluoroacetic acid (3 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-2-acetoxy-4-(((4R,4aS,7aR,12bS)-4a,9-dihydroxy-3-methyl-2, 3,4,4a,5,7a-hexahydro-1H-4,12-methanobenzofuro[3,2-e]isoquinolin-7-yl)oxy)-4-oxobutanoic acid trifluoroacetic acid salt (100 mg, 60%) as a fluffy white solid: $^1$H NMR (300 MHz, DMSO-$d_6$) δ 13.4 (br s, 1H), 9.29 (s, 1H), 9.14 (br s, 1H), 6.65 (apparent q, J=8.1 Hz, 2H), 6.24 (s, 1H), 5.55 (dd, J=5.7, 2.1 Hz, 1H), 5.28 (dd, J=8.4, 4.5 Hz, 1H), 4.96 (s, 1H), 3.12-2.94 (m, 4H), 2.84 (d, J=3.6 Hz, 3H), 2.67-2.42 (m, 4H), 2.27 (dd, J=17.7, 6.0 Hz, 1H), 2.09-2.03 (m, 4H), 1.63 (d, J=11.7 Hz, 1H); ESI MS m/z 460 $[C_{23}H_{25}NO_9+H]^+$; HPLC (Method A) 96.8% (AUC), $t_R$=6.88 min.

Scheme 144: (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((S)-2-acetoxy-2-phenylacetoxy)propanoate trifluoroacetic acid salt

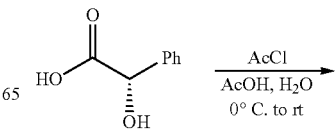

827
-continued

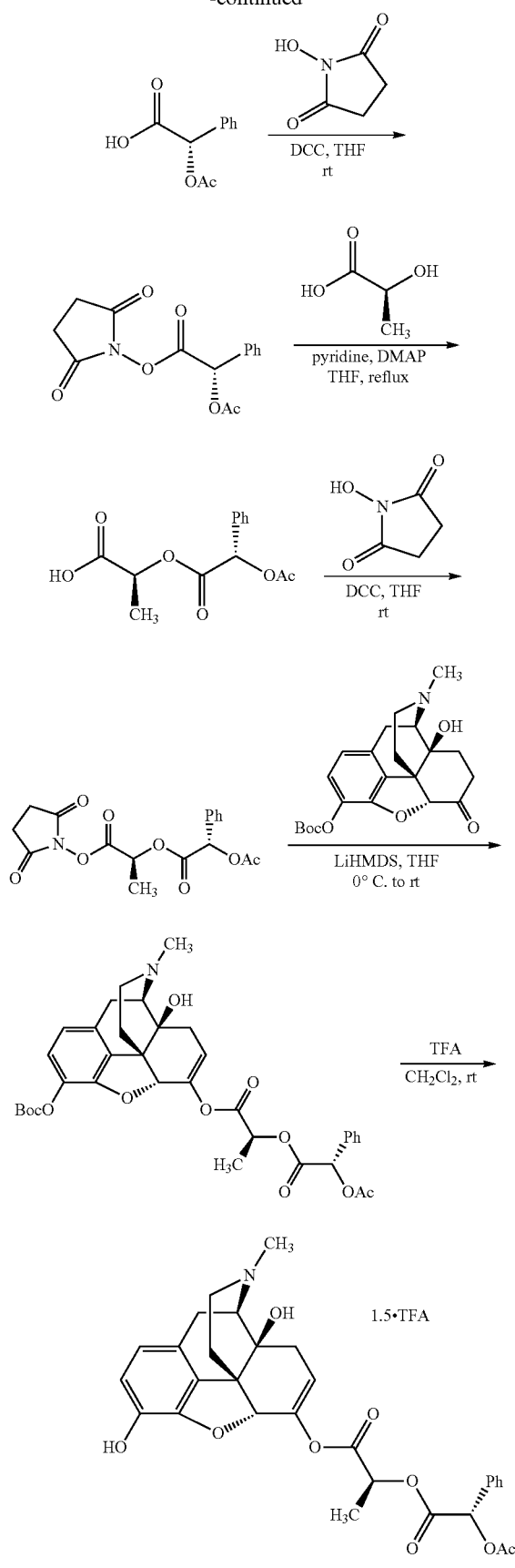

828

Preparation of (S)-2-Acetoxy-2-phenylacetic acid

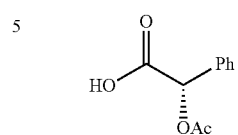

A solution of (S)-2-hydroxy-2-phenylacetic acid (16.4 g, 108 mmol) in acetic acid (30 mL) and water (1.3 mL) at 0° C. was treated dropwise with acetyl chloride (23.0 mL, 32.4 mmol). The reaction mixture was stirred at 0° C. for 1 h and then at room temperature for 18 h. After this time, the mixture was concentrated under reduced pressure, and the residue was dissolved in ethyl acetate, washed with water and brine, dried over sodium sulfate, filtered, and concentrated under reduced pressure to provide (S)-2-acetoxy-2-phenylacetic acid (22.0 g, 97%): $^1$H NMR (300 MHz, CDCl$_3$) δ 7.50-7.45 (m, 2H), 7.42-7.37 (m, 3H), 5.94 (s, 1H), 2.20 (s, 3H), CO$_2$H proton not observed.

Preparation of (S)-2,5-Dioxopyrrolidin-1-yl 2-acetoxy-2-phenylacetate

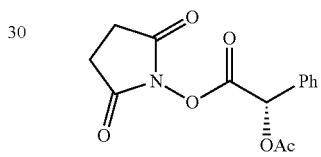

A mixture of (S)-2-acetoxy-2-phenylacetic acid (6.50 g, 31.0 mmol) and N-hydroxysuccinimide (4.00 g, 34.8 mmol) in tetrahydrofuran (150 mL) at 0° C. was added N,N-dicyclohexylcarbodiimide (7.00 g, 33.9 mmol). The ice bath was removed, and the reaction mixture was stirred at ambient temperature for 4 h. After this time, diethyl ether (100 mL) was added, and the mixture was filtered. The filtrate was concentrated under reduced pressure to provide (S)-2,5-dioxopyrrolidin-1-yl 2-acetoxy-2-phenylacetate (10.0 g) that was used without purification: $^1$H NMR (300 MHz, CDCl$_3$) δ 7.57-7.52 (m, 2H), 7.46-7.43 (m, 3H), 6.33 (s, 1H), 2.80 (s, 4H), 2.20 (s, 3H).

Preparation of (S)-2-((S)-2-Acetoxy-2-phenylacetoxy)propanoic acid

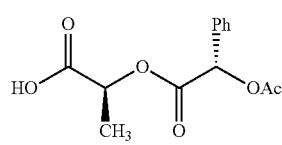

A mixture of (S)-2,5-dioxopyrrolidin-1-yl 2-acetoxy-2-phenylacetate (3.40 g, 11.6 mmol), (S)-2-hydroxypropanoic acid (1.30 g, 14.4 mmol), pyridine (1.1 mL, 13.6 mmol), and 4-dimethylaminopyridine (100 mg, 0.8 mmol) in tetrahydrofuran (50 mL) was stirred at reflux for 18 h. After this time, the mixture was cooled to room temperature, partially concentrated under reduced pressure, diluted with ethyl acetate, and washed with 10% citric acid. The organic layer was extracted with saturated sodium bicarbonate. The aqueous extract was carefully treated with 2 N hydrochloric acid until acidic by pH paper analysis, and then extracted with ethyl acetate. The organic extracts were dried over sodium carbonate, filtered and concentrated. The residue was purified by reversed phase column chromatography (150 g C18 column, 5-100% acetonitrile/water) to provide (S)-2-((S)-2-acetoxy-2-phenylacetoxy)propanoic acid (1.15 g, 37%): ESI MS m/z 531 [2×($C_{13}H_{14}O_6$)–H]⁻.

Preparation of (S)-2,5-Dioxopyrrolidin-1-yl 2-((S)-2-acetoxy-2-phenylacetoxy)propanoate

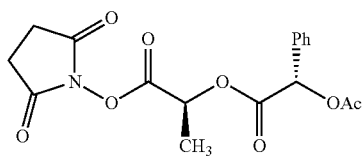 [SMILES: CC(=O)O[C@H](C(=O)O[C@@H](C)C(=O)ON1C(=O)CCC1=O)c1ccccc1]

A mixture of (S)-2-((S)-2-acetoxy-2-phenylacetoxy)propanoic acid (1.15 g, 4.32 mmol) and N-hydroxysuccinimide (545 mg, 4.74 mmol) in tetrahydrofuran (20 mL) was treated with N,N'-dicyclohexylcarbodiimide (975 mg, 4.74 mmol), and the reaction mixture was stirred at ambient temperature for 4 h. After this time, diethyl ether (20 mL) was added, and the mixture was filtered. The filtrate was concentrated under reduced pressure to provide (S)-2,5-dioxopyrrolidin-1-yl 2-((S)-2-acetoxy-2-phenylacetoxy)propanoate (1.64 g) that was used without purification: ¹H NMR (300 MHz, CDCl₃) δ 7.50-7.46 (m, 2H), 7.42-7.35 (m, 3H), 5.99 (s, 1H), 5.49 (q, J=7.1 Hz, 1H), 2.79 (s, 4H), 2.19 (s, 3H), 1.68 (d, J=7.1 Hz, 3H).

Preparation of (S)-(4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 2-((S)-2-acetoxy-2-phenylacetoxy)propanoate

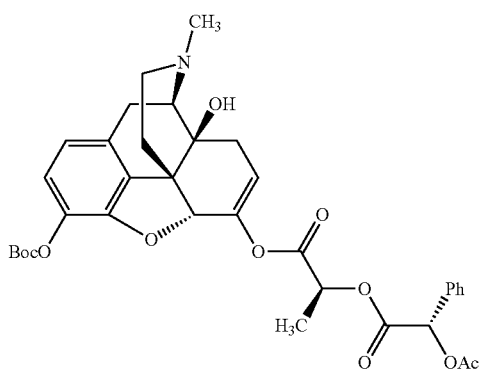

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (400 mg, 1.00 mmol) in tetrahydrofuran (8 mL) was cooled to –10° C. and treated dropwise with a 1.0 M solution of lithium bis(trimethylsilyl)amidein tetrahydrofuran (1.1 mL, 1.1 mmol). After addition was complete, the mixture was stirred at ambient temperature for 10 min. The mixture was re-cooled to –10° C. and (S)-2,5-dioxopyrrolidin-1-yl 2-((S)-2-acetoxy-2-phenylacetoxy)propanoate (400 mg, 1.1 mmol) was added in one portion. The mixture was stirred at –10° C. to ambient temperature over 45 min. After this time, the reaction mixture was cooled in an ice bath, treated with saturated aqueous ammonium chloride, and extracted with ethyl acetate. The combined organics were dried over sodium sulfate, filtered, and concentrated under reduced pressure. The residue was purified by reverse phase column chromatography (50 g C18 column, 5-100% acetonitrile/water) to provide (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-((S)-2-acetoxy-2-phenylacetoxy)propanoate (257 mg, 40%): ESI MS m/z 650 [$C_{35}H_3NO_{11}$+H]⁺.

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((S)-2-acetoxy-2-phenylacetoxy)propanoate trifluoroacetic acid salt

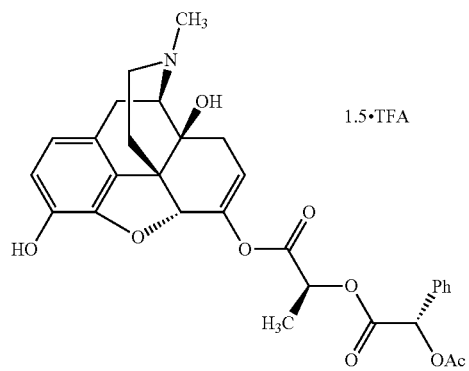 [SMILES: CC(=O)O[C@H](C(=O)O[C@@H](C)C(=O)OC1=CC[C@@]2(O)[C@H]3Cc4ccc(O)c5c4[C@@]2(CCN3C)[C@H]1O5)c1ccccc1]

A solution of (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-((S)-2-acetoxy-2-phenylacetoxy)propanoate (250 mg, 0.38 mmol) in methylene chloride (6 mL) was treated with trifluoroacetic acid (2 mL) and stirred at ambient temperature for 2 h. After this time, the reaction mixture was concentrated under reduced pressure. The residue was purified by reversed phase column chromatography (50 g C18 column, 5-30% acetonitrile/water, with 0.1% trifluoroacetic acid) and freeze dried to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((S)-2-acetoxy-2-phenylacetoxy)propanoate trifluoroacetic acid salt (95 mg, 35% over two steps) as a fluffy white solid: ¹H NMR (300 MHz, DMSO-d₆) δ 9.30 (br s, 1H), 9.16 (br s, 1H), 7.53-7.49 (m, 2H), 7.42-7.39 (m, 3H), 6.68 (d, J=8.2 Hz, 1H), 6.63 (d, J=8.2 Hz, 1H), 6.25 (s, 1H), 6.06 (s, 1H), 5.46 (dd, J=5.9, 2.0 Hz, 1H), 5.26 (q, J=7.1 Hz, 1H), 4.79 (s, 1H), 6.61 (d, J=6.1 Hz, 1H), 3.36 (d, J=20.0 Hz, 1H), 3.12-3.01 (m, 2H), 2.87-2.82 (m, 3H), 2.69-2.57 (m, 1H), 2.41 (dd, J=13.2, 4.7 Hz, 1H), 2.26 (dd, J=18.0, 6.2 Hz, 1H), 2.13 (s, 3H), 2.03 (d, J=18.0 Hz, 1H), 1.59 (d, J=10.9 Hz, 1H), 1.50 (d, J=7.1 Hz, 3H); ESI MS m/z 550 [$C_{30}H_{31}NO_9$+H]⁺; HPLC (Method A) 97.4% (AUC), $t_R$=9.46 min.

Scheme 145: (S)-2-((4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt
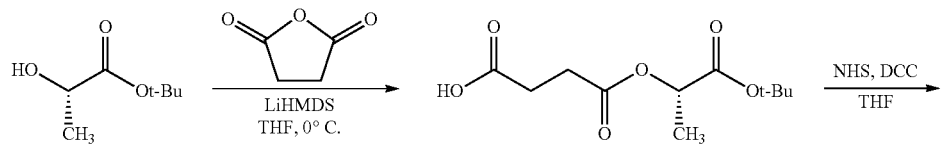
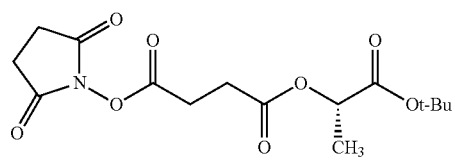
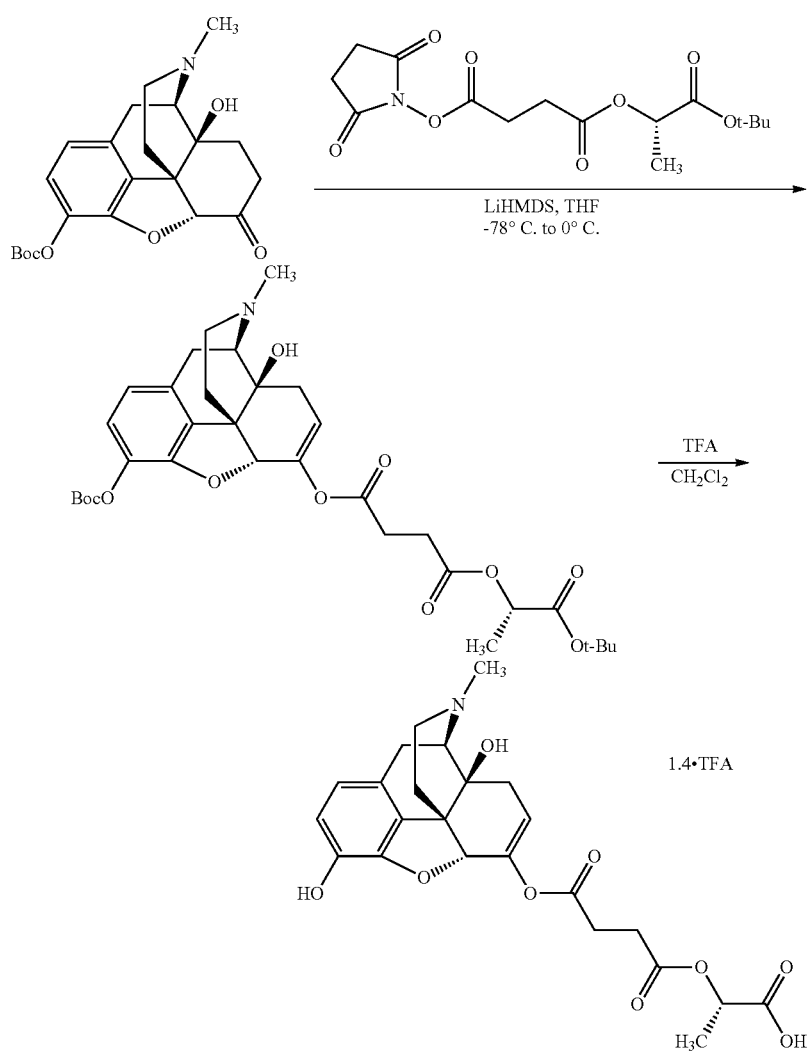

Preparation of (S)-4-((1-(tert-Butoxy)-1-oxopropan-2-yl)oxy)-4-oxobutanoic acid

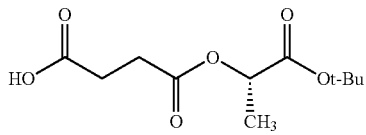

A solution of (S)-tert-butyl 2-hydroxypropanoate (3.40 g, 23.3 mmol) in tetrahydrofuran (50 mL) was cooled in an ice bath and treated with a 1.0 M solution of lithium bis(trimethylsilyl)amide in tetrahydrofuran (30.3 mL, 30.3 mmol) under a nitrogen atmosphere. After 10 min, the mixture was treated dropwise with a solution of succinic anhydride (2.80 g, 27.9 mmol) in tetrahydrofuran (25 mL) and stirred at 0° C. for 45 min. After this time, the reaction mixture was poured into saturated aqueous ammonium chloride and extracted with ethyl acetate. The combined organics were dried over sodium sulfate, filtered, and concentrated under reduced pressure. The crude residue was purified by column chromatography (silica gel, 0-20% methanol/methylene chloride) and triturated with ether, filtered, and concentrated under reduced pressure to provide (S)-4-((1-(tert-butoxy)-1-oxopropan-2-yl)oxy)-4-oxobutanoic acid (0.600 g, 10%) as a colorless oil: $^1$H NMR (300 MHz, DMSO-$d_6$) δ 12.18 (br s, 1H), 4.81 (q, J=7.2 Hz, 1H), 2.51-2.49 (m, 4H, partially obscured by solvent peak), 1.40 (s, 9H), 1.36 (d, J=7.2 Hz, 3H).

Preparation of (S)-1-(tert-Butoxy)-1-oxopropan-2-yl (2,5-dioxopyrrolidin-1-yl) succinate

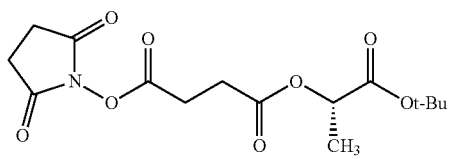 [SMILES: C[C@H](OC(=O)CCC(=O)ON1C(=O)CCC1=O)C(=O)OC(C)(C)C]

A solution of (S)-4-((1-(tert-butoxy)-1-oxopropan-2-yl)oxy)-4-oxobutanoic acid (0.700 mg, 2.84 mmol) in tetrahydrofuran (12 mL) was treated with N-hydroxysuccinimide (0.459 mg, 3.98 mmol) and N,N'-dicyclohexylcarbodiimide (0.822 mg, 3.98 mmol) and stirred under a nitrogen atmosphere for 5 h. After this time, the reaction mixture was filtered to remove the solid dicyclohexylurea byproduct. The solid was washed with diethyl ether, and the combined filtrate and washings were concentrated under reduced pressure. The crude residue was triturated with diethyl ether. The resulting solid was isolated by filtration and washed with diethyl ether. The combined filtrate and washings were concentrated under reduced pressure to provide (S)-1-(tert-butoxy)-1-oxopropan-2-yl (2,5-dioxopyrrolidin-1-yl) succinate (0.900 g, 92%) as a yellow oil: $^1$H NMR (300 MHz, CDCl$_3$) δ 5.00 (q, J=7.2 Hz, 1H), 2.99-2.96 (m, 2H), 2.85-2.80 (m, 6H), 1.48-1.45 (m, 12H).

Preparation of (S)-1-(tert-Butoxy)-1-oxopropan-2-yl ((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) succinate

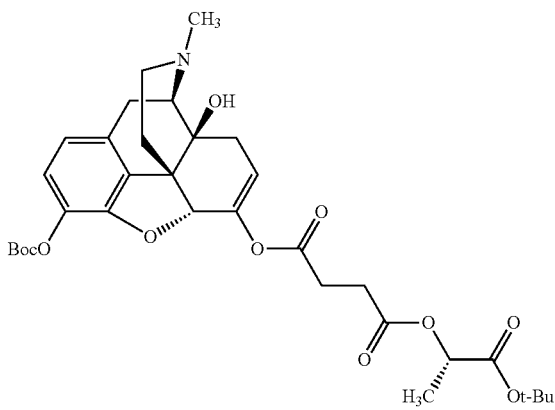

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (12 mL) was cooled to 0° C. and treated dropwise with a 1.0 M solution of lithium bis(trimethylsilyl)amidein tetrahydrofuran (1.46 mL, 1.46 mmol). After addition was complete, the mixture was stirred at 0° C. for 25 min and then at ambient temperature for 25 min. The mixture was re-cooled to −78° C., and (S)-1-(tert-butoxy)-1-oxopropan-2-yl (2,5-dioxopyrrolidin-1-yl) succinate (500 mg, 1.46 mmol) was added. The mixture was allowed to warm to 0° C. over 2 h. After this time, the mixture was treated with saturated aqueous ammonium chloride and extracted with ethyl acetate. The combined organics were dried over sodium sulfate, filtered, and concentrated under reduced pressure. The residue was purified by reversed phase column chromatography (150 g C18 column, 5-100% acetonitrile/water) to provide (S)-1-(tert-butoxy)-1-oxopropan-2-yl ((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) succinate (356 mg, 45%): ESI MS m/z 630 [$C_{33}H_{43}NO_{11}$+H]$^+$.

Preparation of (S)-2-((4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt

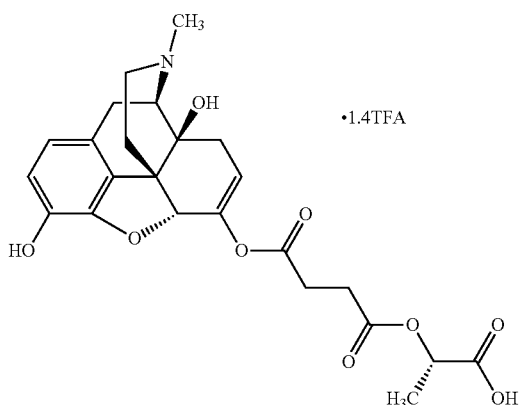

A solution of (S)-1-(tert-butoxy)-1-oxopropan-2-yl ((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) succinate (350 mg, 0.56 mmol) in methylene chloride (6 mL) was treated with trifluoroacetic acid (3 mL) and stirred at ambient temperature for 2 h. After this time, the reaction mixture was concentrated under reduced pressure. The residue was purified by reversed phase column chromatography (50 g C18 column, 5-30% acetonitrile/water, with 0.1% trifluoroacetic acid) and freeze dried to provide (S)-2-((4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt (186 mg, 52% over two steps) as a fluffy white solid: $^1$H NMR (300 MHz, DMSO-$d_6$) δ 13.05 (br s, 1H), 9.33 (br s, 1H), 9.18 (br s, 1H), 6.68 (d, J=8.2 Hz, 1H), 6.62 (d, J=8.2 Hz, 1H), 6.28 (s, 1H), 5.52 (dd, J=5.7, 1.8 Hz, 1H), 4.98-4.89 (m, 2H), 3.63 (d, J=6.2 Hz, 1H), 3.37 (d, J=19.9 Hz, 1H), 3.13-3.00 (m, 2H), 3.84 (s, 3H), 2.76-2.55 (m, 5H), 2.43 (dd, J=13.2, 4.6 Hz, 1H), 2.27 (dd, J=17.9, 6.1 Hz, 1H), 2.05 (d, J=16.2 Hz, 1H), 1.62 (d, J=11.0 Hz, 1H), 1.40 (d, J=7.1 Hz, 3H); ESI MS m/z 474 [$C_{24}H_{27}NO_9$+H]$^+$; HPLC (Method A) 96.8% (AUC), $t_R$=7.28 min.

Scheme 146: (S)-2-((S)-2-Acetoxypropanamido)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

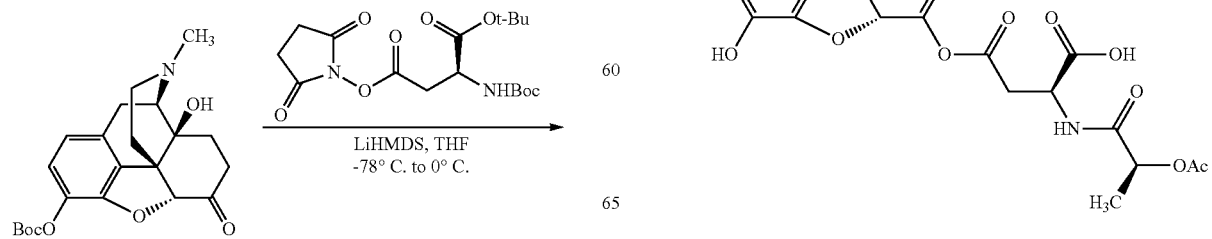

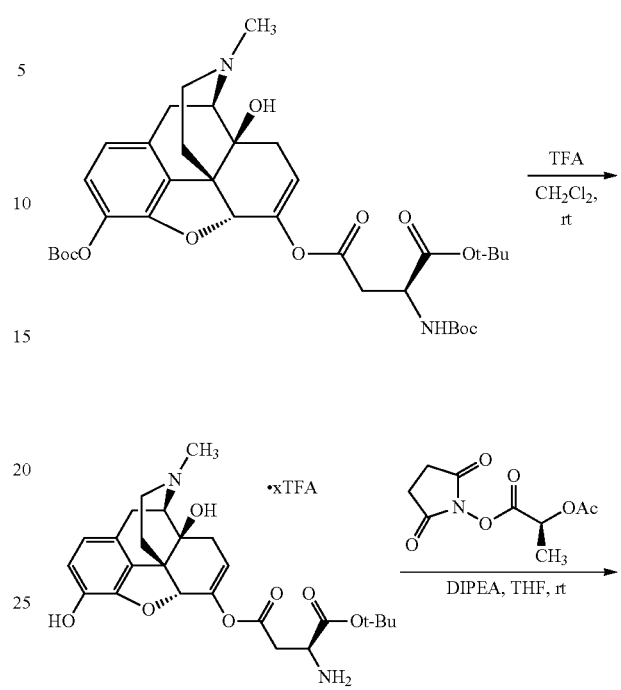

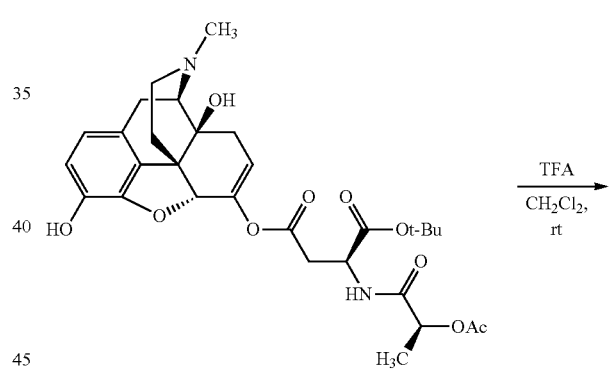

Preparation of (S)-4-((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl) 1-tert-butyl 2-((tert-butoxycarbonyl)amino)succinate

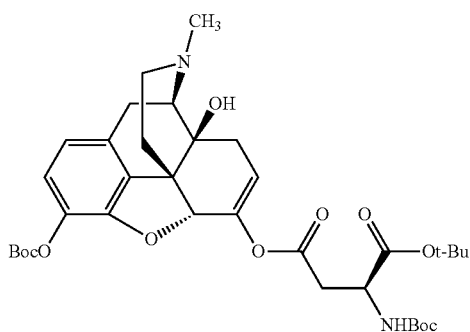

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (870 g, 2.17 mmol) in tetrahydrofuran (15 mL) was cooled to 0° C. and treated dropwise with a 1.0 M solution of lithium bis(trimethylsilyl)amide in tetrahydrofuran (2.37 mL, 2.37 mmol). After addition was complete, the mixture was stirred at 0° C. for 25 min and then at ambient temperature for 25 min. The mixture was re-cooled to −78° C. and (S)-1-tert-butyl 4-(2,5-dioxopyrrolidin-1-yl) 2-((tert-butoxycarbonyl)amino)succinate (870 mg, 2.25 mmol) was added. The mixture was allowed to warm to 0° C. over 2 h. After this time, the mixture was treated with saturated aqueous ammonium chloride, and extracted with ethyl acetate. The combined organics were dried over sodium sulfate, filtered, and concentrated under reduced pressure. The residue was purified by reversed phase column chromatography (150 g C18 column, 5-100% acetonitrile/water) to provide (S)-4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 1-tert-butyl 2-((tert-butoxycarbonyl)amino)succinate (610 mg, 38%): ESI MS m/z 673 $[C_{35}H_{48}N_2O_{11}+H]^+$.

Preparation of (S)-1-tert-Butyl 4-((4R,4aS,7aR,12bS)-4a,9-dihydroxy-3-methyl-2,3,4,4a,5,7a-hexahydro-1H-4,12-methanobenzofuro[3,2-e]isoquinolin-7-yl) 2-aminosuccinate trifluoroacetic acid salt

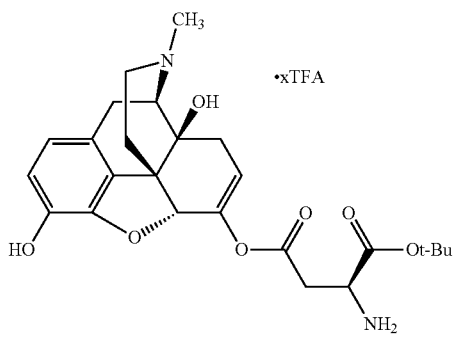 [SMILES: CN1CC[C@]23c4c5ccc(O)c4O[C@H]2C(OC(=O)C[C@H](N)C(=O)OC(C)(C)C)=CC[C@@]3(O)[C@H]1C5]

A solution (S)-4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 1-tert-butyl 2-((tert-butoxycarbonyl)amino)succinate (610 mg, 0.91 mmol) in methylene chloride (7 mL) was treated with trifluoroacetic acid (1 mL) and stirred at ambient temperature for 2 h. After this time, the reaction mixture was concentrated under reduced pressure to obtain (S)-1-tert-butyl 4-((4R,4aS,7aR,12bS)-4a,9-dihydroxy-3-methyl-2,3,4,4a,5,7a-hexahydro-1H-4,12-methanobenzofuro[3,2-e]isoquinolin-7-yl) 2-aminosuccinate trifluoroacetic acid salt (600 mg) that was used in the next step without purification: ESI MS m/z 473 $[C_{25}H_{32}N_2O_7+H]^+$.

Preparation of (S)-1-tert-Butyl 4-((4R,4aS,7aR,12bS)-4a,9-dihydroxy-3-methyl-2,3,4,4a,5,7a-hexahydro-1H-4,12-methanobenzofuro[3,2-e]isoquinolin-7-yl) 2-((S)-2-acetoxypropanamido)succinate

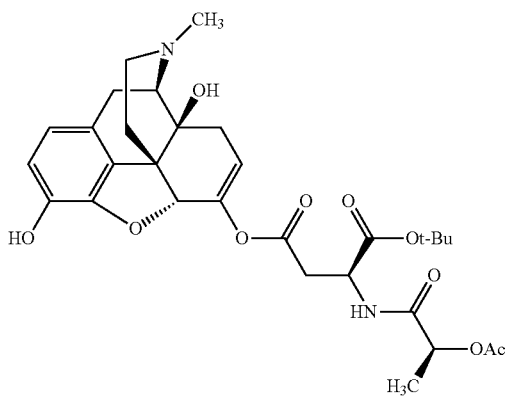 [SMILES: CC(=O)O[C@@H](C)C(=O)N[C@@H](CC(=O)OC1=CC[C@@]2(O)[C@H]3Cc4ccc(O)c5c4[C@@]2(CCN3C)[C@H]1O5)C(=O)OC(C)(C)C]

A mixture of (S)-1-tert-butyl 4-((4R,4aS,7aR,12bS)-4a,9-dihydroxy-3-methyl-2,3,4,4a,5,7a-hexahydro-1H-4,12-methanobenzofuro[3,2-e]isoquinolin-7-yl) 2-aminosuccinate trifluoroacetic acid salt (600 mg) and (S)-2,5-dioxopyrrolidin-1-yl 2-acetoxypropanoate (230 mg, 1.00 mmol) in tetrahydrofuran (8 mL) was treated with N,N-diisopropylethylamine (0.6 mL, 3.44 mmol). The reaction mixture was stirred at room temperature for 1 h. After this time, the mixture was diluted with ethyl acetate and washed with water and brine. The organic extracts were dried over sodium sulfate, filtered, and concentrated. The residue was purified by reversed phase column chromatography (15.5 g C18 column, 5-100% acetonitrile/water) to provide (S)-1-tert-butyl 4-((4R,4aS,7aR,12bS)-4a,9-dihydroxy-3-methyl-2,3,4,4a,5,7a-hexahydro-1H-4,12-methanobenzofuro[3,2-e]isoquinolin-7-yl) 2-((S)-2-acetoxypropanamido)succinate (135 mg, 26%): ESI MS m/z 587 $[C_{30}H_{36}N_2O_{10}+H]^+$.

839

Preparation of (S)-2-((S)-2-Acetoxypropanamido)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

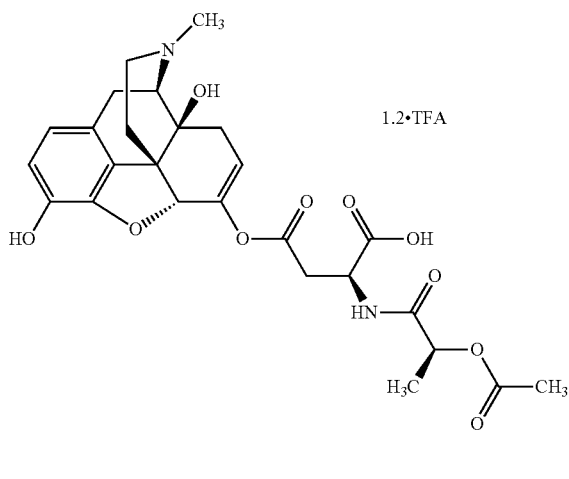 [SMILES: CC(=O)O[C@@H](C)C(=O)N[C@@H](CC(=O)OC1=CC[C@@]2(O)[C@H]3Cc4ccc(O)c5c4[C@@]2(CCN3C)[C@H]1O5)C(=O)O]

840

A solution of (S)-1-tert-butyl 4-((4R,4aS,7aR,12bS)-4a,9-dihydroxy-3-methyl-2,3,4,4a,5,7a-hexahydro-1H-4,12-methanobenzofuro[3,2-e]isoquinolin-7-yl) 2-((S)-2-acetoxypropanamido)succinate (135 mg, 0.230 mmol) in methylene chloride (5 mL) was treated with trifluoroacetic acid (1.5 mL) and stirred at room temperature for 3 h. After this time, the mixture was concentrated. The residue was purified by reversed phase column chromatography (15.5 g C18 column, 3-25% acetonitrile/water, with 0.1% trifluoroacetic acid) and freeze dried to provide (S)-2-((S)-2-acetoxypropanamido)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt (92 mg, 62%): $^1$H NMR (300 MHz, DMSO-$d_6$) δ 9.28 (br s, 1H), 9.16 (br s, 1H), 8.45 (d, J=8.3 Hz, 1H), 6.68 (d, J=8.2 Hz, 1H), 6.63 (d, J=8.2 Hz, 1H), 6.24 (s, 1H), 5.52 (dd, J=5.9, 1.9 Hz, 1H), 4.98 (q, J=6.8 Hz, 1H), 4.93 (s, 1H), 4.65 (q, J=6.9 Hz, 1H), 3.61 (d, J=6.3 Hz, 1H), 3.11-2.93 (m, 3H), 2.91-2.74 (m, 4H), 2.70-2.58 (m, 1H), 2.48-2.39 (m, 1H), 2.28 (dd, J=17.7, 6.2 Hz, 1H), 2.06 (d, J=14.0 Hz, 1H), 1.62 (d, J=11.0 Hz, 1H), 1.33 (d, J=6.9 Hz, 3H), $CO_2$H proton not observed, four protons obscured by solvent peaks; ESI MS m/z 531 [$C_{26}H_{30}N_2O_{10}$+H]$^+$; HPLC (Method A) 95.2% (AUC), $t_R$=7.00 min.

Scheme 147: (S,2S,2'S)-4,4'-(((4R,4aS,7aR,12bS)-9-Hydroxy-3-methyl-2,3,4,4a,5,7a-hexahydro-1H-4,12-methanobenzofuro[3,2-e]isoquinoline-4a,7-diyl)bis(oxy))bis(2-((S)-2-hydroxy-2-phenylacetamido)-4-oxobutanoic acid) trifluoroacetic acid salt

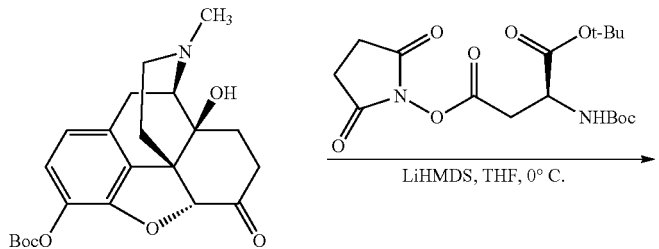

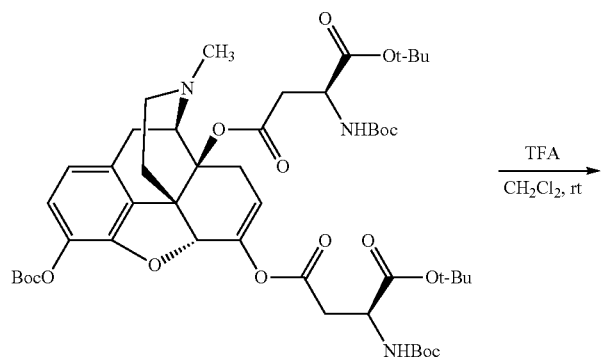

-continued
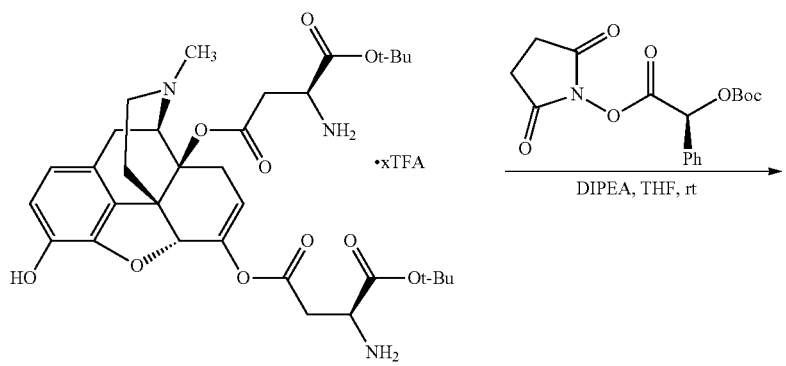
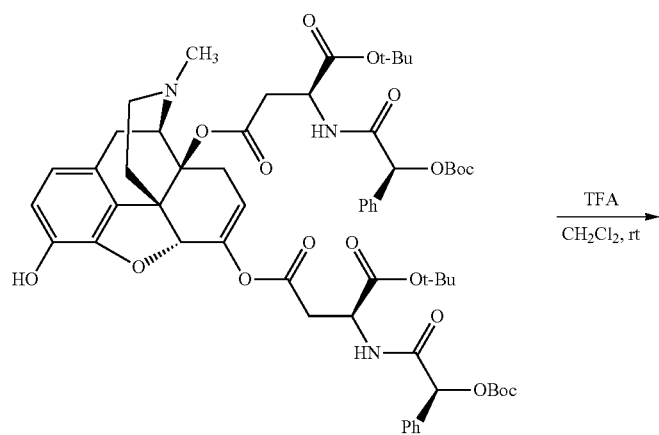
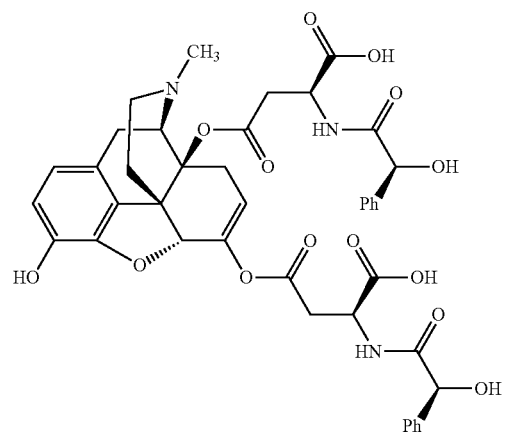 [SMILES: CN1CC[C@]23c4c5ccc(O)c4O[C@H]2C(OC(=O)C[C@H](NC(=O)[C@@H](O)c2ccccc2)C(=O)O)=CC[C@@]3(OC(=O)C[C@H](NC(=O)[C@@H](O)c2ccccc2)C(=O)O)[C@H]1C5]

Preparation of (2S,2'S)-O'⁴, O⁴-((4R,4aS,7aR, 12bS)-9-((tert-Butoxycarbonyl)oxy)-3-methyl-2,3,4, 4a,5,7a-hexahydro-1H-4, 12-methanobenzofuro[3,2-e]isoquinolin-4a,7-diyl) 1-di-tert-butyl bis(2-((tert butoxycarbonyl)amino)succinate)

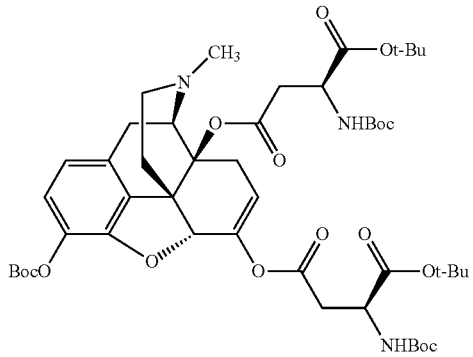

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-y) carbonate (1.60 g, 3.99 mmol) in tetrahydrofuran (25 mL) was cooled in an ice bath and treated dropwise with a 1.0 M solution of lithium bis(trimethylsilyl)amidein tetrahydrofuran (8.5 mL, 8.5 mmol). After addition was complete, the mixture was stirred at ambient temperature for 10 min. The mixture was re-cooled to 0° C., and (S)-1-tert-butyl 4-(2,5-dioxopyrrolidin-1-yl) 2-((tert-butoxycarbonyl)amino)succinate (3.10 g, 8.0 mmol) was added in one portion. The mixture was stirred at 0° C. for 30 min and then at ambient temperature for 30 min. After this time, the reaction mixture was cooled in an ice bath, treated with saturated aqueous ammonium chloride, and extracted with ethyl acetate. The combined organics were dried over sodium sulfate, filtered, and concentrated under reduced pressure. The residue was purified by reverse phase column chromatography (150 g C18 column, 5-100% acetonitrile/water) to provide (2S,2'S)-O'⁴, O⁴-((4R,4aS, 7aR,12bS)-9-((tert-butoxycarbonyl)oxy)-3-methyl-2,3,4,4a, 5,7a-hexahydro-1H-4,12-methanobenzofuro[3,2-e]isoquinoline-4a,7-diyl) 1-di-tert-butyl bis(2-((tert-butoxycarbonyl)amino)succinate) (1.95 g, 52%): ESI MS m/z 944 [C4H₆₉N₃O₁₆+H]⁺.

Preparation of (2S,2'S)-1-di-tert-Butyl O'⁴,O'-((4R, 4aS,7aR,12bS)-9-Hydroxy-3-methyl-2,3,4,4a,5,7a-hexahydro-1H-4,12-methanobenzofuro[3,2-e]isoquinoline-4a,7-diyl) bis(2-aminosuccinate) trifluoroacetic acid salt

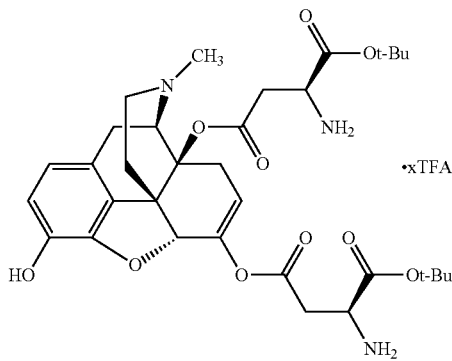 [SMILES: CN1CC[C@]23c4c5ccc(O)c4O[C@H]2C(OC(=O)C[C@H](N)C(=O)OC(C)(C)C)=CC[C@@]3(OC(=O)C[C@H](N)C(=O)OC(C)(C)C)[C@H]1C5]

A solution of (2S,2'S)-O'⁴,O⁴-((4R,4aS,7aR,12bS)-9-((tert-butoxycarbonyl)oxy)-3-methyl-2,3,4,4a,5,7a-hexahydro-1H-4,12-methanobenzofuro[3,2-e]isoquinoline-4a,7-diyl) 1-di-tert-butyl bis(2-((tert-butoxycarbonyl)amino)succinate) (1.22 g, 1.29 mmol) in methylene chloride (15 mL) was treated with trifluoroacetic acid (2.5 mL) and stirred at ambient temperature for 2.5 h. After this time, the reaction mixture was concentrated under reduced pressure to provide (2S,2'S)-1-di-tert-butyl O'⁴,O⁴-((4R,4aS,7aR, 12bS)-9-hydroxy-3-methyl-2,3,4,4a,5,7a-hexahydro-1H-4, 12-methanobenzofuro[3,2-e]isoquinoline-4a,7-diyl) bis(2-aminosuccinate) trifluoroacetic acid salt (900 mg) that was used without purification: ESI MS m/z 644 [C₃₃H₄₅N₃O₁₀+H]⁺.

Preparation of (S,2S,2'S)-1-Di-tert-butyl O',O'⁴-((4R,4aS,7aR,12bS)-9-Hydroxy-3-methyl-2,3,4,4a,5, 7a-hexahydro-1H-4,12-methanobenzofuro[3,2-e] isoquinoline-4a,7-diyl) bis(2-((S)-2-((tert-butoxycarbonyl)oxy)-2-phenylacetamido)succinate)

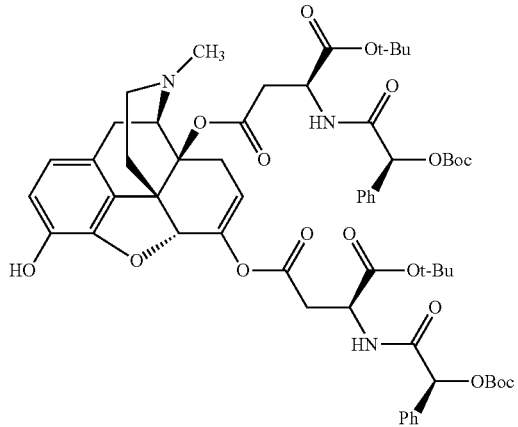

A mixture of (2S,2'S)-1-di-tert-butyl O'⁴,O⁴-((4R,4aS, 7aR,12bS)-9-hydroxy-3-methyl-2,3,4,4a,5,7a-hexahydro-1H-4,12-methanobenzofuro[3,2-e]isoquinoline-4a,7-diyl) bis(2-aminosuccinate) trifluoroacetic acid salt (590 mg, 0.60 mmol) and (S)-2,5-dioxopyrrolidin-1-yl 2-((tert-butoxycarbonyl)oxy)-2-phenylacetate (560 mg, 1.59 mmol) in tetrahydrofuran (7 mL) was treated with N,N-diisopropylethylamine (0.90 mL, 5.2 mmol) and stirred at room temperature for 2.5 h. After this time, the reaction mixture was diluted with ethyl acetate and washed with water and brine. The organic extracts were dried over sodium sulfate, filtered, and concentrated under reduced pressure. The residue was purified by reversed phase column chromatography (50 g C18 column, 5-100% acetonitrile/water) to provide (S,2S,2'S)-1-di-tert-butyl O'⁴,O⁴-((4R,4aS,7aR,12bS)-9-hydroxy-3-methyl-2,3,4,4a,5,7a-hexahydro-1H-4,12-methanobenzofuro[3,2-e]isoquinoline-4a,7-diyl) bis(2-((S)-2-((tert-butoxycarbonyl)oxy)-2-phenylacetamido)succinate) (100 mg, 15%): ESI MS m/z 1112 [C₅₉H₇₃N₃O₁₈+H]⁺.

845

Preparation of (S,2S,2'S)-4,4'-(((4R,4aS,7aR,12bS)-9-Hydroxy-3-methyl-2,3,4,4a,5,7a-hexahydro-1H-4,12-methanobenzofuro[3,2-e]isoquinoline-4a,7-diyl)bis(oxy))bis(2-((S)-2-hydroxy-2-phenylacetamido)-4-oxobutanoic acid) trifluoroacetic acid salt

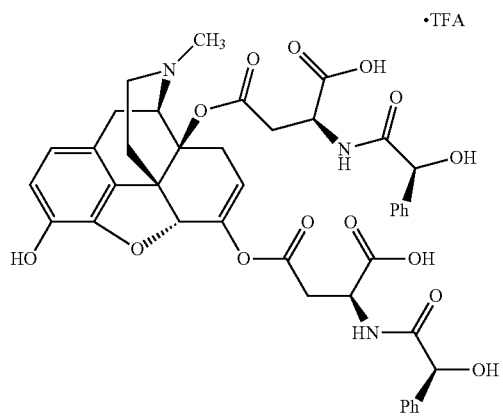 [SMILES: CN1CC[C@]23c4c5ccc(O)c4O[C@H]2C(OC(=O)C[C@H](NC(=O)[C@@H](O)c2ccccc2)C(=O)O)=CC[C@@]3(OC(=O)C[C@H](NC(=O)[C@@H](O)c2ccccc2)C(=O)O)[C@H]1C5]

A solution of (S,2S,2'S)-1-di-tert-butyl $O'^4,O^4$-((4R,4aS,7aR,12bS)-9-hydroxy-3-methyl-2,3,4,4a,5,7a-hexahydro-1H-4,12-methanobenzofuro[3,2-e]isoquinoline-4a,7-diyl) bis(2-((S)-2-((tert-butoxycarbonyl)oxy)-2-phenylacetamido)succinate) (100 mg, 0.09 mmol) in methylene chloride (5 mL) was treated with trifluoroacetic acid (1.5 mL) and stirred at ambient temperature for 4 h. After this time, the reaction mixture was concentrated under reduced pressure. The residue was purified by reversed phase column chromatography (15.5 g C18 column, 3-30% acetonitrile/water, with 0.1% trifluoracetic acid) and freeze dried to provide (S,2S,2'S)-4,4'-(((4R,4aS,7aR,12bS)-9-hydroxy-3-methyl-2,3,4,4a,5,7a-hexahydro-1H-4,12-methanobenzofuro[3,2-e]isoquinoline-4a,7-diyl)bis(oxy))bis(2-((S)-2-hydroxy-2-phenylacetamido)-4-oxobutanoic acid) trifluoroacetic acid salt (18 mg, 22%): $^1$H NMR (300 MHz, DMSO-$d_6$, Mixture of diastereomers) δ 9.35 (s, 1H), 8.48 (d, J=8.4 Hz, 0.18H), 8.43 (d, J=8.3 Hz, 0.82H), 8.25 (d, J=7.2 Hz, 1H), 7.44-7.17 (m, 10H), 6.69 (d, J=8.2 Hz, 1H), 6.63 (d, J=8.2 Hz, 1H), 6.41-6.30 (m, 2H), 5.34 (d, J=5.9 Hz, 0.18H), 5.25 (d, J=4.5 Hz, 0.82H), 5.00-4.89 (m, 3H), 4.74-4.47 (m, 3H), 3.18-2.94 (m, 4H), 2.93-2.67 (m, 8H), 2.45-2.43 (m, 2H), 2.09-1.98 (m, 1H), 1.73-1.61 (m, 1H), $CO_2H$ protons not observed; ESI MS m/z 800 $[C_{41}H_{41}N_3O_{14}+H]^+$; HPLC (Method A) 94.4% (AUC), $t_R$=8.52 min.

Scheme 148: (R)-2-((4-(((4R,4aS,7aR,12bS)-4a,9-Dihydroxy-3-methyl-2,3,4,4a,5,7a-hexahydro-1H-4, 12-methanobenzofura[3-2-e]isoquinolin-7-yl)oxy)-4-oxobutanoyl)oxy)succinic acid trifluoroacetic acid salt

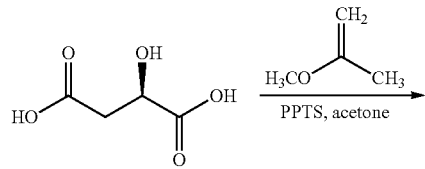

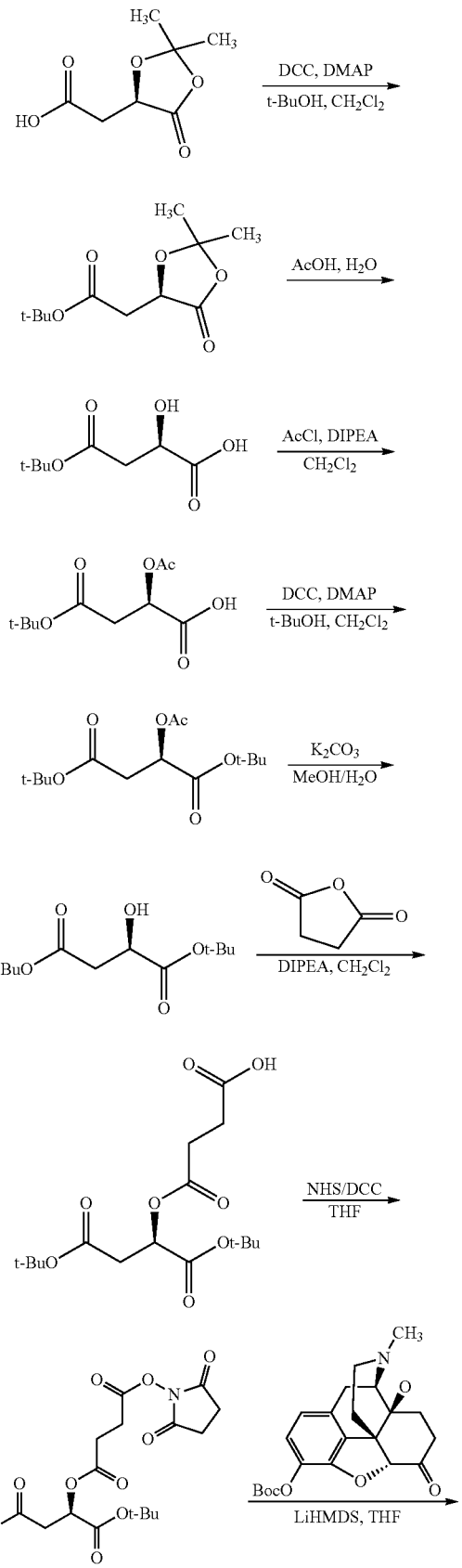

-continued

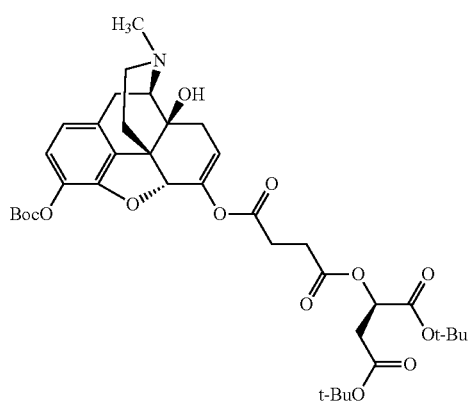

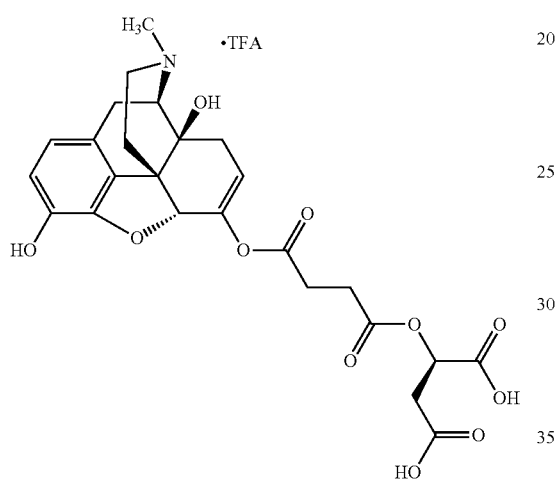

Preparation of (R)-2-(2,2-Dimethyl-5-oxo-1,3-dioxolan-4-yl)acetic acid

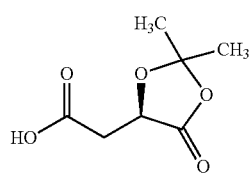

A solution of (R)-malic acid (4.50 g, 33.6 mmol), 2-methoxyprop-1-ene (9.68 g, 134 mmol) and pyridinium p-toluenesulfonate (844 mg, 3.36 mmol) in acetone (50 mL) was stirred at 35° C. for 16 h. After this time, water (200 mL) was added, and the aqueous solution was extracted with ethyl acetate (2×200 mL). The combined organics were dried over sodium sulfate, filtered, and concentrated under reduced pressure. The residue was recrystallized from ethyl acetate/heptane to provide (R)-2-(2,2-dimethyl-5-oxo-1,3-dioxolan-4-yl)acetic acid (2.92 g, 50%) as an off-white solid: $^1$H NMR (300 MHz, DMSO-d$_6$) δ 4.72 (dd, J=6.6, 3.9 Hz, 1H), 3.01 (dd, J=17.4, 3.9 Hz, 1H), 2.86 (dd, J=17.4, 6.6 Hz, 1H), 1.63 (s, 3H), 1.58 (s, 3H), CO$_2$H proton not observed.

Preparation of (R)-tert-Butyl 2-(2,2-dimethyl-5-oxo-1,3-dioxolan-4-yl)acetate

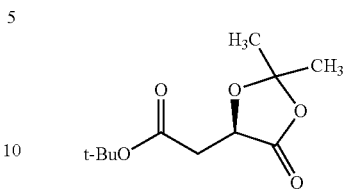

A solution of (R)-2-(2,2-dimethyl-5-oxo-1,3-dioxolan-4-yl)acetic acid (2.92 g, 16.8 mmol) and tert-butanol (1.86 g, 25.2 mmol) in methylene chloride (40 mL) was treated with N,N'-dicyclohexylcarbodiimide (4.16 g, 20.2 mmol) and 4-(dimethylamino)pyridine (616 mg, 5.04 mmol) and stirred at room temperature under a nitrogen atmosphere for 4 h. After this time, the reaction mixture was filtered to remove the solid dicyclohexylurea byproduct. The solid was washed with diethyl ether (100 mL), and the combined filtrate and washings were concentrated under reduced pressure. The crude residue was purified by column chromatography (80 g silica gel column, 0-30% ethyl acetate/heptane) to provide (R)-tert-butyl 2-(2,2-dimethyl-5-oxo-1,3-dioxolan-4-yl)acetate (3.19 g, 82%) as a white solid: $^1$H NMR (300 MHz, CDCl$_3$) δ 4.66 (dd, J=6.0, 3.9 Hz, 1H), 2.84 (dd, J=17.1, 4.2 Hz, 1H), 2.72 (dd, J=16.8, 6.3 Hz, 1H), 1.63 (s, 3H), 1.56 (s, 3H), 1.47 (s, 9H).

Preparation of (R)-4-(tert-Butoxy)-2-hydroxy-4-oxobutanoic acid

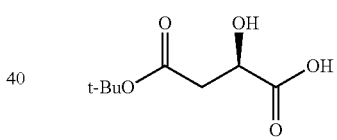

A solution of (R)-tert-butyl 2-(2,2-dimethyl-5-oxo-1,3-dioxolan-4-yl)acetate (3.19 g, 13.9 mmol) in acetic acid (21 mL) and water (9 mL) was stirred at 60° C. for 4 h. After this time, the solvent was removed under reduced pressure. The residue was dried under vacuum to provide (R)-4-(tert-butoxy)-2-hydroxy-4-oxobutanoic acid (2.81 g) as a colorless oil: $^1$H NMR (300 MHz, DMSO-d$_6$) δ 4.48 (dd, J=5.7, 5.4 Hz, 1H), 2.83 (m, 2H), 1.48 (m, 9H), CO$_2$H and OH protons not observed.

Preparation of (R)-2-Acetoxy-4-(tert-butoxy)-4-oxobutanoic acid

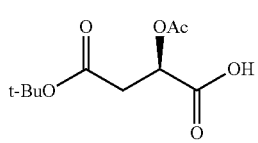 [SMILES: CC(=O)O[C@H](CC(=O)OC(C)(C)C)C(=O)O]

(R)-4-(tert-Butoxy)-2-hydroxy-4-oxobutanoic acid (2.81 g, 14.8 mmol), acetyl chloride (1.28 g, 16.3 mmol), N,N-diisopropylethylamine (5.74 g, 44.4 mmol), and methylene chloride (150 mL) were combined at 0° C. and then stirred at room temperature under a nitrogen atmosphere for 4 h. After this time, 10% aqueous citric acid (100 mL) was added. The organic layer was separated and extracted with methylene chloride (2×100 mL). The combined organics were washed with brine (50 mL), dried over sodium sulfate, filtered, and concentrated under reduced pressure to provide (R)-2-acetoxy-4-(tert-butoxy)-4-oxobutanoic acid (3.44 g) as a black oil, which was used without purification.

Preparation of (R)-Di-tert-butyl 2-acetoxysuccinate

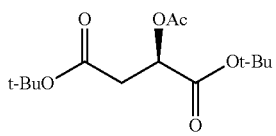 [SMILES: CC(=O)O[C@H](CC(=O)OC(C)(C)C)C(=O)OC(C)(C)C]

A solution of (R)-2-acetoxy-4-(tert-butoxy)-4-oxobutanoic acid (3.44 g, 14.8 mmol) and tert-butanol (2.41 g, 32.6 mmol) in methylene chloride (70 mL) was treated with N,N'-dicyclohexylcarbodiimide (3.69 g, 19.2 mmol) and 4-(dimethylamino)pyridine (597 mg, 4.88 mmol) and stirred at room temperature under a nitrogen atmosphere for 16 h. After this time, the reaction mixture was filtered to remove the solid dicyclohexylurea byproduct. The solid was washed with diethyl ether (100 mL), and the combined filtrate and washings were concentrated under reduced pressure. The crude residue was purified by column chromatography (80 g silica gel column, 0-30% ethyl acetate/heptane) to provide (R)-di-tert-butyl 2-acetoxysuccinate (1.70 g, 40%) as a colorless oil: $^1$H NMR (300 MHz, CDCl$_3$) δ 5.30 (dd, J=7.5, 5.4 Hz, 1H), 2.75 (m, 2H), 2.12 (s, 3H), 1.46 (s, 18H).

Preparation of (R)-Di-tert-butyl 2-hydroxysuccinate

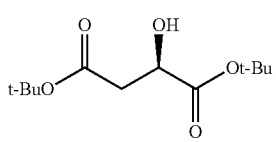 [SMILES: CC(C)(C)OC(=O)C[C@@H](O)C(=O)OC(C)(C)C]

(R)-Di-tert-butyl 2-acetoxysuccinate (1.70 g, 5.90 mmol), potassium carbonate (2.44 g, 17.7 mmol), methanol (90 mL) and water (15 mL) were combined and stirred at 0° C. for 3 h. After this time, water (200 mL) was added, and the aqueous solution was extracted with methylene chloride (2×200 mL). The combined organics were washed with brine (50 mL), dried over sodium sulfate, filtered, and concentrated under reduced pressure to provide (R)-di-tert-butyl 2-hydroxysuccinate (1.16 g, 80%) as a white solid: $^1$H NMR (300 MHz, CDCl$_3$) δ 4.30 (dd, J=10.2, 5.7 Hz, 1H), 3.19 (d, J=5.4 Hz, 1H), 2.75-2.66 (m, 2H), 1.47 (s, 9H), 1.45 (s, 9H).

Preparation of (R)-4-((1,4-Di-tert-butoxy-1,4-dioxobutan-2-yl)oxy)-4-oxobutanoic acid

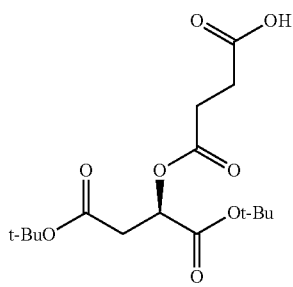 [SMILES: CC(C)(C)OC(=O)C[C@@H](OC(=O)CCC(=O)O)C(=O)OC(C)(C)C]

(R)-Di-tert-butyl 2-hydroxysuccinate (1.16 g, 4.71 mmol), dihydrofuran-2,5-dione (1.41 g, 14.1 mmol), N,N-diisopropylethylamine (1.82 g, 14.1 mmol), and methylene chloride (30 mL) were combined and stirred at room temperature under a nitrogen atmosphere for 16 h. After this time, 10% aqueous citric acid (100 mL) was added. The organic layer was separated and extracted with methylene chloride (2×50 mL). The combined organics were washed with brine (50 mL), dried over sodium sulfate, filtered, and concentrated under reduced pressure to provide (R)-4-((1,4-di-tert-butoxy-1,4-dioxobutan-2-yl)oxy)-4-oxobutanoic acid (2.05 g) as a brown oil: $^1$H NMR (300 MHz, CDCl$_3$) δ 5.32 (dd, J=7.5, 5.1 Hz, 1H), 2.77-2.66 (m, 6H), 1.45 (s, 18H), CO$_2$H proton not observed.

Preparation of (R)-Di-tert-butyl 2-((4-((2,5-dioxopyrrolidin-1-yl)oxy)-4-oxobutanoyl)oxy)succinate

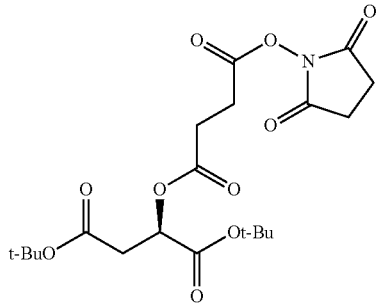 [SMILES: CC(C)(C)OC(=O)C[C@@H](OC(=O)CCC(=O)ON1C(=O)CCC1=O)C(=O)OC(C)(C)C]

A solution of (R)-4-((1,4-di-tert-butoxy-1,4-dioxobutan-2-yl)oxy)-4-oxobutanoic acid (2.05 g, 5.92 mmol) in tetrahydrofuran (60 mL) was treated with N-hydroxysuccinimide (681 mg, 5.92 mmol) and N,N'-dicyclohexylcarbodiimide (1.22 g, 5.92 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (R)-di-tert-butyl 2-((4-((2,5-dioxopyrrolidin-1-yl)oxy)-4-oxobutanoyl)oxy)succinate (2.75 g) as a brown oil: $^1$H NMR (300 MHz, CDCl$_3$) δ 5.34 (dd, J=6.9, 5.7 Hz, 1H), 3.01-2.96 (m, 2H), 2.87-2.70 (m, 8H), 1.45 (s, 18H).

851

Preparation (R)-Di-tert-butyl 2-((4-(((4R,4aS,7aR, 12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-4-oxobutanoyl)oxy)succinate

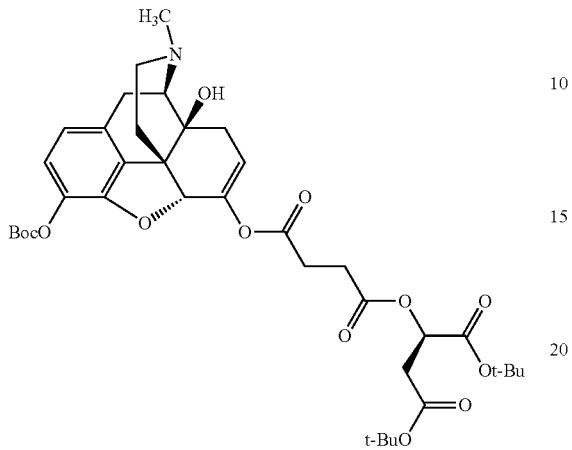

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at ambient temperature for 15 min. The mixture was re-cooled to −45° C. and treated dropwise with a solution of (R)-di-tert-butyl 2-((4-((2,5-dioxopyrrolidin-1-yl)oxy)-4-oxobutanoyl)oxy)succinate (608 mg, 1.37 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (R)-di-tert-butyl 2-((4-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-4-oxobutanoyl)oxy)succinate (100 mg, 11%) as a white solid: ESI MS m/z 730 $[C_{36}H_{51}NO_{13}+H]^+$.

852

Preparation of (R)-2-((4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-4-oxobutanoyl)oxy)succinic acid trifluoroacetic acid salt

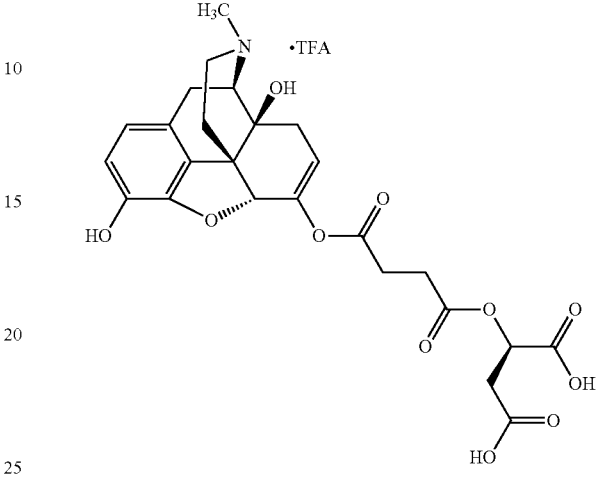

A solution of (R)-di-tert-butyl 2-((4-(((4R,4aS,7aR, 12bS)-9-((tert-butoxycarbonyl)oxy)-4a-hydroxy-3-methyl-2,3,4,4a,5,7a-hexahydro-1H-4,12-methanobenzofuro[3,2-e] isoquinolin-7-yl)oxy)-4-oxobutanoyl)oxy)succinate (100 mg, 0.137 mmol) in methylene chloride (2 mL) was treated with trifluoroacetic acid (1 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (R)-2-((4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)succinic acid trifluoroacetic acid salt (48 mg, 55%) as a fluffy white solid: $^1$H NMR (300 MHz, DMSO-$d_6$) δ 13.2 (br s, 1H), 12.6 (br s, 1H), 9.30 (s, 1H), 9.17 (br s, 1H), 6.64 (q, J=8.1 Hz, 2H), 6.24 (br s, 1H), 5.53 (dd, J=6.3, 2.1 Hz, 1H), 5.22 (dd, J=7.8, 4.5 Hz, 1H), 4.95 (s, 1H), 3.41-3.32 (m, 1H), 3.04 (m, 1H), 2.86-2.61 (m, 10H), 2.51-2.42 (m, 3H), 2.26 (m, 1H), 2.06 (d, J=18.0 Hz, 1H), 1.62 (d, J=10.8 Hz, 1H); ESI MS m/z 518 $[C_{25}H_{27}NO_{11}+H]^+$; HPLC (Method A) 95.3% (AUC), $t_R$=6.81 min.

Scheme 149: (S)-4-(((4R,4aS,7aR,12bS)-4a,9-Dihydroxy-3-methyl-2,3,4,4a,5,7a-hexahydro-1H-4, 12-methanobenzofuro[3,2-e]isoquinolin-7-yl)oxy)-2-((S)-2-hydroxy-2-phenylacetamido)-4-oxobutanoic acid trfluoro acid salt and (S)-1-tert-Butyl 4-((4R,4aS,7aR,12bS)-4a,9-dihydroxy-3-methyl-2,3,4,4a,5,7a-hexahydro-1H-4, 12-methanobenzofuro[3,2-e]isoquinolin-7-yl) 2-((S)-2-hydroxy-2-phenylacetamido)succinate trifluoroacetic acid salt

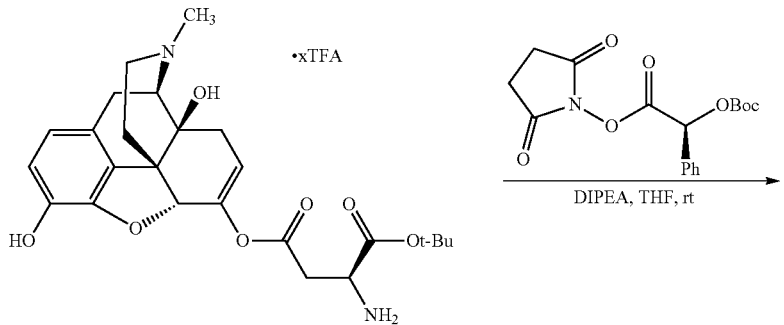

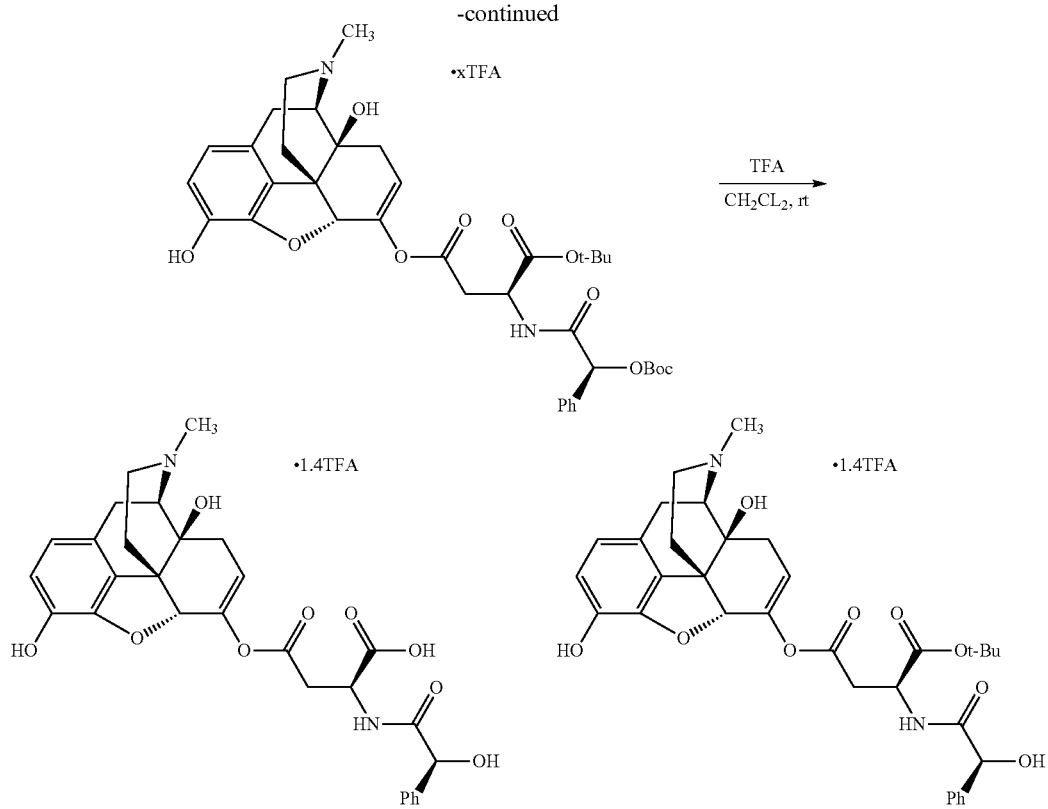

Preparation of (S)-1-tert-Butyl 4-((4R,4aS,7aR,12bS)-4a,9-dihydroxy-3-methyl-2,3,4,4a,5,7a-hexahydro-1H-4,12-methanobenzofuro[3,2-e]isoquinolin-7-yl) 2-((S)-2-((tert-butoxycarbonyl)oxy)-2-phenylacetamido)succinate

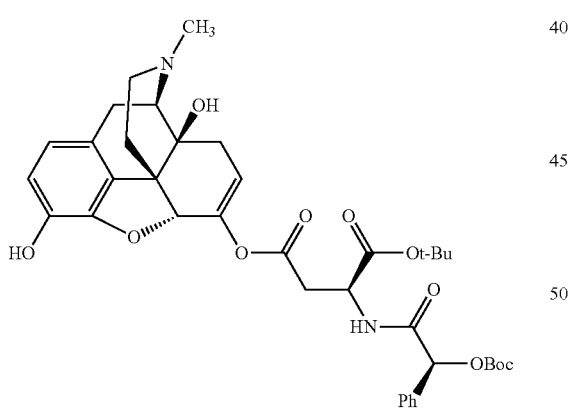

A mixture of (S)-1-tert-butyl 4-((4R,4aS,7aR,12bS)-4a,9-dihydroxy-3-methyl-2,3,4,4a,5,7a-hexahydro-1H-4,12-methanobenzofuro[3,2-e]isoquinolin-7-yl) 2-aminosuccinate trifluoroacetic acid salt (490 mg, 0.70 mmol) and (S)-2,5-dioxopyrrolidin-1-yl 2-((tert-butoxycarbonyl)oxy)-2-phenylacetate (315 mg, 0.901 mmol) in tetrahydrofuran (8 mL) was treated with N,N-diisopropylethylamine (0.60 mL, 3.4 mmol) and stirred at room temperature for 1 h. After this time, the reaction mixture was diluted with ethyl acetate and washed with water and brine. The organic extracts were dried over sodium sulfate, filtered, and concentrated. The residue was purified by reversed phase column chromatography (50 g C18 column, 5-100% acetonitrile/water) to provide (S)-1-tert-butyl 4-((4R,4aS,7aR,12bS)-4a,9-dihydroxy-3-methyl-2,3,4,4a,5,7a-hexahydro-1H-4,12-methanobenzofuro[3,2-e]isoquinolin-7-yl) 2-((S)-2-((tert-butoxycarbonyl)oxy)-2-phenylacetamido)succinate (160 mg, 30%): ESI MS m/z 707 $[C_{36}H_{46}N_2O_{11}+H]^+$.

Preparation of (S)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-((S)-2-hydroxy-2-phenylacetamido)-4-oxobutanoic acid trifluoroacetic acid salt and (S)-1-tert-Butyl 4-((4R,4aS,7aR,12bS)-4a,9-dihydroxy-3-methyl-2,3,4,4a,5,7a-hexahydro-1H-4,12-methanobenzofuro[3,2-e]isoquinolin-7-yl) 2-((S)-2-hydroxy-2-phenylacetamido)succinate trifluoroacetic acid salt

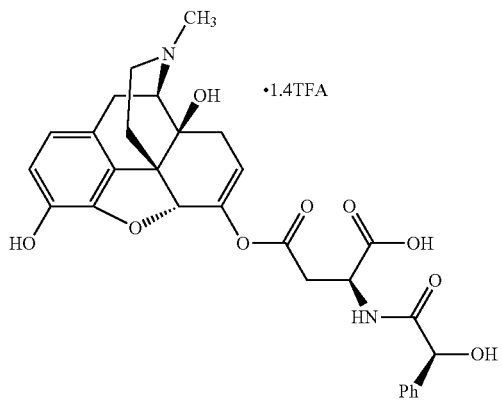

-continued

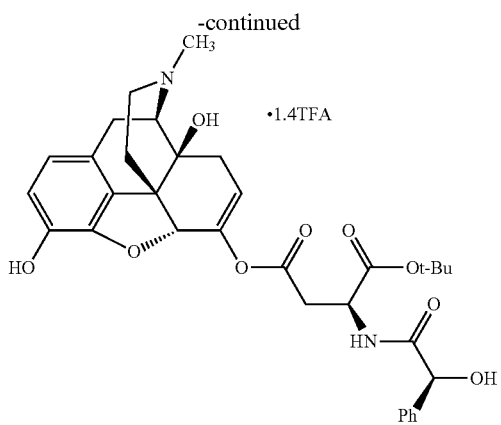

A solution of (S)-1-tert-butyl 4-((4R,4aS,7aR,12bS)-4a,9-dihydroxy-3-methyl-2,3,4,4a,5,7a-hexahydro-1H-4,12-methanobenzofuro[3,2-e]isoquinolin-7-yl) 2-((S)-2-((tert-butoxycarbonyl)oxy)-2-phenylacetamido)succinate (160 mg, 0.23 mmol) in methylene chloride (7 mL) was treated with trifluoroacetic acid (1 mL) and stirred at room temperature for 1.5 h. After this time, the mixture was concentrated. The residue was purified by reversed phase column chromatography (15.5 g C18 column, 3-30% acetonitrile/water, with 0.1% trifluoroacetic acid) and freeze dried to provide (S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-((S)-2-hydroxy-2-phenylacetamido)-4-oxobutanoic acid trifluoroacetic acid salt (33 mg, 20%) as a white solid: $^1$H NMR (300 MHz, DMSO-$d_6$) δ 13.01 (br s, 1H), 9.30 (br s, 1H), 9.15 (br s, 1H), 8.37 (d, J=8.3 Hz, 1H), 7.46-7.18 (m, 5H), 6.68 (d, J=8.1 Hz, 1H), 6.62 (d, J=8.1 Hz, 1H), 6.38 (br s, 1H), 6.21 (s, 1H), 5.35 (d, J=4.2 Hz, 1H), 4.96 (s, 1H), 4.89 (s, 1H), 4.67 (q, J=6.3 Hz, 1H), 3.64-3.58 (m, 1H), 3.18-2.79 (m, 8H), 2.77-2.60 (m, 2H), 2.30-2.18 (dd, J=17.6, 6.1 Hz, 1H), 2.03 (d, J=18.32 Hz, 1H), 1.62 (d, J=12.2 Hz, 1H); ESI MS m/z 551 $[C_{29}H_{30}N_2O_9+H]^+$; HPLC (Method A) 89.8% (AUC), $t_R$=7.45 min; and (S)-1-tert-butyl 4-((4R,4aS,7aR,12bS)-4a,9-dihydroxy-3-methyl-2,3,4,4a,5,7a-hexahydro-1H-4,12-methanobenzofuro[3,2-e]isoquinolin-7-yl) 2-((S)-2-hydroxy-2-phenylacetamido)succinate trifluoroacetic acid salt (23 mg, 13%) as a white solid: $^1$H NMR (300 MHz, DMSO-$d_6$) δ 9.29 (br s, 1H), 9.14 (br s, 1H), 8.41 (d, J=8.1 Hz, 1H), 7.43-7.38 (m, 2H), 7.34-7.24 (m, 3H), 6.68 (d, J=8.1 Hz, 1H), 6.63 (d, J=8.1 Hz, 1H), 6.32 (br s, 1H), 6.22 (s, 1H), 5.41-5.39 (m, 1H), 4.96 (s, 1H), 4.90 (s, 1H), 4.61-4.52 (m, 1H), 3.63-3.59 (m, 1H), 3.12-2.95 (m, 3H), 2.88-2.78 (m, 4H), 2.70-2.59 (m, 1H), 2.45-2.40 (m, 1H), 2.25 (dd, J=17.5, 6.3 Hz, 1H), 2.04 (d, J=18.6 Hz, 1H), 1.62 (d, J=11.6 Hz, 1H), 1.33 (s, 9H), one proton obscured by solvent peaks; ESI MS m/z 607 $[C33H_{38}N_2O_9+H]^+$; HPLC (Method A) 97.0% (AUC), $t_R$=9.05 min.

Scheme 150: (S)-3-Acetoxy-4-(((S)-1-(((4R,4aS,7aR,12bS-4a,9-dyhydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid

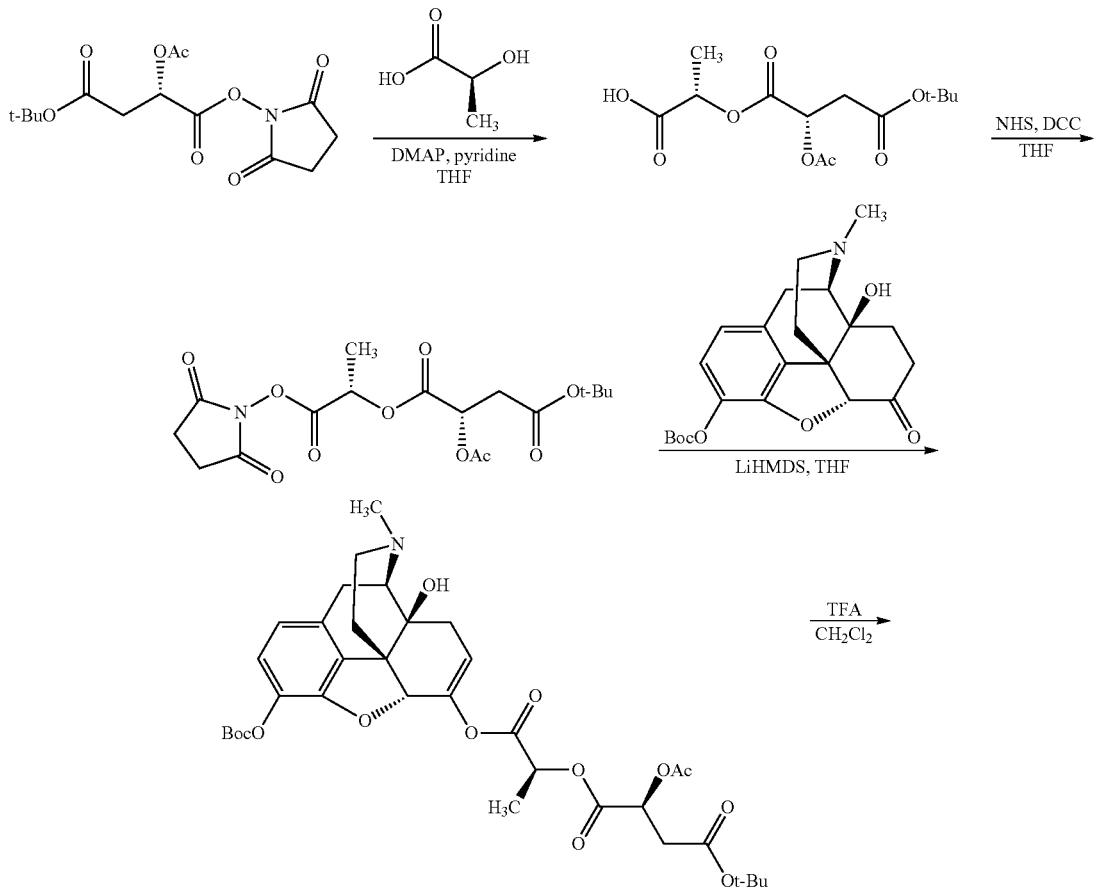

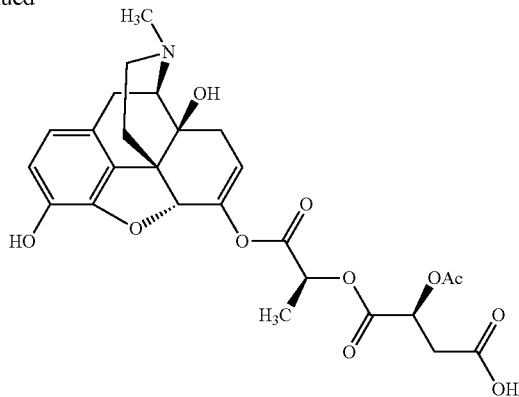

Preparation of (S)-2-(((S)-2-Acetoxy-4-(tert-butoxy)-4-oxobutanoyl)oxy)propanoic acid

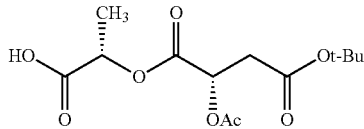 [SMILES: CC(=O)O[C@@H](CC(=O)OC(C)(C)C)C(=O)O[C@@H](C)C(=O)O]

(S)-Lactic acid (109 mg, 1.21 mmol), (S)-4-tert-butyl 1-(2,5-dioxopyrrolidin-1-yl) 2-acetoxysuccinate (400 mg, 1.21 mmol), 4-(dimethylamino)pyridine (15 mg, 0.121 mmol), pyridine (115 mg, 1.45 mmol) and tetrahydrofuran (8 mL) were combined and heated at 60° C. under a nitrogen atmosphere for 24 h. After this time, the solvent was removed under reduced pressure, and the residue was partitioned between ethyl acetate (20 mL) and 10% aqueous citric acid. The organic layer was separated and extracted with saturated aqueous sodium bicarbonate (20 ml). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (S)-2-(((S)-2-acetoxy-4-(tert-butoxy)-4-oxobutanoyl)oxy)propanoic acid (247 mg, 67%) as a colorless oil: $^1$H NMR (300 MHz, CDCl$_3$) δ 5.47 (m, 1H), 5.21 (m, 1H), 2.95-2.77 (m, 2H), 2.13 (s, 3H), 1.56 (d, J=6.9 Hz, 3H), 1.45 (s, 9H), CO$_2$H proton not observed.

Preparation of (S)-4-tert-Butyl 1-((S)-1-((2,5-dioxopyrrolidin-1-yl)oxy)-1-oxopropan-2-yl) 2-acetoxysuccinate

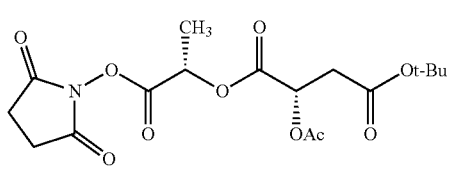 [SMILES: CC(=O)O[C@@H](CC(=O)OC(C)(C)C)C(=O)O[C@@H](C)C(=O)ON1C(=O)CCC1=O]

A solution of (S)-2-(((S)-2-acetoxy-4-(tert-butoxy)-4-oxobutanoyl)oxy)propanoic acid (247 mg, 0.812 mmol) in tetrahydrofuran (10 mL) was treated with N-hydroxysuccinimide (103 mg, 0.893 mmol) and N,N'-dicyclohexylcarbodiimide (184 mg, 0.893 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-4-tert-butyl 1-((S)-1-((2,5-dioxopyrrolidin-1-yl)oxy)-1-oxopropan-2-yl) 2-acetoxysuccinate (384 mg) as a white solid: $^1$H NMR (300 MHz, CDCl$_3$) δ 5.38-5.45 (m, 2H), 2.97-2.81 (m, 6H), 2.12 (s, 3H), 1.71 (q, J=6.9 Hz, 3H), 1.46 (s, 9H).

Preparation of (S)-1-((S)-1-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 4-tert-butyl 2-acetoxysuccinate

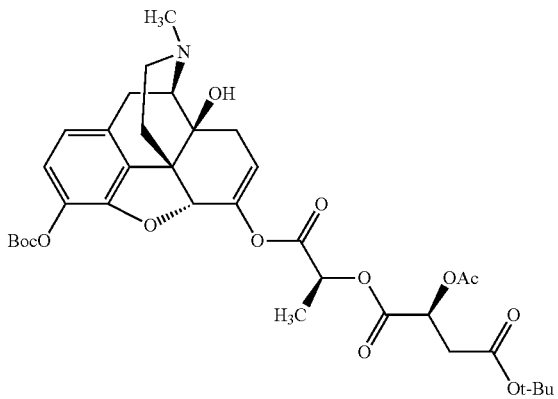

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (349 mg, 0.870 mmol) in tetrahydrofuran (8 mL) was cooled in an ice bath and treated dropwise with a 1.0 M solution of lithium bis(trimethylsilyl)amide in tetrahydrofuran (1.0 mL, 1.0 mmol). After addition was complete, the mixture was stirred at 0° C. for 1 h. The mixture was re-cooled to −45° C. and treated dropwise with a solution of (S)-4-tert-butyl 1-((S)-1-((2,5-dioxopyrrolidin-1-yl)oxy)-1-oxopropan-2-yl) 2-acetoxysuccinate (384 mg, 0.957 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-1-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 4-tert-butyl 2-acetoxysuccinate (182 mg, 30%) as a white solid: ESI MS m/z 688 $[C_{35}H_{45}NO_{13}+H]^+$.

Preparation of (S)-3-Acetoxy-4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid

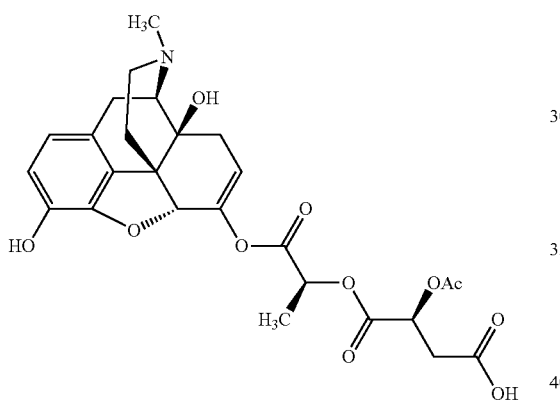

A solution of (S)-1-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 4-tert-butyl 2-acetoxysuccinate (182 mg, 0.265 mmol) in methylene chloride (3 mL) was treated with trifluoroacetic acid (3 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-3-acetoxy-4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid (84.2 mg, 60%) as a fluffy white solid: $^1$H NMR (300 MHz, DMSO-$d_6$) δ 6.55 (apparent q, J=8.1 Hz, 2H), 5.56 (dd, J=5.7, 2.4 Hz, 1H), 5.35 (dd, J=9.0, 3.6 Hz, 1H), 5.23 (q, J=8.1 Hz, 1H), 3.09 (d, J=18.6 Hz, 1H), 2.94-2.72 (m, 3H), 2.60 (dd, J=18.6, 6.3 Hz, 1H), 2.51-2.44 (m, 4H), 2.35 (s, 3H), 2.27 (m, 1H), 2.13-2.00 (m, 6H), 1.53 (d, J=6.9 Hz, 3H), 1.39 (d, J=10.8 Hz, 1H), CO$_2$H proton not observed; ESI MS m/z 532 $[C_{26}H_{29}NO_{11}+H]^+$; HPLC (Method A) 96.8% (AUC), $t_R$=7.73 min.

Scheme 151: (R)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-hydroxy-4-oxobutanoic acid trifluoroacetic acid salt

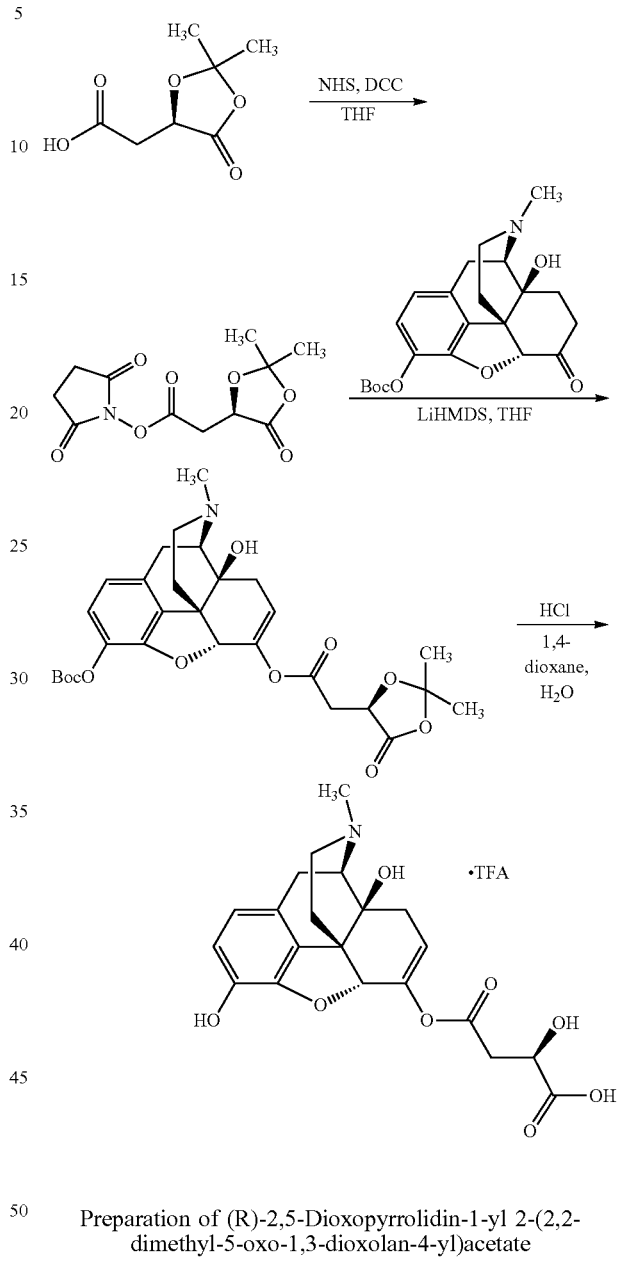

Preparation of (R)-2,5-Dioxopyrrolidin-1-yl 2-(2,2-dimethyl-5-oxo-1,3-dioxolan-4-yl)acetate

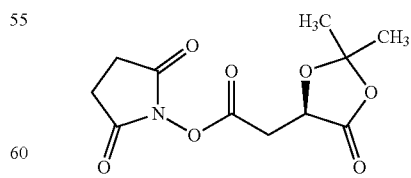

A solution of (R)-2-(2,2-dimethyl-5-oxo-1,3-dioxolan-4-yl)acetic acid (696 mg, 4.00 mmol) in tetrahydrofuran (40 mL) was treated with N-hydroxysuccinimide (506 mg, 4.40 mmol) and N,N'-dicyclohexylcarbodiimide (906 mg, 4.40 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (R)-2,5-dioxopyrrolidin-1-yl 2-(2,2-dimethyl-5-oxo-1,3-dioxolan-4-yl)acetate (1.40 g, quantitative) as a yellow solid: $^1$H NMR (300 MHz, CDCl$_3$) δ 4.77 (dd, J=6.3, 3.6 Hz, 1H), 3.28 (dd, J=17.4, 3.9 Hz, 1H), 3.10 (dd, J=17.1, 6.3 Hz, 1H), 2.85 (s, 4H), 1.63 (s, 3H), 1.58 (s, 3H).

Preparation (4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 2-((R)-2,2-dimethyl-5-oxo-1,3-dioxolan-4-yl)acetate

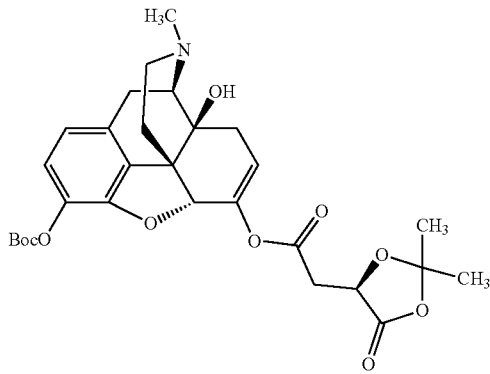

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at ambient temperature for 15 min. The mixture was re-cooled to −45° C. and treated dropwise with a solution of (R)-2,5-dioxopyrrolidin-1-yl 2-(2,2-dimethyl-5-oxo-1,3-dioxolan-4-yl)acetate (372 mg, 1.37 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-((R)-2,2-dimethyl-5-oxo-1,3-dioxolan-4-yl)acetate (270 mg, 38%) as a white solid: ESI MS m/z 558 [C$_{29}$H$_{35}$NO$_{10}$+H]$^+$.

Preparation of (R)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-hydroxy-4-oxobutanoic acid trifluoroacetic acid salt

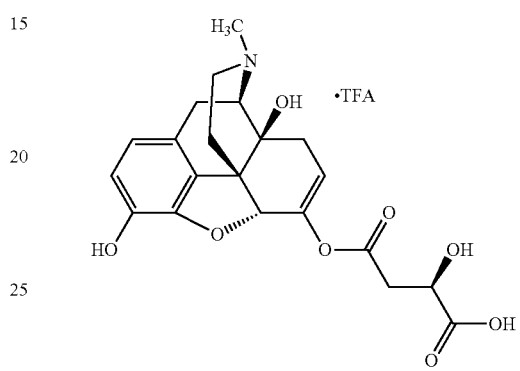

A solution of (4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-((R)-2,2-dimethyl-5-oxo-1,3-dioxolan-4-yl)acetate (270 mg, 0.484 mmol) was treated with a 4.0 M solution of hydrochloric acid in 1,4-dioxane (5 mL, 20.0 mmol) and water (0.2 mL). The reaction mixture was stirred under a nitrogen atmosphere at ambient temperature for 2 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (R)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-hydroxy-4-oxobutanoic acid trifluoroacetic acid salt (75 mg, 29%) as a fluffy white solid: $^1$H NMR (300 MHz, DMSO-d$_6$) δ 12.7 (s, 1H), 9.31 (s, 1H), 9.15 (br s, 1H), 6.65 (apparent q, J=7.8 Hz, 2H), 6.22 (s, 1H), 5.64 (s, 1H), 5.52 (dd, J=6.0, 2.1 Hz, 1H), 4.95 (s, 1H), 4.35 (m, 1H), 3.41-3.33 (m, 2H), 3.03 (m, 1H), 2.89 (d, J=4.5 Hz, 1H), 2.83 (s, 3H), 2.72-2.61 (m, 1H), 2.44-2.42 (m, 1H), 2.27 (m, 1H), 2.06 (d, J=17.7 Hz, 3H), 1.63 (d, J=10.8 Hz, 1H); ESI MS m/z 418 [C$_{21}$H$_{23}$NO$_8$+H]$^+$; HPLC (Method A)>99% (AUC), t$_R$=6.16 min.

Scheme 152: (S)-4-Amino-5-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid bis(trifluoroacetic acid salt)

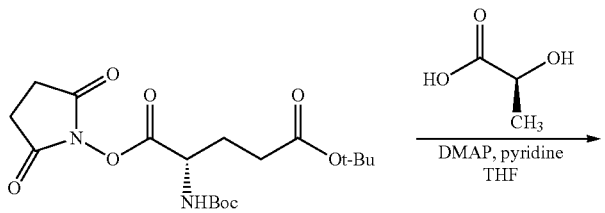

863

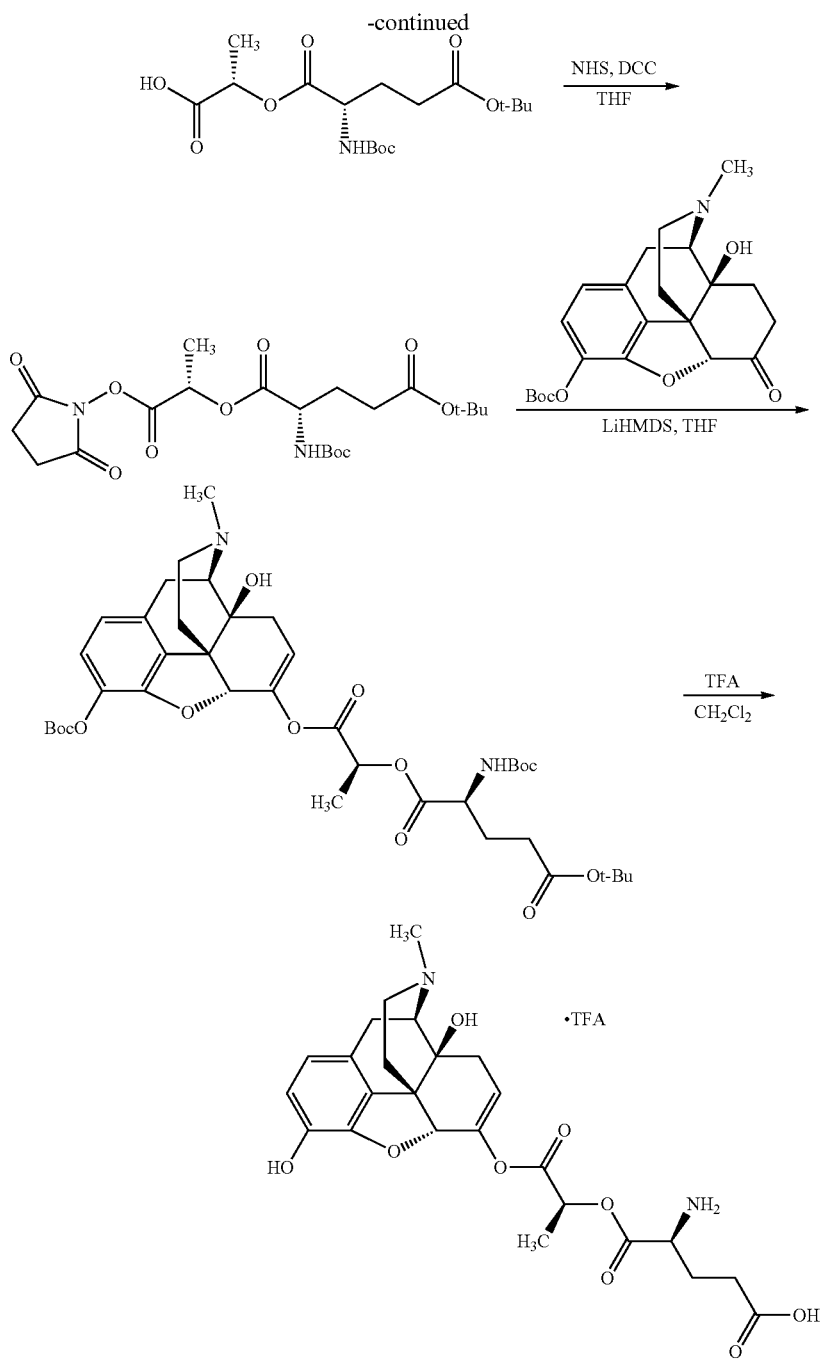

864

Preparation of (S)-2-(((S)-5-(tert-Butoxy)-2-((tert-butoxycarbonyl)amino)-5-oxopentanoyl)oxy)propanoic acid

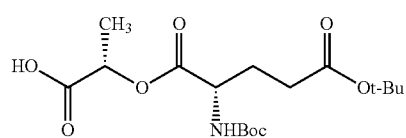 [SMILES: C[C@H](OC(=O)[C@H](CCC(=O)OC(C)(C)C)NC(=O)OC(C)(C)C)C(=O)O]

(S)-Lactic acid (135 mg, 1.50 mmol), (S)-5-tert-butyl 1-(2,5-dioxopyrrolidin-1-yl) 2-((tert-butoxycarbonyl)amino)pentanedioate (500 mg, 1.25 mmol), 4-(dimethylamino)pyridine (15 mg, 0.125 mmol), and pyridine (119 mg, 1.50 mmol) were combined and heated at 60° C. under a nitrogen atmosphere for 48 h. After this time, the solvent was removed under reduced pressure, and the residue was participated between ethyl acetate (20 mL) and 10% aqueous citric acid. The organic layer was separated and extracted with saturated aqueous sodium bicarbonate (20 ml). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (S)-2-(((S)-5-(tert-butoxy)-2-((tert-butoxycarbonyl)amino)-5-oxopentanoyl)oxy)propanoic acid (385 mg, 82%) as a colorless oil: $^1$H NMR (300 MHz, CDCl$_3$) δ 5.24 (m, 2H), 4.32 (m, 1H), 2.40 (m, 2H), 2.20 (m, 1H), 1.99 (m, 1H), 1.56 (d, J=6.9 Hz, 3H), 1.45 (s, 18H), CO$_2$H proton not observed.

Preparation of (S)-5-tert-Butyl 1-((S)-1-((2,5-dioxopyrrolidin-1-yl)oxy)-1-oxopropan-2-yl) 2-((tert-butoxycarbonyl)amino)pentanedioate

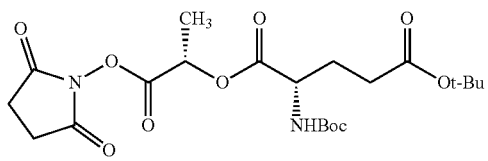 [SMILES: C[C@H](OC(=O)[C@H](CCC(=O)OC(C)(C)C)NC(=O)OC(C)(C)C)C(=O)ON1C(=O)CCC1=O]

A solution of (S)-2-(((S)-5-(tert-butoxycarbonyl)amino)-5-oxopentanoyl)oxy)propanoic acid (385 mg, 1.03 mmol) in tetrahydrofuran (8 mL) was treated with N-hydroxysuccinimide (130 mg, 1.13 mmol) and N,N'-dicyclohexylcarbodiimide (233 mg, 1.13 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-5-tert-butyl 1-((S)-1-((2,5-dioxopyrrolidin-1-yl)oxy)-1-oxopropan-2-yl) 2-((tert-butoxycarbonyl)amino)pentanedioate (542 mg) as a white solid that was used without purification.

Preparation of (S)-1-((S)-1-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 5-tert-butyl 2-((tert-butoxycarbonyl)amino)pentanedioate

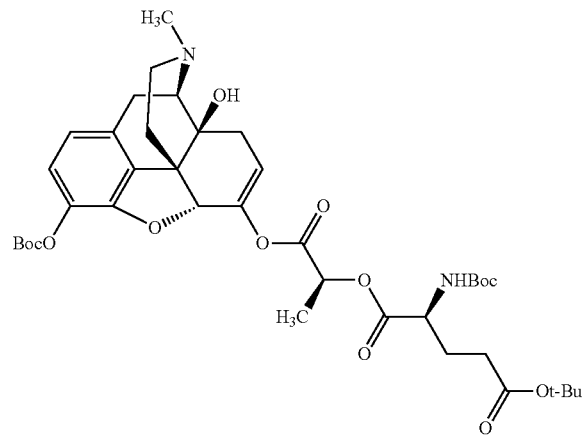

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at 0° C. for 1 h. The mixture was re-cooled to −45° C. and treated dropwise with a solution of (S)-5-tert-butyl 1-((S)-1-((2,5-dioxopyrrolidin-1-yl)oxy)-1-oxopropan-2-yl) 2-((tert-butoxycarbonyl)amino)pentanedioate (647 mg, 1.37 mmol) in tetrahydrofuran (5 mL). After addition was complete, the reaction was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-1-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 5-tert-butyl 2-((tert-butoxycarbonyl)amino)pentanedioate (402 mg, 42%) as a white solid: ESI MS m/z 759 [C$_{39}$H$_{54}$N$_2$O$_{13}$+H]$^+$.

Preparation of (S)-4-Amino-5-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid bis(trifluoroacetic acid salt)

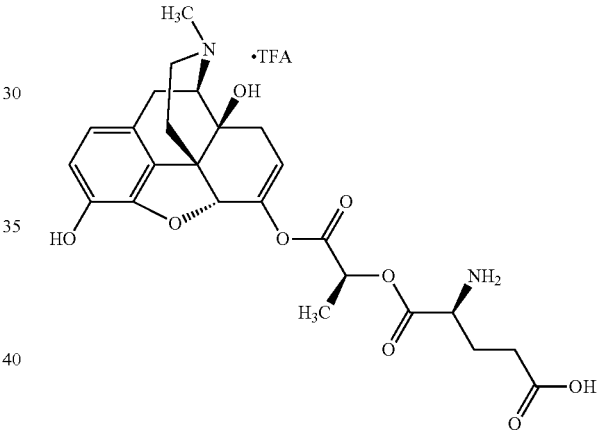

A solution of (S)-1-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 5-tert-butyl 2-((tert-butoxycarbonyl)amino)pentanedioate (210 mg, 0.277 mmol) in methylene chloride (3 mL) was treated with trifluoroacetic acid (3 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-4-amino-5-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid bis(trifluoroacetic acid salt) (95 mg, 46%) as a fluffy white solid: $^1$H NMR (300 MHz, DMSO-d$_6$) δ 12.3 (br s, 1H), 9.32 (br s, 1H), 9.16 (br s, 1H), 8.44 (br s, 3H), 6.66 (apparent q, J=8.1 Hz, 2H), 6.25 (s, 1H), 5.61 (dd, J=6.0, 2.1 Hz, 1H), 5.34 (q, J=7.2 Hz, 1H), 4.99 (s, 1H), 4.23 (m, 1H), 3.62 (m, 3H), 3.08 (m, 1H), 2.84 (s, 3H), 2.63-2.26 (m, 4H), 2.11-2.05 (m, 3H), 1.76 (m, 1H), 1.63-1.58 (m, 4H); ESI MS m/z 503 [C$_{25}$H$_{30}$N$_2$O$_9$+H]$^+$.

Scheme 153: (S)-1-((S)-4-(tert-Butoxy)-1-(((4R,4aS,7aR,12bS)-4a,9-dihydroxy-3-methyl-2,3,4,4a,5,7a-hexahydro-1H-4,12-methanobenzofura[3,2-e]isoquinolin-7-yl)oxy)-1,4-dioxobutan-2-yl) 4-tert-butyl 2-acetoxysuccinate trifluoroacetic acid salt

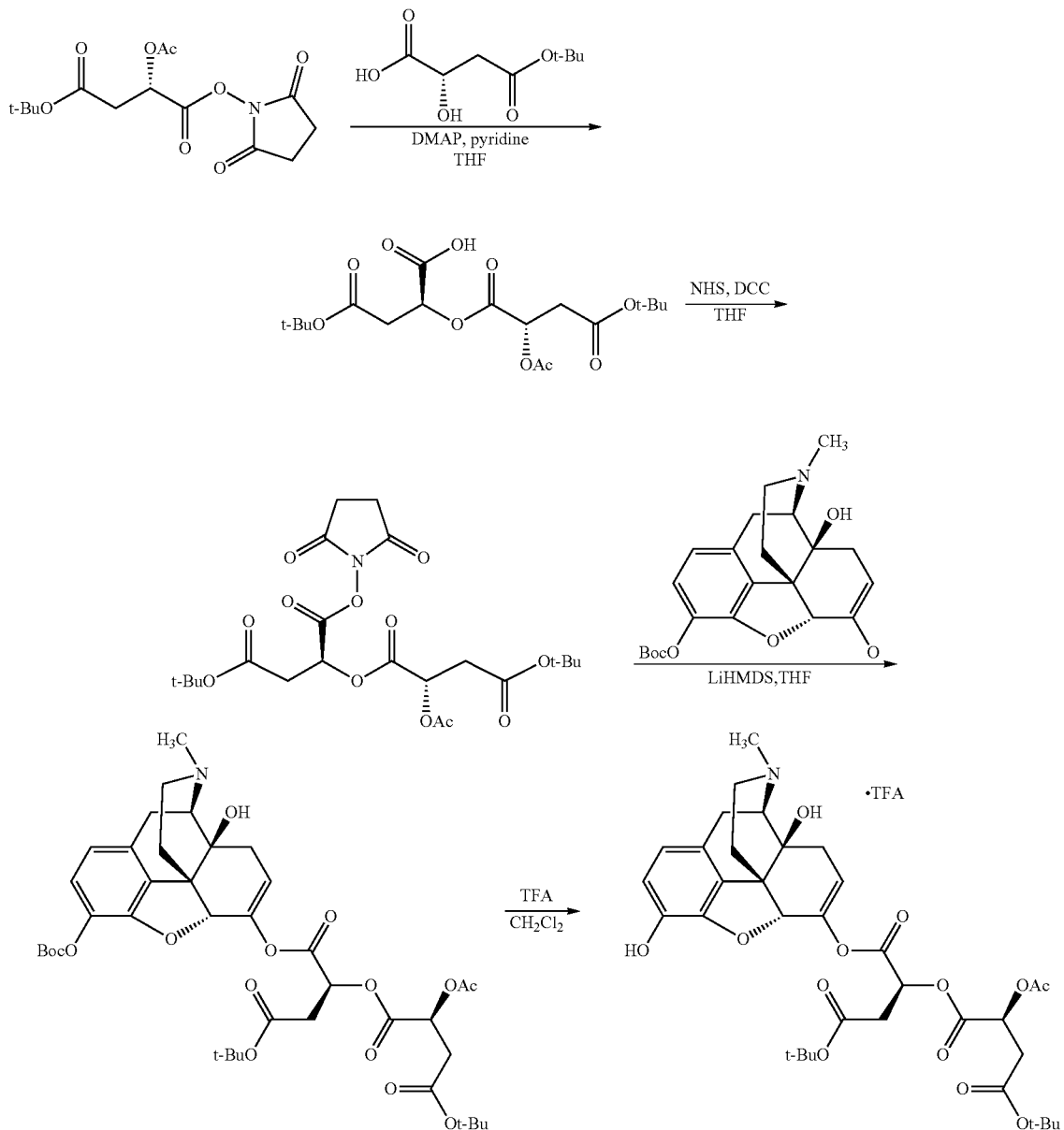

Preparation of (S)-2-(((S)-2-Acetoxy-4-(tert-butoxy)-4-oxobutanoyl)oxy)-4-(tert-butoxy)-4-oxobutanoic acid

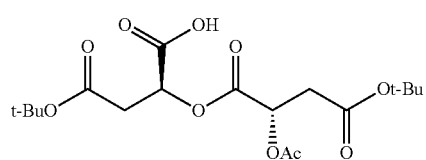 [SMILES: CC(=O)O[C@@H](CC(=O)OC(C)(C)C)C(=O)O[C@@H](CC(=O)OC(C)(C)C)C(=O)O]

(S)-4-(tert-Butoxy)-2-hydroxy-4-oxobutanoic acid (762 mg, 4.01 mmol), (S)-4-tert-butyl 1-(2,5-dioxopyrrolidin-1-yl) 2-acetoxysuccinate (1.32 g, 4.01 mmol), 4-(dimethylamino)pyridine (49 mg, 0.40 mmol), pyridine (381 mg, 4.81 mmol), and tetrahydrofuran (20 mL) were combined and heated at 60° C. under a nitrogen atmosphere for 72 h. After this time, the solvent was removed under reduced pressure, and the residue was partitioned between ethyl acetate (20 mL) and 10% aqueous citric acid. The organic layer was separated and extracted with ethyl acetate (2×20 mL). The combined organics were washed with brine (50 mL), dried over sodium sulfate, filtered, and concentrated under reduced pressure to provide (S)-2-(((S)-2-acetoxy-4-(tert-butoxy)-4-oxobutanoyl)oxy)-4-(tert-butoxy)-4-oxobutanoic acid (1.62 g) as a yellow oil: $^1$H NMR (300 MHz, CDCl$_3$) δ 5.49-5.45 (m, 2H), 2.92-2.72 (m, 4H), 2.13 (s, 3H), 1.46 (s, 18H), CO$_2$H proton not observed.

Preparation of (S)-1-((S)-4-(tert-Butoxy)-1-((2,5-dioxopyrrolidin-1-yl)oxy)-1,4-dioxobutan-2-yl) 4-tert-butyl 2-acetoxysuccinate

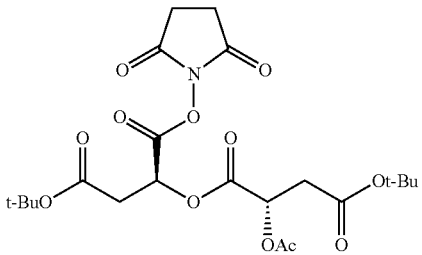 [SMILES: CC(=O)O[C@@H](CC(=O)OC(C)(C)C)C(=O)O[C@@H](CC(=O)OC(C)(C)C)C(=O)ON1C(=O)CCC1=O]

A solution of (S)-2-(((S)-2-acetoxy-4-(tert-butoxy)-4-oxobutanoyl)oxy)-4-(tert-butoxy)-4-oxobutanoic acid (1.62 g, 4.15 mmol) in tetrahydrofuran (30 mL) was treated with N-hydroxysuccinimide (477 mg, 4.15 mmol) and N,N′-dicyclohexylcarbodiimide (855 mg, 4.15 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-1-((S)-4-(tert-butoxy)-1-((2,5-dioxopyrrolidin-1-yl)oxy)-1,4-dioxobutan-2-yl) 4-tert-butyl 2-acetoxysuccinate (2.01 g) as a white solid: $^1$H NMR (300 MHz, CDCl$_3$) δ 5.84 (m, 1H), 5.47 (m, 1H), 2.98-2.75 (m, 8H), 2.12 (s, 3H), 1.46 (s, 9H), 1.45 (s, 9H).

Preparation of (S)-1-((S)-4-(tert-Butoxy)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1,4-dioxobutan-2-yl) 4-tert-butyl 2-acetoxysuccinate

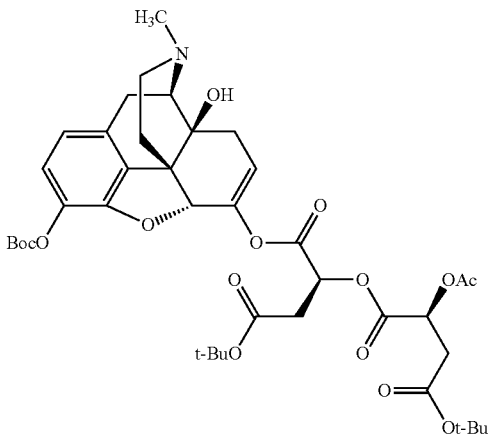

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at 0° C. for 1 h. The mixture was re-cooled to −45° C. and treated dropwise with a solution of (S)-1-((S)-4-(tert-butoxy)-1-((2,5-dioxopyrrolidin-1-yl)oxy)-1,4-dioxobutan-2-yl) 4-tert-butyl 2-acetoxysuccinate (668 mg, 1.37 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-1-((S)-4-(tert-butoxy)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1,4-dioxobutan-2-yl) 4-tert-butyl 2-acetoxysuccinate (83 mg, 11%) as a white solid: ESI MS m/z 788 [C$_{40}$H$_{53}$NO$_{15}$+H]$^+$.

Preparation of (S)-1-((S)-4-(tert-Butoxy)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1,4-dioxobutan-2-yl) 4-tert-butyl 2-acetoxysuccinate trifluoroacetic acid salt

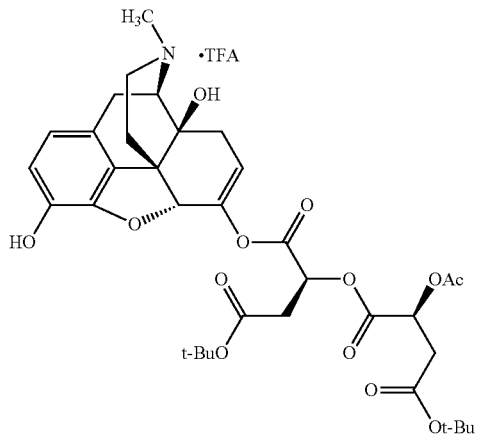 [SMILES: CC(=O)O[C@@H](CC(=O)OC(C)(C)C)C(=O)O[C@@H](CC(=O)OC(C)(C)C)C(=O)OC1=CC[C@@]2(O)[C@H]3Cc4ccc(O)c5c4[C@@]2(CCN3C)[C@H]1O5]

A solution of (S)-1-((S)-4-(tert-butoxy)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1,4-dioxobutan-2-yl) 4-tert-butyl 2-acetoxysuccinate (80 mg, 0.102 mmol) in methylene chloride (5.0 mL) was treated with trifluoroacetic acid (0.25 mL) and stirred under a nitrogen atmosphere at ambient temperature for 30 min. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-1-((S)-4-(tert-butoxy)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1,4-dioxobutan-2-yl) 4-tert-butyl 2-acetoxysuccinate trifluoroacetic acid salt (22 mg, 25%) as a fluffy white solid: $^1$H NMR (300 MHz, DMSO-d$_6$) δ 9.26 (s, 1H), 9.14 (br s, 1H), 6.65 (apparent q, J=8.1 Hz, 2H), 6.23 (s, 1H), 5.62 (dd, J=6.0, 2.4 Hz, 1H), 5.52 (dd, J=7.2, 4.5 Hz, 1H), 5.36 (dd, J=8.7, 3.9 Hz, 1H), 4.92 (s, 1H), 3.62-3.31 (m, 1H), 3.11-3.01 (m, 2H), 2.97-2.63 (m, 8H), 2.47-2.27 (m, 2H), 2.08-2.03 (m, 4H), 1.63 (m, 1H), 1.44 (s, 9H), 1.39 (s, 9H), one proton obscured by solvent peaks; ESI MS m/z 688 [C$_3$H$_{45}$NO$_{13}$+H]$^+$; HPLC (Method A) 95.3% (AUC), t$_R$=11.03 min.

Scheme 154: (2R,3R)-2,3-Diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

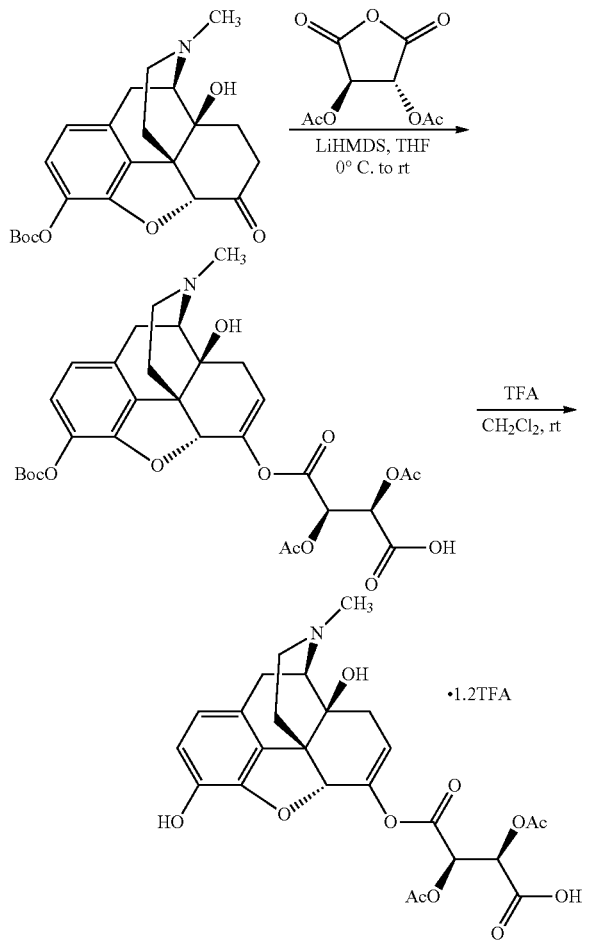

Preparation of (2R,3R)-2,3-Diacetoxy-4-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-4-oxobutanoic acid

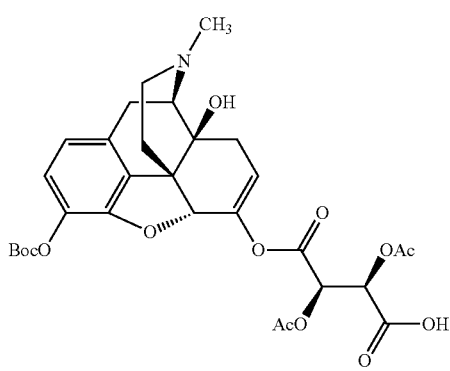

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (110 mg, 0.27 mmol) in tetrahydrofuran (2.5 mL) at 0° C. was treated with a 1.0 M solution of lithium bis(trimethylsilyl)amide in tetrahydrofuran (0.3 mL, 0.3 mmol), and the mixture was stirred for 5 min at 0° C. and 10 min at room temperature. The reaction mixture was cooled to 0° C., and (3R,4R)-2,5-dioxotetrahydrofuran-3,4-diyl diacetate (89 mg, 0.41 mmol) was added in one portion. The mixture was stirred at 0° C. for 20 min and then at room temperature for 30 min. After this time, the mixture was poured into a saturated solution of ammonium chloride and extracted with ethyl acetate. The organic extract was dried over sodium sulfate, filtered, and concentrated under reduced pressure to provide (2R,3R)-2,3-diacetoxy-4-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-4-oxobutanoic acid (100 mg): ESI MS m/z 618 $[C_{30}H_{35}NO_{13}+H]^+$.

Preparation of (2R,3R)-2,3-Diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

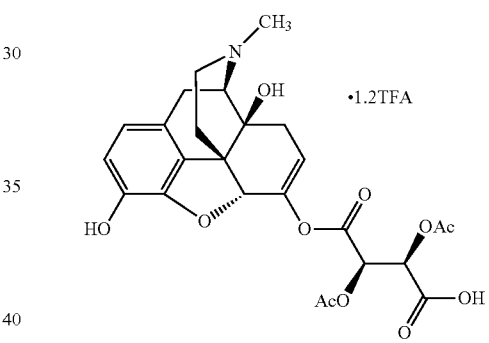

A solution of (2R,3R)-2,3-diacetoxy-4-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-4-oxobutanoic acid (100 mg) in methylene chloride (4 mL) was treated with trifluoroacetic acid (0.8 mL) and stirred at ambient temperature for 1.5 h. After this time, the reaction mixture was concentrated under reduced pressure. The residue was purified by reversed phase column chromatography (50 g C18 column, 3-25% acetonitrile/water, with 0.1% trifluoracetic acid) and freeze dried to provide (2R,3R)-2,3-diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt (28 mg, 20% over two steps): $^1$H NMR (300 MHz, DMSO-$d_6$) δ 9.34 (s, 1H), 9.15 (br s, 1H), 6.68 (d, J=8.1 Hz, 1H), 6.63 (d, J=8.1 Hz, 1H), 6.29 (br s, 1H), 5.77 (d, J=2.8 Hz, 1H), 5.68 (d, J=2.8 Hz, 1H), 5.52 (d, J=4.1 Hz, 1H), 4.83 (s, 1H), 3.62 (d, J=6.0 Hz, 1H), 3.12-3.01 (m, 3H), 2.83 (s, 3H), 2.70-2.56 (m, 1H), 2.46-2.39 (m, 1H), 2.28 (dd, J=17.7, 6.0 Hz, 1H), 2.19 (s, 3H), 2.15 (s, 3H), 2.07 (d, J=16.4 Hz, 1H), 1.62 (d, J=11.2 Hz, 1H), CO$_2$H proton not observed; ESI MS m/z 518 $[C_{25}H_{27}NO_{11}+H]^+$; HPLC (Method A) 83.9% (AUC), $t_R$=6.99 min.

Scheme 155: (S)-2-(((S)-3-Acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt

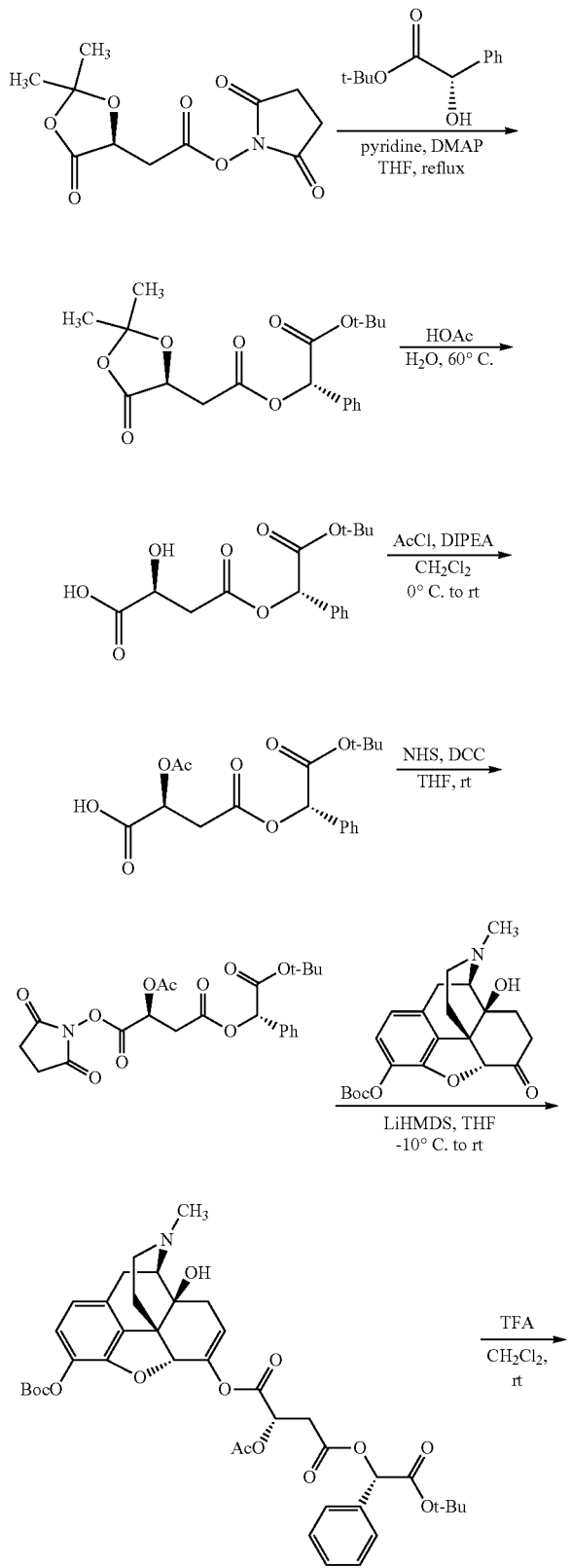

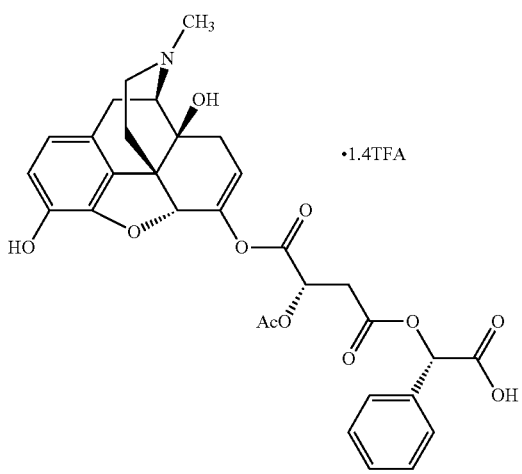 [SMILES: CC(=O)O[C@@H](CC(=O)O[C@H](C(=O)O)c1ccccc1)C(=O)OC1=CC[C@@]2(O)[C@H]3Cc4ccc(O)c5c4[C@@]2(CCN3C)[C@H]1O5]

Preparation of (S)-tert-Butyl 2-(2-((S)-2,2-dimethyl-5-oxo-1,3-dioxolan-4-yl)acetoxy)-2-phenylacetate

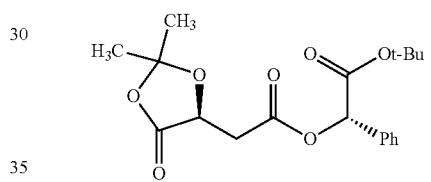

A mixture of (S)-2,5-dioxopyrrolidin-1-yl 2-(2,2-dimethyl-5-oxo-1,3-dioxolan-4-yl)acetate (2.0 g, 7.3 mmol), (S)-tert-butyl 2-hydroxy-2-phenylacetate (1.5 g, 7.3 mmol), pyridine (0.6 mL, 7.4 mmol), and 4-dimethylaminopyridine (80 mg, 0.65 mmol) in tetrahydrofuran (30 mL) was stirred at reflux for 36 h. After this time, the mixture was cooled to room temperature, concentrated under reduced pressure, and purified by column chromatography (80 g silica gel column, 5-80% ethyl acetate/heptane) to provide (S)-tert-butyl 2-(2-((S)-2,2-dimethyl-5-oxo-1,3-dioxolan-4-yl)acetoxy)-2-phenylacetate (1.18, 44%) as a 7:3 mixture of epimers: $^1$H NMR (300 MHz, CDCl$_3$) δ 7.47-7.41 (m, 2H), 7.41-7.36 (m, 3H), 5.87 (s, 0.3H), 5.82 (s, 0.7H), 4.78-4.73 (m, 1H), 3.17-3.03 (m, 1H), 2.99-2.87 (m, 1H), 1.55 (s, 6H), 1.40 (s, 2.7H), 1.39 (s, 6.3H).

Preparation of (S)-4-((S)-2-(tert-Butoxy)-2-oxo-1-phenylethoxy)-2-hydroxy-4-oxobutanoic acid

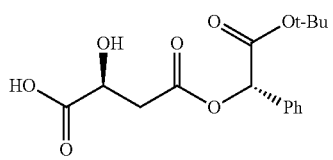

A mixture of (S)-tert-butyl 2-(2-((S)-2,2-dimethyl-5-oxo-1,3-dioxolan-4-yl)acetoxy)-2-phenylacetate (1.15 g, 3.16 mmol) in acetic acid (13 mL) and water (8 mL) was stirred at 60° C. for 4 h. After this time the mixture was concentrated to dryness to provide (S)-4-((S)-2-(tert-butoxy)-2-oxo-1-phenylethoxy)-2-hydroxy-4-oxobutanoic acid (1.09 g, quantitative, 7:3 mixture of epimers): ESI MS m/z 647 [2×($C_{16}H_{20}O_7$)–H]⁻.

Preparation of (S)-2-Acetoxy-4-((S)-2-(tert-butoxy)-2-oxo-1-phenylethoxy)-4-oxobutanoic acid

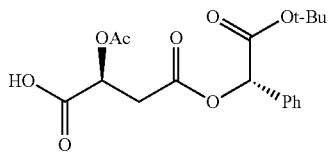 [SMILES: CC(C)(C)OC(=O)[C@@H](OC(=O)C[C@H](O)C(=O)O)c1ccccc1]

A solution of (S)-4-((S)-2-(tert-butoxy)-2-oxo-1-phenylethoxy)-2-hydroxy-4-oxobutanoic acid (1.09 g, 3.36 mmol) and N,N-diisopropylethylamine (1.7 mL, 9.8 mmol) in methylene chloride (30 mL) at 0° C. was treated dropwise with acetyl chloride (0.29 mL, 4.1 mmol). The reaction mixture was stirred at 0° C. for 10 min and then at room temperature for 40 min. After this time, the mixture was diluted with methylene chloride and washed with saturated ammonium chloride and brine. The organic layer was dried over sodium sulfate, filtered, and concentrated to provide (S)-2-acetoxy-4-((S)-2-(tert-butoxy)-2-oxo-1-phenylethoxy)-4-oxobutanoic acid (1.15 g, 92%): ESI MS m/z 384 [$C_{18}H_{22}O_8$+$NH_4$]⁺.

Preparation of (S)-4-((S)-2-(tert-Butoxy)-2-oxo-1-phenylethyl) 1-(2,5-dioxopyrrolidin-1-yl) 2-acetoxysuccinate

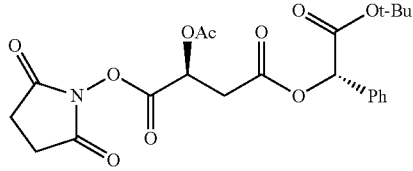 [SMILES: CC(=O)O[C@@H](CC(=O)O[C@H](C(=O)OC(C)(C)C)c1ccccc1)C(=O)ON1C(=O)CCC1=O]

A mixture of (S)-2-acetoxy-4-((S)-2-(tert-butoxy)-2-oxo-1-phenylethoxy)-4-oxobutanoic acid (1.1 g, 3.0 mmol) and N-hydroxysuccinimide (380 mg, 3.30 mmol) in tetrahydrofuran (15 mL) was treated with N,N'-dicyclohexylcarbodiimide (680 mg, 3.30 mmol), and the reaction mixture was stirred at ambient temperature for 4 h. After this time, diethyl ether (20 mL) was added, and the mixture was filtered. The filtrate was concentrated under reduced pressure to provide (S)-4-((S)-2-(tert-butoxy)-2-oxo-1-phenylethyl) 1-(2,5-dioxopyrrolidin-1-yl) 2-acetoxysuccinate (1.4 g) that was used without purification.

Preparation of (S)-4-((S)-2-(tert-Butoxy)-2-oxo-1-phenylethyl) 1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2-acetoxysuccinate

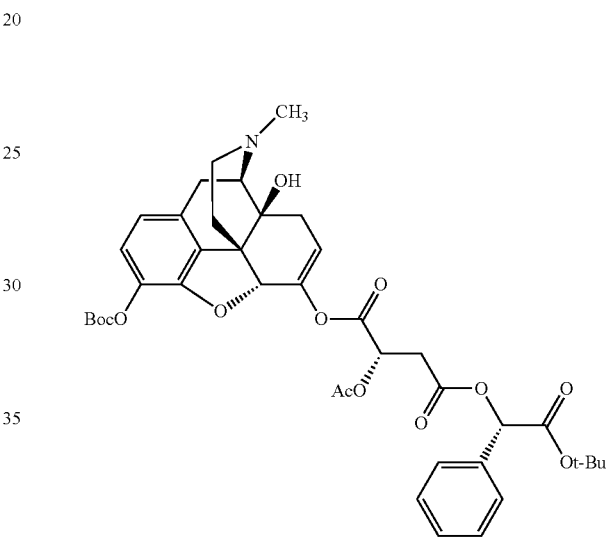

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (420 mg, 1.05 mmol) in tetrahydrofuran (8 mL) was cooled to 0° C. and treated dropwise with a 1.0 M solution of lithium bis(trimethylsilyl)amidein tetrahydrofuran (1.1 mL, 1.1 mmol). After addition was complete, the mixture was stirred at ambient temperature for 10 min. The mixture was re-cooled to 0° C., and (S)-4-((S)-2-(tert-butoxy)-2-oxo-1-phenylethyl) 1-(2,5-dioxopyrrolidin-1-yl) 2-acetoxysuccinate (500 mg, 1.08 mmol) was added. The mixture was stirred at 0° C. for 1 h. After this time, the mixture was treated with saturated aqueous ammonium chloride and extracted with ethyl acetate. The combined organics were dried over sodium sulfate, filtered, and concentrated under reduced pressure. The residue was purified by reversed phase column chromatography (50 g C18 column, 5-100% acetonitrile/water) to provide (S)-4-((S)-2-(tert-butoxy)-2-oxo-1-phenylethyl) 1-((4R,4aS,7aR,12bS)-9-((tert-butoxycarbonyl)oxy)-4a-hydroxy-3-methyl-2,3,4,4a,5,7a-hexahydro-1H-4,12- methanobenzofuro[3,2-e]isoquinolin-7-yl)
2-acetoxysuccinate (140 mg, 18%, 7:3 mixture of epimers): ESI MS m/z 750 [$C_{40}H_{47}NO_{13}$+H]$^+$.

Preparation of (S)-2-(((S)-3-Acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt

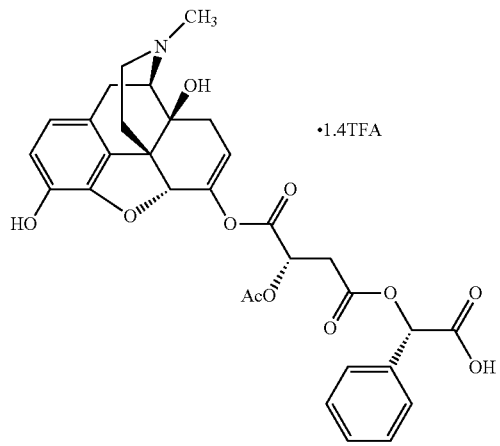 [SMILES: CC(=O)O[C@@H](CC(=O)O[C@H](C(=O)O)c1ccccc1)C(=O)OC1=CC[C@@]2(O)[C@H]3Cc4ccc(O)c5c4[C@@]2(CCN3C)[C@H]1O5]

A solution of (S)-4-((S)-2-(tert-butoxy)-2-oxo-1-phenylethyl) 1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2-acetoxysuccinate (140 mg, 0.18 mmol) in methylene chloride (6 mL) was treated with trifluoroacetic acid (1 mL) and stirred at ambient temperature for 4 h. After this time, the reaction mixture was concentrated under reduced pressure. The residue was purified by reversed phase column chromatography (15.5 g C18 column, 3-30% acetonitrile/water, with 0.1% trifluoracetic acid) and freeze dried to provide (S)-2-(((S)-3-acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt (43 mg, 32%) as a 7:3 mixture of epimers: $^1$H NMR (300 MHz, DMSO-$d_6$) δ 9.30 (s, 1H), 9.15 (s, 1H), 7.51-7.39 (m, 5H), 6.68 (d, J=8.1 Hz, 1H), 6.63 (d, J=8.1 Hz, 1H), 6.27 (s, 1H), 5.92-5.87 (m, 1H), 5.61-5.47 (m, 2H), 4.94 (m, 0.7H), 4.90 (s, 0.3H), 3.62 (d, J=6.4 Hz, 1H), 3.24-3.01 (m, 5H), 2.83 (s, 3H), 2.71-2.56 (m, 1H), 2.48-2.36 (m, 1H), 2.33-2.21 (m, 1H), 2.12-2.02 (m, 4H), 1.66-1.57 (m, 1H), $CO_2H$ proton not observed; ESI MS m/z 594 [$C_{31}H_{31}NO_{11}$+H]$^+$; HPLC (Method A) 91.0% (AUC), $t_R$=8.91 min.

Scheme 156: (S)-2-(((S)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-hydroxy-4-oxobutanoyl)oxy)propanoic acid trifluoroacetic acid salt

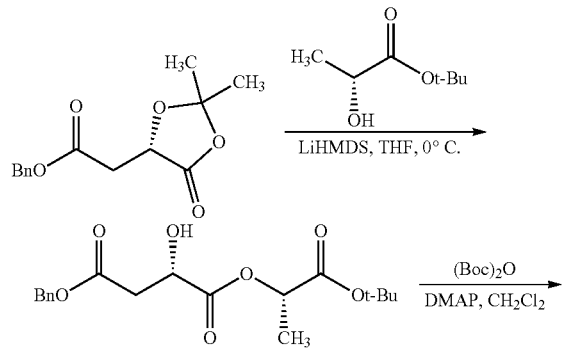

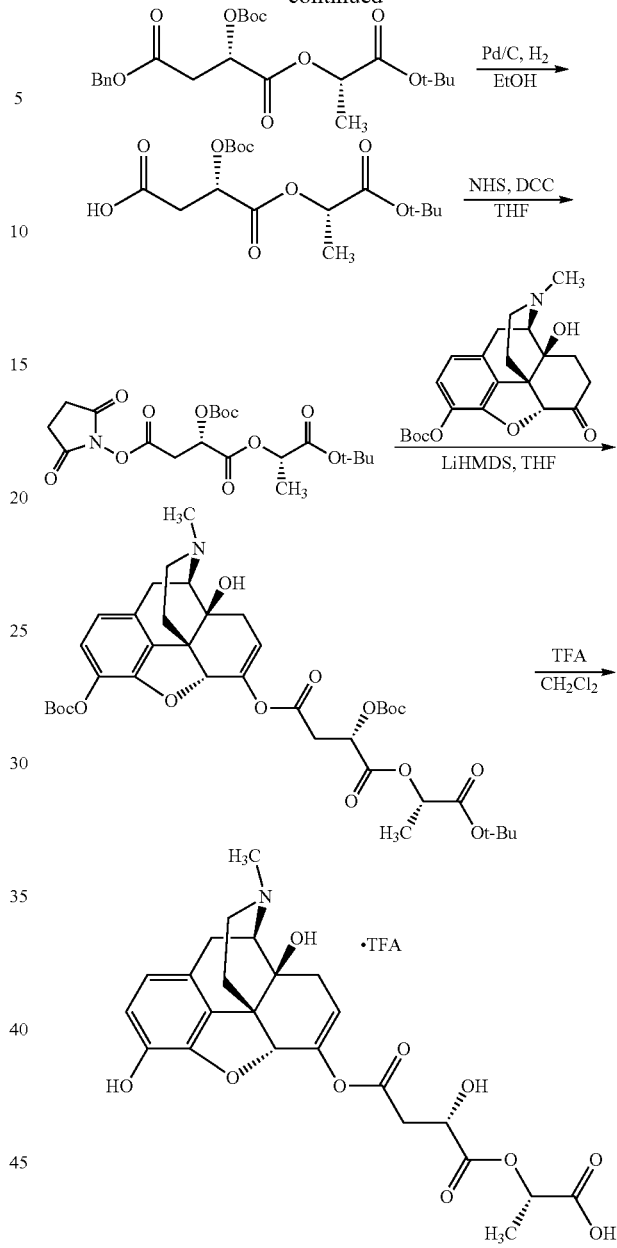

Preparation of (S)-4-Benzyl 1-((S)-1-(tert-butoxy)-1-oxopropan-2-yl) 2-hydroxysuccinate

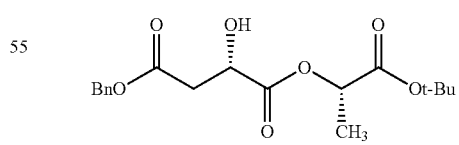

A solution of (S)-tert-butyl 2-hydroxypropanoate (1.11 g, 7.61 mmol) in tetrahydrofuran (15 mL) was cooled in an ice bath and treated dropwise with a 1.0 M solution of lithium bis(trimethylsilyl)amide in tetrahydrofuran (7.6 mL, 7.6 mmol). After addition was complete, the mixture was stirred at ambient temperature for 15 min. The mixture was re-cooled in the ice bath and treated dropwise with a solution of (S)-benzyl 2-(2,2-dimethyl-5-oxo-1,3-dioxolan-4-yl)acetate (2.01 g, 7.61 mmol) in tetrahydrofuran (10 mL). After addition was complete, the mixture was stirred at 0° C. for 4 h. After this time, the reaction mixture was treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (silica gel, 0-30% ethyl acetate/heptanes) to provide (S)-4-benzyl 1-((S)-1-(tert-butoxy)-1-oxopropan-2-yl) 2-hydroxysuccinate (0.89, 33%) as a colorless oil: $^1$H NMR (300 MHz, CDCl$_3$) δ 7.38-7.35 (m, 5H), 5.17 (d, J=1.0 Hz, 1H), 5.05 (dd, J=14.1, 8.4 Hz, 1H), 4.69-4.53 (m, 1H), 3.15 (dd, J=18.0, 6.0 Hz, 1H), 3.02 (dd, J=15.9, 3.9 Hz, 1H), 2.90-2.80 (m, 1H), 1.46 (d, J=8.1 Hz, 3H), 1.45 (s, 9H), OH proton not observed.

Preparation of (S)-4-Benzyl 1-((S)-1-(tert-butoxy)-1-oxopropan-2-yl) 2-((tert-butoxycarbonyl)oxy)succinate

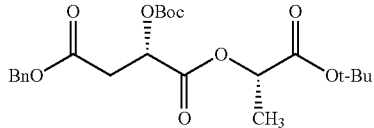

(S)-4-Benzyl 1-((S)-1-(tert-butoxy)-1-oxopropan-2-yl) 2-hydroxysuccinate (1.86 g, 5.28 mmol), di-tert-butyl dicarbonate (1.38 g, 6.34 mmol), and N,N-dimethylpyridin-4-amine (64 mg, 0.53 mmol) were combined and stirred in methylene chloride (60 mL) at ambient temperature for 3 h. After this time, the mixture was concentrated under reduced pressure. The crude residue was purified by column chromatography (silica gel, 0-30% ethyl acetate/heptanes) to provide (S)-4-benzyl 1-((S)-1-(tert-butoxy)-1-oxopropan-2-yl) 2-((tert-butoxycarbonyl)oxy)succinate (1.91 g, 80%) as a colorless oil: $^1$H NMR (300 MHz, CDCl$_3$) δ 7.38-7.33 (m, 5H), 5.41 (dd, J=9.6, 3.3 Hz, 1H), 5.21 (d, J=12.3 Hz, 1H), 5.13 (d, J=12.3 Hz, 1H), 5.02 (dd, J=14.1, 3.6 Hz, 1H), 3.12 (dd, J=17.8, 3.6 Hz, 1H), 2.95 (dd, J=18.1, 8.1 Hz, 1H), 1.49 (s, 9H), 1.45 (d, J=6.2 Hz, 3H), 1.44 (s, 9H).

Preparation of (S)-4-(((S)-1-(tert-Butoxy)-1-oxopropan-2-yl)oxy)-3-((tert-butoxycarbonyl)oxy)-4-oxobutanoic acid

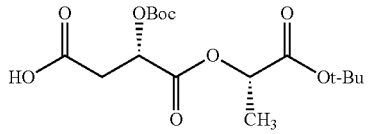

A solution of (S)-4-benzyl 1-((S)-1-(tert-butoxy)-1-oxopropan-2-yl) 2-((tert-butoxycarbonyl)oxy)succinate (0.27 g, 0.60 mmol) in ethyl alcohol (5 mL) was treated with palladium on carbon (10%, 30 mg). The mixture was stirred with under a hydrogen atmosphere at ambient temperature for 2 h. After this time, the reaction mixture was filtered and concentrated under reduced pressure to provide (S)-4-(((S)-1-(tert-butoxy)-1-oxopropan-2-yl)oxy)-3-((tert-butoxycarbonyl)oxy)-4-oxobutanoic acid (0.22 g, 99%) as a colorless oil: $^1$H NMR (300 MHz, CDCl$_3$) δ 5.38 (dd, J=9.3, 3.6 Hz, 1H), 5.05 (dd, J=14.1, 6.9 Hz, 1H), 3.13 (dd, J=17.1, 3.3 Hz, 1H), 2.95 (dd, J=17.1, 9.3 Hz, 1H), 1.50 (s, 9H), 1.47 (d, J=6.2 Hz, 3H), 1.46 (s, 9H), CO$_2$H proton not observed.

Preparation of (S)-1-((S)-1-(tert-Butoxy)-1-oxopropan-2-yl) 4-(2,5-dioxopyrrolidin-1-yl) 2-((tert-butoxycarbonyl)oxy)succinate

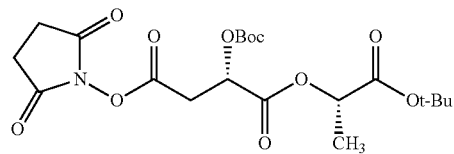

(S)-4-(((S)-1-(tert-Butoxy)-1-oxopropan-2-yl)oxy)-3-((tert-butoxycarbonyl)oxy)-4-oxobutanoic acid (0.21 g, 0.58 mmol), 1-hydroxypyrrolidine-2,5-dione (77 mg, 0.67 mmol) and dicyclohexylcarbodiimide (0.13 g, 0.64 mmol) were combined and stirred in tetrahydrofuran (4 mL) at ambient temperature for 4 h. After this time, the mixture was filtered and concentrated under reduced pressure to provide (S)-1-((S)-1-(tert-butoxy)-1-oxopropan-2-yl) 4-(2,5-dioxopyrrolidin-1-yl) 2-((tert-butoxycarbonyl)oxy)succinate (0.3 g, 99%) as a sticky solid: $^1$H NMR (300 MHz, CDCl$_3$) δ 5.45 (dd, J=9.6, 3.3 Hz, 1H), 5.05 (dd, J=14.1, 6.9 Hz, 1H), 3.46 (dd, J=17.1, 3.3 Hz, 1H), 3.18 (dd, J=17.1, 9.3 Hz, 1H), 2.87-2.82 (m, 4H), 1.50 (s, 9H), 1.47 (d, J=6.2 Hz, 3H), 1.46 (s, 9H).

Preparation of (S)-1-((S)-1-(tert-Butoxy)-1-oxopropan-2-yl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2-((tert-butoxycarbonyl)oxy)succinate

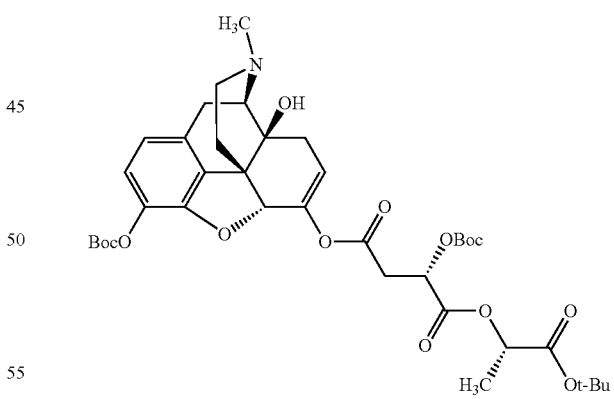

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (650 mg, 1.62 mmol) in tetrahydrofuran (10 mL) was cooled in an ice bath and treated dropwise with a 1.0 M solution of lithium bis(trimethylsilyl)amide in tetrahydrofuran (1.9 mL, 1.9 mmol). After addition was complete, the mixture was stirred at 0° C. for 1 h. The mixture was re-cooled to −45° C. and treated dropwise with a solution of (S)-1-((S)-1-(tert-butoxy)-1-oxopropan-2-yl) 4-(2,5-dioxopyrrolidin-1-yl)

2-((tert-butoxycarbonyl)oxy)succinate (818 mg, 1.78 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-1-((S)-1-(tert-butoxy)-1-oxopropan-2-yl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2-((tert-butoxycarbonyl)oxy)succinate (235 mg, 19%) as a white solid: ESI MS m/z 746 $[C_{38}H_{51}NO_{14}+H]^+$.

Preparation of (S)-2-(((S)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-hydroxy-4-oxobutanoyl)oxy)propanoic acid trifluoroacetic acid salt

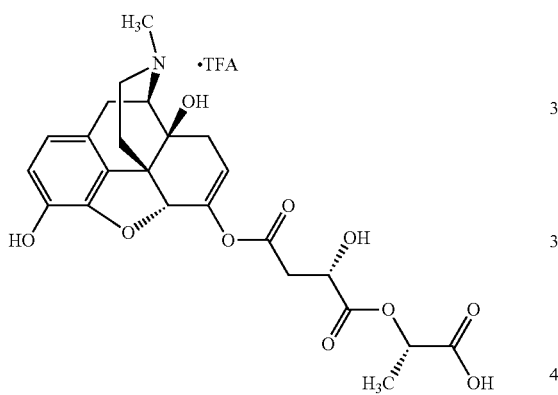

A solution of (S)-1-((S)-1-(tert-butoxy)-1-oxopropan-2-yl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2-((tert-butoxycarbonyl)oxy)succinate (157 mg, 0.210 mmol) in methylene chloride (4 mL) was treated with trifluoroacetic acid (3 mL) and stirred under a nitrogen atmosphere at ambient temperature for 2 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-hydroxy-4-oxobutanoyl)oxy)propanoic acid trifluoroacetic acid salt (54 mg, 42%) as a fluffy white solid: $^1$H NMR (300 MHz, DMSO-$d_6$) δ 13.1 (br s, 1H), 9.30 (s, 1H), 9.14 (br s, 1H), 6.64 (apparent q, J=8.1 Hz, 2H), 6.22 (s, 1H), 5.96 (d, J=6.3 Hz, 1H), 5.55 (dd, J=6.0, 1.8 Hz, 1H), 5.03-4.97 (m, 2H), 4.52 (m, 1H), 3.41-3.33 (m, 1H), 3.04 (m, 1H), 2.95 (dd, J=15.9, 4.2 Hz, 1H), 2.84 (s, 3H), 2.73-2.64 (m, 2H), 2.51-2.42 (m, 3H), 2.27 (m, 1H), 2.05 (d, J=17.7 Hz, 1H), 1.63 (m, 1H), 1.42 (d, J=6.9 Hz, 3H); ESI MS m/z 490 $[C_{24}H_{27}NO_{10}+H]^+$; HPLC (Method A) 97.7% (AUC), $t_R$=6.92 min.

Scheme 157: (S)-2-(((S)-2-Acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt

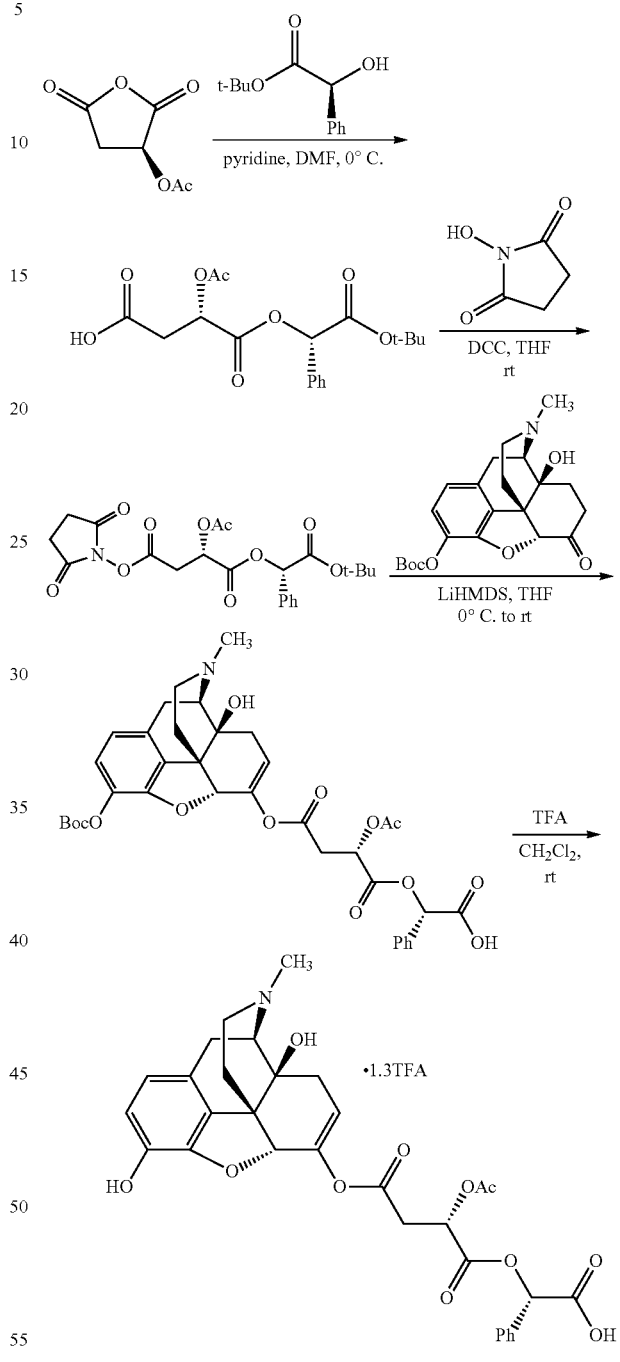

Preparation of (S)-3-Acetoxy-4-((S)-2-(tert-butoxy)-2-oxo-1-phenylethoxy)-4-oxobutanoic acid

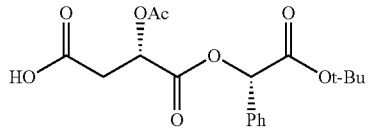 [SMILES: CC(=O)O[C@@H](CC(=O)O)C(=O)O[C@H](C(=O)OC(C)(C)C)c1ccccc1]

A solution of (S)-2,5-dioxotetrahydrofuran-3-yl acetate (720 mg, 4.56 mmol) in N,N-dimethylformamide (4 mL) at 0° C. was treated with (S)-tert-butyl 2-hydroxy-2-phenylacetate (1.10 g, 5.29 mmol) followed by pyridine (0.37 mL, 4.59 mmol), and the mixture was allowed to warm to room temperature and stirred for 18 h. After this time, the reaction mixture was diluted with ethyl acetate and extracted with saturated sodium bicarbonate. The aqueous layer was collected, carefully treated with 6 N hydrochloric acid until acidic by pH paper analysis, and then extracted with ethyl acetate. The organic extracts were dried over sodium sulfate, filtered, and concentrated to provide (S)-3-acetoxy-4-((S)-2-(tert-butoxy)-2-oxo-1-phenylethoxy)-4-oxobutanoic acid (810 mg, 49%): ESI MS m/z 750 $[2\times(C_{18}H_{22}O_8)+NH_4]^+$.

Preparation of (S)-1-((S)-2-(tert-Butoxy)-2-oxo-1-phenylethyl) 4-(2,5-dioxopyrrolidin-1-yl) 2-acetoxysuccinate

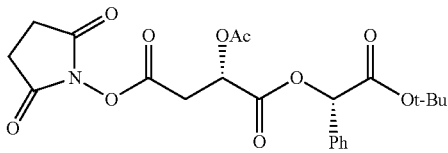 [SMILES: CC(=O)O[C@@H](CC(=O)ON1C(=O)CCC1=O)C(=O)O[C@H](C(=O)OC(C)(C)C)c1ccccc1]

A mixture of (S)-3-acetoxy-4-((S)-2-(tert-butoxy)-2-oxo-1-phenylethoxy)-4-oxobutanoic acid (1.03 g, 2.73 mmol) and N-hydroxysuccinimide (340 mg, 2.95 mmol) in tetrahydrofuran (15 mL) was treated with N,N'-dicyclohexylcarbodiimide (610 mg, 2.95 mmol), and the reaction mixture was stirred at ambient temperature for 4 h. After this time, diethyl ether (20 mL) was added, and the mixture was filtered. The filtrate was concentrated under reduced pressure to provide (S)-1-((S)-2-(tert-butoxy)-2-oxo-1-phenylethyl) 4-(2,5-dioxopyrrolidin-1-yl) 2-acetoxysuccinate (1.3 g) that was used without purification.

Preparation of (S)-1-((S)-2-(tert-Butoxy)-2-oxo-1-phenylethyl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2-acetoxysuccinate

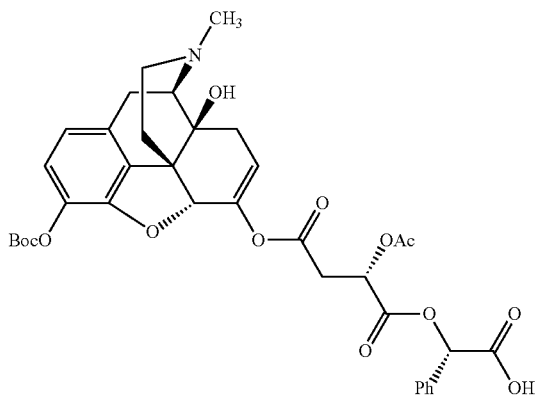

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (400 mg, 1.00 mmol) in tetrahydrofuran (8 mL) was cooled to 0° C. and treated dropwise with a 1.0 M solution of lithium bis(trimethylsilyl)amide in tetrahydrofuran (1.1 mL, 1.1 mmol). After addition was complete, the mixture was stirred at ambient temperature for 10 min. The mixture was re-cooled to 0° C., and (S)-1-((S)-2-(tert-butoxy)-2-oxo-1-phenylethyl) 4-(2,5-dioxopyrrolidin-1-yl) 2-acetoxysuccinate (500 mg, 1.09 mmol) was added in one portion. The mixture was stirred at 0° C. for 1 h. After this time, the mixture was treated with saturated aqueous ammonium chloride, and extracted with ethyl acetate. The combined organics were dried over sodium sulfate, filtered, and concentrated under reduced pressure. The residue was purified by reversed phase column chromatography (50 g C18 column, 5-100% acetonitrile/water) to provide (S)-1-((S)-2-(tert-butoxy)-2-oxo-1-phenylethyl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2-acetoxysuccinate (230 mg, 33%): ESI MS m/z 750 $[C_{40}H_{47}NO_{13}+H]^+$.

Preparation of (S)-2-(((S)-2-Acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt

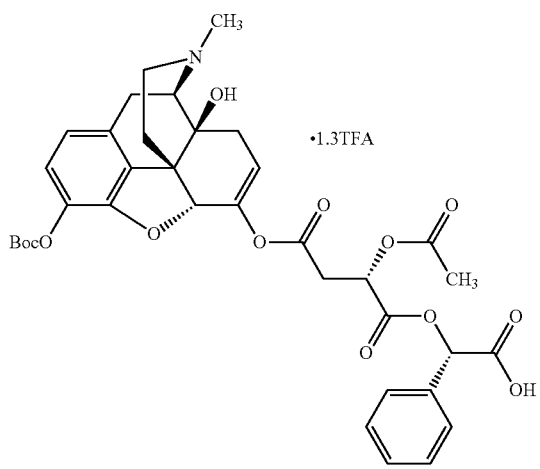

A solution of (S)-1-((S)-2-(tert-butoxy)-2-oxo-1-phenylethyl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2-acetoxysuccinate (225 mg, 0.300 mmol) in methylene chloride (7 mL) was treated with trifluoroacetic acid (1 mL) and stirred at ambient temperature for 3 h. After this time, the reaction mixture was concentrated under reduced pressure. The residue was purified by reversed phase column chromatography (50 g C18 column, 3-30% acetonitrile/water, with 0.1% trifluoracetic acid) and freeze dried to provide (S)-2-(((S)-2-acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt (100 mg, 45%): $^1$H NMR (300 MHz, DMSO-$d_6$) δ 9.30 (br s, 1H), 9.15 (br s, 1H), 7.52-7.39 (m, 5H), 6.68 (d, J=8.2 Hz, 1H), 6.63 (d, J=8.2 Hz, 1H), 6.23 (s, 1H), 5.97 (s, 1H), 5.57-5.47 (m, 2H), 4.96 (s, 1H), 6.31 (d, J=6.0 Hz, 1H), 3.12-3.00 (m, 4H), 2.84 (s, 3H), 2.71-2.49 (m, 1H), 2.50-2.40 (m, 1H), 2.34-2.21 (m, 1H), 2.15-2.00 (m, 4H), 1.63 (d, J=11.8 Hz, 1H), $CO_2H$ proton not observed; ESI MS m/z 594 $[C_{31}H_{31}NO_{11}+H]^+$; HPLC (Method A) 99.5% (AUC), $t_R$=8.96 min.

Scheme 158: (S)-2-Acetoxy-4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt

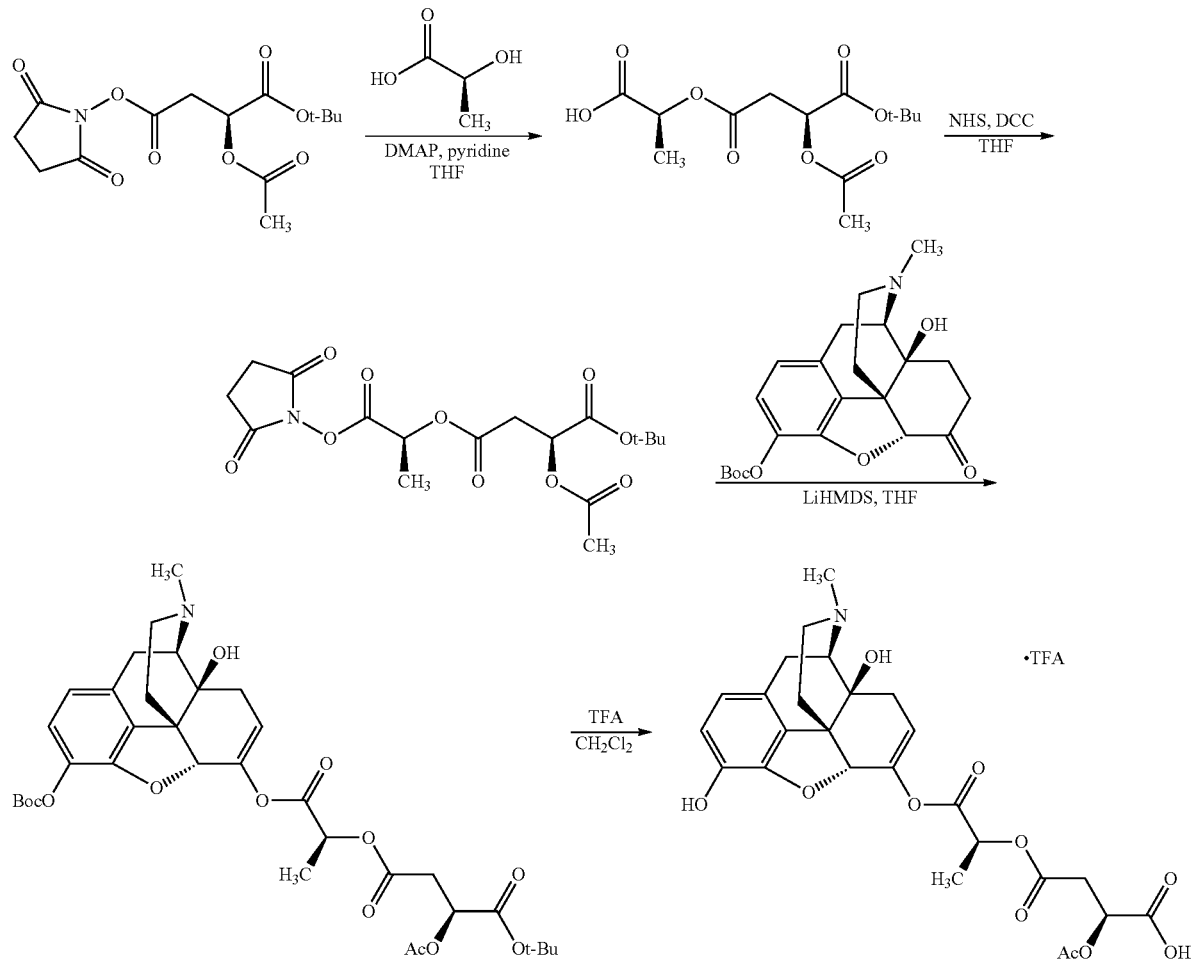

Preparation of (S)-2-(((S)-3-Acetoxy-4-(tert-butoxy)-4-oxobutanoyl)oxy)propanoic acid

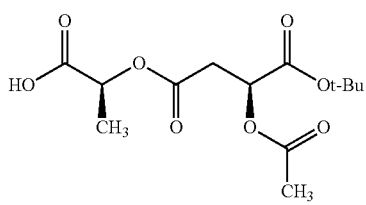 [SMILES: CC(=O)O[C@@H](CC(=O)O[C@@H](C)C(=O)O)C(=O)OC(C)(C)C]

A solution of (S)-1-tert-butyl 4-(2,5-dioxopyrrolidin-1-yl) 2-acetoxysuccinate (1.46 g, 4.44 mmol), lactic acid (447 mg, 4.96 mmol), and 4-dimethylaminopyridine (57 mg, 0.47 mmol) in tetrahydrofuran (30 mL) was treated with pyridine (0.72 g, 8.9 mmol) and heated at 50° C. under a nitrogen atmosphere for 48 h. After this time, the reaction mixture was cooled to room temperature and concentrated under reduced pressure. The residue was dissolved in ethyl acetate (50 mL) and washed with aqueous 10% citric acid (2×25 mL) and water (25 mL), dried over sodium sulfate, filtered, and concentrated under reduced pressure. The crude residue was purified by column chromatography (silica gel, 0-10% methanol/methylene chloride) to (S)-2-(((S)-3-acetoxy-4-(tert-butoxy)-4-oxobutanoyl)oxy)propanoic (455 mg, 34%) as a colorless oil: $^1$H NMR (300 MHz, DMSO-d$_6$) δ 13.07 (br s, 1H), 5.17 (dd, J=7.8, 4.8 Hz, 1H), 4.96 (q, J=6.9 Hz, 1H), 2.98-2.83 (m, 2H), 2.05 (s, 3H), 1.41 (s, 9H), 1.39 (d, J=6.9 Hz, 3H).

Preparation of (S)-1-tert-Butyl 4-((S)-1-((2,5-dioxopyrrolidin-1-yl)oxy)-1-oxopropan-2-yl) 2-acetoxysuccinate

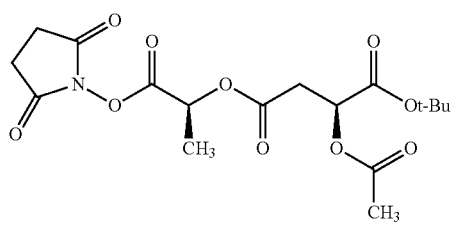 [SMILES: CC(=O)O[C@@H](CC(=O)O[C@@H](C)C(=O)ON1C(=O)CCC1=O)C(=O)OC(C)(C)C]

A solution of (S)-2-(((S)-3-acetoxy-4-(tert-butoxy)-4-oxobutanoyl)oxy)propanoic (450 mg, 1.48 mmol) in tetrahydrofuran (15 mL) was treated with N-hydroxysuccinimide (185 mg, 1.61 mmol) and N,N'-dicyclohexylcarbodiimide (338 mg, 1.64 mmol) and stirred under a nitrogen atmosphere for 7 h. After this time, the reaction mixture was filtered to remove the solid dicyclohexylurea byproduct. The solid was washed with diethyl ether, and the combined filtrate and washings were concentrated under reduced pressure to provide (S)-1-tert-butyl 4-((S)-1-((2,5-dioxopyrrolidin-1-yl)oxy)-1-oxopropan-2-yl) 2-acetoxysuccinate (703 mg, quantitative) as an off-white solid: $^1$H NMR (300 MHz, DMSO-d$_6$) δ 5.52 (q, J=6.9 Hz, 1H), 5.18 (dd, J=7.5, 5.1 Hz, 1H), 3.05-2.91 (m, 2H), 2.82 (br s, 4H), 2.05 (s, 3H), 1.56 (d, J=6.9 Hz, 3H), 1.41 (s, 9H).

Preparation of (S)-4-((S)-1-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 1-tert-butyl 2-acetoxysuccinate

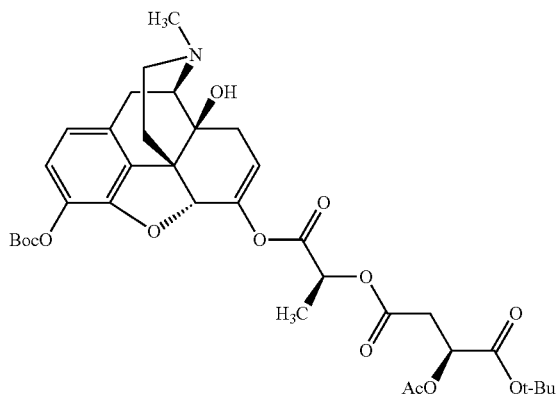

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (387 mg, 0.964 mmol) in tetrahydrofuran (8 mL) was cooled in an ice bath and treated dropwise with a 1.0 M solution of lithium bis(trimethylsilyl)amide in tetrahydrofuran (1.2 mL, 1.2 mmol). After addition was complete, the mixture was stirred at 0° C. for 1 h. The mixture was re-cooled to −45° C. and treated dropwise with a solution of (S)-1-tert-butyl 4-((S)-1-((2,5-dioxopyrrolidin-1-yl)oxy)-1-oxopropan-2-yl) 2-acetoxysuccinate (425 mg, 1.06 mmol) in tetrahydrofuran (4 mL). After addition was complete, the mixture was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-4-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 1-tert-butyl 2-acetoxysuccinate (271 mg, 40%) as a white solid: ESI MS m/z 688 [C$_{35}$H$_{45}$NO$_{13}$+H]$^+$.

Preparation of (S)-2-Acetoxy-4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt

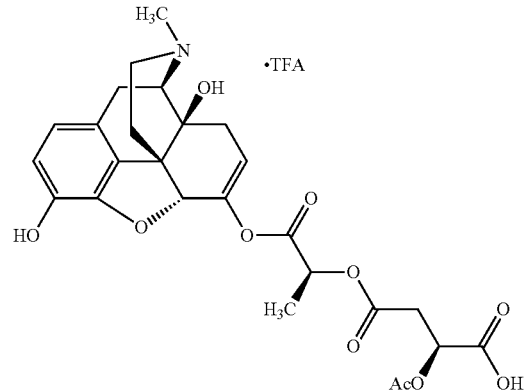 [SMILES: CC(=O)O[C@@H](CC(=O)O[C@@H](C)C(=O)OC1=CC[C@@]2(O)[C@H]3Cc4ccc(O)c5c4[C@@]2(CCN3C)[C@H]1O5)C(=O)O]

A solution of (S)-4-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 1-tert-butyl 2-acetoxysuccinate (170 mg, 0.247 mmol) in methylene chloride (5.0 mL) was treated with trifluoroacetic acid (3.0 mL) and stirred under a nitrogen atmosphere at ambient temperature for 2 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-2-acetoxy-4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt (50 mg, 30%) as a fluffy white solid: $^1$H NMR (300 MHz, DMSO-d$_6$) δ 13.3 (br s, 1H), 9.29 (s, 1H), 9.15 (br s, 1H), 6.65 (apparent q, J=8.1 Hz, 2H), 6.24 (s, 1H), 5.58 (dd, J=5.7, 2.1 Hz, 1H), 5.27 (dd, J=8.4, 4.5 Hz, 1H), 5.18 (q, J=6.9 Hz, 1H), 4.97 (s, 1H), 3.11-2.96 (m, 4H), 2.83 (d, J=3.9 Hz, 3H), 2.73-2.41 (m, 4H), 2.29 (m, 1H), 2.09-2.04 (m, 4H), 1.63 (m, 1H), 1.52 (d, J=7.2 Hz, 3H); ESI MS m/z 532 [C$_{26}$H$_{29}$NO$_{11}$+H]$^+$; HPLC (Method A) 95.1% (AUC), t$_R$=7.64 min.

Scheme 159: (S)-3-Acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

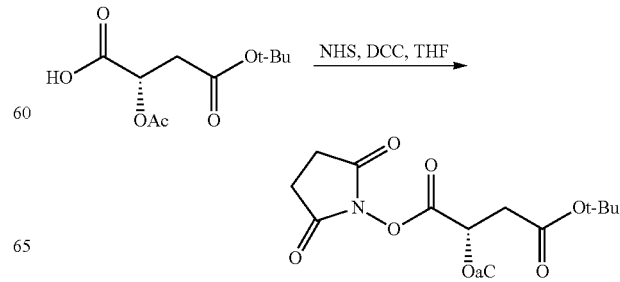

889

-continued

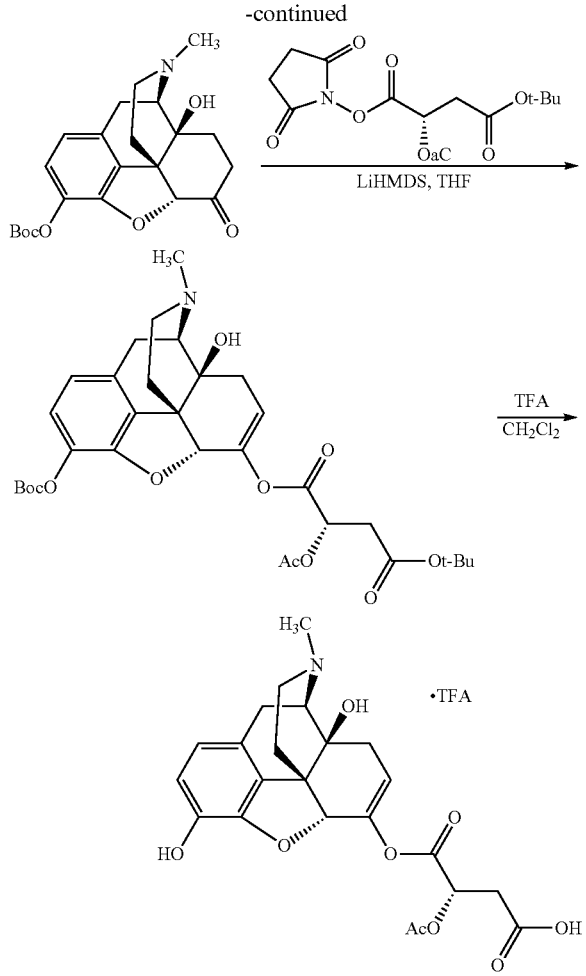

Preparation of (S)-4-tert-Butyl 1-(2,5-dioxopyrrolidin-1-yl) 2-acetoxysuccinate

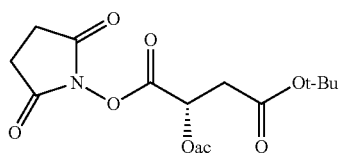

A solution of (S)-2-acetoxy-4-(tert-butoxy)-4-oxobutanoic acid (2.00 g, 8.61 mmol) in tetrahydrofuran (60 mL) was treated with N-hydroxysuccinimide (1.09 g, 9.47 mmol) and N,N'-dicyclohexylcarbodiimide (1.95 g, 9.47 mmol) and stirred under a nitrogen atmosphere for 4 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-4-tert-butyl 1-(2,5-dioxopyrrolidin-1-yl) 2-acetoxysuccinate (3.37 g) as a brown oil: $^1$H NMR (300 MHz, CDCl$_3$) δ 5.76 (dd, J=8.1, 4.8 Hz, 1H), 3.01-2.88 (m, 2H), 2.84 (s, 4H), 2.14 (s, 3H), 1.46 (s, 9H).

890

Preparation of (S)-1-((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2-acetoxysuccinate

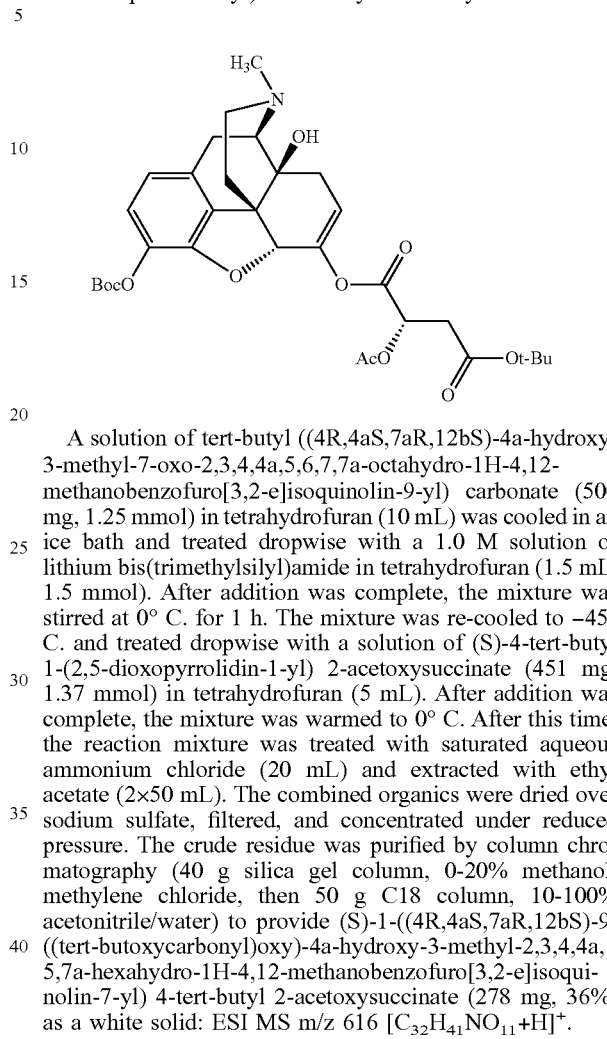

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at 0° C. for 1 h. The mixture was re-cooled to −45° C. and treated dropwise with a solution of (S)-4-tert-butyl 1-(2,5-dioxopyrrolidin-1-yl) 2-acetoxysuccinate (451 mg, 1.37 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2-acetoxysuccinate (278 mg, 36%) as a white solid: ESI MS m/z 616 [C$_{32}$H$_{41}$NO$_{11}$+H]$^+$.

Preparation of (S)-3-Acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

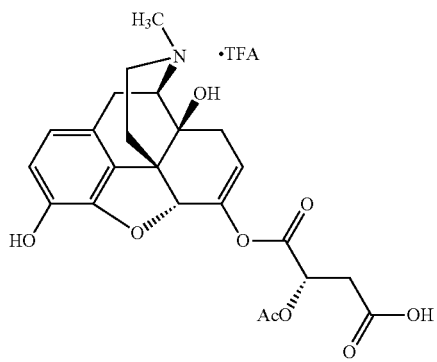 [SMILES: CC(=O)O[C@@H](CC(=O)O)C(=O)OC1=CC[C@@]2(O)[C@H]3Cc4ccc(O)c5c4[C@@]2(CCN3C)[C@H]1O5]

A solution of (S)-1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2-acetoxysuccinate (139 mg, 0.226 mmol) in methylene chloride (3 mL) was treated with trifluoroacetic acid (3 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-3-acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt (38 mg, 28%) as a fluffy white solid: $^1$H NMR (300 MHz, DMSO-$d_6$) δ 12.8 (br s, 1H), 9.29 (s, 1H), 9.16 (br s, 1H), 6.65 (apparent q, J=8.1 Hz, 2H), 6.26 (s, 1H), 5.60 (dd, J=5.7, 2.1 Hz, 1H), 5.39 (dd, J=7.2, 4.2 Hz, 1H), 4.92 (s, 1H), 3.62-3.34 (m, 1H), 3.11-2.83 (m, 7H), 2.73-2.39 (m, 3H), 2.29 (m, 1H), 2.11 (s, 3H), 2.06 (m, 1H), 1.62 (m, 1H); ESI MS m/z 460 $[C_{23}H_{25}NO_9+H]^+$.

Scheme 160: (S)-3-Acetoxy-4-((S)-2-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoroacetic acid salt

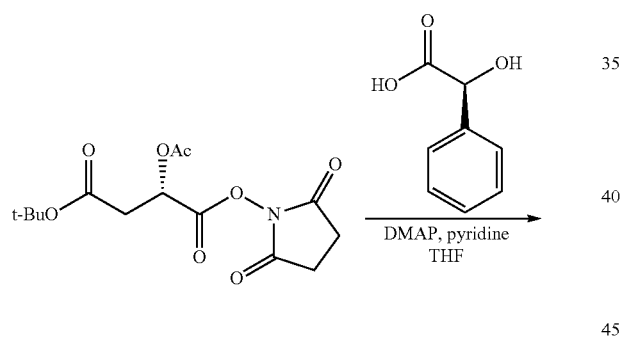

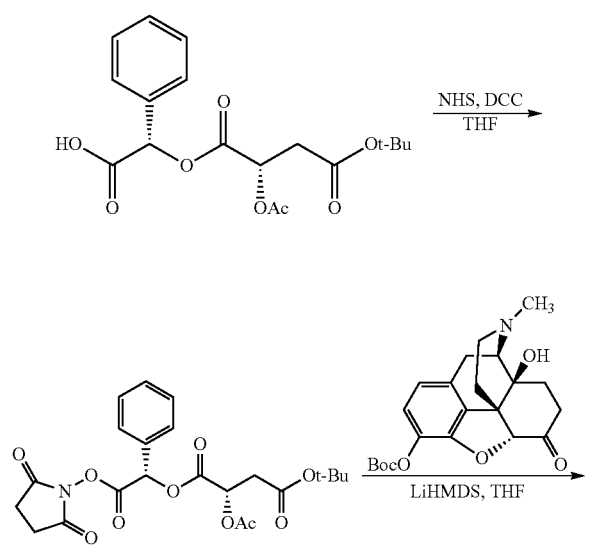

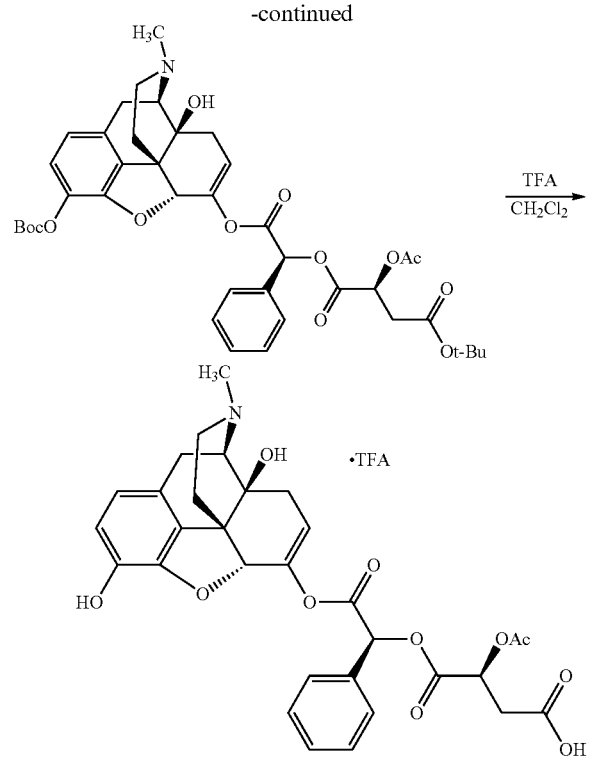

Preparation of (S)-2-(((S)-2-Acetoxy-4-(tert-butoxy)-4-oxobutanoyl)oxy)-2-phenylacetic acid (S)-Mandelic acid (770 mg, 5.06 mmol), (S)-4-tert-butyl 1-(2,5-dioxopyrrolidin-1-yl) 2-acetoxysuccinate (2.00 g, 6.07 mmol), 4-(dimethylamino)pyridine (62 mg, 0.506 mmol), pyridine (480 mg, 6.07 mmol) and tetrahydrofuran (34 mL) were combined and heated at 60° C. under a nitrogen atmosphere for 24 h. After this time, the solvent was removed under reduced pressure, and the residue was participated between ethyl acetate (20 mL) and 10% aqueous citric acid. The organic layer was separated and extracted with saturated aqueous sodium bicarbonate (20 ml). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (S)-2-(((S)-2-acetoxy-4-(tert-butoxy)-4-oxobutanoyl)oxy)-2-phenylacetic acid (754 mg, 41%) as a colorless oil: $^1$H NMR (300 MHz, CDCl$_3$) δ 7.48-7.39 (m, 5H), 6.03 (s, 1H), 5.54 (m, 1H), 3.01-2.76 (m, 2H), 2.13 (s, 3H), 1.45 (s, 9H), CO$_2$H proton not observed.

Preparation of (S)-4-tert-Butyl 1-((S)-2-((2,5-dioxopyrrolidin-1-yl)oxy)-2-oxo-1-phenylethyl) 2-acetoxysuccinate

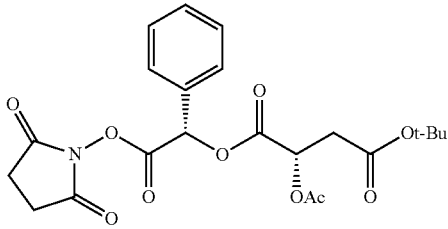 [SMILES: CC(=O)O[C@@H](CC(=O)OC(C)(C)C)C(=O)O[C@H](C(=O)ON1C(=O)CCC1=O)c1ccccc1]

A solution of (S)-2-(((S)-2-acetoxy-4-(tert-butoxy)-4-oxobutanoyl)oxy)-2-phenylacetic acid (754 mg, 2.06 mmol) in tetrahydrofuran (15 mL) was treated with N-hydroxysuccinimide (260 mg, 2.26 mmol) and N,N'-dicyclohexylcarbodiimide (466 mg, 2.26 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-4-tert-butyl 1-((S)-2-((2,5-dioxopyrrolidin-1-yl)oxy)-2-oxo-1-phenylethyl) 2-acetoxysuccinate (930 mg) as a yellow oil: $^1$H NMR (300 MHz, CDCl$_3$) δ 7.55-7.43 (m, 5H), 6.39 (s, 1H), 5.53 (m, 1H), 2.98-2.76 (m, 6H), 2.15 (s, 3H), 1.46 (s, 9H).

Preparation of (S)-1-((S)-2-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl) 4-tert-butyl 2-acetoxysuccinate

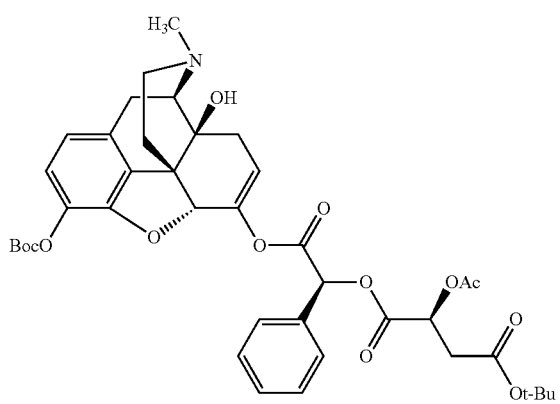

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (400 mg, 0.996 mmol) in tetrahydrofuran (8 mL) was cooled in an ice bath and treated dropwise with a 1.0 M solution of lithium bis(trimethylsilyl)amide in tetrahydrofuran (1.2 mL, 1.2 mmol). After addition was complete, the mixture was stirred at 0° C. for 1 h. The mixture was re-cooled to −45° C. and treated dropwise with a solution of (S)-4-tert-butyl 1-((S)-2-((2,5-dioxopyrrolidin-1-yl)oxy)-2-oxo-1-phenylethyl) 2-acetoxysuccinate (508 mg, 1.10 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-1-((S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl) 4-tert-butyl 2-acetoxysuccinate (160 mg, 21%) as a white solid: ESI MS m/z 750 [C$_{40}$H$_{47}$NO$_{13}$+H]$^+$.

Preparation of (S)-3-Acetoxy-4-((S)-2-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoroacetic acid salt

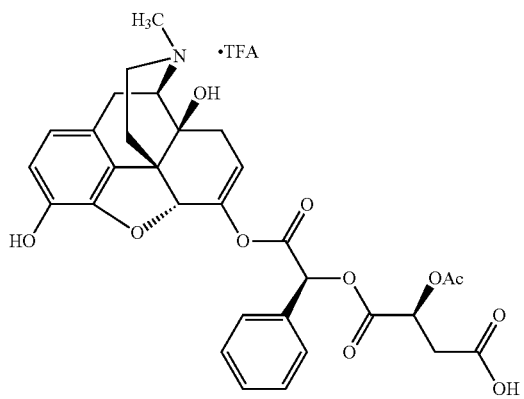 [SMILES: CC(=O)O[C@@H](CC(=O)O)C(=O)O[C@H](C(=O)OC1=CC[C@@]2(O)[C@H]3Cc4ccc(O)c5c4[C@@]2(CCN3C)[C@H]1O5)c1ccccc1]

A solution of (S)-1-((S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl) 4-tert-butyl 2-acetoxysuccinate (160 mg, 0.213 mmol) in methylene chloride (3 mL) was treated with trifluoroacetic acid (3 mL) and stirred under a nitrogen atmosphere at ambient temperature for 2 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-3-acetoxy-4-((S)-2-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoroacetic acid salt (86 mg, 57%) as a fluffy white solid: $^1$H NMR (300 MHz, DMSO-d$_6$) δ 12.8 (br s, 1H), 9.34 (s, 1H), 9.27 (br s, 1H), 7.60-7.54 (m, 2H), 7.49-7.45 (m, 3H), 6.68 (d, J=8.1 Hz, 1H), 6.66 (d, J=8.1 Hz, 1H), 6.24 (s, 2H), 5.58 (dd, J=5.7, 2.1 Hz, 1H), 5.44 (dd, J=9.0, 3.6 Hz, 1H), 4.86 (s, 1H), 3.40-3.33 (m, 2H), 3.07-2.99 (m, 2H), 2.89-2.82 (m, 4H), 2.63-2.39 (m, 4H), 2.25 (m, 1H), 2.09-2.02 (m, 3H), 1.59 (m, 1H); ESI MS m/z 594 [C$_{31}$H$_{31}$NO$_{11}$+H]$^+$; HPLC (Method A) 98.9% (AUC), t$_R$=8.92 min.

Scheme 161: (S)-2-(((2R,3R)-2,3-Diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt

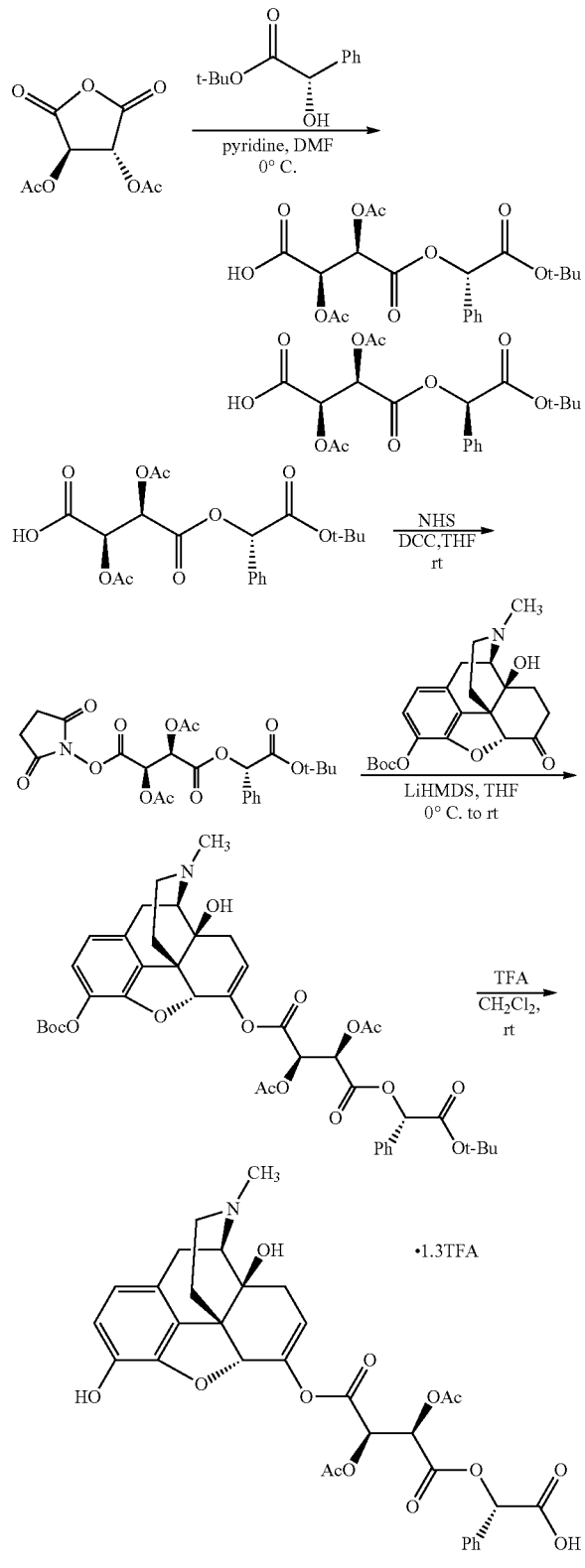

Preparation of (2R,3R)-2,3-Diacetoxy-4-((S)-2-(tert-butoxy)-2-oxo-1-phenylethoxy)-4-oxobutanoic acid and (2R,3R)-2,3-Diacetoxy-4-((R)-2-(tert-butoxy)-2-oxo-1-phenylethoxy)-4-oxobutanoic acid

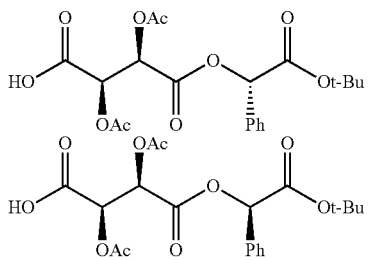

A solution of (3R,4R)-2,5-dioxotetrahydrofuran-3,4-diyl diacetate (1.35 g, 6.25 mmol) in N,N-dimethylformamide (1.5 mL) at 0° C. was treated with (S)-tert-butyl 2-hydroxy-2-phenylacetate (~7:3 S/R mixture, 1.02 g, 4.90 mmol) followed by pyridine (0.36 mL, 4.47 mmol), and the mixture was stirred at 0° C. for 1 h. After this time, the reaction mixture was diluted with ethyl acetate; washed with 10% citric acid, water, and brine; filtered; and concentrated. The residue was purified by reversed phase column chromatography (150 g C18 column, 3-20% acetonitrile/water) to provide (2R,3R)-2,3-diacetoxy-4-((S)-2-(tert-butoxy)-2-oxo-1-phenylethoxy)-4-oxobutanoic acid (dr 95:5, 1.47 g, 54%) and (2R,3R)-2,3-diacetoxy-4-((R)-2-(tert-butoxy)-2-oxo-1-phenylethoxy)-4-oxobutanoic acid (dr 85:15, 0.55 g, 18%). (2R,3R)-2,3-Diacetoxy-4-((S)-2-(tert-butoxy)-2-oxo-1-phenylethoxy)-4-oxobutanoic acid: $^1$H NMR (300 MHz, CDCl$_3$) δ 7.26 (s, 5H), 5.94 (s, 1H), 5.90 (d, J=2.6 Hz, 1H), 5.81 (s, J=2.6 Hz, 1H), 2.17 (s, 3H), 1.92 (s, 3H), 1.40 (s, 9H), CO$_2$H proton not observed.

Preparation of (2R,3R)-1-((S)-2-(tert-Butoxy)-2-oxo-1-phenylethyl) 4-(2,5-dioxopyrrolidin-1-yl) 2,3-diacetoxysuccinate

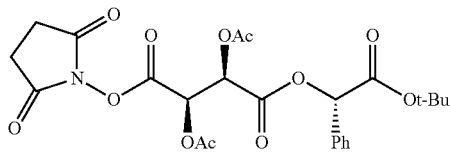 [SMILES: CC(=O)O[C@@H](C(=O)O[C@H](C(=O)OC(C)(C)C)c1ccccc1)[C@@H](OC(C)=O)C(=O)ON1C(=O)CCC1=O]

A mixture of (2R,3R)-2,3-diacetoxy-4-((S)-2-(tert-butoxy)-2-oxo-1-phenylethoxy)-4-oxobutanoic acid (1.07 g, 2.52 mmol) and N-hydroxysuccinimide (320 mg, 2.78 mmol) in tetrahydrofuran (14 mL) was treated with N,N'-dicyclohexylcarbodiimide (570 mg, 2.76 mmol), and the reaction mixture was stirred at ambient temperature for 4 h. After this time, diethyl ether (20 mL) was added, and the mixture was filtered. The filtrate was concentrated under reduced pressure to provide (2R,3R)-1-((S)-2-(tert-butoxy)-2-oxo-1-phenylethyl) 4-(2,5-dioxopyrrolidin-1-yl) 2,3-diacetoxysuccinate (1.41 g, 80%) that was used without purification: $^1$H NMR (300 MHz, CDCl$_3$) δ 7.38 (s, 5H), 6.14 (d, J=2.8 Hz, 1H), 6.02 (d, J=2.8 Hz, 1H), 5.92 (s, 1H), 2.83 (s, 4H), 2.24 (s, 3H), 1.97 (s, 3H), 1.41 (s, 9H).

897

Preparation of (2R,3R)-1-((S)-2-(tert-Butoxy)-2-oxo-1-phenylethyl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2,3-diacetoxysuccinate

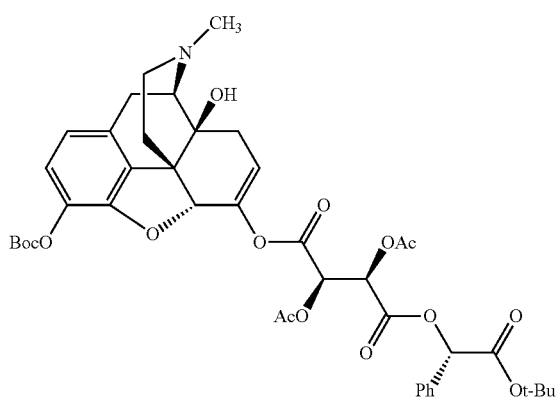

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (400 mg, 1.00 mmol) in tetrahydrofuran (8 mL) was cooled to 0° C. and treated dropwise with a 1.0 M solution of lithium bis(trimethylsilyl)amidein tetrahydrofuran (1.1 mL, 1.1 mmol). After addition was complete, the mixture was stirred at ambient temperature for 10 min. The mixture was re-cooled to 0° C., and (2R,3R)-1-((S)-2-(tert-butoxy)-2-oxo-1-phenylethyl) 4-(2,5-dioxopyrrolidin-1-yl) 2,3-diacetoxysuccinate (550 mg, 1.06 mmol) was added in one portion. The mixture was stirred at 0° C. for 45 min. After this time, the mixture was treated with saturated aqueous ammonium chloride and extracted with ethyl acetate. The combined organics were dried over sodium sulfate, filtered, and concentrated under reduced pressure. The residue was purified by reversed phase column chromatography (50 g C18 column, 10-100% acetonitrile/water) to provide (2R,3R)-1-((S)-2-(tert-butoxy)-2-oxo-1-phenylethyl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2,3-diacetoxysuccinate (270 mg, 33%): ESI MS m/z 808 [C$_{42}$H$_{49}$NO$_{15}$+H]$^{+}$.

898

Preparation of (S)-2-(((2R,3R)-2,3-Diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt

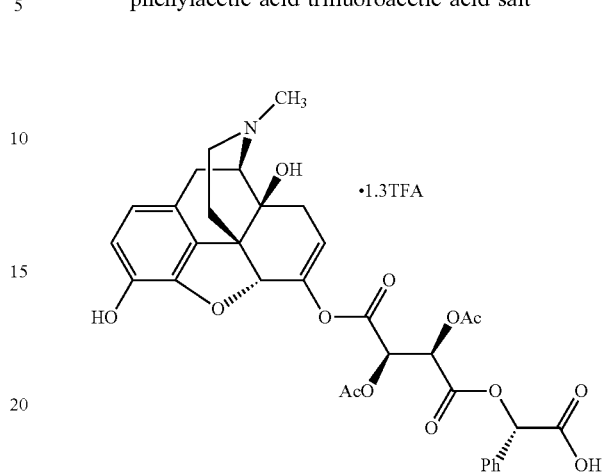

A solution of (2R,3R)-1-((S)-2-(tert-butoxy)-2-oxo-1-phenylethyl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2,3-diacetoxysuccinate (270 mg, 0.33 mmol) in methylene chloride (6 mL) was treated with trifluoroacetic acid (1 mL) and stirred at ambient temperature for 4 h. After this time, the reaction mixture was concentrated under reduced pressure. The residue was purified by reversed phase column chromatography (50 g C18 column, 3-30% acetonitrile/water, with 0.1% trifluoroacetic acid) and freeze dried to provide (S)-2-(((2R,3R)-2,3-diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt (42 mg, 20%): $^1$H NMR (300 MHz, DMSO-d$_6$) δ 9.35 (s, 1H), 9.15 (br s, 1H), 7.46-7.40 (m, 5H), 6.68 (d, J=8.2 Hz, 1H), 6.63 (d, J=8.2 Hz, 1H), 6.30 (s, 1H), 6.01 (s, 1H), 5.96 (d, J=2.7 Hz, 1H), 5.86 (d, J=2.7 Hz, 1H), 5.56-5.51 (m, 1H), 4.83 (s, 1H), 3.62 (d, J=6.2 Hz, 1H), 3.11-3.01 (m, 1H), 3.83 (s, 3H), 2.70-2.54 (m, 1H), 2.49-2.39 (m, 1H), 2.32-2.16 (m, 5H), 2.07 (d, J=18.0 Hz, 1H), 2.01 (s, 3H), 1.62 (d, J=12.0 Hz, 1H), CO$_2$H proton not observed; ESI MS m/z 652 [C33H$_{33}$NO$_{13}$+H]$^{+}$; HPLC (Method A) 98.7% (AUC), t$_R$=9.12 min.

Scheme 162: (S)-2-Amino-5-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid bis(trifluoroacetic acid salt)

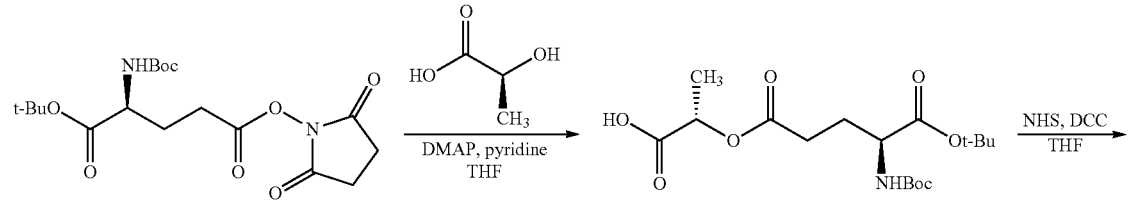

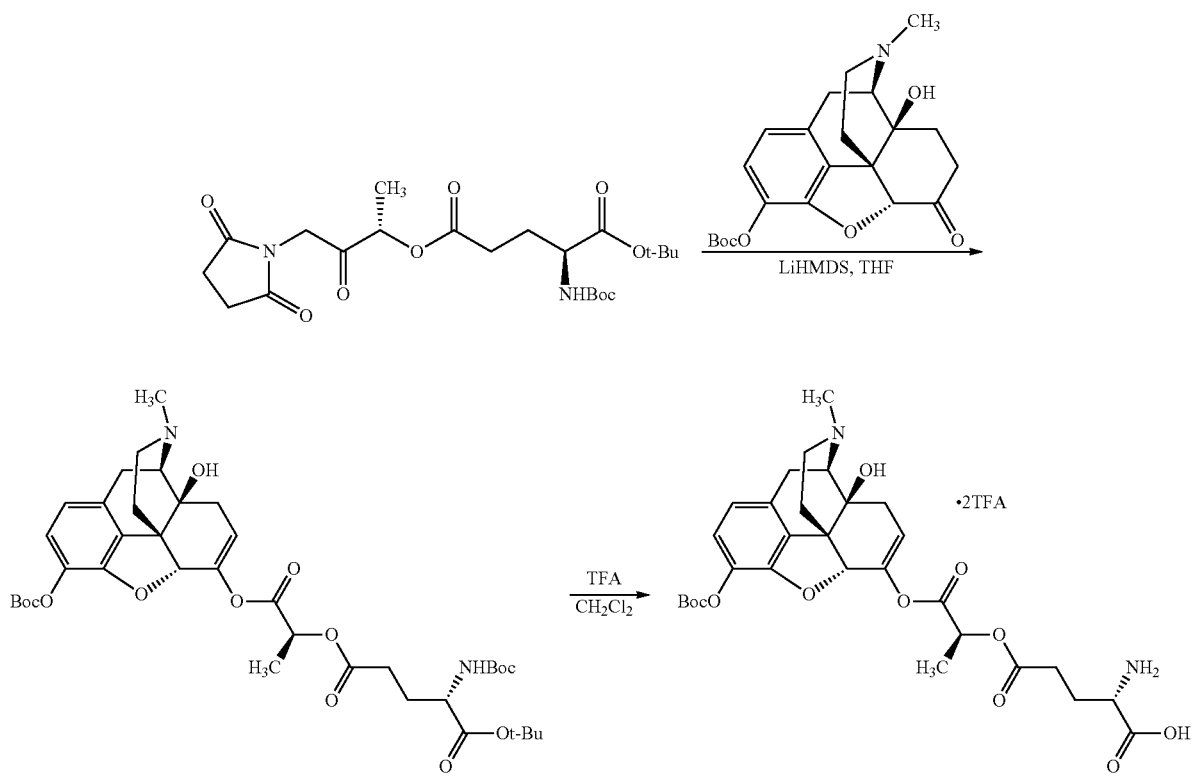

Preparation of (S)-2-(((S)-5-(tert-Butoxy)-4-((tert-butoxycarbonyl)amino)-5-oxopentanoyl)oxy)propanoic acid

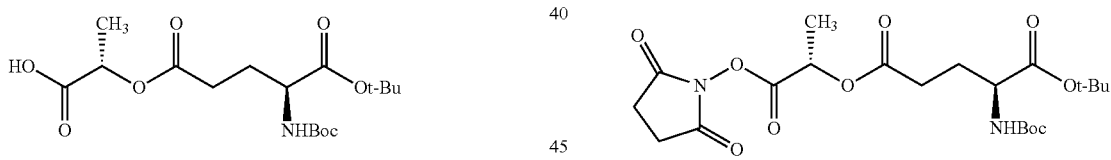

(S)-Lactic acid (270 mg, 3.00 mmol), (S)-1-tert-butyl 5-(2,5-dioxopyrrolidin-1-yl) 2-((tert-butoxycarbonyl)amino)pentanedioate (1.00 g, 2.50 mmol), 4-(dimethylamino)pyridine (31 mg, 0.250 mmol), and pyridine (237 mg, 3.00 mmol) were combined and heated at 60° C. under a nitrogen atmosphere for 48 h. After this time, the solvent was removed under reduced pressure, and the residue was participated between ethyl acetate (20 mL) and 10% aqueous citric acid. The organic layer was separated and extracted with saturated aqueous sodium bicarbonate (20 ml). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (S)-2-(((S)-5-(tert-butoxy)-4-((tert-butoxycarbonyl)amino)-5-oxopentanoyl)oxy)propanoic acid (726 mg, 77%) as a colorless oil: $^1$H NMR (300 MHz, CDCl$_3$) δ 5.19-5.12 (m, 2H), 2.51-2.42 (m, 2H), 2.18 (m, 1H), 1.91 (m, 1H), 1.54 (d, J=7.2 Hz, 3H), 1.47 (s, 9H), 1.45 (s, 9H), CO$_2$H and NH protons not observed.

Preparation of (S)-1-tert-Butyl 5-((S)-1-((2,5-dioxopyrrolidin-1-yl)oxy)-1-oxopropan-2-yl) 2-((tert-butoxycarbonyl)amino)pentanedioate A solution of (S)-2-(((S)-5-(tert-butoxy)-4-((tert-butoxycarbonyl)amino)-5-oxopentanoyl)oxy)propanoic acid (726 mg, 1.93 mmol) in tetrahydrofuran (15 mL) was treated with N-hydroxysuccinimide (245 mg, 2.13 mmol) and N,N'-dicyclohexylcarbodiimide (439 mg, 2.13 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-1-tert-butyl 5-((S)-1-((2,5-dioxopyrrolidin-1-yl)oxy)-1-oxopropan-2-yl) 2-((tert-butoxycarbonyl)amino)pentanedioate (1.03 g, quantitative) as a white solid: $^1$H NMR (300 MHz, CDCl$_3$) δ 5.42 (dd, J=14.1, 7.2 Hz, 1H), 5.08 (m, 1H), 2.84 (s, 4H), 2.53-2.46 (m, 2H), 2.20 (m, 1H), 1.91 (m, 1H), 1.67 (d, J=7.2 Hz, 3H), 1.47 (s, 9H), 1.45 (s, 9H), NH proton not observed.

901

Preparation of (S)-5-((S)-1-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 1-tert-butyl 2-((tert-butoxycarbonyl)amino)pentanedioate

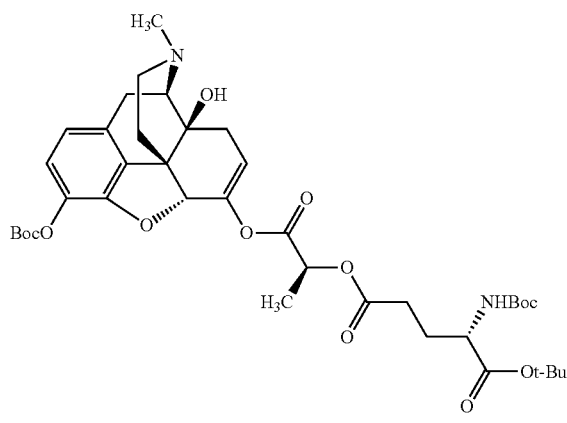

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (400 mg, 0.996 mmol) in tetrahydrofuran (8 mL) was cooled in an ice bath and treated dropwise with a 1.0 M solution of lithium bis(trimethylsilyl)amide in tetrahydrofuran (1.2 mL, 1.2 mmol). After addition was complete, the mixture was stirred at 0° C. for 1 h. The mixture was re-cooled to −45° C. and treated dropwise with a solution of (S)-1-tert-butyl 5-((S)-1-((2,5-dioxopyrrolidin-1-yl)oxy)-1-oxopropan-2-yl) 2-((tert-butoxycarbonyl)amino)pentanedioate (518 mg, 1.10 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-5-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 1-tert-butyl 2-((tert-butoxycarbonyl)amino)pentanedioate (264 mg, 35%) as a white solid: ESI MS m/z 759 $[C_{39}H_{54}N_2O_{13}+H]^+$.

902

Preparation of (S)-2-Amino-5-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid bis(trifluoroacetic acid salt)

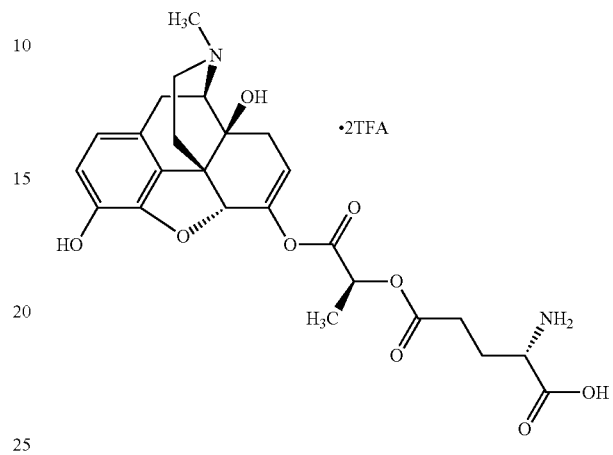

A solution of (S)-5-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 1-tert-butyl 2-((tert-butoxycarbonyl)amino)pentanedioate (160 mg, 0.211 mmol) in methylene chloride (3 mL) was treated with trifluoroacetic acid (3 mL) and stirred under a nitrogen atmosphere at ambient temperature for 3 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-2-amino-5-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-5-oxopentanoic acid bis(trifluoroacetic acid salt) (76 mg, 47%) as a fluffy white solid: $^1$H NMR (300 MHz, DMSO-$d_6$) δ 9.30 (br s, 1H), 9.16 (br s, 1H), 8.27 (br s, 3H), 6.66 (apparent q, J=8.1 Hz, 2H), 6.26 (s, 1H), 5.58 (dd, J=6.0, 2.1 Hz, 1H), 5.13 (q, J=4.2 Hz, 1H), 4.96 (s, 1H), 3.96 (m, 1H), 3.44 (m, 2H), 3.05 (m, 1H), 2.84 (s, 3H), 2.73-2.41 (m, 5H), 2.28 (m, 1H), 2.18-2.00 (m, 3H), 1.62 (m, 1H), 1.53 (d, J=7.2 Hz, 3H), CO$_2$H proton not observed; ESI MS m/z 503 $[C_{25}H_{30}N_2O_9+H]^+$; HPLC (Method A) 95.0% (AUC), $t_R$=6.38 min.

Scheme 163: (S)-2-(((S)-2-Acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt

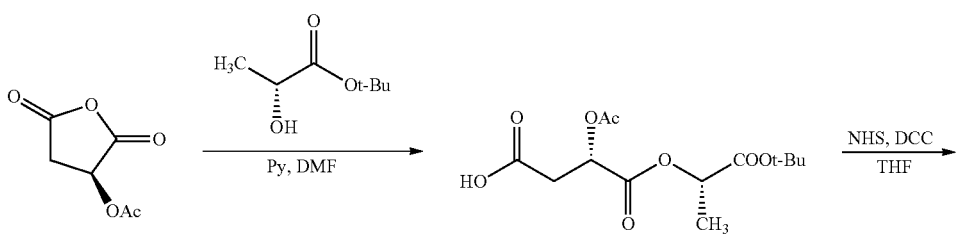

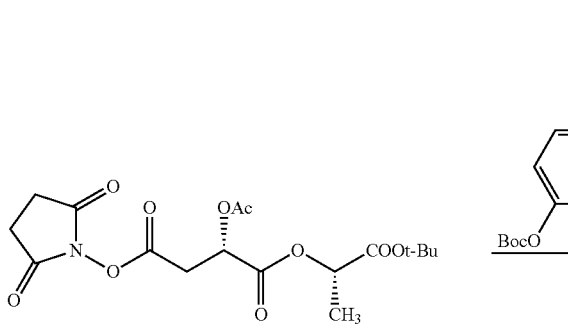
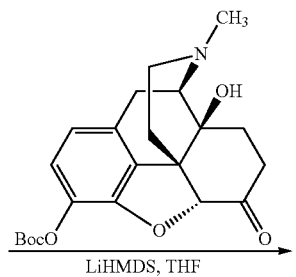

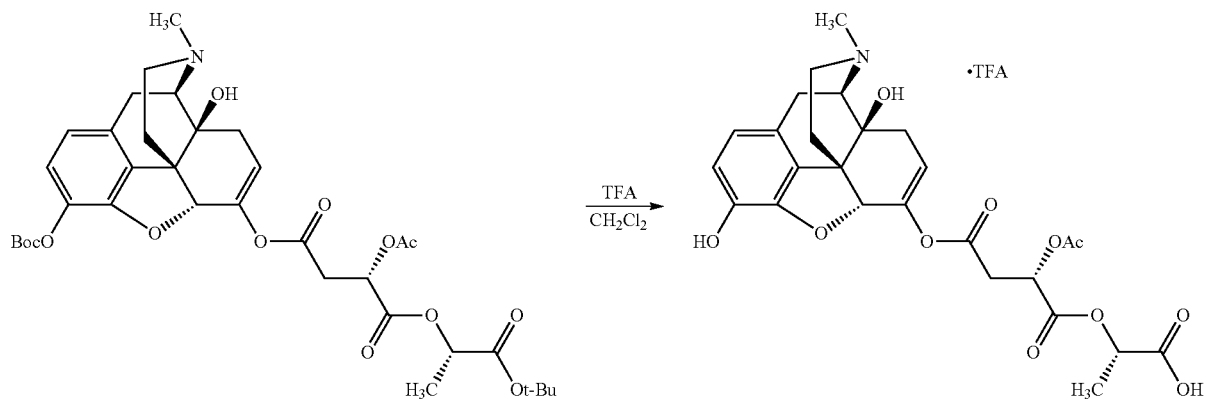

Preparation of (S)-3-Acetoxy-4-(((S)-1-(tert-butoxy)-1-oxopropan-2-yl)oxy)-4-oxobutanoic acid

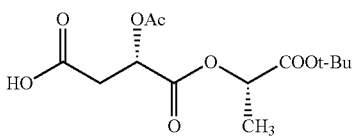

A solution of (S)-2,5-dioxotetrahydrofuran-3-yl acetate (0.70 g, 3.4 mmol) and (S)-tert-butyl 2-hydroxypropanoate (0.50 g, 3.4 mmol) in N,N-dimethylformamide (4 mL) was cooled in an ice bath and treated with pyridine (0.36 mL, 4.4 mmol). After addition was complete, the mixture was stirred at ambient temperature for 16 h. After this time, the mixture was diluted with water (20 mL) and extracted with ethyl acetate (2×20 mL). The combined organics were washed with brine (50 mL), dried over sodium sulfate, filtered, and concentrated under reduced pressure to provide (S)-3-acetoxy-4-(((S)-1-(tert-butoxy)-1-oxopropan-2-yl)oxy)-4-oxobutanoic acid (0.6 g, 58%) as a brown oil: $^1$H NMR (300 MHz, CDCl$_3$) $^1$H NMR (300 MHz, CDCl$_3$) δ 5.49 (dd, J=9.3, 3.3 Hz, 1H), 5.03 (dd, J=14.1, 6.9 Hz, 1H), 3.13 (dd, J=17.1, 3.3 Hz, 1H), 2.95 (dd, J=17.1, 9.3 Hz, 1H), 2.13 (s, 3H), 1.48 (d, J=7.2 Hz, 3H), 1.46 (s, 9H), CO$_2$H proton not observed.

Preparation of (S)-1-((S)-1-(tert-Butoxy)-1-oxopropan-2-yl) 4-(2,5-dioxopyrrolidin-1-yl) 2-acetoxysuccinate

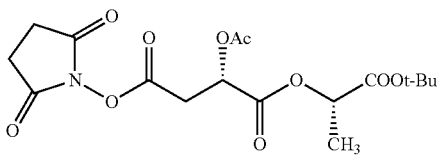

(S)-3-Acetoxy-4-(((S)-1-(tert-butoxy)-1-oxopropan-2-yl)oxy)-4-oxobutanoic acid (1.8 g, 6.01 mmol), 1-hydroxypyrrolidine-2,5-dione (0.81 g, 7.0 mmol) and dicyclohexylcarbodiimide (1.36 g, 6.61 mmol) were combined and stirred in tetrahydrofuran (40 mL) at ambient temperature for 4 h. After this time, the mixture was filtered and concentrated under reduced pressure to provide (S)-1-((S)-1-(tert-butoxy)-1-oxopropan-2-yl) 4-(2,5-dioxopyrrolidin-1-yl) 2-acetoxysuccinate (2.64 g, 99%) as a sticky solid: $^1$H NMR (300 MHz, DMSO-d$_6$) δ 5.50 (dd, J=8.7, 4.2 Hz, 1H), 5.00 (dd, J=14.1, 6.9 Hz, 1H), 3.40 (dd, J=17.1, 3.3 Hz, 1H), 3.30 (dd, J=17.1, 9.3 Hz, 1H), 2.77 (s, 4H), 2.10 (s, 3H), 1.46 (d, J=6.9 Hz, 3H), 1.41 (s, 9H).

905

Preparation of (S)-1-((S)-1-(tert-Butoxy)-1-oxopropan-2-yl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2-acetoxysuccinate

906

Preparation of (S)-2-(((S)-2-Acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt

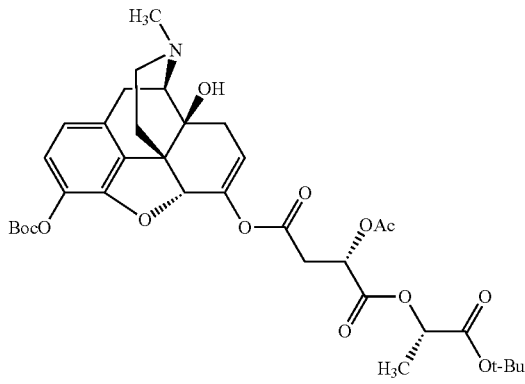

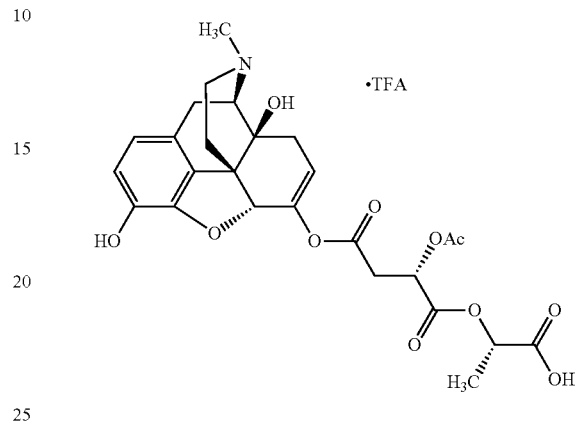

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at 0° C. for 1 h. The mixture was re-cooled to −45° C. and treated dropwise with a solution of (S)-1-((S)-1-(tert-butoxy)-1-oxopropan-2-yl) 4-(2,5-dioxopyrrolidin-1-yl) 2-acetoxysuccinate (550 mg, 1.37 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-1-((S)-1-(tert-butoxy)-1-oxopropan-2-yl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2-acetoxysuccinate (293 mg, 34%) as a white solid: ESI MS m/z 688 [$C_{35}H_{45}NO_{13}$+H]$^+$.

A solution of (S)-1-((S)-1-(tert-butoxy)-1-oxopropan-2-yl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2-acetoxysuccinate (150 mg, 0.218 mmol) in methylene chloride (3 mL) was treated with trifluoroacetic acid (3 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-2-(((S)-2-acetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt (55 mg, 37%) as a fluffy white solid: $^1$H NMR (300 MHz, DMSO-$d_6$) δ 13.2 (br s, 1H), 9.29 (s, 1H), 9.15 (br s, 1H), 6.65 (apparent q, J=8.1 Hz, 2H), 6.23 (s, 1H), 5.58 (dd, J=6.3, 2.1 Hz, 1H), 5.42 (dd, J=9.3, 3.6 Hz, 1H), 5.09-4.97 (m, 2H), 3.43-3.33 (m, 1H), 3.18 (dd, J=17.1, 3.6 Hz, 1H), 3.11-2.93 (m, 3H), 2.84 (s, 3H), 2.73-2.42 (m, 3H), 2.28 (m, 1H), 2.13-2.04 (m, 4H), 1.63 (m, 1H), 1.43 (d, J=7.2 Hz, 3H); ESI MS m/z 532 [$C_{26}H_{29}NO_{11}$+H]$^+$.

Scheme 164: (R)-2-(((2R,3R)-2,3-Diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt

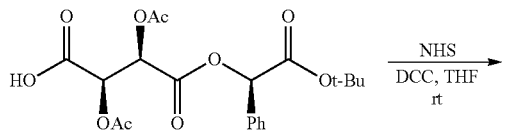

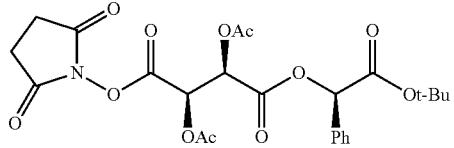
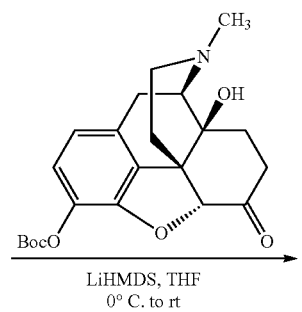

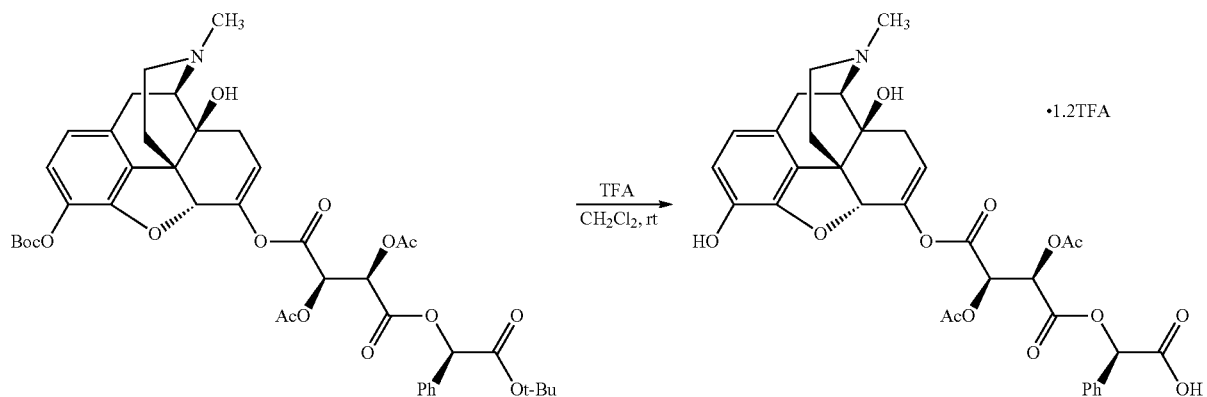

Preparation of (2R,3R)-1-((R)-2-(tert-Butoxy)-2-oxo-1-phenylethyl) 4-(2,5-dioxopyrrolidin-1-yl) 2,3-diacetoxysuccinate

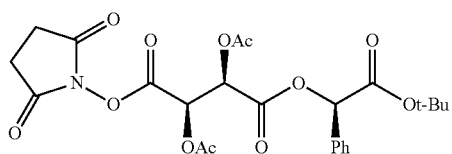 [SMILES: CC(=O)O[C@@H](C(=O)O[C@@H](C(=O)OC(C)(C)C)c1ccccc1)[C@@H](OC(C)=O)C(=O)ON1C(=O)CCC1=O]

A mixture of (2R,3R)-2,3-diacetoxy-4-((R)-2-(tert-butoxy)-2-oxo-1-phenylethoxy)-4-oxobutanoic acid (550 mg, 1.30 mmol) and N-hydroxysuccinimide (165 mg, 1.43 mmol) in tetrahydrofuran (8 mL) was treated with N,N'-dicyclohexylcarbodiimide (295 mg, 1.43 mmol), and the reaction mixture was stirred at ambient temperature for 4 h. After this time, diethyl ether (10 mL) was added and the mixture was filtered. The filtrate was concentrated under reduced pressure to provide (2R,3R)-1-((R)-2-(tert-butoxy)-2-oxo-1-phenylethyl) 4-(2,5-dioxopyrrolidin-1-yl) 2,3-diacetoxysuccinate (1.41 g, 80%) that was used without purification: $^1$H NMR (300 MHz, CDCl$_3$) δ 7.41-7.38 (m, 5H), 6.33 (d, J=2.8 Hz, 1H), 5.95 (d, J=2.8 Hz, 1H), 5.79 (s, 1H), 2.83 (s, 4H), 2.29 (s, 3H), 2.28 (s, 3H), 1.35 (s, 9H).

Preparation of (2R,3R)-1-((R)-2-(tert-Butoxy)-2-oxo-1-phenylethyl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2,3-diacetoxysuccinate

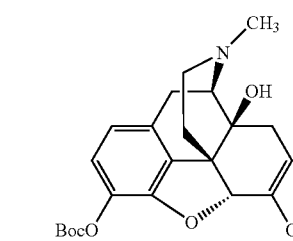

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (300 mg, 0.75 mmol) in tetrahydrofuran (6 mL) was cooled to 0° C. and treated dropwise with a 1.0 M solution of lithium bis(trimethylsilyl)amidein tetrahydrofuran (0.75 mL, 0.75 mmol). After addition was complete, the mixture was stirred at ambient temperature for 10 min. The mixture was re-cooled to 0° C., and (2R,3R)-1-((R)-2-(tert-butoxy)-2-oxo-1-phenylethyl) 4-(2,5-dioxopyrrolidin-1-yl) 2,3-diacetoxysuccinate (355 mg, 0.681 mmol) was added in one portion. The mixture was stirred at 0° C. for 45 min. After this time, the mixture was treated with saturated aqueous ammonium chloride and extracted with ethyl acetate. The combined organics were dried over sodium sulfate, filtered, and concentrated under reduced pressure. The residue was purified by reversed phase column chromatography (50 g C18 column, 10-100% acetonitrile/water) to provide (2R,3R)-1-((R)-2-(tert-butoxy)-2-oxo-1-phenylethyl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2,3-diacetoxysuccinate (260 mg, 47%): ESI MS m/z 808 $[C_{42}H_{49}NO_{15}+H]^+$.

Preparation of (R)-2-(((2R,3R)-2,3-Diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt

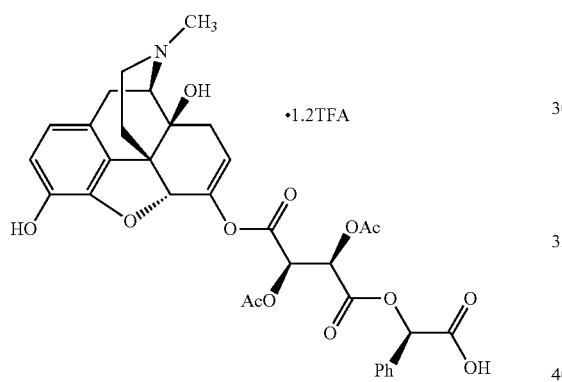

A solution of (2R,3R)-1-((R)-2-(tert-butoxy)-2-oxo-1-phenylethyl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2,3-diacetoxysuccinate (260 mg, 0.32 mmol) in methylene chloride (6 mL) was treated with trifluoroacetic acid (1 mL) and stirred at ambient temperature for 3 h. After this time, the reaction mixture was concentrated under reduced pressure. The residue was purified by reversed phase column chromatography (50 g C18 column, 3-30% acetonitrile/water, with 0.1% trifluoroacetic acid) and freeze dried to provide (R)-2-(((2R,3R)-2,3-diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)-2-phenylacetic acid trifluoroacetic acid salt (74 mg, 36%): $^1$H NMR (300 MHz, DMSO-$d_6$) δ 13.51 (br s, 1H), 9.33 (s, 1H), 9.15 (br s, 1H), 7.51-7.40 (m, 5H), 6.67 (d, J=8.2 Hz, 1H), 6.62 (d, J=8.2 Hz, 1H), 6.30 (s, 1H), 6.03 (d, J=2.7 Hz, 1H), 5.98-5.94 (m, 2H), 5.56-5.53 (m, 1H), 4.83 (s, 1H), 3.62 (d, J=6.0 Hz, 1H), 3.40-3.33 (m, 1H), 3.12-3.02 (m, 2H), 3.83 (apparent d, J=3.5 Hz, 3H), 2.67-2.56 (m, 1H), 2.47-2.38 (m, 1H), 2.31-2.21 (m, 4H), 2.11 (s, 3H), 2.08 (d, J=17.7 Hz, 1H), 1.63 (d, J=11.1 Hz, 1H); ESI MS m/z 652 $[C_{33}H_{33}NO_{13}+H]^+$; HPLC (Method A) 98.0% (AUC), $t_R$=9.16 min.

Scheme 165: (2R,3R)-4-(((4R,4aS,7aR,12bS)-4a,9-Dihydroxy-3-methyl-2,3,4,4a,5,7a-hexahyrdo-1H-4,12-methanobenzofuro[3,2-e]isoquinolin-7-yl)oxy)-2,3-dihydroxy-4-oxobutanoic acid trifluoracetic acid salt

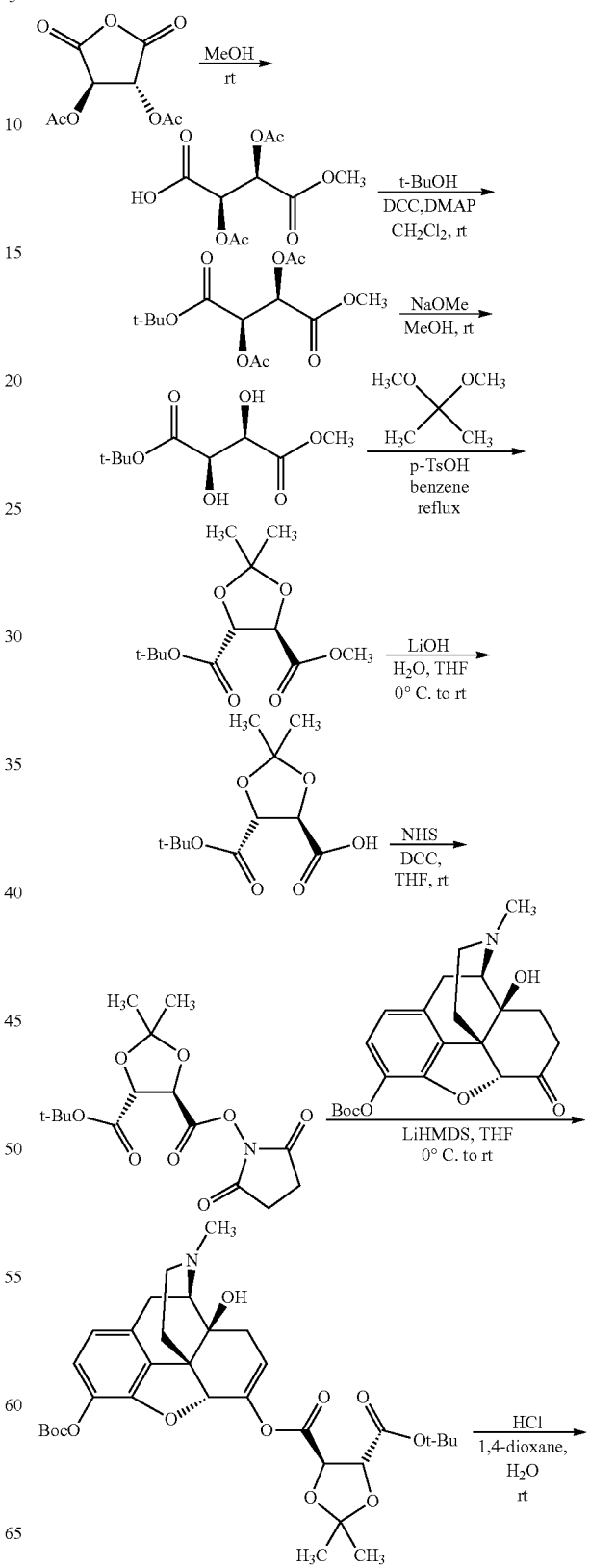

-continued

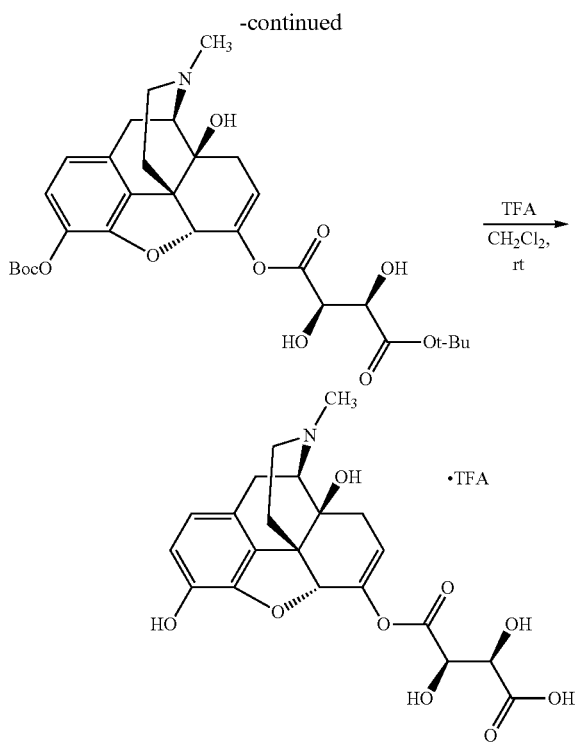

Preparation of (2R,3R)-2,3-Diacetoxy-4-methoxy-4-oxobutanoic acid

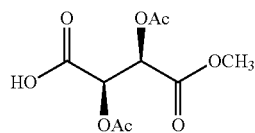

A mixture of (3R,4R)-2,5-dioxotetrahydrofuran-3,4-diyl diacetate (5.66 g, 26.2 mmol) in methanol (26 mL) was stirred at room temperature for 30 min. After this time, the mixture was concentrated to dryness to provide (2R,3R)-2,3-diacetoxy-4-methoxy-4-oxobutanoic acid (6.30 g, 97%): $^1$H NMR (300 MHz, DMSO-$d_6$) δ 5.63 (d, J=2.9 Hz, 1H), 5.52 (d, J=2.9 Hz, 1H), 3.70 (s, 3H), 2.12 (s, 3H), 2.10 (s, 3H), CO$_2$H proton not observed.

Preparation of (2R,3R)-1-tert-Butyl 4-methyl 2,3-diacetoxysuccinate

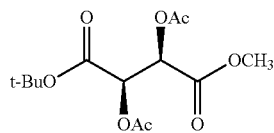 [SMILES: COC(=O)[C@H](OC(C)=O)[C@@H](OC(C)=O)C(=O)OC(C)(C)C]

A mixture of (2R,3R)-2,3-diacetoxy-4-methoxy-4-oxobutanoic acid (6.30 g, 25.4 mmol) and tert-butanol (6.5 mL, 68 mmol) in methylene chloride (50 mL) at 0° C. was treated with N,N'-dicyclohexylcarbodiimide (6.70 g, 32.5 mmol).

After stirring for 1 h, the ice bath was removed and the reaction mixture was stirred at ambient temperature for 18 h. After this time, the mixture was filtered, and the filtrate was concentrated under reduced pressure. The residue was purified by column chromatography (120 g silica gel column, 5-70% ethyl acetate/heptane) to provide (2R,3R)-1-tert-butyl 4-methyl 2,3-diacetoxysuccinate (4.2 g, 54%): $^1$H NMR (300 MHz, CDCl$_3$) δ 5.73 (d, J=2.8 Hz, 1H), 5.60 (d, J=2.8 Hz, 1H), 3.78 (s, 3H), 2.18 (s, 3H), 2.16 (s, 3H), 1.45 (s, 9H).

Preparation of (2R,3R)-1-tert-Butyl 4-methyl 2,3-dihydroxysuccinate

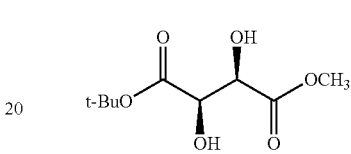

A solution of (2R,3R)-1-tert-butyl 4-methyl 2,3-diacetoxysuccinate (4.15 g, 13.7 mmol) in methanol (28 mL) was treated with sodium methoxide (25% in methanol, 0.30 mL, 1.3 mmol), and the mixture was stirred at room temperature for 19 h. After this time, the reaction mixture was treated with a few drops of 2 N hydrochloric acid, until neutral by pH paper analysis. The mixture was partially concentrated, and the residue was dissolved in ethyl acetate, washed with saturated ammonium chloride and brine, dried over sodium sulfate, filtered, and concentrated under reduced pressure to provide (2R,3R)-1-tert-butyl 4-methyl 2,3-dihydroxysuccinate (2.62 g, 87%): $^1$H NMR (300 MHz, CDCl$_3$) δ 4.51 (dd, J=7.5, 1.7 Hz, 1H), 4.41 (d, J=6.3, 1.7 Hz, 1H), 3.86 (s, 3H), 3.19 (d, J=6.3 Hz, 1H), 3.05 (d, J=7.5 Hz, 1H), 1.52 (s, 9H).

Preparation of (4R,5R)-4-tert-Butyl 5-methyl 2,2-dimethyl-1,3-dioxolane-4,5-dicarboxylate

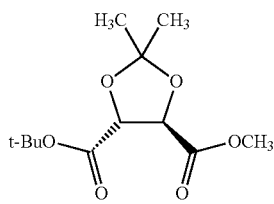

A mixture of (2R,3R)-1-tert-butyl 4-methyl 2,3-dihydroxysuccinate (2.62 g, 11.9 mmol), 2,2-dimethoxypropane (2.2 mL, 18 mmol), and p-toluenesulfonic acid (50 mg, 0.26 mmol) in benzene (30 mL) was stirred at reflux for 20 h. After this time, the mixture was cooled to room temperature, and saturated sodium bicarbonate was added. The mixture was stirred for 5 min and then extracted with ethyl acetate. The organic extracts were washed with water and brine and then concentrated. The residue was purified by column chromatography (80 g silica gel column, 5-70% ethyl acetate/heptane) to provide (4R,5R)-4-tert-butyl 5-methyl 2,2-dimethyl-1,3-dioxolane-4,5-dicarboxylate (1.63 g, 53%): $^1$H NMR (300 MHz, CDCl$_3$) δ 4.71 (d, J=5.9 Hz, 1H), 4.64 (d, J=5.9 Hz, 1H), 3.82 (s, 3H), 1.50 (s, 15H).

913

Preparation of (4R,5R)-5-(tert-Butoxycarbonyl)-2,2-dimethyl-1,3-dioxolane-4-carboxylic acid

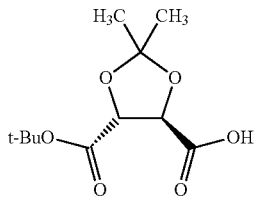

A solution of (4R,5R)-4-tert-butyl 5-methyl 2,2-dimethyl-1,3-dioxolane-4,5-dicarboxylate (4.96 g, 19.1 mmol) in tetrahydrofuran (35 mL) was treated with a solution of lithium hydroxide (940 mg, 22.4 mmol) in water (15 mL), and the mixture was stirred at room temperature for 1 h. After this time, 2 N hydrochloric acid was added until the mixture tested neutral by pH paper analysis. The mixture was partially concentrated and then extracted with ethyl acetate. The organic extracts were washed with 10% citric acid and brine, dried over sodium sulfate, filtered and concentrated to provide (4R,5R)-5-(tert-butoxycarbonyl)-2,2-dimethyl-1,3-dioxolane-4-carboxylic acid (2.00 g, 43%): $^1$H NMR (300 MHz, CDCl$_3$) δ 4.80 (d, J=5.7 Hz, 1H), 4.66 (d, J=5.7 Hz, 1H), 1.53 (s, 3H), 1.52 (s, 9H), 1.50 (s, 3H), CO$_2$H proton not observed.

Preparation of (4R,5R)-4-tert-Butyl 5-(2,5-dioxopyrrolidin-1-yl) 2,2-dimethyl-1,3-dioxolane-4,5-dicarboxylate

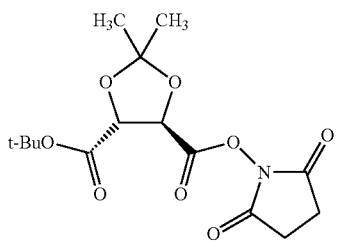

A mixture of (4R,5R)-5-(tert-butoxycarbonyl)-2,2-dimethyl-1,3-dioxolane-4-carboxylic acid (410 mg, 1.67 mmol) and N-hydroxysuccinimide (210 mg, 1.82 mmol) in tetrahydrofuran (10 mL) was treated with N,N'-dicyclohexylcarbodiimide (380 mg, 1.84 mmol), and the reaction mixture was stirred at ambient temperature for 4 h. After this time, diethyl ether (20 mL) was added, and the mixture was filtered. The filtrate was concentrated under reduced pressure to provide (4R,5R)-4-tert-butyl 5-(2,5-dioxopyrrolidin-1-yl) 2,2-dimethyl-1,3-dioxolane-4,5-dicarboxylate (650 mg) that was used without purification: $^1$H NMR (300 MHz, CDCl$_3$) δ 5.09 (d, J=4.9 Hz, 1H), 4.87 (d, J=4.9 Hz, 1H), 2.87 (s, 4H), 1.54 (s, 3H), 1.52 (s, 3H), 1.51 (s, 9H).

914

Preparation of (4R,5R)-4-((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl) 5-tert-butyl 2,2-dimethyl-1,3-dioxolane-4,5-dicarboxylate

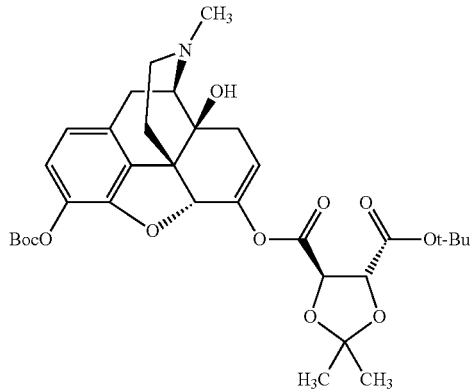

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (400 mg, 1.00 mmol) in tetrahydrofuran (8 mL) was cooled to 0° C. and treated dropwise with a 1.0 M solution of lithium bis(trimethylsilyl)amide in tetrahydrofuran (1.1 mL, 1.1 mmol). After addition was complete, the mixture was stirred at ambient temperature for 10 min. The mixture was re-cooled to 0° C. and (4R,5R)-4-tert-butyl 5-(2,5-dioxopyrrolidin-1-yl) 2,2-dimethyl-1,3-dioxolane-4,5-dicarboxylate (500 mg, 1.09 mmol) was added in one portion. The mixture was stirred at 0° C. for 1 h. After this time, the mixture was treated with saturated aqueous ammonium chloride and extracted with ethyl acetate. The combined organics were dried over sodium sulfate, filtered, and concentrated under reduced pressure. The residue was purified by reversed phase column chromatography (50 g C18 column, 5-100% acetonitrile/water) to provide (4R,5R)-4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 5-tert-butyl 2,2-dimethyl-1,3-dioxolane-4,5-dicarboxylate (254 mg, 40%): ESI MS m/z 630 [C$_{33}$H$_{43}$NO$_{11}$+H]$^+$.

Preparation of (2R,3R)-1-((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2,3-dihydroxysuccinate

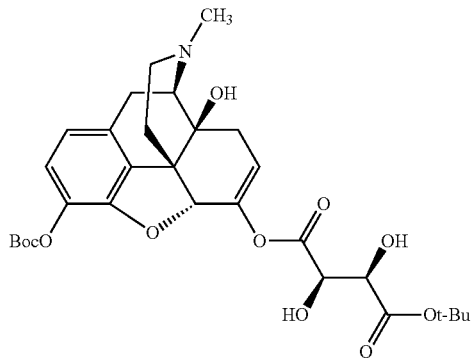

A solution of (4R,5R)-4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin- 7-yl) 5-tert-butyl 2,2-dimethyl-1,3-dioxolane-4,5-dicarboxylate (245 mg, 0.390 mmol) in 1,4-dioxane (2 mL) and water (0.1 mL) was treated with a 1 N solution of hydrogen chloride in 1,4-dioxane (2 mL, 8 mmol) and stirred at ambient temperature for 3 h. After this time, the reaction mixture was concentrated under reduced pressure to provide (2R,3R)-1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2,3-dihydroxysuccinate (240 mg): ESI MS m/z 590 $[C_{30}H_{39}NO_{11}+H]^+$.

Preparation of (2R,3R)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoic acid trifluoroacetic acid salt

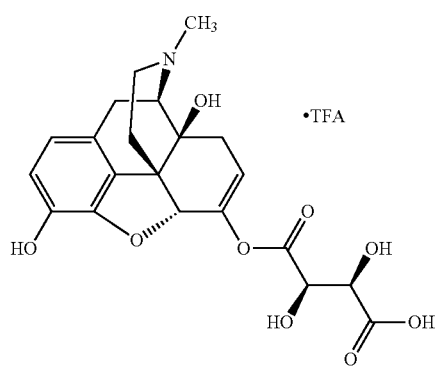 [SMILES: CN1CC[C@]23c4c5ccc(O)c4O[C@H]2C(OC(=O)[C@H](O)[C@@H](O)C(=O)O)=CC[C@@]3(O)[C@H]1C5]

A solution of (2R,3R)-1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 4-tert-butyl 2,3-dihydroxysuccinate (240 mg) in methylene chloride (5 mL) was treated with trifluoroacetic acid (1.5 mL) and stirred at ambient temperature for 1 h. After this time, the reaction mixture was concentrated under reduced pressure. The residue was purified by reversed phase column chromatography (50 g C18 column, 3-10% acetonitrile/water, with 0.1% trifluoroacetic acid) and freeze dried to provide (2R,3R)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoic acid trifluoroacetic acid salt (7 mg, 3% over two steps): $^1$H NMR (300 MHz, CD$_3$OD) δ 6.65-6.57 (m, 2H), 5.55 (dd, J=5.4, 2.8 Hz, 1H), 4.99 (s, 1H), 4.65 (d, J=2.2 Hz, 1H), 4.53 (d, J=2.2 Hz, 1H), 3.56 (d, J=6.5 Hz, 1H), 3.35 (d, J=20.0 Hz, 1H), 3.13-3.03 (m, 2H), 2.83 (s, 3H), 2.82-2.74 (m, 1H), 2.57 (dt, J=13.4, 4.9 Hz, 1H), 2.25-2.17 (m, 2H), 1.71 (dd, J=13.5, 3.0 Hz, 1H), CO$_2$H, CF$_3$CO$_2$H, and four OH protons not observed; ESI MS m/z 434 $[C_{21}H_{23}NO_9+H]^+$; HPLC (Method A) 93.3% (AUC), $t_R$=5.83 min.

Scheme 166: (2S,3S)-2,3-Diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

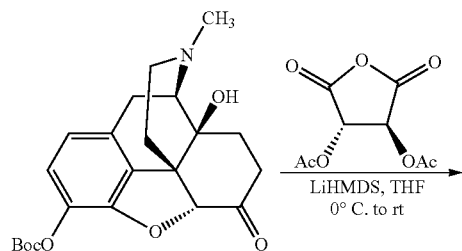

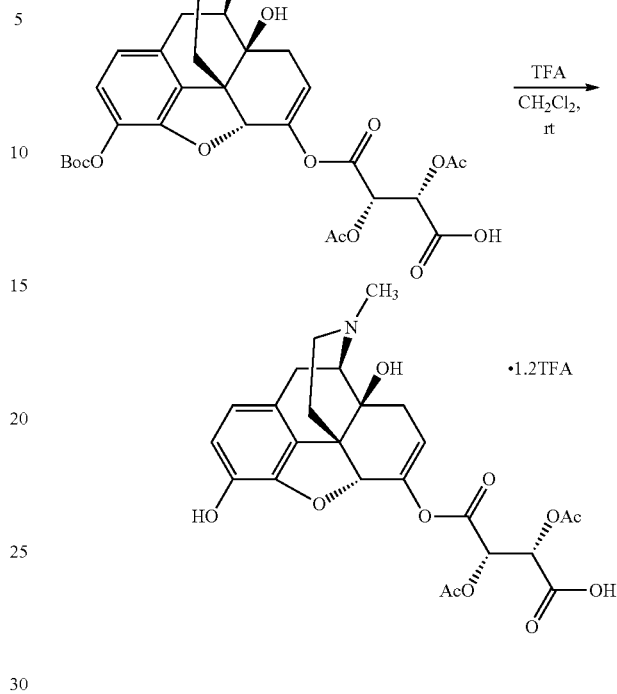

Preparation of (2S,3S)-2,3-Diacetoxy-4-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-4-oxobutanoic acid

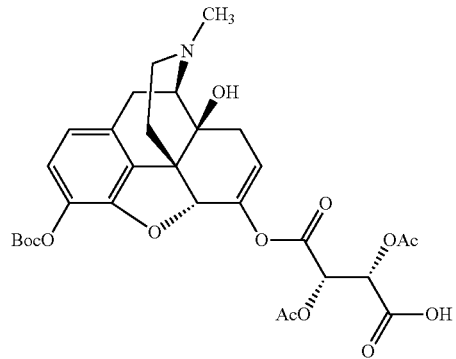

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (370 mg, 0.92 mmol) in tetrahydrofuran (8 mL) at 0° C. was treated with a 1.0 M solution of lithium bis(trimethylsilyl) amide in tetrahydrofuran (0.95 mL, 0.95 mmol), and the mixture was stirred for 5 min at 0° C. and 10 min at room temperature. The reaction mixture was cooled to 0° C. and (3S,4S)-2,5-dioxotetrahydrofuran-3,4-diyl diacetate (89 mg, 0.41 mmol) was added in one portion. The mixture was stirred at 0° C. for 20 min and then at room temperature for 30 min. After this time, the mixture was poured into a saturated solution of ammonium chloride and extracted with ethyl acetate. The organic extract was dried over sodium sulfate, filtered, and concentrated under reduced pressure. The residue was purified by reversed phase column chromatography (50 g C18 column, 5-80% acetonitrile/water) and freeze dried to provide (2S,3S)-2,3-diacetoxy-4-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-4-oxobutanoic acid (50 mg, 9%): ESI MS m/z 618 $[C_{30}H_{35}NO_{13}+H]^+$.

Preparation of (2S,3S)-2,3-Diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt

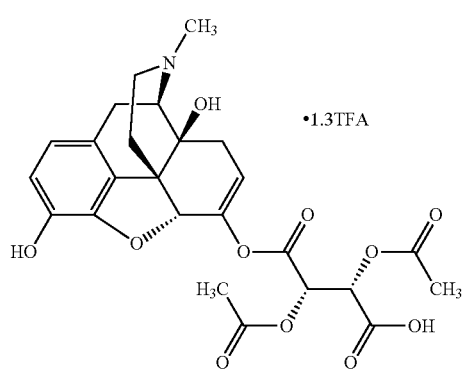 [SMILES: CC(=O)O[C@H](C(=O)O)[C@H](OC(C)=O)C(=O)OC1=CC[C@@]2(O)[C@H]3Cc4ccc(O)c5c4[C@@]2(CCN3C)[C@H]1O5]

A solution of (2S,3S)-2,3-diacetoxy-4-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-4-oxobutanoic acid (45 mg, 0.073 mmol) in methylene chloride (2 mL) was treated with trifluoroacetic acid (0.8 mL) and stirred at ambient temperature for 45 min. After this time, the reaction mixture was concentrated under reduced pressure. The residue was purified by reversed phase column chromatography (15.5 g C18 column, 3-30% acetonitrile/water, with 0.1% trifluoroacetic acid) and freeze dried to provide (2S,3S)-2,3-diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoic acid trifluoroacetic acid salt (30 mg, 62%): $^1$H NMR (300 MHz, DMSO-$d_6$) δ 9.24 (br s, 1H), 9.16 (br s, 1H), 6.87 (d, J=8.2 Hz, 1H), 6.62 (d, J=8.2 Hz, 1H), 6.30 (s, 1H), 5.82 (d, J=2.9 Hz, 1H), 5.60 (dd, J=6.0, 1.9 Hz, 1H), 5.56 (d, J=2.9 Hz, 1H), 4.94 (s, 1H), 3.63 (d, J=6.0 Hz, 1H), 3.42-3.30 (m, 1H), 3.11-3.02 (m, 2H), 2.84 (apparent d, J=3.8 Hz, 3H), 2.70-2.56 (m, 1H), 2.48-2.39 (m, 1H), 2.28 (d, J=18.0, 6.1 Hz, 1H), 2.18 (s, 3H), 2.15 (s, 3H), 2.11-2.02 (m, 1H), 1.63 (d, J=11.3 Hz, 1H), $CO_2H$ proton not observed; ESI MS m/z 518 $[C_{25}H_{27}NO_{11}+H]^+$; HPLC (Method A) 96.8% (AUC), $t_R$=7.19 min.

Scheme 167: (S)-2-(((2R,3R)-2,3-Diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)succinic acid trifluoroacetic acid salt

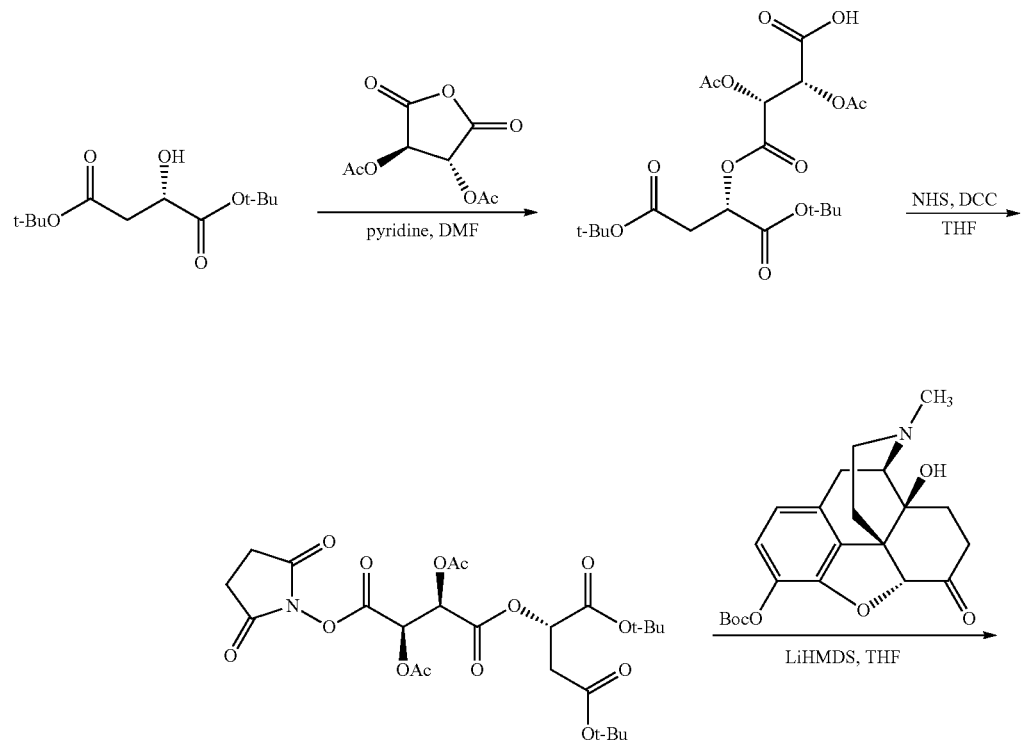

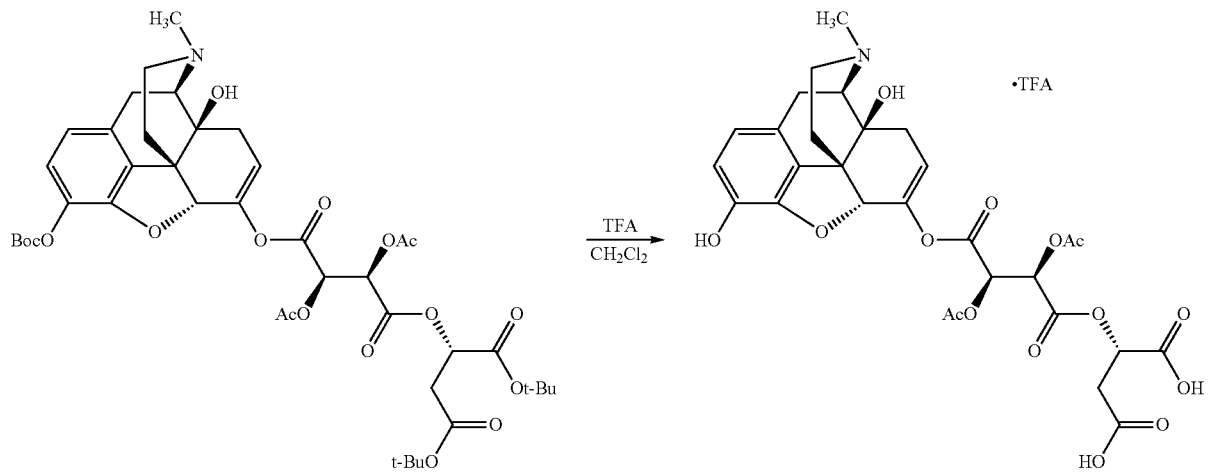

Preparation of (2R,3R)-2,3-Diacetoxy-4-(((S)-1,4-di-tert-butoxy-1,4-dioxobutan-2-yl)oxy)-4-oxobutanoic acid Preparation of (2R,3R)-1-((S)-1,4-Di-tert-butoxy-1,4-dioxobutan-2-yl) 4-(2,5-dioxopyrrolidin-1-yl) 2,3-diacetoxysuccinate

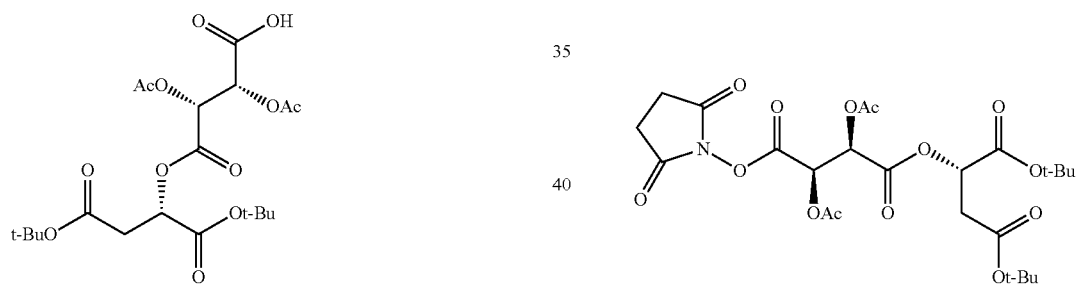

(S)-Di-tert-butyl 2-hydroxysuccinate (968 mg, 3.93 mmol), (3R,4R)-2,5-dioxotetrahydrofuran-3,4-diyl diacetate (1.06 g, 4.91 mmol), pyridine (279 mg, 3.54 mmol), and N,N-dimethylformamide (2 mL) were combined and stirred at 0° C. under a nitrogen atmosphere for 2 h. After this time, saturated sodium bicarbonate (15 mL) was added, and the resulting aqueous solution was washed with ethyl acetate (10 mL). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (2R,3R)-2,3-diacetoxy-4-(((S)-1,4-di-tert-butoxy-1,4-dioxobutan-2-yl)oxy)-4-oxobutanoic acid (1.74 g, 95%) as a yellow oil: $^1$H NMR (300 MHz, CDCl$_3$) δ 5.80 (d, J=3.0 Hz, 1H), 5.68 (d, J=3.0 Hz, 1H), 5.30 (dd, J=7.2, 5.1 Hz, 1H), 2.77-2.74 (m, 2H), 2.20 (s, 3H), 2.18 (s, 3H), 1.46 (s, 9H), 1.44 (s, 9H), CO$_2$H proton not observed.

A solution of (2R,3R)-2,3-diacetoxy-4-(((S)-1,4-di-tert-butoxy-1,4-dioxobutan-2-yl)oxy)-4-oxobutanoic acid (1.74 g, 3.76 mmol) in tetrahydrofuran (25 mL) was treated with N-hydroxysuccinimide (476 mg, 4.14 mmol) and N,N'-dicyclohexylcarbodiimide (929 mg, 4.51 mmol) and stirred under a nitrogen atmosphere for 4 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (2R,3R)-1-((S)-1,4-di-tert-butoxy-1,4-dioxobutan-2-yl) 4-(2,5-dioxopyrrolidin-1-yl) 2,3-diacetoxysuccinate (2.06 g) as a yellow solid: $^1$H NMR (300 MHz, CDCl$_3$) δ 6.04 (d, J=3.0 Hz, 1H), 5.95 (d, J=2.7 Hz, 1H), 5.32 (dd, J=8.1, 4.2 Hz, 1H), 2.85-2.74 (m, 6H), 2.25 (s, 3H), 2.23 (s, 3H), 1.46 (s, 9H), 1.44 (s, 9H).

921

Preparation (2R,3R)-1-((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl) 4-((S)-1,4-di-tert-butoxy-1,4-dioxobutan-2-yl) 2,3-diacetoxysuccinate

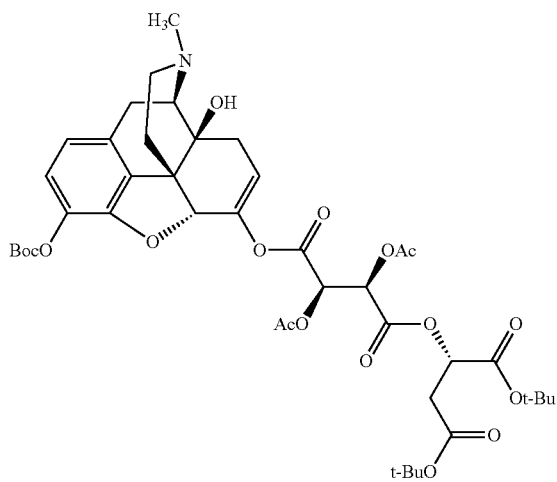

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at ambient temperature for 15 min. The mixture was re-cooled to −45° C. and treated dropwise with a solution of (2R,3R)-1-((S)-1,4-di-tert-butoxy-1,4-dioxobutan-2-yl) 4-(2,5-dioxopyrrolidin-1-yl) 2,3-diacetoxysuccinate (766 mg, 1.37 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (2R,3R)-1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 4-((S)-1,4-di-tert-butoxy-1,4-dioxobutan-2-yl) 2,3-diacetoxysuccinate (290 mg, 27%) as a white solid: ESI MS m/z 846 $[C_{42}H_{55}NO_{17}+H]^+$.

922

Preparation of (S)-2-(((2R,3R)-2,3-Diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy) succinic acid trifluoroacetic acid salt

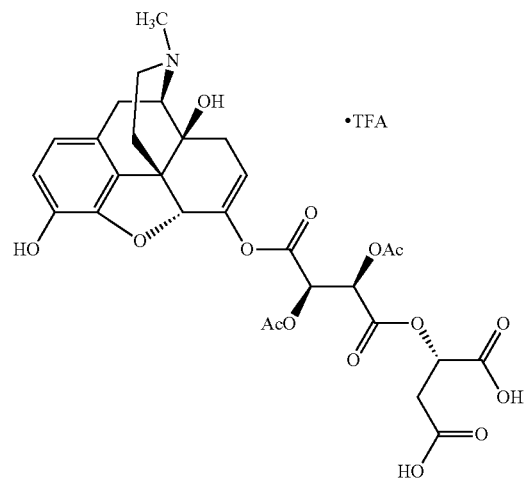 [SMILES: CC(=O)O[C@@H](C(=O)OC1=CC[C@@]2(O)[C@H]3Cc4ccc(O)c5c4[C@@]2(CCN3C)[C@H]1O5)[C@@H](OC(C)=O)C(=O)O[C@@H](CC(=O)O)C(=O)O]

A solution of (2R,3R)-1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 4-((S)-1,4-di-tert-butoxy-1,4-dioxobutan-2-yl) 2,3-diacetoxysuccinate (290 mg, 0.343 mmol) in methylene chloride (5.0 mL) was treated with trifluoroacetic acid (5.0 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-2-(((2R,3R)-2,3-diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)succinic acid trifluoroacetic acid salt (189 mg, 73%) as a fluffy white solid: $^1$H NMR (300 MHz, DMSO-d$_6$) δ 9.35 (s, 1H), 9.15 (br s, 1H), 6.64 (apparent q, J=8.1 Hz, 2H), 6.27 (br s, 1H), 5.85 (d, J=2.7 Hz, 1H), 5.77 (d, J=2.7 Hz, 1H), 5.53 (dd, J=5.7, 1.8 Hz, 1H), 5.29 (dd, J=8.4, 3.9 Hz, 1H), 4.83 (s, 1H), 3.32 (m, 1H), 3.03 (m, 1H), 2.90-2.63 (m, 6H), 2.51-2.41 (m, 3H), 2.27 (m, 1H), 2.21 (s, 3H), 2.13 (s, 3H), 2.04 (m, 1H), 1.62 (m, 1H), CO$_2$H protons not observed; ESI MS m/z 634 $[C_{29}H_{31}NO_{15}+H]^+$.

Scheme 168: 4-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-4-ethoxy-1,4-dioxobutan-2-yl)oxy)-4-oxobutanoic acid trifluoroacetic acid salt

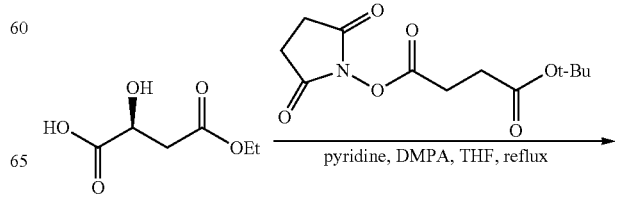

923
-continued

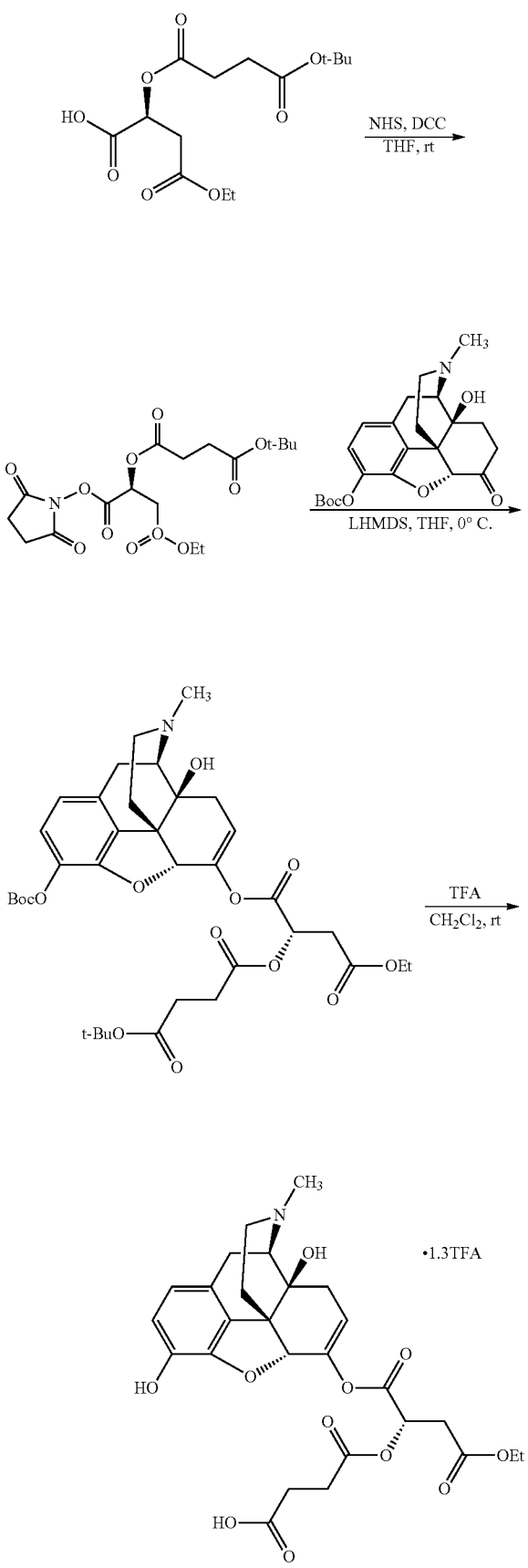

924

Preparation of (S)-2-((4-(tert-Butoxy)-4-oxobutanoyl)oxy)-4-ethoxy-4-oxobutanoic acid

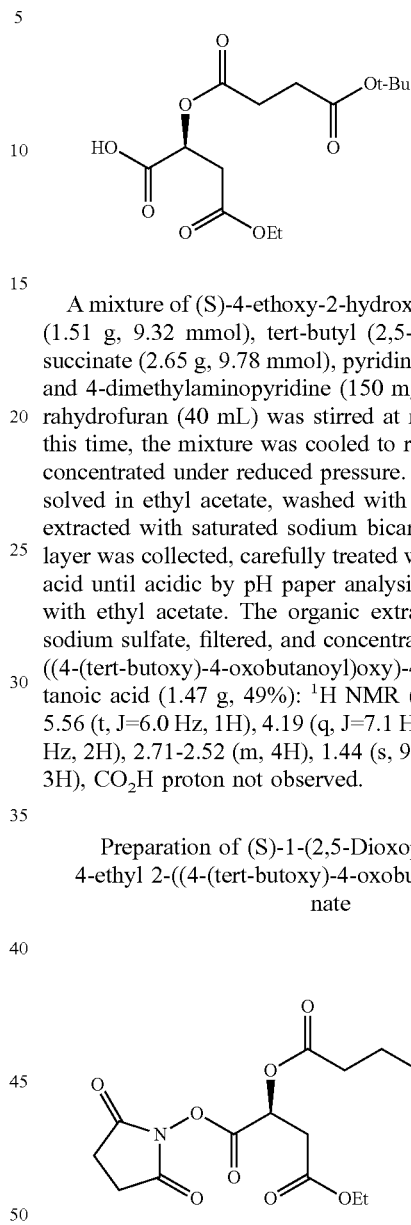

A mixture of (S)-4-ethoxy-2-hydroxy-4-oxobutanoic acid (1.51 g, 9.32 mmol), tert-butyl (2,5-dioxopyrrolidin-1-yl) succinate (2.65 g, 9.78 mmol), pyridine (1.0 mL, 12 mmol), and 4-dimethylaminopyridine (150 mg, 1.23 mmol) in tetrahydrofuran (40 mL) was stirred at reflux for 24 h. After this time, the mixture was cooled to room temperature and concentrated under reduced pressure. The residue was dissolved in ethyl acetate, washed with 10% citric acid, and extracted with saturated sodium bicarbonate. The aqueous layer was collected, carefully treated with 6 N hydrochloric acid until acidic by pH paper analysis, and then extracted with ethyl acetate. The organic extracts were dried over sodium sulfate, filtered, and concentrated to provide (S)-2-((4-(tert-butoxy)-4-oxobutanoyl)oxy)-4-ethoxy-4-oxobutanoic acid (1.47 g, 49%): $^1$H NMR (300 MHz, CDCl$_3$) δ 5.56 (t, J=6.0 Hz, 1H), 4.19 (q, J=7.1 Hz, 2H), 2.93 (d, J=6.0 Hz, 2H), 2.71-2.52 (m, 4H), 1.44 (s, 9H), 1.27 (t, J=7.1 Hz, 3H), CO$_2$H proton not observed.

Preparation of (S)-1-(2,5-Dioxopyrrolidin-1-yl) 4-ethyl 2-((4-(tert-butoxy)-4-oxobutanoyl)oxy)succinate A mixture of (S)-2-((4-(tert-butoxy)-4-oxobutanoyl)oxy)-4-ethoxy-4-oxobutanoic acid (1.40 g, 4.40 mmol) and N-hydroxysuccinimide (560 mg, 4.87 mmol) in tetrahydrofuran (25 mL) was treated with N,N'-dicyclohexylcarbodiimide (1.00 g, 4.85 mmol), and the reaction mixture was stirred at ambient temperature for 4 h. After this time, diethyl ether (20 mL) was added, and the mixture was filtered. The filtrate was concentrated under reduced pressure to provide (S)-1-(2,5-dioxopyrrolidin-1-yl) 4-ethyl 2-((4-(tert-butoxy)-4-oxobutanoyl)oxy)succinate (1.9 g) that was used without purification: $^1$H NMR (300 MHz, CDCl$_3$) δ 5.82 (dd, J=7.1, 5.2 Hz, 1H), 4.22 (dd, J=7.1 Hz, 2H), 3.05-3.03 (m, 2H), 2.84 (s, 4H), 2.72-2.65 (m, 2H), 2.60-2.53 (m, 2H), 1.44 (s, 9H), 2.28 (t, J=7.1 Hz, 3H).

925

Preparation of (S)-1-((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl) 4-ethyl 2-((4-(tert-butoxy)-4-oxobutanoyl)oxy)succinate

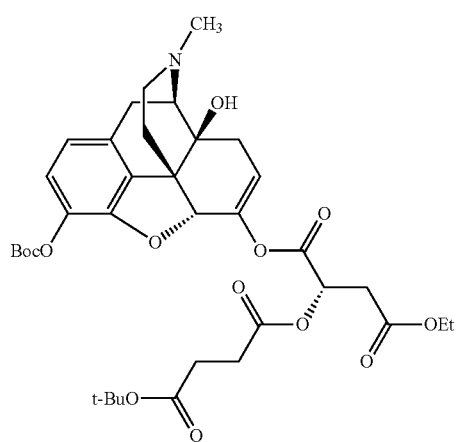

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled to 0° C. and treated dropwise with a 1.0 M solution of lithium bis(trimethylsilyl)amide in tetrahydrofuran (1.35 mL, 1.35 mmol). After addition was complete, the mixture was stirred at ambient temperature for 10 min. The mixture was re-cooled to 0° C. and (S)-1-(2,5-dioxopyrrolidin-1-yl) 4-ethyl 2-((4-(tert-butoxy)-4-oxobutanoyl)oxy)succinate (570 mg, 1.37 mmol) was added in one portion. The mixture was stirred at 0° C. for 1 h. After this time, the mixture was treated with saturated aqueous ammonium chloride and extracted with ethyl acetate. The combined organics were dried over sodium sulfate, filtered, and concentrated under reduced pressure. The residue was purified by reversed phase column chromatography (50 g C18 column, 5-100% acetonitrile/water) to provide (S)-1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 4-ethyl 2-((4-(tert-butoxy)-4-oxobutanoyl)oxy)succinate (384 mg, 44%): ESI MS m/z 702 [$C_{36}H_{47}NO_{13}$+H]$^+$.

926

Preparation of 4-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-4-ethoxy-1,4-dioxobutan-2-yl)oxy)-4-oxobutanoic acid trifluoroacetic acid salt

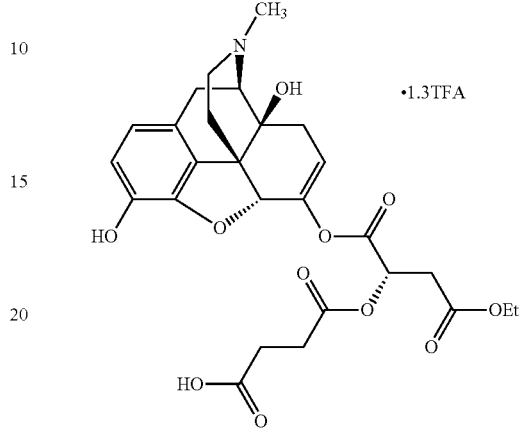

A solution of (S)-1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 4-ethyl 2-((4-(tert-butoxy)-4-oxobutanoyl)oxy)succinate (380 mg, 0.54 mmol) in methylene chloride (6 mL) was treated with trifluoroacetic acid (1.2 mL) and stirred at ambient temperature for 1.5 h. After this time, the reaction mixture was concentrated under reduced pressure. The residue was purified by reversed phase column chromatography (50 g C18 column, 3-20% acetonitrile/water, with 0.1% trifluoracetic acid) and freeze dried to provide 4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-ethoxy-1,4-dioxobutan-2-yl)oxy)-4-oxobutanoic acid trifluoroacetic acid salt (128 mg, 34%): $^1$H NMR (300 MHz, DMSO-$d_6$) δ 12.30 (br s, 1H), 9.30 (br s, 1H), 9.17 (br s, 1H), 6.68 (d, J=8.2 Hz, 1H), 6.63 (d, J=8.2 Hz, 1H), 6.27 (s, 1H), 5.60 (dd, J=6.0, 1.9 Hz, 1H), 5.45 (t, J=5.9 Hz, 1H), 4.93 (s, 1H), 4.14 (q, J=7.1 Hz, 2H), 3.62 (d, J=6.0 Hz, 1H), 3.14-2.98 (m, 4H), 2.84 (apparent d, J=4.7 Hz, 3H), 2.70-2.57 (m, 3H), 2.43 (dd, J=13.3, 4.5 Hz, 1H), 2.28 (dd, J=17.9, 6.0 Hz, 1H), 2.05 (d, J=17.9 Hz, 1H), 1.63 (d, J=11.1 Hz, 1H), 1.21 (t, J=7.1 Hz, 3H), three protons obscured by solvent peaks; ESI MS m/z 546 [$C_{27}H_{31}NO_{11}$+H]$^+$; HPLC (Method A) 97.4% (AUC), $t_R$=7.94 min.

Scheme 169: (S)-2-(((2R,3R)-2,3-Diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt

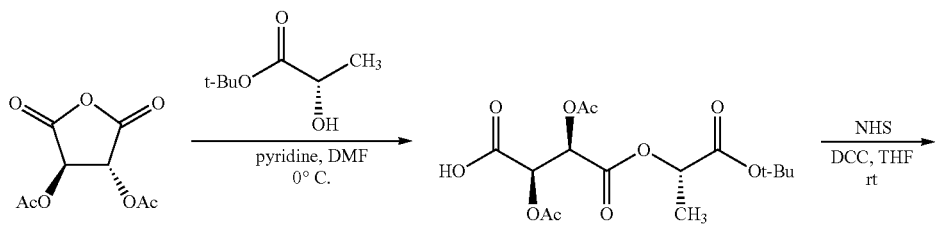

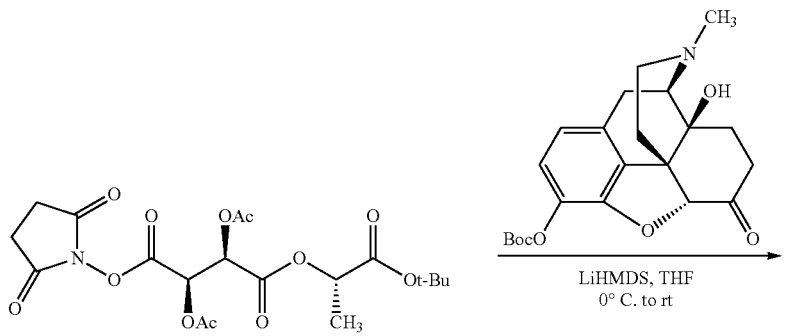

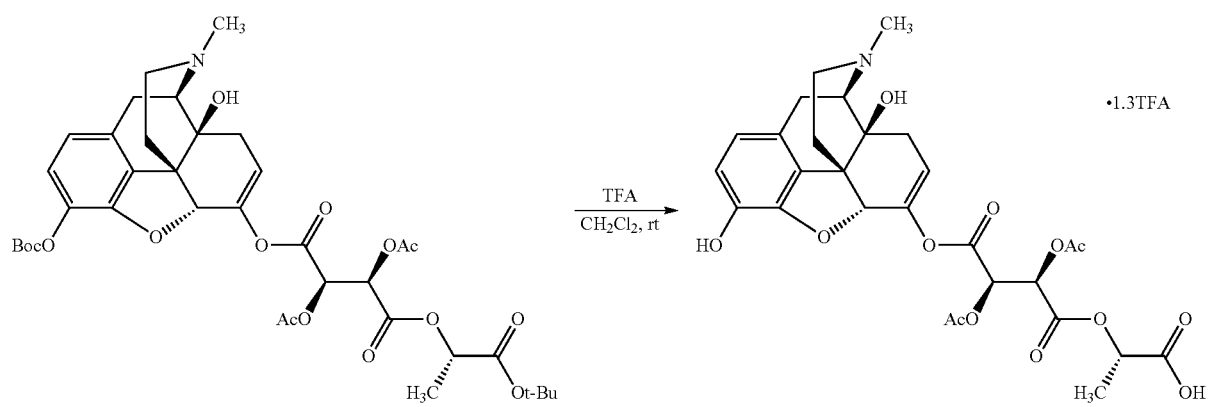

Preparation of (2R,3R)-2,3-Diacetoxy-4-(((S)-1-(tert-butoxy)-1-oxopropan-2-yl)oxy)-4-oxobutanoic acid

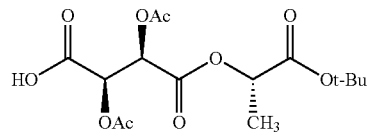

A solution of (3R,4R)-2,5-dioxotetrahydrofuran-3,4-diyl diacetate (1.25 g, 5.78 mmol) in N,N-dimethylformamide (1.5 mL) at 0° C. was treated with (S)-tert-butyl 2-hydroxypropanoate (675 mg, 4.62 mmol) followed by pyridine (0.36 mL, 4.47 mmol), and the mixture was stirred at 0° C. for 1 h. After this time, the reaction mixture was diluted with ethyl acetate and extracted with saturated sodium bicarbonate. The aqueous extracts were acidified with 6 N hydrochloric acid and then extracted with ethyl acetate. The organic extracts were dried over sodium sulfate, filtered, and concentrated to provide (2R,3R)-2,3-diacetoxy-4-(((S)-1-(tert-butoxy)-1-oxopropan-2-yl)oxy)-4-oxobutanoic acid (1.66 g, quantitative): $^1$H NMR (300 MHz, CDCl$_3$) δ 5.85 (d, J=2.6 Hz, 1H), 5.83 (d, J=2.6 Hz, 1H), 5.02 (q, J=7.0 Hz, 1H), 2.19 (s, 3H), 2.19 (s, 3H), 1.47-1.43 (m, 12H), CO$_2$H proton not observed.

Preparation of (2R,3R)-1-((S)-1-(tert-Butoxy)-1-oxopropan-2-yl) 4-(2,5-dioxopyrrolidin-1-yl) 2,3-diacetoxysuccinate

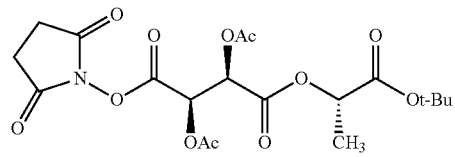 [SMILES: CC(=O)O[C@@H](C(=O)O[C@@H](C)C(=O)OC(C)(C)C)[C@@H](OC(C)=O)C(=O)ON1C(=O)CCC1=O]

A mixture of (2R,3R)-2,3-diacetoxy-4-(((S)-1-(tert-butoxy)-1-oxopropan-2-yl)oxy)-4-oxobutanoic acid (1.20 g, 3.31 mmol) and N-hydroxysuccinimide (410 mg, 3.56 mmol) in tetrahydrofuran (20 mL) was treated with N,N'-dicyclohexylcarbodiimide (740 mg, 3.58 mmol), and the reaction mixture was stirred at ambient temperature for 4 h. After this time, diethyl ether (20 mL) was added, and the mixture was filtered. The filtrate was concentrated under reduced pressure to provide (2R,3R)-1-((S)-1-(tert-butoxy)-1-oxopropan-2-yl) 4-(2,5-dioxopyrrolidin-1-yl) 2,3-diacetoxysuccinate (1.60 g) that was used without purification: $^1$H NMR (300 MHz, CDCl$_3$) δ 6.20 (d, J=2.7 Hz, 1H), 5.95 (d, J=2.7 Hz, 1H), 5.01 (q, J=7.0 Hz, 1H), 2.84 (s, 4H), 2.26 (s, 3H), 2.22 (s, 3H), 1.47-1.43 (m, 12H).

929

Preparation of (2R,3R)-1-((S)-1-(tert-Butoxy)-1-oxopropan-2-yl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2,3-diacetoxysuccinate

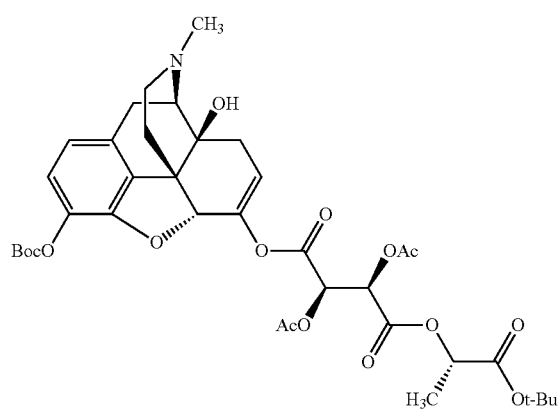

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled to 0° C. and treated dropwise with a 1.0 M solution of lithium bis(trimethylsilyl)amidein tetrahydrofuran (1.1 mL, 1.1 mmol). After addition was complete, the mixture was stirred at ambient temperature for 10 min. The mixture was re-cooled to 0° C., and (2R,3R)-1-((S)-1-(tert-butoxy)-1-oxopropan-2-yl) 4-(2,5-dioxopyrrolidin-1-yl) 2,3-diacetoxysuccinate (550 mg, 1.06 mmol) was added in one portion. The mixture was stirred at 0° C. for 45 min. After this time, the mixture was treated with saturated aqueous ammonium chloride, and extracted with ethyl acetate. The combined organics were dried over sodium sulfate, filtered, and concentrated under reduced pressure. The residue was purified by reversed phase column chromatography (50 g C18 column, 5-100% acetonitrile/water) to provide (2R,3R)-1-((S)-1-(tert-butoxy)-1-oxopropan-2-yl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2,3-diacetoxysuccinate (324 mg, 35%): ESI MS m/z 746 [$C_{37}H_{47}NO_{15}$+H]r.

930

Preparation of (S)-2-(((2R,3R)-2,3-Diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy) propanoic acid trifluoroacetic acid salt

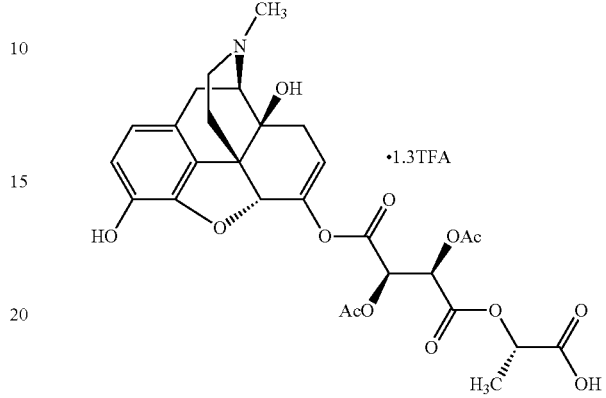

A solution of (2R,3R)-1-((S)-1-(tert-butoxy)-1-oxopropan-2-yl) 4-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2,3-diacetoxysuccinate (320 mg, 0.43 mmol) in methylene chloride (6 mL) was treated with trifluoroacetic acid (1.5 mL) and stirred at ambient temperature for 4 h. After this time, the reaction mixture was concentrated under reduced pressure. The residue was purified by reversed phase column chromatography (50 g C18 column, 3-20% acetonitrile/water, with 0.1% trifluoroacetic acid) and freeze dried to provide (S)-2-(((2R,3R)-2,3-diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)propanoic acid trifluoroacetic acid salt (154 mg, 49%): $^1$H NMR (300 MHz, DMSO-$d_6$) δ 9.37 (br s, 1H), 9.17 (br s, 1H), 6.68 (d, J=8.2 Hz, 1H), 6.63 (d, J=8.2 Hz, 1H), 6.33 (br s, 1H), 5.89 (d, J=2.7 Hz, 1H), 5.85 (d, J=2.7 Hz, 1H), 5.55-5.53 (m, 1H), 5.05 (q, J=7.0 Hz, 1H), 4.84 (s, 1H), 3.63 (d, J=6.2 Hz, 1H), 3.11-3.03 (m, 2H), 3.83 (apparent d, J=1.8 Hz, 3H), 2.71-2.57 (m, 1H), 2.47-2.39 (m, 1H), 2.43 (dd, J=18.0, 6.3 Hz, 1H), 2.22 (s, 3H), 2.15 (s, 3H), 2.07 (d, J=18.0 Hz, 1H), 1.62 (d, J=11.2 Hz, 1H), 1.39 (d, J=7.0 Hz, 3H), $CO_2H$ proton not observed; ESI MS m/z 590 [$C_{28}H_{31}NO_{13}$+H]$^+$; HPLC (Method A) 98.5% (AUC), $t_R$=8.04 min.

Scheme 170: (2R,3R)-2,3-Diacetoxy-4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt

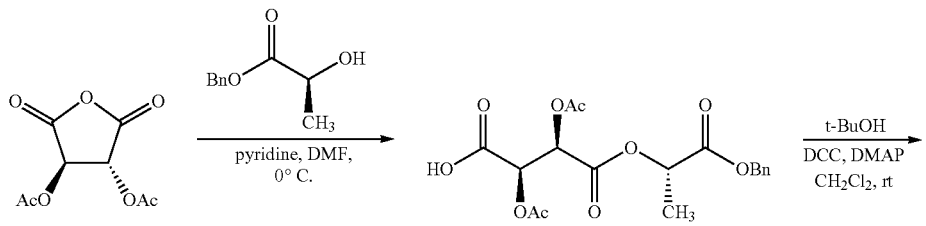

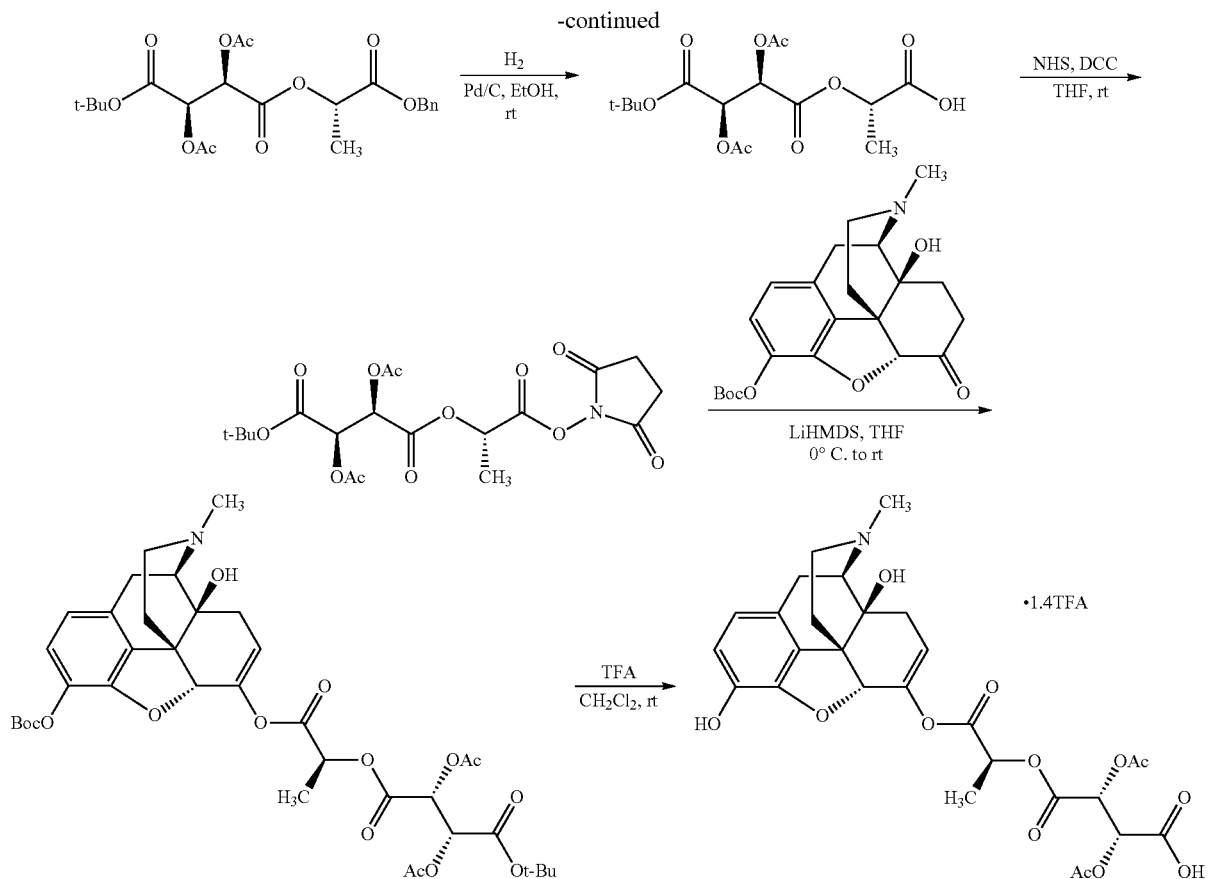

Preparation of (2R,3R)-2,3-Diacetoxy-4-(((S)-1-(benzyloxy)-1-oxopropan-2-yl)oxy)-4-oxobutanoic acid

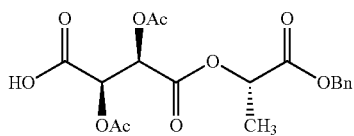

A solution of (3R,4R)-2,5-dioxotetrahydrofuran-3,4-diyl diacetate (1.85 g, 8.56 mmol) in N,N-dimethylformamide (2.2 mL) at 0° C. was treated with (S)-benzyl 2-hydroxypropanoate (1.30 g, 7.21 mmol) followed by pyridine (0.53 mL, 6.58 mmol), and the mixture was stirred at 0° C. for 1 h. After this time, the reaction mixture was diluted with ethyl acetate and extracted with saturated sodium bicarbonate. The aqueous layer was collected, carefully treated with 6 N hydrochloric acid until acidic by pH paper analysis, and then extracted with ethyl acetate. The organic extracts were dried over sodium sulfate, filtered and concentrated to give (2R,3R)-2,3-diacetoxy-4-(((S)-1-(benzyloxy)-1-oxopropan-2-yl)oxy)-4-oxobutanoic acid (2.80 g, 98%): $^1$H NMR (300 MHz, CDCl$_3$) δ 7.38-7.33 (m, 5H), 5.84-5.83 (m, 2H), 5.23-5.13 (m, 3H), 2.18 (s, 3H), 2.17 (s, 3H), 1.49 (d, J=7.1 Hz, 3H), CO$_2$H proton not observed.

Preparation of (2R,3R)-1-((S)-1-(Benzyloxy)-1-oxopropan-2-yl) 4-tert-butyl 2,3-diacetoxysuccinate

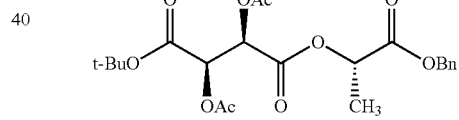

A mixture of (2R,3R)-2,3-diacetoxy-4-(((S)-1-(benzyloxy)-1-oxopropan-2-yl)oxy)-4-oxobutanoic acid (2.80 g, 7.07 mmol), tert-butanol (1.8 mL, 19 mmol), and 4-dimethylaminopyridine (280 mg, 2.29 mmol) in methylene chloride (16 mL) at 0° C. was treated with N,N'-dicyclohexylcarbodiimide (1.70 g, 8.24 mmol). The ice bath was removed, and the reaction mixture was stirred at ambient temperature for 4 h. After this time, the mixture was filtered, and the filtrate was concentrated under reduced pressure. The residue was purified by column chromatography (80 g silica gel column, 0-70% ethyl acetate/heptane) to provide (2R,3R)-1-((S)-1-(benzyloxy)-1-oxopropan-2-yl) 4-tert-butyl 2,3-diacetoxysuccinate (1.38 g, 43%): $^1$H NMR (300 MHz, CDCl$_3$) δ 7.38-7.31 (m, 5H), 5.85 (d, J=2.7 Hz, 1H), 5.69 (d, J=2.7 Hz, 1H), 5.23-5.13 (m, 3H), 2.17 (s, 3H), 2.16 (s, 3H), 1.49 (d, J=7.1 Hz, 3H), 1.45 (s, 9H).

Preparation of (S)-2-(((2R,3R)-2,3-Diacetoxy-4-(tert-butoxy)-4-oxobutanoyl)oxy)propanoic acid

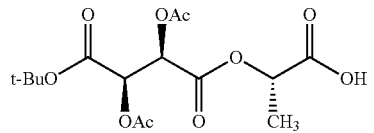 [SMILES: CC(=O)O[C@@H](C(=O)O[C@@H](C)C(=O)O)[C@@H](OC(C)=O)C(=O)OC(C)(C)C]

A mixture of (2R,3R)-1-((S)-1-(benzyloxy)-1-oxopropan-2-yl) 4-tert-butyl 2,3-diacetoxysuccinate (1.35 g, 2.99 mmol) and palladium (5% on carbon, 180 mg) in ethanol (15 mL) was stirred at room temperature under balloon pressure hydrogen for 2 h. After this time, the reaction mixture was purged with nitrogen and filtered through diatomaceous earth. The filtrate was concentrated under reduced pressure to provide (S)-2-(((2R,3R)-2,3-diacetoxy-4-(tert-butoxy)-4-oxobutanoyl)oxy)propanoic acid (1.01 g, 93%): $^1$H NMR (300 MHz, CDCl$_3$) δ 5.80 (d, J=2.7 Hz, 1H), 5.69 (d, J=2.7 Hz, 1H), 5.16 (q, J=7.1 Hz, 1H), 2.18 (s, 3H), 2.17 (s, 3H), 1.53 (d, J=7.1 Hz, 3H), 1.46 (s, 9H), CO$_2$H proton not observed.

Preparation of (2R,3R)-1-tert-Butyl 4-((S)-1-((2,5-dioxopyrrolidin-1-yl)oxy)-1-oxopropan-2-yl) 2,3-diacetoxysuccinate

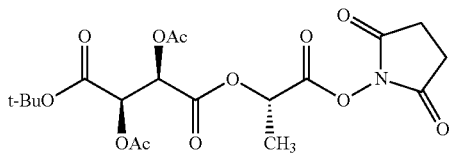 [SMILES: CC(=O)O[C@@H](C(=O)O[C@@H](C)C(=O)ON1C(=O)CCC1=O)[C@@H](OC(C)=O)C(=O)OC(C)(C)C]

A mixture of (S)-2-(((2R,3R)-2,3-diacetoxy-4-(tert-butoxy)-4-oxobutanoyl)oxy)propanoic acid (1.00 g, 2.76 mmol) and N-hydroxysuccinimide (350 mg, 3.04 mmol) in tetrahydrofuran (20 mL) was treated with N,N'-dicyclohexylcarbodiimide (627 mg, 3.04 mmol), and the reaction mixture was stirred at ambient temperature for 4 h. After this time, diethyl ether (20 mL) was added, and the mixture was filtered. The filtrate was concentrated under reduced pressure to provide (2R,3R)-1-tert-butyl 4-((S)-1-((2,5-dioxopyrrolidin-1-yl)oxy)-1-oxopropan-2-yl) 2,3-diacetoxysuccinate (960 mg, 76%) that was used without purification: $^1$H NMR (300 MHz, CDCl$_3$) δ 5.82 (d, J=2.7 Hz, 1H), 5.66 (d, J=2.7 Hz, 1H), 5.49 (q, J=7.1 Hz, 1H), 2.85 (s, 4H), 2.18 (s, 3H), 2.16 (s, 3H), 1.67 (d, J=7.1 Hz, 3H), 1.46 (s, 9H).

Preparation of (2R,3R)-1-((S)-1-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 4-tert-butyl 2,3-diacetoxysuccinate

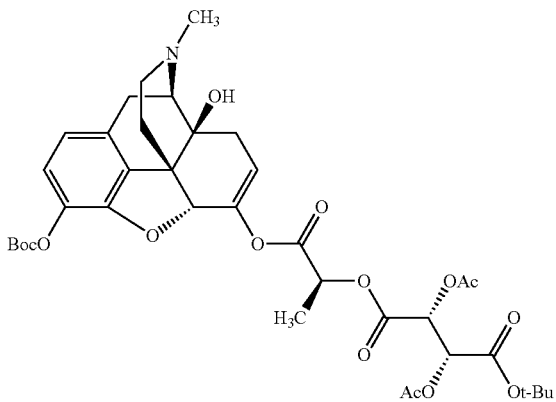

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (400 mg, 1.00 mmol) in tetrahydrofuran (8 mL) was cooled to 0° C. and treated dropwise with a 1.0 M solution of lithium bis(trimethylsilyl)amide in tetrahydrofuran (1.1 mL, 1.1 mmol). After addition was complete, the mixture was stirred at ambient temperature for 10 min. The mixture was re-cooled to 0° C., and (2R,3R)-1-tert-butyl 4-((S)-1-((2,5-dioxopyrrolidin-1-yl)oxy)-1-oxopropan-2-yl) 2,3-diacetoxysuccinate (500 mg, 1.09 mmol) was added in one portion. The mixture was stirred at 0° C. for 45 min. After this time, the mixture was treated with saturated aqueous ammonium chloride, and extracted with ethyl acetate. The combined organics were dried over sodium sulfate, filtered, and concentrated under reduced pressure. The residue was purified by reversed phase column chromatography (50 g C18 column, 5-100% acetonitrile/water) to provide (2R,3R)-1-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 4-tert-butyl 2,3-diacetoxysuccinate (280 mg, 38%): ESI MS m/z 746 [C$_{37}$H$_{47}$NO$_{15}$+H]$^+$.

Preparation of (2R,3R)-2,3-Diacetoxy-4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt

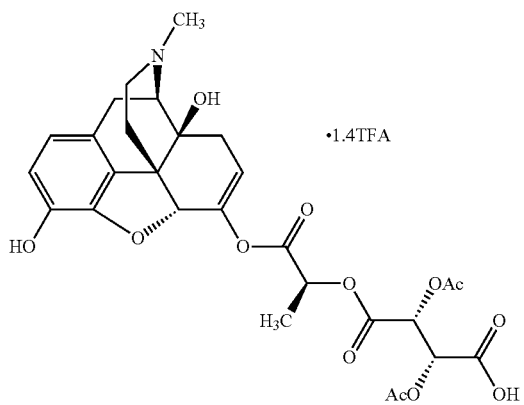 [SMILES: CC(=O)O[C@@H](C(=O)O)[C@@H](OC(C)=O)C(=O)O[C@@H](C)C(=O)OC1=CC[C@@]2(O)[C@H]3Cc4ccc(O)c5c4[C@@]2(CCN3C)[C@H]1O5]

A solution of (2R,3R)-1-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 4-tert-butyl 2,3-diacetoxysuccinate (280 mg, 0.38 mmol) in methylene chloride (5 mL) was treated with trifluoroacetic acid (1 mL) and stirred at ambient temperature for 5 h. After this time, the reaction mixture was concentrated under reduced pressure. The residue was purified by reversed phase column chromatography (50 g C18 column, 3-20% acetonitrile/water, with 0.1% trifluoroacetic acid) and freeze dried to provide (2R,3R)-2,3-diacetoxy-4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt (86 mg, 30%): $^1$H NMR (300 MHz, DMSO-d$_6$) δ 13.9 (br s, 1H), 9.29 (br s, 1H), 9.17 (br s 1H), 6.68 (d, J=8.2 Hz, 1H), 6.63 (d, J=8.2 Hz, 1H), 6.26 (s, 1H), 5.72 (d, J=2.8 Hz, 1H), 5.62 (d, J=2.8 Hz, 1H), 5.59 (dd, J=6.0, 2.2 Hz, 1H), 5.28 (q, J=7.0 Hz, 1H), 5.00 (s, 1H), 3.62 (d, J=6.3 Hz, 1H), 3.37 (d, J=20.0 Hz, 1H), 3.13-3.01 (m, 2H), 2.83 (apparent d, J=4.6 Hz, 3H), 2.70-2.57 (m, 1H), 2.43 (dd, J=14.5, 4.7 Hz, 1H), 2.29 (dd, J=17.9, 6.4 Hz, 1H), 2.14 (s, 3H), 2.11-2.02 (m, 4H), 1.63 (d, J=10.8 Hz, 1H), 1.50 (d, J=7.0 Hz, 3H); ESI MS m/z 590 [C$_{28}$H$_{31}$NO$_{13}$+H]$^+$; HPLC (Method A) 96.8% (AUC), t$_R$=7.82 min.

Scheme 171: (S)-3-Amino-4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt

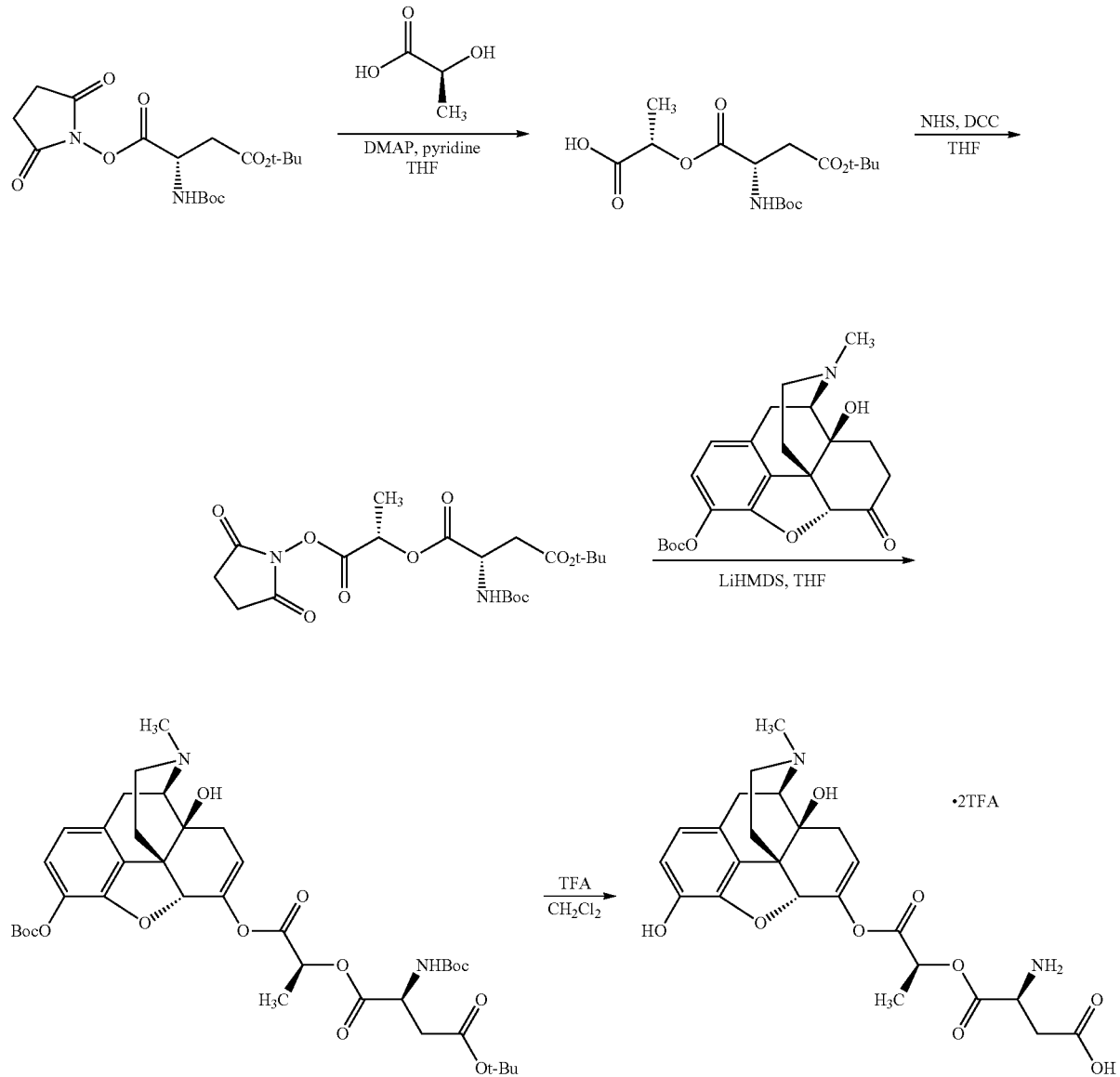

Preparation of (S)-2-(((S)-4-(tert-Butoxy)-2-((tert-butoxycarbonyl)amino)-4-oxobutanoyl)oxy)propanoic acid

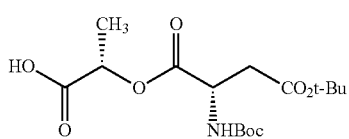 [SMILES: C[C@H](OC(=O)[C@H](CC(=O)OC(C)(C)C)NC(=O)OC(C)(C)C)C(=O)O]

(S)-Lactic acid (280 mg, 3.11 mmol), (S)-4-tert-butyl 1-(2,5-dioxopyrrolidin-1-yl) 2-((tert-butoxycarbonyl)amino)succinate (1.00 g, 2.59 mmol), 4-(dimethylamino) pyridine (32 mg, 0.259 mmol), pyridine (248 mg, 3.11 mmol), and tetrahydrofuran (17 mL) were combined and heated at 60° C. under a nitrogen atmosphere for 24 h. After this time, the solvent was removed under reduced pressure, and the residue was participated between ethyl acetate (30 mL) and 10% aqueous citric acid. The organic layer was separated and washed with water (50 mL), dried over sodium sulfate, filtered, and concentrated under reduced pressure to provide (S)-2-(((S)-4-(tert-butoxy)-2-((tert-butoxycarbonyl)amino)-4-oxobutanoyl)oxy)propanoic acid (858 mg, 91%) as a colorless oil: $^1$H NMR (300 MHz, CDCl$_3$) δ 5.51 (m, 1H), 4.58 (m, 1H), 2.96-2.69 (m, 2H), 1.55 (m, 3H), 1.45 (s, 18H), CO$_2$H and NH protons not observed.

Preparation of (S)-4-tert-Butyl 1-((S)-1-((2,5-dioxopyrrolidin-1-yl)oxy)-1-oxopropan-2-yl) 2-((tert-butoxycarbonyl)amino)succinate

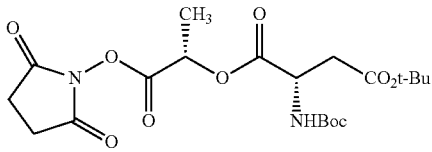 [SMILES: C[C@H](OC(=O)[C@H](CC(=O)OC(C)(C)C)NC(=O)OC(C)(C)C)C(=O)ON1C(=O)CCC1=O]

A solution of (S)-2-(((S)-4-(tert-butoxy)-2-((tert-butoxycarbonyl)amino)-4-oxobutanoyl)oxy)propanoic acid (858 mg, 2.37 mmol) in tetrahydrofuran (30 mL) was treated with N-hydroxysuccinimide (300 mg, 2.61 mmol) and N,N'-dicyclohexylcarbodiimide (538 mg, 2.61 mmol) and stirred at room temperature under a nitrogen atmosphere for 5 h. After this time, the reaction mixture was filtered to remove the solid dicyclohexylurea byproduct. The solid was washed with diethyl ether (50 mL), and the combined filtrate and washings were concentrated under reduced pressure. The residue was triturated with diethyl ether to provide (S)-4-tert-butyl 1-((S)-1-((2,5-dioxopyrrolidin-1-yl)oxy)-1-oxopropan-2-yl) 2-((tert-butoxycarbonyl)amino)succinate (1.24 g, quantitative) as a white solid: $^1$H NMR (300 MHz, CDCl$_3$) δ 5.52 (m, 1H), 4.63 (m, 1H), 2.97-2.73 (m, 6H), 1.68 (m, 3H), 1.45 (s, 18H); NH proton not observed.

Preparation of (S)-1-((S)-1-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 4-tert-butyl 2-((tert-butoxycarbonyl)amino)succinate

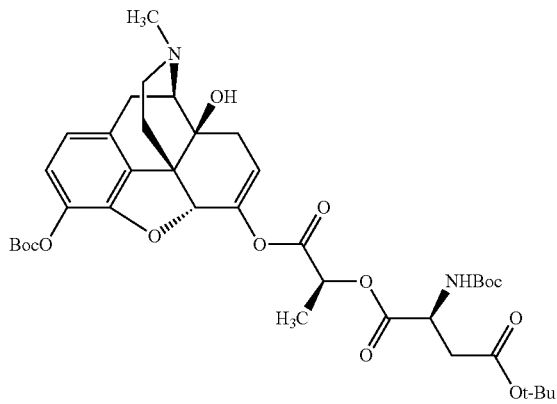

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at 0° C. for 1 h. The mixture was re-cooled to −45° C. and treated dropwise with a solution of (S)-4-tert-butyl 1-((S)-1-((2,5-dioxopyrrolidin-1-yl)oxy)-1-oxopropan-2-yl) 2-((tert-butoxycarbonyl)amino)succinate (628 mg, 1.37 mmol) in tetrahydrofuran (2.5 mL). After addition was complete, the mixture was warmed to 0° C. After this time, the reaction mixture was treated with saturated aqueous ammonium chloride (10 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-1-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 4-tert-butyl 2-((tert-butoxycarbonyl)amino)succinate (304 mg, 32%) as a white solid: ESI MS m/z 745 [C$_{36}$H$_{52}$N$_2$O$_{13}$+H]$^+$.

Preparation of (S)-3-Amino-4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt

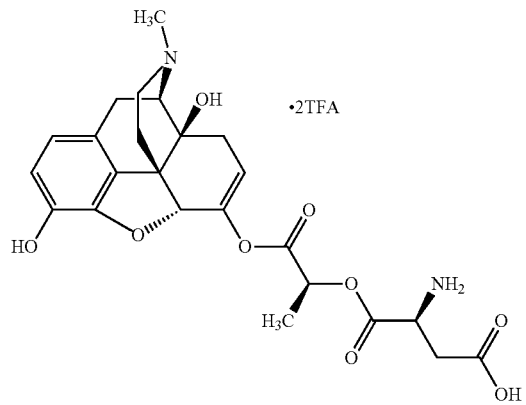

A solution of (S)-1-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 4-tert-butyl 2-((tert-butoxycarbonyl)amino)succinate (300 mg, 0.403 mmol) in methylene chloride (5.0 mL) was treated with trifluoroacetic acid (3.0 mL) and stirred under a nitrogen atmosphere at ambient temperature for 3 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-3-amino-4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-4-oxobutanoic acid trifluoroacetic acid salt (170 mg, 58%) as a fluffy white solid: $^1$H NMR (300 MHz, DMSO-d$_6$) δ 9.15 (br s, 2H), 8.44 (br s, 2H), 6.66 (apparent q, J=8.1 Hz, 2H), 6.26 (s, 2H), 5.59 (m, 1H), 5.33 (q, J=7.2 Hz, 1H), 4.98 (s, 1H), 4.45 (m, 1H), 3.35 (m, 2H), 3.11-2.88 (m, 4H), 2.84 (s, 3H), 2.73-2.42 (m, 3H), 2.29 (m, 1H), 2.06 (m, 1H), 1.64-1.53 (m, 4H); ESI MS m/z 489 [C$_{24}$H$_{28}$N$_2$O$_9$+H]$^+$.

Scheme 172: (2S,2′S)-4,4′-(((((4R,4aS,7aR,12bS)-9-Hydroxy-3-methyl-2,3,4,4a,5,7a-hexahydro-1H-4,12-methanobenzofuro[3,2-e]isoquinoline-4a,7-diyl)bis(oxy))bis(3-oxopropane-3,1-diyl))bis(azanediyl))bis(2-hydroxy-4-oxobutanoic acid trifluoroacetic acid salt
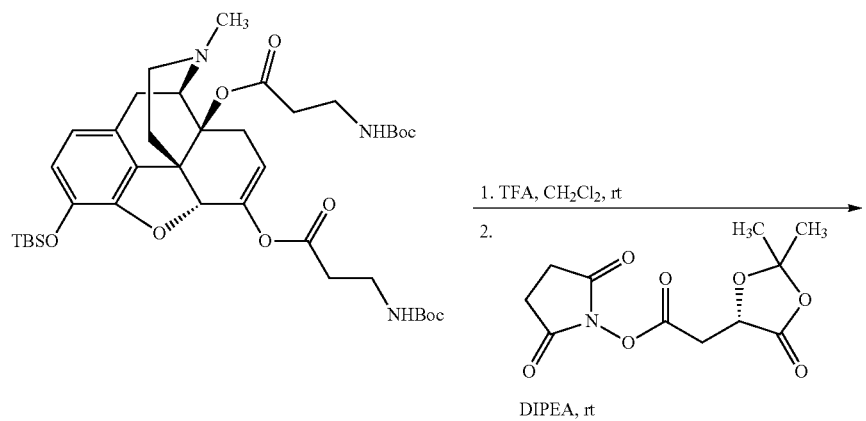
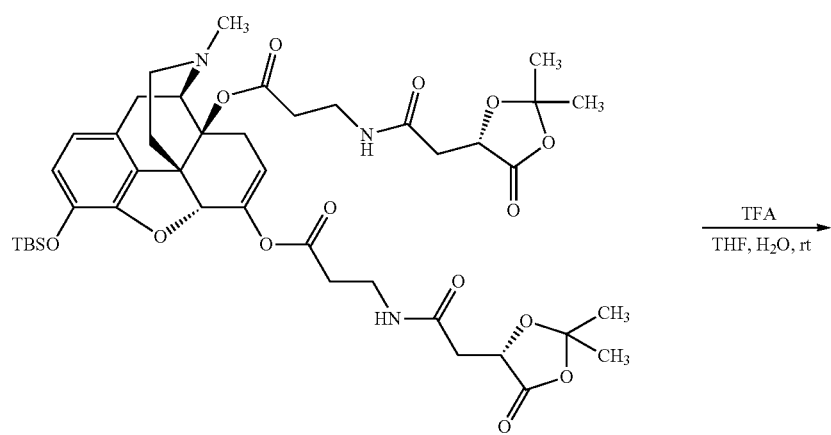
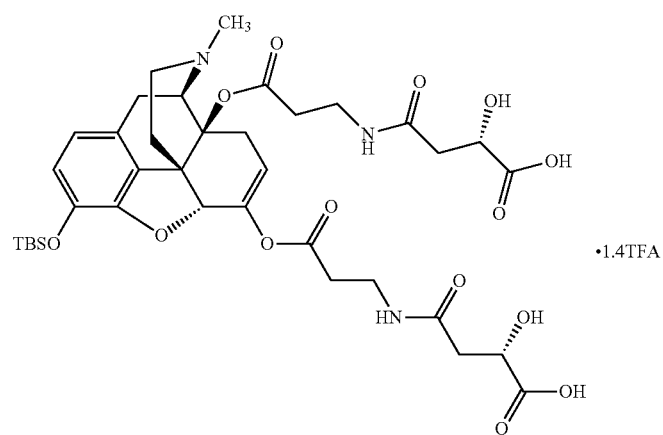

941

Preparation of (S)-(4R,4aS,7aR,12bS)-9-((tert-Butyldimethylsilyl)oxy)-3-methyl-2,3,4,4a,5,7a-hexahydro-1H-4,12-methanobenzofuro[3,2-e]isoquinoline-4a,7-d yl bis(3-(2-((S)-2,2-dimethyl-5-oxo-1,3-dioxolan-4-yl)acetamido)propanoate)

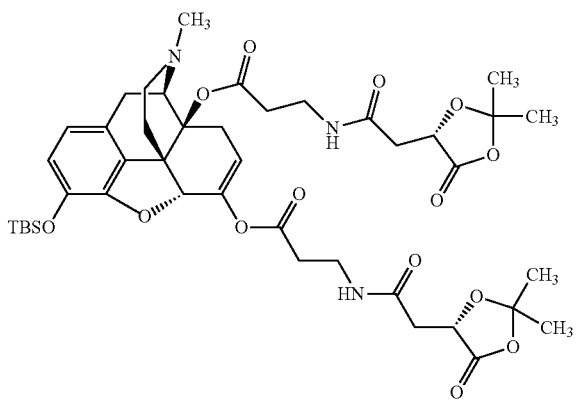

A solution of (4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl bis(3-((tert-butoxycarbonyl)amino)propanoate) (2.05 g, 2.70 mmol), in methylene chloride (30 mL) was treated with trifluoroacetic acid (3 mL) and the mixture was stirred at room temperature for 2 h. After this time, LC-MS analysis of the reaction mixture showed cleavage of the Boc protecting groups. N,N-Diisopropylethylamine was added slowly until the reaction mixture tested basic by pH paper analysis (~5 mL of base added). The mixture was treated with (S)-2,5-dioxopyrrolidin-1-yl 2-(2,2-dimethyl-5-oxo-1,3-dioxolan-4-yl)acetate (2.15 g, 7.93 mmol) in one portion and stirred at room temperature for 2 h. After this time, the mixture was diluted with ethyl acetate and washed with water and brine. The organic extracts were dried over sodium sulfate, filtered, and concentrated. The residue was purified by reversed phase column chromatography (150 g C18 column, 5-100% acetonitrile/water) to provide (S)-(4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl bis(3-(2-((S)-2,2-dimethyl-5-oxo-1,3-dioxolan-4-yl)acetamido)propanoate) (1.20 g, 51%): ESI MS m/z 870 $[C_{43}H_{59}N_3O_{14}Si+H]^+$.

942

Preparation of (2S,2'S)-4,4'-(((((4R,4aS,7aR,12bS)-9-Hydroxy-3-methyl-2,3,4,4a,5,7a-hexahydro-1H-4,12-methanobenzofuro[3,2-e]isoquinoline-4a,7-diyl)bis(oxy))bis(3-oxopropane-3,1-diyl))bis(azanediyl))bis(2-hydroxy-4-oxobutanoic acid) trifluoroacetic acid salt

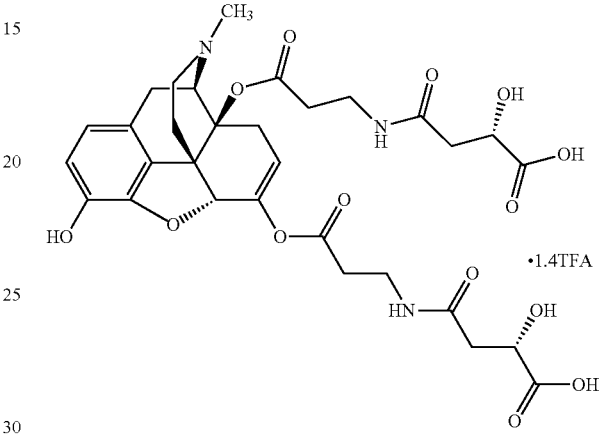

A solution of (S)-(4R,4aS,7aR,12bS)-9-((tert-butyldimethylsilyl)oxy)-3-methyl-2,3,4,4a,5,7a-hexahydro-1H-4,12-methanobenzofuro[3,2-e]isoquinoline-4a,7-diyl bis(3-(2-((S)-2,2-dimethyl-5-oxo-1,3-dioxolan-4-yl)acetamido)propanoate) (1.10 g, 1.26 mmol) in tetrahydrofuran (25 mL) was treated with water (12 mL) followed by trifluoroacetic acid (8 mL), and the mixture was stirred at room temperature for 3 h. After this time, the mixture was concentrated, and the residue was purified by reversed phase column chromatography (150 g C18 column, 3-20% acetonitrile/water, with 0.1% trifluoracetic acid) and freeze dried to provide (2S,2'S)-4,4'-(((((4R,4aS,7aR,12bS)-9-hydroxy-3-methyl-2,3,4,4a,5,7a-hexahydro-1H-4,12-methanobenzofuro[3,2-e]isoquinoline-4a,7-diyl)bis(oxy))bis(3-oxopropane-3,1-diyl))bis(azanediyl))bis(2-hydroxy-4-oxobutanoic acid) trifluoroacetic acid salt (277 mg, 26%): $^1$H NMR (300 MHz, DMSO-$d_6$) δ 12.5 (br s, 2H), 9.51-9.28 (m, 2H), 8.13 (t, J=5.7 Hz, 1H), 8.02 (t, J=5.5 Hz, 1H), 6.72 (d, J=8.2 Hz, 1H), 6.66 (d, J=8.2 Hz, 1H), 5.50 (dd, J=6.6, 1.7 Hz, 1H), 5.06 (s, 1H), 4.78-4.65 (m, 1H), 4.32-4.27 (m, 2H), 3.56-3.43 (m, 2H), 3.40-3.15 (m, 6H), 3.08-2.88 (m, 4H), 2.87-2.69 (m, 2H), 2.67-2.57 (m, 3H), 2.48-2.30 (m, 4H), 2.08 (d, J=18.8 Hz, 1H), 1.78 (d, J=12.9 Hz, 1H), two protons obscured by solvent peaks; ESI MS m/z 676 $[C_{31}H_{37}N_3O_{14}+H]^+$; HPLC (Method A) 97.2% (AUC), $t_R$=6.32 min.

Scheme 173: (S)-2-Acetoxy-4-((S)-2-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoroacetic acid salt

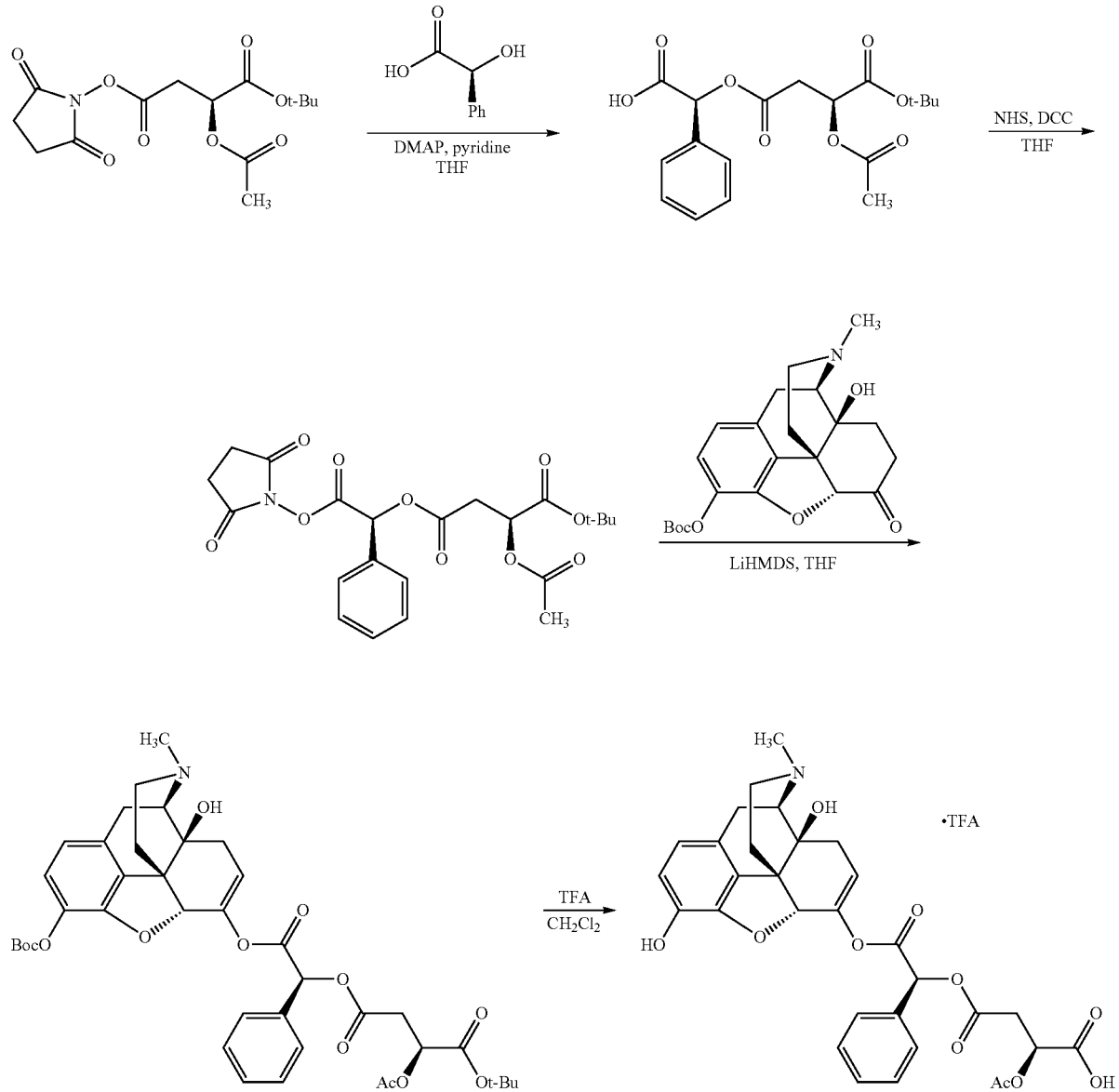

Preparation of (S)-2-(((S)-3-Acetoxy-4-(tert-butoxy)-4-oxobutanoyl)oxy)-2-phenylacetic acid

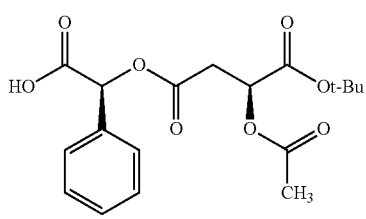 [SMILES: CC(=O)O[C@@H](CC(=O)O[C@H](C(=O)O)c1ccccc1)C(=O)OC(C)(C)C]

A solution of (S)-1-tert-butyl 4-(2,5-dioxopyrrolidin-1-yl) 2-acetoxysuccinate (1.66 g, 5.05 mmol), (S)-mandelic acid (861 mg, 5.66 mmol), and 4-dimethylaminopyridine (68 mg, 0.56 mmol) in tetrahydrofuran (30 mL) was treated with pyridine (0.82 mL, 10 mmol) and heated at 50° C. under a nitrogen atmosphere for 64 h. After this time, the reaction mixture was cooled to room temperature and concentrated under reduced pressure. The residue was dissolved in ethyl acetate (50 mL); washed with aqueous 10% citric acid (2×25 mL), water (25 mL), and brine (25 mL); dried over sodium sulfate; filtered; and concentrated under reduced pressure. The crude residue was purified by column chromatography (silica gel, 0-10% methanol/methylene chloride) to provide (S)-2-(((S)-3-acetoxy-4-(tert-butoxy)-4-oxobutanoyl)oxy)-2-phenylacetic acid (849 mg, 46%) as a colorless oil: $^1$H NMR (300 MHz, DMSO-d$_6$) δ 13.31 (s, 1H), 7.47-7.40 (m, 5H), 5.88 (s, 1H), 5.23 (dd, J=8.7, 4.2 Hz, 1H), 3.05 (dd, J=16.8, 4.2 Hz, 1H), 2.94 (dd, J=16.8, 8.7 Hz, 1H), 2.05 (s, 3H), 1.38 (s, 9H); ESI MS m/z 731 [(2×C$_{18}$H$_{22}$O$_8$)–H]$^-$.

Preparation of (S)-1-tert-Butyl 4-((S)-2-((2,5-dioxopyrrolidin-1-yl)oxy)-2-oxo-1-phenylethyl) 2-acetoxysuccinate

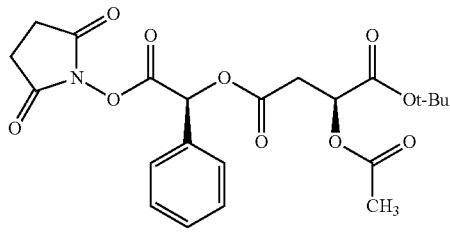 [SMILES: CC(=O)O[C@@H](CC(=O)O[C@H](C(=O)ON1C(=O)CCC1=O)c1ccccc1)C(=O)OC(C)(C)C]

A solution of (S)-2-(((S)-3-acetoxy-4-(tert-butoxy)-4-oxobutanoyl)oxy)-2-phenylacetic acid (845 mg, 2.31 mmol) in tetrahydrofuran (23 mL) was treated with N-hydroxysuccinimide (292 mg, 2.54 mmol) and N,N'-dicydohexylcarbodiimide (541 mg, 2.62 mmol) and stirred under a nitrogen atmosphere for 16 h. After this time, the reaction mixture was filtered to remove the solid dicyclohexylurea byproduct. The solid was washed with diethyl ether, and the combined filtrate and washings were concentrated under reduced pressure to provide (S)-1-tert-butyl 4-((S)-2-((2,5-dioxopyrrolidin-1-yl)oxy)-2-oxo-1-phenylethyl) 2-acetoxysuccinate (1.20 g, quantitative) as a white semi-solid: $^1$H NMR (300 MHz, DMSO-$d_6$) δ 7.59-7.56 (m, 2H), 7.50-7.47 (m, 3H), 6.57 (s, 1H), 5.22 (dd, J=8.1, 4.5 Hz, 1H), 3.10 (dd, J=16.8, 4.5 Hz, 1H), 3.00 (dd, J=16.8, 8.4 Hz, 1H), 2.78 (br s, 4H), 2.04 (s, 3H), 1.37 (s, 9H).

Preparation of (S)-4-((S)-2-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl) 1-tert-butyl 2-acetoxysuccinate

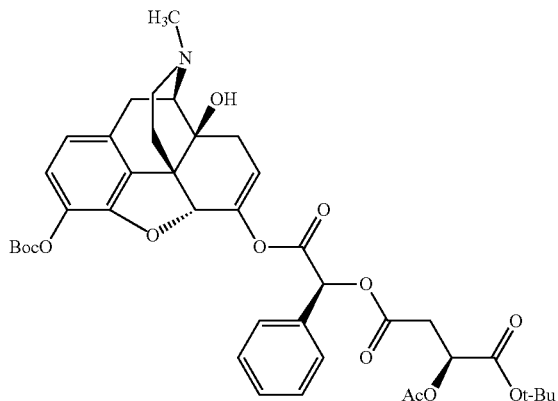

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (510 mg, 1.27 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at 0° C. for 1 h. The mixture was re-cooled to −45° C. and treated dropwise with a solution of (S)-1-tert-butyl 4-((S)-2-((2,5-dioxopyrrolidin-1-yl)oxy)-2-oxo-1-phenylethyl) 2-acetoxysuccinate (648 mg, 1.40 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-4-((S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl) 1-tert-butyl 2-acetoxysuccinate (382 mg, 40%) as a white solid: ESI MS m/z 750 $[C_{40}H_{47}NO_{13}+H]^+$.

Preparation of (S)-2-Acetoxy-4-((S)-2-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoroacetic acid salt

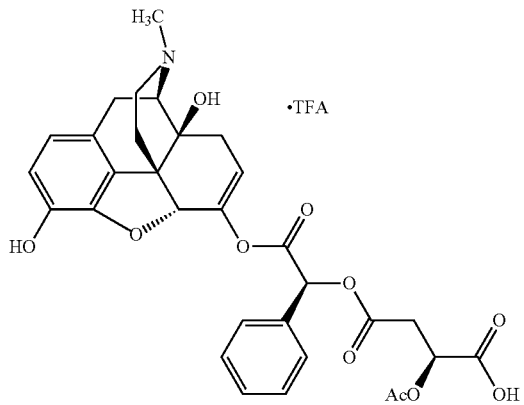

A solution of (S)-4-((S)-2-(((4R,4aS,7aR,12bS)-9-((tert-butoxycarbonyl)oxy)-4a-hydroxy-3-methyl-2,3,4,4a, 5,7a-hexahydro-1H-4,12-methanobenzofuro[3,2-e]isoquinolin-7-yl)oxy)-2-oxo-1-phenylethyl) 1-tert-butyl 2-acetoxysuccinate (190 mg, 0.253 mmol) in methylene chloride (5 mL) was treated with trifluoroacetic acid (3 mL) and stirred under a nitrogen atmosphere at ambient temperature for 2 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-2-acetoxy-4-((S)-2-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-oxo-1-phenylethoxy)-4-oxobutanoic acid trifluoroacetic acid salt (124 mg, 67%) as a fluffy white solid: $^1$H NMR (300 MHz, DMSO-$d_6$) δ 13.4 (br s, 1H), 9.28 (s, 1H), 9.14 (br s, 1H), 7.59-7.54 (m, 2H), 7.52-7.45 (m, 3H), 6.64 (apparent q, J=8.1 Hz, 2H), 6.25 (s, 1H), 6.17 (s, 1H), 5.60 (dd, J=5.7, 2.1 Hz, 1H), 5.31 (dd, J=8.7, 3.9 Hz, 1H), 4.87 (s, 1H), 3.62-3.33 (m, 2H), 3.14-2.96 (m, 4H), 2.82 (d, J=4.2 Hz, 3H), 2.64-2.38 (m, 2H), 2.25 (m, 1H), 2.09-2.02 (m, 4H), 1.60 (m, 1H); ESI MS m/z 594 $[C_{31}H_{31}NO_{11}+H]^+$.

Scheme 174: (R)-2-(((2R,3R)-2,3-Diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)succinic acid trifluoroacetic acid salt

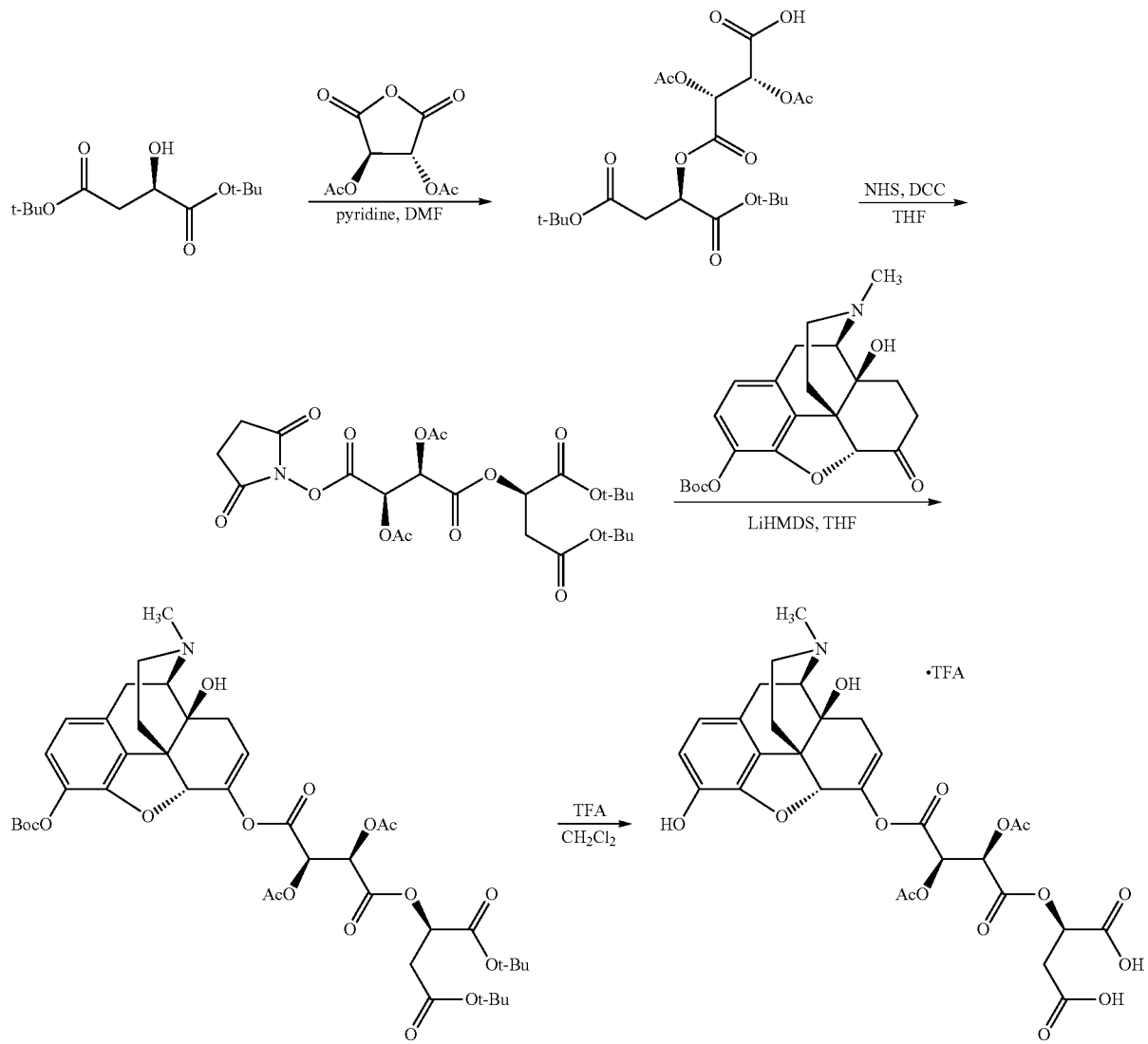

Preparation of (2R,3R)-2,3-Diacetoxy-4-(((R)-1,4-di-tert-butoxy-1,4-dioxobutan-2-yl)oxy)-4-oxobutanoic acid

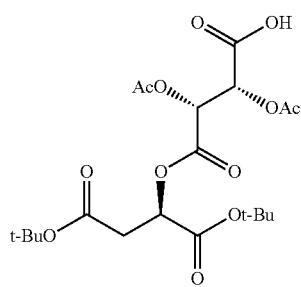 [SMILES: CC(=O)O[C@@H](C(=O)O)[C@@H](OC(C)=O)C(=O)O[C@H](CC(=O)OC(C)(C)C)C(=O)OC(C)(C)C]

(R)-Di-tert-butyl 2-hydroxysuccinate (1.60 g, 6.50 mmol), (3R,4R)-2,5-dioxotetrahydrofuran-3,4-diyl diacetate (1.76 g, 8.12 mmol), pyridine (462 mg, 5.85 mmol), and N,N-dimethylformamide (4 mL) were combined and stirred at 0° C. under a nitrogen atmosphere for 3 h. After this time, saturated sodium bicarbonate (15 mL) was added, and the resulting aqueous solution was washed with ethyl acetate (10 mL). The aqueous phase was collected and acidified to pH=3 with 6 N hydrochloric acid, and the mixture was extracted with ethyl acetate (2×20 mL). The combined organics were washed with brine (50 mL), dried over sodium sulfate, filtered, and concentrated under reduced pressure to provide (2R,3R)-2,3-diacetoxy-4-(((R)-1,4-di-tert-butoxy-1,4-dioxobutan-2-yl)oxy)-4-oxobutanoic acid (2.28 g, 75%) as a yellow oil: $^1$H NMR (300 MHz, CDCl$_3$) δ 5.80 (d, J=2.7 Hz, 1H), 5.75 (d, J=2.4 Hz, 1H), 5.36 (dd, J=7.8, 5.1 Hz, 1H), 2.78-2.74 (m, 2H), 2.21 (s, 3H), 2.19 (s, 3H), 1.46 (s, 9H), 1.44 (s, 9H), CO$_2$H proton not observed.

Preparation of (2R,3R)-1-((R)-1,4-Di-tert-butoxy-1,4-dioxobutan-2-yl) 4-(2,5-dioxopyrrolidin-1-yl) 2,3-diacetoxysuccinate

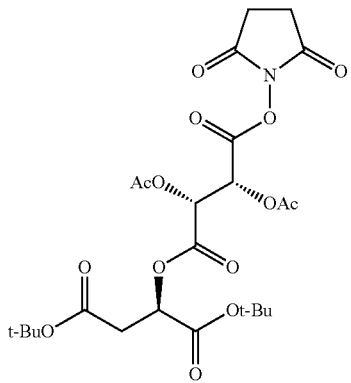 [SMILES: CC(=O)O[C@@H](C(=O)O[C@H](CC(=O)OC(C)(C)C)C(=O)OC(C)(C)C)[C@@H](OC(C)=O)C(=O)ON1C(=O)CCC1=O]

A solution of (2R,3R)-2,3-diacetoxy-4-(((R)-1,4-di-tert-butoxy-1,4-dioxobutan-2-yl)oxy)-4-oxobutanoic acid (2.28 g, 4.93 mmol) in tetrahydrofuran (40 mL) was treated with N-hydroxysuccinimide (624 mg, 5.42 mmol) and N,N'-dicyclohexylcarbodiimide (1.12 g, 5.42 mmol) and stirred under a nitrogen atmosphere for 4 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (2R,3R)-1-((R)-1,4-di-tert-butoxy-1,4-dioxobutan-2-yl) 4-(2,5-dioxopyrrolidin-1-yl) 2,3-diacetoxysuccinate (3.39 g, quantitative) as a yellow solid: $^1$H NMR (300 MHz, CDCl$_3$) δ 6.14 (d, J=3.0 Hz, 1H), 5.88 (d, J=3.0 Hz, 1H), 5.38 (dd, J=8.1, 3.3 Hz, 1H), 2.88-2.68 (m, 6H), 2.24 (s, 3H), 2.23 (s, 3H), 1.46 (s, 9H), 1.44 (s, 9H).

Preparation (2R,3R)-1-((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl) 4-((R)-1,4-di-tert-butoxy-1,4-dioxobutan-2-yl) 2,3-diacetoxysuccinate

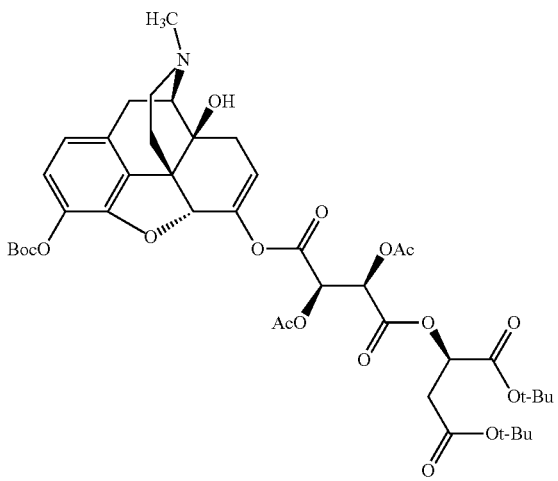

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (500 mg, 1.25 mmol) in tetrahydrofuran (10 mL) was cooled in an ice bath and treated dropwise with a 1.0 M solution of lithium bis(trimethylsilyl)amide in tetrahydrofuran (1.5 mL, 1.5 mmol). After addition was complete, the mixture was stirred at ambient temperature for 15 min. The mixture was re-cooled to −45° C. and treated dropwise with a solution of (2R,3R)-1-((R)-1,4-di-tert-butoxy-1,4-dioxobutan-2-yl) 4-(2,5-dioxopyrrolidin-1-yl) 2,3-diacetoxysuccinate (766 mg, 1.37 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×25 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (2R,3R)-1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 4-((S)-1,4-di-tert-butoxy-1,4-dioxobutan-2-yl) 2,3-diacetoxysuccinate (288 mg, 27%) as a white solid: ESI MS m/z 846 [C$_{42}$H$_{55}$NO$_{17}$+H]$^+$.

Preparation of (R)-2-(((2R,3R)-2,3-Diacetoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)succinic acid trifluoroacetic acid salt

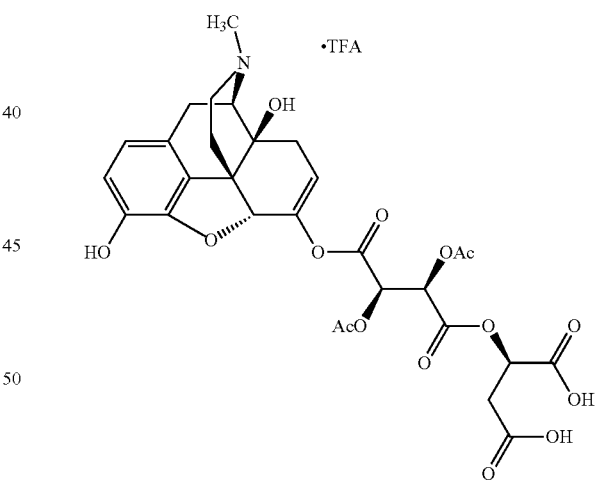

A solution of (2R,3R)-1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 4-((R)-1,4-di-tert-butoxy-1,4-dioxobutan-2-yl) 2,3-diacetoxysuccinate (288 mg, 0.340 mmol) in methylene chloride (5.0 mL) was treated with trifluoroacetic acid (5.0 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (R)-2-(((2R,3R)-2,3-diac-

951 etoxy-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-4-oxobutanoyl)oxy)succinic acid trifluoroacetic acid salt (175 mg, 68%) as a fluffy white solid: $^1$H NMR (300 MHz, DMSO-$d_6$) δ 13.5 (br s, 1H), 12.8 (br s, 1H), 9.36 (s, 1H), 9.16 (br s, 1H), 6.65 (apparent q,

952

J=8.1 Hz, 2H), 6.28 (br s, 1H), 5.82 (d, J=2.4 Hz, 1H), 5.78 (d, J=2.4 Hz, 1H), 5.54 (dd, J=6.0, 1.8 Hz, 1H), 5.35 (dd, J=7.5, 3.9 Hz, 1H), 4.84 (s, 1H), 3.62-3.34 (m, 2H), 3.02 (m, 1H), 2.93-2.72 (m, 5H), 2.63-2.40 (m, 3H), 2.27 (m, 1H), 2.22 (s, 3H), 2.11 (s, 3H), 2.07 (m, 1H), 1.62 (m, 1H); ESI MS m/z 634 $[C_{29}H_{31}NO_{15}+H]^+$.

Scheme 175: (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((3-((S)-2-acetamido-6-aminohexanamido)propanoyl)oxy)propanoate trifluoroacetic acid salt

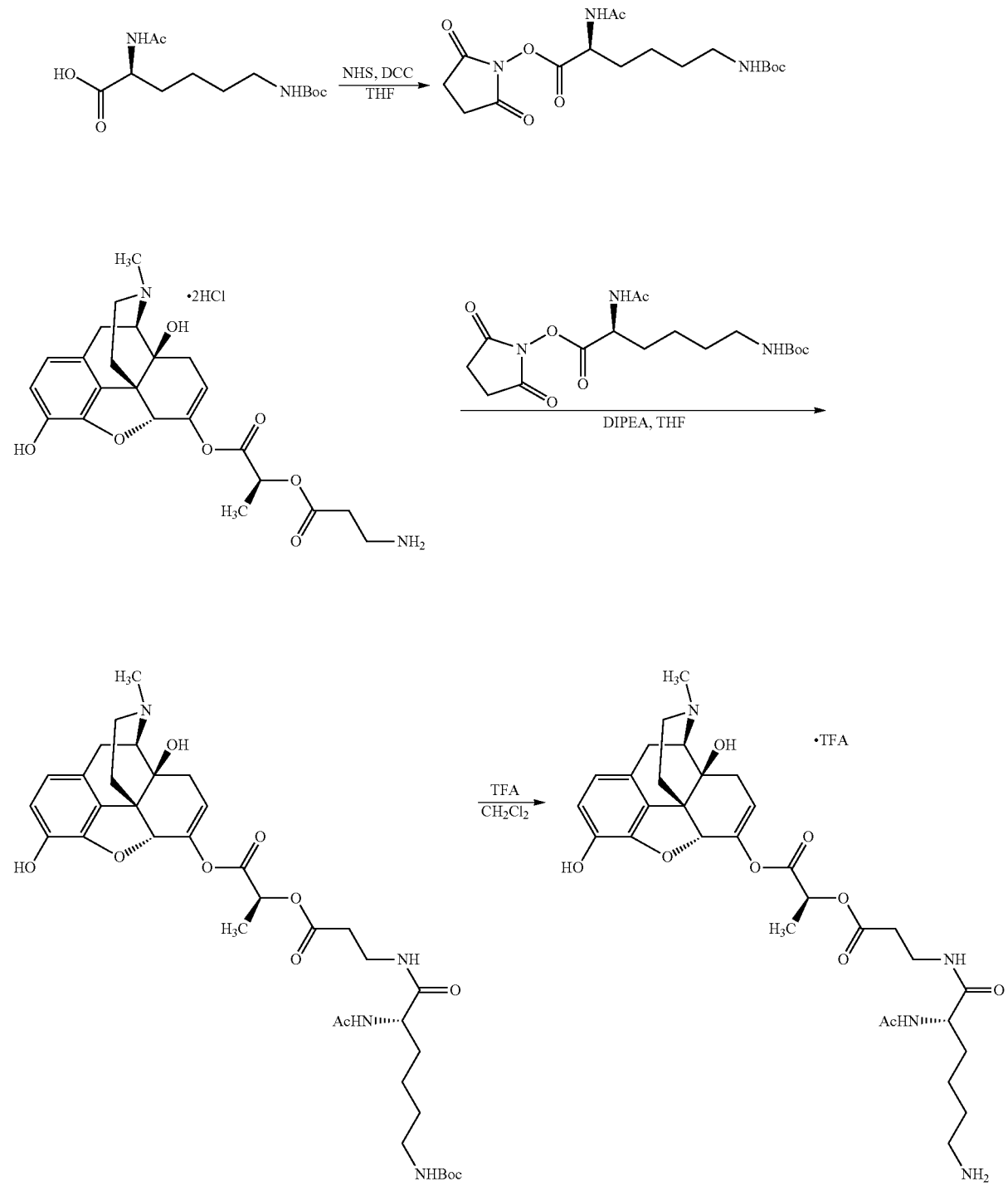

Preparation of (S)-2,5-Dioxopyrrolidin-1-yl 2-acet-amido-6-((tert-butoxycarbonyl)amino)hexanoate

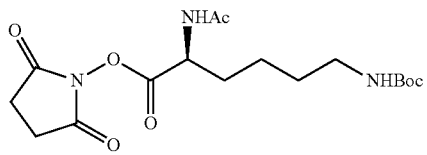 [SMILES: CC(=O)N[C@@H](CCCCNC(=O)OC(C)(C)C)C(=O)ON1C(=O)CCC1=O]

A solution of (S)-2-acetamido-6-((tert-butoxycarbonyl) amino)hexanoic acid (1.00 g, 3.47 mmol) in tetrahydrofuran (20 mL) was treated with N-hydroxysuccinimide (439 mg, 3.81 mmol) and N,N'-dicyclohexylcarbodiimide (785 mg, 3.81 mmol) and stirred under a nitrogen atmosphere for 2 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-2,5-dioxopyrrolidin-1-yl 2-acetamido-6-((tert-butoxycarbonyl)amino)hexanoate (1.49 mg) as a white solid: $^1$H NMR (300 MHz, CDCl$_3$) δ 6.27 (m, 1H), 4.94 (m, 1H), 4.69 (m, 1H), 3.15-3.13 (m, 2H), 2.87 (s, 4H), 2.08 (s, 3H), 2.02-1.83 (m, 2H), 1.55-1.22 (m, 4H), 1.45 (s, 9H).

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((3-((S)-2-acetamido-6-((tert-butoxycarbonyl)amino)hexanamido)propanoyl)oxy)propanoate

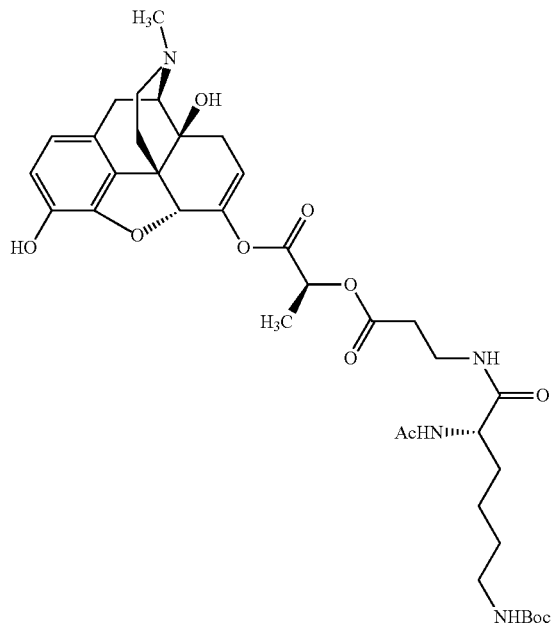

A solution of (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-aminopropanoyl)oxy)propanoate hydrochloride (121 mg, 0.233 mmol) in tetrahydrofuran (6 mL) was treated with (S)-2,5-dioxopyrrolidin-1-yl 2-acetamido-6-((tert-butoxycarbonyl)amino) hexanoate (90 mg, 0.23 mmol) and N,N-diisopropylethylamine (60 mg, 0.47 mmol) at 0° C. and stirred under a nitrogen atmosphere for 1 h. After this time the reaction mixture was concentrated under reduced pressure. The residue was purified by column chromatography (40 g silica gel column, 0-20% methanol/methylene chloride) to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-((S)-2-acetamido-6-((tert-butoxycarbonyl)amino)hexanamido)propanoyl)oxy)propanoate (126 mg, 75%) as a white solid: ESI MS m/z 715 [C$_{36}$H$_{50}$N$_4$O$_{11}$+H]$^+$.

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((3-((S)-2-acetamido-6-aminohexanamido)propanoyl)oxy)propanoate trifluoroacetic acid salt

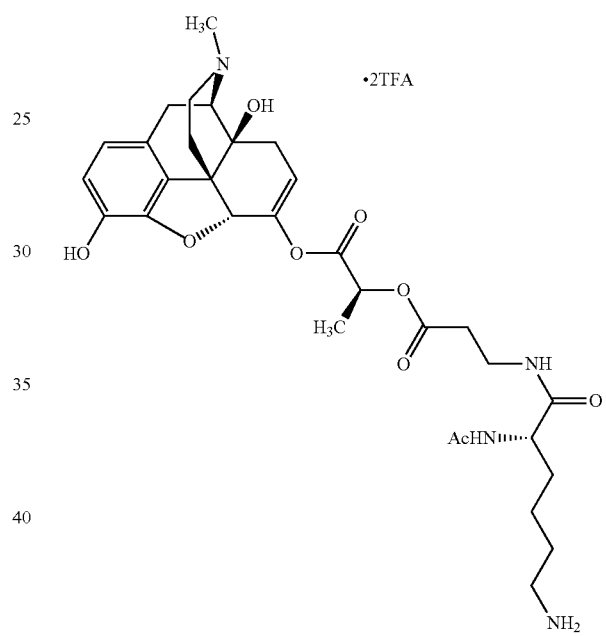

A solution of (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-((S)-2-acetamido-6-((tert-butoxycarbonyl)amino)hexanamido)propanoyl)oxy) propanoate (126 mg, 0.176 mmol) in methylene chloride (3 mL) was treated with trifluoroacetic acid (3 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-((S)-2-acetamido-6-aminohexanamido)propanoyl)oxy)propanoate trifluoroacetic acid salt (51 mg, 32%) as a fluffy white solid: $^1$H NMR (300 MHz, DMSO-d$_6$) δ 9.30 (s, 1H), 9.16 (br s, 1H), 8.05-7.98 (m, 2H), 7.64 (br s, 3H), 6.65 (apparent q, J=8.1 Hz, 2H), 6.25 (s, 2H), 5.58 (dd, J=5.7, 1.8 Hz, 1H), 5.10 (q, J=7.2 Hz, 1H), 4.96 (s, 1H), 4.15 (m, 1H), 3.67-3.27 (m, 4H), 3.11-3.03 (m, 2H), 2.84 (d, J=4.8 Hz, 3H), 2.78-

2.72 (m, 2H), 2.67-2.46 (m, 2H), 2.29 (m, 1H), 2.06 (m, 1H), 1.84 (s, 3H), 1.65-1.25 (m, 11H); ESI MS m/z 615 [C$_{31}$H$_{42}$N$_4$O$_9$+H]$^+$.

Scheme 176: (2R,3R)-4-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-2,3-dihydroxy-4-oxobutanoic acid trifluoroacetic acid salt

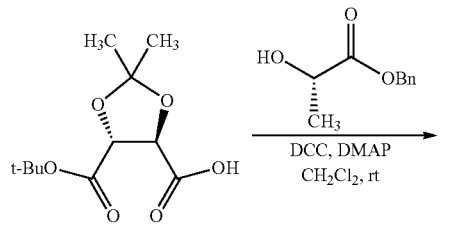

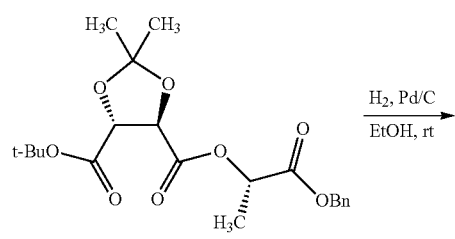

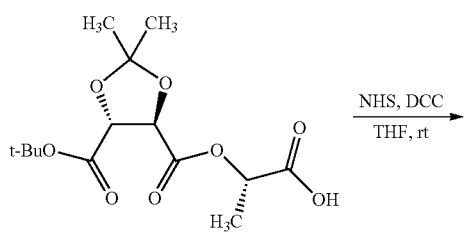

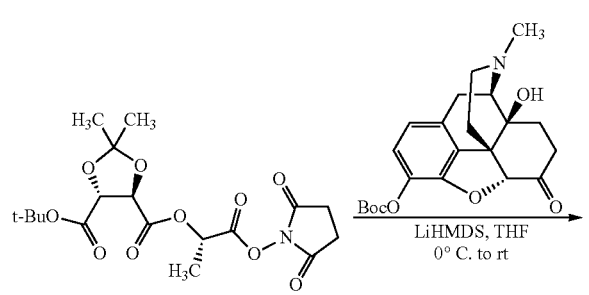

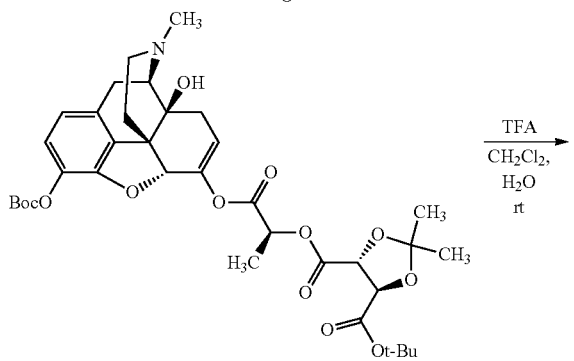

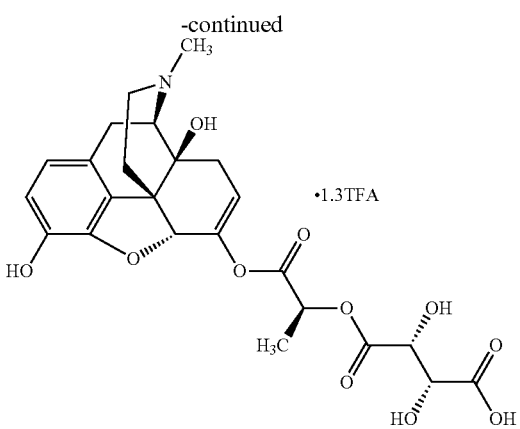

Preparation of (4R,5R)-4-((S)-1-(Benzyloxy)-1-oxopropan-2-yl) 5-tert-butyl 2,2-dimethyl-1,3-dioxolane-4,5-dicarboxylate

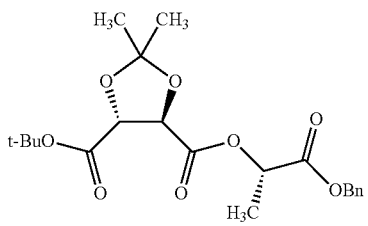 [SMILES: C[C@H](OC(=O)[C@@H]1OC(C)(C)O[C@H]1C(=O)OC(C)(C)C)C(=O)OCc1ccccc1]

A mixture of (4S,5S)-5-(tert-butoxycarbonyl)-2,2-dimethyl-1,3-dioxolane-4-carboxylic acid (1.00 g, 4.07 mmol), (S)-benzyl 2-hydroxypropanoate (1.20 g, 6.66 mmol), and 4-dimethylaminopyridine (150 mg, 1.23 mmol) in methylene chloride (10 mL) was treated with N,N'-dicyclohexylcarbodiimide (1.10 g, 5.33 mmol), and the reaction mixture was stirred at ambient temperature for 18 h. After this time, the mixture was filtered, and the filtrate was concentrated under reduced pressure. The residue was purified by column chromatography (40 g silica gel column, 0-50% ethyl acetate/heptane) to provide (4S,5S)-4-((S)-1-(benzyloxy)-1-oxopropan-2-yl) 5-tert-butyl 2,2-dimethyl-1,3-dioxolane-4,5-dicarboxylate (780 mg, 47%): $^1$H NMR (300 MHz, CDCl$_3$) δ 7.39-7.32 (m, 5H), 5.23 (q, J=7.1 Hz, 1H), 5.18 (s, 2H), 4.77 (d, J=5.7 Hz, 1H), 4.65 (d, J=5.7 Hz, 1H), 1.56 (d, J=7.1 Hz, 3H), 1.52-1.49 (m, 15H).

Preparation of (S)-2-(((4R,5R)-5-(tert-Butoxycarbonyl)-2,2-d methyl-1,3-dioxolane-4-carbonyl)oxy) propanoic acid

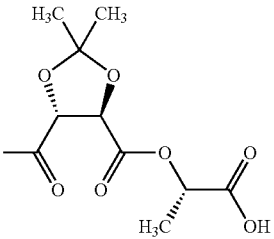

A mixture of (4S,5S)-4-((S)-1-(benzyloxy)-1-oxopropan-2-yl) 5-tert-butyl 2,2-dimethyl-1,3-dioxolane-4,5-dicarboxylate (770 mg, 1.89 mmol) and palladium (10% on carbon, 200 mg) in ethanol (25 mL) was stirred at room temperature under balloon pressure hydrogen for 2 h. After this time, the reaction mixture was purged with nitrogen and filtered through diatomaceous earth. The filtrate was concentrated under reduced pressure to provide (S)-2-(((4S,5S)-5-(tert-butoxycarbonyl)-2,2-dimethyl-1,3-dioxolane-4-carbonyl)oxy)propanoic acid: $^1$H NMR (300 MHz, CDCl$_3$) δ 5.20 (q, J=7.0 Hz, 1H), 4.77 (d, J=5.7 Hz, 1H), 4.67 (d, J=5.7 Hz, 1H), 1.59 (d, J=7.0 Hz, 3H), 1.53-1.48 (m, 15H), CO$_2$H proton not observed.

Preparation of (4R,5R)-4-tert-Butyl 5-((S)-1-((2,5-dioxopyrrolidin-1-yl)oxy)-1-oxopropan-2-yl) 2,2-dimethyl-1,3-dioxolane-4,5-dicarboxylate

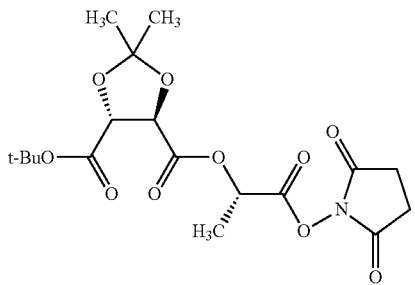 [SMILES: C[C@H](OC(=O)[C@@H]1OC(C)(C)O[C@H]1C(=O)OC(C)(C)C)C(=O)ON1C(=O)CCC1=O]

A mixture of (S)-2-(((4S,5S)-5-(tert-butoxycarbonyl)-2,2-dimethyl-1,3-dioxolane-4-carbonyl)oxy)propanoic acid (580 mg, 1.82 mmol) and N-hydroxysuccinimide (230 mg, 2.00 mmol) in tetrahydrofuran (15 mL) was treated with N,N'-dicyclohexylcarbodiimide (413 mg, 2.00 mmol), and the reaction mixture was stirred at ambient temperature for 4 h. After this time, diethyl ether (15 mL) was added, and the mixture was filtered. The filtrate was concentrated under reduced pressure to provide (4S,5S)-4-tert-butyl 5-((S)-1-((2,5-dioxopyrrolidin-1-yl)oxy)-1-oxopropan-2-yl) 2,2-dimethyl-1,3-dioxolane-4,5-dicarboxylate (960 mg, 76%) that was used without purification: $^1$H NMR (300 MHz, CDCl$_3$) δ 5.53 (q, J=7.1 Hz, 1H), 4.80 (d, J=5.6 Hz, 1H), 4.70 (d, J=5.6 Hz, 1H), 2.85 (s, 4H), 1.75 (d, J=7.1 Hz, 3H), 1.52-1.49 (m, 15H).

Preparation of (4R,5R)-4-((S)-1-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 5-tert-butyl 2,2-dimethyl-1,3-dioxolane-4,5-d carboxylate

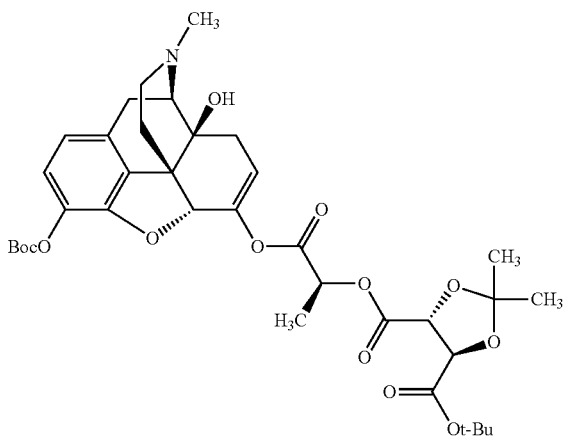

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (600 mg, 1.50 mmol) in tetrahydrofuran (8 mL) was cooled to 0° C. and treated dropwise with a 1.0 M solution of lithium bis(trimethylsilyl)amide in tetrahydrofuran (1.6 mL, 1.6 mmol). After addition was complete, the mixture was stirred at ambient temperature for 10 min. The mixture was re-cooled to 0° C. and (4S,5S)-4-tert-butyl 5-((S)-1-((2,5-dioxopyrrolidin-1-yl)oxy)-1-oxopropan-2-yl) 2,2-dimethyl-1,3-dioxolane-4,5-dicarboxylate (600 mg, 1.45 mmol) was added in one portion. The mixture was stirred at 0° C. for 45 min. After this time, the mixture was treated with saturated aqueous ammonium chloride and extracted with ethyl acetate. The combined organics were dried over sodium sulfate, filtered, and concentrated under reduced pressure. The residue was purified by reverse phase column chromatography (50 g C18 column, 5-100% acetonitrile/water) to provide (4R,5R)-4-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 5-tert-butyl 2,2-dimethyl-1,3-dioxolane-4,5-dicarboxylate (495 mg, 49%): ESI MS m/z 702 [C$_{36}$H$_{47}$NO$_{13}$+H]$^+$.

Preparation of (2R,3R)-4-(((S)-1-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-2,3-dihydroxy-4-oxobutanoic acid trifluoroacetic acid salt

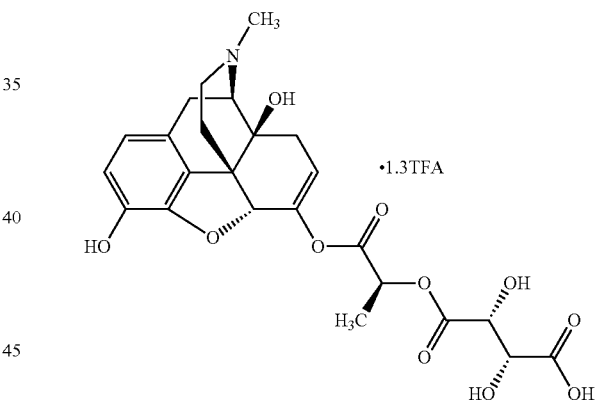

A solution of (4R,5R)-4-((S)-1-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-1-oxopropan-2-yl) 5-tert-butyl 2,2-dimethyl-1,3-dioxolane-4,5-dicarboxylate (495 mg, 0.706 mmol) in methylene chloride (10 mL) was treated with trifluoroacetic acid (2 mL), and the mixture was stirred at room temperature for 1 h. LC-MS analysis of the reaction mixture indicated cleavage of the Boc and tert-butyl protecting groups. Water (0.1 mL) was added, and the mixture was stirred at ambient temperature for 6 h. After this time, the reaction mixture was concentrated under reduced pressure. The residue was purified by reversed phase column chromatography (50 g C18 column, 3-20% acetonitrile/water, with 0.1% trifluoracetic acid) and freeze dried to provide (2R,3R)-4-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-2,3-dihydroxy-4-oxobutanoic acid trifluoroacetic acid salt (163 mg, 41%): ¹H NMR (300 MHz, DMSO-d₆) δ 12.83 (br s, 1H), 9.30 (br s, 1H), 9.17 (br s, 1H), 6.69 (d, J=8.1 Hz, 1H), 6.63 (d, J=8.1 Hz, 1H), 6.27 (s, 1H), 5.60 (dd, J=6.0, 2.0 Hz, 1H), 5.18 (q, J=7.0 Hz, 1H), 4.99 (s, 1H), 4.48 (d, J=2.2 Hz, 1H), 4.39 (d. J=2.1 Hz, 1H), 3.63 (d, J=6.3 Hz, 1H), 3.38 (d, J=20.0 Hz, 1H), 3.14-3.00 (m, 2H), 2.84 (apparent d, J=4.2 Hz, 3H), 2.70-2.57 (m, 1H), 2.44 (dd, J=13.6, 4.9 Hz, 1H), 2.29 (dd, J=17.9, 6.1 Hz, 1H), 2.07 (d, J=17.9 Hz, 1H), 1.63 (d, J=11.3 Hz, 1H), 1.53 (d, J=7.0 Hz, 3H), two protons obscured by solvent peaks; ESI MS m/z 506 [C₂₄H₂₇NO₁₁+H]⁺; HPLC (Method A) 94.4% (AUC), $t_R$=6.71 min.

Scheme 177: (S)-2-(((S)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-3-hydroxy-4-oxobutanoyl)oxy)propanoic acid trifluoroacetic acid salt

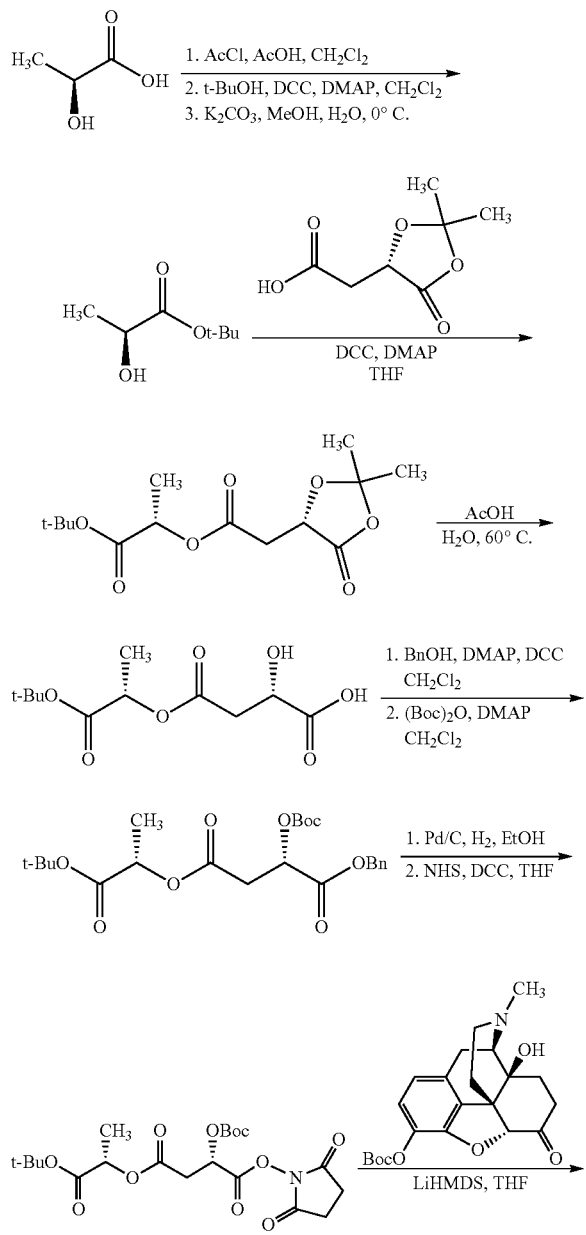

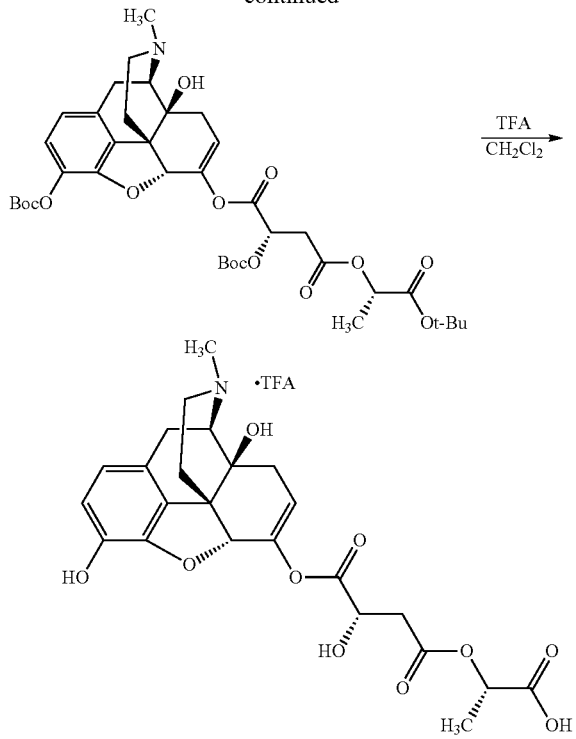

Preparation of (S)-tert-Butyl 2-hydroxypropanoate

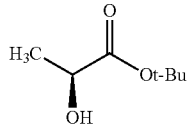

A solution of (S)-2-hydroxypropanoic acid (5.0 g, 55 mmol) and acetic acid (1 mL) in dichloromethane (40 mL) was cooled in an ice bath and treated dropwise with acetyl chloride (4.5 mL, 61 mmol). After addition was complete, the mixture was stirred at ambient temperature for 16 h. After this time, the mixture was diluted with water (50 mL) and extracted with methylene chloride (2×50 mL). The combined organics were washed with brine (50 mL), dried over sodium sulfate, filtered, and concentrated under reduced pressure to provide (S)-2-acetoxypropanoic acid (6.0 g) as a colorless oil.

(S)-2-acetoxypropanoic acid (6.0 g, 55 mmol), tert-butyl alcohol (8.10 g, 110 mmol),N,N-dimethylpyridin-4-amine (2.0 g, 16 mmol) and N,N'-dicyclohexylcarbodiimide (14.7 g, 71.5 mmol) were combined and stirred at ambient temperature for 16 h. After this time, the mixture was filtered and concentrated under reduced pressure to provide (S)-tert-butyl 2-acetoxypropanoate (12 g) as a colorless oil.

A solution of (S)-tert-butyl 2-acetoxypropanoate (12 g, 55 mmol) in methanol (40 mL) was cooled in an ice bath and treated with a solution of potassium carbonate (22.8 g, 165 mmol) in water (40 mL). After addition was complete, the mixture was stirred in an ice bath for 5 h. After this time, the mixture was diluted with water (50 mL) and extracted with ethyl acetate (3×50 mL). The combined organics were washed with brine (50 mL), dried over sodium sulfate, filtered, and concentrated under reduced pressure. The crude residue was purified by column chromatography (silica gel, 0-30% ethyl acetate/heptanes) to provide (S)-tert-butyl 2-hydroxypropanoate (1.14 g, 15% in three steps) as a white solid: ¹H NMR (300 MHz, CDCl₃) δ 4.13 (dd, J=6.9, 5.4 Hz, 1H), 2.82 (d, J=5.4 Hz, 1H), 1.49 (s, 9H), 1.37 (d, J=6.9 Hz, 3H).

Preparation of (S)-tert-Butyl 2-(2-((S)-2,2-dimethyl-5-oxo-1,3-dioxolan-4-yl)acetoxy)propanoate

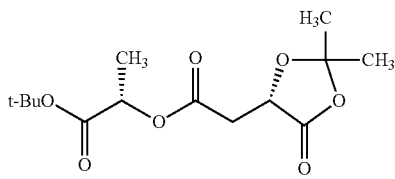 [SMILES: C[C@H](OC(=O)C[C@@H]1OC(C)(C)OC1=O)C(=O)OC(C)(C)C]

A solution of (S)-2-(2,2-dimethyl-5-oxo-1,3-dioxolan-4-yl)acetic acid (0.66 g, 3.8 mmol) in dichloromethane (20 mL) was treated with (S)-tert-butyl 2-hydroxypropanoate (0.50 g, 3.4 mmol),N,N-dimethylpyridin-4-amine (0.13 g, 1.0 mmol) and N,N'-dicyclohexylcarbodiimide (0.85 g, 4.1 mmol). The mixture was stirred at ambient temperature for 16 h. After this time, the mixture was filtered and concentrated under reduced pressure. The crude residue was purified by column chromatography (silica gel, 0-30% ethyl acetate/heptanes) to provide (S)-tert-butyl 2-(2-((S)-2,2-dimethyl-5-oxo-1,3-dioxolan-4-yl)acetoxy)propanoate (0.22 g, 21%) as a colorless oil: ¹H NMR (300 MHz, CDCl₃) δ 4.99 (dd, J=14.1, 8.4 Hz, 1H), 4.74 (dd, J=6.6, 3.6 Hz, 1H), 3.04 (dd, J=14.1, 3.6 Hz, 1H), 2.85 (dd, J=17.4, 8.4 Hz, 1H), 1.62 (s, 3H), 1.55 (s, 3H), 1.47 (d, J=6.2 Hz, 3H), 1.46 (s, 9H).

Preparation of (S)-4-(((S)-1-(tert-Butoxy)-1-oxopropan-2-yl)oxy)-2-hydroxy-4-oxobutanoic acid

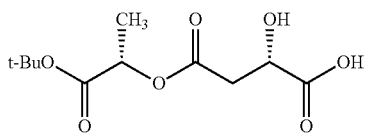 [SMILES: C[C@H](OC(=O)C[C@H](O)C(=O)O)C(=O)OC(C)(C)C]

A solution of (S)-tert-butyl 2-(2-((S)-2,2-dimethyl-5-oxo-1,3-dioxolan-4-yl)acetoxy)propanoate (3.07 g, 10.2 mmol), acetic acid (35 mL), and water (15 mL) was heated at 60° C. for 1 h. After this time, the mixture was concentrated under reduced pressure. The residue was diluted with toluene and concentrated under reduced pressure to provide of (S)-4-(((S)-1-(tert-butoxy)-1-oxopropan-2-yl)oxy)-2-hydroxy-4-oxobutanoic acid (2.99 g, 99%) as a colorless oil: ¹H NMR (300 MHz, DMSO-d₆) δ 12.6 (s, 1H), 5.51 (s, 1H), 4.82 (dd, J=14.1, 6.9 Hz, 1H), 4.31-4.30 (m, 1H), 2.72 (dd, J=15.9, 4.5 Hz, 1H), 2.60 (dd, J=15.9, 7.8 Hz, 1H), 1.40 (s, 9H), 1.36 (d, J=7.2 Hz, 3H).

Preparation of (S)-1-Benzyl 4-((S)-1-(tert-butoxy)-1-oxopropan-2-yl) 2-((tert-butoxycarbonyl)oxy)succinate

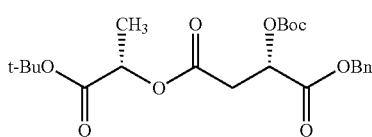

(S)-4-(((S)-1-(tert-Butoxy)-1-oxopropan-2-yl)oxy)-2-hydroxy-4-oxobutanoic acid (0.26 g, 1.0 mmol), benzylalcohol (0.15 g, 1.2 mmol),N,N-dimethylpyridin-4-amine (44 mg, 0.30 mmol), and N,N'-dicyclohexylcarbodiimide (0.30 g, 1.2 mmol) were combined and stirred in methylene chloride (10 mL) at ambient temperature for 16 h. After this time, the mixture was filtered and concentrated under reduced pressure to provide to provide (S)-1-benzyl 4-((S)-1-(tert-butoxy)-1-oxopropan-2-yl) 2-hydroxysuccinate (0.32 g) as a colorless oil.

(S)-1-Benzyl 4-((S)-1-(tert-butoxy)-1-oxopropan-2-yl) 2-hydroxysuccinate (0.32 g, 0.91 mmol), di-tert-butyl dicarbonate (0.22 g, 1.0 mmol), and 4-dimethylaminopyridine (12 mg, 0.098 mmol) were combined and stirred in methylene chloride (10 mL) at ambient temperature for 3 h. After this time, the mixture was concentrated under reduced pressure. The crude residue was purified by column chromatography (silica gel, 0-30% ethyl acetate/heptanes) to provide (S)-1-benzyl 4-((S)-1-(tert-butoxy)-1-oxopropan-2-yl) 2-((tert-butoxycarbonyl)oxy)succinate (0.21 g, 46% in two steps) as a colorless oil: ¹H NMR (300 MHz, CDCl₃) δ 7.34-7.32 (m, 5H), 5.41 (dd, J=8.1, 4.5 Hz, 1H), 5.26 (d, J=12 Hz, 1H), 5.14 (d, J=12 Hz, 1H), 4.96 (dd, J=14.1, 7.2 Hz, 1H), 2.98-2.94 (m, 2H), 1.46 (s, 9H), 1.45 (s, 9H), 1.42 (d, J=7.2 Hz, 3H).

Preparation of (S)-4-((S)-1-(tert-Butoxy)-1-oxopropan-2-yl) 1-(2,5-dioxopyrrolidin-1-yl) 2-((tert-butoxycarbonyl)oxy)succinate

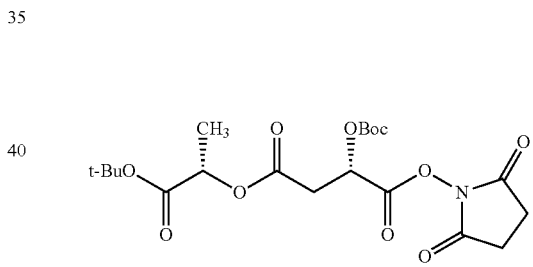

A solution of (S)-1-benzyl 4-((S)-1-(tert-butoxy)-1-oxopropan-2-yl) 2-((tert-butoxycarbonyl)oxy)succinate (0.54 g, 1.2 mmol) in ethyl alcohol (8 mL) was treated with palladium on carbon (10%, 0.1 g). The mixture was stirred under a hydrogen atmosphere at ambient temperature for 2 h. After this time, the reaction mixture was filtered and concentrated under reduced pressure to provide (S)-4-(((S)-1-(tert-butoxy)-1-oxopropan-2-yl)oxy)-2-((tert-butoxycarbonyl)oxy)-4-oxobutanoic acid (0.5 g) as a colorless oil.

(S)-4-(((S)-1-(tert-Butoxy)-1-oxopropan-2-yl)oxy)-2-((tert-butoxycarbonyl)oxy)-4-oxobutanoic acid (0.50 g, 1.2 mmol), 1-hydroxypyrrolidine-2,5-dione (0.16 g, 1.4 mmol) and N,N'-dicyclohexylcarbodiimide (0.27 g, 1.3 mmol) were combined and stirred in tetrahydrofuran (10 mL) at ambient temperature for 4 h. After this time, the mixture was filtered and concentrated under reduced pressure to provide (S)-4-((S)-1-(tert-butoxy)-1-oxopropan-2-yl) 1-(2,5-dioxopyrrolidin-1-yl) 2-((tert-butoxycarbonyl)oxy)succinate (0.8 g) as a sticky solid, which was used without purification.

Preparation of (S)-4-((S)-1-(tert-Butoxy)-1-oxopropan-2-yl) 1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2-((tert-butoxycarbonyl)oxy)succinate

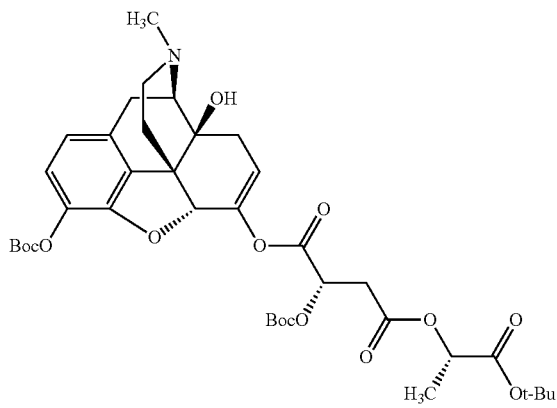

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (400 mg, 0.996 mmol) in tetrahydrofuran (10 mL) was cooled in an ice bath and treated dropwise with a 1.0 M solution of lithium bis(trimethylsilyl)amide in tetrahydrofuran (1.2 mL, 1.2 mmol). After addition was complete, the mixture was stirred at 0° C. for 1 h. The mixture was re-cooled to −45° C. and treated dropwise with a solution of (S)-4-((S)-1-(tert-butoxy)-1-oxopropan-2-yl) 1-(2,5-dioxopyrrolidin-1-yl) 2-((tert-butoxycarbonyl)oxy)succinate (504 mg, 1.10 mmol) in tetrahydrofuran (5 mL). After addition was complete, the mixture was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g silica gel column, 0-20% methanol/methylene chloride, then 50 g C18 column, 10-100% acetonitrile/water) to provide (S)-4-((S)-1-(tert-butoxy)-1-oxopropan-2-yl) 1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2-((tert-butoxycarbonyl)oxy)succinate (37 mg, 5%) as a white solid: ESI MS m/z 746 $[C_{38}H_{51}NO_{14}+H]^+$.

Preparation of (S)-2-(((S)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-3-hydroxy-4-oxobutanoyl)oxy)propanoic acid trifluoroacetic acid salt

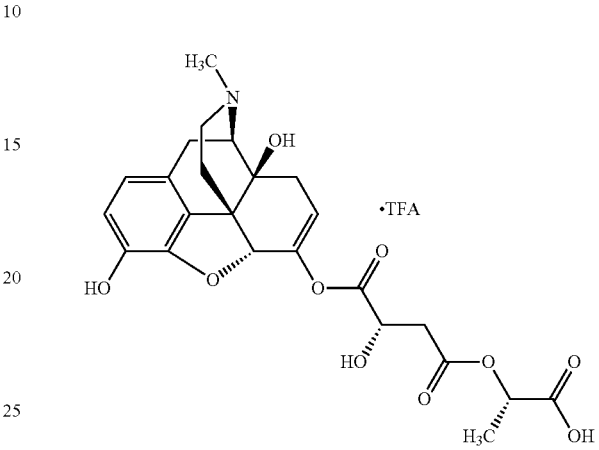

A solution of (S)-4-((S)-1-(tert-butoxy)-1-oxopropan-2-yl) 1-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2-((tert-butoxycarbonyl)oxy)succinate (37 mg, 0.050 mmol) in methylene chloride (3 mL) was treated with trifluoroacetic acid (1 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-2-(((S)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-3-hydroxy-4-oxobutanoyl)oxy)propanoic acid trifluoroacetic acid salt (27 mg, 90%) as a fluffy white solid: $^1$H NMR (300 MHz, DMSO-$d_6$) δ 9.30 (s, 1H), 9.14 (br s, 1H), 6.64 (apparent q, J=8.4 Hz, 2H), 6.24 (br s, 1H), 5.97 (d, J=6.0 Hz, 1H), 5.57 (d, J=3.9 Hz, 1H), 5.00-4.93 (m, 2H), 4.53 (m, 1H), 3.41-3.33 (m, 2H), 3.05 (m, 1H), 2.89-2.72 (m, 6H), 2.63-2.41 (m, 3H), 2.27 (m, 1H), 2.07 (m, 1H), 1.62 (m, 1H), 1.40 (d, J=7.2 Hz, 3H); ESI MS m/z 490 $[C_{24}H_{27}NO_{10}+H]^+$.

Scheme 178: (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((3-((S)-2-amino-4-methylpentanamido)propanoyl)oxy)propanoate bis(trifluoroacetic acid salt)

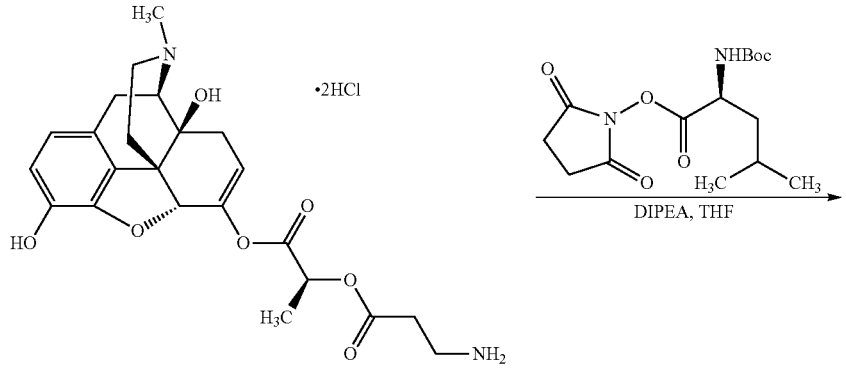

-continued
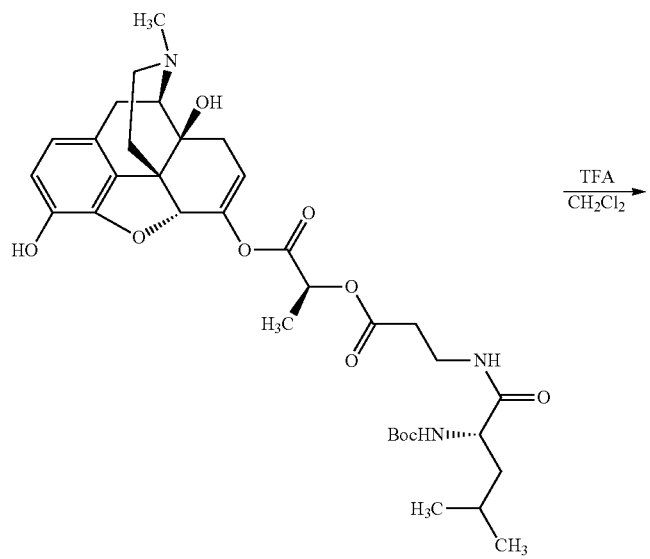
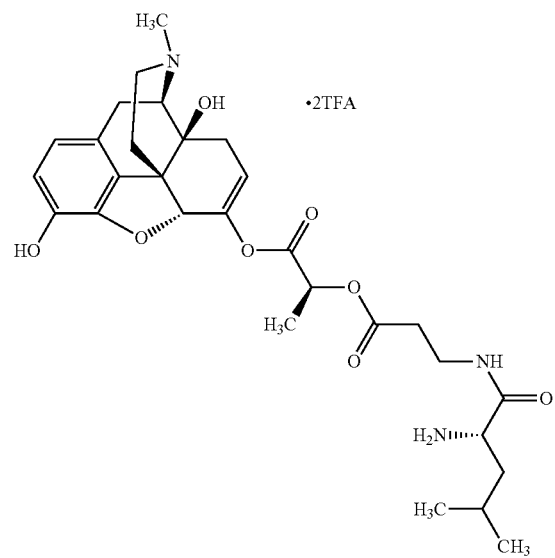

967

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((3-((S)-2-((tert-butoxycarbonyl)amino)-4-methylpentanamido)propanoyl)oxy)propanoate

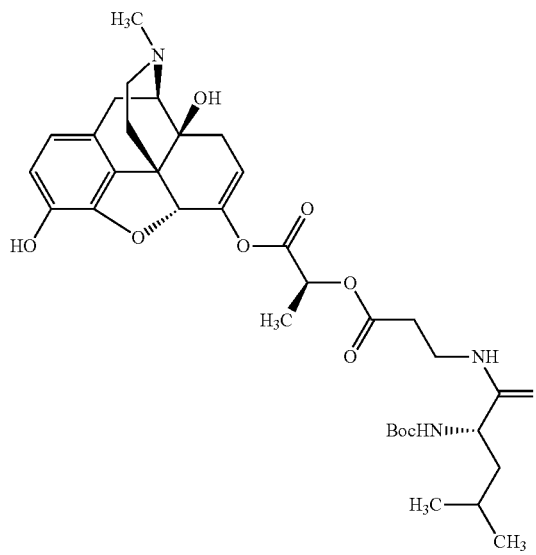

A solution of (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-aminopropanoyl)oxy)propanoate dihydrochloride (121 mg, 0.233 mmol) in tetrahydrofuran (6 mL) was treated with (S)-2,5-dioxopyrrolidin-1-yl 2-((tert-butoxycarbonyl)amino)-4-methylpentanoate (63 mg, 0.23 mmol) and N,N-diisopropylethylamine (60 mg, 0.47 mmol) at 0° C. and stirred under a nitrogen atmosphere for 1 h. After this time, the reaction mixture was concentrated under reduced pressure. The residue was purified by column chromatography (40 g silica gel column, 0-20% methanol/methylene chloride) to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-((S)-2-((tert-butoxycarbonyl)amino)-4-methylpentanamido)propanoyl)oxy)propanoate (76 mg, 54%) as a white solid: ESI MS m/z 658 $[C_{34}H_{47}N_3O_{10}+H]^+$.

968

Preparation of (S)-(4R,4aS,7aR,12bS)-4a,9-Dihydroxy-3-methyl-2,3,4,4a,5,7a-hexahydro-H-4,12-methanobenzofuro[3,2-e]isoquinolin-7-yl 2-((3-((S)-2-amino-4-methylpentanamido)propanoyl)oxy)propanoatebis(trifluoroacetic acid salt)

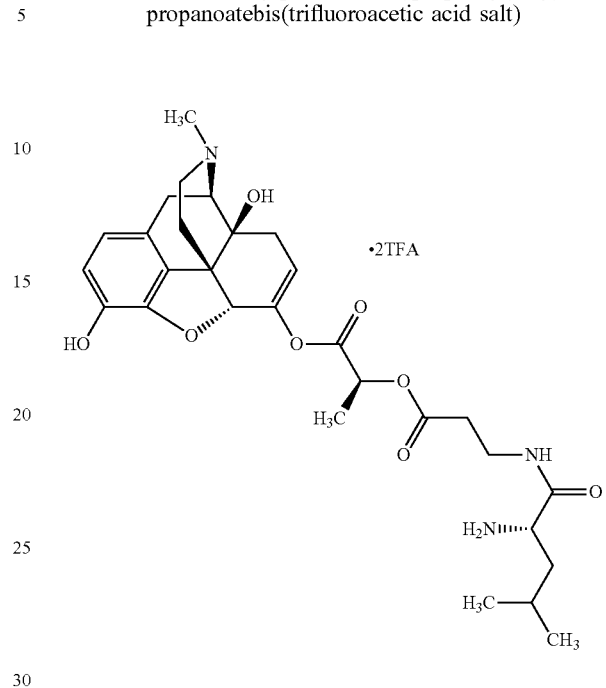

A solution of (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-((S)-2-((tert-butoxycarbonyl)amino)-4-methylpentanamido)propanoyl)oxy)propanoate (76 mg, 0.12 mmol) in methylene chloride (2 mL) was treated with trifluoroacetic acid (2 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-((S)-2-amino-4-methylpentanamido)propanoyl)oxy)propanoate bis(trifluoroacetic acid salt) (50 mg, 50%) as a fluffy white solid: $^1$H NMR (300 MHz, DMSO-$d_6$) δ 9.31 (s, 1H), 9.16 (br s, 1H), 8.62 (t, J=5.4 Hz, 1H), 8.09 (br s, 3H), 6.65 (apparent q, J=8.1 Hz, 2H), 6.24 (s, 1H), 5.58 (dd, J=6.0, 2.1 Hz, 1H), 5.12 (q, J=6.9 Hz, 1H), 4.96 (s, 1H), 3.67-3.27 (m, 4H), 3.05 (m, 1H), 2.84 (d, J=4.8 Hz, 3H), 2.63-2.41 (m, 6H), 2.28 (m, 1H), 2.05 (m, 1H), 1.64-1.52 (m, 7H), 0.89 (dd, J=6.0, 2.1 Hz, 6H); ESI MS m/z 558 $[C_{29}H_{39}N_3O_8+H]^+$.

Scheme 179: (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-(((S)-2-((S)-2-acetamido-6-aminohexanamido)propanoyl)oxy)propanoate bis(trifluoroacetic acid salt)

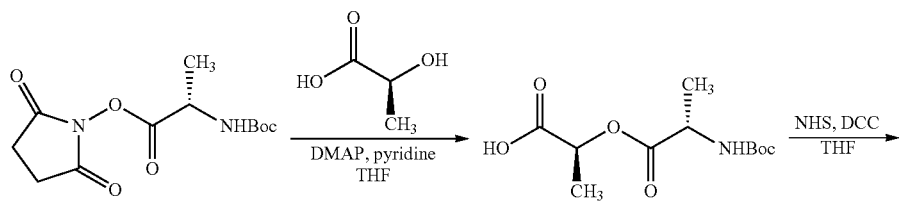

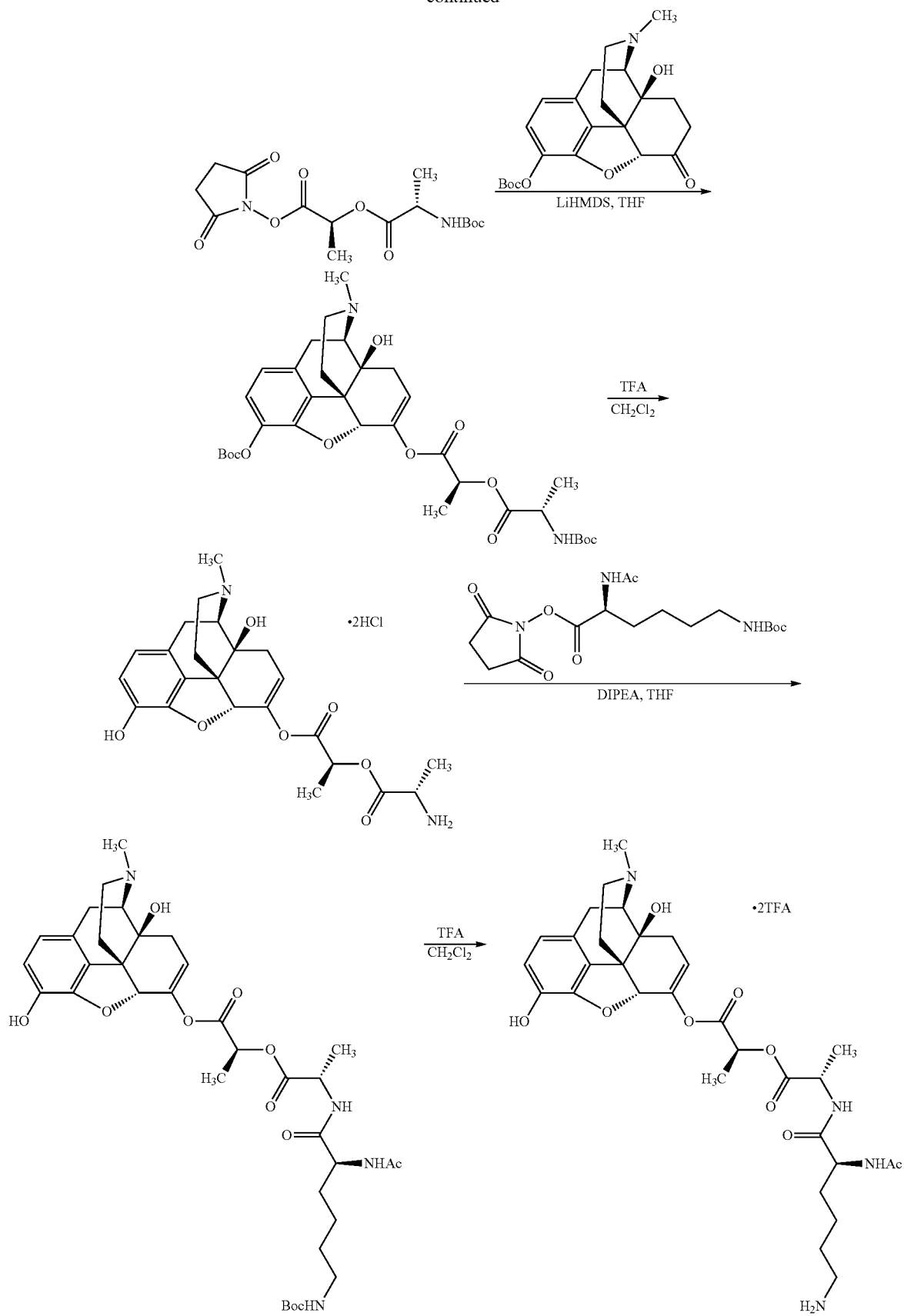

Preparation of (S)-2-(((S)-2-((tert-Butoxycarbonyl)amino)propanoyl)oxy)propanoic acid

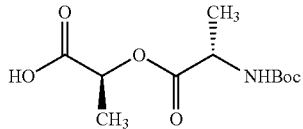

(S)-Lactic acid (944 mg, 10.5 mmol), (S)-2,5-dioxopyrrolidin-1-yl 2-((tert-butoxycarbonyl)amino)propanoate (2.50 g, 8.73 mmol), 4-(dimethylamino)pyridine (107 mg, 0.873 mmol), pyridine (831 mg, 10.5 mmol), and tetrahydrofuran (40 mL) were combined and heated at 75° C. under a nitrogen atmosphere for 24 h. After this time, the solvent was removed under reduced pressure, and the residue was partitioned between ethyl acetate (20 mL) and 10% aqueous citric acid. The organic layer was separated and extracted with saturated aqueous sodium bicarbonate (20 ml). The aqueous phase was collected and acidified to pH=2 with 6 N hydrochloric acid, and the mixture was extracted with ethyl acetate (2×20 mL). The combined organics were washed with brine (50 mL), dried over sodium sulfate, filtered, and concentrated under reduced pressure to provide (S)-2-(((S)-2-((tert-butoxycarbonyl)amino)propanoyl)oxy)propanoic acid (2.10 g, 92%) as a colorless oil: $^1$H NMR (300 MHz, CDCl$_3$) δ 5.19 (t, J=6.9 Hz, 1H), 5.01 (m, 1H), 4.35 (m, 1H), 1.56 (d, J=7.2 Hz, 3H), 1.46-1.43 (s, 12H), CO$_2$H proton not observed.

Preparation of (S)-2,5-Dioxopyrrolidin-1-yl 2-(((S)-2-((tert-butoxycarbonyl)amino)propanoyl)oxy)propanoate

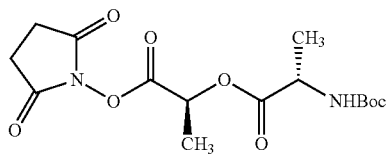 [SMILES: C[C@H](NC(=O)OC(C)(C)C)C(=O)O[C@@H](C)C(=O)ON1C(=O)CCC1=O]

A solution of (S)-2-(((S)-2-((tert-butoxycarbonyl)amino)propanoyl)oxy)propanoic acid (2.10 g, 8.04 mmol) in tetrahydrofuran (40 mL) was treated with N-hydroxysuccinimide (1.02 g, 8.84 mmol) and N,N'-dicyclohexylcarbodiimide (1.82 g, 8.84 mmol) and stirred under a nitrogen atmosphere for 5 h. After this time, the reaction mixture was filtered to remove the solid dicyclohexylurea byproduct. The solid was washed with diethyl ether (100 mL), and the combined filtrate and washings were concentrated under reduced pressure. The residue was triturated with diethyl ether to provide (S)-2,5-dioxopyrrolidin-1-yl 2-(((S)-2-((tert-butoxycarbonyl)amino)propanoyl)oxy)propanoate (2.73 g) as a white powder: $^1$H NMR (300 MHz, CDCl$_3$) δ 5.46 (m, 1H), 5.02 (m, 1H), 4.38 (m, 1H), 2.82 (s, 4H), 1.69 (d, J=6.6 Hz, 3H), 1.46-1.42 (s, 12H).

Preparation of (S)-(4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl 2-(((S)-2-((tert-butoxycarbonyl)amino)propanoyl)oxy)propanoate

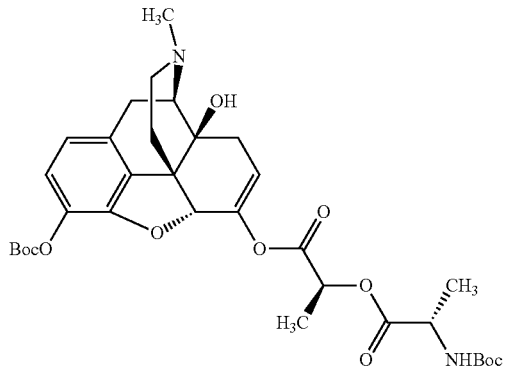

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (1.50 g, 3.74 mmol) in tetrahydrofuran (30 mL) was cooled in an ice bath and treated dropwise with a 1.0 M solution of lithium bis(trimethylsilyl)amide in tetrahydrofuran (4.5 mL, 4.5 mmol). After addition was complete, the mixture was stirred at 0° C. for 1 h. The mixture was re-cooled to −45° C. and treated dropwise with a solution of (S)-2,5-dioxopyrrolidin-1-yl 2-(((S)-2-((tert-butoxycarbonyl)amino)propanoyl)oxy)propanoate (1.47 g, 4.11 mmol) in tetrahydrofuran (15 mL). After addition was complete, the mixture was warmed to 0° C. After this time, the reaction mixture was treated with saturated aqueous ammonium chloride (20 mL) and extracted with ethyl acetate (2×50 mL). The combined organics were dried over sodium sulfate, filtered, and concentrated under reduced pressure. The crude residue was purified by column chromatography (40 g, silica gel, 0-20% methanol/methylene chloride, then 50 g, C18, 10-100% acetonitrile/water) to provide (S)-(4R,4aS,7aR,12bS)-9-((tert-butoxycarbonyl)oxy)-4a-hydroxy-3-methyl-2,3,4,4a,5, 7a-hexahydro-1H-4,12-methanobenzofuro[3,2-e]isoquinolin-7-yl 2-(((S)-2-((tert-butoxycarbonyl)amino)propanoyl)oxy)propanoate (1.04 g, 43%) as a white solid: ESI MS m/z 645 [C$_{33}$H$_{44}$N$_2$O$_{11}$+H]$^+$.

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-(((S)-2-aminopropanoyl)oxy)propanoate dihydrochloride

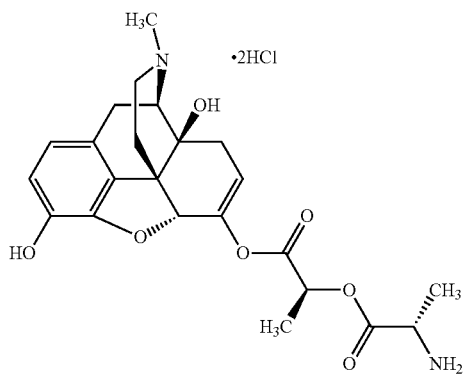 [SMILES: C[C@H](N)C(=O)O[C@@H](C)C(=O)OC1=CC[C@@]2(O)[C@H]3Cc4ccc(O)c5c4[C@@]2(CCN3C)[C@H]1O5]

A solution of (S)-(4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl 2-(((S)-2-((tert-butoxycarbonyl)amino)propanoyl)oxy)propanoate (150 mg, 0.233 mmol) was treated with a 4.0 M solution of hydrogen chloride in 1,4-dioxane (5 mL) and stirred under a nitrogen atmosphere at ambient temperature for 1 h. After this time, the reaction mixture concentrated under vacuum to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-(((S)-2-aminopropanoyl)oxy)propanoatedihydrochloride (121 mg, 100%) as a white solid: ESI MS m/z 445 $[C_{23}H_{28}N_2O_7+H]^+$.

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-(((S)-2-((S)-2-acetamido-6-((tert-butoxycarbonyl)amino)hexanamido)propanoyl)oxy)propanoate

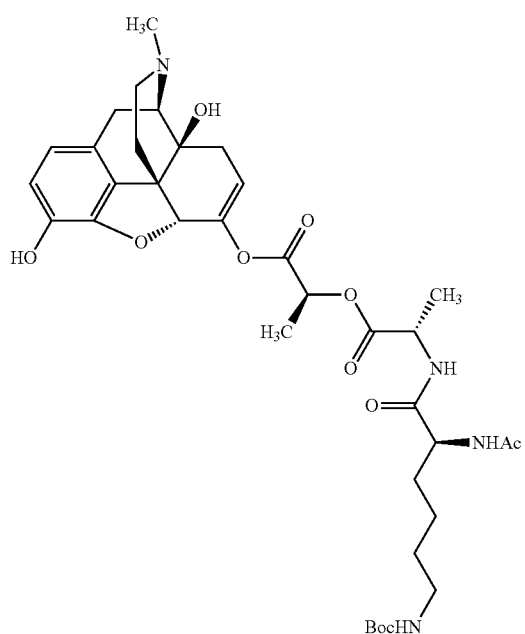 [SMILES: CC(=O)N[C@@H](CCCCNC(=O)OC(C)(C)C)C(=O)N[C@@H](C)C(=O)O[C@@H](C)C(=O)OC1=CC[C@@]2(O)[C@H]3Cc4ccc(O)c5c4[C@@]2(CCN3C)[C@H]1O5]

A solution of (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-(((S)-2-aminopropanoyl)oxy)propanoate hydrochloride (121 mg, 0.233 mmol) in tetrahydrofuran (6 mL) was treated with (S)-2,5-dioxopyrrolidin-1-yl 2-acetamido-6-((tert-butoxycarbonyl)amino)hexanoate (90 mg, 0.23 mmol) and N,N-diisopropylethylamine (60 mg, 0.47 mmol) at 0° C. and stirred under a nitrogen atmosphere for 1 h. After this time, the reaction mixture was concentrated under reduced pressure. The residue was purified by reversed phase column chromatography (50 g C18 column, 10-100% acetonitrile/water) to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-(((S)-2-((S)-2-acetamido-6-((tert-butoxycarbonyl)amino)hexanamido)propanoyl)oxy)propanoate (34 mg, 20%) as a white solid: ESI MS m/z 715 $[C_{36}H_{50}N_4O_{11}+H]^+$.

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-(((S)-2-((S)-2-acetamido-6-aminohexanamido)propanoyl)oxy)propanoatebis(trifluoroacetic acid salt)

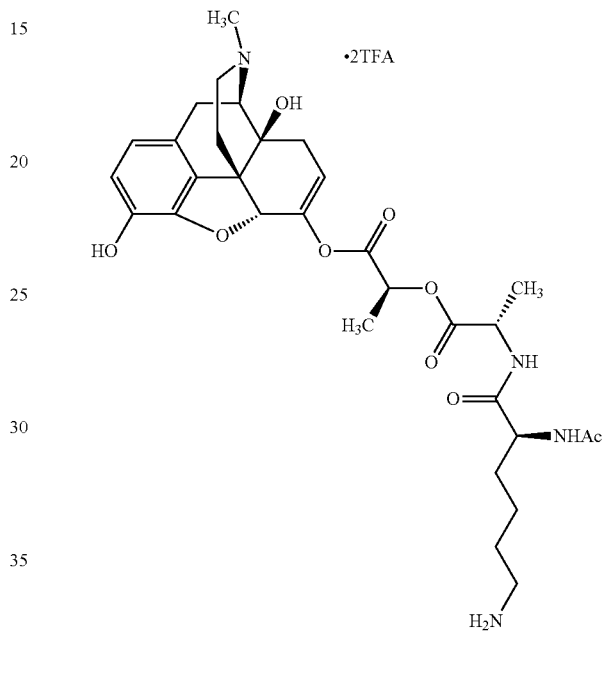

A solution of (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-(((S)-2-((S)-2-acetamido-6-((tert-butoxycarbonyl)amino)hexanamido)propanoyl)oxy)propanoate (34 mg, 0.048 mmol) in methylene chloride (2 mL) was treated with trifluoroacetic acid (1 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-(((S)-2-((S)-2-acetamido-6-aminohexanamido)propanoyl)oxy)propanoate bis (trifluoroacetic acid salt)(12 mg, 24%) as a fluffy white solid: $^1$H NMR (300 MHz, DMSO-d$_6$) δ 9.30 (s, 1H), 9.16 (br s, 1H), 8.43 (d, J=6.3 Hz, 1H), 7.99 (d, J=7.8 Hz, 1H), 7.61 (br s, 3H), 6.65 (apparent q, J=8.1 Hz, 2H), 6.22 (s, 1H), 5.57 (dd, J=6.0, 2.1 Hz, 1H), 5.14 (q, J=6.9 Hz, 1H), 4.35-4.30 (m, 3H), 3.46-3.33 (m, 2H), 3.11 (m, 1H), 2.84 (d, J=5.1 Hz, 3H), 2.74-2.41 (m, 3H), 2.27 (in, 1H), 2.07 (in, 1H), 1.84 (s, 3H), 1.64-1.32 (in, 14H); ESI MS m/z 615 $[C_{31}H_{42}N_4O_9+H]^+$.

Scheme 180: (2R,3R)-4-((S)-2-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-oxo-1-phenylethoxy)-2,3-dihydroxy-4-oxobutanoic acid trifluoroacetic acid salt
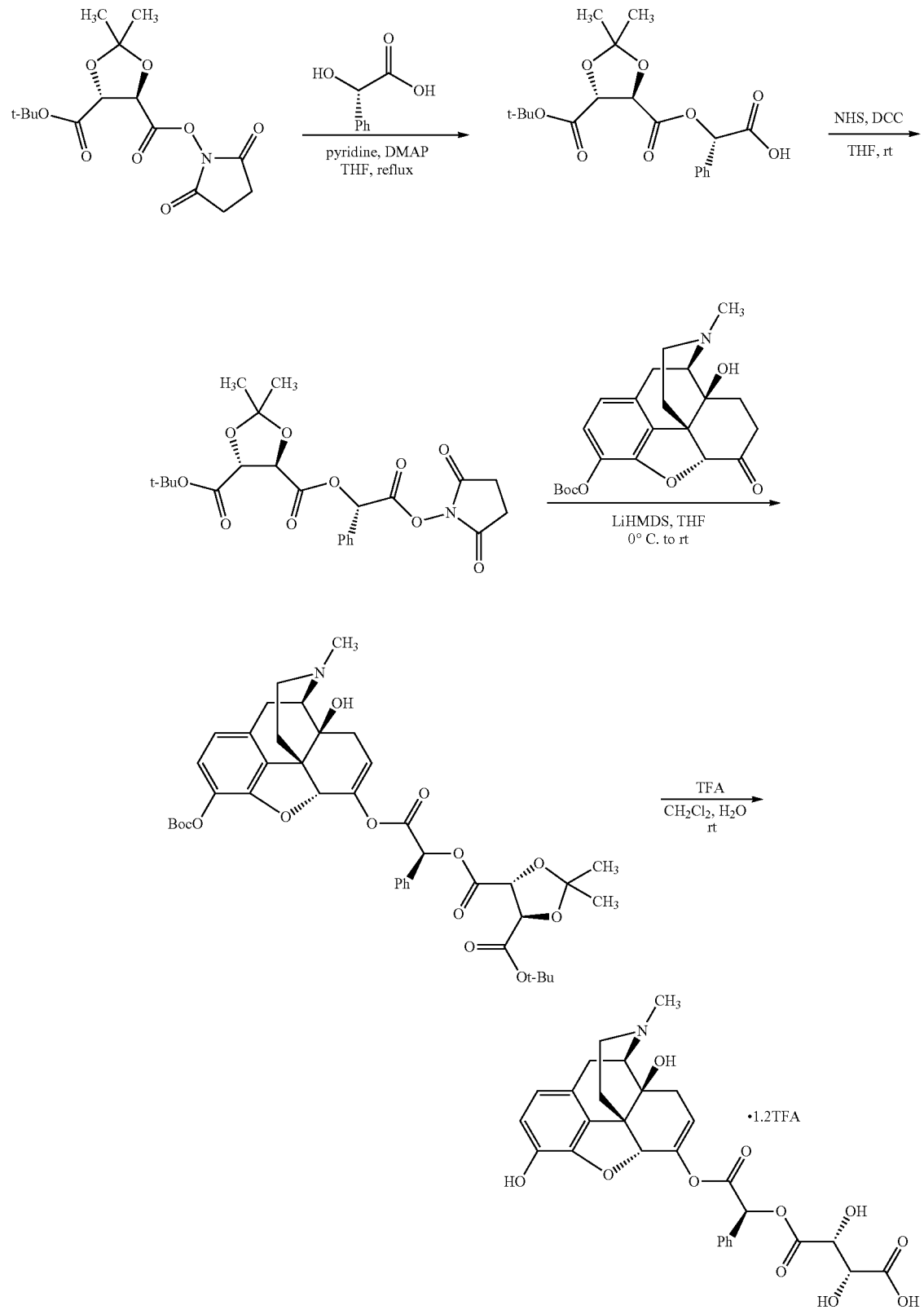

Preparation of (S)-2-(((4R,5R)-5-(tert-Butoxycarbonyl)-2,2-d methyl-1,3-dioxolane-4-carbonyl)oxy)-2-phenylacetic acid

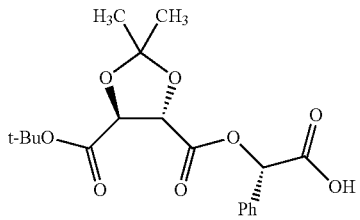 [SMILES: CC(C)(C)OC(=O)[C@H]1OC(C)(C)O[C@@H]1C(=O)O[C@H](C(=O)O)c1ccccc1]

A mixture of (4R,5R)-4-tert-butyl 5-(2,5-dioxopyrrolidin-1-yl) 2,2-dimethyl-1,3-dioxolane-4,5-dicarboxylate (1.42 g, 4.15 mmol), (S)-2-hydroxy-2-phenylacetic acid (900 mg, 5.92 mmol), pyridine (0.45 mL, 5.60 mmol), and 4-dimethylaminopyridine (60 mg, 0.49 mmol) in tetrahydrofuran (25 mL) was stirred at reflux for 18 h. After this time, the mixture was cooled to room temperature, partially concentrated under reduced pressure, diluted with ethyl acetate, washed with 10% citric acid and brine, and concentrated under reduced pressure. The residue was purified by reversed phase column chromatography (50 g C18 column, 5-100% acetonitrile/water) and freeze dried to provide (S)-2-(((4R,5R)-5-(tert-butoxycarbonyl)-2,2-dimethyl-1,3-dioxolane-4-carbonyl)oxy)-2-phenylacetic acid (425 mg, 27%): $^1$H NMR (300 MHz, CDCl$_3$) δ 7.53-7.46 (m, 2H), 7.43-7.35 (m, 3H), 6.02 (s, 1H), 4.85 (d, J=5.8 Hz, 1H), 4.67 (d, J=5.8 Hz, 1H), 1.52 (s, 3H), 1.51 (s, 3H), 1.42 (s, 9H), CO$_2$H proton not observed.

Preparation of (4R,5R)-4-tert-Butyl 5-((S)-2-((2,5-dioxopyrrolidin-1-yl)oxy)-2-oxo-1-phenylethyl) 2,2-dimethyl-1,3-dioxolane-4,5-dicarboxylate

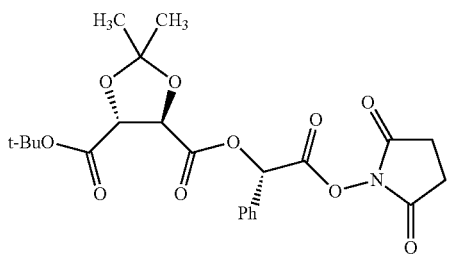 [SMILES: CC(C)(C)OC(=O)[C@@H]1OC(C)(C)O[C@H]1C(=O)O[C@H](C(=O)ON1C(=O)CCC1=O)c1ccccc1]

A mixture of (S)-2-(((4R,5R)-5-(tert-butoxycarbonyl)-2,2-dimethyl-1,3-dioxolane-4-carbonyl)oxy)-2-phenylacetic acid (425 mg, 1.12 mmol) and N-hydroxysuccinimide (142 mg, 1.23 mmol) in tetrahydrofuran (10 mL) was treated with N,N'-dicyclohexylcarbodiimide (255 mg, 1.23 mmol), and the reaction mixture was stirred at ambient temperature for 4 h. After this time, diethyl ether (10 mL) was added, and the mixture was filtered. The filtrate was concentrated under reduced pressure to provide (4R,5R)-4-tert-butyl 5-((S)-2-((2,5-dioxopyrrolidin-1-yl)oxy)-2-oxo-1-phenylethyl) 2,2-dimethyl-1,3-dioxolane-4,5-dicarboxylate (600 mg) that was used without purification: $^1$H NMR (300 MHz, CDCl$_3$) δ 7.58-7.52 (m, 2H), 7.48-7.43 (m, 3H), 6.43 (s, 1H), 4.86 (d, J=5.6 Hz, 1H), 4.67 (d, J=5.6 Hz, 1H), 2.81 (s, 4H), 1.50 (s, 6H), 1.43 (s, 9H).

Preparation of (4R,5R)-4-((S)-2-(((4R,4aS,7aR,12bS)-9-((tert-Butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl) 5-tert-butyl 2,2-dimethyl-1,3-dioxolane-4,5-dicarboxylate

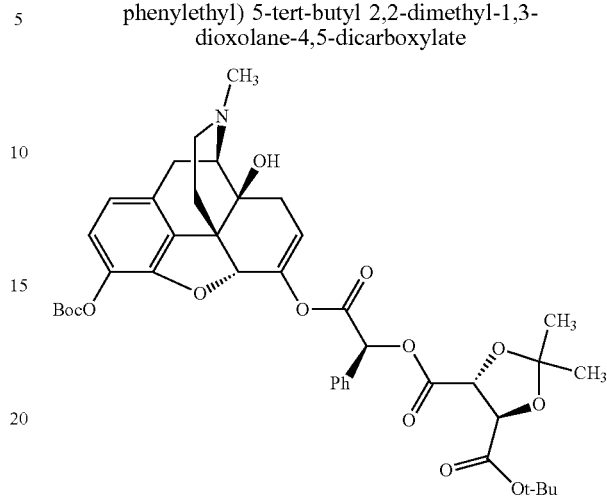

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (450 mg, 1.12 mmol) in tetrahydrofuran (8 mL) was cooled to 0° C. and treated dropwise with a 1.0 M solution of lithium bis(trimethylsilyl)amide in tetrahydrofuran (1.2 mL, 1.2 mmol). After addition was complete, the mixture was stirred at ambient temperature for 10 min. The mixture was re-cooled to 0° C., and (4R,5R)-4-tert-butyl 5-((S)-2-((2,5-dioxopyrrolidin-1-yl)oxy)-2-oxo-1-phenylethyl) 2,2-dimethyl-1,3-dioxolane-4,5-dicarboxylate (535 mg, 1.12 mmol) was added in one portion. The mixture was stirred at 0° C. for 45 min. After this time, the mixture was treated with saturated aqueous ammonium chloride and extracted with ethyl acetate. The combined organics were dried over sodium sulfate, filtered, and concentrated under reduced pressure. The residue was purified by reversed phase column chromatography (50 g C18 column, 5-100% acetonitrile/water) to provide (4R,5R)-4-((S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl) 5-tert-butyl 2,2-dimethyl-1,3-dioxolane-4,5-dicarboxylate (425 mg, 51%): ESI MS m/z 764 [C$_{41}$H$_{49}$NO$_{13}$+H]4.

Preparation of (2R,3R)-4-((S)-2-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2-oxo-1-phenylethoxy)-2,3-dihydroxy-4-oxobutanoic acid trifluoroacetic acid salt

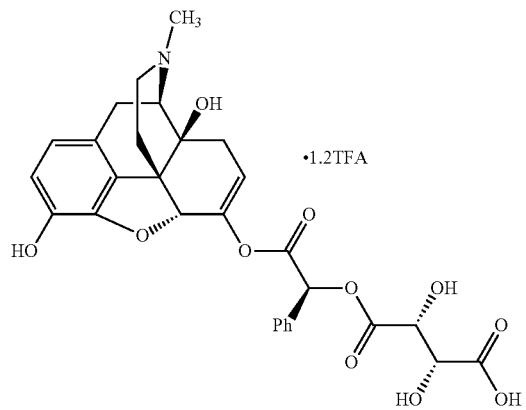 [SMILES: CN1CC[C@]23c4c5ccc(O)c4O[C@H]2C(OC(=O)[C@@H](OC(=O)[C@H](O)[C@@H](O)C(=O)O)c2ccccc2)=CC[C@@]3(O)[C@H]1C5]

A solution of (4R,5R)-4-((S)-2-(((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl)oxy)-2-oxo-1-phenylethyl) 5-tert-butyl 2,2-dimethyl-1,3-dioxolane-4,5-dicarboxylate (425 mg, 0.556 mmol), in methylene chloride (10 mL) was treated with trifluoroacetic acid (2 mL), and the mixture was stirred at room temperature for 1 h. LC-MS analysis of the reaction mixture indicated cleavage of the Boc and tert-butyl protecting groups. Water (0.1 mL) was added, and the mixture was stirred at ambient temperature for 7 h. After this time, the reaction mixture was concentrated under reduced pressure. The residue was purified by reversed phase column chromatography (50 g C18 column, 3-20% acetonitrile/water, with 0.1% trifluoroacetic acid) and freeze dried to provide (2R,3R)-4-((S)-2-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2-oxo-1-phenylethoxy)-2,3-dihydroxy-4-oxobutanoic acid trifluoroacetic acid salt (186 mg, 47%): $^1$H NMR (300 MHz, DMSO-$d_6$) δ 12.86 (br s, 1H), 9.30 (br s, 1H), 9.14 (br s, 1H), 7.62-7.56 (m, 2H), 7.50-7.43 (d, 3H), 6.68 (d, J=8.1 Hz, 1H), 6.62 (d, J=8.1 Hz, 1H), 6.27 (s, 1H), 6.16 (s, 1H), 5.61 (dd, J=6.0, 2.0 Hz, 1H), 4.90 (s, 1H), 4.58 (d, J=2.0 Hz, 1H), 4.38 (d, J=2.3 Hz, 1H), 3.61 (d, J=6.2 Hz, 1H), 3.37 (d, J=19.8 Hz, 1H), 3.13-3.00 (m, 2H), 2.83 (d, J=4.3 Hz, 3H), 2.68-2.56 (m, 1H), 2.41 (dd, J=13.0, 4.7 Hz, 1H), 2.26 (dd, J=18.0, 6.2 Hz, 1H), 2.07 (d, J=18.0 Hz, 1H), 1.60 (d, J=10.8 Hz, 1H),two protons obscured by solvent peaks; ESI MS m/z 568 [$C_{29}H_{29}NO_{11}$+H]$^+$; HPLC (Method A) 98.9% (AUC), $t_R$=7.65 min.

Scheme 181: (S)-2-(((2R,3R)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy)propanoic acid trifluoroacetic acid salt

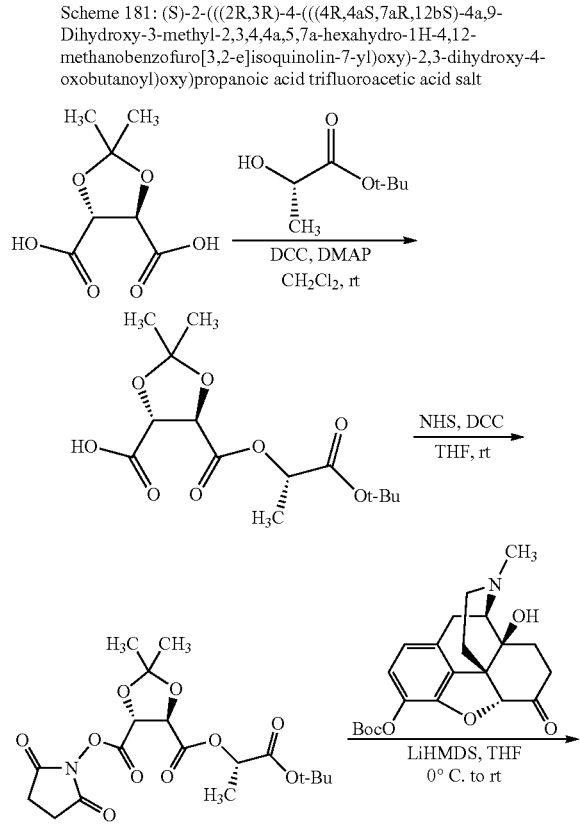

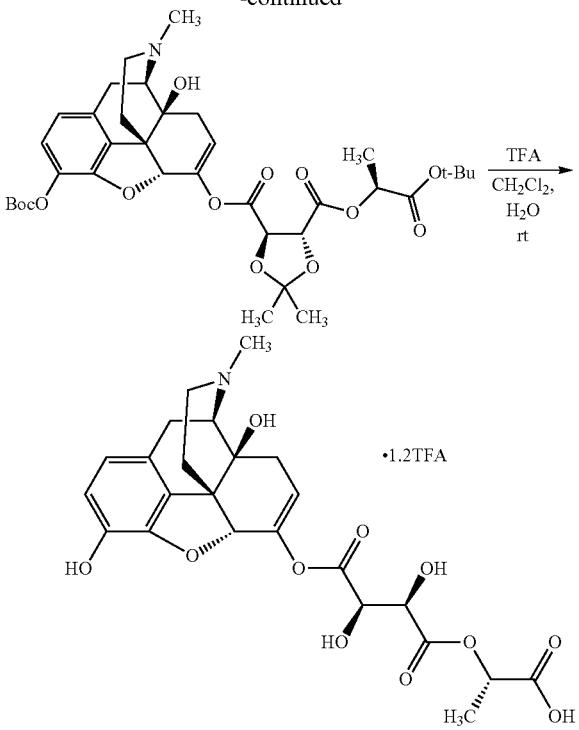

Preparation of (4R,5R)-5-(((S)-1-(tert-Butoxy)-1-oxopropan-2-yl)oxy)carbonyl)-2,2-dimethyl-1,3-dioxolane-4-carboxylic acid

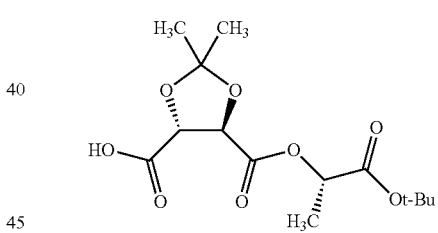

A mixture of (4R,5R)-2,2-dimethyl-1,3-dioxolane-4,5-dicarboxylic acid (770 mg, 4.05 mmol), (S)-tert-butyl 2-hydroxypropanoate (595 mg, 4.08 mmol), and 4-dimethylaminopyridine (150 mg, 1.23 mmol) in methylene chloride (12 mL) was treated with N,N'-dicyclohexylcarbodiimide (920 mg, 4.46 mmol), and the reaction mixture was stirred at ambient temperature for 18 h. After this time, the mixture was filtered, and the filtrate was concentrated under reduced pressure. The residue was dissolved in ethyl acetate, washed with 2 N hydrochloric acid, and then extracted with saturated sodium bicarbonate. The aqueous layer was collected, carefully treated with 6N hydrochloric acid until acidic by pH paper analysis, and then extracted with ethyl acetate. The organic extracts were dried over sodium sulfate, filtered, and concentrated to provide (4R,5R)-5-(((((S)-1-(tert-butoxy)-1-oxopropan-2-yl)oxy)carbonyl)-2,2-dimethyl-1,3-dioxolane-4-carboxylic acid (780 mg, 61%): $^1$H NMR (300 MHz, CDCl$_3$) δ 5.05 (q, J=7.1 Hz, 1H), 4.91 (d, J=5.4 Hz, 1H), 4.87 (d, J=5.4 Hz, 1H), 1.54 (s, 6H), 1.53 (d, J=7.1 Hz, 3H), 1.47 (s, 9H), CO$_2$H proton not observed.

Preparation of (4R,5R)-4-((S)-1-(tert-Butoxy)-1-oxopropan-2-yl) 5-(2,5-dioxopyrrolidin-1-yl) 2,2-dimethyl-1,3-dioxolane-4,5-dicarboxylate

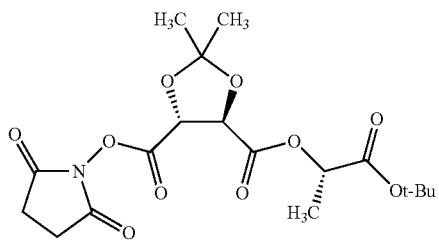

A mixture of (4R,5R)-5-((((S)-1-(tert-butoxy)-1-oxopropan-2-yl)oxy)carbonyl)-2,2-dimethyl-1,3-dioxolane-4-carboxylic acid (780 mg, 2.45 mmol) and N-hydroxysuccinimide (310 mg, 2.69 mmol) in tetrahydrofuran (20 mL) was treated with N,N'-dicyclohexylcarbodiimide (555 mg, 2.69 mmol), and the reaction mixture was stirred at ambient temperature for 4 h. After this time, diethyl ether (15 mL) was added, and the mixture was filtered. The filtrate was concentrated under reduced pressure to provide (4R,5R)-4-((S)-1-(tert-butoxy)-1-oxopropan-2-yl) 5-(2,5-dioxopyrrolidin-1-yl) 2,2-dimethyl-1,3-dioxolane-4,5-dicarboxylate (1.0 g) that was used without purification: $^1$H NMR (300 MHz, CDCl$_3$) δ 5.22 (d, J=4.7 Hz, 1H), 5.08 (d, J=4.7 Hz, 1H), 5.03 (q, J=7.1 Hz, 1H), 2.87 (s, 4H), 1.57 (s, 3H), 1.56 (s, 3H), 1.53 (d, J=7.1 Hz, 3H), 1.47 (s, 9H).

Preparation of (4R,5R)-4-((S)-1-(tert-Butoxy)-1-oxopropan-2-yl) 5-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2,2-dimethyl-1,3-dioxolane-4,5-dicarboxylate

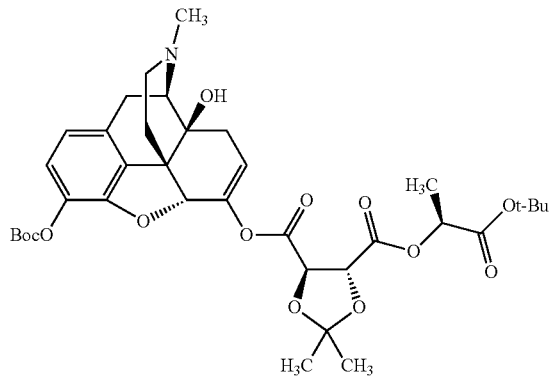

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (480 mg, 1.19 mmol) in tetrahydrofuran (8 mL) was cooled to 0° C. and treated dropwise with a 1.0 M solution of lithium bis(trimethylsilyl)amide in tetrahydrofuran (1.3 mL, 1.3 mmol). After addition was complete, the mixture was stirred at ambient temperature for 10 min. The mixture was re-cooled to 0° C., and (4R,5R)-4-((S)-1-(tert-butoxy)-1-oxopropan-2-yl) 5-(2,5-dioxopyrrolidin-1-yl) 2,2-dimethyl-1,3-dioxolane-4,5-dicarboxylate (500 mg, 1.20 mmol) was added in one portion. The mixture was stirred at 0° C. for 45 min. After this time, the reaction mixture was treated with saturated aqueous ammonium chloride and extracted with ethyl acetate. The combined organics were dried over sodium sulfate, filtered, and concentrated under reduced pressure. The residue was purified by reversed phase column chromatography (50 g C18 column, 5-100% acetonitrile/water) to provide (4R,5R)-4-((S)-1-(tert-butoxy)-1-oxopropan-2-yl) 5-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2,2-dimethyl-1,3-dioxolane-4,5-dicarboxylate (289 mg, 35%): ESI MS m/z 702 [C36H47NO13+H]$^+$.

Preparation of (S)-2-(((2R,3R)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy) propanoic acid trifluoroacetic acid salt

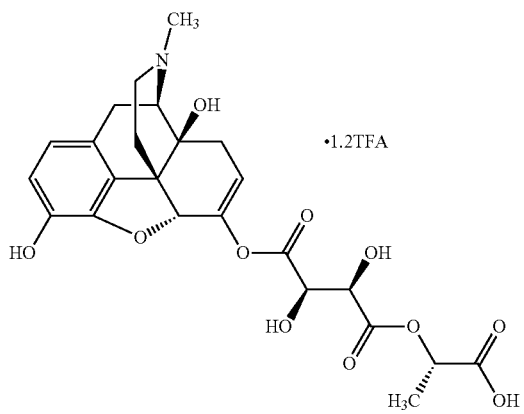 [SMILES: C[C@H](OC(=O)[C@H](O)[C@@H](O)C(=O)OC1=CC[C@@]2(O)[C@H]3Cc4ccc(O)c5c4[C@@]2(CCN3C)[C@H]1O5)C(=O)O]

A solution of (4R,5R)-4-((S)-1-(tert-butoxy)-1-oxopropan-2-yl) 5-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2,2-dimethyl-1,3-dioxolane-4,5-dicarboxylate (288 mg, 0.410 mmol) in methylene chloride (8 mL) was treated with trifluoroacetic acid (1.5 mL), and the mixture was stirred at room temperature for 1 h. LC-MS analysis of the reaction mixture indicated cleavage of the Boc and t-butyl protecting groups. Water (0.1 mL) was added, and the mixture was stirred at ambient temperature for 6 h. After this time, the reaction mixture was concentrated under reduced pressure. The residue was purified by reversed phase column chromatography (50 g C18 column, 3-20% acetonitrile/water, with 0.1% trifluoracetic acid) and freeze dried to provide (S)-2-(((2R,3R)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy) propanoic acid trifluoroacetic acid salt (160 mg, 61%): $^1$H NMR (300 MHz, DMSO-d$_6$) δ 13.4 (br s, 1H), 9.32 (s, 1H), 9.17 (br s, 1H), 6.69 (d, J=8.2 Hz, 1H), 6.63 (d, J=8.2 Hz, 1H), 6.26 (s, 1H), 5.83 (br s, 2H), 5.56 (dd, J=5.9, 1.9 Hz, 1H), 5.03 (s, 1H), 4.99 (q, J=7.1 Hz, 1H), 4.62 (s, 1H), 4.56 (s, 1H), 3.62 (d, J=6.1 Hz, 1H), 3.38 (d, J=20.0 Hz, 1H), 3.13-3.01 (m, 2H), 2.84 (apparent d, J=4.1 Hz, 3H), 2.71-2.58 (m, 1H), 2.45 (dd, J=14.1, 5.6 Hz, 1H), 2.30 (dd, J=18.0, 6.1 Hz, 1H), 2.06 (d, J=18.0 Hz, 1H), 1.64 (d, J=10.7 Hz, 1H), 1.43 (d, J=7.1 Hz, 3H); ESI MS m/z 506 [C24H27NO11+H]$^+$; HPLC (Method A) 98.7% (AUC), t$_R$=6.42 min.

Scheme 182: (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2((3-((S)-pyrrolidine-2-carboxamido)propanoyl)oxy)propanoate bis(trifluoroacetic acid salt)

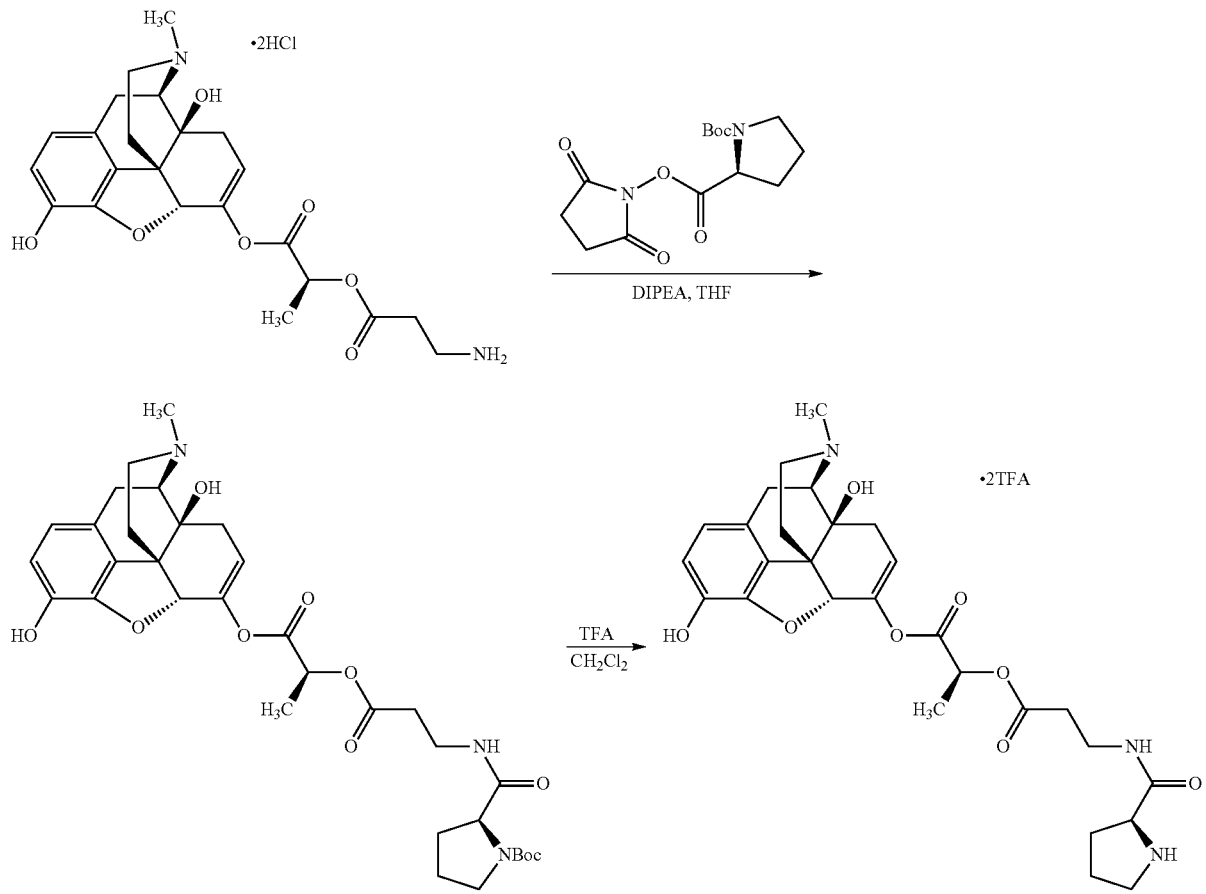

Preparation of (S)-tert-Butyl 2-((3-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)carbamoyl)pyrrolidine-1-carboxylate

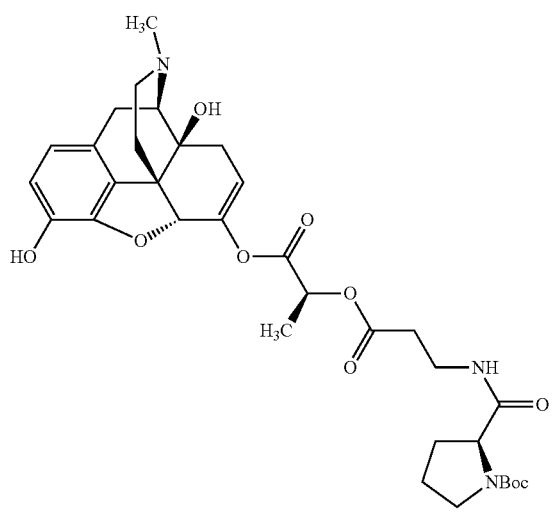

A solution of (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-aminopropanoyl)oxy)propanoate dihydrochloride (121 mg, 0.233 mmol) in tetrahydrofuran (6 mL) was treated with (S)-1-tert-butyl 2-(2,5-dioxopyrrolidin-1-yl) pyrrolidine-1,2-dicarboxylate (87 mg, 0.28 mmol) and N,N-diisopropylethylamine (60 mg, 0.47 mmol) at 0° C. and stirred under a nitrogen atmosphere for 1 h. After this time, the reaction mixture was concentrated under reduced pressure. The residue was purified by column chromatography (40 g silica gel column, 0-20% methanol/methylene chloride) to provide (S)-tert-butyl 2-((3-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)carbamoyl)pyrrolidine-1-carboxylate (81 mg, 54%) as a white solid: ESI MS m/z 642 [$C_{33}H_{43}N_3O_{10}$+H]$^+$.

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((3-((S)-pyrrolidine-2-carboxamido)propanoyl)oxy)propanoate bis(trifluoroacetic acid salt)

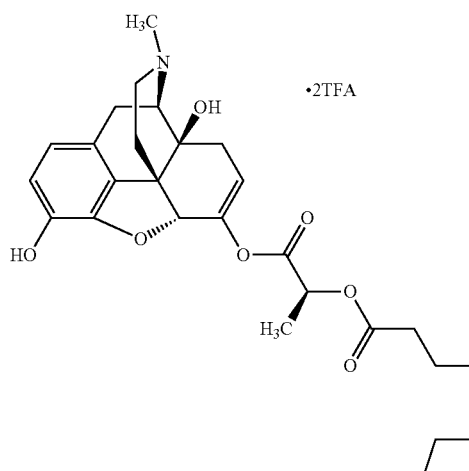

A solution of (S)-tert-butyl 2-((3-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)carbamoyl)pyrrolidine-1-carboxylate (81 mg, 0.13 mmol) in methylene chloride (2 mL) was treated with trifluoroacetic acid (1 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-((S)-pyrrolidine-2-carboxamido)propanoyl)oxy)propanoate bis(trifluoroacetic acid salt) (55 mg, 53%) as a fluffy white solid: $^1$H NMR (300 MHz, DMSO-$d_6$) δ 9.31 (s, 1H), 9.19 (br s, 2H), 8.61 (t, J=5.7 Hz, 1H), 8.54 (br s, 1H), 6.66 (apparent q, J=8.1 Hz, 2H), 6.25 (s, 1H), 5.58 (dd, J=6.0, 2.1 Hz, 1H), 5.12 (q, J=6.9 Hz, 1H), 4.96 (s, 1H), 4.13-3.03 (m, 10H), 2.84 (d, J=4.5 Hz, 3H), 2.64-2.19 (m, 5H), 2.05 (m, 1H), 1.92-1.77 (m, 3H), 1.62 (m, 1H), 1.53 (d, J=7.2 Hz, 3H); ESI MS m/z 542 $[C_{28}H_{35}N_3O_8+H]^+$.

Scheme 183: (S)-2-(((2R,3R)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy)-2-phenylacetic acid trifluoroacetic acid salt and (R)-2-(((2R,3R)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy)-2-phenylacetic acid trifluoroacetic acid salt

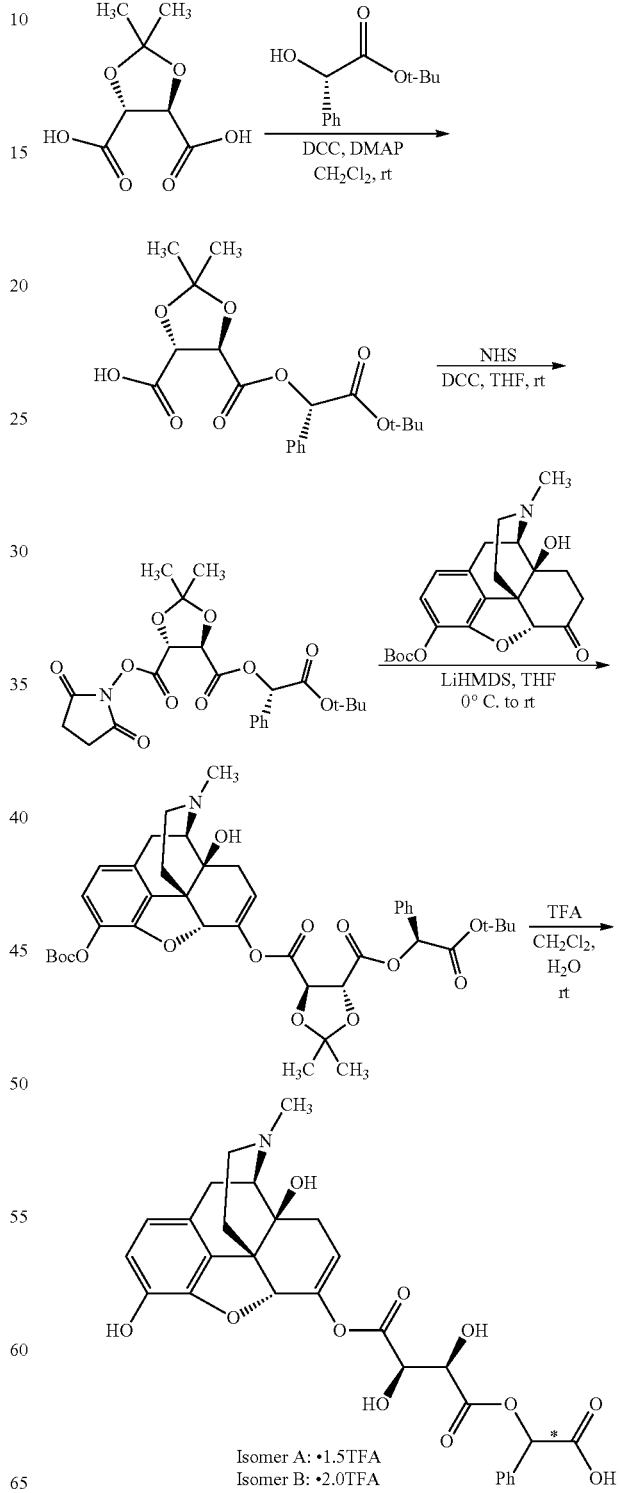

Preparation of (4R,5R)-5-(((S)-2-(tert-Butoxy)-2-oxo-1-phenylethoxy)carbonyl)-2,2-dimethyl-1,3-dioxolane-4-carboxylic acid

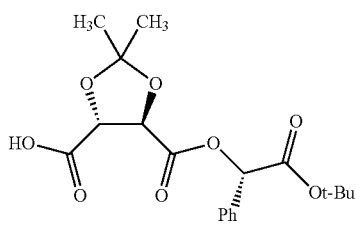 [SMILES: CC(C)(C)OC(=O)[C@@H](OC(=O)[C@@H]1OC(C)(C)O[C@H]1C(=O)O)c1ccccc1]

A mixture of (4R,5R)-2,2-dimethyl-1,3-dioxolane-4,5-dicarboxylic acid (765 mg, 4.03 mmol), (S)-tert-butyl 2-hydroxy-2-phenylacetate (enantiomeric ratio=~6:4, 843 mg, 4.05 mmol), and 4-dimethylaminopyridine (150 mg, 1.23 mmol) in methylene chloride (12 mL) was treated with N,N'-dicyclohexylcarbodiimide (920 mg, 4.46 mmol), and the reaction mixture was stirred at ambient temperature for 18 h. After this time, the mixture was filtered, and the filtrate was concentrated under reduced pressure. The residue was dissolved in ethyl acetate, washed with 2 N hydrochloric acid, and then extracted with saturated sodium bicarbonate. The aqueous layer was collected, carefully treated with 6N hydrochloric acid until acidic by pH paper analysis, and then extracted with ethyl acetate. The organic extracts were dried over sodium sulfate, filtered, and concentrated to provide (4R,5R)-5-(((S)-2-(tert-butoxy)-2-oxo-1-phenylethoxy)carbonyl)-2,2-dimethyl-1,3-dioxolane-4-carboxylic acid (550 mg, 36%) as a ~6:4 mixture of diastereomers: $^1$H NMR (300 MHz, CDCl$_3$) δ 7.50-7.42 (m, 2H), 7.42-7.34 (m, 3H), 5.92 (s, 0.4H), 5.89 (s, 0.6H), 5.08 (d, J=5.5 Hz, 0.4H), 4.98-4.91 (m, 1.6H), 1.58-1.51 (m, 6H), 1.40 (s, 9H), CO$_2$H proton not observed.

Preparation of (4R,5R)-4-((S)-2-(tert-Butoxy)-2-oxo-1-phenylethyl) 5-(2,5-dioxopyrrolidin-1-yl) 2,2-dimethyl-1,3-dioxolane-4,5-dicarboxylate

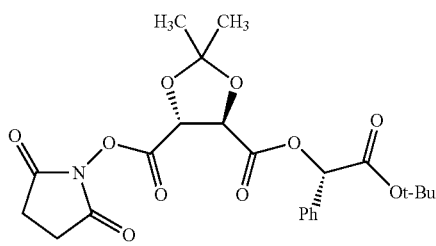 [SMILES: CC(C)(C)OC(=O)[C@@H](OC(=O)[C@@H]1OC(C)(C)O[C@H]1C(=O)ON1C(=O)CCC1=O)c1ccccc1]

A mixture of (4R,5R)-5-(((S)-2-(tert-butoxy)-2-oxo-1-phenylethoxy)carbonyl)-2,2-dimethyl-1,3-dioxolane-4-carboxylic acid (550 mg, 1.45 mmol) and N-hydroxysuccinimide (185 mg, 1.61 mmol) in tetrahydrofuran (10 mL) was treated with N,N'-dicyclohexylcarbodiimide (330 mg, 1.60 mmol), and the reaction mixture was stirred at ambient temperature for 4 h. After this time, diethyl ether (10 mL) was added, and the mixture was filtered. The filtrate was concentrated under reduced pressure to provide (4R,5R)-4-((S)-2-(tert-butoxy)-2-oxo-1-phenylethyl) 5-(2,5-dioxopyrrolidin-1-yl) 2,2-dimethyl-1,3-dioxolane-4,5-dicarboxylate (700 mg) that was used without purification: $^1$H NMR (300 MHz, CDCl$_3$, Mixture of diastereomers) δ 7.49-7.43 (m, 2H), 7.43-7.34 (m, 3H), 5.89 (s, 0.4H), 5.88 (s, 0.6H), 5.46 (d, J=4.3 Hz, 0.4H), 5.25 (d, J=4.3 Hz, 0.6H), 5.17 (d, J=4.3 Hz, 1H), 2.85 (s, 4H), 1.59-1.54 (m, 6H), 1.40 (s, 9H).

Preparation of (4R,5R)-4-((S)-2-(tert-Butoxy)-2-oxo-1-phenylethyl) 5-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2,2-dimethyl-1,3-dioxolane-4,5-dicarboxylate

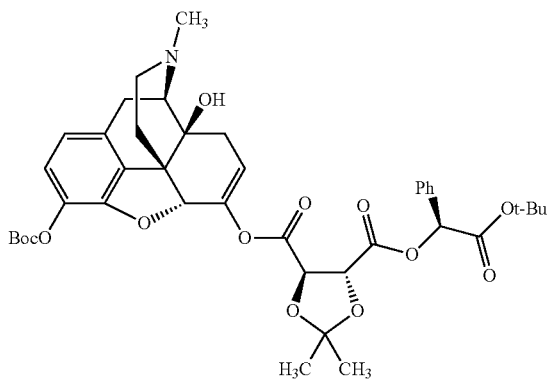

A solution of tert-butyl ((4R,4aS,7aR,12bS)-4a-hydroxy-3-methyl-7-oxo-2,3,4,4a,5,6,7,7a-octahydro-1H-4,12-methanobenzofuro[3,2-e]isoquinolin-9-yl) carbonate (310 mg, 0.77 mmol) in tetrahydrofuran (5 mL) was cooled to 0° C. and treated dropwise with a 1.0 M solution of lithium bis(trimethylsilyl)amidein tetrahydrofuran (0.8 mL, 0.8 mmol). After addition was complete, the mixture was stirred at ambient temperature for 10 min. The mixture was re-cooled to 0° C., and (4R,5R)-4-((S)-2-(tert-butoxy)-2-oxo-1-phenylethyl) 5-(2,5-dioxopyrrolidin-1-yl) 2,2-dimethyl-1,3-dioxolane-4,5-dicarboxylate (343 mg, 0.72 mmol) was added in one portion. The mixture was stirred at 0° C. for 45 min. After this time, the mixture was treated with saturated aqueous ammonium chloride and extracted with ethyl acetate. The combined organics were dried over sodium sulfate, filtered, and concentrated under reduced pressure. The residue was purified by reversed phase column chromatography (50 g C18 column, 5-100% acetonitrile/water) to provide (4R,5R)-4-((S)-2-(tert-butoxy)-2-oxo-1-phenylethyl) 5-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2,2-dimethyl-1,3-dioxolane-4,5-dicarboxylate (270 mg, 49%, ~6:4 mixture of diastereomers): ESI MS m/z 764 [C$_{41}$H$_{49}$NO$_{13}$+H]$^+$.

Preparation of (S)-2-(((2R,3R)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy)-2-phenylacetic acid trifluoroacetic acid salt and (R)-2-(((2R,3R)-4-(((4R,4aS,7aR,12bS)-4a,9-Dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy)-2-phenylacetic acid trifluoroacetic acid salt

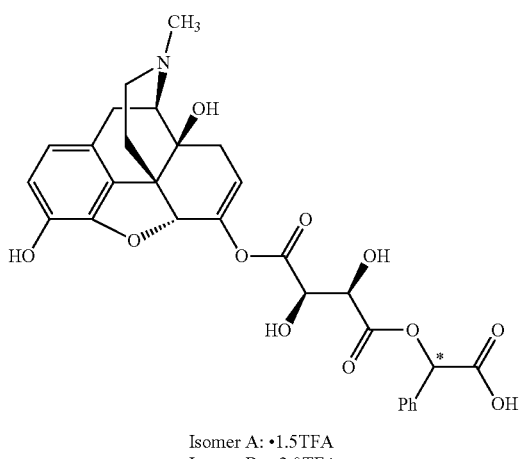

Isomer A: •1.5TFA
Isomer B : •2.0TFA

A solution of (4R,5R)-4-((S)-2-(tert-butoxy)-2-oxo-1-phenylethyl) 5-((4R,4aS,7aR,12bS)-9-((tert-butoxycarbonyl)oxy)-4a-hydroxy-3-methyl-2,3,4,4a,5,7a-hexahydro-1H-4,12-methanobenzofuro[3,2-e]isoquinolin-7-yl) 2,2-dimethyl-1,3-dioxolane-4,5-dicarboxylate (270 mg, 0.35 mmol) in methylene chloride (8 mL) was treated with trifluoroacetic acid (1.5 mL), and the mixture was stirred at room temperature for 1 h. LC-MS analysis of the reaction mixture indicated cleavage of the Boc and tert-butyl protecting groups. Water (0.1 mL) was added, and the mixture was stirred at ambient temperature for 3 h. After this time, the reaction mixture was concentrated under reduced pressure. The residue was purified by reversed phase column chromatography (50 g C18 column, 3-20% acetonitrile/water, with 0.1% trifluoroacetic acid) and freeze dried to provide of (S)-2-(((2R,3R)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy)-2-phenylacetic acid trifluoroacetic acid salt and (R)-2-(((2R,3R)-4-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-2,3-dihydroxy-4-oxobutanoyl)oxy)-2-phenylacetic acid trifluoroacetic acid salt.

Isomer A (86 mg, 33%): $^1$H NMR (300 MHz, DMSO-$d_6$) δ 13.38 (br s, 1H), 9.32 (s, 1H), 9.17 (br s, 1H), 7.54-7.47 (m, 2H), 7.47-7.39 (m, 3H), 6.69 (d, J=8.2 Hz, 1H), 6.63 (d, J=8.2 Hz, 1H), 6.26 (s, 1H), 5.99-5.80 (m, 3H), 5.54 (dd, J=6.1, 2.0 Hz, 1H), 5.02 (s, 1H), 4.67 (d, J=1.6 Hz, 1H), 4.59 (d, J=1.5 Hz, 1H), 3.62 (d, J=7.1 Hz, 1H), 3.38 (d, J=18.7 Hz, 1H), 3.13-3.00 (m, 2H), 2.84 (s, 3H), 2.70-2.57 (m, 1H), 2.43 (dd, J=14.2, 5.5 Hz, 1H), 2.28 (dd, J=17.5, 6.2 Hz, 1H), 2.05 (d, J=17.7 Hz, 1H), 1.63 (d, J=10.5 Hz, 1H); ESI MS m/z 568 $[C_{29}H_{29}NO_{11}+H]^+$; HPLC (Method A) 95.2% (AUC), $t_R$=7.79 min.

Isomer B (49 mg, 18%): $^1$H NMR (300 MHz, DMSO-$d_6$) δ 13.28 (br s, 1H), 9.32 (s, 1H), 9.15 (br s, 1H), 7.56-7.47 (m, 2H), 7.47-7.37 (m, 3H), 6.68 (d, J=8.2 Hz, 1H), 6.63 (d, J=8.2 Hz, 1H), 6.29 (br s, 1H), 5.94-5.89 (m, 3H), 5.56-5.35 (m, 1H), 5.03 (s, 1H), 4.70 (s, 1H), 4.64 (dd, J=8.0, 2.4 Hz, 1H), 3.61 (d, J=5.6 Hz, 1H), 3.41-3.38 (m, 1H), 3.14-2.99 (m, 2H), 2.83 (s, 3H), 2.71-2.58 (m, 1H), 2.47-2.38 (m, 1H), 2.27 (dd, J=17.4, 6.5 Hz, 1H), 2.05 (d, J=18.0 Hz, 1H), 1.63 (d, J=12.8 Hz, 1H); ESI MS m/z 568 $[C_{29}H_{29}NO_{11}+H]^+$; HPLC (Method A) 98.7% (AUC), $t_R$=7.96 min.

Scheme 184: (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-(((S)-2-((S)-2-amino-4-methylpentanamido)propanoyl)oxy)propanoate bis(trifluoroacetic acid salt)

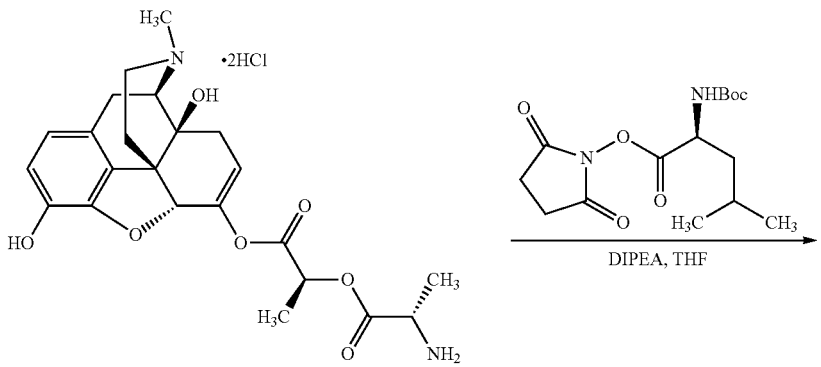

991

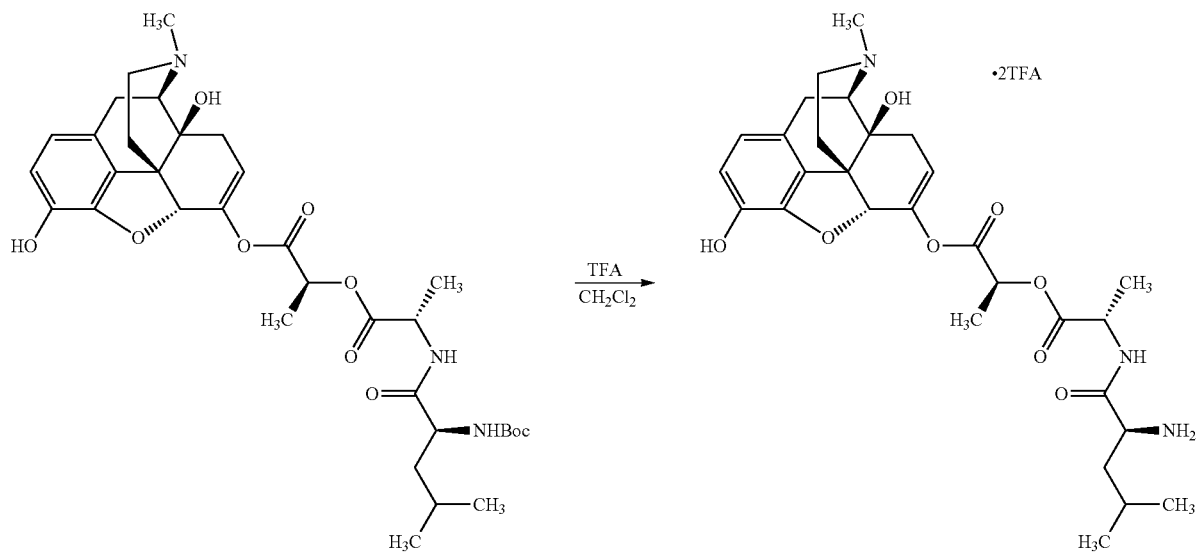

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-(((S)-2-((S)-2-((tert-butoxycarbonyl)amino)-4-methylpentanamido)propanoyl)oxy)propanoate

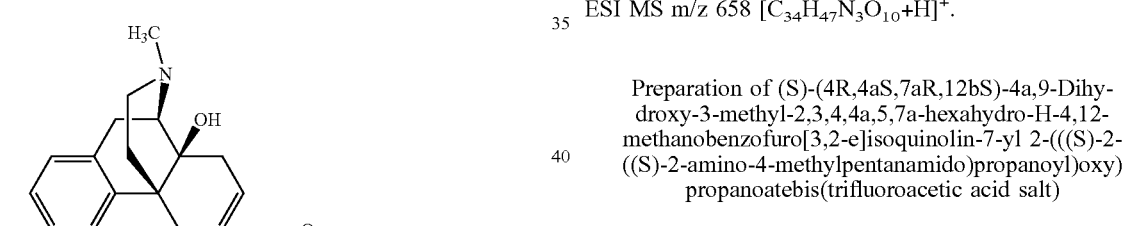

A solution of (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-(((S)-2-aminopropanoyl)oxy)propanoate hydrochloride (121 mg, 0.233 mmol) in tetrahydrofuran (6 mL) was treated with (S)-2,5-dioxopyrrolidin-1-yl 2-((tert-butoxycarbonyl)amino)-4-methylpentanoate (92 mg, 0.280 mmol) and diisopropylethylamine (75 mg, 0.583 mmol) at 0° C. and stirred under a nitrogen

992 atmosphere for 1 h. After this time the reaction mixture was concentrated under reduced pressure. The residue was purified by column chromatography (50 g, C18, 10-100% acetonitrile/water) to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-(((S)-2-((S)-2-((tert-butoxycarbonyl)amino)-4-methylpentanamido)propanoyl)oxy)propanoate (77 mg, 50%) as a white solid: ESI MS m/z 658 $[C_{34}H_{47}N_3O_{10}+H]^+$.

Preparation of (S)-(4R,4aS,7aR,12bS)-4a,9-Dihydroxy-3-methyl-2,3,4,4a,5,7a-hexahydro-H-4,12-methanobenzofuro[3,2-e]isoquinolin-7-yl 2-(((S)-2-((S)-2-amino-4-methylpentanamido)propanoyl)oxy)propanoatebis(trifluoroacetic acid salt)

A solution of (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-(((S)-2-((S)-2-((tert-butoxycarbonyl)amino)-4-methylpentanamido)propanoyl)oxy)propanoate (77 mg, 0.117 mmol) in methylene chloride (3 mL) was treated with trifluoroacetic acid (2 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-(((S)-2-((S)-2-amino-4-methylpentanamido)propanoyl)oxy)propanoate bis(trifluoroacetic acid salt)(48 mg, 48%) as a fluffy white solid: $^1$H NMR (300 MHz, DMSO-$d_6$) δ 9.32 (s, 1H), 9.15 (br s, 1H), 8.93 (d, J=6.9 Hz, 1H), 8.13 (br s, 3H), 6.65 (apparent q, J=8.1 Hz, 2H), 6.24 (s, 1H), 5.58 (dd, J=6.0, 2.1 Hz, 1H), 5.19 (q, J=6.9 Hz, 1H), 4.95 (s, 1H), 4.47 (m, 1H), 3.75 (m, 1H), 3.64-3.52 (m, 2H), 3.05 (m, 1H), 2.84 (d, J=4.5 Hz, 3H), 2.73-2.41 (m, 3H), 2.27 (m, 1H), 2.07 (m, 1H), 1.73-1.51 (m, 7H), 1.41 (d, J=7.5 Hz, 3H), 0.91 (t, J=6.6 Hz, 6H); ESI MS m/z 558 [$C_{29}H_{39}N_3O_8$+H]$^+$.

Scheme 185: (S)-4-Amino-5-((3-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoic acid bis(trifluoroacetic acid salt)

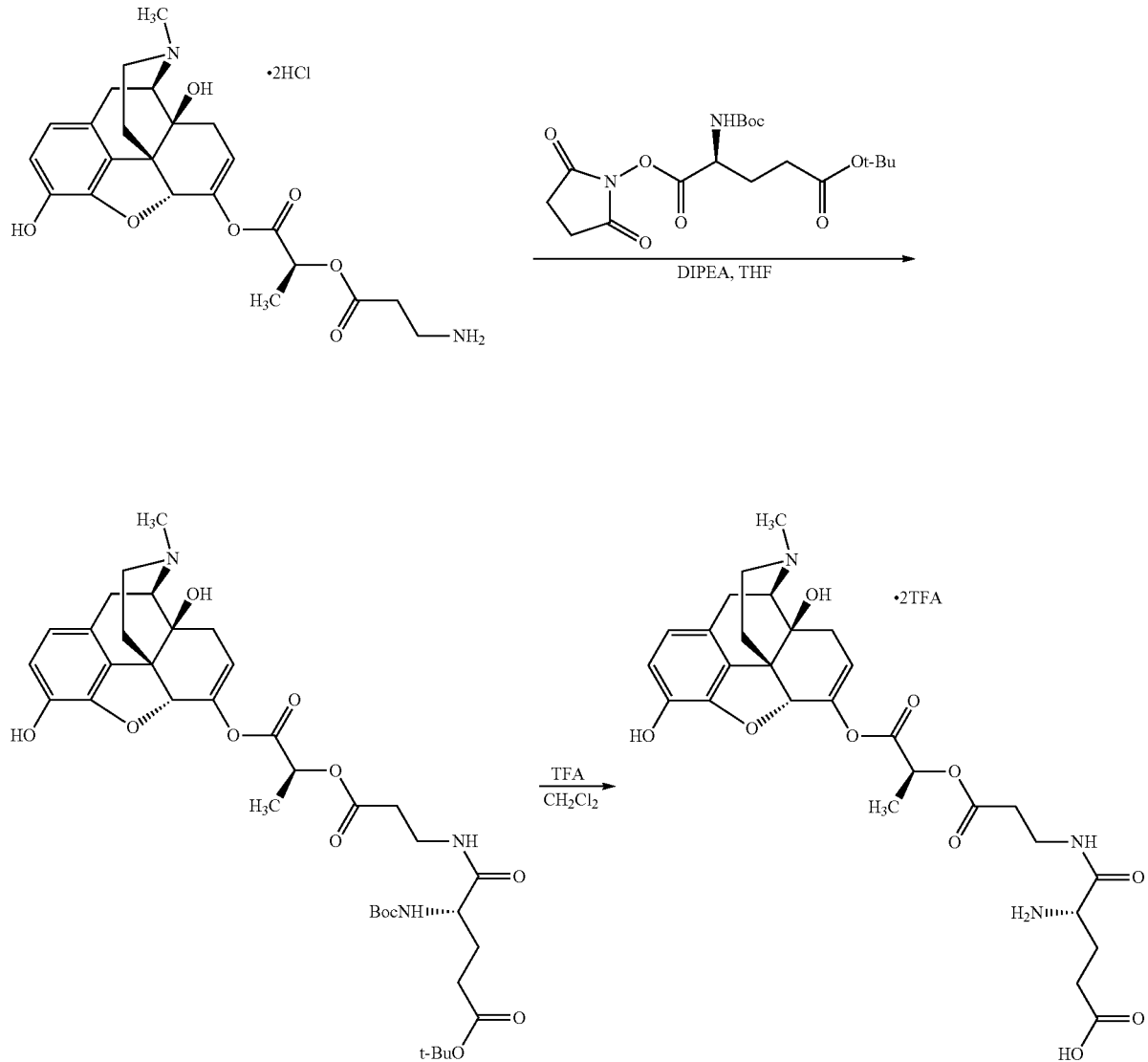

995

Preparation of (S)-tert-Butyl 4-((tert-butoxycarbonyl)amino)-5-((3-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoate

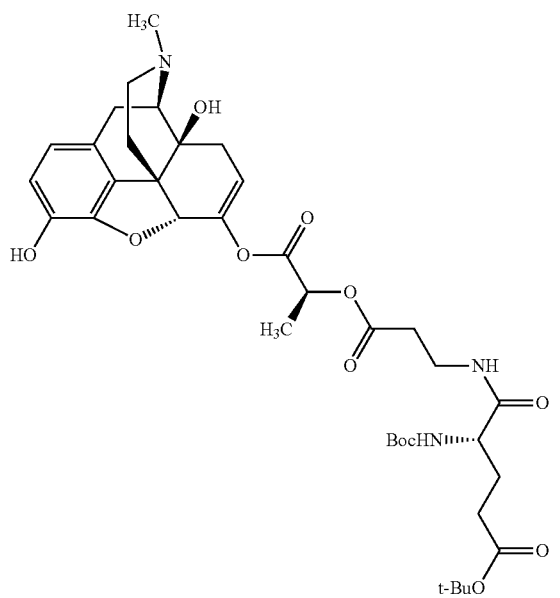 [SMILES: C[C@H](OC(=O)CCNC(=O)[C@H](CCC(=O)OC(C)(C)C)NC(=O)OC(C)(C)C)C(=O)OC1=CC[C@@]2(O)[C@H]3Cc4ccc(O)c5c4[C@@]2(CCN3C)[C@H]1O5]

A solution of (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-aminopropanoyl)oxy)propanoate dihydrochloride (121 mg, 0.233 mmol) in tetrahydrofuran (6 mL) was treated with (S)-5-tert-butyl 1-(2,5-dioxopyrrolidin-1-yl) 2-((tert-butoxycarbonyl)amino)pentanedioate (112 mg, 0.280 mmol) and N,N-diisopropylethylamine (75 mg, 0.58 mmol) at 0° C. and stirred under a nitrogen atmosphere for 1 h. After this time the reaction mixture was concentrated under reduced pressure. The residue was purified by column chromatography (40 g, silica gel, 0-20% methanol/methylene chloride) to (S)-tert-butyl 4-((tert-butoxycarbonyl)amino)-5-((3-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoate (91 mg, 53%) as a white solid: ESI MS m/z 730 $[C_{37}H_{51}N_3O_{12}+H]^+$.

996

Preparation of (S)-4-Amino-5-((3-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoic acidbis(trifluoroacetic acid salt)

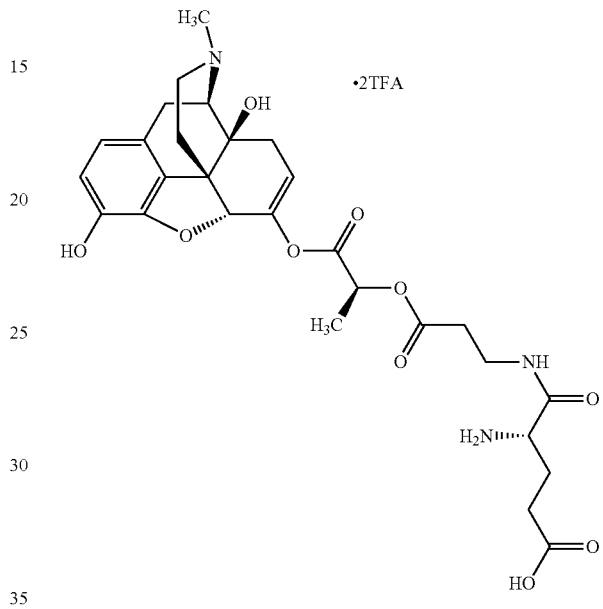

A solution of (S)-tert-butyl 4-((tert-butoxycarbonyl)amino)-5-((3-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoate (91 mg, 0.13 mmol) in methylene chloride (3 mL) was treated with trifluoroacetic acid (2 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-4-amino-5-((3-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-3-oxopropyl)amino)-5-oxopentanoic acid bis(trifluoroacetic acid salt)(44 mg, 42%) as a fluffy white solid: $^1$H NMR (300 MHz, DMSO-d$_6$) δ 12.35 (br s, 1H), 9.32 (s, 1H), 9.17 (br s, 1H), 8.61 (t, J=5.4 Hz, 1H), 8.14 (br s, 3H), 6.66 (apparent q, J=8.1 Hz, 2H), 6.26 (s, 1H), 5.58 (dd, J=6.0, 2.1 Hz, 1H), 5.11 (q, J=7.2 Hz, 1H), 4.96 (s, 1H), 3.74 (m, 1H), 3.67-3.27 (m, 4H), 3.06 (m, 1H), 2.84 (s, 3H), 2.63-2.41 (m, 5H), 2.32-2.26 (m, 3H), 2.05 (m, 1H), 1.96-1.88 (m, 2H), 1.62 (m, 1H), 1.53 (d, J=7.2 Hz, 3H); ESI MS m/z 574 $[C_{28}H_{35}N_3O_{10}+H]^+$.

Scheme 186: (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-(((S)-2-(((S)-pyrrolidine-2-carboxamido)propanoyl)oxy)propanoate bis(trifluoroacetic acid salt)

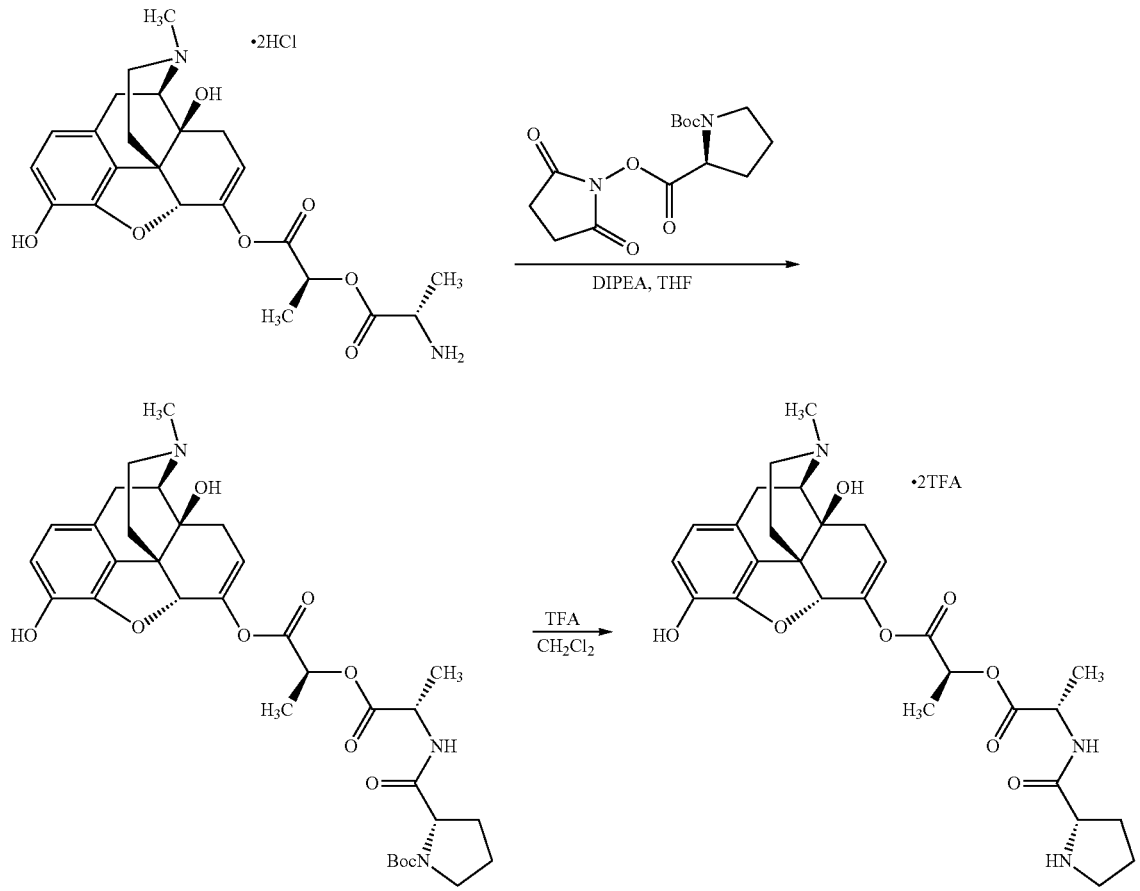

Preparation of (S)-tert-Butyl 2-(((S)-1-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-y)oxy)-1-oxopropan-2-yl)carbamoyl)pyrrolidine-1-carboxylate

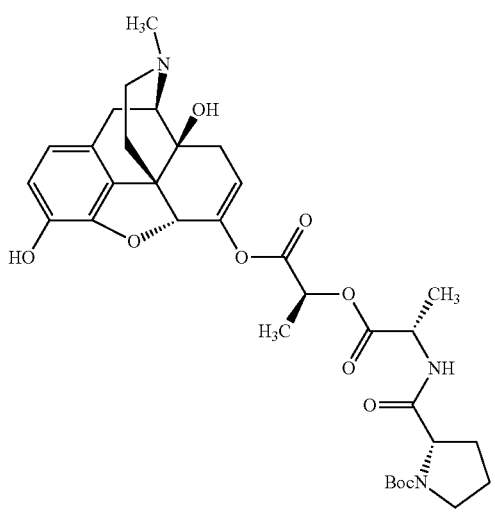 [SMILES: C[C@H](NC(=O)[C@@H]1CCCN1C(=O)OC(C)(C)C)C(=O)O[C@@H](C)C(=O)OC1=CC[C@@]2(O)[C@H]3Cc4ccc(O)c5c4[C@@]2(CCN3C)[C@H]1O5]

A solution of (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-(((S)-2-aminopropanoyl)oxy)propanoate hydrochloride (121 mg, 0.233 mmol) in tetrahydrofuran (6 mL) was treated with (S)-1-tert-butyl 2-(2,5-dioxopyrrolidin-1-yl) pyrrolidine-1,2-dicarboxylate (87 mg, 0.28 mmol) and diisopropylethylamine (75 mg, 0.58 mmol) at 0° C. and stirred under a nitrogen atmosphere for 1 h. After this time the reaction mixture was concentrated under reduced pressure. The residue was purified by column chromatography (50 g, C18, 10-100% acetonitrile/water) to provide (S)-tert-butyl 2-(((S)-1-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl)carbamoyl) pyrrolidine-1-carboxylate (59 mg, 39%) as a white solid: ESI MS m/z 642 $[C_{33}H_{43}N_3O_{10}+H]^+$.

999

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-(((S)-2-((S)-pyrrolidine-2-carboxamido)propanoyl)oxy)propanoatebis(trifluoroacetic acid salt)

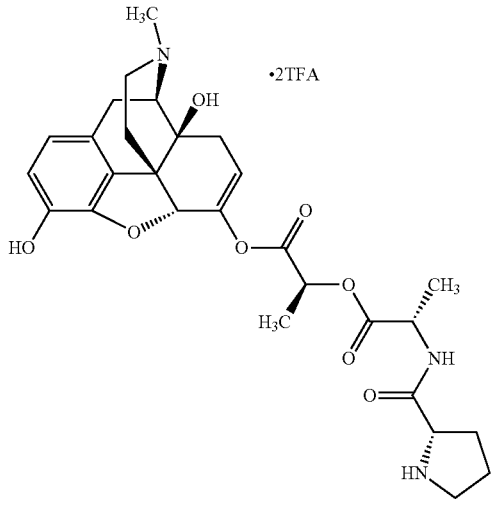 [SMILES: C[C@H](NC(=O)[C@@H]1CCCN1)C(=O)O[C@@H](C)C(=O)OC1=CC[C@@]2(O)[C@H]3Cc4ccc(O)c5c4[C@@]2(CCN3C)[C@H]1O5]

1000

A solution of (S)-tert-butyl 2-(((S)-1-(((S)-1-(((4R,4aS,7aR,12bS)-4a,9-dihydroxy-3-methyl-2,3,4,4a,5,7a-hexahydro-1H-4,12-methanobenzofuro[3,2-e]isoquinolin-7-yl)oxy)-1-oxopropan-2-yl)oxy)-1-oxopropan-2-yl)carbamoyl)pyrrolidine-1-carboxylate (59 mg, 0.092 mmol) in methylene chloride (3 mL) was treated with trifluoroacetic acid (1 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-(((S)-2-((S)-pyrrolidine-2-carboxamido)propanoyl)oxy)propanoate bis(trifluoroacetic acid salt)(25 mg, 32%) as a fluffy white solid: $^1$H NMR (300 MHz, DMSO-$d_6$) δ 9.32 (s, 1H), 9.25 (br s, 1H), 9.17 (br s, 1H), 8.97 (d, J=6.6 Hz, 1H), 8.56 (br s, 1H), 6.66 (apparent q, J=8.1 Hz, 2H), 6.25 (s, 1H), 5.58 (dd, J=6.0, 2.4 Hz, 1H), 5.18 (q, J=6.9 Hz, 1H), 4.95 (s, 1H), 4.44 (m, 1H), 4.21 (m, 1H), 3.67-3.03 (m, 4H), 2.84 (d, J=4.5 Hz, 3H), 2.72-2.41 (m, 3H), 2.31-2.27 (m, 2H), 2.07 (m, 1H), 1.91-1.84 (m, 3H), 1.62 (m, 1H), 1.54 (d, J=7.2 Hz, 3H), 1.41 (d, J=7.2 Hz, 3H); ESI MS m/z 542 $[C_{28}H_{35}N_3O_8+H]^+$.

Scheme 187: (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((3-((S)-2-amino-3-phenylpropanamido)propanoyl)oxy)propanoate bis(trifluoroacetic acid salt)

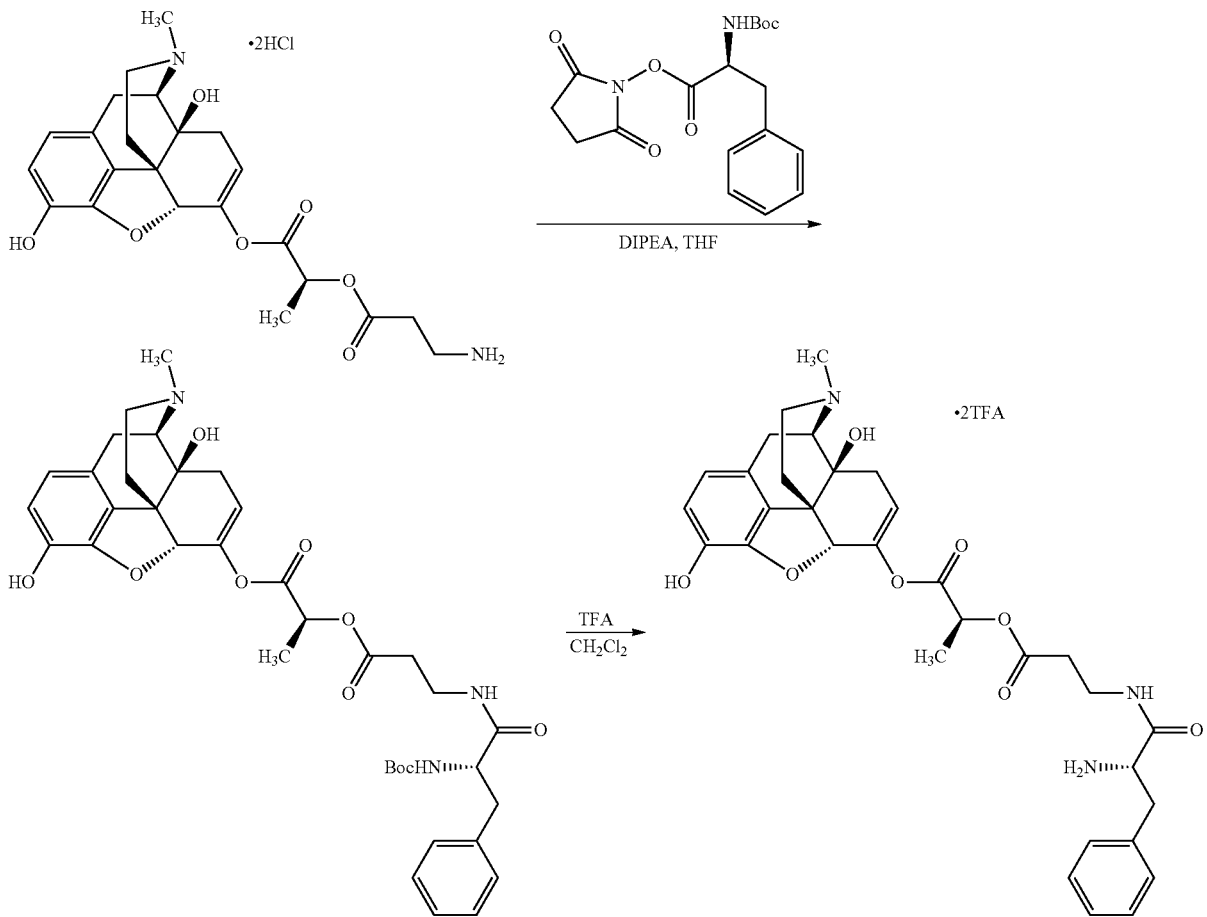

1001

Preparation of (S)-(4R,4aS,7aR,12bS)-4a,9-Dihydroxy-3-methyl-2,3,4,4a,5,7a-hexahydro-1H-4,12-methanobonzofuro[3,2-e]isoquinolin-7-yl 2-((3-((S)-2((tert-butoxycarbonyl)amino-3-phenylpropanamido)propanoyl)oxy)propanoate

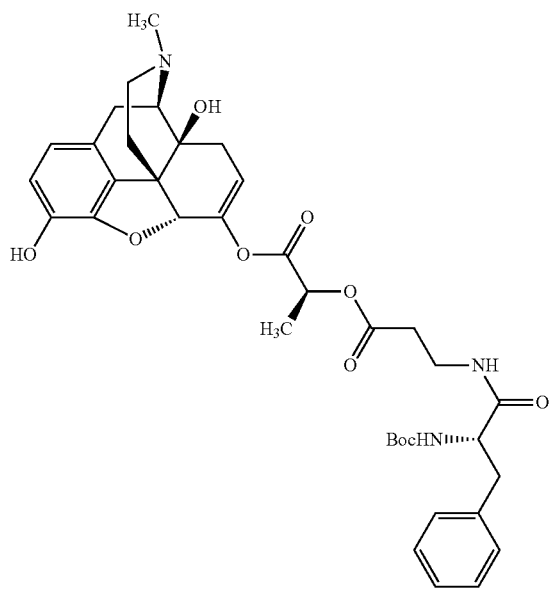 [SMILES: C[C@H](OC(=O)CCNC(=O)[C@H](Cc1ccccc1)NC(=O)OC(C)(C)C)C(=O)OC1=CC[C@@]2(O)[C@H]3Cc4ccc(O)c5c4[C@@]2(CCN3C)[C@H]1O5]

A solution of (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-aminopropanoyl)oxy)propanoate dihydrochloride (121 mg, 0.233 mmol) in tetrahydrofuran (6 mL) was treated with (S)-2,5-dioxopyrrolidin-1-yl 2-((tert-butoxycarbonyl)amino)-3-phenylpropanoate (98 mg, 0.28 mmol) and N,N-diisopropylethylamine (75 mg, 0.58 mmol) at 0° C. and stirred under a nitrogen atmosphere for 1 h. After this time, the reaction mixture was concentrated under reduced pressure. The residue was purified by column chromatography (40 g silica gel column, 0-20% methanol/methylene chloride) to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-((S)-2-((tert-butoxycarbonyl)amino)-3-phenylpropanamido)propanoyl)oxy)propanoate (45 mg, 28%) as a white solid: ESI MS m/z 692 [$C_{37}H_{45}N_3O_{10}$+H]$^+$.

1002

Preparation of (S)-(4R,4aS,7aR,12bS)-4a,9-Dihydroxy-3-methyl-2,3,4,4a,5,7a-hexahydro-1H-4,12-methanobenzofuro[3,2-e]isoquinolin-7-yl 2-((3-((S)-2-amino-3-phenylpropanamido)propanoyl)oxy)propanoatebis(trifluoroacetic acid salt)

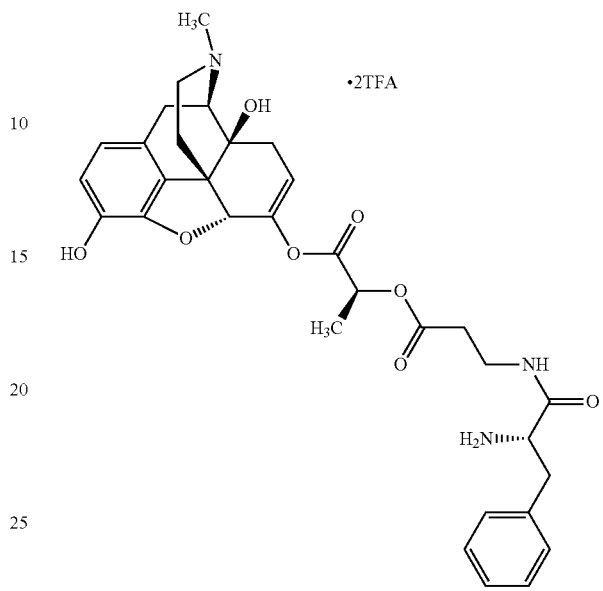

A solution of (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-((S)-2-((tert-butoxycarbonyl)amino)-3-phenylpropanamido)propanoyl)oxy)propanoate (45 mg, 0.066 mmol) in methylene chloride (3 mL) was treated with trifluoroacetic acid (1 mL) and stirred under a nitrogen atmosphere at ambient temperature for 1 h. After this time, the reaction mixture was concentrated under reduced pressure. The residue was purified by reversed phase column chromatography (50 g C18 column, 0-100% acetonitrile/water with 0.1% trifluoroacetic acid) and freeze dried to provide (S)-(4R,4aS,7aR,12bS)-4a,9-dihydroxy-3-methyl-2,3,4,4a,5,7a-hexahydro-1H-4,12-methanobenzofuro[3,2-e]isoquinolin-7-yl 2-((3-((S)-2-amino-3-phenylpropanamido)propanoyl)oxy)propanoate bis(trifluoroacetic acid salt)(40 mg, 70%) as a fluffy white solid: $^1$H NMR (300 MHz, DMSO-d$_6$) δ 9.32 (s, 1H), 9.16 (br s, 1H), 8.49 (t, J=5.4 Hz, 1H), 8.19 (br s, 3H), 7.37-7.24 (m, 5H), 6.65 (apparent q, J=8.1 Hz, 2H), 6.25 (s, 1H), 5.57 (dd, J=5.7, 1.8 Hz, 1H), 5.08 (q, J=6.9 Hz, 1H), 3.94 (m, 1H), 3.64-3.16 (m, 6H), 3.11-2.92 (m, 4H), 2.84 (d, J=3.3 Hz, 3H), 2.73-2.24 (m, 3H), 2.28 (m, 1H), 2.05 (m, 1H), 1.61 (m, 1H), 1.53 (d, J=7.2 Hz, 3H); ESI MS m/z 592 [$C_{32}H_{37}N_3O_8$+H]$^+$.

Test Preparation, Procedures, and Analysis

Animal studies were conducted on *Rattus norvegicus*, specifically of the Sprague Dawley strain. Three male Sprague Dawley rats per test article were jugular vein cannulated (JVC) for blood collection. The rats weighed approximately 225-250 g at treatment. The rats were allowed a minimum of 2 day acclimation period and were fasted approximately 16-20 hours before dosing. Fasting continued until 4 hours post-dose.

The dosing formulations were prepared on the day of dosing. The test article concentration was equivalent to 2 mg/mL oxymorphone HCl or 10 mg/mL oxycodone HCl. For test articles that were provided as salt forms, the dosing vehicle was 0.5% methylcellulose in water. For test articles that were provided as free base forms, the dosing vehicle was 0.5% methylcellulose in dilute HCl. Each dosing formulation was prepared by weighing the test article into the formulation container, followed by addition of the appropriate volume of vehicle based on the weighed amount. If the test article appeared undissolved, the dosing formulation was sonicated to aid dissolution. The dosing formulations were mixed well and continuously stirred until filling the dosing syringes. Following dosing, any remaining formulation was stored at approximately −20° C.

Each animal was administered a single oral gavage (PO) dose. Any obviously mis-dosed animals were replaced. The volume of dosing formulation that was administered to each animal was calculated based on the pre-dose body weight obtained on the day of dosing.

Samples were collected at 15 min., 30 min., 1 h, 2 h, 3 h, 4, h, and 6 h post-dose. $K_2EDTA$ was used as an anticoagulant. At each non-terminal sample time, a 0.5 mL blood sample was collected from the JVC. After each non-terminal sample removal, 0.4 mL strain-matched donor blood was transfused via the JVC to replace removed blood, followed by a flush of the cannula with heparinized saline. If the cannula failed, retroorbital or tail bleeding was used. The terminal sample was collected by cardiac puncture and was approximately 0.5 mL volume.

Blood collection tubes were placed on ice immediately and centrifuged within 30 minutes at 4° C. to separate plasma. Samples were centrifuged at approximately 6000 rpm for 3 minutes at 4° C. Plasma was removed, placed into labeled polypropylene tubes, and quick frozen over dry ice. The plasma tubes were labeled with the study number, animal number, and sample time. Plasma specimens were stored at −70° C. until analysis.

Plasma samples were analyzed for oxymorphone/oxycodone concentrations using LC-MS/MS methods using the following steps: (1) Quantitation by LC-MS/MS with internal standard; (2) Determine anticipated calibration curve range; (3) Prepare calibration curve before and after sample analysis (N=2) in blank plasma using the following standards: (a) Minimum of 6 standard concentration; and (b) Acceptance criteria: Five standard concentrations minimum within the curve, must contain at least one standard at both bottom and top of the range back calculated to ±20% of their nominal concentrations. It is acceptable to remove the upper or lower standards to bring the curve into ±20% nominal. Each batch also contained at least double blank, single blank, and carryover blank controls.

Example 1

Three Sprague Dawley rats were administered a dose of 1.77 mg/kg Oxymorphone HCl Oral. The plasma concentrations of oxymorphone in each rat, the mean plasma concentration of oxymorphone, and the standard deviation at the seven time points are summarized in Table 2:

TABLE 2

| Group 1: 1.77 mg/kg Oxymorphone HCl Oral | | | | | |
|---|---|---|---|---|---|
| | Plasma oxymorphone (ng/mL) | | | | |
| Time (h) | Rat 1 | Rat 2 | Rat 3 | Mean | SD |
| 0.25 | 0.379 | 0.862 | 1.144 | 0.795 | 0.387 |
| 0.5 | 0.343 | 0.925 | 0.799 | 0.689 | 0.306 |
| 1 | 0.545 | 1.557 | 1.110 | 1.071 | 0.507 |
| 2 | 0.728 | 1.826 | 0.621 | 1.058 | 0.667 |
| 3 | 0.457 | 0.676 | BQL | 0.378 | 0.345 |
| 4 | 0.508 | 0.429 | BQL | 0.312 | 0.273 |

TABLE 2-continued

| Group 1: 1.77 mg/kg Oxymorphone HCl Oral | | | | | |
|---|---|---|---|---|---|
| | Plasma oxymorphone (ng/mL) | | | | |
| Time (h) | Rat 1 | Rat 2 | Rat 3 | Mean | SD |
| 6 | BQL | 1.800 | BQL | 0.600 | 1.039 |
| $C_{max}$ (ng/mL) | 0.728 | 1.826 | 1.144 | 1.233 | 0.554 |
| $T_{max}$ (h) | 2.00 | 2.00 | 0.25 | 1.417 | 1.010 |
| $AUC_{last}$ (h*ng/mL) | | | | | |

BQL: <0.200 ng/mL

Example 2

Three Sprague Dawley rats were administered a dose of 3.54 mg/kg Oxymorphone HCl Oral. The plasma concentrations of oxymorphone in each rat, the mean plasma concentration of oxymorphone, and the standard deviation at the seven time points are summarized in Table 3:

TABLE 3

| Group 2: 3.54 mg/kg Oxymorphone HCl Oral | | | | | |
|---|---|---|---|---|---|
| | Plasma oxymorphone (ng/mL) | | | | |
| Time (h) | Rat 4 | Rat 5 | Rat 6 | Mean | SD |
| 0.25 | 4.958 | 3.246 | 1.767 | 3.324 | 1.597 |
| 0.5 | 4.716 | 2.469 | 2.095 | 3.093 | 1.418 |
| 1 | 3.423 | 2.146 | 0.913 | 2.161 | 1.255 |
| 2 | 1.273 | 2.434 | 1.639 | 1.782 | 0.594 |
| 3 | 0.577 | 1.635 | 1.276 | 1.163 | 0.538 |
| 4 | 0.335 | 0.545 | 0.618 | 0.499 | 0.147 |
| 6 | 0.453 | 0.796 | 0.774 | 0.674 | 0.192 |
| $C_{max}$ (ng/mL) | | | | | |
| $T_{max}$ (h) | | | | | |
| $AUC_{last}$ (h*ng/mL) | | | | | |

BQL: <0.200 ng/mL

Example 3

Three Sprague Dawley rats were administered a dose of 7.12 mg/kg Oxymorphone Oleate (Ex No. B3) Oral. The plasma concentrations of oxymorphone in each rat, the mean plasma concentration of oxymorphone, and the standard deviation at the seven time points are summarized in Table 4:

TABLE 4

| Group 3: 7.12 mg/kg Oxymorphone Oleate Oral | | | | | |
|---|---|---|---|---|---|
| | Plasma oxymorphone (ng/mL) | | | | |
| Time (h) | Rat 7 | Rat 8 | Rat 9 | Mean | SD |
| 0.25 | 1.718 | 0.256 | BQL | 0.987 | ND |
| 0.5 | BQL | 0.203 | BQL | 0.068 | ND |
| 1 | 0.242 | 0.245 | 0.448 | 0.312 | 0.118 |
| 2 | BQL | BQL | 0.239 | 0.080 | ND |
| 3 | 0.424 | 0.662 | 0.462 | 0.516 | 0.128 |
| 4 | 0.290 | 0.643 | 0.514 | 0.482 | 0.179 |
| 6 | 1.828 | 0.614 | 1.167 | 1.203 | 0.608 |
| $C_{max}$ (ng/mL) | | | | | |
| $T_{max}$ (h) | | | | | |
| $AUC_{last}$ (h*ng/mL) | | | | | |

BQL: <0.200 ng/mL
ND: Not determined (N < 3)

Example 4

Three Sprague Dawley rats were administered a dose of 5.56 mg/kg Oxymorphone Malate (Ex No. B5) Oral. The plasma concentrations of oxymorphone in each rat, the mean plasma concentration of oxymorphone, and the standard deviation at the seven time points are summarized in Table 5:

TABLE 5

Group 4: 5.56 mg/kg Oxymorphone Malate Oral

| Time (h) | Plasma oxymorphone (ng/mL) | | | | |
|---|---|---|---|---|---|
| | Rat 10 | Rat 11 | Rat 12 | Mean | SD |
| 0.25 | 3.309 | 1.469 | 2.289 | 2.356 | 0.922 |
| 0.5 | 6.131 | 2.268 | 2.821 | 3.740 | 2.089 |
| 1 | 7.497 | 3.572 | 4.122 | 5.064 | 2.125 |
| 2 | 5.038 | 2.696 | 2.605 | 3.446 | 1.379 |
| 3 | 4.153 | 2.808 | 2.173 | 3.045 | 1.011 |
| 4 | 2.480 | 1.884 | 2.094 | 2.153 | 0.302 |
| 6 | 0.861 | 1.553 | 0.926 | 1.113 | 0.382 |
| $C_{max}$ (ng/mL) | | | | | |
| $T_{max}$ (h) | | | | | |
| $AUC_{last}$ (h*ng/mL) | | | | | |

BQL: <0.200 ng/mL

Example 5

Three Sprague Dawley rats were administered a dose of 6.72 mg/kg Oxymorphone Mandelate (Ex No. B1a) Oral. The plasma concentrations of oxymorphone in each rat, the mean plasma concentration of oxymorphone, and the standard deviation at the seven time points are summarized in Table 6:

TABLE 6

Group 5: 6.72 mg/kg Oxymorphone Mandelate Oral (not completely soluble)

| Time (h) | Plasma oxymorphone (ng/mL) | | | | |
|---|---|---|---|---|---|
| | Rat 13 | Rat 14 | Rat 15 | Mean | SD |
| 0.25 | 0.649 | 0.889 | 0.824 | 0.787 | 0.124 |
| 0.5 | 0.660 | 1.017 | 0.705 | 0.794 | 0.194 |
| 1 | 0.500 | 1.434 | 0.612 | 0.849 | 0.510 |
| 2 | 0.543 | 1.445 | 0.691 | 0.893 | 0.484 |
| 3 | 0.546 | 0.870 | 0.718 | 0.711 | 0.162 |
| 4 | 0.667 | 0.799 | 0.477 | 0.648 | 0.162 |
| 6 | 0.354 | 1.482 | 0.836 | 0.891 | 0.566 |
| $C_{max}$ (ng/mL) | | | | | |
| $T_{max}$ (h) | | | | | |
| $AUC_{last}$ (h*ng/mL) | | | | | |

BQL: <0.200 ng/mL

Example 6

Three Sprague Dawley rats were administered a dose of 5.48 mg/kg Oxymorphone Mandelate (Ex No. B1b) Oral. The plasma concentrations of oxymorphone in each rat, the mean plasma concentration of oxymorphone, and the standard deviation at the seven time points are summarized in Table 7:

TABLE 7

Group 6: 5.48 mg/kg Oxymorphone Mandelate Oral

| Time (h) | Plasma oxymorphone (ng/mL) | | | | |
|---|---|---|---|---|---|
| | Rat 16 | Rat 17 | Rat 18 | Mean | SD |
| 0.25 | 0.976 | 2.781 | 3.377 | 2.378 | 1.250 |
| 0.5 | 1.162 | 2.229 | 3.898 | 2.430 | 1.379 |
| 1 | 1.320 | 2.385 | 4.951 | 2.885 | 1.866 |
| 2 | 1.273 | 1.607 | 2.615 | 1.832 | 0.699 |

TABLE 7-continued

Group 6: 5.48 mg/kg Oxymorphone Mandelate Oral

| Time (h) | Plasma oxymorphone (ng/mL) | | | | |
|---|---|---|---|---|---|
| | Rat 16 | Rat 17 | Rat 18 | Mean | SD |
| 3 | 0.884 | 0.821 | 0.623 | 0.776 | 0.136 |
| 4 | 0.465 | 0.471 | 0.223 | 0.386 | 0.141 |
| 6 | 0.594 | 0.321 | 2.896 | 1.270 | 1.414 |
| $C_{max}$ (ng/mL) | | | | | |
| $T_{max}$ (h) | | | | | |
| $AUC_{last}$ (h*ng/mL) | | | | | |

BQL: <0.200 ng/mL

Example 7

Three Sprague Dawley rats were administered a dose of 6.01 mg/kg Oxymorphone Lactate (Ex No. B2a) Oral. The plasma concentrations of oxymorphone in each rat, the mean plasma concentration of oxymorphone, and the standard deviation at the seven time points are summarized in Table 8:

TABLE 8

Group 7: 6.01 mg/kg Oxymorphone Lactate Oral

| Time (h) | Plasma oxymorphone (ng/mL) | | | | |
|---|---|---|---|---|---|
| | Rat 19 | Rat 20 | Rat 21 | Mean | SD |
| 0.25 | 3.689 | 1.782 | 1.836 | 2.436 | 1.086 |
| 0.5 | 4.377 | 2.711 | 1.514 | 2.867 | 1.438 |
| 1 | 2.485 | 2.347 | 1.989 | 2.274 | 0.256 |
| 2 | 1.351 | 2.022 | 0.995 | 1.456 | 0.521 |
| 3 | 0.501 | 1.422 | 0.408 | 0.777 | 0.561 |
| 4 | 0.218 | 0.998 | 0.451 | 0.556 | 0.400 |
| 6 | 1.128 | 1.784 | 0.466 | 1.126 | 0.659 |
| $C_{max}$ (ng/mL) | | | | | |
| $T_{max}$ (h) | | | | | |
| $AUC_{last}$ (h*ng/mL) | | | | | |

BQL: <0.200 ng/mL

Example 8

Three Sprague Dawley rats were administered a dose of 4.93 mg/kg Oxymorphone Lactate (Ex No. B2a) Oral. The plasma concentrations of oxymorphone in each rat, the mean plasma concentration of oxymorphone, and the standard deviation at the seven time points are summarized in Table 9:

TABLE 9

Group 8: 4.93 mg/kg Oxymorphone Lactate Oral

| Time (h) | Plasma oxymorphone (ng/mL) | | | | |
|---|---|---|---|---|---|
| | Rat 22 | Rat 23 | Rat 24 | Mean | SD |
| 0.25 | 4.760 | 0.740 | 3.488 | 2.996 | 2.055 |
| 0.5 | 3.470 | 2.347 | 2.514 | 2.777 | 0.606 |
| 1 | 3.749 | 2.839 | 1.846 | 2.811 | 0.952 |
| 2 | 1.698 | 2.279 | 2.062 | 2.013 | 0.294 |
| 3 | 1.325 | 1.306 | 1.199 | 1.277 | 0.068 |

TABLE 9-continued

Group 8: 4.93 mg/kg Oxymorphone Lactate Oral

| | Plasma oxymorphone (ng/mL) | | | | |
|---|---|---|---|---|---|
| Time (h) | Rat 22 | Rat 23 | Rat 24 | Mean | SD |
| 4 | 1.504 | 0.728 | 0.642 | 0.958 | 0.475 |
| 6 | 1.323 | 0.915 | 1.915 | 1.384 | 0.503 |
| $C_{max}$ (ng/mL) | | | | | |
| $T_{max}$ (h) | | | | | |
| $AUC_{last}$ (h*ng/mL) | | | | | |

BQL: <0.200 ng/mL

Example 9

Three Sprague Dawley rats were administered a dose of 7.4 mg/kg Oxymorphone Stearate (Ex No. B4) Oral. The plasma concentrations of oxymorphone in each rat, the mean plasma concentration of oxymorphone, and the standard deviation at the seven time points are summarized in Table 10:

TABLE 10

Group 9: 7.4 mg/kg Oxymorphone Stearate Oral (not completely soluble)

| | Plasma oxymorphone (ng/mL) | | | | |
|---|---|---|---|---|---|
| Time (h) | Rat 25 | Rat 26 | Rat 27 | Mean | SD |
| 0.25 | 0.372 | 1.047 | 2.369 | 1.263 | 1.016 |
| 0.5 | 0.938 | 1.560 | 3.332 | 1.943 | 1.242 |
| 1 | 0.640 | 1.484 | 3.230 | 1.785 | 1.321 |
| 2 | 0.745 | 1.031 | 2.208 | 1.328 | 0.775 |
| 3 | 0.732 | 0.763 | 1.927 | 1.141 | 0.681 |
| 4 | 0.680 | 0.986 | 0.845 | 0.837 | 0.153 |
| 6 | 6.220 | 3.176 | 1.077 | 3.491 | 2.586 |
| $C_{max}$ (ng/mL) | | | | | |
| $T_{max}$ (h) | | | | | |
| $AUC_{last}$ (h*ng/mL) | | | | | |

BQL: <0.200 ng/mL

Example 10

Three Sprague Dawley rats were administered a dose of 6.16 mg/kg Oxymorphone Alanine (Ex No. B6) Oral. The plasma concentrations of oxymorphone in each rat, the mean plasma concentration of oxymorphone, and the standard deviation at the seven time points are summarized in Table 11:

TABLE 11

Group 10: 6.16 mg/kg Oxymorphone Alanine Oral

| | Plasma oxymorphone (ng/mL) | | | | |
|---|---|---|---|---|---|
| Time (h) | Rat 28 | Rat 29 | Rat 30 | Mean | SD |
| 0.25 | 4.594 | 1.841 | 2.008 | 2.814 | 1.543 |
| 0.5 | 3.106 | 6.227 | 3.877 | 4.403 | 1.626 |
| 1 | 2.794 | 2.901 | 3.409 | 3.035 | 0.329 |
| 2 | 1.863 | 3.212 | 1.688 | 2.254 | 0.834 |
| 3 | 0.997 | 1.247 | 0.683 | 0.976 | 0.283 |
| 4 | 0.642 | 0.600 | 0.772 | 0.671 | 0.090 |
| 6 | 0.394 | 1.042 | 0.259 | 0.565 | 0.419 |
| $C_{max}$ (ng/mL) | | | | | |
| $T_{max}$ (h) | | | | | |
| $AUC_{last}$ (h*ng/mL) | | | | | |

BQL: <0.200 ng/mL

Example 11

Three Sprague Dawley rats were administered a dose of 5.41 mg/kg Oxymorphone Alanine (Ex No. B6) Oral. The plasma concentrations of oxymorphone in each rat, the mean plasma concentration of oxymorphone, and the standard deviation at the seven time points are summarized in Table 12:

TABLE 12

Group 11: 5.41 mg/kg Oxymorphone Alanine Oral

| | Plasma oxymorphone (ng/mL) | | | | |
|---|---|---|---|---|---|
| Time (h) | Rat 31 | Rat 32 | Rat 33 | Mean | SD |
| 0.25 | 7.162 | 3.700 | 8.770 | 6.544 | 2.591 |
| 0.5 | 5.382 | 2.835 | 5.058 | 4.425 | 1.386 |
| 1 | 5.630 | 2.846 | 8.661 | 5.712 | 2.908 |
| 2 | 2.536 | 3.074 | 5.179 | 3.596 | 1.397 |
| 3 | 1.497 | No Sample | 2.029 | 1.763 | ND |
| 4 | 0.348 | 1.496 | 0.722 | 0.855 | 0.585 |
| 6 | 0.516 | 0.442 | BQL | 0.319 | 0.279 |
| $C_{max}$ (ng/mL) | | | | | |
| $T_{max}$ (h) | | | | | |
| $AUC_{last}$ (h*ng/mL) | | | | | |

BQL: <0.200 ng/mL

Example 12

Three Sprague Dawley rats were administered a dose of 6.01 mg/kg Oxymorphone Mandelate (Ex No. B8) Oral. The plasma concentrations of oxymorphone in each rat, the mean plasma concentration of oxymorphone, and the standard deviation at the seven time points are summarized in Table 13:

TABLE 13

Group 12: 6.01 mg/kg Oxymorphone Mandelate Oral

| | Plasma oxymorphone (ng/mL) | | | | |
|---|---|---|---|---|---|
| Time (h) | Rat 34 | Rat 35 | Rat 36 | Mean | SD |
| 0.25 | 5.294 | 1.391 | 1.909 | 2.865 | 2.120 |
| 0.5 | 2.736 | 1.530 | 1.429 | 1.898 | 0.727 |
| 1 | 3.083 | 2.104 | 2.436 | 2.541 | 0.498 |
| 2 | 1.423 | 1.562 | 1.786 | 1.590 | 0.183 |
| 3 | 0.351 | 1.146 | 1.050 | 0.849 | 0.434 |
| 4 | 0.383 | 0.969 | 0.436 | 0.596 | 0.324 |
| 6 | 0.355 | 1.426 | 0.421 | 0.734 | 0.600 |
| $C_{max}$ (ng/mL) | | | | | |
| $T_{max}$ (h) | | | | | |
| $AUC_{last}$ (h*ng/mL) | | | | | |

BQL: <0.200 ng/mL

Example 13

Three Sprague Dawley rats were administered a dose of 6.02 mg/kg Oxymorphone Malate (Ex No. B9) Oral. The plasma concentrations of oxymorphone in each rat, the mean plasma concentration of oxymorphone, and the standard deviation at the seven time points are summarized in Table 14:

TABLE 14

Group 13: 6.02 mg/kg Oxymorphone Malate Oral

| Time (h) | Plasma oxymorphone (ng/mL) | | | | |
|---|---|---|---|---|---|
| | Rat 37 | Rat 38 | Rat 39 | Mean | SD |
| 0.25 | 4.115 | 4.829 | 6.096 | 5.013 | 1.003 |
| 0.5 | 2.805 | 4.386 | 2.200 | 3.130 | 1.129 |
| 1 | 2.379 | 3.955 | 2.999 | 3.111 | 0.794 |
| 2 | 3.028 | 1.615 | 2.540 | 2.394 | 0.718 |
| 3 | 1.059 | 1.410 | 1.128 | 1.199 | 0.186 |
| 4 | 0.456 | 0.856 | 0.755 | 0.689 | 0.208 |
| 6 | 0.490 | 0.310 | 2.493 | 1.098 | 1.212 |
| $C_{max}$ (ng/mL) | | | | | |
| $T_{max}$ (h) | | | | | |
| $AUC_{last}$ (h*ng/mL) | | | | | |

BQL: <0.200 ng/mL

Example 14

Three Sprague Dawley rats per group were administered a 0.89 mg/kg dose of an oxycodone compound. The plasma concentrations of oxycodone in each rat, the mean plasma concentration of oxymorphone, and the standard deviation at the seven time points are summarized in Table 15:

TABLE 15

| Group | Test Article | Dose$^a$ (mg/kg) | Time (h) | Plasma Concentration (ng/mL) by Subject | | | | | |
|---|---|---|---|---|---|---|---|---|---|
| | | | | 1M001 | 1M002 | 1M003 | Mean | SD | N |
| 1 | Oxycodone HCl Oral | 0.89 | 0.25 | 2.39 | 1.19 | 1.26 | 1.61 | 0.67 | 3 |
| | | | 0.5 | 1.97 | 0.682 | 1.04 | 1.23 | 0.66 | 3 |
| | | | 1 | 1.40 | BLQ | 0.678 | 1.04 | 0.51 | 2 |
| | | | 2 | BLQ | BLQ | BLQ | BLQ | — | 0 |
| | | | 3 | BLQ | BLQ | BLQ | BLQ | — | 0 |
| | | | 4 | BLQ | BLQ | BLQ | BLQ | — | 0 |
| | | | 6 | BLQ | BLQ | BLQ | BLQ | — | 0 |

| Group | Test Article | Dose (mg/kg) | Time (h) | Plasma Concentration (ng/mL) by Subject | | | | | |
|---|---|---|---|---|---|---|---|---|---|
| | | | | 2M001 | 2M002 | 2M003 | Mean | SD | N |
| 2 | Oxycodone Mandelate Oral | 0.89 | 0.25 | 3.07 | 1.53 | 3.31 | 2.64 | 0.97 | 3 |
| | | | 0.5 | 3.29 | 1.73 | 2.98 | 2.67 | 0.83 | 3 |
| | | | 1 | 1.48 | BLQ | 2.37 | 1.93 | 0.63 | 2 |
| | | | 2 | 0.908 | BLQ | 0.596 | 0.752 | 0.221 | 2 |
| | | | 3 | 0.671 | BLQ | BLQ | 0.671 | n = 1 | 1 |
| | | | 4 | BLQ | BLQ | BLQ | BLQ | — | 0 |
| | | | 6 | BLQ | BLQ | BLQ | BLQ | — | 0 |

| Group | Test Article | Dose (mg/kg) | Time (h) | Plasma Concentration (ng/mL) by Subject | | | | | |
|---|---|---|---|---|---|---|---|---|---|
| | | | | 3M001 | 3M002 | 3M003 | Mean | SD | N |
| 3 | Oxycodone Malate Oral | 0.89 | 0.25 | 0.742 | 1.14 | 1.09 | 0.991 | 0.217 | 3 |
| | | | 0.5 | 0.696 | 1.06 | 1.36 | 1.04 | 0.33 | 3 |
| | | | 1 | 0.767 | 1.14 | 1.62 | 1.18 | 0.43 | 3 |
| | | | 2 | 0.955 | 0.782 | 1.22 | 0.986 | 0.221 | 3 |
| | | | 3 | BLQ | BLQ | 0.792 | 0.792 | n = 1 | 1 |
| | | | 4 | BLQ | BLQ | 0.788 | 0.788 | n = 1 | 1 |
| | | | 6 | BLQ | BLQ | BLQ | BLQ | — | 0 |

| Group | Test Article | Dose (mg/kg) | Time (h) | Plasma Concentration (ng/mL) by Subject | | | | | |
|---|---|---|---|---|---|---|---|---|---|
| | | | | 4M001 | 4M002 | 4M003 | Mean | SD | N |
| 4 | Oxycodone Dimalate Oral | 0.89 | 0.25 | BLQ | BLQ | BLQ | BLQ | — | 0 |
| | | | 0.5 | BLQ | BLQ | BLQ | BLQ | — | 0 |
| | | | 1 | 0.933 | BLQ | BLQ | 0.933 | n = 1 | 1 |
| | | | 2 | BLQ | BLQ | BLQ | BLQ | — | 0 |
| | | | 3 | BLQ | BLQ | BLQ | BLQ | — | 0 |
| | | | 4 | BLQ | BLQ | BLQ | BLQ | — | 0 |
| | | | 6 | BLQ | BLQ | BLQ | BLQ | — | 0 |

| Group | Test Article | Dose (mg/kg) | Time (h) | Plasma Concentration (ng/mL) by Subject | | | | | |
|---|---|---|---|---|---|---|---|---|---|
| | | | | 5M001 | 5M002 | 5M003 | Mean | SD | N |
| 5 | Oxycodone Lactate | 0.89 | 0.25 | 5.59 | 7.27 | 3.09 | 5.32 | 2.10 | 3 |
| | | | 0.5 | 5.19 | 8.71 | 4.32 | 6.07 | 2.32 | 3 |

TABLE 15-continued

|  | Oral | | 1 | 3.61 | 6.31 | 2.12 | 4.01 | 2.12 | 3 |
|---|---|---|---|---|---|---|---|---|---|
|  |  | | 2 | 0.790 | 2.11 | BLQ | 1.45 | 0.93 | 2 |
|  |  | | 3 | BLQ | 1.24 | BLQ | 1.24 | n = 1 | 1 |
|  |  | | 4 | BLQ | 1.69 | BLQ | 1.69 | n = 1 | 1 |
|  |  | | 6 | BLQ | BLQ | BLQ | BLQ | — | 0 |

| | Test | Dose | Time | Plasma Concentration (ng/mL) by Subject | | | | | |
|---|---|---|---|---|---|---|---|---|---|
| Group | Article | (mg/kg) | (h) | 6M001 | 6M002 | 6M003 | Mean | SD | N |
| 6 | Oxycodone | 0.89 | 0.25 | BLQ | 4.92 | 1.90 | 3.41 | 2.14 | 2 |
|  | Stearate | | 0.5 | 2.83 | 7.57 | 4.73 | 5.04 | 2.39 | 3 |
|  | Oral | | 1 | 1.92 | 4.86 | 4.74 | 3.84 | 1.66 | 3 |
|  |  | | 2 | 1.41 | 2.13 | 1.93 | 1.82 | 0.37 | 3 |
|  |  | | 3 | 1.14 | 1.31 | 1.75 | 1.40 | 0.31 | 3 |
|  |  | | 4 | 1.02 | 1.44 | 1.39 | 1.28 | 0.23 | 3 |
|  |  | | 6 | 0.914 | BLQ | 1.48 | 1.20 | 0.40 | 2 |

| | Test | Dose | Time | Plasma Concentration (ng/mL) by Subject | | | | | |
|---|---|---|---|---|---|---|---|---|---|
| Group | Article | (mg/kg) | (h) | 7M001 | 7M002 | 7M003 | Mean | SD | N |
| 7 | Oxycodone | 0.89 | 0.25 | 0.912 | 3.12 | BLQ | 2.02 | 1.56 | 2 |
|  | Palmitate | | 0.5 | 2.79 | 6.17 | 1.87 | 3.61 | 2.26 | 3 |
|  | Oral | | 1 | 3.45 | 4.49 | 1.65 | 3.20 | 1.44 | 3 |
|  |  | | 2 | 1.84 | 2.02 | 1.17 | 1.68 | 0.45 | 3 |
|  |  | | 3 | 2.11 | 1.51 | BLQ | 1.81 | 0.42 | 2 |
|  |  | | 4 | 1.93 | 1.75 | BLQ | 1.84 | 0.13 | 2 |
|  |  | | 6 | 1.44 | BLQ | BLQ | 1.44 | n = 1 | 1 |

| | Test | Dose | Time | Plasma Concentration (ng/mL) by Subject | | | | | |
|---|---|---|---|---|---|---|---|---|---|
| Group | Article | (mg/kg) | (h) | 8M001 | 8M002 | 8M003 | Mean | SD | N |
| 8 | Oxycodone | 0.89 | 0.25 | 2.34 | BLQ | 2.31 | 2.33 | 0.02 | 2 |
|  | Oleate | | 0.5 | 3.40 | 1.82 | 3.02 | 2.75 | 0.82 | 3 |
|  | Oral | | 1 | 2.35 | 2.03 | 2.20 | 2.19 | 0.16 | 3 |
|  |  | | 2 | 1.03 | 1.21 | 1.34 | 1.19 | 0.16 | 3 |
|  |  | | 3 | BLQ | BLQ | 1.01 | 1.01 | n = 1 | 1 |
|  |  | | 4 | BLQ | BLQ | BLQ | BLQ | — | 0 |
|  |  | | 6 | BLQ | BLQ | 0.900 | 0.900 | n = 1 | 1 |

These and other modifications and variations to the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

What is claimed is:

1. An abuse-resistant opioid compound represented by Formula I:

$$O\text{-}X_n\cdot T_c \tag{I}$$

wherein,
O is an opioid selected from the group consisting of oxycodone and oxymorphone;
each X is an independent chemical moiety that is safe for human consumption having a hydrolyzable point of linkage to O though oxygen of an enol tautomer of O, such that hydrolysis releases activated opioid, and X consists of α-hydroxy acid;
T is a pharmaceutically acceptable salt;
c is from 0 to 5; and
n is from 1 to 10.

2. The abuse-resistant opioid compound of claim 1, wherein X consists of lactic acid, mandelic acid, malic acid, or tartaric acid.

3. A pharmaceutical composition, comprising:
an abuse-resistant opioid compound; and
at least one pharmaceutical additive,
wherein the abuse-resistant opioid compound is represented by Formula I:

$$O\text{-}X_n\cdot T_c \tag{I}$$

wherein,
O is an opioid selected from the group consisting of oxycodone and oxymorphone;
each X is an independent chemical moiety that is safe for human consumption having a hydrolyzable point of linkage to O though oxygen of an enol tautomer of O, such that hydrolysis releases activated opioid, and X consists of α-hydroxy acid;
T is a pharmaceutically acceptable salt;
c is from 0 to 5; and
n is from 1 to 10.

4. The pharmaceutical composition of claim 3, wherein X consists of lactic acid, mandelic acid, malic acid, or tartaric acid.

5. The abuse-resistant opioid compound of claim 1, wherein the abuse-resistant compound is selected from the group consisting of:

1013
A3
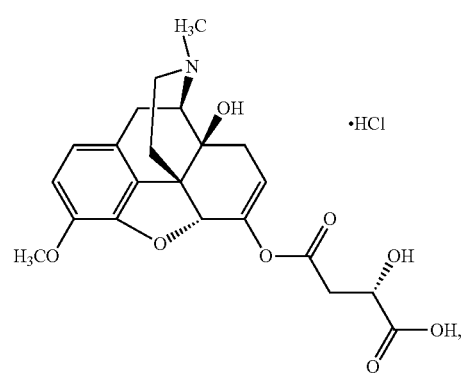
·HCl
A31
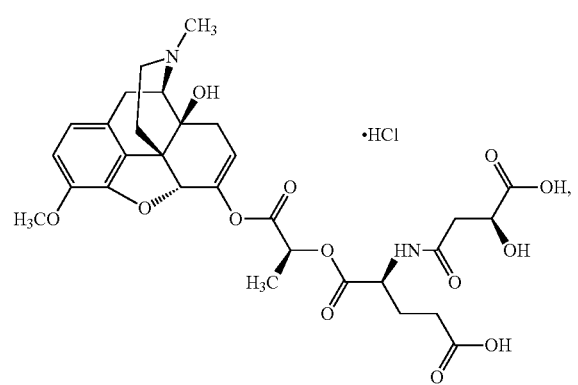
·HCl
B5
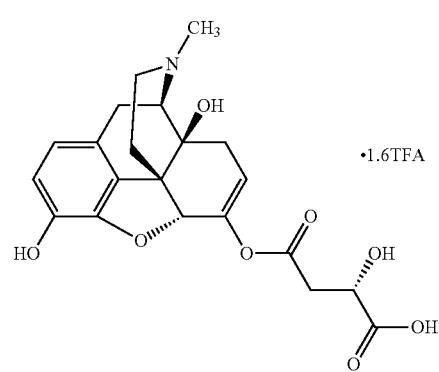
·1.6TFA
1014
-continued
B9
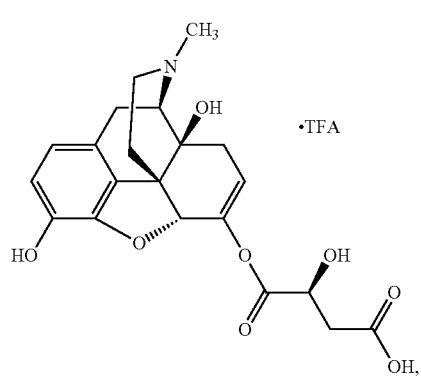
·TFA
B29
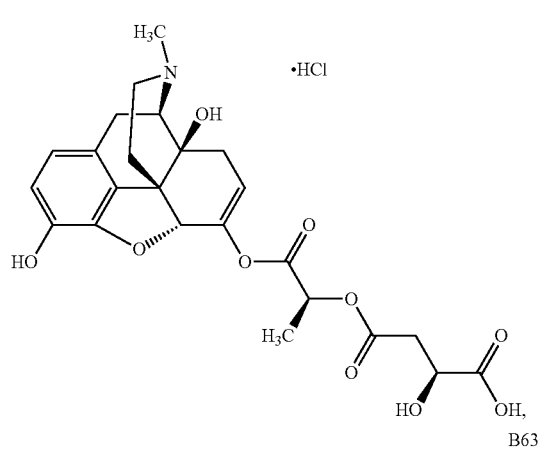
·HCl
B63
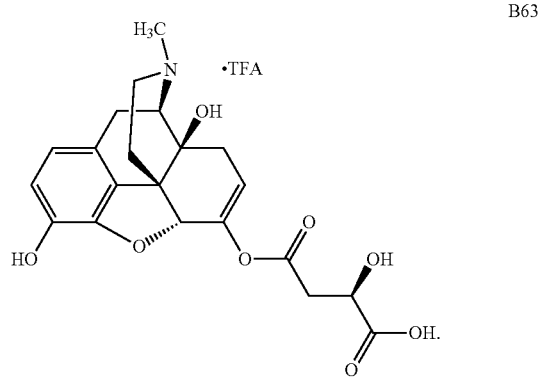 [SMILES: CN1CC[C@]23c4c5ccc(O)c4O[C@H]2C(OC(=O)C[C@@H](O)C(=O)O)=CC[C@@]3(O)[C@H]1C5]
·TFA
* * * * *

UNITED STATES PATENT AND TRADEMARK OFFICE
CERTIFICATE OF CORRECTION

PATENT NO. : 10,226,456 B2
APPLICATION NO. : 15/139836
DATED : March 12, 2019
INVENTOR(S) : John K. Thottathil Page 1 of 1

It is certified that error appears in the above-identified patent and that said Letters Patent is hereby corrected as shown below:

Column 1011, Claim 1, Line 56, Formula I should read, "$O - X_n \cdot \bullet T_c$."

Column 1011, Claim 1, Line 62, before "oxygen of" delete "though" and insert --through--

Column 1012, Claim 3, Line 48, Formula I should read, "$O - X_n \cdot \bullet T_c$."

Column 1012, Claim 3, Line 55, before "oxygen of" delete "though" and insert --through--

Signed and Sealed this
Sixteenth Day of April, 2019

Andrei Iancu
*Director of the United States Patent and Trademark Office*